US012209132B2

(12) United States Patent
Kastelein et al.

(10) Patent No.: US 12,209,132 B2
(45) **Date of Patent: *Jan. 28, 2025**

(54) COMPOSITIONS AND METHODS RELATED TO IL27 RECEPTOR BINDING

(71) Applicant: Synthekine, Inc., Menlo Park, CA (US)

(72) Inventors: Robert Kastelein, Menlo Park, CA (US); Patrick Lupardus, Menlo Park, CA (US); Deepti Rokkam, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,998

(22) Filed: Sep. 11, 2023

(65) Prior Publication Data

US 2024/0209101 A1 Jun. 27, 2024

Related U.S. Application Data

(63) Continuation of application No. 18/164,386, filed on Feb. 3, 2023, now Pat. No. 11,873,349, which is a continuation of application No. PCT/US2021/044577, filed on Aug. 4, 2021.

(60) Provisional application No. 63/061,562, filed on Aug. 5, 2020, provisional application No. 63/078,745, filed on Sep. 15, 2020, provisional application No. 63/135,884, filed on Jan. 11, 2021.

(51) Int. Cl.

| | |
|---|---|
| ***C07K 16/28*** | (2006.01) |
| ***A61P 37/02*** | (2006.01) |
| ***C07K 14/715*** | (2006.01) |
| ***C07K 16/46*** | (2006.01) |
| ***C07K 19/00*** | (2006.01) |
| ***C12N 15/63*** | (2006.01) |
| ***C12N 15/86*** | (2006.01) |
| *A61K 39/00* | (2006.01) |

(52) U.S. Cl.

CPC .......... *C07K 16/2866* (2013.01); *A61P 37/02* (2018.01); *C07K 14/7155* (2013.01); *C07K 16/2803* (2013.01); *C07K 16/46* (2013.01); *C07K 16/468* (2013.01); *C07K 19/00* (2013.01); *C12N 15/63* (2013.01); *C12N 15/86* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/569* (2013.01); *C07K 2319/40* (2013.01)

(58) Field of Classification Search

CPC .............. C07K 16/2866; C07K 16/468; C07K 2317/22; C07K 2317/31; C07K 2317/569

USPC ...................................................... 424/136.1

See application file for complete search history.

(56) References Cited

U.S. PATENT DOCUMENTS

| | | | |
|---|---|---|---|
| 8,258,268 | B2 | 9/2012 | Wu et al. |
| 8,921,528 | B2 | 12/2014 | Holt et al. |
| 8,975,382 | B2 | 3/2015 | Revets et al. |
| 9,334,331 | B2 | 5/2016 | Igawa |
| 10,421,807 | B2 | 9/2019 | Gonzales |
| 10,927,186 | B2 | 2/2021 | Roobrouck et al. |
| 2006/0024295 | A1 | 2/2006 | Brunetta |
| 2010/0297127 | A1 | 11/2010 | Ghilardi et al. |
| 2011/0028695 | A1 | 2/2011 | Revets et al. |
| 2011/0053865 | A1 | 3/2011 | Saunders et al. |
| 2011/0142831 | A1 | 6/2011 | Cua et al. |
| 2012/0201746 | A1 | 8/2012 | Liu et al. |
| 2012/0316324 | A1 | 12/2012 | Adams et al. |
| 2013/0189262 | A1 | 7/2013 | Wong et al. |
| 2014/0065142 | A1 | 3/2014 | Roschke et al. |
| 2015/0079088 | A1 | 3/2015 | Lowman et al. |
| 2016/0046730 | A1 | 2/2016 | Ghayur et al. |
| 2016/0251440 | A1 | 9/2016 | Roobrouck et al. |
| 2017/0106051 | A1 | 4/2017 | Oh et al. |
| 2017/0298149 | A1 | 10/2017 | Baeuerle et al. |
| 2018/0362655 | A1 | 12/2018 | Wang et al. |
| 2019/0185562 | A1 | 6/2019 | Regeneron |
| 2019/0330366 | A1 | 10/2019 | Eckelman et al. |
| 2019/0352404 | A1 | 11/2019 | Suzhou |
| 2019/0382500 | A1 | 12/2019 | Abujoub et al. |
| 2020/0016202 | A1 | 1/2020 | Kuchroo |
| 2020/0055946 | A1 | 2/2020 | Timmer et al. |

(Continued)

FOREIGN PATENT DOCUMENTS

| | | | |
|---|---|---|---|
| CN | 111018985 | A | 6/2019 |
| WO | 2008/011081 | A2 | 1/2008 |
| WO | 2009/068631 | A1 | 6/2009 |

(Continued)

OTHER PUBLICATIONS

Cairo, et al. "Control of multivalent interactions by binding epitope density." Journal of the American Chemical Society 124, No. 8 (2002): 1615-1619.

De Weerd, et al. "The interferons and their receptors-distribution and regulation." Immunology and cell biology 90, No. 5 (2012): 483-491.

Fan, et al. "Bispecific antibodies and their applications." Journal of hematology & oncology 8 (2015): 1-14.

Goel, et al. "Plasticity within the antigen-combining site may manifest as molecular mimicry in the humoral immune response." The Journal of Immunology 173, No. 12 (2004): 7358-7367.

(Continued)

*Primary Examiner* — Lynn A Bristol

(74) *Attorney, Agent, or Firm* — Kilpatrick Townsend & Stockton LLP

(57) ABSTRACT

Provided herein are IL27R binding proteins that bind to IL27Rα and gp130 and comprise an anti-IL27Rα $V_H$H antibody and an anti-gp130 $V_H$H antibody.

19 Claims, 4 Drawing Sheets

Specification includes a Sequence Listing.

(56) References Cited

U.S. PATENT DOCUMENTS

2020/0157237 A1 5/2020 Regev et al.
2024/0026014 A1* 1/2024 Kastelein .......... C07K 14/7156

FOREIGN PATENT DOCUMENTS

WO 2013/006544 A1 1/2013
WO 2013/059299 A1 4/2013
WO 2015/142675 A2 9/2015
WO 2016/097313 A1 6/2016
WO 2017/198212 A1 11/2017
WO 2019/129221 A1 7/2019
WO 2019/242632 A1 12/2019
WO 2020/144164 A1 7/2020
WO 2020/187711 A1 9/2020
WO 2022/031871 A1 2/2022
WO 2022/055641 A1 3/2022

OTHER PUBLICATIONS

Heldin, Carl-Henrik. "Dimerization of cell surface receptors in signal transduction." Cell 80, No. 2 (1995): 213-223.
Holliger, et al. ""Diabodies": small bivalent and bispecific antibody fragments." Proceedings of the National Academy of Sciences 90, No. 14 (1993): 6444-6448.
Khan, et al. "Adjustable locks and flexible keys: plasticity of epitope-paratope interactions in germline antibodies." The Journal of Immunology 192, No. 11 (2014): 5398-5405.
Kontermann, Roland. "Dual targeting strategies with bispecific antibodies." In MAbs, vol. 4, No. 2, pp. 182-197. Taylor & Francis, 2012.
Lo, et al. "Conformational epitope matching and prediction based on protein surface spiral features." BMC genomics 22, No. 2 (2021): 1-16.
Lloyd, et al. "Modelling the human immune response: performance of a 1011 human antibody repertoire against a broad panel of therapeutically relevant antigens." Protein Engineering, Design & Selection 22, No. 3 (2009): 159-168.
Marks, et al. "How repertoire data are changing antibody science." Journal of Biological Chemistry 295, No. 29 (2020): 9823-9837.
Nie, et al. "Biology drives the discovery of bispecific antibodies as innovative therapeutics." Antibody therapeutics 3, No. 1 (2020): 18-62.
Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.
Saerens, et al. "Single-domain antibodies as building blocks for novel therapeutics." Current opinion in pharmacology 8, No. 5 (2008): 600-608.
Shahangain et al., VVH Against VEGF-RBD, Genbank entry (online) National Center for Biotechnology Information, 12 May 215, retrieved from the internet www.ncbi.nlm.nih.gov/protein/BAR73350.1, 2 pages.
Shouval, et al. "Interleukin 10 receptor signaling: master regulator of intestinal mucosal homeostasis in mice and humans." Advances in immunology 122 (2014): 177-210.
U.S. Appl. No. 18/006,370 , Advisory Action, Mailed On Jun. 4, 2024, 3 pages.
U.S. Appl. No. 18/006,370 , Final Office Action, Mailed On Mar. 15, 2024, 12 pages.
U.S. Appl. No. 18/006,370 , Non-Final Office Action, Mailed On Dec. 4, 2023, 36 pages.
Bhattacharya et al., "Impact of Genetic Variation on Three Dimensional Structure and Function of Proteins", PLoS One, vol. 12, No. 3, Mar. 15, 2017, pp. 1-22.
Bork et al., "Go Hunting in Sequence Databases but Watch Out for the Traps", Trends in Genetics, vol. 12, No. 10, Oct. 1996, pp. 425-427.
Bork , "Powers and Pitfalls in Sequence Analysis: The 70% Hurdle", Genome Research, vol. 10, No. 4, Apr. 2000, pp. 398-400.
Brenner , "Errors in Genome Annotation", Trends in Genetics, vol. 15, No. 4, Apr. 1999, pp. 132-133.
Brorson et al., "Mutational Analysis of Avidity and Fine Specificity of Anti-Levan Antibodies", The Journal of Immunology, vol. 163, No. 12, Dec. 15, 1999, pp. 6694-6701.
Brummell et al., "Probing the Combining Site of an Anti-Carbohydrate Antibody by Saturation-Mutagenesis: Role of the Heavy-Chain CDR3 Residues", Biochemistry, vol. 32, No. 4, Feb. 1993, pp. 1180-1187.
Burks et al., "In Vitro Scanning Saturation Mutagenesis of an Antibody Binding Pocket", Proceedings of the National Academy of Sciences, vol. 94, No. 2, Jan. 21, 1997, pp. 412-417.
Colman , "Effects of Amino Acid Sequence Changes on Antibody-Antigen Interactions", Research in Immunology, vol. 145, No. 1, Jan. 1994, pp. 33-36.
Doerks et al., "Protein Annotation: Detective Work for Function Prediction", Trends in Genetics, vol. 14, No. 6, Jun. 1998, pp. 248-250.
Fenton et al., "Rheostat Positions: A New Classification of Protein Positions Relevant to Pharmacogenomics", Medicinal Chemistry Research, vol. 29, Jun. 7, 2020, pp. 1133-1146.
Guo et al., "Protein Tolerance to Random Amino Acid Change", Proceedings of the National Academy of Sciences, vol. 101, No. 25, Jun. 14, 2004, pp. 9205-9210.
Ikeuchi et al., "Delicate Balance Among Thermal Stability, Binding Affinity, and Conformational Space Explored by Single-domain VHH Antibodies", Scientific Reports, vol. 11, No. 1, Oct. 18, 2021, 9 pages.
Jang et al., "The Structural Basis for DNA Binding by an Anti-DNA Autoantibody", Molecular Immunology, vol. 35, No. 18, Dec. 15, 1998, pp. 1207-1217.
Kobayashi et al., "Tryptophan H33 Plays an Important Role in Pyrimidine (6-4) Pyrimidone Photoproduct Binding by a High-Affinity Antibody", Protein Engineering, vol. 12, No. 10, Oct. 1, 1999, pp. 879-884.
Rudikoff et al., "Single Amino Acid Substitution Altering Antigen-Binding Specificity", Proceedings of the National Academy of Sciences, vol. 79, No. 6, Mar. 1, 1982, pp. 1979-1983.
Skolnick et al., "From Genes to Protein Structure and Function: Novel Applications of Computational Approaches in the Genomic Era", Trends in Biotechnology, vol. 18, No. 1, Jan. 1, 2000, pp. 34-39.
Smith et al., "The Challenges of Genome Sequence Annotation or "The Devil is in the Details"", Nature Biotechnology, vol. 15, No. 12, Nov. 1997, pp. 1222-1223.
Tokuriki et al., "Stability Effects of Mutations and Protein Evolvability", Current Opinion in Structural Biology, vol. 19, No. 5, Oct. 2009, pp. 596-604.
Vasudevan et al., "A Single Amino Acid Change in the Binding Pocket Alters Specificity of an Anti-Integrin Antibody AP7.4 as Revealed by Its Crystal Structure", Blood Cells, Molecules, and Diseases, vol. 32, No. 1, Jan.-Feb. 2004, pp. 176-181.
Zhang et al., "Comprehensive Optimization of a Single-Chain Variable Domain Antibody Fragment as a Targeting Ligand for a Cytotoxic Nanoparticle", mAbs, vol. 7, No. 1, Jan. 2015, pp. 42-52.
U.S. Appl. No. 18/006,370 , Notice of Allowance, Mailed On Jul. 26, 2024, 9 pages.
Akbar et al., "A Compact Vocabulary of Paratope-Epitope Interactions Enables Predictability of Antibodyantigen Binding", Cell Reports, vol. 34, Mar. 16, 2021, 21 pages.
Cairo et al., "Control of Multivalent Interactions by Binding Epitope Density", Journal of the American Chemical Society, vol. 124, No. 8, Feb. 2, 2002, pp. 1615-1619.
Edwards et al., "The Remarkable Flexibility of the Human Antibody Repertoire; Isolation of Over One Thousand Different Antibodies to a Single Protein, BLyS", Journal of Molecular Biology, vol. 334, No. 1, Nov. 14, 2003, pp. 103-118.
Application No. PCT/US2021/044575 , International Preliminary Report on Patentability, Mailed On Feb. 16, 2023, 10 pages.
Application No. PCT/US2021/044575 , International Search Report and Written Opinion, Mailed On Feb. 2, 2022, 14 pages.
PCT/US2021/044575 "Invitation to Pay Additional Fees and, Where Applicable, Protest Fee", Nov. 18, 2021, 2 pages.

(56) References Cited

OTHER PUBLICATIONS

Application No. PCT/US2021/044576 , International Preliminary Report on Patentability, Mailed On Feb. 16, 2023, 8 pages.
Application No. PCT/US2021/044576 , International Search Report and Written Opinion, Mailed On Jan. 12, 2022, 12 pages.
PCT/US2021/044576 , "Invitation to Pay Additional Fees and, Where Applicable, Protest Fee", Nov. 12, 2021, 2 pages.
Application No. PCT/US2021/044577 , International Preliminary Report on Patentability, Mailed On Feb. 16, 2023, 7 pages.
Application No. PCT/US2021/044577 , International Search Report and Written Opinion, Mailed On Dec. 9, 2021, 10 pages.
Poosarla et al., "Computational de novo Design of Antibodies binding to a Peptide with High Affinity", Biotechnology and Bioengineering, vol. 114, No. 6, Jan. 6, 2017, pp. 1331-1342.
Vajda et al., "Progress Toward Improved Understanding of Antibody Maturation", Current Opinion in Structural Biology, vol. 67, Apr. 2021, pp. 226-231.

* cited by examiner

FIGURE 3A
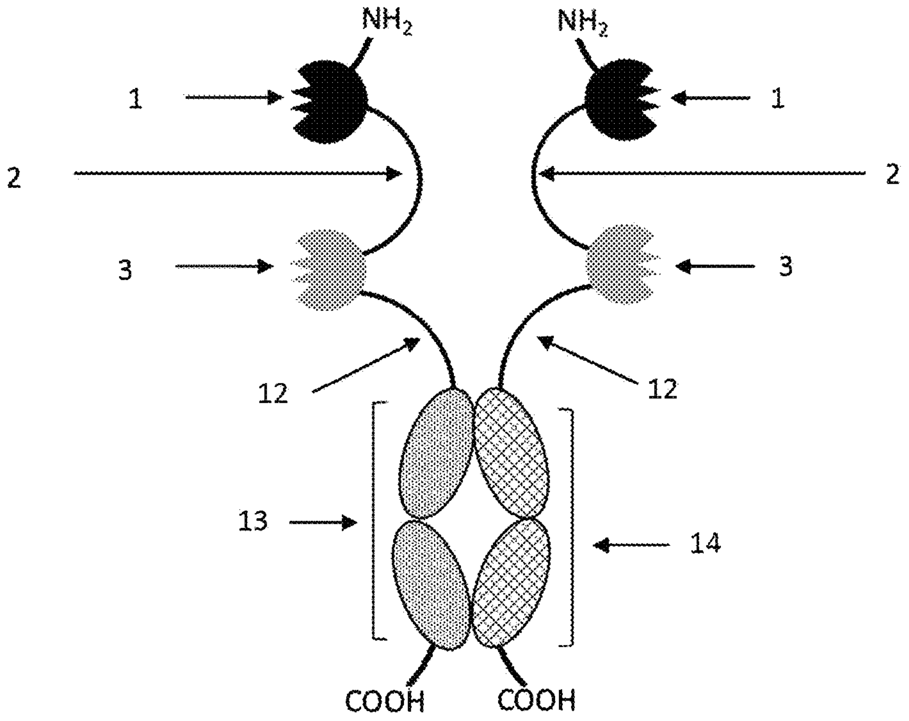
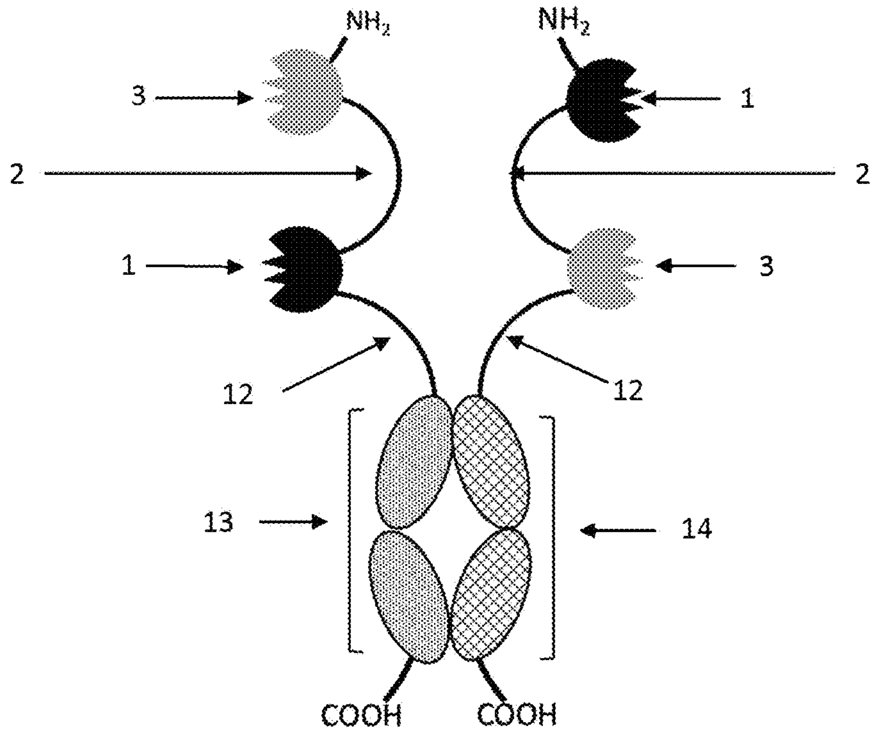
FIGURE 3B

COMPOSITIONS AND METHODS RELATED TO IL27 RECEPTOR BINDING

CROSS-REFERENCES TO RELATED APPLICATIONS

This application is a continuation of U.S. application Ser. No. 18/164,386, filed Feb. 3, 2023 which is a continuation of PCT/US2021/044577, filed Aug. 4, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in XML format and is hereby incorporated by reference in its entirety. Said XML file, created on Feb. 2, 2023, is named 106249-1361753-006820US_SL.xml, and is 2,426,545 bytes in size.

BACKGROUND OF THE DISCLOSURE

The interleukin-27 receptor (IL27R) is a type I cytokine receptor for interleukin-27 (IL27). It is a heterodimer composed of the IL27Rα subunit and glycoprotein 130 (gp130). IL27 is expressed by antigen presenting cells and induces differentiation of a diverse populations of T cells in the immune system. When IL27 binds to the IL27R, signaling pathways, such as the JAK-STAT and p38 MAPK pathways, are turned on to induce pro-inflammatory or anti-inflammatory responses, which involve different types of cells, such as macrophages, dendritic cells, T cells, and B cells. The response that is activated can be dependent on the external surrounding of IL27.

IL-27 is a heterodimeric cytokine consisting of two non-covalently linked subunits, p28 and EBI3. The p28 subunit belongs to the 4-helix bundle cytokine family, while EBI3 is the shortest form possible of a soluble cytokine receptor, with two typical cytokine binding domains (Pflanz S, et al., Immunity. 2002 June; 16(6):779-90).

The primary binding receptor for IL-27 is the IL-27R1 (also known as TCCR- or WSX-1 receptor). IL-27 and IL-27R1 form a complex of considerable affinity (nM). Gp130 is the second receptor that binds the complex of IL-27/IL-27R to create the active signaling complex. Gp130 binding to the IL-27/IL-27R1 complex is much weaker than the interaction between IL-27 and IL-27R1 (Pflanz S, et al., J Immunol. 2004 Feb. 15; 172(4):2225-31).

The IL-27 extracellular domain has 5 domains. The first two domains form the IL-27 binding domains. Typically the loops between D1 and D2 provide most of the binding energy.

The other 3 domains are called Fibronectin type III domains (Fn3). The sequence of each Fn3 domain varies.

The gp130 receptor has 6 domains. The top domain D1 of gp130 binds p28 of IL-27. D2 and D3 contribute little to binding IL-27. The membrane proximal 3 domains are Fn3 domains. The sequence of each Fn3 domain varies.

The structure of the IL-27R is not known but the domain structure is known. The structure of gp130 is known as complexed with IL-6. Based on that structure it is evident that the Fn3 domains do not energetically contribute to IL-27R complex formation. Rather the structure of the gp130 forms a 'C' with the domain 4 and 5 at 80% angle of each other. Certain residues in each of the 'tall' receptors are conserved similar to D4 and D5 in gp130. This indicates that all tall receptors of the gp130 family, including IL-27R, forms this 'C' structure. (Yibin Xu, et al., J Biol Chem. 2010 Jul. 9; 285(28):21214-8).

IL-27R has 5 extracellular domains. D1 and D2 are the cytokine binding domains. D3, D4 and D5 are Fn3 domains. The D5 domain of IL-27R and the D6 domain of gp130 will come close together at the membrane because of the 'C' shape of each receptor. This is required to be able for the receptor complex to trigger binding of JAKs at the intracellular domains of both receptors.

SUMMARY OF THE DISCLOSURE

The present disclosure provides compositions useful in the pairing of cellular receptors to generate desirable effects useful in treatment of disease in mammalian subjects.

Several advantages flow from the binding molecules described herein. The natural ligand of the IL-27R, IL-27, causes gp130 and IL-27Ra to come into proximity (i.e., by their simultaneous binding of IL-27). However, when IL-27 is used as a therapeutic in mammalian, particularly human, subjects, it may also trigger a number of adverse and undesirable effects by a variety of mechanisms including the presence of gp130 and IL-27Ra on other cell types and the binding to gp130 and IL-27Ra on the other cell types may result in undesirable effects and/or undesired signaling on cells expressing gp130 and IL-27Ra. The present disclosure is directed to methods and compositions that modulate the multiple effects of gp130 and IL-27Ra binding so that desired therapeutic signaling occurs, particularly in a desired cellular or tissue subtype, while minimizing undesired activity and/or intracellular signaling.

In some embodiments, the IL-27R binding molecules described herein are partial agonists of the IL-27 receptor. In some embodiments, the binding molecules described herein are designed such that the binding molecules are full agonists. In some embodiments, the binding molecules described herein are designed such that the binding molecules are super agonists.

In some embodiments, the binding molecules provide the maximal desired IL-27 intracellular signaling from binding to gp130 and IL-27Ra on the desired cell types, while providing significantly less IL-27 signaling on other undesired cell types. This can be achieved, for example, by selection of binding molecules having differing affinities or causing different $E_{max}$ for gp130 and IL-27Ra as compared to the affinity of IL-27 for gp130 and IL-27Ra. Because different cell types respond to the binding of ligands to its cognate receptor with different sensitivity, by modulating the affinity of the dimeric ligand (or its individual binding moieties) for the IL-27 receptor relative to wild-type IL-27 binding may facilitate the stimulation of desired activities while reducing undesired activities on non-target cells.

The present disclosure provides bivalent binding molecules that are agonists of the IL-27 receptor, the bivalent binding molecule comprising:

- a first single domain antibody (sdAb) that specifically binds to the extracellular domain of gp130 (an "anti-gp130 sdAb"), and
- a second single domain antibody that specifically binds to extracellular domain IL-27Ra (an "anti-IL-27Ra sdAb"), wherein the anti-gp130 sdAb and anti-IL-27Ra sdAb are stably associated and first wherein contacting a cell expressing gp130 and IL-27Ra with an effective amount of the bivalent binding molecule results the dimerization of gp130 and IL-27Ra and results in intracelullar signaling characteristic of the IL-27 receptor when activated by its natural cognate IL-27. In some embodiments, one or both of the sdAbs is an scFv. In some embodiments, one or both of the sdAbs is a VHH.

In some embodiments, one sdAb of the bivalent binding molecule is an scFv and the other sdAb is a VHH.

In some embodiments, the first and second sdAbs are covalently bound via a chemical linkage.

In some some embodiments, the first and second sdAbs are provided as single continuous polypeptide.

In some embodiments, the first and second sdAbs are provided as single continuous polypeptide optionally comprising an intervening polypeptide linker between the amino acid sequences of the first and second sdAbs.

In some embodiments the bivalent binding molecule optionally comprising a linker, is optionally expressed as a fusion protein with an additional amino acid sequence. In some embodiments, the additional amino acid sequence is a purification handle such as a chelating peptide or an additional protein such as a subunit of an Fc molecule.

In one aspect, the disclosure provides an IL27 receptor (IL27R) binding protein that specifically binds to IL27Rα subunit (IL27Rα) and glycoprotein 130 subunit (gp130), wherein the binding protein causes the multimerization of IL27Rα and gp130 when bound to IL27Rα and gp130 and the multimerization results in the activation of JAK kinases associated with the intracellular domains of IL27Rα and gp130 and intracelullar signaling, and wherein the binding protein comprises a single-domain antibody (sdAb) that specifically binds to IL27Rα (an anti-IL27Rα sdAb) and a sdAb that specifically binds to gp130 (an anti-gp130 sdAb). In some embodiments, the multimerization of IL27Rα and gp130 can cause downstream signaling.

In some embodiments, the anti-IL27Rα sdAb is a $V_HH$ antibody (an antiIL27Rα $V_HH$ antibody) and/or the anti-gp130 sdAb is a $V_HH$ antibody (an anti gp130 $V_HH$ antibody). In some embodiments, the anti-IL27Rα sdAb and the anti-gp130 sdAb are joined directly or via a peptide linker. In some embodiments, the peptide linker comprises between 1 and 50 amino acids. In particular embodiments, the peptide linker comprises a sequence of GGGS (SEQ ID NO:108).

In some embodiments, the IL27R binding protein comprises:

- a first $V_HH$ antibody comprising a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR1 from a row of Table 1A; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR2 from the same row of Table 1A; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR3 from the same row of Table 1A; and
- a second $V_HH$ antibody comprising a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR4 from the same row of Table 1A; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR5 from the same row of Table 1A; and a CDR3 having at least 90% (e.g., 91%, 92%, 93%, 94%, 95%, 96%, 97%, 98%, 99%, or 100%) sequence identity, or having 0, 1, 2, or 3 amino acid changes optionally conservative amino acid changes relative, to the sequence of a CDR6 from the same row of Table 1A.

In some embodiments, the IL27R binding protein comprises a sequence at least 90% (e.g., 91%, 92%, 93%, 94%, 95%, 96%, 97%, 98%, 99%, or 100%) identical to any one of the dual VHH dimer sequences shown in Table 1A.

In certain embodiments, the anti IL27Rα $V_HH$ antibody comprises a CDR1 having 0, 1, 2, or 3 amino acid changes relative to the sequence of any one of SEQ ID NOS:193-198; a CDR2 having 0, 1, 2, or 3 amino acid changes relative to the sequence of any one of SEQ ID NOS:199-204; and a CDR3 having 0, 1, 2, or 3 amino acid changes relative to the sequence of any one of SEQ ID NOS:205-210. In further embodiments, the anti gp130 $V_HH$ antibody comprises a CDR1 having 0, 1, 2, or 3 amino acid changes relative to the sequence of any one of SEQ ID NOS:211-217; a CDR2 having 0, 1, 2, or 3 amino acid changes relative to the sequence of any one of SEQ ID NOS:218-224; and a CDR3 having 0, 1, 2, or 3 amino acid changes relative to the sequence of any one of SEQ ID NOS:225-231.

In particular embodiments, the IL27R binding protein comprises a CDR1, a CDR2, and a CDR3 in the anti IL27Rα $V_HH$ antibody and a CDR1, a CDR2, and a CDR3 in the anti gp130 $V_HH$ antibody as listed in a row of Table 1.

In some embodiments, the binding protein comprises an anti gp130 $V_HH$ antibody linked to the N-terminus of a linker and an anti IL27Rα $V_HH$ antibody linked to the C-terminus of the linker. In some embodiments, the anti gp130 $V_HH$ antibody comprises a sequence having at least 90% (e.g., 91%, 92%, 93%, 94%, 95%, 96%, 97%, 98%, 99%, or 100%) sequence identity to a sequence of any one of SEQ ID NOS:232-237. In some embodiments, the anti IL27Rα $V_HH$ antibody comprises a sequence having at least 90% (e.g., 91%, 92%, 93%, 94%, 95%, 96%, 97%, 98%, 99%, or 100%) sequence identity to a sequence of any one of SEQ ID NOS:238-244.

In particular embodiments, each of the anti-gp130 $V_HH$ antibody and the anti-IL27Rα $V_HH$ antibody comprises a sequence having at least 90% (e.g., 91%, 92%, 93%, 94%, 95%, 96%, 97%, 98%, 99%, or 100%) identity to a sequence listed in a row of Table 2A.

In certain embodiments, the binding protein comprises a sequence that is substantially identical to a sequence of any one of SEQ ID NOS:1-42. In certain embodiments, the binding protein comprises a sequence having at least 90% (e.g., 91%, 92%, 93%, 94%, 95%, 96%, 97%, 98%, 99%, or 100%) identity to a sequence of any one of SEQ ID NOS:1-42.

In some embodiments, the binding protein comprises an anti IL27Rα $V_HH$ antibody linked to the N-terminus of a linker and an anti gp130 $V_HH$ antibody linked to the C-terminus of the linker. In some embodiments, the anti IL27Rα $V_HH$ antibody comprises a sequence having at least 90% (e.g., 91%, 92%, 93%, 94%, 95%, 96%, 97%, 98%, 99%, or 100%) sequence identity to a sequence of any one of SEQ ID NOS:245-251. In certain embodiments, the anti gp130 $V_HH$ antibody comprises a sequence having at least 90% sequence identity to a sequence of any one of SEQ ID NOS:252-257.

In particular embodiments, each of the anti IL27Rα $V_HH$ antibody and the anti gp130 $V_HH$ antibody comprises a sequence having at least 90% (e.g., 91%, 92%, 93%, 94%, 95%, 96%, 97%, 98%, 99%, or 100%) identity to a sequence listed in a row of Table 3A.

In certain embodiments, the binding protein comprises a sequence that is substantially identical to a sequence of any one of SEQ ID NOS:43-84. In certain embodiments, the binding protein comprises a sequence having at least 90% (e.g., 91%, 92%, 93%, 94%, 95%, 96%, 97%, 98%, 99%, or 100%) identity to a sequence of any one of SEQ ID NOS:43-84.

In another aspect, the disclosure provides an isolated nucleic acid encoding the IL27R binding protein described herein. In certain embodiments, the isolated nucleic acid comprises a sequence having at least 90% (e.g., 91%, 92%, 93%, 94%, 95%, 96%, 97%, 98%, 99%, or 100%) sequence identity to a sequence of any one of SEQ ID NOS:109-192 or a sequence from Table 1B. The disclosure also provides an expression vector comprising the nucleic acid. The disclosure also provides an isolated host cell comprising the expression vector.

In another aspect, the disclosure provides a pharmaceutical composition comprising the IL27R binding protein described herein and a pharmaceutically acceptable carrier.

In another aspect, the disclosure provides a method of treating an autoimmune or inflammatory disease, disorder, or condition, a neoplastic disease, or a viral infection in a subject in need thereof, comprising administering to the subject a therapeutically effective amount of an IL27R binding protein described herein or a pharmaceutical composition described herein.

In some embodiments, the method further comprises administering one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52, IgEIL12/IL23, IL17a, IL1ß, IL4Rα, IL5, IL6R, integrin-α4β7, RANKL, TNFα, VEGF-A, and VLA-4.

In certain embodiments, the disease, disorder, or condition is selected from viral infections, heliobacter pylori infection, HTLV, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome, psoriasis, psoriatic arthritis, dermatitis (eczema), exfoliative dermatitis or atopic dermatitis, *Pityriasis rubra* pilaris, *Pityriasis rosacea*, parapsoriasis, *Pityriasis* lichenoiders, *Lichen planus, Lichen nitidus*, ichthyosiform dermatosis, keratodermas, dermatosis, alopecia areata, pyoderma gangrenosum, vitiligo, pemphigoid, urticaria, prokeratosis, rheumatoid arthritis; seborrheic dermatitis, solar dermatitis, seborrheic keratosis, senile keratosis, actinic keratosis, photo-induced keratosis, keratosis follicularis; acne vulgaris; keloids; nevi; warts including verruca, condyloma or condyloma acuminatum, and human papilloma viral (HPV) infections.

An IL27R binding proteins described herein are useful in the treatment of neoplastic diseases, such as cancer (e.g., a solid tumor cancer; e.g., non-small-cell lung carcinoma (NSCLC), renal cell carcinoma (RCC), or melanoma) and/or infectious diseases (e.g., bacterial infections and viral infections (e.g., viral infections caused by hepatitis C virus (HCV), human papillomavirus (HPV), or human immunodeficiency virus (HIV)) in a subject in need thereof. The IL27R binding protein binds to and activates $CD8^+$ T cells, $CD4^+$ T cells, and/or T regulatory (Treg) cells. The IL27R binding protein can trigger different levels of downstream signaling in different cell types. For example, by varying the length of the linker between the antiIL27Rα $V_HH$ antibody and the antigp130 $V_HH$ antibody in the IL27R binding protein, the IL27R binding protein can cause a higher level of downstream signaling in desired cell types compared to undesired cell types. In some embodiments, by varying the linker length, an IL27R binding protein can cause a higher level of downstream signaling in T cells (e.g., $CD8^+$ T cells) compared to the level of downstream signaling in other cells. In other embodiments, different antiIL27Rα $V_HH$ antibodies with different binding affinities and different antigp130 $V_HH$ antibodies with different binding affinities can be combined to make different IL27R binding proteins. Further, the orientation of the two antibodies in the binding protein can also be changed to make a different binding protein (i.e., antiIL27Rα $V_HH$ antibody-linker-antigp130 $V_HH$ antibody, or antigp130 $V_HH$ antibody-linker-antiIL27Rα $V_HH$ antibody). Different IL27R binding proteins can be screened to find the ideal binding protein that causes a higher level of downstream signaling in desired cell types compared to undesired cell types. In some embodiments, the level of downstream signaling in T cells (e.g., $CD8^+$ T cells) is at least 1.1, 1.5, 2, 3, 5, or 10 times of the level of downstream signaling in other cells.

In particular, the IL27R binding protein binds to and activates $CD8^+$ T cells. In some embodiments, the IL27R binding protein binds to and activates $CXCR5^+$ $CD8^+$ T cells. It is known that IL27 can promote and sustain a rapid division of memory-like $CXCR5^+$ $CD8^+$ T cells during, for example, viral infection. The $CXCR5^+$ $CD8^+$ T cells can sustain T cell responses during persistent infection or cancer and drive the proliferative burst of $CD8^+$ T cells after anti-PD1 treatment. Accordingly, an IL27R binding protein described herein is useful to sustain and augment self-renewing T cells in chronic infections and neoplastic diseases, such as cancer.

BRIEF DESCRIPTION OF THE FIGURES

FIG. 2A provides a schematic representation of an illustrative single polypeptide chain bivalent binding molecule comprising, from amino to carboxy, a first single domain antibody (1) and a second single domain antibody (3) and a linker (2). FIG. 2B provides a schematic representation of a bivalent binding molecule comprising a first single domain antibody (1) and a second single domain antibody (3) and a linker (2) and a knob-into-hole Fc domain, the Fc domain comprising a first subunit which is a Fc knob (13) and a second subunit which is a Fc hole (14) wherein the bivalent binding molecule is covalently linked to an Fc domain subunit via a IgG hinge sequence (12).

FIGS. 3A and 3B of the attached drawings provides a schematic representations of two illustrative configurations of bivalent binding molecules of the present disclosure. FIG. 3A provides a schematic representation of an illustrative bivalent binding molecule construct comprising two bivalent binding molecules each attached to a subunit of a knob-into-hole Fc domain, the construct comprising two polypeptide chains, the first polypeptide chain comprising, from amino to carboxy, a first single domain antibody (1), a linker (2) and a second single domain antibody (3), a IgG hinge sequence (12) and a Fc knob subunit (13) and a second polypeptide chain comprising, from amino to carboxy, a first single domain antibody (1), a linker (2) and a second single domain antibody (3), a IgG hinge sequence (12) and a Fc hole subunit (14) wherein the first and second polypeptides are in stable associate via the interaction of the knob-into-hole Fc domain. FIG. 3B provides schematic representation of a an alternative arrangement of a bivalent binding molecule construct comprising two polypeptides a first polypeptide chain comprising, from amino to carboxy, a first single domain antibody (1), a linker (2) and a second single domain antibody (3), an IgG hinge sequence (12) and a Fc knob subunit (13) and a second polypeptide chain comprising, from amino to carboxy, a first second domain antibody (3), a linker (2) and a first single domain antibody (1), a IgG hinge sequence (12) and a Fc hole subunit (14), wherein the first and second polypeptides are in stable association via the interaction of the knob-into-hole Fc domain.

DETAILED DESCRIPTION OF THE DISCLOSURE

I. Introduction

Figure 1:
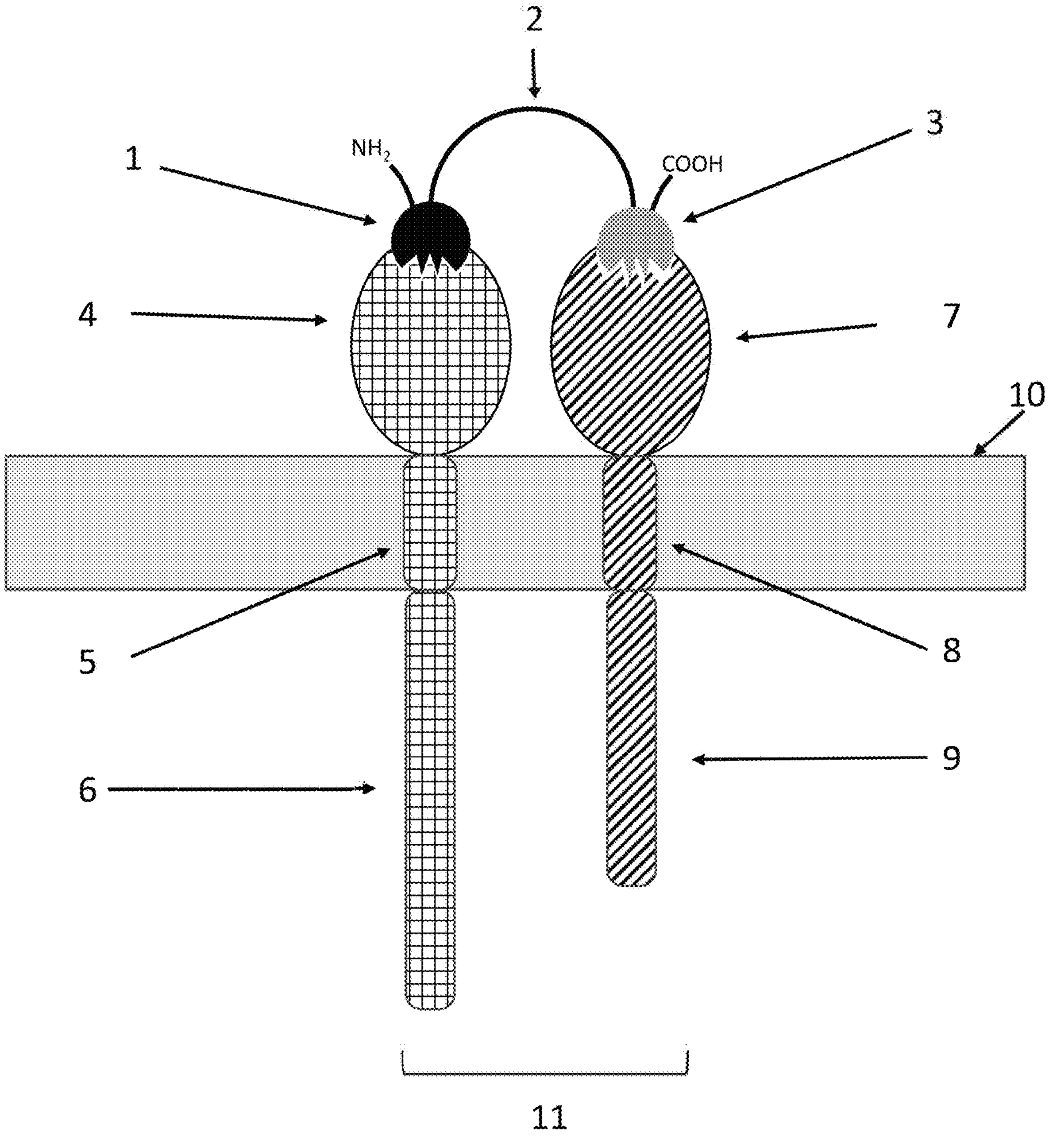
FIG. 1 of the attached drawings provides a schematic representation of one embodiment of the bivalent binding molecule of the present disclosure comprising a first single domain antibody (1) and a second single domain antibody (3) and a linker (2) depicted as interacting with a cell membrane (10) associated heterodimeric receptor comprising a first receptor subunit comprising an extracellular domain (4), and transmembrane domain (5) and an intracellular domain (6) interaction of a bivalent binding molecule and a second first receptor subunit comprising an extracellular domain (7), and transmembrane domain (8) and an intracellular domain (9) wherein the intracellular domain of the first receptor (6) and the intracellular domain of the second receptor (9) on of a bivalent binding molecule are within a proximal distance (11).
Figure 2A:
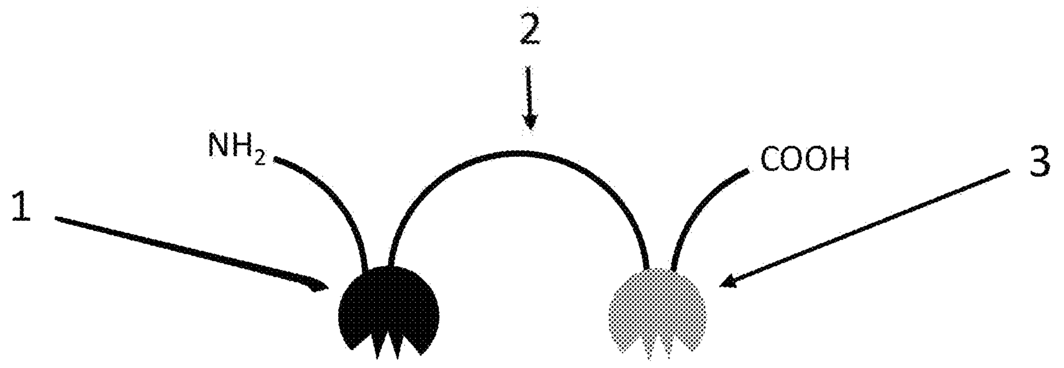
FIGS. 2A and 2B of the attached drawings provides a schematic representation of two illustrative configurations of bivalent binding molecules of the present disclosure.
Figure 2B:
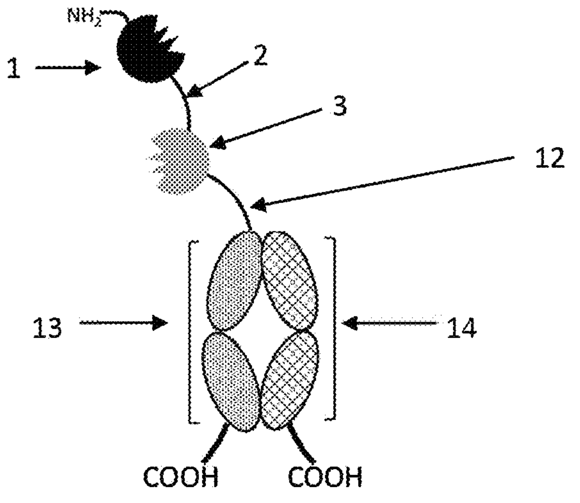
Figure 4A:
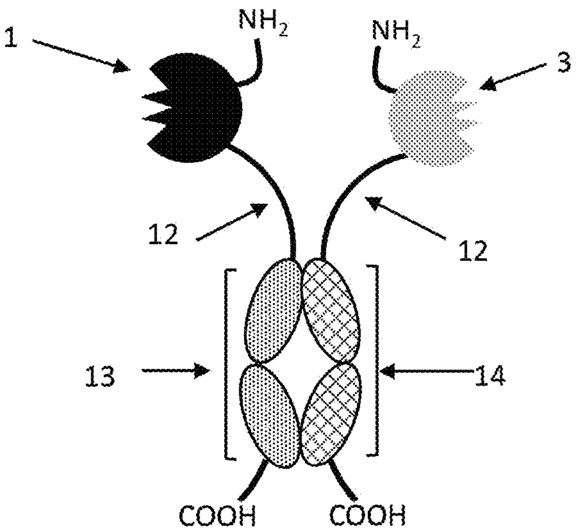
FIG. 4A provides alternative schematic representations of configurations of the bivalent binding molecules of the present disclosure where one single domain antibody is attached to each subunit of a knob-into-hole Fc domain comprising two polypeptides, the first polypeptide comprising from amino to carboxy, a first single domain antibody (1), an IgG hinge sequence (12) and a Fc knob subunit (13), the second polypeptide comprising from amino to carboxy, a second single domain antibody (3), an IgG hinge sequence (12) and a Fc hole subunit (13), wherein the first and second single domain antibodies are in stable associate via the interaction of the knob-into-hole Fc domain.
Figure 4B:
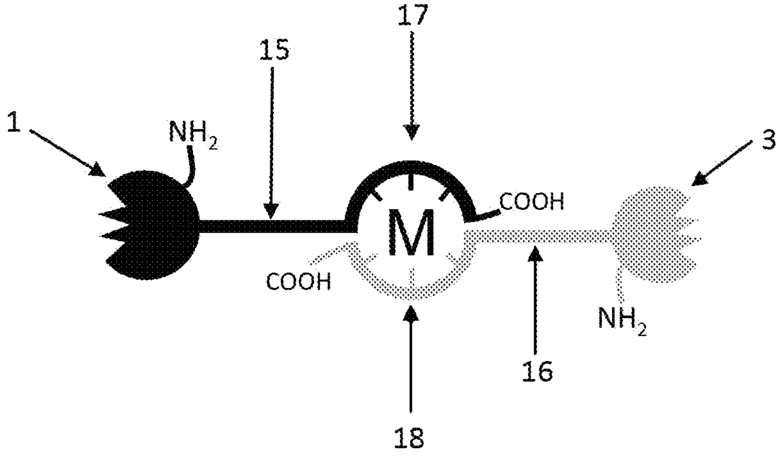
FIG. 4B provides a schematic representation of a binding molecule the binding domains are single domain antibodies associated via transition metal coordinate covalent complex. As illustrated, the binding molecules comprises two polypeptide subunits: the first subunit comprising a first single domain antibody (1) is attached via a first linker (15) to a first chelating peptide (17) and second subunit comprising a second single domain antibody (3) is attached via a second linker (16) to a second chelating peptide (18), wherein the first chelating peptide (17) and second chelating peptide (18) form a coordinate covalent complex with a single transition metal ion ("M"). The transition metal ion may be in a kinetically labile or kinetically inert oxidation state.

The present disclosure provides compositions useful in the pairing of cellular receptors to generate desirable effects useful in treatment of diseases. In general, binding proteins are provided that comprise a first domain that binds to IL27Rα and a second domain that binds to gp130, such that upon contacting with a cell expressing IL27Rα and gp130, the binding protein causes the functional association of IL27Rα and gp130, thereby resulting in functional dimerization of the receptors and downstream signaling.

Several advantages flow from the binding proteins described herein. The natural ligand of IL27R, IL27, causes IL27Rα and gp130 to come into proximity (i.e., by their simultaneous binding of IL27). However, when IL27 is used as a therapeutic in mammalian, particularly human, subjects, it may also trigger a number of adverse and undesirable effects by a variety of mechanisms including the presence of IL27Rα and gp130 on other cell types and the binding to IL27Rα and gp130 on the other cell types may result in undesirable effects and/or undesired signaling on cells expressing IL27Rα and gp130. The present disclosure is directed to methods and compositions that modulate the multiple effects of IL27Rα and gp130 binding so that desired therapeutic signaling occurs, particularly in a desired cellular or tissue subtype, while minimizing undesired activity and/or intracellular signaling.

In some embodiments, the binding proteins described herein are designed such that the binding proteins provide the maximal desired IL27 intracellular signaling from binding to IL27Rα and gp130 on the desired cell types, while providing significantly less IL27 signaling on other undesired cell types. This can be achieved, for example, by selection of binding proteins having differing affinities or causing different $E_{max}$ for IL27Rα and gp130 as compared to the affinity of IL27 for IL27Rα and gp130. Because different cell types respond to the binding of ligands to its cognate receptor with different sensitivity, by modulating the affinity of the dimeric ligand (or its individual binding moieties) for the IL27 receptor relative to wild-type IL27 binding facilitates the stimulation of desired activities while reducing undesired activities on non-target cells. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signalinging caused by the binding protein, can also be measured.

Interleukin 27 (IL27) Structure:

IL27 is a member of the IL-12 cytokine family. IL27 is a heterodimeric cytokine comprised of two subunits: IL27A (also referred to as IL-27p28) and IL27B (also referred to as Epstein-Barr Virus induced gene 3 or "EBI3"). The human p28 (hIL27A) is expressed as a 243 amino acid pre-protein comprising 28 amino acid signal sequence which is post-translationally removed to render a 215 amino acid mature protein. UniProtKB—Q8NEV9 (IL27A_HUMAN). The mature form of p28 (less the signal peptide) possesses the amino acid sequence;

(SEQ ID NO: 400)

FPRPPGRPQLSLQELRREFTVSLHLARKLLSEVRGQAHRFAESHL

PGVNLYLLPLGEQLPDVSLTFQAWRRLSDPERLCFISTTLQPFHA

LLGGLGTQGRWTNMERMQLWAMRLDLRDLQRHLRFQVLAAGFNLP

EEEEEEEEEEEEERKGLLPGALGSALQGPAQVSWPQLLSTYRLLH

SLELVLSRAVRELLLLSKAGHSVWPLGFPTLSPQP

The human IL27B (hIL27B) is expressed as a 229 amino acid pre-protein comprising 20 amino acid signal sequence which is post-translationally removed to render a 209 amino acid mature protein. UniProtKB—Q14213 (IL27B_HUMAN). The mature form of hIL27B (less the signal peptide) possesses the amino acid sequence (SEQ ID NO: 401)

RKGPPAALTLPRVQCRASRYPIAVDCSWTLPPAPNSTSPVSFIAT

YRLGMAARGHSWPCLQQTPTSTSCTITDVQLFSMAPYVLNVTAVH

PWGSSSSFVPFITEHIIKPDPPEGVRLSPLAERQLQVQWEPPGSW

PFPEIFSLKYWIRYKRQGAARFHRVGPIEATSFILRAVRPRARYY

VQVAAQDLTDYGELSDWSLPATATMSLGK

Interleukin 27 (IL27) Receptor:

IL27 results in intracellular signaling via its interaction with a heterodimeric receptor consisting of: IL-27Ra (or IL27RA) and gp130. The binding of IL27 to IL27 receptor activates signaling pathways including the JAK/STAT and p38 MAPK pathways. IL27 stimulates both pro-inflammatory and anti-inflammatory response in different cell types such as macrophages, dendritic cells, T cells and B cells. The type of response is dependent on the environment.

The human IL27 receptor subunit alpha (hIL27RA) is expressed as a 636 amino acid pre-protein comprising 32 amino acid signal sequence which is post-translationally removed to render a 604 amino acid mature protein. UniProtKB—Q6UWB1 (I27RA_HUMAN)

The mature form of hIL27RA (less the signal peptide) possesses the amino acid sequence:

(SEQ ID NO: 402)

QGSAGPLQCYGVGPLGDLNCSWEPLGDLGAPSELHLQSQKYRSNK

TQTVAVAAGRSWVAIPREQLTMSDKLLVWGTKAGQPL WPPVFVN

LETQMKPNAPRLGPDVDFSEDDPLEATVHWAPPTWPSHKVLICQF

HYRRCQEAAWTLLEPELKTIPLTPVEIQDLELATGYKVYGRCRME

KEEDLWGEWSPILSFQTPPSAPKDVWVSGNLCGTPGGEEPLLLWK

APGPCVQVSYKVWFWVGGRELSPEGITCCCSLIPSGAEWARVSAV

NATSWEPLINLSLVCLDSASAPRSVAVSSIAGSTELLVTWQPGPG

EPLEHVVDWARDGDPLEKLNWVRLPPGNLSALLPGNFTVGVPYRI

TVTAVSASGLASASSVWGFREELAPLVGPTLWRLQDAPPGTPAIA

-continued

WGEVPRHQLRGHLTHYTLCAQSGTSPSVCMNVSGNTQSVTLPDLP

WGPCELWVTASTIAGQGPPGPILRLHLPDNTLRWKVLPGILFLWG

LFLLGCGLSLATSGRCYHLRHKVLPRWVWEKVPDPANSSSGQPHM

EQVPEAQPLGDLPILEVEEMEPPPVMESSQPAQATAPLDSGYEKH

FLPTPEELGLLGPPRPQVLA

The extracellular domain of hIL27RA (IL27RA-ECD) is a 484 amino acid polypeptide corresponding to amino acids 33-516 of the hIL27RA preprotein and possesses the amino acid sequence:

(SEQ ID NO: 403)

QGSAGPLQCYGVGPLGDLNCSWEPLGDLGAPSELHLQSQKYRSNK

TQTVAVAAGRSWVAIPREQLTMSDKLLVWGTKAGQPLWPPVFVNL

ETQMKPNAPRLGPDVDFSEDDPLEATVHWAPPTWPSHKVLICQFH

YRRCQEAAWTLLEPELKTIPLTPVEIQDLELATGYKVYGRCRMEK

EEDLWGEWSPILSFQTPPSAPKDVWVSGNLCGTPGGEEPLLLWKA

PGPCVQVSYKVWFWVGGRELSPEGITCCCSLIPSGAEWARVSAVN

ATSWEPLTNLSLVCLDSASAPRSVAVSSIAGSTELLVTWQPGPGE

PLEHVVDWARDGDPLEKLNWVRLPPGNLSALLPGNFTVGVPYRIT

VTAVSASGLASASSVWGFREELAPLVGPTLWRLQDAPPGTPAIAW

GEVPRHQLRGHLTHYILCAQSGTSPSVCMNVSGNTQSVTLPDLPW

GPCELWVTASTIAGQGPPGPILRLHLPDNTLRWK

The human gp130 receptor subunit (hGP130) is also referred as the IL6 receptor beta subunit. UniProtKB—P40189 (IL6RB_HUMAN. hGP130 is expressed as a 918 amino acid pre-protein comprising 22 amino acid signal sequence which is post-translationally removed to render a 896 amino acid mature protein. The mature form of hGP130 possess the amino acid sequence:

(SEQ ID NO: 404)

ELLDPCGYISPESPVVQLHSNFTAVCVLKEKCMDYFHVNANYIVW

KTNHFTIPKEQYTIINRTASSVTFTDIASLNIQLTCNILTFGQLE

QNVYGITIISGLPPEKPKNLSCIVNEGKKMRCEWDGGRETHLETN

FTLKSEWATHKFADCKAKRDIPTSCTVDYSTVYFVNIEVWVEAEN

ALGKVTSDHINEDPVYKVKPNPPHNLSVINSEELSSILKLTWINP

SIKSVIILKYNIQYRTKDASTWSQIPPEDTASTRSSFTVQDLKPF

TEYVFRIRCMKEDGKGYWSDWSEEASGITYEDRPSKAPSFWYKID

PSHTQGYRTVQLVWKTLPPFEANGKILDYEVTLTRWKSHLQNYTV

NATKLTVNLTNDRYLATLTVRNLVGKSDAAVLTIPACDFQATHPV

MDLKAFPKDNMLWVEWTTPRESVKKYILEWCVLSDKAPCITDWQQ

EDGTVHRTYLRGNLAESKCYLITVTPVYADGPGSPESIKAYLKQA

PPSKGPTVRTKKVGKNEAVLEWDQLPVDVQNGFIRNYTIFYRTII

GNETAVNVDSSHTEYTLSSLTSDTLYMVRMAAYTDEGGKDGPEFT

FTTPKFAQGEIEAIVVPVCLAFLLTTLLGVLFCFNKRDLIKKHIW

-continued

```
PNVPDPSKSHIAQWSPHTPPRHNFNSKDQMYSDGNFTDVSVVEIE

ANDKKPFPEDLKSLDLFKKEKINTEGHSSGIGGSSCMSSSRPSIS

SSDENESSQNTSSTVQYSTVVHSGYRHQVPSVQVFSRSESTQPLL

DSEERPEDLQLVDHVDGGDGILPRQQYFKQNCSQHESSPDISHFE

RSKQVSSVNEEDFVRLKQQISDHISQSCGSGQMKMFQEVSAADAF

GPGTEGQVERFETVGMEAATDEGMPKSYLPQTVRQGGYMPQ
```

The extracellular domain of hGP130 (hGP130-ECD) is a 597 amino acid polypeptide corresponding to amino acids 23-619 of the hGP130 preprotein and possesses the amino acid sequence:

```
                                      (SEQ ID NO: 405)
ELLDPCGYISPESPVVQLHSNFTAVCVLKEKCMDYFHVNANYIVW

KTNHFTIPKEQYTIINRTASSVTFTDIASLNIQLICNILTFGQLE

QNVYGITIISGLPPEKPKNLSCIVNEGKKMRCEWDGGRETHLETN

FTLKSEWATHKFADCKAKRDTPTSCTVDYSTVYFVNIEVWVEAEN

ALGKVTSDHINFDPVYKVKPNPPHNLSVINSEELSSILKLTWTNP

SIKSVIILKYNIQYRTKDASTWSQIPPEDTASTRSSFTVQDLKPF

TEYVFRIRCMKEDGKGYWSDWSEEASGITYEDRPSKAPSFWYKID

PSHTQGYRTVQLVWKTLPPFEANGKILDYEVTLTRWKSHLQNYTV

NATKLTVNLINDRYLATLTVRNLVGKSDAAVLTIPACDFQATHPV

MDLKAFPKDNMLWVEWTTPRESVKKYILEWCVLSDKAPCITDWQQ

EDGTVHRTYLRGNLAESKCYLITVTPVYADGPGSPESIKAYLKQA

PPSKGPTVRTKKVGKNEAVLEWDQLPVDVQNGFIRNYTIFYRTII

GNETAVNVDSSHTEYTLSSLTSDTLYMVRMAAYTDEGGKDGPEFT

FTTPKFAQGEIE
```

IL27 Activity

IL27 is expressed by antigen presenting cells. hIL27 induces differentiation of the diverse populations of T cells in the immune system and also upregulates IL10. hIL27 has pro- and anti-inflammatory properties, that can regulate T-helper cell development, suppress T-cell proliferation, stimulate cytotoxic T-cell activity, induce isotype switching in B-cells, and that have diverse effects on innate immune cells. Among its target cells are CD4 T-helper cells which can differentiate in type 1 effector cells (TH1), type 2 effector cells (TH2) and IL17 producing helper T-cells (TH17).

T Cell Differentiation

IL27 plays a significant role in the differentiation through inducing or suppressing of T cell subtypes including Th1, Th2, Th17, Tr1 and Treg cells. IL-27 is greatly involved in differentiation through inducing or suppressing of each T cell subset. Interferon gamma (IFNg) expressing Th1 cells are generated in response IL27 through STAT1 signaling via expression of T-bet and signature Th1 genes. IL4 expressing Th2 cells are inhibited by IL27 through the transcription factor GATA-3. Th17 cells, which express IL17, IL22, and GM-CSF, are inhibited by IL27 through STAT1 and expression of transcription factor RORγt. Treg cells are inhibited by IL27 through STAT1 and STAT3.

IL27 drives rapid clonal expansion of naive but not memory CD4 T-cells. IL27 also strongly synergizes with IL-12 to trigger interferon-gamma/IFN-gamma production of naive CD4 T-cells, binds to the cytokine receptor WSX-1/TCCR. Another important role of IL-27 is its antitumor activity as well as its antiangiogenic activity with activation of production of antiangiogenic chemokines Induction of IL10

Tr1 cells which express IL-10, are induced by IL-27 through the transcription factor c-Maf providing an anti-inflammatory response. A primary activity of IL-10 is the suppression of inflammatory responses. Also involved are the STAT1 and STAT3 transcription factors that bind specifically to the IL-27a. The activation of STAT3 by IL-27 leads to an increase of IL-10 secretion from Treg cells.

II. Definitions

To facilitate the understanding of present disclosure, certain terms and phrases are defined below as well as throughout the specification. The definitions provided herein are non-limiting and should be read in view of the knowledge of one of skill in the art would know.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); AA or aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar, kDa=kilodalton; i.m.=intramuscular(ly); i.p.=intraperitoneal (ly); SC or SQ=subcutaneous(ly); QD=daily; BID=twice daily; QW=once weekly; QM=once monthly; HPLC=high performance liquid chromatography; BW=body weight; U=unit; ns=not statistically significant; PBS=phosphate-buffered saline; PCR=polymerase chain reaction; HSA=human serum albumin; MSA=mouse serum albumin; DMEM=Dulbeco's Modification of Eagle's Medium; EDTA=ethylenediaminetetraacetic acid.

It will be appreciated that throughout this disclosure reference is made to amino acids according to the single letter or three letter codes. For the reader's convenience, the single and three letter amino acid codes are provided in the Table below:

TABLE

| Amino Acid Abbreviations | | |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York. N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g. an assay) or biological or chemical property (e.g. the degree of binding of the molecule to another molecule) or of a physical property of a material or cell (e.g. modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc. As used herein, the term "proliferative activity" referes to an activity that promotes cell proliferation and replication.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g. an ortholog, an IL2 ortholog, an engineered cell expressing an orthogonal receptor, an engineered cell expressing an orthogonal IL2 receptor, a CAR-T cell expressing an orthogonal IL2 receptor, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, inhalation and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant (KD), a ratio of the dissociation rate constant between the molecule and its target (Koff) and the association rate constant between the molecule and its target (Kon).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state, resulting in a biological response. The response mimics the effect of the endogenous activator of the receptor. The term "agonist" includes partial agonists, full agonists and superagonists. An agonist may be described as a "full agonist" when such agonist which leads to a substantially full biological response (i.e., the response associated with the naturally occurring ligand/receptor binding interaction) induced by receptor under study, or a partial agonist. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate. e.g., a gene, protein, ligand, receptor, biological pathway, or cell.

Antibody: As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4) delta$C_H2$, $F(ab')_2$, Fab, ScFv, $V_H$, $V_L$, tetrabodies, triabodies, diabodies, dsFv, $F(ab')_3$, scFv-Fc and $(scFv)_2$ that competes with the immunoglobulin from which it was derived for binding to the target molecule. The term antibody is not restricted to immunoglobulins derived from any particular mammalian species and includes murine, human, equine, and camelids antibodies (e.g., human antibodies). The term "antibody" encompasses antibodies isolatable from natural sources or from animals following immunization with an antigen and as well as engineered antibodies including monoclonal antibodies, bispecific antibodies, trispecific, chimeric antibodies, humanized antibodies, human antibodies, CDR-grafted, veneered, or deimmunized (e.g., to remove T-cell epitopes) antibodies. The term "human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries.

Binding molecule: As used herein, the term "binding molecule" refers to a bivalent molecule that can bind to the extracellular domain of two cell surface receptors. In some embodiments, a binding molecule specifically binds to two different receptors (or domains or subunits thereof) such that the receptors (or domains or subunits) are maintained in proximity to each other such that the receptors (or domains or subunits), including domains thereof (e.g., intracellular domains) interact with each other and result in downstream signaling.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chen.* 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Clonotype: A clonotype is defined as a collection of binding molecules that originate from the same B-cell progenitor cell. The term "clonotype" is used herein to refer to a collection of antigen binding molecules that belong to the same germline family, have the same CDR3 lengths, and have 70% or greater homology in CDR3 sequence.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

As used herein, the term "downstream signaling" refers to the cellular signaling process that is caused by the interaction of two or more cell surface receptors that are brought into proximity of each other.

Effective Concentration (EC): As used herein, the terms "effective concentration" or its abbreviation "EC" are used interchangeably to refer to the concentration of an agent (e.g., an hIL2 mutein) in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect. The EC of a particular effective concentration of a test agent may be abbreviated with respect to the with respect to particular parameter and test system.

Extracellular Domain: As used herein the term "extracellular domain" or its abbreviation "ECD" refers to the portion of a cell surface protein (e.g. a cell surface receptor) which is outside of the plasma membrane of a cell. The term "ECD" may include the extra-cytoplasmic portion of a transmembrane protein or the extra-cytoplasmic portion of a cell surface (or membrane associated protein).

Identity: As used herein, the term "percent (%) sequence identity" or "substantially identical" used in the context of nucleic acids or polypeptides, refers to a sequence that has at least 50% sequence identity with a reference sequence. Alternatively, percent sequence identity can be any integer from 50% to 100%. In some embodiments, a sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined with BLAST using standard parameters, as described below. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned. Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff. *Proc. Natl. Acad. Sci. USA* 89:10915 (1989)). The BLAST algorithm also performs a statistical analysis of the similarity between two sequences (see. e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about $10^{-20}$.

As used herein, the term "interleukin 27 receptor" or "IL27R" refers to a heterodimeric receptor formed by subunits IL27Rα (IL27Rα) and glycoprotein 130 (gp130) and bound by the ligand IL27. The human sequence of IL27Rα is listed as UniProt ID NO. Q6UWB1. The human sequence of gp130 is listed as UniProt ID NO. Q13514.

Intracellular Signaling: As used herein, the terms "intracellular signaling" and "downstream signaling" are used interchangeably to refer to the to the cellular signaling process that is caused by the interaction of the intracellular domains (ICDs) of two or more cell surface receptors that are in proximity of each other. In receptor complexes via the JAK/STAT pathway, the association of the ICDS of the receptor subunits brings the JAK domains of the ICDs into proximit which initiates a phosphorylation cascade in which STAT molecules are phosphorylated and translocate to the nucleus associating with particular nucleic acid sequences resulting in the activation and expression of particular genes in the cell. The binding molecules of the present disclosure provide intracelullar signaling characteristic of the IL-27 receptor when activated by its natural cognate IL27. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signalinging caused by the binding molecule, can also be measured.

Ligand: As used herein, the term "ligand" refers to a molecule that exhibits specific binding to a receptor and results in a change in the biological activity of the receptor so as to effect a change in the activity of the receptor to which it binds. In one embodiment, the term "ligand" refers to a molecule, or complex thereof, that can act as an agonist or antagonist of a receptor. As used herein, the term "ligand" encompasses natural and synthetic ligands. "Ligand" also encompasses small molecules, e.g., peptide mimetics of cytokines and peptide mimetics of antibodies. The complex of a ligand and receptor is termed a "ligand-receptor complex."

As used herein, the term "linker" refers to a linkage between two elements, e.g., protein domains. A linker can be a covalent bond or a peptide linker. The term "bond" refers to a chemical bond, e.g., an amide bond or a disulfide bond, or any kind of bond created from a chemical reaction, e.g., chemical conjugation. The term "peptide linker" refers to an amino acid or polypeptide that may be employed to link two protein domains to provide space and/or flexibility between the two protein domains.

Modulate: As used herein, the terms "modulate", "modulation" and the like refer to the ability of a test agent to affect a response, either positive or negative or directly or indirectly, in a system, including a biological system or biochemical pathway.

Multimerization: As used herein, the term "multimerization" refers to two or more cell surface receptors, or domains or subunits thereof, being brought in close proximity to each other such that the receptors, or domains or subunits thereof, can interact with each other and cause intracellular signaling.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. The terms "immediately N-terminal" or "immediately C-terminal" are used to refers to a position of a first amino acid residue relative to a second amino acid residue where the first and second amino acid residues are covalently bound to provide a contiguous amino acid sequence.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the Operably Linked: The term "operably linked" is used herein to refer to the relationship between nucleic acid sequences encoding differing functions when combined into a single nucleic acid sequence that, when introduced into a cell, provides a nucleic acid which is capable of effecting the transcription and/or translation of a particular nucleic acid sequence in a cell. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, certain genetic elements such as enhancers need not be contiguous with respect to the sequence to which they provide their effect.

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. A In some embodiments, the IL-27 binding molecule has a reduced $E_{max}$ compared to the $E_{max}$ caused by IL-27. $E_{max}$ reflects the maximum response level in a cell type that can be obtained by a ligand (e.g., a binding molecule described herein or the native cytokine (e.g., IL-27)). In some embodiments, the IL-27 binding molecule described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IL-27. In other embodiments, the $E_{max}$ of the IL-27 binding molecule described herein is greater (e.g., at least 1%, 5%, 10%, 15%, 20%, 25%, 30%, 35%, 40%, 45%, or 50% greater) than the $E_{max}$ of the natural ligand, IL-27. In some embodiments, by varying the linker length of the IL-27 binding molecule, the $E_{max}$ of the IL-27 binding molecule can be changed. The IL-27 binding molecule can cause $E_{max}$ in the most desired cell types, and a reduced $E_{max}$ in other cell types.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; fusion proteins of immunologically active proteins (e.g. antigenic diphtheria or tetanus toxin fragments) and the like.

As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Proximity: As used herein, the term "proximity" refers to the spatial proximity or physical distance between two cell surface receptors, or domains or subunits thereof, after a binding molecule described herein binds to the two cell surface receptors, or domains or subunits thereof. In some embodiments, after the binding molecule binds to the cell surface receptors, or domains or subunits thereof, the spatial proximity between the cell surface receptors, or domains or subunits thereof, can be, e.g., less than about 500 angstroms, such as e.g., a distance of about 5 angstroms to about 500 angstroms. In some embodiments, the spatial proximity amounts to less than about 5 angstroms, less than about 20 angstroms, less than about 50 angstroms, less than about 75 angstroms, less than about 100 angstroms, less than about 150 angstroms, less than about 250 angstroms, less than about 300 angstroms, less than about 350 angstroms, less than about 400 angstroms, less than about 450 angstroms, or less than about 500 angstroms. In some embodiments, the spatial proximity amounts to less than about 100 angstroms. In some embodiments, the spatial proximity amounts to less than about 50 angstroms. In some embodiments, the spatial proximity amounts to less than about 20 angstroms. In some embodiments, the spatial proximity amounts to less than about 10 angstroms. In some embodiments, the spatial proximity ranges from about 10 to 100 angstroms, from about 50 to 150 angstroms, from about 100 to 200 angstroms, from about 150 to 250 angstroms, from about 200 to 300 angstroms, from about 250 to 350 angstroms, from about 300 to 400 angstroms, from about 350 to 450 angstroms, or about 400 to 500 angstroms. In some embodiments, the spatial proximity amounts to less than about 250 angstroms, alternatively less than about 200 angstroms, alternatively less than about 150 angstroms, alternatively less than about 120 angstroms, alternatively less than about 100 angstroms, alternatively less than about 80 angstroms, alternatively less than about 70 angstroms, or alternatively less than about 50 angstroms.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. In some embodiments, the receptor is a cell surface receptor that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multicomponent complex to facilitate intracellular signaling. For example, the ligand may bind a cell surface molecule having not associated with any intracellular signaling alone but upon ligand binding facilitates the formation of a multimeric complex that results in intracellular signaling.

Recombinant: As used herein, the term "recombinant" is used as an adjective to refer to the method by a polypeptide, nucleic acid, or cell that was modified using recombinant DNA technology. A recombinant protein is a protein produced using recombinant DNA technology and may be designated as such using the abbreviation of a lower case "r" (e.g., rhIL2) to denote the method by which the protein was produced. Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response." for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors. In contrast, the terms "inhibition", "down-regulation" and the like refer to the opposite effects.

Single Domain Antibody (sdAb): The term "single-domain antibody" or "sdAbs," refers to an antibody having a single (only one) monomeric variable antibody domain. A sdAb is able to bind selectively to a specific antigen. A $V_HH$ antibody, further defined below, is an example of a sdAb.

Specifically Binds: As used herein, the term "specifically bind" refers to the degree of selectivity or affinity for which one molecule binds to another. In the context of binding pairs (e.g., a binding molecule described herein/receptor, a ligand/receptor, antibody/antigen, antibody/ligand, antibody/receptor binding pairs), a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample.

Stably Associated: As used herein, the term "stably associated" or "in stable association with" are used to refer to the various means by which one molecule (e.g., a polypeptide) may be associated with another molecule over an extended period of time. The stable association of one molecule to another may be effected by a variety of means, including covalent bonding and non-covalent interactions. In some embodiments, stable association of two molecules may be effected by covalent bonds such as peptide bonds. In other embodiments, stable association of two molecules may be effected b non-covalent interactions. Examples of non-covalent interactions which may provide a stable association between two molecules include electrostatic interactions (e.g., hydrogen bonding, ionic bonding, halogen binding, dipole-dipole interactions, Van der Waals forces and π-effects including cation-π interactions, anion-π interactions and π-π interactions) and hydrophobilic/hydrophilic interactions. In some embodiments, the stable association of sdAbs of the bivalent binding molecules of the present disclosure may be effected by non-covalent interactions. In one embodiment, the non-covalent stable association of the sdAbs of the bivalent binding molecules may be achieved by conjugation of the sdAbs to "knob-into-hole" modified Fc monomers. An Fc "knob" monomer stably associates non-covalently with an Fc "hole" monomer. Conjugation of a first sdAb which specifically binds to the extracellular domain of a first subunit of a heterodimeric receptor to an "Fc knob" monomer and conjugation of an second sdAb which specifically binds to the extracellular domain of a second subunit of a heterodimeric receptor to an "Fc hole" monomer provides stable association of the first and second sdAbs. The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 on one chain and Y349 on the second chain which results in a stabilizing disulfide bridge between the two antibody heavy chains in the Fc region (Carter, et al. (2001) Immunol Methods 248, 7-15). The knob-into-hole format is used to facilitate the expression of a first polypeptide (e.g., an IL27Rα binding sdAb) on a first Fc monomer with a "knob" modification and a second polypeptide on the second Fc monomer possessing a "hole" modification to facilitate the expression of heterodimeric polypeptide conjugates.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially: As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g., blood count), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

Therapeutically Effective Amount: As used herein, the term The phrase "therapeutically effective amount" is used in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, modification of biomarker levels, increase in duration of survival, extended duration of progression free survival, extension of the time to progression, increased time to treatment failure, extended duration of event free survival, extension of time to next treatment, improvement objective response rate, improvement in the duration of response, and the like that that are relied upon by clinicians in the field for the assessment of an improvement in the condition of the subject in response to administration of an agent.

Treat: The terms "treat", "treating", treatment" and the like refer to a course of action (such as administering a binding molecule described herein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

VHH: As used herein, the term "$V_H$H" is a type of sdAb that has a single monomeric heavy chain variable antibody domain. Such antibodies can be found in or produced from Camelid mammals (e.g., camels, llamas) which are naturally devoid of light chains $V_H$Hs can be obtained from immunization of camelids (including camels, llamas, and alpacas (see, e.g., Hamers-Casterman, et al. (1993) Nature 363:446-448) or by screening libraries (e.g., phage libraries) constructed in $V_H$H frameworks. Antibodies having a given specificity may also be derived from non-mammalian sources such as $V_H$Hs obtained from immunization of cartilaginous fishes including, but not limited to, sharks. In a particular embodiment, a $V_H$H in a bispecific $V_HH^2$ binding molecule described herein binds to a receptor (e.g., the first receptor or the second receptor of the natural or non-natural receptor pairs) if the equilibrium dissociation constant between the $V_H$H and the receptor is greater than about $10^{-6}$M, alternatively greater than about $10^{-8}$ M, alternatively greater than about $10^{-10}$ M, alternatively greater than about $10^{-11}$ M, alternatively greater than about $10^{-10}$ M, greater than about $10^{-12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a $V_H$H described herein can be humanized to contain human framework regions. Examples of human germlines that could be used to create humanized $V_H$Hs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

$V_HH^2$: As used herein, the term "$V_HH^2$" and "bispecific $V_HH^2$" and "VHH dimer" refers to are used interchangeably to refer to a subtype of the binding molecules of the present disclosure wherein the first and second sdAbs are both VHHs and first $V_H$H binding to a first receptor, or domain or subunit thereof, and a second $V_H$H binding to a second receptor, or domain or subunit thereof.

Wild Type: As used herein, the term "wild type" or "WT" or "native" is used to refer to an amino acid sequence or a nucleotide sequence that is found in nature and that has not been altered by the hand of man.

III. IL27 Receptor Binding Proteins

The IL27 receptor (IL27R) includes IL27Rα subunit (IL27Rα) and glycoprotein 130 subunit (gp130). Provided herein is an IL27R binding protein that specifically binds to IL27Rα and gp130. In some embodiments, the IL27R binding protein binds to a mammalian cell expressing both IL27Rα and gp130. In some embodiments, the IL27R binding protein can be a bispecific $V_HH^2$ as described below.

The IL27R binding protein can be a bispecific $V_HH^2$ that has a first $V_H$H binding to IL27Rα (an anti-IL27Rα $V_H$H antibody) and a second $V_H$H binding to gp130 (an anti-gp130 $V_H$H antibody) and causes the dimerization of the two receptor subunits and downstream signaling when bound to a cell expressing IL27Rα and gp130, e.g., a $CD8^+$ T cells, a $CD4^+$ T cells, and/or a T regulatory (Treg) cell.

A $V_H$H is a type of single-domain antibody (sdAb) containing a single monomeric variable antibody domain. Like a full-length antibody, it is able to bind selectively to a specific antigen. The complementary determining regions (CDRs) of $V_H$Hs are within a single-domain polypeptide. $V_H$Hs can be engineered from heavy-chain antibodies found in camelids.

An exemplary $V_H$H has a molecular weight of approximately 12-15 kDa which is much smaller than traditional mammalian antibodies (150-160 kDa) composed of two heavy chains and two light chains. $V_H$Hs can be found in or produced from Camelidae mammals (e.g., camels, llamas, dromedary, alpaca, and guanaco) which are naturally devoid of light chains. Descriptions of sdAbs and $V_H$HS can be found in, e.g., De Greve et al., *Curr Opin Biotechnol.* 61:96-101, 2019; Ciccarese, et al., *Front Genet.* 10:997, 2019; Chanier and Chames, *Antibodies* (*Basel*) 8(1), 2019; and De Vlieger et al., *Antibodies* (*Basel*) 8(1), 2018.

To prepare a binding protein that is a bispecific $V_HH^2$, in some embodiments, the two $V_H$Hs can be synthesized separately, then joined together by a linker. Alternatively, the bispecific $V_HH^2$ can be synthesized as a fusion protein. $V_H$Hs having different binding activities and receptor targets can be paired to make a bispecific $V_HH^2$. The binding proteins can be screened for signal transduction on cells carrying one or both relevant receptors.

In some embodiments, a bispecific $V_HH^2$ comprises:

A first $V_H$H antibody comprising a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR1 from a row of Table 1A; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR2 from the same row of Table 1A; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR3 from the same row of Table 1A; and a second $V_HH$ antibody comprising a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR4 from the same row of Table 1A; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of a CDR5 from the same row of Table 1A; and a CDR3 having at least 90% (e.g., 91%, 92%, 93%, 94%, 95%, 96%, 97%, 98%, 99%, or 100%) sequence identity, or having 0, 1, 2, or 3 amino acid changes optionally conservative amino acid changes relative, to the sequence of a CDR6 from the same row of Table 1A. In some embodiments, the bispecific $V_HH^2$ comprises a sequence at least 90% (e.g., 91%, 92%, 93%, 94%, 95%, 96%, 97%, 98%, 99%, or 100%) identical to any one of the dual VHH dimer sequences shown in Table 1A.

In some embodiments, a $V_HH$ described herein can be humanized to contain human framework regions. Examples of human germlines that could be used to create humanized $V_HH$s include, but are not limited to, VH3-23 (e.g., UniProt ID: P01764). VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Table 1A:

TABLE 1A

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH1-DR591 | 406 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGGSQVQLQESGGGSVQAGGSERLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 211 | FTFSSYPMS | 218 | TISAGGDTTLYADSVKG | 947 | RIDCNSGYCYRRNY | 943 | AIASGYIDSRWCMA | 199 | AIWPGGGLTVYADSVKG | 205 | GSPRMCPSLEFGFDY |
| hIL27Ra_VHH2-DR591 | 407 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGGSQVQLQESGGGSVQAGGSLRLSCTASGAIASGYIDSRWCMAWFRQAPGKEREGVAAIWPGGGLTVYADSVKGRETISRDHAKNTLYLQMNNLKPEDTAMYYCAAGSPRMCPSLEFGEDYWGQGTQVTVSS | 940 | FTFSLSGMS | 224 | AISSGGASTYYTDSMS | 231 | GGSGYGDASRMTSPVKG | 943 | AIASGYIDSRWCMA | 199 | AIWPGGGLTVYADSVKG | 205 | GSPRMCPSLEFGFDY |
| hIL27Ra_VHH3-DR591 | 408 | QVQLQESGGGSVQAGGSLRISCVASGYVSCDYFLPSWYRQAPGKEREFVSIIDGTGSTSYAASVKGRETASEDKGKNIAYLQMNSLKPEDTAMYYCKASCVRGRAVSEYWGQGTQVTVSSGGGSQVQLQESGGGSVQAGGSLRLSCTASGAIASGYIDSRWCMAWFRQAPGKEREGVAAIWPGGGLIVYADSVKGRETISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 948 | SCVRGRAVSEY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH4-DR591 | 409 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 212 | FTFSNYAMS | 219 | GINVAYGITSYADSVKG | 226 | HSGTTIPRGFISYTK | 943 | AIASGYIDSRWCMA | 199 | AIWPGGGLTVYADSVKG | 205 | GSPRMCPSLEFGFDY |
| hIL27Ra_VHH5-DR591 | 410 | QVQLQESGGGSVQAGGSLRLSCTASGYVSCDYFLPSWYRQAPGKEREFVSVIDGTGSTSYAASVKGRETASQDKGKNIAYLQMNSLKPEDTAMYYCKASCVRGRAISEYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLS | 944 | VIDGTGSTSYAASVKG | 229 | SCVRGRAISEY | 943 | AIASGYIDSRWCMA | 199 | AIWPGGGLTVYADSVKG | 205 | GSPRMCPSLEFGFDY |
| hIL27Ra_VHH6-DR591 | 411 | QVQLQESGGGLVQPGGSLPLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 213 | FSFSSYAMK | 220 | TISSGGSSTNYADSVKG | 227 | AIVPTGATME | 943 | AIASGYIDSRWCMA | 199 | AIWPGGGLTVYADSVKG | 205 | GSPRMCPSLEFGFDY |
| hIL27Ra_VHH7-DR591 | 412 | QVQLQESGGGLVQPGGSLRLSCAASGFTFSSYPMSWVRQAPGKGLEWISTISAG | 211 | FTFSSYPMS | 218 | TISAGG | 947 | RIDCNS | 943 | AIASGYIDS | 199 | AIWPGGGLT | 205 | GSPRMC |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GDTTLYADSVKGRFTSSRDNAKNTLYLQLNSLKTEDTAIYYCAKRIDCNSGYCYRRNYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | | | | DTTLYADSVKG | | GYCYRRNY | | RWCMA | | VYADSVKG | | PSLEFGFDY |
| hIL27Ra_VHH8-DR591 | 413 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 211 | FTFSSYPMS | 218 | TISAGGDTTLYADSVKG | 947 | RIDCNSGYCYRRNY | 943 | AIASGYIDSRWCMA | 199 | AIWPGGGLTVYADSVKG | 205 | GSPRMCPSLEFGFDY |
| hIL27Ra_VHH9-DR591 | 414 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 214 | FTYSTSNSWMA | 221 | AIYTVGGSIFYADSVRG | 228 | ASGRLRGKWFWPYEYNY | 943 | AIASGYIDSRWCMA | 199 | AIWPGGGLTVYADSVKG | 205 | GSPRMCPSLEFGFDY |
| hIL27Ra_VHH10-DR591 | 415 | QVQLQESGGGSVQAGGSLRLSCRASGSTYSNYCLGWFRQITGKEREGVAVINWVGGMLYFADSVKGRFTVSQDQAKNTLYLQMNSLKPED | 216 | STYSNYCLG | 223 | VINWVGGMLY | 230 | ESVSSFSCGG | 943 | AIASGYIDSRWCMA | 199 | AIWPGGGLTVYADSV | 205 | GSPRMCPSLE |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TAMYYCAAESVSSFSCGGWLTRPDRVPYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | | | | FADSVKG | | WLTRPDRVPY | | | | KG | | FGFDY |
| hIL27Ra_VHH11-DR591 | 416 | QVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 949 | ESVSSFSCGGWLTRPGRVPY | 943 | AIASGYIDSRWCMA | 199 | AIWPGGGLTVYADSVKG | 205 | GSPRMCPSLEFGFDY |
| hIL27Ra_VHH12-DR591 | 417 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGGSQVQLQESGGGSVQAGGSLRLSCTASGAIASGYIDSPWCMAWFRQAPGKEREGVAAIWPGGGLTVYADSVAGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 230 | ESVSSFGGWLTRPDRVPY | 943 | AIASGYIDSRWCMA | 199 | AIWPGGGLTVYADSVKG | 205 | GSPRMCPSLEFGFDY |
| hIL27Ra_VHH13-DR591 | 418 | QVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISE | 215 | YVSCDYFLPS | 222 | IIDGTGSTSYAA | 950 | SCVRGRTISEY | 943 | AIASGYIDSRWCMA | 199 | AIWPGGGLTVYADSVKG | 205 | GSPRMCPSLEFG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | YWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | | | | SVKG | | | | | | | | FDY |
| hIL27Ra_VHH14-DR591 | 419 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 229 | SCVRGRAISEY | 943 | AIASGYIDSRWCMA | 199 | AIWPGGGLTVYADSVKG | 205 | GSPRMCPSLEFGFDY |
| hIL27Ra_VHH15-DR591 | 420 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 229 | SCVRGRAISEY | 943 | AIASGYIDSRWCMA | 199 | AIWPGGGLTVYADSVKG | 205 | GSPRMCPSLEFGFDY |
| hIL27Ra_VHH16-DR591 | 421 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGGSQVQLQESGGGS | 216 | STYSNYCLG | 223 | VINWVGGMLYFADSVK | 951 | ESASSFSCGGWLTRPD | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | | | | G | | RVPY | | | | | | |
| hIL27Ra_VHH17-DR591 | 422 | QVQLQESGGGLVQPGGSLRLSCAASGFTFSLSGMSWVRQAPGKGLEWYSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 940 | FTFSLSGMS | 224 | AISSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |
| hIL27Ra_VHH18-DR591 | 423 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 952 | SCVRGRGISEY | 943 | AIASGYIDSRWCMA | 199 | AIWPGGGLTVYADSVKG | 205 | GSPRMCPSLEFGFDY |
| hIL27Ra_VHH19-DR591 | 424 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLRLSCTASGAIASGYIDSPWCMAWFRQAPG | 216 | STYSNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | KEREGVAAIWPGGGLTVYADSVKGRFTISRDHAKNTLYLQMNNLKPEDTAMYYCAAGSPRMCPSLEFGFDYWGQGTQVTVSS | | | | | | | | | | | | |
| hIL27Ra_VHH20-DR591 | 425 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 211 | FTFSSYPMS | 945 | TISSGGDTTLYADSVKG | 953 | RIDCNSGYCYKRSY | 943 | AIASGYIDSRWCMA | 199 | AIWPGGGLTVYADSVKG | 205 | GSPRMCPSLEFGFDY |
| hIL27Ra_VHH21-DR591 | 426 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 217 | FTFSLSSMS | 224 | AISSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |
| hIL27Ra_VHH22-DR591 | 427 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLRLSCTASGAIASGYIDSRWCMAWERQAPGKEREGVAAIWPGGGLTVYADSVKGRFTISRDHAKNT | 216 | STYSNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | LYLQMNNLKPEDTAMYYCAAGSPRMCPSLEFGFDYWGQGTQVTVSS | | | | | | | | | | | | |
| hIL27Ra_VHH23-DR591 | 428 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGGSQVQLQESGGGSVQAGGSIRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 941 | SPYGNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |
| hIL27Ra_VHH24-DR591 | 429 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 942 | FTFSHSGMS | 946 | TINSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |
| hIL27Ra_VHH1-DR592 | 430 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYPPNYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 211 | FTFSSYPMS | 218 | TISAGGDTTLYADSVKG | 947 | RIDCNSGYCYRRNY | 194 | FTSNSCGMD | 200 | SISTDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH2-DR592 | 431 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKIKDGTIATMELCDFGYWGQGTQVTVSS | 940 | FTFSLSGMS | 224 | AISSGGASTYYTDSVKG | 231 | GGSGYGDASRMTSP | 194 | FTSNSCGMD | 200 | SISTDGTTGYADSVKG | 206 | KDGTIATMELCDFGY |
| hIL27Ra_VHH3-DR592 | 432 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 215 | YVSCDYFLPS | 222 | IIDGTGSTSYAASVKG | 948 | SCVRGRAVSEY | 194 | FTSNSCGMD | 200 | SISTDGTTGYADSVKG | 206 | KDGTIATMELCDFGY |
| hIL27Ra_VHH4-DR592 | 433 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKASGTTIPRGFISYTKRGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 212 | FTFSNYAMS | 219 | GINVAYGITSYADSVKG | 226 | HSGTTIPRGFISYTK | 194 | FTSNSCGMD | 200 | SISTDGTTGYADSVKG | 206 | KDGTIATMELCDFGY |
| hIL27Ra_VHH5-DR592 | 434 | QVQLQESGGGSVQAGGSLRLSCTASGYVSCDYFLPSWYRQAPGKEREFVSVIDGTGSTSYAASVKGRFTASQ | 215 | YVSCDYFLPS | 944 | VIDGTGST | 229 | SCVRGRAI | 194 | FTSNSCGMD | 200 | SISTDGTTGYAD | 206 | KDGTIATM |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DKGKNIAYLQMNSLKPED<br>TAMYYCKASCVRGRAISE<br>YWGQGTQVTVSSGGGSQV<br>QLQESGGGSVQAGGSLRL<br>SCTAPGFTSNSCGMDWYR<br>QAPGKEREFVSSISTDGT<br>TGYADSVKGRFTISKDKA<br>KDTVYLQMNSLKPEDTGM<br>YSCKTKDGTIATMELCDF<br>GYWGQGTQVTVSS | | | | SY<br>AA<br>SV<br>KG | | SE<br>Y | | | | SVK<br>G | | EL<br>CD<br>FG<br>Y |
| hIL27Ra_<br>VHH6-<br>DR592 | 435 | QVQLQESGGGLVQPGGSL<br>RLSCAASGFSFSSYAMKW<br>VRQAPGKGLEWVSTISSG<br>GSSTNYADSVKGRFTISR<br>DNAKNTLYLQLNSLKIED<br>TAMYYCAKAIVPTGATME<br>RGQGTQVTVSSGGGSQVQ<br>LQESGGGSVQAGGSLRLS<br>CTAPGFTSNSCGMDWYRQ<br>APGKEREFVSSISTDGTT<br>GYADSVKGRFTISKDKAK<br>DTVYLQMNSLKPEDTGMY<br>SCKTKDGTIATMELCDFG<br>YWGQGTQVTVSS | 213 | FSFSSYAMK | 220 | TI<br>SS<br>GG<br>SS<br>TN<br>YA<br>DS<br>VK<br>G | 227 | AI<br>VP<br>TG<br>AT<br>ME | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH7-<br>DR592 | 436 | QVQLQESGGGLVQPGGSL<br>RLSCAASGFTFSSYPMSW<br>VPQAPGKGLEWISTISAG<br>GDTTLYADSVKGRFTSSR<br>DNAKNTLYLQLNSLKTED<br>TAIYYCAKRIDCNSGYCY<br>RRNYWGQGTQVTVSSGGG<br>SQVQLQESGGGSVQAGGS<br>LRLSCTAPGFTSNSCGMD<br>WYRQAPGKEREFVSSIST<br>DGTTGYADSVKGRFTISK<br>DKAKDTVYLQMNSLKPED<br>TGMYSCKTKDGTIATMEL<br>CDFGYWGQGTQVTVSS | 211 | FTFSSYPMS | 218 | TI<br>SA<br>GG<br>DT<br>TL<br>YA<br>DS<br>VK<br>G | 947 | RI<br>DC<br>NS<br>GY<br>CY<br>RR<br>NY | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH8-<br>DR592 | 437 | QVQLQESGGGSVQVGGSL<br>RLSCAASGFTFSSYPMSW<br>VRQAPGKGLEWISTISAG<br>GDTTLYADSVKGRFTSSR<br>DNAKNTLYLQLNSLKTED<br>TAIYYCAKRIDCNSGYCY<br>RRNYWGQGTQVTVSSGGG<br>SQVQLQESGGGSVQAGGS<br>LRLSCTAPGFTSNSCGMD | 211 | FTFSSYPMS | 218 | TI<br>SA<br>GG<br>DT<br>TL<br>YA<br>DS<br>VK<br>G | 947 | RI<br>DC<br>NS<br>GY<br>CY<br>RR<br>NY | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | WYRQAPGKEREFVSSISTDGTTGYADSVKGRFTISKDKAKDTVYLQMNSLKPEDTGMYSCKTKDGTIATMELCDFGYWGQGTQVTVSS | | | | | | | | | | | | |
| hIL27Ra_VHH9-DR592 | 438 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 214 | FTYSTSNSWMA | 221 | AIYTVGGSIFYADSVRG | 228 | ASGRLRGKWFWPYEYNY | 194 | FTSNSCGMD | 200 | SISTDGTTGSVKG | 206 | KDGTIAELCDFGY |
| hIL27Ra_VHH10-DR592 | 439 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 216 | STYSNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |
| hIL27Ra_VHH11-DR592 | 440 | QVQLQESGGGSVQAGGSLRLSCRASGSTYSNYCLGWFRQSTGKEREGVAVINWVGGMLYFADSVKGRFTVSQDHAKNIVTLQMNSLKPEDTAMYYCAAESVSSFSCGGWLTRPGRVPYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMN | 216 | STYSNYCLG | 223 | VINWVGGMLYFADSVKG | 949 | ESVSSFSCGGWLTRPGRVPY | 194 | FTSNSCGMD | 200 | SISTDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SLKPEDTGMYSCKTKDGT IATMELCDFGYWGQGTQV TVSS | | | | | | | | | | | | |
| hIL27Ra_ VHH12- DR592 | 441 | QVQLQESGGGSVQAGESL RLSCRASGSTYSNYCLGW FRQITGKEREGVAVINWV GGMLYFADSVKGRFTVSQ DQAKNTVYLEMNSLKPED TAMYYCATESVSSFSCGG WLTRPDRVPYWGQGTQVT VSSGGGSQVQLQESGGGS VQAGGSLRLSCTAPGFTS NSCGMDWYRQAPGKEREF VSSISTDGTTGYADSVKG RFTISKDKAKDTVYLQMN SLKPEDIGMYSCKTKDGT IATMELCDFGYWGQGTQV TVSS | 216 | STYSNYCLG | 223 | VI NW VG GM LY FA DS VK G | 230 | ES VS SF SC GG WL TR PD RV PY | 194 | FTS NSC GMD | 200 | SIS TDG TTG YAD SVK G | 206 | KD GT IA TM EL CD FG Y |
| hIL27Ra_ VHH13- DR592 | 442 | QVQLQESGGGSVQAGGSL RLSQVASGYVSCDYFLPS WYRQAPGKEREFVSIIDG TGSTSYAASVKGRFTASQ DRGKNIAYLQMNSLKPED TAMYYCKASCVRGRTISE YWGQGTQVTVSSGGGSQV QLQESGGGSVQAGGSLRL SCTAPGFTSNSCGMDWYR QAPGKEREFVSSISTDGT TGYADSVKGRFTISKDKA KDTVYLQMNSLKPEDTGM YSCKTKDGTIATMELCDF GYWGQGTQVTVSS | 215 | YVSCDYFLPS | 222 | II DG TG ST SY AA SV KG | 950 | SC VR GR TI SE Y | 194 | FTS NSC GMD | 200 | SIS TDG TTG YAD SVK G | 206 | KD GT IA TM EL CD FG Y |
| hIL27Ra_ VHH14- DR592 | 443 | QVQLQESGGGSVQAGGSL RLSCVASGYVSCDYFLPS WYRQAPGKEREFVSIIDG TGSTSYAASVKGRFTASQ DKGKNIAYLQMNSLKPED TAMYYCKASCVRGRAISE YWGQGTQVTVSSGGGSQV QLQESGGGSVQAGGSLRL SCTAPGFTSNSCGMDWYR QAPGKEREFVSSISTDGT TGYADSVKGRFTISKDKA KDTVYLQMNSLKPEDTGM YSCKTKDGTIATMELCDF GYWGQGTQVTVSS | 215 | YVSCDYFLPS | 222 | II DG TG ST SY AA SV KG | 229 | SC VR GR AI SE Y | 194 | FTS NSC GMD | 200 | SIS TDG TTG YAD SVK G | 206 | KD GT IA TM EL CD FG Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_<br>VHH15-<br>DR592 | 444 | QVQLQESGGGSVQAGGSL<br>RLSCVASGYVSCDYFLPS<br>WYRQAPGKEREFVSIIDG<br>TGSTSYAASVKGRFTASQ<br>DKGKNIAYLQMNTLKPED<br>TAMYYCKASCVRGRAISE<br>YWGQGTQVTVSSGGGSQV<br>QLQESGGGSVQAGGSLRL<br>SCTAPGFTSNSCGMDWYR<br>QAPGKEREFVSSISTDGT<br>TGYADSVKGRFTISKDKA<br>KDTVYLQMNSLKPEDTGM<br>YSCKTKDGTIATMELCDF<br>GYWGQGTQVTVSS | 215 | YVSCDYFLPS | 222 | II<br>DG<br>TG<br>ST<br>SY<br>AA<br>SV<br>KG | 229 | SC<br>VR<br>GR<br>AI<br>SE<br>Y | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH16-<br>DR592 | 445 | QVQLQESGGGSVQAGGSL<br>RLSCRASGSTYSNYCLGW<br>FRQITGKEREGVAVINWV<br>GGMLYFADSVKGRFTVSQ<br>DQAKNTVYLQMNSLKPED<br>TAMYYCAAESASSFSCGG<br>WLTRPDRVPYWGQGTQVT<br>VSSGGGSQVQLQESGGGS<br>VQAGGSIRLSCTAPGFTS<br>NSCGMDWYRQAPGKEREF<br>VSSISTDGTTGYADSVKG<br>RFTISKDKAKDTVYLQMN<br>SLKPEDTGMYSCKIKDGT<br>IATMELCDFGYWGQGTQV<br>TVSS | 216 | STYSNYCLG | 223 | VI<br>NW<br>VG<br>GM<br>LY<br>FA<br>DS<br>VK<br>G | 951 | ES<br>AS<br>SF<br>SC<br>GG<br>WL<br>TR<br>PD<br>RV<br>PY | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH17-<br>DR592 | 446 | QVQLQESGGGIVQPGGSL<br>RLSCAASGFTFSLSGMSW<br>VRQAPGKGLEWVSAISSG<br>GASTYYTDSVKGRFTISR<br>DNAKNMLYLQLNSLKTED<br>TAMYYCAKGGSGYGDASR<br>MTSPGSQGTQVTVSSGGG<br>SQVQLQESGGGSVQAGGS<br>LRLSCTAPGFTSNSCGMD<br>WYRQAPGKEREFVSSIST<br>DGTTGYADSVKGRFTISK<br>DKAKDTVYLQMNSLKPED<br>TGMYSCKIKDGTIATMEL<br>CDFGYWGQGTQVTVSS | 940 | FTFSLSGMS | 224 | AI<br>SS<br>GG<br>AS<br>TY<br>YT<br>DS<br>VK<br>G | 231 | GG<br>SG<br>YG<br>DA<br>SR<br>MT<br>SP | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH18-<br>DR592 | 447 | QVQLQESGGGSVQAGGSL<br>RLSCVASGYVSCDYFLPS<br>WYRQAPGKEREFVSIIDG<br>TGSTSYAASVKGRFTASQ | 215 | YVSCDYFLPS | 222 | II<br>DG<br>TG<br>ST | 952 | SC<br>VR<br>GR<br>GI | 194 | FTS<br>NSC<br>GMD | 200 | SIS<br>TDG<br>TTG<br>YAD | 206 | KD<br>GT<br>IA<br>TM |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DKGKNIAYLQMNSLKPEDTAMYYCKASCVRGRGISEYWGQGTQVTVSSGGGSQVQLQESGGGSVQAGGSLRLSCTAPGFTSNSCGMDWYRCAPGKEREFVSSISTDGTTGYADSVKGRFTISKDKAKDTVYLQMNSLKPEDTGMYSCKTKDGTIATMELCDFGYWGQGTQVTVSS | | | | SYAASVKG | | SEY | | | | SVKG | | ELCDFGY |
| hIL27Ra_VHH19-DR592 | 448 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 216 | STYSNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |
| hIL27Ra_VHH20-DR592 | 449 | QVQLQESGGGLVQPGGSLRLSCAASGFTFSSYPMSWVPQAPGKGLEWVSTISSGGDTTLYADSVKGRFTSSRDNAKNTLYLQLNSLKTEDTAMYYCAKRIDCNSGYCYKRSYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 211 | FTFSSYPMS | 945 | TISSGGDTTLYADSVKG | 953 | RIDCNSGYCYKRSY | 194 | FTSNSCGMD | 200 | SISTDGTTGYADSVKG | 206 | KDGTIATMELCDFGY |
| hIL27Ra_VHH21-DR592 | 450 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGG | 217 | FTFSLSSMS | 224 | AISSGGASTYYTDS | 231 | GGSGYGDASRMTSP | 194 | FTSNSCGMD | 200 | SISTDGTTGYADSVKG | 206 | KDGTIATMELCDFG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SQVQLQESGGGSVQAGGSLRLSCTAPGFTSNSCGMDWYRQAPGKEPEFVSSISTDGTTGYADSVKGRFTISKDKAKDTVYLQMNSLKPEDTGMYSCKTKDGTIATMELCDFGYWGQGTQVTVSS | | | | VKG | | | | | | | | Y |
| hIL27Ra_VHH22-DR592 | 451 | QVQLQESGGGSVQAGGSLRLSCRASGSTYSNYCLGWFRQTIGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLPLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 216 | STYSNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |
| hIL27Ra_VHH23-DR592 | 452 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGGSQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 941 | SPYGNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |
| hIL27Ra_VHH24-DR592 | 453 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCTAPGFTSNSCGMDWYRQAPGKEREFVSSIST | 942 | FTFSHSGMS | 946 | TINSGGASTYYTDSVKG | 231 | GGSGYGDASRMTSP | 194 | FESNSCGMD | 200 | SISTDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DGTTGYADSVKGRFTISKDKAKDTVYLQMNSLKPEDTGMYSCKTKDGTIATMELCDFGYWGQGTQVTVSS | | | | | | | | | | | | |
| hIL27Ra_VHH1-DR593 | 454 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH2-DR593 | 455 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH3-DR593 | 456 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGGSQVQLQESGGGSVQAGGSLRL | 942 | FTFSHSGMS | 946 | TINSGGASTYYTDSVK | 231 | GGSGYGDASRMTSP | 195 | YPYSNGYMG | 201 | TIYTGDGRTYYADSVKG | 207 | RAAPLYSSGSPLTRAR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SCAASGYPYSNGYNGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | G | | | | | | | | YNV |
| hIL27Ra_VHH4-DR593 | 457 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH5-DR593 | 458 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH6-DR593 | 459 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAM | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | YYCAARAAPLYSSGSPLTRARYNVWGQGTQVTVSS | | | | | | | | | | | | |
| hIL27Ra_VHH7-DR593 | 460 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGSVQAGGSLPLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH8-DR593 | 461 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH9-DR593 | 462 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 204 | RAAPLYSSGSPLTRARYNV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH10- DR593 | 463 | QVQLQESGGGSVQAGGSL RLSCRASGSTYSNYCLGW FRQITGKEREGVAVINWV GGMLYFADSVKGRETVSQ DQAKNTLYLQMNSLKPED TAMYYCAAESVSSFSCGG WLTRPDRVPYWGQGTQVT VSSGGGSQVQLQESGGGS VQAGGSLRLSCAASGYPY SNGYMGWFRQAPGKEREG VATIYTGDGRTYYADSVK GRFTISRDNAKNTVDLQM SSLKPEDTAMYYCAARAA PLYSSGSPLTRARYNVWG QGTQVTVSS | 942 | FTFSHSGMS | 946 | TI NS GG AS TY YT DS VK G | 231 | GG SG YG DA SR MT SP | 195 | YPY SNG YMG | 201 | TIY TGD GRT YYA DSV KG | 207 | RA AP LY SS GS PL TR AR YN V |
| hIL27Ra_ VHH11- DR593 | 464 | QVQLQESGGGSVQAGGSL RLSCRASGSTYSNYCLGW FRQSTGKEREGVAVINWV GGMLYFADSVKGRFTVSQ DHAKNTVTLQMNSLKPED TAMYYCAAESVSSFSCGG WLTRPGRVPYWGQGTQVT VSSGGGSQVQLQESGGGS VQAGGSLRLSCAASGYPY SNGYMGWFRQAPGKEREG VATIYTGDGRTYYADSVK GRFTISRDNAKNTVDLQM SSLKPEDTAMYYCAARAA PLYSSGSPLTRARYNVWG QGTQVTVSS | 942 | FTFSHSGMS | 946 | TI NS GG AS TY YT DS VK G | 231 | GG SG YG DA SR MT SP | 195 | YPY SNG YMG | 201 | TIY TGD GRT YYA DSV KG | 207 | RA AP LY SS GS PL TR AR YN V |
| hIL27Ra_ VHH12- DR593 | 465 | QVQLQESGGGSVQAGESL RLSCRASGSTYSNYCLGW FRQITGKEREGVAVINWV GGMLYFADSVKGRFTVSQ DQAKNTVYLEMNSLKPED TAMYYCATESVSSFSCGG WLTRPDRVPYWGQGTQVT VSSGGGSQVQLQESGGGS VQAGGSLRLSCAASGYPY SNGYMGWFRQAPGKEREG VATIYTGDGRTYYADSVK GRFTISRDNAKNTVDLQM SSLKPEDTAMYYCAARAA PLYSSGSPLTRARYNVWG QGTQVTVSS | 942 | FTFSHSGMS | 946 | TI NS GG AS TY YT DS VK G | 231 | GG SG YG DA SR MT SP | 195 | YPY SNG YMG | 201 | TIY TGD GRT YYA DSV KG | 207 | RA AP LY SS GS PL TR AR YN V |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH13- DR593 | 466 | QVQLQESGGGSVQAGGSL RLSCVASGYVSCDYFLPS WYRQAPGKEREFVSIIDG TGSTSYAASVKGRFTASQ DRGKNIAYLQMNSLKPED TAMYYCKASCVRGRTISE YWGQGTQVTVSSGGGSQV QLQESGGGSVQAGGSLRL SCAASGYPYSNGYMGWFR QAPGKEREGVATIYTGDG RTYYADSVKGRFTISRDN AKNTVDLQMSSLKPEDTA MYYCAARAAPLYSSGSPL TRARYNVWGQGTQVTVSS | 942 | FTFSHSGMS | 946 | TI NS GG AS TY YT DS VK G | 231 | GG SG YG DA SR MT SP | 195 | YPY SNG YMG | 201 | TIY TGD GRT YYA DSV KG | 207 | RA AP LY SS GS PL TR AR YN V |
| hIL27Ra_ VHH14- DR593 | 467 | QVQLQESGGGSVQAGGSL RLSCVASGYVSCDYFLPS WYRQAPGKEREFVSIIDG TGSTSYAASVKGRFTASQ DKGKNIAYLQMNSLKPED TAMYYCKASCVRGRAISE YWGQGTQVTVSSGGGSQV QLQESGGGSVQAGGSLRL SCAASGYPYSNGYMGWFR QAPGKEREGVATIYTGDG RTYYADSVKGRETISRDN AKNTVDLQMSSLKPEDTA MYYCAARAAPLYSSGSPL TRARYNVWGQGTQVTVSS | 942 | FTFSHSGMS | 946 | TI NS GG AS TY YT DS VK G | 231 | GG SG YG DA SR MT SP | 195 | YPY SNG YMG | 201 | TIY TGD GRT YYA DSV KG | 207 | RA AP LY SS GS PL TR AR YN V |
| hIL27Ra_ VHH15- DR593 | 468 | QVQLQESGGGSVQAGGSL RLSCVASGYVSCDYFLPS WYRQAPGKEREFVSIIDG TGSTSYAASVKGRFTASQ DKGKNIAYLQMNTLKPED TAMYYCKASCVRGRAISE YWGQGTQVTVSSGGGSQV QLQESGGGSVQAGGSLRL SCAASGYPYSNGYMGWFR QAPGKEREGVATIYTGDG RTYYADSVKGRFTISRDN AKNTVDLQMSSLKPEDTA MYYCAARAAPLYSSGSPL TRARYNVWGQGTQVTVSS | 942 | FTFSHSGMS | 946 | TI NS GG AS TY YT DS VK G | 231 | GG SG YG DA SR MT SP | 195 | YPY SNG YMG | 201 | TIY TGD GRT YYA DSV KG | 207 | RA AP LY SS GS PL TR AR YN V |
| hIL27Ra_ VHH16- DR593 | 469 | QVQLQESGGGSVQAGGSL RLSCRASGSTYSNYCLGW FRQITGKEREGVAVINWV GGMLYFADSVKGRFTVSQ | 942 | FTFSHSGMS | 946 | TI NS GG AS | 231 | GG SG YG DA | 195 | YPY SNG YMG | 201 | TIY TGD GRT YYA | 207 | RA AP LY SS |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DQAKNTVYLQMNSLKPEDTAMYYCAAESASSFSCGGWLTRPDRVPYWGQGTQVTVSSGGGSQVQLQESGGGSVQAGGSLPLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | TYYTDSVKG | | SRMTSP | | | | DSVKG | | GSPLTRARYNV |
| hIL27Ra_VHH17-DR593 | 470 | QVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH18-DR593 | 471 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH19-DR593 | 472 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVT | 942 | FTFSHSGMS | 946 | TINSGGASTYYTDS | 231 | GGSGYGDASRMTSP | 195 | YPYSNGYMG | 201 | TIYTGDGRTYYADSVKG | 207 | RAAPLYSSGSPLTR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | VKG | | | | | | | | ARYNV |
| hIL27Ra_VHH20-DR593 | 473 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH21-DR593 | 474 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH22-DR593 | 475 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLRLSCAASGYPY | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYN |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | | | | | | | | | V |
| hIL27Ra_VHH23-DR593 | 476 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH24-DR593 | 477 | QVQLQESGGGLVQPGGSLRLSCAASGFTFSHSGMSWVPQAPGKGLEWVSTINSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH1-DR594 | 478 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGGSQVQLQESGGGSVQAGGSLRLSCVASASTYCTYDMHWYRQAPGKGREFVSAIDSDGTTRYADSVKGRFTISQ | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GTAKNTVYLQMNSLQPEDTAMYYCKTVCVVGSRWSDYWGQGTQVTVSS | | | | | | | | | | | | |
| hIL27Ra_VHH2-DR594 | 479 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH3-DR594 | 480 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH4-DR594 | 481 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPE | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH5-DR594 | 482 | QVQLQESGGGSVQAGGSLRLSCTASGYVSCDYFLPSWYRQAPGKEREFVSVIDG | 942 | FTFSHSGMS | 946 | TINSGG | 231 | GGSGYG | 196 | STYCTYDMH | 202 | AIDSDGTTR | 954 | VCVVGS |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TGSTSYAASVKGRFTASQDKGKNIAYLQMNSLKPEDTAMYYCKASCVRGRAISEYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | ASTYYTDSVKG | | DASRMTSP | | | | YADSVKG | | RWSDY |
| hIL27Ra_VHH6-DR594 | 483 | QVQLQESGGGLVQPGGSLRLSCAASGFSFSSYAMKWVPQAPGKGLEWVSTISSGGSSTNYADSVKGRFTISRDNAKNTLYLQLNSLKIEDTAMYYCAKAIVPTGATMERGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH7-DR594 | 484 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH8-DR594 | 485 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGSVQAGGS | 942 | FTFSHSGMS | 946 | TINSGGASTYYTDSVK | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | LRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | G | | | | | | | | |
| hIL27Ra_VHH9-DR594 | 486 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGGSQVQLQESGGGSVQAGGSLRISCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH10-DR594 | 487 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH11-DR594 | 488 | QVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGGSQVQLQESGGGSVQAGGSLRLSCVASASTYCTYDMHWYRQAPGKGREFVSAIDSDGTTRYADSVKG | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | RFTISQGTAKNTVYLQMNSLQPEDTAMYYCKTVCVVGSRWSDYWGQGTQVTVSS | | | | | | | | | | | | |
| hIL27Ra_VHH12-DR594 | 489 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGGSQVQLQESGGGSVQAGGSLPLSCVASASTYCTYDMHWYRQAPGKGREFVSAIDSDGTTRYADSVKGRFTISQGIAKNTVYLQMNSLQPEDTAMYYCKTVCVVGSRWSDYWGQGTQVTVSS | 942 | FTFSHSGMS | 946 | FINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH13-DR594 | 490 | QVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH14-DR594 | 491 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH15-DR594 | 492 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH16-DR594 | 493 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSGSGNS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH17-DR594 | 494 | QVQLQESGGGLVQPGGSLRLSCAASGFTFSLSGMSWVRQAPGKGLEWYSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH18-DR594 | 495 | QVQLQESGGGSVQAGGSLRLSCVASGYVSCDYFLPSWYRQAPGKEREFVSIIDGTGSTSYAASVKGRFTASQ | 942 | FTFSHSGMS | 946 | TINSGGAS | 231 | GGSGYGDA | 196 | STYCTYDMH | 202 | AIDSDGTTRYAD | 954 | VCVVGSRW |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DKGKNIAYLQMNSLKPEDTAMYYCKASCVRGRGISEYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | TYYTDSVKG | | SRMTSP | | | | SVKG | | SDY |
| hIL27Ra_VHH19-DR594 | 496 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSGSGNS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH20-DR594 | 497 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSGSGNS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH21-DR594 | 498 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCVASASTYCTYDMH | 942 | FTFSHSGMS | 946 | TINSGGASTYYTDSVKG | 231 | GGSGYGDASRMTSP | 196 | STYCTYDMA | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | WYRQAPGKGREFVSAIDSDGTTRYADSVKGRFTISQGTAKNTVYLQMNSLQPEDTAMYYCKTVCVVGSRWSDYWGQGTQVTVSS | | | | | | | | | | | | |
| hIL27Ra_VHH22-DR594 | 499 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH23-DR594 | 500 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH24-DR594 | 501 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGGSQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH1-DR595 | 502 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYPRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH2-DR595 | 503 | QVQLQESGGGLVQPGGSLRLSCAASGFTFSLSGMSWVRQAPGKGLEWYSAISSGGASTYYTDSVKGRFTISRDNAKNILYLQLNSLKTEDTAMYYCAKGGSGYGDASRMTSPGSQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH3-DR595 | 504 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH4-DR595 | 505 | QVQLQESGGGLVQPGESLRLSCTASGFTFSNYAMSWVRQAPGKGLEWVSGINVAYGITSYADSVKGRFTISR | 942 | FTFSHSGMS | 946 | TINSGGAS | 231 | GGSGYGDA | 197 | YAYSTCNMG | 203 | AFISDGSTYYAD | 209 | NCYRRLRN |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DNTKNTLYLQLNSLKTEDTAIYYCVKASGTTIPRGFISYTKRGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | | | | TYYTDSVKG | | SRMTSP | | | | SVKG | | Y |
| hIL27Ra_VHH5-DR595 | 506 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH6-DR595 | 507 | QVQLQESGGGLVQPGGSLRISCAASGESESSYAMKWVRQAPGKGLEWVSTISSGGSSTNYADSVKGRETISRDNAKNTLYLQLNSLKIEDRGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYDSVKG | 231 | GGSGYGDASRMTSP | 197 | YAYSTCNMG | 203 | AFISDGSTYYADSVK | 209 | NCYRRLRNY |
| hIL27Ra_VHH7-DR595 | 508 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGSVQAGGSLTLSCAASEYAYSTCNMGWYRQAPGKERELVSAFIS | 942 | FTFSHSGMS | 9466 | TINSGGASTYYTDSVKG | 231 | GGSGYGDASRMTSP | 197 | YAYSTCNMG | 203 | AFISDGSTYYADSVKG | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DGSTYYADSVKGRFTITR<br>DNAKNTVYLQMNSLKPED<br>TAIYYCSANCYRRLRNYW<br>GQGTQVTVSS | | | | | | | | | | | | |
| hIL27Ra_<br>VHH8-<br>DR595 | 509 | QVQLQESGGGSVQVGGSL<br>RLSCAASGFTFSSYPMSW<br>VRQAPGKGLEWISTISAG<br>GDTTLYADSVKGRFTSSR<br>DNAKNTLYLQLNSLKTED<br>TAIYYCAKRIDCNSGYCY<br>RRNYWGQGTQVTVSSGGG<br>SQVQLQESGGGSVQAGGS<br>LTLSCAASEYAYSTCNMG<br>WYRQAPGKERELVSAFIS<br>DGSTYYADSVKGRFTITR<br>DNAKNTVYLQMNSLKPED<br>TAIYYCSANCYRRLRNYW<br>GQGTQVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 197 | YAY<br>STC<br>NMG | 203 | AFI<br>SDG<br>STY<br>YAD<br>SVK<br>G | 209 | NC<br>YR<br>RL<br>RN<br>Y |
| hIL27Ra_<br>VHH9-<br>DR595 | 510 | QVQLQESGGGSVQSGGSL<br>RLSCAASGFTYSTSNSWM<br>AWFRQAPGKEREGVAAIY<br>TVGGSIFYADSVRGRFTI<br>SQDATKNMFYLQMNTLKP<br>EDTAMYYCAAASGRLRGK<br>WFWPYEYNYWGQGTQVTV<br>SSGGGSQVQLQESGGGSV<br>QAGGSLTLSCAASEYAYS<br>TCNMGWYRQAPGKERELV<br>SAFISDGSTYYADSVKGR<br>FTITRDNAKNTVYLQMNS<br>LKPEDTAIYYCSANCYRR<br>LRNYWGQGTQVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 197 | YAY<br>STC<br>NMG | 203 | AFI<br>SDG<br>STY<br>YAD<br>SVK<br>G | 209 | NC<br>YR<br>RL<br>RN<br>Y |
| hIL27Ra_<br>VHH10-<br>DR595 | 511 | QVQLQESGGGSVQAGGSL<br>RLSCRASGSTYSNYCLGW<br>FRQITGKEREGVAVINWV<br>GGMLYFADSVKGRFTVSQ<br>DQAKNTLYLQMNSLKPED<br>TAMYYCAAESVSSFSCGG<br>WLTRPDRVPYWGQGTQVT<br>VSSGGGSQVQLQESGGGS<br>VQAGGSLTLSCAASEYAY<br>STCNMGWYRQAPGKEREL<br>VSAFISDGSTYYADSVKG<br>RFTITRDNAKNTVYLQMN<br>SLKPEDTAIYYCSANCYR<br>RLRNYWGQGTQVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 197 | YAY<br>STC<br>NMG | 203 | AFI<br>SDG<br>STY<br>YAD<br>SVK<br>G | 209 | NC<br>YR<br>RL<br>RN<br>Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH11- DR595 | 512 | QVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDIAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_ VHH12- DR595 | 513 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_ VHH13- DR595 | 514 | QVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_ VHH14- DR595 | 515 | QVQLQESGGGSVQAGGSLRLSCVASGYVSCDYFLPSWYRQAPGKEREFVSIIDGTGSTSYAASVKGRFTASQDKGKNIAYLQMNSLKPED | 942 | FTFSGSGMS | 946 | TINSGGASTY | 231 | GGSGYGDASR | 197 | YAYSTCNMG | 203 | AFISDGSTYYADSVK | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TAMYYCKASCVRGRAISEYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLPNYWGQGTQVTVSS | | | | YTDSVKG | | MTSP | | | | G | | |
| hIL27Ra_VHH15-DR595 | 516 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLPNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH16-DR595 | 517 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH17-DR595 | 518 | QVQLQESGGGLVQPGGSLRLSCAASGFTFSISGMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLTLSCAASEYAYSTCNMGWYRQAPGKERELVSAFIS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DGSTYYADSVKGRFTITRDNAKNTVYLQMNSLKPEDTAIYYCSANCYRRLRNYWGQGTQVTVSS | | | | | | | | | | | | |
| hIL27Ra_VHH18-DR595 | 519 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH19-DR595 | 520 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLILSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH20-DR595 | 521 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYPPLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH21-DR595 | 522 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH22-DR595 | 523 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYVADSVKG | 209 | NCYRRLRNY |
| hIL27Ra_VHH23-DR595 | 524 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH24-DR595 | 525 | QVQLQESGGGLVQPGGSLRLSCAASGFTFSHSGMSWVRQAPGKGLEWVSTINSGGASTYYTDSVKGRFTISRDNAKNMLYLQLNSLKTED | 942 | FTFSHSGMS | 946 | TINSGGASTY | 231 | GGSGYGDASR | 197 | YAYSTCNMG | 203 | AFISDGSTYYADSVK | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TAMYYCAKGGSGYGDASRMTSPGSQGTQVTVSSGGGSQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYPPLRNYWGQGTQVTVSS | | | | YTDSVKG | | MTSP | | | | G | | |
| hIL27Ra_VHH1-DR596 | 526 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH2-DR596 | 527 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH3-DR596 | 528 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGGSQVQLQESGGGLVQPGGSLRLSCTASGLTFDDSVMGWFRQAPGKGREAVSCISSSGA | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NAFYADSVKGRFTISRDNAKNTLYLQMNSLKPEDTATYYCKRGHACAGYYPIPYDDYWGQGTQVTVSS | | | | | | | | | | | | |
| hIL27Ra_VHH4-DR596 | 529 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH5-DR596 | 530 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH6-DR596 | 531 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH7- DR596 | 532 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH8- DR596 | 533 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH9- DR596 | 534 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH10- DR596 | 535 | QVQLQESGGGSVQAGGSLRLSCRASGSTYSNYCLGWFRQITGKEREGVAVINWVGGMLYFADSVKGRFTVSQ | 942 | FTFSHSGMS | 946 | TINSGGAS | 231 | GGSGYGDA | 198 | LTFDDSVMG | 204 | CISSSGANAFYA | 210 | GHACAGYY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DQAKNTLYLQMNSLKPED<br>TAMYYCAAESVSSFSCGG<br>WLTRPDRVPYWGQGTQVT<br>VSSGGGSQVQLQESGGGL<br>VQPGGSLRLSCTASGLTF<br>DDSVMGWFRQAPGKGREA<br>VSCISSSGANAFYADSVK<br>GRFTISRDNAKNTLYLQM<br>NSLKPEDTATYYCKRGHA<br>CAGYYPIPYDDYWGQGTQ<br>VTVSS | | | | TY<br>YT<br>DS<br>VK<br>G | | SR<br>MT<br>SP | | | | DSV<br>KG | | PI<br>PY<br>DD<br>Y |
| hIL27Ra_<br>VHH11-<br>DR596 | 536 | QVQLQESGGGSVQAGGSL<br>RLSCRASGSTYSNYCLGW<br>FRQSTGKEREGVAVINWV<br>GGMLYFADSVKGRFTVSQ<br>DHAKNTVTLQMNSLKPED<br>TAMYYCAAESVSSFSCGG<br>WLTRPGRVPYWGQGTQVT<br>VSSGGGSQVQLQESGGGL<br>VQPGGSLRLSCTASGLTF<br>DDSVMGWFRQAPGKGREA<br>VSCISSSGANAFYADSVK<br>GRFTISRDNAKNTLYLQM<br>NSLKPEDTATYYCKRGHA<br>CAGYYPIPYDDYWGQGTQ<br>VTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 198 | LTF<br>DDS<br>VMG | 204 | CIS<br>SSG<br>ANA<br>FYA<br>DSV<br>KG | 210 | GH<br>AC<br>AG<br>YY<br>PI<br>PY<br>DD<br>Y |
| hIL27Ra_<br>VHH12-<br>DR596 | 537 | QVQLQESGGGSVQAGESL<br>RLSCRASGSTYSNYCLGW<br>FRQITGKEREGVAVINWV<br>GGMLYFADSVKGRFTVSQ<br>DQAKNTVYLEMNSLKPED<br>TAMYYCATESVSSFSCGG<br>WLTRPDRVPYWGQGTQVT<br>VSSGGGSQVQLQESGGGL<br>VQPGGSLRLSCTASGLTF<br>DDSVMGWFRQAPGKGREA<br>VSCISSSGANAFYADSVK<br>GRFTISRDNAKNTLYLQM<br>NSLKPEDTATYYCKRGHA<br>CAGYYPIPYDDYWGQGTQ<br>VTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 198 | LTF<br>DDS<br>VMG | 204 | CIS<br>SSG<br>ANA<br>FYA<br>DSV<br>KG | 210 | GH<br>AC<br>AG<br>YY<br>PI<br>PY<br>DD<br>Y |
| hIL27Ra_<br>VHH13-<br>DR596 | 538 | QVQLQESGGGSVQAGGSL<br>RLSCVASGYVSCDYFLPS<br>WYRQAPGKEREFVSIIDG<br>TGSTSYAASVKGRFTASQ<br>DRGKNIAYLQMNSLKPED<br>TAMYYCKASCVRGRTISE | 942 | FTFSHSGMS | 946 | TI<br>NS<br>GG<br>AS<br>TY<br>YT | 231 | GG<br>SG<br>YG<br>DA<br>SR<br>MT | 198 | LTF<br>DDS<br>VMG | 204 | CIS<br>SSG<br>ANA<br>FYA<br>DSV<br>KG | 210 | GH<br>AC<br>AG<br>YY<br>PI<br>PY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | YWGQGTQVTVSSGGGSQVQLQESGGGLVQPGGSLRLSCTASGLTFDDSVNGWFRQAPGKGREAVSCISSSGANAFYADSVKGRFTISRDNAKNTLYLQMNSLKPEDTATYYCKRGHACAGYYPIPYDDYWGQGTQVTVSS | | | | DSVKG | | SP | | | | | | DDY |
| hIL27Ra_VHH14-DR596 | 539 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSSGGGSQVQLQESGGGLVQPGGSLRLSCTASGLTFDDSVMGWFRQAPGKGREAVSCISSSGANAFYADSVKGRFTISRDNAKNTLYIQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH15-DR596 | 540 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH16-DR596 | 541 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGGSQVQLQESGGGLVQPGGSLRLSCTASGLTFDDSVMGWFRQAPGKGREAVSCISSSGANAFYADSVK | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GRFTISRDNAKNTLYLQMNSLKPEDTATYYCKRGHACAGYYPIPYDDYWGQGTQVTVSS | | | | | | | | | | | | |
| hIL27Ra_VHH17-DR596 | 542 | QVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH18-DR596 | 543 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGGSQVQLQESGGGLVQPGGSLRLSCTASGLTFDDSVNGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH19-DR596 | 544 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGGSQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH20- DR596 | 545 | QVQLQESGGGLVQPGGSL RLSCAASGFTFSSYPMSW VRQAPGKGLEWVSTISSG GDTTLYADSVKGRFTSSR DNAKNTLYLQLNSLKTED TAMYYCAKRIDCNSGYCY KRSYWGQGTQVTVSSGGG SQVQLQESGGGLVQPGGS LRLSCTASGLTFDDSVMG WFRQAPGKGREAVSCISS SGANAFYADSVKGRFTIS RDNAKNTLYLQMNSLKPE DTATYYCKRGHACAGYYP IPYDDYWGQGTQVTVSS | 942 | FTFSHSGMS | 946 | TI NS GG AS TY YT DS VK G | 231 | GG SG YG DA SR MT SP | 198 | LTF DDS VMG | 204 | CIS SSG ANA FYA DSV KG | 210 | GH AC AG YY PI PY DD Y |
| hIL27Ra_ VHH21- DR596 | 546 | QVQLQESGGGLVQPGGSL RLSCAASGFTFSISSMSW VRQAPGKGLEWVSAISSG GASTYYTDSVKGRFTISR DNAKNMLYLQLNSLKTED TAMYYCAKGGSGYGDASR MTSPGSQGTQVTVSSGGG SQVQLQESGGGLVQPGGS LRLSCTASGLTFDDSVMG WFRQAPGKGREAVSCISS SGANAFYADSVKGRFTIS RDNAKNTLYLQMNSLKPE DTATYYCKRGHACAGYYP IPYDDYWGQGTQVTVSS | 942 | FTFSHSGMS | 946 | TI NS GG AS TY YT DS VK G | 231 | GG SG YG DA SR MT SP | 198 | LTF DDS VMG | 204 | CIS SSG ANA FYA DSV KG | 210 | GH AC AG YY PI PY DD Y |
| hIL27Ra_ VHH22- DR596 | 547 | QVQLQESGGGSVQAGGSL RLSCRASGSTYSNYCLGW FRQTTGKEREGVAVINWV GGMLYFADSVKGRFTVSQ DQAKNTVYLQMNSLKPED TAMYYCAAESVSSFSCGG WLTRPDRVPYWGQGTQVT VSSGGGSQVQLQESGGGL VQPGGSLRLSCTASGLTF DDSVMGWFRQAPGKGREA VSCISSSGANAFYADSVK GRFTISRDNAKNTLYLQM NSLKPEDTATYYCKRGHA CAGYYPIPYDDYWGQGTQ VTVSS | 942 | FTFSHSGMS | 946 | TI NS GG AS TY YT DS VK G | 231 | GG SG YG DA SR MT SP | 198 | LTF DDS VMG | 204 | CIS SSG ANA FYA DSV KG | 210 | GH AC AG YY PI PY DD Y |
| hIL27Ra_ VHH23- DR596 | 548 | QVQLQESGGGSVQAGGSL RLSCRASRSPYGNYCLGW FRQSTGKEREGVAVINWV | 942 | FTFSHSGMS | 946 | TI NS GG | 231 | GG SG YG | 198 | LTF DDS VMG | 204 | CIS SSG ANA | 210 | GH AC AG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GGMLYFADSVKGRFTVSQ DHAKNTVTLQMNSLKPED TAMYYCAAESVSSFSCGG WLTRPDRVPYWGQGTQVT VSSGGGSQVQLQESGGGL VQPGGSLRLSCTASGLTF DDSVMGWFRQAPGKGREA VSCISSSGANAFYADSVK GRFTISRDNAKNTLYLQM NSLKPEDTATYYCKRGHA CAGYYPIPYDDYWGQGTQ VTVSS | | | | AS TY YT DS VK G | | DA SR MT SP | | | | FYA DSV KG | | YY PI PY DD Y |
| hIL27Ra_ VHH24- DR596 | 549 | QVQLQESGGGLVQPGGSL RLSCAASGFTFSHSGMSW VRQAPGKGLEWVSTINSG GASTYYTDSVKGRFTISR DNAKNMLYLQLNSLKTED TAMYYCAKGGSGYGDASR MTSPGSQGTQVTVSSGGG SQVQLQESGGGLVQPGGS LRLSCTASGLTFDDSVMG WFRQAPGKGREAVSCISS SGANAFYADSVKGRFTIS RDNAKNTLYLQMNSLKPE DTATYYCKRGHACAGYYP IPYDDYWGQGTQVTVSS | 942 | FTFSHSGMS | 946 | TI NS GG AS TY YT DS VK G | 231 | GG SG YG DA SR MT SP | 198 | LTF DDS VMG | 204 | CIS SSG ANA FYA DSV KG | 210 | GH AC AG YY PI PY DD Y |
| DR591- hIL27Ra_ VHH1 | 1 | QVQLQESGGGSVQAGGSL RLSCTASGAIASGYIDSR WCMAWFRQAPGKEREGVA AIWPGGGLTVYADSVKGR FTISRDHAKNTLYLQMNN LKPEDTAMYYCAAGSPRM CPSLEFGFDYWGQGTQVT VSSGGGSQVQLQESGGGL VQPGGSLRLSCAASGFTF SSYPMSWVRQAPGKGLEW ISTISAGGDTTLYADSVK GRFTSSRDNAKNTLYLQL NSLKTEDAAIYYCAKRID CNSGYCYRRNYWGQGTQV TVSS | 943 | AIASGYIDSRWCMA | 199 | AI WP GG GL TV YA DS VK G | 205 | GS PR MC PS LE FG FD Y | 211 | FTF SSY PMS | 218 | TIS AGG DTT LYA DSV KG | 947 | RI DC NS GY CY RR NY |
| DR591- hIL27Ra_ VHH2 | 550 | QVQLQESGGGSVQAGGSL RLSCTASGAIASGYIDSR WCMAWFRQAPGKEREGVA AIWPGGGLTVYADSVKGR | 943 | AIASGYIDSRWCMA | 199 | AI WP GG GL | 205 | GS PR MC PS | 940 | FTF SLS GMS | 224 | AIS SGG AST YYT | 231 | GG SG YG DA |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | FTISRDHAKNTLYLQMNNLKPEDTAMYYCAAGSPRMCPSLEFGFDYWGQGTQVTVSSGGGSQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | | | | TVYADSVKG | | LEFGFDY | | | | DSVKG | | SRMTSP |
| DR591-hIL27Ra_VHH3 | 551 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 948 | SCVRGRAVSEY |
| DR591-hIL27Ra_VHH4 | 2 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGLVQPGESLRLSCTASGFTFSNYAMSWVRQAPGKGLEWVSGINVAYGITSYADSVKGRFTISRDNTANTLYLQLNSLKTEDTAIYYCVKHSGTTIPRGFISYTKRGQGTQVTVSS | 943 | AIASGYIDSRWCMA | 199 | AIWPGGGLTVYADSVKG | 205 | GSPRMCPSLEFGFDY | 212 | FTFSNYAMS | 219 | GINVAYGITSYADSVKG | 226 | HSGTTIPRGFISYTK |
| DR591-hIL27Ra_VHH5 | 552 | QVQLQESGGGSVQAGGSLRLSCTASGAIASGYIDSRWCMAWFPQAPGKEREGVAAIWPGGGLTVYADSVKGRFTISRDHAKNTLYLQMNNLKPEDTAMYYCAAGSPRM | 943 | AIASGYIDSRWCMA | 199 | AIWPGGGLTVYA | 205 | GSPRMCPSLEFG | 215 | YVSCDYFLPS | 944 | VIDGTGSTSYAASVKG | 229 | SCVRGRAISEY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | CPSLEFGFDYWGQGTQVTVSSGGGSQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | | | | DSVKG | | FDY | | | | | | |
| DR591-hIL27Ra_VHH6 | 3 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS | 943 | AIASGYIDSRWCMA | 199 | AIWPGGGLTVYADSVKG | 205 | GSPRMCPSLEFGFDY | 213 | FSFSSYAMK | 220 | TISSGGSSTNYADSVKG | 227 | AIVPTGATME |
| DR591-hIL27Ra_VHH7 | 553 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGLVQPGGSIRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 943 | AIASGYIDSRWCMA | 199 | AIWPGGGLTVYADSVKG | 205 | GSPRMCPSLEFGFDY | 211 | FTFSSYPMS | 218 | TISAGGDTTLYADSVKG | 947 | RIDCNSGYCYRRNY |
| DR591-hIL27Ra_VHH8 | 554 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQVGGSIRLSCAASGFTF | 943 | AIASGYIDSRWCMA | 199 | AIWPGGGLTVYADSVKG | 205 | GSPRMCPSLEFGFDY | 211 | FTFSSYPMS | 218 | TISAGGDTTLYADSVKG | 947 | RIDCNSGYCYRRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SSYPMSWVRQAPGKGLEW<br>ISTISAGGDTTLYADSVK<br>GRFTSSRDNAKNTLYLQL<br>NSLKTEDTAIYYCAKRID<br>CNSGYCYRRNYWGQGTQV<br>TVSS | | | | | | | | | | | | |
| DR591-<br>hIL27Ra_<br>VHH9 | 4 | QVQLQESGGGSVQAGGSL<br>RLSCTASGAIASGYIDSR<br>WCMAWFRQAPGKEREGVA<br>AIWPGGGLTVYADSVKGR<br>FTISRDHAKNTLYLQMNN<br>LKPEDTAMYYCAAGSPRM<br>CPSLEFGFDYWGQGTQVT<br>VSSGGGSQVQLQESGGGS<br>VQSGGSLRLSCAASGFTY<br>STSNSWMAWFRQAPGKER<br>EGVAAIYTVGGSIFYADS<br>VRGRFTISQDATKNMFYL<br>QMNTLKPEDTAMYYCAAA<br>SGRLRGKWFWPYEYNYWG<br>QGTQVTVSS | 943 | AIASGYIDSRWCMA | 199 | AI<br>WP<br>GG<br>GL<br>TV<br>YA<br>DS<br>VK<br>G | 205 | GS<br>PR<br>MC<br>PS<br>LE<br>FG<br>FD<br>Y | 214 | FTY<br>STS<br>NSW<br>MA | 221 | AIY<br>TVG<br>GSI<br>FYA<br>DSV<br>RG | 228 | AS<br>GR<br>LR<br>GK<br>WF<br>WP<br>YE<br>YN<br>Y |
| DR591-<br>hIL27Ra_<br>VHH10 | 555 | QVQLQESGGGSVQAGGSL<br>RLSCTASGAIASGYIDSR<br>WCMAWFRQAPGKEREGVA<br>AIWPGGGLTVYADSVKGR<br>FTISRDHAKNTLYLQMNN<br>LKPEDTAMYYCAAGSPRM<br>CPSLEFGFDYWGQGTQVT<br>VSSGGGSQVQLQESGGGS<br>VQAGGSLRLSCRASGSTY<br>SNYCLGWFRQITGKEREG<br>VAVINWVGGMLYFADSVK<br>GRFTVSQDQAKNTLYLQM<br>NSLKPEDTAMYYCAAESV<br>SSFSCGGWLTRPDRVPYW<br>GQGTQVTVSS | 943 | AIASGYIDSRWCMA | 199 | AI<br>WP<br>GG<br>GL<br>TV<br>YA<br>DS<br>VK<br>G | 205 | GS<br>PR<br>MC<br>PS<br>LE<br>FG<br>FD<br>Y | 216 | STY<br>SNY<br>CLG | 223 | VIN<br>WVG<br>GML<br>YFA<br>DSV<br>KG | 230 | ES<br>VS<br>SF<br>SC<br>GG<br>WL<br>TR<br>PD<br>RV<br>PY |
| DR591-<br>hIL27Ra_<br>VHH11 | 556 | QVQLQESGGGSVQAGGSL<br>RLSCTASGAIASGYIDSR<br>WCMAWFPQAPGKEREGVA<br>AIWPGGGLTVYADSVKGR<br>FTISRDHAKNTLYLQMNN<br>LKPEDTAMYYCAAGSPRM<br>CPSLEFGFDYWGQGTQVT<br>VSSGGGSQVQLQESGGGS<br>VQAGGSLRLSCRASGSTY<br>SNYCLGWFRQSTGKEREG<br>VAVINWVGGMLYFADSVK | 943 | AIASGYIDSRWCMA | 199 | AI<br>WP<br>GG<br>GI<br>TV<br>YA<br>DS<br>VK<br>G | 205 | GS<br>PR<br>MC<br>PS<br>LE<br>FG<br>FD<br>Y | 216 | STY<br>SNY<br>CLG | 223 | VIN<br>WVG<br>GML<br>YFA<br>DSV<br>KG | 949 | ES<br>VS<br>SF<br>SC<br>GG<br>WL<br>TR<br>PG<br>RV<br>PY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GRFTVSQDHAKNTVTLQMNSLKPEDTAMYYCAAESVSSFSCGGWLTRPGRVPYWGQGTQVTVSS | | | | | | | | | | | | |
| DR591-hIL27Ra_VHH12 | 557 | QVQLQESGGGSVQAGGSLRLSCTASGAIASGYIDSRWCMAWFRQAPGKEREGVAAIWPGGGLTVYADSVKGRFTISRDHAKNTLYIQMNNLKPEDTAMYYCAAGSPRMCPSLEFGFDYWGQGTQVTVSSGGGSQVQLQESGGGSVQAGESLRLSCRASGSTYSNYCLGWFRQITGKEREGVAVINWVGGMLYFADSVKGRFTVSQDQAKNIVYLEMNSLKPEDTAMYYCATESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |
| DR591-hIL27Ra_VHH13 | 558 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 950 | SCVRGRTISEY |
| DR591-hIL27Ra_VHH14 | 559 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQM | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 229 | SCVRGRAISEY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSLKPEDTAMYYCKASCVRGRAISEYWGQGTQVTVSS | | | | | | | | | | | | |
| DR591-hIL27Ra_VHH15 | 5 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 229 | SCVRGRAISEY |
| DR591-hIL27Ra_VHH16 | 560 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCRASGSTYSNYCLGWERQITGKEREGVAVINWVGGMLYFADSVKGRFTVSQDQAKNTVYLQMNSLKPEDTAMYYCAAESASSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 951 | ESASSFSCGGWLTRPDRVPY |
| DR591-hIL27Ra_VHH17 | 561 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGEDYWGQGTQVTVSSGGGSQVQLQESGGGLVQPGGSLRLSCAASGFTFSLSGMSWVRQAPGKGLEWVSAISSGGASTYYTDSVKGRFTISRDNAKNMLYLQL | 943 | AIASGYIDSRWCMA | 199 | AIWPGGGLTVYADSVKG | 205 | GSPRMCPSLEFGFDY | 940 | FTFSLSGMS | 224 | AISSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSLKTEDTAMYYCAKGGSGYGDASRMTSPGSQGTQVTVSS | | | | | | | | | | | | |
| DR591-hIL27Ra_VHH18 | 562 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 952 | SCVRGRGISEY |
| DR591-hIL27Ra_VHH19 | 6 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGSVQAGGSLRLSCRASGSTYSNYCLGWFRQITGKEREGVAVINWVGGMLYFADSVKGRFTVSQDQARNTVYLQMNSLKPEDTAMYYCAAESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |
| DR591-hIL27Ra_VHH20 | 563 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGLVQPGGSLRLSCAASGFTFSSYPMSWVRQAPGKGLEWVSTISSGGDTTLYADSVKGRFTSSRDNAKNTLYLQL | 943 | AIASGYIDSRWCMA | 199 | AIWPGGGLTVYADSVKG | 205 | GSPRMCPSLEFGFDY | 211 | FTFSSYPMS | 945 | TISSGGDTTLYADSVKG | 953 | RIDCNSGYCYKRSY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSLKTEDTAMYYCAKRIDCNSGYCYKRSYWGQGTQVTVSS | | | | | | | | | | | | |
| DR591-hIL27Ra_VHH21 | 7 | QVQLQESGGGSVQAGGSLRLSCTASGAIASGYIDSRWCMAWFPQAPGKEREGVAAIWPGGGLTVYADSVKGRFTISRDHAKNTLYLQMNNLKPEDTAMYYCAAGSPRMCPSLEFGFDYWGQGTQVTVSSGGGSQVQLQESGGGLVQPGGSIRLSCAASGFTFSLSSMSWVRQAPGKGLEWVSAISSGGASTYYTDSVKGRFTISRDNAKNMLYLQLNSLKTEDTAMYYCAKGGSGYGDASPMTSPGSQGTQVTVSS | 943 | AIASGYIDSRWCMA | 199 | AIWPGGGLTVYADSVKG | 205 | GSPRMCPSLEFGFDY | 217 | FTFSLSSMS | 224 | AISSGGASTYYTDSVKG | 231 | GGSGYGDASRMTSP |
| DR591-hIL27Ra_VHH22 | 564 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGEDYWGQGTQVTVSSGGGSQVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |
| DR591-hIL27Ra_VHH23 | 565 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGEDYWGQGTQVTVSSGGGSQVQLQESGGGSVQAGGSLRLSCRASRSPYGNYCLGWFRQSTGKEREGVAVINWVGGMLYFADSVKGRFTVSQDHAKNTVTLQM | 943 | AIASGYIDSRWCMA | 199 | AIWPGGGLTVYADSVKG | 205 | GSPRMCPSLEFGFDY | 941 | SPYGNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSLKPEDTAMYYCAAESV<br>SSFSCGGWLTRPDRVPYW<br>GQGTQVTVSS | | | | | | | | | | | | |
| DR591-<br>hIL27Ra_<br>VHH24 | 566 | QVQLQESGGGSVQAGGSL<br>RLSCTASGAIASGYIDSR<br>WCMAWFRQAPGKEREGVA<br>AIWPGGGLTVYADSVKGR<br>FTISRDHAKNTLYLQMNN<br>LKPEDTAMYYCAAGSPRM<br>CPSLEFGEDYWGQGTQVT<br>VSSGGGSQVQLQESGGGL<br>VQPGGSIRLSCAASGFTF<br>SHSGMSWVRQAPGKGLEW<br>VSTINSGGASTYYTDSVK<br>GRFTISRDNAKNMLYLQL<br>NSLKTEDTAMYYCAKGGS<br>GYGDASRMTSPGSQGTQV<br>TVSS | 943 | AIASGYIDSRWCMA | 199 | AI<br>WP<br>GG<br>GL<br>TV<br>YA<br>DS<br>VK<br>G | 205 | GS<br>PR<br>MC<br>PS<br>LE<br>FG<br>FD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR592-<br>hIL27Ra_<br>VHH1 | 8 | QVQLQESGGGSVQAGGSL<br>RLSCTAPGFTSNSCGMDW<br>YRQAPGKEREFVSSISTD<br>GTTGYADSVKGRFTISKD<br>KAKDTVYLQMNSLKPEDT<br>GMYSCKIKDGTIATMELC<br>DFGYWGQGTQVTVSSGGG<br>SQVQLQESGGGLVQPGGS<br>LRLSCAASGFTFSSYPMS<br>WVRQAPGKGLEWISTISA<br>GGDTTLYADSVKGRFTSS<br>RDNAKNILYLQLNSLKTE<br>DAAIYYCAKRIDCNSGYC<br>YRRNYWGQGTQVTVSS | 194 | FTSNSCGMD | 200 | SI<br>ST<br>DG<br>TT<br>GY<br>AD<br>SV<br>KG | 206 | KD<br>GT<br>IA<br>TM<br>EL<br>CD<br>FG<br>Y | 211 | FTF<br>SSY<br>PMS | 218 | TIS<br>AGG<br>DTT<br>LYA<br>DSV<br>KG | 947 | RI<br>DC<br>NS<br>GY<br>CY<br>RR<br>NY |
| DR592-<br>hIL27Ra_<br>VHH2 | 567 | QVQLQESGGGSVQAGGSL<br>RLSCTAPGFTSNSCGMDW<br>YRQAPGKEREFVSSISTD<br>GTTGYADSVKGRFTISKD<br>KAKDTVYLQMNSLKPEDT<br>GMYSCKTKDGTIATMELC<br>DFGYWGQGTQVTVSSGGG<br>SQVQLQESGGGLVQPGGS<br>LRLSCAASGFTFSLSGMS<br>WVRQAPGKGLEWVSAISS<br>GGASTYYTDSVKGRFTIS<br>RDNAKNILYLQLNSLKTE<br>DTAMYYCAKGGSGYGDAS<br>RMTSPGSQGTQVTVSS | 194 | FTSNSCGMD | 200 | SI<br>ST<br>DG<br>TT<br>GY<br>AD<br>SV<br>KG | 206 | KD<br>GT<br>IA<br>TM<br>EL<br>CD<br>FG<br>Y | 940 | FTF<br>SLS<br>GMS | 224 | AIS<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR592-hIL27Ra_VHH3 | 568 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 948 | SCVRGRAVSEY |
| DR592-hIL27Ra_VHH4 | 9 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKIKDGTIATMELCDFGYWGQGTQVTVSSGGGSQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 194 | FTSNSCGMD | 200 | SISTDGTTGYADSVKG | 206 | KDGTIATMELCDFGY | 212 | FTFSNYAMS | 219 | GINVAYGITSYADSVKG | 226 | HSGTTIPRGFISYTK |
| DR592-hIL27Ra_VHH5 | 569 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | 194 | FTSNSCGMD | 200 | SISTDGTTGYADSVKG | 206 | KDGTIATMELCDFGY | 215 | YVSCDYFLPS | 944 | VIDGTGSTSYAASVKG | 229 | SCVRGRAISEY |
| DR592-hIL27Ra_VHH6 | 10 | QVQLQESGGGSVQAGGSLRLSCTAPGFTSNSCGMDWYRQAPGKEREFVSSISTDGTTGYADSVKGRFTISKDKAKDTVYLQMNSLKPEDT | 194 | FTSNSCGMD | 200 | SISTDGTTGY | 206 | KDGTIATMEL | 213 | FSFSSYAMK | 220 | TISSGGSSTNYADSV | 227 | AIVPTGATME |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GMYSCKTKDGTIATMELCDFGYWGQGTQVTVSSGGGSQVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS | | | | ADSVKG | | CDFGY | | | | KG | | |
| DR592-hIL27Ra_VHH7 | 570 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 194 | FTSNSCGMD | 200 | SISTDGTTGYADSVKG | 206 | KDGTIATMELCDFGY | 211 | FTFSSYPMS | 218 | TISAGGDTTLYADSVKG | 947 | RIDCNSGYCYRRNY |
| DR592-hIL27Ra_VHH8 | 571 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 194 | FTSNSCGMD | 200 | SISTDGTTGYADSVKG | 206 | KDGTIATMELCDFGY | 211 | FTFSSYPMS | 218 | TISAGGDTTLYADSVKG | 947 | RIDCNSGYCYRRNY |
| DR592-hIL27Ra_VHH9 | 11 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKIKDGTIATMELCDFGYWGQGTQVTVSSGGGSQVQLQESGGGSVQSGGSLRLSCAASGFTYSTSNSWMAWFRQAPGKEREGVAAI | 194 | FTSNSCGMD | 200 | SISTDGTTGYADSVKG | 206 | KDGTIATMELCDFGY | 214 | FTYSTSNSWMA | 221 | AIYTVGGSIFYADSVRG | 228 | ASGRLRGKWFWPYEYNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | YTVGGSIFYADSVRGRFTISQDATKNMFYLQMNTLKPEDTAMYYCAAASGRLRGKWFWPYEYNYWGQGTQVTVSS | | | | | | | | | | | | |
| DR592-hIL27Ra_VHH10 | 572 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 194 | FTSNSCGMD | 200 | SISTDGTTGYADSVKG | 206 | KDGTIATMELCDFGY | 216 | STYSNYCLG | 223 | VINWVGGMLYFADSVKG | 230 | ESVSSFSCGGWLTRPDRVPY |
| DR592-hIL27Ra_VHH11 | 573 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSS | 194 | FTSNSCGMD | 200 | SISTDGTTGYADSVKG | 206 | KDGTIATMELCDFGY | 216 | STYSNYCLG | 223 | VINWVGGMLYFADSVKG | 949 | ESVSSFSCGGWLTRPGRVPY |
| DR592-hIL27Ra_VHH12 | 574 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGESLRLSCRASGSTYSNYCLGWFRQITGKEREGVAVINWVGGMLYFADSVKGRFTVSQDQAKNTVYLEMNSLKPE | 194 | FTSNSCGMD | 200 | SISTDGTTGYADSVKG | 206 | KDGTIATMELCDFGY | 216 | STYSNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DTAMYYCATESVSSFSCGGWLTRPDRVPYWGQGTQVTVSS | | | | | | | | | | | | |
| DR592-hIL27Ra_VHH13 | 575 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 950 | SCVRGRTISEY |
| DR592-hIL27Ra_VHH14 | 576 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 229 | SCVRGRAISEY |
| DR592-hIL27Ra_VHH15 | 12 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCVASGYVSCDYFLPSWYRQAPGKEREEVSIIDGTGSTSYAASVKGRFTASQDKGKNIAYLQMNTLKPEDTAMYYCKASCVRGRAISEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 229 | SCVRGRSEY |
| DR592- | 577 | QVQLQESGGGSVQAGGSL | 194 | FTSNSCGMD | 200 | SI | 206 | KD | 216 | STY | 223 | VIN | 951 | ES |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH14 | | RLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | | | | STDGTTGYADSVKG | | GTIATMELCDFGY | | SNYCLG | | WVGGMLYFADSVKG | | ASSFSCGGWLTRPDRVPY |
| DR592-hIL27Ra_VHH17 | 578 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 194 | FTSNSCGMD | 200 | SISTDGTTGYADSVKG | 206 | KDGTIATMELCDFGY | 940 | FTFSLSGMS | 224 | AISSGGASTYYTDSVKG | 231 | GGSGYGDASRMTSP |
| DR592-hIL27Ra_VHH18 | 579 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 952 | SCVRGRGISEY |
| DR592-hIL27Ra_VHH19 | 13 | QVQLQESGGGSVQAGGSLRLSCTAPGFTSNSCGMDWYRQAPGKEREFVSSISTDGTTGYADSVKGRFTISKDKAKDTVYLQMNSLKPEDT | 194 | FTSNSCGMD | 200 | SISTDGTTGY | 206 | KDGTIATMEL | 216 | STYSNYCLG | 223 | VINWVGGMLYFADSV | 230 | ESVSSFSCGG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GMYSCKTKDGTIATMELC DFGYWGQGTQVTVSSGGG SQVQLQESGGGSVQAGGS LRLSCRASGSTYSNYCLG WFRQITCKEREGVAVINW VGGMLYFADSVKGRFTVS QDQAKNIVYLQMNSLKPE DTAMYYCAAESVSSFSCG GWLTRPDRVPYWGQGTQV TVSS | | | | AD SV KG | | CD FG Y | | | | KG | | WL TR PD RV PY |
| DR592-hIL27Ra_VHH20 | 580 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKIKDGTIATMELC DFGYWGQGTQVTVSSGGG SQVQLQESGGGLVQPGGS LRLSCAASGFTFSSYPMS WVRQAPCKGLEWVSTISS GGDTTLYADSVKGRFTSS RDNAKNTLYLQLNSLKTE DTAMYYCAKRIDCNSGYC YKRSYWGQGTQVTVSS | 194 | FTSNSCGMD | 200 | SI ST DG TT GY AD SV KG | 206 | KD GT IA TM EL CD FG Y | 211 | FTF SSY PMS | 945 | TIS SGG DTT LYA DSV KG | 953 | RI DC NS GY CY KR SY |
| DR592-hIL27Ra_VHH21 | 14 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGG SQVQLQESGGGLVQPGGS LRLSCAASGFTFSLSSMS WVRQAPGKGLEWVSAISS GGASTYYTDSVKGRFTIS RDNAKNMLYLQLNSLKTE DTAMYYCAKGGSGYGDAS RMTSPGSQGTQVTVSS | 194 | FTSNSCGMD | 200 | SI ST DG TT GY AD SV KG | 206 | KD GT IA TM EL CD FG Y | 217 | FTF SLS SMS | 224 | AIS SGG AST YYT DSV KG | 231 | GG SG YG DA SR MT SP |
| DR592-hIL27Ra_VHH22 | 581 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGG SQVQLQESGGGSVQAGGS LRLSCRASGSTYSNYCLG | 194 | FTSNSCGMD | 200 | SI ST DG TT GY AD SV KG | 206 | KD GT IA TM EL CD FG Y | 216 | STY SNY CLG | 223 | VIN WVG GML YFA DSV KG | 230 | ES VS SF SC GG WL TR PD RV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | WFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | | | | | | | | | | | | PY |
| DR592-hIL27Ra_VHH23 | 582 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGSVQAGGSLRLSCRASRSPYGNYCLGWFRQSTGKEREGVAVINWVGGMLYFADSVKGRETVSQDHAKNTVTLQMNSLKPEDTAMYYCAAESVSSFSCGGWLTRPDRVPYWGQGTQVTVSS | 194 | FTSNSCGMD | 200 | SISTDGTTGYADSVKG | 206 | KDGTIATMELCDFGY | 941 | SPYGNYCLG | 223 | VINWVGGMLYFADSVKG | 230 | ESVSSFSCGGWLTRPDRVPY |
| DR592-hIL27Ra_VHH24 | 583 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGGSQVQLQESGGGLVQPGGSLRLSCAASGETFSHSGMSWVPQAPGKGLEWVSTINSGGASTYYTDSVKGRFTISRDNAKNMLYLQLNSLKTEDTAMYYCAKGGSGYGDASRMTSPGSQGTQVTVSS | 194 | FTSNSCGMD | 200 | SISTDGTTGYADSVKG | 206 | KDGTIATMELCDFGY | 942 | FTFSHSGMS | 946 | TINSGGASTYYTDSVKG | 231 | GGSGYGDASRMTSP |
| DR593-hIL27Ra_VHH1 | 15 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGLVQPGGSLRLSCAASGFTFSSYPMSWVRQAPGKGLEWISTISAGGDTTLYADSVKGRFTSSRDNAKNTLYLQLN | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SLKTEDAAIYYCAKRIDCNSGYCYPRNYWGQGTQVTVSS | | | | | | | | | | | | |
| DR593-hIL27Ra_VHH2 | 584 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMISPGSQGTQVTVSS | 195 | YPYSNGYMG | 201 | TIYTGDGRTYYADSVKG | 207 | RAABLYSSGSPLTRARYNV | 942 | FTFSHSGMS | 946 | TINSGGASTYYTDSVKG | 231 | GGSGYGDASRMTSP |
| DR593-hIL27Ra_VHH3 | 585 | QVQLQESGGGSVQAGGSLPLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH4 | 16 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-<br>hIL27Ra_<br>VHH5 | 586 | QVQLQESGGGSVQAGGSL<br>PLSCAASGYPYSNGYMGW<br>FRQAPGKEREGVATIYTG<br>DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGSV<br>QAGGSLRLSCTASGYVSC<br>DYFLPSWYRQAPGKEREF<br>VSVIDGTGSTSYAASVKG<br>RFTASQDKGKNIAYLQMN<br>SLKPEDTAMYYCKASCVR<br>GRAISEYWGQGTQVTVSS | 195 | YPYSNGYMG | 201 | TI<br>YT<br>GD<br>GR<br>TY<br>YA<br>DS<br>VK<br>G | 207 | RA<br>AP<br>LY<br>SS<br>GS<br>PL<br>TR<br>AR<br>YN<br>V | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR593-<br>hIL27Ra_<br>VHH6 | 17 | QVQLQESGGGSVQAGGSL<br>RLSCAASGYPYSNGYMGW<br>FPQAPGKEREGVATIYTG<br>DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGLV<br>QPGGSLRLSCAASGFSFS<br>SYAMKWVRQAPGKGLEWV<br>STISSGGSSTNYADSVKG<br>RFTISRDNAKNTLYLQLN<br>SIKIEDTAMYYCAKAIVP<br>TGATMERGQGTQVTVSS | 195 | YPYSNGYMG | 201 | TI<br>YT<br>GD<br>GR<br>TY<br>YA<br>DS<br>VK<br>G | 207 | RA<br>AP<br>LY<br>SS<br>GS<br>PL<br>TR<br>AR<br>YN<br>V | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR593-<br>hIL27Ra_<br>VHH7 | 587 | QVQLQESGGGSVQAGGSL<br>RLSCAASGYPYSNGYMGW<br>FRQAPGKEREGVATIYTG<br>DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGLV<br>QPGGSLRLSCAASGFTFS<br>SYPMSWVRQAPGKGLEWI<br>STISAGGDTTLYADSVKG<br>RFTSSRDNAKNTLYLQLN<br>SLKTEDTAIYYCAKRIDC<br>NSGYCYRRNYWGQGTQVT<br>VSS | 195 | YPYSNGYMG | 201 | TI<br>YT<br>GD<br>GR<br>TY<br>YA<br>DS<br>VK<br>G | 207 | RA<br>AP<br>LY<br>SS<br>GS<br>PL<br>TR<br>AR<br>YN<br>V | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SR |
| DR593-<br>hIL27Ra_<br>VHH8 | 588 | QVQLQESGGGSVQAGGSL<br>RLSCAASGYPYSNGYMGW<br>FRQAPGKEREGVATIYTG | 195 | YPYSNGYMG | 201 | TI<br>YT<br>GD | 207 | RA<br>AP<br>LY | 942 | FTF<br>SHS<br>GMS | 946 | TIN<br>SGG<br>AST | 231 | GG<br>SG<br>YG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGSV<br>QVGGSLRLSCAASGFTFS<br>SYPMSWVRQAPGKGLEWI<br>STISAGGDTTLYADSVKG<br>RFTSSRDNAKNTLYLQLN<br>SLKTEDTAIYYCAKRIDC<br>NSGYCYRRNYWGQGTQVT<br>VSS | | | | GR<br>TY<br>YA<br>DS<br>VK<br>G | | SS<br>GS<br>PL<br>TR<br>AR<br>YN<br>V | | | | YYT<br>DSV<br>KG | | DA<br>SR<br>MT<br>SP |
| DR593-<br>hIL27Ra_<br>VHH9 | 18 | QVQLQESGGGSVQAGGSL<br>RLSCAASGYPYSNGYMGW<br>FRQAPGKEREGVATIYTG<br>DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGSV<br>QSGGSLRLSCAASGFTYS<br>TSNSWMAWFRQAPGKERE<br>GVAAIYTVGGSIFYADSV<br>RGRFTISQDATKNMFYLQ<br>MNTLKPEDTAMYYCAAAS<br>GRLRGKWFWPYEYNYWGQ<br>GTQVTVSS | 195 | YPYSNGYMG | 201 | TI<br>YT<br>GD<br>GR<br>TY<br>YA<br>DS<br>VK<br>G | 207 | RA<br>AP<br>LY<br>SS<br>GS<br>PL<br>TR<br>AR<br>YN<br>V | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR593-<br>hIL27Ra_<br>VHH10 | 589 | QVQLQESGGGSVQAGGSL<br>RLSCAASGYPYSNGYMGW<br>FRQAPGKEREGVATIYTG<br>DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGSV<br>QAGGSLRLSCRASGSTYS<br>NYCLGWFRQITGKEREGV<br>AVINWVGGMLYFADSVKG<br>RFTVSQDQAKNTLYLQMN<br>SLKPEDTAMYYCAAESVS<br>SFSCGGWLTRPDRVPYWG<br>QGTQVTVSS | 195 | YPYSNGYMG | 201 | TI<br>YT<br>GD<br>GR<br>TY<br>YA<br>DS<br>VK<br>G | 207 | RA<br>AB<br>LY<br>SS<br>GS<br>PL<br>TR<br>AR<br>YN<br>V | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR593-<br>hIL27Ra_<br>VHH11 | 590 | QVQLQESGGGSVQAGGSL<br>RLSCAASGYPYSNGYMGW<br>FRQAPGKEREGVATIYTG<br>DGRTYYADSVKGRFTISR<br>DNAKNTVDLQMSSLKPED | 195 | YPYSNGYMG | 201 | TI<br>YT<br>GD<br>GR<br>TY | 207 | RA<br>AP<br>LY<br>SS<br>GS | 942 | FTF<br>SHS<br>GMS | 946 | TIN<br>SGG<br>AST<br>YYT<br>DSV | 231 | GG<br>SG<br>YG<br>DA<br>SR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TAMYYCAARAAPLYSSGSPLTRARYNVWGQGTQVTVSSGGGSQVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSS | | | | YADSVKG | | PLTRARYNV | | | | KG | | MTSP |
| DR593-hIL27Ra_VHH12 | 591 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGESLPLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH13 | 592 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH14 | 593 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSV | 195 | YPYSNGYMG | 201 | TIYTGDGRTYYADSVK | 207 | RAAPLYSSGSPLTRAR | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | QAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | | | | G | | YNV | | | | | | |
| DR593-hIL27Ra_VHH15 | 19 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH16 | 594 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 195 | YPYSNGYMG | 201 | TIYTGDGRTYYADSVKG | 207 | RAABLYSSGSPLTRARYNV | 942 | FTFSHSGMS | 946 | TINSGGASTYYTDSVKG | 231 | GGSGYGDASRMTSP |
| DR593-hIL27Ra_VHH17 | 595 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGLVQPGGSLRLSCAASGFTFSLSGMSWVRQAPGKGLEWVSAISSGGASTYYTDSVKGRFTISRDNAKNMLYLQLN | 195 | YPYSNGYMG | 201 | TIYTGDGRTYYADSVKG | 207 | RAABLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SLKTEDTAMYYCAKGGSG YGDASRMTSPGSQGTQVT VSS | | | | | | | | | | | | |
| DR593- hIL27Ra_ VHH18 | 596 | QVQLQESGGGSVQAGGSL RLSCAASGYPYSNGYMGW FRQAPGKEREGVATIYTG DGRTYYADSVKGRFTISR DNAKNTVDLQMSSLKPED TAMYYCAARAAPLYSSGS PLTRARYNVWGQGTQVTV SSGGGSQVQLQESGGGSV QAGGSLRLSCVASGYVSC DYFLPSWYRQAPGKEREF VSIIDGTGSTSYAASVKG RFTASQDKGKNIAYLQMN SLKPEDTAMYYCKASCVR GRGISEYWGQGTQVTVSS | 195 | YPYSNGYMG | 201 | TI YT GD GR TY YA DS VK G | 207 | RA AP LY SS GS PL TR AR YN V | 942 | FTF SHS GMS | 946 | TIN SGG AST YYT DSV KG | 231 | GG SG YG DA SR MT SP |
| DR593- hIL27Ra_ VHH19 | 20 | QVQLQESGGGSVQAGGSL RLSCAASGYPYSNGYMGW FRQAPGKEREGVATIYTG DGRTYYADSVKGRFTISR DNAKNTVDLQMSSLKPED TAMYYCAARAAPLYSSGS PLTRARYNVWGQGTQVTV SSGGGSQVQLQESGGGSV QAGGSLRLSCRASGSTYS NYCLGWFRQITGKEREGV AVINWVGGMLYFADSVKG RFTVSQDQAKNTVYLQMN SLKPEDTAMYYCAAESVS SFSCGGWLTRPDRVPYWG QGTQVTVSS | 195 | YPYSNGYMG | 201 | TI YT GD GR TY YA DS VK G | 207 | RA AP LY SS GS PL TR AR YN V | 942 | FTF SHS GMS | 946 | TIN SGG AST YYT DSV KG | 231 | GG SG YG DA SR MT SP |
| DR593- hIL27Ra_ VHH20 | 597 | QVQLQESGGGSVQAGGSL RLSCAASGYPYSNGYMGW FRQAPGKEREGVATIYTG DGRTYYADSVKGRFTISR DNAKNTVDLQMSSLKPED TAMYYCAARAAPLYSSGS PLTRARYNVWGQGTQVTV SSGGGSQVQLQESGGGLV QPGGSLRLSCAASGFTFS SYPMSWVRQAPGKGLEWV STISSGGDTTLYADSVKG RFTSSRDNAKNTLYLQLN SLKTEDTAMYYCAKRIDC NSGYCYKRSYWGQGTQVT VSS | 195 | YPYSNGYMG | 201 | TI YT GD GR TY YA DS VK G | 207 | RA AP LY SS GS PL TR AR YN V | 942 | FTF SHS GMS | 946 | TIN SGG AST YYT DSV KG | 231 | GG SG YG DA SR MT SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH21 | 21 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH22 | 598 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGGSLPLSCRASGSTYSNYCLGWERQTTGKEREGYAVINWVGGMLYFADSVKGRFTVSQDQAKNTVYLQMNSLKPEDTAMYYCAAESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH23 | 599 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGGSQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593- | 600 | QVQLQESGGGSVQAGGSL | 195 | YPYSNGYMG | 201 | TI | 207 | RA | 942 | FTF | 946 | TIN | 231 | GG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_<br>VHH24 | | RLSCAASGYPYSNGYMGW<br>FRQAPGKEREGVATIYTG<br>DGRTYYADSVKGRFTISR<br>DNAKNTVDLQMSSLKPED<br>TAMYYCAARAAPLYSSGS<br>PLTRARYNVWGQGTQVTV<br>SSGGGSQVQLQESGGGLV<br>QPGGSLRLSCAASGFTFS<br>HSGMSWVRQAPGKGLEWV<br>STINSGGASTYYTDSVKG<br>RFTISRDNAKNMLYLQLN<br>SLKTEDTAMYYCAKGGSG<br>YGDASRMTSPGSQGTQVT<br>VSS | | | | YT<br>GD<br>GR<br>TY<br>YA<br>DS<br>VK<br>G | | AP<br>LY<br>SS<br>GS<br>PL<br>TR<br>AR<br>YN<br>V | | SHS<br>GMS | | SGG<br>AST<br>YYT<br>DSV<br>KG | | SG<br>YG<br>DA<br>SR<br>ME<br>SP |
| DR594-<br>hIL27Ra_<br>VHH1 | 22 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGGSQVQ<br>LQESGGGLVQPGGSLRLS<br>CAASGFTFSSYPMSWVRQ<br>APGKGLEWISTISAGGDT<br>TLYADSVKGRFTSSRDNA<br>KNTLYLQLNSLKTEDAAI<br>YYCAKRIDCNSGYCYRRN<br>YWGQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-<br>hIL27Ra_<br>VHH2 | 601 | QVQLQESGGGSVQAGGSL<br>RLSCVASASTYCTYDMHW<br>YRQAPGKGREFVSAIDSD<br>GTTRYADSVKGRFTISQG<br>TAKNIVYLQMNSLQPEDT<br>AMYYCKTVQVVGSRWSDY<br>WGQGTQVTVSSGGGSQVQ<br>LQESGGGLVQPGGSLRLS<br>CAASGFTFSLSGMSWVRQ<br>APGKGLEWVSAISSGGAS<br>TYYTDSVKGRFTISRDNA<br>KNILYLQLNSLKTEDTAM<br>YYCAKGGSGYGDASRMTS<br>PGSQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-<br>hIL27Ra_<br>VHH3 | 602 | QVQLQESGGGSVQAGGSL<br>RLSCVASASTYCTYDMHW<br>YPQAPGKGREFVSAIDSD<br>GTTRYADSVKGRFTISQG<br>TAKNTVYLQMNSLQPEDT | 196 | STYCTYDMH | 202 | AI<br>DS<br>DG<br>TT<br>RY | 954 | VC<br>VV<br>GS<br>RW<br>SD | 942 | FTF<br>SHS<br>GMS | 946 | TIN<br>SGG<br>AST<br>YYT<br>DSV | 231 | GG<br>SG<br>YG<br>DA<br>SR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AMYYCKTVCVVGSRWSDYWGQGTQVTVSSGGGSQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | | | | ADSVKG | | Y | | | | KG | | MTSP |
| DR594-hIL27Ra_VHH4 | 23 | QVQLQESGGGSVQAGGSLRLSCVASASTYCTYDMHWYRQAPGKGREFVSAIDSDGTTRYADSVKGRFTISQGTAKNIVYLQMNSLQPEDTAMYYCKTVCVVGSRWSDYWGQGTQVTVSSGGGSQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH5 | 603 | QVQLQESGGGSVQAGGSLRLSCVASASTYCTYDMHWYPQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH6 | 24 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGLVQPGGSLRLSCAASGFSFSSYAMKWVRQAPGKGLEWVSTISSGGSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TNYADSVKGRFTISRDNA<br>KNTLYLQLNSLKIEDTAM<br>YYCAKAIVPTGATMERGQ<br>GTQVTVSS | | | | | | | | | | | | |
| DR594-<br>hIL27Ra_<br>VHH7 | 604 | QVQLQESGGGSVQAGGSL<br>PLSCVASASTYCTYDMHW<br>YRQAPGKGREFVSAIDSD<br>GTTRYADSVKGRFTISQG<br>TAKNIVYLQMNSLQPEDT<br>AMYYCKTVQVVGSRWSDY<br>WGQGTQVTVSSGGGSQVQ<br>LQESGGGLVQPGGSLRLS<br>CAASGFTFSSYPMSWVRQ<br>APGKGLEWISTISAGGDT<br>TLYADSVKGRFTSSRDNA<br>KNTLYLQLNSLKTEDTAI<br>YYCAKRIDCNSGYCYRRN<br>YWGQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-<br>hIL27Ra_<br>VHH8 | 605 | QVQLQESGGGSVQAGGSL<br>RLSCVASASTYCTYDMHW<br>YPQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGGSQVQ<br>LQESGGGSVQVGGSLRLS<br>CAASGFTFSSYPMSWVRQ<br>APGKGLEWISTISAGGDT<br>TLYADSVKGRFTSSRDNA<br>KNTLYLQLNSLKTEDTAI<br>YYCAKRIDCNSGYCYRRN<br>YWGQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-<br>hIL27Ra_<br>VHH9 | 25 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGGSQVQ<br>LQESGGGSVQSGGSLRLS<br>CAASGFTYSTSNSWMAWF<br>RQAPGKEREGVAAIYTVG<br>GSIFYADSVRGRFTISQD<br>ATKNMFYLQMNTLKPEDT<br>AMYYCAAASGRLRGKWFW<br>PYEYNYWGQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR594-hIL27Ra_VHH10 | 606 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH11 | 607 | QVQLQESGGGSVQAGGSLRLSCVASASTYCTYDMHWYRQAPGKGREFVSAIDSDGTTRYADSVKGRFTISQGTARNTVYLQMNSLQPEDTAMYYCKTVQVVGSRWSDYWGQGTQVTVSSGGGSQVQLQESGGGSVQAGGSLRLSCRASGSTYSNYCLGWFRQSTGKEREGVAVINWVGGMLYFADSVKGRETVSQDHAKNTVTLQMNSLKPEDTAMYYCAAESVSSFSCGGWLTRPGRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH12 | 608 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH13 | 609 | QVQLQESGGGSVQAGGSLRLSCVASASTYCTYDMHWYRQAPGKGREFVSAIDSDGTTRYADSVKGRFTISQGTAKNTVYLQMNSLQPEDT | 196 | STYCTYDMH | 202 | AIDSDGTTRY | 954 | VCVVGSRWSD | 942 | FTFSHSGMS | 946 | TINSGGASTYYTDSV | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AMYYCKTVCVVGSRWSDY<br>WGQGTQVTVSSGGGSQVQ<br>LQESGGGSVQAGGSLRLS<br>CVASGYVSCDYFT PSWYR<br>QAPGKEREFVSIIDGTGS<br>TSYAASVKGRFTASQDRG<br>KNIAYLQMNSLKPEDTAM<br>YYCKASCVRGRTISEYWG<br>QGTQVTVSS | | | | AD<br>SV<br>KG | | Y | | | | KG | | MT<br>SP |
| DR594-<br>hIL27Ra_<br>VHH14 | 610 | QVQLQESGGGSVQAGGSL<br>RLSCVASASTYCTYDMHW<br>YRQAPGKGREFVSAIDSD<br>GTTRYADSVKGRETISQG<br>TAKNTVYLQMNSLQPEDT<br>AMYYCKTVQVVGSRWSDY<br>WGQGTQVTVSSGGGSQVQ<br>LQESGGGSVQAGGSLRLS<br>CVASGYVSCDYFLPSWYR<br>QAPGKEREFVSIIDGTGS<br>TSYAASVKGRFTASQDKG<br>KNIAYLQMNSLKPEDTAM<br>YYCKASCVRGRAISEYWG<br>QGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-<br>hIL27Ra_<br>VHH15 | 26 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGGSQVQ<br>LQESGGGSVQAGGSLRLS<br>CVASGYVSCDYELPSWYR<br>QAPGKEREFVSIIDGTGS<br>TSYAASVKGRFTASQDKG<br>KNIAYLQMNTLKPEDTAM<br>YYCKASCVRGRAISEYWG<br>QGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-<br>hIL27Ra_<br>VHH16 | 611 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGGSQVQ<br>LQESGGGSVQAGGSLRLS<br>CRASGSTYSNYCLGWFRQ<br>ITGKEREGVAVINWVGGM | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | LYFADSVKGRFTVSQDQAKNTVYLQMNSLKPEDTAMYYCAAESASSFSCGGWLTRPDRVPYWGQGTQVTVSS | | | | | | | | | | | | |
| DR594-hIL27Ra_VHH17 | 612 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH18 | 613 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH19 | 27 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGGSQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR594-hIL27Ra_VHH20 | 614 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGLVQPGGSLRLSCAASGFTFSSYPMSWVRQAPGKGLEWVSTISSGGDTTLYADSVKGRFTSSRDNAKNTLYLQENSLKTEDTAMYYCAKRIDCNSGYCYKRSYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH21 | 28 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH22 | 615 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH23 | 616 | QVQLQESGGGSVQAGGSLRLSCVASASTYCTYDMHWYRQAPGKGREFVSAIDSDGTTRYADSVKGRFTISQGTAKNTVYLQMNSLQPEDT | 196 | STYCTYDMH | 202 | AIDSDGTTRY | 954 | VCVVGSRWSD | 942 | FTFSHSGMS | 946 | TINSGGASTYYTDSV | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AMYYCKTVCVVGSRWSDYWGQGTQVTVSSGGGSQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | | | | ADSVKG | | Y | | | | KG | | MTSP |
| DR594-hIL27Ra_VHH24 | 617 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGGSQVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR595-hIL27Ra_VHH1 | 29 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH2 | 618 | QVQLQESGGGSVQAGGSLTLSCAASEYAYSTCNMGWYRQAPGKERELVSAFISDGSTYYADSVKGRFTITRDNARNTVYLQMNSLKPEDTAIYYCSANCYRRLRNYWGQGTQVTVSSGGGSQVQLQESGGGLVQPGGSLRLSCAASGFTFSLSGMSWVRQAPGKGLEWVSAISSGGASTY | 197 | YAYSTCNMG | 203 | AFISDGSTYYADSVKG | 209 | NOYRRLRNY | 942 | FTFSHSGMS | 946 | TINSGGASTYYTDSVKG | 231 | GGSGYGDASRMPSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | YTDSVKGRFTISRDNAKNILYLQLNSLKTEDTAMYYCAKGGSGYGDASRMTSPGSQGTQVTVSS | | | | | | | | | | | | |
| DR595-hIL27Ra_VHH3 | 619 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH4 | 30 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH5 | 620 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQAGGSLRLSCTASGYVSCDYFLPSWYRQAPGKEREEVSVIDGTGSTSYAASVKGRFTASQDKGKNIAYLQMNSLKPEDTAMYYCKASCVRGPAISEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR595-hIL27Ra_VHH6 | 31 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH7 | 621 | QVQLQESGGGSVQAGGSLTLSCAASEYAYSTCNMGWYRQAPGKERELVSAFISDGSTYYADSVKGRFTITRDNAKNIVYLQMNSIKPEDTAIYYCSANCYRRLRNYWGQGTQVTVSSGGGSQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 197 | YAYSTCNMG | 203 | AFISDGSTYYADSVKG | 209 | NCYRRLRNY | 942 | FTFSHSGMS | 946 | TINSGGASTYYPDSVKG | 231 | GGSGYGDASRMTSP |
| DR595-hIL27Ra_VHH8 | 622 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH9 | 32 | QVQLQESGGGSVQAGGSLTLSCAASEYAYSTCNMGWYRQAPGKERELVSAFISDGSTYYADSVKGRFTITRDNARNTVYLQMNSLKPEDT | 197 | YAYSTCNMG | 203 | AFISDGSTYY | 209 | NOYRRLRNY | 942 | FTFSHSGMS | 946 | TINSGGASTYYTDSV | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AIYYCSANCYRRLRNYWG<br>QGTQVTVSSGGGSQVQLQ<br>ESGGGSVQSGGSLRLSCA<br>ASGFTYSTSNSWMAWFRQ<br>APGKEREGVAAIYTVGGS<br>IFYADSVRGRFTISQDAT<br>KNMFYLQMNTLKPEDTAM<br>YYCAAASGRLRGKWFWPY<br>EYNYWGQGTQVTVSS | | | | AD<br>SV<br>KG | | | | | | KG | | MP<br>SP |
| DR595-<br>hIL27Ra_<br>VHH10 | 623 | QVQLQESGGGSVQAGGSL<br>TLSCAASEYAYSTCNMGW<br>YPQAPGKERELVSAFISD<br>GSTYYADSVKGRFTITRD<br>NAKNTVYLQMNSLKPEDT<br>AIYYCSANCYRRLRNYWG<br>QGTQVTVSSGGGSQVQLQ<br>ESGGGSVQAGGSLRLSCR<br>ASGSTYSNYCLGWFRQIT<br>GKEREGVAVINWVGGMLY<br>FADSVKGRFTVSQDQAKN<br>TLYLQMNSLKPEDTAMYY<br>CAAESVSSFSCGGWLTRP<br>DRVPYWGQGTQVTVSS | 197 | YAYSTCNMG | 203 | AF<br>IS<br>DG<br>ST<br>YY<br>AD<br>SV<br>KG | 209 | NO<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR595-<br>hIL27Ra_<br>VHH11 | 624 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGGSQVQLQ<br>ESGGGSVQAGGSLRLSCR<br>ASGSTYSNYCLGWFRQST<br>GKEREGVAVINWVGGMLY<br>FADSVKGRFTVSQDHAKN<br>TVTLQMNSLKPEDTAMYY<br>CAAESVSSFSCGGWLTRP<br>GRVPYWGQGTQVTVSS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR595-<br>hIL27Ra_<br>VHH12 | 625 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGGSQVQLQ<br>ESGGGSVQAGESLRLSCR<br>ASGSTYSNYCLGWFRQIT<br>GKEREGVAVINWVGGMLY | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | FADSVKGRFTVSQDQAKN<br>TVYLEMNSLKPEDTAMYY<br>CATESVSSFSCGGWLTRP<br>DRVPYWGQGTQVTVSS | | | | | | | | | | | | |
| DR595-<br>hIL27Ra_<br>VHH13 | 626 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGGSQVQLQ<br>ESGGGSVQAGGSLRLSCV<br>ASGYVSCDYFLPSWYRQA<br>PGKEREFVSIIDGTGSTS<br>YAASVKGRFTASQDRGKN<br>IAYLQMNSLKPEDTAMYY<br>CKASCVRGRTISEYWGQG<br>TQVTVSS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR595-<br>hIL27Ra_<br>VHH14 | 627 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGGSQVQLQ<br>ESGGGSVQAGGSLRLSCV<br>ASGYVSCDYFLPSWYRQA<br>PGKEREEVSIIDGTGSTS<br>YAASVKGRFTASQDKGKN<br>IAYLQMNSLKPEDTAMYY<br>CKASCVRGRAISEYWGQG<br>TQVTVSS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR595-<br>hIL27Ra_<br>VHH15 | 33 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGGSQVQLQ<br>ESGGGSVQAGGSLRLSCV<br>ASGYVSCDYFLPSWYRQA<br>PGKEREFVSIIDGTGSTS<br>YAASVKGRFTASQDKGKN<br>IAYLQMNTLKPEDTAMYY<br>CKASCVRGRAISEYWGQG<br>TQVTVSS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR595-hIL27Ra_VHH16 | 628 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH17 | 629 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH18 | 630 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH19 | 34 | QVQLQESGGGSVQAGGSLTLSCAASEYAYSTCNMGWYRQAPGKERELVSAFISDGSTYYADSVKGRFTITRDNAKNTVYLQMNSLKPEDT | 197 | YAYSTCNMG | 203 | AFISDGSTYY | 209 | NCYRRLRNY | 942 | FTFSHSGMS | 946 | TINSGGASTYYTDSV | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AIYYCSANCYRRLRNYWGQGTQVTVSSGGGSQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS | | | | ADSVKG | | | | | | KG | | MTSP |
| DR595-hIL27Ra_VHH20 | 631 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH21 | 35 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | 197 | YAYSTCNMG | 203 | AFISDGSTYYADSVKG | 209 | NOYRRLRNY | 942 | FTFSHSGMS | 946 | TINSGGASTYYTDSVKG | 231 | GGSGYGDASRMTSP |
| DR595-hIL27Ra_VHH22 | 632 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQAGGSLRLSCRASGSTYSNYCLGWFRQTTGKEREGVAVINWVGGMLY | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | FADSVKGRFTVSQDQAKNTVYLQMNSLKPEDTAMYYCAAESVSSFSCGGWLTRPDRVPYWGQGTQVTVSS | | | | | | | | | | | | |
| DR595-hIL27Ra_VHH23 | 633 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH24 | 634 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGGSQVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR596-hIL27Ra_VHH1 | 36 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR596-hIL27Ra_VHH2 | 635 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH3 | 636 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH4 | 37 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH5 | 637 | QVQLQESGGGLVQPGGSLRLSCTASGLTFDDSVMGWFRQAPGKGREAVSCISSSGANAFYADSVKGRFTISRDNAKNTLYLQMNSLKPED | 198 | LTFDDSVMG | 204 | CISSSGANAF | 210 | GHACAGYYPI | 942 | FTFSHSGMS | 946 | TINSGGASTYYTDSV | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TATYYCKRGHACAGYYPI<br>PYDDYWGQGTQVTVSSGG<br>GSQVQLQESGGGSVQAGG<br>SLRLSCTASGYVSCDYFL<br>PSWYRQAPGKEREFVSVI<br>DGTGSTSYAASVKGRFTA<br>SQDKGKNIAYLQMNSLKP<br>EDTAMYYCKASCVRGRAI<br>SEYWGQGTQVTVSS | | | | YA<br>DS<br>VK<br>G | | PY<br>DD<br>Y | | | | KG | | MT<br>SP |
| DR596-<br>hIL27Ra_<br>VHH6 | 38 | QVQLQESGGGLVQPGGSL<br>RLSCTASGLTFDDSVMGW<br>FRQAPGKGREAVSCISSS<br>GANAFYADSVKGRFTISR<br>DNAKNTLYLQMNSLKPED<br>TATYYCKRGHACAGYYPI<br>PYDDYWGQGTQVTVSSGG<br>GSQVQLQESGGGLVQPGG<br>SLRLSCAASGFSFSSYAM<br>KWVRQAPGKGLEWVSTIS<br>SGGSSTNYADSVKGRFTI<br>SRDNAKNTLYLQLNSLKI<br>EDTAMYYCAKAIVPTGAT<br>MERGQGTQVTVSS | 198 | LTFDDSVMG | 204 | CI<br>SS<br>SG<br>AN<br>AF<br>YA<br>DS<br>VK<br>G | 210 | GH<br>AC<br>AG<br>YY<br>PI<br>PY<br>DD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR596-<br>hIL27Ra_<br>VHH7 | 638 | QVQLQESGGGLVQPGGSL<br>RLSCTASGLTFDDSVMGW<br>FRQAPGKGREAVSCISSS<br>GANAFYADSVKGRFTISR<br>DNAKNTLYLQMNSLKPED<br>TATYYCKRGHACAGYYPI<br>PYDDYWGQGTQVTVSSGG<br>GSQVQLQESGGGLVQPGG<br>SLRLSCAASGFTFSSYPM<br>SWVRQAPGKGLEWISTIS<br>AGGDTTLYADSVKGRFTS<br>SRDNAKNTLYLQLNSLKT<br>EDTAIYYCAKRIDCNSGY<br>CYRRNYWGQGTQVTVSS | 198 | LTFDDSVMG | 204 | CI<br>SS<br>SG<br>AN<br>AF<br>YA<br>DS<br>VK<br>G | 210 | GH<br>AC<br>AG<br>YY<br>PI<br>PY<br>DD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR596-<br>hIL27Ra_<br>VHH8 | 639 | QVQLQESGGGLVQPGGSL<br>RLSCTASGLTFDDSVMGW<br>FRQAPGKGREAVSCISSS<br>GANAFYADSVKGRFTISR<br>DNAKNTLYLQMNSLKPED<br>TATYYCKRGHACAGYYPI<br>PYDDYWGQGTQVTVSSGG<br>GSQVQLQESGGGSVQVGG<br>SLRLSCAASGFTFSSYPM<br>SWVRQAPGKGLEWISTIS | 198 | LTFDDSVMG | 204 | CI<br>SS<br>SG<br>AN<br>AF<br>YA<br>DS<br>VK<br>G | 210 | GH<br>AC<br>AG<br>YY<br>PI<br>PY<br>DD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AGGDTTLYADSVKGRFTSSRDNAKNTLYLQLNSLKTEDTAIYYCAKRIDCNSGYCYRRNYWGQGTQVTVSS | | | | | | | | | | | | |
| DR596-hIL27Ra_VHH9 | 39 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS | 198 | LTFDDSVMG | 210 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH10 | 640 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH11 | 641 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCPASGSTYSNYCLGWFRQSTGKEREGVAVINWVGGMLYFADSVKGRFTVSQDHAKNTVTLQMNSLKP | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | EDTAMYYCAAESVSSFSCGGWLTRPGRVPYWGQGTQVTVSS | | | | | | | | | | | | |
| DR596-hIL27Ra_VHH12 | 642 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGESLRLSCRASGSTYSNYCLGWFRQITGKEREGVAVINWVGGMLYFADSVKGRFTVSQDQARNTVYLEMNSLKPEDTAMYYCATESVSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH13 | 643 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH14 | 644 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR596-hIL27Ra_VHH15 | 40 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH16 | 645 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMISP |
| DR596-hIL27Ra_VHH17 | 646 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH18 | 647 | QVQLQESGGGLVQPGGSLRLSCTASGLTFDDSVMGWFRQAPGKGREAVSCISSSGANAFYADSVKGRFTISR | 198 | LTFDDSVMG | 204 | CISSSGAN | 210 | GHACAGYY | 942 | FTFSHSGMS | 946 | TINSGGASTYYI | 231 | GGSGYGDA |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DNAKNTLYLQMNSLKPEDTATYYCKRGHACAGYYPIPYDDYWGQGTQVTVSSGGGSQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | | | | AFYADSVKG | | PIPYDDY | | | | DSVKG | | SRMTSP |
| DR596-hIL27Ra_VHH19 | 41 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGSVQAGGSLRLSCPASGSTYSNYCLGWFRQITGKEREGVAVINWVGGMLYFADSVKGRFTVSQDQAKNIVYLQMNSLKPEDTAMYYCAAESVSSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH20 | 648 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH21 | 42 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGGSQVQLQESGGGLVQPGG | 198 | LTFDDSVMG | 204 | CISSSGANAFYADSVK | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SLRLSCAASGFTFSLSSM<br>SWVRQAPGKGLEWVSAIS<br>SGGASTYYTDSVKGRFTI<br>SRDNAKNMLYLQLNSLKT<br>EDTAMYYCAKGGSGYGDA<br>SRMTSPGSQGTQVTVSS | | | | G | | | | | | | | |
| DR596-<br>hIL27Ra_<br>VHH22 | 649 | QVQLQESGGGLVQPGGSL<br>RLSCTASGLTFDDSVMGW<br>FRQAPGKGREAVSCISSS<br>GANAFYADSVKGRFTISR<br>DNAKNTLYLQMNSLKPED<br>TATYYCKRGHACAGYYPI<br>PYDDYWGQGTQVTVSSGG<br>GSQVQLQESGGGSVQAGG<br>SLRLSCRASGSTYSNYCL<br>GWFRQTTGKEREGVAVIN<br>WVGGMLYFADSVKGRFTV<br>SQDQAKNTVYLQMNSLKP<br>EDTAMYYCAAESVSSFSC<br>GGWLTRPDRVPYWGQGTQ<br>VTVSS | 198 | LTFDDSVMG | 204 | CI<br>SS<br>SG<br>AN<br>AF<br>YA<br>DS<br>VK<br>G | 210 | GH<br>AC<br>AG<br>YY<br>PI<br>PY<br>DD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR596-<br>hIL27Ra_<br>VHH23 | 650 | QVQLQESGGGLVQPGGSL<br>RLSCTASGLTFDDSVMGW<br>FRQAPGKGREAVSCISSS<br>GANAFYADSVKGRFTISR<br>DNAKNTLYLQMNSLKPED<br>TATYYCKRGHACAGYYPI<br>PYDDYWGQGTQVTVSSGG<br>GSQVQLQESGGGSVQAGG<br>SLRLSCRASRSPYGNYCL<br>GWFRQSTGKEREGVAVIN<br>WVGGMLYFADSVKGRFTV<br>SQDHAKNTVTLQMNSLKP<br>EDTAMYYCAAESVSSFSC<br>GGWLTRPDRVPYWGQGTQ<br>VTVSS | 198 | LTFDDSVMG | 204 | CI<br>SS<br>SG<br>AN<br>AF<br>YA<br>DS<br>VK<br>G | 210 | GH<br>AC<br>AG<br>YY<br>PI<br>PY<br>DD | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR596-<br>hIL27Ra_<br>VHH24 | 651 | QVQLQESGGGLVQPGGSL<br>RLSCTASGLTFDDSVMGW<br>FRQAPGKGREAVSCISSS<br>GANAFYADSVKGRFTISR<br>DNAKNTLYLQMNSLKPED<br>TATYYCKRGHACAGYYPI<br>PYDDYWGQGTQVTVSSGG<br>GSQVQLQESGGGLVQPGG<br>SLRLSCAASGFTFSHSGM<br>SWVRQAPGKGLEWVSTIN<br>SGGASTYYTDSVKGRFTI | 198 | LTFDDSVMG | 204 | CI<br>SS<br>SG<br>AN<br>AF<br>YA<br>DS<br>VK<br>G | 210 | GH<br>AC<br>AG<br>YY<br>PI<br>PY<br>DD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SRDNAKNMLYLQLNSLKTEDTAMYYCAKGGSGYGDASRMTSPGSQGTQVTVSS | | | | | | | | | | | | |
| hIL27Ra_VHH1-DR591 | 652 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGSGGSGGSGQVQLQESGGGSVQAGGSLRLSCTASGAIASGYIDSRWCMAWFRQAPGKEREGVAAIWPGGGLTVYADSVKGRETISRDHAKNTLYLQMNNLKPEDTAMYYCAAGSPRMCPSLEFGFDYWGQGTQVTVSS | 211 | FTFSSYPMS | 218 | TISAGGDTTLYADSVKG | 947 | RIDCNSGYCYRRNY | 943 | AIASGYIDSRWCMA | 199 | AIWPGGGLTVYADSVKG | 205 | GSPRMCPSLEFGFDY |
| hIL27Ra_VHH2-DR591 | 653 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGSGGSGGSGQVQLQESGGGSVQAGGSLRLSCTASGAIASGYIDSRWCMAWFRQAPGKEREGVAAIWPGGGLTVYADSVKGRFTISPDHAKNTLYLQMNNLKPEDTAMYYCAAGSPRMCPSLEFGFDYWGQGTQVTVSS | 940 | FTFSSYPMS | 224 | AISSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |
| hIL27Ra_VHH3-DR591 | 654 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYL | 215 | YVSCDYFLPS | 222 | IIDGTGSTSYAASVKG | 948 | SCVRGRAVSEY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | QMNNLKPEDTAMYYCAAGSPRMCPSLEFGFDYWGQGTQVTVSS | | | | | | | | | | | | |
| hIL27Ra_VHH4-DR591 | 655 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPPMCPSLEFGFDYWGQGTQVTVSS | 212 | FTFSSNYAMS | 219 | GINVAYGITSYADSVKG | 226 | HSGTTIPRGFISYTK | 943 | AIASGYIDSRWCMA | 199 | AIWPGGGLTVYADSVKG | 205 | GSPRMCPSLEFGFDY |
| hIL27Ra_VHH5-DR591 | 656 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 944 | VIDGTGSTSYAASVKG | 229 | SCVRGRAISEY | 943 | AIASGYIDSRWCMA | 199 | AIWPGGGLTVYADSVKG | 205 | GSPRMCPSLEFGFDY |
| hIL27Ra_VHH6-DR591 | 657 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGSGGSGGSGQVQLQESGGGSVQAGGSLRLSCTASGAIASGYIDSRWCMAWFRQAPGKEREGVAAIWPGGGLTVYADSVKGRETISRDHAKNTLYLQMNNLKPEDTAMYYCAAGS | 213 | FSFSSYAMK | 220 | TISSGGSSTNYADSVKG | 227 | AIVPTGATME | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | PRMCPSLEFGFDYWGQGTQVTVSS | | | | | | | | | | | | |
| hIL27Ra_VHH7-DR591 | 658 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCTASGAIASGYIDSPWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 211 | FTFSSYPMS | 218 | TISAGGDTTLYADSVKG | 947 | RIDCNSGYCYRRNY | 943 | AIASGYIDSRWCMA | 199 | AIWPGGGLTVYADSVKG | 205 | GSPRMCPSLEFGFDY |
| hIL27Ra_VHH8-DR591 | 659 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 211 | FTFSSYPMS | 218 | TISAGGDTTLYADSVKG | 947 | RIDCNSGYCYRRNY | 943 | AIASGYIDSRWCMA | 199 | AIWPGGGLTVYADSVKG | 205 | GSPRMCPSLEFGFDY |
| hIL27Ra_VHH9-DR591 | 660 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 214 | FTYSTSNSWMA | 221 | AIYTVGGSIFYADSVRG | 228 | ASGRLRGKWFWPYEYNY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH10-DR591 | 661 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGSGGSGGSGQVQLQESGGGSVQAGGSLRLSCTASGAIASGYIDSRWCMANFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |
| hIL27Ra_VHH11-DR591 | 662 | QVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 949 | ESVSSFSCGGWLTRPGRVPY | 943 | AIASGYIDSRWCMA | 199 | AIWPGGGLTVYADSVKG | 205 | GSPRMCPSLEFGFDY |
| hIL27Ra_VHH12-DR591 | 663 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH13-DR591 | 664 | QVQLQESGGGSVQAGGSLRLSQVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 950 | SCVRGRTISEY | 943 | AIASGYIDSRWCMA | 199 | AIWPGGGLTVYADSVKG | 205 | GSPRMCPSLEFGFDY |
| hIL27Ra_VHH14-DR591 | 665 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 229 | SCVRGRAISEY | 943 | AIASGYIDSRWCMA | 199 | AIWPGGGLTVYADSVKG | 205 | GSPRMCPSLEFGFDY |
| hIL27Ra_VHH15-DR591 | 666 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 229 | SCVRGRAISEY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH16-DR591 | 667 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 951 | ESASSFSCGGWLTRPDRVPY | 943 | AIASGYIDSRWCMA | 199 | AIWPGGGLTVYADSVKG | 205 | GSPRMCPSLEFGFDY |
| hIL27Ra_VHH17-DR591 | 668 | QVQLQESGGGLVQPGGSLRLSCAASGFTFSLSGMSWVRQAPGKGLEWYSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 940 | FTFSKSGNS | 224 | AISSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |
| hIL27Ra_VHH18-DR591 | 669 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGSGGSGGSGQVQLQESGGGSVQAGGSLRLSCTASGAIASGYIDSRWCMAWFRQAPGKEREGVAAIWPSGGLTVYADSVKGRFTISRDHAKNTLYLQMNNLKPEDTAMYYCAAGSPRMCPSLEFGFDYWGQGTQVTVSS | 215 | YVSCDYFLPS | 222 | IIDGTGSTSYAASVKG | 952 | SCVRGRGISEY | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH19-DR591 | 670 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |
| hIL27Ra_VHH20-DR591 | 671 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 211 | FYFSSYPMS | 945 | TISSGGDTTLYADSVKG | 953 | RIDCNSGYCYKRSY | 943 | AIASGYIDSRWCMA | 199 | AIWPGGGLIVYADSVKG | 205 | GSPRMCPSLEFGFDY |
| hIL27Ra_VHH21-DR591 | 672 | QVQLQESGGGLVQPGGSLRLSCAASGFTFSLSSMSWVRQAPGKGLEWVSAISSGGASTYYEDSVKGRFTISPDNAKNMLYLQLNSLKTEDTAMYYCAKGGSGYGDASRMTSPGSQGTQVTVSSGGSGGSGGSGQVQLQESGGGSVQAGGSLRLSCTASGAIASGYIDSPWCMAWFRQAPGKEREGVAAIWPGGGLTVYADSVKGRFTISRDHAKNTLYLQMNNLKPEDTAMYYCAAGSPRMCPSLEFGEDYWGQGTQVTVSS | 217 | FTFSKSSNS | 224 | AISSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH22-DR591 | 673 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 216 | STYSNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |
| hIL27Ra_VHH23-DR591 | 674 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS | 941 | SPYGNYCLG | 223 | VINWVGGMLYFADSVKG | 230 | ESVSSFSCGGWLTRPDRVPY | 943 | AIASGYIDSRWCMA | 199 | AIWPGGGLTVYADSVKG | 205 | GSPRMCPSLEFGFDY |
| hIL27Ra_VHH24-DR591 | 675 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGEDYWGQGTQVTVSS | 942 | FTFSGSGMS | 946 | TINSGGASTYYTDSVKG | 231 | GGSGYGDASRMTSP | 943 | AIASGYIDSRWCMA | 199 | AIWPGGGLTVYADSVKG | 205 | GSPRMCPSLEFGFDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH1-DR592 | 676 | QVQLQESGGGLVQPGGSL RLSCAASGFTFSSYPMSW VRQAPGKGLEWISTISAG GDTTLYADSVKGRFTSSR DNAKNTLYLQLNSLKTED AAIYYCAKRIDCNSGYCY RRNYWGQGTQVTVSSGGS GGSGGSGQVQLQESGGGS VQAGGSLRLSCTAPGFTS NSCGMDWYRQAPGKEREF VSSISTDGTTGYADSVKG RFTISKDKAKDTVYLQMN SLKPEDIGMYSCKTKDGT IATMELCDFGYWGQGTQV TVSS | 211 | FTFSSYPMS | 218 | TI SA GG DT TL YA DS VK G | 947 | RI DC NS GY CY RR NY | 194 | FTS NSC GMD | 200 | SIS TDG TTG YAD SVK G | 206 | KD GT IA TM EL CD FG Y |
| hIL27Ra_ VHH2-DR592 | 677 | QVQLQESGGGLVQPGGSL RLSCAASGFTFSLSGMSW VRQAPGKGLEWVSAISSG GASTYYTDSVKGRFTISR DNAKNILYLQLNSLKTED TAMYYCAKGGSGYGDASR MTSPGSQGTQVTVSSGGS GGSGGSGQVQLQESGGGS VQAGGSLRLSCTAPGFTS NSCGMDWYRQAPGKEREF VSSISTDGTTGYADSVKG RFTISKDKAKDTVYLQMN SLKPEDTGMYSCKTKDGT IATMELCDFGYWGQGTQV TVSS | 940 | FTFSLSGMS | 224 | AI SS GG AS TY YT DS VK G | 231 | GG SG YG DA SR MT SP | 194 | FTS NSC GMD | 200 | SIS TDG TTG YAD SVK G | 206 | KD GT IA TM EL CD FG Y |
| hIL27Ra_ VHH3-DR592 | 678 | QVQLQESGGGSVQAGGSL RLSCVASGYVSCDYFLPS WYRQAPGKEREFVSIIDG TGSTSYAASVKGRFTASE DKGKNIAYLQMNSLKPED TAMYYCKASCVRGRAVSE YWGQGTQVTVSSGGSGGS GGSGQVQLQESGGGSVQA GGSLRLSCTAPGFTSNSC GMDWYRQAPGKEREFVSS ISTDGTTGYADSVKGRFT ISKDKAKDTVYLQMNSLK PEDTGMYSCKTKDGTIAT MELCDFGYWGQGTQVTVS S | 215 | YVSCDYFLPS | 222 | II DG TG ST SY AA SV KG | 948 | SC VR GR AV SE Y | 194 | FTS NSC GMD | 200 | SIS TDG TTG YAD SVK G | 206 | KD GT IA TM EL CD FG Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH4-DR592 | 679 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 212 | FTFSNYAMS | 219 | GINVAYGITSYADSVKG | 226 | HSGTTIPRGFISYTK | 194 | FTSNSCGMD | 200 | SISTDGTTGYADSVKG | 206 | KDGTIATMELCDFGY |
| hIL27Ra_VHH5-DR592 | 680 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 215 | YVSCDYFLPS | 944 | VIDGTGSTSYAASVKG | 229 | SCVRGRAISEY | 194 | FTSNSCGMD | 200 | SISTDGTTGYADSVKG | 206 | KDGTIATMELCDFGY |
| hIL27Ra_VHH6-DR592 | 681 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 213 | FSFSSYAMK | 220 | TISSGGSSTNYADSVKG | 227 | AIVPTGATME | 194 | FTSNSCGMD | 200 | SISIDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH7-DR592 | 682 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKIKDGTIATMELCDFGYWGQGTQVTVSS | 211 | FTFSSYPMS | 218 | TISAGGDTTLYADSVKG | 947 | RIDCNSGYCYRRNY | 194 | FTSNSCGMD | 200 | SISTDGTTGYADSVKG | 206 | KDGTIATMELCDFGY |
| hIL27Ra_VHH8-DR592 | 683 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKIKDGTIATMELCDFGYWGQGTQVTVSS | 211 | FTFSSYPMS | 218 | TISAGGDTTLYADSVKG | 947 | RIDCNSGYCYRRNY | 194 | FTSNSCGMD | 200 | SISTDGTTGYADSVKG | 206 | KDGTIATMELCDFGY |
| hIL27Ra_VHH9-DR592 | 684 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGSGGSGGSGQVQLQESGGGSVQAGGSLPLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 214 | FTYSTSNSWMA | 221 | AIYTVGGSIFYADSVRG | 228 | ASGRLRGKWFWPYEYNY | 194 | FTSNSCGMD | 200 | SISTDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH10-DR592 | 685 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 216 | STYSNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |
| hIL27Ra_VHH11-DR592 | 686 | QVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 216 | STYSNYCLG | 223 | VINWVGGMLYFADSVKG | 949 | ESVSSFSCGGWLTRPGRVPY | 194 | FTSNSCGMD | 200 | SISTDGTTGYADSVKG | 206 | KDGTIATMELCDFGY |
| hIL27Ra_VHH12-DR592 | 687 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 216 | STYSNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH13- DR592 | 688 | QVQLQESGGGSVQAGGSL RLSCVASGYVSCDYFLPS WYRQAPGKEREFVSIIDG TGSTSYAASVKGRFTASQ DRGKNIAYLQMNSLKPED TAMYYCKASCVRGRTISE YWGQGTQVTVSSGGSGGS GGSGQVQLQESGGGSVQA GGSLRLSCTAPGFTSNSC GMDWYRQAPGKEREFVSS ISTDGTTGYADSVKGRFT ISKDKAKDTVYLQMNSLK PEDTGMYSCKTKDGTIAT MELCDFGYWGQGTQVTVS S | 215 | YVSCDYFLPS | 222 | II DG TG ST SY AA SV KG | 950 | SC VR GR TI SE Y | 194 | FTS NSC GMD | 200 | SIS TDG TTG YAD SVK G | 206 | KD GT IA TM EL CD FG Y |
| hIL27Ra_ VHH14- DR592 | 689 | QVQLQESGGGSVQAGGSL RLSCVASGYVSCDYFLPS WYRQAPGKEREFVSIIDG TGSTSYAASVKGRFTASQ DKGKNIAYLQMNSLKPED TAMYYCKASCVRGRAISE YWGQGTQVTVSSGGSGGS GGSGQVQLQESGGGSVQA GGSLRLSCTAPGFTSNSC GMDWYRQAPGKEREFVSS ISTDGTTGYADSVKGRFT ISKDKAKDTVYLQMNSLK PEDTGMYSCKTKDGTIAT MELCDFGYWGQGTQVTVS S | 215 | YVSCDYFLPS | 222 | II DG TG ST SY AA SV KG | 229 | SC VR GR AI SE Y | 194 | FTS NSC GMD | 200 | SIS TDG TTG YAD SVK G | 206 | KD GT IA TM EL CD FG Y |
| hIL27Ra_ VHH15- DR592 | 690 | QVQLQESGGGSVQAGGSL RLSCVASGYVSCDYFLPS WYRQAPGKEREFVSIIDG TGSTSYAASVKGRFTASQ DKGKNIAYLQMNTLKPED TAMYYCKASCVRGRAISE YWGQGTQVTVSSGGSGGS GGSGQVQLQESGGGSVQA GGSLRLSCTAPGFTSNSC GMDWYRQAPGKEREFVSS ISTDGTTGYADSVKGRFT ISKDKAKDTVYLQMNSLK PEDTGMYSCKTKDGTIAT MELCDFGYWGQGTQVTVS S | 215 | YVSCDYFLPS | 222 | II DG TG ST SY AA SV KG | 229 | SC VR GR AI SE Y | 194 | FTS NSC GMD | 200 | SIS TDG TTG YAD SVK G | 206 | KD GT IA TM EL CD FG Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH16- DR592 | 691 | QVQLQESGGGSVQAGGSL RLSCRASGSTYSNYCLGW FRQITGKEREGVAVINWV GGMLYFADSVKGRFTVSQ DQAKNTVYLQMNSLKPED TAMYYCAAESASSFSCGG WLTRPDRVPYWGQGTQVT VSSGGSGGSGGSGQVQLQ ESGGGSVQAGGSLRLSCT APGFTSNSCGMDWYRQAP GKEREFVSSISTDGTTGY ADSVKGRFTISKDKAKDT VYLQMNSLKPEDIGMYSC KTKDGTIATMELCDFGYW GQGTQVTVSS | 216 | STYSNYCLG | 223 | VI NW VG GM LY FA DS VK G | 951 | ES AS SF SC GG WL TR PD RV PY | 194 | FTS NSC GMD | 200 | SIS TDG TTG YAD SVK G | 206 | KD GT IA TM EL CD FG Y |
| hIL27Ra_ VHH17- DR592 | 692 | QVQLQESGGGLVQPGGSL RLSCAASGFTFSLSGMSW VRQAPGKGLEWVSAISSG GASTYYTDSVKGRFTISR DNAKNMLYLQLNSLKTED TAMYYCAKGGSGYGDASR MTSPGSQGTQVTVSSGGS GGSGGSGQVQLQESGGGS VQAGGSLRLSCTAPGFTS NSCGMDWYRQAPGKEREF VSSISTDGTTGYADSVKG RFTISKDKARDTVYLQMN SLKPEDTGMYSCKTKDGT IATMELCDFGYWGQGTQV TVSS | 940 | FTFSLSGMS | 224 | AI SS GG AS TY YT DS VK G | 231 | GG SG YG DA SR MT SP | 194 | FTS NSC GMD | 200 | SIS TDG TTG YAD SVK G | 206 | KD GT IA TM EL CD FG Y |
| hIL27Ra_ VHH18- DR592 | 693 | QVQLQESGGGSVQAGGSL RLSCVASGYVSCDYFLPS WYRQAPGKEREFVSIIDG TGSTSYAASVKGRFTASQ DKGKNIAYLQMNSLKPED TAMYYCKASCVRGRGISE YWGQGTQVTVSSGGSGGS GGSGQVQLQESGGGSVQA GGSLALSCTAPGFTSNSC GMDWYRQAPGKEREFVSS ISTDGTTGYADSVKGRFT ISKDKAKDTVYLQMNSLK | 215 | YVSCDYFLPS | 222 | II DG TG ST SY AA SV KG | 952 | SC VR GR GI SE Y | 194 | FTS NSC GMD | 200 | SIS TDG TTG YAD SVK G | 206 | KD GT IA TM EL CD FG Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | PEDTGMYSCKTKDGTIATMELCDFGYWGQGTQVTVSS | | | | | | | | | | | | |
| hIL27Ra_VHH19-DR592 | 694 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSS | 216 | STYSNYCLG | 223 | VINWVGGMLYFADSVKG | 230 | ESVSSFSCGGWLTRPDRVPY | 194 | FTSNSCGMD | 200 | SISTDGTTGYADSVKG | 206 | KDGTIATMELCDFGY |
| hIL27Ra_VHH20-DR592 | 695 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS | 211 | FTFSSYPMS | 945 | TISSGGDTTLYADSVKG | 953 | RIDCNSGYCYKRSY | 194 | FTSNSCGMD | 200 | SISTDGTTGYADSVKG | 206 | KDGTIATMELCDFGY |
| hIL27Ra_VHH21-DR592 | 696 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCTAPGFTSNSCGMDWYRQAPGKEREFVSSISTDGTTGYADSVKGRFTISKDKAKDTVYLQMN | 217 | FTFSKSSMS | 224 | AISSGGASTYYTDSVKG | 231 | GGSGYGDASRMTSP | 194 | FTSNSCGMD | 200 | SISTDGTTGYADSVKG | 206 | KDGTIATMELCDFGY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SLKPEDTGMYSCKTKDGT<br>IATMELCDFGYWGQGTQV<br>TVSS | | | | | | | | | | | | |
| hIL27Ra_<br>VHH22-<br>DR592 | 697 | QVQLQESGGGSVQAGGSL<br>RLSCRASGSTYSNYCLGW<br>FRQTTGKEREGVAVINWV<br>GGMLYFADSVKGRFTVSQ<br>DQAKNTVYLQMNSLKPED<br>TAMYYCAAESVSSFSCGG<br>WLTRPDRVPYWGQGTQVT<br>VSSGGSGGSGGSGQVQLQ<br>ESGGGSVQAGGSLRLSCT<br>APGFTSNSCGMDWYRQAP<br>GKEREFVSSISTDGTTGY<br>ADSVKGRFTISKDKAKDT<br>VYLQMNSLKPEDIGMYSC<br>KTKDGTIATMELCDFGYW<br>GQGTQVTVSS | 216 | STYSNYCLG | 223 | VI<br>NW<br>VG<br>GM<br>LY<br>FA<br>DS<br>VK<br>G | 230 | ES<br>VS<br>SF<br>SC<br>GG<br>WL<br>TR<br>PD<br>RV<br>PY | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH23-<br>DR592 | 698 | QVQLQESGGGSVQAGGSL<br>RLSCRASRSPYGNYCLGW<br>FRQSTGKEREGVAVINWV<br>GGMLYFADSVKGRFTVSQ<br>DHAKNTVTLQMNSLKPED<br>TAMYYCAAESVSSFSCGG<br>WLTRPDRVPYWGQGTQVT<br>VSSGGSGGSGGSGQVQLQ<br>ESGGGSVQAGGSLRLSCT<br>APGFTSNSCGMDWYRQAP<br>GKEREFVSSISTDGTTGY<br>ADSVKGRFTISKDKAKDT<br>VYLQMNSLKPEDTGMYSC<br>KTKDGTIATMELCDFGYW<br>GQGTQVTVSS | 941 | SPYGNYCLG | 223 | VI<br>NW<br>VG<br>GM<br>LY<br>FA<br>DS<br>VK<br>G | 230 | ES<br>VS<br>SF<br>SC<br>GG<br>WL<br>TR<br>PD<br>RV<br>PY | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |
| hIL27Ra_<br>VHH24-<br>DR592 | 699 | QVQLQESGGGLVQPGGSL<br>RLSCAASGFTFSHSGMSW<br>VRQAPGKGLEWVSTINSG<br>GASTYYTDSVKGRFTISR<br>DNAKNMLYLQLNSLKTED<br>TAMYYCAKGGSGYGDASR<br>MTSPGSQGTQVTVSSGGS<br>GGSGGSGQVQLQESGGGS<br>VQAGGSLRLSCTAPGFTS<br>NSCGMDWYRQAPGKEREF<br>VSSISTDGTTGYADSVKG<br>RFTISKDKAKDTVYLQMN | 942 | FTFSGSGMS | 946 | TI<br>NS<br>GG<br>AS<br>TY<br>YT<br>DS<br>VK<br>G | 231 | GG<br>SG<br>YG<br>DA<br>SR<br>MT<br>SP | 194 | FTS<br>NSC<br>GMD | 200 | SIS<br>TDG<br>TTG<br>YAD<br>SVK<br>G | 206 | KD<br>GT<br>IA<br>TM<br>EL<br>CD<br>FG<br>Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SLKPEDTGMYSCKTKDGTIATMELCDFGYWGQGTQVTVSS | | | | | | | | | | | | |
| hIL27Ra_VHH1-DR593 | 700 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSGSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH2-DR593 | 701 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSGSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH3-DR593 | 702 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSL | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | KPEDTAMYYCAARAAPLYSSGSPLTRARYNVWGQGTQVTVSS | | | | | | | | | | | | |
| hIL27Ra_VHH4-DR593 | 703 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKASGTTIPRGFISYTKRGQGTQVTVSSGGSGGSGGSGQVQLQESGGGSVQAGGSLRLSCAASGYPYSNGYMGWFPQAPGKEREGVATIYTGDGRTYYADSVKGRFTISRDNAKNIVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH5-DR593 | 704 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH6-DR593 | 705 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SGSPLTRARYNVWGQGTQVTVSS | | | | | | | | | | | | |
| hIL27Ra_VHH7-DR593 | 706 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNIVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH8-DR593 | 707 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCAASGYPYSNGYMGWFRQAPGKEREGVATIYTGDGRTYYADSVKGRFTISPDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH9-DR593 | 708 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMASLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH10- DR593 | 709 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_ VHH11- DR593 | 710 | QVQLOESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_ VHH12- DR593 | 711 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_ | 712 | QVQLQESGGGSVQAGGSL | 942 | FTFSHSGMS | 946 | TI | 231 | GG | 195 | YPY | 201 | TIY | 207 | RA |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| VHH13-DR593 | | RLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | NSGGASTYYTDSVKG | | SGYGDASRMTSP | | SNGYMG | | TGDGRTYYADSVKG | | APLYSSGSPLTRARYNV |
| hIL27Ra_VHH14-DR593 | 713 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH15-DR593 | 714 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH16-DR593 | 715 | QVQLQESGGGSVQAGGSLRLSCRASGSTYSNYCLGWFRQITGKEREGVAVINWV | 942 | FTFSHSGMS | 946 | TINSGG | 231 | GGSGYG | 195 | YPYSNGYMG | 201 | TIYTGDGRT | 207 | RAAPLY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GGMLYFADSVKGRFTVSQDQAKNTVYLQMNSLKPEDTAMYYCAAESASSFSCGGWLTRPDRVPYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | ASTYYTDSVKG | | DASRMTSP | | | | YYADSVKG | | SSGSPLTRARYNV |
| hIL27Ra_VHH17-DR593 | 716 | QVQLQESGGGLVQPGGSLRLSCAASGFTFSISGMSWVRQAPGKGLEWVSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH18-DR593 | 717 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH19-DR593 | 718 | QVQLQESGGGSVQAGGSLRLSCRASGSTYSNYCLGWFRQITGKEREGVAVINWVGGMLYFADSVKGRFTVSQDQAKNTVYLQMNSLKPED | 942 | FTFSHSGMS | 946 | TINSGGASTY | 231 | GGSGYGDASR | 195 | YPYSNGYMG | 201 | TIYTGDGRTYYADSV | 207 | RAAPLYSSGS |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TAMYYCAAESVSSFSCGGWLTRPDRVPYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | YTDSVKG | | MTSP | | | | KG | | PLTRARYNV |
| hIL27Ra_VHH20-DR593 | 719 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH21-DR593 | 720 | QVQLQESGGGLVQPGGSLRLSCAASGFTFSLSSMSWVRQAPGKGLEWYSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH22-DR593 | 721 | QVQLQESGGGSVQAGGSLRLSCRASGSTYSNYCLGWFRQTTGKEREGVAVINWYGGMLYFADSVKGRFTVSQDQAKNTVYLQMNSLKPEDTAMYYCAAESVSSFSCGGWLTRPDRVPYWGQGTQVT | 942 | FTFSHSGMS | 946 | TINSGGASTYYTDS | 231 | GGSGYGDASRMTSP | 195 | YPYSNGYMG | 201 | TIYTGDGRTYYADSVKG | 207 | RAAPLYSSGSPLTR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | | | | VKG | | | | | | | | ARYNV |
| hIL27Ra_VHH23-DR593 | 722 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS | 942 | FTFSHSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH24-DR593 | 723 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCAASGYPYSNGYMGWFRQAPGKEREGVATIYTGDGRTYYADSVKGRFTISRDNAKNIVDLQMSSLKPEDTAMYYCAARAAPLYSSGSPLTRARYNVWGQGTQVTVSS | 942 | FTFSGSGMS | 946 | TINSGGASTYYTDSVKG | 231 | GGSGYGDASRMTSP | 195 | YPYSNGYMG | 201 | TIYTGDGRTYYADSVKG | 207 | RAAPLYSSGSPLTRARYNV |
| hIL27Ra_VHH1-DR594 | 724 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGSGGSGGSGQVQLQESGGGSVQAGGSLRLSCVASASTY | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | CTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | | | | | | | | | |
| hIL27Ra_VHH2-DR594 | 725 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH3-DR594 | 726 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH4-DR594 | 727 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGSGGSGGSGQVQLQESGGGSVQAGGSLRLSCVASASTYCTYDMHWYPQAPGKGREFVSAIDSDGTTRYADSVKGRFTISQGTAKNIVYLQMNSLQPEDTAMYYCKTVCV | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VGSRWSDYWGQGTQVTVSS | | | | | | | | | | | | |
| hIL27Ra_VHH5-DR594 | 728 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDME | 202 | AIDSDGTTRYADSVKG | 954 | VCVVGSRWSDY |
| hIL27Ra_VHH6-DR594 | 729 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH7-DR594 | 730 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH8-DR594 | 731 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VOVVGSRWSDY |
| hIL27Ra_VHH9-DR594 | 732 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSGSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH10-DR594 | 733 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH11- | 734 | QVQLQESGGGSVQAGGSLRLSCRASGSTYSNYCLGW | 942 | FTFSGSGMS | 946 | TINS | 231 | GGSG | 196 | STYCTY | 202 | AIDSDG | 954 | VCVV |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR594 | | FRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | GGASTYYTDSVKG | | YGDASRMTSP | | DMH | | TTRYADSVKG | | GSRWSDY |
| hIL27Ra_VHH12-DR594 | 735 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH13-DR594 | 736 | QVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH14-DR594 | 737 | QVQLQESGGGSVQAGGSLRLSCVASGYVSCDYFLPSWYRQAPGKEREFVSIIDGTGSTSYAASVKGRFTASQDKGKNIAYLQMNSLKPED | 942 | FTFSGSGMS | 946 | TINSGGASTY | 231 | GGSGYGDASR | 196 | STYCTYDMH | 202 | AIDSDGTTRYADSVK | 954 | VCVVGSRWSD |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TAMYYCKASCVRGRAISEYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | YTDSVKG | | MTSP | | | | G | | Y |
| hIL27Ra_VHH15-DR594 | 738 | QVQLQESGGGSVQAGGSLRLSQVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH16-DR594 | 739 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH17-DR594 | 740 | QVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLRLSCVASASTY | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | CTYDMHWYRQAPGKGREFVSAIDSDGTTRYADSVKGRFTISQGTAKNTVYLQMNSLQPEDTAMYYCKTVCVVGSRWSDYWGQGTQVTVSS | | | | | | | | | | | | |
| hIL27Ra_VHH18-DR594 | 741 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGSGGSGGSGQVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH19-DR594 | 742 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGSVQAGGSLRLSCVASASTYCTYDMAWYRQAPGKGREFVSAIDSDGTTRYADSVKGRFTISQGTAKNTVYLQMNSLQPEDTAMYYCKTVCVVGSPWSDYWGQGTQVTVSS | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |
| hIL27Ra_VHH20-DR594 | 743 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGSGGSGGSGQVQLQESGGGSVQAGGSLRLSCVASASTYCTYDMHWYRQAPGKGREFVSAIDSDGTTRYADSVKG | 942 | FTFSHSGMS | 946 | TINSGGASTYYTDSVKG | 231 | GGSGYGDASRMTSP | 196 | STYCTYDMH | 202 | AIDSDGTTRYADSVKG | 954 | VCVVGSRWSDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | RFTISQGTAKNTVYLQMN<br>SLQPEDTAMYYCKTVCVV<br>GSRWSDYWGQGTQVTVSS | | | | | | | | | | | | |
| hIL27Ra_<br>VHH21-<br>DR594 | 744 | QVQLQESGGGLVQPGGSL<br>RLSCAASGFTFSLSSMSW<br>VRQAPGKGLEWVSAISSG<br>GASTYYTDSVKGRFTISR<br>DNAKNMLYLQLNSLKTED<br>TAMYYCAKGGSGYGDASR<br>MTSPGSQGTQVTVSSGGS<br>GGSGGSGQVQLQESGGGS<br>VQAGGSLRLSCVASASTY<br>CTYDMHWYRQAPGKGREF<br>VSAIDSDGTTRYADSVKG<br>RFTISQGTAKNTVYLQMN<br>SLQPEDTAMYYCKTVCVV<br>GSRWSDYWGQGTQVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 196 | STY<br>CTY<br>DMH | 202 | AID<br>SDG<br>TTR<br>YAD<br>SVK<br>G | 954 | VC<br>VV<br>GS<br>RW<br>SD<br>Y |
| hIL27Ra_<br>VHH22-<br>DR594 | 745 | QVQLQESGGGSVQAGGSL<br>RLSCRASGSTYSNYCLGW<br>FRQTIGKEREGVAVINWV<br>GGMLYFADSVKGRFTVSQ<br>DQAKNTVYLQMNSLKPED<br>TAMYYCAAESVSSFSCGG<br>WLTRPDRVPYWGQGTQVT<br>VSSGGSGGSGGSGQVQLQ<br>ESGGGSVQAGGSLRLSCV<br>ASASTYCTYDMHWYRQAP<br>GKGREFVSAIDSDGTTRY<br>ADSVKGRFTISQGTAKNT<br>VYLQMNSLQPEDTAMYYC<br>KTVCVVGSRWSDYWGQGT<br>QVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 196 | STY<br>CTY<br>DMH | 202 | AID<br>SDG<br>TTR<br>YAD<br>SVK<br>G | 954 | VC<br>VV<br>GS<br>SD<br>Y |
| hIL27Ra_<br>VHH23-<br>DR594 | 746 | QVQLQESGGGSVQAGGSL<br>RLSCRASRSPYGNYCLGW<br>FRQSTGKEREGVAVINWV<br>GGMLYFADSVKGRFTVSQ<br>DHAKNTVTLQMNSLKPED<br>TAMYYCAAESVSSFSCGG<br>WLTRPDRVPYWGQGTQVT<br>VSSGGSGGSGGSGQVQLQ<br>ESGGGSVQAGGSLRLSCV<br>ASASTYCTYDMHWYRQAP<br>GKGREFVSAIDSDGTTRY<br>ADSVKGRETISQGTAKNT<br>VYLQMNSLQPEDTAMYYC<br>KTVCVVGSRWSDYWGQGT<br>QVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 196 | STY<br>CTY<br>DMH | 202 | AID<br>SDG<br>TTR<br>YAD<br>SVK<br>G | 954 | VC<br>VV<br>GS<br>RW<br>SD<br>Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH23- DR594 | 747 | QVQLQESGGGLVQPGGSL RLSCAASGFTFSHSGMSW VRQAPGKGLEWVSTINSG GASTYYTDSVKGRFTISR DNAKNMLYLQLNSLKTED TAMYYCAKGGSGYGDASR MTSPGSQGTQVTVSSGGS GGSGGSGQVQLQESGGGS VQAGGSLRLSCVASASTY CTYDMHWYRQAPGKGREF VSAIDSDGTTRYADSVKG RFTISQGTAKNTVYLQMN SLQPEDTAMYYCKTVCVV GSRWSDYWGQGTQVTVSS | 942 | FTFSHSGMS | 946 | TI NS GG AS TY YT DS VK G | 231 | GG SG YG DA SR MT SP | 196 | STY CTY DMH | 202 | AID SDG TTR YAD SVK G | 954 | VC VV GS RW SD Y |
| hIL27Ra_ VHH1- DR595 | 748 | QVQLQESGGGLVQPGGSL RLSCAASGFTFSSYPMSW VRQAPGKGLEWISTISAG GDTTLYADSVKGRFTSSR DNAKNTLYLQLNSLKTED AAIYYCAKRIDCNSGYCY PRNYWGQGTQVTVSSGGS GGSGGSGQVQLQESGGGS VQAGGSLTLSCAASEYAY STCNMGWYRQAPGKEREL VSAFISDGSTYYADSVKG RFTITRDNAKNTVYLQMN SLKPEDTAIYYCSANCYR RLRNYWGQGTQVTVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH2- DR595 | 749 | QVQLQESGGGLVQPGGSL RLSCAASGFTFSLSGMSW VRQAPGKGLEWVSAISSG GASTYYTDSVKGRFTISR DNAKNILYLQLNSLKTED TAMYYCAKGGSGYGDASR MTSPGSQGTQVTVSSGGS GGSGGSGQVQLQESGGGS VQAGGSLTLSCAASEYAY STCNMGWYRQAPGKEREL VSAFISDGSTYYADSVKG RFTITRDNAKNTVYLQMN SLKPEDTAIYYCSANCYR RLRNYWGQGTQVTVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH3- DR595 | 750 | QVQLQESGGGSVQAGGSL RLSCVASGYVSCDYFLPS WYRQAPGKEREFVSIIDG TGSTSYAASVKGRFTASE | 942 | FTFSHSGMS | 946 | TI NS GG AS | 231 | GG SG YG DA | 197 | YAY STC NMG | 203 | AFI SDG STY YAD | 209 | NC YR RL RN |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DKGKNIAYLQMNSLKPEDTAMYYCKASCVRGRAVSEYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | | | | TYYTDSVKG | | SRMTSP | | | | SVKG | | Y |
| hIL27Ra_VHH4-DR595 | 751 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH5-DR595 | 752 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH6-DR595 | 753 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGSGGSGGSGQVQLQESGGGSVQAGGSLTLSCAASEYAYSTCN | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | MGWYRQAPGKERELVSAFISDGSTYYADSVKGRFTITRDNAKNTVYLQMNSLKPEDTAIYYCSANCYRRLRNYWGQGTQVTVSS | | | | | | | | | | | | |
| hIL27Ra_VHH7-DR595 | 754 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH8-DR595 | 755 | QVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGSVQAGGSLILSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH9-DR595 | 756 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH10- DR595 | 757 | QVQLQESGGGSVQAGGSL RLSCRASGSTYSNYCLGW FRQITGKEREGVAVINWV GGMLYFADSVKGRFTVSQ DQAKNTLYLQMNSLKPED TAMYYCAAESVSSFSCGG WLTRPDRVPYWGQGTQVT VSSGGSGGSGGSGQVQLQ ESGGGSVQAGGSLTLSCA ASEYAYSTCNMGWYRQAP GKERELVSAFISDGSTYY ADSVKGRFTITRDNAKNT VYLQMNSLKPEDTAIYYC SANCYRRLRNYWGQGTQV TVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH11- DR595 | 758 | QVQLQESGGGSVQAGGSL RLSCRASGSTYSNYCLGW FRQSTGKEREGVAVINWV GGMLYFADSVKGRFTVSQ DHAKNTVTLQMNSLKPED TAMYYCAAESVSSFSCGG WLTRPGRVPYWGQGTQVT VSSGGSGGSGGSGQVQLQ ESGGGSVQAGGSLTLSCA ASEYAYSTCNMGWYRQAP GKERELVSAFISDGSTYY ADSVKGRFTITRDNAKNT VYLQMNSLKPEDTAIYYC SANCYRRLRNYWGQGTQV TVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH12- DR595 | 759 | QVQLQESGGGSVQAGESL RLSCRASGSTYSNYCLGW FRQITGKEREGVAVINWV GGMLYFADSVKGRFTVSQ DQAKNTVYLEMNSLKPED TAMYYCATESVSSFSCGG WLTRPDRVPYWGQGTQVT VSSGGSGGSGGSGQVQLQ ESGGGSVQAGGSLTLSCA ASEYAYSTCNMGWYRQAP GKERELVSAFISDGSTYY ADSVKGRFTITRDNAKNT VYLQMNSLKPEDTAIYYC SANCYRRLRNYWGQGTQV TVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH13- DR595 | 760 | QVQLQESGGGSVQAGGSL RLSCVASGYVSCDYFLPS WYRQAPGKEREFVSIIDG TGSTSYAASVKGRFTASQ DRGKNIAYLQMNSLKPED TAMYYCKASCVRGRTISE YWGQGTQVTVSSGGSGGS GGSGQVQLQESGGGSVQA GGSLTLSCAASEYAYSTC NMGWYRQAPGKERELVSA FISDGSTYYADSVKGRFT ITRDNAKNTVYLQMNSLK PEDTAIYYCSANCYRRLR NYWGQGTQVTVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH14- DR595 | 761 | QVQLQESGGGSVQAGGSL RLSCVASGYVSCDYFLPS WYRQAPGKEREFVSIIDG TGSTSYAASVKGRFTASQ DKGKNIAYLQMNSLKPED TAMYYCKASCVRGRAISE YWGQGTQVTVSSGGSGGS GGSGQVQLQESGGGSVQA GGSLTLSCAASEYAYSTC NMGWYRQAPGKERELVSA FISDGSTYYADSVKGRFT ITRDNAKNTVYLQMNSLK PEDTAIYYCSANCYRRLR NYWGQGTQVTVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH15- DR595 | 762 | QVQLQESGGGSVQAGGSL RLSCVASGYVSCDYFLPS WYRQAPGKEREFVSIIDG TGSTSYAASVKGRFTASQ DKGKNIAYLQMNTLKPED TAMYYCKASCVRGRAISE YWGQGTQVTVSSGGSGGS GGSGQVQLQESGGGSVQA GGSLTLSCAASEYAYSTC NMGWYRQAPGKERELVSA FISDGSTYYADSVKGRFT ITRDNAKNTVYLQMNSLK PEDTAIYYCSANCYRRLR NYWGQGTQVTVSS | 942 | FTFSHSGMS | 946 | TI NS GG AS TY YT DS VK G | 231 | GG SG YG DA SR MT SP | 197 | YAY STC NMG | 203 | AFI SDG STY YAD SVK G | 209 | NC YR RL RN Y |
| hIL27Ra_ VHH16- DR595 | 763 | QVQLQESGGGSVQAGGSL RLSCRASGSTYSNYCLGW FRQITGKEREGVAVINWV GGMLYFADSVKGRFTVSQ | 942 | FTFSHSGMS | 946 | TI NS GG AS | 231 | GG SG YG DA | 197 | YAY STC NMG | 203 | AFI SDG STY YAD | 209 | NC YR RL RN |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | DQAKNTVYLQMNSLKPED<br>TAMYYCAAESASSFSCGG<br>WLTRPDRVPYWGQGTQVT<br>VSSGGSGGSGGSGQVQLQ<br>ESGGGSVQAGGSLTLSCA<br>ASEYAYSTCNMGWYRQAP<br>GKERELVSAFISDGSTYY<br>ADSVKGRFTITRDNAKNT<br>VYLQMNSLKPEDTAIYYC<br>SANCYRPLRNYWGQGTQV<br>TVSS | | | | TY<br>YT<br>DS<br>VK<br>G | | SR<br>MT<br>SP | | | | SVK<br>G | | Y |
| hIL27Ra_<br>VHH17-<br>DR595 | 764 | QVQLQESGGGLVQPGGSL<br>RLSCAASGFTFSLSGMSW<br>VRQAPGKGLEWVSAISSG<br>GASTYYTDSVKGRFTISR<br>DNAKNMLYLQLNSLKTED<br>TAMYYCAKGGSGYGDASR<br>MTSPGSQGTQVTVSSGGS<br>GGSGGSGQVQLOESGGGS<br>VQAGGSLTLSCAASEYAY<br>STCNMGWYRQAPGKEREL<br>VSAFISDGSTYYADSVKG<br>RFTITRDNAKNTVYLQMN<br>SLKPEDTAIYYCSANCYR<br>RLRNYWGQGTQVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 197 | YAY<br>STC<br>NMG | 203 | AFI<br>SDG<br>STY<br>YAD<br>SVK<br>G | 209 | NC<br>YR<br>RL<br>RN<br>Y |
| hIL27Ra_<br>VHH18-<br>DR595 | 756 | QVQLQESGGGSVQAGGSL<br>RLSQVASGYVSCDYFLPS<br>WYRQAPGKEREFVSIIDG<br>TGSTSYAASVKGRFTASQ<br>DKGKNIAYLQMNSLKPED<br>TAMYYCKASCVRGRGISE<br>YWGQGTQVTVSSGGSGGS<br>GGSGQVQLQESGGGSVQA<br>GGSLTLSCAASEYAYSTC<br>NMGWYRQAPGKERELVSA<br>FISDGSTYYADSVKGRFT<br>ITRDNAKNTVYLQMNSLK<br>PEDTAIYYCSANCYRRLR<br>NYWGQGTQVTVSS | 942 | FTFSHSGMS | 946 | TI<br>NS<br>GG<br>AS<br>TY<br>YT<br>DS<br>VK<br>G | 231 | GG<br>SG<br>YG<br>DA<br>SR<br>MT<br>SP | 197 | YAY<br>STC<br>NMG | 203 | AFI<br>SDG<br>STY<br>YAD<br>SVK<br>G | 209 | NC<br>YR<br>RL<br>RN<br>Y |
| hIL27Ra_<br>VHH19-<br>DR595 | 766 | QVQLQESGGGSVQAGGSL<br>RLSCRASGSTYSNYCLGW<br>FRQITGKEREGVAVINWV<br>GGMLYFADSVKGRFTVSQ<br>DQAKNTVYLQMNSLKPED<br>TAMYYCAAESVSSFSCGG<br>WLTRPDRVPYWGQGTQVT<br>VSSGGSGGSGGSGQVQLQ | 942 | FTFSHSGMS | 946 | TI<br>NS<br>GG<br>AS<br>TY<br>YT<br>DS<br>VK | 231 | GG<br>SG<br>YG<br>DA<br>SR<br>MT<br>SP | 197 | YAY<br>STC<br>NMG | 203 | AFI<br>SDG<br>STY<br>YAD<br>SVK<br>G | 209 | NC<br>YR<br>RL<br>RN<br>Y |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | ESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | | | | G | | | | | | | | |
| hIL27Ra_VHH20-DR595 | 767 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH21-DR595 | 768 | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH22-DR595 | 769 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNT | 942 | FTFSHSGMS | 946 | TINSGGASTYYTDSVKG | 2311 | GGSGYGDASRMTSP | 197 | YAYSTCNMG | 203 | AFISDGSTYYADSVKG | 209 | NCYRRLRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VYLQMNSLKPEDTAIYYCSANCYRRLPNYWGQGTQVTVSS | | | | | | | | | | | | |
| hIL27Ra_VHH23-DR595 | 770 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSIKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH24-DR595 | 771 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGSGGSGGSGQVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS | 942 | FTFSHSGMS | 946 | TINSGGASTYYTDSVKG | 231 | GGSGYGDASRMTSP | 197 | YAYSTCNMG | 203 | AFISDGSTYYADSVKG | 209 | NCYRRLRNY |
| hIL27Ra_VHH1-DR596 | 772 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH2-DR596 | 773 | QVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSSGGSGGSGGSGQVQLQESGGGLVQPGGSLRLSCTASGLTFDDSVMGWERQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH3-DR596 | 774 | QVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH4-DR596 | 775 | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH5-DR596 | 776 | QVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH6-DR596 | 777 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSSGGSGGSGGSGQVQLQESGGGLVQPGGSLALSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH7-DR596 | 778 | QVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNELYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH8- DR596 | 779 | QVQLQESGGGSVQVGGSLRLSCAASGFTFSSYPMSWVRQAPGKGLEWISTISAGGDTTLYADSVKGRFTSSPDNAKNTLYLQLNSLKTEDTAIYYCAKRIDCNSGYCYRRNYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH9- DR596 | 780 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH10- DR596 | 781 | QVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_ VHH11- DR596 | 782 | QVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH12- DR596 | 783 | QVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_ VHH13- DR596 | 784 | QVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH14-DR596 | 785 | QVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH15-DR596 | 786 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH16-DR596 | 787 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH17-DR596 | 788 | QVQLQESGGGLVQPGGSLRLSCAASGFTFSLSGMSWVRQAPGKGLEWYSAISSGGASTYYTDSVKGRFTISRDNAKNMLYLQLNSLKTEDTAMYYCAKGGSGYGDASRMTSPGSQGTQVTVSSGGSGGSGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH18-DR596 | 789 | QVQLQESGGGSVQAGGSLRLSQVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH19-DR596 | 790 | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH20-DR596 | 791 | QVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSSGGSGGSGGSGQVQLQESGGGLVQPGGSLRLSCTASGLTFDDSVMGWERQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH21-DR596 | 792 | QVQLQESGGGLVQPGGSLRLSCAASGFTFSLSSMSWVRQAPGKGLEWYSAISSGGASTYYTDSVKGRFTISRDNAKNMLYLQLNSLKTEDTAMYYCAKGGSGYGDASRMTSPGSQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPYDDY |
| hIL27Ra_VHH22-DR596 | 793 | QVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| hIL27Ra_VHH23-DR596 | 794 | QVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| hIL27Ra_VHH24-DR596 | 795 | QVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSSGGSGGSGGSGQVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS | 942 | FTFSHSGMS | 946 | TINSGGASTYYTDSVKG | 231 | GGSGYGDASRMTSP | 198 | LTFDDSVMG | 204 | CISSSGANAFYADSVKG | 210 | GHACAGYYPIPYDDY |
| DR591-hIL27Ra_VHH1 | 796 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS | 943 | AIASGYIDSRWCMA | 199 | AIWPGGGLTVYADSVKG | 205 | GSPRMCPSLEFGFDY | 211 | FTFSSYPMS | 218 | TISAGGDTTLYADSVKG | 947 | RIDCNSGYCYRRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH2 | 797 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | 943 | AIASGYIDSRWCMA | 199 | AIWPGGGLTVYADSVKG | 205 | GSPRMCPSLEFGFDY | 940 | FTFSLSGMS | 224 | AISSGGASTYYTDSVKG | 231 | GGSGYGDASRMTSP |
| DR591-hIL27Ra_VHH3 | 798 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 948 | SCVRGRAVSEY |
| DR591-hIL27Ra_VHH4 | 799 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 943 | AIASGYIDSRWCMA | 199 | AIWPGGGLTVYADSVKG | 205 | GSPRMCPSLEFGFDY | 212 | FTFSNYAMS | 219 | GINVAYGITSYADSVKG | 226 | HSGTTIPRGFISYTK |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH5 | 800 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 944 | VIDGTGSTSYAASVKG | 229 | SCVRGRAISEY |
| DR591-hIL27Ra_VHH6 | 801 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGESFSSYAMKWVRQAPGKGLEWVSTISSGGSSTNYADSVKGRFTISRDNAKNTLYLQLNSLKIEDTAMYYCAKAIVPTGATMERGQGTQVTVSS | 943 | AIASGYIDSRWCMA | 199 | AIWPGGGLTVYADSVKG | 205 | GSPRMCPSLEFGFDY | 213 | FSFSSYAMK | 220 | TISSGGSSTNYADSVKG | 227 | AIVPTGATME |
| DR591-hIL27Ra_VHH7 | 802 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 943 | AIASGYIDSRWCMA | 199 | AIWPGGGLTVYADSVKG | 205 | GSPRMCPSLEFGFDY | 211 | FTFSSYPMS | 218 | TISAGGDTTLYADSVKG | 947 | RIDCNSGYCYRRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH8 | 803 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 943 | AIASGYIDSRWCMA | 199 | AIWPGGGLTVYADSVKG | 205 | GSPRMCPSLEFGFDY | 211 | FTFSSYPMS | 218 | TISAGGDTTLYADSVKG | 947 | RIDCNSGYCYRRNY |
| DR591-hIL27Ra_VHH9 | 804 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS | 943 | AIASGYIDSRWCMA | 199 | AIWPGGGLTVYADSVKG | 205 | GSPRMCPSLEFGFDY | 214 | FTYSTSNSWMA | 221 | AIYTVGGSIFYADSVRG | 228 | ASGRLRGKWFWPYEYNY |
| DR591-hIL27Ra_VHH10 | 805 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH11 | 806 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 949 | ESVSSFSCGGWLTRPGRVPY |
| DR591-hIL27Ra_VHH12 | 807 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |
| DR591-hIL27Ra_VHH13 | 808 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 950 | SCVRGRTISEY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH14 | 809 | QVQLQESGGGSVQAGGSLRLSCTASGAIASGYIDSRWCMAWFPQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 229 | SCVRGRSEY |
| DR591-hIL27Ra_VHH15 | 810 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGEDYWGQGTQVTVSSGGSGGSGGSGQVQLQESGGGSVQAGGSLRLSCVASGYVSCDYFLPSWYRQAPGKEREEVSIIDGTGSTSYAASVKGRFTASQDKGKNIAYLQMNTLKPEDTAMYYCKASCVRGRAISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 229 | SCVRGRSEY |
| DR591-hIL27Ra_VHH16 | 811 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSGRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 951 | ESASSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH17 | 812 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 943 | AIASGYIDSRWCMA | 199 | AIWPGGGLTVYADSVKG | 205 | GSPRMCPSLEFGFDY | 940 | FTFSLSGMS | 224 | AISSGGASTYYTDSVKG | 231 | GGSGYGDASRMTSP |
| DR591-hIL27Ra_VHH18 | 813 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 943 | AIASGYIDSRWCMA | 199 | AIWPGGGLTVYADSVKG | 205 | GSPRMCPSLEFGFDY | 215 | YVSCDYFLPS | 222 | IIDGTGSTSYAASVKG | 952 | SCVRGRGISEY |
| DR591-hIL27Ra_VHH19 | 814 | QVQLQESGGGSVQAGGSLRLSCTASGAIASGYIDSRWCMAWFPQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH20 | 815 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSS | 943 | AIASGYIDSRWCMA | 199 | AIWPGGGLTVYADSVKG | 205 | GSPRMCPSLEFGFDY | 211 | FTFSSYPMS | 945 | TISSGGDTTLYADSVKG | 953 | RIDCNSGYCYKRSY |
| DR591-hIL27Ra_VHH21 | 816 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | 943 | AIASGYIDSRWCMA | 199 | AIWPGGGLTVYADSVKG | 205 | GSPRMCPSLEFGFDY | 217 | FTFSLSSMS | 224 | AISSGGASTYYTDSVKG | 231 | GGSGYGDASRMTSP |
| DR591-hIL27Ra_VHH22 | 817 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 216 | STYSNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR591-hIL27Ra_VHH23 | 818 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 943 | AIASGYIDSRWCMA | 199 | AIWPGGGLTVYADSVKG | 205 | GSPRMCPSLEFGFDY | 941 | SPYGNYCLG | 223 | VINWVGGMLYFADSVKG | 230 | ESVSSFSCGGWLTRPDRVPY |
| DR591-hIL27Ra_VHH24 | 819 | QVQLQESGGGSVQAGGSLRLSCTASGAIASGYIDSRWCMAWFPQAPGKEREGVAAIWPGGGLTVYADSVKGRFTISRDHAKNTLYLQMNNLKPEDTAMYYCAAGSPRMCPSLEFGFDYWGQGTQVTVSSGGSGGSGGSGQVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSS | 943 | AIASGYIDSRWCMA | 199 | AIWPGGGLTVYADSVKG | 205 | GSPRMCPSLEFGFDY | 942 | FTFSHSGMS | 946 | TINSGGASTYYTDSVKG | 231 | GGSGYGDASRMESP |
| DR592-hIL27Ra_VHH1 | 820 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS | 194 | FTSNSCGMD | 200 | SISTDGTTGYADSVKG | 206 | KDGTIATMELCDFGY | 211 | FTFSSYPMS | 218 | TISAGGDTTLYADSVKG | 947 | RIDCNSGYCYRRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR592-hIL27Ra_VHH2 | 821 | QVQLQESGGGSVQAGGSLRLSCTAPGFTSNSCGMDWYRQAPGKEREFVSSISTDGTTGYADSVKGRFTISKDKAKDIVYLQMNSLKPEDTGMYSCKTKDGTIATMELCDFGYWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | 194 | FTSNSCGMD | 200 | SISTDGTTGYADSVKG | 206 | KDGTIATMELCDFGY | 940 | FTFSLSGMS | 224 | AISSGGASTYYTDSVKG | 231 | GGSGYGDASRMTSP |
| DR592-hIL27Ra_VHH3 | 822 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSURLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 948 | SCVRGRAVSEY |
| DR592-hIL27Ra_VHH4 | 823 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSG | 194 | FTSNSCGMD | 200 | SISTDGTTGYADSVKG | 206 | KDGTIATMELCDFGY | 212 | FTFSNYAMS | 219 | GINVAYGITSYADSVKG | 226 | HSGTTIPRGEISYTK |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | TTIPRGFISYTKRGQGTQVTVSS | | | | | | | | | | | | |
| DR592-hIL27Ra_VHH5 | 824 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGPAISEYWGQGTQVTVSS | 194 | FTSNSCGMD | 200 | SISTDGTTGYADSVKG | 206 | KDGTIATMELCDFGY | 215 | YVSCDYFLPS | 944 | VIDGTGSTSYAASVKG | 229 | SCVRGRAISEY |
| DR592-hIL27Ra_VHH6 | 825 | QVQLQESGGGSVQAGGSLRLSCTAPGETSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS | 194 | FTSNSCGMD | 200 | SISTDGTTGYADSVKG | 206 | KDGTIATMELCDFGY | 213 | FSFSSYAMK | 220 | TISSGGSSTNYADSVKG | 227 | AIVPTGATME |
| DR592-hIL27Ra_VHH7 | 826 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 194 | FTSNSCGMD | 200 | SISTDGTTGYADSVKG | 206 | KDGTIATMELCDFGY | 211 | FTFSSYPMS | 218 | TISAGGDTTLYADSVKG | 947 | RIDCNSGYCYRRNY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR592-hIL27Ra_VHH8 | 827 | QVQLQESGGGSVQAGGSLRLSCTAPGFTSNSCGMDWYPQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 194 | FTSNSCGMD | 200 | SISTDGTTGYADSVKG | 206 | KDGTIATMELCDFGY | 211 | FTFSSYPMS | 218 | TISAGGDTTLYADSVKG | 947 | RIDCNSGYCYRRNY |
| DR592-hIL27Ra_VHH9 | 828 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVIVSS | 194 | FTSNSCGMD | 200 | SISTDGTTGYADSVKG | 206 | KDGTIATMELCDFGY | 214 | FTYSTSNSWMA | 221 | AIYTVGGSIFYADSVRG | 228 | ASGRLRGKWFWPYEYNY |
| DR592-hIL27Ra_VHH10 | 829 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 194 | FTSNSCGMD | 200 | SISTDGTTGYADSVKG | 206 | KDGTIATMELCDFGY | 216 | STYSNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR592-hIL27Ra_VHH11 | 830 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCRASGSTYSNYCLGWFRQSTGKEREGVAVINWYGGMLYFADSVKGRFTVSQDHAKNTVTLQMNSLKPEDTAMYYCAAESVSSFSCGGWLTRPGRVPYWGQGTQVTVSS | 194 | FTSNSCGMD | 200 | SISTDGTTGYADSVKG | 206 | KDGTIATMELCDFGY | 216 | STYSNYCLG | 223 | VINWVGGMLYFADSVKG | 949 | ESVSSFSCGGWLTRPGRVPY |
| DR592-hIL27Ra_VHH12 | 831 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 194 | FTSNSCGMD | 200 | SISTDGTTGYADSVKG | 206 | KDGTIATMELCDFGY | 216 | STYSNYCLG | 223 | VINWVGGMLYFADSVKG | 230 | ESVSSFSCGGWLTRPDRVPY |
| DR592-hIL27Ra_VHH13 | 832 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDRGKNIAYLQM | 194 | FTSNSCGMD | 200 | SISTDGTTGYADSVKG | 206 | KDGTIATMELCDFGY | 215 | YVSCDYFLPS | 222 | IIDGTGSTSYAASVKG | 950 | SCVRGRTISEY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSLKPEDTAMYYCKASCVRGRTISEYWGQGTQVTVSS | | | | | | | | | | | | |
| DR592-hIL27Ra_VHH14 | 833 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSYAASVKG | 229 | SCVRGRAISEY |
| DR592-hIL27Ra_VHH15 | 834 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 194 | FTSNSCGMD | 200 | SISTDGTTGYADSVKG | 206 | KDGTIATMELCDFGY | 215 | YVSCDYFLPS | 222 | IIDGTGSTSVAASVKG | 229 | SCVRGRAISEY |
| DR592-hIL27Ra_VHH16 | 835 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQM | 194 | FTSNSCGMD | 200 | SISTDGTTGYADSVKG | 206 | KDGTIATMELCDFGY | 216 | STYSNYCLG | 223 | VINWVGGMLYFADSVKG | 951 | ESASSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSLKPEDTAMYYCAAESA SSFSCGGWLTRPDRVPYW GQGTQVTVSS | | | | | | | | | | | | |
| DR592-hIL27Ra_VHH17 | 836 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGS GGSGGSGQVQLQESGGGL VQPGGSLRLSCAASGFTF SLSGMSWVRQAPGKGLEW VSAISSGGASTYYTDSVK GRFTISRDNAKNMLYLQL NSLKTEDTAMYYCAKGGS GYGDASRMTSPGSQGTQV TVSS | 194 | FTSNSCGMD | 200 | SISTDGTTGYADSVKG | 206 | KDGTIATMELCDFGY | 940 | FTFSLSGMS | 224 | AISSGGASTYYTDSVKG | 231 | GGSGYGDASRMTSP |
| DR592-hIL27Ra_VHH18 | 837 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGS GGSGGSGQVQLQESGGGS VQAGGSLRLSCVASGYVS CDYFLPSWYRQAPGKERE FVSIIDGTGSTSYAASVK GRFTASQDKGKNIAYLQM NSLKPEDTAMYYCKASCV RGRGISEYWGQGTQVTVS S | 194 | FTSNSCGMD | 200 | SISTDGTTGYADSVKG | 206 | KDGTIATMELCDFGY | 215 | YVSCDYFLPS | 222 | IIDGTGSTSYAASVKG | 952 | SCVRGRGISEY |
| DR592-hIL27Ra_VHH19 | 838 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGS GGSGGSGQVQLQESGGGS VQAGGSLRLSCRASGSTY SNYCLGWFRQITGKEREG VAVINWVGGMLYFADSVK GRFTVSQDQAKNTVYLQM NSLKPEDTAMYYCAAESV | 194 | FTSNSCGMD | 200 | SISTDGTTGYADSVKG | 206 | KDGTIATMELCDFGY | 216 | STYSNYCLG | 223 | VINWVGGMLYFADSVKG | 230 | ESVSSFSCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | SSFSCGGWLTRPDRVPYW GQGTQVTVSS | | | | | | | | | | | | |
| DR592-hIL27Ra_VHH20 | 839 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGS GGSGGSGQVQLQESGGGL VQPGGSLRLSCAASGFTF SSYPMSWYRQAPGKGLEW VSTISSGGDTTLYADSVK GRFTSSRDNAKNTLYLQL NSLKTEDTAMYYCAKRID CNSGYCYKRSYWGQGTQV TVSS | 194 | FTSNSCGMD | 200 | SISTDGTTGYADSVKG | 206 | KDGTIATMELCDFGY | 211 | FTFSSYPMS | 945 | TISSGGDTTLYADSVKG | 953 | RIDCNSGYCYKRSY |
| DR592-hIL27Ra_VHH21 | 840 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGS GGSGGSGQVQLQESGGGL VQPGGSLRLSCAASGFTF SLSSMSWVRQAPGKGLEW VSAISSGGASTYYTDSVK GRFTISRDNAKNMLYLQL NSLKTEDTAMYYCAKGGS GYGDASRMTSPGSQGTQV TVSS | 194 | FTSNSCGMD | 200 | SISTDGTTGYADSVKG | 206 | KDGTIATMELCDFGY | 217 | FTFSLSSMS | 224 | AISSGGASTYYTDSVKG | 231 | GGSGYGDASRMTSP |
| DR592-hIL27Ra_VHH22 | 841 | QVQLQESGGGSVQAGGSL RLSCTAPGFTSNSCGMDW YRQAPGKEREFVSSISTD GTTGYADSVKGRFTISKD KAKDTVYLQMNSLKPEDT GMYSCKTKDGTIATMELC DFGYWGQGTQVTVSSGGS GGSGGSGQVQLQESGGGS VQAGGSERLSCRASGSTY SNYCLGWFRQTTGKEREG VAVINWVGGMLYFADSVK GRFTVSQDQAKNTVYLQM NSLKPEDTAMYYCAAESV SSFSCGGWLTRPDRVPYW GQGTQVTVSS | 194 | FTSNSCGMD | 200 | SISTDGTTGYADSVKG | 206 | KDGTIATMELCDFGY | 216 | STYSNYCLG | 223 | VINWVGGMLYFADSVKG | 230 | ESVSSESCGGWLTRPDRVPY |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR592-hIL27Ra_VHH23 | 842 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 194 | FTSNSCGMD | 200 | SISTDGTTGYADSVKG | 206 | KDGTIATMELCDFGY | 941 | SPYGNYCLG | 223 | VINWVGGMLYFADSVKG | 230 | ESVSSFSCGGWLTRPDRVPY |
| DR592-hIL27Ra_VHH24 | 843 | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVSSGGSGGSGGSGQVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSS | 194 | FTSNSCGMD | 200 | SISTDGTTGYADSVKG | 206 | KDGTIATMELCDFGY | 942 | FTFSHSGMS | 946 | TINSGGASTYYTDSVKG | 231 | GGSGYGDASRMTSP |
| DR593-hIL27Ra_VHH1 | 844 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH2 | 845 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH3 | 846 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH4 | 847 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH5 | 848 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH6 | 849 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFSFSSYAMKWVRQAPGKGLEWVSTISSGGSSTNYADSVKGRFTISRDNAKNTLYLQLNSEKIEDTAMYYCAKAIVPTGATMERGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH7 | 850 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYPRNYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH8 | 851 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQVGGSLRLSCAASGFTFSSYPMSWVRQAPGKGLEWISTISAGGDTTLYADSVKGRFTSSPDNAKNTLYLQLNSLKTEDTAIYYCAKRIDCNSGYCYRRNYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH9 | 852 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH10 | 853 | QVQLQESGGGSVQAGGSLRLSCAASGYPYSNGYMGWFPQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH11 | 854 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH12 | 855 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGESERLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH13 | 856 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 195 | YPYSNGYMG | 201 | TIYTGDGRTYYADSVKG | 207 | RAABLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH14 | 857 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH15 | 858 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH16 | 859 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH17 | 860 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH18 | 861 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH19 | 862 | QVQLQESGGGSVQAGGSLRLSCAASGYPYSNGYMGWFRQAPGKEREGVATIYTGDGRTYYADSVKGRFTISPDNAKNTVDLQMSSLKPEDTAMYYCAARAAPLYSSGSPLTRARYNVWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH20 | 863 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH21 | 864 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH22 | 865 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR593-hIL27Ra_VHH23 | 866 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR593-hIL27Ra_VHH24 | 867 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSSGGSGGSGGSGQVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSS | 195 | YPYSNGYMG | 201 | TIYTGDGRTYYADSVKG | 207 | RAAPLYSSGSPLTRARYNV | 942 | FTFSHSGMS | 946 | TINSGGASTYYTDSVKG | 231 | GGSGYGDASRMTSP |
| DR594-hIL27Ra_VHH1 | 868 | QVQLQESGGGSVQAGGSLRLSQVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCARRIDCNSGYCYRRNYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR594-hIL27Ra_VHH2 | 869 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH3 | 870 | QVQLQESGGGSVQAGGSLRLSQVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH4 | 871 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 1 | GGSGYGDASRMTSP |
| DR594-hIL27Ra_VHH5 | 872 | QVQLQESGGGSVQAGGSLRLSQVASASTYCTYDMHWYRQAPGKGREFVSAIDSD | 196 | STYCTYDMH | 202 | AIDSDG | 954 | VCVVGS | 942 | FTFSHSGMS | 946 | TINSGGAST | 231 | GGSGYG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GTTRYADSVKGRFTISQGTAKNTVYLQMNSLQPEDTAMYYCKTVCVVGSRWSDYWGQGTQVTVSSGGSGGSGGSGQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | | | | TTRYADSVKG | | RWSDY | | | | YYTDSVKG | | DASRMTSP |
| DR594-hIL27Ra_VHH6 | 873 | QVQLQESGGGSVQAGGSLRLSQVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH7 | 874 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH8 | 875 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGSVQVG | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | | | | | | | | | | | | |
| DR594-hIL27Ra_VHH9 | 876 | QVQLQESGGGSVQAGGSLPLSCVASASTYCTYDMHWYPQAPGKGREFVSAIDSDGTTRYADSVKGRFTISQGTAKNIVYLQMNSLQPEDTAMYYCKTVCVVGSRWSDYWGQGTQVTVSSGGSGGSGGSGQVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH10 | 877 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGSVQAGGSLRLSCPASGSTYSNYCLGWFRQITGKEREGVAVINWVGGMLYFADSVKGRFTVSQDQAKNTLYLQMNSLKPEDTAMYYCAAESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH11 | 878 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGSVQAGGSLRLSCRASGSTYSNYCLGWFRQSTGKEREGVAVINWVGGMLYFADSVKGRFT | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VSQDHAKNTVTLQMNSLKPEDTAMYYCAAESVSSFSCGGWLTRPGRVPYWGQGTQVTVSS | | | | | | | | | | | | |
| DR594-hIL27Ra_VHH12 | 879 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH13 | 880 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH14 | 881 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR594-hIL27Ra_VHH15 | 882 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGSGGSG<br>GSGQVQLQESGGGSVQAG<br>GSLRLSCVASGYVSCDYF<br>LPSWYRQAPGKEREFVSI<br>IDGTGSTSYAASVKGRFT<br>ASQDKGKNIAYLQMNTLK<br>PEDTAMYYCKASCVRGRA<br>ISEYWGQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-hIL27Ra_VHH16 | 883 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGSGGSG<br>GSGQVQLQESGGGSVQAG<br>GSLRLSCRASGSTYSNYC<br>LGWFRQITGKEREGVAVI<br>NWVGGMLYFADSVKGRFT<br>VSQDQAKNTVYLQMNSLK<br>PEDTAMYYCAAESASSFS<br>CGGWLTRPDRVPYWGQGT<br>QVTVSS | 196 | STYCTYDMH | 202 | AI<br>DS<br>DG<br>TT<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-hIL27Ra_VHH17 | 884 | QVQLQESGGGSVQAGGSL<br>RLSCVASASTYCTYDMHW<br>YRQAPGKGREFVSAIDSD<br>GTTRYADSVKGRFTISQG<br>TAKNTVYLQMNSLQPEDT<br>AMYYCKTVCVVGSRWSDY<br>WGQGTQVTVSSGGSGGSG<br>GSGQVQLQESGGGLVQPG<br>GSLRLSCAASGFTFSLSG<br>MSWVRQAPGKGLEWVSAI<br>SSGGASTYYTDSVKGRFT<br>ISRDNAKNMLYLQLNSLK<br>TEDTAMYYCAKGGSGYGD<br>ASRMTSPGSQGTQVTVSS | 196 | STYCTYDMH | 202 | AI<br>DS<br>DG<br>TT<br>RY<br>AD<br>SV<br>KG | 954 | VC<br>VV<br>GS<br>RW<br>SD<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR594-hIL27Ra_VHH18 | 885 | QVQLQESGGGSVQAGGSL<br>RLSCVASASTYCTYDMHW<br>YRQAPGKGREFVSAIDSD | 196 | STYCTYDMH | 202 | AI<br>DS<br>DG | 954 | VC<br>VV<br>GS | 942 | FTF<br>SHS<br>GMS | 946 | TIN<br>SGG<br>AST | 231 | GG<br>SG<br>YG |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GTTRYADSVKGRFTISQG TAKNTVYLQMNSLQPEDT AMYYCKTVCVVGSRWSDY WGQGTQVTVSSGGSGGSG GSGQVQLQESGGGSVQAG GSLRLSCVASGYVSCDYF LPSWYRQAPGKEREFVSI IDGTGSTSYAASVKGRFT ASQDKGKNIAYLQMNSLK PEDTAMYYCKASCVRGRG ISEYWGQGTQVTVSS | | | | TT RY AD SV KG | | RW SD Y | | | | YYT DSV KG | | DA SR MT SP |
| DR594-hIL27Ra_VHH19 | 886 | QVQLQESGGGSVQAGGSL RLSCVASASTYCTYDMHW YRQAPGKGREFVSAIDSD GTTRYADSVKGRFTISQG TAKNTVYLQMNSLQPEDT AMYYCKTVCVVGSRWSDY WGQGTQVTVSSGGSGGSG GSGQVQLQESGGGSVQAG GSLRLSCRASGSTYSNYC LGWFRQITGKEREGVAVI NWVGGMLYFADSVKGRFT VSQDQAKNTVYLQMNSLK PEDTAMYYCAAESVSSFS CGGWLTRPDRVPYWGQGT QVTVSS | 196 | STYCTYDMH | 202 | AI DS DG TT RY AD SV KG | 954 | VC VV GS RW SD Y | 942 | FTF SHS GMS | 946 | TIN SGG AST YYT DSV KG | 231 | GG SG YG DA SR MT SP |
| DR594-hIL27Ra_VHH20 | 887 | QVQLQESGGGSVQAGGSL RLSCVASASTYCTYDMHW YRQAPGKGREFVSAIDSD GTTRYADSVKGRFTISQG TAKNTVYLQMNSLQPEDT AMYYCKTVCVVGSRWSDY WGQGTQVTVSSGGSGGSG GSGQVQLQESGGGLVQPG GSLRLSCAASGFTFSSYP MSWVRQAPGKGLEWVSTI SSGGDTTLYADSVKGRFT SSRDNAKNTLYLQLNSLK TEDTAMYYCAKRIDCNSG YCYKRSYWGQGTQVTVSS | 196 | STYCTYDMH | 202 | AI DS DG TT RY AD SV KG | 954 | VC VV GS RW SD Y | 942 | FTF SHS GMS | 946 | TIN SGG AST YYT DSV KG | 231 | GG SG YG DA SR MT SP |
| DR594-hIL27Ra_VHH21 | 888 | QVQLQESGGGSVQAGGSL RLSCVASASTYCTYDMHW YRQAPGKGREFVSAIDSD GTTRYADSVKGRFTISQG TAKNTVYLQMNSLQPEDT AMYYCKTVCVVGSRWSDY WGQGTQVTVSSGGSGGSG | 196 | STYCTYDMH | 202 | AI DS DG TT RY AD SV | 954 | VC VV GS RW SD Y | 942 | FTF SHS GMS | 946 | TIN SGG AST YYT DSV KG | 231 | GG SG YG DA SR MT SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | GSGQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | | | | KG | | | | | | | | |
| DR594-hIL27Ra_VHH22 | 889 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH23 | 890 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |
| DR594-hIL27Ra_VHH24 | 891 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVQVVGSRWSDYWGQGTQVTVSSGGSGGSGGSGQVQLQESGGGLVQPGGSLRLSCAASGFTFSHSGMSWVRQAPGKGLEWVSTI | 196 | STYCTYDMH | 202 | AIDSDGTTRYADSVKG | 954 | VCVVGSRWSDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NSGGASTYYTDSVKGRFTISRDNAKNMLYLQLNSLKTEDTAMYYCAKGGSGYGDASRMTSPGSQGTQVTVSS | | | | | | | | | | | | |
| DR595-hIL27Ra_VHH1 | 892 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH2 | 893 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNILYLQLNSLKTEDTAMYYCAKGGSGYGDASRMTSPGSQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH3 | 894 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCVASGYVSCDYFLPSWYRQAPGKEREFVSIIDGTGSTSYAASVKGRFTASEDKGKNIAYLQMNSLKPEDTAMYYCKASCVRGRAVSEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR595-hIL27Ra_VHH4 | 895 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGLVQPGESLRLSCTASGFTFSNYAMSWVRQAPGKGLEWVSGINVAYGITSYADSVKGRFTISRDNTKNILYLQLNSLKTEDTAIYYCVKHSGTTIPRGFISYTKRGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH5 | 896 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCTASGYVSCDYFLPSWYRQAPGKEREFVSVIDGTGSTSYAASVKGRFTASQDKGKNIAYLQMNSLKPEDTAMYYCKASCVRGRAISEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH6 | 897 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRPLRNYWGQGTQVTVSSGGSGGSGGSGQVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH7 | 898 | QVQLQESGGGSVQAGGSLTLSCAASEYAYSTCNMGWYRQAPGKERELVSAFISDGSTYYADSVKGRFTITRDNAKNTVYLQMNSLKPEDT | 197 | YAYSTCNMG | 203 | AFISDGSTYY | 209 | NCYRRLRNY | 942 | FTFSHSGMS | 946 | TINSGGASTYYTDSV | 231 | GGSGYGDASR |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | AIYYCSANCYRRLRNYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | | | | ADSVKG | | | | | | KG | | MTSP |
| DR595-hIL27Ra_VHH8 | 899 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQVGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH9 | 900 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH10 | 901 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCRASGSTYSNYCLG | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | WFRQITGKEREGVAVINWVGGMLYFADSVKGRFTVSQDQAKNTLYLQMNSLKPEDTAMYYCAAESVSSFSCGGWLTRPDRVPYWGQGTQVTVSS | | | | | | | | | | | | |
| DR595-hIL27Ra_VHH11 | 902 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCRASGSTYSNYCLGWFRQSTGKEREGVAVINWVGGMLYFADSVKGRFTVSQDHAKNTVTLQMNSLKPEDTAMYYCAAESVSSFSCGGWLTRPGRVPYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH12 | 903 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH13 | 904 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCVASGYVSCDYFLPSWYRQAPGKEREFVSIIDGTGSTSYAASVKGRFTAS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | QDRGKNIAYLQMNSLKPEDTAMYYCKASCVRGRTISEYWGQGTQVTVSS | | | | | | | | | | | | |
| DR595-hIL27Ra_VHH14 | 905 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRAISEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH15 | 906 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMESP |
| DR595-hIL27Ra_VHH16 | 907 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR595-hIL27Ra_VHH17 | 908 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGLVQPGGSLRLSCAASGFTFSLSGMSWVRQAPGKGLEWVSAISSGGASTYYTDSVKGRFTISPDNAKNMLYLQLNSLKTEDTAMYYCAKGGSGYGDASRMTSPGSQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH18 | 909 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH19 | 910 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNIVYLQMNSLKPEDTAMYYCAAESVSSSFSCGGWLTRPDRVPYWGQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR595-hIL27Ra_VHH20 | 911 | QVQLQESGGGSVQAGGSLTLSCAASEYAYSTCNMGWYRQAPGKERELVSAFISDGSTYYADSVKGRFTITRD | 197 | YAYSTCNMG | 203 | AFISDGST | 209 | NCYRRLRN | 942 | FTFSHSGMS | 946 | TINSGGASTYYT | 231 | GGSGYGDA |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | NAKNTVYLQMNSLKPEDT<br>AIYYCSANCYRRLRNYWG<br>QGTQVTVSSGGSGGSGGS<br>GQVQLQESGGGLVQPGGS<br>LRLSCAASGFTFSSYPMS<br>WVRQAPGKGLEWVSTISS<br>GGDTTLYADSVKGRFTSS<br>RDNAKNTLYLQLNSLKTE<br>DTAMYYCAKRIDCNSGYC<br>YKRSYWGQGTQVTVSS | | | | YY<br>AD<br>SV<br>KG | | Y | | | | DSV<br>KG | | SR<br>MT<br>SP |
| DR595-<br>hIL27Ra_<br>VHH21 | 912 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRIRNYWG<br>QGTQVTVSSGGSGGSGGS<br>GQVQLQESGGGLVQPGGS<br>LRLSCAASGFTFSLSSMS<br>WVRQAPGKGLEWVSAISS<br>GGASTYYTDSVKGRFTIS<br>RDNAKNMLYLQLNSLKTE<br>DTAMYYCAKGGSGYGDAS<br>RMTSPGSQGTQVTVSS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR595-<br>hIL27Ra_<br>VHH22 | 913 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGSGGSGGS<br>GQVQLQESGGGSVQAGGS<br>LRLSCRASGSTYSNYCLG<br>WFRQTTGKEREGVAVINW<br>VGGMLYFADSVKGRFTVS<br>QDQAKNTVYLQMNSLKPE<br>DTAMYYCAAESVSSFSCG<br>GWLTRPDRVPYWGQGTQV<br>TVSS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |
| DR595-<br>hIL27Ra_<br>VHH23 | 914 | QVQLQESGGGSVQAGGSL<br>TLSCAASEYAYSTCNMGW<br>YRQAPGKERELVSAFISD<br>GSTYYADSVKGRFTITRD<br>NAKNTVYLQMNSLKPEDT<br>AIYYCSANCYRRLRNYWG<br>QGTQVTVSSGGSGGSGGS<br>GQVQLQESGGGSVQAGGS | 197 | YAYSTCNMG | 203 | AF<br>IS<br>DG<br>ST<br>YY<br>AD<br>SV<br>KG | 209 | NC<br>YR<br>RL<br>RN<br>Y | 942 | FTF<br>SHS<br>GMS | 946 | TIN<br>SGG<br>AST<br>YYT<br>DSV<br>KG | 231 | GG<br>SG<br>YG<br>DA<br>SR<br>MT<br>SP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | LRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | | | | | | | | | | | | |
| DR595-hIL27Ra_VHH24 | 915 | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSSGGSGGSGGSGQVQLQESGGGLVQPGGSLRLSCAASGFTFSHSGMSWVPQAPGKGLEWVSTINSGGASTYYTDSVKGRFTISRDNAKNMLYLQLNSLKTEDTAMYYCAKGGSGYGDASRMTSPGSQGTQVTVSS | 197 | YAYSTCNMG | 203 | AFISDGSTYYADSVKG | 209 | NCYRRLRNY | 942 | FTFSHSGMS | 946 | TINSGGASTYYTDSVKG | 231 | GGSGYGDASRMTSP |
| DR596-hIL27Ra_VHH1 | 916 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTOVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH2 | 917 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSLSGMSWVRQAPGKGLEWVSAISSGGASTYYTDSV | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 1 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | KGRFTISRDNAKNILYLQ LNSLKTEDTAMYYCAKGG SGYGDASRMTSPGSQGTQ VTVSS | | | | | | | | | | | | |
| DR596-hIL27Ra_VHH3 | 918 | QVQLQESGGGLVQPGGSL RLSCTASGLTFDDSVMGW FRQAPGKGREAVSCISSS GANAFYADSVKGRFTISR DNAKNTLYLQMNSLKPED TATYYCKRGHACAGYYPI PYDDYWGQGTQVTVSSGG SGGSGGSGQVQLQESGGG SVQAGGSLRLSCVASGYV SCDYFLPSWYRQAPGKER EFVSIIDGTGSTSYAASV KGRFTASEDKGKNIAYLQ MNSLKPEDTAMYYCKASC VRGRAVSEYWGQGTQVTV SS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH4 | 919 | QVQLQESGGGLVQPGGSL RLSCTASGLTFDDSVMGW FRQAPGKGREAVSCISSS GANAFYADSVKGRFTISR DNAKNTLYLQMNSLKPED TATYYCKRGHACAGYYPI PYDDYWGQGTQVTVSSGG SGGSGGSGQVQLQESGGG LVQPGESERLSCTASGFT FSNYAMSWVRQAPGKGLE WVSGINVAYGITSYADSV KGRFTISRDNTKNTLYLQ LNSLKTEDTAIYYCVKHS GTTIPRGFISYTKRGQGT QVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH5 | 920 | QVQLQESGGGLVQPGGSL PLSCTASGLTFDDSVMGW FRQAPGKGREAVSCISSS GANAFYADSVKGRFTISR DNAKNTLYLQMNSLKPED TATYYCKRGHACAGYYPI PYDDYWGQGTQVTVSSGG SGGSGGSGQVQLQESGGG SVQAGGSLRLSCTASGYV SCDYFLPSWYRQAPGKER EFVSVIDGTGSTSYAASV KGRFTASQDKGKNIAYLQ | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | MNSLKPEDTAMYYCKASCVRGRAISEYWGQGTQVTVSS | | | | | | | | | | | | |
| DR596-hIL27Ra_VHH6 | 921 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFSFSSYAMKWVPQAPGKGLEWVSTISSGGSSTNYADSVKGRFTISRDNAKNTLYLQINSLKIEDTAMYYCAKAIVPTGATMERGQGTQVEVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH7 | 922 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSSYPMSWVRQAPGKGLEWISTISAGGDTTLYADSVKGRFTSSRDNAKNTLYLQLNSLKTEDTAIYYCAKRIDCNSGYCYRRNYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH8 | 923 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQVGGSLRLSCAASGFTFSSYPMSWVRQAPGKGLEWISTISAGGDTTLYADSVKGRFTSSRDNAKNTLYLQ | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | LNSLKTEDTAIYYCAKRI DCNSGYCYRRNYWGQGTQ VTVSS | | | | | | | | | | | | |
| DR596-hIL27Ra_VHH9 | 924 | QVQLQESGGGLVQPGGSL RLSCTASGLTFDDSVMGW FRQAPGKGREAVSCISSS GANAFYADSVKGRFTISR DNAKNTLYLQMNSLKPED TATYYCKRGHACAGYYPI PYDDYWGQGTQVTVSSGG SGGSGGSGQVQLQESGGG SVQSGGSLRLSCAASGFT YSTSNSWMAWFRQAPGKE REGVAAIYTVGGSIFYAD SVRGRFTISQDATKNMFY LQMNTLKPEDTAMYYCAA ASGRLRGKWFWPYEYNYW GQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH10 | 925 | QVQLQESGGGLVQPGGSL RLSCTASGLTFDDSVMGW FRQAPGKGREAVSCISSS GANAFYADSVKGRFTISR DNAKNTLYLQMNSLKPED TATYYCKRGHACAGYYPI PYDDYWGQGTQVTVSSGG SGGSGGSGQVQLQESGGG SVQAGGSLRLSCRASGST YSNYCLGWFRQITGKERE GVAVINWVGGMLYFADSV KGRFTVSQDQAKNTLYLQ MNSLKPEDTAMYYCAAES VSSFSCGGWLTRPDRVPY WGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH11 | 926 | QVQLQESGGGLVQPGGSL RLSCTASGLTFDDSVMGW FRQAPGKGREAVSCISSS GANAFYADSVKGRFTISR DNAKNTLYLQMNSLKPED TATYYCKRGHACAGYYPI PYDDYWGQGTQVTVSSGG SGGSGGSGQVQLQESGGG SVQAGGSLRLSCRASGST YSNYCLGWFRQSTGKERE GVAVINWVGGMLYFADSV | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | KGRFTVSQDHAKNTVTLQMNSLKPEDTAMYYCAAESVSSFSCGGWLTRPGRVPYWGQGTQVTVSS | | | | | | | | | | | | |
| DR596-hIL27Ra_VHH12 | 927 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGESLRLSCRASGSTYSNYCLGWFRQITGKEREGVAVINWVGGMLYFADSVKGRFTVSQDQAKNTVYLEMNSLKPEDTAMYYCATESVSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH13 | 928 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDRGKNIAYLQMNSLKPEDTAMYYCKASCVRGRTISEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH14 | 929 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASC | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| | | VRGRAISEYWGQGTQVTVSS | | | | | | | | | | | | |
| DR596-hIL27Ra_VHH15 | 930 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH16 | 931 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESASSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH17 | 932 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSLSGMSWVRQAPGKGLEWVSAISSGGASTYYTDSVKGRFTISRDNAKNMLYLQLNSLKTEDTAMYYCAKGGSGYGDASRMTSPGSQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR596-hIL27Ra_VHH18 | 933 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCVASGYVSCDYFLPSWYRQAPGKEREFVSIIDGTGSTSYAASVKGRFTASQDKGKNIAYLQMNSLKPEDTAMYYCKASCVRGRGISEYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH19 | 934 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMESP |
| DR596-hIL27Ra_VHH20 | 935 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSSYPMSWVRQAPGKGLEWVSTISSGGDTTLYADSVKGRFTSSRDNAKNTLYLQLNSLKTEDTAMYYCAKRIDCNSGYCYKRSYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR596-hIL27Ra_VHH21 | 936 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH22 | 937 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCRASGSTYSNYCLGWFRQTTGKEREGVAVINWVGGMLYFADSVKGRFTVSQDQAKNTVYLQMNSLKPEDTAMYYCAAESVSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |
| DR596-hIL27Ra_VHH23 | 938 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGSVQAGGSLRLSCRASRSPYGNYCLGWFRQSTGKEREGVAVINWVGGMLYFADSVKGRFTVSQDHAKNTVTLQMNSLKPEDTAMYYCAAESVSSFSCGGWLTRPDRVPYWGQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

TABLE 1A-continued

| Name | SEQ ID NO: | Sequence of dual VHH dimer | SEQ ID NO: | CDR1 | SEQ ID NO: | CDR2 | SEQ ID NO: | CDR3 | SEQ ID NO: | CDR4 | SEQ ID NO: | CDR5 | SEQ ID NO: | CDR6 |
|---|---|---|---|---|---|---|---|---|---|---|---|---|---|---|
| DR596-hIL27Ra_VHH24 | 939 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSSGGSGGSGGSGQVQLQESGGGLVQPGGSLRLSCAASGFTFSHSGMSWVRQAPGKGLEWVSTINSGGASTYYTDSVKGRFTISRDNAKNMLYLQLNSLKTEDTAMYYCAKGGSGYGDASRMTSPGSQGTQVTVSS | 198 | LTFDDSVMG | 204 | CISSSGANAFYADSVKG | 210 | GHACAGYYPIPYDDY | 942 | FTFSHSGMS | 946 | TINSGGASTYYTDSVKG | 231 | GGSGYGDASRMTSP |

In some embodiments, an IL27R binding protein described herein (e.g., in Table 1A) is encoded by an isolated nucleic acid that is substantially identical to a sequence of any one of Table 1B below. In some embodiments, an IL27R binding protein described herein (e.g., an IL27R binding protein comprising a sequence of Table 1A) is encoded by an isolated nucleic acid comprising a sequence having at least 90% (e.g., 91%, 92%, 93%, 94%, 95%, 96%, 97%, 98%, 99%, or 100%) sequence identity to a sequence of Table 1B below.

TABLE 1B

| Name | SEQ ID NO: | Sequence |
|---|---|---|
| DR591-hIL27 Ra_VH H1 | 955 | CAGGTTCAGCTCCAGGAGAGCGGGGGGGGCTCCGTGCAGGCTGGCGGATCACTG CGTCTGTCCTGTACTGCGAGCGGCGCTATCGCGAGCGGGTACATTGATAGCAGA TGGTGTATGGCTTGGTTCCGTCAGGCACCAGGCAAGGAGCGTGAGGGCGTGGCA GCTATCTGGCCTGGAGGGGGTCTCACCGTGTACGCCGACTCCGTGAAGGGCCGT TTCACAATTAGTAGAGACCATGCCAAGAATACGCTCTATCTTCAGATGAATAAC CTGAAACCCGAGGATACGGCTATGTACTATTGTGCTGGGGGATCACCCCGGATG TGCCCGTCTCTGGAGTTTGGATTCGACTATTGGGGACAGGGGACCCAGGTCACC GTCAGTTCCGGTGGGGGCTCCCAAGTCCAGCTCCAGGAGTCCGGCGGGGGCTTG GTCCAGCCCGGAGGCTCCCCCCGCCTGAGTTGTGCTGCCAGCGGATTCACTTTT TCCAGTTACCCTATGTCCTGGGTGAGACAGGCCCCTGGGAAGGGCCTGGAGTGG ATCTCTACCATCAGGGGGGGGGGGGATACCACTCTGTATGCCGACTCAGTGAAG GGCAGGTTCACGTCTTCCCGCGATAACGCTAAGAATACTCTCTATCTGCAACTC AATTCCCTGAAGACAGAGGACGCAGCTATCTACTATTGTGCTAAGCGTATTGAT TGCAACAGCGGATACTGCTACCGTAGGAACTATTGGGGCCAGGGCACCCAGGTG ACTGTGTCCTCC |
| DR591-hIL27 Ra_VH H1 | 956 | CAGGTACAGCTCCAGGAGTCTGGTGGAGGCTCTGTGCAAGCAGGGGGTAGCCTG AGGCTGTCATGCACAGCCTCCGGTGCCATCGCCAGCGGTTACATTGACAGCAGG TGGTGTATGGCTTGGTTCAGGCAGGCCCCCGGCAAAGAACGTGAAGGCGTGGCC GCTATCTGGCCCGGCGGTGGACTGACTGTCTATGCCGATAGTGTGAAAGGCAGA TTCACCATCTCTCGGGATCACGCGAAGAATACACTGTACCTTCAGATGAATAAC CTGAAGCCTGAGGACACCGCCATGTACTATTGCGCTGCGGGCTCTCCGAGGATG TGCCCCAGCCTGGAGTTCGGGTTCGATTATTGGGGTCAGGGCACCCAAGTGACT GTGAGCAGTGGGGGATCTGGCGGGTCCGGTGGCTCTGGTCAGGTGCAGCTGCAA GAGTCTGGAGGGGGGCCTCGTACAACCTGGAGGTAGTCTGCGCCTCAGTTGTGCT GCATCTGGCTTCACCTTCAGCTCCTATCCCATGTCTTGGGTTCGGCAGGCTCCC GGCAAGGGGCTGGAGTGGATCTCCACCATCAGGGGGGGGGGGGACACAACTCTG TACGCCGATTCTGTGAAGGGGCGTTTCACAAGCTCAAGAGATAACGCAAAAAAC ACGCTCTACCTCCAGCTTAATTCATTGAAGACCGAAGACGCAGCTATTTATTAC TGCGCTAAGCGCATCGACTGTAACTCCGGCTACTGCTATAGAAGGAATTACTGG GGCCAGGGAACACAGGTTACCGTGAGTTCA |
| DR591-hIL27 Ra_VH H2 | 957 | CAGGTGCAGCTCCAGGAGTCCGGTGGCGGAAGCGTCCAGGCTGGCGGAAGTCTG AGGCTCTCATGCACCGCCTCTGGTGCCATCGCCAGCGGATACATCGACTCCAGA TGGTGTATGGCTTGGTTTAGGCAAGCCCCTGGCAAGGAAAGGGAGGGGGGTTGCT GCCATCTGGCCCGGCGGAGGCCTGACGGTGTATGCAGACAGCGTCAAAGGGAGA TTCACCATTTCTCGCGACCACGCTAAGAACACCCTTTACTTGCAGATGAATAAC CTCAAGCCCGAGGACACCGCCATGTATTACTGCGCCGCTGGTTCACCGAGGATG TGCCCGAGCCTGGAGTTCGGCTTCGACTACTGGGGCCAAGGTACACAAGTGACT GTGTCCAGCGGGGGGGGTAGCCAGGTTCAGCTGCAAGAGAGCGGCGGTGGATTG GTGCAGCCAGGCGGTAGCCTGCGCCTGTCTTGCGCGGCCAGCGGATTCACATTC TCCCTGAGCGGCATGTCTTGGGTGCGCCAAGCTCGGGGCAAAGGCCTGGAGTGG GTCAGCGCCATCTCTAGCGGAGGTGCCTCTACGTATTACACAGATTCCGTTAAG GGCCGCTTCACTATCAGCCGCGATAACGCCAAGAACATCCTGTATCTCCAGTTG AACAGCCTGAAAACGGAGGACACAGCCATGTACTATTGCGCTAAAGGGGGTTCA GGCTATGGTGACGCTTCTCGCATGACCTCACCCGGCTCACAGGGAACCCAGGTG ACAGTGTCAAGT |
| DR591-hIL27 Ra_VH H2 | 958 | CAGGTGCAGCTGCAAGAGTCCGGCGGAGGTAGCGTTCAAGCCGGAGGCTCACTG AGACTGTCTTGCACCGCCTCTGGTGCAATCGCCCCTGGCTATATTGATTCTCGC TGGTGTATGGCGTGGTTTAGGCAAGCGCCTGGGAAAGAGCGTGAAGGAGTTGCA GCCATCTGGCCGGGAGGCGGACTGACCGTGTACGCTGACTCTGTGAAGGGCAGA TTCACCATCAGTCGTGACCACGCCAAGAACACTCTGTACCTTCAGATGAATAAC CTCAAACCAGAGGACACAGCTATGTACTATTGTGCGGCTGGATCTCCGCGCATG TGCCCTAGTCTGGAGTTCGGTTTTGATTACTGGGGCCAGGGAACTCAAGTGACC GTGTCTAGCGGGGGTTCTGGAGGCAGTGGTGGGTCAGGTCAGGTTCAGCTCCAA GAGTCAGGTGGGGGACTCGTGCAACCAGGGGGCTCCCTGCGCCTGTCTTGCGCT GCCTCCGGCTTCACTTTCAGCCTGAGCGGTATGTCCTGGGTTCGCCAGGCTCCC GGTAAAGGGCTGGAGTGGGTTAGTGCTATCAGCTCCGGCGGAGCTTCTACCTAT TACACCGACTCTGTTAAGGGTCGCTTCACTATCAGCCGCGACAACGCCAAAAAT ATTTTGTATCTGCAACTCAACTCCTTGAAGACAGAGGACACCGCGATGTATTAC TGCGCCAAGGGAGGTAGCGGCTACGGCGATGCTAGTCGTATGACGAGCCCCGGC TCTCAGGGTACACAAGTCACCGTAAGCTCC |
| DR591-hIL27 Ra_VH H3 | 959 | CAGGTTCAGTTGCAGGAGTCTGGGGGAGGGAGCGTTCAGGCTGGCGGTTCCCTG AGGCTCTCTTGCACAGCCTCTGGCGCTATCGCCTCAGGATATATTGATTCCCGT TGGTGTATGGCATGGTTCCGTCAGGCCCCTGGCAAGGAACGCGAGGGAGTCGCT GCCATCTGGCCCGGGGGGGGCCTGACAGTCTACGCTGATTCAGTTAAGGGCCGC TTCACTATCAGCCGCGACCACGCTAAAAACACGCTGTACCTGCAAATGAATAAC CTCAAACCAGAGGACACTGCAATGTATTACTGCGCCGCAGGCTCTCCCAGAATG |

TABLE 1B-continued

| Name | SEQ ID NO: | Sequence |
|---|---|---|
| | | TGCCCGAGCCTGGAGTTTGGTTTCGATTACTGGGGTCAGGGCACGCAGGTAACC GTGAGTTCTGGTGGAGGCTCCCAGGTGCAGCTCCAAGAGTCCGGGGGAGGCTCT GTGCAAGCAGGCGGAAGCCTGAGATTGTCCTGCGTGGCCAGCGGTTATGTGTCC TGTGATTACTTCCTGCCTTCTTGGTATCGGCAGGCCCCAGGCAAGGAGCGCGAG TTCGTCTCCATCATTGATGGCACCGGATCAACAAGCTACGCTGCGTCCGTGAAG GGTCGGTTTACAGCAAGCGAGGATAAGGGAAAGAACATCGCGTACCTCCAGATG AACAGCCTGAAGCCTGAAGACACTGCTATGTATTACTGTAAGGCTAGTTGTGTG CGGGGCCGCGCAGTTTCTGAATATTGGGGTCAGGGAACACAAGTAACCGTGTCC TCA |
| DR591-hIL27 Ra_VH H3 | 960 | CAGGTCCAGCTCCAGGAATCAGGAGGTGGCTCCGTACAGGGGGGAGGGAGTCTC CGCCTCTCCTGTACTGCCAGTGGTGCCATCGCAAGCGGCTATATCGACAGCCGT TGGTGCATGGCCTGGTTCAGGCAGGCACCCGGCAAAGAGAGAGAAGGAGTCGCT GCGATCTGGCCGGGTGGAGGTTTGACCGTCTACGCCGACAGCGTCAAGGGCAGA TTTACTATCAGCCGTGACCACGCGAAGAACACCCTCTATCTTCAGATGAATAAC CTCAAACCTGAGGATACCGCCATGTATTACTGCGCAGCCGGGAGCCCTCGGATG TGCCCTAGCCTGGAGTTCGGCTTCGACTACTGGGGCCAAGGGACACAGGTAACA GTTAGTAGCGGTGGCTCCGGTGGCTCCGGGGGTTCTGGTCAGGTCCAGCTCCAG GAGTCTGGAGGCGGTTCAGTGCAGGCTGGCGGTTCACTGCGCCTCAGCTGCGTG GCCTCCGGCTACGTATCATGCGACTATTTCCTGCCCTCCTGGTATCGCCAGGCC CCCGGAAAAGAGAGGGAGTTTGTGTCTATTATCGACGGGACCGGAAGCACCAGC TACGCTGCCTCAGTGAAGGGTCGCTTCACCGCCTCCGAGGATAAGGGCAAGAAC ATTGCCTACTTGCAGATGAACTCATTGAAACCGGAAGACACTGCGATGTATTAC TGTAAGGCTTCTTGCGTTCGCGGACGTGCTGTGAGCGAGTACTGGGGCCAAGGG ACCCAAGTGACGGTCTCTTCT |
| DR591-hIL27 Ra_VH H4 | 961 | CAGGTGCAACTTCAGGAGTCTGGCGGTGGCAGCGTGCAGGCCGGGGGCTCCCTG CGGCTGTCATGTACGGCCTCCGGCGCTATTGCCAGGGGTTACATTGACTCCAGG TGGTGCATGGCCTGGTTCCGTCAGGCTCCGGGCAAGGAGAGGGAAGGCGTGGCA GCCATCTGGCCCGGGGGGGCCTCACCGTTTATGCCGATTCCGTGAAGGGACGT TTTACAATCAGCCGTGACCATGCTAAGAACACCCTGTATTTGCAGATGAATAAC CTGAAACCCGAGGACACCGCCATGTATTACTGCGCCGCAGGCAGCCCCCGTATG TGCCCGTCCCTGGAGTTTGGCTTCGATTACTGGGGCCAGGGGACCCAGGTGACA GTCAGCTCCGGGGGTGGCTCTCAGGTGCAACTTCAGGAATCCGGTGGAGGTCTG GTGCAGCCGGGAGAGTCTCTGCGTCTGTCATGCACTGCCTCAGGCTTCACGTTT AGTAACTATGCTATGTCCTGGGTGAGGCAAGCTCCTGGAAAGGGCCTCGAATGG GTGTCAGGAATCAACGTGGCCTACGGCATTACTTCTTATGCCGATTCTGTTAAG GGTCGCTTCACTATCTCAAGAGACAACACTAAAAACACTCTTTACTTGCAGCTG AACAGCCTGAAAACAGAGGACACAGCCATTTATTACTGCGTGAAGCACTCTGGC ACAACCATCCCACGCGGTTTCATTTCATACACGAAGCGCGGCCAGGGGACCCAG GTGACTGTGAGCAGC |
| DR591-hIL27 Ra_VH H4 | 962 | CAGGTCCAACTTCAGGAATCTGGAGGTGGCTCAGTACAGGCTGGAGGCTCCCTG AGACTGAGCTGCACCGCCTCAGGAGCAATCGCATCCGGCTATATCGACTCCCGT TGGTGTATGGCCTGGTTTCGCCAGGCCCCCGGCAAGGAGCGTGAGGGCGTGGCC GCTATCTGGCCAGGGGGGGGCCTGACCGTGTACGCTGACAGTGTTAAAGGAAGG TTCACAATTTCCCGCGATCACGCTAAGAATACATTGTATCTTCAGATGAATAAC CTCAAGCCAGAGGACACCGCCATGTATTACTGCGCAGCCGGTTCACCCCGCATG TGCCCCAGCCTGGAGTTCGGCTTCGACTACTGGGGACAGGGCACCCAGGTTACC GTGTCTTCCGGGGGTTCTGGCGGATCTGGTGGCTCGGGGCAGGTGCAGCTCCAG GAATCTGGTGGGGGCCTGGTTCAGCCGGGTGAAAGCCTGAGGCTGTCTTGCACC GCCTCTGGTTTCACCTTCAGCAACTATGCGATGTCTTGGGTGGGGCAAGCACCG GGTAAGGGCCTGGAGTGGGTGAGCGGCATCAACGTGGCCTACGGTATTACAAGC TACGCCGATTCCGTTAAAGGTCGTTTCACCATCTCTAGGGACAACACAAAGAAC ACACTGTACTTGCAGCTGAACTCTCTGAAGACCGAAGATACCGCCATCTATTAC TGTGTGAAGCATTCCGGCACAACCATCCCTCGCGGCTTCATCTCCTATACCAAG CGCGGCCAGGGCACCCAGGTCACGGTTTCCTCC |
| DR591-hIL27 Ra_VH H5 | 963 | CAGGTGCAGCTGCAAGAGTCCGGTGGGGGGTCCGTCCAGGCCGGGGGCTCTCTG CGTCTTAGCTGCACCGCTTCTGGGGCCATTGCTTCTGGCTACATTGATTCCAGA TGGTGTATGGCCTGGTTCCGCCAAGCGCCCGGCAAGGAGCGCGAGGGCGTGGCC GCTATCTGGCCCGGTGGAGGCCTTACCGTCTATGCTGACAGCGTGAAAGGACGC TTCACCAACTCCCGCGACCACGCCAAAAACACCCTGTACTTGCAGATGAACAAT TTGAAGCCCGAGGACACGGCCATGTATTACTGCGCCGCTGGTAGCCCCCGCATG TGTCCGTCCCTGGAGTTCGGTTTCGACTACTGGGGGCAGGGCACCCAGGTGACA GTCAGCTCTGGAGGGGGCTCCCAGGTGCAGCTCCAGGAGAGCGGCGGAGGCAGC GTGCAGGCCGGGGGAAGCCTCAGGCTGAGCTGCACCGCGAGCGGCTACGTTTCC TGTGATTATTTTCTCCCATCATGGTATCGCCAAGCGCCAGGAAAGGAGCGTGAG TTCGTATCCGTGATTGACGGTACAGGTTCAACATCCCATGCGGCCTCCGTGAAG GGGCGCTTCACCGCGAGCCAAGATAAGGGGAAGAACATCGCCTATTTGCAGATG AACTCACTGAAGCCTGAGGACACCGCTATGTATTACTGCAAGGCTTCCTGTGTG CGTGGCCGCGCCATCTCTGAGTACTGGGGGCAGGGCACCCAGGTGACCGTGTCC TCC |
| DR591-hIL27 Ra_VH | 964 | CAGGTGCAGCTGCAAGAATCTGGAGGCGGTAGCGTACAGGCAGGTGGCAGCCTG AGGCTGTCTTGTACTGCGTCCGGCGCTATCGCATCAGGATACATTGACTCACGT TGGTGCATGGCCTGGTTTCGTCAGGCTCCAGGAAAGGAGCGTGAAGGCGTCGCT |

TABLE 1B-continued

| Name | SEQ ID NO: | Sequence |
|---|---|---|
| H5 | | GCCATTTGGCCTGGTGGAGGCCTGACCGTGTATGCCGATAGCGTCAAGGGACGT TTCACCATCAGCCGTGACCACGCTAAGAATACCCTGTACTTGCAAATGAACAAT TTGAAGCCAGAGGACACTGCGATGTACTATTGCGCGGCAGGCTCCCCCAGGATG TGTCCCAGCCTGGAGTTTGGTTTCGATTACTGGGGGCAGGGCACCCAGGTCACC GTTAGCTCCGGGGGTTCTGGAGGTTCCGGGGGTTCAGGACAGGTGCAGCTTCAG GAGTCTGGGGGAGGGTCCGTACAAGCCGGGGGCTCCTTGCGCCTGTCTTGCACA GCTTCCGGCTATGTTAGTTGTGACTACTTCCTGCCTAGCTGGTATCGCCAAGCC CCTGGCAAGGAGAGGGAGTTCGTTTCCGTGATTGATGGCACTGGGTCTACTTCC TACGCTGCCAGTGTGAAGGGGCGCTTCACCGCTTCTCAAGACAAGGGCAAGAAC ATCGCGTACCTCCAGATGAACAGCCTGAAGCCAGAAGATACCGCAATGTACTAT TGTAAGGCCTCCTGCGTTCGCGGGGGGGCCATCTCAGAATACTGGGGCCAGGGG ACTCAGGTCACCGTGTCCAGT |
| DR591-<br>hIL27<br>Ra_VH<br>H6 | 965 | CAGGTGCAGTTGCAGGAATCTGGCGGAGGCTCCGTCCAGGCTGGTGGCAGTTTG CGTCTGTCCTGCACAGCTTCAGGCGCGATTGCCTCTGGCTACATTGATAGTAGA TGGTGCATGGCTTGGTTCAGACAGGCTCCTGGAAAGGAGAGAGAGGGGGTGGCC GCGATCTGGCCCGGAGGCGGGCTGACTGTCTACGCCGATAGCGTTAAGGGTCGC TTCACGATTTCTGGGGATCACGCCAAGAACACCCTGTACTTGCAAATGAATAAC CTGAAACCCGAAGACACCGCAATGTATTACTGCGCCGCTGGTTCACCAAGGATG TGCCCTTCCCTGGAGTTCGGTTTCGACTACTGGGGACAGGGCACCCAGGTAACC GTGAGTAGCGGCGGGGGTAGTCAGGTGCAGCTTCAGGAGTCAGGCGGGGGCTTG GTCCAACCTGGAGGGAGCCTCAGGCTCTCCTGTGCCGCTTCCGGCTTCAGTTTC AGCTCCTATGCCATGAAGTGGGTAAGACAGGCCCCTGGCAAGGGCCTGGAGTGG GTTTCCACCATTAGTAGCGGAGGCAGCTCAACCAACTACGCCGATCCCGTTAAG GGCCGCTTTACGATCAGCCGTGACAATGCAAAGAACACCTTGTACCTCCAGCTG AACTCCCTGAAAATTGAAGACACCGCAATGTATTACTGCGCCAAGGCAATCGTC CCTACAGGGGCCACAATGGAGCGCGGTCAGGGAACTCAGGTGACCGTGTCCAGC |
| DR591-<br>hIL27<br>Ra_VH<br>H6 | 966 | CAGGTTCAGCTCCAGGAATCTGGAGGGGGAAGTGTGCAGGCTGGAGGTTCCCTC CGCCTCAGCTGCACTGCCAGCGGAGCTATCGCTTCCGGTTACATTGACAGCCGC TGGTGTATGGCTTGGTTTCGCCAAGCGCCCGGCAAGGAACGCGAAGGGGTGGCG GCCATCTGGCCTGGGGGAGGCCTGACAGTGTACGCCGACAGCGTCAAGGGTAGG TTTACTATCAGCAGAGACCACGCAAAGAACACCCTGTATCTGCAAATGAACAAT CTGAAGCCGGAAGACACTGCAATGTATTACTGTGCTGGGGGCTCCCCCAGGATG TGTCCCAGCCTGGAGTTCGGGTTTGACTACTGGGGTCAGGGGACGCAGGTGACC GTCAGCTCCGGCGGTTCGGGGGGCAGCGGAGGCAGCGGACAGGTCCAGCTTCAG GAGTCCGGTGGGGGCCTGGTCCAGCCTGGGGGCTCTCTGCGGCTGAGCTGTGCG GCCAGCGGGTTTAGTTTCTCCAGTTACGCTATGAAATGGGTGCGTCAGGCACCG GGTAAGGGACTCGAATGGGTCAGCACAATCAGTAGCGGAGGCAGCCCCACGAAC TATGCTGATAGCGTGAAGGGAAGATTCACCATTAGCCGCGACAACGCCAAGAAT ACATTGTATCTTCAGCTGAACAGCCTGAAGATCGAAGACACCGCGATGTATTAC TGTGCTAAGGCCATCGTGCCCACTGGGGCCACAATGGAGAGGGGCCAGGGCACC CAGGTCACGGTATCCAGC |
| DR591-<br>hIL27<br>Ra_VH<br>H7 | 967 | CAGGTCCAGTTGCAGGAAAGCGGAGGCGGATCTGTGCAGGCAGGTGGCTCCCTT CGCCTGAGCTGCACCGCAAGCGGGGCCATTGCGTCTGGATACATCGACTCCAGA TGGTGCATGGCCTGGTTCCGCCAAGCGCCAGGCAAAGAGCGCGAAGGAGTGGCA GCCATCTGGCCTGGAGGGGGCCTCACAGTTTACGCTGACTCCGTTAAGGGCAGA TTCACCATCTCCCGCGACCACGCCAAGAACACACTCTACCTCCAGATGAATAAC CTGAAGCCCGAGGATACCGCCATGTATTACTGCGCAGCTGGAAGCCCACGTATG TGCCCGTCCTTGGAGTTCGGCTTCGACTACTGGGGGCAAGGAACCCAGGTGACC GTTTCCAGCGGGGGCGGGATCTCAGGTCCAGTTGCAAGAGTCCGGGGGGGGCTG GTGCAGCCTGGGGGCTCTCTGCGCCTGTCCTGCGCAGCGAGCGGCTTCACCTTC TCATCCTATCCTATGTCTTGGGTGCGTCAGGCCCCAGGTAAGGGACTGGAGTGG ATTTCCACGATCAGTGCCGGTGGCGATACTACCCTCTACGCCGACTCTGTGAAA GGACGGTTCACCAGTAGCCGTGACAACGCGAAGAACACATTGTATTTGCAGCTG AACAGCCTCAAGACCGAAGATACCGCCATCTATTACTGCGCCAAGAGAATTGAT TGTAACTCTGGATACTGCTACCGTCGCAACTACTGGGGACAGGGCACCCAGGTC ACCGTCAGTTCC |
| DR591-<br>hIL27<br>Ra_VH<br>H7 | 968 | CAGGTGCAGTTGCAGGAATCCGGGGGAGGCAGTGTTCAGGCTGGCGGAAGCCTG CGCCTTTCCTGCACAGCCAGGGGGGCTATTGCCTCCGGCTACATTGATAGTCGT TGGTGCATGGCCTGGTTCCGCCAAGCACCGGGTAAGGAGAGGGAAGGCGTCGCC GCAATCTGGCCGGGAGGGGGTCTGACCGTGTATGCTGACAGCGTGAAGGGCAGA TTCACCATCTCTAGGGACCACGCCAAGAACACCCTCTATTTGCAGATGAACAAT CTCAAACCCGAGGATACCGCGATGTATTACTGCGCTGCGGGTAGCCCACGTATG TGTCCATCTCTGGAGTTCGGCTTCGATTATTGGGGTCAGGGCACTCAGGTGACC GTCAGCTCCGGGGGCTCCGGCGGTTCTGGTGGGTCAGGCCAGGTGCAGCTCCAG GAGTCCGGCGGTGGCCTGGTGCAGCCCGGTGGGTCCCTTCGTCTGAGCTGTGCA GCCAGCGGATTTACATTTAGCTCCTACCCCATGTCCTGGGTAAGACAGGCCCCC GGAAAGGGCCTGGAATGGATTTCCACCATCTCTGCCGGTGGAGACACCACACTG TATGCTGACTCTGTGAAGGGAAGATTCACTTCCTCTCGGGACAACGCCAAGAAC ACCCTGTACTTGCAGTTGAACAGCCTGAAGACAGAGGATACCGCCATTTATTAC TGTGCCAAGAGGATTGATTGTAACAGCGGATACTGTTATCGCAGGAACTATTGG GGACAGGGAACTCAGGTGACCGTCTCTTCA |

TABLE 1B-continued

| Name | SEQ ID NO: | Sequence |
|---|---|---|
| DR591-hIL27Ra_VHH8 | 969 | CAGGTCCAGCTTCAGGAGTCCGGCGGAGGCTCTGTGCAGGCAGGCGGTTCACTGCGCCTGTCATGCACGGCGAGCGGAGCCATCGCCAGCGGTTACATTGATTCCCCGTTGGTGCATGGCGTGGTTCCGTCAGGCACCCGGCAAGGAACGCGAGGGCGTGGCTGCCATCTGGCCTGGGGGGGGCTTACAGTGTACGCCGATTCCGTGAAAGGTCGCTTCACCAACTCCCGCGACCACGCCAAGAATACTCTTTACCTGCAAATGAATAACTTGAAGCCGGAGGACACCGCTATGTATTACTGTGCCGCTGGCAGCCCACGCATGTGTCCCTCTCTGGAGTTCGGCTTTGATTACTGGGGCCAGGGCACCCAGGTGACCGTATCTAGCGGTGGAGGCTCCCAAGTGCAGCTGCAAGAATCTGGAGGGGGGAGCGTCCAGGTGGGAGGCTCCCTGCGCCTGAGCTGCGCCGCTTCCGGCTTTACCTTTAGTAGCTACCCCATGTCCTGGGTCCGCCAGGCACCCGGCAAAGGCCTTGAGTGGATCTCCACGATCAGCGCAGGGGGTGACACCACTCTGTACGCCGACAGCGTTAAAGGCAGGTTCACCAGCTCCCGCGACAACGCGAAAAACACCCTGTACTTGCAGCTCAACTCACTCAAGACGGAGGACACTGCTATCCATTACTGCGCCAAGCGCATTGATTGTAACAGCGGTTACTGTTACCGGCGTAACTACTGGGGTCAGGGCACTCAGGTCACCGTCTCCTCT |
| DR591-hIL27Ra_VHH8 | 970 | CAAGTGCAGCTCCAGGAATCCGGTGGAGGCAGCGTGCAGGCCGGAGGTTCCCTGCGCCTGTCTTGCACTGCCTCAGGAGCCATTGCCTCCGGTTACATTGATTCCCCGTTGGTGCATGGCCTGGTTTCGCCAGGCCCCAGGAAAAGAGCGCGAGGGGGTGGCCGCTATCTGGCCCGGCGGTGGCCTGACTGTGTACGCTGATTCCGTAAAGGGCCGGTTTACCATCTCCAGGGATCATGCAAAAAACACACTCAACCTCCAGATGAATAACCTGAAGCCTGAGGACACCGCCATGTATTACTGCGCCGCTGGCTCACCTCGTATGTGTCCCAGCCTCGAATTTGGCTTTGACTATTGGGGCCAGGGCACCCAGGTTACCGTCTCTTCCGGTGGCTCAGGAGGTTCCGGGGGCTCTGGTCAGGTGCAGTTGCAGGAAAGTGGAGGTGGCAGTGTGCAGGTAGGGGGCAGCCTGCGTCTGAGCTGTGCTGCCAGCGGCTTTACATTCAGCCCCTATCCTATGAGCTGGGTGAGACAGGCCCCTGGGAAAGGCCTGGAGTGGATCAGCACTATCAGCGCCGGTGGCGATACGACTCTCTATGCCGATAGCGTCAAGGGCCGCTTCACGTCCTCAAGGGACAATGCTAAAAACACCTTGTATCTCCAGTTGAACAGTCTCAAGACGGAGGACACCGCTATCTACTATTGTGCCAAGAGAATTGATTGCAACAGCGGCTACTGTTACAGACGTAATTATTGGGGCAGGGCACCCAGGTAACTGTGTCCTCA |
| DR591-hIL27Ra_VHH9 | 971 | CAGGTGCAGTTGCAGGAGTCAGGCGGTGGCTCCGTGCAGGCAGGCGGAAGCCTGCGCCTGTCTTGCACTGCCTCTGGGGCTATTGCATCAGGGTACATTGATAGCCGCTGGTGTATGGCGTGGTTTAGGCAGGCTCCAGGAAAGGAAAGAGAGGGAGTGGCCGCGATCTGGCCCGGTGGAGGTCTGACGGTGTATGCTGATTCAGTGAAGGGCCGGTTCACTATTTCTCGCGACCATGCCAAGAACACCCTCTACCTTCAGATGAATAACCTGAAACCCGAGGACACCGCTATGTATTACTGCGCTGCGGGTTCTCCCCGCATGTGTCCTAGTCTTGAGTTCGGATTTGACTATTGGGGCCAGGGCACCCAAGTGACGGTCAGCTCCGGGGGGGGTAGTCAGGTCCAACTGCAAGAATCCGGGGGGGGTAGCGTGCAGTCCGGTGGCTCCCTGAGACTCAGCCGCGCCGCTTCCGGGTTTACCTACTCCACTTCCAACTCTTGGATGGCGTGGTTCCGTCAGGCCCCAGGAAAGGAGAGGGAGGGCGTGGCCGCTATCTATACGGTGGGTGGCTCCATCCTCTACGCCGATTCTGTACGCGGAAGATTCACAATCTCTCAGGACGCAACAAAAAATATGTTTTACTTGCAGATGAACACTCTGAAGCCTGAAGACACTGCGATGTACTATTGTGCGGCTGCGAGCGGCAGACTGCGCGGTAAGTGGTTCTGGCCCCACGAGTACAACTACTGGGGGCAGGGCACTCAGGTCACAGTCTCTAGC |
| DR591-hIL27Ra_VHH9 | 972 | CAGGTGCAGTTGCAGGAATCTGGGGGTGGCAGTGTCCAGGCCGGTGGCTCCCTCAGGCTGTCCTGCACTGCCAGCGGAGCCATCGCTTCAGGCTACATTGACTCTAGGTGGTGCATGGCTTGGTTTCGCCAGGCTCCGGGCAAAGAGCGCGAGGGCGTCGCAGCCATCTGGCCAGGTGGGGTTTGACGGTCTATGCTGATTCCGTGAAGGGGGGGTTCACTATCTCCCGTGACCACGCCAAGAACACCCTGTACCTCCAGATGAATAACCTGAAGCCTGAGGATACAGCGATGTACTATTGCGCTGCCGGTAGCCCGCGCATGTGCCCCAGTCTTGAGTTCGGCTTTGACTATTGGGGGCAGGGCACGCAAGTGACCGTGTCCTCTGGGGGCAGTGGCGGTTCTGGTGGCTCAGGTCAGGTCCAGCTCCAGGAAAGCGGGGGTGGGTCCGTCCAATCTGGTGGCTCCTTGCGTCTGAGCTGCGCTGCCTCTGGCTTCACTTATTCAACGTCCAACTCTTGGATGGCCTGGTTTCGCCAAGCGCCAGGCAAGGAGCGTGAAGGCGTCGCTGCCATCTATACCGTTGGTGGCAGCATTTTCTACGCTGACTCAGTGAGGGGCAGATTTACCATTTCTCAGGATGCAACCAAGAATATGTCTTACTTGCAGATGAACACACTGAAGCCCGAGGACACAGCTATGTACTATTGTGCAGCCGCTTCTGGCCGTCTTCGCGGCAAGTGGTTCTGGCCCTACGAGTACAATTATTGGGGCCAGGGTACGCAGGTGACCGTGTCCAGT |
| DR591-hIL27Ra_VHH10 | 973 | CAAGTTCAGTTGCAGGAGTCCGGTGGCGGTAGTGTGCAGGCGGGCGGAAGCCTGCGCCTGTCTTGTACCGCCTCTGGGGCCATTGCCTCTGGCTACATTGATTCTCGCTGGTGTATGGCCTGGTTTAGGCAGGCACCAGGCAAGGAACGCGAAGGCGTGGCCGCTATCTGGCCTGGGGGGGACTGACCGTGTACGCTGACTCAGTCAAAGGCCGCTTCACTATCTCACGCGACCACGCCAAGAATACTCTGTACCTCCAGATGAATAACCTGAAGCCTGAGGACACCGCGATGTATTACCGCGCTGCCGGTTCCCCAAGAATGTGCCCTTCACTTGAGTTTGGCTTTGACTATTGGGGCCAAGGAACTCAGGTGACCGTAAGCTCTGGAGGGGGCAGCCAGGTCCAGCTCCAGGAGTCTGGAGGGGGCTCCGTGCAGGCCGGAGGGTCTCTCCGCCTCAGCTGTCGTGCCTCAGGCTCCACGTACTCTAACTACTGCCTGGGGTGGTTCCGCCAGATCACAGGTAAAGAGCGCGAAGGCGTAGCTGTCATCAACTGGGTCGGGGGAATGCTGTACTTCGCCGACTCCGTTAAGGGTCGGTTCACCGTCTCTCAGGATCAGGCCAAAAATACCCTGTATCTCCAGATG |

TABLE 1B-continued

| Name | SEQ ID NO: | Sequence |
|---|---|---|
| | | AACAGCCTGAAGCCGGAGGACACCGCTATGTATTACTGTGCCGCAGAGAGCGTG TCCTCCTTCTCCTGCGGGGGTTGGCTGACCCGCCCGGACAGAGTACCCTACTGG GGTCAGGGGACTCAGGTGACAGCGAGCAGC |
| DR591-hIL27 Ra_VH H10 | 974 | CAGGTGCAACTGCAAGAGTCCGGCGGAGGCTCTGTGCAAGCCGGAGGCTCTCTG CGCCTGTCCTGTACCGCTAGTGGAGCCATCGCCAGCGGTTACATTGACAGCAGA TGGTGTATGGCCTGGTTCCGCCAGGCCCCCGGCAAAGAGCGCGAGGGCGTCGCT GCAATCTGGCCTGGGGGGGCCTTACCGTATATGCCGATTCAGTCAAAGGCCGC TTCACAATCTCACGCGACCACGCCAAGAACACCCTGTACTTGCAGATGAATAAC CTGAAGCCGGAGGACACCGCAATGTATTACTGCGCAGCCGGGTCTCCGCGCATG TGTCCCAGCTTGGAGTTCGGATTCGACTACTGGGGCCAAGGGACCCAGGTGACG GTTAGCTCTGGCGGTTCCGGGGGGAGTGGGGGCTCTGGCCAGGTGCAGCTGCAA GAGTCTGGGGGAGGTTCTGTCCAGGGGGGAGGCTCCCTGAGGCTGAGTTGTCGT GCAAGCGGTTCTACCTACTCCAACTATTGCCTGGGTTGGTTTCGTCAGATTACG GGGAAGGAACGCGAGGGGGTCGCCGTCATAAATTGGGTTGGCGGTATGCTTTAT TTTGCCGACTCTGTCAAAGGTCGGTTCACCGTGTCTCAAGACCAGGCTAAGAAC ACTCTGTACCTCCAGATGAACTCCCTGAAACCAGAGGACACCGCAATGTATTAC TGCGCTGCCGAAAGCGTGTCCAGCTTCAGCTGTGGCGGTTGGCTCACCCGCCCT GACCGTGTGCCCTATTGGGGTCAGGGGACACAGGTGACCGTCAGCAGC |
| DR591-hIL27 Ra_VH H11 | 975 | CAGGTGCAGTTGCAGGAAAGCGGAGGGGGCTCCGTGCAAGCCGGAGGGTCTCTG CGTCTTTCTTGCACTGCCTCTGGGGCCATCGCTTCCGGCTACATTGATAGCCGT TGGTGCATGGCCTGGTTCCGTCAAGCGCCTGGAAAGGAGCGCGAGGGCGTGGCC GCTATTTGGCCTGGTGGAGGCCTCACTGTGTATGCTGATAGTGTGAAGGGACGT TTCACAATCTCCCGTGACCACGCGAAGAACACGCTGTACCTCCAGATGAACAAT CTCAAACCCGAGGATACAGCTATGTATTACTGTGCCGCTGGTAGTCCACGCATG TGTCCCAGTCTGGAGTTCGGGTTTGATTATTGGGGACAAGGCACGCAGGTTACA GTGTCTTCCGGGGGTGGCTCCCAAGTTCAGCTTCAAGAGAGCGGCGGAGGCTCC GTGCAGGCGGGTGGCTCACTGAGACTGTCCTGCCGTGCCTCCGGGTCCACTTAT AGTAACTATTGTCTGGGTTGGTTCCGTCAAAGTACTGGTAAAGAGCGCGAGGGC GTGGCAGTAATCAACTGGGTCGGCGGAATGCTGTACTTCGCGGATTCTGTGAAG GGAAGATTCACTGTGTCACAGGACCACGCCAAAAATACCGTGACCCTTCAGATG AATAGCCTGAAGCCTGAGGACACGGCAATGTATTACTGTGCCGCTGAATCCGTG TCTAGCTTTAGCTGCGGAGGTTGGCTGACACGTCCTGGTAGAGTGCCATATTGG GGCCAAGGCACTCAAGTGACTGTATCTTCC |
| DR591-hIL27 Ra_VH H11 | 976 | CAGGTTCAGCTTCAGGAATCCGGTGGAGGCAGTGTGCAGGCCGGTGGAAGCCTC CGCCTCTCTTGCACAGCCTCCGGGGCCATCGCATCTGGCTATATTGACAGCCGC TGGTGTATGGCTTGGTTCCGCCAAGCGCCCGGTAAGGAGCGCGAAGGGGTCGCT GCCATTTGGCCTGGTGGGGGATTGACTGTGTATGCAGATAGCGTGAAAGGTCGT TTCACTATCAGCCGTGACCACGCCAAGAACACCCTGTATCTGCAAATGAACAAT CTGAAGCCTGAGGACACCGCCATGTATTACTGTGCGGCAGGCAGCCCTCGCATG TGCCCGTCCCTGGAGTTCGGTTTCGACTACTGGGGCCAGGGCACACAGGTGACT GTTAGCTCCGGGGGTTCTGGAGGTTCTGGGGGCTCTGGCCAGGTACAGCTCCAG GAGAGCGGAGGGGGCTCCGTTCAAGCAGGTGGCTCTTTGCGTTTGAGCTGCCGT GCCAGCGGGTCTACCTACTCCAATTACTGTCTGGGATGGTTCCGCCAATCCACC GGCAAAGAACGTGAGGGTGTGGCCGTTATCAACTGGGTTGGGGGAATGCTTTAC TTTGCGGACAGTGTGAAAGGGCGCTTCACCGTGTCCCAGGATCATGCTAAGAAC ACTGTGACCCTCCAGATGAACAGCCTGAAGCCCGAGGATACGGCAATGTATTAC TGCGCCGCTGAATCAGTAAGCCCCTTCTCATGTGGGGGATGGCTGACCCGCCCT GGCCGCGTGCCCTATTGGGGACAGGGCACCCAGGTGACAGTCAGCAGC |
| DR591-hIL27 Ra_VH H12 | 977 | CAGGTGCAGTTGCAGGAATCCGGTGGCGGAAGTGTGCAGGCCGGGGGCTCCCTC CGTCTGTCCTGCACCGCGTCAGGCGCTATCGCCTCCGGGTACATCGACTCCCGC TGGTGCATGGCCTGGTTTCGTCAAGCGCCCGGCAAGGAGAGAGAGAAGGTGTGGCC GCGATTTGGCCGGGGGGAGGCCTGACCGTGTACGCTGACTCCGTTAAGGGGCGT TTTACTATCTCCCGTGACCACGCCAAGAATACATTGTATCTGCAAATGAATAAC CTCAAGCCCGAGGACACTGCTATGTACTATTGTGCTGCCGGTTCCCCGCGCATG TGTCCGAGCCTGGAGTTTGGCTTCGACTATTGGGGTCAAGGCACTCAGGTCACC GTCTCCTCAGGCGGAGGGAGCCAAGTGCAGCTCCAGGAAAGCGGAGGTGGCTCC GTGCAGGCTGGAGAGAGCCTGAGGCTGTCATGCCGCGCCAGGGGGTCTACCTAC TCTAACTACTGTCTGGGCTGGTTTAGGCAGATTACCGGCAAAGAGAGAGAGGGG GTCGCTGTTATCAACTGGGTGGGAGGGATGTTGTACTTCGCCGACAGCGTCAAG GGTAGATTTACCGTCTCTCAGGACCAGGCTAAGAACACAGTATATCTGGAGATG AACTCTCTTAAACCCGAGGACACTGCTATGTACTATTGTGCCACCGAGTCCGTG TCTTCCTTCTCCTGCGGGGGCTGGCTGACTAGACCTGATCGGGTGCCCTACTGG GGTCAGGGTACACAGGTGACAGTCTCTAGC |
| DR591-hIL27 Ra_VH H12 | 978 | CAAGTTCAGCTTCAGGAAAGTGGCGGTGGCTCCGTACAGGCCGGGGGCAGTCTG CGCCCGAGCTGCACCGCCAGCGGTGCCATCGCCAGCGGCTACATCGACTCCAGG TGGTGTATGGCTTGGTTCCGCCAAGCACCGGGCAAGGAGCGCGAAGGAGTTGCC GCTATCTGGCCCGGGGGGGGCCCGACCGTCTACGCCGACAGCGTGAAAGGTCGC TTCACTATCTCTCGCGACCACGCCAAGAACACCCTGTACCTCCAAATGAATAAC CTGAAGCCAGAGGACACTGCTATGTATTACCGCGCTGCCGGAAGTCCCCGTATG TGTCCCTCTCTGGAGTTTGGGTTTGATTATTGGGGGCAGGGCACACAGGTCACT GTGTCAAGCGGGGGTAGTGGCGGTTCCGGGGGTAGCGGCCAGGTGCAGCTTCAA GAGAGCGGGGGCGGAAGCGTGCAGGGGGGCGAATCTCTCCGGTTGTCATGTAGA |

TABLE 1B-continued

| Name | SEQ ID NO: | Sequence |
|---|---|---|
| | | GCGTCTGGCTCCACCTACTCTAACTACTGCCTGGGGTGGTTCAGACAGATTACG GGGAAAGAGAGGGAAGGCGTGGCCGTTATAAATTGGGTAGGCGGAATGCTCTAC TTCGCTGACTCTGTCAAGGGCCGGTTCACAGTGTCTCAGGACCAGGCCAAAAAT ACTGTGTATCTGGAGATGAACTCTCTGAAACCCGAGGACACTGCCATGTATTAC TGCGCCACGGAGAGCGTCTCCAGCTTCTCATGTGGAGGGTGGCTGACCCGCCCG GACCGTGTACCCTACTGGGGTCAGGGAACACAGGTGACAGTGAGCAGC |
| DR591-hIL27Ra_VH H13 | 979 | CAGGTGCAGTTGCAGGAGAGCGGAGGCGGGAGCGTCCAGGCCGGAGGCTCCCTT CGCCTCAGCTGTACCGCGTCTGGAGCAATCGCCAGGGGCTACATTGACTCCCGT TGGTGCATGGCATGGTTCCGCCAAGCGCCAGGCAAAGAGAGAGAAGGCGTGGCC GCTATTTGGCCTGGGGGTGGACTCACAGTTTATGCAGACTCTGTGAAGGGCCGC TTTACCATCAGTAGAGACCACGCCAAGAACACCCTGTATCTGCAAATGAACAAT CTGAAGCCAGAGGACACCGCGATGTACTATTGCGCTGCCGGTTCTCCCAGGATG TGTCCCTCATTGGAGTTCGGCTTTGATTACTGGGGCCAGGGAACCCAGGTCACC GTATCTTCCGGTGGCGGATCACAGGTTCAGCTCCAGGAATCAGGAGGTGGCTCT GTGCAGGCCGGGGGGTCCCTGCGGCTGTCTTGCGTGGCCTCCGGCTACGTCTCT TGCGACTACTTTCTGCCTTCTTGGTATCGGCAGGCCCCTGGGAAAGAGCGGGAG TTCGTCTCTATCATTGACGGCACCGGCTCCACATCCTACGCTGCGAGCGTGAAG GGCCGCTTCACAGCATCCCAGGACAGGGGAAAGAACATCGCTTATTTGCAGATG AACAGCCTGAAGCCTGAGGACACAGCTATGTATTACTGTAAGGCCTCTTGTGTG CGCGGCAGAACCATCAGCGAGTACTGGGGACAAGGGACCCAGGTGACCGTATCT TCA |
| DR591-hIL27Ra_VH H13 | 980 | CAGGTGCAGTTGCAGGAGTCCGGCGGGGGCTCTGTCCAAGCTGGAGGCTCCTTG CGTTTGAGCTGTACCGCTAGTGGAGCCATCGCGAGTGGCTACATCGACAGCAGA TGGTGCATGGCCTGGTTCCGCCAAGCTCCCGGCAAGGAGAGGGAAGGCGTTGCT GCAATCTGGCCCGGCGGTGGCCTGACCGTGTACGCGGATTCTGTCAAGGGGCGC TTTACTATCAGCCGCGATCATGCTAAAAACACGCTTTATCTGCAAATGAATAAC CTCAAACCAGAAGATACCGCGATGTACTATTGCGCAGCTGGTTCTCCCCGGATG TGTCCCAGTTTGGAGTTTGGTTTCGATTACTGGGGTCAGGGCACTCAGGTGACC GTGAGTTCCGGCGGATCTGGAGGCTCAGGAGGCTCCGGCCAGGTGCAGCTCCAG GAGTCCGGCGGTGGCAGCGTACAAGCTGGCGGGTCCCTCCGTCTGAGCTGTGTG GCAAGCGGTTATGTTAGCTGTGACTACTTTCTGCCAAGCTGGTATCGCCAAGCG CCAGGCAAGGAGCGCGAGTTCGTGAGTATCATTGATGGCACCGGCAGCACCTCC TACGCAGCCAGCGTGAAGGGACGGTTTACCGCCTCCCAGGATAGAGGAAAGAAC ATCGCATACCCCCAGATGAACAGCCTGAAGCCGGAGGACACAGCCATGTATTAC TGCAAGGCCTCTTGCGTGAGGGGCCGCACCATCAGCGAGTACTGGGGGCAGGGC ACTCAGGTAACTGTCAGCTCA |
| DR591-hIL27Ra_VH H14 | 981 | CAGGTGCAGCTTCAGGAGAGCGGTGGAGGCTCTGTCCAAGCTGGCGGTTCCCTG AGACTTTCCTGCACCGCCTCCGGGGCCATCGCTTCCGGCTACATTGATAGCAGA TGGTGTATGGCATGGTTCAGGCAGGCCCCTGGTAAAGAGCGCGAGGGCGTTGCC GCAATCTGGCCTGGGGGAGGCCTGACCGTGTACGCCGACTCCGTGAAGGGCCGT TTCACCATCTCTCGTGACCACGCCAAGAATACTCTGTATCTTCAGATGAATAAC TTGAAACCTGAAGACACAGCTATGTATTACTGCGCAGCCGGAAGCCCACGCATG TGCCCATCCCTGGAGTTTGGCTTCGATTATTGGGGCCAAGGCACCCAAGTGACA GTCAGCAGTGGAGGCGGTTCCCAGGTTCAGTTGCAAGAGTCCGGTGGCGGAAGC GTGCAGGCAGGCGGTAGCTTGCGCTTGTCCTGTGTGGCCTCCGGCTATGTGAGT TGCGACTATTTCCTGCCTTCCTGGTATAGACAGGCCCCCGGCAAGGAACGCGAG TTCGTGTCTATTATCGACGGCACCGGGAGCACATCCTACGCTGCGAGCGTCAAG GGCCGCTTCACTGCGTCACAGGACAAGGGCAAGAACATCGCTTATCTCCAGATG AACTCCCTGAAACCTGAGGATACAGCAATGTATTACTGTAAGGCTTCCTGCGTG AGAGGCCGCGCCATTAGCGAGTACTGGGGGCAGGGCACTCAGGTAACCGTAAGC AGC |
| DR591-hIL27Ra_VH H14 | 982 | CAGGTTCAGCTTCAGGAGTCTGGGGGAGGCAGCGTGCAGGCAGGTGGCTCCCTT CGCCTCAGCTGTACGGCTTCAGGTGCCATTGCTTCCGGTTACATTGATAGCAGG TGGTGTATGGCCTGGTTCCGGCAAGCGCCCGGCAAAGAAAGAGAGGGTGTGGCA GCCATCTGGCCAGGCGGTGGGCTTACCGTGTATGCCGATTCTGTTAAGGGCAGG TTCACGATCTCCAGGGACCACGCCAAGAATACCCTGTATCTCCAAATGAATAAC CTGAAGCCCGAGGACACTGCCATGTATTACTGTGCTGCGGGCTCCCCTCGTATG TGTCCCTCTCTGGAGTTCGGGTTTGACTACTGGGGACAAGGAACACAGGTGACC GTCTCCAGCGGGGGCAGCGGAGGTAGCGGCGGAAGCGGACAGGTACAGTTGCAG GAGTCTGGCGGTGGCTCCGTGCAGGCTGGCGGTTCACTCAGACTGTCCTGTGTG GCCAGCGGATACGTGAGCTGCGATTATTTCTTGCCTTCCTGGTATCGCCAGGCC CCTGGGAAGGAACGCGAGTTCGTGTCTATCATTGACGGAACCGGCTCCACGTCC TATGCCGCTTCTGTCAAGGGTCGCTTTACAGCTTCCCAGGACAAGGGTAAAAAC ATCGCTTACCTTCAGATGAACTCCCTGAAGCCTGAAGATACCGCCATGTACTAT TGTAAGGCCAGCTGCGTGCGGGGCAGGGCTATCTCAGAGTATTGGGGTCAGGGC ACGCAGGTGACAGTGTCCTCT |
| DR591-hIL27Ra_VH H15 | 983 | CAGGTGCAGCTCCAGGAAAGCGGGGGAGGCTCCGTGCAGGCGGGGGGTAGCCTC CGTCTGTCCTGCACTGCCTCAGGAGCCATTGCCTCTGGCTACATTGACTCCCGC TGGTGTATGGCCTGGTTCCGCCAAGCGCCCGGAAAGGARAGGGAGGGCGTGGCT GCAATTTGGCCAGGAGGTGGCCTGACCGTGTATGCGGATTCTGTGAAGGGACGC TTCACCATCAGCAGGGACCACGCTAAGAACACCCTGTACCTGCAAATGAATAAC CTGAAACCCGAGGACACCGCCATGTACTATTGTGCCGCAGGCTCCCCCAGAATG |

TABLE 1B-continued

| Name | SEQ ID NO: | Sequence |
|---|---|---|
| | | TGCCCTTCTCTGGAGTTCGGGTTCGACTATTGGGGTCAGGGGACCCAGGTGACC GTCTCCTCTGGTGGGGGTAGCCAGGTGCAACTCCAGGAATCCGGGGGGGGCTCC GTGCAGGCTGGCGGGTCTCTGCGCCTGAGCTGTGTGGCTTCCGGGTATGTGTCC TGCGACTACTTCCCGCCTTCTTGGTATCGCCAAGCGCCGGGGAAGGAACGCGAG TTCGTAAGCATCAATGATGGCACTGGATCAACAAGCTACGCGGCCCCTGTGAAA GGCCGCTTCACAGCGAGCCAGGATAAGGGTAAGAACATCGCGTATTTGCAGATG AACACTCTCAAGCCAGAAGACACCGCGATGTATTACTGCAAGGCCAGTTGTGTG CGTGGCCGGGCCATCTCCGAGTATTGGGGGCAGGGCACCCAGGTCACCGTGTCC TCC |
| DR591-hIL27 Ra_VH H15 | 984 | CAGGTCCAACTTCAGGAGTCTGGAGGCGGTTCCGTGCAGGGGGGCGGTAGCTTG CGCCTGAGCTGTACCGCTTCAGGTGCCATCGCGAGCGGATACATCGACTCTCGC TGGTGTATGGCCTGGTTCCGCCAGGCCCCTGGCAAGGAACGTGAGGGTGTGGCT GCCATTTGGCCCGGGGGGGGACTTACTGTGTACGCCGACTCCGTGAAGGGCCGT TTCACCATCTCCCGTGACCACGCGAAGAACACCCTGTACTTGCAGATGAATAAC CTCAAACCCGAGGATACCGCGATGTATTACTGTGCCGCTGGCAGCCCACGCATG TGTCCCAGTCTGGAGTTCGGTTTTGACTATTGGGGGCAGGGTACACAAGTCACA GTGTCTAGCGGAGGCTCTGGTGGCTCCGGGGGTAGCGGACAGGTGCAGTTGCAG GAATCTGGCGGTGGCAGTGTGCAGGCGGGTGGCAGCCTGCGCCTGTCCTGCGTT GCTAGTGGGTATGTGAGCTGTGATTATTTCCTGCCATCTTGGTATCGCCAGGCC CCCGGCAAAGAAAGAGAGTTCGTGTCCATCATTGATGGCACCGGCTCCACCAGT TATGCAGCGTCTGTCAAAGGCAGGTTCACTGCCAGCCAGGACAAGGGTAAGAAC ATTGCTTATTTGCAGATGAACACCCTGAAGCCCGAGGACACGGCTATGTATTAC TGTAAGGCCTCATGTGTGCGTGGCCGGGCGATTTCCGAGTACTGGGGACAAGGC ACACAAGTGACCGTGTCCAGC |
| DR591-hIL27 Ra_VH H16 | 985 | CAAGTGCAACTCCAGGAGTCCGGGGGCGGGTCTGTGCAAGCTGGAGGCTCCCTG CGCCTGAGTTGTACCGCGTCCGGTGCCATCGCTTCTGGTTATATTGATAGCAGA TGGTGTATGGCTTGGTTCCGTCAAGCGCCAGGGAAAGAGAGGGAGGGCGTGGCA GCTATCTGGCCAGGAGGGGGACTGACCGTCTACGCAGACCCCGTCAAAGGCGGG TTTACAATCTCCAGAGACCACGCGAAAAACACTCTGTATCTCCAGATGAATAAC CTGAAGCCAGAGGATACAGCAATGTACTATTGCGCCGCTGGCTCACCCCGTATG TGCCCCAGTCTGGAGTTCGGGTTTGACTACTGGGGCCAGGGCACCCAAGTCACT GTAAGCTCCGGGGGTGGCTCCCAGGTGCAGTTGCAGGAAAGTGGGGGAGGCAGC GTGCAGGCCGGGGGCAGCCTGCGCCTCTCTTGTCGCGCATCCGGCAGTACCTAT TCTAACTACTGTTTGGGTTGGTTTAGGCAGATTACCGGCAAGGAGAGGGAGGGG GTGGCCGTTATCAACTGGGTCGGGGGCATGTTGTACTTTGCCGACTCTGTGAAG GGTAGGTTCACTGTTTCTCAGGATCAGGCTAAGAACACTGTTTATCTTCAGATG AACTCTCTGAAGCCAGAGGACACCGCTATGTATTACTGTGCCGCAGAGTCAGCC AGCTCCTTTAGTTGTGGGGGCTGGCTGACCCGTCCCGACCGCGTCCCATACTGG GGCCAGGGTACACAAGTGACTGTCTCCAGC |
| DR591-hIL27 Ra_VH H16 | 986 | CAGGTGCAACTTCAGGAGAGTGGGGGAGGCTCTGTTCAGGCAGGGGGGTCCCTG CGCCTGAGCTGCACCGCCTCAGGTGCCATCGCCTCTGGCCATATTGATAGCCGT TGGTGTATGGCCTGGTTCCGGCAGGCACCCGGCAAAGAACGCGAAGGGGTGGCC GCTATCTGGCCTGGAGGTGGCCTGACCGTTTACGCTGACAGCGTGAAAGGAAGG TTCACCATCTCCAGGGACCACGCTAAGAACACTCTGTACTTGCAGATGAATAAC CTGAAACCTGAAGATACCGCCATGTATTACTGCGCCGCTGGCTCTCCACGCATG TGTCCATCCCTGGAGTTCGGATTCGATTATTGGGGACAGGGCACCCAGGTCACC GTGTCCTCTGGCGGATCTGGTGGCTCAGGGGGCTCTGGCCAGGTCCAGTTGCAG GAATCCGGTGGAGGCAGTGTTCAGGCCGGGGGCTCCCTGCGCCTGTCATGTCGG GCCTCCGGCAGCACCTACTCCAATTACTGCCTCGGATGGTTCCGCCAGATCACC GGCAAAGAGCGTGAAGGCGTGGCCGTCATCAACTGGGTGGGCGGGATGCTTTAC TTTGCAGATTCCGTGAAGGGCAGATTTACGGTGTCTCAGGACCAGGCGAAGAAC ACAGTGTATCTCCAGATGAACAGCCTCAAGCCTGAAGATACCGCTATGTATTAC TGCGCCGCAGAGAGCGCTTCTTCCTTTAGCTGCGGCGGTTGGCTGACCAGGCCC GACCGTGTTCCGTACTGGGGTCAGGGCACCCAGGTGACCGTATCCAGT |
| DR591-hIL27 Ra_VH H17 | 987 | CAAGTCCAGCTCCAGGAATCCGGCGGAGGTAGCGTGCAGGCGGGTGGCAGCCTG CGCCTGTCCTGTACTGCAAGCGGAGCCATCGCCTCTGGCTACATCGACTCACGC TGGTGTATGGCCTGGTTTCGCCAAGCGCCGGGTAAGGAGCGCGAAGGGGTGGCC GCGATTTGGCCGGGGGGGGGCCTGACCGTCTACGCTGACAGTGTCAAGGGCCGC TTCACCATCTCTCGGGATCACGCCAAGAACACTTTGTATCTGCAAATGAATAAC CTGAAACCCGAAGACACCGCAATGTATTACTGCGCCGCTGGTAGTCCGCGTATG TGTCCATCACTGGAGTTCGGCTTCGACTACTGGGGTCAGGGAACCCAGGTCACC GTGTCCTCTGGTGGCGGTAGCCAGGTCCAGCTGCAAGAATCCGGTGGGGGGCTG GTGCAGCCAGGTGGATCTCTGCGCTTGTCCTGTGCCGCAAGCGGTTTTACTTTC TCACTGAGCGGCATGTCCTGGGTGAGGCAGGCTCCAGGCAAGGGCCTCGAATGG GTCTCAGCCATTAGTAGCGGGGGCGCATCCACCTATTACACAGATTCCGTGAAG GGTAGATTCACGATTAGCCGCGACAATGCTAAGAATATGCTGTATCTTCAGTTG AATAGCCTGAAGACAGAGGACACCGCTATGTATTACTGCGCGAAGGGCGGATCT GGCTACGGCGACGCCTCCAGGATGACAAGTCCGGGTTCCCAGGGCACACAGGTC ACGGTCTCTAGC |
| DR591-hIL27 Ra_VH | 988 | CAGGTGCAGCTCCAGGAGTCCGGCGGAGGCTCAGTCCAGGCTGGGGGCTCCCTC CGCCTGTCCTGTACGGCAAGTGGCGCTATCGCGAGCGGCTACATTGATTCACGC TGGTGCATGGCCTGGTTCAGGCAAGCTCCTGGGAAGGAGCGCGAGGGAGTGGCT |

TABLE 1B-continued

| Name | SEQ ID NO: | Sequence |
|---|---|---|
| H17 | | GCCATCTGGCCAGGGGGTGGCCTGACTGTGTACGCGGACAGCGTGAAGGGTCGC<br>TTCACAATCTCAAGGGACCACGCCAAGAATACCTTGTATCTTCAGATGAATAAC<br>CTGAAACCCGAGGACACAGCCATGTACTATTGTGCAGCCGGTTCCCCGAGAATG<br>TGCCCTAGTTTGGAGTTCGGCTTCGACTACTGGGGTCAGGGAACCCAGGTGACC<br>GTGTCCAGTGGCGGGTCTGGGGGTTCCGGCGGGTCAGGCCAGGTCCAGCTTCAG<br>GAATCCGGGGGAGGCCTGGTTCAGCCAGGTGGAAGCCTTCGCCTGTCCTGCGCT<br>GCATCCGGGTTCACATTCAGCCTGAGTGGCATGTCCTGGGTGAGACAGGCCCCA<br>GGAAAGGGTCTGGAGTGGGTCTCTGCAATCAGCTCCGGCGGTGCTTCTACCTAT<br>TACACCGACTCCGTGAAGGGCCGGTTCACTATTAGTCGCGACAACGCTAAGAAC<br>ATGCTGTACCTGCAACTGAACTCCTTGAAGACAGAAGACACGGCCATGTATTAC<br>TGCGCCAAGGGAGGTTCAGGTTACGGCGACGCCAGCCGCATGACCTCCCCTGGC<br>TCTCAGGGGACTCAGGTTACAGTCTCCTCC |
| DR591-<br>hIL27<br>Ra_VH<br>H18 | 989 | CAGGTCCAGCCCCAGGAAAGCGGAGGCGGGTCCGTCCAGGCTGGCGGTAGTTTG<br>CGCCTCTCATGTACCGCCAGCGGCGCAATCGCTTCTGGATATATCGACTCTCGC<br>TGGTGTATGGCCTGGTTCCGGCAGGCCCCCGGCAAGGAGAGGGAGGGAGTGGCA<br>GCCATCTGGCCGGGTGGGGGGTTGACCGTGTATGCCGACTCTGTCAAGGGCCGC<br>TTCACAATCAGCAGAGACCATGCCAAGAACACCCTGTACCTTCAGATGAATAAC<br>CTGAAGCCCGAAGACACCGCCATGTATTACTGCGCCGCAGGCTCCCCAAGAATG<br>TGCCCTAGTCTGGAGTTCGGCCTCGACTACTGGGGCCAGGGGACCCAGGTGACC<br>GTCAGCTCTGGTGGAGGTAGCCAGGTGCAACTCCAGGAGAGCGGAGGGGGTAGC<br>GTGCAGGCTGGCGGTTCCCCGCGCCTGAGCTGCGTGGCCTCTGGTTACGTTAGT<br>TGCGACTATTTTCTGCCCAGCTGGTATCGTCAGGCTCCGGGCAAGGAAAGAGAA<br>TTTGTCTCCATCATTGACGGAACTGGCTCTACAAGTTACGCCGCAAGTGTCAAG<br>GGTCGCTTCACCGCCAGCCAGGACAAGGGTAAGAACATCGCCTACCTGCAAATG<br>AACTCCCTCAAGCCAGAAGACACCGCGATGTACTATTGCAAGGCCAGCTGTGTA<br>AGGGGCAGGGGCATTAGCGAGTACTGGGGCCAGGGAACCCAGGTGACCGTGTCC<br>TCC |
| DR591-<br>hIL27<br>Ra_VH<br>H18 | 990 | CAGGTCCAGCTCCAGGAGTCAGGGGGTGGATCTGTGCAGGCGGGGGGGAGCCTC<br>AGGCTGAGCTGTACTGCCAGCGGCGCTATTGCCTCCGGTTACATTGACAGCCGC<br>TGGTGTATGGCTTGGTTTCGCCAAGCCCCTGGAAAGGAGAGGGAGGGCGTTGCT<br>GCCATCTGGCCTGGTGGGGACTGACCGTCTATGCTGATTCAGTGAAGGGGCGT<br>TTTACCATCTCCCGCGATCACGCTAAGAACACACTGTACCTCCAGATGAACAAT<br>TTGAAGCCCGAAGACACAGCCATGTACTATTGCGCCGCTGGGAGTCCCCGCATG<br>TGCCCTAGCCTGGAGTTTGGCTTCGACTATTGGGGGCAGGGCACTCAGGTCACT<br>GTTAGTTCCGGTGGCTCTGGTGGCAGCGGTGGCAGTGGCCAAGTGCAGCTCCAG<br>GAGTCCGGCGGAGGCTCAGTACAGGCCGGTGGCTCCCTTCGCCTGTCCTGCGTC<br>GCCTCCGGTTACGTTAGTTGCGACTATTTCCTGCCCAGCTGGTATCGCCAGGCA<br>CCAGGGAAGGAGCGCGAGTTCGTGTCCATTATCGACGGAACAGGGTCTACATCT<br>TATGCTGCCAGCGTGAAAGGAAGGTTCACCGCCCCCCAGGATAAGGGAAAAAAC<br>ATCGCCTACCCCCAGATGAACAGCCTGAAGCCAGAGGACACGGCCATGTACTAT<br>TGCAAGGCCTCCTGCGTGCGCGGCAGAGGTATCTCCGAATATTGGGGCCAGGGA<br>ACACAGGTGACCGTGAGCAGC |
| DR591-<br>hIL27<br>Ra_VH<br>H19 | 991 | CAGGTCCAGCTCCAGGAATCTGGTGGGGGAAGCGTGCAGGCCGGTGGGTCCCTG<br>AGACTGAGCTGTACCGCGAGCGGAGCTATCGCTTCTGGGTACATTGACTCCCGG<br>TGGTGCATGGCGTGGTTCCGTCAGGCTCCAGGTAAGGAGCGGGAGGGCGTTGCT<br>GCGATCTGGCCAGGAGGGGGATTGACTGTGTACGCTGACTCTGTCAAGGGTCGC<br>TTTACTATCTCCCGCGACCACGCAAAGAATACCCTGTACTTGCAAATGAACAAT<br>CTGAAGCCTGAGGACACCGCCATGTATTACTGTGCCGCTGGTAGCCCCACGCATG<br>TGTCCCAGTCTGGAGTTCGGGTTCGATTATTGGGGCCAGGGCACGCAGGTGACT<br>GTGTCCTCTGGTGGAGGCAGCCAAGTGCAGTTGCAGGAGTCAGGCGGAGGGAGC<br>GTGCAGGCGGGAGGTTCCCTGCGGCTGTCCTGTCGCGCGTCCGGTTCCACCTAC<br>TCTAACTATTGCCTCGGTTGGTTCCGCCAGATCACCGGCAAGGAGCGCGAGGGA<br>GTGGCGGTTATCAACTGGGTCGGGGGTATGCTGTACTTTGCAGACTCAGTTAAA<br>GGACGCTTCACTGTGAGCCAGGACCAGGCAAAGAATACTGTGTACTTGCAGATG<br>AACTCCCTGAAGCCAGAAGACACCGCCATGTATTACTGTGCTGCGGAATCTGTG<br>AGTTCCTTCAGTTGCGGTGGGTGGCTCACTAGACCCGATAGAGTCCCATATTGG<br>GGACAGGGTACTCAGGTGACTGTTAGCTCC |
| DR591-<br>hIL27<br>Ra_VH<br>H19 | 992 | CAGGTGCAGTTGCAGGAGAGTGGCGGTGGCAGCGTGCAGGCGGGGGGGAGCCTG<br>AGGCTGTCCTGTACTGCCTCTGGTGCAATCGCTTCAGGTTACATTGACTCACGC<br>TGGTGCATGGCTTGGTTTCGCCAGGCTCCAGGCAAGGAGCGCGAGGGTGTGGCC<br>GCTATCTGGCCGGGTGGAGGCCTCACCGTGTACGCCGATAGTGTCAAGGGACGC<br>TTTACAATCTCCCGTGACCATGCGAAGAACACATTGTATCTTCAGATGAATAAC<br>CTCAAACCCGAGGACACCGCTATGTATTACTGTGCAGCCGGAAGCCCTCGTATG<br>TGTCCAAGCCTGGAGTTCGGCTTTGATTACTGGGGACAAGGCACCCAGGTGACA<br>GTTTCTAGTGGAGGCTCTGGCGGTTCAGGAGGCTCCGGGCAAGTGCAGTTGCAG<br>GAATCCGGGGGTGGCTCCGTGCAGGCTGGGGGCTCTCTGCGGCTGTCTTGTCGT<br>GCATCTGGTTCCACATATAGCAACTACTGCCTGGGCTGGTTCCGCCAGATTACG<br>GGCAAGGAAAGAGAAGGTGTTGCAGTGATAAATTGGGTAGGTGGAATGCTGTAC<br>TTTGCCGACTCAGTGAAAGGGCGCTTTACAGTGAGCCAGGACCAGGCCAAGAAC<br>ACAGTCTACTTGCAGATGAACAGCCTCAAGCCTGAAGACACCGCAATGTACTAT<br>TGTGCTGCCGAGAGCGTCTCATCCTTTTCCTGCGGAGGCTGGCTGACCCGTCCA<br>GACCGCGTCCCCTACTGGGGCCAGGGCACCCAGGTGACTGTGTCCTCA |

TABLE 1B-continued

| Name | SEQ ID NO: | Sequence |
| --- | --- | --- |
| DR591-hIL27Ra_VH H20 | 993 | CAAGTGCAGCTGCAAGAGTCCGGTGGAGGCAGCGTACAAGCGGGTGGCTCACTG CGCCTGAGTTGTACCGCTTCTGGTGCAATCGCAAGCGGCTACATTGATTCCAGA TGGTGCATGGCATGGTTTCGCCAAGCCCCAGGCAAGGAAAGGGAGGGCGTGGCC GCAATCTGGCCTGGGGGTGGACTGACCGTGTATGCCGACAGCGTGAAGGGGGGC TTTACCATCTCCCGTGACCACGCTAAGAACACACTGTACTTGCAGATGAATAAC CTCAAGCCTGAAGACACTGCTATGTACTATTGCGCTGCCGGAAGTCCCCGCATG TGTCCTAGTCTGGAGTTTGGTTTTGATTACTGGGGCCAGGGCACCCAGGTGACC GTTTCAAGCGGAGGGGGCAGTCAGGTTCAGCTCCAGGAATCTGGAGGTGGGCTT GTCCAGCCAGGGGGCAGCCCCCGCCTGTCCTGTGCAGCGTCTGGCTTTACTTTC AGCTCCTATCCCATGTCTTGGGTTAGACAGGCACCAGGCAAGGGCCTGGAGTGG GTGTCCACAATCTCAAGCGGGGGCGATACAACCCTCTATGCCGATTCCGTGAAG GGCAGATTCACAAGCTCTAGGGACAACGCCAAGAATACCTTGTACCTCCAGCTG AACTCCCTGAAGACCGAGGACACTGCGATGTATTACTGCGCTAAGCGCATTGAT TGTAACTCTGGGTATTGTTACAAGCGCTCTTATTGGGGACAGGGCACGCAGGTG ACTGTCAGTTCC |
| DR591-hIL27Ra_VH H20 | 994 | CAGGTGCAGTTGCAAGAGAGCGGCGGAGGCTCCGTTCAGGCAGGGGGCTCCTTG CGCTTGTCTTGCACCGCATCCGGGGCCATTGCCTCAGGCTATATCGACTCCCGC TGGTGTATGGCTTGGTTCCGGCAAGCGCCGGGTAAGGAGCGTGAGGGGGTGGCA GCCATCTGGCCCGGAGGCGGTTTGACCGTGTATGCCGACTCTGTGAAGGGCCGG TTCACCATCTCTAGGGACCATGCGAAGAACACACTGTATCTCCAGATGAATAAC CTGAAGCCCGAAGACACCGCGATGTATTACTGTGCCGCTGGCTCCCCCAGGATG TGCCCCTCATTGGAGTTCGGTTTCGACTATTGGGGGCAGGGAACTCAAGTGACC GTAAGCTCCGGCGGGGTCCGGGGTAGTGGAGGCTCTGGGCAGGTGCAGTTGCAG GAGTCAGGGGGGGGCTTGGTGCAGCCCGGCGGTAGCCTGAGGCTGAGTTGCGCC GCCTCAGGCTTTACCTTTTCCAGCTACCCTATGTCTTGGGTGCGCCAGGCTCCG GGCAAGGGCTTGGAGTGGGTGTCCACCATCTCCAGCGGAGGCGATACGACCCTC TATGCGGATTCCGTCAAAGGGCGCTTTACCTCCAGCCGCGATAACGCCAAGAAC ACCTTGTACCTCCAGCTGAACTCCCTGAAGACCGAGGATACCGCAATGTACTAT TGTGCAAAGCGGATTGATTGTAACAGCGGCTATTGCTACAAGAGGTCTTACTGG GGCCAGGGCACCCAGGTGACAGTCTCCAGT |
| DR591-hIL27Ra_VH H21 | 995 | CAGGTCCAGCCCCAGGAGAGCGGTGGCGGTTCCGTGCAGGCTGGTGGCAGTCTT CGTCTCTCCTGTACCGCGTCCGGTGCCATCGCCAGTGGCTACATTGATTCTCGC TGGTGCATGGCATGGTTCCGCCAAGCTCCCGGCAAGGAGCGCGAGGGCGTCGCT GCCATTTGGCCAGGTGGGGGGCTGACCGTGTACGCGGACCCTGTGAAGGGTCGG TTTACGATCAGCCGGGACCATGCTAAGAATACGCTCTACCTGCAAATGAACAAT CTGAAACCCGAGGACACAGCAATGTACTATTGCGCAGCCGGAAGTCCACGCATG TGCCCATCTTTGGAGTTTGGCCTCGATTATTGGGGCCAGGGCACCCAGGTCACT GTGTCCAGTGGGGGGGGTTCTCAGGTGCAGTTGCAGGAAAGTGGAGGTGGCCTT GTCCAACCTGGAGGGAGTCTGCGTCTCTCCTGCGCTGCCTCCGGGTTCACCTTT AGTCTGTCCAGTATGTCTTGGGTCCGCCAAGCGCCCGGAAAGGGTCTGGAGTGG GTCAGCGCGATTAGCTCCGGTGGAGCCAGTACTTATTACACCGACAGCGTGAAA GGACGGTTTACCATCTCCCGCGATAATGCTAAGAATATGCTCTACTTGCAGCTG AACAGCCTGAAGACCGAGGACACAGCGATGTATTACTGTGCCAAGGGAGGTTCC GGCTATGGTGATGCCAGCCGCATGACCTCCCCTGGCTCCCAGGGAACTCAGGTT ACTGTGTCCTCC |
| DR591-hIL27Ra_VH H21 | 996 | CAAGTGCAGTTGCAGGAGAGCGGTGGCGGTAGCGTCCAAGCTGGGGGCAGCTTG CGCCTGAGCTGTACTGCGTCTGGCGCTATTGCGAGCGGTTACATTGATTCCAGG TGGTGTATGGCCTGGTTCAGGCAGGCACCGGGTAAAGAGCGTGAGGGGGTGGCA GCCATTTGGCCTGGCGGTGGACTGACCGTCTACGGGGACTCTGTCAAGGGACGT TTCACGATCAGCCGCGATCACGCTAAAAACACCCTCTACCTCCAGATGAATAAC CTGAAGCCTGAGGACACAGCTATGTATTACTGTGCTGCGGGCAGTCCCAGAATG TGTCCCAGCCTGGAGTTCGGCTTCGACTACTGGGGGCAAGGCACCCAGGTGACA GTGTCCAGCGGGGGCTCCGGCGGGTCTGGGGGCAGCGGCCAGGTGCAACTGCAA GAGTCTGGCGGTGGACTTGTTCAGCCAGGGGGATCTCTGAGGCTCTCCTGCGCC GCTTCCGGTTTTACCTTCTCCCTCAGCAGTATGTCCTGGGTCCGTCAGGCTCCA GGCAAAGGCCTGGAATGGGTTTCCGCTATTAGCTCTGGCGGTGCCTCCACCTAC TATACGGACTCAGTCAAAGGCCGTTTCACGATCTCCAGGGACAATGCTAAGAAT ATGCTCTACCTCCAGTTGAACTCTCTGAAAACGGAGGACACCGCTATGTACTAT TGCGCCAAAGGGGGTTCCGGCTACGGCGACGCCTCCCGGATGACATCCCCTGGG TCCCAGGGAACCCAGGTGACCGTGTCCAGC |
| DR591-hIL27Ra_VH H22 | 997 | CAGGTGCAGTTGCAGGAGTCCGGCGGAGGCTCCGTGCAAGCTGGCGGTAGCTTG CGGCTGAGTTGCACTGCCAGCGGTGCCATCGCGAGGGGGTACATCGACAGCAGG TGGTGCATGGCCTGGTTCCGTCAAGCGCCAGGAAAGGAGAGGGAGGGCGTCGCA GCCATCTGGCCGGGCGGAGGCCTGACCGTGTACGCAGATTCCGTCAAAGGCCGT TTCACCATCTCCCGCGACCACGCCAAGAACACCCTGTATCTTCAGATGAATAAC CTGAAACCCGAGGACACCGCCATGTACTATTGTGCTGCGGGCTCACCCCGGATG TGTCCCTCTCTGGAGTTCGGCTTCGATTATTGGGGCCAGGGCACCCAGGTCACC GTGTCAAGTGGTGGCGGTTCCCAGGTGCAGCTGCAAGAGAGCGGCGGTGGCAGC GTGCAGGCGGGGGGTAGCTTGCGCCTGAGCTGTCGCGCCTCCGGCAGCACTTAC AGCAACTACTGCCTGGGCTGGTTCCGTCAGACTACAGGTAAGGAGCGTGAGGGC GTAGCGGTAATCAACTGGGTCGGGGGAATGCTTTACTTTGCGGACAGTGTGAAA GGCCGTTTCACCGTGTCTCAGGACCAGGCTAAGAACACTGTGTACCTCCAGATG AACTCCCTGAAGCCTGAGGACACGGCCATGTATTACTGTGCAGCGGAGTCCGTT |

TABLE 1B-continued

| Name | SEQ ID NO: | Sequence |
|---|---|---|
| | | AGCTCCTTCTCTTGTGGCGGATGGCTGACCCGGCCAGACCGCGTGCCATATTGG GGCCAAGGGACCCAAGTGACCGTGTCATCC |
| DR591-hIL27 Ra_VH H22 | 998 | CAGGTGCAGCTCCAGGAGTCCGGCGGTGGGTCCGTGCAGGCTGGTGGATCTCTT AGACTGTCCTGTACCGCTTCTGGAGCGATTGCCTCAGGTTACATTGACAGTAGG TGGTGTATGGCTTGGTTCCGTCAGGCTCCAGGCAAGGAACGCGAGGGCGTTGCT GCCATTTGGCCAGGAGGCGGTCTGACTGTCTACGCTGACAGCGTAAAGGGCCGC TTTACCATCTCTCGGGATCACGCGAAAAATACACTGTACCTCCAGATGAATAAC CTGAAGCCGGAGGACACCGCCATGTATTACTGCGCTGCCGGGAGCCCCCGTATG TGCCCTTCCCTGGAGTTCGGATTTGACTATTGGGGCCAGGGCACCCAAGTGACC GTCAGCTCCGGTGGCTCTGGCGGTTCCGGGGGCTCTGGCCAAGTGCAGCTTCAG GAGTCAGGGGGTGGCTCTGTGCAGGCCGGTGGCAGCCTGCGTCTGAGCTGCCGT GCCAGCGGCTCTACCTATTCCAACTACTGCCTGGGGTGGTTTCGGCAGACCACA GGAAAGGAAAGAGAGGGTGTGGCAGTTATCAACTGGGTGGGAGGGATGTTGTAC TTCGCCGACTCCGTCAAGGGGCGCTTCACCGTCAGTCAGGACCAGGCAAAGAAC ACCGTGTACCCCCAGATGAACTCCCTGAAGCCTGAGGATACCGCCATGTATTAC TGCGCCGCTGAGTCTGTGTCATCTTTCTCATGCGGTGGCTGGCTCACCCGCCCA GACCGCGTGCCTTATTGGGGCCAGGGCACACAGGTCACCGTCAGCTCA |
| DR591-hIL27 Ra_VH H23 | 999 | CAGGTTCAACTCCAGGAAAGCGGGGGGGGCTCTGTGCAAGCTGGCGGAAGTTTG CGTCTGTCCTGCACCGCCTCTGGAGCCATCGCCAGCGGCTACATCGACTCAAGA TGGTGTATGGCCTGGTTCAGACAGGCTCCAGGAAAAGAACGCGAAGGCGTGGCC GCTATCTGGCCCGGAGGTGGCCTGACCGTGTACGCTGACTCCGTCAAGGGCCGC TTCACCATCTCCCGTGACCACGCAAAGAACACACTGTACCTCCAGATGAATAAC CTGAAGCCCGAGGATACCGCCATGTACTATTGCGCTGCGGGCTCCCCTCGGATG TGTCCCAGCCTGGAGTTCGGCTTCGACTATTGGGGACAGGGAACTCAGGTCACA GTCAGCTCCGGCGGAGGCTCTCAGGTCCAGCTCCAGGAATCAGGTGGAGGCTCC GTTCAGGGGGGGCGGATCTCTTCGCCTGTCATGCCGTGCATCCAGATCCCCGTAT GGCAACTATTGCCTGGGGTGGTTCCGCCAGAGTACAGGTAAGGAGCGCGAGGGC GTGGCTGTTATCAACTGGGTCGGCGGAATGCTGTATTTTGCCGATTCCGTGAAG GGTCGTTTCACAGTGAGCCAGGATCACGCCAAGAACACCGTGACCTTGCAGATG AACTCCCTGAAGCCTGAAGATACCGCCATGTATTACTGTGCTGCGGAGAGCGTG TCCTCTTTCTCTTGCGGCGGTTGGCTGACCAGGCCTGATCGTGTCCCCTACTGG GGGCAGGGCACCCAGGTGACCGTCTCTAGC |
| DR591-hIL27 Ra_VH H23 | 1000 | CAAGTGCAGTTGCAGGAGTCAGGCGGAGGCTCTGTCCAGGCTGGAGGCTCCCTG AGACTCTCCTGCACCGCATCCGGGGCCATCGCCAGCGGATATATCGACTCCAGA TGGTGTATGGCGTGGTTTCGCCAAGCTCCGGGGAAGGAGCGTGAGGGTGTCGCT GCGATCTGGCCTGGGGGGGGACTGACCGTGTATGCTGATTCCGTAAAGGGCCGT TTCACCATCAGCCGCGACCATGCCAAGAACACACTCTACCTCCAGATGAACAAT CTTAAACCCGAGGACACTGCAATGTACTATTGTGCGGCTGGTTCTCCCCGCATG TGTCCTTCCCTGGAGTTCGGCTTCGACTACTGGGGGCAGGGCACCCAGGTCACC GTGAGTAGGGGGGGGGAGCGGGGGGAGCGGTGGCTCCGGCCAGGTGCAGCTTCAA GAGTCCGGGGGTGGCTCCGTGCAAGCTGGTGGAAGTCTTCGCCTGAGTTGCCGC GCGTCCCGCTCCCCTTACGGCAATTATTGCCTGGGATGGTTTCGCCAATCCACC GGGAAGGAGCGCGAGGGCGTGGCAGTAATCAACTGGGTGGGGGGTATGCTGTAC TTTGCCGATTCTGTGAAGGGCAGATTTACCGTGTCTCAAGACCACGCCAAGAAC ACTGTCACCTTGCAGATGAACTCACTGAAGCCAGAGGATACCGCTATGTATTAC TGCGCTGCCGAATCAGTCAGCTCCTTCTCTTGCGGTGGCTGGCTGACCCGCCCT GATAGGGTCCCCTATTGGGGCCAGGGCACCCAGGTCACCGTGTCCAGT |
| DR591-hIL27 Ra_VH H24 | 1001 | CAGGTCCAGCTCCAGGAGTCCGGCGGAGGTTCTGTCCAGGCCGGTGGATCACTG CGTCTGTCTTGCACCGCCAGCGGCGCAATCGCGTCTGGCTATATCGACAGCCGT TGGTGCATGGCTTGGTTTCGCCAGGCTCCCGGCAAGGAAAGGGAAGGGGTGGCC GCGATTTGGCCTGGGGGCGGTCTGACCGTCTACGCCGACAGCGTGAAGGGCCGC TTTACCATCTCCCGCGACCACGCCAAGAACACATTGTACCTGCAAATGAATAAC CTCAAGCCTGAGGACACAGCGATGTATTACTGTGCCGCTGGCTCACCCCGCATG TGTCCGTCCCTGGAGTTTGGGTTTGATTATTGGGGCCAGGGCACACAGGTGACT GTGTCATCTGGAGGCGGTTCCCAGGTCCAGTTGCAGGAGTCTGGCGGAGGTCTG GTGCAGCCAGGAGGCAGCCTGCGGCTGTCTTGTGCTGCGTCTGGTTTCACCTTC TCTCACAGCGGCATGTCTTGGGCGCGCCAAGCACCGGGCAAGGGCCTGGAGTGG GTCTCCACAATTAACTCCGGCGGGGCCTCCACCCATTACACCGACCCTGTAAAG GGTCGGTTTACCATTAGCCGCGATAACGCCAAAAATATGTTGTATTTGCAGCTT AACTCCCTGAAGACCGAAGATACCGCTATGTATTACTGCGCAAAGGGTGGGAGC GGTTACGGCGACGCCTCCCGCATGACCTCTCCGGGATCTCAGGGAACCCAAGTT ACCGTGAGTAGT |
| DR591-hIL27 Ra_VH H24 | 1002 | CAGGTGCAGCTCCAGGAATCTGGAGGCGGTTCCGTGCAGGCAGGCGGTTCCCTG AGGCTTAGTTGTACCGCCTCTGGGGCTATCGCCTCCGGCTACATTGACTCTCGC TGGTGTATGGCCTGGTTCAGGCAGGCTCCAGGTAAGGAGCGCGAGGGTGTCGCG GCTATTTGGCCTGGTGGCGGACTGACTGTGTACGCCGATTCTGTGAAGGGCCGG TTTACTATTACCAGGGATCATGCGAAAAATACCCTTTACTTGCAGATGAACAAT CTGAAGCCGGAGGACACGGCCATGTACTATTGCGCCGCTGGCTCACCTAGAATG TGTCCTAGCTTGGAGTTCGGGTTTGATTACTGGGGCCAGGGAACCCAGGTGACC GTCTCTAGCGGTGGGAGCGGGAGCGGGGGGGGAAGCGGGCAGGTTCAGTTGCAG GAATCAGGAGGGGGACTGGTGCAACCGGGAGGCTCCCTGCGCCTGTCTTGTGCT GCCTCTGGTTTTACTTTTAGCCATAGGGGGATGTCCTGGGTTCGCCAGGCTCCA |

TABLE 1B-continued

| Name | SEQ ID NO: | Sequence |
|---|---|---|
| | | GGCAAGGGCCTGGAGTGGGTATCTACCATCAACTCTGGAGGTGCCAGCACCTAT TACACCGACAGCGTGAAGGGGAGGTTCACCATCTCCCGCGACAACGCTAAGAAC ATGCTGTACCTCCAGCTCAACTCTCTGAAGACCGAGGACACCGCTATGTATTAC TGCGCGAAGGGCGGTTCCGGTTACGGAGACGCCCCCCGCATGACCAGTCCGGGT TCCCAAGGTACACAGGTGACCGTGTCTAGC |
| DR592-hIL27 Ra_VH H1 | 1003 | CAGGTTCAACTCCAGGAGTCCGGGGGGGGTTCCGTGCAAGCTGGAGGTTCACTG CGCCTGAGCTGCACTGCGCCAGGCTTCACATCAAATTCTTGTGGTATGGATTGG TATCGGCAAGCCCCCGGAAAAGAGCGGGAGTTCGTGTCCAGTATTAGCACAGAC GGTACGACCGGATATGCGGACTCTGTGAAAGGACGCTTCACGATTTCCAAAGAC AAGGCCAAGGACACCGTGTACCTTCAGATGAACTCACTGAAACCAGAGGACACG GGCATGTACTCCTGTAAGACGAAGGACGGAACAATCGCCACTATGGAATTGTGC GATTTCGGCTATTGGGGCCAGGGGACGCAGGTTACCGTTTCTTCAGGGGGAGGG AGTCAGGTTCAGTTGCAGGAGTCCGGCGGTGGCCTGGTGCAACCTGGGGGAAGC CTGCGTCTTTCTTGTGCAGCCAGCGGCTTCACCTTCAGTTCATACCCCATGAGC TGGGTCCGTCAGGCCCCCGGTAAAGGGCTGGAGTGGATCTCAACCATCTCTGCC GGTGGCGACACCACGCTTTACGCTGACTCCGTCAAAGGCAGATTCACCAGTAGC AGAGACAACGCGAAGAACACCCTCTATTTGCAGCTTAACTCCCTCAAGACCGAG GACGCAGCTATCTACTATTGTGCTAAGAGGATTGACTGTAACAGCGGCTACTGT TATCGTCGCAACTATTGGGGCCAGGGCACTCAGGTCACAGTGTCTTCC |
| DR592-hIL27 Ra_VH HI | 1004 | CAGGTCCAGCTCCAGGAGAGCGGCGGAGGGTCTGTGCAGGCGGGGGGTAGTTTG CGCTTGAGCTGTACCGCACCCGGATTCACCTCCAACAGCCGCGGTATGGACTGG TATCGCCAGGCTCCTGGTAAAGAGCGTGAGTTCGTGTCTTCAATCAGCACCGAC GGTACAACTGGGTATGCCGATTCCGTGAAAGGAAGATTCACCATCTCCAAGGAC AAGGCCAAAGACACAGTTTATCTTCAGATGAACAGTCTGAAGCCCGAGGACACC GGCATGTATTCTTGTAAGACTAAGGACGGGACGATTGCGACAATGGAACTGTGC GACTTCGGTTACTGGGGCCAGGGGACTCAGGTAACTGTGTCAAGCGGAGGCTCT GGCGGAAGTGGAGGCTCAGGACAGGTGCAGCTCCAGGAGTCAGGAGGGGGCCTG GTCCAGCCGGGCGGGTCTCTGCGCCTCTCTTGCGCTGCCTCTGGGTTCACATTC AGCAGTTACCCTATGTCCTGGGTACGCCAGGCTCCAGGCAAAGGTCTGGAGTGG ATCTCCACCATCAGTGCCGGAGGCGATACCACTCTGTATGCCGACAGCGTGAAG GGACGCTTTACCTCCTCACGCGATAATGCCAAGAACACTCTGTACCTGCAACTC AATAGTCTGAAGACTGAGGACGCGGCCATCTATTACTGCGCCAAGCGCATTGAT TGCAATAGTGGCTACTGTTACCGGGGCAACTATTGGGGACAGGGTACTCAGGTA ACAGTCAGCTCC |
| DR592-hIL27 Ra_VH H2 | 1005 | CAGGTCCAACTGCAAGAGTCTGGAGGGGGCTCTGTGCAGGCCGGAGGCTCCCTT CGCCTGTCTTGTACCGCCCCAGGTTTTACCCCAAACTCCTGCGGCATGGATTGG TATAGACAGGCTCCTGGGAAAGAGAGGGAGTTCGTGTCTTCCATCAGCACCGAC GGTACAACCGGCTACGCGGATTCCGTGAAAGGTCGCTTTACCATTTCAAAGGAC AAAGCTAAAGATACCGTGTACCTCCAGATGAACTCACTGAAGCCCGAGGACACT GGCATGTACTCTTGTAAGACCAAGGATGGCACCATCGCCACTATGGAGTTGTGT GATTTCGGGTACTGGGGCCAGGGCACACAAGTGACCGTCTCCAGCGGTGGAGGC AGCCAGGTGCAGCTTCAAGAGTCCGGCGGGGGGCTGGTCCAGCCAGGAGGCTCA CTCCGCCTGTCCTGTGCGGCTTCCGGGTTTACCTTCTCACTGTCCGGCATGTCC TGGGTCCGCCAGGCCCCCGGCAAAGGCCTTGAGTGGGTGTCCGCTATTAGCTCC GGTGGAGCCAGCACTTACTATACTGACTCTGTTAAAGGCCGGTTTACAATCTCC CGTGACAATGCCAAGAACATCCCGTATCTTCAGCTGAACAGTCTCAAGACAGAG GATACTGCCATGTACTATTGTGCTAAAGGTGGCTCCGGCTACGGCGACGCGAGC CGTATGACTTCTCCTGGCTCCCAGGGCACTCAGGTGACTGTTTCCAGC |
| DR592-hIL27 Ra_VH H2 | 1006 | CAGGTCCAGCTTCAGGAGAGCGGGGGTGGGAGCGTGCAGGCCGGGGGCTCTCTG CGCCTGTCCTGCACAGCGCCCGGTTTTACGTCCAACTCTTGGGGCATGGATTGG TATCGCCAAGCGCCTGGCAAGGAAAGAGAGTTTGTCAGCTCCATCAGCACCGAT GGCACTACCGGCTACGCGGATTCTGTAAAGGGTCGTTTCACCATCAGTAAGGAT AAGGCTAAGGACACGGTGTACCTCCAGATGAACCCCCTCAAGCCCGAGGATACC GGGATGTACTCTTGCAAGACCAAGGACGGCACCATCGCCACTATGGAGCTTTGC GACTTCGGCTATTGGGGCCAGGGAACTCAGGTGACTGTGTCAAGTGGTGGGTCA GGAGGTAGCGGAGGTTCTGGCCAGGTGCAGCTTCAGGAATCTGGCGGTGGGCTC GTCCAGCCGGGAGGCTCTCTGCGCCTGAGCTGCGCAGCCTCTGGCTTTACCTTT TCTCTGTCTGGCATGTCTTGGGTCCGCCAGGCACCTGGAAAGGGGCTGGAGTGG GTTTCCGCCATCTCCTCTGGTGGCGCATCCACATATTACACCGACTCAGTCAAG GGCCGCTTCACCATTTCACGCGATAATGCCAAGAACATCCTGTACCTTCAGCTG AACTCCCTGAAGACCGAGGACACAGCTATGTATTACTGCGCTAAGGGAGGGTCC GGCTACGGGGATGCGAGCAGAATGACCAGCCCTGGTTCACAAGGCACCCAGGTA ACTGTTAGCAGT |
| DR592-hIL27 Ra_VH H3 | 1007 | CAAGTCCAACTTCAGGAGTCCGGGGGGGGCTCTGTGCAGGCTGGAGGGTCTCTG CGCCTGTCCTGCACTGCACCTGGGTTCACTTCAAACTCTTGCGGCATGGACTGG TATCGCCAGGCCCCAGGCAAGGAACGTGAGTTTGTGTCCAGCATTTCAACTGAC GGCACAACCGGGTATGCTGATAGCGTGAAGGGTAGGTTTACCATCTCCAAGGAT AAGGCCAAGGATACCGTGTACTTGCAGATGAACTCCCTCAAACCTGAGGATACC GGAATGTATAGCTGCAAGACCAAAGATGGAACCATCGCTACTATGGAGCTGTGT GACTTTGGCTACTGGGGCAGGGCACCCAGGTGACCGTGTCCAGCGGCGGTGGA TCTCAGGTCCAGCTCCAGGAGAGCGGGGGGGGGTCTGTGCAGGCAGGGGGGTCC CTGCGTCTGTCATGCGTCGCGTCAGGCTACGTCTCCTGCGATTACCTCCTGCCT |

TABLE 1B-continued

| Name | SEQ ID NO: | Sequence |
|---|---|---|
| | | TCCTGGTATCGCCAGGCCCCTGGCAAGGAAAGGGAGTTCGTCAGTATCATTGAC GGAACCGGCTCCACCAGCTACGCTGCCTCCGTCAAGGGCCGCTTCACCGCCTCC GAGGACAAAGGGAAGAACATCGCCTACCTCCAGATGAACAGTCTGAAACCAGAG GATACTGCAATGTACTATTGCAAGGCCTCCTGTGTCCGTGGCCGTGCCGTTTCT GAGTACTGGGGCCAAGGGACTCAGGTGACTGTCTCCTCC |
| DR592-hIL27 Ra_VH H3 | 1008 | CAGGTTCAGTTGCAGGAGAGTGGAGGGGGCTCCGTGCAGGCCGGTGGCTCCCTG AGGCTGTCCTGCACAGCTCCCGGCTTCACCAGTAATTCCTGTGGCATGGACTGG TATCGCCAGGCCCCCGGTAAGGAAAGAGAGTTTGTGTCCAGTATCTCAACCGAC GGCACCACTGGCTATGCGGACTCCGTCAAGGGCAGGTTCACTATCTCCAAGGAT AAGGCCAAAGACACAGTGTACCTCCAAATGAACTCTCTCAAGCCCGAGGACACG GGCATGTATTCCTGTAAAACCAAGGACGGCACCATCGCTACTATGGAGCTGTGT GATTTCGGATACTGGGGCCAGGGAACCCAGGTGACCGTGTCAAGCGGAGGTAGT GGTGGCTCAGGCGGGTCCGGGCAGGTCCAACTCCAGGAGTCTGGAGGGGGGAGT GTGCAGGCTGGTGGCTCCCTGCGGCTGAGCTGCGTGGCTTCCGGGTATGTTTCT TGCGATTACTTCCTGCCGAGCTGGTACAGGCAGGCTCCCGGTAAGGAGCGTGAG TTCGTTTCCATCATTGACGGCACCGGGAGCACAAGCTACGCCGCTAGTGTGAAG GGACGCTTCACGGCAAGCGAAGACAAGGGCAAAAACATCGCGTACTTGCAGATG AACTCCTTGAAGCCCGAGGACACCGCTATGTATTACTGTAAAGCCTCATGCGTC AGAGGCAGGGCTGTCTCAGAGTACTGGGGTCAGGGCACGCAAGTGACAGTCTCT TCC |
| DR592-hIL27 Ra_VH H4 | 1009 | CAAGTGCAACTCCAGGAGTCCGGCGGTGGGTCTGTGCAGGCTGGGGGCTCACTG CGTCTGAGCTGCACCGCTCCCGGTTTTACCAGTAACTCTTGTGGTATGGACTGG TATCGCCAGGCCCCCGGCAAGGAGAGGGAATTTGTCAGTTCCATCTCTACAGAC GGCACTACAGGATACGCCGACTCCGTCAAGGGGCGGTTCACCATCTCAAAAGAT AAAGCAAAGGACACAGTCTACCTTCAGATGAACAGCCTGAAACCTGAGGACACT GGAATGTATAGCTGCAAGACAAAGGATGGAACAATCGCCACGATGGAGCTGTGT GACTTCGGATACTGGGGCCAGGGGACACAGGTCACTGTGTCCTCTGGAGGCGGG TCCCAGGTGCAGCTCCAGGAGAGGGGCGGAGGCCTGGTGCAGCCCGGCGAGTCC CTTAGGCTGAGCTGTACGGCGAGCGGCTTTACTTTCAGCAACTACGCCATGAGC TGGGTCCGTCAAGCGCCGGGGAAGGGGCTGGAGTGGGTTTCTGGCATCAACGTG GCATACGGCATCACCTCCTATGCTGATAGCGTCAAGGGCCGCTTCACCATTTCC AGAGATAATACCAAGAATACCCCCTACCTCCAGCTCAATTCCCTGAAGACCGAG GACACTGCTATTTATTACTGTGTGAAGCACTCTGGCACCACAATTCCTCGCGGC TTTATCAGCTATACAAAGAGAGGCCAGGGAACTCAGGTCACCGTCAGCTCT |
| DR592-hIL27 Ra_VH H4 | 1010 | CAGGTCCAGTTGCAGGAATCTGGGGGGGGATCAGTGCAGGCCGGGGGCTCCCTG CGTCTTTCTTGCACAGCCCCTGGCTTTACCTCCAATTCCTGTGGCATGGATTGG TATCGGCAGGCCCCCGGCAAGGAGCGCGAGTTTGTCTCTAGCATTAGCACCGAC GGCACCACTGGTTACGCTGACTCAGTGAAGGGACGGTTCACCATTTCCAAGGAC AAGGCTAAAGACACAGTCTACCTTCAGATGAACAGTCTGAAGCCCGAGGATACA GGGATGTACTCCTGTAAGACCAAGGACGGCACCATCGCAACGATGGAGCTGTGC GACTTCGGCTATTGGGGGCAAGGGACCCAGGTGACTGTGTCCTCTGGGGGCTCC GGGGGCAGCGGAGGCTCCGGCCAAGTGCAACTCCAGGAGAGCGGCGGTGGACTG GTGCAGCCAGGCGAGAGCCTCCGGCTTTCCTGCACCGCAAGCGGCTTCACTTTT AGCAACTACGCTATGTCCTGGGTAAGGCAGGCTCCAGGTAAGGGCCTGGAGTGG GTGAGCGGTATTAACGTGGCATACGGCATCACTTCCCACGCGGACAGCGTCAAG GGCCGTTTTACTATCAGCAGGGATAATACTAAGAATACTCTGTACTTGCAGCTG AACAGCCTGAAGACTGAAGATACTGCCATCTATTACTGCGTGAAGCACTCTGGA ACAACCATTCCACGGGGCTTCATCAGTTACACCAAGCGGGGCCAGGGCACTCAG GTCACCGTGTCTTCC |
| DR592-hIL27 Ra_VH H5 | 1011 | CAAGTGCAGCTCCAGGAGTCCGGCGGTGGAAGCGTGCAGGCCGGAGGCTCTCTG CGCTTGAGTTGCACCGCCCCTGGATTCACATCTAACTCCCGTGGTATGGATTGG TACAGGCAGGCACCAGGCAAGGAACGTGAGTTCGTGTCTTCCATCAGTACCGAC GGTACTACCGGCTACGCGGACTCCGTCAAAGGTAGATTTACGATCAGCAAAGAT AAGGCTAAGGATACCGTGTATCTCCAGATGAACCCCCTGAAACCCGAGGATACA GGTATGTATAGCTGCAAGACCAAGGACGGCACTATCGCGACTATGGAATTGTGT GACTTTGGTTACTGGGGCCAAGGAACCCAGGTGACCGTCAGTAGCGGTGGCGGT TCCCAAGTACAGCTGCAAGAGTCTGGAGGTGGATCTGTGCAGGCTGGGGGTAGT CTTCGCCTGTCTTGTACCGCCAGCGGTTACGTGTCCCGTGACTACTTTCTGCCC TCCTGGTACAGACAGGCTCCTGGTAAGGAGCGCGAGTTCGTGAGCGTCATCGAC GGCACAGGGTCCACCAGTTACGCGGCATCCGTAAAGGGACGTTTCACCGCTTCC CAAGATAAGGGCAAAAACATCGCTTATCTCCAGATGAACAGTTTGAAGCCTGAG GACACAGCGATGTATTACTGTAAGGCTTCCTGCGTGAGAGGCCGCGCTATCTCT GAATATTGGGGACAGGGCACTCAGGTGACTGTGTCTTCA |
| DR592-hIL27 Ra_VH H5 | 1012 | CAGGTGCAGCCCCAGGAGTCTGGGGGTGGCTCCGTCCAGGCTGGCGGAAGCCTG CGCCTGTCCTGTACCGCTCCGGGTTTCACAAGTAACAGTTGTGGAATGGATTGG TATCGCCAGGCCCCCGGAAAGGAACGGGAGTTCGTCTCTAGCATCTCAACTGAC GGCACTACCGGCTACGCCGACTCCGTGAAGGGCCGTTTCACCATTAGCAAGGAC AAGGCCAAAGACACGGTGTACCTCCAGATGAACTCCCTGAAGCCCGAGGATACC GGGATGTATAGCTGTAAGACCAAGGACGGTACTATCGCTACGATGGAGCTGTGT GACTTCGGATACTGGGGCCAGGGGACCCAGGTGACTGTTTCCAGCGGTGGCTCC GGTGGGTCCGGCGGTTCTGGCCAGGTGCAGCTTCAGGAGTCCGGCGGTGGGAGC GTCCAAGCTGGCGGTTCCCTGCGCTTGAGTTGCACAGCATCTGGCTATGTGTCC |

TABLE 1B-continued

| Name | SEQ ID NO: | Sequence |
| --- | --- | --- |
| | | TGTGACTATTTCTTGCCATCCTGGTACAGACAAGCGCCTGGTAAGGAGAGAGAG TTCGTGTCCGTGATTGATGGGACGGGCTCAACAAGCTATGCCGCTTCCGTTAAA GGAAGGTTTACCGCTTCTCAAGATAAAGGGAAGAACATCGCTTATCTCCAGATG AATAGCCTCAAACCAGAGGATACTGCTATGTATTACTGCAAGGCATCTTGTGTG CGTGGACGTGCAATCTCCGAGTATTGGGGACAAGGCACCCAGGTTACAGTGTCT TCA |
| DR592-hIL27 Ra_VH H6 | 1013 | CAGGTGCAGCTCCAGGAGTCTGGAGGTGGCTCCGTTCAGGCTGGCGGAAGCCTG CGGTTGAGCTGTACTGCCCCTGGATTTACCTCCAATTCTTGTGGCATGGATTGG TATAGACAGGCTCCAGGGAAAGAGCGCGAGTTTGTCTCCAGCATTTCCACCGAT GGTACGACTGGTTATGCCGACAGCGTTAAGGGTAGATTTACAATCAGTAAGGAC AAAGCTAAGGACACAGTGTATTTGCAGATGAACTCTCTGAAACCGGAGGATACA GGTATGTATAGTTGTAAGACAAAAGATGGCACCATTGCTACTATGGAACTTTGT GACTTCGGCTACTGGGGACAGGGCACTCAGGTAACAGTCTCTAGCGGTGGAGGC TCTCAAGTGCAGCTTCAGGAGTCTGGGGGAGGCCTCGTCCAGCCGGGAGGCTCC TTGCGCCTGAGCTGTGCCGCTTCTGGTTTTTCATTTAGCTCCTATGCTATGAAA TGGGTGCGCCAGGCTCCCGGCAAGGGCCTGGAGTGGGTCTCCACGATTTCCTCT GGGGGCTCAAGCACCAACTACGCCGACAGCGTAAAGGGCCGTTTACCATCTCT CGGGACAACGCCAAAAACACCCTGTACCTTCAGTTGAACTCACTGAAAATCGAG GATACTGCAATGTATTACTGTGCCAAGGCCATCGTCCCAACCGGAGCTACAATG GAAAGGGGCCAGGGGACCCAGGTCACCGTGAGTAGC |
| DR592 hIL27 Ra_VH H6 | 1014 | CAGGTGCAGTTGCAGGAATCTGGTGGAGGCAGCGTGCAAGCTGGAGGCTCTCTG AGGTTGAGCTGCACCGCCCCTGGGTTTACAAGCAACCCATGTGGCATGGACTGG TATCGGCAAGCGCCTGGGAAAGAGCGCGAATTTGTAAGCTCTATCTCTACTGAC GGCACAACCGGCTACGCAGATAGCGTGAAGGGCAGGTTCACCATCTCAAAGGAT AAAGCCAAGGATACCGTGTACCTGCAAATGAACTCCCTTAAACCCGAGGATACC GGCATGTATAGCTGCAAGACCAAGGACGGCACCATCGCAACGATGGAGCTGTGC GACTTCGGTTATTGGGGACAGGGAACCCAGGTGACCGTTAGTTCCGGTGGCTCA GGCGGTAGCGGAGGCAGTGGCCAGGTGCAGTTGCAAGAGAGCGGAGGTGGGCTG GTGCAGCCAGGGGGCTCCCTGCGTCTGTCCTGCGCAGCCAGCGGCCTTAGCTTT TCCAGCTATGCCATGAAATGGGTTCGGCAAGCGCCTGGGAAGGGTCTGGAATGG GTGTCCACTATCTCCTCAGGGGGCTCCTCTACAAACTACGCAGATTCAGTGAAG GGTCGGTTTACTATTTCTAGGGACAACGCGAAGAACACCCTGTACCTTCAGTTG AACTCCCTCAAGATTGAGGATACTGCCATGTACTATTGCGCGAAGGCCATCGTA CCCACCGGCGCTACAATGGAGAGGGGCCAGGGCACCCAAGTAACTGTCTCCTCA |
| DR592-hIL27 Ra_VH H7 | 1015 | CAAGTGCAGTTGCAGGAGAGCGGTGGGGGATCTGTCCAGGCCGGAGGCAGTCTC CGCCTGTCCTGCACTGCCCCTGGCTTCACCTCTAACAGTTGTGGCATGGACTGG TATCGCCAGGCCCCTGGTAAAGAGCGCGAATTTGTCAGCTCAATCAGTACAGAT GGCACAACTGGTTATGCTGACAGCGTTAAGGGCCGCTTTACGATCAGCAAAGAC AAGGCTAAAGATACTGTGTACCTCCAGATGAACAGCCTCAAGCCTGAAGACACC GGAATGTATAGCTGTAAGACCAAGGACGGCACCATTGCGACAATGGAACTGTGC GACTTTGGCTATTGGGGCCAAGGGACCCAGGTCACAGTCAGCAGTGGAGGGGGC AGCCAGGTGCAGTTGCAGGAATCAGGGGGTGGCCTTGTGCAGCCTGGGGGGAGT CTGCGCCTGTCATGTGCGGCCTCCGGGTTCACCCTCAGCTCCTACCCAATGTCT TGGGTGAGGCAGGCACCTGGCAAGGGCCTGGAGTGGATCAGCACTATCAGCGCA GGCGGTGACACCACTCTGTACGCAGACAGCGTGAAGGGAAGATTCACCAGTAGC CGCGATAACGCGAAGAACACACTGTATCTCCAGCTCAATTCACTCAAGACCGAG GACACTGCCATCTACTATTGTGCCAAACGCATTGATTGTAATTCTGGCTACTGC TATCGGCGTAACTACTGGGGACAGGGCACCCAGGTTACCGTCAGTTCC |
| DR592-hIL27 Ra_VH H7 | 1016 | CAGGTTCAGCTTCAAGAGAGTGGAGGTGGGTCCGTCCAGGGGGGAGGCTCACTG CGGCTGTCTTGCACCGCTCCTGGTTTCACTAGCAACTCCTGCGGCATGGATTGG TATAGGCAAGCCCCTGGTAAGGAAGGTGAGTTTGTTTCTTCCATCTGCACAGAT GGTACTACCGGGTATGCTGACAGTGTGAAAGGCCGTTTTACCATCTCCAAGGAC AAGGCAAAGGACACCGTGTACCTCCAGATGAACAGTCTTAAACCCGAGGACACC GGCATGTACTCTTGTAAGACAAAGGATGGCACAATCGCCACTATGGAGCTGTGT GATTTCGGGTACTGGGGCCAGGGCACACAGGTGACTGTGTCAAGCGGGGGAAGC GGAGGCAGCGGTGGCTCAGGCCAGGTCCAGCTCCAGGAGTCCGGCGGTGGACTG GTTCAACCGGGTGGCAGCCTCCGTGTGTCCTGCGCCGCGAGTGGATTCACGTTC AGTAGCTACCCCATGTCTTGGGTCAGACAGGCTCCCGGCAAAGGTCTCGAATGG ATCTCTACAATCTCTGCCGGTGGGGACACAACCCTGTATGCGGATAGCGTGAAA GGGAGATTCACCAGCAGTAGGGACAACGCTAAGAACACCCTGTATCTTCAGCTG AACAGCCTGAAAACCGAAGACACAGCGATCTATTACTGTGCAAAGAGAATTGAT TGCAACAGCGGGTATTGCTACCGTCGCAACTATTGGGGGCAGGGAACCCAAGTC ACTGTGTCCTCC |
| DR592-hIL27 Ra_VH H8 | 1017 | CAGGTGCAGCCCCAGGAATCCGGTGGAGGTTCTGTGCAGGCCGGTGGCAGCCTC CGTCTTAGCTGCACCGCTCCGGGGTTTACCTCCAACAGCTGTGGTATGGATTGG TATCGTCAGGCCCCTGGTAAGGAGCGGGAGTTTGTGTCTTCCATTTCAACTGAT GGCACCACTGGTTACGCCGACAGCGTAAAGGGTCGTTTCACAATCAGTAAGGAT AAGGCAAAGGACACCGTCTATTTGCAGATGAACAGCCTGAAGCCGGAAGACACA GGGATGTACTCTTGCAAGACAAAGGACGGCACGATTGCTACGATGGAGCTGTGT GACTTCGGCTACTGGGGCCAGGGTACACAGGTGACCGTGTCCAGCGGGGGGGGC AGTCAGGTTCAGTTGCAGGAGTCCGGCGGTGGCAGCGTCCAGGTGGGGGTAGC CTGCGCCTGTCCTGTGCTGCATCCGGCTTTACCTTCTCTAGTTATCCAATGAGT |

TABLE 1B-continued

| Name | SEQ ID NO: | Sequence |
|---|---|---|
| | | TGGGTCCGCCAGGCTCCAGGGAAAGGTCTGGAATGGATCTCCACCATTTCCGCA GGTGGGGACACCACACTGTACGCCGATAGCGTGAAGGGCAGATTCACCAGCTCC AGAGACAATGCCAAAAACACTTTGTACCTCCAGCTGAATAGCCTGAAGACCGAG GATACCGCCATCTACTATTGTGCCAAGCGTATTGATTGTAATTCCGGCTATTGT TATCGCAGAAACTACTGGGGCCAGGGCACACAGGTCACTGTATCTAGC |
| DR592-hIL27 Ra_VH H8 | 1018 | CAGGTGCAGCTCCAGGAGAGCGGCGGTGGCTCTGTCCAGGCTGGGGGAAGTCTG CGTTTGTCTTGCACTGCACCCGGATTCACCTCAAATTCCCGCGGTATGGATTGG TACAGACAAGCGCCTGGCAAGGAGCGTGAATTTGTAAGCTCCATTAGCACCGAC GGGACCACTGGCTATGCTGATAGCGTGAAGGGCCGCTTCACCATTTCTAAGGAT AAGGCTAAAGACACCGTGTACCTCCAGATGAACTCCTTGAAGCCAGAGGATACC GGGATGTATTCTTGTAAGACCAAGGACGGCACCATCGCAACTATGGAACTCTGT GACTTCGGTTACTGGGGGCAGGGAACCCAAGTGACAGTCTCTTCCGGGGGCTCC GGCGGTTCTGGCGGATCTGGGCAGGTGCAACTTCAGGAATCCGGTGGAGGTAGC GTCCAGGTGGGAGGCTCCCTGCGCCTGAGTTGTGCCGCAAGTGGCTTCACCTTC TCATCCTACCCCATGTCTTGGGTACGCCAGGCTCCCGGCAAGGGCCTGGAGTGG ATCTCCACCATCTCCGCCGGAGGTGACACTACCCTGTACGCCGACTCCGTGAAG GGCCGCTTTACAAGCTCCCGTGACAACGCTAAGAATACACTGTACCTCCAGCTT AATTCACTGAAGACCGAAGACACGGCTATCTACTATTGCGCCAAGCGCATTGAT TGTAACAGCGGGTACTGTTACAGGAGAAACTATTGGGGACAGGGCACACAGGTG ACTGTGTCCTCC |
| DR592-hIL27 Ra_VH H9 | 1019 | CAGGTTCAGCTCCAGGAGAGCGGCGGAGGCAGCGTGCAGGCTGGTGGCAGTCTG CGCCTGAGCTGCACAGCCCCCGGCTTCACCAGTAACAGCCGTGGAATGGACTGG TATCGTCAAGCGCCTGGCAAGGAAAGGGAGTTCGTGTCTAGTATCAGCACCGAT GGCACCACAGGATACGCCGACTCCGTGAAGGGACGCTTCACTATCTCAAAGGAT AAGGCAAAAGATACAGTGTATCTCCAGATGAACTCCCTCAAGCCTGAAGACACA GGCATGTACTCTTGTAAGACCAAGGACGGCACTATCGCTACTATGGAGTTGTGC GACTTCGGATACTGGGGACAAGGAACCCAGGTCACCGTATCCTCAGGGGGAGGT TCACAGGTGCAGCTTCAGGAGTCCGGTGGCGGTTCTGTGCAGAGTGGAGGCTCC CTGCGTTTGAGTTGCGCAGCCAGTGGCTTCACCTACTCTACTAGCAACAGCTGG ATGGCGTGGTTCCGCCAGGCCCCCGGCAAAGAACGCGAGGGCGTTGCCGCTATT TACACCGTGGGCGGTTCCATTTTCTACGCCGATTCCGTGCGTGGCAGGTTTACT ATCTCTCAGGATGCCACTAAAAATATGTTCTACCTGCAAATGAACACACTGAAG CCCGAGGACACCGCTATGTATTACTGCGCAGCCGCTTCTGGCCGCCTGAGAGGC AAGTGGTTTTGGCCCTACGAGTACAATTACTGGGGTCAGGGCACCCAGGTGACG GTGTCTAGC |
| DR592-hIL27 Ra_VH H9 | 1020 | CAGGTGCAACTCCAGGAGTCTGGAGGGGGCTCTGTCCAGGCCGGAGGCTCTCTC CGTCTGAGCTGCACCGCTCCCGGCTTCACCAGTAATAGCTGCGGTATGGACTGG TACAGACAGGCTCCAGGCAAGGAGAGAGAATTTGTCAGCTCCATTTCTACTGAT GGGACTACGGGCTACGCCGACTCCGTGAAGGGCCGCTTTACCATCTCTAAGGAT AAGGCTAAGGACACCGTATATTTGCAGATGAACTCCCTGAAGCCAGAAGATACT GGCATGTATAGCTGCAAGACGAAGGATGGAACCATCGCCACTATGGAATTGTGC GATTTCGGTTACTGGGGCCAGGGAACACAGGTGACTGTGAGTTCCGGGGGCTCA GGCGGGGTCTGGAGGCTCTGGACAGGTGCAACTCCAGGAGAGCGGAGGGGGTTCA GTCCAGTCTGGGGGCTCCCTTCGCCTGAGTTGCGCTGCCAGTGGCTTTACCTAC AGTACCAGCAACTCCTGGATGGCGTGGTTCAGACAGGCACCCGGAAAGGAACGC GAAGGCGTGGCTGCCATCTACACAGTCGGGGGCTCCATCTTCTACGCTGACTCC GTTAGAGGCCGCTTCACCATTTCTCAGGATGCCACCAAAAATATGTTCTATCTG CAAATGAACACCTTGAAGCCCGAGGACACCGCCATGTATTACTGCGCAGCTGCC AGCGGACGGCTTCGCGGTAAGTGGTTCTGGCCGTATGAGTATAACTACTGGGGA CAGGGCACCCAGGTCACGGTGAGTTCT |
| DR592-hIL27 Ra_VH H10 | 1021 | CAAGTGCAGTTGCAGGAAAGTGGAGGGGGGTTCCGTGCAGGCAGGAGGCAGTCTG AGGCTGAGTTGTACCGCGCCTGGCTTTACCTCAAACAGTTGCGGCATGGACTGG TATAGGCAGGCCCCAGGCAAGGAGCGCGAGTTTGTCTCAAGCATCTCCACCGAT GGAACCACTGGCTACGCCGACTCCGTCAAGGGAAGGTTCACTATCTCCAAGGAT AAGGCCAAGGACACCGTGTATCTCCAGATGAACTCATTGAAGCCAGAAGACACC GGGATGTACTCCTGTAAAACCAAGGACGGCACGATTGCGACAATGGAACTGTGT GATTTCGGTTACTGGGGTCAGGGAACGCAGGTGACCGTGTCTAGCGGGGGGGGT TCCCAGGTTCAGCTCCAGGAGAGCGGTGGGGCTCTGTGCAGGCCGGTGGAAGT CTGCGTCTGAGCTGTCGCGCCTCTGGCTCCACATACTCCAACTATTGCCTGGGA TGGTTTCGGCAAATCACGGGTAAAGAAAGAGAGGGCGTGGCTGTCATCAACTGG GTGGGCGGAATGCTGTACTTCGCCGATAGTGTGAAGGGGCGCTTCACCGTTTCC CAGGATCAAGCTAAAAACACACTTTACCTTCAGATGAACAGTCTGAAACCCGAA GACACCGCAATGTATTACTGTGCCGCTGAGAGTGTCAGTTCCTTCTCATGCGGA GGTTGGCTTACGAGGCCTGATCGCGTGCCGTATTGGGGCCAGGGGACCCAGGTG ACCGTGAGTTCT |
| DR592-hIL27 Ra_VH H10 | 1022 | CAGGTGCAGTTGCAGGAATCCGGGGGAGGCTCCGTGCAGGCTGGGGGAAGCCTG AGACTTAGCTGCACTGCTCCCGGGATTTACGAGCAACAGCTGTGGCATGGACTGG TACAGACAGGCCCCTGGGAAGGAGCGCGAGTTCGTGTCAAGCATCAGCACTGAC GGCACAACTGGGTACGCTGATAGCGTGAAGGGCCGTTTTACCATCTCCAAGGAT AAGGCCAAAGACACTGTCTACCTGCAAATGAACTCCCTCAAGCCTGAGGACACC GGAATGTACTCCTGTAAGACTAAGGACGGGACCATTGCCACGATGGAGCTTTGT GACTTCGGCTATTGGGGACAGGGAACCCAGGTCACCGTCTCTAGTGGAGGCAGC |

TABLE 1B-continued

| Name | SEQ ID NO: | Sequence |
|---|---|---|
| | | GGCGGTAGTGGCGGGTCCGGCCAGGTTCAGCTCCAGGAGTCCGGTGGCGGATCT<br>GTGCAAGCAGGAGGCAGCCTGCGCCTTAGCTGCCGTGCGAGCGGCAGCACTTAC<br>AGCAATTATTGTCTGGGTTGGTTTCGTCAGATCACTGGTAAAGAACGGGAGGGC<br>GTGGCCGTCATCAACTGGGTCGGCGGTATGCTGTACTTCGCGGACAGCGTCAAA<br>GGCCGGTTTACCGTGTCTCAGGACCAGGCGAAGAACACATTGTACCTCCAGATG<br>AATAGCCTGAAGCCTGAGGATACAGCTATGTATTACTGTGCAGCGGAGTCCGTC<br>TCTTCATTCAGCTGTGGTGGATGGCTCACGAGACCGGATAGAGTGCCATACTGG<br>GGCCAGGGCACCCAGGTGACCGTGTCCAGC |
| DR592-<br>hIL27<br>Ra_VH<br>H11 | 1023 | CAGGTGCAGTTGCAGGAGTCTGGTGGCGGTTCCGTTCAGGCAGGCGGTTCCCTG<br>AGACTGTCCTGCACCGCCCCTGGTTTTACCTCCAACTCCTGTGGCATGGATTGG<br>TATCGCCAGGCACCAGGCAAGGAACGCGAGTTCGTATCTTCCATTAGCACTGAC<br>GGCACAACTGGTTACGCCGATTCAGTCAAGGGGCGCTTTACAATCAGTAAGGAC<br>AAGGCTAAGGATACCGTTTACTTGCAGATGAATAGCCTGAAACCAGAGGACACC<br>GGAATGTACTCTTGCAAAACTAAAGACGGCACCATTGCAACTATGGAACTCTGT<br>GACTTTGGGTATTGGGGTCAAGGCACTCAAGTGACCGTCTCCTCTGGGGGGGGC<br>TCTCAGGTCCAGTTGCAGGAAAGCGGGGGAGGGAGCGTGCAGGCTGGAGGTAGT<br>CTCAGGCTGTCTTGCCGCGCCAGCGGAAGCACCTACTCAAACTACTGCCTTGGC<br>TGGTTTAGACAGAGCACTGGTAAGGAGCGGGAGGGAGTGGCCGTCATCAACTGG<br>GTCGGTGGGATGCTGTATTTCGCTGATAGCGTAAAGGGAAGATTTACGGTAAGC<br>CAGGATCACGCAAAGAACACCGTGACCCTCCAGATGAACTCTCTGAAGCCCGAG<br>GACACTGCCATGTACTATTGCGCAGCCGAATCCGTCAGTTCCTTCTCCTGCGGC<br>GGATGGCTGACCCGCCCCGGAAGAGTTCCATATTGGGGTCAGGGGACCCAGGTG<br>ACAGTTTCTTCT |
| DR592-<br>hIL27<br>Ra_VH<br>H11 | 1024 | CAGGTGCAACTCCAGGAGAGCGGTGGAGGTAGCGTGCAGGCTGGCGGTTCCCTG<br>CGGCTGTCCTGCACCGCTCCGGGTTTTACCTCCAACTCCCGGGGGATGGATTGG<br>TACAGACAGGCCCCCGGAAAGGAGCGCGAGTTTGTGTCTTCCATTAGCACCGAC<br>GGCACAACCGGCTATGCAGACAGTGTCAAGGGACGGTTCACAATCCCCAAGGAC<br>AAAGCTAAAGACACGGTGTATCTTCAGATGAACAGCTTGAAGCCTGAAGATACT<br>GGTATGTATTCCTGCAAAACCAAGGATGGTACTATCGCCACTATGGAACTCTGC<br>GATTTCGGATATTGGGGACAGGGGACCCAGGTGACGGTGTCTAGCGGGGGCTCA<br>GGTGGGTCTGGAGGCTCTGGTCAGGTGCAACTCCAGGAGAGCGGGGGGGGAAGC<br>GTTCAGGCCGGGGGCAGCCTGCGGCTGTCCTGCCGGGCTAGTGGATCTACGTAC<br>TCCAACTACTGCCTGGGATGGTTTCGCCAATCTACTGGAAAGGAGCGTGAGGGG<br>GTGGCCGTCATCAACTGGGTGGGCGGAATGTTGTATTTTGCCGATTCTGTCAAA<br>GGAAGGTTCACTGTGTCTCAGGACCATGCCAAGAACACCGTCACCCTCCAGATG<br>AACTCTTTGAAGCCGGAAGATACCGCTATGTATTACTGGGGGGCAGAAAGCGTG<br>AGTAGCTTCTCTTGCGGTGGGTGGCTGACACGTCCGGGTAGGGTGCCGTACTGG<br>GGCCAGGGAACTCAGGTAACCGTCTCATCC |
| DR592-<br>hIL27<br>Ra_VH<br>H12 | 1025 | CAGGTCCAACTCCAGGAATCCGGGGGGGGCTCCGTACAGGCAGGTGGCAGTCTG<br>AGGCTTTCCTGCACTGCCCCTGGTTTCACCAGCAACAGCTGTGGGATGGACTGG<br>TATCGCCAGGCTCCCGGCAAAGAGCGGGAGTTCGTCAGCTCTATCTCAACCGAC<br>GGCACAACCGGGTATGCCGACTCCGTTAAAGGCCGGTTCACCATCAGCAAAGAC<br>AAGGCCAAGGATACAGTCTACCTCCAGATGAACAGCCTGAAGCCTGAGGATACC<br>GGAATGTATAGTTGCAAAACTAAGGATGGCACTATCGCCACTATGGAGTTGTGC<br>GATTTCGGATACTGGGGACAGGGCACCCAGGTTACCGTCTCATCTGGAGGGGGC<br>TCCCAGGTGCAGCTGCAAGAATCCGGCGGAGGCAGTGTCCAGGCTGGCGAATCC<br>CTCCGCTTGAGCTGTCGTGCCAGCGGTAGTACCTACTCCAATTACTGCCTGGGT<br>TGGTTTCGCCAGATCACCGGCAAGGAACGTGAAGGCGTGGCCGTCATCAACTGG<br>GTAGGGGGTATGCTCTACTTCGCTGACTCCGTGAAGGGACGCTTCACGGTGAGT<br>CAGGACCAGGCTAAAAACACCGTGTACCTTGAAATGAACTCCTTGAAGCCCGAG<br>GACACCGCTATGTATTACTGCGCCACAGAGTCTGTTTCTTCCTTCTCATGCGGA<br>GGCTGGCTGACTCGTCCAGACCGCGTGCCCTACTGGGGCCAGGGGACCCAGGTG<br>ACCGTGTCCTCA |
| DR592-<br>hIL27<br>Ra_VH<br>H12 | 1026 | CAAGTTCAGTTGCAGGAGAGTGGAGGCGGTTCTGTCCAGGCTGGGGGTAGTTTG<br>CGGTTGAGTTGCACCGCGCCTGGGTTCACCTCCAACAGCTGTGGTATGGATTGG<br>TATCGCCAGGCCCCCGGCAAGGAGCGCGAGTTCGTGAGTTCCATCAGCACCGAC<br>GGCACCACTGGTTACGCAGACTCAGTGAAGGGAAGATTCACCATCAGCAAGGAC<br>AAAGCCAAGGACACTGTGTATCTTCAGATGAATAGCCTCAAGCCGGAGGATACT<br>GGCATGTATTCCTGCAAGACCAAGGACGGCACCATCGCTACGATGGAGTTGTGT<br>GATTTCGGGTACTGGGGACAGGGAACCCAGGTAACTGTGAGTAGCGGAGGTAGC<br>GGGGGAAGCGGCGGGGTCAGGGCAGGTACAGCTTCAGGAGTCCGGGGGGGGTCC<br>GTTCAGGCCGGTGAGTCCTTGCGCCTGAGCTGCCGCGCCAGCGGTTCCACCTAC<br>AGTAACTATTGTCTGGGCTGGTTTCGTCAGATCACAGGCAAGGAGCGCGAGGGC<br>GTTGCTGTCATTAACTGGGTTGGCGGAATGCTGTATTTTGCCGACAGCGTGAAG<br>GGTCGTTTCACGGTATCCCAAGACCAAGCAAAGAACACTGTCTATCTTGAAATG<br>AACAGTCTGAAACCAGAAGACACCGCCATGTACTATTGTGCCACCGAGTCCGTA<br>TCCAGTTTCTCCTGCGGCGGATGGCTGACCAGACCTGACCGTGTGCCATACTGG<br>GGACAGGGGACACAGGTGACTGTGTCCAGC |
| DR592-<br>hIL27<br>Ra_VH<br>H13 | 1027 | CAGGTGCAGCTCCAGGAGTCCGGGGGAGGCCCTGTGCAGGCCGGGGGTTCCCTG<br>AGACTTTCATGTACTGCACCAGGCTTTACCTCAAATTCTTGCGGGATGGACTGG<br>TACAGGCAGGCCCCCGGTAAGGAGCGGGAGTTTGTGTCTTCCATTTCCACCGAT<br>GGTACAACCGGCTACGCGGACTCTGTGAAGGGCCGCCTTACCATTTCTAAGGAC |

TABLE 1B-continued

| Name | SEQ ID NO: | Sequence |
|---|---|---|
| | | AAGGCTAAAGACACCGTCTATCTCCAGATGAACTCTTTGAAGCCTGAAGACACA GGCATGTATAGCTGCAAGACAAAGGATGGCACCATTGCCACGATGGAGTTGTGC GACTTTGGCTATTGGGGTCAGGGCACCCAGGTCACTGTGTCTTCCGGGGGGGGC TCTCAGGTCCAACTCCAGGAGAGCGGGGGAGGGTCTGTTCAGGCTGGTGGCTCA CTGCGCCTCAGTTGCGTGGCCTCTGGATACGTGTCCTGTGACTACTTTCTGCCC TCTTGGTACAGACAGGCCCCAGGCAAAGAGCGCGAGTTCGTGAGCATCATTGAC GGTACTGGCTCTACAAGCTACGCGGCCTCCGTCAAGGGCCGTTTCACTGCCTCC CAAGACAGAGGTAAAAACATCGCTTATCTCCAGATGAACAGCCTGAAGCCCGAG GATACGGCTATGTACTATTGCAAGGCCAGCTGTGTACGTGGACGCACTATCTCT GAGTACTGGGGCCAGGGGACACAAGTGACGGTGTCCTCC |
| DR592-hIL27 Ra_VH H13 | 1028 | CAGGTGCAGCTTCAAGAGAGCGGAGGCGGGTCTGTGCAGGCTGGTGGGTCCCTC CGCCTGTCATGCACTGCCCCCGGCTTCACTTCTAACAGCCGCGGCATGGACTGG TATCGCCAGGCCCCAGGCAAAGAGCGCGAGTTTGTATCATCCATCTCCACCGAC GGCACGACTGGCTACGCCGACTCCGTGAAGGGCCGGTTCACCATCAGCAAGGAC AAAGCCAAGGATACCGTGTACCTCCAGATGAACTCCCTCAAACCCGAAGACACT GGGATGTACTCATGCAAGACAAAAGACGGTACGATTGCCACTATGGAGCTGTGT GATTTCGGATACTGGGGACAGGGAACTCAGGTGACCGTTTCCTCTGGAGGCAGT GGAGGGAGCGGAGGCTCCGGCCAGGTGCAGCTGCAAGAGAGCGGTGGCGGTAGC GTGCAAGCCGGAGGCTCCCTCCGTCTTTCTTGTGTCGCGAGCGGCTACGTGAGC TGTGATTACTTTCTGCCCAGCTGGTATCGTCAAGCGCCAGGCAAAGAGCGCGAA TTTGTGTCTATTATCGACGGCACCGGCAGCACGAGCTACGCAGCCCCCCGTGAAG GGACGTTTCACTGCTTCACAGGATCGCGGCAAAAACATTGCTTACCTCCAGATG AACTCCCTGAAGCCTGAGGACACAGCAATGTATTACTGTAAGGCCTCCTGTGTG CGTGGACGCACCATCTCAGAGTACTGGGGACAGGGAACCCAGGTGACCGTATCT TCC |
| DR592-hIL27 Ra_VH H14 | 1029 | CAGGTTCAGCTTCAGGAGTCCGGGGGTGGGTCCGTCCAAGCTGGTGGCTCACTG CGCCTGTCCTGCACCGCCCCTGGCTTCACCTCCAATTCCTGCGGAATGGACTGG TATCGCCAGGCCCCAGGCAAAGAACGCGAGTTCGTCAGTAGCATCTCTACTGAT GGAACCACAGGCTACGCGGACAGCGTGAAGGGGCGTTTCACTATCTCCAAGGAC AAGGCCAAGGACACCGTGTACCTTCAAATGAACTCCCTGAAGCCCGAGGATACT GGAATGTACTCCTGTAAGACCAAGGACGGGACTATCGCCACTATGGAGCTGTGT GACTTCGGATATTGGGGCCAGGGCACGCAGGTGACCGTCAGCTCTGGGGGGGGG TCCCAGGTCCAGCTTCAGGAAAGTGGAGGCGGGTCCGTGCAGGCCGGAGGTTCC CTCCGCCTGTCATGTGTCGCAAGCGGCTACGTGTCTTGCGACTACTTCCTGCCC TCCTGGTATCGCCAGGCTCCGGGCAAGGAGAGAGAGTTCGTAAGCATCATTGAT GGCACCGGCTCTACTTCTTACGCCGCTAGTGTGAAGGGCCGCTTCACAGCGTCC CAGGATAAGGGTAAAAACATCGCTTACTTGCAGATGAATAGCCTGAAGCCCGAG GACACGGCAATGTATTACTGTAAGGCCTCCTGTGTTAGAGGCCGCGCTATTTCT GAATACTGGGGACAGGGCACTCAGGTGACAGTCTCCTCC |
| DR592-hIL27 Ra_VH H14 | 1030 | CAGGTGCAGCTTCAGGAGTCCGGTGGGGGCTCTGTGCAGGCTGGAGGTTCCCTT CGCCTGTCATGTACTGCCCCTGGGTTCACTTCTAACTCCTGTGGTATGGACTGG TATCGTCAGGCCCCTGGGAAGGAGCGTGAGTTCGTCAGCTCCATCTCTACTGAT GGCACTACCGGCTATGCCGATTCTGTGAAGGGGCGTTTTACCATCAGCAAGGAC AAGGCCAAGGATACCGTGTACCTGCAAATGAACAGCTTGAAGCCTGAGGACACT GGCATGTATTCTTGTAAAACCAAAGACGGCACCATCGCCACAATGGAGCTGTGT GACTTTGGCTACTGGGGCCAGGGCACTCAAGTGACCGTGTCCTCAGGGGGGTCT GGCGGATCTGGGGGAAGCGGACAGGTGCAGCTTCAGGAGAGCGGAGGTGGCTCT GTCCAGGCCGGTGGGTCCCTGAGACTGTCTTGCGTGGCCAGTGGGTACGTGAGC TGCGATTACTTCCTCCCCAGTTGGTATAGGCAGGCCCCTGGAAAGGAACGTGAG TTCGTAAGCATCATTGACGGCACCGGCTCTACTTCTTATGCGGCCTCCGTAAAG GGCCGCTTCACTGCTTCCCAGGACAAGGGTAAGAATATCGCCTACCTTCAGATG AACAGCCTGAAACCCGAAGACACGGCTATGTATTACTGCAAGGCTTCCTGCGTA AGAGGGAGAGCAATCTCCGAGTATTGGGGCCAGGGCACCCAGGTGACTGTGTCT TCA |
| DR592-hIL27 Ra_VH H15 | 1031 | CAGGTGCAGCTCCAGGAGAGCGGGGGGGGCTCCGTACAAGCGGGGGGTTCCCTC CGTCTGTCTTGTACCGCCCCAGGCTTCACCAGTAACTCCTGTGGCATGGACTGG TACAGACAGGCTCCTGGCAAAGAAAGAGAGTTCGTATCCAGCATCTCCACCGAC GGCACCACAGGCTACGCGGATTCAGTTAAGGGCAGATTTACGATCTCCAAGGAT AAGGCTAAAGATACTGTGTACCTCCAGATGAATAGCCTGAAGCCGGAAGACACC GGCATGTATAGCTGTAAGACTAAGGATGGCACCATTGCCACAATGGAGCTGTGC GACTTCGGCTACTGGGGTCAGGGAACACAGGTGACGGTGTCCTCTGGTGGCGGT AGCCAGGTTCAGTTGCAGGAATCTGGAGGTGGCTCTGTGCAGGCCGGTGGATCT CTGCGTCTGTCTTGCGTGGCCTCCGGCTACGTGAGTTGCGACTATTTCCTTCCC AGCTGGTATCGCCAGGCTCCAGGCAAGGAACGCGAGTTTGTGTCCATTATCGAC GGAACAGGCAGCACATCCTACGCAGCTAGTGTTAAGGGTAGATTCACTGCGAGC CAGGACAAGGGCAAAAACATCGCTTATCTTCAGATGAATACCCTCAAACCTGAG GACACCGCCATGTATTACTGCAAGGCCAGCTGTGTGCGTGGCCGCGCTATCTCT GAATATTGGGGCCAGGGCACCCAGGTGACAGTTTCCTCT |
| DR592-hIL27 Ra_VH H15 | 1032 | CAGGTGCAGCTCCAGGAGAGCGGGGGAGGCTCAGTGCAGGCCGGGGGTTCATTG AGGCTGTCCTGCACCGCCCCAGGGTTTACTAGCAACTCTTGTGGGATGGATTGG TATCGTCAGGCCCCTGGGAAGGAACGTGAGTTCGTTTCTAGTATCTCAACCGAT GGTACAACCGGCTATGCAGACTCCGTAAAGGGCCGGTTCACGATCTCCAAAGAT |

TABLE 1B-continued

| Name | SEQ ID NO: | Sequence |
|---|---|---|
| | | AAGGCTAAGGACACTGTTTATCCGCAAATGAACTCCCTGAAGCCTGAGGACACC GGCATGTACTCCTGTAAGACTAAGGACGGCACCATCGCTACGATGGAGTTGTGC GACTTCGGATATTGGGGTCAGGGAACCCAGGTTACTGTGTCTAGCGGGGGCAGC GGTGGCAGCGGGGGATCTGGCCAGGTGCAGTTGCAGGAATCCGGGGGGGGTTCA GTGCAGGCAGGAGGCTCTCTTCGGTTGTCCTGCGTCGCGAGTGGCTATGTGTCT TGTGATTACTTCCTGCCATCCTGGTATCGTCAGGCCCCAGGGAAGGAACGTGAG TTCGTGTCCATCATTGATGGCACTGGCAGTACTTCCTACGCCGCCTCCGTGAAG GGTAGGTTTACAGCGAGTCAGGATAAGGGTAAGAACATCGCCTATCTCCAGATG AACACCCTGAAACCGGAGGACACAGCCATGTACTATTGCAAGGCCTCTTGTGTG CGTGGCCGCGCAATTAGCGAGTACTGGGGACAGGGTACACAGGTTACCGTCTCC TCC |
| DR592-hIL27 Ra_VH H16 | 1033 | CAGGTCCAGCTCCAGGAGAGTGGTGGGGGCAGCGTGCAGGCCGGAGGCTCTCTT AGACTCTCTTGCACCGCCCCCGGCTTCACATCCAACTCCTGTGGCATGGACTGG TATCGCCAGGCTCCCGGCAAGGAGAGGGAATTTGTGTCCAGCATTTCTACCGAC GGAACCACAGGCTACGCTGACAGCGTTAAGGGACGTTTCACTATCAGCAAGGAT AAGGCCAAGGACACCGTATACCTCCAGATGAACTCCCTCAAACCCGAGGACACC GGCATGTATAGCTGTAAAACCAAGGATGGAACCATCGCGACTATGGAGCTGTGC GATTTCGGCTACTGGGGCCAGGGCACTCAAGTGACTGTTTCTAGCGGGGGGGGC AGCCAGGTGCAGCTTCAGGAGTCTGGCGGAGGCAGCGTCCAAGCTGGAGGTAGC CTGCGGCTCTCCTGTCGCGCTTCTGGCTCTACGTACAGTAATTATTGCCTGGGT TGGTTCAGACAGATCACCGGCAAAGAACGCGAGGGTGTTGCAGTCATCAACTGG GTTGGGGGAATGCTGTATTTTGCCGACAGTGTGAAGGGCAGGTTCACGGTCAGC CAAGACCAGGCCAAGAATACCGTCTACCTCCAGATGAACTCTTTGAAACCCGAA GACACCGCCATGTACTATTGTGCTGCGGAGTCAGCTTCATCTTTCTCTTGCGGA GGCTGGCTGACCCGTCCAGACCGCGTACCTTACTGGGGCCAGGGGACCCAGGTG ACCGTCTCCTCC |
| DR592-hIL27 Ra_VH H16 | 1034 | CAAGTCCAGCTGCAAGAGAGTGGAGGGGGCAGCGTTCAGGCCGGAGGCTCTCTG CGTCTTTCATGCACCGCGCCCGGTTTCACTTCCAACTCCTGGGGCATGGACTGG TATCGGCAGGCCCCAGGCAAGGAAAGGGAGTTCGTAAGCTCCATCTCCACTGAT GGAACAACCGGCTATGCCGATTCCGTCAAGGGCCGCTTCACCATCAGCAAGGAT AAGGCAAAAGACACTGTCTATCTGCAAATGAACTCTCTGAAGCCCGAAGACACC GGAATGTACTCTTGTAAAACTAAGGACGGCACCATTGCCACTATGGAGCTGTGT GATTTCGGGTACTGGGGCCAGGGCACCCAGGTGACGGTCTCTAGCGGGGGCTCA GGGGGCTCTGGTGGCTCTGGTCAGGTGCAGCTCCAGGAGTCCGGTGGCGGAAGC GTGCAGGCTGGAGGTAGTCTGCGCCTGTCTTGTCGTGCCAGCGGCAGCACATAT AGCAATTACTGCCCTGGCTGGTTTAGACAGATTACTGGTAAGGAGCGGGAGGGC GTGGCCGTAATAAATTGGGTTGGCGGGATGCTCTATTTTGCAGACTCAGTCAAG GGCCGCTTCACAGTGTCCCAGGATCAGGCCAAGAACACCGTGTATCTCCAGATG AACTCCCTGAAGCCGGAAGACACCGCCATGTACTATTGTGCCGCAGAGTCCGCT TCCTCCTTCTCTTGCGGCGGATGGCTGACACGTCCTGATCGTGTGCCCTATTGG GGACAGGGCACACAGGTCACCGTGTCCTCC |
| DR592-hIL27 Ra_VH H17 | 1035 | CAGGTTCAGCTGCAAGAGAGCGGCGGTGGCTCTGTGCAGGCTGGTGGCAGCTTG AGACTGTCCTGTACTGCGCCTGGCTTCACTTCCAATTCTTGGGGCATGGACTGG TATAGACAAGCTCCGGGAAAAGAACGCGAATTTGTGTCTTCCATTAGCACCGAC GGAACTACAGGCTATGCTGACAGCGTGAAGGGACGCTTTACCATCTCCAAGGAC AAGGCGAAGGATACCGTCTATTTGCAGATGAACAGTCTGAAACCAGAAGACACC GGCATGTATTCCTGCAAAACCAAAGATGGCACAATCGCCACTATGGAACTCTGT GATTTTGGCTACTGGGGCCAAGGGACCCAAGTTACCGTGTCTTCCGGCGGAGGC AGCCAAGTCCAGTTGCAAGAGTCAGGTGGGGGTCTGGTCCAGCCCGGAGGCTCT CTGAGGCTGAGTTGTGCCGCTTCCGGTTTCACATTCCCCCTGAGCGGTATGTCC TGGGTACGCCAGGCTCCCGGCAAGGGCCTCGAATGGGTGTCCGCGATCAGCTCT GGCGGGGCCTCCACTTATTACACAGACAGCGTTAAGGGGCGCTTCACAATCAGC CGCGATAACGCAAAGAATATGTTGTACTTGCAACTCAATTCTCTCAAGACAGAA GACACCGCGATGTATTACTGTGCTAAAGGGGGTTCCGGCTATGGCGATGCCTCT CGTATGACTTCACCCGGTAGCCAGGGAACCCAGGTGACCGTCTCTAGC |
| DR592-hIL27 Ra_VH H17 | 1036 | CAGGTGCAGCTCCAAGAGTCTGGGGGGGGTTCTGTGCAGGCAGGCGGGTCCTTG AGACTCTCTTGCACCGCCCCAGGCTTTACCAGCAATTCCTGTGGAATGGATTGG TACAGGCAAGCGCCCGGTAAAGAACGCGAGTTCGTCAGCTCTATTAGCACAGAC GGAACCACTGGCTATGCTGACTCAGTTAAGGGCCGGTTCACCATCAGTAAGGAT AAAGCCAAGGACACCGTGTACCTTCAGATGAACTCTCTGAAGCCCGAGGACACT GGCATGTATAGCTGTAAGACAAAAGACGGAACAATCGCGACTATGGAGTTGTGT GACTTCGGATACTGGGGTCAGGGAACGCAGGTGACCGTGTCCAGCGGCGGTTCT GGGGGTAGCGGGGGCAGCGGACAAGTTCAGCTCCAGGAAAGCGGAGGGGGGCTC GTGCAGCCTGGGGGCTCCCTCCGCCTGTCCTGTGCAGCCTCAGGCTTCACGTTT TCACTGTCTGGCATGAGCTGGGTTCGCCAGGCTCCCGGCAAAGGACTCGAATGG GTGTCCGCCATCTCTTCCGGCGGAGCCCCCACCTATTACACAGATTCCGTCAAA GGACGCTTCACTATCTCACGTGATAACGCGAAGAATATGTTGTACCTTCAGTTG AACTCCCTGAAAACCGAGGATACAGCCATGTATTACTGCGCTAAGGGCGGAAGC GGATACGGAGACGCCTCCCGCATGACATCCCCTGGTTCCCAGGGGACACAGGTG ACCGTGTCCTCA |
| DR592-hIL27 | 1037 | CAGGTCCAGCTCCAGGAATCCGGGGGCGGGGTCCGTGCAGGGGGGGGCTCCCTT AGGCTCTCCTGTACCGCCCCCGGCTTCACCAGCAACTCCTGtGGGATGGATTGG |

TABLE 1B-continued

| Name | SEQ ID NO: | Sequence |
|---|---|---|
| Ra_VH<br>H18 | | TATCGGCAAGCACCGGGCAAGGAGCGCGAGTTTGTGTCCTCTATCAGCACCGAC<br>GGCACTACCGGCTACGCAGACAGCGTAAAGGGTCGTTTCACAATCTCCAAGGAT<br>AAGGCAAAGGACACAGTGTATCTTCAGATGAACAGCCTGAAGCCCGAGGATACT<br>GGCATGTATTCCTGCAAGACCAAAGACGGAACCATCGCCACTATGGAACTCTGT<br>GATTTCGGCTACTGGGGCAAGGCACCCAGGTGACGGTGTCTAGCGGCGGTGGC<br>AGCCAGGTGCAGTTGCAGGAGTCTGGAGGGGCTCCGTGCAGGCTGGAGGCAGC<br>CTGCGCCTGTCTTGCGTTGCTTCCGGGTATGTCTCTTGCGATTACTTCCTGCCT<br>AGCTGGTACAGACAGGCCCCTGGGAAGGAGCGCGAGTTCGTTTCAATCATTGAT<br>GGGACGGGCTCCACCTCCTATGCTGCATCCGTTAAGGGGCGCTTTACAGCCTCT<br>CAGGATAAGGGAAAAAATATCGCCTACCTCCAGATGAACTCTCTGAAGCCTGAG<br>GACACTGCCATGTACTATTGCAAGGCCTCATGTGTTCGCGGGGGGGGTATTAGT<br>GAGTACTGGGGGCAGGGCACCCAGGTGACTGTCTCCAGC |
| DR592-<br>hIL27<br>Ra_VH<br>H18 | 1038 | CAAGTTCAGCTCCAGGAGAGCGGAGGTGGGTCAGTCCAGGCTGGTGGCAGTCTG<br>CGTCTGTCCTGCACTGCCCCCGGTTTCACCTCCAACAGCTGCGGCATGGATTGG<br>TACAGGCAGGCACCTGGCAAAGAAAGGGAGTTCGTGTCCTCTATTTCCACTGAC<br>GGAACGACCGGCTACGCCGACAGTGTGAAGGGAAGGTTCACAATCTCCAAGGAC<br>AAGGCCAAGGACACCGTGTATCTTCAGATGAACTCACTGAAGCCCGAAGACACC<br>GGGATGTATAGCTGCAAGACAAAGGACGGGACTATCGCTACTATGGAGCTGTGT<br>GATTTCGGTTACTGGGGCAAGGCACTCAGGTGACCGTTAGCTCCGGCGGTAGC<br>GGCGGATCAGGAGGCTCTGGGCAAGTGCAGCTTCAAGAGTCTGGCGGTGGCTCC<br>GTACAAGCGGGCGGAAGCCTGAGACTGAGTTGCGTGGCTTCCGGCTACGTTAGC<br>TGCGACTACTTTCTGCCAAGCTGGTATCGCCAAGCTCCCGGCAAGGAGGGGGAG<br>TTCGTGTCAATTATCGACGGCACTGGTTCTACCTCTTACGCCGCTTCTGTAAAG<br>GGACGCTTTACCGCCAGCCAGGATAAGGGCAAAAACATCGCATACCTTCAGATG<br>AACTCTCTGAAGCCAGAGGACACAGCAATGTATTACTGTAAGGCTTCCTGCGTT<br>CGCGGTCGCGGTATCTCTGAATATTGGGGCCAGGGGACCCAGGTAACTGTGTCT<br>TCT |
| DR592-<br>hIL27<br>Ra_VH<br>H19 | 1039 | CAGGTGCAACTTCAGGAATCTGGAGGGGGATCAGTCCAGGCCGGGGGTAGTCTG<br>AGATTGTCTTGCACCGCTCCCGGATTTACGTCAAACTCTTGCGGTATGGACTGG<br>TATCGCCAGGCTCCCGGCAAGGAACGTGAGTTCGTGTCCAGCATTAGTACCGAA<br>GGCACCACGGGCTATGCTGACAGTGTGAAGGGTCGGTTTACCATCTCCAAGGAC<br>AAGGCCAAGGACACCGTGTATCCTCAGATGAACAGCCTGAAGCCCGAAGACACC<br>GGCATGTATTCCTGCAAGACCAAGGATGGCACCATCGCTACGATGGAACTGTGC<br>GATTTCGGTTACTGGGGTCAGGGAACCCAGGTCACCGTGTCTAGCGGAGGCGGT<br>TCTCAAGTGCAGCTCCAGGAATCTGGGGGGGGCTCCGTGCAGGCTGGGGGGTCC<br>CTGCGCCTGTCCTGTCGGGCGAGCGGTTCCACCTACTCCAATTATTGTCTGGGC<br>TGGTTTAGACAGATCACAGGCAAGGAAAGAGAGGGCGTGGCCGTTATCAACTGG<br>GTCGGAGGTATGCTTTACTTCGCCGACAGCGTCAAGGGCAGGTTCACCGTCTCT<br>CAGGACCAAGCTAAGAATACCGTGTACCTTCAGATGAACTCCCTGAAGCCTGAG<br>GATACCGCGATGTATTACTGTGCAGCTGAGTCCGTCAGCTCTTTCTCTTGCGGA<br>GGTTGGTTGACTAGGCCTGATCGGGTGCCATACTGGGGCCAGGGGACACAGGTC<br>ACCGTATCTAGC |
| DR592-<br>hIL27<br>Ra_VH<br>H19 | 1040 | CAGGTACAGTTGCAGGAAAGCGGCGGTGGATCTGTCCAGGGGGGGGGTAGCCTC<br>CGCCTGTCCTGCACAGCCCCTGGGTTCACCAGCAACTCATGTGGCATGGACTGG<br>TATCGCCAGGCTCCGGGTAAAGAGCGTGAGTTCGTGTCCTCTATCTCCACAGAT<br>GGAACGACAGGCTATGCAGACAGCGTCAAAGGGAGGTTTACAATCTCCAAGGAC<br>AAGGCCAAGGATACGGTTTACCTTCAGATGAACTCTCTGAAGCCCGAGGACACC<br>GGCATGTACTCCTGTAAGACTAAGGACGGAACCATCGCCACTATGGAACTCTGC<br>GATTTCGGCTATTGGGGACAGGGAACCCAGGTGACGGTGTCCAGCGGAGGCTCA<br>GGAGGGTCCGGTGGCAGCGGACAGGTCCAACTCCAGGAGTCTGGTGGAGGCTCC<br>GTCCAGGCCGGAGGTTCTCTGAGACTGTCTTGTCGGGCATCTGGATCTACTTAC<br>AGCAACTACTGCCTGGGATGGTTCAGACAAATCACAGGAAAGGAGCGCGAAGGT<br>GTGGCCGTGATTAACTGGGTGGGGGGTATGCTGTATTTCGCAGACTCCGTCAAG<br>GGCCGCTTCACCGTGTCTCAGGATCAGGCTAAAAACACTGTTTATCTCCAGATG<br>AACTCCCTCAAGCCTGAGGATACTGCCATGTATTACTGTGCCGCAGAGTCCGTA<br>AGCTCCTTCTCTTGCGGGGGCTGGCTGACTCGCCCCGACCGTGTACCGTACTGG<br>GGCCAGGGAACACAGGTCACAGTGTCCTCT |
| DR592-<br>hIL27<br>Ra_VH<br>H20 | 1041 | CAGGTGCAGCTCCAGGAATCTGGCGGTGGCTCCGTGCAGGCCGGTGGCTCCCTC<br>AGACTGTCCTGCACAGCGCCAGGCTTCACGTCCAACTCTTGCGGCATGGATTGG<br>TATCGGCAAGCACCGGGCAAGGAAAGAGAGTTCGTTTCTTCCATCTCCACGGAC<br>GGCACGACAGGCTATGCGGACTCAGTCAAAGGCCGTTTCACTATTTCTAAGGAT<br>AAAGCCAAGGATACAGTCTACCTTCAGATGAACTCCTTGAAACCAGAGGACACC<br>GGAATGTATAGTTGCAAGACTAAGGACGGCACAATCGCCACTATGGAACTGTGC<br>GACTTCGGGTACTGGGGCCAGGGCACACAGGTCACTGTTAGCTCCGGTGGCGGT<br>TCACAGGTCCAGCTCCAGGAGAGCGGCGGGGGGCTGGTTCAGCCGGGAGGGAGC<br>CTGCGCCTGTCCTGTGCCGCTTCCGGGTTCACGTTTTCTTCCTACCCTATGTCT<br>TGGGTTCGCCAGGCCCCTGGTAAGGGTCTTGAATGGGTCTCTACAATTTCTAGT<br>GGTGGCGACACAACGCTGTATGCCGACTCCGTCAAGGGTCGCTTTACCTCAAGC<br>AGGGATAATGCTAAGAACACCCTCTATTTGCAGTTGAACTCTCTTAAAACCGAG<br>GATACCGCAATGTATTACTGTGCAAAACGTATCGACTGTAATAGCGGTTATTGC<br>TATAAGCGTAGCTACTGGGGTCAGGGCACCCAGGTGACGGTGTCTAGT |

TABLE 1B-continued

| Name | SEQ ID NO: | Sequence |
|---|---|---|
| DR592-hIL27 Ra_VH H20 | 1042 | CAGGTGCAACTCCAGGAATCCGGCGGGGGCAGCGTTCAGGCGGGAGGCTCTCTC CGTCTGTCCTGCACCGCCCCCGGCTTCACAAGTAATTCCTGCGGCATGGACTGG TATCGTCAGGCCCCTGGCAAAGAACGGGAGTTCGTAAGCTCCATCCCAACCGAT GGCACAACCGGCTATGCAGACTCCGTGAAGGGGCGCTTCACCATCTCAAAGGAC AAGGCCAAAGATACAGTGTACCTTCAGATGAACAGCCTTAAACCGGAGGATACA GGCATGTATTCTTGCAAGACCAAGGACGGCACCATCGCAACAATGGAGCTGTGC GACTTCGGATACTGGGGTCAAGGCACCCAGGTGACTGTCTCATCTGGGGGTAGC GGAGGGAGCGGAGGCAGTGGTCAGGTGCAGCTTCAGGAGAGCGGTGGAGGGCTC GTGCAACCCGGGGGTAGCCTGCGCCTGTCCTGCGCAGCTTCTGGGCTTACGTTT TCTTCCTACCCTATGAGCTGGGTGAGGCAGGCCCCTGGCAAGGGGCTGGAGTGG GTCTCAACCATTTCCAGCGGTGGGGATACCACACTCTACGCCGATTCCGTCAAG GGACGCTTCACCAGTTCCCGCGATAATGCCAAGAACACCCTGTACCTTCAGCTG AACAGCCTGAAGACTGAGGACACTGCCATGTACTATTGTGCGAAGCGGATTGAC TGCAATTCTGGGTACTGTTATAAGCGTTCTTACTGGGGGCAAGGAACCCAGGTG ACCGTGTCCAGT |
| DR592-hIL27 Ra_VH H21 | 1043 | CAAGTGCAGCCTCAAGAAAGCGGGGGGGGTTCCGTGCAGGCAGGGGGGGAGCCTG CGCTTGAGTTGCACCGCTCCGGGCTTTACAAGTAACAGCTGCGGGATGGATTGG TATCGCCAGGCACCTGGAAAGGAGCGCGAGTTCGTGTCCTCTATTTCCACGGAC GGGACTACCGGGTATGCCGATTCCGTGAAGGGCCGGTTTACTATCTCCAAGGAC AAAGCCAAGGACACCGTTTACCTTCAGATGAACAGCCTCAAGCCTGAAGATACC GGAATGTATAGTTGTAAGACCAAGGACGGCACCATCGCCACGATGGAGCTGTGT GATTTCGGATACTGGGGTCAGGGCACACAGGTTACTGTGTCCAGTGGAGGCGGT AGCCAGGTGCAGTTGCAGGAATCTGGGGGGGGCTTGGTCCAGCCTGGGGGCTCT CTGCGCCTCAGCTGCGCGGCCTCCGGCTTCACGTTTAGCCTGAGTAGCATGTCT TGGGTTCGGCAAGCACCGGGTAAGGGCCTGGAGTGGGTCTCCGCTATTTCCAGC GGCGGTGCTAGTACCTATTACACCGACTCTGTGAAAGGCCGCTTCACGATTTCC CGCGACAACGCAAAGAACATGCTTTATCTCCAGCTGAACTCACTGAAGACAGAG GACACAGCAATGTATTACTGTGCCAAGGGAGGTTCCGGCTACGGGGATGCGTCA CGTATGACATCCCCTGGTTCACAGGGCACCCAGGTGACGGTGAGCAGC |
| DR592-hIL27 Ra_VH H21 | 1044 | CAAGTCCAGCTCCAGGAGTCCGGGGGGGGGTTCCGTCCAGGCTGGCGGTAGCCTG AGGCTGTCCTGTACCGCCCCCGGTTTCACATCTAACTCCTGCGGCATGGACTGG TATCGCCAGGCTCCCGGAAAAGAACGCGAGTTCGTGAGTTCCATCTCCACAGAC GGCACCACTGGCTATGCAGACAGTGTGAAGGGAAGGTTCACCATCTCTAAGGAT AAAGCTAAGGACACCGTTTACTTGCAGATGAACTCTCTCAAGCCAGAGGACACC GGAATGTACTCCTGTAAGACCAAAGATGGGACCATCGCGACAATGGAGCTGTGT GACTTTGGATACTGGGGACAAGGGACCCAGGTGACTGTTTCATCCGGCGGTTCC GGCGGGTCTGGTGGGTCCGGTCAGGTGCAGCTCCAGGAGTCCGGGGGGGGACTG GTGCAGCCTGGGGGATCACTGCGCCTCAGCTGCGCTGCCTCAGGTTTCACATTT AGTCTTAGCTCTATGAGCTGGGTGCGCCAGGCACCCGGAAAGGGGCTGGAATGG GTCAGCGCAATCAGCTCAGGGGGGGGTTCTACGTATTACACGGATAGCGTGAAA GGGCGCTTCACCATCAGCCGTGACAACGCCAAGAACATGCTGTACCTTCAGCTG AACTCACTGAAGACGGAAGATACTGCCATGTACTATTGTGCCAAGGGTGGATCT GGGTATGGTGATGCCTCCCGTATGACCTCACCTGGAAGCCAGGGTACACAGGTC ACCGTCTCCTCC |
| DR592-hIL27 Ra_VH H22 | 1045 | CAGGTGCAGTTGCAGGAGAGCGGGGGGGGCAGCGTGCAAGCCGGTGGCAGCCTG CGGCTGTCTTGTACCGCCCCCGGTTTTACTAGCAATTCTTGCGGCATGGATTGG TATCGCCAGGCCCCAGGCAAGGAAAGAGAGTTCGTGTCCTCTATCAGCACTGAC GGCACAACCGGCTACGCCGATTCAGTGAAGGGCCGCTTCACCATCTCAAAGGAT AAGGCCAAGGACACCGTGTACCTTCAGATGAACTCTCTTAAACCGGAGGACACT GGTATGTACTCTTGCAAGACCAAAGACGGGACCATCGCGACTATGGAGCTGTGC GATTTCGGGTACTGGGGCCAGGGAACACAGGTCACTGTCTCTTCCGGCGGAGGT TCTCAGGTTCAGTTGCAGGAGAGCGGTGGGGGTAGCGTTCAGGCTGGCGGAAGC CTGCGGTTGAGTTGTCGCGCATCTGGCTCTACCTATAGCAACTATTGCCTGGGA TGGTTCAGACAGACAACCGGCAAGGAGCGCGAGGGTGTGGCCGTCATCAACTGG GTCGGGGGTATGCTGTATTTTGCTGATTCCGTGAAGGGCCGTTTCACCGTGAGC CAGGACCAGGCTAAGAACACAGTTTATCTCCAGATGAACAGCCTGAAACCCGAG GATACTGCCATGTACTATTGTGCGGCAGAATCCGTGTCCTCTTTTAGCTGTGGT GGCTGGCTCACACGCCCTGACCGCGTCCCGTACTGGGGTCAGGGAACCCAAGTG ACCGTGAGTTCA |
| DR592-hIL27 Ra_VH H22 | 1046 | CAAGTGCAGCTTCAGGAGTCTGGGGGGGGCTCCGTACAGGCTGGGGGCAGCCTT AGATTGTCATGCACTGCCCCTGGATTCACAAGCAACAGCTGTGGCATGGATTGG TATCGCCAAGCACCTGGGAAGGAGCGGGAGTTCGTCCCCAGCATTTCTACTGAT GGTACGACCGGCTACGCTGACAGTGTGAAGGGACGCTTCACTATCTCCAAGGAC AAGGCCAAAGATACCGTGTATTTGCAGATGAACAGTCTCAAGCCGGAGGACACC GGAATGTATTCCTGCAAGACTAAGGACGGGACTATCGCCACTATGGAACTTTGC GACTTTGGCTATTGGGGCCAGGGCACCCAGGTGACCGTAAGTTCCGGGGGTTCC GGCGGAAGCGGCGGTAGCGGCCAGGTTCAACTTCAGGAGTCCGGGGGAGGCTCT GTGCAGGCCGGGGGCTCTCTGAGACTGTCCTGCCGGGCCTCCGGCTCCACATAC TCTAACTACTGCCAGGGATGGTTCCGTCAGACTACAGGCAAGGAGCGCGAGGGT GTTGCAGTCATCAACTGGGTAGGGGGAATGCTGTATTTCGCCGATTCAGTCAAA GGACGCTTCACTGTGTCCCAAGACCAGGCCAAGAACACAGTCTATCTTCAGATG AACAGCCTCAAGCCCGAGGATACCGCTATGTACTATTGCGCAGCTGAGAGCGTG |

TABLE 1B-continued

| Name | SEQ ID NO: | Sequence |
|---|---|---|
| | | TCCAGCTTCTCTTGCGGAGGCTGGCTGACCAGGCCGGATCGGGTGCCCTATTGG GGTCAAGGCACACAGGTGACAGTTTCAAGT |
| DR592-hIL27 Ra_VH H23 | 1047 | CAGGTGCAGCTCCAGGAGAGTGGAGGTGGGTCCGTGCAGGGGGGAGGTAGCCTG CGGCTGTCCTGTACTGCGCCCGGCTTTACCAGTAACAGCTGCGGCATGGACTGG TATAGACAGGCCCCCGGAAAGGAACGCGAGTTTGTCAGCAGTATCTCTACTGAT GGCACCACTGGATATGCGGACTCCGTGAAGGGTCGGTTCACCATTAGCAAGGAC AAGGCAAAGGATACCGTGTATTTGCAGATGAACAGTCTCAAACCAGAGGACACA GGCATGTATAGTTGCAAAACCAAGGACGGGACCATCGCCACTATGGAACTCTGT GATTTTGGGTATTGGGGCCAGGGGACTCAGGTGACCGTCAGCTCCGGGGGGGGT TCCCAAGTTCAGTTGCAAGAGTCTGGAGGCGGATCAGTGCAGGCCGGGGGCTCT CTGCGGCTTAGCTGCCGTGCTTCTCGCAGCCCTTATGGGAACTACTGTCTTGGC TGGTTCAGGCAGAGTACAGGTAAGGAACGCGAAGGGGTGGCCGTCATCAACTGG GTGGGCGGAATGCTCTATTTCGCTGACTCTGTGAAGGGCCGTTTCACAGTGTCC CAGGACCATGCTAAGAACACTGTCACCCTCCAGATGAACAGCCTGAAGCCAGAG GACACCGCTATGTATTACTGCGCAGCCGAGTCTGTGTCCAGTTTCTCATGCGGT GGGTGGCTGACCAGACCTGATCGCGTTCCATACTGGGGACAAGGGACTCAGGTC ACAGTGTCCTCT |
| DR592-hIL27 Ra_VH H23 | 1048 | CAGGTGCAGCTCCAGGAGTCCGGGGGTGGCTCCGTTCAGGCGGGAGGCTCTTTG CGTTTGTCCTGCACCGCACCCGGTTTCACAAGTAACTCCTGCGGCATGGACTGG TATCGTCAGGCTCCAGGCAAGGAGCGCGAGTTCGTGAGTTCTATCTCCACAGAC GGCACCAGGGGCTACGCCGACAGTGTTAAGGGTCGCTTTACTATCTCAAAGGAT AAGGCGAAGGACACCGTATACCTTCAGATGAACTCCCTCAAGCCTGAAGACACC GGAATGTATAGCTGTAAGACCAAGGACGGCACCATCGCCACAATGGAGCTGTGC GACTTTGGATACTGGGGGCAGGGAACACAGGTGACAGTATCCAGCGGGGGCTCT GGCGGTTCCGGGGGTTCCGGCCAGGTCCAGTTGCAGGAGTCTGGTGGCGGTAGC GTCCAGGCTGGGGGCAGCCCGCGGCTGTCCTGTCGCGCATCAAGAAGCCCTTAC GGCAATTATTGTTTGGGCTGGTTCCGCCAATCAACTGGTAAGGAGAGAGAAGGA GTCGCTGTCATTAACTGGGTGGGCGGTATGCTTTATTTTGCCGATAGCGTGAAG GGGCGCTTCACGGTGTCTCAGGACCATGCCAAGAATACCCTTACGTTGCAGATG AACAGCCTGAAACCCGAAGACACCGCAATGTATTACTGTGCCGCTGAGTCCGTA TCCTCTTTCTCCTGTGGAGGCTGGCTGACACGCCCCGACCGCGTGCCTTATTGG GGCCAAGGGACCCAGGTTACCGTGTCCTCC |
| DR592-hIL27 Ra_VH H24 | 1049 | CAGGTGCAGTTGCAGGAAAGTGGTGGAGGCAGCGTGCAGGCAGGAGGCTCTCTG CGCCTGAGCTGCACAGCGCCTGGCTTTACCCCCAACAGCTGTGGAATGGACTGG TATCGCCAGGCTCCCGGTAAGGAGCGGGAATTTGTCAGCTCCATTTCCACCGAC GGCACCACTGGCTACGCCGATTCCGTCAAGGGCAGGTTCACAATCTCAAAGGAC AAAGCCAAGGACACAGTGTATCTCCAGATGAACTCCCTGAAGCCTGAGGACACA GGTATGTATAGCTGCAAGACTAAGGACGGCACAATCGCCACGATGGAATTGTGC GACTTCGGATATTGGGGACAAGGTACTCAGGTGACCGTCTCCTCTGGAGGGGGC TCCCAGGTGCAGCTCCAGGAGTCTGGCGGTGGCCTGGTGCAGCCCGGTGGGTCT CTGCGGCTGAGTTGTGCTGCGTCTGGATTCACCTTTTCCCACAGCGGGATGTCA TGGGTGAGGCAGGCACCCGGCAAGGGCCTGGAGTGGGTGAGCACAATTAACTCC GGGGGTGCTTCCACGTACTATACCGATAGCGTGAAGGGCAGGTTTACCATCTCA CGCGACAACGCGAAGAACATGCTGTATCTTCAGCTGAATAGTTTGAAGACCGAG GACACCGCTATGTATTACTGCGCCAAAGGCGGTTCTGGCTACGGGGACGCCTCC CGCATGACAAGCCCTGGGTCTCAGGGCACACAGGTGACCGTGTCTTCT |
| DR592-hIL27 Ra_VH H24 | 1050 | CAAGTTCAGCTTCAGGAATCAGGTGGCGGTAGCGTGCAGGCTGGGGGCTCCTTG AGATTGTCCTGCACGGCCCCAGGATTCACCAGCAACTCTTGGGGGATGGATTGG TATCGCCAGGCTCCGGGGAAGGAGAGGGAGTTCGTAAGCTCCATTTCAACCGAA GGGACCACTGGATACGCTGACTCCGTTAAGGGTAGGTTCACGATCAGTAAGGAC AAGGCCAAGGATACAGTGTATCCTCAAATGAACTCACTGAAGCCCGAGGACACC GGGATGTACTCCTGTAAGACCAAAGATGGCACTATCGCAACGATGGAGCTGTGC GACTTCGGCTATTGGGGCCAGGGAACCCAGGTTACTGTGTCCAGCGGAGGCAGC GGCGGTTCTGGAGGCTCTGGACAGGTCCAACTCCAGGAATCTGGGGGCGGTCTC GTGCAGCCAGGTGGGTCACTGCGCTTGTCATGTGCGGCCTCCGGTTTCACCTTC AGCCATTCTGGAATGAGCTGGGTGCGTCAAGCACCGGGCAAAGGCCTCGAATGG GTCTCTACTATTAACAGCGGAGGTGCATCTACCCACTATACAGACAGCGTTAAG GGGAGGTTCACCATCTCTCGCGATAATGCTAAAAACATGCTGTATTTGCAGCTT AATTCACTGAAGACGGAGGACACGGCCATGTACTATTGTGCCAAGGGTGGGTCC GGGTACGGTGACGCCTCTCGCATGACCCCCCCAGGAAGTCAGGGCACCCAGGTG ACCGTGTCATCC |
| DR593-hIL27 Ra_VH H1 | 1051 | CAGGTGCAGCTCCAGGAATCTGGCGGTGGCAGCGTGCAGGCCGGTGGCTCCCTG AGGCTGTCCTGTGCTGCCTCTGGATACCCATACTCCAACGGGTACATGGGCTGG TTCCGTCAGGCCCCTGGAAAGGAACGTGAGGGCGTGGCCACTATTTACACCGGC GACGGTCGTACTTATTACGCCGACTCCGTGAAAGGCCGCTTCACCATTTCTAGG GATAACGCTAAGAACACAGTTGACCTCCAGATGTCTAGCCTGAAACCTGAGGAT ACCGCCATGTATTACTGCGCTGCCAGGGCTGCCCCACTCTACAGCTCTGGTTCA CCCCTGACACGCGCCAGGTATAACGTGTGGGGACAGGGGACCCAGGTCACAGTG AGTTCTGGGGGGGGTTCTCAGGTGCAACTCCAGGAATCTGGCGGAGGCCTGGTC CAGCCTGGTGGCTCCCTTCGCCTGAGCTGTGCAGCCTCTGGCTTCACATTCAGC TCCTATCCTATGTCCTGGGTGCGCCAGGCCCCTGGGAAGGGCCTGGAGTGGATC TCCACCATCTCTGCGGGTGGCGACACTACACTCTACGCCGACAGCGTGAAGGGC |

TABLE 1B-continued

| Name | SEQ ID NO: | Sequence |
|---|---|---|
| | | CGCTTTACCTCCAGTCGCGATAACGCTAAGAATACACTGTACCTCCAGCTTAAC<br>AGCCTGAAGACAGAGGACGCTGCAATCTATTACTGTGCCAAGAGGATCGACTGC<br>AACAGCGGATATTGCTACCGTAGGAATTATTGGGGCCAGGGAACCCAGGTTACC<br>GTATCATCC |
| DR593-<br>hIL27<br>Ra_VH<br>H1 | 1052 | CAAGTTCAGTTGCAGGAATCCGGTGGCGGTAGCGTGCAGGCTGGTGGCAGCCTG<br>CGTCTGAGCTGCGCTGCATCCGGGTATCCGTACAGCAACGGTTACATGGGATGG<br>TTCCGCCAAGCTCCTGGGAAGGAGCGCGAAGGCGTGGCGACCATTTACACCGGA<br>GACGGACGCACTTATTACGCCGACTCAGTGAAGGGCCGCTTTACGAACTCTCGG<br>GACAACGCTAAGAATACCGCGGACTTGCAGATGAGTTCCCTGAAGCCTGAGGAC<br>ACCGCAATGTATTACTGTGCCGCACGCGCTGCGCCCCTCCACAGCTCTGGTTCT<br>CCCCTGACCCGTGCCCGTTACAATGTATGGGGACAAGGCACCCAGGTGACCGTG<br>AGTAGCGGGGGAAGCGGAGGCAGCGGGGGATCTGGCCAGGTGCAGCTCCAGGAA<br>AGCGGCGGGGGCCTGGTCCAGCCCGGTGGCAGCCTGCGCCTGTCCTGTGCTGCC<br>AGTGGATTCACCTTTTCTTCCTATCCTATGTCATGGGTCCGCCAGGCACCTGGC<br>AAGGGCCTGGAGTGGATTTCCACTATCTCAGCTGGCGGAGACACAACTCTCTAC<br>GCGGACTCTGTAAAGGGTCGGTTTACGTCTTCCCGCGACAACGCCAAGAATACC<br>CTGTACCTTCAGTTGAACTCCCTTAAAACCGAAGATGCAGCTATCTACTATTGT<br>GCGAAGCGTATTGATTGCAACTCCGGTTACTGCTACCGGCGTAACTACTGGGGT<br>CAAGGCACACAGGTCACAGTCCCCTCC |
| DR593-<br>hIL27<br>Ra_VH<br>H2 | 1053 | CAAGTCCAGCTCCAAGAGAGTGGGGGGGGTTCCGTGCAGGCTGGAGGCTCCCTC<br>AGATTGAGTTGTGCGGCTAGTGGCTATCCCTATAGCAACGGCTACATGGGCTGG<br>TTCCGCCAGGCCCCCGGCAAGGAAAGGGAGGGTGTTGCAACCATCTACACAGGA<br>GATGGCCGCACTTACTATGCAGACTCCGTTAAGGGTCGTTTCACCATTTCCCGC<br>GATAACGCTAAGAATACAGTGGATCTTCAGATGTCCAGCCTCAAACCAGAGGAT<br>ACTGCAATGTATTACTGCGCAGCGCGGGCCGCGCCCCTGTACTCTTCCGGCTCT<br>CCACTGACCCGCGCTCGCTACAACGTGTGGGGCCAAGGCACGCAGGTCACAGTT<br>TCTTCCGGGGGGGGCAGCCAGGTCCAGCTCCAGGAAAGTGGCGGGGGCCTGGTT<br>CAGCCCGGGGGTTCCCTGCGCCTCAGCTGTGCTGCCTCTGGGTTTACCTTCAGC<br>CTGTCAGGCATGAGCTGGGTGCGGCAGGCTCCTGGCAAGGGTCTGGAATGGGTT<br>TCCGCCATTTCAAGGGGGGGGGCCTCTACCTATTACACAGACTCCGTGAAGGGC<br>CGTTTCACGATCAGTCGCGACAACGCGAAAAACATTCTCTATCTCCAGCTGAAC<br>AGCTTGAAGACCGAGGACACTGCGATGTATTACTGTGCCAAAGGGGGATCAGGA<br>TACGGCGATGCGTCTCGCATGACTTCCCCAGGTTCACAGGGCACTCAGGTTACC<br>GTCTCTTCC |
| DR593-<br>hIL27<br>Ra_VH<br>H2 | 1054 | CAGGTACAGCTTCAAGAAAGCGGGGGGGGAAGCGTGCAAGCTGGCGGGAGCCTT<br>AGGCTGAGTTGCGCGGCCTCAGGTTACCCCTATAGCAACGGATATATGGGATGG<br>TTCCGGCAGGCACCGGGGAAGGAACGCGAGGGAGTGGCCACCATTTACACCGGG<br>GACGGGAGGACCTACTATGCCGACTCTGTGAAGGGCCGTTTCACTATCTCTAGG<br>GATAACGCGAAGAACACAGTGGACTTGCAGATGTCATCTCTCAAGCCGGAGGAC<br>ACTGCCATGTATTACTGTGCGGCTCGTGCCGCTCCTCTCTACAGCTCCGGGAGT<br>CCACTGACCCGCGCAAGGTACAACGTGTGGGGTCAGGGAACTCAGGTGACCGTT<br>TCATCCGGGGGCAGCGGTGGCTCCGGTGGCTCTGGTCAGGTTCAGCTCCAGGAA<br>AGCGGGGGCGGGCTGGTGCAGCCCGGAGGCTCCCTGCGTCTTTCTTGCGCTGCC<br>AGTGGCTTTACCTTTTCCCTGAGTGGAATGAGCTGGGTGAGGCAAGCGCCAGGC<br>AAGGGACTGGAATGGGTGAGCGCAATCAGTTCAGGGGGGGCCAGTACTTATTAC<br>ACTGACTCCGTCAAGGGTCGGTTTACCATCCCTCGGGATAACGCTAAGAACATC<br>CTTTATTTGCAGCTCAACTCCTTGAAGACGGAAGACACCGCTATGTATTACTGC<br>GCTAAAGGAGGGAGTGGATACGGAGACGCATCTCGCATGACCAGTCCAGGCTCC<br>CAGGGAACCCAGGTGACTGTGTCAAGC |
| DR593-<br>hIL27<br>Ra_VH<br>H3 | 1055 | CAGGTCCAGCTTCAGGAAAGCGGCGGTGGGTCTGTCCAGGCAGGTGGCTCCCTG<br>AGACTGTCCTGTGCTGCCAGGGGGTATCCGTACTCAAATGGCTACATGGGCTGG<br>TTCCGCCAGGCCCCTGGAAAGGAGCGCGAGGGCGTGGCCACGATCTATACCGGG<br>GACGGACGCACCTATTACGCTGACAGTGTCAAAGGTAGATTCACTATCAGCCGG<br>GACAACGCGAAGAACACCGTTGACCTTCAGATGTCAAGCCTGAAGCCTGAGGAC<br>ACTGCCATGTATTACTGCGCTGCAAGGGCTGCCCCTCTTTACAGCTCCGGCTCA<br>CCCCTTACAAGAGCCCGGTACAACGTCTGGGGCCAGGGAACTCAGGTGACCGTT<br>AGCTCCGGGGGGGGCTCCCAGGTGCAGCTCCAGGAGTCCGGTGGCGGAAGTGTT<br>CAGGCGGGGGGAAGTCTGCGCCTGTCTTGCGTGGCCTCTGGATACGTCTCCTGT<br>GACTATTTCTTGCCCAGCTGGTATCGCCAGGCTCCGGGAAAAGAGAGAGAGTTC<br>GTGAGCATCATTGACGGCACTGGCTCCACCAGCTACGCAGCCTCCGTTAAGGGT<br>CGCTTTACCGCCTCAGAGGATAAGGGTAAGAACATCGCATACTTGCAGATGAAC<br>AGTCTCAAGCCCGAGGATACCGCTATGTATTACTGCAAGGCCAGCTGCGTCCGG<br>GGTCGCGCTGTCTCCGAATACTGGGGACAGGGCACCCAGGTGACCGTATCTAGT |
| DR593-<br>hIL27<br>Ra_VH<br>H3 | 1056 | CAGGTTCAGCTCCAGGAGAGTGGCGGAGGGAGTGTGCAAGCTGGCGGTTCTTTG<br>CGCCTCTCTTGTGCTGCCTCCGGTTATCCCTACAGTAACGGCTATATGGGCTGG<br>TTTCGCCAAGCACCAGGGAAGGAACGGGAGGGGGTCGCCACCATTTATACTGGC<br>GATGGCCGCACCTATTACGCCGACTCCGTGAAAGGTCGCTTCACCATCAGTCGG<br>GACAATGCAAAGAACACTGTAGACTTGCAAATGTCTTCCCTCAAGCCTGAGGAT<br>ACTGCTATGTACTATTGCGCTGCAAGGGCAGCTCCCCTGTACTCTAGTGGCTCC<br>CCTCTGACCCGCGCTCGGTACAACGTCTGGGGTCAGGGAACCCAGGTTACCGTC<br>TCTAGCGGGGGCTCAGGTGGCAGCGGCGGTTCCGGCCAGGTCCAACTCCAGGAG<br>TCCGGCGGTGGCTCCGTTCAAGCCGGAGGCAGTCTGAGACTGAGCTGCGTGGCG |

TABLE 1B-continued

| Name | SEQ ID NO: | Sequence |
|---|---|---|
| | | TCCGGTTACGTCTCCTGTGACTACTTCCTGCCTAGCTGGTATCGGCAAGCGCCT<br>GGTAAGGAAAGAGAGTTCGTGAGTATCATTGATGGGACCGGCTCCACCTCCTAC<br>GCCGCATCTGTTAAGGGGCGCTTCACAGCTTCCGAAGACAAGGGAAAGAACATC<br>GCTTATCTTCAGATGAACTCTCTCAAACCTGAAGACACGGCTATGTACTATTGC<br>AAGGCCTCCTGTGTACGGGGTCGCGCCGTGTCCGAGTACTGGGGGCAGGGGACA<br>CAGGTTACCGTATCCAGC |
| DR593-<br>hIL27<br>Ra_VH<br>H4 | 1057 | CAGGTGCAGCTGCAAGAGAGCGGCGGAGGCAGCGTGCAAGCTGGAGGCTCTCTC<br>CGGCTTTCATGCGCTGCCAGGGGCTATCCTTATAGCAACGGCTACATGGGCTGG<br>TTCCGCCAAGCGCCCGGCAAGGAGCGCGAGGGGGTGGCGACGATTTATACGGGG<br>GACGGCAGGACTTATTACGCAGACTCCGTCAAAGGGCGCTTCACCATCTCCCGC<br>GACAACGCCAAAAATACCGTCGATCTTCAGATGTCAAGCCTCAAGCCCGAGGAT<br>ACAGCCATGTACTATTGGGCAGCCCGCGCCGCACCCCTCTATTCCTCAGGATCT<br>CCACTCACACGCGCCCGGTACAATGTGTGGGGTCAAGGAACCCAGGTGACCGTA<br>TCCAGCGGGGGGGGTTCTCAAGTCCAGCTTCAGGAGTCCGGCGGAGGCCTTGTG<br>CAGCCCGGAGAATCTCTGAGACCGTCCTGTACTGCCAGCGGGTTCACCTTTTCT<br>AACTACGCGATGAGCTGGGTACGGCAAGCGCCCGGAAAGGGTCTGGAATGGGTC<br>AGCGGAATCAATGTTGCCTACGGCATCACTTCTTACGCCGACAGTGTTAAGGGC<br>CGCTTCACTATTAGTCGTGACAACACCAAAAACACTCTGTATCTCCAGCTCAAC<br>AGCCTGAAAACAGAGGATACTGCGATTTACTATTGTGTCAAACACTCTGGCACC<br>ACTATCCCAAGGGGGTTCATCTCCTACACTAAGCGCGGTCAGGGAACCCAGGTG<br>ACCGTGTCATCC |
| DR593-<br>hIL27<br>Ra_VH<br>H4 | 1058 | CAGGTGCAGTTGCAGGAGAGTGGTGGCGGAAGCGTGCAAGCTGGCGGAAGCCTG<br>AGACTGAGCTGCGCTGCGAGCGGCTACCCTTACTCAAATGGCTACATGGGGTGG<br>TTCCGTCAGGCCCCCGGCAAGGAGCGTGAGGGGGTGGCCACGATCTACACTGGA<br>GATGGCCGCACTTATTACGCCGATTCTGTTAAGGGGAGATTCACAATCAGCCGC<br>GACAATGCTAAGAACACCGTGGACCTTCAGATGTCCAGCCTCAAACCGGAAGAC<br>ACTGCAATGTATTACTGTGCGGCCCGTGCCGCGCCGCTTTACTCTTCAGGGTCA<br>CCTCTGACCCGCGCTCGGTACAATGTATGGGGCCAGGGTACACAGGTGACCGTG<br>TCTAGCGGAGGCAGCGGTGGCTCAGGAGGTTCTGGGCAAGTCCAGCTCCAAGAG<br>TCAGGTGGGGGTCTGGTGCAGCCAGGTGAAAGCCTGCGTCTTTCCTGCACTGCC<br>AGCGGCTTTACCTTCTCCAACTATGCCATGTCCTGGGTGCGCCAAGCTCCGGGG<br>AAGGGCCTGGAATGGGTATCCGGCATTAACGTGGCCTATGGGATCACAAGTTAC<br>GCTGACTCTGTGAAGGGCAGATTTACTATTAGCAGAGACAACACCAAGAATACC<br>TTGTACTTGCAACTGAACTCCCCCAAGACCGAGGATACAGCCATCTACTATTGC<br>GTGAAACACAGCGGCACTACAATCCCGCGCGGCTTTATTAGTTATACGAAGAGG<br>GGACAAGGTACGCAGGTGACCGTGTCCAGC |
| DR593-<br>hIL27<br>Ra_VH<br>H5 | 1059 | CAGGTGCAGTTGCAGGAGTCCGGGGGGGGCAGCGTTCAGGCTGGGGGCTCTCTC<br>AGACTGTCCTGTGCCGCGAGCGGCTATCCATACAGTAACGGATACATGGGCTGG<br>TTCCGCCAAGCGCCCGGCAAGGAGAGGGAGGGTGTCGCCACTATCTACACGGGG<br>GATGGCCGGACTTATTACGCGGATAGCGTGAAAGGTCGTTTTACCATCTCCCGC<br>GACAACGCGAAGAACACCGTGGATTTGCAGATGTCTAGCCTCAAACCCGAGGAC<br>ACGGCTATGTACTATTGCGCAGCCCGTGCCGCACCTTTGTATTCCTCTGGTTCA<br>CCCCTCACTAGGGCCAGATATAACGTGTGGGGACAGGGGACCCAGGTGACTGTG<br>AGTTCTGGGGGTGGCTCCCAGGTGCAGCTCCAGGAGAGCGGAGGTGGCTCCGTT<br>CAGGCGGGAGGCTCCCTGAGGCTGTCTTGCACCGCCTCTGGATACGTTTCCTGC<br>GACTATTTCCTCCCCTCCTGGTACAGACAGGCACCCGGAAAGGAACGCGAGCTT<br>GTGAGCGTCATCGACGGAACAGGGAGCACCTCCTATGCGGCCTCAGTGAAGGGC<br>AGATTCACAGCTTCCCAAGACAAGGGTAAGAACATCGCATACCTTCAGATGAAC<br>TCCCTGAAACCCGAAGATACCGCCATGTATTACTGCAAAGCATCTTGCGTTCGG<br>GGAAGGGCAATCAGCGAATACTGGGGCCAGGGCACGCAGGTGACCGTGTCCTCT |
| DR593-<br>hIL27<br>Ra_VH<br>H5 | 1060 | CAGGTGCAGCTTCAAGAGAGTGGTGGAGGGTCCGTCCAGGCCGGGGGTTCTCTG<br>AGGTTGTCCTGCGCAGCCAGCGGTTACCCCTACTCCAACGGCTATATGGGGTGG<br>TTCCGTCAGGCCCCAGGCAAGGAACGCGAAGGGGTCGCAACAATCTACACAGGT<br>GATGGCCGCACTTATTACGCTGATAGCGTGAAAGGTCGGTTCACCATTTCTCGG<br>GACAACGCCAAGAACACCGTAGATTTGCAGATGTCTTCCTTGAAACCCGAGGAC<br>ACTGCCATGTATTACTGCGCTGCACGGGCTGCCCCACTCTATAGTTCCGGCTCC<br>CCACTCACACGCGCCAGATACAACGTGTGGGGGCAAGGGACACAGGTCACTGTG<br>TCTAGTGGGGGCTCCGGTGGCAGCGGAGGTAGCGGCCAGGTTCAGCTTCAGGAA<br>TCTGGCGGAGGCTCCGTGCAAGCCGGTGGGAGCCTCAGACTGTCTTGTACTGCC<br>AGCGGGTACGTAAGCTGCGACTACTTCCTGCCTTCCTGGTATCGCCAAGCTCCA<br>GGGAAGGAACGTGAGTTCGTATCTGTGATCGACGGAACAGGCTCTACATCTTAT<br>GCAGCTTCAGTGAAGGGGAGATTCACAGCCAGCCAGGACAAGGGTAAAAACATT<br>GCTTATCCCCAGATGAACTCACTCAAGCCGGAGGACACCGCTATGTATTACTGT<br>AAAGCATCCTGCGTGAGAGGACGGGCTATCAGCGAATACTGGGGGCAGGGAACC<br>CAGGTGACCGTGAGCAGC |
| DR593-<br>hIL27<br>Ra_VH<br>H6 | 1061 | CAGGTGCAGTTGCAGGAGTCCGGGGGAGGTTCCGTCCAGGGGGGGGGAAGTCTG<br>CGCTTGTCATGCGCTGCCAGCGGCTATCCCTACTCCAACGGCTATATGGGCTGG<br>TTTAGGCAGGCCCCTGGGAAGGAACGCGAAGGCGTCGCGACGATCTACACGGGC<br>GATGGGAGGACCTATTACGCAGATTCCGTAAAGGGCAGATTTACCATCTCCCGT<br>GATAACGCCAAGAATACCGTTGACCTCCAGATGTCCACTCTGAAACCCGAGGAT<br>ACCGCCATGTACTATTGCGCCGCTCGCGCCGCTCCCCTCTACAGCTCTGGATCA<br>CCACTGACCCGCGCTAGGTATAACGTGTGGGGTCAGGGGACACAGGTGACCGTC |

TABLE 1B-continued

| Name | SEQ ID NO: | Sequence |
|---|---|---|
| | | AGCTCTGGGGGAGGCTCCCAGGTTCAGCTCCAGGAGTCTGGAGGGGGCCTTGTG CAGCCCGGCGGGTCCCTCCGTCTGAGTTGTGCTGCCCCAGGCTTTAGTTTCTCT TCCTACGCTATGAAATGGGTCCGTCAAGCGCCCGGCAAAGGCCTGGAGTGGGTC TCTACCATTAGCTCCGGGGGTTCCAGCACGAATTATGCTGACTCCGTCAAAGGC AGGTTCACTATCAGCCGCGACAACGCCAAGAATACCCTGTACTTGCAGCTCAAC AGCCTGAAGATCGAGGACACCGCGATGTATTACTGCGCTAAAGCCATCGTGCCT ACTGGAGCGACGATGGAACGCGGACAGGGCACTCAGGTCACCGTGTCCAGC |
| DR593-hIL27Ra_VH H6 | 1062 | CAAGTGCAGCTGCAAGAATCAGGCGGAGGCAGTGTCCAAGCTGGCGGTAGTCTG CGCCTGAGCTGCGCCGCATCAGGCTACCCATACTCTAACGGCTATATGGGGTGG TTTAGGCAAGCCCCCGGCAAGGAGCGCGAAGGCGTGGCGACCATCTACACTGGT GATGGCCGCACTTACTATGCGGACTCTGTGAAAGGACGCTTCACAATTTCTCGT GACAATGCTAAGAACACTGTGGATCTTCAGATGAGTTCCCTGAAGCCCGAAGAC ACGGCGATGTATTACTGTGCTGCCAGAGCCGCTCCGCTGTACTCCAGCGGCAGC CCCCTCACCCGCGCCCGTTATAACGTCTGGGGCCAGGGCACCCAGGTCACTGTT TCTTCCGGTGGCAGTGGAGGCTCTGGGGGCAGCGGACAAGTACAACTCCAGGAG TCAGGCGGGGGCCTGGTTCAGCCAGGGGGTTCCCTGCGCCTGAGCTGTGCCGCT TCTGGCTTTTCATTCTCTTCCTATGCCATGAAGTGGGTGCGCCAGGCCCCTGGG AAGGGACTGGAGTGGGTGAGCACCATTTCAAGTGGAGGTAGCTCCACCAACTAC GCGGATTCCGTCAAAGGCCGCTTCACCATTTCCAGGGACAACGCTAAAAACACC CTGTATCTTCAGCTCAACTCCCTGAAGATCGAAGACACTGCTATGTACTATTGC GCCAAGGCCATCGTCCCCACAGGTGCCACAATGGAGAGGGGCCAGGGCACGCAG GTGACAGTCAGCAGT |
| DR593-hIL27Ra_VH H7 | 1063 | CAGGTGCAGCTCCAGGAATCCGGGGGAGGCTCCGTGCAGGCTGGCGGGTCCCTT AGGTTGTCTTGCGCTGCCAGCGGATACCCTTACAGCAATGGATATATGGGTTGG TTCCGCCAGGCCCCTGGCAAGGAGAGAGAGGGAGTGGCCACCATCTACACGGGT GACGGGCGTACCTACTATGCCGATTCCGTTAAGGGCAGGTTCACAATCTCCCGC GACAACGCCAAGAACACCGTGGACCTGCAAATGTCTTCCCTTAAACCCGAAGAC ACTGCCATGTATTACTGCGCTGCCCGCGCGGCCCCACTCTACAGCTCTGGGAGC CCTTTGACCCGTGCTCGCTATAACGTGTGGGGCCAGGGTACTCAGGTGACCGTC TCAAGCGGCGGAGGCTCTCAGGTGCAGCTCCAGGAGTCAGGTGGAGGTTTGGTG CAGCCAGGAGGCTCACTGAGACTGAGCTGCGCTGCCAGCGGGTTCACTTTCTCC TCTTATCCTATGTCCTGGGTTCGCCAGGCACCCGGCAAAGGCTTGGAGTGGATC AGCACCATCAGTGCGGGTGGCGACACAACTTTGTACGCCGACTCTGTGAAGGGT CGTTTTACCTCCAGTCGCGACAATGCTAAAAACACACTGTATCTGCAACTGAAC TCTCTGAAGACCGAGGACACCGCCATCTATTACTGTGCCAAAAGAATTGACTGT AACAGCGGATATTGCTATAGACGCAACTATTGGGGTCAGGGCACACAGGTTACC GTGTCCTCA |
| DR593-hIL27Ra_VH H7 | 1064 | CAAGTCCAGCCCCAGGAATCCGGCGGTGGCAGCGTTCAAGCCGGTGGCTCCCTG CGCCTGAGTTGTGCAGCTTCAGGTTATCCCTACAGCAACGGATACATGGGATGG TTCCGTCAGGCTCCCGGTAAGGAGCGTGAGGGTGTGGCAACTATCTATACGGGA GATGGCAGGACCTACTATGCGGACTCTGTGAAGGGCAGGTTCACGATCTCTCGT GATAACGCTAAGAACACCGTCGATCTCCAGATGTCTTCCTTGAAGCCCGAGGAT ACGGCTATGTATTACTGCGCCGCGAGAGCTGCCCCGCTCTATTCCTCCGGCAGT CCTCTGACTCGGGCACGGTACAACGTGTGGGGCCAAGGCACCCAGGTCACTGTG TCCTCTGGGGGTAGCGGTGGCTCTGGCGGTTCAGGTCAGGTGCAGCTGCAAGAA TCCGGTGGAGGCCTGGTGCAGCCCGGGGGTTCCCTCCGTCTGTCCTGTGCTGCA TCTGGATTCACTTTTTCTAGCTACCCAATGTCATGGGTGCGCCAGGCCCCAGGC AAAGGGCTGGAGTGGATCTCAACTATCTCCGCAGGTGGCGATACTACCCTCTAC GCTGACTCCGTGAAGGGGCGGTTTACCAGTTCCCGTGACAACGCCAAGAACACT TTGTATCTTCAGCTGAACTCATTGAAGACTGAGGACACCGCCATCTATTACTGC GCTAAGAGAATCGACTGCAACTCAGGGTACTGCTATAGACGCAACTATTGGGGC CAGGGGACTCAGGTGACCGTGTCAAGC |
| DR593-hIL27Ra_VH H8 | 1065 | CAGGTGCAGTTGCAGGAAAGCGGCGGTGGCTCCGTGCAGGCTGGGGGCTCTCTG CGTTTGTCATGTGCCGCAAGTGGATACCCCTACAGCAACGGCTACATGGGCTGG TTCAGGCAGGCTCCCGGAAAGGAGCGCGAAGGGGTGGCCACCATCTACACTGGG GATGGAAGGACTTACTATGCGGATAGCGTAAAGGGGCGTTTTACTATCTCCAGA GACAATGCCAAAAACACAGTTGACCTCCAGATGTCTAGCTTGAAGCCTGAAGAC ACTGCCATGTACTATTGTGCAGCGCGGGCAGCCCCGCTGTATAGCTCCGGCTCC CCTCTGACACGCGCCCGCTACAACGTGTGGGGACAGGGCACCCAGGTTACCGTG AGTTCCGGCGGTGGGTCCCAGGTCCAGCTTCAGGAGTCCGGGGGGGGTTCCGTC CAAGTTGGTGGCAGCCTGCGCCTGTCCTGCGCTGCCTCCGGGTTTACTTTCAGT TCCTACCCAATGTCATGGGTGCGCCAGGCTCCTGGTAAGGGGCTGGAATGGATT TCTACTATCAGTGCAGGCGGAGATACGACCCTCTACGCCGATAGCGTGAAGGGG CGGTTCACTTCATCTCGTGATAACGCCAAGAACACCCTGTACCTTCAGCTGAAC TCCCTGAAGACGGAAGACACCGCCATTTATTACTGCGCGAAGAGGATCGACTGC AACTCCGGCTACTGCTATCGTCGCAACTATTGGGGCCAGGGTACGCAGGTGACG GTCAGTTCC |
| DR593-hIL27Ra_VH H8 | 1066 | CAGGTGCAGCTCCAGGAGTCAGGCGGTGGCTCTGTGCAGGCCGGAGGGTCTCTC CGGTTGAGTTGTGCAGCTTCAGGCTACCCTTATAGCAACGGCTACATGGGATGG TTCAGACAGGCACCCGGTAAGGAACGCGAGGGCGTAGCCACGATCTACACTGGT GATGGGAGGACCTATTACGCTGACTCTGTGAAAGGTCGCTTCACAATTAGCCGC GATAACGCTAAGAACACCGTGGATCTCCAGATGAGCAGTTTGAAGCCTGAGGAC |

TABLE 1B-continued

| Name | SEQ ID NO: | Sequence |
|---|---|---|
| | | ACCGCAATGTACTATTGTGCTGCACGCGGGGCCCCTCTCTACAGTTCCGGCAGC CCACTGACTAGAGCCCGGTACAACGTCTGGGGCCAAGGCACCCAGGTCACCGTC AGTAGCGGGGGGAGGGGAGGCTCCGGTGGCTCCGGCCAGGTGCAGCTCCAGGAG TCTGGAGGCGGATCTGTCCAGGCTGGAGGGAGCCTGCGCTTGAGTTGCGCTGCC AGCGGATTCACCTTTTCTTCATACCCCATGAGCTGGGTGCGCCAAGCGCCCGGA AAGGGGCTGGAGTGGATCTCAACGATCAGCGCCGGAGGTGATACAACCCTCTAC GCAGACAGCGTCAAAGGCAGGTTTACATCTAGCCGCGACAACGCAAAGAACACC CTGTATTTGCAGCTGAACAGCCTGAAAACGGAAGACACCGCCATCTATTACTGC GCCAAAAGAATTGATTGCAATTCTGGTTATTGTTACAGACGCAATTACTGGGGA CAGGGGACCCAGGTTACAGTCTCCAGT |
| DR593-hIL27 Ra_VH H9 | 1067 | CAGGTCCAGCTTCAGGAAAGCGGGGGGGGTAGCGTCCAGGCAGGTGGCAGCCTG CGTCTGAGCTGTGCGGCCAGCGGTTATCCTTACTCCAACGGTTACATGGGCTGG TTCCGCCAGGCCCCTGGCAAGGAGCGTGAGGGAGTGGCCACCATCTACACTGGA GATGGAAGAACCTACTATGCAGATTCAGTTAAGGGCAGGTTTACAATCAGCCGC GATAATGCCAAGAACACAGTCGATCTCCAGATGTCCTCTCTGAAGCCCGAAGAC ACTGCCATGTATTACTGTGCTGCACGCGCTGCCCCGCTGTATTCTTCAGGTAGT CCCCTCACACGCGCCCGCTACAACGTGTGGGGGCAGGGTACACAGGTAACTGTG TCTAGCGGCGGTGGGAGCCAGGTCCAGCTCCAGGAGTCTGGTGGCGGATCTGTG CAGAGCGGGGGTTCCCTGCGCCTGTCCTGTGCTGCCTCTGGGTTCACGTATAGC ACTTCCAACAGCTGGATGGCCTGGTTCCGTCAAGCGCCTGGAAAGGAGCGTGAG GGGGTGGCTGCCATCTATACAGTGGGAGGTTCTATCTTTTACGCAGACAGCGTG CGTGGACGTTTCACAATCTCTCAAGACGCTACTAAGAATATGTTTTACCTTCAG ATGAACACTCTCAAGCCCGAGGACACCGCAATGTATTACCGCGCTGCGGCATCT GGCCGCCTGAGAGGCAAGTGGTTTTGGCCCTACGAGTATAATTACTGGGGCCAG GGCACGCAGGTGACGGTCTCTAGT |
| DR593-hIL27 Ra_VH H9 | 1068 | CAAGTTCAACTTCAGGAGAGTGGGGGTGGCTCTGTGCAGGCCGGTGGCTCTCTG AGACTCAGTTGTGCTGCCTCCGGTTACCCTTATTCCAACGGCTACATGGGCTGG TTCCGTCAGGCCCCAGGCAAGGAGCGCGAAGGCGTCGCCACCATTTACACAGGC GACGGACGCACATACTATGCTGATTCTGTGAAGGGCAGATTTACCATCAGCCGG GATAACGCCAAAAATACCGTGGACCTTCAAATGAGTTCTCTGAAGCCTGAGGAT ACCGCCATGTATTACTGGGCCGCGCGGGCAGCTCCCCTCCACAGCAGTGGCTCC CCGCTGACCCGCGCCCGCTATAACGTGTGGGGCCAAGGCACACAGGTGACCGTG TCCAGCGGGGGCTCCGGGGGCTCTGGGGGCTCAGGACAGGTCCAGTTGCAGGAA TCTGGCGGTGGCAGCGTTCAGAGTGGAGGTTCCCTGCGGCTCTCTTGTGCCGCT TCCGGCTTCACCTACTCAACCTCTAATAGCTGGATGGCCTGGTTCCGTCAAGCC CCCGGCAAGGAGCGCGAAGGCGTGGCTGCAATCTACACCGTAGGCGGATCTATC TTCTACGCCGATTCAGTGCGCGGCAGGTTTACCATCTCACAGGACGCCACTAAG AATATGTTTTATTTGCAGATGAATACTCTGAAGCCTGAGGACACCGCTATGTAT TACTGCGCTGCGGCCAGTGGCCGCCTGAGGGGCAAGTGGTTCTGGCCATACGAA TACAACTACTGGGGACAGGGGACCCAGGTTACAGTTAGTAGC |
| DR593-hIL27 Ra_VH H10 | 1069 | CAGGTGCAGTTGCAGGAATCTGGGGGTGGCAGTGTGCAGGCTGGAGGCTCCCTG CGCCTGTCCTGTGCGGCCTCTGGCTATCCATATAGTAATGGTTACATGGGATGG TTTAGGCAGGCTCCGGGCAAGGAGCGCGAGGGCGTGGCCACTATCTACACTGGT GATGGTCGGACCTACTATGCTGACTCTGTGAAGGGGCGCCTCACAATTTCTGGG GATAACGCCAAAAATACCGTGGACTTGCAGATGAGTTCCCTCAAACCGGAAGAC ACCGCCATGTATTACTGTGCAGCTAGGGCGGCACCGCTGTATAGTTCTGGCAGC CCTCTGACTCGGGCTCGCTATAATGTCTGGGGCCAGGGAACCCAGGTTACAGTC TCCAGCGGGGGTGGGTCCCAAGTGCAGTTGCAGGAATCCGGTGGGGGTTCCGTT CAGGCCGGAGGCTCACTGGGGCTGTCTTGCAGAGCGTCCGGCTCCACTTACTCT AACTATTGCCTGGGCTGGTTCCGTCAGATTACTGGCAAGGAGAGGGAGGGCGTG GCCGTCATAAATTGGGTGGGAGGTATGCTGTACTTTGCCGATTCAGTTAAAGGA CGTTTTACGGTGAGCCAGGACCAGGCTAAGAACACCCTTTACCTTCAGATGAAC AGCCTGAAGCCCGAAGACACAGCCATGTACTATTGTGCTGCGGAGTCCGTGTCT AGCTTTTCTTGCGGAGGCTGGCTCACGAGACCGGATAGAGTGCCATACTGGGGC CAGGGCACCCAGGTGACCGTCTCCAGC |
| DR593-hIL27 Ra_VH H10 | 1070 | CAGGTGCAGCTCCAGGAAAGCGGAGGCGGGTCTGTCCAGGCAGGGGGCTCCCTG AGACTCTCTTGTGCTGCGAGCGGTTATCCTTATAGCAACGGGTATATGGGATGG TTTCGCCAGGCTCCGGGGAAGGAGCGCGAGGGTGTGGCTACCATCTATACGGGT GATGGTCGGACTTACTATGCAGACAGTGTCAAGGGCCGCTTCACCATCAGCAGA GACAACGCAAAAAATACCGTGGACTTGCAGATGTCATCCCTCAAGCCAGAGGAC ACAGCAATGTATTACTGCGCCGCGAGAGCTGCGCCCCTGTACTCCTCTGGATCT CCCTTGACCAGAGCCCGCTATAATGTCTGGGGACAGGGAACCCAGGTAACAGTG TCCAGCGGAGGTTCCGGGGGTTCTGGAGGTTCTGGACAGGTTCAACTCCAGGAG TCTGGCGGGGGCTCAGTCCAGGCTGGGGGGTCTTTGCGCCTGTCCTGTCGGGCC AGCGGCTCCACCTACTCCAACTACTGCCTCGGTTGGTTCCGCCAGATTACTGGC AAAGAGCGTGAGGGCGTGGCTGTTATCAACTGGGTGGGCGGAATGCTGTACTTC GCCGATTCTGTTAAGGGACGCTTCACCGTCTCTCAGGACCAGGCCAAGAACACG CTGTATTTGCAGATGAACAGTCTGAAGCCAGAGGATACAGCAATGTATTACTGT GCTGCGGAGTCTGTTAGCTCTTTTTCCCGTGGTGGCTGGCTGACCAGGCCGGAT CGCGTGCCTTACTGGGGGCAGGGAACCCAGGTGACTGTCAGCAGT |
| DR593-hIL27 | 1071 | CAGGTGCAGCTTCAGGAGTCCGGCGGAGGCAGTGTCCAGGCAGGGGGCTCCCTG CGCCTCTCTTGTGCGGCCTCTGGATATCCCTACTCTAACGGATACATGGGCTGG |

TABLE 1B-continued

| Name | SEQ ID NO: | Sequence |
|---|---|---|
| Ra_VH<br>H11 | | TTTCGTCAGGCCCCAGGAAAAGAGCGGGAGGGGGTGGCGACAATCTACACTGGC<br>GATGGCCGCACCTACTATGCTGATTCCGTTAAGGGGCGCTTCACCATCAGCAGA<br>GACAACGCAAAGAACACTGTCGATCTTCAGATGAGTTCCCTCAAACCTGAAGAC<br>ACAGCCATGTATTACTGTGCAGCCCGCGCGGCCCCTCTTTACAGCTCTGGGAGC<br>CCCCTGACACGCGCTCGCTACAATGTTTGGGGTCAGGGCACACAGGTGACAGTC<br>TCCTCTGGGGGAGGCTCCCAAGTCCAGCTTCAGGAATCCGGCGGTGGGAGTGTG<br>CAAGCTGGTGGATCTCTGCGCCTGAGCTGTAGGGCCTCCGGCAGCACATACTCT<br>AACTACTGCCTGGGCTGGTTTAGGCAGTCCACAGGAAAAGAACGCGAAGGAGTC<br>GCGGTAATAAATTGGGTCGGGGGTATGCTCTACTTCGCCGACTCCGTGAAAGGC<br>CGCTTCACAGTGTCTCAGGATCACGCCAAAAATACCGTAACCCTTCAGATGAAC<br>TCCTTGAAGCCAGAGGACACCGCGATGTATTACTGCGCTGGGGAGTCCGTATCC<br>AGCTTCAGCTGTGGTGGCTGGCTGACCCGCCCAGGACGGGTTCCATACTGGGGC<br>CAGGGTACACAGGTCACAGTGTCTAGC |
| DR593-<br>hIL27<br>Ra_VH<br>H11 | 1072 | CAGGTGCAGCTCCAGGAGTCCGGCGGAGGGTCCGTCCAGGCCGGAGGCTCCCTC<br>CGTCTGTCTTGCGCCGCGTCCGGTTATCCTTACAGCAACGGCTATATGGGTTGG<br>TTCCGTCAGGCCCCCGGAAAGGAAAGAGAAGGCGTCGCCACGATCTACACCGGG<br>GATGGCAGGACCTACTATGCTGACTCCGTGAAGGGCCGCTTCACAATTAGTCGC<br>GACAATGCCAAGAACACGGTGGACCTCCAGATGTCTTCACTTAAACCCGAGGAC<br>ACCGCTATGTATTACTGTGCAGCCAGAGCAGCTCCTCTGTACTCCTCAGGCTCT<br>CCCCTCACCCGTGCTCGCTACAACGTGTGGGGACAGGGCACACAGGTCACAGTG<br>TCATCCGGGGGTTCCGGTGGCAGTGGAGGCAGCGGACAGGTACAGCTTCAGGAG<br>TCCGGCGGGGGTTCTGTGCAGGCTGGAGGCTCTTTGCGCCTTAGCTGTCGCGCG<br>AGCGGTTCCACCTACTCCAATTACTGCCTGGGTTGGTTCAGGCAGAGCACCGGC<br>AAGGAGCGCGAAGGAGTGGCCGTCATCAACTGGGTCGGTGGGATGCTCTATTTT<br>GCTGACTCTGTGAAGGGCAGGTTTACTGTGAGCCAGGACCATGCCAAGAACACT<br>GTGACTCTCCAGATGAATAGTCTTAAACCAGAGGACACGGCTATGTATTACTGT<br>GCAGCCGAATCAGTCTCCTCTTTCACTTGTGGTGGGTGGTTGACGAGGCCGGGT<br>CGTGTTCCCTATTGGGGCCAGGGGACCCAGGTGACTGTATCCTCT |
| DR593-<br>hIL27<br>Ra_VH<br>H12 | 1073 | CAGGTGCAGCTCCAAGAGTCCGGTGGGGGGAGCGTGCAGGGGGGCGGTTCCCTT<br>CGCCTGTCTTGTGCTGCCTCCGGCTACCCCTACTCTAATGGCTACATGGGCTGG<br>TTCCGCCAAGCTCCAGGGAAGGAAAGGGAAGGCGTGGCCACTATTTACAGGGGC<br>GACGGTCGCACATATTACGCTGACTCTGTTAAAGGCCGCCTCACTATCTCCAGA<br>GACAACGCAAAGAACACGGTGGACCTCCAGATGTCCTCTCTGAAGCCCGAAGAC<br>ACCGCTATGTATTACTGCGCTGCAAGGGCTGCCCCTCTGTACTCCAGCGGTTCC<br>CCTCTGACCAGAGCCCGCTATAACGTCTGGGGCCAAGGAACACAGGTCACTGTC<br>AGCTCCGGTGGCGGGTCACAGGTGCAGCTTCAGGAGAGCGGGGGGGGCAGTGTC<br>CAAGCTGGTGAGAGCCTCAGACTGAGTTGCAGAGCCAGCGGTTCCACCTACTCC<br>AACTACTGCTTGGGTTGGTTCAGGCAGATCACAGGCAAGGAGCGTGAGGGCGTC<br>GCTGTCATCAACTGGGTGGGGGGGATGCTCTACTTTGCTGACAGCGTTAAGGGC<br>CGGTTCACCGCGAGCCAGGATCAGGCGAAGAACACGGTTTATCTGGAGATGAAC<br>TCACCGAAGCCCGAGGATACAGCTATGTATTACTGTGCAACTGAGTCAGTTTCC<br>TCTTTCTCCTGGGGGGGGTGGCTGACCAGGCCGGATAGGGTGCCGTATTGGGGC<br>CAAGGGACTCAGGTTACCGTCTCCTCT |
| DR593-<br>hIL27<br>Ra_VH<br>H12 | 1074 | CAAGTGCAGCTCCAAGAATCAGGAGGCGGTTCCGTGCAGGCCGGGGGCTCCCTG<br>CGCTTGTCTTGCGCGGCCAGCGGGTATCCCTACTCTAATGGTTACATGGGCTGG<br>TTCCGTCAGGCTCCTGGCAAGGAACGGGAGGGAGTGGCCACTATCTATACTGGC<br>GACGGGAGGACCTACTATGCCGACTCCGTGAAGGGCCGGCTCACCATCAGCCGC<br>GACAACGCAAAAAATACCGTGGACTTGCAAATGAGTTCCCTGAAGCCCGAGGAC<br>ACCGCGATGTACTATTGTGCGGCCGGCGCCGCGCCTCTGTACTCCAGTGGGAGC<br>CCTCTCACCCGCGCCAGATACAACGTGTGGGGCCAGGGCACCCAGGTCACGGTG<br>TCTAGCGGAGGCAGCGGTGGATCTGGTGGCTCTGGACAAGTGCAACTCCAGGAG<br>TCAGGCGGTGGCTCCGTGCAGGCTGGCGAGAGCTTGCGGCTGTCCTGCCGCGCG<br>TCTGGCAGCACGTACAGCAATTACTGCCTGGGATGGTTCCGGCAGATCACCGGG<br>AAAGAGCGTGAGGGAGTCGCCGTGATTAACTGGGTCGGGGGCATGTTGTATTTT<br>GCTGATTCCGTGAAAGGGCGCCTTACCGTCAGCCAGGACCAGGCCAAGAACACG<br>GTGTATCTTGAGATGAACTCACTCAAGCCTGAGGACACAGCTATGTATTACTGT<br>GCGACCGAGTCCGTGTCATCTTTTTCCTGTGGCGGTTGGCTTACAAGGCCTGAT<br>CGCGTTCCTTACTGGGGCCAGGGCACTCAGGTGACCGTGTCTAGC |
| DR593-<br>hIL27<br>Ra_VH<br>H13 | 1075 | CAGGTACAGTTGCAGGAAAGTGGCGGAGGCAGCGTGCAGGCCGGGGGCAGTCTC<br>CGTCTGTCTTGTGCCGCTAGTGGCTATCCCTATTCTAACGGCTATATGGGATGG<br>TTCCGCCAGGCACCCGGCAAAGAGAGGGAAGGCGTCGCCACCATCTACACAGGT<br>GATGGAAGGACATACTATGCAGACAGCGTGAAGGGCCGCTTCACGATTAGCCGC<br>GACAACGCGAAGAACACTGTGGATCTCCAAATGAGTTCCCTCAAGCCTGAGGAC<br>ACTGCGATGTATTACTGCGCAGCCAGAGCAGCTCCCCTTTACAGCAGTGGAAGC<br>CCGCTGACTCGGGCAAGATACAACGTCTGGGGCCAGGGAACTCAGGTTACGGTA<br>TCTTCCGGCGGTGGATCTCAGGTTCAGCTTCAGGAATCAGGGGGTGGATCAGTG<br>CAGGCGGGCGGAAGTTTGCGCCTGTCCTGTGTAGCCTCCGGGTACGTCTCCTGT<br>GACTATTTCCCGCCCAGCTGGTATAGGCAGGCCCCCGGCAAGGAGCGCGAGTTC<br>GTGTCCATCATTGATGGCACCGGGTCCACGTCCTACGCCGCTTCCGTGAAGGGG<br>AGATTCACGGCGAGCCAAGATCGCGGCAAAAACATCGCATACTTGCAGATGAAC<br>TCACTCAAGCCCGAGGATACCGCCATGTATTACTGTAAGGCCAGCTGCGTTCGC<br>GGTCGCACTATCTCTGAATATTGGGGCCAGGGAACCCAGGTGACAGTAAGCAGT |

TABLE 1B-continued

| Name | SEQ ID NO: | Sequence |
|---|---|---|
| DR593-hIL27Ra_VH H13 | 1076 | CAAGTGCAGCTCCAGGAGAGTGGTGGGGGCTCCGTACAGGGGGGCGGTTCCCTG<br>CGCCTTAGTTGCGCGGCCAGCGGCTACCCTTATTCCAACGGTTACATGGGCTGG<br>TTCCGCCAGGCACCAGGCAAAGAGAGAGAGGGGGTTGCAACCATCTACACTGGC<br>GATGGTAGAACTTATTACGCCGACTCTGTAAAGGGGCGCTTCACAATTTCCCGT<br>GATAATGCCAAGAACACCGTTGACCTCCAGATGAGCAGTCTGAAGCCAGAGGAT<br>ACAGCCATGTATTACTGCGCCGCTCGGGCAGCCCCACTCTACAGCTCCGGTAGC<br>CCCCTGACCCGTGCCCGCTACAACGTGTGGGGACAGGGCACACAGGTCACCGTG<br>TCCTCTGGTGGCTCCGGGGGCAGCGGCGGATCAGGCCAGGTGCAGCTCCAGGAA<br>AGCGGAGGCGGATCTGTGCAAGCCGGAGGCTCTCTGAGACTCTCCTGTGTTGCC<br>AGCGGCTACGTGTCCTGTGACTACTTCTTGCCTTCTTGGTATCGTCAGGCACCT<br>GGAAAGGAGCGTGAGTTCGTGTCCATCATTGACGGCACAGGCTCTACCTCCTAC<br>GCCGCGAGCGTGAAGGGTCGTTTCACCGCTTCACAGGATCGCGGTAAGAACATC<br>GCGTATCTCCAGATGAACTCCCTGAAACCCGAAGACACCGCCATGTATTACTGC<br>AAAGCCTCCTGTGTGCGCGGGCGCACGATCAGCGAATACTGGGGGCAGGGTACA<br>CAGGTCACCGTGTCCTCC |
| DR593-hIL27Ra_VH H14 | 1077 | CAGGTGCAGTTGCAGGAGAGCGGTGGAGGCTCCGTTCAGGCAGGTGGCAGCCTG<br>CGGCTCTCCTGCGCCGCATCCGGTTACCCATACAGCAATGGCTACATGGGATGG<br>TTCCGCCAAGCGCCTGGAAAAGAAAGGGAAGGTGTGGCCACTATCTACACTGGT<br>GATGGCCGGACGTACTATGCCGACTCAGTGAAGGGCCGGCTCACAATCAGCCGG<br>GATAACGCTAAGAACACAGTGGATCTTCAGATGAGTTCCCTGAAACCCGAGGAC<br>ACTGCCATGTATTACTGTGCGGCCAGGGGGGCTCCCCTGTACTCTTCCGGCTCC<br>CCCTTGACCCGTGCCCGTTATAATGTGTGGGGTCAAGGCACACAGGTCACTGTG<br>TCTTCCGGGGGAGGCTCCCAGGTCCAACTCCAGGAAAGTGGTGGAGGCTCTGTG<br>CAGGCAGGCGGTTCCCTCCGCCTGAGCTGTGTGGCCTCCGGCTACGTGTCATGT<br>GATTACTTTCTGCCAAGCTGGTAACGTCAGGCTCCCGGTAAGGAGCGCGAGTTC<br>GTTAGCATTATCGACGGCACCGGCTCCACCAGCTATGCGGCCAGCGTCAAGGGG<br>CGCTTCACCGCCTCTCAGGACAAAGGTAAGAACATCGCCTACCTGCAAATGAAC<br>TCCCTGAAGCCCGAGGACACAGCCATGTATTACTGCAAGGCCTCCTGTGTCAGA<br>GGTAGGGCGATCTCAGAGTACTGGGGTCAGGGAACCCAGGTGACCGTGTCCTCC |
| DR593-hIL27Ra_VH H14 | 1078 | CAAGTGCAGTTGCAGGAGAGCGGCGGAGGCTCTGTGCAGGGGGGAGGCAGTCTG<br>AGACTGTCCTGTGCCGCTTCCGGCTACCCCTATAGCAACGGTTATATGGGTTGG<br>TTCCGCCAGGCCCCAGGAAAAGAGCGCGAGGGCGTAGCGACTATTTACACGGGT<br>GATGGTAGAACTTACTATGCAGATTCAGTAAAGGGCCGTTTCACCATTTCCCGT<br>GACAACGCTAAGAATACCGTAGATTTGCAGATGTCTTCCCTGAAGCCGGAAGAC<br>ACTGCCATGTATTACTGCGCTGCACGCGCGGCTCCCCTTTATTCTTCCGGGTCA<br>CCACTCACCCGTGCCCGCTACAACGTGTGGGGCCAGGGCACGCAGGTCACTGTA<br>TCCAGCGGAGGCAGCGGCGGAAGCGGGGGCTCTGGCCAAGTCCAGCTCCAGGAG<br>TCAGGCGGTGGCTCAGTCCAGGCTGGGGGCTCACTGCGCCTGAGCTGCGTGGCC<br>TCTGGCTATGTCAGTTGTGATTACTTCCTTCCGAGCTGGTATCGCCAAGCGCCT<br>GGGAAGGAGAGGGAGTTCGTGTCTATTATCGACGGGACCGGCAGCACCAGCTAT<br>GCGGCTAGTGTGAAGGGCCGTTTCACCGCTTCCCAGGATAAGGGCAAGAACATC<br>GCCTATTTGCAAATGAACAGTCTTAAACCGGAGGATACTGCTATGTACTATTGC<br>AAGGCCTCCTGCGTGCGGGGAAGAGCCATCAGTGAGTACTGGGGGGAGGGCACC<br>CAGGTCACGGTATCCTCC |
| DR593-hIL27Ra_VH H15 | 1079 | CAGGTTCAGCCTCAGGAGAGTGGAGGCGGTAGCGTGCAGGCCGGGGGCAGCTTG<br>CGCCTGTCTTGCGCTGCCTCCGGTTACCCTTATAGTAACGGATACATGGGTTGG<br>TTCAGGCAGGCCCCCGGCAAAGAGAGAGAGGGCGTTGCTACCATTTACACCGGC<br>GATGGCCGCACCTACTATGCTGACTCTGTGAAGGGTCGCCTCACAATCTCCCGT<br>GATAACGCTAAAAATACCGTCGATCTCCAGATGTCTTCCCTGAAACCCGAGGAT<br>ACTGCAATGTATTACTGTGCTGCCCGCGCCGCTCCTCTGTACTCTTCAGGTTCT<br>CCTCTGACCCGCGCCAGGTACAACGTCTGGGGTCAGGGCACCCAGGTTACCGTA<br>AGCTCCGGTGGAGGCTCTCAAGTGCAGTTGCAGGAATCAGGAGGTGGCTCCGTC<br>CAGGCAGGTGGGAGCCTCCGCCTCTCATGCGTCGCAAGCGGCTACGTGAGCTGC<br>GACTACTTCTTGCCCTCATGGTATCGCCAGGCTCCTGGGAAGGAGCGTGAGTTC<br>GTGAGCATCATTGACGGCACCGGCTCCACCAGCTATGCCGCTTCCGTGAAGGGC<br>CGGTTCACTGCGTCCCAGGATAAGGGCAAGAACATCGCGTACCTTCAGATGAAC<br>ACCCTGAAGCCGGAGGATACAGCTATGTACTATTGCAAGGCATCTTGCGTGAGG<br>GGTAGAGCCATCAGCGAGTATTGGGGCCAAGGAACCCAGGTGACTGTTTCCTCT |
| DR593-hIL27Ra_VH H15 | 1080 | CAGGTGCAGTTGCAGGAGTCCGGTGGGGGATCTGTGCAGGCGGGAGGGAGCCTG<br>CGTCTTAGCTGCGCCGCAAGCGGATACCCCTACTCCAACGGATACATGGGTTGG<br>TTTCGCCAAGCCCCTGGGAAGGAAAGGGAGGGCGTGGCCACCATCTATACCGGA<br>GATGGCCGCACCTATTACGCTGATTCCGTGAAGGGACGTTTCACAATCAGCAGA<br>GATAACGCTAAGAACACTGTGGACCTCCAGATGTCTAGCCTGAAACCCGAAGAC<br>ACTGCCATGTATTACTGCGCGGCCAGAGCAGCCCCTCTGTATTCCCCTGGAAGC<br>CCGTTGACCAGAGCCCGCTACAATGTGTGGGGACAGGGCACCCAGGTCACTGTG<br>TCATCCGGCGGAAGCGGGGGTAGTGGGGGCTCTGGCCAAGTTCAGCTCCAGGAA<br>AGCGGCGGAGGCAGCGTGCAGGCTGGCGGATCACTGAGATTGAGCTGTGTTGCT<br>TCCGGCTATGTGAGCTGTGATTATTTCCTCCCCAGCTGGTACAGACAGGCTCCC<br>GGCAAGGAACGCGAGTTTGTCAGTATCATTGATGGCACCGGCTCTACCAGTTAC<br>GCTGCGTCAGTTAAAGGACGCTTCACCGCGTCCCAAGACAAAGGCAAGAACATC<br>GCCTATTTGCAGATGAACACCCTGAAGCCAGAAGACACTGCCATGTATTACTGC<br>AAGGCTTCTTGCGTGCGCGGTCGCGCCATTTCTGAATACCGGGGCCAGGGCACT<br>CAAGTCACCGTGTCTTCC |

TABLE 1B-continued

| Name | SEQ ID NO: | Sequence |
|---|---|---|
| DR593-<br>hIL27<br>Ra_VH<br>H16 | 1081 | CAGGTGCAGCTCCAGGAGTCTGGAGGCGGAAGTGTCCAGGCTGGCGGTAGCCTG<br>CGGCTTTCATGTGCCGCTTCCGGCTACCCGTACTCAAACGGCTACATGGGCTGG<br>TTCAGACAAGCGCCTGGAAAAGAGAGAGAAGGCGTGGCCACCATCTATACAGGT<br>GATGGCCGTACTTATTACGCTGACTCCGTCAAGGGCCGCTTCACCATCAGCCGG<br>GATAACGCTAAGAATACCGTCGATCTTCAAATGAGTTCCTTGAAGCCGGAAGAC<br>ACCGCTATGTATTACTGTGCCGCGCGGGCTGCCCCGCTGTATAGTAGCGGCTCT<br>CCCCTCACCCGCGCTCGCTACAACGTGTGGGGACAGGGGACTCAAGTAACCGTG<br>AGTTCCGGCGGTGGCTCTCAGGTGCAGCTGCAAGAAAGCGGGGGGGGCTCCGTG<br>CAGGCAGGCGGAAGCCTGCGCCTGTCTTGCAGAGCCTCCGGCAGTACCTACAGT<br>AACTATTGTCTGGGCTGGTTTCGCCAGATCACAGGTAAAGAGAGAGAAGGTGTT<br>GCCGTTATCAACTGGGTAGGTGGAATGCTGTACTTTGCCGATTCCGTGAAGGGT<br>CGCTTCACCGTGTCCCAAGACCAAGCCAAGAATACTGTATATTTGCAGATGAAC<br>TCCCTGAAGCCCGAGGACACAGCTATGTACTATTGTGCCGCTGAGTCTGCTAGT<br>AGCTTTTCCTGCGGGGGTTGGCTGACCCGCCCGGACCGCGTCCCCTACTGGGGA<br>CAGGGCACCCAGGTAACCGTGAGTTCT |
| DR593-<br>hIL27<br>Ra_VH<br>H16 | 1082 | CAGGTGCAGTTGCAGGAGTCTGGGGGTGGAAGCGTGCAAGCCGGGGGATCTCTG<br>CGGCTGAGCTGCGCTGCCAGTGGATATCCATATTCCAACGGCTATATGGGCTGG<br>TTTCGCCAAGCGCCCGGCAAGGAGCGCGAAGGCGTCGCCACAATCTACACAGGC<br>GATGGCCGCACCTATTACGCTGATTCCGTTAAAGGACGGTTCACGATCAGCCGC<br>GACAACGCCAAGAACACAGTTGACCTCCAGATGTCCAGCCTGAAGCCCGAGGAT<br>ACTGCGATGTATTACTGTGCCGCGAGAGCTGCCCCACTCCACAGTTCCGGGAGC<br>CCCCTTACTCGCGCCCGTTACAATGTTTGGGGACAGGGCACTCAAGTGACAGTG<br>TCCAGCGGAGGTTCCGGTGGCTCCGGGGGGTCTGGACAGGTGCAGTTGCAGGAG<br>TCCGGCGGAGGGAGCGTACAGGCCGGGGGCTCTTTGCGTCTGTCCTGCAGAGCT<br>TCCGGGTCTACCTATTCCAATTATTGTCTGGGTTGGTTCCGCCAGATTACTGGC<br>AAGGAGCGTGAAGGGGTCGCCGTCATCAACTGGGTGGGTGGGATGCTCTATTTC<br>GCGGATAGTGTGAAGGGCCGCTTTACAGTCTCTCAGGACCAGGCTAAGAATACT<br>GTCTATCTTCAGATGAACTCTTTGAAGCCCGAGGATACGGCCATGTACTATTGC<br>GCTGCGGAAAGTGCCTCTAGCTTCAGCTGTGGCGGTTGGCTCACCCGCCCAGAC<br>CGCGTCCCCTACTGGGGCCAGGGAACCCAGGTGACAGTGTCCAGT |
| DR593-<br>hIL27<br>Ra_VH<br>H17 | 1083 | CAGGTTCAGCTGCAAGAATCCGGGGGAGGGTCCGTCCAAGCGGGAGGCAGTCTC<br>AGACTTTCCTGCGCAGCTTCTGGATACCCTTACTCTAACGGATATATGGGTTGG<br>TTTAGACAGGCACCCGGCAAGGAGAGGGAAGGCGTGGCCACGATCTACACTGGG<br>GATGGCAGGACCTATTACGCAGACAGCGTGAAGGGCCGCCTCACCATTTCCAGA<br>GATAATGCTAAGAACACCGTTGATCTCCAGATGAGTTCCCTGAAGCCAGAAGAT<br>ACCGCCATGTATTACTGCGCTGCCCGCGCCCGCGCCTCTTTACAGCTCTGGGAGC<br>CCGCTGACTCGTGCTAGGTATAACGTCTGGGGCCAGGGAACCCAGGTGACTGTC<br>AGCTCTGGGGGCGGGAGCCAGGTGCAGCTCCAGGAGAGTGGCGGTGGCCTTGTT<br>CAGCCCGGTGGCTCCTTGCGGCTGTCATGTGCTGCCTCCGGCTTCACATTTTCC<br>CTGAGCGGGATGTCCTGGGTGCGGCAGGCCCCCGGCAAGGGCCTTGAGTGGGTC<br>TCCGCTATCTCCAGCGGCGGTGCAAGCACTTACTATACCGACAGCGTCAAGGGC<br>CGTTTCACTATCTCACGCGATAACGCCAAAAACATGCTGTATCTCCAGCTGAAC<br>TCCCTCAAGACCGAGGATACCGCTATGTACTATTGTGCCAAAGGCGGTTCCGGC<br>TATGGCGATGCGTCCCGCATGACTTCTCCCGGCTCCCAGGGCACTCAGGTTACC<br>GTGTCTAGC |
| DR593-<br>hIL27<br>Ra_VH<br>H17 | 1084 | CAAGTTCAGCTTCAGGAGAGTGGAGGCGGATCTGTCCAGGCAGGTGGCTCACTT<br>AGGCTGTCTTGTGCTGCCAGTGGCTACCCCTACTCCAACGGATATATGGGTTGG<br>TTTCGCCAGGCACCAGGGAAGGAGCGCGAGGGCGTCGCTACCATCTACACCGGC<br>GACGGACGCACCTACTATGCGGACAGCGTGAAGGGCCGGTTCACCATCAGCCGC<br>GACAACGCCAAAAACACCGTCGATTTGCAGATGTCTTCCCTGAAGCCAGAAGAC<br>ACAGCCATGTATTACTGTGCCGCGCGTGCTGCCCCACTCTACTCCTCTGGGAGC<br>CCCCTCACCCGTGCCCGCTACAACGTGTGGGGCCAGGGCACACAGGTGACCGTT<br>TCCAGTGGTGGCAGCGGTGGCAGCGGGGGTTCCGGCCAGGTCCAGCTCCAGGAG<br>TCAGGGGGTGGGCTGGTGCAGCCCGGGGGTAGCCTGCGCTTGTCCTGCGCTGCC<br>AGCGGGTTCACCTTCAGTCTGTCAGGTATGTCCTGGGTAAGGCAGGCTCCCGGT<br>AAGGGCCTGGAGTGGGTATCCGCCATCTCTAGCGGTGGAGCCAGCACCTATTAC<br>ACTGATTCAGTAAAAGGACGCTTCACCATTAGCAGGGACAACGCCAAAAACATG<br>CTGTATCTTCAACTGAACTCCCTCAAGACTGAGGACACAGCCATGTACTATTGC<br>GCCAAGGGAGGGTCTGGCTACGGCGATGCCTCCAGGATGACCTCCCCCGGTAGC<br>CAGGGCACTCAGGTGACAGTGTCAAGC |
| DP593-<br>hIL27<br>Ra_VH<br>H18 | 1085 | CAGGTGCAGCTCCAGGAGAGCGGTGGGGGAAGCGTGCAGGCTGGCGGAAGCCTC<br>CGCCTGTCCTGTGCGGCATCTGGCTACCCATATTCTAACGGCTATATGGGCTGG<br>TTTCGGCAAGCGCCTGGGAAGGAGCGCGAGGGGGTCGCCACCATTTATACTGGC<br>GATGGCCGCACCTATTACGCCGATTCTGTGAAGGGCCGCTTCACGATTTCTAGG<br>GATAACGCTAAAAACACCGTGGATCTGCAAATGTCCAGCCTGAAGCCAGAAGAC<br>ACAGCCATGTACTATTGCGCCGCTGGGGCCGCTCCTTTGTACTCATCCGGCTCA<br>CCTCTCACTAGAGCCCGTTACAACGTCTGGGGACAGGGTACTCAGGTTACCGTA<br>AGCTCTGGGGGTGGCTCACAAGTGCAGTTGCAGGAGAGCGGTGGAGGTTCCGTT<br>CAGGCTGGAGGCTCCCTGCGGCTTTCCCGCGTGGCTTCCGGCTACGTGTCATGC<br>GACTACTTCCTGCCTAGCTGGTATCGCCAGGCTCCTGGGAAGGAGCGTGAATTT<br>GTTAGCATCATTGATGGCACAGGCAGCACTAGCTACGCGGCTTCTGTTAAGGGA<br>CGTTTTACAGCGTCTCAGGACAAAGGGAAGAACATCGCCTACCTCCAGATGAAC |

TABLE 1B-continued

| Name | SEQ ID NO: | Sequence |
|---|---|---|
| | | TCCCTGAAACCGGAGGATACCGCCATGTACTATTGCAAGGCCTCCTGCGTGCGC<br>GGTCGCGGTATTAGCGAATACTGGGGACAGGGCACCCAGGTCACTGTGTCTTCA |
| DR593-<br>hIL27<br>Ra_VH<br>H18 | 1086 | CAGGTCCAGCTCCAGGAATCCGGTGGAGGCTCCGTGCAGGCCGGAGGGTCTCTC<br>AGACTCAGCTGCGCTGCCAGTGGTTATCCGTACTCTAATGGGTACATGGGTTGG<br>TTCCGCCAGGCCCCCGGCAAGGAGAGGGAAGGCGTGGCCACAATCTATACCGGC<br>GACGGGCGTACATATTACGCGGATAGTGTGAAGGGACGCTTCACCATCAGCCGT<br>GACAACGCCAAGAACACCGTGGACCTTCAGATGTCTTCCTTGAAGCCAGAAGAC<br>ACCGCGATGTATTACTGCGCGGCTCGCGCAGCTCCCCTCTATTCCTCAGGCTCC<br>CCACTGACCCGCGCCAGATACAATGTTTGGGGCCAGGGCACTCAGGTCACTGTG<br>TCCAGTGGCGGTAGCGGGGGTAGTGGTGGCTCCGGTCAGGTGCAGCTCCAGGAG<br>TCAGGGGGTGGCTCCGTACAGGCTGGTGGCTCACTCCGTCTGAGTTGTGTAGCC<br>AGCGGTTACGTCTCCTGCGATTATTTCCTTCCTTCCCGGTATCGCCAGGCTCCC<br>GGCAAAGAGCGGGAGTTCGTTTCCATTATCGACGGAACTGGATCAACATCCTAT<br>GCCGCTTCTGTCAAGGGGCGCTTCACCGCCTCACAGGATAAGGGCAAGAATATC<br>GCTTACCTCCAGATGAACAGCCTGAAACCAGAAGACACCGCGATGTATTACTGT<br>AAGGCGAGCTGTGTTCGGGGGCGGGGGATCTCAGAGTATTGGGGCCAGGGCACA<br>CAGGTGACCGTATCCTCC |
| DR593-<br>hIL27<br>Ra_VH<br>H19 | 1087 | CAAGTGCAGCTCCAGGAGTCAGGCGGTGGCAGCGTACAGGCCGGAGGCTCCCTG<br>AGACTGAGCTGTGCAGCCTCTGGCTACCCATACAGCAATGGCTATATGGGATGG<br>TTCCGCCAGGCTCCGGGTAAAGAGCGCGAGGGCGTGGCCACTATTTATACCGGG<br>GACGGAAGAACCTATTACGCGGATTCCGTGAAAGGCCGCTTCACAATTTCCCGT<br>GACAACGCGAAGAACACCGTCGATCTCCAGATGTCTTCCCTGAAGCCAGAGGAC<br>ACCGCTATGTATTACTGCGCCGCTAGGGCAGCTCCGCTTTACAGTAGCGGATCT<br>CCCCTCACCCGCGCCCGCTACAACGTGTGGGGACAGGGAACACAAGTGACAGTT<br>TCCTCAGGCGGTGGCTCTCAGGTGCAGCTCCAGGAATCTGGGGGAGGGTCCGTA<br>CAGGCCGGAGGCTCCCTGAGATTGAGCTGCCGCGCAAGTGGGTCCACCTACAGC<br>AACTATTGTCTGGGGTGGTTTCGCCAGATTACTGGTAAGGAGAGGGAGGGCGTG<br>GCCGTCATCAACTGGGTGGGCGGAATGCTCTACTTCGCCGACTCCGTGAAGGGT<br>CGGTTCACCGTTTCACAGGACCAAGCAAAGAACACCGTGTACCTCCAGATGAAC<br>AGTCTGAAGCCCGAGGATACCGCCATGTATTACTGTGCGGCTGAATCCGTCAGC<br>TCCTTCTCCTGCGGCGGGGGGCTGACACGGCCAGATCGGGTCCCTTACTGGGGA<br>CAGGGCACACAGGTGACTGTGTCCTCC |
| DR593-<br>hIL27<br>Ra_VH<br>H19 | 1088 | CAGGTGCAGTTGCAGGAGAGTGGAGGTGGCAGCGTGCAGGCCGGAGGCAGCCTT<br>CGCCTCTCTTGCGCTGCGAGTGGCTACCCCTACAGCAATGGGTACATGGGCTGG<br>TTCCGTCAGGCACCCGGTAAAGAAAGAGAGGGCGTGGCTACTATCTACACTGGG<br>GATGGCAGGACCTATTACGCCGATAGCGTCAAGGGCCGGTTCACGATTAGCCGT<br>GACAACGCCAAAAATACTGTGGACCTCCAGATGTCTTCACTGAAACCTGAGGAC<br>ACAGCAATGTATTACTGCGCTGCCCGTGCCGCTCCTCTCTACAGCTCCGGCTCT<br>CCATTGACCCGCGCCCGTTACAATGTTTGGGGGCAGGGCACCCAAGTCACCGTG<br>TCATCCGGCGGTTCCGGCGGAAGCGGTGGCAGCGGCCAGGTGCAGCTTCAGGAG<br>TCTGGTGGCGGTAGCGTTCAGGCAGGTGGCAGTCTGCGTCTGAGCTGCCGGGCG<br>AGCGGCAGCACATACTCCAACTATTGCCTGGGCTGGTTTCGGCAGATCACTGGT<br>AAGGAGCGCGAGGGCGTGGCTGTCATAAATTGGGTCGGAGGTATGCTGTACTTC<br>GCCGACTCAGTTAAAGGACGCTTCACCGTGTCCCAGGACCAGGCTAAGAATACT<br>GTGTATCTCCAGATGAACAGTCTGAAACCAGAGGACACAGCAATGTATTACTGT<br>GCTGCCGAAAGCGTCTCATCTTTCTCCTGTGGGGGCTGGCTCACACGCCCGGAC<br>CGTGTTCCGTATTGGGGTCAGGGAACCCAGGTGACCGTAAGCTCC |
| DR593-<br>hIL27<br>Ra_VH<br>H20 | 1089 | CAAGTGCAGCTCCAGGAGTCCGGGGGCGGGTCTGTGCAAGCTGGCGGTTCTCTG<br>AGGCTGTCCTGCGCTGCATCCGGCTACCCTTACTCCAATGGCTACATGGGTTGG<br>TTCAGACAAGCTCCCGGAAAGGAGAGGGAGGGTGTGGCTACCATCTACACCGGC<br>GACGGACGCACTTATTACGCAGACTCCGTGAAGGGCCGCCTCACCATTTCTGGG<br>GATAACGCTAAGAACACCGTGGACCTTCAGATGTCTTCCCTTAAACCTGAGGAC<br>ACTGCCATGTATTACTGTGCCGCTCGGGCCGCGCCACTGTACTCTTCCGGGTCC<br>CCACTTACACGTGCTCGTTACAATGTGTGGGGTCAAGGAACCCAGGTGACTGTG<br>TCCAGCGGAGGCGGTTCACAAGTGCAGCTTCAGGAAAGCGGAGGCGGGTTGGTG<br>CAGCCTGGGGGCTCACTCCGTCTGAGCTGTGCCGCTTCTGGTTTCACCTTCTCT<br>TCATATCCTATGAGTTGGGTGAGACAAGCGCCGGGCAAAGGACTGGAGTGGGTC<br>TCCACTATTTCTTCCGGCGGTGATACTACCTTGTATGCTGACTCCGTGAAGGGT<br>CGTTTCACCTCCAGTCGCGACAATGCGAAGAATACCCTGTACCTCCAGCTCAAC<br>TCCCTGAAGACCGAGGACACAGCGATGTATTACCGCGCTAAGCGTATCGACTGC<br>AATTCCGGGTACTGCTACAAGAGAAGCTACTGGGGGCAAGGGACTCAGGTGACA<br>GTGTCTAGC |
| DR593-<br>hIL27<br>Ra_VH<br>H20 | 1090 | CAGGTCCAACTTCAGGAGTCTGGTGGAGGCTCCGTTCAGGCGGGGGGGTCCCTG<br>CGCTTGTCTTGTGCAGCCAGCGGTTACCCATACAGCAACGGATATATGGGCTGG<br>TTCCGGCAGGCCCCTGGGAAAGAACGTGAGGGCGTCGCGACTATCTATACTGGA<br>GATGGACGCACTTATTACGCCGATAGCGTCAAGGGACGGTTTACCATCAGCAGG<br>GACAACGCCAAAAACACCGTGGACCTTCAGATGTCTTCCCTGAAACCCGAGGAC<br>ACGGCTATGTACTATTGCGCGGCCCGCGCTGCCCCTCTCTATAGTTCTGGGAGT<br>CCCTTGACAAGGGCCAGATACAACGTGTGGGGGCAGGGGACTCAGGTTACTGTC<br>TCCTCTGGTGGCTCCGGTGGCAGCGGAGGCTCTGGCCAGGTGCAGTTGCAGGAG<br>AGTGGGGGTGGCCTGGTGCAGCCTGGTGGCAGCCTGCGCCTGTCTTGCGCAGCC<br>TCTGGGTTTACCTTTAGCTCTTACCCCATGTCCTGGGTCCGCCAGGCCCCCGGC |

TABLE 1B-continued

| Name | SEQ ID NO: | Sequence |
|---|---|---|
| | | AAAGGACTGGAGTGGGTGTCCACCATTTCTAGCGGAGGCGATACTACCCTGTAC<br>GCCGACTCTGTGAAGGGGCGCTTCACTAGCTCACGGGACAATGCTAAGAACACA<br>CTGTACCTTCAGCTGAACTCACTGAAAACCGAAGACACTGCTATGTATTACTGC<br>GCTAAACGCATTGATTGCAACAGCGGCTATTGTTATAAAAGATCCTACTGGGGC<br>CAGGGCACCCAGGTCACGGTCTCCAGC |
| DR593-<br>hIL27<br>Ra_VH<br>H21 | 1091 | CAAGTTCAGCTCCAGGAGAGTGGAGGGGGCAGTGTTCAGGCCGGAGGTAGCCTG<br>CGCCTCAGCTGTGCAGCCAGTGGCTACCCCTACTCTAATGGCTACATGGGCTGG<br>TTCAGGCAGGCCCCCGGAAAAGAGCGTGAGGGTGTGGCTACAATTTATACCGGA<br>GACGGCAGAACCTACTATGCCGACTCCGTGAAGGGCCGCTTCACAATCTCTCGG<br>GACAACGCTAAGAACACAGTGGATCTTCAGATGAGCAGTCTCAAGCCAGAGGAT<br>ACCGCCATGTATTACTGTGCCGCGCGGGCTGCCCCTTTGTACTCATCTGGGAGC<br>CCTCCGACCCGCGCCCGCTATAATGTGTGGGGCCAGGGGACCCAAGTGACGGTA<br>TCCTCTGGGGGGGGTAGCCAGGTGCAGCTCCAGGAAAGCGGAGGGGGACTGGTG<br>CAGCCCGGGGGGAGCCTGCGGCTTAGCTGCGCAGCCTCCGGCTTCACCTTCTCC<br>CTCAGTTCCATGAGTTGGGTTCGCCAGGCTCCAGGGAAGGGACTGGAATGGGTG<br>TCAGCCATCTCCTCTGGCGGGGCGTCCACTTATTACACAGACTCCGTGAAGGGC<br>AGGTTCACCATTTCTAGGGATAATGCCAAGAACATGCTGTACCTCCAGCTGAAG<br>AGTCTGAAAACAGAAGACACAGCTATGTACTATTGCGCCAAAGGTGGGTCCGGT<br>TATGGCGATGCGTCCAGGATGACTTCCCCTGGGTCCCAGGGCACACAGGTCACC<br>GTGAGTAGC |
| DR593-<br>hIL27<br>Ra_VH<br>H21 | 1092 | CAGGTGCAACTCCAGGAGAGCGGGGGAGGCTCTGTCCAAGCAGGGGGGTCTCTC<br>CGTCTGTCTTGCGCCGCAAGCGGATACCCCTACAGCAACGGTTATATGGGTTGG<br>TTCCGCCAGGCCCCCGGAAAGGAGCGTGAGGGTGTGGCCACCATCTACACTGGC<br>GATGGAAGAACCTATTACGCAGACAGCGTGAAGGGCCGGTTTACCATCAGCCGC<br>GACAACGCCAAGAACACCGTTGACTTGCAGATGTCCAGCCTGAAACCTGAGGAC<br>ACAGCTATGTACTATTGTGCTGCCAGAGCGGCTCCTCTCTACAGTTCTGGATCT<br>CCCCTTACACGGGCTAGGTACAATGTTTGGGGGCAGGGCACCCAGGTCACCGTG<br>TCCTCTGGCGGATCAGGAGGCAGCGGGGGCTCTGGTCAAGTGCAGCTCCAGGAG<br>TCCGGCGGGGGACTGGTTCAGCCTGGAGGTTCCCTGCGCCTTTCTTGTGCTGCC<br>AGCGGCTTCACGTTCTCCCTGAGTTCCATGAGCTGGGTCCGGCAGGCCCCCGGC<br>AAAGGCCTGGAGTGGGTTTCCGCTATCTCCAGCGGGGGGGCCTCCACCTACTAT<br>ACCGACTCCGTGAAGGGACGGTTCACAATCTCCAGGGACAATGCTAAGAATATG<br>TTGTACCTTCAGTTGAACTCCCCGAAAACCGAAGACACGGCCATGTATTACTGC<br>GCCAAGGGAGGCTCCGGTTACGGCGATGCCAGCAGAATGACCTCCCCCGGTAGC<br>CAGGGGACACAGGTGACTGTATCCAGC |
| DR593-<br>hIL27<br>Ra_VH<br>H22 | 1093 | CAGGTGCAGTTGCAGGAGTCCGGGGGAGGCTCCGTTCAGGCCGGTGGCAGCCTC<br>AGACTGTCATGTGCAGCCTCCGGTTATCCCTATTCCAATGGTTACATGGGATGG<br>TTCCGTCAGGCCCCTGGGAAAGAGAGGGAGGGCGTCGCCACGATCTACACCGGC<br>GATGGACGCACATATTACGCCGACAGTGTTAAGGGCCGTTTCACCATCTCTGGC<br>GACAACGCCAAAAACACAGTTGATTTGCAGATGAGTTCCCTCAAGCCCGAAGAC<br>ACCGCTATGTACTATTGTGCAGCCCGCGCCGCTCCTCTCTACAGCTCTGGCTCC<br>CCACTGACGAGGGCGCGGTACAACGTGTGGGGCCAGGGCACCCAGGTTACCGTT<br>TCTAGTGGCGGGGGCTCCCAGGTCCAGCTCCAGGAGAGTGGCGGAGGCAGCGTG<br>CAGGCAGGGGGTAGCCTTCGCCTGAGCTGCCGGGCCTCCGGGAGCACGTACTCT<br>AACTACTGTCTTGGATGGTTCCGGCAGACAACTGGGAAGGAGCGCGAGGGAGTC<br>GCCGTTATCAACTGGGTAGGGGGAATGCTGTACTTTGCCGATTCCGTCAAGGGA<br>CGCTTTACCGTCTCTCAGGATCAGGCCAAGAACACCGTCTACCTCCAGATGAAC<br>AGTCTGAAGCCCGAGGACACCGCTATGTACTATTGCGCTGCGGAGAGCGTTTCC<br>TCTTTCTCCTGCGGCGGTTGGCTTACCCGCCCCGACCGGGTGCCTTACTGGGGT<br>CAGGGCACACAGGTGACCGTCTCCTCC |
| DR593-<br>hIL27<br>Ra_VH<br>H22 | 1094 | CAGGTTCAGCTTCAGGAAAGTGGAGGGGGCTCCGTTCAAGCCGGGGGTTCCCTT<br>AGGCTGTCCTGCGCCGCTTCTGGTTATCCGTATTCAAATGGGTACATGGGATGG<br>TTCCGCCAGGCTCCCGGCAAGGAGCGCGAGGGTGTCGCAACAATCTATACGGGC<br>GACGGTCGGACCTACTATGCAGACTCTGTCAAGGGCCGGTTCACAATCTCCCGC<br>GATAACGCCAAGAACACAGTGGACCTCCAGATGTCATCCCTGAAGCCAGAGGAT<br>ACAGCAATGTATTACTGTGCTGCACGTGCCGCTCCCCTGTACTCTAGTGGGAGC<br>CCCCTCACCAGAGCGCGGTATAACGTGTGGGGTCAGGGGACTCAGGTAACCGTG<br>TCCAGCGGCGGTTCCGGGGGTAGCGGAGGCTCCGGCCAGGTACAGCTCCAGGAG<br>AGGGGAGGGGGCTCCGTCCAGGCTGGGGGGTCCCTGCGCCTGTCCTGCCGGGCC<br>TCCGGTAGCACATACTCTAACTACTGCCTGGGCTGGTTCAGGCAGACCACTGGA<br>AAGGAACGCGAGGGCGTCGCTGTAATCAACTGGGTCGGAGGTATGCTTTACTTC<br>GCAGACTCCGTGAAGGGTCGCTTCACAGTGAGCCAGGACCAAGCTAAGAACACT<br>GTGTACCTCCAGATGAACTCTCTCAAGCCGGAGGATACCGCCATGTATTACTGT<br>GCAGCCGAGAGTGTGTCTAGCTTCTCCTGGGGAGGCTGGCTGACGAGACCCGAT<br>AGGGTCCCGTACTGGGGGCAGGGCACTCAAGTCACTGTGAGCAGC |
| DR593-<br>hIL27<br>Ra_VH<br>H23 | 1095 | CAGGTACAACTTCAGGAAAGCGGGGGAGGCTCCGTACAGGGGGGAGGCAGCTTG<br>CGCCTGAGCTGTGCCGCAAGTGGTTACCCGTACAGCAACGGCTACATGGGCTGG<br>TTTCGTCAGGCTCCTGGGAAAGAGAGAGAGGGCGTGGCTACGATCTACACGGGT<br>GACGGACGCACCTATTACGCCGACTCCGTGAAAGGAAGATTCACCATCAGCCGC<br>GATAACGCTAAGAACACAGTTGACCTGCAAATGTCTAGCCTGAAACCGGAGGAC<br>ACTGCTATGTACTATTGTGCCGCACGCGCTGCCCCTCTCTATTCTTCCGGCAGC<br>CCCCTCACCAGGGCTCGCTACAACGTCTGGGGCCAAGGGACCCAGGTGACTGTG |

TABLE 1B-continued

| Name | SEQ ID NO: | Sequence |
|---|---|---|
| | | TCCAGCGGTGGAGGGAGCCAGGTGCAGCTCCAGGAGAGCGGCGGGGGCTCTGTC CAGGCCGGTGGCAGTCTGCGCCTGTCCTGCCGGGCCTCCCGTTCCCCATACGGG AATTATTGCCTGGGCTGGTTCAGACAGTCTACGGGTAAGGAGGGGGAAGGCGTG GCAGTTATCAACTGGGTCGGCGGAATGCTGTACTTTGCCGACTCCGTCAAAGGC CGCTTCACTGTGTCTCAGGACCATGCAAAGAACACCGTAACCTTGCAGATGAAC TCTCTGAAACCCGAAGACACGGCGATGTATTACTGCGCTGCCGAGTCCGTTTCT AGCTTCAGCTGTGGCGGTTGGTTGACAAGGCCAGATCGCGTCCCGTACTGGGGC CAAGGAAGCCAGGTAACCGTAAGCAGT |
| DR593-hIL27Ra_VH H23 | 1096 | CAAGTCCAGCTGCAAGAGAGCGGAGGGGGGAGCGTTCAGGCTGGTGGCAGCCTG CGGCTGAGTTGTGCTGCCAGCGGATACCCCTATTCCAATGGTTATATGGGCTGG TTTAGACAGGCACCTGGAAAGGAACGCGAGGGCGTAGCTACTATTTACACTGGA GACGGCAGGACTTATTACGCGGATAGCGTGAAGGGGCGTTTCACAATTTCACGC GACAATGCCAAAAACACCGTGGATCTGCAAATGTCCAGCCTGAAGCCCGAGGAC ACCGCCATGTACTATTGCGCCGCACGCGCGGCTCCCCTGTACTCCTCAGGTAGC CCTTTGACTCGCGCACGCTATAATGTGTGGGGCCAGGGCACCCAGGTGACGGTT TCTAGCGGAGGGAGCGGGGGTTCTGGTGGCTCAGGTCAGGTGCAGCTTCAGGAA TCTGGAGGTGGCTCCGTACAGGCTGGGGGCTCCCTGCGTCTGAGCTGCCGGGCG AGCAGGTCCCCTTATGGTAACTACTGTCTCGGTTGGTTCCGCCAATCCACCGGC AAGGAGCGCGAGGGAGTGGCCGTTATAAATTGGGTGGGCGGTATGCTGTACTTT GCTGACAGTGTTAAGGGACGTTTCACCGTATCTCAGGACCACGCCAAGAACACC GTGACATTGCAGATGAACTCTCTCAAGCCAGAGGACACCGCTATGTATTACTGT GCCGCTGAGTCAGTGTCCTCTTTCAGCTGGGGGGGGCGGCTCACTCGCCCTGAC AGAGTACCCTATTGGGGGCAGGGGACACAGGTCACGGTTTCCAGC |
| DR593-hIL27Ra_VH H24 | 1097 | CAAGTACAGTTGCAGGAGTCCGGCGGTGGCAGTGTTCAGGGGGGGGGGTCCCTG CGCCTCAGCTGCGCAGCCAGCGGATACCCATACTCTAACGGTTACATGGGTTGG TTCCGCCAGGCCCCAGGTAAGGAAAGAGAGGGAGTGGCGACTATTTATACCGGG GATGGCCGCACCTACTATGCCGATTCTGTAAAAGGTAGGTTCACGATCTCTCGC GATAACGCCAAAAACACAGTCGATCTCCAGATGTCTTCCCTGAAGCCCGAGGAC ACCGCCATGTATTACTGTGCGGCACGGGCAGCTCCCCTTTACAGCTCCGGCTCC CCGCTGACTCGTGCCCGTTACAACGTCTGGGGGCAGGGCACACAGGTAACCGTG TCCAGCGGCGGAGGTTCACAGGTGCAGCTCCAGGAGTCTGGTGGCGGACTGGTG CAGCCCGGAGGCTCCCTGCGTCTCAGCTGTGCAGCCAGCGGCTTTACATTTAGC CACTCCGGTATGAGCTGGGTACGGCAGGCACCTGGAAAGGGTCTGGAGTGGGTG TCCACAATCAACTCAGGGGGAGCCTCTACATACTATACTGACTCAGTCAAGGGA CGTTTCACCATCTCCCGCGACAACGCTAAAAACATGCTGTACCTTCAGTTGAAC AGTCTGAAGACTGAGGATACAGCCATGTATTACTGTGCCAAAGGGGGCTCTGGC TACGGGGATGCCTCCAGAATGACTAGCCCTGGCTCCCAGGGCACCCAGGTGACC GTGTCTTCC |
| DR593-hIL27Ra_VH H24 | 1098 | CAGGTGCAGTTGCAAGAGTCTGGGGGAGGCTCCGTCCAAGCAGGGGGGAGTCTT CGGCTGTCTTGTGCAGCCTCCGGGTATCCGTACTCTAATGGTTACATGGGCTGG TTCAGGCAGGCCCCAGGTAAAGAACGGGAGGGCGTGGCCACCATTTACACCGGC GATGGCCGCACATACTATGCCGACTCCGTGAAGGGTAGGTTCACCATTTCACGT GACAATGCCAAGAATACCGTGGATCTCCAGATGTCTAGCCTGAAGCCGGAGGAC ACAGCCATGTATTACTGTGCTGCCCGCGCTGCCCCTCTGTACTCCAGCGGTTCT CCTCTGACTAGAGCCCGGTACAACGTGTGGGGCCAGGGCACCCAAGTCACTGTG TCTAGTGGGGGGTCCGGCGGAAGCGGTGGCTCAGGCCAAGTTCAGCTCCAGGAA TCAGGTGGGGGCCTGGTCCAGCCCGGTGGATCTCTGCGGCTGTCCTGTGCTGCC AGCGGATTCACGTTTAGCCACAGCGGCATGAGCTGGGTACGCCAGGCTCCAGGC AAAGGATTGGAATGGGTGTCCACAATTAACTCTGGCGGGGCCAGCACCTATTAC ACTGACAGCGTTAAAGGGCGCCSTACAATCTCTCGCGACAACGCCAAGAATATG TTGTACCTCCAGCTGAACTCACTCAAGACCGAGGATACTGCCATGTATTACTGT GCTAAAGGCGGAAGGGGCTACGGCGACGCTTCCAGGATGACCAGTCCTGGCTCC CAGGGCACACAGGTGACCGTGTCCTCC |
| DR594-hIL27Ra_VH HI | 1099 | CAGGTCCAGCTTCAGGAGTCCGGCGGAGGCAGCGTACAGGGGGGCGGGTCCTTG CGCCTGTCCTGTGTGGCCTCCGCATCTACGTATTGCACCTATGATATGCACTGG TATCGTCAGGCCCCTGGCAAAGGTCGGGAGTTCGTGAGCGCCATTGATTCTGAT GGCACTACCCGCTACGCCGACAGTGTGAAGGGACGGTTTACCATTTCCCAGGGA ACCGCGAAGAATACCGTGTACCTCCAGATGAACAGCCTGCAACCCGAGGACACA GCTATGTACTATTGTAAGACCGTGTGTGTCGTGGGTTCCCGCTGGAGCGACTAT TGGGGACAGGGCACCCAAGTGACCGTCAGCTCCGGGGGGGGCTCTCAGGTGCAG TTGCAGGAGAGCGGGGGTGGATTGGTGCAGCCCGGCGGATCTCTGCGCCTGAGC TGCGCCGCTTCCGGGTTCACTTTTTCATCTTACCCAATGTCCTGGGTGCGCCAA GCGCCGGGCAAGGGACTGGAGTGGATCTCCACGATCAGCGCTGGCGGTGATACA ACCCTTTACGCCGACTCCGTGAAGGGCCGCTTTACCAGCTCAAGAGACAACGCA AAAAACACTCTGTACTTGCAGCTGAACTCTCTCAAGACCGAGGATGGGGCCATT TATTACTGCGCCAAGCGCATTGATTGTAACTCTGGGTACTGTTATAGACGCAAC TATTGGGGTCAGGGCACGCAGGTGACCGTGTCTTCC |
| DR594-hIL27Ra_VH H1 | 1100 | CAGGTTCAGCTCCAGGAAAGCGGCGGAGGCAGTGTGCAGGCAGGCGGAAGCCTG AGACTGTCCTGTGTAGCGTCAGCCAGTACCTACTGCACATACGATATGCACTGG TATCGCCAAGCTCCTGGGAAAGGAAGAGAGTTCGTTTCCGCCATCGACTCTGAC GGCACTACAAGATATGCCGATAGCGTTAAAGGCCGCTTTACAATTTCCCAGGGC ACCGCGAAGAACACCGTCTACCTGCAAATGAATAGTTTGCAGCCAGAAGACACT |

TABLE 1B-continued

| Name | SEQ ID NO: | Sequence |
|---|---|---|
| | | GCTATGTACTATTGCAAGACCGTGTGCGTGGTCGGGTCAAGGTGGAGCGATTAC<br>TGGGGCCAAGGTACTCAGGTCACCGTCAGCCCCGGTGGAAGCGGGGGCTCCGGG<br>GGCTCTGGACAGGTCCAGCACCAGGAGTCTGGCGGAGGCCTCGTTCAGCCAGGG<br>GGCTCATTGAGGCTTTCCTGTGCGGCCTCCGGCTTCACATTTTCTAGCTACCCG<br>ATGAGTTGGGTACGCCAGGCTCCTGGAAAAGGCCTGGAATGGATCAGCACAATC<br>AGCGCAGGTGGGGACACAACCCCGTACGCTGATAGCGTGAAGGGTAGGTTTACA<br>TCTTCCCGCGACAACGCTAAGAACACCCTTTACTTGCAGCTCAATTCCCTCAAG<br>ACCGAGGACGCGGCCATCTATTACTGCGCCAAACGTATTGACTGCAACTCTGGT<br>TATTGTTACAGAAGGAATTACTGGGGCCAGGGGACCCAGGTGACCGTATCTTCC |
| DR594-<br>hIL27<br>Ra_VH<br>H2 | 1101 | CAGGTGCAGCTCCAAGAATCCGGGGGTGGCAGTGTGCAGGCCGGTGGCTCTCTG<br>AGGTTGAGCTGCGTCGCCTCAGCCAGCACTTACTGCACCTATGACATGCACTGG<br>TACAGACAGGCACCCGGTAAGGGACGTGAGTTCGTGTCTGCTATTGATTCCGAT<br>GGCACTACCAGATATGCCGATTCCGTGAAAGGCAGATTCACGATTTCCCAAGGA<br>ACCGCTAAGAACACCGTGTATCTCCAAATGAACTCCCTTCAGCCCGAAGACACC<br>GCTATGTATTACTGTAAGACCGTGTGCGTAGTGGGCAGTCGTTGGTCAGACTAT<br>TGGGGCCAGGGCACCCAGGTCACCGTCAGTTCCGGCGGAGGCTCTCAGGTCCAA<br>CTTCAGGAATCTGGGGGAGGTTTGGTGCAGCCGGGTGGCTCCCTGCGGCTGTCC<br>TGTGCGGCAAGTGGCTTCACCTTCAGCCTCTCCGGCATGTCCTGGGTGGGCCAA<br>GCGCCCGGTAAGGGGCTGGAGTGGGTGTCCGCCATTAGCTCTGGCGGTGCTTCT<br>ACCTATTACACCGACTCCGTCAAGGGTCGGTTTACCATCTCTCGCGACAACGCC<br>AAGAACATCTTGTACCTTCAGCTCAATTCTCTGAAGACTGAGGACACTGCCATG<br>TATTACTGTGCGAAAGGTGGCTCCGGCTACGGAGATGCCTCTCGCATGACCTCC<br>CCTGGGTCCCAGGGCACACAGGTTACCGTGTCCTCC |
| DR594-<br>hIL27<br>Ra_VH<br>H2 | 1102 | CAGGTCCAGCTCCAGGAGTCTGGCGGAGGGAGCGTTCAGGCCGGGGGCTCTCTG<br>AGGCTCTCCTGTGTGGCGAGCGCCTCTACTTACTGTACTTACGACATGCACTGG<br>TATCGCCAAGCCCCAGGCAAGGGCAGGGAGTTCGTCAGTGCCATCGACTCCGAC<br>GGCACAACTCGCTACGCCGACTCCGTCAAGGGACGTTTCACAATCTCTCAGGGC<br>ACGGCTAAGAACACTGTGTATCTCCAAATGAACAGTCTCCAGCCTGAAGATACA<br>GCCATGTACTATTGCAAAACTGTGTGTGTGGTCGGCTCACGGTGGTCTGACTAC<br>TGGGGTCAGGGGACCCAGGTCACAGTAAGCTCAGGAGGTTCCGGCGGTTCTGGC<br>GGTTCAGGACAGGTGCAACTTCAGGAAAGCGGTGGCGGACTCGTCCAGCCCGGA<br>GGTTCACTGCGTCTCAGCTGTGCTGCCAGCGGTTTTACCTTCAGCCTCAGTGGA<br>ATGAGCTGGGTCAGACAGGCCCCTGGCAAAGGGCTGGAGTGGGTGAGTGCCATT<br>TCCTCAGGAGGTGCCTCTACCTATTACACCGACTCTGTCAAAGGCAGGTTTACC<br>ATCAGCCGCGATAACGCCAAGAACATCCTGTATCTCCAGCTTAATTCCCTCAAG<br>ACAGAAGACACAGCTATGTATTACTGTGCGAAAGGGGGCTCCGGTTACGGGGAC<br>GCTTCCAGAATGACATCCCCTGGTTCTCAGGGCACACAGGTGACCGTGTCCTCA |
| DR594-<br>hIL27<br>Ra_VH<br>H3 | 1103 | CAAGTTCAGCTCCAGGAATCTGGCGGTGGGTCTGTTCAAGCCGGTGGCTCCCTG<br>CGCCTTTCATGTGTCGCCTCTGCTTCTACATACTGCACCTACGACATGCACTGG<br>TATCGTCAGGCTCCCGGCAAGGGCCGCGAATTTGTTAGTGCTATCGACTCCGAC<br>GGCACTACACGCTATGCCGACAGTGTTAAAGGCCGCTTCACCATCTCTCAGGGC<br>ACGGCGAAAAACACCGTGTACCTCCAGATGAACTCCCTGCAACCCGAGGATACA<br>GCCATGTATTACTGCAAGACAGTCTGTGTCGTGGGATCTCGCTGGTCTGACTAC<br>TGGGGACAGGGGACCCAGGTTACTGTCTCCACTGGCGGAGGCAGCCAGGTGCAG<br>CTTCAGGAGTCCGGTGGGGGCTCCGTGCAGGCTGGCGGAAGCCTGCGCCTGTCC<br>TGCGTTGCATCCGGTTATGTTAGCTGCGATTACTTCCTGCCCTCCTGGTATCGT<br>CAAGCTCCCGGCAAGGAGCGCGAGTTTGTTTCCATTATCGACGGCACCGGCAGC<br>ACGTCATACGCTGCGAGCGTTAAGGGCCGCTTCACCGCTTCCGAAGACAAGGGC<br>AAGAACATCGCCTACTTGCAGATGAACTCCCTGAAGCCTGAGGATACCGCCATG<br>TATTACTGCAAGGCCAGCTGCGTCCGGGGGGGGGCCGTGTCCGAGTATTGGGGG<br>CAGGGCACCCAGGTGACAGTGAGTAGC |
| DR594-<br>hIL27<br>Ra_VH<br>H3 | 1104 | CAAGTCCAACTCCAGGAAAGTGGCGGTGGGTCCGTACAGGCCGGGGGCAGTCTG<br>CGGCTTTCCTGTGTGGCCTCTGCATCTACTTACTGTACTTACGACATGCACTGG<br>TATCGCCAGGCCCCAGGTAAGGGTCGGGAGTTTGTTAGCGCAATCGACTCAGAC<br>GGGACTACCCGCTACGCGGATAGCGTCAAGGGCCGGTTCACCATCTCTCAGGGC<br>ACCGCCAAGAACACCGTTTATTTGCAGATGAATAGCCTCCAACCTGAAGATACT<br>GCAATGTATTACTGCAAGACAGTGTGCGTGGTTGGCAGCCGCTGGTCAGACTAT<br>TGGGGTCAGGGCACCCAGGTCACCGTTAGCTCTGGAGGCAGCGGCGGTAGCGGT<br>GGCAGCGGACAGGTCCAGCTCCAGGAGTCAGGAGGGGGCTCTGTCCAGGCCGGG<br>GGCTCTCTCCGTCTTTCTTGCGTCGCCTCAGGCTACGTCAGCTGCGATTACTTC<br>CTCCCTAGCTGGTATCGTCAAGCGCCGGGGAAGGAACGGGAGTTTGTGTCAATC<br>ATTGACGGCACCGGCTCTACTTCCTATGCTGCCAGCGTGAAGGGCCGCTTTACA<br>GCCTCCGAAGACAAGGGCAAGAACATCGCTTACCTCCAGATGAACTCTCTGAAG<br>CCCGAAGACACCGCTATGTACTATTGCAAGGCCAGCTGCGTCAGAGGTAGGGCT<br>GTGTCCGAATATTGGGGTCAGGGCACGCAGGTTACCGTGTCTTCT |
| DR594-<br>hIL27<br>Ra_VH<br>H4 | 1105 | CAGGTCCAACTCCAGGAGAGCGGAGGGGGTTCCGTGCAAGCAGGTGGCTCCCTG<br>CGCTTGAGCTGTGTGGCCTCCGCTAGTACTTACTGCACTTACGATATGCACTGG<br>TATAGGCAAGCCCCAGGGAAGGGGCGCGAGTTCGTGTCCGCCATTGACAGCGAC<br>GGTACAACCCGGTATGCCGACTCTGTGAAAGGCCGTTTCACAATCTCCCAGGGA<br>ACAGCCAAGAACACCGTATACCTCCAGATGAACTCCTTGCAGCCTGAGGATACA<br>GCCATGTACTATTGTAAAACCGTGTGCGTGGTCGGCCCACGCTGGAGTGATTAC<br>TGGGGCCAAGGAACCCAGGTCACTGTCTCCTCAGGGGGAGGTAGCCAGGTCCAG |

TABLE 1B-continued

| Name | SEQ ID NO: | Sequence |
|---|---|---|
| | | CTTCAGGAGTCCGGCGGTGGCCTGGTTCAGCCTGGGGAATCACTGCGTCTCTCT TGCACTGCCAGTGGATTCACATTTTCAAACTATGCTATGTCTTGGGTGGGGCAG GCCCCTGGGAAGGGGCTCGAATGGGTATCCGGTATTAACGTGGCATACGGCATC ACCTCCTACGCTGATTCCGTGAAGGGCAGGTTCACCATCTCTCGCGACAACACC AAGAACACACTGTACTTGCAACTTAACAGTCTTAAAACTGAAGACACTGCTATC TACTATTGCGTCAAGCACAGCGGTACGACTATCCCGCGTGGATTCATCAGCTAT ACAAAGAGGGGCCAAGGCACCCAAGTCACTGTGAGCAGC |
| DR594-hIL27 Ra_VH H4 | 1106 | CAGGTCCAACCTCAGGAATCTGGGGGAGGCTCTGTGCAGGCTGGAGGGAGTCTT AGACTGTCCTGTGTCGCAAGCGCAAGCACGTACTGCACCTACGACATGCACTGG TATCGCCAGGCTCCGGGTAAGGGACGCGAATTTGTGAGCGCAATCGACTCCGAC GGGACCACAAGGTACGCCGATAGCGTTAAGGGACGTTTCACCATCAGTCAGGGT ACTGCCAAGAACACGGTCTACCTCCAGATGAATAGCCTCCAGCCGGAAGATACC GCTATGTATTACTGCAAGACAGTGTGCGTAGTGGGCAGCCGTTGGTCCGATTAT TGGGGCCAGGGTACACAGGTGACAGTCTCCAGTGGAGGCTCCGGCGGATCTGGG GGCAGCGGTCAGGTGCAGTTGCAGGAGAGCGGCGGTGGCTTGGTGCAACCCGGT GAATCTTTGCGTCTGAGCTGCACAGCGAGCGGATTCACATTTAGCAACTACGCC ATGTCCTGGGTGCGCCAGGCTCCCGGTAAGGGTCTGGAGTGGGTGAGTGGTATC AATGTGGCCTATGGGATCACCAGTTATGCGGATAGCGTGAAGGGCCGGTTTACC ATCAGCCGGGACAACACCAAGAACACCCTGTACCTTCAGCTTAACTCCCTGAAG ACCGAAGATACAGCCATCTATTACTGTGTGAAGCACTCAGGGACTACCATCCCT CGTGGTTTTATTAGCTACACTAAGCGTGGGCAAGGAACACAAGTGACGGTGTCT TCC |
| DR594-hIL27 Ra_VH H5 | 1107 | CAGGTGCAGCTCCAGGAATCCGGGGGGGGCAGCGTGCAGGCCGGAGGCTCCTTG CGTCTGTCTTGCGTCGCATCCGCCAGCACGTACTGCACCTACGATATGCACTGG TATCGTCAGGCTCCCGGTAAGGGGAGGGAGTTTGTCAGTGCTATCGACAGCGAT GGGACCACTCGCTACGCTGACTCCGTGAAGGGTCGTTTTACCATCAGCCAGGGC ACAGCTAAGAACACGGTGTACTTGCAGATGAACTCTCTCCAGCCGGAAGACACC GCGATGTATTACTGCAAGACTGTTTGCGTCGTGGGCTCTCGTTGGTCTGACTAT TGGGGTCAGGGCACCCAAGTCACGGTGAGTAGCGGGGGGGGTAGCCAAGTGCAG CTTCAGGAGTCCGGTGGCGGAAGCGTGCAGGCTGGGGGCAGCCTTCGGCTGTCA TGTACCGCCTCCGGTTACGTGTCTTGTGACTACTTCTTGCCAAGCTGGTATCGT CAGGCCCCTGGTAAAGAGGGGGAGTTCGTCAGCGTGATTGATGGCACTGGGTCC ACCAGCTACGCTGCCAGCGTTAAGGGCCGCTTCACCGCCAGCCAGGACAAGGGA AAGAATATTGCATATCTCCAGATGAACTCCCTGAAGCCTGAAGATACCGCTATG TATTACTGCAAGGCCTCATGCGTCCGTGGACGCGCTATTTCCGAGTATTGGGGA CAGGGTACTCAGGTCACCGTGAGTTCT |
| DR594-hIL27 Ra_VH H5 | 1108 | CAGGTGCAGCTGCAAGAAAGCGGTGGGGGCTCCGTCCAGGGGGGCGGTAGCCTG AGGCTGAGTTGCGTCGCCAGCGCTAGTACATACTGTACCTACGACATGCACTGG TATCGCCAGGCCCCCGGCAAAGGCAGGGAGTTCGTGTCAGCCATCGACTCCGAC GGGACTACCAGATACGCCGACTCCGTGAAAGGGCGGTTTACCATCAGTCAGGGT ACAGCTAAGAATACCGTGTACCTCCAGATGAACTCCTTGCAGCCTGAGGACACT GCAATGTATTACTGCAAGACCGTGTGTGTTGTCGGCAGCCGTTGGTCCGACTAC TGGGGACAGGGAACCCAGGTCACAGTCTCTAGCGGCGGAAGCGGGGGCTCAGGA GGCTCTGGGCAAGTGCAGTTGCAGGAGAGTGGCGGAGGCAGTGTGCAGGCCGGG GGCTCCCTCCGCCTGAGCTGTACTGCGAGGGGCTACGTCAGCTGTGACTACTTT CTGCCATCTTGGTATCGTCAGGCTCCCGGAAAGGAACGCGAGTTTGTGTCTGTG ATCGACGGGACCGGCTCTACCTCTTACGCCGCTTCCGTCAAGGGCCGCTTTACC GCTTCCCAAGATAAGGGGAAGAATATCGCTTACTTGCAGATGAACTCCCTGAAG CCAGAAGACACCGCCATGTACTATTGCAAGGCTTCCTGTGTTCGTGGCCGCGCC ATTAGCGAGTACTGGGGCCAGGGCACCCAGGTCACCGTGTCCAGT |
| DR594-hIL27 Ra_VH H6 | 1109 | CAGGTACAACTCCAGGAGAGTGGTGGGGGGAGCGTGCAAGCAGGGGGCTCCCTG CGCCTGTCCTGCGTCGCGTCCGCCAGCACATATTGCACCTACGATATGCACTGG TATCGCCAGGCCCCTGGGAAGGGTCGCGAGTTCGTGTCCGCCATCGACTCAGAC GGCACTACCCGCTACGCGGATTCTGTGAAGGGCAGATTCACAATTTCCCAGGGG ACCGCCAAGAACACGGTGTATCTCCAGATGAACTCTTTGCAGCCCGAGGACACT GCCATGTATTACTGCAAGACCGTGTGTGTCGTGGGCTCCAGGTGGAGCGACTAT TGGGGCCAGGGGACACAGGTTACCGTGTCCAGCGGTGGGGGTTCCCAGGTACAG CTCCAGGAGTCTGGCGGTGGCCTGGTACAGCCCGGTGGAAGCCTGCGCCTCAGC TGTGCCGCTTCCGGCTTTAGCTTCAGTTCTTATGCCATGAAGTGGGTCCGCCAG GCCCCCGGCAAGGGCCTGGAATGGGTCTCCACCATCTCCAGTGGGGGTAGCTCC ACCAACTATGCTGATAGCGTGAAGGGACGCTTTACCATCAGTCGTGATAACGCG AAGAACACCCTTTACCTTCAGCTGAACTCTCTGAAGATCGAAGACACCGCCATG TACTATTGTGCCAAGGCTATCGTGCCTACCGGGGCCACTATGGAAAGAGGACAG GGCACCCAGGTGACAGTGTCCTCC |
| DR594-hIL27 Ra_VH H7 | 1110 | CAGGTGCAGTTGCAGGAGTCTGGTGGCGGGTCAGTGCAGGCTGGAGGCTCCCTC AGGCTGAGTTGTGTCGCAAGCGCAAGCACATACTGCACCTATGATATGCACTGG TATCGCCAAGCTCCTGGCAAAGGTCGGGAGTTTGTGTCTGCTATTGATAGCGAC GGCACCACGCGCTACGCGGACCCCGTGAAGGGCAGATTTACAATCTCACAAGGG ACGGCGAAAAATACCGTGTACCTCCAGATGAACTCTCTCCAGCCCGAGGATACC GCTATGTATTACTGCAAGACCGTCTGCGTCGTGGGTAGCAGGTGGTCCGACTAC TGGGGTCAGGGCACTCAGGTGACGGTGTCTTCAGGAGGCTCGGGGGGCTCTGGC GGTAGCGGACAGGTGCAGTTGCAGGAGAGCGGGGGGGGTCTGGTGCAGCCTGGG |

TABLE 1B-continued

| Name | SEQ ID NO: | Sequence |
|---|---|---|
| | | GGTTCCCTGAGACTGAGCTGCGCCGCTTCTGGTTTCAGTTTTAGTTCTTACGCT ATGAAGTGGGTACGCCAAGCCCCTGGTAAGGGTCTGGAGTGGGTTTCTACGATT TCTAGCGGGGGCAGCTCTACAAACTACGCGGATAGCGTGAAAGGACGCTTTACC ATCTCCCGCGACAATGCAAAGAACACTTTGTACCTCCAGCTTAATTCACTGAAG ATCGAGGACACGGCTATGTACTATTGCGCTAAGGCCATCGTGCCGACCGGAGCC ACTATGGAAAGAGGTCAAGGCACCCAGGTGACTGTGTCCTCA |
| DP594-hIL27 Ra_VH H7 | 1111 | CAGGTCCAGCTCCAGGAGTCCGGGGGAGGCTCTGTGCAGGCAGGGGGCTCTCTG AGGCTGAGCTGCGTCGCCTCAGCCTCTACCTACTGCACCTATGACATGCACTGG TATCGTCAGGCTCCTGGCAAGGGTCGCGAGTTCGTTTCTGCCATTGATTCCGAC GGCACCACTAGATACGCTGACTCCGTCAAGGGCCGCTTCACCATCTCCCAGGGG ACTGCTAAGAACACCGTGTACCTTCAGATGAACTCTCTTCAGCCCGAAGATACT GCGATGTATTACTGCAAGACTGTTTGCGTTGTGGGAAGTCGTTGGTCCGATTAC TGGGGCCAGGGTACTCAAGTGACTGTAAGCCCAGGTGGCGGATCTCAGGTCCAG CTCCAGGAGTCAGGCGGTGGCCTCGTTCAGCCAGGGGGGTCTCTGAGACTGAGC TGCGCTGCCTCTGGATTCACCTTCTCATCTTACCCCATGTCTTGGGTGCGTCAA GCGCCTGGGAAAGGTCTGGAGTGGATCAGCACAATTTCAGCTGGCGGAGATACC ACTCTCTACGCTGACAGCGTGAAAGGCCGGTTCACCCCCAGCCGCGACAACGCC AAGAATACCCCGTACCTCCAGCTTAACTCCCTCAAGACAGAGGACACTGCAATT TACTATTGCGCTAAGCGGATTGATTGTAACTCCGGCTACTGCTACAGGCGTAAC TATTGGGGCCAGGGGACGCAGGTGACAGTGTCATCC |
| DR594-hIL27 Ra_VH H7 | 1112 | CAGGTCCAGCTCCAGGAGAGTGGAGGCGGATCTGTGCAGGCCGGGGGCTCCCTG CGTCTCTCATGCGTCGCCAGCGCATCTACTTACTGCACATACGACATGCACTGG TATCGTCAGGCACCGGGCAAGGGCCGTGAGTTCGTCTCTGCGATTGACTCTGAC GGAACTACCCGCTACGCCGATTCTGTGAAAGGGGGGTTCACCATCTCTCAGGGC ACTGCCAAGAATACCGTCTACCTGCAAATGAACAGCCTCCAGCCAGAGGATACC GCCATGTACTATTGCAAGACGGTCTGCGTCGTGGGCTCCAGATGGTCCGATTAC TGGGGCCAGGGAACACAAGTGACAGTTAGTTCCGGTGGCTCAGGAGGTTCCGGG GGCAGCGGTCAAGTGCAGTTGCAGGAGAGGGGAGGCGGTCTGGTTCAGCCTGGC GGTTCTCTTCGCCTGAGCTGCGCTGCCTCAGGCTTTACGCTCTCCTCTTACCCC ATGTCCTGGGTGCGGCAAGCTCCGGGGAAGGGCCTGGAGTGGATCTCCACCATT AGTGCAGGTGGCGACACCACTCCGTACGCTGACAGTGTAAAGGGCCGCTTCACA TCCTCTCGGGACAACGCCAAAAATACACTCTATTTGCAGCTGAATAGCCTGAAA ACCGAGGACACGGCCATTTACTATTGTGCAAAGAGAATTGATTGCAACAGCGGA TACTGTTATCGCAGGAACTACTGGGGCCAGGGCACCCAGGTGACAGTGTCCTCT |
| DR594-hIL27 Ra_VH H8 | 1113 | CAGGTGCAGCTCCAGGAGTCCGGGGGGGGCTCAGTGCAGGCCGGAGGCAGCTTG AGGCTGAGTTGTGTGGCCAGTGCCTCCACATATTGCACCTACGACATGCACTGG TATCGGCAAGCCCCTGGTAAGGGACGGGAATTTGTAAGTGCTATTGATTCTGAT GGCACTACCCGTTACGCCGACAGCGTGAAAGGCCGCTTCACTATTTCACAGGGG ACTGCCAAAAATACCGTGTACCTTCAGATGAACTCTCTTCAGCCCGAGGACACG GCGATGTACTATTGCAAGACCGTTTGTGTTGTGGGTAGTCGCTGGTCCGACTAT TGGGGCCAGGGTACTCAGGTGACTGTATCCAGCGGCGGAGGCAGCCAGGTGCAG TTGCAGGAGTCCGGCGGTGGAAGCGTCCAGGTGGGTGGCAGTCTGCGCCTCTCA TGTGCCGCATCCGGCTTCACCTTCTCTAGTTACCCTATGTCCTGGGTCCGTCAG GCCCCTGGAAAGGGTCTTGAGTGGATTTCCACAATCTCTGCTGGGGGCGACACA ACCCTGTATGCCGACTCCGTGAAAGGCCGCTTCACCTCCAGTCGCGACAATGCG AAGAACACCCTTTATTTGCAGCTGAACTCACTGAAGACCGAGGACACCGCAATT TACTATTGTGCTAAGCGCATTGATTGCAATAGCGGCTACCGTTACCGGCGCAAT TATTGGGGCCAGGGTACTCAGGTGACTGTGTCCTCT |
| DR594-hIL27 Ra_VH H8 | 1114 | CAGGTGCAACTGCAAGAGAGCGGCGGTGGCAGCGTACAGGCCGGTGGCTCCCTC CGCCTTAGCTGCGTCGCCAGCGCTTCCACTTACTGTACTTACGACATGCACTGG TACAGGCAAGCGCCCGGCAAGGGACGCGAGTTCGTCTCCGCCATCGACAGCGAC GGCACCACTCGCTACGCCGATAGCGTTAAGGGTCGCTTCACCATTTCACAGGGC ACCGCCAAGAACACCGTCTATCTTCAGATGAACAGCCTCCAGCCAGAGGATACA GCCATGTACTATTGCAAGACCGTCTGCGTCGTGGGCTCTCGTTGGAGTGACTAT TGGGGCCAGGGCACTCAAGTGACCGTGTCCTCTGGAGGCTCGGGGGGCAGCGGC GGGTCCGGTCAGGTGCAACTCCAGGAGTCCGGCGGAGGCTCTGTGCAGGTTGGT GGAAGCCTGCGTCTCTCCTGCGCGGCCTCCGGCCTCACTTTCTCCTCTTACCCT ATGAGCTGGGTCAGGCAGGCCCCCGGCAAGGGGCTGGAGTGGATCTCTACCATT TCTGCCGGAGGGGACACTACCCTGTACGCAGATTCTGTGAAAGGCCGCTTCACC AGCTCTAGGGACAACGCCAAGAATACCCTGTATCTCCAGCTCAACTCCCTCAAG ACCGAGGACACAGCTATCTATTACTGTGCTAAGAGGATCGACTGTAACTCTGGT TATTGTTATCGCAGGAACTATTGGGGACAGGGGACCCAAGTGACCGTCAGCTCA |
| DR594-hIL27 Ra_VH H9 | 1115 | CAGGTGCAGCTTCAGGAGTCTGGCGGTGGCAGCGTCCAAGCTGGCGGGAGCCTG CGGCTGTCTTGTGTGGCCTCCGCCTCAACATACTGTACCTATGATATGCACTGG TATAGACAAGCGCCCGGCAAGGGCAGGGAGTTCGTCTCCGCTATTGATAGCGAT GGAACCACTCGTTACGCGGACTCCGTGAAGGGCCGCTTTACGATCAGCCAGGGC ACCGCGAAGAACACCGTGTATCTTCAGATGAACTCTTTGCAGCCCGAGGACACT GCCATGTATTACTGCAAGACTGTTTGTGTAGTGGGCAGCAGGTGGAGCGACTAC TGGGGCCAGGGAACACAGGTCACAGTAAGCACTGGTGGAGGGTCTCAGGTGCAG CTTCAAGAATCTGGTGGAGGCTCCGTGCAATCCGGTGGCAGCCTGAGGCTGTCC TGCGCTGCCTCAGGATTCACTTACAGCACCTCTAACTCCTGGATGGCCTGGTTT |

TABLE 1B-continued

| Name | SEQ ID NO: | Sequence |
|---|---|---|
| | | CGCCAAGCGCCCGGAAAAGAGAGGGAAGGCGTGGCCGCTATTTACACTGTCGGT<br>GGCTCCATCTTCTACGCGGATAGTGTAAGGGGCCGCTTCACCATCTCTCAGGAC<br>GCCACAAAAAATATGTTCTACCTCCAGATGAATACCCTTAAACCGGAGGACACC<br>GCTATGTATTACTGTGCAGCGGCAAGTGGAAGGCTTCGCGGGAAGTGGTTCTGG<br>CCTTACGAATACAACTACTGGGGTCAGGGAACTCAGGTCACAGTTTCCTCC |
| DR594-<br>hIL27<br>Ra_VH<br>H9 | 1116 | CAGGTCCAGTTGCAGGAATCTGGTGGCGGTTCCGTCCAGGGGGGAGGTTCCCTG<br>CGCCTCTCCTGCGTGGCCTCTGCCTCTACGTATTGTACCTACGACATGCACTGG<br>TATCGCCAGGCCCCAGGTAAGGGCCGCGAGTTCGTTTCCGCCATTGATTCCGAT<br>GGGACCACACGCTATGCTGATTCCGTGAAGGGCCGGTTCACCATCAGTCAAGGC<br>ACCGCCAAGAACACAGTGTACCTCCAGATGAACTCCCTCCAGCCTGAGGACACA<br>GCCATGTACTATTGTAAGACAGTGTGTGTAGTCGGTTCCCGCTGGAGCGACTAA<br>TGGGGACAGGGAACCCAGGTGACGGTTTCATCCGGTGGCAGGGGAGGTAGCGGC<br>GGTAGCGGACAGGTGCAGTTGCAAGAATCCGGCGGTGGCTCCGTGCAGAGCGGA<br>GGCTCTCTGCGGCTCTCTTGTGCGGCCAGTGGCCTCACCTACTCCACCAGCAAC<br>TCTTGGATGGCTTGGTTCCGCCAAGCCCCTGGCAAAGAACGCGAAGGCGTCGCT<br>GCCATCTACACTGTTGGGGGAAGTATTTTTTACGCTGACTCCGTCCGTGGCCGT<br>TTTACCATCTCCCAGGATGCCACAAAAAATATGTTCTACCTCCAGATGAACACC<br>CTGAAGCCCGAGGATACCGCAATGTACTATTGTGCTGCCGCATCTGGTCGTCTG<br>CGCGGCAAGTGGTTCTGGCCCTACGAATACAACTACTGGGGTCAAGGTACACAG<br>GTGACGGTGTCTTCC |
| DR594-<br>hIL27<br>Ra_VH<br>H10 | 1117 | CAGGTGCAGCCTCAGGAATCCGGCGGGAGGCTCTGTGCAGGGGGGGGAAGCCTT<br>CGGCTGTCTTGTGTTGCCTCCGCGAGCACCTACCGCACCTACGATATGCACTGG<br>TATCGCCAGGCTCCTGGCAAGGGCCGTGAGTTTGTGAGCGCCATTGATTCCGAC<br>GGAACTACGAGATATGCCGACAGTGTGAAAGGTCGTTTCACTATTTCACAGGGC<br>ACCGCCAAGAATACCGTCTATCTCCAAATGAACAGTCTCCAGCCGGAGGACACC<br>GCCATGTATTACTGTAAGACGGTATGTGTTGTGGGGTCTCGCTGGTCAGACTAC<br>TGGGGCCAGGGGACACAGGTGACTGTCAGCTCCGGGGGGGGCTCACAGGTGCAG<br>CTGCAAGAGAGGGGCGGTGGCAGTGTTCAGGCGGGGGGTTCTCTCCGCCTGTCT<br>TGCAGGGCCTCCGGGAGCACTTACAGCAATTATTGTTTGGGGTGGTTTAGACAA<br>ATCACCGGCAAGGAGCGCGAGGGGGTGGCCGTGATAAATTGGGTGGGCGGTATG<br>CTCTACTTCGCTGACTCTGTGAAGGGCCGTTTCACAGTGTCCCAGGACCAGGGG<br>AAAAACACCCTTTACCTCCAGATGAACTCTCTCAAGCCCGAGGACACCGCCATG<br>TATTACTGTGCTGCCGAGTCCGTGTCCTCTTTCAGCTGCGGGGCCGGCTGACC |
| | | CGCCCTGATAGGGTGCCGTATTGGGGTCAAGGAACTCAGGTCACAGTGTCCAGC |
| DR594-<br>hIL27<br>Ra_VH<br>H10 | 1118 | CAAGTGCAGCTCCAGGAGTCCGGGGGAGGTTCTGTCCAGGCCGGAGGCTCACTG<br>CGCCTGTCCTGTGTCGCTTCTGCGTCTACTTACTGTACTTATGATATGCACTGG<br>TATCGCCAGGCTCCAGGTAAGGGCAGGGAGTTCGTGTCTGCTATTGATTCCGAT<br>GGCACGACCCGCTATGCCGATTCAGTGAAAGGCCGTTTCACAATCTCTCAGGGA<br>ACAGCCAAGAACACGGTGTACTTGCAGATGAACTCTCTGCAACCCGAGGACACC<br>GCCATGTATTACTGTAAGACTGTCTGCGTGGTCGGCTCACGCTGGTCCGACTAT<br>TGGGGCCAGGGGACCCAAGTTACTGTTTCCAGCGGAGGCAGCGGTGGATCTGGG<br>GGCTCCGGCCAGGTGCAGCTCCAGGAATCTGGGGGGGGGTCCGTGCAGGCTGGG<br>GGATCTCTGCGCCTGAGTTGTCGCGCAAGTGGGAGTACCTACAGTAATTATTGC<br>CTGGGATGGTTCCGCCAGATCACAGGTAAGGAGCGCGAGGGCGTGGCCGTGATT<br>AACTGGGTGGGTGGCATGTTGTACTTCGCTGATTCCGTCAAGGGACGTTTCACT<br>GTCTCTCAGGACCAGGCTAAGAATACCTTGTATCTTCAGATGAACTCCCTGAAG<br>CCTGAAGATACTGCTATGTATTACTGTGCGGCTGAGAGCGTCAGTTCCTTCTCC<br>TGTGGGGGCTGGCTGACTCGCCCGGACCGTGTGCCCTACTGGGGCCAGGGCACT<br>CAGGTGACCGTGAGCAGC |
| DR594-<br>hIL27<br>Ra_VH<br>H11 | 1119 | CAGGTGCAGCTTCAGGAGAGCGGAGGGGGGTCCGTGCAGGCTGGTGGGTCACTG<br>AGACTGTCATGTGTGGCTTCAGCTTCAACGTACTGTACCTATGACATGCACTGG<br>TACAGGCAAGCTCCTGGGAAAGGCCGCGAGTTCGTGTCCGCTATTGACAGCGAC<br>GGTACTACCCGTTATGCCGACAGCGTCAAGGGCAGATTTACCATCTCCCAAGGC<br>ACGGCCAAAAACACCGTGTATCTCCAGATGAACAGCCTTCAGCCCGAGGACACC<br>GCAATGTATTACTGCAAGACCGTGTGTGTTGTGGGGAGCCGTTGGTCCGACTAC<br>TGGGGCCAGGGCACCCAAGTGACCGTCTCCTCTGGGGGTGGCTCCCAGGTCCAG<br>CTTCAGGAGTCCGGGGGAGGCAGTGTTCAGGCCGGAGGGAGCCTGAGACTGAGC<br>TGCCGTGCTTCTGGTAGTACTTACTCTAACTACTGTTTGGGCTGGTTTCGCCAA<br>TCCACCGGCAAAGAGCGTGAGGGGGTCGCGGTCATCAACTGGGTCGGAGGTATG<br>CTGTACTTTGCCGATAGCGTCAAGGGAAGATTTACCGTCTCCCAAGACCACGCC<br>AAGAACACCGTGACCCTGCAAATGAACAGCCTGAAGCCAGAGGATACCGCCATG<br>TACTATTGCGCGGCAGAATCCGTCTCCAGCCTTTCTTGCGGAGGCTGGCTCACA<br>AGACCAGGGCGCGTGCCTTACTGGGGACAAGGCACCCAGGTGACAGTCAGCTCA |
| DR594-<br>hIL27<br>Ra_VH<br>H11 | 1120 | CAGGTGCAGTTGCAGGAGTCTGGGGGGGGAAGTGTCCAGGCTGGAGGCTCCCTG<br>CGCCTGAGTTGTGTGGCCAGCGCCAGCACTTACTGCACTTATGACATGCACTGG<br>TACAGACAAGCCCCTGGCAAGGGTAGGGAGTTCGTGTCTGCTATTGACTCCGAC<br>GGGACCACACGTTATGCCGACTCTGTCAAGGGCCGTTTCACTATCTCCCAGGGA<br>ACGGCCAAGAACACAGTGTACTTGCAGATGAACTCTTTGCAACCCGAAGACACC<br>GCTATGTATTACTGTAAGACTGTGTGCGTCGTGGGTTCCAGGTGGTCAGACTAC<br>TGGGGTCAGGGTACTCAGGTCACTGTTAGCTCAGGGGGTTCTGGGGGCTCCGGG<br>GGTTCCGGCCAGGTGCAGCTTCAGGAGTCTGGAGGCGGTTCCGTCCAGGGGGGA<br>GGCTCTCTTAGACTGTCCTGCCGCGCCAGCGGCAGCACCTACTCCAACTACTGC |

TABLE 1B-continued

| Name | SEQ ID NO: | Sequence |
|---|---|---|
| | | CTCGGATGGTTTCGTCAGTCCACAGGTAAGGAGCGCGAAGGCGTGGCCGTTATC AACTGGGTGGGGGGAATGCTGTACTTTGCTGACTCCGTGAAAGGCCGCTTCACT GTGTCACAAGACCATGCAAAGAACACCGTCACATTGCAGATGAACTCTCTGAAA CCAGAGGATACTGCCATGTATTACTGCGCAGCTGAATCTGTGTCCTCTTTCTCC TGCGGTGGCTGGCTGACCCGCCCTGGGAGAGTGCCGTACTGGGGCCAGGGCACC CAAGTGACAGTCAGTTCT |
| DR594-hIL27Ra_VH H12 | 1121 | CAAGTACAGCTCCAGGAATCTGGAGGCGGTAGCGTGCAGGCCGGGGGCTCCTTG CGCTTGTCCTGCGTTGCCTCAGCCAGCACCTACTGCACCTACGACATGCACTGG TATCGCCAAGCACCAGGGAAGGGCAGAGAGTTCGTGTCTGCCATCGACAGTGAT GGCACTACCCGCTACGCCGACCCCGTTAAGGGGCGCATTACCATTTCCCAGGGA ACAGCCAAGAACACCGTGTACTTGCAGATGAACAGCTTGCAGCCTGAAGACACC GCCATGTATTACTGCAAGACCGTGTGTGTAGTGGGTTCAAGGTGGTCCGACTAT TGGGGACAGGGCACTCAGGTGACTGTGTCTTCCGGCGGAGGCAGCCAGGTACAG CTCCAGGAATCCGGTGGGGGCTCCGTTCAGGCTGGCGAGTCCCTGCGCCTGTCC TGTAGGGCCTCCGGCTCCACGTATAGTAACTACTGTCTGGGCTGGTTCCGCCAG ATCACCGGCAAGGAACGCGAGGGAGTGGCGGTAATAAATTGGGTTGGGGGAATG CTGTATTTCGCCGACAGCGTGAAAGGCAGATTCACCGTGTCCCAGGACCAGGCG AAGAACACCGTGTATTTGGAAATGAACTCTCTGAAGCCCGAGGATACCGCCATG TATTACTGCGCTACCGAAAGCGTAAGCTCCTTCAGCTGTGGGGGTTGGCTGACA CGCCCTGATCGGGTTCCCTACTGGGGCCAGGGTACGCAGGTCACCGTTTCCTCC |
| DR594-hIL27Ra_VH H12 | 1122 | CAGGTCCAGCTGCAAGAGTCCGGTGGAGGCAGTGTGCAGGCAGGCGGTAGCCTG CGTTTGTCCTGTGTGGCATCCGCCAGTACCTACCGCACTTACGATATGCACTGG TACAGACAAGCCCCCGGCAAAGGCCGGGAGTTCGTTTCAGCTATCGACTCTGAC GGGACCACTAGGTATGCGGACTCTGTCAAGGGCCGCTTTACAATTAGCCAGGGC ACGGCCAAAAACACCGTATATCTCCAGATGAACAGCCTCCAACCAGAAGACACA GCCATGTATTACTGCAAGACTGTATGCGTGGTCGGCTCCCGTTGGTCTGACTAT TGGGGCCAGGGAACTCAGGTCACCGTCTCATCCGGTGGCTCTGGTGGGAGGGGG GGTTCCGGCCAGGTGCAGCTCCAGGAGTCAGGTGGGGGGAGCGTGCAGGCGGGG GAGTCCCTCCGGCTGAGTTGTAGGGCTTCCGGTAGCACTTACTCCAACTACTGC CTCGGCTGGTTTCGCCAGATCACGGGCAAGGAGCGCGAGGGCGGGGGCGTAATT AACTGGGTCGGAGGGATGCTGTATTTCGCGGACAGCGTTAAGGGACGCTTCACC GTGTCCCAGGATCAGGCCAAGAACACCGTCTATCTGGAGATGAACTCCCTGAAG CCGGAGGACACAGCCATGTATTACTGCGCAACGGAATCCGTGTCTAGCTTCAGC TGCGGTGGGTGGCTCACCCGTCCCGACCGCGTGCCGTATTGGGGGCAGGGGACC CAGGTGACTGTGTCCTCC |
| DR594-hIL27Ra_VH H13 | 1123 | CAGGTGCAACTCCAGGAGTCAGGCGGTGGCTCCGTCCAGGCGGGAGGTTCCCTG CGCCTTTCTTGCGTTGCATCTGCGTCCACCTACTGTACCTATGACATGCACTGG TATCGTCAGGCACCAGGCAAGGGGAGGGAGTTCGTGTCTGCGATTGATTCTGAT GGCACAACTAGGTATGCTGACTCCGTCAAGGGACGGTTCACAATCTCTCAAGGG ACCGCCAAGAATACCGTGTATCTCCAGATGAACTCCCTTCAGCCCGAGGACACG GCCATGTATTACTGCAAGACCGTTTGCGTCGTGGGTTCCAGGTGGTCTGACTAC TGGGGGCAAGGCACGCAGGTGACCGTTAGCTCTGGGGGGGGTAGCCAGGTGCAG TTGCAGGAATCTGGTGGAGGTTCTGTGCAAGCAGGAGGGTCTCTGCGCTTGAGT TGCGTAGCAAGTGGGTACGTGAGTTGTGATTACTTCCTGCCTTCTTGGTACAGG CAGGCTCCGGGCAAGGAACGCGAGTTCGTGTCCATTATCGACGGGACCGGCTCC ACCAGCTATGCCGCGAGCGTCAAGGGGCGCTTCACAGCCAGCCAGGATCGCGGG AAGAACATCGCCTACTTGCAGATGAACAGCCTGAAACCGGAAGATACAGCTATG TATTACTGTAAGGCCTCCTGCGTCCGTGGCCGTACTATTAGTGAATACTGGGGC CAAGGCACGCAGGTGACCGTATCTTCC |
| DR594-hIL27Ra_VH H13 | 1124 | CAGGTTCAGCTCCAGGAGAGCGGAGGTGGCAGCGTTCAAGCCGGTGGCTCCCTG CGCCTGTCTTGTGTCGCGTCTGCTTCCACGTACTGCACCTACGACATGCACTGG TATCGGCAGGCTCCTGGAAAGGGCCGCGAGTTCGTCTCCGCTATCGACTCTGAC GGAACCACTCGCTATGCCGATAGCGTGAAGGGCCGCTTCACCATTAGCCAAGGC ACAGCCAAGAACACAGTGTACTTGCAGATGAACAGCCTCCAGCCGGAAGACACT GCTATGTACTATTGCAAGACTGTGTGTGTTGTGGGGTCCCGTTGGTCTGATTAT TGGGGCCAGGGCACCCAGGTGACCGTCAGTAGCGGGGGCAGTGGGGGGTCAGGA GGCTCCGGTCAGGTGCAGTTGCAGGAGAGCGGAGGGGGCAGTGTTCAGGCCGGG GGCAGCCTGAGACTGTCTTGTGTCGCCTCCGGCTATGTGTCTTGTGACTACTTT CTGCCATCCTGGTATCGGCAGGCCCCTGGGAAAGAAAGAGAGTTCGTGTCCATT ATCGACGGCACTGGAAGCACCTCTTATGCTGCCTCTGTGAAGGGTAGGTTTACT GCCTCCCAAGACAGGGGGAAGAACATTGCTTATGTCCAGATGAACAGTCTGAAG CCCGAGGACACTGCGATGTATTACTGTAAGGCCTCTTGCGTTCGCGGTCGCACA ATTTCCGAGTACTGGGGCCAGGGAACACAGGTGACGGTGAGTAGC |
| DR594-hIL27Ra_VH H14 | 1125 | CAGGTACAGCTCCAGGAGTCTGGGGGAGGTTCAGTGCAGGCTGGCGGTTCTTTG CGCCTGTCCTGTGTAGCCTCCGCCAGCACATATTGCACTTACGACATGCACTGG TATCGCCAGGCTCCGGGTAAGGGCCGCGAGTTTGTTAGCGCCATCGACTCCGAT GGAACAACCCGTTATGCTGACTCTGTGAAGGGCCGCTTTACAATTAGTCAGGGA ACCGCAAAGAATACTGTTTATTTGCAGATGAATAGCCTGCAACCCGAGGACACC GCTATGTATTACTGTAAGACAGTGTGCGTTGTGGGCTCCCGCTGGAGCGACTAT TGGGGTCAGGGCACACAGGTTACCGTGTCCAGCGGAGGGGGGAGCCAGGTGCAG CTCCAGGAGTCAGGTGGCGGATCTGTCCAAGCTGGAGGTTCCCTGCGGTTGTCT TGTGTGGCCTCTGGTTATGTGTCATGCGATTATTTCTTGCCCAGCTGGTATCGC |

TABLE 1B-continued

| Name | SEQ ID NO: | Sequence |
|---|---|---|
| | | CAGGCTCCGGGCAAGGAGCGCGAATTTGTGTCTATCATTGACGGCACCGGCTCC<br>ACCTCCTACGCAGCCAGTGTCAAGGGGCGCTTCACGGCAAGCCAAGACAAGGGA<br>AAGAACATCGCCTATTTGCAGATGAACTCTTTGAAGCCAGAGGACACCGCCATG<br>TATTACTGTAAGGCATCTTGTGTGAGGGGCCGCGCGATCAGCGAGTACTGGGGC<br>CAGGGCACCCAGGTGACCGTGAGCAGC |
| DR594-<br>hIL27<br>Ra_VH<br>H14 | 1126 | CAGGTGCAGCTTCAGGAGTCCGGGGGGGGCAGCGTGCAAGCCGGGGGATCTCTG<br>CGCCTCTCCTGTGTCGCGAGCGCAAGCACATACTGCACCTACGATATGCACTGG<br>TATCGCCAGGCCCCCGGCAAGGGCAGAGAGTTCGTGAGCGCGATTGATTCCGAT<br>GGCACTACCCGCTACGCTGATAGTGTGAAAGGACGGTTCACTATCTCCCAGGGC<br>ACTGCCAAAAACACAGTGTACCTCCAGATGAACTCCCTTCAGCCCGAGGACACC<br>GCCATGTATTACTGCAAAACTGTGTGCGTGGTAGGGTCTCGCTGGAGCGATTAT<br>TGGGGGCAGGGAACCCAGGTGACAGTTTCCTCTGGGGGCAGCGGAGGTTCTGGC<br>GGTTCCGGCCAGGTGCAGCTTCAGGAAAGCGGAGGTGGGAGCGTGCAGGCCGGA<br>GGCAGCCTCAGGCTGAGCTGCGTGGCCCCCGGTTACGTATCATGCGATTACTTC<br>CTCCCCTCCTGGTATCGGCAGGCTCCGGGCAAGGAGCGCGAGTTCGTGAGCATT<br>ATCGACGGTACAGGCTCCACCAGCTATGCCGCATCTGTGAAGGGACGTTTCACA<br>GCTTCCCAGGACAAGGGTAAAAACATTGCCTACTTGCAGATGAACAGCTTGAAG<br>CCGGAAGATACCGCAATGTATTACTGCAAAGCCAGTTGTGTCCGTGGCCGCGCT<br>ATCTCCGAGTATTGGGGACAGGGCACACAGGTGACGGTGTCCTCC |
| DR594-<br>hIL27<br>Ra_VH<br>H15 | 1127 | CAGGTCCAGCTCCAGGAGAGCGGCGGTGGAAGCGTCCAGGCTGGGGGCTCTCTG<br>CGTCTGTCTTGTGTAGCCTCTGCCTCCACTTACTGTACTTACGACATGCACTGG<br>TATCGCCAGGCCCCTGGCAAGGGCCGCGAGTTCGTTTCCGCCATTGATTCCGAC<br>GGTACTACCAGATACGCCGACTCCGTGAAAGGTAGGTTCACGATCAGCCAGGGC<br>ACTGCCAAAAACACAGTTTATCTCCAGATGAACTCCCTCCAGCCTGAGGACACT<br>GCCATGTATTACTGTAAAACCGCTTGTGTGGTCGGATCTCGGTGGTCTGACTAT<br>TGGGGGCAGGGCACCCAGGTGACCGTATCTTCCGGCGGAGGGTCCCAGGTCCAG<br>TTGCAGGAGTCTGGCGGAGGCTCCGTACAGGCAGGGGGCTCCCTGCGCCTCTCC<br>TGCGTGGCCTCCGGCTACGTGTCTTGCGACTATTTCCTGCCATCTTGGTATAGA<br>CAGGCTCCCGGCAAGGAGCGCGAGTTTGTGTCTATTATCGACGGCACCGGCTCA<br>ACTTCCTACGCTGCCTCTGTGAAGGGCCGCTTTACCGCCAGCCAGGACAAAGGC<br>AAGAACATCGCGTACCTCCAGATGAACACCCTGAAGCCCGAGGACACCGCCATG<br>TATTACTGTAAGGCCTCCTGTGTGCGTGGACGTGCCATCTCCGAATACTGGGGC<br>CAGGGCACCCAGGTGACCGTAAGCTCA |
| DR594-<br>hIL27<br>Ra_VH<br>H15 | 1128 | CAGGTGCAGCTGCAAGAGAGCGGTGGGGGCAGCGTGCAAGCTGGGGGCAGCCTG<br>CGCCTCTCCTGCGTCGCGTCTGCTTCCACTTACTGTACTTACGACATGCACTGG<br>TATCGCCAGGCCCCTGGCAAGGGCCGCGAGTTCGTGTCTGCCATTGACAGCGAT<br>GGAACGACCCGCTACGCGGACAGCGTTAAGGGTCGCTTCACTATCTCTCAGGGC<br>ACTGCTAAAAACACTGTGTACCCCCAGATGAACTCTTTGCAGCCCGAGGATACT<br>GCCATGTATTACTGTAAGACCGTTTGCGTTGTGGGTTCCCGTTGGTCCGATTAT<br>TGGGGCCAGGGCACCCAGGTGACCGTATCAAGCGGGGGGTCCGGGGGCAGCGGA<br>GGTTCAGGTCAGGTGCAGTTGCAGGAAAGCGGAGGTGGCAGCGTACAGGCCGGG<br>GGCTCCCTGAGGCTGAGCTGCGTGGCGAGTGGCTACGTCAGTTGCGACTACTTC<br>TTGCCTTCTTGGTATCGGCAAGCCCCCGGTAAGGAGCGCGAGTTCGTGAGTATT<br>ATCGACGGCACTGGTAGCACCTCCTATGCTGCCAGCGTGAAAGGTCGTTTTACC<br>GCCTCCCAGGACAAGGGTAAAAACATTGCCTATTTGCAAATGAACACCCTTAAA<br>CCTGAGGACACTGCCATGTATTACTGTAAGGCTTCATGTGTGAGAGGTCGTGCT<br>ATCTCAGAATACTGGGGCCAGGGCACCCAAGTCACTGTTTCTTCT |
| DR594-<br>hIL27<br>Ra_VH<br>H16 | 1129 | CAGGTTCAGCTCCAGGAATCCGGCGGTGGCTCCGTTCAGGCAGGGGGCAGCCTG<br>CGTCTGTCCTGTGTCGCATCCGCCTCTACCTACTGCACTTAGGATATGCACTGG<br>TATCGGCAGGCTCCTGGTAAGGGCCGCGAGTTCGTCAGTGCTATTGACTCCGAC<br>GGTACAACCCGGTATGCGGATTCTGTGAAAGGAAGATTTACGATCTCCCAAGGG<br>ACCGCAAAAAACACCGTGTACCTTCAGATGAACTCTCTCCAGCCCGAAGATACA<br>GCGATGTATTACTGCAAGACTGTATGCGTGGTAGGTTCTCGTTGGAGCGACTAC<br>TGGGGCCAGGGTACACAAGTCACCGTCTCCAGCGGGGGGGGCAGCCAGGTCCAG<br>CTCCAGGAATCTGGCGGAGGTTCCGTGCAGGCCGGAGGTAGCCTTCGCCTCTCT<br>TGCCGCGCATCCGGCAGCACCTACTCCAACTACTGTCTGGGCTGGTTCAGGCAG<br>ATCACCGGCAAGGAGCGCGAGGGCGTAGCCGTAATAAATTGGGTAGGCGGTATG<br>CTGTACTTTGCTGACAGCGTTAAGGGTCGGTTTACGGTGTCCCAGGATCAGGCC<br>AAGAACACCGTGTATCTCCAGATGAACTCCCTGAAGCCGGAGGATACCGCTATG<br>TACTATTGCGCAGCCGAGTCAGCTAGTTCCTTCAGCTGCGGTGGCTGGCTCACG<br>AGACCAGATCGCGTCCCCTACTGGGGACAAGGCACACAGGTTACCGTGTCCTCC |
| DR594-<br>hIL27<br>Ra_VH<br>H16 | 1130 | CAGGTCCAGCTTCAGGAGAGCGGGGGAGGCTCCGTGCAAGCTGGAGGTTCCCTC<br>CGCTTGTCCTGCGTTGCGTCCGCAAGCACCTACTGCACTTATGACATGCACTGG<br>TATCGCCAGGCTCCTGGCAAAGGGAGAGAGTTCGTCTCCGCCATTGATAGCGAT<br>GGTACAACTAGGTACGCAGATTCCGTTAAAGGTAGGTTTACTATCAGCCAGGGC<br>ACGGCCAAAAACACCGTCTATCTGCAAATGAACTCTCTCCAGCCCGAGGATACC<br>GCGATGTACTATTGCAAGACCGTGTGTGTAGTGGGCAGCCGCTGGTCAGACTAT<br>TGGGGCCAGGGAACGCAGGTGACAGTGTCTAGCGGGGGGTCCGGCGGTTCCGGT<br>GGCTCCGGCCAGGTACAGCCCCAGGAGTCAGGCGGAGGCCCCGTGCAAGCCGGG<br>GGTTCTCTGCGGCTCTCCTGTCGCGCTTCTGGGTCCACCTATTCCAATTACTGC<br>CTGGGCTGGTTCCGTCAAATTACGGGCAAGGAGCGCGAAGGCGTGGCCGTGATA<br>AATTGGGTGGGCGGGATGTTGTACTTTGCTGACAGCGTTAAGGGACGTTTTACT |

TABLE 1B-continued

| Name | SEQ ID NO: | Sequence |
|---|---|---|
| | | GTGTCCCAGGACCAGGCCAAGAACACCGTGTACCTGCAGATGAACTCCTTGAAG CCAGAGGACACAGCAATGTATTACTGTGCCGCTGAAAGCGCCAGCTCTTTCAGT TGTGGGGGCTGGCTGACTAGACCAGACCGTGTCCCTTACTGGGGTCAGGGCACC CAGGTTACCGTGTCCTCC |
| DR594-hIL27Ra_VHH17 | 1131 | CAAGTCCAGCTCCAGGAGTCCGGCGGTGGCTCCGTCCAGGGGGGCGGATCTCTG CGCCTGTCCTGTGTCGCCTCCGCTTCCACATACTGCACCCATGACATGCACTGG TATCGGCAGGCTCCTGGTAAGGGCCGCGAGTTCGTCAGCGCCATCGACTCCGAC GGAACGACCCGGTACGCTGATAGCGTGAAAGGTAGGTTTACCATCTCACAGGGC ACCGCCAAAAATACCGTCTACTTGCAGATGAACAGTTTGCAGCCCGAGGACACC GCCATGTATTACTGCAAGACTGTGTGTGTAGTGGGGTCACGCTGGTCTGATTAT TGGGGCCAGGGTACTCAGGTGACTGTGTCTAGTGGCGGTGGCAGCCAGGTGCAG TTGCAGGAGAGTGGAGGCGGTCTCGTCCAGCCAGGAGGCAGTCTGCGCCTGTCA TGCGCTGCCTCCGGCTTTACTTTTTCCCTGTCTGGTATGTCATGGGTGCGGCAG GCCCCCGGCAAGGGTCTGGAGTGGGTCAGTGCAATCAGCAGTGGAGGGGCCTCT ACTTATTACACCGACAGCGTCAAAGGCAGATTCACCATCAGTAGGGATAATGCC AAGAACATGCTGTACCTCCAGCTGAACTCTCTGAAGACAGAGGACACGGCTATG TACTATTGTGCTAAAGGGGGCAGCGGTTAGGGGGATGCTTCCAGAATGACTTCT CCGGGATCTCAGGGTACTCAAGTCACCGTTAGTTCT |
| DR594-hIL27Ra_VHH17 | 1132 | CAAGTCCAGCTCCAGGAGAGCGGAGGGGGTTCCGTGCAGGCAGGGGGTTCACTT CGCCTGTCCTGTGTGGCTTCTGCTTCCACCTATTGCACGTATGATATGCACTGG TATCGCCAGGCTCCCGGCAAGGGCCGCGAGTTCGTCTCAGCGATTGATTCTGAC GGCACCACTCGCTACGCTGACTCTGTGAAGGGCCGCTTTACCATCAGTCAAGGT ACTGCGAAGAACACCGTGTACCTTCAGATGAACTCACTGCAACCGGAGGACACC GCGATGTACTATTGCAAGACTGTTTGTGTGGTCGGTTCCCGCTGGTCCGATTAC TGGGGGCAGGGCACTCAGGTGACGGTCAGTTCCGGCGGGGAGTGGGGGTCCGGG GGCTCTGGCCAAGTGCAGTTGCAGGAGAGCGGGGGAGGCCTCGTGCAGCCAGGT GGATCTCTGCGGCTGTCTTGTGCCGCTTCCGGCTTCACTTTTTCCCTGTCCGGC ATGAGTTGGGTCCGCCAGGCCCCAGGGAAAGGCCTGGAGTGGGTGTCCGCCATC TCTAGCGGCGGTGCCTCCACATATTACACTGACAGCGTCAAGGGTCGCTTTACG ATTTCCCGCGATAACGCTAAGAACATGCTCTACCTCCAGCTGAACAGCCTGAAG ACCGAGGATACTGCCATGTATTACTGTGCCAAAGGGGGTAGCGGCTATGGGGAC GCCAGCAGGATGACCAGTCCCGGAAGTCAGGGAACTCAGGTCACCGTTTCTTCC |
| DR594-hIL27Ra_VHH18 | 1133 | CAGGTACAGCTTCAGGAGAGCGGGGGAGGCACTGTGCAGGCCGGAGGCTCTCTG CGCCTCTCTTGTGTCGCCTCCGCGTCTACCTATTGCACCTACGACATGCACTGG TATCGCCAGGCCCCCGGAAAAGGTCGCGAGTTCGTGTCTGCTATCGACTCCGAC GGGACCACTCGCTACGCTGACTCCGTAAAAGGACGTTTTACAATTAGTCAGGGT ACAGCCAAGAATACAGTATACCTGCAAATGAACTCCTTGCAGCCAGAGGACACC GCCATGTATTACTGCAAGACCGTGTGCGTGGTCGGCAGTCGCTGGTCCGACTAC TGGGGCCAGGGAACCCAGGTCACGGTCTCAAGCGGAGGGGGGATCACAGGTCCAG CTGCAAGAATCAGGAGGTGGAAGCGTGCAGGCAGGGGGAAGCCTGAGGCTGTCC TGCGTGGCCAGGGGCTACGTGTCCTGCGATTACTTTCTCCCTAGCTGGTATCGC CAGGCACCCGGAAAAGAGAGGGAGTTCGTCTCAATTATCGACGGAACTGGAAGC ACCTCTTACGCCGCTTCCGTGAAGGGCCGCCTTACTGCATCACAGGATAAGGGC AAGAATATCGCCTACCTCCAGATGAACTCACTGAAGCCTGAGGACACTGCTATG TATTACTGCAAGGCTTCCTGTGTGCGGGGTCGCGGAATCTCTGAGTACTGGGGT CAGGGTACTCAGGTCACCGTCTCTTCT |
| DR594-hIL27Ra_VHH18 | 1134 | CAGGTGCAGTTGCAGGAGAGCGGAGGTGGGAGTGTCCAGGCTGGTGGCTCCTTG CGCCTGAGCTGCGTGGCCTCCGCCTCCACTTATTGCACCTACGACATGCACTGG TACAGGCAAGCCCCTGGTAAGGGTAGGGAGTTCGTCAGCGCCATTGATAGCGAT GGCACAACCCGTTACGCGGATAGCGTGAAGGGCCGTTTCACAATCTCACAGGGC ACCGCCAAGAACACCGTTTATTTGCAGATGAACAGCCTCCAGCCCGAAGATACA GCTATGTATTACTGTAAGACCGTGTGTGTGGTTGGTAGCAGATGGTCCGACTAC TGGGGTCAAGGCACTCAAGTCACCGTATCCAGCGGCGGATCAGGAGGCAGCGGG GGTTCCGGGCAGGTGCAGCTCCAGGAATCAGGCGGTGGCAGCGTGCAGGCAGGG GGTTCCTTGCGTCTGAGTTGTGTGGCAAGTGGCTATGTAAGCTGTGACTACTTC CTCCCCAGTTGGTATCGCCAGGCTCCCGGCAAGGAGCGGGAGTTCGTGAGTATC ATTGATGGCACTGGTAGCACCTCCTACGCAGCGAGCGTCAAGGGTCGTTTTACC GCGTCTCAGGACAAGGGAAAAAACATCGCGTACCTCCAGATGAACAGCCTGAAG CCTGAGGACACAGCCATGTATTACTGCAAGGCCCCCCGCGTGCGCGGTCGCGGA ATTTCCGAGTATTGGGGCCAGGGCACCCAAGTAACAGTAAGCTCT |
| DR594-hIL27Ra_VHH19 | 1135 | CAGGTCCAACTTCAAGAGTCTGGCGGTGGGTCCGTCCAGGCCGGGGGTTCCCTC AGACTGTCATGCGTGGCCTCCGCTTCCACCTATTGTACCTACGACATGCACTGG TATCGCCAGGCTCCTGGCAAGGGCCGCGAGTTCGTGTCTGCCATTGATTCAGAC GGGACAACCCGCTACGCAGACTCCGTGAAAGGTCGTTTTACCATCTCACAGGGC ACTGCAAAAAACACTGTCTATCTGCAAATGAACTCCTTGCAGCCAGAAGACACC GCCATGTATTACTGCAAGACCGTATGTGTCGTGGGAAGCCGTTGGTCAGACTAC TGGGGGCAGGGCACCCAAGTTACGGTGTCCTCTGGCGGGGGCAGTCAGGTGCAG TTGCAGGAGAGGGGGGGCGGTTCTGTGCAAGCTGGGGGTTCCCTGCGCCTGAGC TGTCGCGCCTCTGGATCTACGTATAGCAACTACTGCCTGGGCTGGTTCCGCCAG ATCACCGGAAAGGAACGTGAGGGAGTGGCCGTCATCAACTGGGTGGGCGGAATG CTGTACTTCGCCGATTCTGTCAAGGGCCGGTTTACTGTCTCCCAGGATCAGGGG AAGAACACGGTATACCTTCAGATGAACAGCCTGAAACCAGAAGATACCGCTATG |

TABLE 1B-continued

| Name | SEQ ID NO: | Sequence |
|---|---|---|
| | | TATTACTGTGCCGCAGAGAGCGTCTCCAGCTTTTCCTGCGGAGGCTGGCTCACC<br>CGCCCAGATCGTGTGCCTTACTGGGGGCAGGGGACCCAGGTGACCGTTTCCTCC |
| DR594-<br>hIL27<br>Ra_VH<br>H19 | 1136 | CAAGTCCAGCTCCAGGAGTCCGGGGGGGGTTCCGTCCAGGCTGGGGGCTCTTTG<br>CGGTTGTCTTGTGTCGCATCAGCCTCCACTTATTGTACCTATGATATGCACTGG<br>TATCGCCAGGCTCCGGGGAAGGGCAGGGAATTTGTGTCAGCTATTGATTCCGAC<br>GGAACCACACGGTATGCAGATTCTGTGAAAGGCCGCTTCACTATCTCACAGGGT<br>ACTGCCAAGAACACCGTCTACTTGCAGATGAACTCCCTCCAGCCAGAGGACACT<br>GCCATGTATTACTGCAAGACCGTCTGTGTGGTTGGGAGTAGGTGGAGTGACTAC<br>TGGGGCCAGGGCACACAGGTCACGGTATCTTCCGGCGGGAAGCGGGGAAGTGGT<br>GGCTCTGGACAAGTGCAGTTGCAGGAGAGCGGGGGGGGTTCCGTGCAGGCAGGC<br>GGAAGCCTGAGGCTGAGCTGTCGTGCTTCTGGCTCCACCTATTCCAACTATTGC<br>TTGGGTTGGTTTCGCCAAATTACCGGCAAGGAGCGTGAAGGGGTTGCTGTCATC<br>AACTGGGTTGGGGGTATGCTCTACTTTGCTGACTCCGTGAAGGGTCGCTTCACA<br>GTCAGCCAAGACCAGGCTAAGAACACAGTGTATCTCCAGATGAACTCTCTTAAA<br>CCGGAAGACACTGCTATGTATTACTGCGCCGCAGAAAGCGTCAGCCCCTTCAGT<br>TGCGGTGGCTGGCTGACCAGGCCAGATCGCGTACCATATTGGGGACAGGGAACC<br>CAGGTCACCGTGTCCTCC |
| DR594-<br>hIL27<br>Ra_VH<br>H20 | 1137 | CAAGTGCAGCTGCAAGAGAGGGGCGGTGGCCCCGTGCAGGCCGGGGGCTCCCTG<br>CGCCTGAGCTGTGTGGCAAGCGCCTCAACATACTGCACCTATGACATGCACTGG<br>TATCGTCAGGCTCCCGGAAAGGGCAGAGAGTTCGTGTCCGCCATCGACAGCGAT<br>GGGACAACCCGCTACGCAGACAGCGTGAAGGGCCGCTTCACTATCTCTCAGGGC<br>ACAGCTAAGAACACCGTGTACCCTCAGATGAACTCCTTGCAGCCTGAGGATACT<br>GCCATGTACTATTGCAAGACCGTGTGTGTAGTGGGCTCCAGATGGTCTGACTAC<br>TGGGGGCAGGGAACACAGGTTACCGTCTCTAGCGGGGGGGGAAGCCAAGTGCAG<br>TTGCAGGAAAGCGGGGGGGGGCTGGTCCAGCCAGGGGGATCTCTGAGGCTGTCT<br>TGCGCCGCATCAGGTTTTACTTTCTCAAGCTACCCCATGTCCTGGGTCAGACAA<br>GCGCCGGGGAAGGGCTTGGAATGGGTGAGCACCATCTCCAGGGGTGGAGACACG<br>ACCCTGTACGCCGACAGCGTCAAAGGGCGCTTCACATCTAGCCGCGACAATGCA<br>AAAAACACCCTGTACCTCCAGCTTAATTCCCTGAAGACAGAGGACACCGCAATG<br>TACTATTGCGCGAAACGGATTGACTGCAACTCCGGTTATTGTTACAAGCGCAGT<br>TACTGGGGCCAGGGGACCCAGGTGACCGTGTCTAGC |
| DR594-<br>hIL27<br>Ra_VH<br>H20 | 1138 | CAGGTTCAGCTTCAGGAATCTGGAGGGGGATGTGTGCAGGCTGGTGGAAGCCTG<br>CGTCTCAGCTGCGTGGCCTCTGCCTCCACGTATTGTACCTACGACATGCACTGG<br>TACAGGCAGGCTCCAGGGAAGGGCCGGGAGTTTGTGAGCGCTATTGATTCAGAC<br>GGCACTACACGGTACGCTGACAGTGTCAAGGGGAGGTTCACCATCAGCCAGGGG<br>ACAGCTAAGAATACCGTCTACCTCCAGATGAACTCCCTTCAGCCGGAGGATACC<br>GCTATGTATTACTGCAAGACGGTGTGCGTGGTCGGCTCCCGTTGGAGCGACTAC<br>TGGGGGCAGGGCACCCAAGTTACCGTGTCCAGCGGAGGTTCAGGCGGTTCTGGT<br>GGCTCTGGCCAGGTGCAGCTCCAGGAGAGCGGAGGCGGTCTGGTGCAGCCGGGT<br>GGCTCCCTGAGACTTTCCTGCGCAGCTTCCGGCTTTACCTTCTCTAGCTATCCA<br>ATGTCTTGGGTGAGACAGGCCCCTGGAAAGGGTCTGGAGTGGGTGTTCTACTAT<br>TCCTCTGGTGGCGATACAACCCTGTACGCGGATTCTGTCAAAGGTCGTTTCACC<br>AGCTCACGCGACAACGCTAAGAACACCTTGTATCTTCAGTTGAACAGCCTGAAG<br>ACAGAGGACACTGCGATGTATTACTGTGCAAAGCGCATTGATTGTAATAGCGGC<br>TACTGTTACAAGCGTAGCTACTGGGGCCAAGGCACCCAGGTCACGGTCAGCAGC |
| DR594-<br>hIL27<br>Ra_VH<br>H21 | 1139 | CAGGTGCAGCTTCAGGAGTCTGGTGGCGGTTCCGTCCAGGCTGGCGGTTCTCTG<br>AGGCTGTCATGCGTGGCATCTGCGAGCACCTACTGTACTTACGACATGCACTGG<br>TATCGTCAGGCCCCCGGTAAGGGTCGGGAGTTCGTGTCCGCCATTGATAGCGAT<br>GGGACAACCCGGTACGCCGACTCCGTGAAGGGTCGCTTCACTATCTCACAGGGA<br>ACCGCTAAGAACACAGTCTACCTTCAGATGAACTCTTTGCAGCCAGAGGACACC<br>GCCATGTATTACTGTAAGACAGTGTGTGTAGTTGGAAGCCGCTGGAGCGACTAC<br>TGGGGCCAAGGCACTCAGGTCACCGTCAGCTCTGGCGGAGGCAGCCAGGTGCAG<br>TTGCAGGAGAGCGGCGGAGGCTTGGTACAGCCCGGAGGCTCCCTCAGGCTCAGC<br>TGTGCTGCCTCCGGTTTCACCTTTTCCCTGTCTTCCATGTCCTGGGTGCGTCAG<br>GCACCAGGCAAGGGTCTGGAGTGGGTGTCTGCTATCAGCTCCGGCGGAGCTTCC<br>ACGTACTATACAGATTCCGTTAAGGGACGGTTCACTATCTCCCGTGACAACGCG<br>AAGAATATGCTGTACCTTCAGCTCAACTCACTGAAGACTGAGGACACCGCCATG<br>TATTACTGCGCCAAAGGGGGCTCCGGCTATGGCGACGCGAGCCGTATGACTAGC<br>CCTGGAAGCCAAGGCACACAGGTCACCGTTAGCTCC |
| DR594-<br>hIL27<br>Ra_VH<br>H21 | 1140 | CAGGTTCAGCTTCAGGAGAGCGGGGGAGGCAGCGTCCAGGCCGGAGGCTCACTG<br>CGCCTGTCTTGTGTCGCCTCTGCATCTACCTACTGCACTTATGACATGCACTGG<br>TATCGCCAAGCGCCGGGTAAAGGACGCGAGTTCGTCTCTGCCATCGACTCCGAC<br>GGCACAACTCGCTACGCCGACTCTGTGAAGGGCAGGTTTACCATCAGCCAGGGA<br>ACCGCTAAGAACACCGTTTACCTCCAGATGAACTCCCTCCAGCCCGAGGACACC<br>GCCATGTATTACTGTAAGACCGTTTGTGTCGTGGGCTCCAGGTGGTCCGACTAC<br>TGGGGACAGGGCACCCAGGTGACAGTCTCCAGCGGTGGAAGTGGTGGCTCCGGC<br>GGTTCAGGCCAGGTCCAGTTGCAGGAGTCTGGCGGTGGACTCGTGCAACCTGGG<br>GGCTCTCTGAGACTGAGCTGTGCGGCTTCTGGGTTCACCTTCAGCCTGAGCAGT<br>ATGAGCTGGGTCCGCCAAGCCCCAGGAAAGGGACTGGAATGGGTGTCCGCCATC<br>TCCTCTGGGGGAGCGAGCACATACTATACAGATAGCGTGAAAGGGAGGTTTACT |

TABLE 1B-continued

| Name | SEQ ID NO: | Sequence |
|---|---|---|
| | | ATCTCTAGGGATAACGCGAAGAACATGCTTTATCTCCAGCTTAATTCCTTGAAG ACTGAGGACACTGCCATGTACTATTGCGCCAAAGGTGGCAGCGGTTATGGAGAC GCCAGTAGAATGACCAGCCCAGGTTCCCAGGGGACTCAAGTGACCGTCAGTTCT |
| DR594-hIL27 Ra_VH H22 | 1141 | CAGGTGCAGCTTCAGGAAAGCGGAGGCGGTAGCGTACAGGCCGGGGGTAGCCTG CGTTTGTCCTGCGTGGCGAGCGCTTCCACGTACTGTACCTACGACATGCACTGG TATCGCCAAGCGCCGGGAAAGGGACGCGAGTTCGTTTCCGCTATTGATTCCGAT GGGACCACACGCTACGCAGATTCCGTGAAGGGCCGCTTCACAATTTCCCAGGGC ACAGCCAAGAACACCGTGTACCTCCAGATGAACTCCTTGCAGCCTGAGGATACC GCCATGTATTACTGCAAAACAGTCTGCGTCGTGGGTTCTCGTTGGTCTGACTAT TGGGGCCAGGGAACTCAGGTTACCGTTTCCTCTGGGGGGGGGTCCCAGGTCCAG CTCCAGGAGTCAGGTGGGGGGTCCGTCCAAGCAGGTGGCTCCCTGCGCCTGTCA TGTCGGGCGAGCGGCAGTACTTATAGCAATTACTGTCTGGGCTGGTTCCGGCAG ACAACCGGCAAAGAGAGAGAGGGCGTTGCCGTTATTAACTGGGTGGGTGGAATG CTGTACTTCGCCGACTCCGTAAAGGGACGCTTCACCGTTAGCCAGGATCAGGCT AAAAATACAGTATACCTGCAAATGAACAGTTTGAAGCCTGAAGACACAGCCATG TACTATTGCGCCGCTGAGTCTGTCAGCTCTTTTTCTTGCGGGGGATGGCTGACT CGCCCGGATCGCGTACCTTATTGGGGCCAGGGAACCCAAGTCACGGTCTCTAGT |
| DR594-hIL27 Ra_VH H22 | 1142 | CAAGTGCAGCTTCAGGAAAGCGGAGGTGGAAGTGTGCAGGCTGGGGGTAGCCTG AGGCTGTCCTGCGTGGCGAGCGCGTCCACTTACTGTACCTACGACATGCACTGG TATCGCCAAGCACCAGGCAAGGGTCGCGAGTTCGTTTCCGCCATTGATAGCGAT GGCACCACTCGTTACGCTGACAGTGTGAAGGGTCGCATTACCATTTCCCAGGGC ACAGCGAAGAACACCGTTTACCTCCAGATGAACAGCCTTCAGCCAGAGGATACA GCCATGTACTATTGCAAAACCGTGTGCGTTGTGGGCAGCCGTTGGTCTGACTAT TGGGGACAAGGCACTCAGGTTACTGTCAGCTCCGGTGGGTCGGGGGGATCTGGG GGCAGCGGCCAGGTCCAGCTGCAAGAGTCTGGTGGCGGTTCCGTCCAGGGGGGC GGGAGTTTGCGGCTCAGCTGCCGCGCCTCAGGCTCAACTTACAGTAACTATTGC CTGGGCTGGTTCAGGCAGACCACAGGCAAGGAGAGAGAGGGTGTCGCCGTCATC AACTGGGTAGGCGGTATGCTGTACTTCGCCGACTCCGTTAAAGGGCGTTTCACG GTTTCCCAAGACCAGGCAAAGAACACTGTGTATCTCCAGATGAACAGCCTCAAA CCCGAAGATACCGCGATGTATTACTGTGCTGCCGAGAGCGTGTCTTCCTTCAGC TGTGGCGGTTGGCTTACACGCCCGGATCGGGTTCCTTACTGGGGCCAGGGCACA CAGGTGACAGTCTCCAGC |
| DR594-hIL27 Ra_VH H23 | 1143 | CAGGTGCAGCTCCAGGAGAGCGGTGGAGGCTCTGTGCAGGCCGGTGGCTCACTT CGCCTGTCCTGCGTGGCTTCAGCCAGCACTTACTGTACCTATGATATGCACTGG TATCGCCAGGCCCCTGGCAAAGGACGCGAGTTCGTGTCTGCCATTGATAGTGAT GGCACCACACGCTACGCCGACTCAGTTAAGGGTAGGTTTACCATTTCCCAAGGC ACGGCCAAGAACACCGTGTACCTGCAAATGAACTCCCTCCAGCCCGAGGACACA GCGATGTATTACTGCAAGACCGTGTGTGTTGTGGGTTCCCGCTGGTCCGACTAT TGGGGTCAGGGCACGCAGGTGACCGTTAGTTCCGGTGGAGGCAGCCAGGTCCAG CTTCAGGAGTCAGGCGGGGGCTCAGTCCAGGCTGGCGGATCTCTCCGCTTGTCC TGTAGGGCCTCCCGTAGCCCCTACGGCAACTATTGTTTGGGTTGGTTCCGCCAG TCCACTGGCAAGGAGCGGGAGGGAGTTGCGGTCATCAACTGGGTGGGCGGGATG CTCTACTTTGCGGACTCCGTGAAAGGCCGCTTCACCGTTAGCCAGGATCACGCT AAGAACACTGTGACACTCCAGATGAACAGCCTGAAGCCTGAGGATACTGCCATG TACTATTGCGCCGCAGAGAGCGTGTCTAGCTTCTCCCGCGGCGGTTGGCTGACC AGACCCGACAGGGTTCCGTATTGGGGTCAAGGCACCCAGGTGACCGTCTCTAGT |
| DR594-hIL27 Ra_VH H23 | 1144 | CAGGTTCAGCTTCAGGAGAGCGGGGGGGGTTCTGTTCAGGCAGGTGGGTCCCTG AGACTGTCTTGCGTTGCCAGCGCCTCCACGTATTGCACCTATGACATGCACTGG TATCGCCAGGCCCCTGGCAAGGGCAGAGAGTTCGTTTCTGCCATTGATTCTGAT GGCACAACCCGCTACGCCGATTCTGTCAAGGGACGCTTCACGATTTCCCAGGGG ACCGCCAAGAACACGGTATATCTGCAAATGAACTCTCTCCAGCCTGAAGACACA GCGATGTACTATTGTAAAACCGTGTGCGTCGTAGGCAGTCGTTGGTCCGATTAC TGGGGCCAGGGCACTCAAGTGACTGTCAGCTCCGGGGGCTCTGGAGGGAGCGGT GGCTCTGGTCAGGTCCAACTGCAAGAGTCAGGGGGGGGCTCCGTGCAGGCCGGA GGCTCCCTGCGCCTTTCCTGTCGCGCAAGCCGTTCTCCATACGGGAACTATTGT CTGGGCTGGTTCAGACAGAGTACTGGGAAGGAGAGGGAGGGCGTGGCCGTCATC AACTGGGTCGGTGGAATGCTGTACTTCGCTGACAGTGTGAAGGGCCGTTTCACT GTGTCCCAGGATCACGCCAAAAACACTGTTACACTCCAGATGAACAGCCTGAAG CCAGAAGATACAGCAATGTATTACTGTGCGGCTGAATCTGTTTCCAGCTTTTCT TGCGGCGGTTGGCTGACGCGCCCTGATCGCGTCCCCTATTGGGGCCAGGGTACT CAGGTTACTGTGTCATCT |
| DP594-hIL27 Ra_VH H24 | 1145 | CAGGTTCAGCTGCAAGAGTCTGGGGGAGGCTCTGTGCAGGCAGGAGGCTCTCTC CGGCTGAGCTGCGTGGCCTCCGCCTCCACTTACTGTACTTACGATATGCACTGG TATCGCCAAGCGCCGGGGAAGGGCCGTGAGTTTGTTAGCGCCATCGACTCCGAC GGTACGACTCGCTACGCCGATTCTGTGAAAGGGCGCTTCACTATTTCCCAAGGC ACCGCCAAAAACACCGTGTACCCTCAGATGAACTCTCTTCAGCCAGAGGACACC GCCATGTATTACTGCAAGACAGTCTGTGTTGTGGGCAGTCGTTGGAGCGATTAC TGGGGTCAGGGTACTCAGGTTACTGTCAGCTCCGGGGGGGGAAGCCAGGTCCAG CTCCAGGAGAGCGGGGGGGGCCTGGTGCAACCTGGCGGTTCTCTGCGCCTTTCC TGCGCTGCGTCTGGCTTCACATTCTCCCACTCCGGCATGAGCTGGGTCCGTCAG GCTCCGGGGAAGGGCCTTGAGTGGGTGTCCACGATCAATAGTGGCGGAGCCAGC ACCTATTACACCGACTCTGTCAAGGGCCGGTTCACTATCAGCCGGGATAACGCC |

TABLE 1B-continued

| Name | SEQ ID NO: | Sequence |
|---|---|---|
| | | AAGAACATGCTGTATTTGCAGCTGAACTCTCTGAAGACGGAGGACACCGCGATG<br>TATTACTGTGCCAAGGGAGGCTCCGGCTATGGGGATGCCTCCAGGATGACTTCT<br>CCGGGTAGCCAGGGAACACAGGTGACAGTCTCAAGC |
| DR594-<br>hIL27<br>Ra_VH<br>H24 | 1146 | CAGGTCCAACTGCAAGAGTCTGGAGGCGGTAGCGTCCAGGCCGGGGGTTCCCTG<br>CGGCTGTCCTGTGTCGCCTCTGCGAGCACATACTGTACCTATGATATGCACTGG<br>TATCGCCAAGCGCCGGGGAAGGGACGCGAGTTCGTCAGCGCCATTGATTCAGAC<br>GGAACGACTCGGTACGCGGACTCTGTCAAGGGACGGTTCACCATCTCACAGGGT<br>ACAGCCAAGAATACAGTCTACTTGCAGATGAACTCCTTGCAGCCCGAGGACACA<br>GCCATGTATTACTGTAAAACCGTTTGCGTAGTGGGCTCCAGGTGGAGCGATTAC<br>TGGGGCCAGGGCACTCAGGTCACCGTCAGCTCCGGCGGTTCCGGGGGGAGCGGA<br>GGCAGCGGTCAGGTACAGCTGCAAGAAAGCGGAGGTGGGCTGGTTCAGCCGGGA<br>GGCAGCCTGCGCCTGTCCTGCGCCGCGTCAGGTTTCACGCTCTCTCACTCTGGG<br>ATGAGCTGGGTGCGGCAAGCGCCGGGCAAGGGCCTCGAATGGGTCTCTACCATC<br>AATTCTGGCGGGGCCTCCACCTATTACACCGATAGCGTTAAAGGCAGATTCACT<br>ATCTCACGTGACAATGCCAAGAATATGCTGTACTTGCAGCTCAACAGTCTGAAG<br>ACCGAAGATACTGCTATGTATTACTGTGCCAAGGGGGGGAGCGGATATGGTGAC<br>GCATCCCGTATGACCAGCCCTGGCTCCCAGGGCACCCAGGTGACCGTCTCTAGC |
| DR595-<br>hIL27<br>Ra_VH<br>H1 | 1147 | CAAGTCCAGCTCCAGGAGAGCGGGGGAGGCTCTGTTCAGGCTGGGGGCAGTCTG<br>ACATTGTCCTGCGCTGCCAGCGAGTACGCCTATTCCACCCGTAACATGGGATGG<br>TATCGGCAAGCCCCAGGTAAGGAACGCGAACTCGTCTCAGCTTTCATCAGCGAT<br>GGCAGCACTTATTACGCCGACTCTGTGAAGGGCCGCCTTACCATCACAAGGGAT<br>AATGCAAAGAATACAGTGTATCTGCAAATGAACTCCCTCAAGCCGGAGGACACA<br>GCTATCTATTACTGTTCCGCGAACTGCTACAGGCGTCTGAGGAACTACTGGGGG<br>CAGGGCACTCAGGTTACCGTTAGCTCCGGCGGTGGAAGCCAGGTGCAGCTCCAG<br>GAGTCTGGAGGCGGGCTGGTGCAGCCTGGGGGCAGCCTTCGCCTGTCTTGCGCG<br>GCCAGCGGATTCACCTTCTCTAGCTACCCAATGTCTTGGGTGAGGCAGGCTCCT<br>GGCAAAGGCCTTGAGTGGATCTCCACAATCAGCGCCGGAGGTGATACCACTCTG<br>TACGCAGACAGTGTGAAGGGCCGCTTCACATCTTCCCGCGACAATGCCAAGAAC<br>ACCCTGTACCTCCAGCTGAACTCACTGAAGACCGAGGACGCAGCGATCTACTAT<br>TGTGCTAAACGTATTGACTGCAACAGTGGGTATTGCTACCGCCGTAACTACTGG<br>GGGCAAGGGACGCAGGTCACCGTCTCTTCG |
| DR595-<br>hIL27<br>Ra_VH<br>H1 | 1148 | CAGGTGCAGCTCCAGGAGTCTGGTGGCGGTTCTGTGCAGGCAGGGGGCTCCCTT<br>ACACTGAGCTGCGCCGCGTCAGAGTATGCGTACAGCACCTGCAACATGGGCTGG<br>TATCGCCAAGCCCCAGGTAAGGAGCGTGAGCTGGTGTCCGCGTTCATCTCCGAT<br>GGCTCTACTTATTACGCTGACTCCGTCAAGGGACGCTTCACAATCACACGTGAC<br>AACGCGAAGAACACCGTGTACCTTCAGATGAACTCTCTGAAACCAGAAGACACA<br>GCGATCTACTATTGCTCTGCTAACTGCTACCGCAGGCTGCGCAACTACTGGGGT<br>CAAGGCACCCAGGTCACCGTCAGCTCCGGTGGGAGTGGTGGCAGCGGTGGCTCC<br>GGCCAGGTGCAGCCCCAGGAGTCTGGGGGGGGGCTGGTGCAGCCAGGTGGCTCC<br>CTTAGATTGTCTTGCGCAGCTAGTGGATTTACCTTTTCTTCCTACCCAATGTCC<br>TGGGTTCGCCAAGCTCCCGGCAAGGGGCTGGAATGGATTAGTACCATCTCTGCG<br>GGAGGCGATACTACACTGTATGCCGATTCCGTCAAAGGCCGGTTCACCTCTTCC<br>AGAGACAACGCCAAGAACACCCTGTATTTGCAGCTGAACAGCCTGAAGACCGAG<br>GATGCTGCCATCTACTATTGCGCTAAGCGTATTGATTGCAACAGCGGCTACTGT<br>TATCGGCGCAACTACTGGGGCCAGGGCACCCAGGTTACTGTTAGCAGT |
| DR595-<br>hIL27<br>Ra_VH<br>H2 | 1149 | CAGGTTCAGCTCCAGGAAAGCGGTGGCGGGAGCGTGCAGGCCGGAGGCTCTCTG<br>ACTCTGTCCTGTGCTGCGAGCGAATACGCCTACTCAACTTGCAACATGGGCTGG<br>TATCGCCAGGCACCCGGCARAGAGCGCGAGTTGGTGAGTGCCTTCATCTCCGAT<br>GGCAGCACCTATTACGCAGATTCCGTTAAGGGGCGCTTCACAATCACCCGCGAC<br>AACGCGAAGAACACCGTGTACCTCCAGATGAACTCTCTGAAGCCCGAGGATACC<br>GCCATTTATTACTGTTCTGCTAACTGTTACAGACGCCTTCSTAATTATTGGGGC<br>CAGGGCACCCAGGTAACCGTTAGCTCTGGCGGGGGCAGCCAGGTGCAGTTGCAG<br>GAGTCCGGGGGGGGACTGGTGCAGCCTGGAGGGTCTCTTAGGCTGTCTTGTGCC<br>GCGTCCGGGTTCACCTTTTCCCTCTCCGGCATGTCATGGGTTAGACAGGCACCA<br>GGCAAGGGCCTTGAGTGGGTATCTGCCATCTCATCCGGGGGGGGCTCTACCTAC<br>TATACCGATTCCGTTAAAGGCCGCTTCACCATTTCTAGGGACAATGCAAAGAAT<br>ATCCTGTACCTCCAGTTGAACAGTCTGAAGACCGAGGATACAGCCATGTACTAT<br>TGTGCAAAAGGGGGCTCCGGCTACGGCGACGCCAGCCGCATGACATCTCCAGGG<br>TCTCAAGGCACCCAAGTGACCGTACTAGC |
| DR595-<br>hIL27<br>Ra_VH<br>H2 | 1150 | CAGGTCCAGCTGCAAGAAAGCGGTGGGGGCAGCGTACAGGCTGGGGGATCTCTG<br>ACCCTGAGCTGTGCTGCCTCAGAGTACGCATATTCAACCCGCAATATGGGCTGG<br>TATCGCCAAGCCCCCGGAAAGGAGCGCGAACTCGTGTCCGCTTTCATCAGTGAC<br>GGGTCCACGTACTATGCCGATTCCGTCAAAGGCCGTTTTACTATCACACGCGAC<br>AACGCCAAGAATACCGTCTACCTCCAGATGAACAGCCTGAAGCCAGAAGATACA<br>GCCATCTATTACTGTAGTGCGAACTGCTACAGACGCCTGCGCAACTACTGGGGA<br>CAGGGCACCCAAGTGACTGTGTCCTCTGGAGGCAGCGGCGGATCTGGAGGGAGT<br>GGACAGGTTCAGCTTCAGGAGAGCGGGGGGGGACTGGTGCAGCCAGGAGGCTCC<br>CTGAGGTTGTCATGCGCGGCCAGCGGTTTCACCTTCAGTTTGTCCGGCATGTCA<br>TGGGTACGCCAAGCGCCCGGTAAGGGTCTGGAATGGGTGTCCGCTATTTCTAGC<br>GGAGGCGCGAGTACCTATTACACCGACAGCGTGAAGGGGCGCTTTACTATCTCT |

TABLE 1B-continued

| Name | SEQ ID NO: | Sequence |
|---|---|---|
| | | CGTGATAACGCCAAGAACATTCTCTATCTCCAACTTAATTCTCTGAAGACCGAG GACACCGCGATGTATTACTGCGCCAAGGGCGGTTCTGGTTATGGCGACGCTTCC CGCATGACATCTCCGGGTAGTCAGGGCACACAGGTGACTGTGTCTAGC |
| DR595-hIL27 Ra_VH H3 | 1151 | CAGGTGCAGCTCCAGGAGTCCGGCGGAGGCAGCGTGCAAGCCGGTGGCTCCCTC ACCCTGTCATGCGCGGCCAGCGAGTACGCCTATAGCACCTGTAACATGGGCTGG TACAGGCAAGCGCCGGGTAAGGAGCGTGAACTCGTCTCTGCCTTTATCTCCGAT GGGTCCACCTATTACGCAGACAGCGTGAAGGGCCGGTTTACGATCACCCGCGAC AACGCCAAAAACACAGTCTATCTCCAGATGAACAGTCTGAAACCCGAGGATACG GCAATTTACTATTGTAGCGCTAACTGCTACCGTAGACTCAGAAACTACTGGGGC CAGGGCACACAGGTGACCGTGAGTTCCGGGGGTGGGTCTCAGGTGCAACTCCAA GAGTCCGGCGGGGGCTCCGTCCAGGCTGGGGGTAGCCTGCGCTTGTCTTGTGTG GCATCTGGATACGTATCTTGCGACTATTTCCTCCCCTCCTGGTATCGTCAAGCT CCGGGAAAAGAGGGGGAGTTCGTGTCCATTATCGAGGGGACCGGCTCCACGAGC TATGCTGCCTCTGTGAAGGGAAGATTTACTGCCAGTGAGGACAAGGGTAAGAAT ATCGCTTATCTGCAAATGAATAGTCTGAAGCCGGAAGACACTGCGATGTATTAC TGCAAGGCGAGTTGCGTCAGAGGACGCGCCGTATCCGAATACTGGGGGCAGGGT ACGCAGGTGACGGTCTCATCT |
| DR595-hIL27 Ra_VH H3 | 1152 | CAAGTCCAGCTTCAAGAGAGTGGCGGAGGCTCCGTTCAGGCCGGTGGCTCTCTG ACTTTGTCCTGCGCCGCAAGCGAGTACGCATACTCTACCTGCAATATGGGCTGG TATAGACAAGCGCCTGGCAAGGAGCGCGAGCTGGTATCAGCCTTCATCAGCGAC GGATCTACCTACTATGCGGATTCAGTGAAGGGGGAGGTTCACCATCACACGCGAC AACGCGAAGAATACTGTGTACCTTCAGATGAACAGCCTGAAACCCGAGGACACC GCAATCTATTACTGCTCTGCCAACTGTTACAGGCGGCTGCGCAATTACTGGGGC CAAGGAACGCAAGTGACAGTATCCAGGGGGGGGAGTGGCGGTAGTGGCGGATCT GGCCAGGTGCAGCCCCAGGAGAGCGGCGGAGGCTCCGTACAGGGGGGTGGCAGT TTGCGCCTGTCCTGTGTCGCTAGTGGTTACGTGTCCTGCGACTATTTTTTGCCC TCTTGGTATCGGCAGGCTCCTGGGAAGGAACGTGAGTTCGTAAGCATCATTGAT GGGACCGGCTCCACCTCCTACGCTGCCAGCGTCAAGGGGAGATTTACTGCATCC GAAGATAAAGGCAAAAACATTGCTTACCTCCAGATGAACTCCCTCAAACCAGAG GATACCGCCATGTATTACTGCAAGGCCTCCCGTGTGAGGGGCCGCGCCGTGTCT GAGTACTGGGGTCAGGGCACTCAGGTGACTGTCTCCTCC |
| DR595-hIL27 Ra_VH H4 | 1153 | CAGGTGCAGCTTCAGGAATCCGGCGGAGGCAGCGTCCAAGGGGGAGGCAGCCTG ACCCTGTCTTGCGCTGCCAGTGAGTATGCTTACTCCACTTGTAACATGGGCTGG TATCGTCAAGCGCCAGGGAAGGAGCGTGAGCTGGTCTCTGCCTTCATCTCAGAT GGTTCCACCTATTACGCTGACAGTGTCAAGGGCAGGTTCACCATCACTCGGGAT AATGCCAAGAACACCGTGTACCTCCAGATGAACTCCCTGAAGCCTGAAGACACT GCCATCTATTACTGCTCCGCCAACTGCTACCGTCGCCTGAGAAATTACTGGGGT CAGGGAACCCAGGTCACCGTGTCTTCCGGGGGAGGCTCCCAGGTCCAGCTGCAA GAGTCTGGTGGCGGTTTGGTGCAGCCTGGCGAGTCCCTGCGCCTGTCTTGCACC GCGAGCGGCTTCACCTTCAGCAATTACGCTATGAGCTGGGTCCGTCAGGCTCCT GGGAAGGGCCTGGAGTGGGTAAGTGGAATCAACGTGGCCTACGGTATCACGTCC TATGCTGATAGCGTGAAGGGCAGATTTACCATCTCTCGGGACAACACCAAGAAC ACACTGTACCTCCAACTCAACAGCCTGAAGACCGAAGACACGGCTATCTATTAC TGTGTCAAGCACAGTGGCACCACGATCCCCAGAGGCTTTATTAGTTATACTAAA CGGGGTCAGGGGACCCAGGTGACCGTCAGCTCC |
| DR595-hIL27 Ra_VH H4 | 1154 | CAAGTTCAGCTTCAGGAAAGCGGCGGAGGCAGCGTCCAGGCCGGTGGAAGCTTG ACGCTGAGCTGTGCGGCTAGTGAATACGCATATTCCACCTGCAATATGGGGTGG TACAGGCAGGCCCCCGGCAAGGAACGCGAACTGGTGAGTGCTTTTATCAGCGAC GGCTCCACGTATTACGCAGATTCCGTGAAAGGAAGGTTTACCATTACCCGCGAT AACGCCAAGAACACTGTGTACCTTCAGATGAACTCTCTCAAACCCGAGGACACT GCCATCTACTATTGCTCAGCCAACTGTTACCGCAGGTTGCGTAACTACTGGGGC CAGGGCACCCAGGTCACAGTCAGCTCCGGGGGGAGTGGTGGATCTGGCGGCTCC GGGCAAGTGCAACTTCAGGAATCCGGGGGGGGCCTGGTGCAGCCTGGGGAGTCC CTGCGCCTTAGCTGTACTGCTTCCGGCTTCACCTTTTCCAACTACGCCATGAGT TGGGTGCGCCAGGCTCCTGGCAAGGGCTTGGAGTGGGTGTCTGGGATTAACGTG GCTTACGGGATTACCTCTTATGCCGACTCAGTCAAGGGTCGTTTCACAATCAGT CGCGACAACACCAAAAACACTCTGTATCTGCAACTGAATAGTCTGAAGACCGAG GATACCGCTATCTATTACTGCGTCAAGCACTCCGGTACTACCATCCCCAGGGGC TTTATTAGTTACACGAAACGGGGTCAGGGGACTCAGGTGACAGTGTCCTCC |
| DR595-hIL27 Ra_VH H5 | 1155 | CAGGTGCAGCTGCAAGAATCCGGCGGAGGCTCCGTGCAGGCAGGTGGCAGTCTG ACACTGAGCTGCGCCGCTTCCGAGTATGCCTATTCCACCTGCAACATGGGTTGG TACAGGCAGGCTCCTGGTAAGGAACGCGAATTGGTGTCCGCCTTCATTTCCGAT GGTAGCACCTACTATGCCGACAGTGTAAAGGGGCGGTTCACCATCACTCGGGAC AACGCAAAAAATACCGTGTACCTGCAAATGAACTCCTTGAAGCCAGAGGACACC GCTATCTATTACTGCTCCGCAAACTGCCATCGCAGGCTGAGGAACTATTGGGGC CAGGGCACCCAGGTGACGGTCTCCTCTGGGGGTGGCTCCCAAGTCCAGCTCCAG GAGTCAGGAGGTGGGAGTGTGCAAGCCGGGGGAAGCCTGCGTCTCTCCTGTACC GCCAGCGGCTACGTGAGCTGTGACTATTTCCTCCCCTCATGGTATAGACAGGCC CCTGGGAAGGAGAGAGAATTTGTTAGCGTGATCGACGGCACCGGGTCCACCAGT TACGCTGCCAGCGTCAAAGGGCGCTTTACCGCTTCTCAGGACAAGGGGAAGAAC |

TABLE 1B-continued

| Name | SEQ ID NO: | Sequence |
| --- | --- | --- |
| | | ATTGCCTACCTGCAAATGAACAGCCTGAAACCCGAGGACACTGCAATGTATTAC<br>TGTAAGGCCAGTTGTGTGCGTGGCCGTGCCATTAGCGAATATTGGGGCCAGGGC<br>ACCCAGGTGACCGTGTCTAGT |
| DR595-<br>hIL27<br>Ra_VH<br>H5 | 1156 | CAGGTCCAGCTCCAGGAGAGCGGAGGTGGCAGTGTGCAGGCTGGTGGCTCCCTG<br>ACCCTTAGTTGTGCAGCCAGCGAATATGCTTACTCCACCTGTAACATGGGATGG<br>TATCGTCAGGCTCCGGGCAAGGAGCGGGAGCTTGTGAGCGCATTTATCAGCGAC<br>GGGTCAACCTATTACGCAGATTCCGTGAAAGGGCGCTTCACCATCACCCGTGAC<br>AACGCTAAGAACACCGTCTACCTCCAGATGAACTCACTGAAGCCCGAGGACACT<br>GCTATCTATTACTGTTCTGCCAACTGCTACAGACGCCTCAGGAATTACTGGGGA<br>CAGGGCACGCAGGTCACTGTTAGCTCCGGTGGCAGTGGTGGCAGCGGGGGCAGT<br>GGACAGGTGCAGTTGCAGGAATCCGGTGGCGGGAGTGTTCAGGCAGGCGGATCT<br>CTGCGCCTGAGCTGCACCGCCTCTGGATATGTGAGCTGTGATTACTTCCTGCCT<br>AGCTGGTATCGGCAGGCCCCCGGCAAGGAACGTGAGTTCGTGAGCGTCATCGAC<br>GGCACCGGCTCCACCTCTTACGCAGCCCCTGTGAAGGGCCGCTTCACAGCCAGC<br>CAAGACAAGGGGAAGAATATCCCCTATCTCCAGATGAACAGCCTGAAACCCGAG<br>GATACAGCCATGTATTACTGTAAAGCCAGCTGTGTGCGCGGCAGAGCTATCTCC<br>GAGTACTGGGGCCAGGGCACCCAGGTTACCGTCTCCTCC |
| DR595-<br>hIL27<br>Ra_VH<br>H6 | 1157 | CAGGTCCAACTCCAGGAGAGCGGAGGGGGCTCTGTTCAGGCCGGAGGCTCCCTG<br>ACCCTCTCCTGGGCAGCCAGTGAATATGCTTACTCCACTTGTAACATGGGATGG<br>TATCGTCAAGCCCCTGGTAAAGAACGTGAGCTGGTCTCCGCCTTTATCTCCGAC<br>GGTTCCACTTATTACGCCGATAGTGTCAAGGGCCGCTTTACCATCACGAGGGAC<br>AATGCCAAGAATACCGTCTACCTCCAGATGAACTCTCTGAAGCCTGAGGATACT<br>GCCATCTACTATTGTAGTGCAAACTGCTACCGGAGATTGAGAAATTATTGGGGT<br>CAGGGCACCCAGGTGACAGTGTCCAGCGGTGGGGGGAGTCAAGTGCAGTTGCAG<br>GAGTCTGGTGGGGGACTGGTGCAGCCGGGGGGAAGTCTGCGTTTGTCTTGCGCC<br>GCGAGCGGTTTCAGTTTTAGCAGTTACGCCATGAAATGGGTGCGTCAGGCCCCC<br>GGGAAGGGCCTGGAGTGGGTGAGTACCATCCCCAGCGGTGGCAGCAGTACTAAC<br>TACGCCGACTCTGTGAAAGGCCGCTTCACAATCTCACGTGATAACGCCAAAAAT<br>ACCCTCTACCTTCAGCTCAACTCCCTGAAAATCGAGGACACTGCCATGTACTAT<br>TGTGCTAAGGCCATTGTGCCGACTGGTGCCACTATGGAACGTGGGCAGGGCACT<br>CAGGTGACCGTTTCTTCC |
| DR595-<br>hIL27<br>Ra_VH<br>H6 | 1158 | CAGGTGCAGCTCCAGGAAAGCGGTGGAGGCTCCGTGCAGGCTGGCGGTTCCCTG<br>ACGCTGTCTTGTGCAGCCTCCGAGTACGCCTATAGCACCTGCAACATGGGCTGG<br>TATCGCCAGGCCCCCGGCAAGGAACGTGAACTGGTATCCGCGTTCATCTCTGAT<br>GGCAGTACCTACTATGCGGATTCTGTGAAGGGCCGCTTCACCATCACAAGAGAC<br>AACGCTAAGAACACCGCGTATCTCCAAATGAACTCCCTCAAGCCCGAGGATACA<br>GCAATCTACTATTGCAGCGCTAACCGCTACAGACGCCTGAGGAACTATTGGGGA<br>CAGGGGACCCAGGTGACAGTTTCTAGTGGAGGCAGCGGAGGCAGCGGAGGGTCT<br>GGCCAGGTTCAGTTGCAGGAGAGTGGGGGGGGTTTGGTGCAGCCAGGGGGCTCC<br>CTGAGGCTCAGTTGCGCTGCCTCTGGATTCTCCTTCTCCTCTTATGCCATGAAG<br>TGGGTGCGCCAAGCGCCCGGCAAGGGCCTGGAGTGGGTATCTACCATCAGCTCT<br>GGGGGCTCCAGCACGAATTACGCAGACAGCGTGAAGGGACGCTTTACTATTTCA<br>AGAGATAATGCCAAGAACACTCTGTATCTTCAGCTCAACTCCCTGAAGATCGAG<br>GATACCGCTATGTACTATTGCGCCAAAGCCATCGTCCCCACTGGGGCAACAATG<br>GAACGCGGCCAAGGAACACAGGTCACCGTCAGTTCT |
| DR595-<br>hIL27<br>Ra_VH<br>H7 | 1159 | CAGGTGCAGTTGCAGGAGAGCGGCGGTGGCTCCGTACAGGCAGGGGGCTCACTG<br>ACCCTGAGCTGTGCAGCTAGTGAGTATGCCTATAGCACTTGCAACATGGGGTGG<br>TATCGTCAGGCCCCTGGCAAGGAGCGCGAGCTTGTGAGCGCGTTCATTAGCGAT<br>GGCTCCACCTACTATGCAGACAGCGTTAAGGGCCGCTTTACCATCACCCGCGAT<br>AACGCTAAAAACACCGTTTACCTCCAGATGAACTCCCTGAAGCCTGAGGATACG<br>GCTATCTATTACTGCTCCGCTAATTGTTATCGCAGGCTGCGTAACTACTGGGGT<br>CAAGGCACCCAGGTGACCGTGTCTTCCGGCGGTGGCTCCCAGGTCCAGCTGCAA<br>GAGTCCGGCGGTGGCCTTGTGCAACCTGGAGGCTCCCTGAGACTTTCCTGCGCT<br>GCCTCCGGCTTCACGTTCAGCTCTTATCCCATGAGCTGGGTGAGACAGGCTCCT<br>GGTAAGGGCCTGGAATGGATTTCCACCATCTCTGCGGGGGGTGACACGACACTC<br>TACGCTGATAGTGTTAAGGGACGTTTCACCTCCTCTCGCGATAACGCGAAGAAC<br>ACCCTGTACCTTCAGCTTAATTCCCTGAAAACCGAAGACACCGCTATCTACTAT<br>TGCGCCAAGAGAATTGACTGCAACTCCGGTTACTGTTATCGTCGCAACTACTGG<br>GGCCAGGGCACCCAGGTGACAGTCTCTTCT |
| DR595-<br>hIL27<br>Ra_VH<br>H7 | 1160 | CAGGTCCAGTTGCAGGAGTCTGGCGGGGGCTCAGTGCAAGCCGGGGGCTCCCTG<br>ACTCTGAGCTGCGCTGCCTCTGAGTATGCTTACTCCACGTGCAACATGGGGTGG<br>TATCGCCAGGCCCCCGGAAAGGAACGCGAGCTGGTGTCTGCCTTCATCTCTGAC<br>GGCAGCACATATTACGCTGACTCCGTAAAAGGTAGATTTACCATCACCCGCGAC<br>AATGCGAAAAACACAGTTTATCTCCAGATGAACTCCCTGAAACCGGAGGACACC<br>GCGATCTACTATTGCAGCGCGAATTGTTACCGCCGTCTTCGTAATTACTGGGGG<br>CAGGGAACCCAGGTGACAGTCTCCAGCGGGGGCCCCGGTGGCTCCGGTGGCTCC<br>GGCCAGGTGCAGCTCCAGGAGTCTGGTGGGGGGTTGGTGCAGCCCGGAGGTAGC<br>CTGAGGCTGTCCTGTGCTGCATCTGGTTTTACCTTCAGCAGTTATCCAATGTCT<br>TGGGTACGCCAAGCGCCCGGTAAGGGCTTGGAGTGGATTTCTACAATTAGCGCC<br>GGAGGCGATACTACCCTGTACGCTGACTCTGTGAAGGGTCGTTTCACATCCTCT |

TABLE 1B-continued

| Name | SEQ ID NO: | Sequence |
|---|---|---|
| | | AGGGATAACGCGAAAAATACACTGTACCTTCAGCTCAATAGACTGAAGACCGAG<br>GACACCGCAATCTATTACTGTGCAAAACGCATCGACTGTAATAGCGGATACTGC<br>TACAGGCGTAACTACTGGGGCCAGGGAACCCAGGTGACCGTCAGTAGC |
| DR595-<br>hIL27<br>Ra_VH<br>H8 | 1161 | CAGGTACAGTTGCAGGAAAGTGGGGGCGGGGTGTGTGCAGGCTGGGGGTCCTTG<br>ACCCTGTCATGTGCCGCTTCTGAGTACGCCTACTCCACCTGTAACATGGGCTGG<br>TATCGTCAGGCTCCCGGCAAGGAGCGCGAGCTGGTATCCGCCTTCATCTCTGAA<br>GGCAGCACCTATTACGCCGATAGCGTGAAGGGTCGTTTCACTATCACACGGGAC<br>AACGCGAAGAACACAGTGTATTTGCAAATGAACAGCTTGAAGCCCGAAGATACC<br>GCTATCTATTACTGCTCTGCTAACTGTTATCGTCGCCTGCGGAACTACTGGGGG<br>CAGGGGACTCAGGTAACTGTTTCCAGGGGAGGCGGTAGCCAGGTCCAGCTTCAG<br>GAGAGCGGCGGAGGCTCCGTGCAGGTCGGTGGCTCTCTCCGCCTCTCATGTGCT<br>GCCAGCGGATTTACTTTCAGCTCCTACCCCATGTCATGGGTGCGGCAGGCTCCC<br>GGAAAGGGCCTTGAATGGATTAGCACGATTAGCGCCGGTGGCGACACAACCCTG<br>TACGCCGACTCTGTCAAGGGTCGTTTCACGTCCTCAAGAGACAACGCGAAGAAC<br>ACTCTGTACTTGCAGCTCAATTCTCTGAAGACAGAGGACACCGCCATCTATTAC<br>TGTGCAAAGAGGATTGACTGCAACAGGGGCTATTGCTACAGACGTAACTATTGG<br>GGTCAGGGCACTCAGGTGACTGTGTCCAGT |
| DR595-<br>hIL27<br>Ra_VH<br>H8 | 1162 | CAGGTGCAGCTGCAAGAGTCTGGGGGCGGGTCCGTGCAGGCCGGAGGTAGTCTG<br>ACTCCTTCCTGCGCTGCGTCTGAGTACGCCTACTCCACCCGTAACATGGGATGG<br>TACAGACAGGCCCCTGGCAAAGAGAGAGAACTGGTGTCCGCTTTTATCAGCGAC<br>GGCAGCACTTACTATGCTGACAGTGTGAAGGGCAGGTTCACCATCACCCGTGAT<br>AACGCCAAGAACACTGTCTACCTTCAGATGAACTCTTTGAAACCAGAGGACACA<br>GCTATCTACTATTGCAGCGCTAACTGCTACAGACGCCTCAGGAACTATTGGGGG<br>CAGGGCACCCAGGTGACCGTTTCTAGTGGAGGTAGCGGAGGCAGCGGTGGAAGC<br>GGCCAGGTGCAGCTCCAGGAGTCCGGTGGCGGGTCCGTCCAGGTCGGGGGGTCT<br>CTCCGCCTGTCCTGCGCTGCCAGCGGGTTCACCTTCTCCAGCTACCCCATGAGC<br>TGGGTCAGGCAGGCCCCTGGCAAGGGCCTCGAATGGATCAGCACTATTTCCGCC<br>GGTGGCGACACAACCCTCTACGCCGACAGCGTCAAGGGACGGTTCACCAGCAGT<br>CGTGACAACGCTAAAAATACCCTGTACCTCCAGCTTAATAGCCTGAAGACCGAA<br>GATACAGCAATCTATTACTGCGCCAAGAGGATCGACTGCAACTCAGGGTACTGT<br>TACCGTCGCAACTACTGGGGACAGGGAACTCAAGTGACTGTGTCTTCC |
| DR595-<br>hIL27<br>Ra_VH<br>H9 | 1163 | CAGGTCCAGTTGCAGGAGTCCGGCGGTGGAAGTGTGCAGGCTGGTGGCAGCCTG<br>ACCTTGTCTTGTGCCGCTAGTGAGTACGCTTATTCAACCTGCAACATGGGCTGG<br>TACAGACAGGCTCCGGGAAAGGAGCGCGAGCTGGTGTCTGCCTTCATCTCCGAT<br>GGTTCAACATACTATGCTGACTCCGTGAAGGGGCGCTTCACCATCACGCGCGAT<br>AATGCAAAGAATACCGTGTACCTTCAAATGAATAGTCTGAAACCCGAGGATACC<br>GCTATCTATTACTGCTCCGCCAACTGCTATCGTCGCCTGCGTAATTACTGGGGC<br>CAGGGCACCCAGGTCACTGTTAGTTCAGGAGGCGGAAGCCAGGTCCAGTTGCAG<br>GAGTCCGGGGGTGGCTCCGTCCAGAGCGGGGGTAGCCTGAGATTGAGTTGCGCG<br>GCCTCAGGCTTCACCTACAGCACCAGCAATAGCTGGATGGCCTGGTTCCGTCAG<br>GCTCCGGGCAAAGAGAGGGAGGGCGTGGCGGCCATCTACACTGTGGGGGGTAGC<br>ATCTTCTACGCGGACAGCGTTCGGGGTCGCTTCACTATCAGCCAAGACGCTACC<br>AAGAATATGTTCTACCTCCAGATGAACACTCTGAAGCCCGAGGACACCGCCATG<br>TACTATTGCGCTGCCGCTTCTGGCCGCCTGCGCGGTAAGTGGTTTTGGCCCTAT<br>GAGTACAACTATTGGGGTCAAGGAACCCAGGTGACCGTGTCTTCC |
| DR595-<br>hIL27<br>Ra_VH<br>H9 | 1164 | CAGGTCCAGTTGCAGGAGAGCGGTGGCGGATCTGTCCAAGCCGGAGGTAGTCTC<br>ACGCTCAGCTGTGCCGCGAGCGAATACGCCTACTCCACCTGTAATATGGGGTGG<br>TATCGTCAGGCACCAGGCAAAGAGCGCGAACTGGTGTCCGCGTTCATCTCCGAC<br>GGCTCAACGTATTACGCCGATAGCGTAAAGGGCCGGTTTACAATCACCCGCGAC<br>AACGCCAAGAATACCGTCTACCTTCAGATGAACCCCCTGAAGCCAGAGGACACT<br>GCAATTTACTATTGCAGCGCTAACTGTTACCGCCGTCTGCGCAACTACTGGGGA<br>CAAGGAACCCAAGTTACCGTGAGTTCTGGTGGCTCTGGTGGCAGCGGAGGCAGC<br>GGACAAGTTCAGCTTCAGGAGTCTGGAGGTGGCTCAGTACAGTCTGGTGGCTCC<br>CTCCGCCTCAGCTGTGCAGCTTCAGGTTTCACCTACTCCACGTCCAACAGTTGG<br>ATGGCCTGGTTTCGGCAAGCTCCGGGAAAAGAGCGTGAGGGAGTGGCTGCGATC<br>TATACAGTCGGGGGATCTATCTTCTACGCGGACTCCGTCAGAGGCAGGTTCACC<br>ATTTCTCAGGATGCTACTAAAAATATGTTCTATCTTCAGATGAACACGCTGAAG<br>CCAGAGGACACAGCCATGTACTATTGCGCCGCAGCCTCAGGCAGGCTGCGCGGT<br>AAATGGTTTTGGCCTTACGAGTACAACTATTGGGGTCAGGGCACCCAGGTGACC<br>GTGAGTTCT |
| DR595-<br>hIL27<br>Ra_VH<br>H10 | 1165 | CAGGTGCAGTTGCAGGAGTCCGGGGGGGGCTCCGTGCAGGGGGGCGGTAGCCTG<br>ACTCTGTCATGTGCCGCGTCCGAGTACGCTTACTCTACCTGCAACATGGGCTGG<br>TATCGCCAGGCTCCTGGAAAAGAACGCGAACTGGTGAGTGCCTTTATCTCTGAC<br>GGTTCCACTTATTACGCCGATTCCGTGAAGGGGCGCTTTACAATCACTCGCGAT<br>AATGCCAAGAACACAGTGTACCTCCAGATGAACAGCCTGAAACCAGAGGACACC<br>GCTATTTACTATTGCAGCGCGAACTGCTACAGACGCCTCAGGAACTATTGGGGA<br>CAGGGCACCCAGGTGACAGTTTCCAGTGGAGGTGGCTCCCAGGTCCAGTTGCAG<br>GAAAGTGGGGGAGGGTCCGTCCAAGCTGGCGGTTCTCTGCGGCTCTCATGCAGG<br>GCCTCCGGTTCCACTTATAGTAACTATTGCTTGGGCTGGTTCAGGCAGATCACC<br>GGCAAGGAGCGCGAGGGAGTGGCTGTCATCAACTGGGTGGGCGGTATGCTTTAT<br>TTCGCCGACTCCGTGAAGGGCCGTTTTACAGTGTCACAAGACCAGGCCAAAAAT<br>ACTCTGTACCTGCAAATGAACAGTTTGAAGCCTGAGGATACCGCGATGTACTAT |

TABLE 1B-continued

| Name | SEQ ID NO: | Sequence |
|---|---|---|
| | | TGTGCCGCTGAGTCCGTAAGTAGCTTTAGCTGCGGCGGTTGGTTGACCAGACCT GACCGCGTGCCATATTGGGGTCAGGGCACACAGGTGACAGTGAGCAGC |
| DR595-hIL27 Ra_VH H10 | 1166 | CAAGTGCAGTTGCAGGAAAGCGGAGGGGGGTCTGTTCAGGCCGGAGGCAGCCTT ACGCTGTCCTGCGCTGCCTCAGAATACGCATACAGTACCTGTAACATGGGCTGG TATCGCCAGGCCCCTGGGAAGGAGAGAGAGCTGGTGAGTGCCTTCATTTCTGAC GGCTCTACCTACTATGCTGATAGCGTGAAGGGTAGGTTTACAATCACCCGCGAC AACGCCAAAAATACCGCTTACCTTCAGATGAACAGCCTGAAGCCGGAAGACACC GCCATCTATTACTGCTCTGCCAACTGCTATCGCCGTCTGCGCAATTACTGGGGC CAGGGCACCCAGGTCACCGTGTCCAGCGGGGGTTCTGGTGGGTCTGGAGGGTCC GGGCAGGTGCAGCTGCAAGAGTCTGGAGGTGGCCCCGTCCAGGCCGGGGGCAGT CTGCGCTTGTCATGTCGGGCCTCTGGTTCCACTTACTCCAACTACTGCTTGGGA TGGTTCCGGCAGATTACAGGCAAGGAACGCGAGGGAGTCGCAGTCATCAACTGG GTGGGCGGAATGCTTTACTTTGCCGATTCCGTCAAGGGCAGGTTCACTGTGAGC CAGGATCAGGCTAAGAACACACTGTACCTTCAGATGAATAGCCTGAAGCCCGAG GACACTGCTATGTATTACTGTGCTGCCGAAAGCGTGTCCTCATTCTCCTGCGGA GGCTGGCTGACCCGCCCTGATCGGGTGCCGTACTGGGGTCAAGGCACTCAAGTG ACTGTCTCATCT |
| DR595-hIL27 Ra_VH H11 | 1167 | CAAGTACAGTTGCAGGAGAGCGGTGGCGGTTCAGTGCAGGCCGGGGGAAGTCTG ACCCTGAGTTGCGCGGCCAGCGAGTATGCCTACAGTACCTGTAACATGGGCTGG TATCGCCAAGCACCTGGCAAGGAACGTGAGCTGGTTTCAGCCTTCATCTCCGAC GGCTCCACCTATTACGCTGACAGCGTGAAGGGTAGGTTCACTATTACTCGGGAC AACGCGAAGAATACCGTATACCTGCAGATGAACTCACTGAAGCCTGAGGACACC GCCATCTATTACTGCTCCGCCAACTGCTACCGTCGCCTTCGTAATTATTGGGGG CAGGGAACCCAGGTCACTGTCAGCTCTGGAGGCGGTTCACAAGTACAGTTGCAG GAGTCTGGTGGGGGTAGCGTCCAGGCCGGGGGAAGCCTTCGCCTTTCTTGCCGC GCCAGCGGCTCCACCTACTCAAATTACTGCCTCGGATGGTTTCGCCAGTCTACC GGAAAGGAACGCGAGGGTGTCGCAGTGATAAATTGGGTCGGCGGTATGCTGTAC TTCGCGGATTCTGTGAAGGGCAGGTTCACAGTTTCCCAGGATCACGCCAAGAAC ACCGTGACCCCCCAGATGAACCCCCTGAAGCCGGAAGATACCGCAATGTATTAC TGTGCCGCTGAGTCTGTGTCATCTTTTTCTCGCGGTGGATGGTTGACTCGCCCC GGTCGCGTGCCTTATTGGGGCCAAGGCACACAAGTGACAGTGTCTAGC |
| DR595-hIL27 Ra_VH H11 | 1168 | CAGGTGCAGTTGCAGGAAAGCGGTGGAGGGTCCGTGCAGGCCGGGGGCTCTCTG ACACTGTCTTGTGCCGCTAGTGAGTACGCATACAGCACATGCAACATGGGCTGG TATCGTCAAGCTCCGGGTAAGGAGCGTGAGCTTGTCTCCGCATTCATCAGTGAC GGCTCAACCTATTACGCGGACAGCGTGAAGGGAAGATTTACCATCACCCGCGAT AACGCCAAGAACACTGTCTACCTCCAGATGAACAGCCTGAAACCCGAGGATACT GCTATTTACTATTGCAGTGCAAACTGTTACCGTCGCCTTCGCAACTATTGGGGC CAGGGCACACAAGTGACTGTGAGTTCAGGTGGCTCCGGTGGCTCAGGTGGCTCC GGTCAGGTCCAGCTCCAGGAGTCCGGCGGAGGCTCCGTGCAGGCAGGGGGCTCT CTGAGGCTGTCCTGTAGGGCATCCGGTTCCACCTATAGTAACTACTGCCTGGGC TGGTTCCGCCAGAGCACCGGAAAGGAACGCGAGGGCGTGGCCGTCATCAACTGG GTCGGGGGCATGTTGTACTTCGCGGACTCTGTGAAGGGCCGCTTCACCGTGTCC CAAGATCACGCCAAAAACACTGTGACTCTCCAGATGAATAGCCTCAAGCCCGAA GATACGGCGATGTACTATTGCGCAGCCGAGTCCGTGAGTTCCTTCTCATGCGGT GGCTGGCTGACCCGCCCCGGTCGCGTGCCTTACTGGGGCCAGGGTACTCAGGTG ACCGTCTCCTCC |
| DR595-hIL27 Ra_VH H12 | 1169 | CAGGTGCAGTTGCAGGAGTCCGGCGGTGGGAGCGTACAGGCTGGCGGTTCTCTG ACACTTTCCTGCGCAGCCAGCGAGTACGCCTACTCCACCCGCAACATGGGGTGG TATCGCCAAGCGCCTGGAAAGGAGCGCGAGCTGGTTAGCGCCTTCATCAGTGAT GGCTCCACATATTACGCGGACAGCGTGAAGGGACGCTTCACCATCACCCGTGAC AACGCGAAAAACACAGTCTACTTGCAGATGAACTCCCTCAAGCCTGAGGATACA GCCATCTACTATTGCTCCGCCAACTGCTATAGGAGATTGCGCAACTACTGGGGG CAAGGAACGCAGGTCACCGTCTCCTCTGGGGGAGGCAGCCAAGTGCAACTCCAG GAGAGCGGGGGTGGCAGCGTGCAGGCGGGTGAGTCTCTCAGACTGTCTTGCCGC GCGTCTGGCTCTACATATTCTAACTATTGCCTGGGTTGGTTCCGGCAGATTACT GGCAAGGAGCGCGAGGGTGTTGCTGTGATTAACTGGGTGGGGGGTATGCTGTAC TTCGCCGATTCCGTCAAGGGACGTTTCACCGTTAGCCAGGACCAGGCCAAAAAC ACCGTCTACCTGGAGATGAATAGCTTGAAGCCCGAAGATACCGCGATGTATTAC TGCGCCACCGAGAGTGTCTCATCTTTTTCCTGTGGGGGTTGGCTTACTCGCCCA GACAGGGTGCCATACTGGGGACAGGGCACTCAGGTGACTGTAAGCAGC |
| DR595-hIL27 Ra_VH H12 | 1170 | CAGGTTCAGTTGCAGGAGAGTGGCGGAGGCAGCGTTCAGGCCGGAGGCTCTCTG ACCCTGTCATGCGCGGCCAGCGAGTACGCCTACAGCACCTGCAACATGGGATGG TATCGCCAGGCACCCGGTAAGGAGAGAGAACTGGTGTCCGCCTTCATCTCTGAC GGCTCCACTTACTATGCTGATAGCGTGAAGGGTCGCTTTACCATCACGCGCGAT AACGCAAAAAATACCGTGTATTTGCAGATGAACTCTCTCAAGCCCGAGGATACC GCCATTTATTACTGTAGCGCTAACTGTTACCGTCGCCTGCGCAACTATTGGGGC CAGGGCACCCAGGTTACTGTCAGCTCCGGTGGCTCCGGCGGTTCTGGGGGCTCC GGCCAGGTGCAGCCCCAGGAGTCTGGTGGAGGCTCCGTGCAGGCAGGTGAGTCC TTGCGTCTGTCCTGCCGGGCCAGCGGTTCAACATATTCTAACTACTGCCTGGGG TGGTTCCGCCAGATTACCGGCAAAGAGCGCGAGGGTGTCGCAGTCATCAACTGG GTCGGAGGTATGCTGTACTTCGCCGATTCTGTGAAGGGACGTTTCACCGTGTCC CAGGACCAGGCCAAGAACACAGTATATCTGGAGATGAACTCCCTGAAGCCTGAA |

TABLE 1B-continued

| Name | SEQ ID NO: | Sequence |
|---|---|---|
| | | GATACAGCCATGTATTACTGCGCCACGGAGTCCGTCAGCTCCTTCTCCTGTGGC<br>GGATGGTTGACCAGGCCCGACAGGGTGCCTTATTGGGGTCAGGGCACCCAAGTC<br>ACCGTGAGCAGC |
| DR595-<br>hIL27<br>Ra_VH<br>H13 | 1171 | CAGGTGCAGCTCCAGGAGTCCGGCGGTGGCTCTGTGCAGGCGGGGGGTAGCCTT<br>ACTCTCAGCTGTGCTGCGTCTGAATACGCTTATTCTACCTGTAATATGGGCTGG<br>TATCGGCAGGCCCCTGGCAAGGAGAGAGAACTCGTGAGCGCCTTCATCTCCGAC<br>GGCTCTACCTACTATGCCGACAGTGTGAAGGGCCGCTTCACTATTACTCGCGAT<br>AACGCCAAGAACACGGTGTACCTCCAGATGAACTCTCTGAAGCCGGAGGACACG<br>GCCATTTATTACTGCTCCGCTAACTGCTACAGACGGCTGCGTAACTACTGGGGC<br>CAGGGCACCCAGGTAACCGTCAGCTCCGGCGGAGGTTCTCAGGTTCAGCTCCAA<br>GAGTCTGGGGGGGGGAGCGTCCAGGCCGGAGGGTCCCTCAGGTTGTCCTGCGTG<br>GCCAGCGGATATGTGTCTTGTGACTACTTCCTGCCCAGCTGGTATCGCCAGGCT<br>CCAGGGAAGGAACGTGAGTTTGTTTCCATCATTGATGGTACAGGCAGCACATCC<br>TACGCCGCATCTGTGAAGGGCCGGTTCACTGCCAGCCAGGACCGTGGCAAAAAC<br>ATCGCTTACTTGCAGATGAACTCCCTGAAGCCCGAGGATACCGCAATGTACTAT<br>TGCAAGGCGAGCTGTGTGCGTGGCAGAACCATTAGCGAATACTGGGGACAGGGC<br>ACGCAGGTGACCGTCTCCTCC |
| DR595-<br>hIL27<br>Ra_VH<br>H13 | 1172 | CAGGTCCAACTCCAGGAGTCTGGCGGAGGTTCCGTTCAGGCCGGTGGGTCCCTT<br>ACCCTGAGTTGCGCCGCTTCAGAATACGCCTACTCAACCTGTAACATGGGCTGG<br>TATCGCCAAGCTCCTGGTAAGGAAAGAGAGTTGGTGTCCGCTTTCATCTCTGAA<br>GGTTCTACCTATTACGCGGACTCTGTGAAGGGCAGATTTACCATCACAAGAGAC<br>AACGCCAAGAATACCGTGTACCTCCAGATGAACTCTCTGAAGCCTGAGGATACT<br>GCCATCTATTACTGTTCAGCAAACTGCTACCGTCGCCTGCGCAATTACTGGGGG<br>CAGGGCACCCAGGTGACAGTATCCAGCGGTGGCAGTGGAGGCTCCGGTGGCTCA<br>GGCCAAGTGCAGCCCCAGGAGTCCGGGGGGGGTTCAGTGCAGGCCGGGGGCTCC<br>CTGCGGCTGTCCTGTGTCGCGTCTGGATACGTGAGTTGCGACTACTTTCTCCCC<br>TCCTGGTATCGCCAGGCTCCAGGAAAGGAGCGCGAGTTTGTCAGCATCATTGAT<br>GGCACCGGGAGTACCAGTTATGCGGCTTCTGTTAAGGGCCGTTTCACCGCTTCT<br>CAGGATCGCGGAAAGAACATCGCCTATTTGCAGATGAACTCTCTGAAGCCGGAA<br>GACACAGCCATGTATTACTGCAAAGCCAGTTGTGTCAGGGGACGGACCATCTCA<br>GAGTATTGGGGACAGGGTACGCAGGTCACTGTGAGTTCC |
| DR595-<br>hIL27<br>Ra_VH<br>H14 | 1173 | CAGGTGCAGCTTCAGGAGTCTGGAGGCGGATCTGTCCAGGCCGGGGGCAGTCTG<br>ACCCTGTCCTGCGCCGCTTCTGAGTATGCCTATAGTACTTGCAACATGGGTTGG<br>TATCGGCAGGCTCCGGGCAAGGAGCGCGAACTGGTTTCAGCGTTCATCTCTGAC<br>GGTAGCACCTACTATGCCGACAGCGTGAAGGGCCGCTTTACTATCACCAGGGAT<br>AACGCAAAGAACACCGTTTACCTCCAGATGAATAGCCTCAAGCCTGAGGATACC<br>GCTATCTATTACTGCTCAGCTAACTGTTATCGTCGGCTGCGTAACTACTGGGGC<br>CAGGGAACTCAAGTTACCGTCAGCAGTGGGGGAGGCAGTCAGGTGCAGTTGCAG<br>GAAAGCGGCGGGGGCAGCGTCCAGGCTGGTGGAAGCCTTCGTCTCTCTTGTGTC<br>GCCAGTGGCTATGTCTCCTGTGATTATTTTCTGCCGTCCTGGTATCGTCAAGCG<br>CCTGGCAAGGAAAGGGAGTTCGTATCCATTATCGACGGAACTGGTAGTACCAGC<br>TACGCTGCCTCCGTGAAGGGAAGGTTCACAGCCTCCCAGGATAAGGGTAAGAAC<br>ATTGCCTACCTCCAGATGAACTCCCTGAAGCCTGAAGATACGGCCATGTACTAT<br>TGCAAAGCCTCTTGTGTCAGGGGCAGAGCCATCAGCGAATACTGGGGCCAAGGC<br>ACTCAGGTCACCGTGAGCAGC |
| DR595-<br>hIL27<br>Ra_VH<br>H14 | 1174 | CAGGTTCAGCTCCAGGAGTCTGGGGGGGGTTCTGTCCAGGCCGGAGGCAGCCTT<br>ACACTGTCTTGCGCTGCCAGCGAGTATGCTTACTCTACCTGCAACATGGGTTGG<br>TATCGGCAAGCGCCGGGCAAGGAAGGGGAACTCGTCTCTGCTTTCATCTCCGAT<br>GGCAGCACATATTACGCTGATAGCGTAAAGGGCCGGTTCACCATCACAAGAGAC<br>AACGCAAAGAACACAGCTTACCTCCAGATGAACTCCCTCAAACCTGAGGATACC<br>GCCATCTATTACTGCTCCGCTAACTGCCACCGCCGTCTGCGCAACTACTGGGGT<br>CAAGGCACCCAGGTTACCGTGTCTAGCGGGGGCTCTGGTGGCAGTGGTGGGTCA<br>GGGCAGGTCCAGCTCCAGGAGAGCGGGGGAGGTAGCGTACAGGCCGGGGGTTCA<br>CTGAGACTGTCTTGTGTGGCCCCTGGATACGTCTCTTGCGATTACTTCCTTCCC<br>AGTTGGTATAGGCAAGCGCCCGGTAAGGAGAGAGAGTTCGTTAGCATCATTGAT<br>GGCACAGGTTCAACAAGTTATGCGGCTTCCGTAAAGGGACGCTTTACTGCGTCT<br>CAGGACAAGGGCAAAAACATCGCCTATCTTCAAATGAACAGTCTGAAGCCTGAA<br>GATACCGCTATGTATTACTGCAAAGCCTCCTGCGTGCGCGGTCGCGCTATCAGC<br>GAATACTGGGGCCAGGGTACGCAAGTGACTGTCAGTTCT |
| DR595-<br>hIL27<br>Ra_VH<br>H15 | 1175 | CAGGTTCAACTCCAGGAATCAGGAGGGGGTTCAGTGCAGGCTGGGGGTAGCCTG<br>ACCCTCAGCTGCGCTGCGAGTGAGTATGCTTATTCCACCTGCAACATGGGGTGG<br>TATCGCCAAGCGCCTGGCAAGGAGAGAGAGCTGGTCAGTGCATTTATTTCCGAT<br>GGCTCCACCTACTATGCTGACTCAGTGAAGGGGCGCTTCACCATCACTCGCGAC<br>AACGCCAAGAATACTGTCTATCTCCAGATGAACAGCCTCAAACCAGAGGATACA<br>GCCATCTACTATTGCAGTGCGAATTGTTATCGTAGGCTGCGCAACTACTGGGGC<br>CAAGGCACACAGGTGACCGTGTCTAGTGGAGGTGGCTCTCAGGTCCAGCTCCAG<br>GAATCTGGTGGAGGCTCCGTCCAGGCTGGCGGTTCCCTTCGTCTGTCCTGCGTG<br>GCCAGCGGCTACGTGAGCTGTGATTATTTCCTCCCTAGCTGGTATCGGCAGGCT<br>CCCGGCAAGGAACGCGAGTTCGTTTCTATCATTGATGGAACGGGTTCTACTAGC<br>TACGCGGCCTCCGTGAAGGGGCGCTTCACAGCAAGCCAGGACAAAGGGAAGAAC |

TABLE 1B-continued

| Name | SEQ ID NO: | Sequence |
|---|---|---|
| | | ATCGCTTACCTGCAAATGAATACCTTGAAGCCTGAGGACACCGCAATGTATTAC TGCAAGGCTTCCTGCGTGAGGGGCCGCGCCATCTCCGAATACTGGGGGCAGGGT ACTCAGGTGACCGTTAGCAGT |
| DR595- hIL27 Ra_VH H15 | 1176 | CAGGTCCAGCTCCAGGAGTCCGGGGGGGGATCAGTCCAGGCTGGGGGGAGTCTG ACACTGTCCTGTGCTGCCTCTGAGTATGCTTACAGCACCTGTAACATGGCTGG TACAGACAAGCCCCTGGGAAGGAGCGCGAACTCGTGTCCGCGTTTATTAGTGAC GGTTCCACCTACTATGCTGACTCCGTGAAGGGTCGCTTCACGATCACCCGCGAC AACGCCAAAAATACCGTGTACTTGCAGATGAACTCCCTGAAGCCGGAGGACACA GCCATCTATTACTGTAGCGCAAATTGCTACCGTCGCCTGCGTAACTATTGGGGT CAGGGCACTCAGGTCACAGTCAGTAGCGGCGGTAGCGGTGGCTCCGGCGGTAGT GGACAGGTGCAGTTGCAGGAATCCGGCGGTGGAAGTGTTCAAGCAGGGGGCTCT CTGCGCCTGTCATGTGTTGCATCAGGCTATGTCTCTTGCGACTACTTCCTGCCA TCTTGGTATCGTCAGGCCCCAGGGAAGGAAAGGGAGTTCGTCTCCATCATTGAT GGCACCGGCTCAACCTCTTACGCTGCCAGCGTAAAGGGGCGCTTCACCGCCTCC CAGGATAAGGGCAAGAACATCGCTTACCTCCAGATGAACACACTCAAGCCTGAG GATACCGCGATGTATTACTGTAAGGCGAGTTGCGTTCGTGGCCGTGCGATCAGC GAGTATTGGGGGCAGGGAACCCAGGTAACAGTCAGCTCC |
| DR595- hIL27 Ra_VH H16 | 1177 | CAAGTGCAGCTCCAGGAGTCCGGGGGCGGTAGCGTGCAGGCCGGTGGCTCCCTC ACTCTGTCCTGCGCTGCCAGCGAGTATGCGTACTCCACCTGCAACATGGGATGG TACAGGCAAGCGCCTGGCAAGGAAAGAGAGCTTGTGAGCGCCTTCATCTCCGAT GGTTCTACCTACTATGCTGACTCCGTTAAGGGCCGGTTCACCATTACTCGCGAT AACGCCAAGAACACCGTGTATCTCCAGATGAACTCCCTCAAGCCAGAGGACACA GCTATCTACTATTGCTCAGCTAACTGTTACCGTCGCCTCCGCAACTATTGGGGC CAGGGCACTCAGGTGACTGTCTCTTCCGGGGGTGGCTCCCAAGTGCAGCTCCAG GAGTCAGGAGGGGGGTCTGTCCAGGGGGGTGGCTCCCTGCGCCTCAGCTGCCGT GCGTCTGGCAGCACCTACAGCAACTACTGTTTGGGCTGGCTCAGACAGATTACT GGAAAAGAACGCGAGGGCGTTGCGGTCATCAACTGGGTGGGGGGGATGCTTTAC TTTGCAGACAGTGTGAAGGGTCGCTTTACCGTCAGCCAGGACCAGGCCAAGAAC ACAGTGTATTTGCAGATGAATAGCCTGAAGCCAGAGGACACTGCCATGTATTAC TGCGCGGCTGAGTCAGCCAGCTCTTTCAGTTGCGGTGGCTGGTTGACGCGCCCT GACCGCGTTCCTTACTGGGGGCAGGGGACTCAGGTTACCGTGAGCAGC |
| DR595- hIL27 Ra_VH H16 | 1178 | CAGGTGCAGCTTCAGGAATCAGGGGGTGGAAGCGTGCAGGCAGGAGGCTCTCTG ACTTTGTCATGTGCCGCTAGTGAGTATGCGTATTCTACGTGCAACATGGGCTGG TATCGTCAAGCCCCCGGAAAAGAGCGTGAACTCGTGTCAGCTTTCATTTCCGAC GGTAGCACATATTACGCCGACAGCGTGAAGGGGCGCTTTACTATCACTCGCGAT AATGCCAAGAATACAGTTTACCTCCAGATGAACTCACTGAAGCCCGAAGACACC GCCATCTACTATTGTAGCGCCAACTGTTATAGGAGACTGCGGAACTACTGGGGT CAAGGCACCCAGGTGACCGTGTCCTCTGGAGGCTCCGGCGGTAGC GGACAGGTGCAGTTGCAGGAGTCCGGTGGTGGGTCAGTGCAGGCCGGGGGCTCA CTCAGGCTTTCCTGCCGCGCCAGTGGTTCCACTTATTCCAACTATTGCCTGGGG TGGTTCAGGCAGATCACAGGTAAGGAACGTGAGGGGGTGGGTGTGATTAACTGG GTCGGGGGGATGCTGTATTTTGCCGACAGTGTGAAAGGGAGATTCACCGTCAGC CAGGATCAGGCCAAAAACACCGTGTACCTGCAAATGAACAGTCTGAAGCCAGAG GATACCGCCATGTATTACTGTGCAGCGGAGAGCGCCTCCAGCTTTTCCTGCGGA GGTTGGCTCACTCGGCCTGACCGCGTTCCCTACTGGGGTCAAGGGACCCAGGTG ACAGTCTCCTCC |
| DR595- hIL27 Ra_VH H17 | 1179 | CAGGTCCAACTCCAAGAAAGCGGTGGCGGTTCCGTCCAGGCCGGAGGCTCCCTG ACCCTGTCCTGTGCTGCAAGTGAGTACGCCTATTCCACCCGTAATATGGGCTGG TATAGGCAGGCACCAGGAAAAGAGCGCGAACTGGTGTCCGCGTTCATCTCCGAC GGCTCCACTTACTATGCTGATAGTGTTAAAGGCCGCATCACCATCACCCGTGAT AACGCGAAGAACACTGTGTACTTGCAGATGAACAGCCTGAAGCCCGAGGATACA GCCATCTACTATTGCTCTGCCAACTGCTATAGAAGGCTGCGGAACTACTGGGGT CAGGGAACCCAGGTGACCGTGAGTTCCGGCGGGGGTTCCCAGGTCCAGCTCCAG GAATCTGGCGGGGGTCTGGTGCAGCCTGGAGGTTCACTCAGATTGTCTTGCGCC GCGTCTGGCTTCACATTCTCCCTCTCCGGGATGAGTTGGGTCCGCCAAGCCCCC GGCAAGGGTCTGGAGTGGGTATCCGCCATCAGTTCCGGCGGAGCCTCAACCTAC TATACGGACTCCGTGAAGGGACGTTTTACCATCAGCCGGGACAACGCTAAGAAC ATGCTGTACCTCCAGCTGAACTCTCTGAAGACTGAAGACACCGCCATGTATTAC TGTGCCAAGGGTGGCTCCGGGTACGGGGATGCCAGCCGCATGACCTCTCCTGGT AGCCAGGGCACGCAGGTCACAGTGTCTTCT |
| DR595- hIL27 Ra_VH H17 | 1180 | CAGGTACAGCTTCAGGAATCTGGAGGCGGAAGCGTGCAGGCTGGTGGCTCTCTG ACACTGTCTTGCGCCGCGAGCGAATACGCATACAGTACGTGTAATATGGGCTGG TACAGGCAAGCTCCGGGCAAGGAAAGAGAACTCGTAAGCGCCTTCATCAGCGAT GGCTCCACTTATTACGCAGACAGCGTGAAGGGCCGCTTCACTATCACGAGGGAT AACGCCAAGAACACTGTCTATCTCCAGATGAACTCCCTCAAACCCGAAGACACC GCCATTTATTACTGCTCCGCTAATTGTTACCGCCGTCTGCGCAATTATTGGGGA CAGGGCACCCAGGTAACAGTGTCCTCTGGAGGGAGCGGTGGATCTGGAGGCTCC GGCCAAGTCCAGTTGCAGGAAAGCGGAGGGGGGTTGGTGCAGCCTGGTGGCAGC CTGCGCCTGTCTTGCGCGGCCTCTGGCTTCACATTCTCCCTGTCTGGAATGTCT TGGGTCCGGCAGGCCCCAGGTAAGGGCCTGGAGTGGGTGAGCGCAATTTCCTCT GGCGGGGCATCCACCTATACACCGACTCCGTGAAGGGCAGGTTTCACTATTAGC CGGGATAATGCGAAGAACATGCTGTACCTTCAGCTGAACTCCTTGAAGACTGAG |

TABLE 1B-continued

| Name | SEQ ID NO: | Sequence |
|---|---|---|
| | | GACACCGCTATGTATTACTGTGCCAAGGGCGGTAGCGGCTACGGTGACGCTTCC CGCATGACCTCTCCGGGTTCCCAGGGCACCCAGGTGACCGTGTCTTCC |
| DR595-hIL27 Ra_VH H18 | 1181 | CAGGTCCAGTTGCAGGAATCCGGGGGGGGTTCCGTCCAAGCAGGCGGTTCCCTT ACACTCAGCTGCGCTGCCAGCGAGTACGCCTATTCTACGTGTAACATGGGCTGG TATCGCCAGGCTCCTGGGAAGGAACGCGAGCTGGTGAGCGCATTTATCTCAGAT GGGTCCACATACTATGCTGACTCTGTTAAGGGTCGTTTCACTATCACCAGGGAC AACGCTAAGAACACTGTCTATCTGCAAATGAACTCCCTGAAACCAGAGGACACC GCTATCTATTACTGCTCTGCCAACTGTTATCGTCGGTTGCGCAATTATTGGGGG CAGGGGACACAGGTGACCGTGTCCTCAGGTGGAGGCTCCCAGGTGCAGTTGCAG GAATCTGGGGGAGGCTCCGTGCAGGCTGGCGGTTCACTGAGGCTGAGTTGTGTT GCATCTGGCTATGTAAGTTGTGATTACTTCTTGCCAAGCTGGTATCGTCAGGCC CCAGGGAAGGAACGCGAGTTCGTCTCTATTATCGACGGCACGGGTTCTACCAGC TACGCTGCCAGCGTTAAGGGGCGGTTTACGGCATCCCAGGACAAGGGAAAGAAC ATCGCTTATTTGCAGATGAACTCCCTGAAACCCGAGGATACTGCGATGTATTAC TGCAAGGCCAGCTGTGTAAGGGGGCGCGGCATCAGCGAATATTGGGGCCAGGGA ACTCAGGTGACCGTGTCCTCT |
| DR595-hIL27 Ra_VH H18 | 1182 | CAGGTGCAGCTCCAGGAAAGCGGGGGGGGCTCCGTGCAGGCTGGGGGCAGCTTG ACACTGTCCTGTGCAGCTTCCGAGTACGCCTACTCAACCTGCAACATGGGCTGG TACAGGCAGGCTCCCGGTAAGGAGCGCGAACTGGTGTCCGCCTTCATTTCTGAC GGCTCCACCTATTACGCCGACTCAGTGAAAGGTAGGTTCACCATTACAAGGGAC AACGCCAAGAACACTGTCTACTTGCAGATGAACAGTTTGAAGCCCGAAGACACT GCTATCTACTATTGCAGCGCCAACTGTTACAGGCGTCTGCGCAACTATTGGGGT CAGGGCACCCAAGTGACTGTGTCTTCCGGTGGGTCCGGTGGCTCCGGGGGCTCC GGCCAGGTGCAGCTGCAAGAGTCCGGCGGTGGCTCCGTACAGGCCGGGGGCAGC CTCAGACTGTCTTGCGTAGCCTCCGGCTACGTTTCTTGCGACTACTTTCTTCCT TCTTGGTACAGACAAGCTCCAGGGAAGGAACGGGAGTTCGTGAGCATTATCGAC GGCACCGGGTCAACCTCTTACGCGGCCTCCGTGAAGGGCCGTTTTACCGCCAGC CAAGACAAGGGCAAAAACATCGCGTATCTTCAGATGAACTCCCTTAAACCTGAG GACACCGCGATGTACTATTGCAAGGCTTCTTGCGTTCGCGGGGGGGGATCAGC GAGTATTGGGGCCAGGGCACCCAGGTGACCGTGTCTTCT |
| DR595-hIL27 Ra_VH H19 | 1183 | CAGGTGCAGTTGCAGGAGTCTGGGGGGGGCTCCGTTCAAGCGGGCGGATCTCTC ACCCTGTCATGTGCCGCTTCTGAGTATGCCTATTCCACTTGCAACATGGGGTGG TATCGCCAGGCACCGGGCAAGGAACGCGAACTCGTGTCTGCCTTCATCTCTGAT GGCTCCACCTATTACGCAGATTCCGTCAAGGGCAGATTTACCATTACCAGAGAC AACGCTAAGAACACCGTTTACCTCCAGATGAACTCCCTGAAACCTGAGGATACA GCCATTTATTACTGTTCCGCCAACTGCTATAGACGCCTGCGGAACTATTGGGGA CAAGGCACGCAGGTTACTGTGTCCTCTGGGGGGGGATCTCAGGTGCAGCTTCAG GAGAGCGGTGGCGGGTCTGTCCAGGCTGGAGGGAGCTTGAGACTGTCCTGTCGT GCGTCCGGGTCAACCTATTCCAACTATTGCCTGGGTTGGTTTCGCCAGATCACT GGTAAGGAGCGTGAGGGGGTCGCTGTTATCAACTGGGTGGGTGGGATGCTGTAT TTCGCTGATTCAGTAAAGGGCCGCTTCACCGTCTCCCAGGACCAGGCGAAGAAC ACCGTGTATCTTCAGATGAACAGCCTCAAGCCTGAGGACACCGCAATGTATTAC TGCGCAGCTGAGTCTGTTTCCAGCTTCAGTTGCGGTGGATGGCTTACACGCCCA GATCGCGTGCCATACTGGGGTCAGGGTACGCAAGTTACCGTCTCCTCC |
| DR595-hIL27 Ra_VH H19 | 1184 | CAGGTGCAGCTCCAGGAGTCCGGTGGGGGTTCCGTCCAGGCTGGTGGCTCTCTG ACGTTGAGTTGCGCGGCCAGCGAGTACGCTTACTCAACGTGCAACATGGGGTGG TATCGCCAAGCGCCAGGGAAAGAGCGCGAACTCGTAAGTGCCTTTATTTCCGAT GGAAGCACCTATTACGCAGACAGTGTGAAGGGGCGCTTTACTATTACCCGTGAC AACGCCAAAAACACCGTCTACCTGCAAATGAACTCCCTGAAACCGGAGGACACC GCCATTTATTACTGTTCCGCCAACTGCTATCGCCGTCTGCGCAATTATTGGGGC CAGGGGACCCAGGTGACAGTGAGTTCTGGGTGGAGCGGGGGGAGCGGAGGGAGC GGGCAGGTCCAGCTTCAGGAGAGCGGGGGAGGCAGCGTGCAGGCTGGGGGTAGC CTGCGCTTGTCTTGCAGAGCCCCCGGTTCCACATACAGTAACTATTGCCTGGGA TGGTTCCGCCAGATTACCGGCAAGGAACGGGAAGGAGTCGCGGTCATCAACTGG GTCGGTGGAATGCTGTATTTTGCTGACTCTGTCAAAGGCCGCTTTACAGTGTCC CAGGATCAGGCTAAGAATACTGTCTATCTCCAGATGAACAGCCTGAAGCCTGAA GACACAGCCATGTATTACTGTGCCGCAGAGTCCGTCAGCTCCTTCTCCTGCGGT GGGTGGCTTACCAGGCCTGATCGCGTTCCTTACTGGGGTCAGGGTACACAGGTG ACGGTGTCCAGT |
| DR595-hIL27 Ra_VH H20 | 1185 | CAGGTACAGCCCCAGGAGAGCGGGGGAGGTTCCGTGCAGGCCGGTGGCAGTCTC ACCCTGTCCTGCGCTGCCTCTGAGTATGCGTATTCTACCTGTAATATGGGCTGG TACAGGCAGGCTCCAGGCAAAGAGAGAGAACTCGTGTCTGCTTTCATCTCTGAC GGTAGTACCTATTACGCGGACAGCGTTAAAGGCAGGTTCACCATCACCAGAGAC AACGCCAAAAACACAGTTTACCTCCAGATGAACTCCCTCAAGCCCGAGGACACC GCAATTTACTATTGTTCCGCTAACTGCTATCGCAGACTGCGTAACTATTGGGGT CAGGGTACTCAGGTTACCGTGTCTAGCGGGGGGGGCAGTCAGGTTCAGCTTCAG GAAAGTGGCGGTGGACTTGTGCAGCCCGGAGGGTCTCTTCGCCTTTCATGTGCT GCCAGCGGCTTCACCTTTTCCAGTTACCCAATGTCCTGGGTCAGACAGGCCCCC GGCAAGGGGCTGGAGTGGGTCAGCACCATCTCTTCCGGCGGTGATACAACCTTG TACGCAGACTCTGTTAAGGGCAGGTTCACATCCAGCCGGGACAATGCTAAGAAT |

TABLE 1B-continued

| Name | SEQ ID NO: | Sequence |
|---|---|---|
| | | ACCCTCTATCTGCAACTCAACAGCCTGAAGACCGAGGACACCGCAATGTACTAT<br>TGCGCCAAACGCATTGATTGCAACAGCGGCTACCGTTACAAACGCCCATACTGG<br>GGCCAGGGCACCCAGGTGACAGTCTCCTCC |
| DR595-<br>hIL27<br>Ra_VH<br>H20 | 1186 | CAGGTCCAGTTGCAGGAATCTGGCGGGTGGCTCCGTACAGGGGGGGGGTCCCTC<br>ACGCTGTCTTGTGCCGCATCCGAATATGCTTATTCCACCTGCAACATGGGCTGG<br>TATCGCCAGGCCCCTGGAAAGGAACGCGAACTTGTGAGCGCCTTTATTAGCGAT<br>GGTTCTACTTATTACGCTGATAGCGTGAAAGGAAGATTTACTATCACACGCGAA<br>AATGCTAAAAATACTGTGTACTTGCAGATGAACTCTTTGAAGCCTGAGGATACG<br>GCCATCTATTACTGCTCTGCAAATTGCTACCGCCGTCTGCGTAATTACTGGGGC<br>CAGGGCACTCAGGTCACAGTGTCAAGGGGCGGGTCAGGAGGCTCCGGCGGAAGC<br>GGCCAGGTCCAGCTCCAGGAGTCTGGAGGTGGCTTGGTGCAGCCTGGTGGCTCT<br>CTTCGTCTGTCTTGCGCTGCCTCCGGTTTCACCTTTAGTTCTTACCCTATGTCC<br>TGGGTGCGTCAGGCCCCCGGAAAAGGGCTGGAATGGGTGTCCACCATTTCCTCT<br>GGCGGTGACACTACACTGTATGCAGACAGTGTGAAGGGGAGATTCACCTCTTCC<br>CGTGACAACGCCAAGAACACCCTGTATCTCCAGCTCAATAGCCTGAAGACTGAG<br>GATACCGCAATGTACTATTGCGCCAAACGGATCGACTGTAACAGTGGATATTGT<br>TACAAGCGTTCCTATTGGGGCCAGGGGACCCAGGTGACTGTGAGTTCT |
| DR595-<br>hIL27<br>Ra_VH<br>H21 | 1187 | CAGGTGCAGCTTCAGGAGTCCGGTGGCGGTTCCGTACAGGCAGGAGGGTCCTTG<br>ACCCTGAGTTGTGCGGCTTCCGAATACGCCCATAGTACATGCAACATGGGTTGG<br>TATCGCCAGGCCCCCGGTAAGGAACGCGAGTTGGTAAGCGCCTTCATCTCCGAT<br>GGAAGTACCTACTATGCCGATTCAGTCAAGGGTCGCTTTACGATCACACGTGAC<br>AACGCTAAGAACACAGTCTATCTCCAGATGAATAGTCTGAAGCCCGAAGATACA<br>GCAATCTATTACTGTTCAGCCAACTGTTATCGGCGTTTGCGTAACTACTGGGGA<br>CAGGGCACCCAAGTCACCGTCTCCAGTGGTGGCGGTTCCCAGGTCCAGCTTCAG<br>GAATCCGGCGGTGGCTTGGTTCAGCCTGGGGGCTCCCTGCGCCTGAGCTGCGCT<br>GCCTCTGGATTTACCTTCTCATTGTCCAGCATGTCATGGGTCCGTCAGGCCCCC<br>GGCAAGGGCCTGGAGTGGGTCAGTGCCATCTCTTCCGGTGGGGCCTCAACGTAC<br>TATACCGATAGCGTGAAGGGACGCTTTACCATCAGCCGGGACAACGCAAAAAAT<br>ATGCTGTATCTCCAGTTGAACAGCCTGAAGACGGAGGACACTGCAATGTACTAT<br>TGCGCAAAGGGAGGGTCCGGGTACGGTGACGCCTCCAGGATGACCTCTCCTGGC<br>TCCCAGGGGACCCAGGTGACTGTCTCCAGC |
| DR595-<br>hIL27<br>Ra_VH<br>H21 | 1188 | CAGGTACAGCTTCAGGAGTCAGGCGGGGGGTAGCGTCCAGGGGGGGGTTCTTTG<br>ACACTCTCCTGCGCCGCGAGCGAGTACGCATACTCTACATGCAACATGGGCTGG<br>TACAGGCAGGCCCCAGGCAAGGAAAGGGAGCTGGTGTCCGCCTTCATTAGCGAC<br>GGAAGCACCTACTATGCTGATTCCGTGAAGGGCCGGTTCACCATCACACGCGAT<br>AACGCTAAGAACACGGTGTACTTGCAGATGAACTCTCTGAAGCCCGAAGACACC<br>GCCATCTATTACTGCTCCGCTAACTGCTATCGCAGACTGCGCAATTATTGGGGG<br>CAGGGCACCCAGGTGACCGTTAGCTCCGGCGGTAGCGGTGGCAGTGGGGGTTCC<br>GGTCAGGTGCAGCTGCAAGAGTCAGGGGGGGGTCTGGTGCAGCCGGGAGGTTCC<br>CTGCGCCTCTCCTGCGCCGCTTCTGGGTTTACCTTCAGCCTCTCTTCCATGTCC<br>TGGGTGCGCCAAGCGCCGGGCAAGGGTCTTGAGTGGGTTTCTGCGATCTCTTCC<br>GGTGGAGCCTCTACATACTATACAGATTCTGTGAAGGGGAGGTTCACTATCAGC<br>CGCGACAACGCCAAAAACATGCTGTACCTTCAGCTCAATTCCCTCAAGACTGAG<br>GACACAGCTATGTATTACTGTGCAAAGGGTGGCAGCGGATATGGGGACGCCTCC<br>CGCATGACTAGCCCTGGTTCCCAGGGGACCCAGGTGACCGTGTCCAGC |
| DR595-<br>hIL27<br>Ra_VH<br>H22 | 1189 | CAGGTGCAGCTGCAAGAGAGCGGGGGGGGGTTCCGTACAGGCTGGTGGCTCTCTG<br>ACCTTGTCTTGCGCGGCTTCAGAGTATGCCTATAGTACCCGTAATATGGGCTGG<br>TATCGCCAGGCACCGGGAAAGGAGCGGGAGCTGGTGTCTGCTTTCATCTCCGAC<br>GGTTCTACCTACTATGCCGATTCTGTAAAGGGGAGGTTTACTATCACTCGGGAT<br>AACGCGAAGAACACCGTCTACCTCCAGATGAACAGCCTGAAACCCGAGGATACT<br>GCGATTTACTATTGCAGCGCCAACTGTTACCGGCGCTTGCGCAACTACTGGGGC<br>CAGGGAACTCAAGTCACTGTCAGTTCTGGCGGAGGCAGCCAGGTCCAGCTCCAG<br>GAGAGCGGGGGGGGATCTGTCCAAGCTGGCGGTTCCCTCCGCCTCAGCTGTCGC<br>GCATCTGGTAGCACTTACTCTAACTACTGTCTCGGCTGGTTTCGTCAGACAACC<br>GGAAAAGAGCGCGAGGGCGTGGCTGTCATCAACTGGCGGGGCGGGATGCTGTAC<br>TTTGCGGATAGCGTCAAGGGCCGCTTTACTGTCTCCCAGGACCAGGCAAAAAAC<br>ACCGTCTACCTCCAGATGAACTCTCTGAAGCCGGAGGACACCGCGATGTACTAT<br>TGTGCTGCCGAGAGCGTCTCCTCATTCTCTTGCGGCGGATGGCTGACCCGCCCA<br>GACCGGGTTCCATACTGGGGCCAGGGCACCCAGGTGACCGTTTCTTCC |
| DR595-<br>hIL27<br>Ra_VH<br>H22 | 1190 | CAGGTGCAGCTCCAGGAGTCTGGAGGGGGTAGCGTGCAGGCCGGAGGCTCCCTT<br>ACCCTGTCCTGTGCGGCCTCCGAGTACGCTTACTCTACCCGTAACATGGGCTGG<br>TATCGGCAAGCGCCCGGCAAAGAACGCGAACTCGTGTCCGCTTTCATCAGTGAC<br>GGTTCCACTTATTACGCTGATTCCGTTAAAGGCCGGTTTACTATCACAAGGGAT<br>AACGCGAAGAACACGGTGTATTTGCAGATGAACTCTTTGAAGCCAGAAGATACA<br>GCTATCTACTATTGCTCCGCCAACTGTTACAGGCGTCTGCGTAACTATTGGGGT<br>CAGGGCACCCAGGTAACAGTGTCATCTGGTGGGAGCGGCGGTTCTGGGGGGTCT<br>GGTCAGGTCCAGTTGCAAGAGAGCGGTGGAGGTAGCGTCCAGGCTGGTGGCTCT<br>CTGCGCCTGTCTTGCCGTGCCTCCGGCAGCACCTACTCCAACTATTGCTTGGGT<br>TGGTTCCGGCAGACAACCGGCAAAGAACGCGAGGGTGTGGCTGTTATCAACTGG<br>GTGGGCGGAATGCTGTACTTTGCAGATAGCGTAAAAGGCCGGTTTACCGTGAGC<br>CAAGACCAGGCTAAGAACACCGTGTACCTCCAGATGAATAGCTTGAAGCCCGAG<br>GACACGGCGATGTATTACTGTGCTGCCGAATCTGTGTCATCTTTCAGCTGCGGA |

TABLE 1B-continued

| Name | SEQ ID NO: | Sequence |
|---|---|---|
| | | GGGTGGCTGACCAGACCAGACCGCGTCCCTTATTGGGGACAGGGCACCCAGGTC ACCGTCTCATCT |
| DR595-hIL27Ra_VH H23 | 1191 | CAGGTGCAGTTGCAGGAGAGCGGGGGGGGAAGTGTTCAGGCTGGCGGGTCCCTT ACACTTAGCTGCGCAGCCAGCGASTACGCATATTCTACCTGCAACATGGGTTGG TATCGCCAGGCCCCTGGAAAAGAGCGCGAACTGGTGTCCGCATTCATCTCTGAT GGCTCCACCTATTACGCTGACTCCGTGAAGGGCAGGTTCACTATCACTCGGGAT AACGCAAAAAATACAGTGTACCTCCAAATGAACTCCATGAAACCCGAGGATACT GCGATTTATTACTGTAGCGCCAACTGTTACCGCAGACTGAGAAACTACTGGGGG CAGGGCACACAGGTGACCGTAAGCTCCGGCGGGGGCAGTCAGGTGCAGCTCCAG GAGAGTGGCGGAGGTTCCGTGCAGGCTGGAGGCTCACTGAGGTTGTCTTGCCGT GCCTCCCGCAGTCCCTACGGTAATTACTGCCTCGGGTGGTTCCGCCAGTCCACG GGTAAGGAGAGAGAGGGTGTGGCCGTTATCAACTGGGTCGGCGGTATGCTGTAT TTTGCCGACAGCGTCAAGGGACGCTTCACCGTAAGCCAGGACCACGCTAAGAAT ACCGTCACTCTGCAAATGAACTCCCTGAAGCCTGAGGATACGGCTATGTACTAT TGTGCAGCGGAGAGCGTGAGTTCCTTCTCTTGTGGCGGGGGGCTGACCAGACCA GACCGGGTGCCCTACTGGGGCCAGGGCACTCAAGTTACCGTCTCATCC |
| DR595-hIL27Ra_VH H23 | 1192 | CAGGTGCAACTTCAGGAATCCGGCGGTGGCAGCGTTCAGGCCGGTGGCTCCCTG ACCCTGTCCTGTGCAGCGAGCGAATATGCGTACTCTACGTGCAATATGGGCTGG TATCGTCAGGCTCCAGGCAAGGAGCGCGAATTGGTGAGTGCGTTCATCTCCGAT GGGTCAACATACTATGCGGACCCTGTGAAGGGCCGCTTTACCATCACCAGAGAC AACGCCAAGAACACGGTCTACCTGCAAATGAACAGCCTGAAGCCCGAGGACACC GCAATCTACTATTGTAGTGCTAATTGTTACCGCAGGCTGAGGAATTACTGGGGT CAAGGCACCCAAGTCACCGTGTCCAGCGGGGGTTCCGGCGGTAGCGGAGGCTCC GGCCAGGTGCAGCTCCAGGAGAGTGGGGGAGGGAGCGTGCAAGCGGGAGGGAGT CTCAGGCTTTCATGCCGTGCTTCTCGCAGCCCTTATGGCAACTATTGTCTGGGC TGGTTCAGGCAGAGTACAGGCAAGGAACGCGAGGGCGTGGCAGTCATCAACTGG GTCGGCGGGATGTTGTACTTCGCTGACTCCGTGAAGGGCCGCTTTACAGTCTCC CAAGACCACGCCAAGAACACCGTCACGCTCCAGATGAACAGTCTCAAGCCCGAA GATACTGCCATGTATTACTGCGCTGCGGAGTCAGTGTCCTCTTTCAGCTGTGGG GGTTGGCTGACTCGCCCAGACCGGGTGCCATATTGGGGCCAGGGTACACAAGTC ACCGTCAGCAGC |
| DR595-hIL27Ra_VH H24 | 1193 | CAAGTCCAGTTGCAGGAGAGCGGGGGGGGAAGCGTGCAGGCTGGAGGGAGCCTC ACCCTGTCCTGCGCCGCTTCCGAGTACGCCTACCCTACTTGTAACATGGGGTGG TATAGGCAGGCTCCCGGCAAAGAACGCGAGCTGGTCTCCGCGTTTATTTCTGAC GGATCTACCTATTACGCGGACAGTGTGAAGGGCAGATTTACAATCACTAGGGAT AACGCAAAAAACACTGTCTATCTCCAGATGAACTCTTTGAAGCCTGAGGACACA GCTATCTATTACTGTTCCGCGAACTGCTACAGACGCCTCCGTAACTATTGGGGT CAGGGTACTCAGGTGACTGTTAGTTCAGGTGGGGGCTCCCAGGTCCAGCTTCAA GAATCTGGGGGTGGATTGGTCCAGCCTGGCGGTTCTCTGCGCCTGTCTTGTGCT GCCAGTGGCTTCACTTTTTCCCACAGCGGCATGTCCTGGGTGCGCCAGGCTCCA GGCAAGGGCCTCGAATGGGTTAGTACCATCAACAGCGGAGGTGCCAGCACCTAC TATACAGATTCTGTGAAGGGCAGATTCACTATTAGTCGCGACAATGCGAAGAAC ATGCCTTACTTGCAGCCGAACTCCCTGAAGACCGAAGACACTGCAATGTATTAC TGCGCCAAGGGCGGTTCTGGCTACGGTGATGCGTCTCGCATGACATCCCCAGGG AGTCAGGGAACCCAGGTGACCGTGAGTTCA |
| DR595-hIL27Ra_VH H24 | 1194 | CAGGTCCAGCTCCAGGAATCTGGAGGGGGTAGCGTACAAGCTGGCGGTTCTCTG ACTCTGAGCTGCGCTGCCTCCGAGTACGCCTACCCAACTTGCAATATGGGCTGG TATAGGCAAGCACCAGGGAAGGAAAGAGAATTGGTTTCCGCCTTCATCTCCGAC GGAAGTACTTATTACGCCGATTCCGTGAAGGGACGCTTCACGATTACACGGGAC AACGCAAAGAACACCGTGTATCTCCAGATGAACAGCCTGAAGCCTGAGGACACC GCAATTTATTACTGTTCCGCCAACTGCTACAGACGCTTGCGCAACTACTGGGGT CAAGGCACCCAGGTGACCGTCTCTAGTGGAGGCTCCGGTGGCTCCGGGGGCTCT GGACAGGTGCAGCTTCAGGAGAGTGGTGGCGGGCTGGTGCAGCCTGGCGGTTCC CTTCGTCTCTCTTGTGCAGCCAGCGGATTCACACTTAGTCACAGCGGCATGAGT TGGGTTCGGCAAGCACCTGGGAAGGGGCTGGAGTGGGTATCCACAATCAACAGC GGAGGTGCCAGCACGTACTATACCGACYCAGTTAAAGGGCGCTTCACCATTAGT CGCGACAACGCGAAGAATATGCTGTACTTGCAGCTGAACAGCCTGAAGACCGAG GACACTGCCATGTACTATTGCGCCAAAGGGGGCAGCGGCTACGGAGATGCGAGC CGTATGACTTCACCTGGGAGCCAGGGCACCCAGGTGACCGTCTCCTCT |
| DR596-hIL27Ra_VH H1 | 1195 | CAGGTGCAGCTTCAGGAGTCTGGGGGAGGCCTGGTACAACCCGGTGGCAGTCTC AGGCTCAGCTGCACAGCCTCCGGCCTGACCTTCGACGATTCCGTGATGGGCTGG TTTAGGCAGGCCCCAGGTAAAGGCCGGGAGGCTGTAAGCTGCATTAGCTCCTCC GGAGCCAACGCCTTCTACGCTGATTCTGTGAAGGGGCGTTTTACCATTTCTCGC GACAACGCCAAGAACACCTTGTATTTGCAGATGAACTCCCTGAAACCCGAGGAC ACCGCCACCTACTATTGTAAGCGTGGCCACGCTTGTGGGGGTTATTACCCCATT CCCTACGATGACTATTGGGGTCAGGGTACGCAAGTCACCGTATCTTCCGGCGGA GGCTCCCAGGTGCAGCTCCAGGAGTCAGGGGGGGGACTGGTGCAGCCCGGAGGT TCCCTGCGGCTGTCTTGTGCGGCATCCGGCTTTACTTTCTCTTCCTACCCCATG AGCTGGGTCCGCCAAGCGCCAGGGAAGGGTCTGGAGTGGATTTCTACAATCTCA GCTGGAGGCGACACTACCCTCTACGCTGACTCTGTTAAAGGCCGCTTCACTAGC |

TABLE 1B-continued

| Name | SEQ ID NO: | Sequence |
|---|---|---|
| | | AGTCGGGATAACGCCAAGAACACGCTGTACCTCCAGCTTAATAGCTTGAAAACC<br>GAGGACGCGGCCATCTATTACTGCGCCAAGCGTATTGACTGTAACTCTGGATAC<br>TGCTATCGTCGCAACTATTGGGGTCAGGGGACCCAAGTTACAGTGAGTTCT |
| DR596-<br>hIL27<br>Ra_VH<br>H1 | 1196 | CAGGTTCAGCCTCAGGAGAGTGGGGGGGGCCTGGTTCAGCCCGGCGGTTCCCTT<br>CGCCTGAGCTGTACGGCAAGCGGTCTGACATTTGACGATTCCGTGATGGGCTGG<br>TTTCGTCAGGCTCCTGGCAAGGGTAGGGAGGGGGTGAGTTGCATCAGCTCCAGC<br>GGAGCCAACGCCTTTTACGCGGATAGCGTCAAGGGAAGGTTTACCATCAGCCGG<br>GACAATGCTAAGAACACCCTGTACTTGCAGATGAACAGTCTGAAACCAGAGGAC<br>ACCGCAACTTATTACTGCAAGCGCGGCCACGCTTGCGCGGGCTATTACCCGATT<br>CCCTATGACGATTACTGGGGCCAGGGCACTCAGGTGACAGTCAGCTCTGGCGGA<br>AGTGGCGGAAGGGGCGGTTCTGGCCAGGTTCAGTTGCAGGAGAGCGGAGGTGGC<br>CTGGTCCAGCCCGGTGGCTCTCTGCGCCTGAGCTGCGCCGCTTCCGGTTTCACT<br>TTCTCTAGCTATCCCATGAGTTGGGTGCGTCAGGCTCCAGGCAAGGGACTGGAG<br>TGGATCAGTACCATCTCAGCTGGGGGCGACACCACATTGTACGCCGATTCTGTG<br>AAGGGCAGATTTACCTCCTCTCGCGATAATGCCAAGAACACCCTGTATCTCCAG<br>TTGAACTCTCTGAAGACCGAGGACGCTGCCATCCACTATTGCGCCAAGCGTATC<br>GACTGTAATTCCGGCTACTGTTACCGTCGGAACTACTGGGGACAAGGCACCCAG<br>GTTACCGTTAGCTCC |
| DR596-<br>hIL27<br>Ra_VH<br>H2 | 1197 | CAGGTCCAACTGCAAGAATCCGGTGGGGGTCTGGTTCAGCCCGGTGGCTCACTG<br>CGCCTGTCATGTACCGCCAGCGGCCTGACTTTCGATGACAGTGTCATGGGATGG<br>TTTCGCCAGGCCCCTGGAAAGGGAAGGGAAGCGGTCAGCTGTATTTCTTCCAGC<br>GGGGCTAATGCCTTCTACGCTGACTCCGTGAAAGGTCGGTTTACCATCAGTAGG<br>GATAATGCCAAGAACACCTTGTACTTGCAGATGAACTCCCTGAAACCTGAGGAC<br>ACCGCCACCTATTACTGTAAGCGTGGCCACGCCTGCGCTGGCTACTAACCCATC<br>CCATACGATGACTACTGGGGCCAGGGTACTCAGGTAACTGTTAGCTCTGGAGGG<br>GGCTCCCAGGTGCAGCTTCAGGAATCTGGTGGCGGACTGGTCCAGCCTGGGGGT<br>TCCCFTCGTCTGAGCTGCGCAGCCTCTGGTTTCACTTTTAGCCTGAGCGGTATG<br>AGCTGGGTGAGGCAGGCCCCTGGCAAGGGTCTGGAGTGGGTCAGCGCGATCTCC<br>AGCGGCGGTGCCTCTACCTACTATACAGATTCCGTGAAGGGCAGATTCACTATC<br>TCCAGAGATAACGCTAAAAACATCCTCTACCTGCAACTGAACTCCCTCAAGACC<br>GAGGATACTGCCATGTATTACTGTGCAAAGGGAGGCTCTGGTTATGGTGATGCC<br>AGTCGGATGACCTCCCCCGGCTCCCAGGGAACACAGGTTACGGTCTCATCC |
| DR596-<br>hIL27<br>Ra_VH<br>H2 | 1198 | CAGGTCCAGCTTCAGGAGAGTGGGGGGGGACTGGTACAGCCCGGAGGCTCCGTG<br>AGACTGAGTTGCACCGCCAGTGGTCTGACATTCGATGACAGCGTGATGGGCTGG<br>TTCAGACAGGCCCCCGGCAAAGGCCGCGAGGCCGTTAGCTGTATCTCTAGTAGC<br>GGGGCCAACGCTTTTTACGCTGACTCTGTTAAGGGCAGGTTCACCATTTCCCGC<br>GACAATGCGAAGAACACCCTGTACTTGCAGATGAACAGTCTGAAACCCGAAGAC<br>ACGGCTACTTACTATTGTAAGAGGGGTCACGCCTGCGCCGGTTATTACCCCATT<br>CCCTACGATGACTATTGGGGGCAAGGGACCCAGGTCACAGTCTCCAGGGGGGGG<br>TCCGGGGGTAGCGGGGGCTCCGGCCAGGTGCAGCTGCAAGAGTCCGGGGGCGGT<br>CTTGTTCAGCCAGGTGGCTCTCTGCGGCTGTCCTGCGCGGCCTCTGGATTCACA<br>TTCTCTCTCAGTGGCATGTCTTGGGTGCGCCAGGCTCCGGGCAAGGGCCTCGAA<br>TGGGTGTCCGCCATCTCCAGCGGTGGCGCTTCCACTTATTACACCGATTCTGTG<br>AAGGGACGCTTCACCATCTCTAGGGACAACGCGAAGAACATTTTGTATCTCCAA<br>CTGAACAGTCTTAAAACCGAGGACACTGCCATGTATTACTGTGGTAAGGGGTGG<br>TCTGGCTACGGAGATGCGTCCAGGATGACGAGCCCAGGCTCCCAGGGCACCCAG<br>GTGACCGTGTCCTCT |
| DR596-<br>hIL27<br>Ra_VH<br>H3 | 1199 | CAGGTCCAGCTCCAGGAGTCCGGTGGGGGCCTCGTTCAGCCCGGCGGATCTCTG<br>AGGCTGAGCTGTACCGCCTCTGGCCTGACCTTCGACGATTCCGTGATGGGCTGG<br>TTCAGACAGGCTCCCGGCAAGGGCCGCGAAGCTGTCTCCTGCATCTCCTCTTCC<br>GGCGCAAATGCGTTCTACGCCGACTCAGTGAAGGGCCGTTTTACCATTTCTCGG<br>GATAACGCTAAAAACACGCTGTATCTGCAAATGAACTCCTTGAAACCGGAGGAT<br>ACCGCCACCTATTACTGCAAACGCGGTCATGCCTGTGCTGGGTATTACCCAATC<br>CCTTACGATGACTATTGGGGCCAAGGCACCCAGGTCACCGTCAGTAGCGGCGGT<br>GGCTCCCAGGCTCAGTTGCAGGAATCAGGGGGGGGCTCCGTCCAAGCCGGAGGC<br>TCTCTGCGTCTGTCATGTGTAGCCAGTGGCTACGTGTCATGCGATTACTTCCTG<br>CCTTCCTGGTATAGACAGGCTCCCGGCAAGGAGCGCGAGTTCGTGAGCATTATC<br>GACGGCACGGGTTCCACGTCCTACGCTGCCCCCGTTAAGGGTCGCTTTACAGCT<br>AGTGAGGACAAGGGCAAGAACATTGCGTACCTCCAGATGAACTCCCTGAAGCCT<br>GAAGATACAGCCATGTACTATTGCAAGGCCAGCTGTGTGAGGGGCCGCGCTGTT<br>TCAGAATACTGGGGCCAGGGCACCCAGGTCACTGTTTCTTCT |
| DR596-<br>hIL27<br>Ra_VH<br>H3 | 1200 | CAGGTTCAGTTGCAGGAATCCGGGGGGGGATTGGTCCAGCCAGGAGGCTCCCTT<br>CGCCTGAGCTGCACTGCCTCTGGACTGACATTTGACGATTCTGTTATGGGCTGG<br>TTCCGCCAAGCACCAGGAAAGGGCAGAGAGGCAGTGTCTTGTATCCCTTCCAGC<br>GGAGCCAATGCGTTTTATGCTGACAGCGTGAAGGGCAGGTTCACCATCTCACGC<br>GACAACGCTAAGAACACCCCCTATCTTCAGATGAACTCTCTCAAACCTGAGGAT<br>ACCGCCACCTATTACTGTAAACGCGGACATGCTTGCGCCGGTTACTATCCCATC<br>CCCTATGATGACTACTGGGGGCAGGGCACCCAGGTGACCGTGTCAAGCGGGGGA<br>TCAGGAGGCAGCGGAGGCAGCGGCCAGGTCCAACTTCAGGAGTCAGGAGGCGGT<br>TCTGTGCAGGCCGGAGGCTCACTGCGGCTGTCCTGTGTGGCGAGTGGCTACGTA<br>AGCTGCGACTACTTCCTGCCTTCTTGGTACAGGCAGGCCCCCGGCAAAGAGAGG<br>GAATTTGTGTCCATCATTGATGGTACAGGCAGCACCTCCTATGCGGCCTCCGTT |

TABLE 1B-continued

| Name | SEQ ID NO: | Sequence |
|---|---|---|
| | | AAGGGCAGATTTACTGCCTCCGAGGACAAGGGCAAGAATATCGCCTATCTCCAG ATGAACTCCCTGAAGCCGGAAGATACCGCAATGTACTATTGCAAAGCCAGTTGT GTGAGAGGGAGAGCGGTAAGTGAGTATTGGGGTCAGGGCACTCAGGTGACGGTT TCCAGC |
| DR596-hIL27 Ra_VH H4 | 1201 | CAGGTGCAACCTCAGGAGTCTGGAGGCGGACTGGTCCAGCCTGGGGGCTCTCTG CGTCTGTCTTGCACCGCCTCCGGCCTGACGTTTGATGACTCAGTCATGGGGTGG TTCCGCCAAGCCCCTGGGAAGGGCAGGGAGGCCGTCAGCTGCATCTCTAGCTCC GGGGCCAACGCTTTCTACGCGGATAGCGTCAAGGGCCGCCTCACCATCAGTAGA GATAACGCAAAAAACACTTTGTATCTCCAGATGAACAGCCTGAAACCCGAGGAT ACCGCAACGTATTACTGTAAGCGCGGACACGCTTGTGCGGGCTATTACCCTATT CCCTATGATGACTACTGGGGTCAGGGCACTCAAGTCACCGTCAGTTCTGGCGGA GGTTCTCAGGTACAGCTCCAGGAGTCTGGCGGGGGCCTGGTGCAGCCCGGCGAA TCTCTGAGACTGTCATGCACCGCATCCGGCTTTACCTTCTCTAATTACGCCATG AGCTGGGTCAGACAGGCCCCTGGTAAGGGGCTGGAGTGGGTCAGTGGAATCAAC GTGGCCTATGGGATCACCTCCTACGCGGACTCCGTCAAGGGTAGATTTACAATC TCTCGCGACAACACCAAGAACACCCTGTACCTTCAGCTGAACTCACTCAAAACC GAAGACACCGCGATCTATTACTGTGTGAAACACTCAGGTACAACCATCCCCAGA GGATTCATCTCATACACAAAACGCGGCCAGGGTACTCAGGTAACCGTGTCCTCA |
| DR596-hIL27 Ra_VH H4 | 1202 | CAGGTCCAGCTCCAGGAGAGCGGGGGGGGCCTGGTGCAGCCTGGCGGTTCCCTG CGGCTCAGCTGTACCGCCTCCGGGCTGACGTTCGACGATTCTGTGATGGGCTGG TTTCGCCAGGCCCCCGGCAAGGGACGCGAAGCTGTAAGCTGCATTAGTTCCTCT GGAGCGAATGCCTTCTACGCCGACTCTGTGAAGGGCCGCTTCACAATCTCCCGC GACAACGCTAAGAACACGCTGTACCTTCAGATGAACTCTCTGAAACCCGAGGAT ACTGCCACCTACTATTGCAAGCGCGGCCATGCCTGTGCTGGGTACTATCCAATC CCGTATGACGATTACTGGGGCCAAGGGACCCAGGTCACCGTAAGTTCAGGAGGT AGCGGTGGCTCTGGGGGCTCTGGTCAAGTACAGTTGCAGGAAAGTGGGGGGGGT CTGGTTCAGCCAGGCGAGTCATTGAGATTGTCTTGTACGGCTAGTGGATTCACA TTTAGTAACTACGCCATGAGCTGGGTCCGTCAAGCACCTGGCAAGGGCCTGGAG TGGGTATCCGGTATTAACGTGGCCTACGGAATTACAAGTTATGCAGACTCTGTG AAGGGCAGGTTCACAATCTCTCGGGACAACACCAAGAACACGCTGTACCTTCAG CTGAACTCTCCGAAAACCGAAGATACTGCTATCCATTACTGCGTGAAGCACAGC GGCACAACCATCCCACGCGGTTTCATCTCTTATACCAAGAGAGGCCAGGGCACC CAAGTCACCGTGTCATCC |
| DR596-hIL27 Ra_VH H5 | 1203 | CAGGTGCAACTCCAGGAGTCCGGCGGTGGCCTCGTGCAACCGGGTGGCTCCTTG AGACTGTCTTGTACCGCCAGCGGACTTACCTTCGACGATTCTGTGATGGGCTGG TTCCGGCAAGCGCCGGGCAAGGGCAGAGAGGCCGTGAGCTGCATCTCTAGTTCT GGTGCTAACGCTTTTTACGCCGACTCCGTGAAAGGCCGTTTCACGATTTCAAGA GATAACGCCAAAAACACTCTCTACCTCCAGATGAACTCCCTCAAGCCTGAGGAC ACTGCCACCTATTACTGTAAGCGGGGCCACGCTTGCGCAGGCTATTACCCTATT CCCTATGACGATTACTGGGGCCAGGGTACACAGGTGACGGTGTCCAGTGGCGGA GGGTCACAAGTTCAACTTCAGGAGAGCGGGGGAGGGTCTGTCCAGGCTGGTGGC TCCCTGCGTCTCTCCTGTACCGCCCCCGGCTACGTGTCATGTGATTACTTTCTG CCTTCCTGGTACAGGCAAGCACCCGGTAAGGAGCGCGAATTTGTCAGCGTTATT GACGGCACGGGTAGTACGTCCTATGCTGCCTCCGTGAAGGGCCGCTTCACGGCA TCCCAGGACAAGGGGAAAAATATCGCATACCTCCAAATGAACAGTCTGAAGCCG GAGGATACAGCTATGTATTACTGCAAGGCTTCATGTGTGCGCGGAAGAGCTATT AGTGAGTATTGGGGCCAGGGTACACAGGTAACGGTCAGCTCC |
| DR596-hIL27 Ra_VH H5 | 1204 | CAGGTCCAGTTGCAGGAGAGCGGCGGTGGCTTGGTGCAGCCCGGTGGGTCACTG AGACTGTCCTGCACTGCAAGGGGCCTTACGTTCGATGACAGCGTGATGGGGTGG TTCCGCCAGGCACCCGGCAAGGGACGTGAGGCCGTGTCCTGCATTAGCTCATCC GGCGCTAATGCCTTTTATGCCGACAGCGTCAAGGGCAGATTTACCATCTCTCGC GACAATGCCAAAAATACCCCGTATCTTCAAATGAATAGCCTGAAGCCAGAGGAT ACCGCTACTTACTATTGTAAGCGCGGCCACGCCTGCGCGGGCTATTACCCTATC CCCTACGATGACTATTGGGGCCAGGGTACTCAAGTGACTGTGAGTTCCGGTGGC TCCGGCGGGTCTGGAGGCTCAGGTCAAGTCCAGTTGCAGGAGTCCGGGGGGGGT AGCGTGCAGGGGGGGGGTTCCCTGCGCCTGTCTTGTACCGCATCTGGGTACGTC TCCTGCGATTACTTCCTGCCTTCCTGGTACAGGCAGGCCCCTGGCAAGGAGCGT GAGTTTGTGTCCGTGATCGACGGGACAGGTTCCACCTCCTACGCTGCATCCGTT AAGGGTCGCTTTACAGCCAGCCAGGACAAAGGAAAGAACATCGCTTACCTGCAA ATGAACTCCCTGAAACCTGAGGATACCGCTATGTATTACCGCAAGGCCTCCTGC GTCCGTGGCCGTGCGATCTCCGAATACTGGGGCCAGGGCACCCAGGTGACTGTT AGCAGC |
| DR596-hIL27 Ra_VH H6 | 1205 | CAGGTGCAGTTGCAGGAGTCTGGGGGAGGTCTCGTGCAGCCAGGAGGGTCACTC CGCCTGAGTTGTACTGCCAGCGGTTTGACATTCGACGATTCTGTCATGGGCTGG TTTCGCCAAGCTCCAGGGAAGGGCCGCGAGGCTGTGTCCTGCATCTCATCCTCC GGGGCCAACGCTTTTTACGCTGATTCTGTCAAAGGCCGCTTCACAATCAGCCGG GACAACGCCAAGAACACTTTGTATCTCCAAATGAACAGCCTGAAGCCTGAGGAC ACTGCAACCTATTACTGTAAGCGCGGACACGCCCGCGCTGGCTATTACCCCATC CCTTACGACGATTATTGGGGTCAAGGAACTCAGGTTACTGTTAGCTCCGGGTGG GGCAGCCAGGTGCAGCTTCAGGAGTCAGGTGGAGGTCTGGTGCAACCTGGAGGC TCCCTGCGCCTGTCCTGTGCCGCATCCGGCTTTAGTTTCTCTAGCTACGCAATG AAATGGGTGCGTCAAGCCCCAGGCAAAGGTCTGGAGTGGGTGTCCACCATCAGT |

TABLE 1B-continued

| Name | SEQ ID NO: | Sequence |
| --- | --- | --- |
| | | AGCGGTGGCTCCAGCACGAACTACGCCGACTCCGTGAAAGGCCGGTTCACCATC<br>AGCCGTGATAACGCTAAGAACACGCTGTACCTCCAGCTGAACTCTCTGAAGATC<br>GAGGACACGGCAATGTATTACTGTGCAAAGGCAATCGTTCCAACTGGTGCCACT<br>ATGGAGAGGGGGCAGGGAACCCAAGTCACCGTTAGCTCC |
| DR596-hIL27 Ra_VH H6 | 1206 | CAAGTGCAGCTCCAAGAAAGCGGCGGAGGCCTGGTGCAGCCTGGCGGTTCTCTG<br>AGACTGAGCTGTACTGCCTCAGGTCTGACTTTTGACGATTCTGTCATGGGATGG<br>TTTAGACAAGCTCCAGGCAAGGGTCGTGAGGCGGTGAGCTGTATTAGCTCCTCT<br>GGCGCGAACGCATTTTATGCCGATTCCGTTAAGGGTCGCTTCACAATCTCACGG<br>GACAACGCGAAGAATACACTGTACCTGCAAATGAACTCCCTGAAGCCCGAGGAC<br>ACAGCTACCTATTACTGCAAGCGCGGCCACGCCTGTGCAGGTTATTACCCTATT<br>CCCTATGATGACTACTGGGGACAAGGGACTCAGGTTACCGTCAGCTCCGGTGGC<br>AGCGGCGGATCTGGTGGCTCCGGCCAGGTGCAGCTTCAGGAGTCCGGGGGAGGC<br>CTGGTGCAGCCGGGGGGTTCATTGCGCCTTTCTTGCGCCGCGAGTGGCTTCTCC<br>TTTTCCAGCTATGCCATGAAGTGGGTCCGCCAGGCTCCTGGGAAGGGCCTGGAG<br>TGGGTGTCCACCATCTCCTCTGGGGGCTCCAGTACCAACTACGCCGACAGCGTG<br>AAGGGTCGCTTCACTATCAGCAGAGATAACGCTAAGAACACACTGTACCTCCAG<br>CTGAATAGCCTGAAGATCGAGGATACGGCTATGTATTACCGTGCCAAGGCGATT<br>GTGCCTACAGGAGCCACTATGGAACGCGGCCAAGGCACCCAGGTGACGGTGTCA<br>AGC |
| DR596-hIL27 Ra_VH H7 | 1207 | CAGGTGCAACTTCAAGAATCTGGAGGTGGACTGGTCCAGCCTGGGGGTTCTCTG<br>CGCCTCTCTTGTACTGCTTCCGGCCTCACATTTGACGATTCTGTTATGGGATGG<br>TTCAGACAGGCCCCAGGTAAGGGTCGCGAGGCCGTGAGTTGTATCAGCTCCAGC<br>GGCGCTAACGCATTCTATGCCGACAGTGTCAAGGGACGCTTTACAATCTCCAGG<br>GACAACGCCAAAAACACGCTCTACCTTCAGATGAACTCACTGAAGCCCGAGGAT<br>ACTGCTACCTATTACTGCAAACGCGGTCATGCTTGTGCCGGTTATTACCCCATC<br>CCATACGATGACTACTGGGGCCAGGGGACCCAGGTAACCGTCAGCTCCGGCGGT<br>GGATCACAGGTGCAGCTTCAGGAGAGTGGTGGAGGTCTCGTGCAACCTGGAGGT<br>AGTCTCCGCTTGTCTTGTGCTGCCTCCGGTTTCACCTTTTCCAGCTACCCCATG<br>AGTTGGGTGCGCCAAGCGCCGGGGAAGGGCCTGGAGTGGATTTCAACTATCAGC<br>GCTGGAGGCGATACCACACTGTACGCCGATAGTGTTAAGGGAAGGTTCACTTCC<br>TCTAGGGATAACGCCAAGAACACCCTGTATCTTCAGCTGAACAGTCTGAAGACG<br>GAGGACACTGCTATCTATTACTGCGCAAAACGCATTGATTGCAACTCCGGCTAT<br>TGCTACCGCCGGAACTACTGGGGCCAGGGGACCCAGGTGACAGTCAGTTCC |
| DR596-hIL27 Ra_VH H7 | 1208 | CAGGTACAGCTCCAGGAGAGCGGCGGTGGCCTGGTACAGCCAGGGGGTTCATTG<br>CGTCTGAGCTGCACTGCTTCTGGTCTGACGTTTGATGACTCTGTTATGGGCTGG<br>TTCCGCCAAGCGCCCGGCAAGGGACGGGAAGCTGTTAGCTGTATCTCCAGTTCC<br>GGGGCCAACGCCTTCTACGCCGATTCTGTGAAGGGTCGCTTCACTATCTCACGC<br>GACAACGCCAAGAACACCCTGTACCTTCAGATGAACAGTCTGAAGCCTGAGGAT<br>ACCGCCACCTACTATTGCAAGCGCGGCCATGCGTGCGCGGGCTATTACCCTATC<br>CCTTACGATGACTATTGGGGGCAGGGCACCCAGGTGACTGTGTCCAGTGGAGGC<br>TCCGGTGGCAGTGGAGGGTCCGGCCAGGTCCAACTCCAGGAGTCTGGTGGGGGC<br>TTGGTCCAGCCTGGGGGTAGCTTGCGCCTGTCTTGCGCTGCCTCCGGGTTCACC<br>TTCTCCAGTTATCCTATGTCTTGGGTGCGGCAAGCGCCGGGTAAGGGCCTGGAG<br>TGGATTTCTACTATCTCTGCTGGCGGTGACACCACGTTGTACGCAGATTCCGTG<br>AAGGGGCGTTTCACCTCCTCAAGAGACAATGCGAAGAACACCTTGTACCTCCAG<br>CTGAACAGCCTGAAGACCGAGGACACCGCTATTTACTATTGTGCCAAGCGTATT<br>GATTGTAATAGCGGTTATTGCTACCGCAGGAACTACTGGGGCCAGGGCACACAG<br>GTCACCGTGAGCAGT |
| DR596-hIL27 Ra_VH H8 | 1209 | CAGGTGCAACTCCAGGAAAGCGGTGGGGGGCTTGTGCAGCCCGGCGGTAGCCTG<br>CGGCTGAGTTGTACTGCAAGCGGTCTCACCATCGACGATAGTGTAATGGGCTGG<br>TTTCGTCAAGCACCCGGAAAGGGAAGGGAGGCGGTGTCTTGCATCTCCAGCAGT<br>GGCGCGAATGCGTTTTATGCCGATTCCGTCAAGGGGCGGTTTACGATCTCCAGG<br>GATAACGCCAAGAACACGCTGTACCTCCAGATGAACAGTCTGAAGCCCGAGGAT<br>ACGGCCACATATTACTGTAAGCGCGGGCACGCCTGTGCCGGATACTATCCCATC<br>CCTTATGACGATTATTGGGGTCAAGGTACGCAGGTCACAGTTAGCTCTGGCGGA<br>GGTTCCCAGGTCCAACTTCAGGAGTCCGGTGGAGGGTCCGTTCAGGTGGGCGGA<br>TCTCTTCGCCTGAGCTGCGCGGCCAGCGGATTTACCTTCAGCTCCTACCCAATG<br>AGTTGGGTGCGTCAGGCTCCGGGTAAGGGCCTGGAGTGGATCTCTACCATTAGT<br>GCTGGCGGAGACACCACGCTGTACGCCGACAGCGTGAAGGGGCGCTTCACCTCC<br>TCTCGCGATAACGCAAAGAATACCCTGTACCTCCAGCTCAATTCCTTGAAGACC<br>GAAGATACGGCCATTTATTACTGCGCCAAGCGCATTGATTGCAATAGCGGCTAT<br>TGCTATCGGAGGAACTACTGGGGACAGGGAACCCAAGTCACTGTTTCATCC |
| DR596-hIL27 Ra_VH H8 | 1210 | CAGGTCCAGCTCCAAGAGTCAGGAGGCGGACTCGTGCAACCGGGTGGCTCCCTG<br>AGGCTGTCTTGTACCGCAAGCGGCCTGACCCTCGATGACAGTGTCATGGGCTGG<br>TTCAGGCAGGCCCCCGGCAAAGGCCGTGAGGCCGTCAGCCGTATCAGTTCTAGT<br>GGAGCCAACGCCTTTTACGCCGATTCCGTAAAGGGCCGTTTCACCATTTCAAGG<br>GACAATGCCAAGAATACCCTGTATCTGCAAATGAACTCCCTCAAGCCCGAAGAT<br>ACCGCCACCTACTATTGCAAGCGCGGACATGCCTGTGCCGGTTATTACCCCATT<br>CCCTATGACGATTATTGGGGTCAGGGAACCCAGGTGACCGTGTCCAGTGGAGGG<br>TCCGGGGGCTCTGGGGGGTCCGGCCAGGTGCAGTTGCAGGAGTCAGGGGGTGGG<br>AGCGTCCAGGTTGGGGGTAGTCTGCGCCTGTCTTGTGCAGCCTCTGGGTTCACC<br>TTCAGCTCCTACCCCATGAGCTGGGTGCGCCAGGCTCCGGGAAAAGGTCTTGAG |

TABLE 1B-continued

| Name | SEQ ID NO: | Sequence |
|---|---|---|
| | | TGGATCTCTACAATCTCCGCCGGTGGCGACACTACCCTGTACGCTGACAGCGTG AAGGGCCGGTTTACAAGTTCTCGCGACAACGCCAAGAACACCTTGTACCTCCAG CTCAACTCCCTGAAGACCGAGGATACCGCCATTTATTACTGTGCAAAAAGGATT GATTGTAACTCCGGCTACTGTTATCGCAGAAATTACTGGGGCCAGGGGACCCAG GTTACAGTGTCTAGC |
| DR596-hIL27 Ra_VH H9 | 1211 | CAGGTTCAGCTGCAAGAGAGCGGAGGGGGTCTCGTGCAGCCGGGTGGGAGCCTG CGCCTTTCCTGTACTGCTTCTGGACTGACCTTCGATGACTCCGTGATGGGTTGG TTCCGGCAGGCCCCTGGAAAGGGCCGTGAAGCTGTGTCCTGTATCAGCTCTTCC GGGGCGAATGCTTTCTACGCCGATAGCGTTAAGGGCCGCTTTACCATCTCCCGC GACAACGCAAAGAATACTCTGTACTTGCAGATGAACAGCCTCAAGCCCGAAGAC ACCGCCACTTATTACTGTAAGCGCGGCCACGCTTGCGCGGGTTACTATCCCATC CCTTACGATGACTACTGGGGACAGGGAACCCAGGTAACCGTGTCATCTGGGGGG GGCAGTCAGGTCCAGTTGCAGGAAAGCGGAGGTGGCAGCGTTCAGAGTGGCGGT TCCCTGCGTCTTAGCTGTGCAGCCTCCGGCTTTACATACAGCACTTCTAATTCC TGGATGGCCTGGTTCAGACAGGCCCCAGGCAAGGAACGCGAAGGCGTGGCTGCC ATTTACACGGTCGGAGGGTCCATCTTTTACGCCGATTCCGTGCGTGGCCGCTTT ACCATCTCCCAGGACGCTACTAAGAATATGTTCTACCTGCAAATGAATACCCTG AAACCGGAGGACACCGCCATGTACTATTGTGCCGCAGCGTCCGGTCGCCTGAGG GGGAAGTGGTTCTGGCCCTATGAATACAATTACTGGGGACAGGGCACCCAGGTT ACCGTGTCTTCA |
| DR596 hIL27 Ra_VH H9 | 1212 | CAGGTACAGCTGCAAGAGAGCGGAGGCGGATTGGTGCAGCCCGGAGGCAGTTTG AGGTTGAGCTGTACCGCTTCCGGCCTCACTTTCGATGACTCCGTCATGGGCTGG TTCCGCCAAGCACCTGGAAAGGGACGGGAAGCTGTCTCCTGCATCAGCAGTAGC GGAGCCAACGCATTCTACGCTGACAGCGTCAAAGGCAGGTTCACAATTAGCCGT GATAATGCAAAGAACACTCTGTACCTGCAAATGAACTCTTTGAAGCCCGAGGAC ACCGCGACGTATTACTGCAAGAGAGGACATGCCTGTGCCGGTTATTACCCCATC CCCTACGATGACTATTGGGGACAGGGTACTCAGGTGACGGTGAGTTCCGGCGGT AGCGGTGGCAGTGGAGGGAGCGGTCAGGTGCAGTTGCAGGAGAGCGGGGGGGGA AGCGTGCAGTCCGGCGGGTCCCTGCGCCTTAGTTGCGCCGCTTCCGGCTTCACT TATAGCACCTCTAACTCTTGGATGGCTTGGTTTCGCCAGGCCCCCGGCAAGGAG AGAGAGGGCGTGGCTGCCAACTACACAGTGGGCGGAAGCATCTTTTACGCGGAT AGCGTGAGAGGCCGTTTCACAATCAGCCAGGATGCAACAAAGAATATGTTCTAT CTCCAGATGAACACACTGAAGCCCGAAGACACCGCTATGTATTACTGTGCTGCC GCTTCAGGACGCTTGAGGGGCAAATGGTTTTGGCCCTATGAATACAACTACTGG GGACAGGGCACCCAGGTGACTGTAAGCAGC |
| DR596-hIL27 Ra_VH H10 | 1213 | CAGGTGCAGTTGCAGGAAAGCGGGGGAGGCCTGGTGCAGCCTGGCGGTTCCCTG CGTCTTTCCTGTACTGCCTCAGGACTTACCTTCGATGACAGTGTGATGGGTTGG TTCCGTCAGGCCCCTGGTAAAGGGGGGGAAGCAGTCAGTTGTATCTCCAGCTCT GGTGCAAACGCATTCTACGCCGACTCTGTCAAGGGACGTTTCACTATCAGTCGC GATAACGCTAAGAATACCCTGTACCTCCAGATGAACAGCCTGAAGCCTGAGGAT ACGGCTACCTATTACTGTAAACGGGGACACGCCTGTGCTGGCTACTATCCCATT CCATACGACGATTATTGGGGCCAGGGAACTCAGGTGACAGTGTCAAGCGGCGGT GGCTCACAGGTTCAGCTCCAGGAATCTGGGGGGGGCTCTGTCCAGGCAGGAGGC AGCTTGCGCCTGTCCTGTAGGGCAAGTGGAAGCACTTACTCCAACTACTGCCTG GGCTGGTTCCGCCAAATTACTGGTAAAGAGCGGGAAGGTGTCGCGGTCATTAAC TGGGTCGGCGGTATGCTGTATTTTGCTGATTCTGTGAAGGGTCGGTTCACTGTG TCCCAGGACCAGGCTAAGAACACCTTGTATCTGCAAATGAACAGCCTGAAGCCA GAGGATACCGCGATGTATTACCGCGCAGCCGAGAGCGTCTCTAGCCTTAGCTGC GGCGGTTGGCTGACCAGGCCGGATCGCGTGCCTTACTGGGGTCAAGGAACCCAG GTGACCGTCTCTTCA |
| DR596-hIL27 Ra_VH H10 | 1214 | CAAGTCCAACTCCAGGAGTCCGGGGGTGGCCTCGTCCAGCCTGGTGGCTCCCTT AGGCTGAGCTGCACTGCATCTGGCCTGACTTTCGATGACCCCGTCATGGGCTGG TTCCGCCAGGCTCCGGGAAAGGGACGCGAGGCCGTGTCTTGTATCAGCTCCAGT GGTGCCAACGCTTTTTACGCTGACTCTGTAAAAGGCCGGTTCACTATCAGCCGC GACAACGCCAAAAACACCCTCCACTTGCAGATGAATAGCCTGAAGCCTGAGGAC ACCGCCACATACTATTGTAAACGTGGCCACGCTTGCGCCGGTTATTACCCTATC CCCTACGATGACTACTGGGGCCAGGGCACCCAGGTGACCGTGAGTTCCGGTGGC AGCGGCGGTTCTGGCGGATCAGGCCAGGTCCAACTTCAGGAAAGCGGAGGGGGG AGTGTTCAGGCTGGTGGCTCCCTGCGTCTGTCCTGCCGTGCTAGTGGCTCTACC TATTCTAACTACTGCCTCGGCTGGTTCCGCCAAATCACGGGTAAGGAGCGTGAG GGGGTTGCCGTCATAAATTGGGTGGGGGGGATGCTTTACTTCGCCGATAGTGTG AAGGGGCGTTTTACTGTGTCCCAGGACCAGGCAAAGAATACCCTGTACCTCCAA ATGAACTCTCTGAAGCCCGAAGACACAGCCATGTACTATTGTGCCGCAGAGAGC GTGTCATCCTTCTCTTGTGGCGGATGGCTGACCCGCCCTGATCGCGTGCCCTAC TGGGGTCAGGGCACCCAGGTGACCGTCTCATCC |
| DR596-hIL27 Ra_VH H11 | 1215 | CAGGTGCAGCTCCAGGAATCAGGCGGGGGCCTCGTGCAGCCAGGGGGCAGCCTG AGACTCTCTTGCACAGCCAGCGGACTCACCTTTGATGACAGCGTCATGGGCTGG TTCAGGCAGGCTCCCGGCAAAGGGAAGGGAGGCCGTCTCCTGCATCTCTTCCTCT GGTGCTAATGCCTTCTACGCTGACTCCGTCAAGGGCCGCTTTACTATCTCCCGC GACAACGCAAAGAACACTCTGTACCTCCAGATGAACTCCCTGAAGCCTGAGGAC ACCGCGACATATTACTGTAAGAGAGGCCACGCCTGTGCGGGCTATTACCCCATC CCCTACGATGACTATTGGGGTCAGGGCACGCAAGTTACAGTCTCCAGCGGGGGA |

TABLE 1B-continued

| Name | SEQ ID NO: | Sequence |
|---|---|---|
| | | GGTTCCCAGGTCCAGCTCCAGGAATCTGGGGGGGGCAGTGTCCAGGCCGGAGGC TCCCTGAGACTGAGCTGCCGGGCCTCCGGTTCCACATACTCCAACTACTGCCTG GGCTGGTTCCGCCAGTCCACAGGTAAAGAGAGAGAGGGCGTCGCAGTGATTAAC TGGGTTGGCGGAATGCTGTACTTTGCTGACTCCGTTAAGGGCCGCTTCACCGTC TCCCAGGATCACGCTAAGAACACTGTCACCTTGCAGATGAACTCATTGAAGCCC GAAGATACCGCCATGTACTATTGTGCTGCCGAGAGCGTTAGTTCATTTTCTTGC GGCGGTTGGCTGACGCGCCCAGGCCGCGTGCCCTACTGGGGCCAGGGAACGCAA GTGACCGTGTCATCC |
| DR596-hIL27 Ra_VH H11 | 1216 | CAGGTACAGTTGCAGGAGTCCGGTGGGGGACTGGTCCAGCCCGGCGGATCACTG CGCCTGAGCTGCACCGCATCCGGGCTGACCTTCGACGATAGCGTTATGGGTTGG TTCCGCCAGGCCCCAGGTAAGGGACGCGAAGCTGTCAGCTGCATTTCTTCCTCC GGGGCCAATGCCTTCTATGCCGATTCTGTGAAAGGAAGATTCACCATCAGCCGC GACAATGCTAAGAATACTCTGTACCTCCAGATGAACAGCCTCAAGCCGGAGGAC ACTGCCACATATTACTGCAAGAGAGGTCATGCTTGCGCAGGTTATTACCCGATT CCCTACGACGATTATTGGGGCCAGGGGACCCAGGTTACGGTTTCTAGCGGAGGG AGCGGAGGGTCCGGTGGCAGTGGACAAGTTCAGCTCCAGGAAAGTGGGGGGGGC TCTGTCCAAGCCGGGGGCTCCCTGCGGCTCTCCTGCCGGGCTTCTGGCTCTACT TATTCTAACTATTGCTTGGGTTGGTTCCGTCAATCCACTGGGAAGGAGAGAGAG GGCGTGGCCGTTATAAATTGGGTTGGGGGGATGCTCTACTTCGCTGATTCCGTC AAAGGAAGGTTCACAGTGTCCCAGGACCACGCTAAGAACACTGTGACTCTGCAA ATGAACTCCCTGAAGCCAGAGGACACTGCTATGTATTACTGTGCCGCTGAGAGC GTCTCATCCTTCTCCTGCGGGGCGGGGCTGACCCGTCCTGGCCGTGTGCCTTAC TGGGGGCAGGGCACCCAGGTGACCGTCTCTAGT |
| DR596-hIL27 Ra_VH B12 | 1217 | CAGGTGCAACTCCAGGAGAGCGGAGGTGGACTTGTTCAGCCCGGCGGAAGCCTT CGCCTTTCATGCACTGCCAGCGGACTGACGTTCGATGACTCAGTCATGGGCTGG TTCAGGCAGGCCCCCGGTAAGGGCCGCGAAGCCGTGTCTTGTATCTCTAGCTCC GGAGCAAACGCTTTCTACGCGGATTCCGTGAAGGGCCGTTTTACAATTAGCAGA GACAACGCCAAGAATACTCTGTACTTGCAGATGAACTCTCTGAAGCCTGAAGAT ACCGCTACCTATTACTGTAAGAGAGGCCATGCGTGTGCAGGGTATTACCCTATT CCTTACGACGATTACTGGGGTCAAGGAACCCAGGTAACCGTGTCTTCAGGGGGG GGTTCCCAGGTGCAGCTCCAGGAGTCCGGGGGAGGCAGTGTGCAAGCAGGCGAG AGCTTGCGTCTGAGTTGCCGCGCTTCCGGTTCAACTTACTCTAACTACTGTCTT GGATGGTTCCGCCAGATCACCGGCAAGGAGCGGGAGGGTGTGGCTGTCATCAAC TGGGTCGGGGGTATGCTTTACTTCGCAGACACTGTGAAGGGCCGCTTTACCGTA TCACAGGACCAAGCAAAGAACACCGTGTACCTGGAGATGAACAGTCTGAAGCCC GAAGACACCGCTATGTACTATTGTGCCACCGAATCCGTCTCATCCTTCTCCTGT GGAGGCTGGCTGACACGCCCCGACCGGGTGCCCTATTGGGGCCAGGGAACTCAG GTCACAGTCTCTAGT |
| DR596-hIL27 Ra_VH H12 | 1218 | CAGGTCCAGCTCCAGGAGTCTGGGGTGGGGCTCGTGCAGCCCGGAGGCTCTTTG AGGCTGAGCTGCACCGCGAGCGGCCTGACTTTCGACGATAGTGTGATGGGCTGG TTCCGTCAAGCCCCTGGCAAAGGCCGCGAGGCGGTTAGCTGTATCTCCTCTTCC GGGGCCAATGCCTTCTATGCTGACAGCGTGAAGGGCCGCCTTACCATCAGCCGT GACAACGCCAAGAACACTCTTTACCTTCAGATGAACTCCTTGAAGCCGGAGGAC ACCGCGACATACTATTGTAAGCGCGGCCACGCTTGTGCAGGCTATTACCCCATC CCCTATGACGATTATTGGGGACAGGGCACCCAGGTGACCGTCTCCTCAGGGGGC AGCGGAGGCTCTGGTGGCTCCGGGCAGGTGCAGCTCCAGGAGTCCGGCGGTGGC TCCGTGCAGGCTGGCGAAAGCCTGCGCCTGTCCTGTCGTGCGTCCGGCAGTACA TATAGCAACTACTGTCTCGGATGGTTCCGTCAAATTACCGGGAAGGAACGCGAG GGAGTGGCCGTTATCAACTGGGCGGGAGGCATGTTGTATTTTGCCGACAGTGTG AAAGGCAGGTTTACAGTGAGCCAGGACCAGGCCAAGAACACGGTGTATCTCGAA ATGAACAGCCTGAAGCCCGAAGACACTGCAATGTATTACTGCGCCACCGAGTCC GTTAGCTCCTTTTCATGTGGTGGGCGGCTGACACGCCCAGACCGCGTGCCATAC TGGGGTCAGGGAACCCAGGTTACCGTGAGTAGT |
| DR596-hIL27 Ra_VH H13 | 1219 | CAGGTGCAGTTGCAGGAGTCCGGTGGCGGACTCGTACAGCCAGGAGGTAGCCTT CGCCTGAGTTGCACTGCCTCCGGTCTGACCTTCGATGACTCCGTTATGGGTTGG TTCCGCCAAGCCCCAGGGAAGGGCAGAGAAGCTGTCTCTTGTATCAGCTCTAGC GGGGCCAACGCCTTCTACGCAGACTCCGTGAAGGGCCGCTTTACCATCAGTCGT GACAACGCCAAGAATACACTCCATTTGCAAATGAACTCTCTCAAGCCTGAGGAT ACCGCTACGTACTATTGCAAACGTGGACACGCTTGTGCCGGTTATTACCCTATC CCTTACGATGACTACTGGGGCCAGGGCACCCAGGTGACCGTGAGTAGCGGCGGA GGCTCTCAGGTGCAGCTCCAGGAGTCTGGTGGCGGGAGCGTCCAGGCCGGGGGG TCTCTGCGCCTGTCCTGCGTGGCTTCCGGGTATGTTTCCTGCGATTACTTTCTG CCCTCCTGGTATCGTCAGGCCCCTGGTAAGGAGCGCGAGTTCGTGAGCATCATT GATGGCACTGGATCTACTTCTTACGCAGCGAGTGTGAAGGGCCGCTTCACCGCC AGCCAGGATAGGGGAAAAAATATCGCATACCTCCAGATGAACAGCCTGAAGCCT GAGGACACTGCCATGTATTACTGCAAGGCGTCCTGTGTGAGGGGAAGGACTATC AGCGAGTATTGGGGCCAAGGTACGCAGGTGACAGTAAGCTCC |
| DR596-hIL27 Ra_VH K13 | 1220 | CAAGTTCAACTTCAGGAGAGTGGTGGAGGCCTGGTGCAGCCAGGGGGTTCCCTC AGGCTCAGCTGTACCGCAAGCGGTCTGACATTTGATGACTCCGTGATGGGATGG TTTCGCCAGGCACCCGGTAAGGGGCGTGAAGCCGTTAGTTGTATTAGTTCCAGC GGAGCCAATGCTTTCTATGCCGACTCCGTGAAGGGTAGATTCACCATCTCCCGT GACAACGCCAAAAACACGCTGTATCTTCAGATGAACTCTCTGAAGCCGGAGGAC |

TABLE 1B-continued

| Name | SEQ ID NO: | Sequence |
|---|---|---|
| | | ACGGCCACCTATTACTGTAAGCGTGGTCATGCCTGCGCGGGGTATTACCCCATC CCCTACGATGACTACTGGGGGCAGGGAACCCAGGTCACTGTTTCCAGCGGTGGC TCCGGTGGCTCAGGAGGCAGTGGCCAGGTACAGTTGCAAGAGTCTGGCGGAGGC AGCGTTCAGGCTGGCGGGTCCCTCAGACTGTCATGCGTGGCATCTGGGTATGTT TCCTGCGACTACTTCCTTCCCAGTTGGTATCGTCAAGGGGGGGGTAAGGAACGC GAATTTGTGAGTATCATTGATGGACCGGGTCTACCTCTTACGCCGCGAGCGTG AAGGGCCGCTTCACCGCGTCTCAGGATCGCGGTAAGAACATTGCCTACCTCCAG ATGAACAGTCTGAAACCAGAAGACACCGCTATGTATTACTGCAAGGCGAGCTGC GTGAGAGGCAGAACCATTTCTGAGTATTGGGGACAGGGAACTCAGGTGACCGTG TCTTCA |
| DR596-hIL27 Ra_VH H14 | 1221 | CAGGTGCAGCTCCAGGAGTCAGGTGGCGGATTGGTGCAGCCCGGTGGCAGCTTG CGCCTGTCCTGCACAGCGAGTGGCTTGACTTTCGACGATTCCGTCATGGGGTGG TTTAGACAGGCTCCTGGCAAGGGCCGTGAGGCAGTCTCCTGTATCTCTTCCAGT GGTGCTAACGCTTTTTACGCCGATAGTGTTAAGGGGAGATTCACGATCTCTCGC GACAACGCCAAGAATACGCTCTACTTGCAGATGAACTCTCTCAAGCCTGAAGAT ACCGCCACCTATTACTGCAAGCGTGGTCACGCTTGCGCAGGCTATTACCCCATC CCCTACGACGATTACTGGGGCCAGGGCACCCAGGTGACCGTCAGTTCCGGTGGG GGAAGCCAGGTCCAGCTTCAGGAGTCCGGCGGTGGCTCCGTCCAGGCAGGTGGC TCCCTGCGCCTGTCTTGCGTGGCTTCTGGGTACGTGAGCTGCGACTACTTTCTC CCCTCTTGGTATCGCCAGGCCCCCGGAAAGGAGCGCGAGTTCGTTTCTATCATT GACGGCACTGGCTCCACCAGCTATGCTGCCAGCGTGAAAGGCCGCTTTACCGCC AGCCAGGACAAAGGCAAGAACATCGCTTACCTCCAGATGAACTCCCTGAAGCCC GAAGATACCGCGATGTATTACTGTAAGGCTTCATGCGTGCGCGGCAGAGCCATC TCCGAGTACTGGGGCCAAGGCACTCAAGTTACAGTCTCTTCA |
| DR596-hIL27 Ra_VH H14 | 1222 | CAGGTGCAGTTGCAGGAGAGCGGTGGGGGCCTGGTGCAGCCCGGTGGCTCCCTG CGTCTTTCTTGCACTGCGTCCGGCTTGACTTTTGACGATAGCGTCATGGGCTGG TTCCGCCAGGCCCCTGGCAAAGGACGTGAGGCCGTGAGCTGCATCTCATCAAGT GGAGCCAACGCATTCTATGCTGACTCCGTGAAAGGCCGCTTCACCATCAGTCGG GACAACGCCAAGAACACCCTCTACTTGCAGATGAACTCCCTGAAGCCCGAGGAC ACCGCCACCTATTACTGTAAGCGCGGCCACGCTTGCGCTGGCTATTACCCGATC CCATACGATGACTACTGGGGACAAGGCACCCAGGTTACCGTGTCTTCCGGGGGC TCTGGTGGCTCAGGGGGCTCTGGCCAGGTCCAACTCCAAGAGTCTGGGGGAGGC TCTGTGCAGGGGGCGGGCTCCCTGCGTCTGAGCTGCGTAGCTTCCGGTTACGTC TCCTGCGATTACTTCCTGCCCTCCTGGTATAGGCAGGCTCCCGGCAAGGAGCGC GAGTTTGTCTCTATTATCGACGGTACAGGCTCTACCTCTTACGCCGCAAGCGTG AAGGGCCGGTTCACAGCCTCTCAGGATAAGGGTAAAAACATCGCCTACTTGCAG ATGAACAGCCTTAAACCAGAGGACACCGCCATGTACTATTGTAAGGCAAGCTGC GTGAGGGGCCGCGCCATCAGCGAGTACTGGGGCCAGGGAACGCAGGTGACCGTC AGCAGC |
| DR596 hIL27 Ra_VH H15 | 1223 | CAGGTCCAGCTCCAGGAGTCGGGCGGGGGCCTGGTCCAGCCCGGGGGGTCTCTG AGACTGTCCTGTACGGCAAGCGGGCTGACCTTCGATGACTCCGTCATGGGCTGG TTTCGTCAAGCCCCTGGTAAGGGCCGCGAGGCGGTTTCTTGCATCAGCTCCTCA GGCGCGAATGCGTTCTACGCCGACTCTGTGAAGGGTCGGTTTACTATCAGCCGC GATAATGCGAAGAACACACTGTACTTGCAAATGAACTCCCTGAAGCCTGAGGAC ACAGCCACTTATTACTGCAAACGTGGACACGCCCGCGCTGGCTATTACCCAATC CCTTACGACGATTACTGGGGCCAGGGCACCCAAGTGACCGTGAGTTCCGGCGGT GGCTCCCAAGTCCAGCTCCAGGAAAGTGGTGGCGGGTCCGTGCAGGGGGGAGGC AGCCCTAGGCTCTCTTGCGTCGCCTCTGGGTACGTCTCTTGCGACTATTTCCTC CCTTCCTGGTATCGCCAAGCGCCGGGCAAGGAGCGCGAGTTCGTCTCCATCATT GATGGCACCGGCTCCACCTCCTACGCTGCCTCCGTGAAAGGCCGCTTCACTGCC TCCCAGGACAAGGGGAAAAACATCGCCTACTTGCAGATGAACACCCTTAAACCC GAAGACACGGCCATGTATTACTGTAAAGCGTCCTGCGTGAGGGGAAGAGCAATC TCCGAGTACTGGGGCCAGGGGACCCAGGTGACAGTGTCCTCA |
| DR596-hIL27 Ra_VH H15 | 1224 | CAGGTGCAGTTGCAGGAGTCCGGTGGCGGACTGGTACAGCCCGGCGGTTCCTTG AGGCTGAGTTGTACCGCTTCCGGCTTGACTTTCGATGACTCAGTGATGGGATGG TTCAGACAAGCGCCCGGTAAGGGTCGCGAGGCGGTCAGTTGCATCAGCTCCAGT GGAGCCAATGCGTTCTACGCTGATTCTGTGAAAGGACGTTTCACCATCTCCAGG GACAATGCTAAGAATACACTGTACCTTCAGATGAACAGCCTGAAGCCTGAAGAT ACAGCTACGTATTACTGCAAGCGCGGACACGCTTGTGCAGGATATTACCCAATT CCTTATGATGACTACTGGGGTCAGGGGACCCAGGTGACTGTATCCAGGGGGGGG TCCGGCGGAAGCGGAGGCAGTGGGCAGGTGCAGCTCCAGGAGTCCGGGGGAGGC TCAGTTCAGGCCGGAGGTTCACTCAGACTGTCATGTGTGGCCTCTGGCTACGTG TCCTGTGACTACTTCCTGCCAAGTTGGTATCGGCAGGCCCCTGGCAAGGAGGGG GAGTTCGTTAGCATTATCGACGGCACGGGCAGCACCAGTTACGCTGCCTCCGTG AAAGGCAGATTCACAGCATCTCAGGATAAGGGGAAAAATATCGCCTACCTCCAG ATGAACACTCTGAAGCCCGAGGACACCGCCATGTACTATTGTAAGGCTTCATGC GTGAGAGGCCGCGCCATTAGCGAGTACTGGGGCCAGGGAACCCAGGTTACTGTC AGTTCC |
| DR596-hIL27 Ra_VH H16 | 1225 | CAGGTGCAGTTGCAGGAATCTGGCGGTGGACTGGTGCAGCCCGGAGGCTCACTG CGCCTCTCTTGTACGGCCAGCGGACTCACTTTCGATGACAGCGTGATGGGGTGG TTCCGCCAGGCCCCTGGCAAAGGCCGCGAGGCTGTCTCCTGTATCTCCAGCAGT GGTGCGAACGCCTTCTACGCTGACTCCGTGAAAGGCCGTTTCACCATCAGCCGT |

TABLE 1B-continued

| Name | SEQ ID NO: | Sequence |
|---|---|---|
| | | GATAACGCTAAGAACACACTCTACTTGCAGATGAACAGCCTGAAGCCGGAGGAC<br>ACTGCCACCTATTACTGTAAGCGCGGTCACGCATGTGCTGGCTATTACCCTATT<br>CCTTACGACGATTACTGGGGCCAGGGCACCCAGGTTACGGTGTCCTCTGGGGGG<br>GGTAGCCAGGTGCAGCTTCAGGAGTCCGGTGGAGGTTCCGTGCAGGCAGGGGGA<br>AGCCTTAGGCTGAGCTGCCGCGCTTCCGGTTCTACCTACAGCAATTACTGCCTG<br>GGGTGGTTCCGGCAGATTACAGGTAAAGAGCGCGAGGGTGTCGCCGTGATTAAC<br>TGGGTGGGCGGGATGCTTTACTTCGCTGATTCAGTGAAGGGCCGCCTCACTGTG<br>AGTCAGGACCAGGCCAAGAACACAGTGTACCTCCAGATGAACTCCCTTAAACCC<br>GAGGACACTGCAATGTACTATTGCGCTGCCGAGTCAGCGTCCTCTTTCAGTTGC<br>GGCGGATGGCTCACTCGTCCTGACCGTGTCCCTTACTGGGGCCAGGGCACGCAG<br>GTGACCGTCTCCTCC |
| DR596-<br>hIL27<br>Ra_VH<br>H16 | 1226 | CAGGTGCAGTTGCAGGAGAGCGGCGGAGGCCTGGTCCAGCCCGGAGGCAGCCTG<br>AGACTTTCTTGCACAGCTTCCGGGCTTACCTTCGATGACTCCGTCATGGGCTGG<br>TTTCGGCAGGCTCCAGGTAAGGGTAGGGAGGCTGTTAGCTGTATCAGTTCCAGC<br>GGCGCTAATGCCTTCTACGCCGACTCTGTGAAGGGCCGGCTTACCATCAGCAGA<br>GACAACGCAAAAAATACGCCCTACTTGCAGATGAACTCTCTGAAGCCCGAAGAT<br>ACCGCCACCTACTATTGCAAGAGGGGCCACGCCTGCGCCGGTTACTATCCAATC<br>CCATACGATGACTACTGGGGCCAGGGTACTCAGGTGACTGTGTCTTCCGGTGGA<br>AGGGGCGGAAGCGGGGGTAGGGGGCAGGTCCAGCTGCAAGAAAGCGGAGGGGGG<br>TCTGTGCAAGCTGGCGGTTCCCTGAGGCTGAGCTGTCGTGCATCAGGCTCAACC<br>TACTCTAACTACTGCTTGGGCGGGTTCCGCCAGATTACCGGCAAGGAGCGCGAG<br>GGCGTGGCCGTCATCAACTGGGTAGGGGGGATGCTGTATTTCGCTGATTCCGTG<br>AAGGGCCGCTTTACCGTCTCACAGGACCAGGCCAAGAACACCGTCTACCTTCAG<br>ATGAACTCCCTGAAACCTGAAGATACTGCCATGTATTACTGTGCAGCGGAGAGC<br>GCCAGCTCCTTCTCCTGTGGAGGGTGGCTGACCCGCCCGGATCGTGTTCCGTAC<br>TGGGGCCAGGGGACTCAAGTGACCGTGTCCTCC |
| DR596-<br>hIL27<br>Ra_VH<br>H17 | 1227 | CAGGTGCAGCTCCAGGAATCAGGGGGGGGACTGGTTCAGCCCGGAGGTTCTCTC<br>AGGCTCAGCTGCACTGCCTCCGGGCTTACTTTTGACGATAGCGTTATGGGCTGG<br>TTCCGCCAGGCTCCCGGCAAAGGCCGCGAGGCCGTGTCTTGTATCTCCAGCTCC<br>GGTGCCAACGCCTTCTACGCTGACTCCGTGAAGGGACGCCTTACCATCTCACGC<br>GACAACGCGAAGAACACACTTTACCTGCAAATGAACAGCTTGAAACCTGAGGAT<br>ACAGCAACCTACTATTGCAAGCGCGGTCACGCTTGCGCCGGTTATTACCCTATC<br>CCTTACGATGACTACTGGGGTCAGGGTACTCAGGTAACGGTGTCAAGTGGGGGC<br>GGGTCCCAGGTCCAGCTTCAAGAGTCCGGCGGGGGACTGGTGCAGCCCGGTGGC<br>TCTCTGAGGCTCTCTTGTGCTGCGAGCGGATTCACTTTCTCTCTGTCAGGGATG<br>TCTTGGGTGCGTCAAGCACCTGGGAAGGGCCTGGAATGGGTCTCAGCAATCTCC<br>AGCGGCGGTGCTTCCACCTATTACACTGACAGCGTGAAGGGCAGGTTTACCATC<br>TCCAGAGACAACGCCAAGAACATGCTGTATCTCCAGTTGAACTCACTGAAAACC<br>GAGGATACAGCCATGTATTACTGTGCCAAAGGAGGGAGCGGCTACGGTGATGCC<br>TCTCGTATGACCAGCCCCGGCTCCCAGGGAACCCAGGTGACGGTGTCTTCC |
| DR596-<br>hIL27<br>Ra_VH<br>H17 | 1228 | CAGGTCCAGCTCCAGGAGTCTGGGGGGGGCCTGGTCCAGCCTGGGGGTAGCCTG<br>AGACTGTCCTGCACTGCTTCTGGTCTTACCTTTGATGACAGCGTGATGGGCTGG<br>TTTAGACAAGCGCCCGGCAAAGGCCGCGAAGCCGTGAGTTGTATCTGCTCTAGC<br>GGCGCGAACGCATTCTACGCTGACTCTGTCAAGGGCCGGTTCACCATTTCCAGG<br>GATAACGCCAAGAACACCCTGTACCTTCAGATGAACAGCCTGAAACCCGAAGAC<br>ACCGCCACTTATTACTGCAAGCGGGGCCACGCCTGTGCTGGCTATTACCCTATT<br>CCTTACGACGATTACTGGGGCCAGGGCACCCAGGTAACTGTCTCTTCAGGCGGA<br>AGCGGCGGTTCCGGGGGGTCTGGGCAGGTGCAGTTGCAAGAGTCCGGCGGTGGG<br>CTGGTCCAGCCGGCGGGCTCACTCCGCTTGTCCTGCGCGGCTTCAGGATTTACT<br>TTCAGTCTGAGTGGTATGAGCTGGGTACGCCAGGCACCCGGCAAGGGCCTGGAG<br>TGGGTGTCCGCCATTTCCTCTGGCGGAGCGAGCACATACTATACCGATTCAGTG<br>AAAGGGGGTTTTACTATCTCTCGCGATAATGCCAAGAACATGCTGTACCTCCAG<br>CTCAACTCTCTGAAGACTGAGGACACCGCCATGTACTATTGCGCCAAAGGCGGA<br>AGTGGATACGGTGACGCCTCAAGGATGACTTCCCCTGGTTCCCAGGGCACGCAG<br>GTGACCGTGAGTAGC |
| DR596-<br>hIL27<br>Ra_VH<br>H18 | 1229 | CAGGTGCAGCTCCAGGAATCCGGTGGCGGGACTCGTCCAGCCAGGGGGTCACTG<br>CGTCTCTCCTGTACCGCGAGTGGACTGACATTCGATGACTCCGTGATGGGGTGG<br>TTCCGCCAGGCCCCCGGCAAGGGCCGCGAGGCGGTGTCTTGCATTTCTAGCTCC<br>GGGGCCAATGCGTTTTACGCTGACTCTGTGAAGGGCAGATTCACTATCAGCAGA<br>GACAACGCGAAGAACACGCTGTATCTGCAAATGAACTCTCTGAAACCCGAGGAT<br>ACTGCCACATACTATTGTAAGCGCGGCCACGCCTGCGCAGGCTACTATCCTATT<br>CCTTACGATGACTACTGGGGCCAGGGAACACAGGTCACCGTTAGCTCAGGGGGA<br>GGCTCCCAGGTGCAGCTCCAGGAGAGCGGAGGTGGCAGCGTCCAGGCTGGCGGA<br>TCTCTGCGCCTGTCTTGTGTCGCCAGCGGATACGTGAGCTGTGACTACTTCCTG<br>CCTAGCTGGTATCGTCAAGCGCCGGGGAAGGAAAGGGAGTTCGTGTCCATTATC<br>GACGGTACTGGGTCTACCTCATACGCGGCCTCCGTCAAGGGCCGTTTCACGGCC<br>TCCCAGGACAAGGGGAAAAACATCGCATATCTGCAAATGAACTCTCTGAAGCCT<br>GAGGACACCGCAATGTATTACTGCAAGGCCTCCCGTGTACGCGGACGTGGAATC<br>TCTGAGTATTGGGGCCAGGGGACCCAGGTGACCGTGTCTTCC |
| DR596-<br>hIL27<br>Ra_VH | 1230 | CAGGTGCAGCTCCAGGAATCCGGGGGCGGTCTGGTTCAGCCAGGTGGCTCTCTC<br>CGTCTGAGCTGCACCGCTTCCGGTCTCACATTCGACGATTCCGTAATGGGGTGG<br>TTCCGCCAGGCCCCTGGAAAAGGTCGCGAGGCCGTGTCTTGCATTTCTTCCAGC |

TABLE 1B-continued

| Name | SEQ ID NO: | Sequence |
|---|---|---|
| H18 | | GGGGCGAACGCATTCTACGCAGACTCTGTGAAGGGTCGTTTTACAATCTCCCGC<br>GACAACGCGAAGAACACCCTTTACTTGCAAATGAACTCCCTCAAGCCCGAGGAC<br>ACCGCGACCTACTATTGCAAGCGTGGCCATGCTTGCGCCGGGTATTACCCCATC<br>CCCTATGATGACTACTGGGGACAGGGAACCCAAGTGACAGTTTCTAGCGGAGGC<br>AGTGGTGGCAGCGGTGGGTCCGGCCAGGTGCAGTTGCAAGAGAGTGGCGGAGGC<br>TCTGTCCAAGCTGGCGGTTCCCTCCGCCTGTCCTGCGTGGCCTCTGGCTACGTT<br>AGCTGCGACTATTTCCTGCCTTCATGGTATCGTCAGGCCCCAGGGAAAGAAAGG<br>GAGTTCGTTAGCATCATTGATGGAACTGGCTCCACCTCCTATGCTGCAAGCGTG<br>AAGGGTCGGTTCACCGCCTCCCAGGATAAGGGCAAGAATATCGCTTATTTGCAG<br>ATGAACTCTCTGAAGCCAGAGGATACCGCCATGTACTATTGCAAGGCATCCTGC<br>GTGCGGGGACGCGGGATCAGCGAATATTGGGGCCAGGGAACTCAGGTGACCGTC<br>AGTTCT |
| DR596-<br>hIL27<br>Ra_VH<br>H19 | 1231 | CAGGTTCAGCTCCAGGAAAGCGGAGGCGGTCTCGTACAGCCTGGCGGTTCCCTG<br>AGGCTGTCCTGCACCGCCAGCGGACTCACGTTTGACGATAGTGTAATGGGATGG<br>TTCAGGCAGGCTCCCGGCAAGGGCCGCGAGGCCGTAAGTTGCATCTCCAGCTCA<br>GGTGCCAATGCGTTCTATGCCGACTCCGTGAAGGGTAGATTCACCATCAGCCGT<br>GATAACGCGAAAAACACGCTCTACCTCCAGATGAACTCACTGAAGCCTGAGGAC<br>ACGGCCACATATTACTGCAAGAGGGGCCACGCCTGTGCTGGGTATTACCCCATC<br>CCCTATGATGACTACTGGGGCCAGGGGACACAAGTGACCGTGTCCAGCGGGGGC<br>GGAAGCCAGGTGCAGTTGCAGGAATCCGGGGGTGGCAGCGTGCAGGCTGGTGGG<br>TCTCTCAGGCTCAGTTGTAGGGCCTCTGGTTCCACCTACAGCAACTACTGTCTG<br>GGCTGGTTCCGTCAGATCACTGGTAAAGAGAGGGAGGGCGTGGCAGTCATCAAC<br>TGGGTTGGCGGAATGTTGTATTTCGCTGACTCTGTCAAGGGCAGATTCACCGTC<br>TCCCAGGATCAGGCTAAGAACACAGTATACTTGCAGATGAACTCCCTGAAGCCC<br>GAGGATACTGCTATGTATTACTGTGCCGCAGAAAGCGTGTCCTCTTTCTCTTGC<br>GGTGGCTGGCTGACACGCCCTGACAGAGTCCCTTATTGGGGTCAGGGGACCCAG<br>GTAACGGTATCTTCC |
| DR596-<br>hIL27<br>Ra_VH<br>H19 | 1232 | CAGGTCCAGCTGCAAGAAAGCGGCGGAGGCCTGGTGCAGCCTGGCGGTTCTCTC<br>CGTCTGAGCTGTACCGCCTCTGGCCTGACATTCGATGACTCCGTTATGGGTTGG<br>TTCCGCCAAGCGCCTGGGAAAGGAAGGGAGGCAGTGAGCTGTATTTCTAGCTCT<br>GGAGCCAATGCTTTCTATGCTGATAGCGTGAAGGGGCGGTTCACTATCTCAAGG<br>GACAACGCCAAGAATACACTGTATCTTCAGATGAACAGCCTGAAGCCAGAGGAT<br>ACAGCCACCTATTACTGTAAGCGCGGACATGCCTGTGCTGGCTATTACCCGATT<br>CCCTACGACGATTACTGGGGCAAGGAACTCAGGTTACTGTGAGTTCCGGGGGG<br>TCTGGGGGCTCAGGGGGTTCCGGCCAGGTACAACTCCAGGAGAGCGGCGGAGGC<br>TCCGTACAGGCCGGGGGCAGCCTGAGACTGAGCTGTCGCGCGAGCGGCAGTACC<br>TACAGCAATTACTGCCTGGGCGGGTTCCGCCAGATTACTGGGAAGGAGCGGGAA<br>GGCGTCGCAGTGATAAATTGGGTCGGTGGAATGCTCTACTTCGCCGATAGCGTC<br>AAGGGACGCTTCACCGTGAGTCAGGATCAGGCCAAAAACACCGTTTATCTTCAG<br>ATGAACTCCTTGAAGCCGGAAGACACAGCAATGTACTATTGCGCCGCTGAAAGT<br>GTCTCCAGCTTCAGCTGCGGAGGGGGCTCACCCGCCCGGATCGCGTGCCTTAC<br>TGGGGGCAGGGCACCCAGGTCACTGTGTCCTCT |
| DR596-<br>hIL27<br>Ra_VH<br>H20 | 1233 | CAGGTGCAGTTGCAGGAGTCCGGGGGAGGCCTCGTGCAGCCTGGGGGCTCCCTG<br>CGCCTCTCTTGTACTGCGTCAGGTCTGACTTTTGACGATTCTGTTATGGGATGG<br>TTCCGGCAAGCGCCCGGCAAGGGCCGCGAGGCGGTGAGTTGCATCTCCAGCTCT<br>GGCGCAAACGCTTTCTATGCTGACAGTGTGAAGGGCCGTTTTACAATTTCCAGG<br>GACAATGCCAAGAATACACTGTACCTCCAGATGAACAGTCTGAAACCCGAAGAT<br>ACCGCAACCTATTACTGCAAGCGCGGCCACGCTTGCGCCGGATACTATCCAATC<br>CCCTATGATGACTACTGGGGCCAGGGCACGCAGGTCACCGTGAGTAGCGGGGGT<br>GGCTCCCAGGTTCAGCTTCAGGAGTCAGGTGGAGGCCTGGTTCAGCCAGGTGGC<br>AGCCTGCGCTTGAGCTGCGCGGCCAGCGGTTTCACCTTTAGCTCTTACCCGATG<br>TCTTGGGTCAGACAGGCTCCCGGCAAGGGCCTGGAGTGGGTGTCTACCATCTCT<br>TCCGGGGGCGATACCACTCAGTACGCGGATTCCGTGAAAGGTCGCTTTACCTCC<br>TCTAGGGATAATGCTAAAAATACGCTGTACCTCCAGCTTAATTCCCTGAAGACA<br>GAAGATACCGCCATGTATTACTGCGCGAAGCGCATCGACTGCAACTCCGGGTAC<br>TGTTACAAACGCAGCTATTGGGGCCAGGGAACACAGGTGACCGTGTCCTCC |
| DR596-<br>hIL27<br>Ra_VH<br>H20 | 1234 | CAGGTGCAACTTCAGGAATCCGGGGGGGGCTTGGTGCAGCCAGGCGGGTCTCTC<br>CGCCTGTCCTGCACGGCCTCTGGCCTGACCTTTGACGATTCCGTGATGGGCTGG<br>TTTCGCCAAGCGCCAGGCAAGGGGGGGGGAGGCCGTTAGTTGCATCAGTTCCTCT<br>GGAGCCAACGCTTTCTACGCCGACTCCGTCAAGGGCCGTTTCACCATCAGCAGA<br>GACAACGCCAAGAATACACTGTATCTCCAGATGAACAGCCTCAAACCGGAGGAC<br>ACGGCCACCTACTATTGTAAGCGCGGTCACGCATGTGGGGGGTATTACCCAATC<br>CCGTATGATGACTACTGGGGTCAGGGCACCCAGGTCACCGTTAGCTCCGGTGGA<br>TCTGGCGGAAGCGGGGGCAGCGGACAGGTCCAGCTCCAGGAGAGCGGGGCGGGA<br>CTGGTTCAGCCTGGGGGGTCTCTGCGTCTGTCCTGCGCCGCTTCAGGCTTCACC<br>TTTTCATCTTATCCGATGTCCTGGGTCAGACAAGCCCCAGGTAAGGGGCTGGAG<br>TGGGTTTCTACGATTAGCTCTGGTGGCGATACCACACTGTACGCGGACAGCGTG<br>AAGGGGCGGTTCACCAGCTCAAGAGACAACGCCAAAAACACCTTGTACCTCCAG<br>CTGAACTCCCCGAAGACCGAGGACACCGCCATGTATTACTGCGCCAAGAGAATT<br>GACTGTAACAGCGGTTATTGTTATAAAAGATCCTACTGGGGCCAGGGAACCCAG<br>GTGACAGTCAGTTCT |

TABLE 1B-continued

| Name | SEQ ID NO: | Sequence |
|---|---|---|
| DP596-hIL27Ra_VH H21 | 1235 | CAGGTGCAGTTGCAGGAGAGCGGTGGAGGCCTGGTCCAGCCAGGTGGCTCTCTG<br>CGGCTGAGCTGCACCGCTTCTGGTCTGACCTTTGATGACAGCGTGATGGGGTGG<br>TTCCGCCAGGCTCCCGGAAAGGGGCGCGAAGGTGTGTCCTGCATCAGCTCCTCT<br>GGTGCCAACGCCTTTTACGCTGATTCCGTGAAGGGTCGCTTCACCATTAGCCGC<br>GACAACGCAAAGAATACCCTCTACTTGCAGATGAACAGCTTGAAGCCCGAGGAC<br>ACAGCGACCTATTACTGTAAGCGCGGCCATGCGTGCGCAGGCTACTATCCGATC<br>CCCTATGATGACTACTGGGGCCAGGGAACCCAGGTGACTGTCTCTTCCGGTGGC<br>GGTTCCCAGGTCCAGCTTCAGGAGAGCGGTGGCGGACTGGTTCAGCCCGGGGGG<br>AGCCTCAGGTTGAGCTGTGCCGCTAGTGGCTTCACCTTCCCCCTCTCTAGCATG<br>AGCTGGGTTCGTCAGGCCCCAGGCAAAGGGCTCGAATGGGTCAGCGCAATCTCC<br>AGCGGGGGTGCCTCCACCTATTACACAGACTCTGTGAAAGGAAGATTCACTATC<br>TCACGTGACAATGCTAAAAACATGCTGTACCTTCAGCTGAACAGCCTGAAGACC<br>GAGGATACCGCTATGTACTATTGTGCCAAGGGTGGCTCCGGCTATGGCGACGCA<br>TCACGCATGACCTCTCCGGGCTCCCAAGGAACCCAAGTTACCGTATCTTCA |
| DR596-hIL27Ra_VH H21 | 1236 | CAGGTGCAGCTCCAGGAGTCCGGTGGAGGCCTGGTACAACCCGGGGGTTCCCTG<br>CGCCTGTCCTGCACAGCAAGCGGGCTTACTCTTGATGACAGTGTCATGGGATGG<br>TTCCGCCAAGCGCCCGGTAAGGGCAGGGAGGCTGTCAGCTGTATCAGTTCCAGC<br>GGGGCTAATGCGTTTTATGCCGATAGTGTCAAGGGCCGGTTTACCATCAGCCGC<br>GACAACGCCAAAAACACCCTGTATTTGCAGATGAATAGCCTCAAACCAGAGGAC<br>ACAGCGACCTATTACTGTAAGCGCGGTCATGCGTGCGCGGGCTATTACCCGATT<br>CCTTACGACGATTATTGGGGACAGGGCACCCAGGTGACCGTCAGCTCCGGTGGC<br>AGTGGCGGTTCCGGTGGCTCCGGCCAGGTGCAGCTTCAGGAGAGCGGTGGGGGG<br>CTGGTGCAGCCCGGAGGTTCCCTCCGCCTGTCCTGTGCTGCCAGCGGCTTCACA<br>TTTTCCCTGTCATCCATGAGCTGGGTGCGCCAGGCACCCGGTAAGGGACTGGAA<br>TGGGTTTCTGCGATTTCTTCCGGCGGTGCCTCCACCTACTATACCGATAGCGTC<br>AAGGGGCGGTTTACGATTTCCAGAGACAACGCCAAGAATATGCTGTACCTTCAG<br>CTCAATTCTCTTAAAACCGAGGACACCGCCATGTATTACTGTGCTAAAGGGGGC<br>TCTGGATATGGTGATGCCTCACGCATGACATCCCCTGGATCTCAGGGCACCCAG<br>GTAACCGTGTCCTCA |
| DR596-hIL27Ra_VH H22 | 1237 | CAGGTCCAACTCCAGGAGAGCGGTGGAGGCTTGGTGCAGCCCGGCGGGTCCCTG<br>CGGCTGTCTTGCACTGCTAGTGGACTGACCTTCGACGATTCCGTGATGGGGTGG<br>TTCCGCCAAGCTCCGGGAAAGGGCCGCGAGGCCGTGAGTTGCATTTCCTCCAGT<br>GGTGCAAACGCCTTTTATGCGGACAGCGTTAAAGGACGGTTCACCATCTCACGC<br>GATAACGCGAAGAATACACCGTATCTTCAGATGAACTCCCTGAAGCCCGAGGAT<br>ACCGCTACCTACTATTGTAAGAGGGGTCATGCGTGTGGGGGATACTATCCAATC<br>CCGTATGACGATTATTGGGGTCAAGGCACTCAGGTTACTGTGTCTTCCGGTGGA<br>GGGTCCCAGGTGCAGTTGCAGGAGTCAGGAGGCGGTAGCGTGCAGGCCGGAGGG<br>AGCCTGCGCCTTGTCTGTCGCGCATCCGGGAGCACATATTCAAATTATTGTCTC<br>GGGGGTTCCGCCAAACCACAGGCAAGGAACGCGGAGGGCGTGGCTGTAATCAAC<br>TGGGTCGGTGGAATGCTCTACTTTGCTGACCCTGTGAAAGGCCGCTTCACTGTC<br>TCCCAGGACCAGGCCAAGAACACCGTTTATCTTCAGATGAACTCCCTGAAGCCC<br>GAAGACACCGCCATGTATTACTGCGCTGCCGAGAGCGTCTCCAGCTTCTCCTGC<br>GGCGGATGGCTGACCCGTCCTGATAGAGTGCCCTATTGGGGCCAAGGCACCCAG<br>GTTACCGTGTCCAGC |
| DR596-hIL27Ra_VH H22 | 1238 | CAGGTGCAGCTCCAGGAGAGTGGGGGCGGCTTGGTGCAGCCAGGCGGATCTCTG<br>AGGCTGTCTTGCACAGCGAGCGGCCTGACATTCGATGACTCCGTGATGGGCTGG<br>TTTCGCCAGGCCCCCGGCAAGGGCCGCGAGGCCGTCTCCTGTATCAGTTCATCT<br>GGAGCAAACGCCTTTTACGCTGATTCCGTGAAGGGACGCTTTACCATTAGCCGG<br>GACAACGCCAAGAACACCCTCTACCTCCAGATGAACAGCCTGAAGCCTGAAGAT<br>ACCGCAACGTATTACTGTAAGAGAGGCCATGCTTGTGGGGGTTACTATCCAATC<br>CCCTATGACGATTACTGGGGTCAGGGCACCCAAGTCACCGTGTCTAGCGGAGGG<br>TCTGGAGGCTCCGGCGGTAGCGGTCAGGTGCAGCTCCAGGAATCTGGTGGCGGA<br>AGCGTGCAGGGGGGCGGTAGCCTGCGCCTGAGCTGTCGCGCCAGCGGTAGCACC<br>TACAGCAATTATTGTCTCGGCTGGTTTCGTCAGACCACTGGCAAGGAACGGGAA<br>GGCGTTGCCGTTATCAACTGGGCGGGCGGTATGCTGTACTTCGCCGATAGTGTG<br>AAGGGTCGCTTCACCGTGTCCCAGGACCAGGCTAAGAACACTGTGTATCTCCAG<br>ATGAACTCCTTGAAGCCCGAGGACACCGCGATGTACTATTGCGCCGCTGAGTCT<br>GTCAGCTCTTTTTCCTGGGGGGGGTGGCTGACGCGGCCCGACCGGGTGCCATAT<br>TGGGGCCAAGGTACTCAGGTGACCGTTAGCAGT |
| DR596-hIL27Ra_VH H23 | 1239 | CAGGTGCAGCTTCAGGAATCCGGCGGAGGCCTGGTGCAACCTGGAGGTAGCTTG<br>CGTCTGTCATGCACAGCCAGTGGACTTACTTTCGACGATAGCGTGATGGGTTGG<br>TTCCGGCAGGCTCCTGGCAAGGGCCGTGAGGCCGTGAGCTGCATCTCCAGCTCC<br>GGTGCCAATGCCTTTTACGCTGATTCCGTCAAAGGACGGTTCACTATCTCCCGC<br>GATAACGCCAAAAACACATTGTATCTCCAGATGAATAGTCTGAAGCCGGAGGAT<br>ACCGCAACCTATTACTGCAAGCGCGGCCACGCTTGCGCAGGATACTATCCTATC<br>CCTTATGACGATTATTGGGGACAGGGAACACAAGTGACGGTGTCCTCTGGCGGA<br>GGTTCCCAGGTGCAGTTGCAGGAGTCTGGGGGCGGGTCCGTCCAGGCCGGAGGC<br>AGCCTGCGCCCTTCCTGTCGCGCCAGCCGCTCCCCCTACGGGAACTATTGTCTG<br>GGCTGGTTTCGCCAGTCCACTGGTAAGGAAAGAGAGGGCGTAGCCGTGATAAAT<br>TGGGTCGGGGGTATGTTGTACTTCGCTGACAGCGTTAAGGGAAGATTCACCGTG<br>AGCCAGGATCACGCGAAGAACACCGTCACCCTCCAGATGAACTCTCTCAAGCCC<br>GAGGATACAGCTATGTATTACTGTGCCGCTGAGTCCGTTAGCTCCTTTTCATGC |

TABLE 1B-continued

| Name | SEQ ID NO: | Sequence |
|---|---|---|
| | | GGCGGATGGCTGACCCGCCCCGACCGTGTCCCCTATTGGGGCCAGGGCACCCAAGTTACTGTGAGTTCT |
| DR596-hIL27Ra_VH H23 | 1240 | CAAGTGCAGCTCCAGGAGTCTGGGGGCGGTCTTGTTCAGCCAGGAGGCTCTTTGCGGCTGTCCTGTACCGCTTCCGGCCTGACATTCGATGACTCTGTCATGGGGTGGTTCAGACAAGCCCCTGGGAAGGACGCGAAGCCGTGAGCTGCATCTCTAGCTCCGGGGCTAACGCCTTTTACGCGGACTCCGTGAAAGGAAGATTCACCATCTCCAGAGACAACGCCAAGAACACACACTACCTCCAGATGAACTCCCTGAAACCCGAGGACACCGCCACCTATTACTGCAAGCGCGGCCATGCGTGCGCGGGCTATTACCCTATTCCTTATGATGACTACTGGGGGCAGGGGACACAGGTGACCGTTTCTAGCGGCGGTTCCGGTGGCTCCGGCGGTTCTGGGCAGGTCCAGCTCCAGGAGAGCGGTGGAGGCTCAGTGCAGGCTGGGGGCTCACTGAGACTGTCCTGCCGCGCCTCCCGCTCTCCGTATGGCAACTACTGCCTTGGCTGGTTTCGCCAGAGCACTGGTAAGGAACGTGAGGGAGTCGCCGTCATCAACTGGGCGGGAGGGATGCTGTATTTCGCTGACAGCGTGAAGGGCCGCTTCACTGTGTCCCAGGACCACGCGAAGAACACAGTGACCCTGCAAATGAATAGTCTCAAACCAGAAGACACTGCTATGTATTACTGTGCTGCCGAATCCGTCAGCTCTTTCAGCTGCGGTGGATGGCTGACAAGGCCAGATCGGGTGCCTTACTGGGGTCAGGGCACCCAGGTGACCGTTAGCAGC |
| DR596-hIL27Ra_VH H24 | 1241 | CAGGTGCAGTTGCAGGAATCCGGGGGGGGATTGGTGCAACCTGGGGGCTCCCTGCGCTTGTCCTGTACTGCAAGCGGACTGACCTTCGATGACTCTGTTATGGGCTGGTTTCGCCAAGCTCCGGGTAAAGGGAGGGAAGCAGTGTCCTGTATCAGCTCCAGCGGGGCCAATGCTTTCTACGCGGATAGCGTGAAGGGTCGTTTTACTATTAGCCGCGACAATGCAAAGAACACCCTGTACTTGCAGATGAACTCACTCAAGCCCGAAGATACAGCCACTTACTATTGTAAGCGCGGCCACGCCCGCGCCGGATATTACCCAATCCCTTACGATGACTACTGGGGCCAGGGCACACAGGTTACCGTGAGTTCTGGCGGTGGCAGTCAGGTGCAGCTCCAGGAGAGCGGGGGTGGCTTGGTGCAGCCGGGAGGCTCTCTGAGGCTGTCCTGTGCTGCCTCAGGTTTCACCTTTTCCCACTCCGGCATGTCCTGGGTGCGCCAGGCCCCCGGCAAGGGTCTGGAATGGGTGAGTACCATCAACAGTGGGGGCGCAAGTACCTACTATACCGACTCTGTTAAGGGACGCTTCACTATCAGCCGCGACAACGCTAAGAACATGCTGTACCTCCAGTTGAACAGCCTTAAAACCGAAGACACGGCCATGTATTACTGCGCGAAAGGGGGCTCTGGCTACGGCGACGCGAGCAGGATGACCAGTCCCGGTTCCCAGGGCACACAGGTGACTGTTAGCAGC |
| DR596-hIL27Ra_VH H24 | 1242 | CAGGTGCAGTTGCAGGAATCTGGGGGTGGCCTGGTGCAACCTGGGGGCAGCCTGCGCCTGAGCTGCACCGCCAGCGGTCTGACCTTCGACGATTCCGTGATGGGATGGTTCCGCCAGGCTCCTGGAAAGGGAAGGGAAGCTGTGAGCTGCATCAGCTCATCCGGCGCGAACGCCTTCTACGCCGATTCTGTGAAGGGCCGTTTTACCATCAGCAGAGACAACGCCAAGAACACTCTTTATTTGCAGATGAACTCCCTGAAACCAGAGGATACAGCAACCTATTACTGTAAGAGGGGTCACGCCCGCGCCGGTTATTACCCCATTCCGTATGACGATTACTGGGGACAGGGCACCCAGGTAACCGTGTCCTCAGGTGGCAGTGGTGGCTCCGGGGGGAGCGGTCAGGTGCAACTCCAGGAGAGCGGGGGGGGCCTGGTCCAGCCCGGTGGCTCCCTGCGTCTGTCCTGCGCGGCCTCTGGGTTCACTTTCAGCCATTCCGGCATGAGCTGGGTCCGCCAGGCCCCTGGCAAGGGTCTGGAGTGGGTTAGCACGATCAACTCAGGGGGGGGCCAGCACTTATTACACCGACTCCGTGAAGGGACGCTTCACCATCTCTCGTGACAATGCTAAGAACATGCTGTATTTGCAGCTGAACTCCCTGAAGACTGAGGACACTGCCATGTACTATTGCGCCAAAGGTGGGTCCGGTTACGGTGACGCGAGCAGAATGACCTCACCTGGGAGCCAGGGCACGCAGGTGACCGTGTCCTCT |
| hIL27Ra_VH H1-DR591 | 1243 | CAGGTGCAGCTGCAAGAGTCTGGGGGGGGCCTGGTGCAGCCTGGAGGCAGCCTGCGCCTGAGCTGTGCGGCATCAGGATTCACGTTTAGCCCCTACCCTATGTCTTGGGTCAGACAGGCACCGGGAAAGGGTTTGGAGTGGATCTCCACAATTTCCGCTGGTGGCGACACCACTCTCTACGCTGATTCTGTGAAGGGCCGCTTCACCTCATCTCGCGACAACGCTAAGAACACCTTGTACCTGCAACTGAACTCTCTCAAGACCGAGGACGCCGCAATTTACTATTGCGCCAAGCGTATTGATTGCAATTCCGGTTACTGCTACCGTAGGAACTACTGGGGCCAGGGTACTCAGGTCACAGTGTCTAGTGGTGGCGGTTCCCAAGTGCAGCTCCAGGAATCTGGAGGTGGGTCTGTGCAGGCTGGAGGCAGCCTGAGGCTGAGCTGTACCGCATCCGGGGCAATCGCCTCTGGCTACATCGACTCCCGCTGGTGCATGGCCTGGTTTCGCCAGGCTCCCGGCAAAGAGCGCGAGGGCGTGGCCGCAATCTGGCCTGGGGGGGGCCTGACCGTTTATGCCGACAGCGTCAAGGGACGCTTCACTATTAGCCGGGACCACGCTAAAAACACACTGTACCTTCAGATGAATAACCTCAAACCGGAGGACACTGCGATGTACTATTGCGCGGCAGGATCACCCCGCATGTGTCCCCCCCGGAGTTCGGTTTCGATTACTGGTGGGCAGGGCACCCAGGTTACCGTAAGTTCC |
| hIL27Ra_VH H1-DR591 | 1244 | CAAGTCCAGCTCCAAGAGAGCGGCGGTGGCCTGGTGCAACCTGGGGGCTCCCTGCGCCTGTCTTGCGCTGCATCCGGGTTCACCTTCTCTAGCTACCCGATGTCTTGGGTGCGTCAGGCTCCGGGTAAGGGCCTGGAATGGATCAGTACCATCCCAGCCGGAGGCGATACCACTCTGTATGCCGATTCTGTGAAAGGCCGCTTTACCTCCAGCCGTGATAACGCAAAGAACACTTTGTACCTCCAGCTGAACTCATTGAAGACTGAGGATGCGGCCATTTATTACTGTGCAAAACGCATTGATTGTAATTCCGGCTACTGCTACCGCCGTAACTATTGGGGTCAAGGTACACAGGTAACCGTGTCCAGTGGTGGCTCTGGCGGTAGTGGTGGGTCTGGCCAGGTGCAGCTTCAGGAAAGTGGTGGAGGTAGCGTGCAAGCTGGAGGCTCCCTGAGGCTCAGCTGTACCGCCTCTGGAGCAATCGCCTCCGGCTACATCGACAGCCGCTGGTGCATGGCTTGGTTCCGCCAGGCTCCAGGGAAGGAGAGGGAAGGTGTGGCTGCAATTTGGCCTGGAGGGGGCTTGACGGTGTAT |

TABLE 1B-continued

| Name | SEQ ID NO: | Sequence |
|---|---|---|
| | | GCTGATAGCGTCAAGGGACGCCTCACCATTTCCAGGGATCACGCGAAAAACACC CTGTACCTGCAAATGAATAACCTGAAACCCGAGGACACCGCAATGTATTACTGC GCTGCGGGTTCCCCGCGCATGTGTCCTTCTCTGGAGTTCGGGTTCGATTACTGG GGGCAGGGTACACAAGTTGACTGTGTCCTCT |
| hIL27 Ra_VH H1-DR592 | 1245 | CAGGTGCAGCTCCAGGAATCAGGGGGTGGACTGGTCCAACCCGGAGGGTCCCTG CGGCTTTCCTGCGCCGCAAGCGGATTTACTTTCTCCTCTTACCCAATGAGCTGG GTGCGCCAAGCGCCAGGGAAGGGTCTGGAGTGGATCTCTACAATTAGTGCGGGG GGTGACACCACACTCTACGCTGACAGCGTCAAGGGTCGGTTTACCTCCTCTCGC GACAACGCCAAGAACACTCTGTATCTTCAGCTGAACTCCCTGAAAACCGAAGAC GCGGCAATTTACTATTGCGCTAAGCGGATCGACTGCAACTCCGGCTACTGTTAC CGTCGGAACTACTGGGGCCAGGGCACACAAGTTACCGTCAGCTCCGGTGGCGGT TCACAAGTACAGCTCCAGGAGTCCGGGGGGGGCAGTGTGCAGGCTGGTGGCTCC CTGCGCCTGTCCTGCACGGCTCCCGGCTTCACGTCCAACTCATGCGGTATGGAT TGGTATCGGCAGGCTCCTGGAAAGGAACGCGAATTTGTGAGTTCAATTTCTACT GACGGCACCACGGGCTACGCTGACAGCGTCAAGGGCAGATTTACTATTTCCAAA GATAAGGCCAAGGATACCGTGTATCTCCAAATGAATAGCTTGAAGCCTGAGGAT ACGGGGATGTACTCTTGCAAGACCAAGGACGGCACCATCGCAACTATGGAACTC TGTGATTTCGGCTATTGGGGGCAAGGGACACAGGTGACCGTCAGCTCT |
| HIL27 Ra_VH H1-DR592 | 1246 | CAAGTACAGCTTCAGGAGTCTGGGGGGGGCCTCGTCCAGCCCGGAGGCAGCCTG CGGTTGTCCTGTGCCGCATCCGGGTTCACCTTCTCCTCTTACCCAATGTCTTGG GTGCGCCAGGCCCCAGGTAAGGGATTGGAGTGGATCTCCACCATCTCTGCGGGC GGAGACACGACTCTTTACGCCGACAGCGTTAAGGGCCGGTTTACCTCTTCCCGC GATAACGCCAAAAACACTCTGTATCTTCAGCTGAACAGTCTGAAGACCGAGGAT GCCGCTATTTATTACTGTGCTAAGCGCATCGACTGCAACAGCGGATATTGCTAC GGGAGGAACTACTGGGGGCAGGGCACCCAGGTTACTGTCAGCTCAGGCGGTTCC GGGGGCTCTGGGGGCTCCGGGCAGGTGCAGCTCCAGGAGTCCGGCGGAGGCAGT GTCCAAGCAGGAGGTTCACTGCGTCTGTCCTGTACCGCCCCCGGTTTTACATCA AACTCATGTGGCATGGACTGGTATCGCCAGGCCCCCGGTAAGGAACGCGAATTT GTCTCAAGCATTTCCACTGACGGCACCACTGGTTACGCTGACTCCGTGAAGGGC CGTTTCACAATCTCCAAGGACAAGGCCAAGGACACCGTGTACCTTCAGATGAAC AGCTTGAAGCCAGAAGACACGGGTATGTACTCTTGCAAGACCAAGGACGGGACC ATCGCTACAATGGAGTTGTGTGACTTCGGTTACTGGGGGCAGGGCACGCAAGTC ACCGTTTCCTCC |
| hIL27 Ra_VH H1-DR593 | 1247 | CAGGTTCAGCTCCAGGAAAGTGGAGGCGGTCTCGTGCAGCCGGTGGGATCTCTT AGACTGAGCTGTGCGGCCAGCGGCTTCACTTTCTCTAGCTACCCCATGTCCTGG GTGCGGCAGGCTCCGGGTAAGGGCCTGGAGTGGATCTCCACCATTTCCGCAGGA GGCGATACTACCCCGTATGCCGACTCTGTCAAAGGCCGGTTCACCTCATCCCGC GACAACGCCAAGAACACTCTGTACCTCCAGCTCAACTCCCTGAAGACCGAAGAC GCCGCTATCTACTATTGTGCCAAGCGCATCGACTGTAATTCCGGCTACTGTTAT AGACGTAACTACTGGGGTCAGGGAACACAGGTTACTGTGTCCTCTGGCGGAGGT TCTCAGGTTCAGCTTCAGGAGTCAGGTGGAGGTTCTGTGCAGGCAGGGGGGAGC TTGAGACTCTCCTGTGCGGCCAGCGGATACCCTTACTCAAATGGCTATATGGGA TGGTTCAGGCAGGCTCCCGGAAAGGAGAGGGAGGGCGTGGCGACTATCTACACA GGGGACGGTAGGACTTATTACGCAGACAGCGTCAAAGGGAGGTTTACTATCTCA CGTGACAATGCGAAGAACACAGTGGACCTCCAAATGTCCAGCCTGAAGCCAGAG GATACTGCCATGTATTACTGTGCAGCTAGGGGGGCACCCCTCTACTCTAGTGGC TCTCCCTTGACACGGGCGAGGTACAATGTTTGGGGTCAGGGGACCCAGGTGACT GTGTCCTCA |
| hIL27 Ra_VH H1-DR593 | 1248 | CAGGTCCAGTTGCAGGAAAGTGGAGGGGGACTCGTGCAACCCGGAGGCAGCCTC CGTTTGTCCTGTGCGGCTTCCGGCTTCACGTTCAGCTCCTACCCAATGTCTTGG GTGCGGCAAGCGCCCGGCAAGGGGCTTGAGTGGATCTCTACAATCAGCGCAGGA GGTGATACTACCCTGTATGCCGACTCTGTCAAGGGCAGATTCACCTCCAGCCGC GACAACGCCAAGAACACCCCTTATCTCCAACTGAACAGCCTCAAGACCGAAGAT GCCGCGATTTACTATTGTGCTAAGCGCATTGACTGCAACCCCGGCTATTGCTAC AGGCGCAACTACTGGGGCCAGGGCACTCAGGTGACTGTGTCCAGCGGCGGTTCT GGAGGCTCCGGGGGCAGCGGCCAGGTGCAGCTCCAGGAGTCTGGTGGAGGCTCC GTTCAGGCCGGAGGTTCCCTTCGCCTGTCTTGTGCTGCAAGCGGCTACCCATAC TCTAACGGCTACATGGGCTGGTTCCGGCAAGCGCCGGGTAAAGAACGCGAAGGG GTGGCCACGATCTACACCGGGGATGGCAGAACCTATTACGCCGATAGCGTGAAG GGTCGTTTCACTATTTCCCGTGACAATGCGAAGAACACCGTGGACCTCCAGATG AGTTCCTTGAAGCCTGAGGATACAGCTATGTACTATTGCGCCGCTCGCGCAGCC CCACTCTATTCCAGCGGTAGTCCCCTGACCCGTGCTCGCTACAACGTATGGGGA CAGGGTACACAGGTGACTGTGTCCTCC |
| hIL27 Ra_VH H1-DR594 | 1249 | CAGGTCCAGCTCCAGGAATCCGGTGGGGGCCTCGTGCAGCCCGGAGGTTCTCTG CGCCTGTCTTGTGCCGCGAGCGGATTTACTTTCAGCTCCTACCCCATGTCCTGG GTGCGTCAAGCCCCAGGTAAGGGGCTGGAGTGGATTTCTACTATTAGCGCTGGA GGCGACACAACCCTGTATGCCGACAGCGTGAAGGGTCGCTTTACTTCTAGCCGC GACAATGCAAAGAACACACTGTACCTTCAGCTCAACTCCCTGAAAACTGAAGAC GCGGCCATCTATTACTGCGCCAAGCGGATTGATTGTAACAGCGGATATTGCTAC AGACGCAACTACTGGGGCCAGGGGACCCAGGTGACAGTGTCAAGCGGGGGGTGG TCTCAGGTGCAGCTTCAGGAGAGCGGGGGAGGCAGCGTCCAGGCTGGTGGCTCC CTGAGGCTTTCTTGTGTGGCCTCCGCCAGTACCTACTGCACCTATGATATGCAC |

TABLE 1B-continued

| Name | SEQ ID NO: | Sequence |
|---|---|---|
| | | TGGTATCGGCAAGCGCCGGGCAAAGGGAGAGAGCTTGTGTCCGCTATCGACTCA GATGGCACAACCAGATACGCCGATAGCGTTAAGGGCAGGTTCACTATCAGTCAG GGGACCGCTAAGAACACCGTGTAACTCCAGATGAATAGCCTCCAGCCAGAGGAT ACCGCCATGTACTATTGTAAGACAGTGTGTGTTGTCGGATCACGCTGGAGCGAC TACTGGGGACAGGGCACCCAGGTGACCGTGTCCTCT |
| hIL27 Ra_VH H1-DR594 | 1250 | CAGGTCCAGTTGCAAGAATCCGGCGGTGGCCTCGTGCAGCGTGGCGGGTCACTG CGTTTGTCTTGTGCCGCTAGTGGCTTCACATTTAGCTCCTACCCCATGAGCTGG GTCCGGCAGGCCCCTGGCAAAGGCCTTGGATGGATCAGTACCATCTGCGCAGGG GGCGACACAACCCTGTATGCGGACTCTGTGAAGGGTAGATTCACATCATCCAGG GACAACGCCAAGAACACACCTTATCTCCAGCTTAACTCTCTGAAGACAGAGGAT GCAGCCATCTACTATTGCGCTAAGCGTATCGACTGCAACCCCGGTTATTGTTAC CGTCGCAATTACTGGGGACAGGGAACACAGGTGACTGTTTCCTCTGGAGGCTCC GGTGGCTCCGGGGGCAGCGGCCAGGTGCAGCTCCAGGAGTCTGGAGGCGGAAGC GTGCAGGCTGGCGGTCTCTGCGCCTGAGCTGTGTCGCAAGTGCCTTCTACCTAC TGCACTTACGACATGCACTGGTATCGGCAAGCGCCCGGAAAAGGCAGGGAGTTT GTTAGCGCCATTGATTCCGACGGTACTACCCGCTATGCCGATAGCGTGAAAGGC AGGTTTACTATCAGCCAGGGCACTGCGAAGAACACCGTGTACCTCCAGATGAAC TCCCTCCAGCCCGAGGACACCGCCATGTATTACTGCAAAACCGTCTGCGTCGTG GGATCACGTTGGTCTGACTATTGGGGGCAGGGGACTCAGGTCACTGTGTCCAGC |
| hIL27 Ra_VH H1-DR595 | 1251 | CAGGTGCAGCTTCAGGAGAGCGGCGGGGGTCTCGTGCAGCCTGGAGGCTCTCTG CGCCTGTCCTGTGCCGCGAGCGGATTCACTTTCCCTTCATACCCGATGTCCTGG GTGCGCCAGGCCCCCGGCAAGGGACTGGAGTGGATCAGCACGATCTCCGCCGGA GGCGACACAACCCTGTATGCCGACTCTGTTAAGGGGAGGTTCACCAGTAGCCGT GACAATGCCAAGAACACTCAGTATCTGCAACTGAACTCTCTCAAGACTGAGGAT GCCGCTATCTATTACTGCGCGAAGCGCATTGACTGCAACAGTGGCTACTGCTAC CGCAGGAACTATTGGGGCCAGGGCACCCAGGTTACCGTTAGTTCTGGAGGCGGA TCACAAGTGCAGCTGCAAGAGTCTGGAGGTGGCAGTGTGCAAGCAGGTGGCTCT CTGACTCTGTCCTGCGCTGCCAGCGAGTATGCTTACTCTACGTGCAACATGGGC TGGTATCGCCAGGCCCCTGGGAAAGAGCGGGAACTGGTTTCCGCGTTCATCTCC GACGGCTCCACTTATTACGCCGACTCCGTGAAGGGGAGATTCACCATCACTGGG GACAACGCAAAAAATACTGTCTATCTCCAGATGAACTCCCTCAAGCCTGAGGAT ACAGCTATCTACTATTGCTCTGCTAACTGCTATCGTCGCCTGCGCAACTATTGG GGACAGGGCACACAGGTGACAGTTAGCAGC |
| hIL27 Ra_VH H1-DR595 | 1252 | CAGGTGCAGTTGCAGGAATCTGGGGGGGGTCTTGTCCAGCCCGGTGGCTCACTC CGCCTGAGCTGCGCTGCCAGCGGTTTCACTTTCAGTTCCTATCCTATGAGTTGG GTGCGGCAGGCCCCAGGCAAAGGACTGGAGTGGATCTCTACAATCTCAGCTGGT GGCGATACCACTCTTTATGCCGATTCTGTGAAGGGTCGTTTCACTTCTTCCAGA GACAACGCGAAGAACACGTTGTATTTGCAGCTGAACAGTCTGAAAACCGAAGAC GCGGCCATCTATTACTGTGCCAAGAGGATTGATTGTAACAGCGGGTATTGTTAT CGCCGTAACTATTGGGGGCAGGGCACTCAAGTTACCGTTAGCTCCGGTGGCTCC GGGGGTAGCGGGGGAAGCGGCCAGGTCCAGCTGCAAGAGTCTGGAGGGGGGTTCC GTTCAGGCGGGAGGGTCTCTGACCCTGTCTTGCGCGGCCTCAGAATACGCCTAC TCCACCTGTAATATGGGTTGGTACAGACAGGCCCCTGGCAAAGAGAGGGAACTC GTTAGCGCTTTCATCTCCGATGGGTCCACTTATTACGCGGACAGCGTCAAGGGC CGCTTCACCATCACACGCGATAACGCCAAGAATACGGTTTAACTCCAGATGAAC TCCCTCAAGCCCGAGGATACTGCGATCTATTACTGTTCCGCGAACTGCTACAGA CGGCTGCGTAACTATTGGGGCCAGGGGACTCAGGTTACCGTGTCCAGC |
| hIL27 Ra_VH H1-DR596 | 1253 | CAGGTTCAGCCCCAGGAGAGCGGTGGAGGTTTGGTCCAACCGGGAGGCAGCCTG AGACTCAGTTGTGCCGCTTCTGGCTTCACTTTCTCCTCTTACCCTATGTCCTGG GTCAGACAAGCACCGGGGAAGGGTCTGGAATGGATCTCCACCATTTCAGCTGGA GGCGATACCACATTGTACGCCGACTCCGTGAAGGGACGCCTCACCTCTTCCCGC GATAATGCCAAGAACACCCTGTATTTGCAGTTGAATAGCCTGAAGACCGAGGAT GCCGCTATTTACTATTGTGCTAAGCGGATCGACTGTAACAGCGGTTACTGTTAC AGGCGCAACTACTGGGGTCAAGGCACCCAGGTAACCGTCAGCTCCGGGGGGTGG TCCCAGGTGCAGCTCCAGGAGTCAGGAGGCGGACTCGTGCAACCCGGTGGCTCC CTCCGCCTCAGCTGTACCGCTTCCGGTCTCACCTTTGATGACTCAGTTATGGGC TGGTTTAGGCAAGCGCCGGGCAAGGGCAGAGAAGCTGTGTCTTGTATCTCCTCA TCCGGTGCTAACGCCTTCTACGCTGACAGCGTGAAGGGTCGCTTTACAATCAGT AGAGATAACGCCAAAAACACTCTTTACTTGCAGATGAACTCACTCAAGCCTGAG GATACCGCCACTTATTACTGTAAGAGGGGTCATGCTTGCGCTGGCTATTACCCC ATCCCCTATGATGACTATTGGGGCCAGGGCACCCAGGTGACTGTGTCTAGT |
| hIL27 Ra_VH H1-DR596 | 1254 | CAGGTGCAGCTTCAGGAGAGCGGGGGAGGCCTCGTGCAGCCAGGAGGCTCCCTG AGACTCTCCTGCGCCGCAAGCGGATTTACATTTTCTAGCTACCCGATGTCCTGG GTGAGACAAGCGCCCGGCAAAGGCCTTGAATGGATCTCTACTATCTCTGCTGGA GGCGACACAACCCTGTATGCCGATAGCGTTAAGGGACGTTTCACCTCTTCCAGA GACAATGCTAAGAACACCCTGTACTTGCAGCTGAACTCCCTCAAGACGGAGGAT GCAGCGATCTACTATTGCGCGAAGAGGATTGACTGTAACAGTGGCTATTGTTAC AGGCGCAATTACTGGGGCCAGGGAACTCAGGTGACCGTCTCCTCTGGCGGTTCC GGGGGATCAGGAGGCAGTGGCCAGGTGCAGTTGCAGGAAAGTGGCGGAGGGCTG GTGCAACCAGGCGGATCTTTGAGATTGTCCTGCACCGCCTCCGGCCTGACATTT GACGATTCAGTGATGGGCTGGTTCCGTCAGGCACCCGGCAAGGGCCGCGAGGCC GTGAGTTGTATCAGCTCCTCAGGCGCAAACGCCTTCTACGCCGACAGTGTTAAG |

TABLE 1B-continued

| Name | SEQ ID NO: | Sequence |
|---|---|---|
| | | GGCAGGTTCACTATCTCCAGAGACAATGCAAAGAACACTCTGTACCTTCAGATG AACAGCCTGAAGCCAGAGGACACAGCCACATACTATTGCAAGCGCGGCCACGCT TGCGCCGGGTACTATCCCATCCCCTACGACGATTACTGGGGACAGGGCACTCAG GTCACAGTGAGTAGC |
| hIL27 Ra_VH H2- DR591 | 1255 | CAAGTACAACTTCAGGAATCTGGGGGCGGTCTCGTTCAGCCTGGGGGCTCTCTG AGGCTGTCTTGCGCCGCGAGCGGATTTACTTTTTCCCTCAGGGGCATGAGCTGG GTCAGACAGGCCCCTGGCAAAGGGCTGGAATGGGTGTCCGCCATCTCCAGGGGG GGCGCTTCTACATACTATACTGACAGCGTGAAGGGCAGGTTCACTATTTCCCGC GACAATGCCAAGAACATTCTTTACCTTCAGCTGAACTCCCTCAAAACAGAGGAC ACCGCGATGTATTACTGTGCTAAGGGCGGGAGCGGTTATGGCGATGCGAGTCGC ATGACCTCCCCCGGCAGTCAGGGAACTCAGGTCACTGTCAGCTCTGGGGGGGGG TCCCAGGTTCAACTCCAGGAGTCAGGAGGGGGCTCTGTTCAGGCTGGCGGTAGC CTGAGGCTGTCCTGCACCGCCTCTGGAGCCATCGCCAGCGGCTATATTGATTCA CGCTGGTGTATGGCGTGGTTCCGCCAGGCTCCTGGCAAAGAAAGGGAAGGTGTA GCCGCTATTTGGCCTGGAGGCGGTCTGACCGTCTATGCCGATAGCGTGAAGGGC AGGTTTACTATCTCTCGGGATCACGCGAAGAACACCCTGTATCTTCAGATGAAC AATCTCAAGCCTGAGGACACAGCTATGTATTACTGCGCAGCGGGTTCCCCGCGC ATGTGCCCCAGCCTGGAGTTCGGATTCGATTACTGGGGGCAAGGCACCCAAGTC ACTGTTTCTAGC |
| hIL27 Ra_VH H2- DR591 | 1256 | CAAGTTCAGCTCCAGGAGTCCGGGCGGTGACTCGTTCAGCCTGGAGGCAGTCTG AGGCTGTCTTGTGCCGCGTCAGGGTTCACCTTCAGCCTGTCTGGGATGAGCTGG GTCCGCCAGGCCCCAGGCAAGGGCCTGGAATGGGTGTCAGCCATCAGCTCCGGC GGTGCCTTCTACTTATACACTGACTCAGTGAAGGGTCGTTTTACCATCTCCCGC GACAACGCCAAGAACATTCTGTATCTCCAGCTCAACAGCCTGAAAACGGAGGAC ACCGCTATGTATTACTGTGCTAAGGGTGGCTCAGGGTACGGGGACGCTTCTCGC ATGACATCTCCTGGCTCCCAGGGCACCCAGGTGACTGTCAGCTCAGGAGGCAGC GGAGGCAGTGGCGGATCTGGGCAGGTCCAGCTCCAAGAGTCTGGAGGGGGTTCA GTGCAGGCTGGAGGTTCTCTTAGGCTGAGCTGTACCGCCAGCGGAGCCATCGCT TCTGGGTATATTGACAGCCGCTGGTGCATGGCTTGGTTCCGGCAAGCTCCAGGT AAGGAGAGGGAGGGAGTGGCAGCCATTTGGCCCGGAGGCGGACTCACAGTGTAT GCCGATAGCGTTAAGGGCAGATTTACCATCAGCCGCGATCACGCAAAAAACACA CTCTACCTTCAGATGAATAACCTGAAGCCGGAGGACACCGCCATGTATTACTGT GCCGCTGGCTCTCCACGCATGTGCCCTAGCCTGGAGTTCGGTTTTGACTACTGG GGTCAAGGCACACAGGTGACCGTGTCTAGT |
| hIL27 Ra_VH H2- DR592 | 1257 | CAGGTCCAGTTGCAGGAATCTGGAGGCGGACTGGTGCAACCTGGCGGTTCCCTG CGGCTGTCCTGTGCAGCCAGTGGCTTTACCTTCAGCCTGAGCGGCATGTCCTGG GTGAGACAGGCCCCCGGAAAGGGTCTGGAATGGGTGAGTGCCATCAGCTCCGGC GGAGCCAGTACCTATTACACCGATAGTGTTAAGGGGCGCTTTACCATCTCCCGT GACAACGCTAAGAATACCCTTTATCTCCAACTGAACAGCCTGAAGACCGAAGAC ACCGCCATGTATTACTGTGCCAAGGGTGGCACTGGATATGGCGATGCCAGCCGC ATGACCAGTCCTGGGTCCCAAGGCACACAGGTAACAGTGTCTAGCGGCGGAGGC AGCCAGGTGCAGCTGCAAGAAAGCGGGGTGGCAGTGTCCAAGCTGGGCGGCAGC TTGCGCCTCTCTTGCACTGCGCCCGGTTTCACCTCTAATAGCTGTGGCATGGAT TGGTATCGCCAGGCACCGGGCAAGGAGAGGGAGTTCGTGAGTTCCATCAGCACC GACGGCACTACGGGATATGCCGACAGCGTTAAGGGCCGCTTCACCATCTCAAAG GACAAGGCCAAGGATACTGTGTACCTGCAAATGAACAGTCTGAAGCCGGAGGAT ACCGGGATGTACTCTTGCAAGACCAAGGACGGAACCATCGCAACTATGGAGCTG TGTGACTTCGGCTACTGGGGCCAGGGAACCCAGGTGACAGTCTCTTCC |
| hIL27 Ra_VH H2- DR592 | 1258 | CAGGTGCAGCTTCAGGAGTCCGGCGGTGGCCTGGTCCAGCCGGGGGGAAGCCTG CGCCTTTCCTGCGCCGCGTCTGGCTTCACCTTCTCTCTCAGCGGTATGAGTTGG GTCCGCCAGGCCCCAGGGAAGGGCCTGGAGTGGGTGTCTGCTATCTCTAGCGGA GGCGCTAGTACCTATTACACAGATTCCGTCAAGGGCCGCTTTACAATCTCACGC GATAACGCCAAGAACATCCTGTACCTTCAGCTGAACAGCCTGAAAACCGAGGAT ACCGCTATGTACTATTGCGCTAAGGGAGGCTCTGGCTACGGAGACGCTTCACGT ATGACCAGTCCTGGCAGCCAGGGAACACAGGTCACAGTCAGCTCCGGCGGTAGC GGTGGCTCCGGGGGGAGCGGCCAGGTTCAACTCCAGGAATCTGGGGGGGGTTCC GTCCAGGCTGGGGGTTCTCTGAGACTGAGCTGCACAGCCCCTGGGTTCACCTCC AACAGTTGCGGAATGGATTGGTATCGTCAGGCCCCCGGCAAGGAGAGAGAGTTT GTTAGCTCTATCTCCACGGACGGGACCACTGGTTATGCTGACAGCGTTAAGGGC CGTTTTACTATCTCCAAGGACAAGGCCAAAGACACCGTGTACTTGCAGATGAAC TCTCTGAAGCCCGAGGATACCGGAATGTACTCATGCAAAACCAAAGATGGTACT ATTGCTACTATGGAGCTGTGTGACTTCGGCTATTGGGGCCAGGGGACCCAGGTG ACTGTGTCCTCT |
| hIL27 Ra_VH H2- DR593 | 1259 | CAGGTTCAACTGCAAGAGTCTGGAGGCGGTCTCGTACAGCCAGGTGGGAGCCTC CGCCTGTCCTGTGCAGCCAGCGGTTTCACCTTCTCCCTCTCCGGTATGTCCTGG GTGCGCCAGGCCCCTGGAAAAGGCTTGGAGTGGGTGTCTGCCATCAGCTCAGGA GGCGCGTCCACATATTACACCGACAGTGTCAAGGGCCGGTTCACCATCTCCAGG GACAATGCGAAGAATATCCTCTACTTGCAGCTGAACTCCCTCAAAACTGAGGAC ACTGCAATGTATTACTGCGCTAAAGGGGGCAGCGGATATGGGGATGCTTCCCGG ATGACATCCCCAGGCAGCCAGGGCACCCAAGTGACCGTGTCTTCCGGTGGGGGC TCCCAGGTGCAGCTCCAGGAAAGCGGAGGGGGAAGCGTGCAGGCAGGGGGTAGC CTTCGTCTGTCTTGTGCAGCCAGCGGCTACCCGTATTCTAATGGATACATGGGC |

TABLE 1B-continued

| Name | SEQ ID NO: | Sequence |
|---|---|---|
| | | TGGTTCAGGCAAGCCCCTGGCAAGGAACGCGAGGGCGTGGCCACGATCTATACC GGAGACGGCAGGACTTACTATGCCGATAGCGTGAAAGGGCGCTTCACCATCTCA CGTGACAACGCGAAAAATACCGTGGATCTTCAGATGTCCTCTCTCAAACCCGAG GACACCGCGATGTACTATTGCGCCGCACGGGCTGCCCCTCTGTACTCATCTGGC TCACCGTTGACTCGGGCAAGATATAACGTGTGGGGTCAGGGCACACAGGTCACC GTGTCTTCC |
| hIL27 Ra_VH H2- DR593 | 1260 | CAGGTCCAACTCCAGGAAAGCGGCGGTGGCCTGGTGCAGCCTGGTGGGTCCCTC AGACTGTCTTGCGCCGCTTCTGGCTTCACCTTTTCTTTGTCCGGGATGTCTTGG GTCCGCCAAGCGCCGGGCAAGGGCCTGGAGTGGGTGTCCGCCATTTCATCTGGT GGAGCTTCAACTTATTACACCGACTCTGTGAAGGCGTCGTTTTACCATCCCCGT GACAACGCGAAGAACATCCCGTATTTGCAGCTGAACTCCTTGAAAACCGAGGAT ACGGCCATGTACTATTGTGCAAAGGGGGGTTCCGGTTACGGCGACGCTTCACGC ATGACCTCCCCCGGTTCCCAGGGCACTCAGGTGACCGTCTCAAGTGGCGGTAGC GGTGGCTCTGGTGGCAGCGGACAGGTCCAGCTTCAGGAATCAGGCGGAGGGAGT GTGCAAGCAGGCGGATCTCTGAGACTGAGCTGTGCTGCCAGCGGTTACCCCTAC TCTAACGGCTATATGGGTTGGTTCAGGCAAGCGCCTGGTAAGGAGCGCGAGGGT GTGGCCACGATCTATACCGGGGATGGCAGGACCTACTATGCCGACTCTGTGAAG GGTCGGTTCACCATCAGCCGGGACAACGCGAAGAACACTGTGGATTTGCAGATG TCTTCCCTGAAACCCGAGGACACCGCCATGTATTACTGCGCTGCAAGAGCCGCT CCCCTGTATAGCTCTGGATCTCCTCTGACCCGTGCAAGATACAATGTATGGGGT CAGGGAACCCAGGTCACCGTCAGCAGT |
| hIL27 Ra_VH H2- DR594 | 1261 | CAGGTGCAGCTTCAGGAGTCAGGTGGGGGCCTGGTCCAGCCAGGCGGTTCCTTG CGCCTGTCATGCGCCGCTAGTGGGTTCACTTTTAGCCTGTCCGGCATGTCCTGG GTTCGGCAAGCACCCGGCAAGGGTTTGGAGTGGGTGTCCGCCATTTCTTCGGGG GGCGCATCTACCTATTACACTGATTCTGTCAAGGGGCGCTTTACCATTTCTCGT GACAACGCTAAAAACATTCTGTATCTGCAACTTAACTCACTGAAGACCGAGGAT ACAGCAATGTACTATTGCGCCAAGGGCGGCCCCGGGTACGGCGATGCGTCACGG ATGACATCTCCTGGGTCCCAGGGAACTCAGGTGACCGTGTCCTCAGGGGGGGGC AGTCAAGTGCAGCTCCAGGAGAGCGGAGGTGGCTCTGTGCAAGCTGGGGGAAGT CTCCGCTTGTCTTGTGTGGCCTCCGCAAGCACATATTGCACCTACGACATGCAC TGGTATAGGCAGGCTCCCGGCAAGGGCCGGGAGTTTGTTTCCGCAATCGACAGC GACGGCACCACTCGCTATGCCGATAGCGTGAAAGGTCGTTTTACCATCTCCCAG GGGACCGCAAAGAACACAGTCTACTTGCAGATGAACTCCCTTCAGCCTGAGGAC ACCGCTATGTATTACTGTAAGACCGTGTGCGTCGTGGGCAGTCGTTGGTCCGAT TACTGGGGCCAGGGAACACAGGTGACAGTCAGTTCT |
| hIL27 Ra_VH H2- DR594 | 1262 | CAGGTGCAGCTCCAGGAGTCTGGGGGGGGCCTGGTCCAACCGGGTGGCTCACTC CGCCTGTCTTGCGCCCGCGTCCGGCTTCACATTCAGTCTCTCCGGGATGTCCTGG GTGCGCCAAGCTCCGGGCAAAGGCTTGGAGTGGGTATCTGCTATCTCTAGCGGT GGAGCTTCCACATACTATACCGACTCCGTGAAGGGCCGCTTCACCATTTCACGT GATAACGCGAAGAACATTCTGTATCTTCAGCTGAACAGCCTGAAAACCGAGGAC ACCGCTATGTACTATTGTGCCAAGGGAGGCAGCGGGTATGGGGACGCTTCCCGG ATGACCTCCCCCGGTTCTCAGGGTACTCAGGTGACCGTCTCTAGCGGTGGCTCA GGTGGCTCCGGCGGATCTGGACAGGTACAGCTCCAGGAGTCAGGTGGAGGGAGT GTGCAGGCAGGTGGCTCCCTGCGGTGTCCTGTGTGGCCAGCGCCTTCTACATAT TGCACCTACGACATGCACTGGTACAGGCAGGCCCCAGGTAAAGGGCGTGAATTT GTGAGTGCCATTGACTCTGATGGAACGACTAGATACGCGGATTCCGTCAAGGGG CGGTTTACAATCTCTCAGGGCACCGCCAAGAACACCGTGTATCTCCAAATGAAC TCATTGCAGCCTGAGGACACTGCCATGTATTACTGCAAGACCGTGTGCGTCGTG GGCTCCCGTTGGTCCGATTATTGGGGCCAGGGCACACAGGTAACCGTATCTTCC |
| hIL27 Ra_VH H2- DR595 | 1263 | CAGGTACAGCTCCAGGAATCCGGTGGGGGCTTGGTCCAGCCAGGGGGTAGTCTG CGCCTTTCCTGCGCTGCCTCCGGCTTCACCTTCAGCCTGTCAGGCATGTCCTGG GTCCGGCAAGCGCCTGGCAAGGGGCTGGAGTGGGTCTCCGCCATTAGCAGTGGT GGAGCGAGCACTTATTACACTGACAGCGTGAAGGGACGCTTTACAATTTCACGT GACAACGCCAAGAACATCCTTCTACTTGCAGCTCAATCTCTGAAGACCGAGGAT ACCGCAATGTACTATTGCGCCAAGGGTGGCTCCGGTTACGGGGACGCCAGCCGC ATGACATCTCCGGGTTCTCAGGGTACACAGGTGACTGTCTCATCCGGGGGCGGG AGCCAGGTCCAGCTCCAGGAGTCTGGTGGGGGCTCCGTGCAAGCTGGCGGTTCA CTGACACTGAGCTGTGCAGCGTCTGAGTATGCGTACTCTACGTGTAACATGGGA TGGTATAGGCAGGCTCCGGGGAAGGAGCGCGAACTCGTGTCAGCCTTTATTAGC GACGGCTCCACGTATTACGCAGATAGCGTCAAGGGACGGTTCACCATCACACGG GACAATGCGAAGAATACCGTGTATCTCCAGATGAACTCCCTCAAGCCCGAGGAC ACCGCAATCTATTACTGTAGCGCAAATTGCTACCGGAGACTGCGGAACTACTGG GGCCAGGGCACCCAGGTAACCGTGTCTTCC |
| hIL27 Ra_VH H2- DR595 | 1264 | CAGGTGCAGTTGCAGGAATCAGGGGGGGGTCTCGTGCAGCCCGGTGGATCACTG AGACTGTCATGTGCTGCCTCCGGCTTCACATTCAGCCTGTCTGGTATGAGCTGG GTCCGCCAGGCACCAGGCAAGGGACTGGAGTGGGTGAGTGCTATCTCATCCGGG GGTGCCAGCACCTATTACACCGACAGCGTAAAAGGACGTTTCACTATCTCCCGC GATAACGCTAAGAACATCCTGTACCTCCAGCTCAATTCTCTGAAAACAGAAGAT ACCGCCATGTATTACTGCGCTAAGGGAGGCAGCGGGTACGGGGATGCGTCCCGC ATGACATCCCCCGGAAGTCAGGGAACCCAAGTGACAGTGTCTTCCGGGGGCTCT GGCGGTTCCGGGGGTTCTGGCCAAGTGCAGCTCCAGGAATCCGGGGGGGGATCT GTGCAGGCGGGGGGGTCTCTGACATTGAGCTGCGCGGCCTCTGAGTATGCTTAC |

TABLE 1B-continued

| Name | SEQ ID NO: | Sequence |
|---|---|---|
| | | TCTACCTGCAACATGGGCTGGTATAGGCAGGCCCCCGGCAAGGAACGCGAACTG<br>GTGTCCGCCTTCATTTCCGACGGGTCCACCTATTACGCCGACTCCGTGAAAGGC<br>AGGTTCACTATCACCCGCGACAACGCCAAGAATACTGTGTACCTCCAGATGAAT<br>AGCTTGAAGCCCGAGGATACCGCGATTTATTACTGCTCCGCAAATTGCTATCGT<br>CGGCTCAGAAATTATTGGGGCCAGGGCACACAGGTTACCGTTAGCTCA |
| hIL27<br>Ra_VH<br>H2-<br>DR596 | 1265 | CAAGTCCAACTCCAGGAGTCCGGCGGTGGCCTGGTGCAGCCCGGTGGGTCCCTG<br>CGCCTGTCATGTGCTGCCAGTGGTTTCACATTCAGCCTCTCAGGCATGTCTTGG<br>GTACGCCAGGCCCCTGGGAAGGGCCTGGAGTGGGTCTCCGCCATCTGCAGCGGT<br>GGCGCAAGTACATATTACACTGATTCCGTGAAGGGTCGTTTCACAATCTCTAGG<br>GATAACGCTAAGAATATCCTGTACCTCCAGCTTAACTCCCTGAAGACCGAAGAT<br>ACCGCTATGTATTACTGTGCGAAGGGCGGTTCTGGCTATGGGGATGCCTCACGC<br>ATGACCTCTCCTGGGTCCCAGGGCACCCAGGTGACTGTCAGCTCAGGGGGGGGC<br>AGCCAGGTGCAGCTCCAGGAGTCCGGGGGCGGGCTGGTGCAGCCTGGCGGAAGC<br>CTCAGACTGTCATGTACCGCGAGTGGACTGACACTTGATGACAGCGTCATGGGC<br>TGGTTCCGGCAGGCCCCAGGAAAGGGGAGGGAAGCTGTGAGCTGTATTTCTTCC<br>TCTGGCGCTAACGCCTTCTACGCTGACAGTGTGAAGGGCCGTTTCACCATTTCC<br>AGAGACAACGCAAAGAACACTCTGTACCTCCAGATGAACTCACTGAAGCCCGAG<br>GACACCGCGACATACTATTGTAAGCGTGGTCACGCTTGTGCTGGCTACTATCCT<br>ATCCCATACGATGACTATTGGGGTCAGGGCACACAGGTGACCGTGAGTAGC |
| hIL27<br>Ra_VH<br>H2-<br>DR596 | 1266 | CAGGTCCAGTTGCAGGAATCTGGAGGTGGCCTGGTTCAGCCCGGAGGCAGCCTG<br>AGACTGAGCTGCGCTGCGAGCGGATTCACCTTTAGCCTGTCTGGCATGAGCTGG<br>GTAAGGCAGGCTCCAGGCAAGGGACTGGAGTGGGTGTCTGCTATCCCCAGCGGA<br>GGCGCTTCCACCTATTACACAGACTCTGTTAAAGGCCGTTTCACTATCAGTAGA<br>GACAACGCGAAGAACATCCTCTATCTTCAGCTGAATAGCCTGAAGACAGAGGAT<br>ACCGCCATGTATTACTGTGCCAAGGGAGGTAGCGGTTACGGCGACGCCAGCCGC<br>ATGACAAGTCCGGGCTCCCAGGGCACACAGGTGACCGTATCCAGCGGTGGCTCC<br>GGTGGGAGCGGGGGTTCCGGCCAGGTGCAGCTGCAAGAAAGCGGCGGTGGCCTG<br>GTGCAGCCAGGGGGTTCTCTGCGTCTGAGCTGCACCGCGAGTGGGCTGACCTTC<br>GACGATTCCGTTATGGGCTGGTTCCGCCAAGCTCCGGGAAAGGGCAGAGAGGCC<br>GTATCCTGCATCAGCTCCAGCGGGGCCAACGCCTTCTATGCCGATAGTGTGAAG<br>GGACGCTTTACCATTTCTCGCGATAACGCGAAAAACACACTGTATCTTCAGATG<br>AACTCACTGAAGCCTGAGGACACCGCCACGTACTATTGTAAACGCGGCCACGCC<br>TGCGCTGGTTATTACCCTATTCCATACGACGATTACTGGGGCCAGGGCACCCAG<br>GTCACTGTGTCCTCA |
| hIL27<br>Ra_VH<br>H3-<br>DR591 | 1267 | CAAGTGCAGCTCCAGGAGAGCGGAGGTGGCTCAGTGCAGGCAGGCGGTTCACTG<br>CGTCTGTCCTGCGTCGCCTCTGGCTACGTTAGCTGTGATTATTTTCTCCCCTCC<br>TGGTATCGGCAGGCTCCTGGGAAAGAGCGCGAATTTGTAAGCATCATTGACGGC<br>ACCGGCTCTACCAGCTATGCGGCCTCCGTCAAAGGACGCCTTACCGCATCCGAA<br>GATAAGGGCAAGAACATCGCTTACTTGCAGATGAACTCTCTGAAACCAGAGGAT<br>ACCGCTATGTACTATTGTAAGGCGTCATGCGTGCGTGGCCGCGCCGTGAGCGAA<br>TACTGGGGCCAAGGAACCCAAGTTACCGTCTCCTCAGGGGGGGGGTCCCAAGTG<br>CAGTTGCAAGAATCCGGTGGCGGATCTGTCCAAGCCGGAGGTTCCCTGAGACTC<br>TCATGTACCGCAAGCGGTGCCATTGCAAGGGGCTATATTGATTCCCGCTGGTGC<br>ATGGCTTGGTTCCGCCAGGCCCCAGGGAAGGAGCGTGAGGGTGTGGCCGCTATC<br>TGGCCCGGAGGGGGCTTGACCGTGTATGCCGATTCCGTCAAAGGACGTTTCACT<br>ATCAGCCGCGACCACGCCAAAAACACTCTTTATCTGCAAATGAATAACCTCAAG<br>CCAGAGGACACAGCTATGTACTATTGCGCCGCAGGCTCCCCACGCATGTGTCCC<br>TCCTTGGAGTTCGGCTTCGACTACTGGGGACAGGGTACTCAGGTTACTGTCTCC<br>TCC |
| hIL27<br>Ra_VH<br>H3-<br>DR591 | 1268 | CAGGTGCAGCTCCAGGAGTCTGGAGGCGGTTCCGTTCAGGCCGGTGGCTCCCTG<br>CGTTTGTCTTGCGTGGCCAGTGGCTACGTCAGTTGTGACTACTTCCTGCCCTCA<br>TGGTATCGTCAAGCGCCAGGTAAGGAGCGCGAGTTCGTCTCCATTATCGACGGA<br>ACAGGTTCTACTAGCTACGCCGCTTCTGTCAAGGGGCGCTTCACCGCTTCCGAG<br>GATAAGGGTAAGAACATCGCGTATCTGCAAATGAACTCATTGAAGCCCGAGGAC<br>ACCGCCATGTATTACTGTAAAGCCTCCTGTGTGCGTGGCCGCGCTGTGTCCGAG<br>TACTGGGGCCAGGGCACACAGGTGACCGTTTCCAGGGGCGGTTCCGGGGGGTCC<br>GGGGGCTCAGGGCAGGTGCAGCTTCAGGAGAGCGGAGGGGGATCTGTGCAGGCC<br>GGTGGCTCCCTGCGGCTGTCCTGCACAGCATCTGGGGCCATCGCGTCCGGGTAC<br>ATCGACTCCCGCTGGTGTATGGCCTGGTTCCGCCAAGCGCCTGGCAAGGAGCGT<br>GAGGGCGTGGCCGCGATCTGGCCGGGGGCGGGACTCACAGTCTACGCTGACAGC<br>GTCAAGGGGCGTTTCACTATTAGCAGAGACCACGCTAAGAACACCCTTTACCTT<br>CAGATGAATAACCTGAAGCCTGAAGACACCGCGATGTACTATTGCGCAGCTGGT<br>TCTCCCCGCATGTGCCCCTCACTTGAATTTGGTTTCGACTACTGGGGGCAGGGT<br>ACGCAGGTCACGGTGTCCTCC |
| hIL27<br>Ra_VH<br>H3-<br>DR592 | 1269 | CAAGTCCAGCTCCAGGAGAGCGGTGGGGGGTCCGTGCAGGGGGGAGGCAGCCTC<br>CGCCTCAGTTGTGTCGCCTCTGGCTACGTGTCCTGCGATTATTTCTTCCGTCC<br>TGGTATCGCCAGGCTCCCGGCAAAGAAAGGGAGTTCGTTAGCATCATTGATGGC<br>ACGGGTTCCACAAGTTACGCTGCCAGCGTGAAAGGTAGGTTTACCGCTTCTGAA<br>GACAAAGGAAAGAACATCGCCTACTTGCAGATGAACTCTCTGAAGCCCGAGGAC<br>ACAGCCATGTACTATTGCAAAGCCTCTTGCGTGAGGGGACGGGCGGTGTCTGAA<br>TACTGGGGGCAAGGAACCCAAGTGACCGTGTCCTCTGGAGGGGGTAGCCAGGTC<br>CAGCTGCAAGAGTCCGGCGGAGGCTCTGTTCAGGCCGGTGGCTCACTGCGCCTG |

TABLE 1B-continued

| Name | SEQ ID NO: | Sequence |
|---|---|---|
| | | TCTTGTACCGCACCTGGCTTCACTAGCAACTCTTGTGGAATGGACTGGTATCGT<br>CAGGCCCCCGGTAAGGAAAGAGAGTTCGTTTCTTCCATTTCTACAGACGGCACA<br>ACGGGGTATGCGGACAGTGTGAAAGGAAGATTCACTATCAGTAAGGATAAGGCC<br>AAAGACACCGTGTATCTCCAGATGAACTCCCTGAAACCAGAGGACACTGGAATG<br>TATAGCTGCAAGACCAAGGACGGGACCATTGCTACGATGGAACTCTGCGATTTC<br>GGCTACTGGGGGCAGGGGACACAGGTGACTGTGTCCTCC |
| hIL27<br>Ra_VH<br>H3-<br>DR592 | 1270 | CAGGTGCAGTTGCAGGAGTCCGGCGGTGGGTCCGTGCAGGGGGCGGGTAGCCTG<br>CGCCTGAGTTGCGTGGCCTCTGGATACGTCTCTTGCGATTACTTCTTGCCCTCT<br>TGGTATCGCCAGGCTCCCGGCAAGGAGCGCGAGTTCGTGAGCATCATTGACGGC<br>ACGGGTAGCACCAGCTACGCTGCCAGCGTGAAGGGACGTTTTACAGCCTCTGAG<br>GACAAGGGGAAGAACATTGCGTATCTTCAGATGAACTCCCTGAAGCCCGAGGAT<br>ACCGCCATGTACTATTGCAAGGCCTCCCGCGTGCGTGGCCGGGCCGTTAGTGAG<br>TATTGGGGCCAGGGGACGCAGGTCACCGTCAGTAGCGGTGGCTCCGGGGGTTCT<br>GGTGGCAGTGGTCAGGTCCAGCTCCAGGAGAGCGGTGGAGGCAGCGTCCAAGCT<br>GGCGGGTCCCTGAGGCTGTCTTGTACTGCGCCGGGATTTACTTCCAACAGCTGC<br>GGTATGGACTGGTATCGGCAGGCCCCTGGGAAAGAGAGGGAGTTCGTGTCTTCC<br>ATCTCTACGGATGGTACTACCGGCTACGCCGACAGCGTGAAGGGCCGTTTTACC<br>ATTAGCAAAGACAAGGCTAAAGACACAGTCTACCTTCAGATGAACTCTCTCAAA<br>CCAGAGGACACTGGTATGTATAGCTGTAAAACCAAAGATGGGACCATCGCTACA<br>ATGGAACTCTGCGATTTCGGGTACTGGGGACAGGGCACCCAAGTCACTGTCTCT<br>AGT |
| hIL27<br>Ra_VH<br>H3-<br>DR593 | 1271 | CAGGTGCAGCTTCAGGAGTCCGGGGGAGGCAGCGTGCAGGCAGGAGGCAGCCTG<br>CGCCTGTCTTGCGTCGCTTCCGGCTACGTGTCCCGCGACTATTTCCTGCCTTCT<br>TGGTACAGACAGGCACCTGGAAAGGAGCGCGAGTTCGTCTCTATTATCGACGGC<br>ACCGGCAGCACTTCTTACGCTGCCTCCGTTAAGGGCCGCCTCACCGCAAGCGAG<br>GACAAGGGAAAGAATATTGCCTACCTCCAGATGAACAGCCTGAAACCAGAGGAC<br>ACCGCGATGTATTACTGTAAGGCATCATGCGTGCGCGGTCGCGCAGTGTCAGAG<br>TATTGGGGTCAGGGAACCCAGGTGACAGTTTCTTCCGGCGGTGGCTCACAGGTG<br>CAGTTGCAGGAGAGTGGTGGAGGGTCAGTCCAGGCTGGAGGCTCCCTCAGACTT<br>TCCTGTGCCGCTAGTGGATACCCCTATTCCAATGGATATATGGGTTGGTTTAGA<br>CAAGCTCCAGGAAAGGAGCGTGAGGGCGTCGCGACCATCTACACTGGCGACGGT<br>CGCACCTACTATGCGGATAGCGTGAAGGGCCGTTTCACCATCAGCCGTGACAAC<br>GCCAAGAATACCGTCGATTTGCAGATGTCTTCCTTGAAACCGGAGGACACCGCT<br>ATGTATTACTGTGCGGCCAGAGCTGCGCCATTGTATAGCTCCGGTTCCCCTCTG<br>ACCCGCGCTCGCTACAATGTGTGGGGACAGGGCACTCAGGTCACCGTCTCATCC |
| hIL27<br>Ra_VH<br>H3-<br>DR593 | 1272 | CAGGTGCAACTCCAGGAGAGCGGGGGGGGTTCCGTCCAGGCTGGTGGCTCTCTG<br>AGGTTGAGCTGTGTAGCCAGCGGCTACGTGTCTTGTGACTACTTCCTCCCCAGC<br>TGGTATCGTCAGGCTCCTGGCAAGGAGCGCGAGTTTGTCAGTATCATTGATGGC<br>ACCGGGAGCACCTCATACGCTGCCTCTGTGAAGGGTCGCTTCACTGCCAGCGAG<br>GATAAGGGCAAGAACATCGCCTACCTTCAGATGAACTCTTTGAAGCCGGAAGAC<br>ACTGCCATGTATTACTGCAAGGCTTCTTGCGTCAGGGGACGCGCAGTGTCAGAG<br>TATTGGGGGCAGGGAACCCAGGTTACCGTCAGCTCCGGCGGAAGCGGAGGCAGC<br>GGGGGCAGGGGGCAGGTGCAACTCCAGGAATCTGGGGGAGGCTCCGTTCAGGCT<br>GGCGGTTCTCTCAGACTCAGCTGCGCGGCCTCCGGCTATCCATATTCCAACGGA<br>TACATGGGCTGGTTCCGTCAGGCTCCCGGAAAGGAACGCGAAGGGGTGGCTACC<br>ATCTACACCGGAGATGGCCGGACTTATTACGCGGACTCTGTGAAGGGTCGCTTC<br>ACCATTTCAAGGGACAACGCAAAGAACACCGTGGACCTGCAAATGTCTTCCCTG<br>AAACCAGAAGACACCGCCATGTACTATTGTGCTGCCCGCGCCGCACCCCTGTAT<br>AGCTCCGGTTCCCCTCTTACGAGGGCACGTTACAACGTCTGGGGCCAGGGCACT<br>CAGGTGACAGTTAGCTCC |
| hIL27<br>Ra_VH<br>H3-<br>DR594 | 1273 | CAAGTGCAGCTGCAAGAGAGTGGCGGAGGCTCTGTGCAGGCTGGCGGTTCCCTG<br>AGACTCAGTTGCGTTGCCTCAGGCTACGTGTCTTGTGACTACTTCTTGCCCTCA<br>TGGTATCGGCAGGCTCCCGGAAAGGAGCGCGAGTTTGTTTCAATCATTGATGGG<br>ACAGGTTCTACCTCCTACGCCGCGTCAGTTAAGGGACGGTTTACTGCGTCCGAG<br>GACAAGGGAAAGAACATTGCATACCTTCAGATGAACTCTCTGAAGCCCGAAGAT<br>ACAGCCATGTATTACTGCAAGGCCTCCTGCGTCAGAGGTAGAGCAGTCTCCGAG<br>TACTGGGGCCAGGGAACCCAGGTGACAGTGAGTAGCGGAGGGGGCTCTCAGGTG<br>CAGCTGCAAGAGAGCGGGGGTGGCTCCGTTCAGGCCGGTGGGAGCCTCAGGCTC<br>AGCTGTGTGGCGAGCGCTTCCACTTATTGCACCTACGACATGCACTGGTATCGG<br>CAGGCTCCGGGAAAGGGCAGAGAGTTCGTATCTGCCATCGACTCAGACGGGACC<br>ACACGTTACGCCGACTCTGTGAAGGGCCGCTTCACTATCAGCCAAGGCACCGCC<br>AAAAACACTGTTTATTTGCAGATGAACAGCTTGCAGCCAGAGGACACCGCCATG<br>TATTACTGTAAGACAGTTTGTGTGGTAGGCAGCAGATGGTCCGACTACTGGGGC<br>CAGGGTACTCAAGTGACCGTCTCCAGC |
| hIL27<br>Ra_VH<br>H3-<br>DR594 | 1274 | CAGGTCCAGCTCCAGGAAAGCGGCGGTGGCAGCGTGCAGGCTGGCGGATCTTTG<br>CGTCTTTCATGCGTGGCCAGCGGTTATGTAAGCTGCGACTATTTTCTGCCAAGC<br>TGGTATCGGCAGGCACCTGGCAAGGAGCGTGAATTTGTCAGCATCATTGATGGC<br>ACCGGATCTACCTCCTACGCAGCGAGCGTCAAGGGAAGATTCACCGCCTCAGAA<br>GATAAGGGCAAAAACATCGCCTACCTCCAGATGAACTCCCTGAAGCCTGAAGAT<br>ACAGCGATGTACTATTGCAAAGCCAGCTGTGTCCGTGGCAGAGCCGTGTCCGAG<br>TATTGGGGCCAGGGAACACAAGTGACTGTTTCCTCTGGTGGATCAGGAGGCAGC<br>GGTGGCTCTGGCCAGGTGCAGCTTCAGGAGAGCGGAGGTGGATCTGTGCAGGCT |

TABLE 1B-continued

| Name | SEQ ID NO: | Sequence |
|---|---|---|
| | | GGCGGTTCACTTCGTCTGTCCTGCGTCGCCTCTGCGTCTACCTATTGTACCTAC GATATGCACTGGTATCGCCAAGCCCCTGGCAAGGGCCGCGAGTTCGTGTCCGCT ATTGATTCCGACGGAACTACCCGGTACGCCGATTCTGTCAAGGGAAGATTTACA ATCTCCCAGGGGACCGCCAAGAATACCGTCTATCTGCAAATGAACAGTTTGCAG CCAGAGGACACTGCTATGTATTACTGCAAGACCGTGTGCGTGGTCGGAAGCCGC TGGTCTGACTATTGGGGTCAGGGCACCCAGGTGACCGTGTCCTCC |
| hIL27 Ra_VH H3-DR595 | 1275 | CAGGTCCAGCTCCAGGAGTCAGGTGGCGGTTCCGTCCAGGGGGGAGGCAGCCTG CGGCTTTCCTGTGTGGCTTCTGGCTATGTTAGCTGCGACTACTTTCTCCCTTCC TGGTATCGTCAAGCGCCTGGAAAGGAGAGGGAGTTCGTCTCCATCATTGACGGG ACGGGTTCCACCAGCTATGCAGCCTCCGTGAAGGGGAGATTCACTGCCAGTGAA GACAAGGGTAAGAACATCGCTTATTTGCAGATGAACTCCCTGAAACCAGAGGAT ACCGCTATGTATTACTGCAAGGCGTCTTGCGTGAGGGGCCGCGCTGTGTCCGAA TACTGGGGCCAGGGGACCCAGGTCACCGTTAGCTCTGGAGGCGGTTCCCAGGTG CAGCTTCAGGAAAGCGGAGGTGGCAGCGTGCAGGCTGGAGGCTCACTGACACTG TCTTGCGCAGCCTCCGAATACGCATATTCAACCCGCAACATGGGCTGGTATCGT CAGGCCCCTGGCAAGGAGAGAGAGCTGGTGTCTGCTTTCATCTCTGATGGCTCC ACGTATTACGCTGATTCTGTTAAGGGTCGTTTTACCATCACACGGGACAACGCT AAGAACACGGTGTATCTTCAGATGAACAGTTTGAAGCCCGAGGATACAGCGATC TACTATTGCAGCGCGAATTGTTATAGACGCCTGCGCAACTATTGGGGTCAGGGC ACACAGGTTACCGTAAGCTCA |
| hIL27 Ra_VH H3-DR595 | 1276 | CAAGTTCAGCTGCAAGAATCTGGAGGGGGGTCTGTGCAGGCTGGCGGTTCCCTG CGTCTCTCATGCGTCGCCTCTGGCTACGTTTCCTGCGACTACTTTCTTCCTTCA TGGTACAGGCAGGCCCCTGGCAAGGAGCGCGAGTTTGTGTCCATTATCGACGGG ACTGGTAGCACATCCTATGCTGCCTCCGTGAAAGGACGCTTTACAGCCAGTGAG GACAAGGCGTAAGAACATCGCTTATTGCAAATGAACTCACTCAAGCCCGAAGAC ACAGCTATGTATTACTGCAAGGCATCCTGTGTGCGTGGCCGCGCCGTGTCTGAG TACTGGGGGCAGGGGACACAGGTGACCGTGTCCTCTGGGGGCTCAGGTGGCTCC GGTGGCTCCGGCCAAGTTCAGCTCCAGGAGTCTGGAGGCGGTAGCGTGCAGGCT GGAGGCTCCCTGACCCTTAGCTGCGCCGCTAGTGAGTATGCGTATTCAACTTGC AACATGGGTTGGTACAGGCAGGCCCCAGGGAAGGAGAGAGAGCTGGTCAGCGCT TTCATTAGTGACGGGTCTACGTATTACGCCGACTCCGTGAAGGGGAGATTTACT ATTACCCGTGATAACGCGAAGAATACTGTGTATTTGCAGATGAACTCTCTCAAG CCGGAGGACACCGCCATCTATTACTGTAGCGCCAACTGTTACAGACGCCTGAGA AACTATTGGGGGCAAGGAACCCAGGTGACCGTGAGCAGC |
| hIL27 Ra_VH H3-DR596 | 1277 | CAGGTGCAACTGCAAGAGTCAGGGGGGGGCAGTGTGCAGGGGGGTGGCAGTCTG CGCCTGTCCTGCGTAGCTTCTGGCTACGTGTCTTGCGACTACTTCCTCCCGTCC TGGTATAGGCAAGCGCCGGGGAAGGAACGGGAGTTTGTCAGTATCATTGATGGT ACTGGTAGCACATCTTATGCTGCCTCTGTCAAGGGAAGATTTACTGCCAGCGAG GATAAGGGCAAGAACATTGCCTACCTGCAAATGAACTCTCTGAAGCCAGAGGAT ACCGCCATGTATTACTGCAAGGCCAGCCGCGTTAGGGGACGTGCTGTCTCTGAA TATTGGGGCCAGGGCACCCAGGTCACCGTGAGTAGCGGTGGGGGCTCTCAGGTT CAACTGCAAGAGTCTGGAGGTGGGCTCGTCCAGCCGGGGGGGTCTCTGAGGTTG TCTTGCACCGCGTCAGGGCTGACCTTCGACGATTCTGTGATGGGCTGGTTTCGC CAGGCCCCTGGCAAAGGGCGTGAGGCTGTGTCCTGCATCAGCTCAAGCGGAGCA AATGCCTTCTATGCCGACAGTGTCAAAGGCCGCCTCACAATCAGCAGAGACAAC GCTAAGAACACCCTGTACCCCCAGATGAACTCACTCAAGCCTGAAGATACGGCA ACCTATTACTGCAAAAGGGGCCACGCCTGCGCCGGGTATTACCCTATCCCCTAA GATGACTACTGGGGCCAGGGTACTCAAGTAACCGTGTCCTCC |
| hIL27 Ra_VH H3-DR596 | 1278 | CAGGTCCAGCTTCAGGAGTCCGGCGGTGGCTCCGTGCAGGCTGGCGGGTCCCTG CGCCTGTCCTGCGTGGCCAGCGGCTACGTGTCCTGCGACTATTTCCTGCCCTCT TGGTATCGCCAAGCGCCGGGCAAAGAAAGAGAGTTCGTATCAATCATTGATGGG ACCGGCTCAACCAGCTACGCAGCTTCCGTAAAGGGGAGATTCACAGCCTCCGAA GATAAAGGCAAGAACATCGCTTACCTCCAGATGAACTCTCTGAAGCCTGAGGAT ACTGCAATGTACTATTGTAAGGCCTCATGCGTGCGTGGCCGCGCAGTGTCTGAA TATTGGGGCCAGGGCACCCAGGTTACCGTCTCAAGCGGAGGCTCAGGAGGCTCA GGAGGCTCAGGACAGGTGCAGCTTCAGGAGTCCGGCGGAGGCCTGGTGCAGCCC GGCGGTAGCCCCCGTCTTAGTTGTACTGCCAGCGGGCTCACCTTTGATGACTCA GTGATGGGGTGGTTTCGCCAGGCTCCGGGCAAAGGCCGGGAGGCCGTGTCCTGC ATCTCTAGCTCCGGTGCCAATGCGTTCTACGCAGATAGCGTGAAGGGCAGATTC ACTATCAGTAGAGATAATGCCAAGAATACACTGTACTTGCAGATGAACTCCCTC AAGCCTGAAGACACGGCCACCTACTATTGTAAACGGGGCCACGCCTGCGCTGGC TATTACCCGATCCCGTATGATGACTACTGGGGACAGGGCACCCAAGTCACCGTC TCCTCT |
| hIL27 Ra_VH H4-DR591 | 1279 | CAGGTTCAGTTGCAGGAATCTGGGGCGGGCCTCGTTCAGCCTGGGGAGAGCCTC CGTCTGTCCTGCACCGCTTCAGGATTCACTTTCTCAAACTACGCAATGTCTTGG GTCCGGCAGGCTCCGGGCAAAGGCTTGGAATGGGTGTCAGGCATCAATGTTGCA TACGGCATTACCTCCTACGCAGATAGCGTGAAGGGCCGTTTCACCATCAGTCGT GACAACACCAAAAACACTCTCTACTTGCAGCTCAATTCACTCAAGACAGAGGAC ACCGCTATTTATTACTGTGTCAAACACTCCGGCACTACCATCCCACGCGGCTTC ATTAGCTATACCAAACGCGGCCAGGGCACCCAGGTCACCGTCTCCTCTGGTGGC GGTTCCCAGGTGCAGTTGCAGGAATCCGGGGGGGGAAGCGTGCAGGCCGGTGGC AGCCTGCGCCTGAGCTGCACAGCTTCCGGGGCTATCGCTTCTGGCTACATTGAT |

TABLE 1B-continued

| Name | SEQ ID NO: | Sequence |
|---|---|---|
| | | TCCCGGTGGTGTATGGCCTGGTTCCGCCAGGCCCCTGGCAAAGAGCGTGAGGGC GTGGCTGCGATCTGGCCTGGAGGGGGCCTGACCGTCTACGCCGATAGCGTTAAA GGCAGGTTTACCATCAGCCGCGACCATGCCAAGAACACCCTGTACCTCCAGATG AATAACCTGAAGCCTGAGGACACGGCCATGTATTACTGCGCCGCAGGCTCACCT AGAATGTGCCCTAGTTTGGAGTTCGGCTTTGACTATTGGGGTCAGGGTACGCAG GTGACTGTGTCCTCC |
| hIL27 Ra_VH H4- DR591 | 1280 | CAAGTGCAGTTGCAGGAGTCCGGTGGCGGACTCGTCCAGCCTGGAGAATCCCTG AGGTTGAGCTGCACCGCGTCCGGGTTCACGTTCAGCAATTACGCCATGTCTTGG GTGAGGCAAGCCCCAGGTAAAGGCCTTGAGTGGGTCAGCGGAATCAACGTGGCT TACGGGATCACCAGTTACGCAGATAGCGTCAAGGGGCGGTTCACTATTAGCAGA GATAACACTAAGAACACTCTGTACCTTCAGCTGAACTCACTCAAGACCGAAGAC ACCGCCATTTATTACTGCGTAAAGCACAGCGGTACTACGATCCCTCGCGGCTTT ATCAGCTATACTAAGCGCGGTCAAGGAACCCAAGTGACCGTGTCAAGCGGAGGG AGCGGTGGATCTGGGGGATCAGGCCAGGTGCAGCTTCAGGAGAGTGGCGGTGGC TCTGTGCAGGCCGGGGGCTCACTGAGACTGTCTTGCACTGCCAGGGGGGCTATC GCGTCTGGCTACATCGACAGTCGCTGGTGCATGGCCTGGTTCAGACAGGCCCCT GGTAAGGAGCGTGAAGGCGTGGCTGCCATTTGGCCTGGAGGCGGACTGACCGTC TATGCGGATAGCGTCAAGGGGAGGTTTACCATTAGCCGCGACCACGCCAAGAAT ACTCTGTACCTTCAGATGAATAACCTGAAACCCGAGGATACCGCGATGTATTAC TGTGCAGCTGGCAGTCCTCGGATGTGTCCGAGCTTGGAGTTCGGGTTCGATTAT TGGGGTCAGGGAACTCAGGTGACTGTGTCCTCC |
| hIL27 Ra_VH H4- DR592 | 1281 | CAGGTACAGCTCCAGGAATCCGGCGGAGGCCTTGTCCAGCCCGGAGAGTCCTTG CGCCTCTCTTGCACCGCAAGCGGCTTCACCTTCTCCAACTATGCTATGTCCTGG GTGCGTCAGGCCCCCGGCAAAGGCCTGGAATGGGTCAGCGGGATCAATGTGGCA TACGGGATCACTTCCTACGCCGATAGTGTCAAGGGTCGTTTTACCATTAGCCGT GATAACACGAAAAACACTCTGTACCTCCAGCTCAACAGCCTGAAGACGGAAGAT ACGGCTATCTATTACTGTGTCAAACACAGTGGCACGACTATTCCGCGCGGCTTC ATCTCATATACTAAGCGCGGACAGGGGACCCAAGTGACTGTCAGCAGTGGCGGA GGCTCCCAGGTGCAGCTCCAGGAATCCGGTGGCGGTTCCGTCCAAGCGGGGGGG TCTCTGCGTCTTTCCTGTACCGCTCCGGGGTTTACCAGCAACTCTTGTGGAATG GACTGGTACAGGCAGGCACCAGGGAAGGAGCGCGAGTTCGTTTCCAGCATCAGC ACCGACGGAACCACTGGCTATGCCGACAGCGTGAAGGGTCGCTTCACGATCTCT AAGGATAAGGCCAAAGATACTGTGTACCTGCAAATGAACTCTCTTAAACCGGAA GATACAGGTATGTACTCATGCAAAACAAAAGACGGCACCATCGCCACGATGGAG CTTTGCGATTTCGGATACTGGGGCCAGGGCACACAAGTGACGGTTAGTAGC |
| hIL27 Ra_VH H4- DR592 | 1282 | CAGGTCCAGCTCCAGGAGAGCGGCGGGGGCCTGGTCCAGCCAGGTGAGTCTCTG CGTCTGTCTTGCACCGCTTCTGGTTTCACATTTTCCAATTATGCCATGTCCTGG GTCCGCCAGGCTCCAGGGAAGGGCCTTGAGTGGGTCTCTGGCATCAACGTGGCC TATGGCATCACCTCTTATGCCGACAGCGTGAAGGGTCGTTTCACCATCTCCCGC GACAACACGAAGAACACACTGTACCTCCAGTTGAACAGCTTGAAGACCGAGGAC ACCGCGATCTACTATTGCGTGAAGCATAGCGGGACCACGATCCCTCGCGGATTC ATCAGCTATACGAAGCGCGGCCAGGGTACACAGGTCACCGTTAGCTCCGGCGGT AGTGGCGGGTCCGGTGGCAGCGGACAGGTGCAGCTCCAGGAGTCCGGTGGGGGT TCCGTACAAGCCGGAGGCTCACTGCGCCTGTCCTGCACAGCTCCGGGCTTCACT TCTAACAGTTGCGGCATGGACTGGTATCGCCAAGCCCCAGGCAAAGAAAGAGAG TTCGTTTCTAGCATCTCCACCGATGGCACCACAGGTTACGCCGACTCTGTCAAG GGCCGCTTTACTATCAGCAAGGATAAGGCCAAGGACACCGTGTATCTTCAGATG AACTCCCTGAAGCCCGAGGATACTGGGATGTACTCATGCAAGACCAAGGATGGA ACTATCGCCACGATGGAGCTGTGTGACTTCGGTTATTGGGGGCAGGGCACCCAG GTGACCGTCAGCAGC |
| hIL27 Ra_VH H4- DR593 | 1283 | CAGGTGCAGCTCCAGGAGAGTGGCGGGGGCCTGGTTCAGCCAGGTGAAAGCCTG CGCTTGAGCTGCACCGCATCCGGCTTCACCTTCTCTAATTATGCCATGAGTTGG GTGAGACAAGCCCCCGGCAAAGGACTGGAGTGGGTGTCTGGAATTAACGTAGCG TATGGCATCACGTCCTACGCTGATAGCGTCAAGGGGCGCTTCACCATCTCCCGC GACAACACGAAAAACACCCTGTACCTCCAGCTGAACTCCCTCAAGACTGAAGAT ACCGCGATTTATTACTGTGTGAAACACTCTGGAACAACCATCCCTCGCGGCTTC ATTAGTTACACCAAGCGCGGCCAGGGCACCCAGGTGACCGTCAGTTCCGGGGGC GGAAGCCAGGTGCAGTTGCAGGAGTCCGGCGGAGGTTCCGTGCAGGCTGGCGGG TCCCTGAGACTGTCCTGCGCAGCCAGCGGCTACCCTTATAGCAATGGCTACATG GGATGGTTTCGCCAGGCTCCTGGCAAGGAGCGCGAAGGTGTGGCCACTATTTAC ACGGGTGATGGACGCACCTATTACGCCGACAGCGTCAAGGGCCGCTTTACCATT AGCCGGGATAACGCCAAGAATACTGTCGATCTCCAGATGTCTTCACTGAAACCT GAAGACACCGCCATGTACTATTGCGCCGCACGCGCCGCGCCGTTGTACTCTTCC GGCAGCCCCCTGACCCGTGCTCGCTACAACGTCTGGGGGCAAGGCACACAGGTG ACAGTCTCCTCT |
| hIL27 Ra_VH H4- DR593 | 1284 | CAGGTCCAGTTGCAGGAGAGCGGAGGGGGCCTGGTGCAGCCTGGGGAATCCCTC CGTCTCTCCTGCACCGCCAGCGGCTTCACCTTCAGCAACTACGCCATGAGCTGG GTGCGCCAGGCTCCAGGGAAGGGCCTGGAGTGGGTGTCAGGCATTAACGTCGCC TACGGCATCACCAGTTATGCCGATAGTGTCAAGGGCCGCTTCACTATCTCCAGG GACAACACAAAGAACACTCTCTATCTTCAGCTTAATTCCCTGAAAACTGAAGAC ACCGCTATCTATTACTGTGTGAAACACAGCGGAACAACCATCCCGCGCGGTTTC ATCTCCTACACTAAGAGAGGCCAGGGCACCCAGGTTACCGTTTCTAGCGGCGGA |

TABLE 1B-continued

| Name | SEQ ID NO: | Sequence |
|---|---|---|
| | | TCTGGGGGCAGCGGGGGCTCCGGTCAGGTCCAACTCCAAGAGTCCGGCGGAGGC<br>TCTGTCCAGGCTGGGGGGTCTTTGCGTCTGTCCTGTGCCGCTTCTGGCTACCCG<br>TACAGCAACGGTTACATGGGTTGGTTCAGACAGGCCCCCGGCAAAGAGAGGGAG<br>GGAGTGGCCACCATCTACACCGGCGACGGCAGGACATATTACGCTGATTCCGTG<br>AAGGGTCGTTTCACTATCTCCCGCGATAACGCCAAGAACACCGTCGATCTTCAG<br>ATGTCATCCCCGAAGCCTGAAGACACTGCGATGTATTACTGTGCAGCTCGCGCC<br>GCGCCCCTCTACAGCTCAGGTAGCCCACTGACACGTGCCCGGTACAACGTCTGG<br>GGGCAGGGCACCCAGGTGACGGTGTCTTCC |
| hIL27<br>Ra_VH<br>H4-<br>DR594 | 1285 | CAGGTGCAGCCCCAGGAAAGCGGGGCGGGGCTGGTTCAGCCTGGCGAGTCCCTC<br>CGTCTGTCCTGCACAGCTAGTGGTTTTACGTTTAGCAACTACGCGATGAGCTGG<br>GTCCGTCAAGCCCCTGGTAAGGGGCTGGAGTGGGTGTCCGGCATCAACGTGGCC<br>TACGGCATCACCTCCTACGCTGACTCTGTGAAGGGCCGGTTCACTATCAGCCGG<br>GATAACACTAAGAACACCTTGTATCTCCAACTGAACTCCCTGAAGACAGAGGAC<br>ACCGCTATTTACTATTGTGTGAAGCACTCTGGCACGACCATCCCCAGGGGCTTC<br>ATCAGCTACACCAAGCGTGGGCAGGGTACACAGGTGACAGTCTCCAGGGCGGGA<br>GGCTCCCAAGTGCAGCTGCAAGAATCTGGCGGGGGAAGCGTCCAGGCCGGTGGA<br>AGTCCGCGCCTTAGTTGCGTGGCTTCTGCAAGCACCTATTGCACCTATGACATG<br>CACTGGTATAGGCAGGCCCCCGGCAAGGGGCGCGAGTTCGTTAGCGCCATCGAC<br>AGTGATGGGACCACGCGCTACGCGGACAGTGTGAAGGGCAGGTTCACCATCAGC<br>CAGGGTACTGCCAAAAATACAGTGTACTTGCAGATGAACTCCCTCCAGCCTGAG<br>GACACCGCCATGTACTATTGCAAGACCGTGTGCGTCGTAGGCTCCCGTTGGAGC<br>GACTACTGGGGCCAGGGCACACAGGTGACCGTCTCCTCC |
| hIL27<br>Ra_VH<br>H4-<br>DR594 | 1286 | CAGGTCCAACTGCAAGAGTCTGGAGGTGGATTGGTCCAGCCCGGCGAAAGCCTG<br>AGGTTGAGCTGCACCGCGAGCGGATTCACCTTTAGCAACTATGCCATGTCCTGG<br>GTTCGCCAAGCCCCTGGGAAGGGCCTGGAGTGGGTCAGTGGGATCAATGTGGCT<br>TATGGAATCACCAGCTATGCGGACTCTGTGAAGGGAAGGTTCACTATCTCTCGT<br>GACAATACTAAAAACACCCTGTACCTCCAGCTCAATTCCCTCAAGACTGAGGAC<br>ACCGCTATTTACTATTGTGTGAAACACTCCGGCACCACGATCCCCCGTGGGTTC<br>ATCAGCTACACCAAACGGGGCCAAGGCACCCAGGTCACCGTATCTAGTGGCGGT<br>AGTGGTGGGAGTGGCGGTTCCGGGCAGGTGCAGCTCCAGGAGTCCGGCGGTGGC<br>TCCGTGCAGGCAGGGGGTAGCCTGCGCCTGTCCTGTGTGGCGTCTGCAAGCACC<br>TATTGTACTTATGATATGCACTGGTATCGTCAGGCTCCAGGCAAGGGCAGAGAG<br>TTCGTCTCCGCAATCGACTCCGATGGCACCACGCGCTACGCCGATTCTGTGAAG<br>GGCCGTTTCACTATCAGCCAGGGTACAGCCAAAAATACCGTGTATCTTCAGATG<br>AACAGTCTCCAGCCAGAGGATACCGCTATGTACTATTGCAAGACTGTGTGCGTG<br>GTTGGCTCCAGGTGGTCCGATTACTGGGGCCAGGGAACCCAGGTGACAGTGTCC<br>AGC |
| hIL27<br>Ra_VH<br>H4-<br>DR595 | 1287 | CAGGTGCAGCTCCAGGAGAGCGGAGGGGGTTTGGTCCAGCCTGGCGAGTCTCTC<br>AGACTTTCTTGTACCGCATCTGGCTTTACTTTCAGCAATTACGCCATGTCCTGG<br>GTGCGGCAAGCCCCCGGCAAGGGCCTGGAATGGGTGAGCGGCATCAACGTGGCC<br>TACGGCATCACCTCATACGCAGATTCCGTCAAGGGGCGTTTTACCATCAGTCGC<br>GATAATACAAAGAACACATTGTACCTCCAACTTGAACTCCCCAAGACCGAGGAT<br>ACCGCGATTTACTATTGCGTGAAACACAGCGGCACTACCATCCCACGCGGGTTT<br>ATCAGCTACACGAAGAGAGGCCAGGGTACACAGGTCACCGTGTCAAGCGGCGGT<br>GGATCTCAGGTACAGCTCCAGGAGTCTGGGGGTGGAAGCGTGCAGGCGGGGGA<br>TCTCCGACATTGTCCTGCGCCGCAAGTGAGTATGCTTATTCCACGTGCAACATG<br>GGATGGTACAGGCAGGCCCCTGGTAAAGAGAGAGAACTCGTGAGCGCTTTTATT<br>TCAGACGGCAGCACTTATTACGCCGACTCCGTCAAAGGACGCTTCACCATCACT<br>CGTGACAACGCTAAGAATACGGTCTACCTTCAGATGAACTCCCTCAAACCTGAA<br>GATACTGCAATCTACTATTGTAGTGCCAACTGCTATAGACGCCTCCGCAACTAT<br>TGGGGGCAGGGAACACAGGTGACCGTTAGCAGC |
| hIL27<br>Ra_VH<br>H4-<br>DR595 | 1288 | CAAGTTCAGCTGCAAGAGTCTGGCGGTGGCCTGGTGCAGCCCGGCGAATCTTTG<br>CGCTTGAGTTGTACCGCCTCTGGTTTTACATTCTCAAACTATGCAATGAGCTGG<br>GTGAGACAGGCCCCAGGCAAGGGCTTGGAATGGGTCTCTGGGATCAACGTCGCT<br>TACGGCATTACCTCATACGCCGATAGCGTCAAGGGTCGCTTCACTATCTCTCGG<br>GATAATACGAAGAATACTCTCTACTTGCAGCTCAACTCACTGAAGACCGAGGAC<br>ACTGCGATCTATTACTGCGTCAAACACTCCGGCACCACTATCCCTCGCGGCTTC<br>ATCTCTTACACTAAACGCGGCCAGGGTACTCAGGTGACTGTGAGTTCAGGTGGC<br>TCTGGAGGTAGCGGGGGTTCCGGTCAGGTGCAGCTCCAGGAGAGCGGGGGGGGA<br>AGCGTACAGGCTGGAGGCAGCCTGACCCTGAGCTGTGCAGCTTCCGAGTATGCC<br>TACTCCACCTGTAACATGGGATGGTATAGACAGGCTCCCGGCAAGGAACGTGAG<br>CTGGTCAGCGCCTTTATCAGTGATGGGTCCACTTACTATGCCGATTCCGTGAAA<br>GGCCGGTTCACCATCACTCGCGACAACGCCAAGAATACAGTGTACTTGCAGATG<br>AACTCCCTCAAGCCCGAGGACACTGCTATCCATTACTGTTCTGCAAACTGCTAC<br>CGTCGCCTGCGCAACTACTGGGGCCAAGGCACTCAGGTTACCGTGAGCAGC |
| hIL27<br>Ra_VH<br>H4-<br>DR596 | 1289 | CAGGTGCAGTTGCAGGAGTCTGGAGGTGGCCTGGTCCAACCTGGAGAATCCCTG<br>CGGCTCTCTTGTACCGCGAGTGGTTTCACCATCAGCAACTATGCAATGAGCTGG<br>GTGCGCCAGGCTCCCGGCAAGGGATTGGAGTGGGTCAGCGGCATCAACGTGGCC<br>TATGGCATCACCAGCTACGCTGATAGTGTGAAGGGCCGGTTTACCATCAGTAGG<br>GACAACACCAAGAACACACTGTATCTTCAGCTCAACTCCCTGAAGACAGAAGAC<br>ACCGCTATCTACTATTGTGTGAAGCATTCCGGCACTACCATCCCACGCGGGTTC<br>ATCTCATACACCAAAAGGGGCCAGGGCACCCAGGTGACAGTTTCTAGCGGTGGC |

TABLE 1B-continued

| Name | SEQ ID NO: | Sequence |
|---|---|---|
| | | GGTTCCCAAGTGCAGTTGCAGGAGTCCGGTGGCGGTCTGGTTCAGCCTGGTGGG TCTCTTCGTCTGAGTTGTACCGCAAGCGGTCTTACCTTCGATGACAGCGTCATG GGGTGGTTCAGGCAGGCCCCCGGCAAGGGTCGCGAGGCAGTGAGCTGCATCAGC TCCAGTGGGGCTAACGCCTTTTATGCAGACTCCGTAAAAGGAAGATTCACTATC AGCAGGGACAACGCAAAGAACACCCTGTATCTCCAAATGAACAGTCTGAAACCG GAAGACACCGCCACTTATTACTGTAAACGGGGCCACGCCCGCGCAGGGTATTAC CCGATTCCTTATGATGACTACTGGGGCCAAGGCACCCAGGTGACAGTGTCTAGC |
| hIL27 Ra_VH H4- DR596 | 1290 | CAGGTGCAGCTCCAGGAAAGCGGAGGGGGGCTGGTGCAGCCGGGAGAGAGTCTC AGGCTTTCTTGTACCGCCTCTGGATTTACATTCAGCAATTACGCCATGTCCTGG GTTCGCCAAGCACCAGGGAAGGGCCTGGAGTGGGTGTCCGGCATCAACGTGGCA TACGGCATCACATCCTACGCGGATTCCGTCAAGGGTCGGTTTACCATCAGCCGC GATAATACAAAGAACACCTTGTATCTCCAGCTTAACAGCCTCAAGACAGAGGAC ACCGCCATCTACTATTGTGTGAAGCACTCCGGCACCACTATCCCTCGCGGCTTC ATTTCCTACACCAAAAGGGGTCAGGGCACTCAGGTAACAGTGTCCTCTGGGGGC TCCGGTGGATCAGGTGGCTCCGGCCAGGTACAACTCCAAGAGTCAGGAGGCGGT CTGGTACAGCCTGGTGGCTCCTCGCGCCTGTCTTGCACAGCAAGCGGCCTGACT TTCGATGACTCTGTGATGGGCTGGTTTCGTCAGGCCCCCAGGGAAGGGCAGGGAG GCCGTCTCCTGCATTAGTAGCTCCGGCGCTAACGCCTTCTATGCCGATAGTGTG AAGGGGCGCTTTACCATCTCTCGTGACAATGCCAAGAACACCCTGTACTTGCAG ATGAACAGCCTGAAGCCGGAGGATACTGCCACCTATTACTGCAAGCGCGGCCAT GCGTGTGCTGGCTACTATCCCATCCCTTACGATGACTATTGGGGTCAGGGCACC CAGGTGACCGTGTCCAGC |
| hIL27 Ra_VH H5- DR591 | 1291 | CAGGTCCAGCTTCAGGAAAGCGGGGGTGGATCTGTCCAGGGGGGCGGATCACTT CGCCTCAGTTGTACGGCCAGTGGCTATGTATCCCGCGACTACTTCCTCCCATCA TGGTATCGCCAGGCTCCGGGAAAGGAAAGGGAGTTCGTGTCTGTGATCGACGGC ACTGGCTCCACCTCCTACGCTGCCAGCGTCAAGGGTCGCTTCACCGCCTCACAG GACAAGGGCAAAAACATCGCCTATCTTCAGATGAACTCCCTGAAACCCGAGGAC ACAGCCATGTATTACTGTAAGGCCTCCTGTGTGCGTGGCCGCGCAATTTCCGAA TATTGGGGCCAGGGCACTCAGGTGACTGTGAGTTCCGGCGGGGGTTCCCAGGTC CAGTTGCAGGAGTCCGGTGGCGGATCTGTGCAGGCCGGAGGGTCCCTGCGCCTG AGCTGCACAGCGAGCGGTGCCATCGCCTCCGGCTATATTGACTCCAGGTGGTGC ATGGCCTGGTTCAGGCAAGCGCCCGGAAAAGAGCGTGAAGGTGTAGCTGCCATC TGGCCTGGGGAGGCCTGACCGTGTATGCCGATTCCGTCAAGGGCCGCTTCACC ATCAGCCGCGACCACGCAAAAAACACTCTGTACCTCCAGATGAATAACCTGAAG CCGGAGGACACCGCCATGTATTACTGTGCTGCCGGTTCTCCCCGTATGTGCCCC AGCCTGGAGTTCGGCTTCGACTACTGGGGCCAGGGAACTCAGGTCACTGTGTCA TCT |
| hIL27 Ra_VH H5- DR591 | 1292 | CAGGTCCAGCTCCAAGAGTCTGGAGGTGGCTCTGTGCAGGCTGGCGGTTCCCTC CGCCTGAGCTGCACAGCGAGCGGGTACGTGAGCTGCGATTATTTTCTGCCGTCT TGGTATCGTCAAGCGCCCGGAAAGGAGCGCGAGTTCGTGTCCGTGATCGACGGT ACGGGTAGCACCAGTTACGCGGCTTCTGTAAAAGGACGGTTCACCGCTTCCCAG GATAAGGGCAAAAACATCGCGTATTTGCAGATGAACAGCCTGAAGCCCGAGGAT ACCGCCATGTATTACTGTAAGGCCAGTTGTGTCAGAGGCCGCGCCATCTCCGAG TACTGGGGACAGGGCACTCAGGTGACCGTGTCCAGCGGTGGAAGCGGTGGCTCC GGGGGCTCCGGTCAGGTCCAGTTGCAAGAGTCAGGGGGTGGCTCCGTCCAGGCG GGCGGGAGCCTGCGCTTGTCCTGCACAGCTTCTGGGGCCATCGCCTCCGGCTAT ATCGACAGCCGCTGGTGCATGGCGTGGTTCCGCCAAGCGCCGGGCAAGGAACGT GAAGGCGTCGCAGCTATTTGGCCTGGGGGGGGGTTGACCGTGTACGCCGACTCC GTGAAGGGCCGTTTCACCATCAGTAGAGACCACGCCAAGAACACTCTCTACCTT CAGATGAATAACCTGAAACCGGAGGACACTGCTATGTATTACTGCGCTGCGGGC TCCCCCAGGATGTGTCCGAGCCTGGAGTTCGGCTTCGACTATTGGGGGCAGGGG ACCCAGGTCACCGTGTCCTCC |
| hIL27 Ra_VH H5- DR592 | 1293 | CAGGTTCAGCTCCAGGAATCCGGCGGAGGCTCTGTCCAGGCTGGGGGTTCTTTG CGTTTGAGCTGTACCGCGAGCGGGTACGTGTCTTGCGACTACTTCTTGCCCTCC TGGTATCGCCAGGCTCCTGGTAAGGAACGCGAGTTCGTCTCCGTCATTGATGGC ACCGGCTCTACGAGCTATGCTGCCTCAGTTAAGGGCCGCTTCACAGCCAGCCAG GATAAGGGCAAAAATATCGCTTACCTCCAGATGAACTCTCTGAAACCTGAAGAC ACTGCCATGTATTACTGTAAAGCGAGCTGCGTAAGAGGACGTGCCATCAGCGAG TACTGGGGCCAAGGGACACAGGTGACAGTTAGTAGCGGTGGCGGGTCCCAGGTG CAGTTGCAAGAGAGCGGTGGCGGAAGCGTGCAGGCAGGCGGATCTCTGCGGCTG TCCTGCACCGCCCCTGGATTCACCAGTAACTCTTGTGGTATGGACTGGTATCGT CAGGCTCCGGGTAAGGAGAGAGAGTTTGTTTCAAGTATCTCCACTGATGGCACA ACCGGGTATGCCGACTCCGTCAAGGGTCGTTTCACCATCTCCAAGGACAAGGCC AAGGACACTGTGTACCTTCAGATGAACTCACTGAAGCCTGAGGACACCGGGATG TATTCTTGCAAGACTAAAGATGGCACCATTGCCACTATGGAGCTGTGCGACTTC GGCTATTGGGGTCAGGGGACACAGGTCACTGTATCTAGC |
| hIL27 Ra_VH H5- DR592 | 1294 | CAGGTGCAGCTTCAGGAGTCCGGCGGTGGGAGCGTTCAGGCTGGAGGCTCTCTC AGGCTGTCATGCACTGCAAGCGGGTACGTTAGTTGTGACTACTTTCTTCCAAGC TGGTATCGCCAGGCTCCCGGAAAAGAGCGCGAGTTTGTTTCCGTTATTGATGGA ACTGGGAGTACGTCCTATGCCGCTTCAGTCAAGGGGCGCTTCACCGCATCCCAG GACAAGGGTAAGAATATCGCTTACCTTCAGATGAACTCCCTGAAGCCCGAAGAC ACCGCCATGTATTACTGTAAGGCTTCTTGCGTGAGGGGCCGCGCTATCAGTGAA |

TABLE 1B-continued

| Name | SEQ ID NO: | Sequence |
|---|---|---|
| | | TACTGGGGTCAGGGGACCCAGGTGACGGTTTCTAGCGGAGGCAGGGGGGGGAGC<br>GGCGGGTCTGGACAGGTCCAGCTTCAGGAAAGTGGTGGGGGCTCCGTTCAGGCT<br>GGCGGATCACTGCGCCTGAGCTGTACTGCTCCCGGCTTCACGAGCAACTCCTGC<br>GGTATGGACTGGTATCGTCAGGCCCCAGGTAAGGAGCGTGAGTTCGTGTCTTCC<br>ATCAGTACAGACGGGACAACCGGCTACGCAGACAGCGTAAAGGGCCGCTTCACC<br>ATCTCCAAGGATAAGGCAAAGGACACCGTCTACCTCCAGATGAACAGCTTGAAG<br>CCAGAGGACACGGGTATGTATAGCTGTAAGACCAAAGACGGTACAATCGCTACA<br>ATGGAGCTGTGTGACTTCGGGTATTGGGGCCAGGGAACTCAGGTTACCGTCTCA<br>TCC |
| hIL27<br>Ra_VH<br>H5-<br>DR593 | 1295 | CAGGTGCAGCTCCAGGAGAGCGGGGGGGGTTCTGTGCAAGCTGGGGGAAGTCTG<br>CGGCTCAGCTGTACCGCTAGTGGTTACGTGTCTTGCGACTATTTCCTGCCTTCA<br>TGGTATCGCCAGGCCCCAGGCAAAGAGCGCGAGTTCGTGTCCGTCATTGACGGA<br>ACCGGGAGTACCTCCTATGCAGCCAGTGTTAAGGGCCGTTTTACAGCCAGCCAG<br>GACAAGGGCAAAAATATCGCTTACCTCCAGATGAACAGCCTGAAGCCCGAGGAC<br>ACTGCCATGTATTACTGTAAAGCGAGCTGTGTCAGGGGTAGAGCAATTAGTGAA<br>TATTGGGGCCAAGGGACACAGGTGACAGTATCTTCAGGGGGGGGATCTCAGGTG<br>CAGCTCCAGGAAAGTGGAGGTGGGTCCGTGCAGGCGGGGGGTTCTCTCAGACTG<br>TCTTGCGCCGCGTCTGGCTATCCTTACAGCAACGGGTACATGGGATGGTTTAGA<br>CAAGCCCCAGGGAAGGAGCGCGAGGGGGTGGCCACCATTTACACCGGCGATGGC<br>CGGACTTACTATGCGGATTCCGTGAAGGGCCGCTTTACCATTTCAAGAGATAAC<br>GCGAAAAATACCGTGGACCTCCAGATGTCCTCTTTGAAGCCAGAGGATACCGCG<br>ATGTACTATTGCGCTGCCCGCGCCGCTCCTCTCTACAGTAGCGGCTCCCCACTT<br>ACCCGCGCTCGCTATAACGTGTGGGGCCAGGGGACACAGGTGACTGTGTCCTCC |
| hIL27<br><br>Ra_VH<br>H5-<br>DR593 | 1296 | CAGGTGCAGCTTCAGGAATCTGGGGGGGGTCCGTCCAGGCTGGCGGATCCTTG<br><br>AGACTGTCTTGCACTGCCAGTGGTTACGTGAGCTGTGATTACTTCCTGCCGTCT<br>TGGTATCGTCAAGCGCCAGGCAAGGAACGTGAGTTCGTGTCCGTGATCGACGGG<br>ACAGGTTCCACATCTTACGCCGCATCTGTTAAGGGGAGGTTCACAGCTTCTCAG<br>GACAAGGGTAAAAATATCGCCTATCTCCAGATGAACTCACTGAAGCCTGAAGAT<br>ACCGCTATGTATTACTGCAAGGCTTCTTGTGTGCGGGGCCGCGCTATCAGCGAG<br>TACTGGGGACAGGGCACTCAGGTGACGGTCTCCAGGGGGGGGGAGCGGGGGCTCC<br>GGGGGCAGCGGCCAGGTGCAGTTGCAGGAGAGCGGGGGAGGCTCTGTGCAAGCT<br>GGAGGCTCTTTGCGCCTGTCCTGCGCTGCCAGCGGATATCCTTACCCTAATGGT<br>TATATGGGATGGTTCAGGCAGGCCCCAGGAAAGGAGAGAGAAGGGGTTGCCACC<br>ATTTATACTGGGGATGGCCGCACCTATTACGCCGATTCCGTGAAGGGGCGGTTC<br>ACAATCTCTCGTGACAACGCCAAGAACACTGTCGATCTTCAGATGTCCAGTCTG<br>AAACCGGAGGACACTGCCATGTATTACTGTGCCGCACGCGCAGCTCCCCTCTAT<br>TCAAGCGGCTCCCCTCTCACTCGCGCACGCTATAACGTGTGGGGGCAGGGAACT<br>CAGGTGACTGTGTCTAGC |
| hIL27<br>Ra_VH<br>H5-<br>DR594 | 1297 | CAGGTGCAGCCGCAAGAGAGGTGGGCGGGCAGCGTGCAAGCCGGAGGTTCTCTG<br>CGGCTGAGTTGTACCGCTTCTGGATACGTGTCCCGCGACTACTTTTTGCCTTCA<br>TGGTATCGGCAGGCCCCAGGCAAAGAACGCGAGTTTGTGTCAGTGATCGACGGC<br>ACTGGCTCCACATCCTACGCAGCCAGCGTGAAGGGCCGTTTTACTGCGTCTCAG<br>GATZAAGGCAAGAACATCGCTTATTTGCAAATGAACAGCCTGAAGCCTGAAGAC<br>ACAGCCATGTATTACTGCAAGGCAAGCTGCGTTCGCGGTCGGGCGATCTCCGAG<br>TACTGGGGGCAGGGTACACAGGTCACCGTCTCCAGTGGAGGTGGCTCCCAGGTG<br>CAGCTTCAGGAAAGCGGTGGGGGAAGCGTCCAAGCTGGGGGCTCTCTCCGCCTC<br>TCATGTGTGGCCTCTGCCTCCACCTACTGCACTTACGATATGCACTGGTATCGT<br>CAGGCACCAGGGAAGGGACGCGAGTTCGTGTCCGCCATCGACAGCGACGGGACA<br>ACCCGGTACGCCGACTCTGTGAAAGGCCGCTTCACCATCAGCCAGGGGACAGCT<br>AAAAACACCGTGTACCTGCAAATGAACTCCCTCCAGCCAGAGGATACCGCCATG<br>TACTATTGTAAGACCGTATGCGTAGTGGGCAGCAGATGGTCCGACTATTGGGGC<br>CAGGGGACGCAGGTCACCGTGTCCAGC |
| hIL27<br>Ra_VH<br>H5-<br>DR594 | 1298 | CAGGTCCAGCTCCAGGAATCCGGTGGCGGTTCCGTGCAGGCAGGGGGGAGCCTG<br>CGTCTGAGTTGCACTGCCAGCGGCTACGTTTCATGTGATTACTTCCTGCCCAGT<br>TGGTACAGGCAGGCTCCTGGTAAAGAGCGCGAGTTCGTGAGCGTGATTGATGGG<br>ACTGGTTCAACCAGTTACGCGGCCAGCGTGAAGGGGCGCTTCACCGCTTCCCAG<br>GACAAGGGTAAGAACATCGCATATCTTCAGATGAACTCTCTCAAGCCTGAAGAC<br>ACCGCTATGTACTATTGCAAAGCCAGCTGCGTGCGTGGCCGCGCCATCAGCGAA<br>TACTGGGGGCAGGGCACCCAGGTCACTGTGTCTAGCGGTGGCTCAGGAGGGAGC<br>GGAGGCTCCGGCCAGGTGCAGCTCCAGGAGTCTGGCGGTGGCAGCGTTCAGGCT<br>GGCGGGAGCCTGCGCCTGAGCTGCGTGGCCACTGCATCCACCTATTGCACCTAC<br>GACATGCACTGGTATCGCCAGGCTCCTGGTAAGGGCCGTGAGTTCGTGAGCGCT<br>ATTGATAGCGACGGGACTACCCGTTACGCGGATTCTGTGAAGGGCAGATTCACC<br>ATCAGCCAGGGCACCGCCAAAAATACTGTTTATCTCCAGATGAATAGCCTGCAA<br>CCAGAAGACACCGCCATGTATTACTGCAAGACCGTGTGCGTAGTGGGAAGTAGG<br>TGGAGTGATTACTGGGGCCAGGGTACACAAGTCACAGTTTCAAGC |
| hIL27<br>Ra_VH<br>H5-<br>DR595 | 1299 | CAGGTCCAGCTCCAGGAGAGGGGGCGGAGGTAGCGTCCAGGCGGGGGGAAGCCTC<br>AGACTGAGCTGCACAGCCTCTGGGTACGTCTCCTGCGACTATTTCCTGCCATCA<br>TGGTATAGGCAAGCACCAGGCAAGGAGAGGGAGTTCGTGAGTGTGATTGACGGA<br>ACAGGGAGTACCTCCTACGCCGCATCTGTTAAGGGGCGGTTCACTGCAAGTCAG<br>GATAAAGGTAAGAACATTGCCTACCTGCAAATGAACCCCCTGAAGCCAGAGGAC |

TABLE 1B-continued

| Name | SEQ ID NO: | Sequence |
|---|---|---|
| | | ACCGCAATGTATTACTGCAAGGCGAGCTGCGTTCGTGGTCGCGCAATCTCCGAG TACTGGGGCCAAGGGACCCAGGTGACCGTGTCTTCCGGTGGCGGTTCCCAGGTG CAGCTCCAGGAGTCCGGGGGTGGCTCTGTGCAGGCCGGGGGCTCTCTGACCCTC TCCTGTGCGGCCAGCGAGTACGCCTACCCTACTTGTAACATGGCGGGGTATCGC CAGGCTCCCGGCAAGGAGCGTGAGCTTGTTAGTGCATTTATCTCCGACGGTTCC ACCTATTACGCCGACAGCGTGAAGGGCCGCTTTACCATTACCCGTGACAATGCG AAGAACACTGTATATTTGCAGATGAACTCCTTGAAGCCCGAAGACACCGCCATC TACTATTGCAGCGCTAACTGTTACCGTCGCCTGCGCAACTATTGGGGGCAGGGG ACACAGGTGACAGTCTCCTCC |
| hIL27 Ra_VH H5- DR595 | 1300 | CAGGTGCAGCTTCAGGAGAGCGGCGGAGGGTCCGTCCAAGCTGGCGGTTCCCTG AGACTGAGTTGCACCGCTTCAGGGTATGTTTCCTGTGACTATTTCCTTCCGAGC TGGTATCGGCAAGCGCCAGGAAAGGAGCGTGAGTTTGTCAGCGTGATCGACGGC ACCGGAAGCACCTCCTACGCCGCGAGTGTGAAAGGCCGTTTTACTGCATCCCAA GACAAAGGCAAGAACATCGCCTACCTTCAAATGAACCTCTGAAGGCGGGAGGAC ACCGCCATGTACTATTGCAAGGCATCTTGCGTCAGGGGCAGGGCCATCTCAGAG TACTGGGGACAGGGAACCCAGGTGACAGTGTCTTCCGGGGGAAGTGGTGGCTCT GGTGGCTCTGGTCAGGCTCAGTTGCAGGAGTCCGGTGGAGGCTCAGTGCAGGCC GGTGGCTCCCTGACGCTGTCTTGCGCGGCCAGCGAGTATGCTTATTCCACCTGC AATATGGGGGGTATCGCCAGGCCCCCGGAAAGGAACGTTGAGCTGGTGAGCGCC TTCATCAGCGACGGGTCTACTTATTACGCTGATTCCGTCAAGGGTAGGTTTACC ATCACACGGGATAATGCCAAGAACACCGTCTACCTCCAGATGAACTCTCTGAAG CCCGAAGACACTGCCATCTACTATTGCTCCGCAAATTGCTACCGCAGACTGAGA AATTATTGGGGCCAGGGAACTCAGGTGACTGTGTCATCA |
| hIL27 Ra_VH H5- DR596 | 1301 | CAGGTGCAGCTTCAGGAATCCGGGCGGGGGTCTGTGCAGGCTGGTGGCTCTCTG CGCCTCTCTTGCACCGCAAGCGGATACGTGTCCTGTGACTACTTCCTGCCGTCT TGGTACAGACAAGCGCCCGGTAAAGAGCGCGAGTTCGTTTCCGTCATTGATGGC ACCGGGAGCACTTCCTACGCAGCCAGCGTAAAGGGCAGATTCACGGCTTCTCAA GACAAGGGCAAGAATATCGCGTACCTCCAGATGAACTCTCTGAAGCCCGAGGAC ACCGCGATGTACTATTGCAAGGCGAGCTGCGTGAGAGGCAGGGCCATCTCCGAA TACTGGGGCCAGGGCACCCAGGTGACCGTGTCTAGCGGTGGGGGTAGCCAGGTA CAGTTGCAGGAATCAGGCGGTGGATTGGTTCAGCCGGGTGGAAGCCTGAGGCTT AGCTGCACCGCCTCCGGGTTGACTTTCGACGATTCTGTAATGGGCTGGTTTCGC CAGGCCCCTGGTAAGGGGAGGGAGGCTGTGAGCTGCATTTCTTCCAGTGGAGCC AATGCTTTCTACGCCGACTCCGTCAAGGGGAGATTCACCATCAGCCGCGACAAT GCAAAAAACACTCTGTACCCCCAGATGAACTCCTTGAAGCCCGAGGACACTGCC ACTTATTACTGTAAAAGAGGACACGCTTGTGCTGGCTACTATCCTATCCCTTAC GATGACTATTGGGGTCAGGGCACTCAAGTGACCGTCTCCTCC |
| hIL27 Ra_VH H5- DR596 | 1302 | CAGGTGCAGTTGCAGGAGTCTGGAGGCGGAAGCGTCCAAGCCGGGGGTTCCCTG AGACTCTCTTGCACCGCCTCCGGCTACGTATCCTGCGACTACTTCCTGCCCAGC TGGTATCGCCAGGCTCCCGGTAAGGAGCGCGAGTTTGTCAGCGTGATCGACGGC ACCGGCTCCACCTCTTATGCCGCTAGTGTTAAGGGCCGCCTTACTGCCTCCCAG GACAAGGGCAAAAACATTGCCTACCTCCAGATGAACAGCCTGAAGCCCGAGGAC ACCGCAATGTATTACTGCAAGGCGTCCTGCGTGAGGGGTCGTGCCATTTCTGAG TACTGGGGCCAGGGGACCCAAGTCACCGTAAGTTCTGGGGGCTCTGGCGGTAGC GGAGGGAGTGGACAGGTGCAGCTCCAGGAGAGCGGCGGAGGCCTGGTGCAGCCT GGTGGGTCACTGAGACTGTCCTGCACAGCTTCAGGCCTGACCTTTGACGATTCT GTCATGGGGTGGTTCAGGCAAGCTCCGGGGAAAGGGCGCGAGGCCGTAAGCTGC ATCAGTAGCTCTGGTGCCAATGCTTTCTACGCGGACTCCGTGAAGGGGCGCTTT ACAATCTCTCGCGATAATGCTAAGAACACCTTGTATCTCCAAATGAACTCTTTG AAGCCCGAGGACACCGCCACCTACTATTGTAAGAGAGGGCACGCATGTGCTGGG TATTACCCTATCCCTTATGATGACTACTGGGGGCAAGGAACACAGGTTACTGTG TCTTCC |
| hIL27 Ra_VH H6- DR591 | 1303 | CAGGTGCAGCTCCAGGAGTCTGGAGGTGGCCTGGTGCAGCCCGGCGGAAGCCTT CGCCTGAGTTGTGCGGCATCCGGCTTTTCCTTCTCATCTTACGCGATGAAGTGG GTCCGCCAGGCCCCAGGGAAAGGCCTGGAGTGGGTGAGTACCATTTCATCCGGC GGTAGCTCCACCAATTATGCTGACAGCGTGAAGGGTAGGTTCACCATCAGCCGC GATAATGCCAAGAACACCCTCTACCTCCAGTTGAACTCCCTGAAGATCGAAGAC ACAGCTATGTATTACTGCGCCAAGGCCATCGTTCCCACTGGGGCCACAATGGAG AGGGGACAGGGGACGCAGGTGACTGTTAGCTCCGGTGGGGGCAGCCAAGTACAG TTGCAGGAGTCTGGTGGGGGTTCCGTGCAGGCCGGGGGCTCACTGCGTCTGTCC TGTACCGCTTCTGGTGCTATCGCCTCTGGATACATTGATTCTCGCTGGTGCATG GCGTGGTTCAGGCAAGCCCCTGGTAAAGAAAGAGAGGGTGTGGCTGCCATCTGG CCAGGAGGCGGGCTCACTGTATACGCAGATTCTGTGAAGGGAAGATTCACTATC TCACGGGATCACGCCAAAAATACGCTGTATTTGCAGATGAACAATTTGAAGCCG GAGGACACCGCGATGTACTATTGTGCTGGGGGCTCTCCTCGTATGTGCCCCTCC CTGGAGTTCGGATTCGATTATTGGGGCCAGGGCACGCAAGTTACCGTAAGCAGT |
| hIL27 Ra_VH H6- DR591 | 1304 | CAGGTCCAGTTGCAGGAGAGTGGTGGCGGTCTCGTGCAACCGGGAGGCAGCCTC AGGCTGTCCTGCGCTGCCAGCGGGTTTTCCTTCAGCCCTTATGCGATGAAATGG GTCCGCCAGGCTCCAGGCAAAGGTCTGGAGTGGGTGAGCACCATCAGCTCAGGA GGCTCCAGCACGAACTACGCTGACTCCGTTAAGGGACGGTTCACTATCTCAAGA GACAATGCAAAAAATACTCTGTATCTCCAGCTGAACTCCCTGAAGATCGAAGAC ACTGCTATGTATTACTGTGCCAAGGCCATCGTTCCTACAGGGGCGACAATGGAG |

TABLE 1B-continued

| Name | SEQ ID NO: | Sequence |
|---|---|---|
| | | CGTGGCCAGGGCACCCAGGTCACAGTGTCTTCAGGAGGCAGGGGTGGAAGCGGGGGCTCTGGCCAAGTGCAACTCCAGGAGTCAGGGGGGGGCTCCGTGCAGGCAGGAGGCAGCCTTCGCCTGTCCTGTACCGCATCAGGCGCTATTGCAAGCGGCTACATCGACTCCCGGTGGTGCATGGCCTGGTTCCGCCAAGCGCCGGGCAAAGAGCGCGAGGGCGTGGCTGCAATCTGGCCTGGTGGAGGCTTGACAGTGTATGCCGATAGTGTGAAGGGCCGCTTCACAATCAGCCGGGATCACGCAAAGAATACCCTGTACCTCCAGATGAATAACCTGAAGCCTGAAGACACCGCCATGTACTATTGCGCAGCTGGCAGTCCTCGCATGTGTCCCAGCCTGGAGTTTGGATTCGATTACTGGGGTCAAGGTACACAGGTGACTGTCTCATCC |
| hIL27 Ra_VH H6-DR592 | 1305 | CAAGTGCAGCTCCAGGAGTCAGGCGGGGGCCTTGTGCAGCCTGGTGGCTCTCTGAGGCTGTCTTGTGCGGCTTCAGGCTTCTCCTTCTCCTCATACGCAATGAAGTGGGTACGTCAGGCCCCCGGCAAAGGCCTTGAGTGGGTCTCCACTATCTCTTCCGGTGGCTCTTCCACCAACTACGCTGATTCAGTCAAAGGCCGGTTCACGATCTCTCGCGATAACGCCAAGAACACGCTGTACCTCCAGCTGAACTCCCTGAAGATCGAAGACACTGCCATGTACTATTGCGCCAAGGCCATTGTTCCCACCGGAGCCACTATGGAACGCGGCCAGGGCACCCAGGTCACCGTGTCCTCTGGAGGCGGTTCACAGGTCCAACTTCAGGAGAGCGGAGGCGGGTCCGTGCAGGGGGGAGGCTCCCTGCGTCTGTCCTGTACCGCTCCCGGTTTCACCAGTAACTCCTGCGGCATGGATTGGTACAGACAGGCCCCTGGTAAGGAAAGGGAATTTGTCAGCTCTATCAGCACCGACGGAACAACCGGCTATGCCGATAGCGTGAAGGGACGCTTTACTATCTCAAAGGACAAGGCTAAGGACACAGTGTACCTCCAGAGAACTCCCTTCAAGCCCGAGGACACCGGCATGTATTCCTGCAAGACAAAAGACGGCACCATTGCAACTATGGAGCTGTGTGATTTTGGTTATTGGGGCCAGGGAACACAGGTCACCGTCTCCAGC |
| hIL27 Ra_VH H6-DR592 | 1306 | CAGGTTCAGCTTCAGGAGTCTGGCGGAGGCCTGGTTCAGCCCGGAGGCAGTCTGCGCCTTTCTTGCGCCGCGAGCGGCTTCTCATTCTCCAGCTACGCCATGAAGTGGGTGCGCCAGGCTCCCGGAAAGGGACTGGAGTGGGTGTCCACAATCTCTTCAGGAGGCTCCAGCACAAATTACGCCGACAGCGTGAAGGGCCGCTTCACGATCTCACGGGATAACGCGAAGAACACTCTGTATCTTCAGCTCAACTCCCTGAAGATCGAGGACACAGCTATGTATTACTGTGCTAAGGCTATCGTTCCTACCGGCGCTACTATGGAAAGAGGGCAGGGCACCCAAGTGACTGTGTCTAGCGGAGGTAGCGGAGGGTCCGGTGGAAGTGGTCAGGTACAGCTCCAGGAATCTGGTGGAGGCAGTGTTCAGGCTGGAGGTTCTTTGAGACTGTCCTGCACAGCTCCTGGATTTACCAGCAACAGCTGTGGGATGGACTGGTATCGCCAGGCACCGGGCAAGGAAAGAGAGTTTGTCTCTAGCATCTCTACCGACGGTACAACCGGCTATGCCGACTCTGTGAAGGGTAGGTTCACTATCTCCAAGGACAAAGCAAAGGATACTGTGTACCTCCAGATGAACTCCTTGAAGCCCGAGGACACCGGCATGTACTCATGTAAGACCAAGGATGGGACCATCGCCACTATGGAGCTGTGTGACTTCGGATACTGGGGCCAGGGTACTCAGGTCACCGTGTCTTCT |
| hIL27 Ra_VH H6-DR593 | 1307 | CAAGTCCAGTTGCAGGAGTCCGGGGGGGGCCTGGTCCAGCCAGGAGGCAGCTTGCGTCTGTCATGTGCTGCCTCTGGTTTCTCATTTTCCAGCTACGCCATGAAGTGGGTGAGACAGGCTCCAGGAAAGGGCCTGGAGTGGGTGTCTACAATCTCCTCTGGAGGGTCTTCCACTAACTATGCCGACTCCGTCAAAGGACGCCTCACAATTTCACGCGACAACGCGAAAAATACCTTGTACCTCCAGTTGAACTCACTCAAGATCGAAGACACGGCCATGTATTACTGCGCCAAAGCCATCGTGCCCACAGGTGCTACTATGGAGCGCGGCCAGGGCACCCAGGTTACCGTCAGCTCTGGGGGAGGCTCCCAAGTGCAGCTGCAAGAGAGGGGGCGGGGGCAGCGTCCAGGCCGGTGGCTCCCTGAGGCTCTCCTGTGCTGCCTCCGGTTACCCATACTCCAATGGGTATATGGGCTGGTTCCGCCAAGCCCCAGGCAAGGAGAGGGAAGGAGTGGCAACCATCTACACCGGCGATGGCCGCACATATTACGCAGACAGCGTCAAGGGCAGGTTTACCATTAGTCGCGACAACGCCAAGAACACTGTGGACCTCCAGATGTCTTCCCTGAAGCCCGAGGACACAGCTATGTATTACTGTGCGGCCAGGGCTGCACCGCTGTACTCCAGCGGTTCACCGCTGACACGCGCCCGGTACAACGTCTGGGGCCAGGGCACACAGGTTACGGTCTCTTCT |
| hIL27 Ra_VH H6-DR593 | 1308 | CAGGTCCAGCTCCAGGAATCCGGTGGGGGCCTGGTGCAGCCCGGTGGCTCCCTGCGCCTGTCCTGCGCTGCATCCGGCTTCAGCCTCAGCTCCTATGCTATGAAGTGGGTCCGGCAAGCGCCTGGCAAGGGACTGGAGTGGGTGAGTACAATCAGCTCCGGGGGCTCCTCTACCAACTATGCCGATAGCGTGAAGGGTAGGTTCACCATTAGCCGCGACAACGCCAAGAACACTCTGTACCTTCAGCTGAACTCCCTGAAAATCGAAGACACAGCGATGTATTACTGCGCGAAGGCCATCGTGCCTACTGGTGCTACTATGGAAAGAGGGCAAGGCACACAGGTGACCGTTAGCTCCGGTGGCTCCGGCGGAAGCGGTGGGTCAGGTCAGGTTCAGCTCCAAGAAAGCGGCGGTGGCAGCGTGCAGGCTGGAGGCTCCCTTAGACTCTCCTGCGCCGCATCTGGATACCCTTATAGCAACGGCTACATGGGATGGTTTCGCCAAGCCCCTGGTAAGGAGCGCGAGGGCGTCGCTACCATTTATACTGGGGATGGCCGCACTTACTATGCCGATTCTGTGAAGGGGCGCTTTACTATCTCACGCGACAACGCAAAGAACACCGTGGACCTCCAGATGTCATCACTCAAGCCGGAAGATACCGCTATGTATTACTGTGCTGCCCGCGCAGCTCCCCTGTACTCCTCCGGCTCCCCACTCACCCGTGCCCGCTATAACGTGTGGGGACAGGGCACTCAGGTGACCGTCTCATCT |
| hIL27 Ra_VH H6-DR594 | 1309 | CAGGTGCAGTTGCAGGAGAGCGGGGGTGGGCTGGTCCAGCCCGGCGGATCTCTGCGCCTCAGCTGCGCCGCAAGCGGCTTCTCCTTCTCCAGCTACGCTATGAAATGGGTCCGCCAGGCCCCCGGTAAGGGGTTGGAGTGGGTGTCTACCATTTCCAGTGGCGGTTCCAGCACCAACTACGCTGACAGCGTGAAGGGCAGATTCACGATCTCTCGCGACAATGCTAAAAATACCCTGTACCTGCAACTCAACAGCCTGAAGATCGAGGATACCGCCATGTATTACTGTGCCAAGGCCATCGTTCCTACTGGGGCCACTATGGAG |

TABLE 1B-continued

| Name | SEQ ID NO: | Sequence |
|---|---|---|
| | | AGGGGACAAGGAACTCAGGTCACCGTCTCTTCCGGTGGGGGCAGCCAAGTCCAG<br>CTCCAAGAATCTGGCGGAGGCTCTGTGCAGGCTGGCGGATCACTCAGACTGTCC<br>TGTGTGGGGTCCGCTTCCACCTATTGCACCTACGACATGCACTGGTATCGCCAG<br>GCCCCTGGCAAAGGCAGGGAATTTGTGTCTGCTATCGACAGCGACGGTACAACC<br>CGCTATGCCGATTCAGTGAAGGGTCGGTTCACCATCTCACAAGGCACCGCCAAG<br>AACACCGTGTACTTGCAGATGAACTCTCTGCAACCCGAGGACACTGCAATGTAT<br>TACTGCAAGACTGTGTGCGTGGTCGGAAGCAGATGGTCTGATTATTGGGGCCAA<br>GGCACACAGGTTACTGTGAGCAGT |
| hIL27<br>Ra_VH<br>H6-<br>DR594 | 1310 | CAGGTGCAGCTCCAGGAGTCCGGGGGAGGCCTGGTGCAGCCTGGTGGGTCTCTG<br>CGGCTGTCCTGTGCCGCTTCAGGATTTAGCTTCTCTTCCTATGCTATGAAGTGG<br>GTGCGCCAGGCTCCTGGTAAGGGACTGGAATGGGTGTCTACAATTAGTTCCGGC<br>GGGTCCTCTACCAACTATGCCGACTCCGTGAAGGGTAGATTCACGATCAGCAGA<br>GACAACGCCAAGAATACCCTCTACTTGCAGCTCAACTCCCTGAAAATTGAAGAC<br>ACCGCGATGTATTACTGTGCCAAGGCCATCGTGCCCACGGGCGCTACAATGGAG<br>CGCGGCCAGGGCACACAGGTGACCGTTTCTTCCGGTGGCAGCGGAGGCTCCGGG<br>GGCTCCGGCCAGGTGCAGCTCCAGGAGTCAGGAGGGGGGTCCGTGCAGGCCGGT<br>GGCAGTCTGCGTTTGTCCTGTGTGGCCAGCGCATCCACCTATTGTACCTACGAT<br>ATGCACTGGTATCGTCAGGCCCCAGGCAAGGGCAGGGAGTTCGTTAGCGCTATT<br>GACTCCGACGGCACCACTCGCTACGCTGACAGTGTCAAAGGCCGCTTCACTATC<br>TCTCAGGGGACTGCCAAGAACACCGTGTATCTCCAGATGAACTCCCTGCAACCA<br>GAGGACACAGCCATGTACTATTGCAAGACAGTGTGCGTTGTGGGCTCTCGCTGG<br>TCCGACTATTGGGGCCAGGGCACCCAGGTGACAGTGTCTTCC |
| hIL27<br>Ra_VH<br>H6-<br>DR595 | 1311 | CAAGTGCAGCTCCAGGAGTCTGGTGGAGGCCTGGTCCAGCCCGGTGGGAGCTTG<br>AGATTGTCTTGCGCAGCCTCTGGATTCCCTTTCTCCAGCTACGCCATGAAATGG<br>GTGCGGCAGGCACCAGGGAAGGGCCTGGAATGGGTGTCTACCATTTCTTCCGGC<br>GGTTCTTCCACTAATTACGCAGACTCCGTGAAGGGCCGGTTCACCATTTCCCGT<br>GACAACGCTAAGAATACCCTGTACTTGCAGCTGAACACCCTGAAGATCGAGGAC<br>ACGGCTATGTATTACTGTGCTAAAGCCATTGTCCCTACAGGGGCCACAATGGAA<br>CGCGGCCAGGGTACTCAAGTGACGGTCAGCTCTGGGGGGGGCAGCCAAGTGCAG<br>CTCCAGGAGAGCGGAGGTGGGTCCGTGCAGGCTGGTGGCTCCCTGACCCTGAGC<br>TGTGCCGCATCTGAATATGCGTATAGCACTTGTAATATGGGATGGTATCGCCAG<br>GCTCCTGGTAAGGAGCGCGAGCTGGTGAGCGCTTTCATTTCCGACGGTAGCACA<br>TATTACGCGGACTCCGTCAAAGGTCGCTTCACCATTACACGCGATAACGCCAAG<br>AATACCGTGTATTTGCAGATGAACTCACTCAAGCCAGAAGACACTGCCATCTAC<br>TATTGTTCAGCCAACTGTTATCGCAGACTCCGCAACTATTGGGGCCAGGGGACG<br>CAGGTAACCGTGTCCTCC |
| hIL27<br>Ra_VH<br>H6-<br>DR595 | 1312 | CAGGTGCAGCTCCAGGAATCTGGCGGTGGCCTGGTGCAGCGGGGGGGGTCCCTG<br>AGACTGAGTTGCGCTGCCAGCGGGTTTTCCTTCAGTTCCTATGCCATGAAGTGG<br>GTCCGCCAAGCTCCGGGGAAGGGCCTGGAATGGGTCTCCACTATTAGTTCCGGT<br>GGCTCTAGCACAAACTATGCGGATTCCGTGAAGGGACGCTTCACCATCTCTCGG<br>GACAACGCCAAGAATACCCTGTACCTCCAGCTGAATAGTCTCAAGATCGAAGAC<br>ACCGCGATGTTACTATTGCGCCAAAGCCATCGTTCCTACTGGGCTACAATGGAG<br>CGTGGCCAGGGCACCCAGGTGACCGTCTCCTCTGGCGGATCTGGGGGTTCCGGG<br>GGCTCCGGCCAGGTCCAGTTGCAGGAAAGCGGGGGGGGCTCCGTTCAGGCCGGG<br>GGCAGTCTGACCCTGTCCTGTGCAGCCTCTGAGCACGCCTATTCCACCTGTAAC<br>ATGGGCTGGTACAGACAAGCGCCCGGAAAAGAGCGCGAATTGGTCTCCGCCTTC<br>ATCTCCGATGGTAGCACTTATTACGCGGACTCTGTAAAAGGCCGTTTCACTATT<br>ACCCGCGACAACGCCAAGAACACCGTCTATCTCCAGATGAACAGCCTGAAGCCA<br>GAAGATACGGCCATTTACTATTGCTCCGCTAACTGCTACAGACGCTTGAGGAAT<br>TATTGGGGCCAGGGCACACAAGTGACTGTTTCCTCC |
| hIL27<br>Ra_VH<br>H6-<br>DR596 | 1313 | CAGGTGCAGCTGCAAGAGAGCGGTGGCGGTCTGGTACAGCCAGGTGGCAGCCTG<br>CGCCTGTCCTGCGCTGCATCAGGCTTCTCCTTCAGTTCCTATGCCATGAAGTGG<br>GTGCGCCAGGCTCCAGGCAAAGGATTGGAGTGGGTGTCTACCATTTCTTCCGGG<br>GGCTCATCCACAAACTACGCCGACAGCGTGAAGGGCCGCTTCACCATCTCCCGC<br>GACAACGCCAAGAACACTCCGTATCTTCAGCTGAACTCCCTGAAGATTGAGGAT<br>ACCGCTATGTATTACTGCGCTAAGGCCATCGTTCCCACAGGCGCTACGATGGAA<br>CGCGGTCAGGGGACACAAGTAACCGTAAGCAGTGGTGGCGGTAGCCAGGTGCAG<br>CTCCAGGAGTCCGGCGGTGGCCTGGTGCAGCCGGGTGGGTCCCTGAGGCTGAGT<br>TGCACAGCCAGCGGTCTGACCTTCGATGACTCCGTGATGGGCGGGTTCCGCCAG<br>GCACCTGGCAAGGGCCGCGAGGCTGTGTCCTGCATTAGCTCTAGCGGTGCCAAT<br>GCCTTCTACGCTGACTCAGTCAAGGGCCGCTTCACCATCTCCCGCGATAACGCC<br>AAGAACACCCTGTACTTGCAGATGAACTCCCTGAAACCCGAGGATACAGCAACA<br>TACTATTGCAAGCGGGGGCACGCCTGTGCAGGATACTATCCTATCCCCTATGAC<br>GATTATTGGGGTCAGGGCACCCAGGTCACCGTCAGCAGC |
| hIL27<br>Ra_VH<br>H6-<br>DR596 | 1314 | CAGGTGCAGCTCCAGGAGTCCGGCGGAGGTCTGGTTCAGCCCGGAGGCTCCCTT<br>CGCCTCTCCTGTGCTGCGTCAGGATTCTCCTTTAGCTCCTACGCTATGAAGTGG<br>GTGCGCCAAGCCCCCGGCAAGGGCCTGGAGTGGGTATCCACCATTTCCAGTGGC<br>GGTTCTTCAACCAACTATGCTGATTCCGTGAAAGGCCGCTTCACCATCTCCCGC<br>GACAACGCAAAAAATACCTTGTATTTGCAGCTGAACAGCCTGAAGATCGAGGAC<br>ACCGCGATGTACTATTGCGCCAAGGCCATCGTGCCTACTGGCGCAACAATGGAG<br>CGTGGACAGGGCACTCAGGTCACTGTGAGTAGCGGAGGGAGTGGCGGTTCCGGC<br>GGTTCAGGACAGGTGCAGCTCCAGGAGAGCGGGGCGGGGCTGGTACAGCCAGGT |

TABLE 1B-continued

| Name | SEQ ID NO: | Sequence |
|---|---|---|
| | | GGCTCTCTCAGGCTGAGTTGCACGGCCTCAGGCCTGACCTTCGATGACAGCGTC ATGGGCTGGTTCCGCCAGGCCCCAGGTAAAGGCCGTGAGGCTGTGTCCTGTATT AGCTCATCTGGGGCCAATGCGTTCTATGCTGACAGTGTCAAAGGCCGCTTCACA ATTTCCCGTGACAACGCCAAGAACACCCTGTATTTGCAGATGAACAGTCTGAAG CCGGAAGACACCGCCACCTACTATTGTAAGCGCGGTCACGCTTGTGCAGGTTAT TACCCTATTCCTTATGATGACTACTGGGGCCAGGGAACGCAGGTGACAGTGTCC TCT |
| hIL27 Ra_VH H7-DR591 | 1315 | CAGGTCCAGTTGCAGGAGTCTGGAGGTGGCCTGGTGCAGCCGGGAGGTTCTCTG CGGCTGTCCTGCGCCGCATCTGGATTCACCTTCAGTTCTTATCCAATGTCTTGG GTCAGGCAAGCGCCGGGCAAGGGCCTGGAATGGATTAGCACTATTTCCGCAGGT GGCGATACCACTCTGTATGCCGATTCAGTGAAAGGCCGCCTCACCAGCTCTGGG GATAACGCTAAGAACACCCTGTATCTCCAGCTGAATAGCCTTAAAACCGAAGAC ACCGCAATCTATTACTGTGCTAAAAGGATTGATTGTAATTCTGGCTATTGTTAC AGACGCAACTACTGGGGACAGGGCACCCAAGTGACCGTTTCCAGTGGGGGGGGG AGCCAGGTACAACTCCAGGAGTCCGGTGGAGGTAGCGTGCAGGCCGGGGGCTCT CTCCGTCTGTCCTGCACCGCATCCGGGGCTATCGCCTCTGGGTACATTGACAGC CGCTGGTGCATGGCCTGGTTCCGTCAGGCCCCCGGCAAGGAACGCGAGGGCGTG GCTGCCATCTGGCCGGGGGGAGGGCTGACTGTGTATGCGGACTCCGTCAAGGGC AGGTTTACCATCAGCCGCGACCATGCTAAGAACACCCTGTACCTCCAGATGAAT AACTTGAAACCTGAAGACACCGCCATGTACTATTGCGCGGCTGGTTCCCCACGC ATGTGCCCCTCACTTGAGTTTGGGTTCGATTACTGGGGCCAGGGCACCCAGGTG ACTGTGTCCAGC |
| hIL27 Ra_VH H7-DR591 | 1316 | CAGGTCCAGCTTCAGGAGTCCGGCGGTGGCCTTGTCCAGCCAGGAGGCAGCCTG CGGCTGTCCTGCGCCGCGAGCGGCTTCACGTTCTCATCCCACCCAATGTCCTGG GTCCGTCAGGCCCCAGGGAAGGGGCTGGAGTGGATCAGTACCATCTCCGCCGGT GGCGATACCACTTTGTACGCCGACTCTGTGAAAGGGCGCTTTACCTCCTCCCGC GATAACGCGAAAAACACATTGTACCTCCAGCTCAACTCCCTGAAGACTGAGGAC ACTGCCATCTACTATTGCGCCAAGAGAATTGATTGCAACAGCGGGTATTGCTAC CGGCGCAACTACTGGGGCCAGGGAACCCAGGTGACGGTATCCTCTGGGGGCTCT GGAGGTTCAGGAGGCAGGGGACAAGTGCAGCTCCAGGAATCAGGAGGCGGTTCT GTGCAGGCGGGTGGCTCTCTGCGTCTGAGCTGCACTGCGTCTGGAGCCATCGCT TCTGGTTACATCGACAGCAGATGGTGCATGGCATGGTTCCGTCAGGCTCCGGGA AAGGAGAGGGAGGGAGTGGCCGCTATCTGGCCCGGAGGGGGCTTGACAGTCTAC GCTGATTCCGTGAAGGGAAGGTTCACGATCTCACGTGACCACGCTAAGAATACC CTGTACCTTCAGATGAATAACCTGAAGCCCGAGGACACCGCAATGTACTATTGT GCTGCCGGAAGCCCCAGGATGTGTCCCAGCCTGGAATTTGGCTTTGACTACTGG GGTCAGGGCACTCAGGTCACAGTCTCCTCT |
| hIL27 Ra_VH H7-DR592 | 1317 | CAGGTGCAGTTGCAGGAGTCCGGGGGGGGCCTGGTGCAGCCAGGAGGGTCTCTG AGGCTGAGTTGCGCCGCTAGTGGCTTCACCTTCTCCAGCTATCCCATGTCTTGG GTGCGCCAGGCTCCCGGTAAAGGACTTGAGTGGATTAGCACGATCTCCGCTGGA GGTGACACGACTCTCTACGCCGATAGCGTGAAGGGACGCTTCACCAGTTCTCGT GACAACGCCAAGAATACCCTGTACCTCCAACTGAACAGCCTGAAGACGGAGGAC ACCGCCATCTATTACTGTGCAAAGCGTATTGATTGTAACTCAGGATACTGCTAT CGGCGCAACTATTGGGGACAGGGCACGCAGGTGACAGTTAGCTCCGGTGGCGGA AGTCAGGTCCAACTTCAGGAAAGCGGAGGTGGCAGCGTTCAGGCTGGCGGTTCC TTGCGCCTGTCTTGTACCGCACCGGGCTTTACAAGCAACAGCTGCGGTATGGAC TGGTATAGACAAGCTCCAGGCAAAGAAAGGGAGTTCGTGTCCAGCATTAGCACT GACGGCACCACAGGCTATGCTGATTCCGTGAAGGGACGCTTCACTATCTCCAAA GATAAGGCGAAGGACACTGTATACCTCCAGATGAACTCCCTGAAGCCTGAGGAT ACCGGCATGTATAGTTGCAAGACCAAGGATGGCACCATCGCAACGATGGAACTC TGTGACTTCGGCTATTGGGGGCAGGGCACCCAGGTGACCGTGTCCTCT |
| hIL27 Ra_VH H7-DR592 | 1318 | CAGGTGCAGCTGCAAGAATCCGGGCGGGGGCTCGTGCAGCCTGGGGGTTCCCTC CGTCTGAGCTGCGCGGCTTCCGGCTTCACTTTCTCTTCCTATCCCATGTCCTGG GTGAGGCAGGCCCCTGGCAAGGGCTTGGAATGGATTAGCACCATCAGCGCCGGG GGCGACACAACCCTGTACGCTGACAGCGTGAAGGGAAGATTCACGTCCAGCCGG GATAACGCCAAGAACACCCTGTACCTCCAGTTGAACTCCCTGAAGACTGAAGAT ACCGCCATCTATTACTGTGCCAAGCGCATTGATTGCAACAGCGGCTACTGCTAT CGCCGGAACTACTGGGGGCAGGTACACAGGTAACGGTGTCCTCAGGGGGCTCC GGCGGGAGTGGGGGCAGGGGGCAAGTTCAGTTGCAGGAGAGGGGCGGGGGCTCC GTCCAAGCAGGCGGAAGCCTTCGCCTCAGCTGCACCGCACCGGGTTTCACATCT AATAGCTGCGGAATGGATTGGTATCGGCAGGCCCCCGGTAAGGAGCGCGAGTTC GTGAGTTCCATCAGTACCGACGGCACAACCGGCTATGCTGACTCCGTGAAGGGT CGCTTCACCATTTCTAAGGATAAGGCCAAAGACACCGTGTACCTTCAGATGAAC TCACTGAAGCCAGAAGACACAGGAATGTACTCTTGTAAAACGAAGGATGGAACC ATCGCTACGATGGAGCTGTGCGACTTTGGCTACTGGGGCCAGGGCACCCAGGTG ACAGTAAGCTCT |
| hIL27 Ra_VH H7-DR593 | 1319 | CAGGTCCAACTCCAGGAAAGCGGCGGTGGCCTGGTGCAGCCAGGTGGGTCTCTC CGTCTGAGCTGTGCTGCATCCGGCTTCACTTTTAGCCCTTACCCGATGAGCTGG GTGCGCCAGGCTCCGGGAAAGGGCCTTGAGTGGATCAGCACCATCCCAGCCGGG GGCGATACAACCCTGTATGCAGACAGTGTTAAAGGCCGTTTTACCCCCTCTCGC GACAATGCTAAAAACACCCCTTATCTTCAGCTCAATAGTCTGAAGACTGAGGAC ACCGCCATTTATTACTGCGCTAAACGCATTGATTGCAACTGGGGGTACTGCTAC |

TABLE 1B-continued

| Name | SEQ ID NO: | Sequence |
|---|---|---|
| | | AGACGTAACTATTGGGGCCAGGGAACACAGGTGACCGTGTCCAGTGGCGGAGGT AGTCAGGTCCAGTTGCAAGAGAGCGGGGGAGGCAGCGTCCAGGGCGGGGGCTCC CTGCGCCTGAGCTGCGCAGCCTCTGGTTACCCATACAGCAACGGCTACATGGGC TGGTTCAGGCAAGCACCGGGTAAGGAGCGGGAAGGCGTGGCAACCATCTATACA GGTGATGGTCGCACCTATTACGCAGATTCCGTCAAGGGCCGGTTCACTATCAGC CGCGACAACGCAAAGAATACAGTCGATCTCCAGATGAGCAGTTTGAAACCTGAA GACACGGCGATGTATTACTGCGCCGCTCGTGCTGCGCCACTCTACTCCTCTGGC TCCCCTCTCACACGTGCTCGTTATAATGTATGGGGCCAGGGCACTCAAGTGACA GTCTCCAGT |
| hIL27 Ra_VH H7- DR593 | 1320 | CAGGTGCAGTTGCAGGAGTCCGGCGGTGGACTGGTCCAACCAGGCGGTAGTCTC AGGCTGTCCTGTGCCGCTTCTGGTTTCACTTTCAGCACCTACCCAATGTCCTGG GTACGGCAAGCTCCTGGGAAGGGTCTGGAGTGGATCTCCACGATCTCCGCAGGC GGGGACACTACCCTCTACGCCGACTCTGTGAAGGGCCGTTTCACTTCTAGCAGA GATAATGCAAAAAACACTCTCTATCTTCAGCTGAACAGTCTGAAAACCGAAGAT ACTGCGATCTATTACTGCGCCAAGCGCATCGACTGCAATTCTGGTTACTGTTAC CGTCGCAATTACTGGGGCCAAGGAACCCAGGTCACGGTGTCCTCAGGTGGCAGC GGAGGTTCCGGGGGGTCCGGTCAGGTCCAGTTGCAGGAAAGCGGCGGAGGTTCT GTCCAAGCCGGAGGCAGCCTGAGGCTGTCTTGCGCTGCCAGTGGATACCCCTAT AGCAACGGCTACATGGGCTGGTTCCGCCAAGCGCCAGGGAAGGAACGTGAAGGT GTGGCCACCATCTACACCGGCGATGGCAGGACCTACTATGCTGACTCCGTGAAG GGTAGGTTCACCATCTCTCGCGATAACGCCAAGAACACTGTGGACCTCCAGATG TCTTCCTTGAAACCTGAGGACACCGCGATGTATTACTGCGCGGCCCGCGCCGCG CCCCTCTACAGTTCAGGCAGCCCCCTGACCAGAGCAAGGTATAACGTGTGGGGT CAGGGCACTCAGGTGACCGTTAGCAGT |
| hIL27 Ra_VH H7- DR594 | 1321 | CAAGTTCAGCCCCAGGAATCTGGGCGGGGCCTGGTCCAGCCAGGTGGCTCCCTG CGCCTGAGTTGTGCGGCTAGTGGCTTCACCTTCAGCTCCTACCCGATGAGTTGG GTGCGTCAGGCTCCAGGGAAGGGTCTGGAGTGGATCTCTACCATCAGCGCCGGT GGCGATACTACCCTGTATGCGGATTCCGTGAAGGGTCGCCTTACCAGCTCTCGG GACAACGCCAAGAACACGCTCTACTTGCAGCTGAACAGTCTGAAGACCGAGGAT ACCGCTACTACTTATTGTGCCAAGCGCATCGACTGTAACAGCGGGTACTGCTAC CGCCGTAACTATTGGGGCCAGGGAACACAAGTTACCGTGTCAAGCGGAGGCGGT TCCCAGGTGCAGCTCCAGGAATCTGGCGGAGGCAGCGTACAGGGGGGAGGCTCA CTGCGCCTGTCTTGTGTCGCATCAGCCAGCACCTACTGCACCTATGACATGCAC TGGTATCGGCAGGCTCCCGGCAAAGGCCGCGAGTTCGTCAGCGCCATTGATTCC GATGGCACCACGAGGTACGCCGATTCTGTAAAGGGCCGCTTTACTATCTCCCAG GGTACTGCCAAGAACACCGTGTACCTCCAGATGAACAGTCTTCAGCCAGAGGAT ACGGCTATGTATTACTGCAAGACTGTTTGTGTCGTTGGCTCCAGGTGGAGCGAC TACTGGGGTCAGGGAACCCAGGTCACTGTGAGTAGC |
| hIL27 Ra_VH H7- DR594 | 1322 | CAGGTCCAACTTCAGGAATCCGGGGGGGGTCTGGTGCAACCTGGCGGTAGCCTC CGGCTTAGTTGCGCCGCAAGTGGATTCACCTTTTCCAGCTATCCCATGTCCTGG GTGCGTCAAGCGCCGGGTAAGGGTCTCGAATGGATTTCAACAATCTCTGCCGGT GGCGACACCACTCTCTAGGCGGATTCCGTGAAAGGGCGCTTCACCTCCTCCCGT GACAATGCCAAGAACACTCTGTATCTCCAGCTTAACTCCTTGAAGACAGAGGAT ACTGCCATCTATTACTGCGCCAAGCGCATCGACTGTAACTCTGGCTATTGTTAC CGCCGTAACTACTGGGGACAGGGCACTCAAGTCACCGTCTCCTCCGGAGGCAGC GGAGGTTCCGGGGGCTCTGGCCAGGTTCAGCTCCAGGAGAGCGGCGGAGGGAGC GTGCAGGCAGGTGGAAGCCTGCGTCTGTCCTGTGTGGCCCCCGCTTCAACCTAC TGCACCTATGATATGCACTGGTATCGTCAGGCCCCCGGCAAAGGTAGAGAGTTC GTGTCCGCCATTGATTCCGATGGTACTACCAGATATGCCGACAGCGTAAAGGGA CGTTTCACGATCTCTCAAGGCACCGCCAAGAACACCGTTTACCTCCAGATGAAT AGCCTCCAGCCGGAAGATACTGCAATGTATTACTGCAAGACTGTTTGCGTGGTT GGCAGCCGCTGGAGCGACTACTGGGGCCAGGGGACCCAGGTGACCGTCTCCTCT |
| hIL27 Ra_VH H7- DR595 | 1323 | CAGGTCCAGTTGCAGGAATCCGGCGGAGGCCTGGTGCAGCCAGGGGGCTCTCTG AGGCTGAGCTGTGCCGCGAGCGGCTTCACATTCTCCAGCTACCCCATGTCTTGG GTGCGTCAGGCCCCTGGCAAGGGTCTGGAGTGGATCTCCACCATCTCTGCTGGC GGTGACACCACTCTGTATGCCGACAGTGTTAAAGGGCGTTTCACGTCTTCCCGT GACAATGCCAAGAACACTCTCTACCTCCAGTTGAACTCACTGAAAACCGAGGAT ACCGCCATTTATTACTGCGCCAAGCGTATCGACTGCAACTCTGGCTACTGTTAT CGCCGGAACTACTGGGGCCAGGGGACCCAGGTGACTGTCAGTTCTGGGGGGGGC TCTCAGGTTCAGCTCCAGGAGTCAGGAGGGGGTTCAGTGCAAGCTGGAGGCTCC CTGACACTCAGCTGTGCCGCGAGTGAGTACGCATACTCCACCTGTAACATGGGT TGGTATCGCCAGGCTCCAGGTAAAGAGCGCGAGCTGGTCTCCGCCTTCATCTCC GACGGCTCCACGTATTACGCCGATTCTGTGAAAGGCCGTTTCACAATCACACGC GACAATGCAAAGAACACAGTGTATCTTCAGATGAACTCACTCAAGCCTGAAGAC ACCGCGATCTATTACTGCTCCGCAAACTGTTACAGACGCCTCCGCAACTACTGG GGGCAAGGCACTCAAGTGACTGTTTCCAGT |
| hIL27 Ra_VH H7- DR595 | 1324 | CAGGTACAGTTGCAGGAGTCAGGAGGTGGCCTGGTGCAGCCTGGTGGCAGCTTG CGCCTGTCTTGCGCAGCCTCTGGCTTCACATTCAGCTCATACCCTATGTCTTGG GTCAGGCAGGCTCCAGGTAAGGGGCTGGAATGGATTTCTACCATTAGTGCAGGC GGTGACACAACCCTGTACGCCGACTCAGTCAAGGGCCGGTTTACGTCCAGCCGC GACAATGCAAAGAACACTCTCTACTTGCAGCTCAACAGTCTGAAGACCGAGGAT ACTGCCATCTACTATTGTGCTAAGAGAATTGATTGCAACAGCGGCTATTGCTAC |

TABLE 1B-continued

| Name | SEQ ID NO: | Sequence |
|---|---|---|
| | | CGCAGAAATTACTGGGGGCAGGGCACCCAGGTGACTGTTTCTTCCGGGGGCAGC<br>GGGGGTAGCGGTGGGTCCGGTCAGGTCCAGCTTCAGGAGTCCGGCGGAGGCAGC<br>GTGCAGGCCGGAGGCAGCCTCACCCTGTCTTGTGCCGCTTCTGAATACGCTTAT<br>TCTACTTGTAACATGGGCTGGTATCGGCAGGCTCCCGGTAAGGAGCGCGAGCTG<br>GTCAGCGCCTTCATCTCTGACGGATCTACTTATTACGCCGAATCCGTCAAGGGT<br>CGCTTCACCATCACCAGAGACAATGCCAAAAACACCGTCTATCTCCAGATGAAC<br>TCTCTCAAGCCGGAGGACACCGCGATTTACTATTGCTCTGCGAACTGTTACCGT<br>CGCCCCCGTAACTATTGGGGTCAGGGCACCCAGGTCACGGTGTCCAGC |
| hIL27 Ra_VH H7- DR596 | 1325 | CAGGTACAACTCCAGGAGTCCGGGGGGGGACTGGTGCAGCCGGGTGGCTCCCTT<br>CGTCTGAGCTGTGCTGCCAGCGGTTTCACCTTCAGCTCCTACCCAATGTCTTGG<br>GTCCGTCAAGCGCCTGGTAAGGGTCTTGAGTGGATTAGTACTATCAGCGCTGGT<br>GGCGATACCACGCTCTACGCTGATTCCGTCAAAGGCCGCTTTACTTCCTCCAGG<br>GATAACGCAAAAAACACTCTTTACCTCCAGCTGAACTCCCTGAAGACCGAAGAT<br>ACCGCAATCTATTACTGTGCTAAACGGATTGATTGCAACTCCGGCTACTGTTAT<br>CGCCGTAATTACTGGGGCCAGGGTACACAGGTGACCGTGTCCTCAGGGGGGGGC<br>TCCCAAGTTCAGCTTCAGGAGAGTGGCGGTTGGCCTGGTCCAGCCGGGGGTTCC<br>CTTCGCCTGTCCTGCACCGCGTCCGGCCTTACCCTCGACGATAGCGTGATGGGT<br>TGGTTCCGCCAGGCTCCCGGCAAGGGCAGGGAAGCCGTGAGCTGCATTTCATCC<br>TCAGGAGCCAACGCTTTCTACGCTGATTCTGTGAAGGGACGTTTTACTATCAGC<br>CGCGATAACGCCAAGAACACTCTGTACCTCCAGATGAACTCCCTGAAGCCTGAG<br>GATACGGCTACATATTACTGCAAGCGCGGTCACGCCTGCGCTGGATATTACCCG<br>ATCCCATACGATGACTACTGGGGCCAGGGAACACAGGTAACAGTCTCCTCT |
| hIL27 Ra_VH H7- DR596 | 1326 | CAGGTTCAACTGCAAGAGTCCGGGGGGGGACTTGTCCAGCCGGGAGGCAGTCTG<br>AGATTGTCCTGCGCAGCGTCCGGGTTCACTTTCAGCTCTTATCCAATGTCATGG<br>GTCCGTCAGGCCCCTGGCAAAGGGCTGGAGTGGATCAGCACCATTTCTGCTGGA<br>GGTGACACTACCCTGTACGCCGACAGCGTTAAGGGCCGCTTCACATCATCCAGG<br>GACAACGCCAAGAACACACTGTACCTTCAGCTGAACTCCCTGAAAACAGAGGAC<br>ACCGCTATCTATTACTGTGCGAAGCGCATTGACTGTAACAGCGGCTATTGTTAT<br>CGCAGGAACTATTGGGGACAGGGAACCCAGGTGACTGTAAGCTCCGGTGGCTCA<br>GGGGGCTCCGGCGGTTCTGGTCAGGTGCAACTCCAGGAGAGCGGGGGTGGCCTG<br>GTGCAGCCTGGCGGGAGTCTGAGGCTTTCCTGCACCGCCAGCGGCCTTACCTTC<br>GATGACTCCGTGATGGGCGGGTTCCGCCAAGCGCCAGGAAAAGGCCGCGAAGCC<br>GTCTCCTGTATCTCCTCAAGCGGCGCGAACGCCTTCTATGCCGACTCAGTGAAG<br>GGCCGTTTCACAATCTCCCGCGATAACGCCAAGAACACCCTGTATCTCCAGATG<br>AACAGCCTGAAGCCGGAAGACACGGCAACCTACTATTGTAAGAGAGGCCACGCT<br>TGCGCTGGGTATTACCCTATCCCTTACGACGATTACTGGGGACAGGGTACTCAG<br>GTGACCGTTAGCTCT |
| hIL27 Ra_VH H8- DR591 | 1327 | CAAGTTCAGCTTCAGGAGTCAGGTGGCGGATCAGTGCAAGTCGGAGGCTCCCTG<br>CGCCTGTCTTGCGCTGCCTCCGGCTTTACATTCCCTTCCTACCCCATGTCCTGG<br>GTAAGGCAGGCTCCCGGCAAAGGCCTGGAGTGGATTAGCACAATCTCAGCCGGT<br>GGCGACACCACTCTGTACGCTGATTCCGTGAAAGGTCGTTTCACGTCTAGCAGA<br>GACAACGCTAAGAACACCCTCTACCTTCAGCTCAACAGCCTGAAGACGGAGGAC<br>ACCGCTATTTATTACTGTGCGAAGCGCATCGACTGTAACTCTGGATACTGCTAT<br>CGGCGCAACTATTGGGGTCAGGGTACTCAGGTTACAGTGTCATCCGGGGGGGGA<br>TCACAAGTGCAACTGCAAGAATCCGGCGGGGGTAGCGTGCAGGCCGGTGGCTCA<br>TTGCGTCTGTCCTGCACCGCCTCTGGCGCTATCGCTTCTGGCTATATCGACAGT<br>CGGTGGTGCATGGCCTGGTTCCGCCAGGCCCCTGGGAAGGAGCGCGAGGGTGTG<br>GCCGCGATCTGGCCCGGTGGGGGCCTCACAGTGTATGCAGACTCCGTAAAAGGC<br>CGCTTCACAATTAGCCGCGACCACGCTAAGAACACCCTTTACTTGCAGATGAAC<br>AATCTGAAGCCAGAAGACACTGCAATGTACTATTGTGCTGCGGGTTCCCCTCGT<br>ATGTGCCCAAGTCTTGAGTTCGGTTTTGATTACTGGGGGCAGGGCACCCAGGTC<br>ACCGTGTCCAGT |
| hIL27 Ra_VH H8- DR591 | 1328 | CAGGTACAACTCCAGGAATCTGGGGCGAGGCTCCGTTCAGGTGGGGGGTCTCTG<br>AGACTGAGCTGCGCTGCCAGCGGATTTACTTTCAGCTCCTACCCCATGAGTTGG<br>GTGAGGCAGGCTCCCGGTAAGGGCCTGGAATGGATTAGCACTATTAGCGCTGGC<br>GGGGACACCACTCTGTACGCTGACAGTGTCAAGGGGCGCCTTACTAGCTCCCGC<br>GACAACGCCAAGAACACTCTGTATCTCCAGCTCAACAGCCTCAAAACTGAGGAC<br>ACAGCTATCTATTACTGTGCTAAGCGCATTGACTGTAACTCAGGCTATTGTTAC<br>CGCCGGAACTACTGGGGACAAGGGACCCAAGTGACAGTTTCCTCTGGGGGTAGC<br>GGCGGATCTGGGGGCTCTGGCCAGGTCCAGCTTCAGGAGTCCGGGGGAGGCTCC<br>GTCCAGGCCGGTGGCTCTTTGAGGCTGTCATGCACAGCTTCCGGTGCCATCGCA<br>AGTGGATATATTGACAGTCGCTGGTGCATGGCTTGGTTCCGGCAAGCCCCCGGA<br>AAGGAGAGAGAGGGCGTTGCTGCAATCTGGCCGGGTGGGGGCTTGACCGTCTAT<br>GCTGATTCTGTGAAGGGCCGTTTTACCATCAGTAGAGACCACGCTAAAAACACC<br>CTGTACTTGCAGATGAATAACTTGAAACCCGAAGACACCGCCATGTATTACTGC<br>GCCGCTGGCTCTCCCCGTATGTGCCCCAGCTTGGAGTTCGGCTTTGATTATTGG<br>GGTCAGGGAACTCAGGTCACTGTGTCCAGC |
| hIL27 Ra_VH H8- DR592 | 1329 | CAGGTGCAGCTCCAGGAGTCTGGCGGTGGAAGCGTGCAAGTAGGAGGCTCTCTG<br>AGGCTGTCATGCGCAGCGAGCGGCTTCACCTTCAGCTCTTATCCAATGTCCTGG<br>GTTCGCCAGGCCCCCGGTAAGGGTCTGGAGTGGATCTCAACTATCAGCGCAGGC<br>GGGGATACAACCCTTTACGCCGATAGTGTGAAGGGACGCTTTACCTCCAGCAGA<br>GATAACGCTAAGAACACTCTGTACTTGCAGCTTAACTCCCTTAAAACCGAGGAC |

TABLE 1B-continued

| Name | SEQ ID NO: | Sequence |
|---|---|---|
| | | ACCGCGATCTATTACTGTGCCAAGCGCATTGACTGCAACCCTGGTTACTGCTAT AGAAGGAACTACTGGGGCCAGGGTACGCAGGTGACGGTTAGTTCCGGTGGAGGC TCACAAGTGCAGCTTCAGGAGTCCGGGGGGGCTCTGTGCAGGCTGGGCGGGTCC CTGCGGCTTTCCTGCACAGCCCCCGGCTTCACGTCTAACTCCTGTGGCATGGAC TGGTATCGCCAGGCCCCTGGTAAAGAGCGTGAGTTCGTGAGCAGTATTTCTACC GATGGAACGACCGGCTATGCTGACTCCGTGAAGGGTCGCTTCACCATCTCCAAG GACAAAGCCAAAGACACCGCTTATTTGCAGATGAACTCCCTCAAGCCAGAGGAC ACTGGCATGTATAGTTGCAAGACCAAGGACGGCACTATTGCGACGATGGAGCTG TGTGACTTCGGCTACTGGGGCCAGGGAACCCAGGTGACGGTGTCTTCT |
| hIL27 Ra_VH H8-DR592 | 1330 | CAGGTGCAGCTCCAAGAGTCTGGTGGGGGAAGCGTTCAAGTGGGGGGCAGCCTG AGACTGTCCTGTGCAGCTTCTGGCTTCACCTTTTCTAGCTACCCTATGTCCTGG GTGCGCCAGGCCCCCGGCAAAGGCCTGGAATGGATCTCCACCATCAGTGCGGGA GGTGACACAACTCTGTACGCGGATTCTGTGAAGGGCCGCTTCACATCTAGCCGT GATAACGCCAAGAATACTTTGTATCTCCAGCTCAACTCTCTGAAGACTGAAGAT ACAGCAATTTATTACTGCGCAAAACGGATTGATTGTAATAGCGGGTACTGTTAC CGCAGGAACTACTGGGGTCAAGGCACTCAGGTTACGGTGTCTTCCGGCGGATCT GGAGGTAGCGGTGGCAGCGGTCAGGTGCAGCTCCAGGAGTCAGGGGGGGGTTCC GTGCAGGCTGGCGGGTCCCTGCGCCTCTCTTGTACTGCCCCTGGGTTTACATCC AACTCCTGTGGTATGGACTGGTATAGGCAAGCTCGGGGAAAGGAGCGCGAGTTC GTGTCTTCCATCAGCACCGATGGCACCACTGGTTACGCCGATTCCGTGAAGGGA CGCTTTACAATTAGCAAGGACAAGGCCAAGGATACTGTGTACTTGCAGATGAAC AGCCTGAAGCCTGAGGACACTGGGATGTACTCTTGCAAGACCAAGGACGGGACC ATCGCCACGATGGAACTCTGCGACTTCGGATACTGGGGCCAGGGCACGCAAGTG ACCGTAAGCTCT |
| hIL27 Ra_VH H8-DR593 | 1331 | CAGGTACAGCTCCAGGAGAGCGGCGGTGGCTCCGTCCAAGTAGGGGGCAGCCTC CGCCTTTCTTGTGCAGCCTCTGGTTTTACATTTTCCAGCTACCCAATGAGCTGG GTCCGGCAAGCGCCTGGGAAAGGTCTGGAGTGGATTTCCACCATCTCCGCCGGG GGCGACACTACCCTGTACGCAGATAGCGTAAAGGGTCGCTTTACCAGTTCTCGT GATAACGCCAAGAACACTCTGTACCTTCAGCTGAATAGCCTCAAGACCGAGGAT ACCGCCATCTACTATTGCGCTAAGCGCATCGACTGCAACTCTGGCTATTGTTAC AGACGTAACTACTGGGGTCAAGGTACGCAGGTAACTGTATCCTCTGGAGGCGGT TCTCAGGTACAGCATCAGGAGAGGGGCGGTGGCAGCGTGCAGGCCGGAGGGTCC CTGCGTCTCTCCTGCGCTGCCTCCGGCTACCCCTACTCCAATGGCTATATGGGT TGGTTCAGACAGGCTCCTGGCAAAGAACGGGAGGGGGTGGCCACAATTTACACT GGTGATGGCCGCACGTACTATGCCGACTCCGTGAAGGGGCGCTTTACCATTTCT CGCGATAACGCTAAAAACACCGTGGACCTCCAGATGTCCAGCCTGAAGCCTGAA GATACTGCAATGTATTACTGTGCCGCACGTGCTGCCCCACTGTACTCAAGTGGG AGCCCACTGACTCGCGCTAGATATAACGTGTGGGGTCAGGGCACTCAGGTGACC GTCTCCTCC |
| hIL27 Ra_VH H8-DR593 | 1332 | CAAGTACAACTCCAGGAATCTGGGGGGGGGAGTGTTCAGGTCGGTGGCAGCCTG CGTCTCAGTTGCGCCGCGTCTGGCTTCACATTTTCTTCCTAACCGATGTCTTGG GTGAGGCAAGCCCCTGGAAAGGGTCTCGAATGGATCTCCACAATCTCAGCTGGC GGTGATACCACGCTCTACGCCGACTCTGTCAAAGGCCGCTTCACTTCTTCACGT GATAACGCCAAAAACACCCCGTACCTTCAGCTCAACTCCCTGAAGACCGAAGAC ACAGCAATCTATTACTGTGCGAAGCGGATTGATTGCAACTCCGGCTATTGTTAT CGGAGGAACTACTGGGGCCAGGGCACCCAAGTGACCGTCTCCTCTGGCGGTTCC GGTGGCTCCGGCGGTTCTGGACAAGTCCAACTCCAGGAGAGCGGCGGAGGCTCC GTTCAGGCAGGGGGGTCCTTGAGGCTGAGTTGTGCTGCATCAGGCTACCCCTAC TCAAACGGCTATATGGGCTGGTTCAGACAGGCTCCGGGCAAGGAGCGCGAGGGA GTGGCCACTATCTATACCGGCGACGGTCGCACTTATTACGCAGATAGCGTAAAG GGTCGCTTCACCATCAGCCGCGATAACGCCAAGAACACGGTTGACCTTCAAATG TCTAGTCTCAAACCTGAAGACACTGCCATGTACTATTGCGCCGCAAGAGCTGCC CCTCTGTATTCCAGCGGGAGCCCCCTGACCCGTGCCCGCTACAACGTGTGGGGT CAGGGCACCCAGGTGACTGTCAGCTCT |
| hIL27 Ra_VH H8-DR594 | 1333 | CAGGTGCAACTCCAGGAGAGTGGGGGGGGCTCCGTACAGGTCGGGGGCTCTCTG AGACTCTCCTGTGCGGCCAGCGGATTTACCTTCAGCAGTTACCCGATGTCTTGG GTGCGTCAGGCCCCAGGCAAGGGCCTGGAGTGGATTTCCACAATCAGCGCTGGC GGTGACACTACACTCTACGCAGATTCCGTGRAAGGGCGTTTCACCTCTAGCCGC GACAACGCTAAGAACACCCTGTACTTGCAGTTGAACTCCCTGAAGACCGAGGAC ACGGCCATCTACTATTGCGCGAAGCGCATCGACTGTAACAGCGGATACTGTTAC AGGCGCAACTATTGGGGACAGGGGACCCAAGTAACCGTGAGTTCAGGTGGGGGC TCCCAGGTGCAGTTGCAGGAGTCAGGTGGAGGCAGCGTCCAGGCCGGGGGCTCT CTTCGCCTGTCCTGTGTGGCCAGCGCCTCTACTTACTGTACGTATGATATGCAC TGGTATAGACAGGCCCCCGGTAAGGGAAGAGAGTTCGTCAGCGCTATTGATAGC GATGGCACCACACGCTATGCGGATTCCGTAAAGGGTAGGTTTACAATCAGCCAG GGAACCGCAAAAAAACACTGTTTACTTGCAGATGAACAGCCTCCAGCCAGAGGAT ACCGCCATGTACTATTGTAAGACTGTGTGTGTCGTGGGTTCCCGTTGGTCCGAT TACTGGGGCCAGGGCACTCAAGTAACAGTTAGTAGT |
| hIL27 Ra_VH H8-DR594 | 1334 | CAAGTTCAACTGCAAGAGTCCGGTGGCGGAAGCGTCCAGGTGGGAGGCTCCCTT CGCCTGAGCTGTGCTGCCAGCGGTTTCACATTCAGTTCCTATCCGATGTCCTGG GTGCGTCAGGCCCCAGGCAAGGGTCTGGAGTGGATCTCTACCATCTCCGCTGGC GGTGACACGACTCTGTACGCTGATAGCGTTAAGGGGCGCTTTACCTCCTCTGGC |

TABLE 1B-continued

| Name | SEQ ID NO: | Sequence |
|---|---|---|
| | | GATAACGCTAAGAACACTCTCTACCTCCAGTTGAATAGCCTCAAGACCGAAGAT<br>ACCGCTATCTACTATTGCGCTAAGGGGATTGATTGCAACTCTGGGTACTGCTAC<br>CGCCGGAACTACTGGGGACAGGCGAACCCAGGTGACTGTGTCCTCTGGGGCTCT<br>GGAGGCTCCGGCGGTTCCGGGCAGGTCCAACTCCAGGAATCCGGCGGTGGCAGC<br>GTGCAGGCCGGTGGCTCCTTGCGTCTGTCCTGCGTGGCGAGCGCTTCCACCTAC<br>TGCACCTACGACATGCACTGGTATCGCCAGGCTCCGGGTAAGGGCCGTGAATTT<br>GTGTCTGCCATTGATTCTGACGGCACCACGCGGTACGCAGACTCTGTTAAGGGG<br>CGCTTTACCATCAGTCAGGGCACGGCTAAGAACACCGTGTACCTGCAAATGAAC<br>TCTCCCCAACCGGAGGACACTGCCATGTATTACTGTAAAACGGTTTGTGTTGTC<br>GGCTCCCGCTGGTCCGATTACTGGGGCCAGGGAACCCAGGTGACAGTCTCAAGC |
| hIL27 Ra_VH H8- DR595 | 1335 | CAGGTTCAACTCCAGGAGAGTGGCGGTGGCCCAGTGCAAGTAGGGGGCAGTCTG<br>CGCCTGAGCTGTTGCTGCATCCGGCTTCACCTCTCTAGTTATCCCATGAGCTGG<br>GTACGTCAGGCTCCAGGCAAAGGTCTGGAGTGGATCAGCACCATTAGCGCTGGC<br>GGAGACACGACTCTCTATGCCGACAGCGTGAAGGGCCGCTTCACCTCCAGTCGG<br>GACAACGCCAAGAACACGCTGTACCTTCAGTTGAACTCACTCAAGACTGAGGAT<br>ACCGCAATCTATTACTGCGCTAAACGCATCGACTGTAACTCCGGGTACTGTTAC<br>CGTCGCAACTACTGGGGTCAGGGGACTCAGGTCACCGTGTCTTCCGGGGGTGGC<br>AGTCAGGTGCAGCTTCAGGAATCCGGGGGAGGCTCTGTCCAGGCTGGCGGTTCC<br>CTGACTCTGTCTTGCGCAGCCTCAGAGTATGCCTACAGCACTTGTAACATGGGT<br>TGGTATCGCCAGGCTCCCGGCAAAGAACGTGAGCTTGTTAGCGCGTTCATCAGC<br>GATGGCAGCACCTATTACGCTGACAGCGTGAAGGGTCGCTTTACAATCACCAGG<br>GACAACGCGAAGAACACCGTGTATCTCCAGATGAACTCCCTCAAGCCCGAGGAC<br>ACCGCCATCTATTACTGCTCCGCTAATTGCTACCGTCGGCTGCGCAACTACTGG<br>GGCCAGGGGACCCAGGTAACAGTCTCCTCT |
| hIL27 Ra_VH H8- DR595 | 1336 | CAGGTCCAGCTCCAGGAGTCCGGTGGGGGAAGCGTCCAAGTAGGGGGATCTCTG<br>AGGCTGTCCTGTGCGGCCTCCGGCTTCACCCTCTCCAGCTACCCCATGTCCTGG<br>GTGAGACAAGCCCCTGGGAAAGGACTGGAATGGATTAGTACCATTTCAGCCGGG<br>GGTGACACAACCCTGTACGCAGACTCCGTGAAAGGACGTTTTACCAGTTCCCGT<br>GATAACGCCAAGAACACCTTGTACCTCCAGTTGAACTCCCTGAAGACAGAAGAC<br>ACAGCCATCTATTACTGTGCCAAGCGCATTGATTGCAACAGCGGATACTGTTAC<br>CGCAGAAACTATTGGGGCCAGGGCACCCAGGTGACAGTATCAAGCGGCGGTTCC<br>GGCGGTAGCGGCGGTAGCGGGCAAGTGCAGTTGCAGGAGAGCGGCGGTGGCTCC<br>GTTCAGGCAGGAGGCTCCCTGACTCTCTCGTGTGCTGCCTCTGAGTATGCGTAC<br>TCCACTTGCAATATGGGCTGGTACAGGCAGGCTCCCGGCAAGGAACGCGAACTG<br>GTGAGTGCATTCATCTCTGATGGCTCCACATATTACGCCGACAGCGTCAAGGGC<br>CGGTTTACCATCACTCGGGATAATGCCAAGAACACCGTCTACTTGCAGATGAAC<br>AGCCTGAAGCCAGAGGACACAGCCATCTATTACTGCTCTGCTAACTGCTACCGC<br>AGACTGCGCAATTACTGGGGCCAGGGAACCCAGGTGACTGTGTCTAGC |
| hIL27 Ra_VH H8- DR596 | 1337 | CAGGTGCAACTCCAGGAATCCGGCGGAGGCAGCGTGCAAGTTGGGGGCAGTCTT<br>CGTCTGTCATGTGCAGCCAGCGGGTTCACCTTCTCAAGCTACCCGATGAGCTGG<br>GTGCGGCAGGCTCCCGGAAAGGGCCTGGAGTGGATTTCCACTATCTCCGCTGGC<br>GGTGACACCACACTGTACGCTGACTCCGTGAAGGGGCGGTTCACGTCATCCCGT<br>GATAACGCTAAGAACACACTGTATCTCCAGCTGAACAGCCTCAAGACCGAGGAC<br>ACTGCAATCTACTATTGCGCTAAGAGAATTGATTGCAACTCCGGGTACTGTTAC<br>AGGCGTAATTACTGGGGGCAGGGCACACAAGTGACCGTGTCCAGTGGCGGTGGC<br>AGCCAGGTGCAGTTGCAGGAGAGTGGGGGTGGCCTTGTGCAGCCCGGTGGGAGT<br>CTGCGCCTGTCCTGCACAGCCTCCGGGCTGACCCTCGACGATTCTGTAATGGGC<br>TGGTTCCGCCAGGCTCCGGGGAAGGGCCGCGAGGCCGTCAGCTGTATCTCCAGC<br>TCTGGAGCCAACGCATTTTACGCGGACAGCGTAAAGGGTAGATTCACAATTTCA<br>CGTGACAACGCCAAGAACACCCTGTACCTCCAGATGAACAGCCTGAAGCCCGAG<br>GATACCGCCACCTACTATTGTAAGCGCGGCCACGCTTGCGCGGGTTACTATCCG<br>ATCCCATACGATGACTATTGGGGCCAGGGCACGCAGGTTACGGTGTCTTCC |
| hIL27 Ra_VH H8- DR596 | 1338 | CAGGTCCAACTGCAAGAGTCTGGGGGGGGTTCCGTTCAGGTCGGTGGCTCCTTG<br>CGGCTGAGCTGTGCTGCCTCCGGCTTTACTTTTAGTTCTTATCCGATGAGCTGG<br>GTGAGGCAGGCTCCTGGCAAGGGCCTGGAGTGGATCTCCACAATCAGCGCTGGC<br>GGGGACACCACATTGTACGCCGACTCCGTCAAGGGCAGGTTCACCTCCTCACGC<br>GATAATGCTAAGAACACTCTGTATCTCCAGCTTAACTCTCTCAAGACCGAGGAC<br>ACCGCCATTTATTACTGCGCGAAGAGAATTGATTGTAACTCCGGCTACTGCTAC<br>CGCCGTAATTACTGGGGTCAGGGAACCCAGGTTACGGTCAGCTCCGGTGGCAGT<br>GGCGGTAGCGGAGGCTCCGGCCAGGTGCAGTTGCAGGAGTCTGGCGGTGGCCTG<br>GTCCAGCCTGGAGGCAGCCTCCGGCTGAGCTGTACTGCTTCAGGCCTGACATTT<br>GACGATAGCGTGAAGGGGTGGTTCCGCCAAGCGCGGGGAAAGGGTCGCGAGGCC<br>GTCTCTTGTATCAGTTCCTCTGGAGCCAACGCTTTCTATGCTGATAGCGTGAAG<br>GGCCGCTTCACAATTAGCCGGGACAATGCAAAGAACACCTTGTACCTGCAAATG<br>AACTCTCTGAAGCCCGAAGATACGGCTACCTACTATTGCAAGCGCGGCCATGCC<br>TGCGCAGGATATTACCCAATCCCCTACGACGATTATTGGGGTCAGGGCACCCAG<br>GTGACCGTGAGCAGC |
| hIL27 Ra_VH H9- DR591 | 1339 | CAGGTCCAACTCCAGGAGAGGGCGGGGGGCAGTGTGCAGTCTGGCGGTTCCCTT<br>AGGCTGAGTTGCGCAGCCAGCGGCTTCACATACAGCACCAGCAATTCATGGATG<br>GCGTGGTTCCGTCAGGCCCCCGGTAAGGAGCGGGAGGGCGTCGCCGCTATCTAC<br>ACAGTGGGTGGGTCCATCTTTTACGCTGATTCCGTGCGTGGCCGTTTCACCATC<br>TCCCAAGATGCGACAAAGAATATGTTCTACCTGCAAATGAACACACTCAAGCCC |

TABLE 1B-continued

| Name | SEQ ID NO: | Sequence |
|---|---|---|
| | | GAAGATACCGCTATGTATTACTGCGCGGCAGCTTCTGGCCGCCTCCGTGGAAAG<br>TGGTTCTGGCCATACGAATATAACTATTGGGGCCAGGGAACTCAGGTGACAGTT<br>AGTAGCGGCGGTGGCTCTCAGGTGCAACTCCAGGAGTCCGGGGGGGGAAGCGTG<br>CAGGCGGGAGGGAGCCTGCGGCTGTCATGTACCGCCAGCGGAGCCATCGCCAGC<br>GGATACATTGATTCCCGCTGGTGTATGGCTTGGTTTCGCCAGGCCCCCGGCAAG<br>GAAAGGGAGGGAGTTCGCCGCTATTGGCCCGGTGGCGGTCTGACAGTGTACGCC<br>GACAGCGTAAAGGGTCGCTTCACTATCAGCCGTGACCACGCTAAGAACACCCTG<br>TACCTCCAGATGAATAACTTGAAGCCAGAGGACACCGCCATGTACTATTGCGCC<br>GCTGGCTCCCCGAGAATGTGCCCTTCTCTCGAATTTGGTTTTGACTACTGGGGG<br>CAGGGGACCCAGGTCACGGTTTCTTCC |
| hIL27<br>Ra_VH<br>H9-<br>DR591 | 1340 | CAGGTGCAACTCCAGGAGAGTGGCGGGGGTTCCGTCCAGAGCGGTGGCAGTCTG<br>AGGCTGTCCTGCGCCGCTTCCGGTTTCACATACTCCACCAGTAACAGCTGGATG<br>GCCTGGTTTCGCCAAGCCCCTGGGAAAGAGAGAGAAGGAGTCGCCGCAATCTAC<br>ACTGTAGGAGGCTCCATTTTCTACGCAGACCCTGTCAGAGGCCGTTTCACCATT<br>AGCCAGGATGCCACTAAGAATATGTTTTACCTCCAGATGAATACACTGAAGCCA<br>GAAGACACCGCTATGTATTACTGTGCTGCGGCTTCCGGCAGGCTGCGCGGCAAG<br>TGGTTCTGGCCTTACGAGTATAACTATTGGGGCCAAGGCACCCAGGTCACCGTG<br>TCAAGCGGGGGTTCCGGTGGCAGCGGAGGGAGCGGCCAGGTGCAGCTGCAAGAG<br>TCTGGTGGGGGTTCCGTCCAGGCTGGGGGCTCTCTCCGGCTGTCTTGTACGGCC<br>AGCGGTGCCATCGCTAGTGGCTACATCGACAGCCGGTGGTGCATGGCCTGGTTC<br>CGTCAGGCTCCTGGAAAGGAACGGGAAGGCGTCGCCGCTATTTGGCCAGGTGGC<br>GGACTGACGGTCTATGCTGACTCTGTCAAGGGACGCTTCACCATCAGTCGCGAT<br>CACGCTAAGAACACCCTCTACCCCCAGATGAATAACCTGAAGCCCGAGGATACG<br>GCCATGTATTACTGCGCCGCTGGTTCCCCAAGAATGTGTCCCAGCCTGGAGTTC<br>GGGTTCGACTATTGGGGACAGGGCACCCAGGTAACCGTGTCATCA |
| hIL27<br>Ra_VH<br>H9-<br>DR592 | 1341 | CAGGTCCAGCTCCAGGAGAGCGGAGGCGGTAGTGTCCAGTCCGGTGGCTCCCTG<br>CGTCTGAGTTGCGCAGCCAGTGGCTTCACTTATTCCACAAGCAACTCTTGGATG<br>GCATGGTTTCGCCAGGCCCCTGGGAAGGAACGCGAGGGTGTCGCTGCCATCTAC<br>ACAGTGGGCGGTTCCATTTTCTACGCAGACTCCGTTAGAGGTAGGTTTACTATC<br>AGCCAGGATGCTACCAAGAATATGTTCTACCTTCAGATGAACACACTCAAGCCC<br>GAAGACACCGCCATGTATTACTGTGCCGCAGCCCCTGGCCGCCTGCGCGGTAAG<br>TGGTTCTGGCCTTACGAGTACAATTACTGGGGTCAGGGCACCCAGGTGACAGTG<br>TCCAGTGGTGGAGGCTCCCAGGTTCAGCTTCAGGAGTCTGGAGGGGGCTCCGTG<br>CAGGCAGGAGGCTCTCTGAGACTCAGCTGCACCGCCCCAGGTTTTACCTCCAAC<br>AGCTGCGGCATGGACTGGTATCGCCAGGCCCCCGGCAAGGAACGCGAGTTCGTG<br>AGTTCTATCTCCACCGATGGAACAACGGGTTACGCCGATTCTGTGAAGGGCCGG<br>TTTACAATCTCCAAGGATAAGGCCAAGGACACTGTGTACCTCCAGATGAACTCT<br>TTGAAACCAGAAGACACAGGCATGTATAGCTGTAAGACCAAGGATGGGACCATC<br>GCGACTATGGAACTGTGTGACTTCGGATACTGGGGCCAGGGGACCCAGGTCACA<br>GTGTCCTCC |
| hIL27<br>Ra_VH<br>H9-<br>DR592 | 1342 | CAGGTCCAGCTGCAAGAGAGCGGAGGCGGTAGTGTGCAGAGGGGCGGAAGCCTG<br>CGCCTCAGCTGCGCCGCGTCCGGCTTTACCTACAGCACAAGTAACTCTTGGATG<br>GCCTGGTTCCGGCAGGCTCCCGGCAAGGAAAGGGAAGGCGTGGCCGCAATCTAC<br>ACGGTCGGAGGTTCTATTTTCTACGCCGATAGCGTCAGAGGCCGCCTCACAATC<br>TCTCAGGACGCAACCAAAAATATGTTCTACTTGCAGATGAACACACTCAAGCCC<br>GAGGACACCGCGATGTATTACTGTGCCGCTGCATCCGGGCGGCTGAGAGGAAAG<br>TGGTTCTGGCCTTATGAGTACAATTATTGGGGTCAGGGCACTCAGGTGACTGTG<br>TCCTCTGGTGGCTCCGGTGGCAGTGGGGGCAGCGGTCAGGTGCAGCTTCAGGAG<br>TCCGGTGGAGGGAGCGTCCAGGCTGGGGGTTCCCTCAGGCTGTCCTGCACAGCA<br>CCGGGCTTCACTAGCAACAGCTGCGGTATGGATTGGTATCGCCAGGCACCGGGT<br>AAGGAGCGCGAATTTGTCTCATCTATCAGCACCGATGGGACAACCGGGTACGCT<br>GATAGCGTGAAAGGTAGGTTCACCATCCCCAAGGACAAGGCAAAAGATACCGTG<br>TACCTCCAGATGAACTCTCTCAAGCCCGAGGACACCGGAATGTATAGCTGCAAG<br>ACAAAGGACGGCACCATTGCAACAATGGAGCTTTGTGACTTTGGCTATTGGGGC<br>CAGGGCACCCAGGTAACGGTCTCTTCA |
| hIL27<br>Ra_VH<br>H9-<br>DR593 | 1343 | CAGGTCCAGCTTCAAGAATCCGGGGGCGGCTCCGTACAATCAGGAGGGTCACTC<br>AGGCTGAGTTGCGCAGCCTCTGGATTCACGTACTCCACAAGCAATTCCTGGATG<br>GCCTGGTTTAGACAGGCACCCGGCAAGGAGCGTGAGGGGGTGGCTGCCATCTAC<br>ACTGTGGGTGGCTCCATCTTCTATGCGGACAGTGTTCGCGGGCGTTTTACAATC<br>TCCCAGGACGCCACCAAGAATATGTTCTACTTGCAGATGAACACACTGAAACCG<br>GAGGACACCGCCATGTATTACTGTGCAGCCGCGTCAGGCCGCCTGCGGGGGAAG<br>TGGTTCTGGCCATACGAGTACAACTACTGGGGTCAGGGCACCCAAGTGACCGTG<br>AGTTCCGGGGGAGGTTCCCAGGTTCAGCTTCAGGAGTCCGGTGGCGGGTCTGTG<br>CAGGCCGGTGGCTCCCTTCGGCTCTCCTGCGCCGCGAGTGGCTATCCTTATTCC<br>AACGGCTACATGGGCTGGTTCCGTCAGGCACCCGGCAAGGAACGGGAAGGCGTC<br>GCTACCATCTATACAGGTGATGGGGGGACTTATTACGCAGACTCCGTGAAGGGC<br>CGCTTTACTATCAGTCGCGACAACGCAAAGAATACAGTGGACTTGCAAATGAGT<br>TCCCTCAAGCCTGAGGACACTGCTATGTACTATTGTGCTGCCCGTGCAGCGCCA<br>CTGTATAGTTCCGGCTCACCGCTGACCCGCGCTAGGTATAACGTATGGGGTCAG<br>GGCACACAAGTGACGGTGTCAAGC |
| hIL27<br>Ra_VH | 1344 | CAGGTGCAACTCCAGGAGTCCGGCGGAGGCAGTGTGCAATCCGGGGGTTCTCTG<br>CGCCTCTCTTGCGCTGCCTCTGGGTTTACATATTCCACATCCAACTCCTGGATG |

TABLE 1B-continued

| Name | SEQ ID NO: | Sequence |
|---|---|---|
| H9-<br>DR593 | | GCCTGGTTCCGCCAGGCTCCCGGCAAGGAGAGAGAGGGGGTGGCCGCGATCTAC<br>ACCGTTGGTGGCTCTATCTTCTATGCCGACAGCGTTCGGGGCCGCCTTACCATT<br>AGCCAGGATGCAACTAAGAATATGTTCTACCTTCAGATGAACACACTGAAGCCA<br>GAGGATACTGCAATGTATTACTGCGCCGCAGCTTCTGGCAGACTGCGCGGAAAA<br>TGGTTCTGGCCTTATGAGTACAATTATTGGGGCAGGGCACCCAGGTCACAGTA<br>AGCTCCGGTGGCTCCGGCGGTAGCGGAGGCTCCGGCCAAGTCCAACTTCAGGAA<br>AGCGGTGGGGGGTCTGTGCAGGCCGGTGGCTCCCTCCGCCTGTCCTGCGCGGCT<br>TCCGGCTATCCATACAGTAACGGCTACATGGGTTGGTTCCGGCAGGCCCCTGGC<br>AAGGAGCGTGAGGGCGTTGCTACGATCTATACAGGTGACGGAAGGACTTACTAT<br>GCTGACAGCGTAAAGGGGCGCTTCACCATTTCTCGTGACAACGCAAAGAACACA<br>GTGGACCTCCAGATGAGCAGTCTGAAGCCTGAGGACACCGCGATGTACTATTGT<br>GCCGCTCGGGCCGCTCCTCTGTATTCCAGCGGCAGCCCTCTGACTAGGGCTAGA<br>TACAACGTCTGGGGACAGGGCACTCAGGTGACTGTGAGCAGC |
| hIL27<br>Ra_VH<br>H9-<br>DR594 | 1345 | CAGGTGCAACCCCAGGAGTCTGGAGGGGGCTCCGTGCAGAGTGGCGGAAGCCTG<br>AGGTTGTCCTGTGCCGCGAGTGGATTCACCTACTCCACCTCCAACAGCTGGATG<br>GCCTGGTTTAGACAGGCTCCAGGTAAGGAAAGAGAGGGCGTGGCCGCGATCTAC<br>ACCGTAGGGGGCTCCATCTTCTATGCAGATAGCGTGAGGGGCCGCTTCACAATC<br>AGTCAGGATGCCACCAAAAATATGTTTTACCTCCAGATGAACACATTGAAGCCA<br>GAGGACACCGCCATGTACTATTGCGCCGCTGCCTCTGGTAGGCTGAGGGGCAAA<br>TGGTTCTGGCCCTATGAATATAACTACTGGGGGCAGGGCACCCAGGTAACGGTG<br>TCAAGCGGTGGGGGCTCTCAGGTGCAGCTCCAGGAGTCCGGGGGGGGCAGCGTA<br>CAGGCTGGAGGTAGTCTGCGCTTGAGTTGCGTCGCGTCAGCCTCTACCTATTGC<br>ACATACGACATGCACTGGTATAGACAGGCCCCAGGCAAGGGAAGGGAGTTCGTG<br>TCCGCAATCGACTCTGATGGCACAACCAGATACGCAGACTCCGTAAAGGGTCGC<br>TTCACCATCAGCCAGGGCACAGCGAAGAACACAGTGTACCTCCAGATGAACTCC<br>TTGCAGCCTGAGGATACTGCCATGTACTATTGCAAGACTGTGTGCGTTGTCGGA<br>TCTCGCTGGTCAGACTACTGGGGCCAGGGAACACAGGTGACAGTGTCCTCC |
| hIL27<br>Ra_VH<br>H9-<br>DR594 | 1346 | CAGGTGCAACTCCAGGAGTCTGGAGGTGGCTCTGTCCAAAGCGGTGGCTCCCTT<br>CGCCTGAGCTGTGCCGCTAGTGGATTCACGTACTCTACGTCAAATAGCTGGATG<br>GCGTGGTTCAGACAGGCCCCTGGCAAGGAGAGGGAGGGTGTGGCTGCGATCTAT<br>ACTGTGGGCGGTTCCATCTTCTATGCCGATTCCGTGCGCGGTCGGTTTACCATC<br>TCTCAGGACGCTACCAAGAATATGTTTTACTTGCAGATGAACACTCTGAAGCCA<br>GAGGATACCGCGATGTACTATTGCGCAGCGGCCTCTGGTAGGCTGAGAGGCAAA<br>TGGTTCTGGCCTTATGAATACAACTATTGGGGACAGGGAACTCAGGTGACGGTC<br>TCTTCCGGTGGCTCTGGGGGCAGGGCGGGGAGCGGCCAAGTGCAGCTTCAGGAG<br>TCTGGCGGAGGCAGCGTTCAAGCAGGGGGTAGCCTGAGACTCTCATGTGTAGCC<br>TCCGCTTCCACTTACTGCACCTACGACATGCACTGGTATCGTCAGGCTCCTGGC<br>AAGGGCCGCGAGTTTGTGTCCGCCATCGACTCCGACGGCACAACGCGGTACGCT<br>GACAGCGTGAAGGGCCGCTTTACCATTAGCCAAGGCACCGCCAAGAATACAGTG<br>TACCTGCAAATGAATAGCCTGCAACCGGAGGATACCGCGATGTACTATTGCAAG<br>ACGGTCTGTGTTGTGGGCAGTCGGTGGAGCGACTACTGGGGGCAAGGTACACAA<br>GTCACTGTGTCTCC |
| hIL27<br>Ra_VH<br>H9-<br>DR595 | 1347 | CAGGTGCAGCTCCAGGAATCTGGAGGTGGCTCTGTGCAGAGTGGGGGCAGCCTT<br>CGCCTGTCCTGCGCTGCCAGCGGCTTCACATACAGTACGTCAAACTCCTGGATG<br>GCCTGGTTCCGTCAAGCGCCTGGAAAGGAACGCGAGGGAGTGGCTGCGATTTAT<br>ACCGTCGGCGGGTCTATTTTTTACGCCGACTCCGTCAGAGGACGTTTCACGATC<br>TCCCAGGACGCCACGAAGAATATGTTTTTATCTCCAGATGAACACACTAAACCC<br>GAAGACACCGCAATGTATTACCGCGCTGCCGCATCTGGCCGCCTCCGGGGCAAA<br>TGGTTTTGGCCTTACGAGTACAATTACTGGGGCCAGGGAACACAGGTTACCGTG<br>AGCAGTGGAGGCGGGTCCCAGGTTCAGTTGCAGGAGTCAGGCGGGGGAAGCGTG<br>CAGGCCGGAGGTTCACTGACCCTGTCTTGTGCAGCGTCTGAATACGCCTACAGC<br>ACCTGTAACATGGGATGGTATCGCCAGGCTCCTGGAAAGGAAAGGGAGCTGGTG<br>TCTGCCTTTATCTCTGACGGCAGCACTTATTACGCTGACTCCGTGAAGGGACGC<br>TTTACCATCACCCGCGACAACGCGAAGAACACTGTGTATCTTCAGATGAACTCC<br>CTGAAGCCCGAAGACACCGCGATCTACTATTGCTCCGCTAATTGTTACCGTCGC<br>CTCCGCAACTATTGGGGCCAAGGGACCCAGGTGACCGTTAGTTCC |
| hIL27<br>Ra_VH<br>H9-<br>DR595 | 1348 | CAAGTCCAGCTTCAGGAGTCCGGCGGTGGCAGCGTGCAGTCTGGAGGCTCCCTG<br>CGCTTGTCCTGCGCCGCTTCCGGTTTCACGTATTCCACAAGTAATAGTTGGATG<br>GCTTGGTTTAGACAGGCCCCCGGCAAAGAGCGCGAGGGTGTGGCTGCCATCTAA<br>ACCGTCGGTGGGAGCATCTTTTACGCCGATTCCGTGCGTGGCCGCTTCACCATC<br>AGCCAGGATGCCACAAAGAATATGTTTTACTTGCAGATGAACACCCTGAAGCCC<br>GAAGACACCGCTATGTACTATTGCGCGGCAGCTTCTGGACGGCTGCGCGGTAAG<br>TGGTTTTGGCCATACGAGTACAACTATTGGGGCCAGGGCACTCAGGTGACCGTG<br>TCTTCCGGGGGCTCCGGGGGGAGCGGTGGCACTGGCCAGGTGCAGCTCCAGGAG<br>TCCGGGGGTGGCTCTGTCCAGGCTGGAGGCAGTCTGACCCTGTCCTGTGCCGCG<br>TCTGAGTACGCCTACTCCACTTGTAATATGGGCTGGTATCGTCAGGCACCTGGC<br>AAAGAACGCGAACTGGTGTCCGCATTTATTTCCGACGGTAGTACCTATTACGCT<br>GATTCCGTGAAGGGACGCTTCACCATCACACGGGATAACGCCAAGAACACTGTG<br>TATCTTCAGATGAACTCCTTGAAGCCCGAAGACACCGCTATCTACTATTGCAGC<br>GCCAACTGCTACAGACGGCTGCGTAACTACTGGGGCCAGGGCACTCAGGTGACT<br>GTCTCCTCT |

TABLE 1B-continued

| Name | SEQ ID NO: | Sequence |
|---|---|---|
| hIL27<br>Ra_VH<br>H9-<br>DR596 | 1349 | CAGGTGCAGCTTCAGGAATCCGGGGGGGGCAGCGTCCAGAGCGGCGGTTCCCTC<br>CGCCTCAGCTGTGCGGCTTCTGGATTCACCTATTCTACAAGCAATTCATGGATG<br>GCGTGGTTTCGCCAAGCGCCGGGCAAAGAGCGTGAGGGCGTTGCGGCTATTTAC<br>ACTGTCGGAGGCTCCATCTTCTACGCAGACTCAGTGCGTGGCCGTTTCACTATC<br>TCCCAGGACGCCACTAAGAATATGTTCTATCTCCAGATGAATACCCTCAAACCA<br>GAAGACACCGCAATGTATTACTGCGCTGCCGCATCTGGCCGTCTGAGAGGTAAG<br>TGGTTTTGGCCTTACGAGTACAACTACTGGGGACAAGGCACTCAGGTCACAGTC<br>TCCTCAGGCGGTGGCTCCCAGGTGCAGCTCCAAGAGTCAGGCGGGGGTCTGGTC<br>CAGCCTGGGGGGTCCCTTAGGCTTAGCTGTACCGCGTCCGGTCTCACCTTCGAT<br>GACAGCGTCATGGGATGGTTCCGCCAGGCCCCAGGCAAGGGGAGGGAGGCAGTG<br>AGCTGCATCTCCAGCTCCGGCGCTAACGCCTTTTATGCGGACAGTGTCAAAGGC<br>AGGTTCACGATTTCTAGGGATAACGCTAAGAACACCCTGTACCTCCAGATGAAC<br>AGCCTCAAACCGGAGGATACCGCGACTTACTATTGCAAACGTGGTCACGCCTGC<br>GCTGGTTATTACCCCATCCCGTATGATGACTATTGGGGCCAAGGCACCCAGGTG<br>ACTGTTTCTTCC |
| hIL27<br>Ra_VH<br>H9-<br>DR596 | 1350 | CAGGTCCAGTTGCAGGAGTCAGGCGGGGGCTCTGTGCAGTCTGGAGGCAGTCTC<br>AGACTGTCTTGCGCGGCTTCCGGCTTCACATACCCCACTTCCAACAGTTGGATG<br>GCCTGGTTCAGGCAAGCGCCGGGCAAGGAGAGAGAGGGTGTAGCGGCAATCTAT<br>ACTGTCGGGGGTTCAATTTTTTACGCGGACTCTGTTCGTGGCAGATTCACCATT<br>TCCCAGGACGCCACAAAAAATATGTTCTACCTCCAAATGAACACCCTCAAGCCT<br>GAGGACACTGCTATGTATTACTGTGCGGCTGCCTCAGGCCGTCTGCGGGGTAAG<br>TGGTTTTGGCCCTACGAGTACAACTACTGGGGCCAGGGGACGCAGGTGACAGTC<br>AGCTCAGGGGGCAGCGGGGGTCCGGGCGGGAGTGGCCAGGTGCAGCTCCAGGAA<br>TCTGGCGGAGGTCTTGTCCAGCCTGGCGGGTCTTTGCGTCTGTCCTGTACCGCA<br>AGTGGTCTGACCTTCGATGACTCAGTTATGGGATGGTTCAGACAAGCGCCTGGT<br>AAGGGCCGCGAGGCGGTGTCATGTATCTCTTCCAGCGGAGCCAACGCTTTTTAC<br>GCCGACTCCGTGAAAGGCAGGTTTACGATTAGTCGGGATAATGCCAAGAACACC<br>TTGTACCTCCAGATGAACAGCTTGAAGCCCGAAGACACTGCTACCTATTACTGT<br>AAGCGCGGTCACGCCTGCGCGGGCTATTACCCAATCCCCTACGATGACTACTGG<br>GGCCAGGGAACCCAGGTGACAGTTTCCAGC |
| hIL27<br>Ra_VH<br>H10-<br>DR591 | 1351 | CAGGTGCAGCTGCAAGAATCCGGGGGTGGCTCCGTTCAGGCCGGAGGCTCATTG<br>CGTCTCTCCTGTCGTGCGTCTGGGTCCACCTACTCTAACTATTGCCTGGGGTGG<br>TTCCGGCAGATTACGGGTAAGGAACGCGAAGGAGTTGCCGTGATTAACTGGGTC<br>GGTGGAATGCTGTACTTTGCTGACTCCGTCAAGGGTCGCCTCACCGTCTCCCAG<br>GACCAGGCTAAGAACACCCTGTACTTGCAGATGAACTCCCTCAAGCCTGAGGAC<br>ACCGCAATGTATTACTGTGCCGCTGAGTCAGTCAGCTCCTTCTCCCGCGGCGGG<br>TGGCTCACTCGCCCCGACAGAGTCCCCTATTGGGGGCAGGGAACCCAGGTGACT<br>GTCTCTAGCGGTGGGGGCTCCCAGGTGCAGTTGCAGGAATCTGGTGGGGGCTCC<br>GTCCAAGCCGGTGGCTCACTTAGGCTGTCCTGTACGGCAAGCGGGGCCATCGCC<br>TCTGGTTATATCGACTCACGGTGGTGTATGGCATGGTTCAGACAGGCTCCAGGG<br>AAGGAGCGGGAGGGAGTCGCTGCCATCTGGCCGGGGGGGGGCCTCACCGTTTAC<br>GCAGATAGCGTGAAGGGTAGGTTTACCATCTCTCGCGACCACGCCAAAAATACT<br>CTGTACCTCCAAATGAATAACCCGAAGCCCGAAGATACCGCCATGTACTATTGC<br>GCCGCTGGCTCCCCGCGCATGTGCCCTTCTCTGGAGTTCGGCTTCGATTATTGG<br>GGACAAGGAACCCAGGTGACAGTGTCTTCC |
| hIL27<br>Ra_VH<br>H10-<br>DR591 | 1352 | CAGGTACAGCTTCAGGAAAGCGGGGGAGGCTCAGTGCAGGCTGGCGGAAGCCTT<br>CGCCTGTCATGTCGGGCCTCTGGTTCCACCTACAGTAACTACTGCCTGGGCTGG<br>TTCCGCCAGATCACTGGCAAGGAACGCGAGGGCGTCGCGGTCATCAACTGGGTC<br>GGCGGAATGTTGTACTTCGCAGATAGCGTCAAGGGCAGGTTCACAGTCTCCCAG<br>GATCAGGCCAAGAACACCCTGTATCTGCAAATGAACTCCCTCAAGCCTGAAGAT<br>ACCGCCATGTATTACTGCGCAGCCGAGTCTGTCTCTTCATTCTCTTGCGGGGGT<br>TGGCTGACCCGTCCTGACAGGGTGCCATACTGGGGCCAGGGTACACAAGTCACC<br>GTGTCTTCAGGAGGTTCCGGTGGGTCAGGAGGTTCCGGGCAAGTTCAGCTCCAA<br>GAGAGTGGTGGCGGTAGCGTGCAGGCAGGGGGTTCACTTCGTCTGTCTTGCACA<br>GCCAGTGGGGCTATCGCCTCCGGCTACATTGACAGCAGATGGTGTATGGCCTGG<br>TTCCGGCAGGCCCCAGGCAAAGAAAGAGAAGGGCGGGCAGCCATCTGGCCGGGT<br>GGGGGCCTGACGGTCTATGCTGACAGCGTGAAGGGCCGCTTCACTATCTCAAGG<br>GATCACGCCAAGAACACCTTGTACTTGCAGATGAACAATCTGAAGCCCGAAGAC<br>ACCGCAATGTATTACTGTGCCGCAGGTAGCCCCCGCATGTGCCCATCCCTGGAG<br>TTTGGATTCGACTACTGGGGCCAGGGAACCCAGGTGACCGTTAGCTCT |
| hIL27<br>Ra_VH<br>H10-<br>DR592 | 1353 | CAGGTTCAGCTTCAGGAGAGCGGGCGGGGGTCCGTGCAGGCCGGTGGCTCCCTG<br>CGCCTGAGCTTGCCGCGCCAGCGGAAGCACTTACAGCAATTATGTCTTGGCTGG<br>TTCCGTCAGATCACAGGCAAAGAGCGCGAAGGCGTGGCCGTTATCAACTGGGTC<br>GGCGGTATGCTGTATTTCGCCGACTCTGTGAAAGGTCGCTTTACGGTCTCTCAG<br>GATCAGGCCAAGAACACGCTTTACTTGCAAATGAACTCACTGAAGCCCGAAGAC<br>ACCGCCATGTATTACTGTGCCGCAGAGTCTGTCAGCTCCCTTTCATGCGGAGGT<br>TGGTTGACTCGCCCCGACCGTGTTCCTTACTGGGGCCAGGGCACGCAAGTGACC<br>GTTTCCTCTGGAGGGGGAAGTCAGGTGCAGTTGCAGGAGTCCGGGGGGGGTAGC<br>GTGCAGGCCGGTGGCAGTCTGCGTCTGAGTTGTACTGCCCCCGGCCTCACCTCC<br>AACTCCTGTGGCATGGACTGGTATCGCCAGGCCCCCGGAAAAGAACGTGAGTTC<br>GTATCTAGCATCTCCACCGATGGGACCACAGGTTATGCTGATTCCGTAAAGGGT<br>AGGTTCACTATCAGCAAGGATAAAGCCAAAGATACCGTGTACCTCCAGATGAAT |

TABLE 1B-continued

| Name | SEQ ID NO: | Sequence |
|---|---|---|
| | | AGCCTTAAACCAGAGGATACGGGAATGTATAGTTGCAAGACCAAGGATGGAACT<br>ATCGCGACAATGGAACTCTGCGACTTCGGCTACTGGGGCCAGGGAACTCAGGTG<br>ACCGTGTCCTCC |
| hIL27<br>Ra_VH<br>H10-<br>DR592 | 1354 | CAGGTTCAGTTGCAGGAATCCGGGGGGGGAAGCGTGCAAGCAGGGGGTAGTTTG<br>CGCCTGTCATGCCGCGCCAGCGGCTCCACCTACAGCAATTATTGTCTGGGTTGG<br>TTCCGCCAGATCACTGGCAAGGAGCGCGAAGGGGTGGCCGTGATTAACTGGGTG<br>GGCGGTATGTTGTACTTCGCTGACTCCGTAAAGGGACGCTTCACTGTCAGCCAG<br>GACCAGGCTAAGAACACTCTGTATCTCCAGATGAACTCACTGAAGCCTGAGGAT<br>ACCGCCATGTATTACTGCGCTGCCGAGTCCGTCTCCAGCTTTTCCTGCGGCGGA<br>TGGCTGACTCGCCCTGACCGCGTGCCGTACTGGGGGCAAGGCACTCAGGTGACA<br>GTGTCTAGCGGAGGGTCTGGGGGCTCTGGTGGAAGCGGGCAGGTGCAGCTTCAG<br>GAATCTGGCGGTGGGAGCGTACAAGCGGGCGGATCTCTTCGTCTGTCCTGTACC<br>GCTCCTGGCTTTACGTCCAATTCCTGTGGGATGGATTGGTACAGACAAGCCCCA<br>GGTAAGGAGCGCGAGTTCGTGTCCTCTATCAGCACCGACGGAACTACCGGGTAC<br>GCTGACTCAGTGAAGGGTCGCTTCACCATCAGCAAGGATAAGGCCAAGGATACC<br>GTGTACCTGCAAATGAACAGTCTGAAGCCAGAAGATACCGGCATGTACTCATGC<br>AAGACGAAAGATGGGACTATCGCCACTATGGAACTGTGCGATTTTGGCTACTGG<br>GGGCAGGGCACTCAGGTGACTGTCTCAAGC |
| hIL27<br>Ra_VH<br>H10-<br>DR593 | 1355 | CAGGTCCAGCTCCAGGAATCTGGTGGAGGTAGCGTTCAGGCCGGGGGCTCCCTC<br>CGCCTGTCATGCAGGGCCAGCGGCTCTACCTATTCCAATTACTGCCTCGGGTGG<br>TTCAGACAGATCACAGGAAAGGAGCGCGAGGGCGTGGCAGTCATCAACTGGGTA<br>GGCGGTATGCTGTATTTCGCGGATAGTGTGAAGGGAAGATTCACCGTGAGTCAG<br>GATCAGGCTAAGAACACCCTGTATCTCCAGATGAACTCCTTGAAGCCCGAGGAC<br>ACTGCCATGTATTACTGCGCAGCCGAATCTGTTAGCTCCCTCAGCTGTGGTGGC<br>TGGCTGACCCGCCCAGATCGCGTGCCATATTGGGGCCAGGGCACACAGGTTACT<br>GTCTCCAGTGGGGGGGGCAGCCAAGTGCAGTTGCAGGAGAGCGGAGGGGGAAGT<br>GTGCAGGCAGGGGGATCTCTGAGACTCTCTTGTGCTGCCTCCGGCTATCCATAT<br>TCTAATGGCTACATGGGATGGTTCCGCCAAGCACCGGGCAAAGAGAGAGAAGGG<br>GTTGCTACCATCTATACCGGCGATGGCAGAACCTATTACGCGGACTCCGTGAAG<br>GGACGCTTCACCATCAGCCGTGATAACGCCAAGAACACTGTGGACCTCCAGATG<br>TCTTCCCTGAAGCCTGAAGACACCGCTATGTACTATTGTGCTGCACGCGCCGCG<br>CCACTTTACAGTAGCGGTTCTCCTCTTACCCGCGCTCGCTACAACGTCTGGGGC<br>CAGGGTACTCAGGTGACAGTTAGTAGC |
| hIL27<br>Ra_VH<br>H10-<br>DR593 | 1356 | CAAGTGCAGTTGCAGGAAAGCGGAGGGGGGAGCGTACAGGGGGGCGGTTCTCTG<br>CGGCTGAGCTGCCGCGCATCTGGTTCCACATACAGCAATTATTGTCTGGGTTGG<br>TTTAGGCAGATCACTGGTAAGGAGAGGGAAGGGGTCGCAGTTATAAATTGGGTG<br>GGTGGGATGCTCTACTTCGCCGATTCAGTGAAGGGCCGCCTCACCGTGAGTCAG<br>GATCAGGCGAAGAATACTCTGTACCTCCAGATGAATAGCCTGAAGCCCGAGGAC<br>ACCGCCATGTATTACTGCGCCGCAGAGAGTGTCAGCTCCTTTAGCTGGGGGGGC<br>TGGCTGACCCGCCCGGACCGCGTGCCCTACTGGGGCCAGGGGACCCAGGTTACC<br>GTTAGCTCTGGCGGTAGCGGGGGCTCTGGAGGCAGCGGACAAGTCCAGCTGCAA<br>GAATCCGGGGGAGGCAGCGTACAGGCTGGGGGGTCTCTGCGCCTGTCCTGCGCC<br>GCTTCAGGATACCCGTATAGCAACGGCTATATGGGTTGGTTCAGACAGGCCCCC<br>GGCAAGGAACGTGAAGGAGTGGCCACCATCTACACCGGCGACGGGCGCACCTAT<br>TACGCTGATTCTGTGAAGGGCCGCTTTACAATCAGCCGCGATAACGCTAAGAAC<br>ACCGTTGACCTTCAAATGTCCAGCCTGAAGCCGGAGGATACCGCCATGTATTAC<br>TGTGCAGCCCGCGCCGCACCACTCTACAGCCCCGGTTCTCCCCTCACAAGGGCT<br>CGGTACAATGTTTGGGGCCAGGGCACCCAGGTCACCGTCTCTAGC |
| hIL27<br>Ra_VH<br>H10-<br>DR594 | 1357 | CAGGTGCAGCTCCAGGAATCAGGTGGGGGCAGCGTACAGGCAGGGGGTTCACTC<br>CGCCCGTCTTGCCGGGCCTCTGGCAGTACATACTCCAATTATTGCCTGGGCTGG<br>TTTCGCCAAATTACCGGCAAGGAGCGGGAGGGCGTCGCTGTAATCAACTGGGTG<br>GGCGGGATGCTCTATTTTGCTGACTCCGTTAAGGGTCGTTTCACGGTCAGCCAG<br>GACCAGGCCAAAAATACACTGTATCTCCAGATGAACTCCCTCAAACCCGAAGAC<br>ACCGCCATGTATTACTGTGCTGCCGAGAGTGTCAGCTCTTTTTCCTGGGGGGGG<br>TGGCTTACCCGCCCGGACCGTGTCCCATACTGGGGTCAAGGCACCCAGGTTACC<br>GTCTCATCCGGCGGAGGCAGCCAGGTGCAACTCCAGGAGAGCGGGGGGGGTAGC<br>GTGCAGGCAGGCGGAAGCCTGCGTCTCTCCTGTGTGGCTTCCGCGTCCACCTAC<br>TGTACCTATGATATGCACTGGTATCGCCAGGCTCCTGGAAAGGGCCGCGAGTTC<br>GTGAGTGCTATTGATTCCGATGGCACCACTCGCTACGCTGACTCCGTGAAGGGA<br>CGTTTCACCATCTCCCAGGGTACAGCTAAGAACACCGTGTACCTCCAGATGAAC<br>TCCCTCCAGCCCGAGGATACCGCAATGTATTACTGCAAGACCGTTTGTGTAGTG<br>GGCTCACGCTGGTCCGACTATTGGGGCCAGGGGACCCAGGTGACTGTATCATCT |
| hIL27<br>Ra_VH<br>H10-<br>DR594 | 1358 | CAGGTCCAGCTTCAGGAAAGCGGTGGGGGCTCCGTGCAGGCCGGAGGCTCCCTG<br>CGTCTGAGCTGTCGGGCCTCTGGTTCCACCTACTCCAACTACTGTCTGGGCTGG<br>TTCCGCCAGATTACAGGCAAGGAACGCGAGGGTGTGGCGGTCATAAATTGGGTG<br>GGTGGAATGTGTATTTCGCGGATAGCGTGAAAGTGGCGCTTCACCGTGTCTCAG<br>GACCAGGCTAAGAACACACTGTACTTGCAGATGAACAGCCTGAAGCCCGAAGAC<br>ACTGCCATGTACTATTGTGCCGCTGAGTCTGTCTCCTCTTTCTCCTGCGGCGGA<br>TGGCTGACCCGCCCCGACAGGGTGCCTTACTGGGGTCAGGGCACCCAGGTGACG<br>GTTTCTAGTGGTGGCTCAGGTGGCTCCGGGGGTTCCGGCCAGGTCCAGTTGCAG<br>GAGTCTGGAGGTGGCAGCGTGCAGGCCGGTGGCAGCCTGCGCCTGTCATGTGTC<br>GCTTCTGCGAGCACCTATTGTACCTATGATATGCACTGGTATCGCCAGGCCCCA |

TABLE 1B-continued

| Name | SEQ ID NO: | Sequence |
|---|---|---|
| | | GGCAAGGGTAGGGAGTTTGTGTCCGCGATTGACTCTGACGGCACCACGCGCTAT<br>GCGGATTCCGTGAAGGGGCGTTTTACAATCCCCCAGGGCACCGCTAAGAACACT<br>GTTTATCTTCAGATGAACAGCTTGCAGCCTGAGGACACCGCGATGTATTACTGT<br>AAAACTGTCTGTGTAGTGGGCTCCAGGTGGTCTGACTACTGGGGTCAGGGCACC<br>CAGGTGACGGTTTCCAGC |
| hIL27 Ra_VH H10-DR595 | 1359 | CAGGTGCAGTTGCAGGAATCTGGGGCGGGCTCTGTGCAGGGGGGCGGGTCCCTG<br>CGCTTGTCCTGCCGCGCTTCTGGTTCTACCTACTCCAACTATTGTCTGGGCTGG<br>TTTAGGCAGATCACCGGAAAGGAGCGCGAAGGTGTGGCTGTTATAAATTGGGTG<br>GGCGGGATGCTCTATTTTGCAGACTCCGTCAAGGGCCGCTTCACCGTCTCACAG<br>GATCAAGCCAAGAATACGCTGTATCTTCAGATGAACAGCCTGAAGCCCGAGGAT<br>ACAGCCATGTATTACTGCGCCGCAGAGTGTGTGTCTTCCTTTTCTTGCGGAGGC<br>TGGCTCACACGCCCGGACCGCGTGCCCTACTGGGGCCAGGGCACCCAGGTGACC<br>GTATCCAGCGGGGGGGGTTCCCAAGTGCAGCTCCAGGAGTCTGGGGGAGGGTCC<br>GTGCAGGCTGGTGGGAGTCTGACCTTGAGTTGCGCAGCCAGCGAATACGCTTAC<br>TCCACTTGCAACATGGGTTGGTATCGTCAGGCTCCCGGTAAAGAGCGCGAGCTG<br>GTCTCTGCATTCATCTCAGATGGCTCTACTTACTATGCTGACTCCGTGAAGGGT<br>CGGTTTACTATCACCCGGGACAACGCCAAGAACACAGTGTACTTGCAGATGAAC<br>TCCCTGAAGCCCGAGGATACCGCCATTTACTATTGTTCCGCCAACTGTTACAGA<br>CGCCTGCGCAACTATTGGGGGCAGGGAACACAGGTTACTGTGTCCTCT |
| hIL27 Ra_VH H10-DR595 | 1360 | CAGGTGCAGTTGCAGGAGAGCGGAGGTGGCAGCGTCCAGGCCGGAGGTTCTCTG<br>CGTCTGAGCTGCCGTGCATCCGGTAGTACATACTCTAACTACTGTCTCGGCTGG<br>TTCAGGCAGATCACAGGCAAGGAAAGGGAGGGTGTTGCCGTAATCAACTGGGTT<br>GGCGGTATGCTCTACTTCGCTGACTCCGTGAAGGGTAGATTTACCGTGTCTCAG<br>GACCAAGCTAAGAACACCCTGTACTTGCAGATGAACAGCCTGAAACCGGAAGAT<br>ACCGCCATGTACTATTGCGCTGCCGAGTCCGTGTCCTCTTTCAGCTGCGGGGGT<br>TGGCTGACCAGACCTGATCGCGTTCCGTACTGGGGTCAAGGCACACAGGTTACC<br>GTGTCAAGCGGTGGCTCTGGAGGCTCCGGTGGCCCGGTCAGGTCCAGTTGCAA<br>GAGTCTGGAGGGGCAGCGTTCCAGGCCGGAGGCTCCCTCACCCTGAGTTGTGCG<br>GCCAGTGAGTACGCCTACTCCACTTGCAACATGGGATGGTATCGCCAGGCCCCA<br>GGAAAGGAGCGCGAGCTGGTCTCCGCTTTCATCTCCGACGGATCTACCTATTAC<br>GCCGACTCTGTGAAGGGACGTTTTACTATCACTAGGGATAACGCGAAAAACACT<br>GTGTACCTCCAGATGAACTCTCTCAAGCCTGAGGACACGGCCATCTACTATTGC<br>TCTGCGAACTGTTACAGACGGCTGAGAAATTATTGGGGACAGGGTACTCAGGTG<br>ACCGTTAGCAGC |
| hIL27 Ra_VH H10-DR596 | 1361 | CAGGTTCAGCTCCAGGAATCTGGGGGAGGCTCTGTCCAAGCTGGCGGTTCCTTG<br>CGTCTGTCTTGTAGGGCCTCTGGGAGCACCTACTCCAATTACTGTCTGGGGTGG<br>TTTCGGCAGATCACCGGCAAAGAACGCGAGGGCGTGGCCGTCATCAACTGGGTG<br>GGCGGAATGCTGTACTTTGCCGACTCTGTGAAGGGCCGCTTCACGGTGTCACAG<br>GACCAGGCCAAGAATACCCTGTATCTTCAGATGAACTCTCTCAAGCCCGAGGAC<br>ACTGCTATGTATTACTGTGCTGCGGAGAGCGTCTCATCCTTCAGCTGTGGTGGC<br>TGGCTGACACGCCCGGACCGTGTCCCTTATTGGGGTCAGGGAACCCAGGTGACC<br>GTTAGCTCAGGAGGTGGATCTCAGGTGCAACTCCAGGAGAGCGGCGGTGGCCTG<br>GTGCAACCCGGAGGTAGCTTGCGCTTGTCCTGTACTGCCCCTGGACTCACCTTC<br>GATGACTCAGTAATGGGTTGGTTCAGACAGGCCCCCGGAAAGGGCAGGGAGGCA<br>GTGTCTTGTATTAGCTCCAGGGGGGCTAATGCGTTCTACGCCGATTCCGTCAAG<br>GGCAGGTTTACCATTAGTCGCGATAACGCCAAGAACACCCTTTACTTGCAGATG<br>AACAGCCTGAAGCCCGAGGACACAGCCACCTATTACTGTAAGAGAGGTCACGCC<br>TGTGCTGGCTATTACCCAATTCCTTACGATGACTACTGGGGACAGGGAACCCAA<br>GTCACTGTCTCTTCT |
| hIL27 Ra_VH H10-DR596 | 1362 | CAGGTCCAGCTTCAGGAGTCCGGGGGGGGTTCCGTCCAGGCCGGGGGATCACTT<br>CGCCTGTCTTGTCGCGCCTCAGGCTCTACTTACTCCAATTATTGCCTCGGTTGG<br>TTCCGCCAAATCACCGGCAAAGAACGGGAGGGAGTAGCCGTAATTAACTGGGTT<br>GGGGGAATGCTGTATTTCGCCGACAGTGTGAAGGGCCGCTTCACCGTGTCTCAG<br>GACCAGGCAAAGAATACCCTGTATCTCCAGATGAACTCCCTGAAGGGGGAGGAC<br>ACTGCCATGTATTACTGCGCCGCTGAGTCCGTGTCCAGCTTCTCCTGCGGTGGC<br>TGGCTGACCCGCCCAGATCGTGTTCCTTATTGGGGCCAGGGCACTCAGGTCACA<br>GTCAGCTCTGGAGGCTCAGGAGGTTCTGGGGGTAGTGGTCAGGTTCAGCTCCAG<br>GAAAGCGGAGGCGGATTGGTTCAGCCTGGTGGAAGTCTGCGCCTCTCTTGCACC<br>GCCTCCGGCCTGACATTTGACGATAGCGTGATGGGCTGGTTCCGCCAGGCTCCG<br>GGAAAGGGTAGAGAGGCTGTGTCTTGTATCAGCTCTTCCGGGGCGAACGCCTTC<br>TACGCCGACTCCGTGAAGGGCCGTTTCACCATCTCACGCGACAACGCAAAGAAC<br>ACTCTGTATCTCCAGATGAACAGTCTGAAGCCCGAAGACACGGCGACCTACTAT<br>TGCAAGCGCGGCCACGCCTGCGCCGGGTACTATCCCATCCCATACGATGACTAA<br>TGGGGCCAGGGAACCCAAGTGACCGTATCTTCA |
| hIL27 Ra_VH H11-DR591 | 1363 | CAGGTGCAGCTTCAGGAGAGTGGTGGAGGCTCCGTGCAGGCCGGTGGCAGCCTC<br>CGTCTCTCTTGCAGAGCCTCAGGAAGCACCTACAGCAATTACTGTTTGGGGTGG<br>TTTCGGCAGTCAACGGGCAAGGAGAGAGAGGGCGTGGCCGTTATCAACTGGGTG<br>GGCGGTATGCTGTACTTCGCCGACTCTGTGAAGGGTCGCTTCACAGTGAGCCAG<br>GACCACGCGAAGAATACAGTGACTCTCCAGATGAACTCCCTCAAGCCCGAGGAC<br>ACCGCCATGTACTATTGTGCGGCTGAGTCCGTATCCTCTTTTTCCTGCGGGGGC<br>TGGCTGACTAGGCCTGGCCGTGTCCCATACTGGGGGCAGGGCACTCAGGTCACA<br>GTCAGCAGTGGAGGGGGTAGTCAGGTCCAGTTGCAGGAAAGCGGCGGAGGTTCC |

TABLE 1B-continued

| Name | SEQ ID NO: | Sequence |
|---|---|---|
| | | GTCCAGGCCGGAGGTTCCCTGCGCCTGAGCTGCACCGCTTCCGGCGCAATCGCC<br>TCTGGTTACATCGACTCCCGCTGGTGTATGGCCTGGTTCCGCCAGGCCCCTGGA<br>AAGGAGCGCGAGGGTGTCGCTGCGATCTGGCCTGGTGGAGGCCTGACTGTCTAT<br>GCTGATTCCGTAAAGGGCCGTTTCACTATCACTCGCGATCATGCCAAAAACACC<br>CTGTACTTGCAGATGAATAACCTGAAGCCCGAAGACACTGCCATGTATTACTGT<br>GCCGCAGGCTCTCCTAGAATGTGCCCTTCCCTGGAGTTCGGGTTTGATTATTGG<br>GGGCAGGGCACCCAGGTTACTGTGTCTTCC |
| hIL27 Ra_VH H11- DR591 | 1364 | CAAGTCCAGCCCCAGGAGAGCGGGGGAGGCTCCGTGCAGGCCGGTGGCAGCCTC<br>CGCCTCAGCTGCCGTGCTTCAGGAAGCACCTACAGCAACTACTGCTTGGGTTGG<br>TTTCGTCAGAGCACCGGAAAAGAGCGCGAGGGTGTGGCTGTGATTAACTGGGTC<br>GGAGGGATGCTGTATTTTGCGGATAGCGTGAAGGGGCGCCTCACAGTGTCTCAG<br>GATCATGCCAAGAACACAGTGACCCTTCAGATGAACAGCCTCAAGCCTGAGGAC<br>ACCGCCATGTATTACTGCGCTGCCGAGTCCGTCAGCTCCTTCAGCCGCGGGGGC<br>TGGCTCACCCGCCCTGGCCGCGTGCCCTATTGGGGCCAGGGAACCCAGGTTACT<br>GTTTCCAGTGGAGGGTCCGGGGGCTCTGGAGGCAGCGGCCAGGTACAGTTGCAG<br>GAATCCGGGGGGGGCTCAGTCCAGGCGGGAGGTTCCTTGCGCCTGTCCTGTACC<br>GCGTCCGGTGCAATCGCCTCCGGCTATATTGATTCCAGATGGTGTATGGCATGG<br>TTCCGCCAGGCTCCCGGTAAGGAACGGGAGGGGGTTGCGGCCATCTGGCCAGGA<br>GGGGGTCTCACCGTGTATGCCGACAGTGTTAAGGGCCGTTTCACTATCAGCAGG<br>GACCATGCAAAGAACACGCTGTACCTCCAAATGAACAATCTGAAGCCGGAAGAC<br>ACCGCCATGTATTACTGTGCTGCCGGTAGTCCTAGAATGTGTCCATCTCTGGAG<br>TTCGGTTTTGATTACTGGGGTCAGGGCACACAAGTTACCGTGTCTAGC |
| hIL27 Ra_VH H11- DR592 | 1365 | CAGGTACAACTCCAGGAGTCTGGTGGGGGCAGCGTACAGGCCGGAGGCTCTCTC<br>AGACTCTCATGTCGCGCGAGCGGCTCCACCTATAGCAACTATTGCCTGGGGTGG<br>TTCAGACAGAGCACTGGTAAGGAGCGTGAAGGTGTGGCAGTTATCAACTGGGTC<br>GGGGGAATGCTGTATTTCGCCGACAGCGTGAAGGGCCGGTTCACTGTGTCCCAG<br>GATCATGCCAAAAACACCGTCACCCTCCAGATGAACTCCCTGAAGCCCGAGGAC<br>ACAGCTATGTATTACTGTGCTGCGGAGAGCGTTAGCTCTTTCAGCTGTGGTGGC<br>TGGCTCACCCGGCCAGGCCGTGTCCCATATTGGGGACAGGGCACCCAGGTGACA<br>GTGTCTAGCGGGCGGGGCTCCCAGGTCCAGCTTCAGGAGTCCGGCGGTGGATCT<br>GTGCAGGCAGGCGGTTCCCCCAGGCTGAGTTGTACCGCCCCCGGCTTCACCAGC<br>AACAGCTGCGGTATGGACTGGTATCGCCAGGCTCCCGGAAAGGAGAGAGAGTTC<br>GTGAGTTCTATCTCCACTGATGGGACGACCGGCTACGCCGACTCCGTGAAGGGG<br>CGCTTCACTATCTCTAAAGATAAGGCTAAGGATACCGTCTACTTGCAGATGAAT<br>AGCTTGAAACCTGAAGATACCGGCATGTACTCCTGCAAGACCAAGGATGGGACC<br>ATTGCTACGATGGAACTCTGTGACTTCGGCTACTGGGGACAGGGCACTCAGGTG<br>ACCGTCTCCAGT |
| hIL27 Ra_VH H11- DR592 | 1366 | CAGGTGCAGCCTCAGGAGTCTGGAGGCGGATCTGTGCAGGCAGGCGGTAGTCTG<br>CGTCTTAGCTGCCGTGCCTCTGGCTCAACCTATTCCAATTATTGCCTCGGCTGG<br>TTTCGGCAGTCCACCGGCAAGGAAAGGGAAGGCGTGGGGGTCATCAACTGGGTT<br>GGGGGTATGCTGTATTTCGCCGACAGCGTGAAGGGCCGTTTTACAGTGTCTCAA<br>GACCATGCTAAGAATACCGTTACCCTCCAGATGAACTCTCTCAAACCGGAAGAC<br>ACTGCTATGTATTACTGCGCAGCCGAATCCGTTTCTAGCTTCAGCCGCGGGGGT<br>TGGCTGACTAGGCCTGGGCGCGTGCCCTATTGGGGGCAGGGTACACAGGTAACC<br>GTTTCCAGCGGAGGCTCTGGGGGGAGTGGCGGATCTGGCCAGGTGCAGTTGCAG<br>GAATCTGGAGGCGGATCTGTCCAAGCTGGGGGCAGCCTCCGTCTGTCATGTACC<br>GCCCCTGGGTTCACTTCCAACTCCTGCGGCATGGATTGGTATCGCCAGGCACCT<br>GGGAAGGAGCGCGAATTTGTAAGCTCAATCTCCACAGATGGCACCACTGGCTAT<br>GCTGACAGTGTTAAAGGCCGGTTCACCATCTCCAAGGATAAGGCTAAGGATACT<br>GTATACCTTCAGATGAACTCTCTGAAACCTGAAGACACAGGAATGTATTCCTGT<br>AAGACGAAGGATGGCACCATCGCTACAATGGAGCTTTGCGATTTTGGCTATTGG<br>GGACAGGGCACACAGGTGACGGTTAGTAGC |
| hIL27 Ra_VH H11- DR593 | 1367 | CAGGTGCAGCTCCAGGAGTCTGGTGGCGGTTCCGTGCAGGCCGGAGGCAGCCTG<br>CGCCTGTCCTGCCGCGCCTCTGGATCTACATACTCCAATTACTGTCTGGGGTGG<br>TTCAGACAGAGTACTGGAAAGAGCGCGAAGGTGTAGCCGTCATAAATTGGGTC<br>GGCGGTATGCTGTACTTCGCCGACAGCGTGAAGGGAAGGTTTACTGTGTCCCAG<br>GACCATGCTAAGAATACCGTGACCCTGCAAATGAACTCCCTTAAACCCGAGGAC<br>ACCGCTATGTACTATTGCGCGGCTGAGTCCGTGTCCAGCTTTTCTTGCGGAGGC<br>TGGCTCACCCGTCCAGGCCGTGTTCCTTATTGGGGACAGGGCACCCAGGTGACG<br>GTCTCCTCTGGTGGAGGTTCCCAGGTGCAGCTCCAGGAGAGTGGAGGGGGGTCA<br>GTACAGGCTGGCGGAAGCCTCCGCTTGAGCTGCGCTGCCTCCGGCTATCCCTAC<br>TCAAACGGCTATATGGGATGGTTTCGCCAGGCCCCCGGAAAGGAACGCGAGGGC<br>GTGGCCACCATTTATACTGGCGATGGCCGGACCTACTATGCTGACTCTGTGAAA<br>GGCCGCTTTACCATCAGCCGTGACAACGCCAAGAACACTGTTGATTTGCAGATG<br>TCTAGCCTGAAGCCCGAAGACACCGCTATGTATTACTGTGCAGCTCGGGCTGCC<br>CCTCTGTACTCCTCTGGAAGCCCCCTCACTCGGGCCAGATACAACGTGTGGGGA<br>CAGGGGACCCAGGTCACCGTGTCAAGT |
| hIL27 Ra_VH H11- DR593 | 1368 | CAGGTGCAGTTGCAGGAGTCTGGCGGTGGGTCCGTCCAGGCTGGGGGTTCCCTT<br>CGCCTGTCTTGCCGTGCCTCAGGCAGTACCTACAGCAACTACTGTCTCGGTTGG<br>TTCCGCCAGTCCACGGGCAAGGAGCGCGAAGGTGTGGCTGTTATCAACTGGCGG<br>GGAGGTATGCTGTACTTTGCCGACTCCGTTAAGGGGCGCTTTACCGTGAGCCAA<br>GACCACGCGAAAAACACGGTAACTTTGCAGATGAACTCTCTTAAACCCGAAGAT |

TABLE 1B-continued

| Name | SEQ ID NO: | Sequence |
|---|---|---|
| | | ACCGCTATGTATTACTGCGCGGCAGAGTCTGTGTCTTCCTTCTCCTGTGGCGGA<br>TGGCTGACCAGGCCTGGGGGCGTCCCGTACTGGGGTCAGGGCACTCAGGTGACA<br>GTCAGCTCCGGCGGAAGCGGTGGCTCCGGTGGCAGTGGGCAAGTGCAACTCCAG<br>GAGTCAGGAGGTGGGAGCGTTCAAGCGGGGGGTAGTCTTCGGCTGAGTTGTGCT<br>GCGAGTGGCTATCCGTACTCCAACGGCTATATGGGTTGGTTCCGCCAGGCCCCT<br>GGCAAGGAGCGGGAGGGCGTGGCCACTATCTACACCGGCGATGGCCGTACCTAT<br>TACGCCGACTCCGTGAAGGGACGGTTTACCATCTCACGCGACAACGCGAAGAAC<br>ACAGTTGACCTCCAGATGTCCTCACTGAAGCCAGAGGATACTGCCATGTATTAC<br>TGTGCTGCCCGCGCAGCCCCTCTGTACTCTAGTGGTTCCCCTCTCACAAGAGCC<br>AGATACAACGTCTGGGGACAAGGCACACAGGTGACTGTGAGTTCC |
| hIL27 Ra_VH H11-DR594 | 1369 | CAGGTACAGCTCCAGGAGTCAGGTGGGGGTTCCGTCCAGGCAGGAGGTAGTTTG<br>CGTCTGTCCTGTCGTGCCAGCGGATCTACCTACTCTAACTACTGCCTGGGATGG<br>TTCCGCCAGTCTACCGGCAAGGAGAGAGAGGGGGTTGCTGTTATCAACTGGGTC<br>GGCGGGATGCTCTATTTCGCCGACTCTGTGAAAGGCCGCTTTACTGTGTCCCAG<br>GATCACGCTAAGAACACCGTAACGCTCCAGATGAACAGCCTGAAGCCTGAAGAC<br>ACAGCCATGTATTACTGTGCCGCTGAGAGCGTGTCCAGCTTCTCTTGTGGCGGA<br>TGGCTCACCCGCCCCGGTCGTGTGCCCTACTGGGGGCAGGGAACCCAGGTCACA<br>GTAAGCTCCGGCGGTGGCAGCCAGGTGCAGTTGCAGGAGTCTGGTGGGGGGTCT<br>GTTCAGGCGGGAGGCTCCCTGAGACTTAGCTGTGTTGCGTCCGCATCCACCTAC<br>TGCACTTACGATATGCACTGGTATCGCCAGGCTCCTGGCAAGGGCCGTGAGTTC<br>GTGTCCGCTATTGATTCCGACGGCACCACTCGCTATGCCGATAGTGTCAAGGGG<br>AGGTTTACCATCTCCCAAGGTACAGCGAAAAATACAGTTTACCTCCAGATGAAC<br>AGCTTGCAGCCCGAGGACACGGCTATGTATTACTGTAAGACGGTGTGCGTCGTG<br>GGCAGTCGGTGGTCCGATTACTGGGGCCAGGGGACCCAGGTTACTGTCTCCAGC |
| hIL27 Ra_VH H11-DR594 | 1370 | CAGGTACAGCCTCAGGAGTCCGGCGGTGGCTCTGTCCAGGCTGGCGGTTCCCTC<br>AGGCTGTCTTGCAGGGCTTCTGGTTCCACCTACAGCAACTACTGTTTGGGATGG<br>TTCCGCCAGTCCACAGGTAAGGAGCGCGAGGGAGTGGCGGTCATCAACTGGGTA<br>GGAGGCATGTTGTACTTCGCCGACTCTGTGAAAGGCAGATTCACTGTCAGCCAG<br>GACCATGCCAAGAACACAGTCACTTTGCAGATGAACTCTCTGAAACCAGAGGAC<br>ACTGCTATGTATTACTGTGCTGCCGAGTCAGTCAGCTCCTTCTCCCGCGGAGGG<br>TGGCTCACCAGACCTGGCCGCGTGCCGTACTGGGGCCAGGGGACGCAGGTGACC<br>GTGTCCAGTGGCGGGAGCGGAGGTTCTGGTGGCTCAGGCCAGGTTCAACTGCAA<br>GAGTCCGGTGGAGGTTCTGTGCAGGCCGGTGGCTCCCTGCGTCTCTCCTGCGTG<br>GCCTCTGCCTCCACTTACTGTACCTATGATATGCACTGGTATCGCCAGGCCCCA<br>GGCAAGGGCCGTGAGTTTGTGAGCGCCATTGACAGTGATGGCACCACTAGGTAT<br>GCCGATTCCGTGAAGGGTCGCTTCACCATCAGTCAGGGCACTGCCAAGAACACT<br>GTGTATCTCCAGATGAACAGCTTGCAGCCCGAGGACACCGCCATGTATTACTGC<br>AAGACCGTCTGCGTCGTGGGAAGCCGCTGGAGCGACTATTGGGGCCAGGGGACC<br>CAGGTGACCGTCTCATCC |
| hIL27 Ra_VH H11-DR595 | 1371 | CAGGTGCAACTGCAAGAGTCCGGGGGAGGCTCCGTTCAGGCTGGCGGGTCTCTG<br>CGGCTCTCCTGCCGCGCCAGCGGCTCTACTTATAGCAACTACTGCCTGGGATGG<br>TTCAGACAGAGTACAGGTAAGGAGAGGGAGGGAGTCGCTGTTATCAACTGGGTT<br>GGCGGTATGCTCTATTTCGCGGACTCCGTGAAGGGCCGGTTCACCGTGAGCCAG<br>GACCACGCCAAGAACACCGTGACACTCCAGATGAACAGCCTTAAACCTGAGGAC<br>ACCGCTATGTACTATTGCGCAGCCGAAAGTGTTAGCTCTTTTTCCTGTGGTGGC<br>TGGCTGACTCGCCCTGGGCGCGTTCCATATTGGGGTCAGGGCACCCAGGTGACG<br>GTTTCATCCGGCGGAGGCAGTCAAGTGCAGCTTCAGGAATCCGGGGGGGGATCT<br>GTGCAGGCTGGGGGCAGTCTGACCCTGTCCTGTGCTGCCAGCGAGTACGCCTAC<br>TCCACTTGCAATATGGGATGGTATCGCCAGGCACCGGGAAAGGAGCGTGAGCTG<br>GTCAGTGCATTTATCAGCGATGGCTCCACCTATTACGCCGATTCTGTTAAGGGC<br>CGCTTCACCATCACCCGCGACAACGCCAAAAACACCGTATATTTGCAGATGAAT<br>AGCTTGAAGCCCGAAGATACTGCCATTTATTACTGCTCTGCTAATTGCTACAGA<br>CGCCTGCGCAACTATTGGGGCCAAGGCACACAGGTGACAGTAAGCTCC |
| hIL27 Ra_VH H11-DR595 | 1372 | CAGGTGCAGCCCCAGGAATCTGGCGGTGGGAGCGTCCAGGGGGGCGGGAGCCTC<br>CGCTTGAGCTGCCGCGCTAGTGGTAGCACCTACAGTAACTATTGCCTCGGCTGG<br>TTCAGGCAGTCCACCGGCAAGGAGCGCGAAGGCGTTGCCGTCATTAACTGGGTT<br>GGAGGTATGCTGTACTTTGCCGACAGCGTAAAGGGTCGTTTTACGGTAAGTCAA<br>GATCATGCTAAGAACACTGTGACATTGCAGATGAACAGCCTGAAGCCGGAGGAT<br>ACTGCCATGTATTACTGCGCGGCTGAGTCTGTAAGCTCTTTCTCATGCGGTGGA<br>TGGCTCACCCGTCCGGGTCGCGTTCCGTACTGGGGTCAGGGCACGCAAGTTACC<br>GTTTCTAGCGGAGGCAGTGGGGGCTCTGGGGGTTCCGGCCAGGTCCAGCTTCAG<br>GAGTCTGGCGGTGGCTCCGTTCAAGCCGGTGGCTCTCTGACACTGTCCTGTGCC<br>GCTTCTGAGTATGCGTACAGCACTTGCAACATGGGATGGTATCGCCAGGCCCCC<br>GGAAAAGAGCGCGAGCTGGTTTCCGCATTTATTTCCGACGGCAGCACCTATTAC<br>GCCGATTCCGTGAAGGGAAGGTTCACTATTACCCGCGACAACGCAAAGAATACC<br>GTCTACTTGCAGATGAACTCCCTGAAGCCCGAGGACACCGCTATCTACTATTGC<br>TCCGCAAATTGCTACCGGCGTCTCCGCAACTACTGGGGCCAGGGTACGCAGGTG<br>ACAGTCAGCTCC |
| hIL27 Ra_VH H11-DR596 | 1373 | CAGGTCCAGCTTCAGGAGAGCGGCGGTGGCTCCGTCCAGGCCGGAGGCTCTCTG<br>CGCTTGTCCTGCCGTGCCTCCGGTTCCACATACAGCAACTACTGTCTGGGGTGG<br>TTCCGTCAGAGCACTGGGAAGGAGAGAGAGGGCGTGGCTGTCATCAACTGGGTT<br>GGCGGGATGCTGTACTTTGCGGATTCAGTCAAGGGAAGGTTCACTGTTAGCCAG |

TABLE 1B-continued

| Name | SEQ ID NO: | Sequence |
|---|---|---|
| | | GACCACGCTAAGAACACCGTAACTCTCCAGATGAACTCCCTGAAGCCCGAGGAT ACAGCCATGTATTACTGTGCTGCCGAGTCCGTGTCCAGCTTCTCCTGTGGTGGC TGGCTCACTCGCCCAGGGAGAGTCCCATACTGGGGACAGGGGACCCAGGTCACA GTGAGTTCCGGCGGAGGCTCTCAGGTGCAGCTGCAAGAGTCTGGCGGAGGTCTT GTGCAGCCTGGCGGTTCCCTGCGTCTGAGTTGTACCGCATCTGGTCTCACTTTT GACGATAGCGTCATGGGATGGTTCCGCCAGGCACGGGGGAAAGGCCGCGAGGCC GTCTCCTGTATTAGTTCCTCTGGTGCCAACGCTTTCTACGCTGATTCCGTGAAA GGACGGTTTACCATCTCCCGCGATAACGCCAAAAACACCCTGTATCTCCAGATG AACTCCCTGAAGCCAGAGGACACTGCGACCTATTACTGTAAACGCGGTCATGCT TGTGCCGGATATTACCCCATCCCCTATGACGATTACTGGGGACAGGGCACCCAA GTTACCGTGTCTAGT |
| hIL27 Ra_VH H11- DR596 | 1374 | CAGGTGCAGCTCCAGGAAAGCGGAGGGGGCTCAGTCCAGGCCGGAGGCTCTCTG AGACTCTCTTGCCGTGCATCCGGCAGCACTTATTCCAACTATTGTCTGGGCTGG TTTAGGCAGAGCACAGGCAAGGAGCGCGAAGGTGTCGCAGTGATTAACTGGGTC GGCGGGATGTTGTACTTCGCCGATAGCGTCAAGGGGCGGTTTACAGTGTCCCAG GACCACGCCAAGAACACCGTGACCCTTCAGATGAATAGCCTGAAGCCCGAAGAT ACAGCAATGTATTACTGTGCGGCTGAGTCCGTGTCTTCCTTCAGCTGCGGGGGC TGGCTGACCAGACCTGGCCGCGCTCCGTACTGGGGACAGGGAACTCAGGTGACC GTTTCCTCTGGGGGATCAGGAGGCTCCGGCGGTTCTGGCCAGGTGCAGTTGCAG GAGTCTGGTGGAGGCCTGGTACAACCCGGCGGTTCTTTGCGCCTCTCATGCACT GCGAGCGGTCTTACATTTGATGACTCTGTAATGGGCTGGTTCCGTCAGGCTCCT GGCAAGGGACGTGAGGCCGTGAGCTGCATTTCCAGCTCCGGCGCGAATGCCTTT TACGCTGATTCCGTGAAGGGAAGATTCACCATTAGTAGAGACAACGCTAAGAAC ACCCTGTATTTGCAGATGAACTCTCTGAAACCTGAGGATACAGCTACCTATTAC TGCAAGCGCGGTCACGCTTGTGCTGGCTATTACCCGATCCCTTACGAGACTAC TGGGGACAGGGCACCCAAGTGACAGTCTCTTCC |
| hIL27 Ra_VH H12- DR591 | 1375 | CAGGTGCAGCCTCAGGAGTCCGGGGGTGGCTCCGTGCAGGGGGGCGAATCCCTT CGTCTGAGCTGCCGCGCTTCTGGCTCCACCTACTCTAACTATTGTCTGGGCTGG TTTCGTCAGATCACCGGCAAAGAGCGCGAGGGAGTGGCCGTTATAAATTGGGTA GGCGGTATGCTGTACTTTGCTGACTCCGTGAAGGGGCGGTTCACAGTTTCCCAG GATCAGGCAAAGAATACTGTTTATCTGGAAATGAACTCCCTGAAGCCTGAGGAC ACTGCTATGTATTACTGCGCCACCGAGTCCGTGTCCAGCTTTTCATGTGGCGGT TGGCTGACCCGCCCTGATCGGGTCCCTTACTGGGGTCAGGGGACACAGGTAACA GTGTCCAGTGGTGGCGGGTCCCAGGTGCAACTCCAGGAATCTGGGGGGGGTTCC GTTCAGGCTGGCGGGTCCCTTCGCCTGTCCTGCACCGCGTCCGGTGCTATCGCT TCAGGTTATATCGACTCCCGTTGGTGTATGGCTTGGTTTAGACAAGCTCCTGGC AAAGAACGCGAGGGCGTCGCTGCCATCTGGCCAGGAGGCGGTCTTACCGTCTAC GCCGACAGCGTGAAGGGCCGGTTTACCATCTCACGTGACCACGCCAAGAACACA CTGTACCTCCAGATGAATAACCTGAAGCCGGAAGATACGGCCATGTATTACTGT GCAGCCGGAAGCCCCCGCATGTGCCCATCTCTTGAGTTCGGGTTTGACTATTGG GGACAGGGAACCCAAGTCACTGTGTCCTCT |
| hIL27 Ra_VH H12- DR591 | 1376 | CAGGTCCAGCTCCAGGAGTCAGGAGGGGGCAGCGTACAGGCCGGAGAGTCCCTG AGACTTAGTTGCCGCGCCAGCGGATCTACCTACTCTAACTACTGCCTCGGCTGG TTCAGGCAGATCACCGGCAAGGAGAGAGAGGGTGTGGCCGTAATCAACTGGGTT GGGGGAATGCTGTACTTCGCCGACTCCGTGAAGGGTAGGTTCACTGTTTCTCAG GACCAGGCAAAGAATACTGTGTATCTGGAGATGAACTCCCTGAAACCCGAAGAT ACTGCCATGTATTACTGTGCCACCGAGAGCGTGTCCTCTTTCTCCTGTGGAGGC TGGCTCACGCGCCCTGATCGCGTGCCCTATTGGGGACAGGGTACTCAAGTCACC GTGTCAAGCGGAGGCAGCGGGGGCTCTGGAGGCAGCGGTCAGGTCCAGCTGCAA GAGAGCGGTGGAGGTTCAGTACAGGCTGGGGGGTCACTGCGTCTGAGTTGTACT GCCAGTGGAGCCATCGCGTCTGGCTACATCGACTCTAGGTGGTGCATGGCCTGG TTCCGGCAGGCTCCTGGGAAGGAGAGAGAGGGAGTGGCCGCGATTTGGCCAGGT GGGGGCCTGACCGTCTACGCCGATAGCGTCAAGGCGGGGTTCACCATCAGCCGC GATCACGCTAAAAATACCCTGTACCTTCAGATGAATAACCTGAAGCCAGAAGAC ACAGCTATGTACTATTGTGCCGCTGGGTCTCCCCGGATGTGTCCAAGTCTGGAA TTTGGCTTCGACTACTGGGGGCAGGGCACACAGGTTACTGTGAGTTCC |
| hIL27 Ra_VH H12- DR592 | 1377 | CAGGTCCAGTTGCAGGAGTCCGGCGGTGGCTCCGTGCAGGCCGGTGAGTCTCTG AGACTGTCTTGCCGCGCTAGTGGGTCCACATACAGTAACTACTGCCTGGGCTGG TTCCGCCAGATCACTGGTAAGGAAAGGGAAGGCGTTGCTGTTATCAACTGGGTG GGCGGTATGCTGTACTTCGCTGACTCCGTCAAGGGCCGCTTCACCGTCTCTCAG GATCAGGCTAAGAATACAGTCTATCTGGAAATGAACAGCCTGAAGCCCGAAGAT ACTGCTATGTACTATTGTGCTACCGAGTCTGTCTCTAGCTTTTCTTGCGGAGGC TGGCTGACCCGCCCGGACAGGGTCCCTTACTGGGGCCAGGGCACTCAGGTGACC GTATCTAGCGGTGGCGGTTCACAGGTGCAACTCCAGGAGAGCGGTGGCGGATCT GTGCAGGCCGGAGGCAGCCTTCGCTTGAGCTGCACGGCCCCCGGCTTTACCAGT AACAGCTGTGGCATGGACTGGTATCGCCAGGCCCCCGGAAAGGAGCGCGAGTTC GTCAGCTCCATCTCCACTGACGGAACTACCGGATATGCTGACTCTGTCAAAGGT CGCTTCACCATCTCTAAGGATAAGGCAAAGGACACAGTCTATCTGCAAATGAAC AGTCTCAAGCCAGAGGACACAGGTATGTACTCCTGCAAGACCAAGGATGGCACT ATTGCCACAATGGAACTTTGTGATTTCGGCTACTGGGGACAGGGCACCCAAGTT ACTGTTTCTAGC |

TABLE 1B-continued

| Name | SEQ ID NO: | Sequence |
|---|---|---|
| hIL27 Ra_VH H12-DR592 | 1378 | CAGGTGCAACTTCAGGAATCAGGGGGTGGCTCCGTGCAGGCTGGTGAGTCACTG CGTCTTTCTTGCAGGGCCTCTGGGTCCACCTACTCCAACTACTGCCTGGGTTGG TTCAGGCAGATCACCGGCAAGGAGAGAGAGGGCGTGGCCGTTATAAATTGGGTA GGAGGTATGCTGTACTTCGCCGACAGCGTCAAGGGACGCTTCACTGTCAGTCAG GATCAGGCCAAGAACACTGTGTACCTTGAGATGAACTCTCTGAAGCCTGAAGAC ACAGCCATGTATTACTGTGCCACAGAGAGTGTCTCTAGCTTCAGCTGCGGTGGA TGGCTGACCCGTCCTGACCGCGTTCCCTACTGGGGCCAGGGCACTCAGGTTACT GTGTCTAGCGGAGGGAGCGGAGGGTCAGGTGGCTCTGGCCAGGTCCAGTTGCAG GAGTCTGGTGGGGGCTCTGTGCAAGCTGGCGGGTCTCTGAGACTGTCCTGTACC GCACCCGGCTTCACATCCAATAGCTGCGGCATGGACTGGTATAGACAAGCGCCC GGGAAGGAGCGCGAGTTTGTTAGCTCCATCAGCACAGACGGCACAACGGGCTAT GCCGACTCTGTGAAAGGGCGCTTTACCATTTCTAAGGACAAGGCCAAGGACACC GTCTATCTCCAGATGAACAGCCTGAAGCCTGAGGACACAGGCATGTATAGCTGC AAAACGAAGGACGGGACCATCGCAACGATGGAGCTGTGTGACTTTGGGTACTGG GGGCAGGGCACCCAGGTTACCGTCACTTCC |
| hIL27 Ra_VH H12-DR593 | 1379 | CAGGTGCAACTCCAGGAGAGCGGTGGAGGTAGCGTGCAAGCTGGTGAGAGTCTG CGCCTCAGCTGCCGCGCTTCCGGCTCAACTTACAGCAATTACTGCCTGGGTTGG TTCCGTCAGATCACCGGAAAGGAGAGAGAGGGGGTAGCAGTCATCAACTGGGTC GGCGGAATGCTCTATTTTGCCGACTCCGTTAAAGGACGCTTCACCGTGTCTCAA GACCAGGCTAAGAACACAGTGTATCTGGAGATGAACTCTCTCAAGCCAGAGGAT ACCGCCATGTACTATTGCGCCACTGAATCCGTGTCTTCCTTCTCATGTGGGGGG TGGCTCACTCGTCCTGATCGGGTGCCATACTGGGGGCAGGGCACCCAGGTCACC GTCTCTAGTGGTGGAGGCAGCCAGGTCCAGTTGCAGGAGTCTGGGGGGGGTTCT GTCCAAGCTGGTGGCTCACTCCGTCTGTCCTGCGCCGCGAGGGGGTATCCATAC TCAAATGGCTACATGGGATGGTTCCGTCAGGCTCCAGGAAAGGAGCGTGAGGGG GTCGCGACCATTTATACCGGCGACGGACGCACCTACTATGCCGACTCCGTGAAG GGGAGGTTTACCATCAGTCGCGATAACGCCAAGAACACCGTGGATCTCCAGATG AGTTCCCTGAAGCCTGAAGACACCGCTATGTATTACTGCGCGGCACGTGCCGCA CCGCTTTACAGTAGCGGCAGTCCCCTGACCCGCGCGAGGTATAACGTGTGGGGC CAGGGCACCCAGGTTACAGTGTCTTCT |
| hIL27 Ra_VH H12-DR593 | 1380 | CAGGTGCAGCTCCAGGAGTCTGGGGGGGGTTCTGTCCAAGCTGGCGAGAGCCTG CGCCCGTCCTGCCGGGCTTCCGGTTCCACCTATTCTAACTATTGTCTGGGCTGG TTTCGCCAGATCACTGGAAAGGAGAGGGAGGGTGTGGCAGTTATCAACTGGGTG GGTGGGATGCTCTATTTCGCCGATTCAGTTAAGGGACGCTTCACAGTGAGCCAA GACCAGGCTAAGAACACAGTCTACCTGGAGATGAACAGCCTGAAACCGGAAGAC ACGGCAATGTATTACTGCGCGACCGAGAGCGTGTCTAGTTTTAGCTGTGGGGGC TGGCTGACGAGACCCGACAGGGGCCTTACTGGGCGGCAGGGTACTCAGGTTACC GTCTCTTCCGGTGGCAGTGGTGGCAGCGGAGGCAGCGGCCAGGTGCAGCTGCAA GAATCTGGCGGTGGCAGCGTTCAGGGGGGAGGTTCCCTTCGCCTGTCTTGTGCT GCATCCGGCTACCCTTACTCTAACGGTTACATGGGCTGGTTTCGTCAAGCCCCC GGCAAGGAACGTGAGGGGGTGGCGACAATTTATACAGGTGATGGCCGCACTTAT TACGCTGACTCCGTTAAGGGACGCTTCACCATCTCCCGCGATAACGCCAAGAAT ACGGTGGACCTCCAGATGTCCTCTCTCAAACCTGAGGACACCGCAATGTACTAT TGCGCCGCTCGCGCCGCGCCGCTCTACAGTAGCGGCAGCCCACTGACTCGCGCC CGCTACAATGTGTGGGGACAGGGAACCCAGGTGACCGTGAGCAGT |
| hIL27 Ra_VH H12-DR594 | 1381 | CAAGTGCAGCTCCAAGAGTCCGGTGGAGGCTCCGTGCAGGCTGGCGAGTCCCTG CGTCTGTCCTGCCGCGCGTCTGGTAGTACTTACTCTAACTATTGTCTCGGTTGG TTCAGGCAGATCACCGGCAAAGAGCGCGAAGGAGTTGCCGTTATCAACTGGGTG GGCGGTATGCTCTATTTCGCCGACAGCGTGAAAGGGAGATTCACTGTGAGCCAG GACCAAGCTAAGAACACAGTGTATCTTGAGATGAACAGCCTCAAGCCTGAGGAC ACCGCTATGTATTACTGTGCCACAGAATCTGTGTCTTCCTTCTCATGTGGGGGT TGGCTCACCAGGCCGGACAGGGTCCCATACTGGGGCCAGGGCACCCAGGTGACC GTGTCTAGCGGAGGTGGCAGCCAGGTGCAGTTGCAGGAGTCCGGTGGGGGCTCC GTGCAGGCTGGAGGCTCACTTCGGCTCAGCTGCGTGGCCTCAGCGTCTACCTAC TGCACATACGATATGCACTGGTATCGTCAAGCACCCGGCAAAGGCCGCGAGTTC GTCAGCGCCATTGATTCCGACGGTACAACCCGTTACGCTGACTCCGTCAAGGGG CGTTTTACCATTTCCCAGGGGACCGCTAAGAACACCGTTTATCTTCAGATGAAC AGCCTCCAGCCGGAAGACACAGCCATGTATTACTGTAAAACCGTGTGCGTAGTG GGCTCCAGATGGTCAGACTATTGGGGGCAGGGCACCCAGGTAACCGTGTCCTCT |
| hIL27 Ra_VH H12-DR594 | 1382 | CAGGTTCAGCTTCAGGAATCAGGAGGTGGCTCAGTGCAGGCAGGAGAGTCTCTC CGCCTGTCCTGTCGTGCCAGCGGATCTACGTATTCCAACTACTGCCTCGGTTGG TTCAGGCAGATCACCGGCAAAGAGCGCGAAGGAGTGGCGGTTATCAACTGGGTT GGCGGAATGCTGTACTTCGCAGACAGTGTCAAGGGCAGATTCACTGTGTCCCAG GACCAGGCCAAAAACACAGTGTACCTGGAGATGAATAGTTTGAAGCCGGAAGAT ACAGCCATGTATTACTGCGCCACCGAGTCTGTCTCCAGCTTTTCTTGCGGAGGC TGGCTGACCCGCCCAGACCGCGTCCCCTACTGGGGCCAGGGAACTCAAGTCACC GTGTCTTCCGGGGGAGTGGTGGCAGCGGCGGGCTCCGGCCAGGTGCAGTTGCAG GAGTCCGGTGGCGGAAGTGTCCAGGCCGGGGGCTCCTTGAGACTTTCATGCGTC GCCTCTGCCTCCACCTACTGCACTTACGACATGCACTGGTATCGCCAGGCTCCG GGTAAGGGACGGGAGTTCGTATCTGCCATCGACTCCGACGGGACCACACGCTAC GCGGACAGCGTGAAAGGCAGGTTCACCATCAGTCAGGGGACCGCCAAGAATACG GTTTACCTCCAGATGAACTCTCTTCAGCCGGAGGACACGGCTATGTATTACTGC |

TABLE 1B-continued

| Name | SEQ ID NO: | Sequence |
|---|---|---|
| | | AAAACTGTGTGCGTGGTTGGAAGCAGATGGTCTGATTACTGGGGTCAGGGCACC CAGGTGACTGTATCAAGC |
| hIL27 Ra_VH H12- DR595 | 1383 | CAAGTGCAGCTGCAAGAAAGTGGCGGTGGCAGTGTGCAAGCTGGAGAGTCCCTC AGACTGAGTTGTAGAGCCAGTGGTAGCACATATAGCAATTACTGCCTGGGTTGG TTTCGTCAGATCACCGGCAAGGAGAGAGAAGGCGTGGCCGTCATAAATTGGGTC GGCGGTATGCTGTACTTTGCAGATTCCGTCAAGGGCCGCTTTACGGTCAGCCAA GATCAGGCCAAGAATACTGTGTATCTGGAAATGAACAGTCTGAAACCGGAGGAC ACCGCTATGTATTACTGCGCTACTGAATCCGTCTCCTCTTTTAGTTGCGGTGGG TGGCTCACCAGACCGGATCGCGTGCCCTATTGGGGCCAGGGCACCCAGGTGACG GTGTCCTCAGGAGGCGGATCACAGGTGCAGCTCCAGGAGAGCGGGGGGGGAGT GTGCAGGCCGGTGGCAGCCTGACCTTGTCATGTGGGGCTAGTGAGTACGCCTAT TCTACCTGTAATATGGGCTGGTATCGCCAGGCACCCGGAAAAGAGCGCGAGCTG GTGTCCGCGTTCATTAGCGATGGGTCTACCTATTACGCCGATTCCGTGAAGGGC AGGTTCACCATCACACGCGACAACGCTAAGAACACCGTATACCTCCAGATGAAC AGCCTGAAGCCAGAAGACACGGCCATCTATTACTGCCCTGCTAATTGCTACCGC AGGCTGCGCAACTACTGGGGACAGGGCACTCAGGTGACTGTGTCTAGT |
| hIL27 Ra_VH H12- DR595 | 1384 | CAGGTGCAACTTCAGGAGTCCGGTGGCGGTAGTGTGCAGGCTGGCGAGTCTCTG CGTCTGTCTTGCCGCGCGTCCGGCTCCACCTACTCCAACTACTGCCTGGGTTGG TTCCGCCAGATTACCGGCAAAGAAAGGGAGGGCGTTGCGGTTATTAACTGGGTG GGCGGGATGCTGTACTTCGCAGATTCTGTGAAGGGTAGGTTTACAGTCTCACAG GACCAGGCTAAGAACACGGTGTACCTGGAAATGAACAGTCTCAAGCCCGAAGAC ACCGCCATGTATTACTGCGCTACAGAGTCTGTTTCCTCTTTTAGCTGCGGTGGG TGGCTGACCCGCCCTGACCGTGTGCCTTACTGGGGACAGGGGACCCAGGTCACT GTAAGCTCTGGAGGGTCCGGTGGCTCCGGGGGGAGGGGCCAGGTACAGCTCCAG GAGTCCGGGGGGGGAAGTGTGCAGGCCGGAGGCAGCCTCACCCTGAGCTGCGCG GCATCCGAGTACGCCTATTCTACCTGTAACATGGGCGGGTACAGGCAGGCTCCG GGCAAGGAGAGAGAGTTGGTTTCTGCTTTTATCAGTGATGGCAGTACCTATTAC GCGGATTCCGTGAAAGGGAGATTCACCATTACACGTGACAACGCTAAGAACACC GTTTATTTGCAGATGAACTCCCTCAAGCCCGAGGATACAGCCATTTACTATTGC TCTGCCAACTGCTATCGTCGCCTGCGCAACTACTGGGGACAGGGGACACAGGTG ACCGTGTCCAGT |
| hIL27 Ra_VH H12- DR596 | 1385 | CAGGTCCAGCTCCAGGAGTCCGGGGGTGGCTCCGTGCAGGCTGGCGAATCTTTG CGCCTCTCATGCAGAGCTTCCGGCTCCACCTATAGCAACTATTGTCTGGGTTGG TTTCGCCAGATCACCGGCAAAGAGCGTGAAGGCGTCGCCGTCATCAACTGGGTC GGGGGATGCTGTACTTTGCGGACTCTGTTAAGGTGTCGTTTCACAGTCAGTCAG GATCAAGCGAAGAACACCGTGTACCTGGAGATGAACTCCCTGAAGCCGGAGGAC ACCGCAATGTATTACTGTGCCACTGAATTCTGTGAGCAGTTTTAGCTGGGCGGT TGGCTGACCCGCCCTGACCGCGTTCCCTACTGGGGGCAGGGCACCCAAGTAACC GTGTCTTCCGGGGGGGGGTCTCAGGTCCAGCTCCAGGAGTCTGGAGGGGGCCTT GTCCAGCCCGGAGGCAGCCTGCGCCTGTCTTGCACGGCTAGTGGCCTGACATTC GACGATAGCGTGATGGGCTGGTTCAGACAGGCTCCGGGGAAGGGCCGTGAGGCC GTTTCTTGTATCTCTAGCTCTGGTGCTAACGCCTTCTATGCCGACTCCGTGAAG GGCCGCTTCACAATCAGCCGTGACAACGCCAAGAACACGCTGTATCTTCAGATG AACTCCCTGAAGCCTGAGGATACCGCCACATATTACTGTAAGCGCGGTCACGCC TGTGCAGGCTATTACCCCATCCCCTACGATGACTACTGGGGTCAGGGAACCCAG GTTACGGTTTCATCT |
| hIL27 Ra_VH H12- DR596 | 1386 | CAGGTGCAACTTCAGGAGAGCGGGGCGGGGAGCGTGCAGGGGGGCGAGAGCCTG CGCCTGTCCTGCCGTGCGTCTGGCTCCACCTACAGTAACTACTGCCTCGGGTGG TTTCGCCAGATTACGGGCAAGGAGCGCGAAGGTGTGGCCGTTATCAACTGGGTG GGTGGAATGCTCTACTTTGCCGATTCTGTGAAAGGACGCTTTACCGTGTCTCAG GATCAGGCTAAGAATACAGTTTACCTGGAGATGAACTCTCTCAAGCCTGAGGAT ACAGCGATGTACTATTGTGCAACCGAGTCCGTCTCTTCCTTCAGCTGCGGGCGG TGGCTGACCCGTCCTGACCGCGTGCCATACTGGGGTCAAGGTACACAGGTGACA GTCAGCTCTGGTGGCAGCGGCGGTAGCGGGGGCAGTGGCCAGGTCCAGTTGCAG GAAAGTGGAGGCGGTCTGGTTCAACCTGGGGGCTCCCTGCGCCTGTCTTGCACA GCCTCTGGACTGACGTTTGATGACTCCGTGATGGGCTGGTTCAGACAGGCTCCT GGTAAGGGCCGCGAGGCCGTCAGCTGTATCAGTAGCTCCGGGGCCAACGCTTTC TATGCAGACTCTGTCAAAGGCAGATTCACTATCAGCCGCGACAACGCCAAGAAC ACACTGTATTTGCAGATGAACAGCCTGAAACCTGAAGATACTGCTACATACTAT TGTAAGCGCGGCCATGCCTGTGCTGGGTATTACCCTATCCCCTACGATGACTAC TGGGGCCAGGGCACGCAGGTTACAGTAAGCAGT |
| hIL27 Ra_VH H13- DR591 | 1387 | CAGGTGCAGCTCCAGGAATCCGGTGGGGGGTCCGTGCAGGCTGGCGGTTCCCTC CGTCTGTCCTGTGTGGCCTCCGGGTACGTCAGCTGTGACTACTTTCTGCCATCC TGGTATCGCCAGGCCCCCGGTAAGGAGAGAGAGCTCGTGTCTATCATTGATGGC ACTGGCAGCACTTCTTACGCCGCATCTGTGAAGGGGCGCTTCACAGCCTCCCAG GATAGAGGCAAAAACATTGCCTACCTTCAGATGAACTCTTTGAAACCCGAGGAT ACTGCCATGTATTACTGCAAAGCGAGCTGTGTCCGGGGCCGCACCATCTCCGAA TACTGGGGACAGGGAACCCAGGTCACGGTCTCCTCTGGTGGGGGGTCCCAGGTG CAGCTTCAGGAGAGCGGGGGAGGTTCCGTGCAGGCCGGAGGCTCTCTCAGGCTC AGCTGCACAGCGTCCGGCGCTATTGCCAGCGGATATATCGACAGTCGTTGGTGT ATGGCCTGGTTTCGCCAGGCTCCGGGCAAGGAGCGTGAGGGAGTCGCTGCCATT TGGCCCGGGGGGGGACTGACCGTGTATGCGGACTCTGTGAAAGGAAGATTCACC |

TABLE 1B-continued

| Name | SEQ ID NO: | Sequence |
|---|---|---|
| | | ATCTCTCGGGATCACGCTAAGAATACCCTGTATCTCCAGATGAATAACCTGAAG CCCGAGGACACCGCCATGTATTACTGCGCCGCAGGATCACCCCGCATGTGTCCG TCTCTGGAGTTCGGTTTCGACTACTGGGGCCAAGGCACCCAAGTCACTGTGTCT TCT |
| hIL27 Ra_VH H13- DR591 | 1388 | CAGGTGCAACTCCAGGAGTCCGGGGGTGGCTCCGTACAGGCTGGAGGCAGCCTC CGTCTCAGTTGTGTTGCCAGCGGCTATGTAAGCTGCGACTATTTCCTGCCTTCT TGGTATCGCCAGGCACCTGGGAAGGAGCGTGAGTTCGTGTCCATCATTGATGGC ACAGGCAGCACCTCCTATGCCGCTTCAGTCAAGGGACGCTTTACAGCCTCCCAG GACCGTGGCAAGAACATCGCCTACCTTCAGATGAACTCCCTGAAGCCTGAGGAC ACAGCCATGTATTACTGTAAGGCTTCCTGTGTGCGTGGCCGGACCATCTCTGAA TACTGGGGACAGGGCACGCAGGTGACGGTCAGCTCTGGGGGTAGTGGGGGGTCC GGCGGGAGTGGACAGGTGCAGCTTCAGGAGAGCGGTGGCGGATCTGTCCAAGCC GGTGGCAGCCTTAGGCTCTCTTGCACTGCCAGCGGGGCCATCGCTTCAGGATAT ATTGATAGCCGCTGGTGCATGGCCTGGTTCCGCCAGGCCCCAGGGAAAGAGCGT GAAGGCGTGGCAGCCATCTGGCCGGGGGCGGGTCTGACCGTCTACGCCGACTCA GTTAAAGGAAGATTTACCATTTCCCGCGATCACGCTAAGAACACTCTGTATCTT CAAATGAATAACCTGAAACCTGAAGACACCGCTATGTATTACTGTGCTGCCGGT AGCCCGAGGATGTGCCCAAGCCCTGAGTTCGGCCTCGACTATTGGGGCCAGGGA ACTCAAGTGACCGTGAGCAGC |
| hIL27 Ra_VH H13- DR592 | 1389 | CAGGTGCAGCTCCAGGAGTCTGGTGGGGGTTCCGTCCAGGCTGGCGGTTCCCTG AGGCTCTCATGCGTGGCCAGCGGTTACGTGTCTTGCGACTATTTCCTGCCCTCA TGGTATCGTCAGGCCCCTGGCAAGGAGCGCGAGTTCGTGTCAATTATCGACGGC ACAGGCAGTACCAGCTATGCAGCCAGCGTTAAGGGCCGTTTTACCGCGTCACAG GATCGCGGGAAGAATATCGCCTACCTCCAGATGAACAGTCTGAAACCTGAAGAT ACAGCGATGTATTACTGTAAGGCCAGCTGTGTGAGGGGTCGGACGATCTCTGAA TACTGGGGCCAAGGAACCCAAGTAACTGTGTCCAGCGGAGGCGGATCTCAGGTG CAGCTTCAGGAATCCGGCGGTGGCAGCGTCCAGGCCGGAGGGAGCCTGCGTCTT TCCTGCACCGCTCCTGGCTTCACCAGCAACAGTTGCGGGATGGATTGGTATCGT CAGGCTCCCGGCAAGGAACGGGAGTTCGTGTCCAGTATCAGCACTGATGGCACT ACCGGATACGCTGATTCCGTTAAGGGTCGTTTCACCATCTCCAAAGATAAGGCC AAAGACACCGTGTATCTCCAGATGAACTCCCTGAAACCAGAAGACACAGGTATG TATTCTTGTAAGACTAAAGACGGCACCATCGCGACAATGGAGCTGTGTGATTTC GGATACTGGGGTCAGGGAACACAGGTGACTGTGTCCTCT |
| hIL27 Ra_VH H13- DR592 | 1390 | CAAGTACAGTTGCAGGAGTCTGGGGGAGGCTCCGTGCAGGCGGGGGGGAGCCTG AGGCTGAGTTGTGTGGCCTCAGGGTATGTGTCCTGTGACTACTTTCTCCCGAGC TGGTATCGCCAGGCTCCAGGGAAGGAGCGTGAGTTCGTGTCTATTATCGACGGG ACTGGATCTACCTCTTATGCCGCATCTGTCAAGGGGCGCTTCACCGCCTCTCAG GATCGCGGAAAGAACATCGCCTACTTGCAAATGAACAGCCTGAAGCCCGAGGAC ACTGCCATGTATTACTGTAAAGCCTCTTGTGTGAGAGGCCGCACTATTTCAGAG TACTGGGGACAGGGAACCCAGGTCACTGTCAGCAGTGGAGGTTCTGGGGGTTCT GGTGGGTCAGGACAGGTACAGTTGCAGGAAAGCGGAGGCGGCTCCGTGCAGGCC GGAGGCTCCCTGAGGCTGTCTTGCACAGCTCCTGGTTTCACATCTAACAGTTGC GGCATGGACTGGTATCGCCAGGCCCCAGGGAAGGAGAGGGAATTTGTGTCTAGC ATCAGCACCGACGGAACCACAGGATACGCCGACTCCGTCAAGGGTCGTTTTACT ATCAGTAAGGACAAGGCTAAGGATACTGTCTACCTGCAAATGAACAGTCTGAAG CCCGAGGACACCGGCATGTATAGCTGTAAGACTAAGGATGGAACTATTGCGACT ATGGAGCTGTGTGACTTCGGGTATTGGGGCCAGGGTACACAAGTAACTGTGAGT TCT |
| hIL27 Ra_VH H13- DR593 | 1391 | CAGGTACAGCTCCAGGAGAGGGGCGGTGGTTCCGTCCAAGCAGGCGGTTCCCTC AGACTGTCATGCGTCGCAAGCGGCTACGTGTCATGTGATTACTTCCTGCCCTCC TGGTACAGGCAAGCGCCAGGAAAGGAAAGGGAGTTTGTCTCCATTATCGACGGC ACCGGAAGCACAAGTTACGCCGCGTCTGTTAAGGGCCGCTTCACCGCTTCTCAA GATCGCGGCAAAAACATCGCCCACCTGCAAATGAACAGCCTCAAACCAGAGGAC ACCGCGATGTATTACTGCAAGGCTTCTTGTGTGCGTGGTCGGACGATTTCCGAA TACTGGGGCCAAGGCACCCAGGTGACTGTTTCTAGCGGTGGGGGCAGCCAGGTC CAGTTGCAGGAGAGTGGGGGTGGCAGCGTTCAGGCTGGGGGGAGCCTGAGACTC AGCTGCGCTGCGTCTGGTTACCCCTATTCCAACGGCTATATGGGCTGGTTCAGA CAGGCACCAGGGAAGGAGCGCGAGGGGGTGGCCACCATCTACACCGGCGATGGC CGCACATATTACGCTGATTCAGTGAAGGGAAGATTCACTATCAGTAGGGACAAC GCTAAGAATACCGTGGATCCCCAGATGAGTTCACTGAAGCCGGAGGATACCGCG ATGTATTACTGCGCGGCTCGCGCAGCCCCTCTCTACAGTAGCGGCTCCCCTCTT ACGCGGGCTAGATACAACGTGTGGGGCCAGGGAACCCAGGTTACTGTGAGCAGT |
| hIL27 Ra_VH H13- DR593 | 1392 | CAGGTTCAGCTGCAAGAGTCCGGGGGGGGCTCCGTTCAGGCCGGAGGCTCTCTC AGGCTGAGCTGTGTCGCCTCCGGCTATGTGAGCTGTGACTACTTTCTGCCATCC TGGTATCGCCAGGCCCCTGGCAAGGAACGCGAGTTTGTCTCCATCATTGACGGC ACCGGCTCCACATCCTACGCGGCTTCCGTGAAGGGGCGTTTCACCGCGTCCCAA GATCGCGGGAAGAATATCGCCTACCTCCAAATGAACTCTCTCAAGCCGGAGGAC ACTGCTATGTATTACTGTAAGGCATCCTGTGTTCGCGGGCGGACAATCAGCGAA TACTGGGGCCAGGGCACCCAGGTAACTGTATCCAGCGGAGGCTCTGGAGGTTCA GGTGGCTCCGGGCAGGTCCAGCTCCAGGAGTCTGGCGGTGGCTCCGTGCAGGCT GGTGGCAGCCTTCGTCTGTCTTGCGCTGCCTCTGGTTATCCTTACTCCAATGGC TACATGGGCTGGTTTCGCCAGGCCCCAGGGAAGGAGAGGGAGGGCGTGGCCACT |

TABLE 1B-continued

| Name | SEQ ID NO: | Sequence |
| --- | --- | --- |
| | | ATCTACACCGGCGATGGCCGCACCTACTATGCTGACAGCGTGAAGGGCAGATTC<br>ACCATCAGCAGGGATAACGCAAAGAACACAGTGGACCTTCAGATGAGTAGCCTG<br>AAGCCAGAGGACACCGCTATGTATTACTGTGCGGCCAGGGCAGCTCCGTTGTAC<br>TCTTCCGGTTCCCCTCTGACCAGAGCGAGATATAATGTGTGGGACAGGGCACC<br>CAGGTTACCGTCAGTTCC |
| hIL27 Ra_VH H13-DR594 | 1393 | CAAGTGCAGTTGCAGGAGAGCGGGCGGGGGTCCGTCCAGGCTGGGGGCTCACTG<br>CGTCTGAGCTGTGTGGCCTCTGGTTACGTGTCCCGTGACTATTTCCTGCCTTCT<br>TGGTATAGACAGGCCCCAGGCAAAGAAAGGGAGTTCGTGTCTATTATCGACGGC<br>ACCGGCAGCACTAGCTATGCGGCCAGCGTTAAGGGGCGTTTCACAGCCAGCCAG<br>GATCGCGGCAAGAACATCGCCTATTTGCAGATGAACTCCCTGAAGCCCGAGGAC<br>ACCGCCATGTACTATTGCAAGGCCAGCTGCGTGCGCGGCAGGACCATTTCCGAG<br>TACTGGGGCCAAGGCACTCAGGTGACAGTGTCTTCCGGTGGCGGTAGTCAGGTG<br>CAGTTGCAGGAGTCCGGGGGAGGCAGCGTGCAGGCCGGTGGGTCCCTCCGCCTG<br>AGCTGTGTGGCGTCCGCAAGCACCTACTGTACCTATGATATGCACTGGTACAGG<br>CAAGCCCCTGGCAAGGGCCGCGAGTTTGTCTCTGCTATCGACTCAGACGGGACC<br>ACTCGCTACGCTGACAGTGTAAAGGGGCGCTTCACTATTAGCCAGGGCACAGCC<br>AAGAACACCGTGTACCTCCAGATGAATAGCCTCCAGCCCGAGGACACTGCCATG<br>TATTACTGCAAGACCGTATGCGTGGTTGGGAGTCGCTGGTCAGATTACTGGGGT<br>CAGGGTACTCAGGTGACCGTCTCCAGC |
| hIL27 Ra_VH H13-DR594 | 1394 | CAGGTGCAGTTGCAGGAATCCGGCGGTGGCTCAGTCCAGGGGGGGGGCTCCCTG<br>AGGCTGTCATGCGTCGCCAGCGGATATGTGTCTTGCGACTATTTTCTGCCCTCC<br>TGGTATCGCCAAGCTCCCGGCAAGGAGAGAGAATTTGTTTCTATCATTGACGGG<br>ACAGGTTCCACTTCCTACGCTGCCAGCGTCAAAGGGCGCTTCACGGCGAGCCAG<br>GATAGGGGCAAAAACATCGCCTACCTGCAAATGAACTCTCTCAAGCCCGAGGAC<br>ACTGCCATGTATTACTGTAAAGCCAGCTGTGTGCGCGGTCGCACTATCTCTGAA<br>TATTGGGGCCAGGGCACCCAGGTGACCGTCACCTCTGGAGGTTCAGGGGGCTCC<br>GGTGGCAGCGGTCAGGTCCAGCTCCAAGAGTCTGGGGGGGGTAGTGTGCAGGCG<br>GGCGGTTCCCTCAGACTCTCCTGCGTGGCCTCCGCCCCTACCTATTGCACCTAC<br>GATATGCACTGGTATCGGCAGGCTCCAGGAAAGGGCCGGGAGTTCGTGAGCGCG<br>ATTGACTCCGATGGCACTACCCGTTATGCCGATTCCGTTAAGGGACGGTTCACA<br>ATTAGCCAGGGAACCGCGAAGAACACCGTGTACCTGCAAATGAACTCTCTCCAG<br>CCGGAGGATACTGCCATGTATTACTGTAAGACTGTGTGCGTCGTTGGGTCCAGG<br>TGGTCCGATTATTGGGGCCAGGGAACTCAGGTTACCGTGTCCAGC |
| hIL27 Ra_VH H13-DR595 | 1395 | CAAGTGCAGCTCCAGGAGTCTGGCGGTGGCTCTGTGCAAGGGGGGGGTTCTCTC<br>AGACTCAGCTGCGTGGCCAGCGGCTACGTGTCCTGCGATTACTTCCTGCCTAGC<br>TGGTATCGTCAGGCCCCCGGCAAGGAACGCGAGTTCGTCAGCATTATCGACGGG<br>ACTGGGTCAACCTCCTATGCAGCCTCCGTAAAAGGCAGGTTCACCGCCAGTCAG<br>GATCGCGGCAAGAATATTCGCGTACCTCCAGATGAACTCTTGAAACCTGAGGAT<br>ACAGCTATGTATTACTGTAAGGCTAGTTGTGTGCGTGGGCGCACCATCTCCGAA<br>TACTGGGGCCAGGGAACTCAGGTCACTGTTTCTAGTGGGGGGGGAAGTCAGGTG<br>CAGTTGCAGGAGTCTGGAGGCGGTTCAGTCCAGGCTGGCGGATCTCTGACGCTC<br>TCTTGTGCAGCCTCTGAGTATGCCTATAGCACCTGCAACATGGGATGGTACAGA<br>CAGGCTCCTGGTAAGGAGCGCGAATTGGTGAGCGCTTTCATCTCTGATGGTTCC<br>ACATATTACGCTGATTCCGTGAAGGGCCGCTTTACGATTACACGCGACAATGCG<br>AAAAACACAGTGTACCTCCAGATGAACTCCCTCAAACCAGAAGACACTGCAATC<br>TACTATTGTTCTGCTAACTGCTATCGCCGTCTGCGCAACTACTGGGGGCAAGGT<br>ACGCAAGTGACCGTCTCCAGC |
| hIL27 Ra_VH H13-DR595 | 1396 | CAGGTCCAGCTGCAAGAGAGCGGCGGTGGGTCTGTGCAGGCCGGAGGCAGCCTG<br>CGTCTCAGCTGCGTCGCTTCTGGATATGTCAGCCGTGACTACTTCCTCCCATCT<br>TGGTACAGACAAGCGCCGGGGAAGGAACGCGAGTTCGTTAGCATTATCGACGGC<br>ACTGGAAGTACCTCTTATGCCGCTTCCGTTAAAGGACGCTTCACGGCCTCTCAG<br>GATCGCGGCAAGAATATCGCCTACCTTCAGATGAACAGCCTGAAGCCAGAGGAC<br>ACCGCTATGTATTACTGCAAGGCCAGCTGTGTGAGAGGGCGCACCATCAGCGAA<br>TACTGGGGCCAGGGCACCCAGGTGACCGTATCTAGTGGGGGGAGCGGTGGCTCC<br>GGTGGCAGTGGCCAGGTGCAGCTGCAAGAGAGTGGTGGGGGCAGTGTGCAGGCT<br>GGGGGTTCCCTGACGCTGTCCTGTGCGGCCAGCGAGTATGCTTACTCAACGTGC<br>AATATGGGTTGGTATCGCCAGGCCCCTGGTAAGGAGCGCGAACTCGTCTCTGCA<br>TTTATTAGCGACGGCTCCACTTATTACGCCGACAGCGTGAAGGGGAGATTCACT<br>ATTACCCGCGACAATGCCAAGAACACTGTGTACCTCCAAATGAACTCCCTGAAG<br>CCCGAGGACACAGCCATCTATTACTGCTCCGCGAACTGCTATCGCCGTCTGCGT<br>AACTACTGGGGCCAGGGGACCCAGGTCACAGTCTCCTCT |
| hIL27 Ra_VH H13-DR596 | 1397 | CAGGTACAGCTCCAGGAGTCCGGCGGTGGCTCTGTGCAGGCAGGAGGCTCACTG<br>CGCTTGAGTTGCGTGGCCAGCGGCTACGTGTCCTGCGACTACTTCCTGCCATCC<br>TGGTATAGGCAGGCTCCGGGTAAGGAAAGGGAGTTCGTCTCCATTATCGACGGT<br>ACTGGCAGCACCTCTTACGCAGCCTCCGTGAAGGGGCGTTTCACCGCCAGCCAG<br>GATCGGGGCAAGAACATCGCCTACTTGCAGATGAACTCCCTGAAGCCAGAGGAC<br>ACTGCAATGTATTACTGCAAAGCCAGCTGTGTGAGAGGACGCACCATCTCTGAG<br>TACTGGGGGCAAGGCACACAGGTCACGGTCTCTAGTGGCGGGGGTAGCCAGGTC<br>CAGCTCCAGGAAAGCGGAGGTGGCCTGGTTCAGCCGGGAGGGTCACTGAGACTG<br>TCCTGTACCGCCAGCGGGCTGACCTTCGATGACAGCGTCATGGGTTGGTTCCGG<br>CAGGCCCCCGGTAAAGGAAGAGAGGCGGTGAGCTGCATCAGCTCCTCTGGAGCT<br>AACGCCTTCTATGCTGACTCCGTGAAGGGTCGCTTCACCATCTCCAGAGATAAC |

TABLE 1B-continued

| Name | SEQ ID NO: | Sequence |
|---|---|---|
| | | GCTAAGAATACTCTCTACCTCCAGATGAACTCTCTGAAACCGGAGGACACCGCA ACCTATTACTGCAAGCGCGGGCACGCCTGCGCGGGATACTATCCAATCCCATAC GATGACTACTGGGGTCAGGGAACCCAGGTCACCGTGAGTTCT |
| hIL27 Ra_VH H13- DR596 | 1398 | CAGGTGCAGCTCCAGGAGAGCGGCGGTGGCTCTGTCCAGGCAGGCGGTTCCCTG CGCCTCTCTTGCGTGGCGAGTGGCTATGTTAGTTGTGACTACTTCCTGCCCTCA TGGTATCGGCAAGCTCCGGGAAAAGAGCGCGAGTTTGTCTCCATCATTGATGGA ACAGGATCTACGTCCTATGCCGCAAGTGTCAAGGGGCGGTTCACCGCTTCTCAG GACAGAGGAAAGAATATCGCTTATCTCCAGATGAACTCCCTGAAGCCAGAAGAC ACCGCTATGTACTATTGCAAGGCTTCTTGTGTGCGCGGCAGAACCATCTCTGAG TACTGGGGCCAGGGCACCCAGGTGACCGTTAGTTCAGGAGGGAGCGGAGGCAGT GGAGGCTCAGGTCAGGTGCAGCTCCAGGAATCTGGGGGAGGTCTGGTCCAGCCA GGTGGGTCCCTGCGCCTCAGCTGTACTGCCTCCGGTCTCACCTTCGATGACAGC GTCATGGGCTGGTTCCGCCAAGCGCCGGGTAAGGGGCGTGAAGCCGTGAGCTGC ATTTCCTCTAGCGGAGCCAACGCTTTTTACGCCGACAGCGTGAAGGGTAGATTT ACAATCTCTCGCGATAACGCGAAGAACACCCTGTATCTCCAAATGAACAGCCTG AAGCCAGAGGACACCGCTACTTATTACTGCAAGAGGGGACATGCGTGTGCGGGG TATTACCCCATTCCCTATGATGACTACTGGGGCCAGGGCACCCAGGTGACCGTT AGTTCT |
| hIL27 Ra_VH H14- DR591 | 1399 | CAGGTGCAACTCCAGGAATCCGGGGGTGGCTCCGTGCAAGCCGGTGGCAGTCTT AGGCTGTCCTGTGTGGCATCAGGGTATGTGTCCTGCGACTACTTCCTGCCTAGC TGGTACAGACAAGCTCCCGGTAAGGAGAGAGAGTTCGTGTCAATCATTGATGGC ACCGGCTCCACTTCCTACGCCGCTTCTGTGAAGGGACGTTTTACTGCCAGCCAA GATAAGGGCAAGAACATTGCCTATTTGCAGATGAACTCCTTGAAGCCGGAGGAC ACCGCTATGTATTACTGCAAGGCCTCCTGTGTACGTGGCCGGGCCATTTCCGAA TACTGGGGCCAAGGAACGCAGGTCACAGTGTCCTCTGGAGGTGGGTCCCAGGTG CAGTTGCAGGAAAGCGGCGGAGGGTCCGTCCAGGCTGGTGGCTCTCTGCGCCTT TCCTGCACCGCCTCTGGGGCTATCGCCCCCGGCTACATTGATTCTCGCTGGTGC ATGGCATGGTTCCGCCAAGCTCCTGGCAAGGAACGCGAGGGAGTGGCCGCGATT TGGCCCGGTGGGGGTCTGACTGTCTACGCAGACTCTGTAAAGGGTCGCTTCACA ATTTCCAGAGATCACGCGAAGAATACCCTCTACCTCCAGATGAACAATCTCAAG CCCGAGGACACTGCCATGTACTATTGCGCCGCTGGATCTCCGCGCATGTGCCCT AGTCTGGAATTTGGCTTCGATTACTGGGGCCAGGGTACTCAGGTGACAGTGTCT AGC |
| hIL27 Ra_VH H14- DR591 | 1400 | CAGGTGCAGTTGCAGGAGTCAGGAGGTGGCAGCGTCCAGGCAGGAGGTAGCTTG CGGCTCTCCTGCGTTGCGTCCGGCTATGTGAGTTGTGACTATTTTCTCCCATCA TGGTATCGTCAAGCGCCAGGTAAGGAACGTGAATTTGTGTCCATCATTGATGGA ACTGGCTCCACTAGCTACGCCGCGAGCGTGAAGGGCCGCTTCACGGCCTCTCAG GATAAGGGGAAGAACATCGCATACCTCCAGATGAACTCCTTGAAGCCAGAGGAT ACCGCCATGTATTACTGCAAGGCCTCCTGCGTCCGTGGTCGGGCGATCTCCGAG TACTGGGGCCAGGGAACTCAGGTGACAGTCAGCTCTGGTGGCAGCGGAGGGTCC GGCGGAAGCGGACAGGTGCAGCTCCAGGAAAGTGGAGGGGGAAGCGTGCAGGCA GGGGGCAGCCTGCGGCTGTCTTGTACCGCATCCGGGGCCATTGCTTCCGGCTAT ATTGATTCCAGATGGTGCATGGCTTGGTTTAGGCAAGCGCCTGGCAAAGAGCGT GAAGGTGTCGCCGCAATCTGGCCGGGGGGGGGTCTGACAGTGTACGCCGACTCC GTGAAGGGTAGATTCACAATCAGCCGCGACCATGCTAAAAACACTTTGTACCTC CAGATGAATAACCTGAAGCCTGAAGACACCGCCATGTATTACTGCGCTGCCGGA AGCCCTCGCATGTGCCCCAGCCTGGAGTTTGGCTTCGATTACTGGGGCCAGGGG ACCCAGGTGACGGTGAGCAGC |
| hIL27 Ra_VH H14- DR592 | 1401 | CAGGTACAGTTGCAAGAGAGCGGAGGCGGTTCTGTGCAGGCTGGAGGCAGCCTT CGCCTGTCCTGCGTGGCCTCTGGATACGTGTCATGTGACTACTTCCTGCCGAGT TGGTATCGCCAGGCTCCTGGGAAGGAGCGGGAGTTCGTGAGCATTATCGACGGC ACAGGCAGTACGTCCTACGCGGCCAGCGTGAAAGGTAGGTTCACTGCTTCCCAG GATAAAGGCAAAAACATCGCGTACTTGCAGATGAACTCACTGAAGCCTGAGGAC ACAGCCATGTATTACTGTAAGGCCAGCCGTGTGCGTGGCCGCGCTATCTCTGAG TACTGGGGGCAAGGCACTCAGGTCACTGTCAGCAGTGGTGGAGGTAGCCAGGTG CAGCTCCAGGAGTCAGGAGGGGGGTCCGTGCAGGCTGGTGGCAGCCTGCGCCTC AGCTGCACCGCTCCCGGCTTCACTTCTAACAGCTGCGGCATGGACTGGTATAGG CAAGCCCCAGGGAAGGAGCGCGAGTTCGTTTCCAGTATCTCCACCGATGGAACC ACGGGCTATGCTGATTCCGTGAAAGGACGTTTCACTATTACCAAGGACAAGGCG AAAGACACTGTGTATCTCCAGATGAACTCTCTGAAGCCTGAGGATACCGGCATG TATAGCTGTAAAACAAAAGATGGGACCATCGCAACTATGGAACTTTGTGACTTC GGCTATTGGGGCCAGGGTACTCAGGTAACCGTGTCCTCT |
| hIL27 Ra_VH H14- DR592 | 1402 | CAGGTTCAGTTGCAAGAAAGTGGTGGGGGCAGCGTGCAGGGGGGAGGCAGCTTG AGGCTGAGCTGCGTGGCATCCGGCTACGTTTCCTGTGATTACTTTCTGCCCTCC TGGTATCGCCAAGCGCCTGGAAAAGAGAGGGAGTTCGTTTCTATTATCGACGGC ACAGGCTCCACGAGTTATGCGGCCTCTGTCAAGGGACGCTTTACTGCTTCCCAA GACAAGGGGAAGAATATCGCCTATCTCCAGATGAACTCTCTGAAGCCTGAAGAC ACCGCTATGTATTACTGCAAGGCCAGCCGTGTGAGAGGTCGCGCTATCTCCGAG TACTGGGGACAAGGCACTCAAGTAACGGTGTCATCCGGTGGCTCTGGAGGCTCC GGGGGGTCTGGCCAAGTCCAGTTGCAGGAATCTGGTGGAGGGTCTGTCCAGGCA GGAGGCAGTCCGCGCCTGTCATGTACCGCGCCCGGATTTACCAGTAATAGCTGC GGAATGGATTGGTATCGCCAGGCTCCTGGCAAGGAAAGAGAGTTCGTCTCTTCC |

TABLE 1B-continued

| Name | SEQ ID NO: | Sequence |
|---|---|---|
| | | ATCAGCACTGACGGCACTACAGGCTACGCCGATTCTGTGAAAGGGCGCTTCACA<br>ATCTCCAAGGACAAAGCTAAGGATACCGTGTATCTGCAAATGAATAGTCTGAAG<br>CCTGAGGATACAGGAATGTACTCCTGTAAGACCAAGGACGGCACCATCGCTACA<br>ATGGAGCTGTGCGACTTTGGCTACTGGGGCCAGGGCACCCAAGTGACCGTCTCT<br>TCA |
| hIL27<br>Ra_VH<br>H14-<br>DR593 | 1403 | CAGGTGCAGCTCCAGGAGAGTGGTGGAGGGAGCGTGCAGGCTGGAGGCTCCCTG<br>CGTCTTAGCTGCGTTGCCAGCGGGTACGTCTCCTGCGACTACTTTCTGCCGTCC<br>TGGTATCGTCAAGCCCCTGGTAAAGAAAGAGAGTTCGTCTCCATCATTGATGGA<br>ACAGGCAGCACATCCTATGCGGCCTCCGTGAAGGGCCGCCTTACCGCAAGCCAA<br>GATAAAGGTAAGAATATCGCCTACCTCCAGATGAACAGTTTGAAGCCCGAGGAT<br>ACAGCCATGTATTACTGTAAGGCCAGTTGTGTGCGCGGGAGAGCCATCAGCGAG<br>TACTGGGGCCAGGGCACACAGGTGACTGTATCTTCCGGCGGTGGCTCCCAGGTG<br>CAGCTGCAAGAGAGCGGAGGGGGGTCCGTGCAGGCCGGAGGTAGCCTGCGCCTG<br>TCATGCGCGGCCTCCGGTTACCCTTACTCCAACGGCTACATGGGGCGGTTTAGA<br>CAGGCCCCAGGTAAGGAGGGGGAGGGGGTCGCCACAATCTACACGGGTGATGGC<br>AGGACTTACTATGCCGACTCAGTGAAAGGCAGGTTTACCATTAGTCGCGACAAC<br>GCCAAGAACACAGTTGACCTTCAGATGTCCTCACTGAAGCCTGAAGACACCGCC<br>ATGTATTACTGCGCTGCACGCGCCGCTCCGCTGTACTCCAGCGGCTCCCCATTG<br>ACTCGCGCACGCTACAATGTGTGGGGGCAAGGAACCCAGGTGACGGTGTCCTCT |
| hIL27<br>Ra_VH<br>H14-<br>DR593 | 1404 | CAGGTGCAGCTCCAAGAGTCAGGGGGGGGTTCCGTTCAAGCCGGTGGGAGCCTG<br>CGCCTGTCATGTGTGGCATCTGGATACGTGTCTTGTGACTACTTCCTGCCATCC<br>TGGTATCGGCAGGCCCCTGGGAAGGAGCGCGAATTTGTGTCTATCATTGATGGA<br>ACCGGATCTACAAGCTACGCCGCATCCGTTAAGGGGAGGCTCACAGCCTCCCAG<br>GACAAGGGAAAGAACATTGCATACCTCCAGATGAACCCCCTCAAGCCCGAGGAT<br>ACTGCTATGTATTACTGTAAGGCCAGTTGTGTGCGTGGACGCGCCATCTCCGAG<br>TACTGGGGCCAGGGAACCCAGGTGACCGTGTCCAGCGGTGGCAGCGGCGGTTCC<br>GGCGGATCTGGACAGGTGCAGCTCCAGGAGTCTGGAGGGGGGTCCGTTCAGGCT<br>GGGGGCAGCTTGCGTTTGAGTTGCGCCGCTTCCGGCTACCCTTACTCTAACGGT<br>TACATGGGCTGGTTTCGCCAAGCACCGGGCAAGGAACGGGAAGGTGTCGCTACG<br>ATTTACACCGGCGACGGACGCACATATTACGCGGATAGCGTGAAGGGGCGCTTC<br>ACAATCTCTAGGGACAACGCGAAGAACACTGTGGACCTCCAGATGTCAAGCCTG<br>AAGCCTGAGGATACCGCCATGTACTATTGCGCCGCTCGTGCTGCGCCCCTGTAT<br>TCTAGCGGCAGCCCTCTTACTCGGGCACGCTACAACGTGTGGGGTCAAGGCACA<br>CAGGTGACCGTCTCCTCC |
| hIL27<br>Ra_VH<br>H14-<br>DR594 | 1405 | CAGGTGCAGCTTCAAGAATCAGGTGGGGGATGTGTGCAGGCAGGGGGGTCACTT<br>CGCCTGTCCTGCGTGGCCTCCGGCTATGTCTCTTGTGATTACTTCCTGCCTAGC<br>TGGTATCGCCAGGCTCCAGGCAAGGAGAGAGAGTTCGTGAGCATCATTGAGGGG<br>ACGGGCTCCACTTCTTACGCCGCAAGCGTCAAGGGGCGCTTCACCGCGTCCCAG<br>GACAAGGGAAAGAACATCGCGTACTTGCAGATGAACTCCCTGAAGCCAGAAGAC<br>ACAGCTATGTATTACTGTAAGGCGTCTTGCGTCCGTGGCCGTGCAATCTCTGAG<br>TACTGGGGCCAGGGCACTCAGGTGACTGTCAGCTCTGGCGGTGGCAGTCAGGTT<br>CAGCTTCAGGAATCTGGGGGGGGCTCTGTGCAGGCAGGGGGTAGCCTGAGGTTG<br>TCCTGTGTGGCTTCCGCTTCTACCTACTGCACCTACGATATGCACTGGTATCGT<br>CAGGCCCCCGGTAAAGGGCGCGAGTTTGTGTCTGCTATTGATTCTGACGGCACC<br>ACACGTTATGCCGACTCTGTCAAAGGCAGGTTCACAATCTCTCAAGGTACTGCT<br>AAAAACACGGTATACCTTCAAATGAACTCTCTGCAACCTGAAGATACAGCGATG<br>TATTACTGTAAGACTGTGTGCGTTGTGGGTAGCAGATGGAGCGACTACTGGGGC<br>CAGGGTACACAGGTGACAGTCTCATCT |
| hIL27<br>Ra_VH<br>H14-<br>DR594 | 1406 | CAGGTCCAGCTTCAGGAGTCTGGGGGGGGTTCTGTGCAGGCTGGGGGCTCTCTC<br>CGGCTGAGCTGTGTGGCAAGCGGTTATGTGTCATGCGACTACTTTCTGCCCAGC<br>TGGTATCGCCAAGCTCCCGGCAAGGAGAGGGAGTTCGTGTCTATTATCGACGGG<br>ACAGGCTCCACCAGTTACGCGGCCTCAGTGAAGGGACGTTTCACTGCATCTCAA<br>GACAAGGGCAAGAACATCGCCCACCTCCAGATGAATAGCCTGAAGCCTGAGGAC<br>ACAGCTATGTATTACTGTAAGGCCTCCTGTGTGCGGGGGCGTGCTATCAGCGAA<br>TACTGGGGTCAGGGGACTCAAGTCACGGTCTCCTCAGGAGGGTCCGGGGGCAGC<br>GGAGGGTCAGGCCAGGTGCAGTTGCAGGAATCTGGAGGCGGTAGTGTTCAGGCC<br>GGTGGCTCTCTGCGCCCGTCCTGCGTCGCGAGTGCATCTACGTACTGTACCTAC<br>GATATGCACTGGTATCGGCAAGCCCCTGGGAAGGGCCGTGAGTTTGTCAGCGCC<br>ATTGATTCTGACGGCACTACCCGCTACGCAGATAGCGTTAAAGGCCGCTTTACT<br>ATCAGTCAGGGCACCGCCAAGAACACCGTCTACCTCCAGATGAACTCTCTCCAG<br>CCCGAGGATACCGCCATGTACTATTGCAAAACAGTGTGCGTCGTGGGCTCCCGG<br>TGGTCCGACTACTGGGGCCAAGGCACTCAAGTGACTGTTTCTTCC |
| hIL27<br>Ra_VH<br>H14-<br>DR595 | 1407 | CAGGTCCAGCTCCAGGAGTCTGGGGGGGGCTCCGTGCAAGCTGGTGGCAGCCTC<br>CGTCTGAGCTGCGTAGCCTCTGGTTACGTGTCATGCGACTACTTCCTGCCGTCC<br>TGGTATCGGCAGGCCCCCGGCAAAGAACGTGAGTTCGTAAGCATCATTGATGGT<br>ACTGGGAGTACGTCCTATGCAGCCAGCGTGAAGGGCCGCTTTACCGCAAGCCAG<br>GACAAGGGTAAAAATATTGCTTATCTTCAGATGAACAGCCTGAAACCTGAAGAT<br>ACCGCAATGTATTACTGTAAGGCCAGCCGCGTAAGGGGCCGTGCCATTTCAGAA<br>TACTGGGGACAGGGTACACAGGTGACTGTGTCATCTGGGGGGGGTAGCCAGGTG<br>CAGCTCCAGGAGTCCGGGGGGGGAGCGTGCAGGCAGGGCGGCTCCCTGACCCTG<br>TCCTGTGCGGCCAGCGAGTACGCCTATAGCACCTGTAATATGGGCGGGTATCGT<br>CAGGCCCCTGGGAAAGAGCGCGAGCTGGTGTCTGCCTTCATCAGTGACGGCTCC |

TABLE 1B-continued

| Name | SEQ ID NO: | Sequence |
| --- | --- | --- |
| | | ACTTATTACGCCGACTCCGTCAAGGGCCGGTTCACCATTACCCGTGATAACGCC AAGAATACCGTTTACCTCCAGATGAATAGCCTCAAACCCGAGGACACCGCGATT TACTATTGCTCCGCTAACTGTTACCGCAGGCTGCGTAACTACTGGGGACAGGGC ACTCAGGTGACTGTCTCTTCC |
| hIL27 Ra_VH H14- DR595 | 1408 | CAGGTCCAGCTCCAGGAGAGCGGGGGGGGTTCCGTCCAGGCCGGTGGCAGCCTG CGTCTCTCTTGTGTGGCGAGCGGGTACGTCAGCTGCGATTACTTCCTGCCCTCC TGGTATCGCCAGGCCCCTGGTAAGGAGAGGGAGTTCGTGTCTATCATTGATGGG ACTGGATCAACTAGCTACGCTGCGTCTGTTAAAGGGCGGTTTACTGCAAGCCAG GACAAGGGCAAGAACATTGCCTACCTTCAGATGAACAGCCTGAAGCCGGAGGAC ACCGCCATGTATTACTGTAAGGCCTCTTGTGTACGCGGTCGCGCCATCTCCGAA TACTGGGGTCAGGGTACACAGGTGACAGTCAGCTCAGGAGGTTCCGGTGGCTCC GGGGGTTCCGGCCAGGTCCAGTTGCAGGAATCCGGTGGCGGAAGCGTGCAGGCT GGTGGCTCCCTGACACTGTCTTGCGCAGCCAGCGAATATGCTTATAGTACTTGC AACATGGGCTGGTATCGCCAGGCCCCCGGCAAAGAACGCGAACTCGTGAGTGCC TTCATCTCCGACGGTAGCACTTATTACGCCGATTCTGTGAAGGGAAGGTTCACT ATTACGCGCGACAACGCCAAGAACACCGTCTACTTGCAGATGAACTCCCTGAAG CCCGAAGACACTGCCATCTACTATTGCTCCGCCAACTGCTACCGTCGCCTGCGG AACTATTGGGGACAGGGCACCCAGGTCACTGTCAGCTCC |
| hIL27 Ra_VH H14- DR596 | 1409 | CAAGTGCAGCTGCAAGAGAGTGGAGGTGGCTCCGTACAGGCAGGCGGGAGCCTC CGCCTCAGCTGCGTAGCCAGCGGCTATGTCAGTTGCGACTACTTCCTCCCCTCA TGGTACAGGCAGGCCCCAGGCAAGGAACGCGAGCTTGTGAGCATTATCGACGGC ACAGGGAGCACGAGTTACGCTGCCAGCGTCAAAGGCAGATTCACAGCCTCTCAA GACAAAGGGAAAAACATCGCCTACTTGCAGATGAACTCTCTGAAGCCCGAGGAT ACCGCCATGTATTACTGCAAGGCCTCTTGTGTGCGGGGCCGCGCTATCTCCGAA TACTGGGGACAGGGGACCCAGGTGACTGTGTCCAGTGGAGGTGGCTCCCAAGTT CAGCTCCAGGAGTCCGGGGGGGGCTTGTGCAGCCGGGCGGGTTCCCTGCGCCTG TCCTGCACTGCATCTGGTCTGACTTTCGACGATTCCGTAATGGGCTGGTTCCGC CAAGCACCTGGCAAAGGTCGCGAGGCTGTATCCTGTATCTCTAGCTCAGGTGCC AACGCATTCTACGCTGACTCCGTCAAAGGCCGTTTTACCATTAGTCGCGATAAC GCTAAAAACACACTGTACCTGCAAATGAACTCCCTCAAACCGGAAGATACTGCC ACCTACTATTGCAAGCGGGGGCACGCGTGTGCGGGCTATTACCCTATCCCATAC GATGACTACTGGGGCCAGGGCACCCAGGTCACTGTTAGCTCC |
| hIL27 Ra_VH H14- DR596 | 1410 | CAGGTCCAACTCCAGGAGTCCGGGGGGGGCAGTGTGCAGGCTGGCGGGTCTCTG CGTCTGTCCTGCGTCGCGAGCGGCTACGTCAGCTGCGACTATTTTCTGCCTAGC TGGTATCGCCAGGCCCCAGGTAAGGAAAGAGAGCTCGTGAGCATTATCGACGGG ACAGGTTCCACCTCCTACGCCGCGTCTGTGAAGGGCCGGTTTACTGCATCCCAG GATAAAGGTAAGAACATTGCATATCTGCAAATGAACTCTCTGAAGCCCGAGGAC ACTGCTATGTATTACTGTAAAGCAAGTTGTGTGCGCGGCAGAGCAATTTCCGAA TACTGGGGCCAGGGCACCCAGGTGACTGTGTCCAGCGGGGGCAGTGGTGGCAGT GGAGGTAGCGGCCAAGTCCAGTTGCAGGAGAGTGGCGGTGGCCTGGTGCAGCCA GGTGGCTCCCCCCGTCTGAGCTGCACAGCCAGCGGGCTGACGTTCGATGACTCT GTGATGGGTTGGTTTCGCCAGGCTCCCGGCAAGGGCCGCGAAGCTGTTTCCTGT ATCTCTTCCTCTGGCGCGAATGCTTTTTACGCCGACTCCGTGAAGGGGAGGTTC ACTATTTCCAGAGACAATGCCAAGAACACTCTGTACCTTCAGATGAACTCCCTC AAGCCTGAAGACACCGCCACCTACTATTGTAAGCGCGGCCATGCCTGTGCCGGG TACTATCCTATTCCTTATGATGACTACTGGGGCCAGGGCACTCAGGTGACCGTG TCCTCC |
| hIL27 Ra_VH H15- DR591 | 1411 | CAGGTGCAGCTCCAGGAGAGCGGGCGGGGGTCCGTGCAGGCCGGTGGCTCCCTC CGCCTCAGCTGCGTGGCCTCAGGTTACGTCAGCCGCGATTACTTTCTGCCAAGC TGGTATCGCCAAGCGCCGGGGAAGGAGCGCGAGTTTGTGTCTATTATCGACGGA ACTGGCTCCACTAGCTATGCTGCCAGCGTGAAGGGACGCCTCACAGCTTCCCAG GATAAGGGAAAAAACATCGCCTACCTCCAGATGAACACCCTGAAACCCGAGGAC ACCGCCATGTATTACTGCAAGGCAAGCTGCGTGCGCGGCAGAGCTATCTCCGAG TACTGGGGCCAGGGAACCCAGGTTACCGTCAGCTCAGGCGGAGGGTCACAGGTT CAGTTGCAAGAAAGCGGCGGTGGGAGCGTGCAGGCTGGTGGAAGCCTGCGTCTG TCCTGCACAGCATCCGGCGCAATCGCTAGTGGATACATTGATAGCCGCTGGTGC ATGGCCTGGTTCCGCCAAGCTCCAGGTAAAGAGCGCGAGGGGGTGGCGGCCATC TGGCCCGGCGGAGGCCTGACTGTTTACGCCGACTCAGTGAAGGGGCGCTTTACC ATCTCACGGGACCATGCTAAGAACACCCTGTACTTGCAGATGAACAATCTGAAA CCTGAGGACACCGCGATGTATTACTGCGCAGCGGGCTCACCTCGTATGTGCCCT AGCTTGGAGTTTGGCTTCGACTACTGGGGCCAAGGCACCCAGGTGACTGTGAGC AGC |
| hIL27 Ra_VH H15- DR591 | 1412 | CAAGTGCAGTTGCAGGAGAGTGGTGGGGGCTCTGTGCAGGCCGGGGGTTCCCTG AGGCTCTCTTGCGTGGCCAGCGGATACGTGTCCTGTGACTACTTCCTGCCCTCT TGGTATCGCCAAGCGCCAGGGAAGGAACGCGAGTTCGTGAGCATTATCGACGGC ACTGGTTCCACCTCTTACGCAGCGTCTGTAAAGGGCCGTTTCACCGCCAGCCAG GACAAGGGGAAGAACATCGCTTACCTTCAGATGAATACGTTGAAGCCTGAGGAC ACTGCGATGTATTACTGTAAAGCGTCTTGCGTTCGTGGCCGTGCCATCTCCGAA TACTGGGGCCAAGGCACTCAGGTAACTGTGTCCAGGGGGGGTTCCGGTGGCTCT GGAGGTAGCGGTCAGGTGCAGCTCCAGGAATCTGGCGGTGGGAGTGTGCAGGCT GGCGGTAGTCTCCGGCTGTCCTGTACCGCCAGTGGAGCTATTGCCAGCGGATAC ATTGATTCCCGGTGGTGTATGGCATGGTTCCGGCAGGCCCCCGGCAAGGAACGC |

TABLE 1B-continued

| Name | SEQ ID NO: | Sequence |
|---|---|---|
| | | GAGGGGGTCGCCGCTATTTGGCCCGGAGGGGGGCTGACCGTGTACGCGGACAGT GTCAAGGGCCGCTCACGATCAGTAGGGATCACGCCAAGAACACCCTTCTACTTG CAGATGAATAACCTCAAACCAGAGGACACTGCAATGTATTACTGCGGCGCTGGC AGCCCGAGGATGTGCCCGTCCCTGGAGTTCGGCTTCGACTATTGGGGTCAGGGC ACTCAGGTCACCGTGTCCTCC |
| hIL27 Ra_VH H15- DR592 | 1413 | CAGGTCCAGCTCCAGGAGAGCGGCGGAGGCTCTGTTCAGGCTGGGGGCAGCCTC CGCCTGTCTTGCGTGGCCTCCGGCTACGTAAGCTGCGACTACTTCTTGCCCTCC TGGTATCGCCAGGCTCCGGGCAAAGAAAGGGAATTTGTATCCATTATCGACGGC ACGGGTAGCACTTCCTACGCCGCTAGTGTAAAGGGTCGGTTCACCGCCTCTCAG GACAAGGGCAAAAACATCGCGTACCTCCAGATGAACACACTGAAGCCAGAGGAT ACCGCCATGTATTACTGCAAGGCTTCCTGCGTGCGGGGGGGGGCCATTAGCGAG TACTGGGGACAAGGAACCCAAGTGACTGTGTCCAGCGGTGGAGGCTCTCAGGTC CAGCTGCAAGAGTCTGGAGGCGGTTCAGTGCAGGCCGGTGGAAGCCTTAGGCTG AGCTGCACCGCCCCTGGATTTACCTCTAACTCTTGCGGCATGGACTGGTATCGT CAGGCCCCCGGCAAGGAACGCGAGTTCGTGTCTAGCATCTCCACCGATGGCACC ACAGGCTATGCTGACAGTGTGAAAGGCCGTTTTACCATCTCCAAGGACAAAGCC AAGGACACGGTGTACCTCCAGATGAACTCCTTGAAGCCTGAAGACACGGGTATG TATTCTTGCAAGACTAAGGACGGCACCATCGCTACTATGGAGCTGTGCGACTTT GGTTATTGGGGACAGGGGACCCAGGTGACTGTATCTTCT |
| hIL27 Ra_VH H15- DR592 | 1414 | CAGGTGCAGCTGCAAGAGTCTGGAGGTGGGTCAGTCCAGGCTGGGGGCAGCCTC AGGCTGTCCTGCGTCGCTTCTGGATACGTGTCCTGCGACTACTTCCTCCCCTCC TGGTATCGCCAGGCCCCAGGTAAAGAACGCGAGTTCGTGTCCATCATTGATGGC ACCGGGTCTACTTCCTATGCTGCGTCCGTGAAGGGCCGTTTTACCGCTTCACAG GATAAAGGAAAGAACATTGCTTACCTCCAGATGAACACACTCAAGCCGGAAGAC ACCGCCATGTATTACTGTAAAGCGAGCTGTGTCCGTGGCAGAGCCATCAGTGAG TATTGGGGCCAGGGAACTCAGGTGACCGTGTCCTCTGGAGGCAGCGGCGGTAGT GGTGGCTCCGGGCAAGTTCAACTTCAGGAGAGTGGGGGTGGGTCCGTGCAGGCT GGGGGTTCTCTCCGCCTCAGCTGTACCGCGCCCGGCTTCACCTCTAACAGCTGC GGTATGGACTGGTATCGCCAAGCGCCGGGTAAAGAGCGTGAGTTCGTTAGCTCC ATCTCCACCGACGGCACCACAGGATATGCCGATAGCGTTAAGGGACGCTTTACT ATTAGTAAGGACAAGGCTAAGGATACCGTCTACCTCCAGATGAACTCTCTGAAA CCTGAAGACACAGGCATGTACTCCTGTAAAACCAAGGACGGCACCATTGCTACA ATGGAGCTTTGTGATTTCGGCTATTGGGGCCAGGGTACACAGGTTACCGTGTCC TCC |
| hIL27 Ra_VH H15- DR593 | 1415 | CAAGTGCAGTTGCAGGAGTCCGGCGGAGGTTCAGTTCAGGCTGGGGGGTCCCTG AGACTGAGTTGTGTGGCCTCCGGCTATGTGAGCTGCGACTACTTTCTGCCTTCT TGGTACAGACAAGCACCAGGCAAAGAGCGGGAGTTCGTGAGTATCATTGATGGG ACCGGCTCCACCAGCTATGCTGCCAGCGTGAAGGGTCGCTTTACCGCTTCTCAG GACAAAGGCAAAAACATCGCTTACCTCCAGATGAATACATTGAAGCCTGAAGAC ACCGCCATGTATTACTGTAAGGCATCATGTGTGCGTGGCCGCGCCATTTCTGAG TACTGGGGCCAGGGAACTCAGGTGACAGTGTCTAGTGGCGGAGGCTCCCAGGTC CAGTTGCAGGAGAGCGGCGGTGGATCTGTCCAGGGGCGGGGCAGCCTCCGTCTG TCCTGTGCGGCCAGCGGGTATCCTTATTCCAACGGGTACATGGGGCGGTTCCGC CAGGCCCCCGGTAAGGAACGCGAGGGCGTGGCCACTATTTACACAGGTGACGGG CGTACCTATTACGCAGACTCTGTAAAGGGTCGCTTCACAATTTCCCGCGACAAC GCCAAGAACACCGTCGATCTCCAGATGTCTAGTCTCAAACCTGAGGACACCGCC ATGTATTACTGTGCCGCTCGCGCCGCGCCACTTTACAGCTCTGGTTCTCCCCTC ACACGCGCTCGCTACAATGTTTGGGGCCAAGGCACACAGGTGACCGTGAGCAGT |
| hIL27 Ra_VH H15- DR593 | 1416 | CAGGTGCAGTTGCAGGAATCTGGTGGAGGCTCCGTGCAGGCTGGGGGCTCCCTG AGGCTTTCATGTGTGGCAAGCGGCTACGTGAGTTGTGATTACTTTCTGCCTTCC TGGTATCGCCAGGCCCCTGGCAAGGAGCGGGAACTTGTCTCAATCATTGATGGT ACTGGTTCCACTTCTTATGCGGCCAGTGTGAAAGGGCGTTTTACTGCCAGCCAG GATAAGGGCAAGAATATTGCTTACTTGCAGATGAACACCCTGAAGCCCGAAGAT ACCGCTATGTACTATTGCAAGGCCAGTTGTGTAAGGGGTCGGGCGATTAGTGAG TATTGGGGCCAGGGCACGCAGGTCACCGTGTCATCCGGGGGCAGCGGCGGGTCC GGGGGTTCTGGCCAGGTGCAGCTCCAGGAGAGCGGTGGAGGCAGCGTGCAGGCC GGTGGAAGCCTTCGTCTGTCCTGCGCCGCTTCAGGCTATCCTTACTCTAATGGC TACATGGGTTGGTTTCGCCAAGCCCCAGGGAAAGAGCGCGAGGGCGTTGCCACA ATTTACACAGGTGATGGAAGGACCTACTATGCGGACAGCGTCAAGGGCCGCTTT ACAATCAGCCGTGATAATGCTAAGAACACCGTCGATCTCCAGATGTCCAGCCTG AAGCCTGAGGATACTGCTATGTACTATTGCGCTGCCCGCGCAGCCCCACTCTAC AGCTCCGGCAGTCCCCTGACGAGGGCTCGCTATAACGTGTGGGGTCAGGGCACA CAGGTCACCGTGTCCAGC |
| hIL27 Ra_VH H15- DR594 | 1417 | CAGGTGCAACCCCAGGAATCCGGGGGAGGCAGCGTGCAAGCCGGTGGCTCCCTG CGCCTGTCCTGCGTCGCCAGCGGCTACGTCAGCTGCGACTACTTTCTGCCCTCC TGGTATCGCCAGGCTCCTGGGAAAGAGCGCGAGTTTGTTTCCATCATTGATGGA ACCGGCAGCACATCCTATGCCGCGAGCGTTAAGGGCAGATTTACCGCCTCTCAA GACAAGGGTAAGAACATCGCCTACCTCCAAATGAACACCCTGAAGCCTGAGGAC ACGGCAATGTATTACTGTAAAGCAAGCTGTGTGGGGGGTCGGGCCATCAGCGAG TACTGGGGTCAGGGCACCCAGGTCACTGTAAGCTCCGGGGGAGGGTCCCAGGTG CAGCTCCAGGAGTCAGGCGGAGGCTCCGTGCAGGCCGGAGGCTCCTTGCGTTTG AGCTGCGTGGCGTCTGCGTCTACCTACTGCACTTACGACATGCACTGGTATCGC |

TABLE 1B-continued

| Name | SEQ ID NO: | Sequence |
|---|---|---|
| | | CAGGCTCCGGGGAAGGGCCGCGAGTTCGTGAGCGCTATCGACTCCGATGGCACA ACTCGCTACGCCGACAGCGTGAAGGGGCGTTTTACCATTTCCCAGGGCACCGCC AAGAACACCGTGTATCTCCAGATGAACTCTCTGCAACCGGAGGATACAGCTATG TATTACTGCAAGACAGTCTGTGTGGTTGGTAGCCGCTGGTCTGACTACTGGGGC CAGGGCACCCAGGTCACGGTGTCCTCT |
| hIL27 Ra_VH H15- DR594 | 1418 | CAGGTGCAGCTTCAAGAGTCTGGGGGCGGGTCCGTCCAGGCGGGTGGCAGTTTG AGACTCAGTTGTGTGGCCAGTGGCTACGTCAGCTGTGACTATTTTCTGCCTAGC TGGTATCGCCAGGCACCCGGTAAAGAGAGGGAGTTCGTGAGCATCATTGATGGG ACAGGGTCTACATCTTATGCTGCCTCCGTGAAAGGGCGGTTCACAGCCTCCCAG GATAAGGGCAAGAACATTGCGTATCTCCAGATGAACACCCTCAAGCCGGAGGAT ACCGCGATGTATTACTGTAAGGCGTCTTGTGTGCGGGGGCGTGCTATTAGCGAG TATTGGGGACAGGGGACGCAAGTGACGGTCTCCTCAGGGGGGTCTGGTGGCTCT GGCGGGTCCGGGCAGGTCCAGCTCCAGGAGTCTGGCGGTGGCTCCGTCCAAGCC GGAGGCAGCCTCCGTCTCTCCTGTGTTGCATCAGCCTCCACGTACTGCACCTAT GATATGCACTGGTATCGGCAAGCGCCCGGCAAGGGCCGCGAGTTTGTGTCTGCC ATCGACAGTGATGGTACAACGCGGTACGCTGATAGCGTGAAAGGCCGCTTCACC ATCAGTCAGGGCACGGCCAAAAACACAGTGTATCTCCAGATGAACTCACTCCAG CCTGAAGATACAGCCATGTACTATTGTAAGACGGTCTGCGTCGTGGGCAGCCGG TGGTCCGACTACTGGGGCCAGGGAACCCAAGTGACTGTCTCAAGT |
| hIL27 Ra_VH H15- DR595 | 1419 | CAGGTGCAGTTGCAGGAGAGCGGCGGAGGCTCTGTGCAGGCAGGAGGCTCACTG AGACTGTCCTGCGTGGCAAGCGGCTATGTGAGCTGCGACTACTTTCTGCCAAGT TGGTATCGTCAGGCTCCTGGCAAAGAAAGGGAGTTTGTGAGCATCATTGATGGA ACCGGAAGCACAAGTTATGCGGCCTCCGTGAAGGGTCGCTTCACCGCCTCACAG GATAAGGGCAAGAACATTGCTTACCTCCAGATGAACACACTCAAGCCTGAAGAC ACCGCGATGTACTATTGTAAAGCAAGTTGTGTGAGAGGCCGCGCCATTAGCGAG TATTGGGGCCAGGGCACTCAGGTGACCGTCAGCTCTGGGGGGGGAAGCCAGGTA CAACCCCAGGAGAGTGGTGGAGGCTCAGTGCAGGCCGGGGGAAGCCTGACCCTG TCCTGTGCCGCTTCCGAGTACGCATACAGCACTTGCAACATGGGCTGGTATCGC CAAGCCCCTGGCAAAGAACGGGAACTCGTGTCCGCCTTCATCTCCGATGGTTCT ACCTATTACGCTGATAGCGTGAAAGGACGCTTCACCATTACCCGTGATAACGCT AAGAACACAGTTTACTTGCAGATGAACTCTCTGAAGCCCGAAGACACCGCCATT TATTACTGTAGCGCCAACTGTTATCGCAGGCTTCGGAATTACTGGGGACAGGGG ACCCAGGTGACAGTGAGTAGC |
| hIL27 Ra_VH H15- DR595 | 1420 | CAGGTGCAGTTGCAGGAGTCTGGGGGCGGTAGCGTCCAGGCTGGCGGATCACTG CGCCTGAGTTGTGTCGCGTCCGGCTACGTCAGCTGCGACTATTTCTTGCCCTCC TGGTATCGCCAGGCCCCTGGCAAGGAACGTGAGTTCGTAAGCATCATTGACGGC ACTGGTAGCACTTCCTACGCCGCTAGTGTGAAGGGGCGGTTCACCGCAAGCCAG GACAAGGGGAAGAACATCGCCTACCTCCAGATGAACACACTGAAGCCCGAGGAC ACGGCCATGTACTATTGCAAAGCCTCTTGCGTGCGGGGGCGTGCGATCTCTGAA TATTGGGGCCAGGGAACTCAGGTGACCGTGTCTAGTGGTGGCAGTGGTGGGTCC GGCGGGAGCGGTCAGGTTCAGTTGCAGGAGAGCGGCGGTGGCTCCGTTCAGGCC GGGGGCTCTCTGACGCTGTCTTGCGCGGCCAGCGAATACGCTTACTCAACTTGT AATATGGGTTGGTATCGTCAGGCACCCGGCAAGGAGCGGGAGCTGGTCTCCGCT TTCATCAGCGACGGCTCCACCTATTACGCAGACAGCGTTAAGGGTCGCTTTACT ATCACGCGCGACAACGCCAAGAACACCGTGTACCTCCAGATGAACTCTCTGAAA CCCGAGGATACCGCCATTTACTATTGCTCTGCTAACTGCTACCGCAGGTTGAGA AATTACTGGGGCCAAGGAACTCAGGTGACGGTCTCAAGC |
| hIL27 Ra_VH H15- DR596 | 1421 | CAGGTGCAGCTCCAGGAATCTGGCGGTGGCTCCGTACAGGCTGGCGGTTCCCTG AGGCTCTCTTGTGTCGCCAGCGGCTACGTCAGCTGTGACTATTTCCTCCCTTCT TGGTATCGTCAGGCCCCAGGGAAGGAGCGCGAGTTCGTGTCCATTATCGACGGG ACCGGAAGCACCTCCTATGCTGCATCAGTGAAAGGCCGGTTTACCGCGTCTCAG GACAAAGGAAAGAACATTGCATATCTGCAAATGAACACACTCAAGCCAGAGGAC ACCGCTATGTACTATTGTAAGGCCTCCTGTGTGAGAGGTCGCGCAATTTCTGAA TATTGGGGCCAGGGAACCCAGGTGACCGTGTCCTCTGGGGGGGGTTCTCAGGTC CAACTTCAGGAAAGCGGTGGGGGGCTCGTGCAACCCGGTGGCAGCCTTCGGCTG TCTTGTACTGCCTCCGGTTTGACATTCGATGACTCTGTGATGGGATGGTTTAGG CAGGCTCCTGGCAAAGGCCGCGAGGCAGTATCTTGTATCAGTTCTTCCGGCGCT AACGCATTTTATGCCGACAGTGTGAAGGGCCGTTTCACAATCTCCCGCGATAAC GCCAAGAACACCCTCTACCTCCAGATGAACTCCCTGAAGCCTGAGGACACCGCC ACTTATTACTGCAAGCGGGGTCATGCCTGTGCTGGCTATTACCCTATTCCATAC GATGACTACTGGGGACAGGGCACCCAAGTTACCGTGTCTAGC |
| hIL27 Ra_VH H15- DR596 | 1422 | CAGGTGCAGCTTCAGGAGTCAGGAGGTGGCTCAGTGCAGGCTGGTGGCAGTCTG CGCCTGTCCTGTGTCGCCAGTGGATATGTCAGTTGTGACTATTTTCTCCCCAGT TGGTATCGCCAAGCGCCCGGTAAAGAGCGGGAGTTTGTCTCAATCATTGACGGC ACCGGCAGCACCTCCTACGCCGCTTCCGTGAAGGGTCGCTTCACCGCGTCCCAG GACAAAGGCAAGAACATCGCGTATCTTCAGATGAACACCCTCAAGCCCGAAGAT ACAGCTATGTATTACTGCAAGGCCTCCTGCGTGCGGGGACGCGCGATCTCTGAA TACTGGGGCCAGGGCACACAGGTCACCGTCTCTTCAGGGGGTTCCGGTGGCTCC GGTGGCTCCGGCCAGGTGCAGTTGCAGGAAAGCGGTGGGGGGCTGGTGCAGCCG GGGGGGAGTCTCCGCCTGTCCTGCACAGCGTCAGGGCTGACTTTTGATGACTCT GTTATGGGCTGGTTTAGGCAGGCTCCGGGTAAGGGCAGAGAGGCCGTTAGCTGC ATCTCTTCCAGGGGGGCTAACGCCTTCTATGCCGACAGCGTGAAGGGTCGCTTC |

TABLE 1B-continued

| Name | SEQ ID NO: | Sequence |
|---|---|---|
| | | ACAATTAGCCGGGACAACGCTAAGAACACTCTGTACCTTCAGATGAACTCCCTG<br>AAGCCCGAAGATACTGCTACTTACTATTGCAAGAGAGGTCATGCTTGCGCCGGA<br>TACTATCCAATCCCTTACGATGACTACTGGGGCCAAGGCACCCAAGTTACCGTG<br>TCTTCT |
| hIL27 Ra_VH H16- DR591 | 1423 | CAGGTGCAGTTGCAGGAAAGTGGCGGTGGATCTGTGCAGGCAGGCGGAAGTCTG<br>AGACTGAGCTGCCGGGCCAGCGGTTCAACTTATAGCAATTACTGTCTGGGTTGG<br>TTCAGGCAGATTACTGGTAAGGAACGCGAAGGCGTTGCTGTTATCAACTGGGTT<br>GGGGGAATGCTGTACTTTGCTGACTCCGTTAAGGGCAGATTCACTGTCAGCCAG<br>GACCAGGCCAAGAATACCGTGTACTTGCAGATGAACAGCCTGAAGCCCGAGGAT<br>ACAGCCATGTATTACTGTGCTGCCGAGTCAGCCTCCTCTTTCTCATGTGGGGGA<br>TGGCTTACAAGGCCCGACCGCGCTCCATATTGGGGCCAGGGCACCCAGGTGACT<br>GTAAGCTCCGGTGGAGGCAGTCAGGTCCAGCTCCAGGAGAGCGGCGGAGGCTCT<br>GTTCAGGCTGGAGGTAGCCTGCGCCTTAGCTGCACAGCCTCAGGTGCCATCGCC<br>AGCGGTTATATTGATTCACGCTGGTGTATGGCCTGGTTTCGCCAGGCCCCTGGG<br>AAGGAGAGGGAAGGTGTGGCTGCCATTCGGCCCGGAGGCGGTCTGACAGTCTAC<br>GCAGACTCCGTGAAGGGCCGCTTTACCATCAGCCGGGACCACGCGAAGAACACT<br>CTGTATTTGCAAATGAATAACCTCAAACCCGAGGACACCGCAATGTACTATTGT<br>GCCGCTGGCTCTCCTCGTATGTGTCCATCTCTGGAGTTCGGCTTTGACTACTGG<br>GGCCAGGGGACCCAGGTGACTGTGAGTAGC |
| hIL27 Ra_VH H16- DR591 | 1424 | CAAGTGCAGTTGCAGGAGTCTGGTGGCGGTTCCGTGCAGGCTGGTGGAAGCCTG<br>AGGCTGTCTTGTCGTGCATCTGGAAGCACCTATTCCAACTATTGTCTTGGGTGG<br>TTCAGACAGATCACTGGCAAAGAGAGAGAAGGGGTTGCGGTTATCAACTGGGTG<br>GGCGGTATGCTGTACTTCGCTGATTCCGTGAAGGGCCGCTTCACGGTATCCCAG<br>GACCAAGCAAAGAATACCGTCTATTTGCAGATGAACAGCCTGAAACCGGAGGAT<br>ACCGCCATGTACTATTGTGCAGCCGAGAGCGCCAGCTCCTTCTCTTGTGGCGGT<br>TGGCTGACTCGTCCAGATCGCGTGCCCTACTGGGGCCAAGGGACCCAGGTGACA<br>GTCAGCTCCGGGGGTAGCGGTGGCTCTGGGGGCTCCGGGCAGGTGCAGCTCCAG<br>GAAAGTGGGGGGGGTTCAGTGCAGGCAGGTGGCAGTCTGCGTCTGTCCTGCACC<br>GCAAGCGGCGCAATCGCTTCCGGTTATATTGATTCTCGCTGGTGCATGGCTTGG<br>TTTCGCCAGGCCCCCGGCAAGGAACGCGAGGGGGTGGCAGCCATCTGGCCGGGA<br>GGGGGACTGACCGTTTACGCTGACAGCGTGAAGGGCCGCTTCACGATCAGTAGG<br>GATCACGCGAAGAACACCCTTTACCTCCAGATGAATAACCTGAAGCCAGAGGAC<br>ACAGCGATGTATTACTGCGCCGCTGGTTCTCCCCGGATGTGTCCATCCCTGGAG<br>TTCGGGTTCGATTACTGGGGCCAGGGGACGCAAGTGACAGTTAGCTCC |
| hIL27 Ra_VH H16- DR592 | 1425 | CAGGTACAGCTGCAAGAAAGCGGGGGAGGGTCCGTGCAGGCTGGCGGTTCTCTT<br>CGTCTGTCTTGCCGCGCCTCCGGTAGTACCTACTCCAACTACTGCTTGGGCTGG<br>TTCCGCCAGATCACAGGCAAGGAGCGTGAGGGGGTGGCCGTAATAAATTGGGTG<br>GGCGGTATGCTGTATTTCGCAGATTCCGTGAAAGGCCGCCTTACCGTCTCCCAG<br>GACCAGGCCAAAAACACCGTGTACCTCCAGATGAACTCTCTGAAGCCGGAGGAC<br>ACAGCGATGTACTATTGTGCTGCCGAAAGCGCTTCTAGTTTTAGCTGTGGCGGT<br>TGGCTGACCCGTCCTGATCGCGTTCCATACTGGGGACAGGGTACTCAGGTCACC<br>GTGTCTTCCGGCGGTGGCTCCCAGGTTCAGCTCCAGGAATCTGGCGGTGGGAGT<br>GTCCAGGCTGGAGGTAGTCTGCGCCTGTCATGTACCGCCCCCGGTTTTACCTCA<br>AACTCTTGCGGTATGGACTGGTATCGCCAGGCTCCCGGTAAGGAGAGGGAGTTC<br>GTCAGCTCTATCAGTACTGACGGCACTACAGGATACGCCGACTCTGTGAAGGGC<br>CGTTTCACCATCTCTAAGGACAAGGCTAAAGACACCGTCTACCTCCAGATGAAC<br>AGTCTCAAGCCCGAGGACACGGGTATGTATTCCTGCAAAACAAAGGATGGGACT<br>ATTGCCACAATGGAGCTTTGTGACTTTGGCTACTGGGGACAGGGAACACAGGTG<br>ACTGTCTCAAGC |
| hIL27 Ra_VH H16- DR592 | 1426 | CAGGTGCAGTTGCAGGAGTCAGGAGGTGGGTCCGTGCAGGCCGGTGGCAGCCTG<br>CGGCCCTCTTGTCGGGCCAGTGGCAGCACTTATAGTAACTACTGTCTGGGGTGG<br>TTCCGCCAGATCACTGGTAAAGAGCGGGAGGGGGTGGCTGTCATTAACTGGGTC<br>GGCGGTATGCTGTACTTCGCCGATTCCGTGAAGGGCCGTTTCACAGTGTCCCAA<br>GACCAGGCCAAGAACACAGTTTACCTTCAGATGAACAGCCTGAAGCCAGAGGAC<br>ACCGCCATGTACTATTGCGCCGCAGAATCTGCTTCTAGCTTCAGCTGCGGCGGT<br>TGGCTGACACGCCCGGACCGCGTGCCGTACTGGGGGCAGGGCACACAGGTAACC<br>GTGTCCTCTGGCGGGAGTGGGGGGTCCGGGGGTAGCGGCCAAGTCCAGCTCCAG<br>GAGTCAGGCGGAGGCTCCGTCCAGGCTGGTGGCAGCTTGAGGTTGTCCTGCACT<br>GCTCCTGGTTTTACATCTAACTCCTGCGGCATGGATTGGTATCGCCAGGCTCCC<br>GGAAAGGAGCGCGAGTTCGTGTCCTCTATTAGTACCGATGGCACTACCGGGTAT<br>GCCGACTCTGTTAAGGGTCGTTTCACAATCAGTAAAGATAAGGCCAAGGACACA<br>GTGTACTTGCAGATGAACTCACTGAAACCAGAGGATACAGGCATGTATAGCTGT<br>AAGACCAAAGACGGGACCATCGCAACTATGGAGCTGCGCGATTTCGGCTACTGG<br>GGCCAGGGCACCCAGGTAACCGTCAGCTCA |
| hIL27 Ra_VH H16- DR593 | 1427 | CAGGTACAGTTGCAGGAGTCCGGCGGGGGAAGCGTGCAGGCTGGAGGTAGCCTG<br>CGTCTGAGCTGTCGCGCCAGCGGCTCCACCTACCCAAACTACTGTCTTGGATGG<br>TTCCGTCAGATTACTGGCAAGGAGAGGGAAGGGGTCGCCGTTATCAACTGGGTG<br>GGCGGTATGCTGTATTTCGCCGACTCTGTTAAAGGCCGTTTCACAGTGAGCCAG<br>GATCAGGCCAAGAACACCGTCTACCTTCAGATGAACTCTTTGAAGCCTGAAGAT<br>ACGGCCATGTATTACTGTGCAGCCGAGTCTGCCTCCAGCTTCTCCTGCGGGGGC<br>TGGCTCACACGCCCCGACCGTGTGCCTTATTGGGGACAGGGGACACAAGTCACT<br>GTCTCCTCTGGAGGGGGATCTCAAGTGCAGCTGCAAGAGTCTGGAGGCGGTAGC |

TABLE 1B-continued

| Name | SEQ ID NO: | Sequence |
|---|---|---|
| | | GTGCAGGCTGGCGGGTCCCTCAGACTGAGCTGTGCTGCCTCCGGTTACCCCTAC<br>TCCAACGGATATATGGGCTGGTTCCGCCAGGCACCAGGCAAGGAGCGCGAGGGC<br>GTGGCTACTATCTATACAGGTGATGGCCGCACCTATTACGCTGATTCCGTGAAG<br>GGTCGCTTCACCATCAGCCGCGACAATGCTAAGAACACCGTGGACCTTCAGATG<br>TCTAGCCTCAAGCCTGAGGACACTGCAATGTATTACTGTGCTGCACGGGCAGCG<br>CCCCTTTATTCCTCTGGCTCCCCTCTCACCCGCGCACGTTACAACGTATGGGGT<br>CAAGGCACCCAGGTGACTGTCTCCAGC |
| hIL27 Ra_VH H16- DR593 | 1428 | CAGGTCCAGCTCCAGGAGAGTGGTGGGGGGTCAGTGCAGGGGGGGAGGCTCACTG<br>CGTCTGTCCTGTCGGGCCTCCGGCTCCACTTACTCTAACTATTGCTTGGGCTGG<br>TTCAGGCAGATTACAGGTAAGGAGCGCGAAGGGGTGGCTGTTATCAACTGGGTA<br>GGGGGTATGCTGTATTTCGCCGATTCAGTTAAGGGCCGTTTCACGGTGAGTCAG<br>GATCAGGCCAAAAACACTGTTTATCTTCAAATGAACTCCCTGAAGCCCGAGGAC<br>ACCGCGATGTACTATTGCGCAGCCGAGAGCGCCTCTAGCTTCAGCTGTGGGGGT<br>TGGCTGACACGGCCTGACCGCGTCCCTTATTGGGGCCAGGGAACCCAAGTGACC<br>GTGTCTAGCGGAGGCTCCGGCGGATCTGGAGGTTCCGGTCAGGTGCAGTTGCAA<br>GAGTCCGGGGGAGGCTCTGTGCAGGCGGCGGGCAGCCTGCGCCTGTCCTGCGCG<br>GCCTCTGGATATCCGTACAGCAACGGCTACATGGGCTGGTTCAGACAAGCACCG<br>GGGAAAGAGAGAGAGGGCGTGGCCACCATCTACACCGGGGAGGGGCGTACTTAG<br>TATGCCGACAGTGTAAAGGGGCGCTTCACTATCTCACGCGACAATGCGAAAAAC<br>ACAGTGGACCCCCAGATGTCAAGTTTGAAGCCGGAGGACACTGCAATGTATTAC<br>TGTGCTGCCAGAGCCGCACCTCTGTACTCCAGCGGCTCTCCTCTGACTCGTGCC<br>CGCTACAACGTGTGGGGTCAGGGCACTCAGGTCACAGTCAGCAGT |
| hIL27 Ra_VH H16- DR594 | 1429 | CAAGTGCAGCCCCAGGAATCTGGAGGCGGAAGCGTCCAGGGGGGCGGTTCTCTG<br>CGTCTGTCTTGTCGGGCCAGCGGCTCTACTTACTCTAATTACTGTCTGGGTTGG<br>TTCCGCCAGATCACTGGTAAGGAGAGAGAGGGGGTGGCCGTTATCAACTGGGTC<br>GGCGGGATGCTGTACTTTGCTGATTCAGTGAAAGGCCGGTTCACAGTAAGCCAG<br>GATCAGGCCAAGAACACAGTTTACCTCCAGATGAACTCTTTGAAGCCCGAGGAC<br>ACCGCCATGTACTATTGTGCGGCAGAATCCGCCCCTAGCTTCAGCTGTGGCGGT<br>TGGCTGACCCGTCCTGACAGAGTGCCATACTGGGGCCAGGGCACCCAGGTGACA<br>GTGTCCTCTGGCGGAGGCTCCCAGGTGCAGCTCCAGGAATCAGGGGGAGGCAGT<br>GTGCAGGGGCGGGGCTCCCTGAGATTGTCCTGTGTCGCCAGCGCGTCCACCTAT<br>TGCACCTACGATATGCACTGGTACAGACAGGCACCCGGAAAGGGCCGTGAGTTT<br>GTGAGTGCTATTGATTCCGACGGTACAACTCGCTACGCGGATTCAGTGAAAGGG<br>AGATTCACGATTTCTCAAGGCACGGCCAAGAATACTGTGTACCTCCAGATGAAC<br>AGCCTCCAGCCAGAAGACACGGCTATGTACTATTGCAAGACCGTGTGTGTGGTC<br>GGCAGCAGGTGGTCCGACTATTGGGGCCAGGGTACACAGGTGACCGTGAGCAGC |
| hIL27 Ra_VH H16- DR594 | 1430 | CAAGTGCAACTCCAGGAGAGCGGCGGTGGCCCCGTGCAGGGCGGGGGAAGCCTC<br>CGCCTTAGTTGCAGAGCGAGCGGCAGCACCTACTCCAACTACTGCTTGGGCTGG<br>TTTAGACAGATTACGGGCAAGGAACGTGAGGGTGTCGCCGTAATCAACTGGGTT<br>GGCGGTATGCTCTACTTTGCTGACTCCGTTAAGGGACGCTTTACTGTTTCTCAG<br>GATCAGGCGAAGAACACCGTCTACCTTCAGATGAACTCCCTCAAACCCGAGGAC<br>ACCGCTATGTACTATTGCGCAGCCGAATCTGCAAGCTCTTTCTCATGCGGTGGG<br>TGGCTGACCCGCCCGGACCGTGTGCCTTACTGGGGCCAGGGGACACAGGTGACC<br>GTTAGCTCCGGGGGCTCGGGGGGTTCAGGTGGATCTGGGCAGGTTCAGCTGCAA<br>GAGTCAGGTGGGGGCTCTGTCCAAGCCGGGGGATCTCTGAGACTGTCATGCGTG<br>GCCTCCGCATCAACCTACTGCACCTATGATATGCACTGGTATCGCCAAGCTCCG<br>GGTAAAGGCAGGGAGTTTGTGAGCGCCATCGACAGCGATGGAACGACCCGCTAC<br>GCCGATAGCGTGAAGGGGAGATTTACTATTTCCCAAGGAACAGCCAAAAACACA<br>GTCTACCTTCAGATGAACTCCCTGCAACCCGAAGACACAGCCATGTATTACTGC<br>AAGACAGTTTGCGTGGTTGGTTCCCGTTGGAGCGACTACTGGGGCCAGGGCACC<br>CAGGTGACTGTCTCCTCT |
| hIL27 Ra_VH H16- DR595 | 1431 | CAGGTCCAGCTGCAAGAATCAGGGGCGGGGTCCGTGCAAGCTGGTGGATCTCTC<br>CGTCTGTCTTGCCGCGCTTCTGGAAGCACTTATTCAAATTATTGCCTGGGCTGG<br>TTTAGGCAGATTACTGGGAAGGAGCGCGAGGGCGTCGCCGTGATAAATTGGGTC<br>GGTGGGATGCTGTATTTCGCGGACAGCGTGAAGGGCCGGCTCACAGTCTCCCAA<br>GATCAGGCTAAGAACACAGTGTACTTGCAGATGAACTCCCTGAAGCCAGAGGAC<br>ACTGCCATGTACTATTGCGCGGCTGAAAGCGCCTCTACCTTCTCCTGTGGGGGC<br>TGGCTCACACGCCCAGATCGCGTACCATACCGGGGTCAGGGCACACAGGTGACC<br>GTGTCATCTGGGGGGGGAGCCAGGTGCAGCTCCAGGAGTCAGGAGCGGGGGTCC<br>GTACAGGCTGGTGGCTCCCTGACCCTGTCTTGCGCTGCATCAGAGTACGCCTAC<br>TCCACCTGCAACATGGGTTGGTATCGTCAGGCTCCCGGCAAAGAAAGGGAACTC<br>GTGAGTGCCTTCATTAGCGATGGATCAACCTATTACGCGGACTCCGTGAAGGGC<br>CGCTTCACCATCACCCGCGACAACGCGAAAAATACGGTCTACTTGCAGATGAAT<br>AGTCTGAAACCAGAGGACACAGCCATCTATTACTGCTCTGCCAACTGTTACCGT<br>CGCCTGCGGAATTATTGGGGCCAGGGCACCCAGGTGACTGTCTCCTCT |
| hIL27 Ra_VH H16- DR595 | 1432 | CAGGTCCAGTTGCAGGAGTCCGGGGGTGGCTCTGTCCAAGCAGGTGGCAGCCTG<br>CGGCTGTCTTGCCGCGCGAGCGGGTCCACTTATAGTAACTATTGCCTGGGCTGG<br>TTTCGTCAGATCACAGGCAAGGAGCGCGAAGGCGTCGCCGTTATCAACTGGGTG<br>GGGGGGATGCTGTATTTCGCCGACAGCGTGAAGGGACGTTTTACAGTGTCACAG<br>GACCAGGCCAAGAACACCGTCTACCTCCAGATGAACTCCCTGAAGCCTGAAGAC<br>ACTGCCATGTACTATTGTGCCGCAGAGTCAGCCAGCTCCTTCAGCTGCGGCGGA<br>TGGTTGACCCGCCCGGACAGGGTTCCCTACTGGGGTCAGGGCACTCAGGTTACG |

TABLE 1B-continued

| Name | SEQ ID NO: | Sequence |
|---|---|---|
| | | GTGAGCAGTGGTGGCTCTGGTGGCTCTGGAGGCTCCGGCCAGGTGCAGCTTCAG<br>GAGAGTGGCGGTGGAAGTGTGCAAGCGGGAGGTAGTCTGACCCTCTCTTGCGCT<br>GCCTCTGAATACGCATACAGTACATGCAATATGGGATGGTATCGCCAGGCCCCT<br>GGCAAAGAGCGTGAACTCGTGAGCGCCTTCATCTCAGATGGGAGCACCTATTAC<br>GCTGACTCTGTCAAGGGCAGGTTCACGATTACCCGCGATAACGCAAAGAACACC<br>GTGTATTTGCAGATGAACTCCCTGAAGCCTGAAGACACAGCCATTTATTACTGC<br>TCCGCCAACTGTTATCGCAGACTGCGGAACTATTGGGGCCAGGGCACCCAGGTC<br>ACCGTGTCTTCC |
| hIL27<br>Ra_VH<br>H16-<br>DR596 | 1433 | CAGGTGCAGTTGCAGGAGTCTGGAGGTGGCTCCGTCCAGGCTGGTGGCTCTCTG<br>CGGCTGAGCTGCCGCGCGAGTGGCAGCACCTACTCCAACTACTGCCTGGGCTGG<br>TTTCGCCAGATTACAGGAAAGGAGAGAGAGGGAGTGGCCGTCATCAACTGGGTG<br>GGCGGGATGTTGTATTTCGCTGACAGTGTGAAGGGAAGATTTACCGTTAGTCAG<br>GACCAGGCTAAGAACACCGTATACCTCCAGATGAACTCTCTGAAGCCAGAGGAT<br>ACAGCCATGTACTATTGTGCCGCAGAGTCTGCCTCCTCTTTTTCATGGGGGGGG<br>TGGTTGACTCGCCCAGACAGAGTACCATACTGGGGCCAGGGGACCCAAGTGACC<br>GTCTCCAGCGGGGGGGGCAGCCAGGTCCAGCTCCAGGAGTCAGGTGGGGGGCTG<br>GTCCAGCCTGGGGGTTCTCTGCGCCTGTCCTGCACCGCCAGTGGGCTCACCTTC<br>GATGACTCCGTGATGGGTTGGTTCCGGCAGGCTCCGGGTAAGGGACGTGAGGCT<br>GTGTCCTGTATTTCTTCCAGCGGAGCCAACGCATTTTATGCGGACAGTGTAAAG<br>GGTCGCTTTACCATCAGTCGTGACAACGCCAAGAACACCCTCTATCTTCAGATG<br>AACTCCCTGAAGCCAGAGGATACTGCCACGTATTACTGCAAGCGTGGTCATGCG<br>TGCGCAGGCTATTACCCCATCCCCTACGACGATTATTGGGGCCAAGGCACGCAG<br>GTGACCGTTTCCTCC |
| hIL27<br>Ra_VH<br>H16-<br>DR596 | 1434 | CAGGTGCAGCTTCAGGAGTCCGGTGGGGGCAGCGTGCAAGCTGGAGGCAGTCTG<br>AGGCTGAGCTGTCGTGCGTCAGGGTCTACCTACTCCAACTATTGTCTGGGCTGG<br>TTTCGCCAGATCACTGGTAAGGAGCGCGAGGGCGTTGCCGTTATCAACTGGGTC<br>GGAGGTATGCTGTACTTCGCTGACTCCGTGAAGGGACGTTTCACTGTGAGCCAG<br>GATCAGGCCAAGAACACCGTGTACCTCCAGATGAACAGCCTGAAGCCTGAAGAT<br>ACCGCCATGTATTACTGTGCAGCCGAATCCGCCTCTTCCTTTAGCTGGGCGGGC<br>TGGCTGACTAGGCCTGACCGCGCGCCTTACTGGGGCCAGGGGACCCAAGTAACC<br>GTCAGCTCTGGTGGCAGCGGAGGTAGCGGTGGGAGTGGCCAGGTTCAGCTTCAG<br>GAGAGCGGTGGAGGTCTGGTGCAGCCAGGGGGTAGTCTGCGCCTTAGCTGCACT<br>GCCTCCGGTCTGACCTTCGATGACAGTGTGATGGGTTGGTTTCGTCAGGCTCCA<br>GGCAAGGGGCGCGAAGCAGTGTCTTGTATCAGCTCCAGCGGCGCTAATGCCTTT<br>TACGCCGATTCCGTGAAAGGCCGCTTTACGATTAGCCGCGATAACGCCAAGAAC<br>ACACTGTATTTGCAGATGAACAGCCTCAAACCCGAAGACACGGCCACCTACTAT<br>TGTAAGCGGGGTCATGCCTGCGCTGGGTATTACCCAATTCCCTACGATGACTAT<br>TGGGGGCAGGGCACCCAGGTTACTGTCTCCTCC |
| hIL27<br>Ra_VH<br>H17-<br>DR591 | 1435 | CAGGTTCAGTTGCAGGAAAGCGGAGGTGGCTTGGTGCAGCCCGGTGGCTCTCTC<br>CGTCTGTCTTGCGCGGCCAGTGGGTTCACATTCTCCCTGAGCGGAATGTCTTGG<br>GTGCGTCAGGCCCCAGGCAAAGGTCTGGAATGGGTTAGCGCGATCAGCTCTGGT<br>GGCGCTTCCACCTACTATACGGACAGCGTTAAGGGCAGATTTACTATTTCTCGC<br>GACAACGCCAAGAACATGCTTTACCTCCAGTTGAACAGCCTGAAGACCGAAGAT<br>ACCGCTATGTATTACTGTGCCAAGGGTGGGTCCGGCTACGGCGATGCCTCCCGT<br>ATGACATCCCCTGGCAGCCAGGGCACTCAAGTGACCGTGTCCAGCGGCGGTGGC<br>AGTCAAGTCCAGCTCCAGGAGTCTGGGGGTGGATCTGTCCAGGCCGGGGGCTCC<br>CTCCGCCTGAGTTGCACTGCGAGCGGTGCTATCGCCAGCGGCTACATCGACTCC<br>AGGTGGTGCATGGCCTGGTTCCGCCAGGCTCCGGGAAAAGAGCGTGAGGGTGTT<br>GCCGCTATCTGGCCCGGAGGGGGGCTGACCGTCTATGCCGACTCCGTAAAGGGC<br>CGGTTCACCATCAGCCGCGACCATGCCAAGAACACCCTGTACCTTCAGATGAAT<br>AACTTGAAACCTGAGGACACTGCTATGTATTACCGCGCGGCTGGTAGCCCTCGC<br>ATGTGCCCGAGCCTGGAATTTGGGTTCGATTACTGGGGACAGGGCACCCAGGTC<br>ACGGTGTCCAGC |
| hIL27<br>Ra_VH<br>H17-<br>DR591 | 1436 | CAGGTGCAGTTGCAAGAAAGTGGGGTGGGTCTGGTACAGCCTGGAGGCTCTCTG<br>CGCCTCTCCTGTGCTGCCAGCGGCTTTACTTTTAGCCTGTCAGGTATGTCCTGG<br>GTCCGCCAGGCCCCCGGTAAAGGTCTTGAGTGGGTCTCCGCTATTTCCAGCGGA<br>GGTGCCAGTACCTATTACACCGACTCAGTGAAAGGACGTTTCACCATTTCCCGC<br>GATAATGCTAAGAATATGTTGTATTTGCAGCTCAACAGCCTGAAGACAGAGGAT<br>ACCGCTATGTACTATTGCGCTAAAGGCGGATCTGGTTATGGAGACGCCTCCCGT<br>ATGACATCCCCTGGGTCTCAGGGAACGCAGGTGACCGTGTCTAGCGGGGGGTCC<br>GGAGGCTCCGGTGGCTCCGGCCAGGTCCAGCTCCAGGAAAGCGGTGGGGGGTCT<br>GTGCAGGCAGGCGGTTCCCTGAGGCTGAGCTGCACAGCCTCCGGGGCAATCGCC<br>AGCGGTTATATCGACAGCAGATGGTGCATGGCCTGGTTCCGTCAGGCCCCCGGC<br>AAAGAGAGGGAGGGAGTGGCGGCCATCTGGCCAGGAGGCGGACTGACCGTGTAT<br>GCCGACTCTGTGAAGGGTCGCTTTACCATCAGCAGAGACCACGCCAAGAACACC<br>CTGTACTTGCAGATGAATAACCTCAAGCCCGAGGACACCGCAATGTATTACTGC<br>GCCGCAGGCAGCCCTCGCATGTGTCCGTCTCTGGAGTTCGGATTCGATTACTGG<br>GGCCAGGGGACCCAGGTGACCGTTTCCTCC |
| hIL27<br>Ra_VH<br>H17-<br>DR592 | 1437 | CAAGTGCAGCTCCAGGAGTCAGGTGGAGGCCTGGTTCAGCCTGGGGGAAGTCTG<br>CGCCTTTCATGTGCAGCTTCTGGTTTTACCTTCTCTCTGAGCGGCATGTCCTGG<br>GTCCGGCAGGCACCGGGCAAGGGCCTGGAGTGGGTGAGTGCCATCTCATCTGGC<br>GGTGCGAGCACCTACTATACCGACTCTGTTAAAGGAAGGTTTACCATCTCCCGC |

TABLE 1B-continued

| Name | SEQ ID NO: | Sequence |
|---|---|---|
| | | GATAACGCTAAAAATATGTTGTACTTGCAGCTCAACTCACTGAAGACCGAAGAC<br>ACCGCTATGTATTACTGGGCCAAGGGTGGCTCCGGGTACGGGGATGCCTCCCGC<br>ATGACCAGCCCCGGTAGTCAGGGCACTCAGGTCACTGTTAGCTCCGGCGGTGGC<br>TCTCAGGTCCAGCTCCAGGAGTCTGGTGGAGGCTCCGTGCAGGCTGGCGGTTCC<br>CTGAGATTGTCTTGTACTGCCCCCGGCTTCACAAGTAACTCCTGTGGTATGGAC<br>TGGTATCGTCAAGCGCCTGGAAAGGAGCGCGAGTTCGTTAGCTCCATTTCTACC<br>GATGGGACCACTGGGTATGCAGACAGCGTGAAAGGTCGCTTTACCATCTCCAAG<br>GACAAGGCTAAGGACACCGTGTACCTCCAAATGAACTCCCTGAAGCCCGAGGAC<br>ACCGGGATGTATTCCTGCAAGACCAAGGACGGGACCATCGCCACTATGGAGTTG<br>TGTGACTTCGGATATTGGGGGCAGGGCACCCAAGTGACTGTGTCTAGC |
| hIL27<br>Ra_VH<br>H17-<br>DR592 | 1438 | CAGGTCCAGCTTCAGGAGTCTGGCGGGGGTCTGGTCCAGCCTGGGGGTTCTCTC<br>CGCCTGTCCTGCGCAGCTAGTGGATTCACCTTCTCTCTCTCCGGTATGTCTTGG<br>GTGCGCCAGGCCCCTGGCAAGGGGCTGGAGTGGGTGAGTGCAATTAGCTCCGGG<br>GGAGCAAGCACCTACTATACAGACTCAGTCAAGGGAAGATTCACAATTTCCCGC<br>GATAACGCTAAAAACATGCTGTATCTCCAGCTCAACAGCCTGAAGACGGAAGAC<br>ACGGCTATGTACTATTGTGCCAAAGGGGGCAGCGGCTATGGCGACGCCAGCCGC<br>ATGACCTCTCCGGGCAGCCAGGGTACGCAGGTGACCGTGTCCAGCGGAGGCTCC<br>GGGGGCTCTGGAGGTTCAGGGCAGGTACAGCTCCAAGAATCCGGGGGGGGTTCT<br>GTGCAGGCTGGAGGCTCCCTGCGCCTGAGCTGCACAGCTCCGGGCTTTACCTCC<br>AACAGTTGCGGAATGGATTGGTACAGGCAAGCGCCCGGCAAGGAGAGGGAGTTC<br>GTGTCCAGTATTTCAACCGACGGCACAACCGGCTACGCGGATTCCGTGAAAGGA<br>CGCTTCACCATTTCCAAAGACAAGGCCAAGGACACCGTGTATTTGCAGATGAAC<br>TCACTGAAGCCCGAGGATACCGGAATGTATTCTTGTAAAACGAAGGATGGGACC<br>ATCGCTACAATGGAGCTGTGTGACTTTGGTTACTGGGGCCAGGGCACTCAGGTC<br>ACTGTCTCTTCT |
| hIL27<br>Ra_VH<br>H17-<br>DR593 | 1439 | CAGGTGCAGCTCCAGGAAAGCGGTGGCGGTTTGGTGCAGCCTGGGGGCTCCCTG<br>CGCCTGTCTTGTGCGGCTAGTGGCTTCACCTTCTCTCTGTCCGGCATGAGCTGG<br>GTGCGGCAAGCGCCGGGCAAGGGCCTCGAATGGGTGAGCGCAATCAGCTCTGGA<br>GGCGCATCAACCTACTATACCGATTCAGTCAAGGGAAGGTTTACCATCTCCAGA<br>GATAACGCCAAGAATATGCTGTACCTCCAGCTCAATTCACTGAAGACCGAGGAT<br>ACCGCCATGTATTACTGCGCTAAGGGCGGCAGCGGATACGGAGATGCGTCCCGC<br>ATGACAAGCCCCGGCTCACAGGGCACACAGGTGACTGTGTCCTCAGGAGGTGGC<br>TCCCAAGTGCAGCTTCAGGAGAGCGGTGGAGGCTCCGTCCAAGCTGGAGGGTCC<br>CTCCGTCTCTCTTGTGCAGCTTCCGGCTATCCTTACTCCAATGGGTACATGGGA<br>TGGTTCCGCCAAGCTCCTGGCAAGGAGAGGGAGGGGGTGGCTACCATCTACACT<br>GGCGATGGCCGCACCTATTACGCCGACAGCGTGAAAGGACGTTTCACCATTTCC<br>CGTGACAATGCAAAGAACACTGTGGACCTCCAGATGTCAAGCCTCAAGCCAGAA<br>GACACCGCGATGTACTATTGTGCTGCCAGAGCAGCGCCCCTGTATTCTTCAGGC<br>TCTCCCCTGACACGCGCACGTTACAACGTCTGGGGCCAGGGTACTCAGGTCACC<br>GTGTCTAGC |
| hIL27<br>Ra_VH<br>H17-<br>DR593 | 1440 | CAGGTGCAGCTCCAGGAATCCGGGGGAGGCCTGGTCCAGCCCGGGGGGTCTCTG<br>CGCCTGTCTTGTGCTGCCAGCGGCTTCACCTTCAGTCTGAGTGGAATGAGCTGG<br>GTGCGTCAGGCTCCAGGAAAGGGCCTGGAGTGGGTGTCCGCCATTAGCTCTGGA<br>GGCGCGTCCACATATTACACCGATAGCGTAAAAGGCCGTTTCACTATCTCACGC<br>GACAACGCTAAGAATATGCTGTATCTCCAGCTGAACTCCCTGAAAACCGAGGAT<br>ACGGCCATGTATTACTGTGCGAAAGGGGGTTCAGGGTACGGCGACGCATCCAGG<br>ATGACCAGCCCAGGTTCCCAAGGGACCCAGGTGACAGTGTCTTCCGGCGGAAGC<br>GGAGGCTCCGGTGGCAGCGGCCAGGTGCAGTTGCAGGAATCTGGCGGTGGGAGC<br>GTGCAGGCTGGCGGGAGCCTGCGCCTGAGCTGTGCTGCGAGCGGCTACCCCTAT<br>TCTAACGGGTACATGGGTTGGTTCCGGCAGGCTCCCGGTAAAGAGCGCGAGGGA<br>GTGGCCACGATTTACACGGGTGATGGGCGCACTTATTACGCAGACTCCGTTAAG<br>GGCCGGTTTACCATTAGTCGTGATAACGCGAAGAACACCGTGGACCTTCAGATG<br>TCCAGCTTGAAGCCAGAGGACACCGCTATGTATTACTGTGCTGCACGCGCCGCG<br>CCTCTCTACAGTAGCGGCTCCCCTCTGACCCGCGCTCGCTATAACGTGTGGGGC<br>CAGGGCACTCAGGTGACAGTAAGCTCC |
| hIL27<br>Ra_VH<br>H17-<br>DR594 | 1441 | CAAGTTCAGCTCCAGGAGTCTGGAGGCGGTCTCGTGCAGCCCGGTGGCTCCCTC<br>CGCCTGTCTTGCGCCGCGAGCGGCTTCACCTTCTCTTTGAGCGGAATGAGCTGG<br>GTCAGGCAGGCTCCCGGCAAAGGCCTGGAGTGGGTGTCCGCCATTAGTAGCGGC<br>GGAGCCTCTACCTATTACACCGATTCTGTGAAGGGTCGTTTCACCATTTCTCGC<br>GATAACGCAAAGAACATGCTGTACCTCCAGCTGAACTCTCTGAAGACCGAGGAT<br>ACTGCAATGTATTACTGCGCCAAAGGCGGTAGTGGTTACGGTGACGCCAGCAGG<br>ATGACCTCCCCAGGATCACAGGGAACCCAGGTCACCGTCAGCTCTGGTGGAGGC<br>AGCCAGGTGCAGTTGCAGGAAAGCGGGGGAGGCAGTGTGCAGGCCGGAGGGTCT<br>CTGAGGCTCTCTTGCGTCGCCAGCGCCTCCACTTACTGCACTTATGACATGCAC<br>TGGTATCGGCAAGCTCCTGGGAAGGGCCGTGAATTTGTGAGCGCTATCGACAGC<br>GACGGCACCACTAGGTATGCTGATTCTGTGAAAGGGAGGTTTACCATTTCCCAG<br>GGCACCGCCAAGAACACGGTGTATCTCCAGATGAACTCTCTCCAGCCGGAAGAC<br>ACTGCCATGTATTACTGTAAGACCGTGTGCGTGGTCGGATCTCGCTGGTCTGAT<br>TATTGGGGCCAGGGAACCCAGGTGACGGTTTCTTCC |
| hIL27<br>Ra_VH<br>H17- | 1442 | CAGGTCCAGTTGCAGGAGTCCGGGGGAGGGCTGGTACAGCCCGGCGGAAGCCTG<br>CGCCTGAGTTGCGCCGCGTCTGGATTTACTTTCTCTCTCTCTGGTATGAGCTGG<br>GTGCGCCAGGCTCCCGGCAAGGGACTTGAGTGGGTAAGCGCAATCTCCTCTGGC |

TABLE 1B-continued

| Name | SEQ ID NO: | Sequence |
| --- | --- | --- |
| DR594 | | GGGGCGAGCACCTATTACACCGACAGCGTTAAGGGCAGGTTCACAATTAGCCGT<br>GACAACGCTAAGAATATGCTTTATCTTCAGCTGAACAGCCTGAAGACTGAAGAC<br>ACGGCCATGTATTACTGTGCCAAGGGGGGTTCCGGCTACGGAGACGCTAGTCGC<br>ATGACCTCCCCAGGCTCCCAGGGCACCCAGGTCACCGTGTCTAGCGGAGGCTCT<br>GGCGGTAGTGGTGGCTCCGGTCAGGTGCAACTTCAGGAGAGTGGCGGTGGCTCC<br>GTTCAAGCTGGGGGTTCCCTGCGTCTGTCTTGTGTCGCTAGTGCGTCCACCTAT<br>TGCACCTACGACATGCACTGGTATCGTCAAGCGCCGGGCAAGGGAAGGGAGTTC<br>GTCAGCGCCATTGATTCCGACGGCACCACTCGCTACGCCGACTCTGTCAAGGGA<br>CGCTTCACCATCTCCCAGGGCACTGCCAAAAATACCGTGTATTTGCAGATGAAC<br>TCACTTCAGCCAGAGGACACTGCCATGTATTACTGCAAGACCGTCTGCGTCGTG<br>GGCAGCAGGTGGTCTGATTACTGGGGCCAAGGCACCCAGGTGACCGTCAGCAGC |
| hIL27<br>Ra_VH<br>H17-<br>DR595 | 1443 | CAGGTGCAACTTCAGGAATCAGGGGGGGGACTGGTGCAGCCAGGTGGCTCTCTG<br>CGCCTCAGCTGTGCGGCCTCTGGCTTTACCTTCTCTTTGAGGGGTATGAGCTGG<br>GTGCGCCAGGCTCCGGGAAAAGGTCTGGAGGCGGTCTCTGCCATCTCTTCCGGC<br>GGTGCCTCCACGTACTATACCGACTCCGTGAAGGGCCGGTTTACCATTTCCAGG<br>GACAACGCCAAGAACATGCTTTATCTCCAGCTGAACTCTCTGAAGACAGAAGAT<br>ACCGCCATGTACTATTGCGCCAAAGGTGGCTCCGGTTACGGCGACGCGAGCCGC<br>ATGACTAGCCCTGGCTCCCAGGGAACCCAGGTCACAGTGTCCTCTGGCGGTGGC<br>TCTCAGGTCCAGCTCCAGGAGTCTGGTGGGGGGTCCGTGCAGGCCGGTGGCTCC<br>CTGACCCTGTCTTGTGCTGCCAGTGAGTATGCGTACAGTACCTGTAATATGGGT<br>TGGTACAGGCAAGCGCCCGGCAAGGAACGCGAGCTGGTCTCCGCTTTTATCTCC<br>GACGGAAGCACCTATTACGCAGACTCAGTGAAGGGTCGTTTCACCATCACCCGT<br>GATAATGCTAAAAACACTGTGTACCTCCAGATGAATAGTCTGAAGCCCGAGGAT<br>ACCGCTATTTATTACTGCTCCGCCAACTGTTACCGTCGCCTGAGAAACTACTGG<br>GGACAAGGCACCCAGGTAACCGTCAGCTCT |
| hIL27<br>Ra_VH<br>H17-<br>DR595 | 1444 | CAGGTGCAGTTGCAGGAGTCTGGCGGAGGTCTGGTACAGCCTGGTGGCAGCCTC<br>CGCTTGAGCTGCGCGGCCAGTGGCTTCACTTTTTCCCTGTCAGGCATGAGCTGG<br>GTGCGTCAGGCTCCTGGCAAAGGACTGGAGTGGGTGTCCGCTATCTCCTCTGGA<br>GGCGCATCCACTTATTACACCGATTCTGTCAAAGGTCGTTTCACCATTTCCCGC<br>GATAATGCTAAGAACATGCTGTATTTGCASTTGAACTCCCTGAAGACAGAGGAC<br>ACCGCTATGTATTACTGCGCTAAGGGTGGCAGCGGGTATGGGGATGCCAGCCGC<br>ATGACAAGCCCCGGCTCCCAGGGTACACAGGTCACCGTCTCCTCAGGAGGCAGT<br>GGAGGTAGCGGGGGCTCCGGCCAAGTCCAGCTCCAGGAGTCGGGCGGGGGATCT<br>GTCCAGGCCGGGGGCAGTCTCACTCTGTCCTGTGCCGCTTCAGAGTACGCCTAT<br>AGTACCTGTAACATGGGCTGGTATAGGCAGGCTCCCGGCAAGGAGAGAGAACTG<br>GTCAGCGCGTTTATCTCCGACGGCAGTACCTACTATGCTGACTCTGTGAAGGGA<br>CGTTTTACCATCACCCGCGACAACGCCAAGAATACCGTCTACCTCCAGATGAAC<br>TCTCCCAAACCGGAGGACACCGCCATCCATTACTGCTCTGCAAACTGTTATAGA<br>AGGCTGCGTAACTACTGGGGACAAGGCACGCAAGTGACAGTGTCCTCA |
| hIL27<br>Ra_VH<br>H17-<br>DR596 | 1445 | CAGGTGCAGTTGCAGGAGAGCGGTGGCGGTCTCGTGCAGCCAGGTGGCTCTCTG<br>CGGCTGAGTTGCGCTGCCTCTGGCTTCACATTCTCTCTGTCCGGCATGTCTTGG<br>GTGCGCCAGGCTCCGGGTAAAGGGCTGGAGTGGGTGAGCGCAATCTCCTCTGGA<br>GGTGCATCCACCTATTACACCGACTCTGTGAAGGGTCGCTTTACGATCTCCCGC<br>GACAACGCAAAGAATATGCCTTACCTGCAACTGAACTCCCTGAAAACAGAGGAC<br>ACGGCCATGTACTATTGTGCCAAGGCGGGGTCTGGCTACGGCGACGCTTCCAGG<br>ATGACCAGTCCGGGCTCTCAGGGCACCCAGGTGACAGTCTCTAGCGGGCGGGGG<br>TCCCAGGTCCAGCTTCAGGAAAGCGGAGGTGGCCTTGTTCAACCGGGGGGTTCA<br>CTTCGCTTGAGCTGCACAGCTTCAGGTCTGACCCTCGACGATTCTGTCATGGGC<br>TGGTTTAGGCAGGCCCCTGGGAAGGGCAGAGAAGGGGTGTCTTGTATCAGTTCC<br>TCAGGGGCCAACGCTTTCTATGCAGACTCCGTGAAGGGACGTTTTACAATTTCA<br>CGCGATAATGCCAAGAACACATTGTACCTCCAGATGAACTCCCTGAAACCCGAG<br>GACACTGCTACATACTATTGTAAACGCGGCCACGCATGTGCAGGCTACTATCCC<br>ATCCCTTACGATGACTACTGGGGTCAGGGAACCCAGGTTACCGTTAGCTCC |
| hIL27<br>Ra_VH<br>H17-<br>DR596 | 1446 | CAGGTTCAGCTCCAGGAGAGCGGAGGTGGCCTGGTTCAGCCTGGTGGCAGCCTG<br>CGCCTGTCTTGCGCTGCCAGCGGTTTTACCCTTAGTTTGTCCGGTATGTCATGG<br>GTTCGTCAAGCTCCTGGCAAGGGTCTCGAATGGGTGTCCGCGATTTCCTCAGGA<br>GGTGCCTTCTACTTATACACCGATAGTGTGAAGGGTCGCTTTACTATCTCTCGC<br>GACAACGCGAAGAACATGCCGTACCTCCAACTGAACAGCCTGAAGACTGAAGAT<br>ACCGCGATGTACTATTGCGCGAAGGGAGGCTCTGGGTATGGAGATGCCTCCCGT<br>ATGACATCTCCTGGCTCTCAAGGCACCCAGGTGACCGTCTCCAGCGGCGGTTCC<br>GGGGGCTCAGGGGGATCTGGCCAGGTTCAGTTGCAGGAGTCCGGCGGTGGCCTG<br>GTCCAACCGGGGGGGAGCCTGAGGCTGTCCTGCACTGCGAGCGGGTTGACATTC<br>GACGATAGCGTGATGGGTTGGTTTCGCCAGGCTCCCGGAAAGGGTCGGGAGGCC<br>GTCAGCTGTATCTCCAGCAGTGGGGCTAATGCCTTCTACGCCGATTCCGTTAAA<br>GGGAGATTTACCATCTCACGGGATAACGCTAAGAACACGCTGTACTTGCAGATG<br>AACAGTCTCAAGCCAGAGGACACAGCGACTTACTATTGTAAACGCGGACATGCC<br>TGTGCCGGGTACTATCCTATTCCCTACGATGACTATTGGGGTCAGGGCACCCAG<br>GTGACCGTATCTTCT |
| hIL27<br>Ra_VH<br>H18-<br>DR591 | 1447 | CAGGTTCAGTTGCAAGAGTCCGGCGGTGGAAGCGTCCAGGCCGGGGGTAGTCTT<br>CGGCTGTCATGCGTGGCGAGTGGCTATGTGTCTCGCGACTATTTTCTGCCGAGC<br>TGGTATCGCCAGGCTCCAGGTAAGGAACGCGAGTTCGTGAGCATCATTGATGGC<br>ACAGGTTCAACATCCTACGCTGCGTCCGTGAAGGGACGGTTCACCGCGAGCCAG |

TABLE 1B-continued

| Name | SEQ ID NO: | Sequence |
|---|---|---|
| | | GACAAGGGTAAGAACATCGCTTACCTCCAGATGAACTCCCTGAAGCCGGAGGAC<br>ACCGCCATGTACTATTGTAAGGCTTCCCGTGTGCGCGGCAGGGGAATCAGTGAA<br>TACTGGGGCCAAGGAACACAGGTGACTGTCAGTTCCGGTGGCGGAAGCCAGGTG<br>CAGTTGCAAGAGTCCGGGGGGGGTTCCGTGCAGGCTGGTGGCTCCCTGAGACTC<br>TCTTGTACCGCTTCAGGTGCTATTGCCAGTGGATACATTGATTCCCCGCTGGTGC<br>ATGGCCTGGTTCCGCCAGGCCCCCGGCAAGGAGAGGGAAGGAGTCGCCGCTATC<br>TGGCCTGGGGGTGGCCTGACCGTGTATGCTGATAGCGTGAAGGGCAGATTCACC<br>ATCAGCCGCGATCATGCTAAGAACACACTCTACCTTCAGATGAATAACCTGAAG<br>CCTGAGGACACCGCTATGTATTACTGCGCAGCCGGTTCCCCTCGCATGTGCCCC<br>TCTTTGGAGTTTGGCTTCGACTACTGGGGCCAGGGCACTCAGGTTACCGTAAGC<br>TCC |
| hIL27 Ra_VH H18- DR591 | 1448 | CAAGTCCAGCTCCAGGAATCCGGGGGTGGCTCCGTCCAGGGGGGCGGTTCCCTC<br>AGGCTCTCCTGCGTGGCCAGCGGCTACGTAAGCTGCGATTATTTCCTGCCATCT<br>TGGTATCGCCAAGCCCCTGGTAAGGAGAGAGAATTTGTCTCAATCATTGATGGT<br>ACAGGTAGCACCTCCTACGCAGCCTCAGTGAAGGGACGTTTTACCGCGAGCCAA<br>GACAAAGGCAAGAACATCGCGTATTTGCAGATGAACTCTCTGAAGCCGGAGGAT<br>ACCGCGATGTACTATTGCAAAGCCTCCTGTGTACGCGGCAGGGGAATCTCAGAG<br>TATTGGGGCCAGGGCACTCAAGTGACAGTCAGCCCTGGCGGGAGCGGGGGGTCT<br>GGAGGTAGCGGTCAGGTGCAACTCCAGGAATCTGGCGGAGGCTCTGTGCAGGCC<br>GGTGGCAGCCTGCGTCTCAGCTGCACAGCCAGCGGGGCCATTGCCAGCGGCTAC<br>ATCGACTCCCGCTGGTGCATGGCTTGGTTCCGGCAAGCGCCGGGAAAGGAAAGA<br>GAGGGAGTCGCCGCGATCTGGCCGGGGGGTGGCCTGACTGTGTACGCTGACAGC<br>GTGAAGGGTCGCTTCACCATCAGTCGGGACCATGCGAAAAACACGCTGTACTTG<br>CAGATGAACAATCTGAAGCCTGAGGACACTGCCATGTATTACTGCGCTGCCGGT<br>AGTCCACGCATGTGCCCGTCTCTGGAGTTCGGCTTTGACTACTGGGGCCAGGGC<br>ACTCAGGTCACGGTTAGCTCT |
| hIL27 Ra_VH H18- DR592 | 1449 | CAGGTGCAACTGCAAGAAAGTGGTGGAGGTTCCGTGCAAGCTGGCGGATCTTTG<br>CGCCTCAGCTGCGTGGCCTCTGGCTATGTGAGTTGTGATTACTTCCTGCCTTCT<br>TGGTATCGTCAGGCCCCTGGTAAGGAACGGGAGTTCGTGTCCATTATCGACGGC<br>ACCGGATCTACGAGCTACGCTGCATCCGTCAAGGGTCGTTTTACCGCTTCCCAA<br>GACAAAGGCAAAAATATTGCCTACTTGCAAATGAACTCTCTGAAACCCGAAGAT<br>ACAGCAATGTATTACTGTAAAGCCAGTTGTGTGCGCGGACGCGGCATTTCCGAG<br>TATTGGGGACAGGGCACTCAGGTGACTGTCTCATCTGGGGGGGGCTCCCAGGTG<br>CAACTTCAGGAATCTGGGGGGGGTTCTGTTCAAGCAGGCGGTTCTCTGCGTCTG<br>AGTTGCACCGCTCCCGGATTTACCTCCAACAGTTGCGGAATGGATTGGTATCGC<br>CAGGCTCCTGGCAAGGAGCGTGAGTTCGTAAGTAGCATTTCAACTGATGGTACT<br>ACCGGATACGCTGACTCAGTTAAGGGTCGGTTCACTATCAGCAAGGATAAAGCT<br>AAGGACACAGTGTACCTTCAGATGAACTCCCTGAAGCCTGAGGACAGCGGAATG<br>TACTCCTGTAAAACCAAAGACGGGACCATCGCCACGATGGAACTGTGTGATTTC<br>GGATATTGGGGTCAGGGCACCCAGGTGACCGTGAGTAGC |
| hIL27 Ra_VH H18- DR592 | 1450 | CAGGTGCAGCTTCAAGAGAGCGGGGGGGGCTCCGTCCAGGCCGGTGGGTCCTTG<br>CGCTTGTCTTGTGTGGCCAGCGGATACGTGTCTTGCGATTATTTCCTGCCCTCT<br>TGGTACAGACAGGCCCCAGGCAAGGAGCGCGAGTTCGTATCCATCATTGACGGC<br>ACTGGTTCTACAAGTTACGCTGCATCTGTGAAGGGCCGCTTTACCGCCTCTCAG<br>GATAAGGGTAAAAACATCGCTTATTTGCAGATGAACTCACTTCAAGCCGAGGAC<br>ACCGCCATGTACTATTGTAAGGCCTCTTGTGTCAGAGGGAGAGGCATTAGTGAA<br>TATTGGGGTCAGGGGACCCAGGTGACTGTGTCCAGCGGGGGGAGCGGGGGCAGC<br>GGTGGCAGCGGCCAGGTTCAACTTCAGGAGAGCGGGGGTGGAAGCGTCCAAGCA<br>GGCGGGTCCCCGCGCTTGAGTTGTACCGCTCCGGGATTCACTAGCAACAGCTGC<br>GGGATGGACTGGTATCGGCAGGCCCCAGGGAAGGAGCGTGAGTTCGTCAGCTCC<br>ATCTCTACAGACGGCACAACCGGCTACGCCGACAGCGTTAAGGGCAGGTTCACA<br>ATCAGCAAGGACAAGGCCAAGGATACCGTGTATTTGCAGATGAACAGCCTGAAG<br>CCAGAGGATACAGGAATGTATAGCTGCAAGACTAAGGACGGCACTATTGCAACC<br>ATGGAACTGTGTGATTTTGGCTACTGGGGTCAAGGCACGCAGGTGACCGTGAGT<br>TCC |
| hIL27 Ra_VH H18- DR593 | 1451 | CAGGTGCAGCTCCAGGAGTCCGGTGGGGGCTCCGTACAGGGGGGCGGTTCCCTG<br>CGCCTTTCTTGTGTGGCCAGCGGTTACGTGAGCTGCGACTACTTCCTCCCTTCC<br>TGGTATCGTCAAGCCCCTGGTAAAGAGAGGGAGTTCGTGTCAATCATTGATGGC<br>ACCGGCTTCTACCTCTATGCTGCCTCTGTGAAAGGACGCTTTACTGCTTCTCAG<br>GATAAGGGCAAGAATATTGCTTACTTGCAGATGAACAGTCTGAAACCTGAGGAT<br>ACTGCCATGTACTATTGCAAGGCCTCCTGTGTGCGTGGCCGGGGCATTAGCGAA<br>TACTGGGGCCAGGGAACCCAGGTCACCGTCAGCTCTGGGGGTGGCTCTCAGGTG<br>CAGCTGCAAGAATCCGGCGGTGGCTCCGTTCAGGCTGGCGGTTCCCTGCGGCTG<br>TCCTGTGCAGCCTCCGGCTACCCGTACTCCAACGGCTATATGGGCTGGTTTCGC<br>CAGGCCCCTGGCAAAGAGCGCGAGGGAGTTGCCACCATCTACACCGGGGATGGC<br>CGCACTTATTACGCTGACTCTGTGAAAGGGCGCTTCACTATCAGCCGGGATAAC<br>GCCAAGAATACCGTGGACCTCCAAATGAGTTCCCTCAAGCCGGAAGACACTGCA<br>ATGTACTATTGCGCGGCTCGTGCAGCTCCACTGTACTCCTCTGGCTCTCCCCTG<br>ACCCGCGCACGTTATAATGTCTGGGGCCAGGGCACCCAGGTGACCGTCTCAAGT |
| hIL27 Ra_VH H18- | 1452 | CAGGTGCAGCTGCAAGAATCTGGGGGGGGCTCCGTGCAGGCAGGGGGTAGCCTG<br>AGGCTGAGCTGCGTGGCTAGTGGCTACGTCTCCTGCGACTACTTTCTGCCCAGC<br>TGGTATCGTCAGGCACCTGGGAAGGAACGCGAGTTCGTATCCATCATTGATGGC |

TABLE 1B-continued

| Name | SEQ ID NO: | Sequence |
|---|---|---|
| DR593 | | ACTGGCTCTACCAGCTACGCAGCCTCCGTGAAAGGACGCTTCACTGCGAGCCAG<br>GACAAGGGCAAGAACATCGCCTACTTGCAGATGAACTCCGTGAAGCCGGAAGAC<br>ACCGCCATGTATTACTGTAAGGCTTCTTGTGTACGCGGGGGGGGTATCTCCGAA<br>TATTGGGGCCAGGGCACTCAGGTGACGGTGTCCAGCGGAGGTAGCGGGGGCTCC<br>GGCGGGAGCGGGCAGGTTCAGCCCCAGGAGTCTGGGGGTGGCTCCGTGCAGGCC<br>GGAGGCTCCCTGCGCCTGTCCTGCGCCGCTTCAGGTTACCCTTATTCTAACGGT<br>TATATGGGTTGGTTCCGTCAAGCGCCCGGCAAAGAAAGGGAGGGTGTGGCTACC<br>ATTTACACTGGTGATGGTCGCACCTACTATGCTGATTCCGTGAAGGGCCGCTTC<br>ACCATCTCTCGCGATAACGCTAAGAATACCGTGGACTTGCAGATGAGTTCTCTG<br>AAACCTGAAGATACCGCCATGTACTATTGTGCCGCACGCGCCGCTCCGCTCTAC<br>TCTAGCGGGTCTCCCCTGACGAGGGCTAGGTACAACGTGTGGGGACAGGGCACC<br>CAGGTGACCGTGTCCAGC |
| hIL27<br>Ra_VH<br>H18-<br>DR594 | 1453 | CAGGTGCAGTTGCAGGAAAGCGGGGGGGGCAGCGTCCAGGCTGGGGGAAGTCTC<br>CGCCTGTCCTGCGTGGCCAGTGGCTACGTCAGCTGTGACTATTTTCTGCCGAGC<br>TGGTACAGGCAGGCCCCTGGGAAGGAGCGGGAGTTCGTGTCTATCATTGATGGG<br>ACCGGCTCCACCAGCTACGCGGCCTCCGTGAAAGGACGTTTCACGGCCAGCCAG<br>GATAAGGGAAAGAATATCGCTTACCTCCAGATGAACTCTCTGAAACCTGAGGAT<br>ACTGCCATGTATTACTGCAAGGCCTCATGTGTGCGCGGACGCGGCATCTCAGAA<br>TATTGGGGTCAGGGAACCCAGGTGACTGTCAGTTCTGGAGGTGGCTCCCAGGTA<br>CAGCTCCAGGAGTCCGGTGGGGGCTCCGTGCAAGCAGGGGGTTCTTTGCGGCTT<br>TCCTGTGTAGCCAGCGCCTCTACCTACTGCACCTACGACATGCACTGGTATCGC<br>CAAGCGCCGGGCAAAGGCCGCGAGTTTGTCTCTGCCATTGATTCCGATGGTACA<br>ACCCGTTATGCAGATTCCGTGAAGGGCAGATTCACCATCAGCCAGGGCACGGCG<br>AAGAATACGGTCTACTTGCAGATGAACTCTTTGCAGCCCGAGGACACAGCCATG<br>TATTACTGTAAGACAGTTTGTGTGGTAGGTTCTCGCTGGTCAGATTACTGGGGT<br>CAGGGCACACAGGTGACGGTTTCTAGT |
| hIL27<br>Ra_VH<br>H18-<br>DR594 | 1454 | CAGGTCCAGCTTCAGGAGTCTGGGGGGGGTTCCGTTCAGGCAGGGGGGTCCCTC<br>AGGCTCTCTTGTGTCGCCTCCGGCTACGTGTCTTGCGACTATTTCCTGCCCTCC<br>TGGTATCGGCAGGCTCCGGGCAAGGAGCGCGAGTTCGTGAGCATCATTGATGGC<br>ACAGGCAGTACTTCCTATGCGGCATCCGTGAAAGGGCGCTTCACTGCCAGTCAA<br>GACAAGGGCAAAAACATTGCATACCTCCAGATGAACTCCCTGAAGCCTGAAGAC<br>ACAGCTATGTATTACTGTAAGGCGAGTTGTGTACGTGGACGTGGTATCAGTGAA<br>TACTGGGGCCAGGGCACCCAGGTGACCGTGTCAAGCGGCGGTTCTGGCGGGTCA<br>GGCGGTTCCGGCCAGGTGCAGCTCCAGGAGTCCGGGGGAGGGAGCGTCCAGGCT<br>GGCGGGTCTCTGCGCCTGTCATGCGTCGCCAGCGCATCTACTTACTGTACCTAC<br>GATATGCACTGGTATCGCCAAGCGCCCGGCAAGGGCCGCGAGTTTGTCTCCGCC<br>ATTGATTCAGAGGGGACAACCCGGTATGCCGATAGTGTGAAGGGCCGTTTTACC<br>ATCAGTCAGGGCACTGCTAAGAACACTGTGTATCTCCAGATGAACAGTCTTCAG<br>CCTGAAGATACTGCTATGTATTACTGCAAAACTGTGTGTGTGGTTGGATCTCGT<br>TGGAGCGACTATTGGGGTCAGGGTACTCAGGTCACAGTGTCTTCT |
| hIL27<br>Ra_VH<br>H18-<br>DR595 | 1455 | CAAGTTCAGTTGCAGGAGTCTGGAGGTGGGTCTGTGCAGGCTGGGGGCTCCCTG<br>CGTTTGTCTTGTGTTGCGAGCGGCTACGTCTCTTGTGACTATTTCCTGCCTAGC<br>TGGTATCGGCAGGCCCCCGGCAAAGAACGCGAGCTTGTGAGCATTATCGACGGT<br>ACTGGCTCCACCAGCTATGCGGCCTCCGTGAAGGGACGCTTTACCGCCTCCCAG<br>GATAAGGGCAAGAACATCGCGTACCTCCAGATGAACTCACTGAAGCCAGAGGAC<br>ACCGCTATGTACTATTGCAAAGCAAGCTGTGTTCGCGGTAGGGGAATTTCAGAG<br>TATTGGGGCCAAGGAACCCAGGTCACCGTCAGCAGTGGAGGTGGCAGCCAGGTG<br>CAGCTCCAGGAGAGTGGGGGGGGTTCTGTGCAGGCCGGAGGCTCCCTGACCCTG<br>TCTTGCGCCGCAAGTGAGTATGCGTACTCCACATGCAACATGGGATGGTATCGC<br>CAGGCTCCCGGTAAGGAGCGCGAGCTGGTGAGCGCTTTTATCTCAGACGGCTCT<br>ACCTACTATGCCGACTCCGTCAAGGGCCGTTTCACAATCACCCGTGATAACGCC<br>AAGAATACCGTCTACTTGCAGATGAACTCTTTGAAGCCTGAGGACACAGCCATT<br>TACTATTGCTCTGCGAACTGTTACCGCCGTCTGCGGAACTATTGGGGCCAGGGC<br>ACCCAGGTGACTGTGTCCTCC |
| hIL27<br>Ra_VH<br>H18-<br>DR595 | 1456 | CAGGTGCAGCTGCAAGAGTCCGGCGGTGGCAGTGTCCAAGCTGGCGGGTCCCTG<br>AGGTTGTCCTGCGTGGCATCCGGCTATGTTAGTTGTGACTACTTTCTGCCCTCC<br>TGGTATCGCCAGGCTCCTGGCAAGGAGCGCGAATTTGTGTCTATCATTGATGGC<br>ACCGGCAGCACTTCTTATGCTGCATCTGTGAAAGGACGGTTCACCGCGAGCCAG<br>GACAAGGGTAAGAATATCGCCTACCTCCAGATGAACAGCCTGAAACCCGAGGAT<br>ACTGCCATGTACTATTGTAAGGCCAGTTGCGTGCGCGGTCGTGGCATCAGCGAG<br>TATTGGGGCCAGGGGACACAGGTGACCGTGTCCAGTGGAGGTAGCGGTGGAAGC<br>GGGGGTTCCGGCCAGGTCCAGCTCCAGGAGAGCGGGGGAGGCTCAGTGCAGGCC<br>GGAGGCAGCCTGACACTGTCCTGCGCCGCAAGCGAATATGCGTACAGCACCTGC<br>AACATGGGCTGGTATCGCCAGGCCCCAGGCAAGGAGCGTGAACTTGTGTCAGCC<br>TTCATCAGCGACGGTAGCACATATTACGCTGACTCAGTGAAGGGACGCTTCACA<br>ATCACCAGGGATAACGCCAAGAACACAGTTTACCTCCAGATGAACTCCCTGAAG<br>CCAGAGGATACCGCTATTTATTACTGTTCCGCAAATTGTTACCGTAGACTGCGC<br>AATTATTGGGGACAAGGCACACAGGTGACAGTGAGTTCT |
| hIL27<br>Ra_VH<br>H18-<br>DR596 | 1457 | CAGGTCCAGTTGCAGGAGTCTGGGGGAGGCAGCGTCCAGGCCGGGGGCAGTCTC<br>CGCCTGTCCTGTGTCGCGAGCGGGTACGTGTCTTGCGATTACTTCCTCCCCTCC<br>TGGTATCGCCAAGCGCCAGGCAAGGAACGCGAGTTCGTTTCCATCATTGACGGC<br>ACCGGAAGCACTTCCTACGCTGCCTCCGTGAAGGGGCGTTTCACAGCGTCCCAG |

TABLE 1B-continued

| Name | SEQ ID NO: | Sequence |
|---|---|---|
| | | GATAAGGGAAAGAATATCGCTTATTTGCAGATGAACTCTCTGAAGCCTGAGGAT<br>ACCGCCATGTACTATTGTAAAGCCTCCTGTGTGAGGGGTCGCGGGATCTCTGAG<br>TACTGGGGCCAAGGAACTCAGGTGACGGTGTCTAGCGGCGGAGGCTCCCAGGTG<br>CAGCTGCAAGAATCTGGCGGAGGCTTGGTGCAGCCGGGAGGCTCACTGCGTCTC<br>TCCTGCACCGCCAGCGGCCTCACTTTTGACGATAGCGTGATGGGATGGTTCCGT<br>CAGGCCCCTGGCAAGGGCCGTGAGGCGGTCAGCTGCATCTCTTCCAGTGGTGCC<br>AACGCTTTCTACGCAGACAGCGTGAAGGGTAGGTTCACCATCAGCAGAGATAAC<br>GCCAAGAACACGCTGTATCTCCAGATGAACTCCCTGAAGCCTGAGGACACTGCC<br>ACCTACTATTGCAAGCGGGGCCATGCGTGTGCTGGCTATTACCCAATTCCCTAC<br>GATGACTACTGGGGCCAGGGCACACAAGTCACGGTAAGCAGC |
| hIL27<br>Ra_VH<br>R18-<br>DR596 | 1458 | CAGGTCCAGCTCCAGGAATCAGGTGGCGGAAGCGTGCAGGCTGGGGGCTCTCTG<br>CGCCTGTCTTGTGTGGCCAGTGGCTACGTTAGCTGCGATTATTTCCTGCCATCT<br>TGGTACAGGCAGGCCCCTGGCAAGGAGCGTGAGTTCGTCTCTATCATTGATGGA<br>ACAGGTTCCACCAGTTACGCCGCTTCTGTTAAGGGCCGCTTCACCGCCTCACAG<br>GATAAGGGCAAGAACATCGCTTACCTCCAAATGAACTCCCTGAAGCCCGAGGAC<br>ACTGCCATGTATTACTGTAAGGCTTCTTGTGTGCGCGGTCGCGGCATTTCCGAA<br>TACTGGGGACAAGGAACCCAGGTAACAGTGTCCTCTGGAGGCAGTGGAGGCTCA<br>GGGGGCTCTGGTCAGGTCCAACTCCAGGAGAGCGGCGGTGGACTGGTGCAGCCC<br>GGTGGCTCTCTCAGGCTGTCCTGTACGGCGAGCGGCCTCACCTTTGATGACTCT<br>GTTATGGGCTGGTTCCGCCAAGCCCCTGGGAAGGGGGGGGAGGCTGTGAGCTGT<br>ATTTCCTCTAGGGGGGCGAACGCTTTCTACGCCGATTCAGTGAAAGGCCGTTTC<br>ACCATCAGTCGCGACAACGCCAAAAACACGCTGTACTTGCAGATGAACTCTTTG<br>AAACCAGAGGACACCGCAACTTACTATTGTAAACGCGGCCACGCATGTGCTGGC<br>TATTACCCTATCCCCTACGATGACTACTGGGGCCAGGGCACCCAGGTTACAGTG<br>TCATCT |
| hIL27<br>Ra_VH<br>H19-<br>DR591 | 1459 | CAAGTCCAGTTGCAGGAATCCGGCGGTGGATCAGTGCAGGCAGGCGGTAGCTTG<br>AGGCTGTCTTGTAGAGCGTCCGGTTCAACTTACTCCAACTACTGCCTGGGCTGG<br>TTTCGGCAGATTACAGGCAAGGAGCGCGAGGGAGTGGCCGTGATAAATTGGGTG<br>GGTGGAATGCTGTATTTTGCCGACTCCGTGAAGGGCCGGTTCACCGTGTCTCAG<br>GACCAGGCCAAGAACACCGTCTACCTTCAGATGAACTCCCTGAAGCCTGAGGAT<br>ACCGCCATGTATTACTGCGCCGCTGAGAGTGTCAGCTCTTTTAGTTGCGGTGGC<br>TGGCTGACCCGCCCCGACCGTGTGCCGTACTGGGGCCAGGGAACACAGGTGACA<br>GTGAGTTCCGGTGGGGGCTCCCAAGTGCAACTTCAGGAGTCTGGCGGTGGCAGC<br>GTGCAGGCAGGGGGCTCTCTGCGTCTGTCATGCACCGCCAGCGGAGCCATCGCC<br>TCCGGTTACATCGACTCCCGCTGGTGTATGGCTTGGTTTCGCCAGGCTCCCGGC<br>AAGGAGCGTGAAGGCGTGGCCGCGATCTGGCCTGGGGGGGGCTGACTGTTTTAT<br>GCTGACTCAGTGAAGGGTCGCTTTACCATCTCCCGCGACCACGCAAAGAACACC<br>CTTTATTTGCAGATGAATAACCTGAAGCCGGAAGACACTGCCATGTACTATTGC<br>GCAGCTGGCTCTCCCCGCATGTGTCCGTCTCTGGAGTTCGGTTTCGATTACTGG<br>GGTCAGGGCACTCAGGTTACCGTGTCCAGC |
| hIL27<br>Ra_VH<br>H19-<br>DR591 | 1460 | CAGGTGCAGTTGCAGGAAAGTGGAGGGGGGTCAGTTCAGGCTGGGGGTTCCCTG<br>AGGCTGTCCTGTCGTGCAAGTGGCTCAACGTATTCAAACTATTGCCTTGGTTGG<br>TTTAGGCAGATCACCGGCAAGGAGCGCGAGGGCGTTGCTGTCATCAACTGGGTC<br>GGCGGGATGCTGTACTTTGCCGACAGCGTCAAGGGCAGATTTACCGTCTCCCAG<br>GATCAGGCCAAGAACACAGTGTATCTCCAGATGAACTCTTTGAAGCCCGAAGAC<br>ACAGCAATGTACTATTGTGCGGCTGAATCTGTTAGCTCCTTTTCCTGCGGCGGT<br>TGGTTGACGAGACCGGATCGGGTCCCGTACTGGGGTCAGGGGACCCAGGTCACG<br>GTCAGCTCCGGGGGCAGCGGCGGTAGTGGAGGCTCCGGTCAGGTGCAGCTCCAG<br>GAGAGCGGGGGGGGTAGCGTGCAAGCAGGGGGCAGTCTGCGGCTGAGCTGTACT<br>GCGAGCGGAGCCATCGCCAGCGGATATATCGACAGCCGCTGGTGTATGGCCTGG<br>TTCCGCCAGGCTCCCGGAAAAGAGCGCGAGGGAGTCGCTGCGATTTGGCCAGGG<br>GGCGGATTGACAGTATACGCCGACTCTGTGAAAGGCAGATTTACTATCAGCCGC<br>GATCACGCCAAGAACACTCTGTACCTCCAGATGAATAACCTCAAACCGGAGGAC<br>ACCGCCATGTATTACTGCGCTGCCGGGTCCCCCAGGATGTGTCCTAGTCTGGAG<br>TTCGGTTTCGACTACTGGGGCCAAGGAACCCAGGTGACCGTCTCTAGC |
| hIL27<br>Ra_VH<br>H19-<br>DR592 | 1461 | CAGGTGCAGTTGCAGGAGTCAGGAGGGCGGAGTGTTCAGGCCGGAGGCAGCCTG<br>CGCTTGAGCTGCCGGGCGTCTGGCAGCACCTACAGCAACTATTGCCTGGGTTGG<br>TTCCGTCAGATCACCGGCAAGGAGCGGGAGGGCGTGGCTGTCATCAACTGGGTG<br>GGTGGAATGCTGTATTTTGCGGATAGTGTGAAGGGACGGCTCACAGTCTCTCAG<br>GATCAGGCAAAGAATACCGTGTACCTTCAGATGAACTCCCTGAAGCCTGAAGAC<br>ACTGCCATGTACTATTGCGCCGCTGAGAGCGTGTCCAGCTTCTCTTGCGGTGGC<br>TGGCTCACCAGGCCTGACCGTGTGCCTTACTGGGGCCAGGGTACGCAGGTGACC<br>GTATCTAGGGGGGGGGGTTCTCAGGTCCAGTTGCAGGAGTCCGGTGGGCGGGTCC<br>GTCCAGGCGGGCGGTAGCCTGCGGCTGAGTTGCACCGCTCCTGGATTTACCAGC<br>AACAGTTGTGGCATGGACTGGTATCGTCAGGCCCCCGGAAAGGAACGCGAGTTC<br>GTGAGCAGTATCTCCACAGACGGCACGACCGGCTACGCTGACTCCGTCAAGGGC<br>CGTTTTACCATCTCCAAAGACAAAGCAAAGGATACAGTGTATCTCCAGATGAAC<br>TCACTGAAGCCCGAGGACACGGGTATGTATAGCTGCAAGACTAAGGACGGAACC<br>ATTGCCACAATGGAGCTTTGTGACTTCGGGTACTGGGGACAGGGAACACAAGTA<br>ACGGTCAGCTCC |
| hIL27<br>Ra_VH | 1462 | CAGGTCCAGTTGCAGGAATCCGGGGGGGGATCAGTGCAGGCTGGCGGGTCTCTG<br>CGCCTCTCATGCAGAGCCTCCGGCTCCACCTATTCTAACCACTGCTTGGGCTGG |

TABLE 1B-continued

| Name | SEQ ID NO: | Sequence |
|---|---|---|
| H19-<br>DR592 | | TTCAGACAGATCACCGGCAAAGAGCGCGAGGGCGTTGCAGTGATAAATTGGGTG<br>GGTGGAATGCTGTATTTTGCAGACTCCGTCAAGGGAAGGTTCACCGTGAGTCAG<br>GATCAAGCCAAGAACACCGTGTATCTGCAAATGAACTCTCTGAAGCCCGAGGAC<br>ACCGCTATGTATTACTGTGCAGCTGAAAGCGTGTCCTCTTTCTCTCGCGGAGGC<br>TGGCTTACTAGACCTGATCGTGTGCCATATTGGGGTCAGGGCACCCAGGTCACA<br>GTTTCTTCCGGTGGCTCAGGCGGATCTGGGGGGTCCGGGCAGGTACAGCTCCAG<br>GAGTCTGGTGGCGGTTCCGTTCAGGCTGGGGGCTCCCTGCGTCTCTCCTGCACC<br>GCGCCCGGCTTCACAAGCAACTCCTGCGGTATGGACTGGTATCGCCAAGCGCCT<br>GGAAAAGAGCGCGAGTTCGTCTCTAGCATTTCCACTGACGGTACTACCGGCTAC<br>GCCGACTCCGTGAAGGGGCGCTTCACTATTTCTAAGGATAAGGCGAAGGATACT<br>GTGTACCTCCAGATGAACTCACTGAAGCCCGAGGACACTGGGATGTATAGTTGC<br>AAGACCAAGGATGGCACAATCGCCACTATGGAATTGTGTGACTTCGGCTACTGG<br>GGGCAGGGCACCCAGGTGACAGTGTCCAGC |
| hIL27<br>Ra_VH<br>H19-<br>DR593 | 1463 | CAGGTCCAGTTGCAGGAGTCCGGGCGGTGTTCCGTCCAAGCCGGAGGCTCACTC<br>AGACTCTCTTGTCGCGCCTCAGGAAGCACTTACTCCAACTACTGCCTGGGGTGG<br>TTTCGCCAGATCACTGGCAAGGAGGGGGAGGGTGTCGCGGTAATAAATTGGGTC<br>GGCGGTATGCTGTATTTCGCGGACTCCGTGAAGGGCCGTTTCACCGTATCACAG<br>GACCAGGCCAAGAACACTGTGTATCTCCAGATGAACTCACTGAAGCCCGAAGAT<br>ACTGCAATGTATTACTGGGGGGCTGAGAGCGTGTCTTCCTTCTCTTGCGGCGGA<br>TGGCTCACACGGCCAGACCGTGTGCCATACTGGGGTCAGGGCACCCAAGTTACA<br>GTCTCCAGGGGGGGGGCTCCCAAGTCCAGCTGCAAGAGAGCGGGGGCGGGCTCC<br>GTGCAGGCTGGAGGTTCTCTGCGTTTGTCCTGTGCTGCCTCAGGATACCCTTAT<br>AGTAACGGTTACATGGGCTGGTTTCGGCAGGCTCCAGGGAAGGAAAGGGAGGGG<br>GTGGCTACAATTTACACCGGCGACGGAAGGACCTATTACGCCGACTCTGTGAAA<br>GGTCGCTTCACCATTTCCCGTGACAACGCGAAGAATACAGTTGATCTTCAGATG<br>TCTTCCCTGAAGCCCGAGGACACAGCGATGTATTACTGCGCTGCCCGTGCTGCC<br>CCTCTCTACAGCTCTGGCTCTCCCCTGACCCGCGCCCGTTACAACGTGTGGGGC<br>CAGGGGACTCAGGTCACAGTCTCATCC |
| hIL27<br>Ra_VH<br>H19-<br>DR593 | 1464 | CAAGTGCAGCTGCAAGAGAGCGGAGGTGGATCTGTGCAGGCTGGTGGGTCTCTG<br>CGCCTCTCTTGCCGTGCGTCAGGCTCCACCTACTCTAATTATTGCCTCGGTTGG<br>TTCCGGCAGATTACGGGCAAGGAGCGCGAGGGTGTGGCAGTTATCAACTGGGTT<br>GGGGGTATGTTGTACTTTGCTGACTCCGTCAAGGGACGTTTCACTGTGAGTCAA<br>GACCAGGCTAAGAACACTGTGTACCTCCAGATGAATAGTCTGAAGCCTGAGGAT<br>ACCGCCATGTATTACTGCGCAGCTGAGAGCGTGAGCAGTTTTTCCTGTGGCGGA<br>TGGCTTACCAGACCTGATCGCGTGCCGTACTGGGGCCAGGGGACCCAGGTGACT<br>GTTAGTTCTGGAGGCAGCGGAGGCTCCGGTGGCAGCGGTCAGGTACAGCTCCAG<br>GAATCTGGTGGGGGTAGCGTGCAGGCAGGGGGCTCTCTTCGCCTGAGCTGTGCA<br>GCTTCTGGATACCCATATAGCAACGGTTACATGGGCTGGTTTCGCCAAGCCCCC<br>GGCAAGGAGAGAGAAGGTGTGGCTACCATTTATACCGGCGACGGGCGCACTTAC<br>TATGCAGACTCCGTCAAAGGGCGGTTTACAATCTCTAGGGACAACGCCAAGAAT<br>ACCGTCGATCTTCAGATGTCTTCCCTGAAGCCGGAGGATACCGCCATGTATTAC<br>TGTGCGGCCAGGGCTGCCCCTCTCTACTCCTCTGGATCACCTCTGACTAGGGCT<br>CGCTATAACGTATGGGGTCAGGGAACACAGGTCACGGTGTCATCT |
| hIL27<br>Ra_VH<br>H19-<br>DR594 | 1465 | CAGGTTCAGCCCCAAGAGAGCGGCGGTGGCTCAGTGCAGGCAGGTGGCTCACTT<br>AGGCTGAGTTGCAGAGCTTCCGGCTCAACATACTCCAACTATTGTCTCGGCTGG<br>TTCAGGCAGATCACTGGTAAGGAGCGCGAGGGGTGGGCCGTCATCAACTGGCGG<br>GGTGGAATGCTGTACTTTGCCGACTCTGTAAAGGGTCGTTTTACTGTGTCTCAG<br>GACCAGGCCAAGAACACAGTGTACCTTCAGATGAACTCTCTGAAGCCGGAGGAT<br>ACGGCAATGTACTATTGCGCTGCCGAGAGTGTTAGTTCATTCTCCTGTGGAGGC<br>TGGCTGACTCGCCCGGATCGTGTGCCGTACTGGGGCCAGGGCACCCAGGTGACC<br>GTTAGCTCCGGCGGTGGCTCCCAGGTGCAGCTGCAAGAGAGTGGTGGAGGCTCC<br>GTGCAGGCAGGTGGCTCCCTTCGTCTTTCTTGTGTCGCCTCTGCTTCAACCTAC<br>TGCACATACGACATGCACTGGTATCGCCAGGCCCCTGGCAAGGGGCGCGAGTTC<br>GTTAGTGCCATCGACAGTGACGGCACTACCAGATACGCCGACAGCGTCAAGGGC<br>CGCTTCACCATCAGCCAGGGAACAGCTAAAAACACCGTCTACCTCCAGATGAAC<br>TCCTTGCAGCCAGAGGACACAGCCATGTATTACTGCAAAACTGTCTGCGTCGTG<br>GGGTCCAGATGGAGCGACTACTGGGGCCAAGGCACGCAGGTTACCGTGAGCAGC |
| hIL27<br>Ra_VH<br>H19-<br>DR594 | 1466 | CAGGTCCAGTTGCAGGAGTCCGGGGGGGGTTCTGTGCAGGCTGGAGGCAGCCTC<br>AGACTCTCTTGCAGGGCTTCTGGATCAACTTATTCTAATTATTGCCTCGGTTGG<br>TTCCGCCAAATCACAGGCAAGGAGAGGGAGGGAGTGGCGGTGATTAACTGGGTG<br>GGCGGTATGCTGTACTTCGCCGACTCCGTGAAAGGTCGTTTCACTGTCTCTCAG<br>GATCAGGCCAAGAACACTGTTTACCTCCAGATGAACTCTCTGAAGCCCGAAGAT<br>ACGGCCATGTACTATTGCGCTGCCGAATCCGTCTCCTCTTTTTCCCGCGGAGGC<br>TGGCTGACACGCCCCGACCGCGTCCCCTATTGGGGTCAGGGGACTCAGGTCACC<br>GTCAGCTCTGGCGGGAGCGGAGGCAGCGGGGGCAGCGGCCAGGTCCAGCTTCAG<br>GAAAGCGGAGGTGGCTCCGTGCAGGCTGGGGGAAGCCTGAGACTGTCCTGCGTG<br>GCTTCAGCTTCCACCTACTGCACCTATGACATGCACCGGTATAGGCAAGCGCCA<br>GGAAAGGGCAGGGAGTTCGTTTCTGCTATTGATTCTGACGGAACAACTAGATAC<br>GCAGACTCCGTCAAGGGAAGGTTCACCATCTCCCAGGGCACCGCCAAGAACACT<br>GTCTACCTCCAGATGAACAGTCTGCAACCAGAAGACACCGCTATGTATTACTGC<br>AAGACCGTGTGCGTGGTCGGGTCCAGATGGTCCGATTACTGGGGCCAGGGAACA<br>CAGGTGACTGTCTCATCT |

TABLE 1B-continued

| Name | SEQ ID NO: | Sequence |
|---|---|---|
| hIL27 Ra_VH H19-DR595 | 1467 | CAGGTGCAGCTCCAGGAATCTGGGGGAGGTTCAGTGCAGGCAGGTGGCTCCCTG CGCCTGAGTTGCAGGGCGTCCGGTAGTACCTACTCAAACTACTGCCTGGGGTGG TTTAGACAAATCACCGGAAAGGAAAGGGAGGGCGTCGCAGTGATAAATTGGGTG GGCGGTATGCTGTACTTCGCCGACTCTGTGAAGGGACGCTTTACCGTCTCCCAG GATCAGGCTAAGAACACTGTGTATTTGCAGATGAACTCCCTGAAACCAGAGGAC ACAGCCATGTATTACTGTGCTGCCGAAAGCGTCTCTAGTTTTTCCTGCGGAGGG TGGCTTACCCGTCCCGACAGAGTTCCTTATTGGGGCCAGGGAACCCAGGTGACA GTTTCCTCTGGTGGGGGTCTCAGGTTCAGCTTCAGGAGTCTGGGGGGGGCTCT GTGCAGGCTGGCGGATCTCTGACTCTGAGCTGCGCCGCGAGCGAGTACGCCTAC TCAACCTGCAACATGGGCTGGTATCGCCAGGCACCGGGCAAGGAACGGGAGCTG GTGTCTGCATTCATCTCAGACGGTTCTACGTATTACGCCGACTCCGTGAAGGGT CGCTTTACTATTACCCGCGACAACGCTAAGAACACGGTGTACTTGCAGATGAAC AGCCTGAAGCCTGAGGATACTGCCATCTATTACTGTTCCGCTAACTGCTATAGA CGCCTGCGCAATTACTGGGGACAGGGGACGCAAGTGACAGTGTCTAGC |
| hIL27 Ra_VH H19-DR595 | 1468 | CAAGTGCAGTTGCAGGAATCCGGGGGAGGCTCCGTACAGGCCGGTGGATCACTG CGCCTGTCTTGTCGGGCCTCCGGGTCAACCTATAGCAACTACTGTCTGGGCTGG TTTCGTCAGATCACAGGTAAAGAGCGCGAGGCGGGTCGCCGTCACAACTGGGTG GGCGGTATGCTGTACTTCGCTGACAGTGTGAAGGGTCGGTTCACCGTTTCCCAG GATCAAGCCAAAAACACCGTCTACCTCCAGATGAACTCCTTGAAGCCCGAAGAC ACCGCCATGTATTACTGCGCCGCAGAGAGTGTGTCCTCTTTCTCCCGCGGTGGG TGGTTGACTAGGCCGGACCGTGTTCCCTACTGGGGCCAGGGAACCCAAGTGACC GTTAGCTCAGGGGGCTCCGGTGGCTCTGGTGGCTCTGGTCAGGTGCAGCTCCAG GAGTCTGGAGGCGGGTCAGTTCAGGCTGGGGGCAGTCTGACTCTGTCCTGTGCA GCAAGCGAGTACGCTTACTCTACCTGTAACATGGGTTGGTATCGCCAGGCCCCA GGGAAGGAACGCGAGCTTGTGTCAGCCTTTATCTCCGATGGCAGCACTTATTAC GCAGATTCCGTAAAGGGACGCTTCACCATCACCCGTGACAACGCCAAGAATACC GTCTACCTCCAGATGAACAGCCTGAAGCCGGAGGACACCGCCATCTATTACTGC TCCGCCAACTGCTACCGGCGTCTGCGCAACTACTGGGGCCAGGGCACCCAGGTG ACCGTCTCATCA |
| hIL27 Ra_VH H19-DR596 | 1469 | CAGGTTCAACTCCAGGAGTCCGGCGGAGGGTCCGTGCAGGCTGGAGGTTCCCTC CGGTTGTCCTGTCGTGCGTCCGGTTCCACCTACTCAAATTATTGTCTGGGCTGG TTCCGCCAGATTACTGGCAAGGAAAGAGAGGGCGTAGCCGTCATCAACTGGGTT GGGGGAATGTTGTACTTCGCCGACAGCGTGAAAGGCCGCTTTACGGTTTCCCAG GACCAGGCTAAGAACACTGTATACCTTCAGATGAACTCCCTGAAGCCGGAGGAC ACCGCTATGTACTATTGCGCCGCTGAGTCTGTCTCCAGCTTCTCTTGCGGGGGA TGGTTGACCCGCCCTGATCGCGTGCCATACTGGGGGCAGGGTACTCAAGTGACA GTGTCCTCTGGCGGAGGCTCCCAGGTTCAGTTGCAGGAGAGGGGCGGTGGACTG GTTCAGCCTGGTGGGAGTCTCCGCCTGAGCTGCACAGCCAGCGGACTGACTTTC GATGACTCAGTGATGGGATGGTTCAGACAGGCTCCGGGAAAGGGCCGTGAGGCG GTCAGCTGTATCTCCTCTTCCGGCGCTAACGCCCTCTACGCTGATTCCGTAAAG GGACGGTTTACCATTTCTCGGGATAACGCCAAGAATACCCTGTATCTCCAGATG AACTCTCTCAAGCCCGAGGATACCGCCACCTATTACTGTAAAAGGGGCCACGCA TGTGCTGGATATTACCCGATTCCCTATGATGACTATTGGGGGCAAGGAACGCAG GTTACCGTTAGTTCT |
| hIL27 Ra_VH H19-DR596 | 1470 | CAGGTGCAGCTCCAGGAGTCCGGTGGGGGTTCCGTCCAGGCAGGTGGCTCCCTG CGGCTGTCTTGTAGGGCTTCTGGCTCTACCTACTCCAACTACTGTCTGGGATGG TTCCGCCAGATCACAGGCAAGGAGAGGGAGGGCGTAGCAGTGATTAACTGGGTT GGGGGTATGCTGTATTTCGCCGATTCCGTGAAGGGTCGCTTCACCGTGTCCCAG GATCAGGCCAAAAACACTGTTTATTTGCAGATGAACTCCCTGAAGCCTGAGGAC ACCGCTATGTATTACTGTGCAGCGGAGTCCGTGTCATCCTTCTCCTGTGGTGGC TGGCTGACTCGTCCAGACCGTGTGCCTTATTGGGGACAGGGCACCCAGGTGACC GTGTCCTCAGGGGGTTCCGGTGGCTCCGGTGGCAGCGGTCAGGTGCAGCTTCAG GAGAGCGGTGGGGGCCTGGTGCAGCCCGGAGGTTCACTGAGACTGAGCTGCACG GCCAGCGGTCTGACCTTCGATGACAGCGTGATGGGTTGGTTCCGTCAAGCGCCG GGCAAGGGACGCGAAGCAGTGTCCTGTATCAGTTCCTCTGGTGCTAACGCCTTC TATGCCGACAGTGTGAAGGGACGCTTTACTATCTCCCGCGACAACGCCAAGAAT ACCCTGTACCTCCAGATGAACTCTCTGAAGCCCGAGGATACCGCCACGTATTAC TGTAAGCGCGGTCACGCCTGTGCAGGGTACTATCCCATCCCCTACGATGACTAC TGGGGCCAGGGAACTCAGGTCACGGTCTCCTCA |
| hIL27 Ra_VH H20-DR591 | 1471 | CAGGTTCAGCTCCAGGAGAGTGGGGGCGGGCTGGTGCAGCCCGGCGGATCACTC CGGCTGTCCTGTGCCGCGAGTGGGTTTACGTTTTCCTCATACCCTATGTCCTGG GTCCGCCAGGCTCCGGGCAAAGGACTGGAATGGGTAAGCACAATTAGCTCTGGG GGCGATACAACTCTGTATGCGGACTCTGTAAAAGGACGCCTCACCAGCTCTCGC GACAACGCAAAGAATACACTCTACCTCCAGCTTAACTCTCTGAAAACAGAGGAC ACAGCAATGTATTACTGTGCAAAGCGCATTGATTGCAATTCCGGCTACTGCTAC AAGCGCTCTTATTGGTGGGCAAGGTACGCAGGTGACGGTTAGCTCCGGGGAGGC TCCCAGGTGCAGTTGCAGGAATCCGGCGGAGGCTCAGTGCAAGCGGGAGGGTCC CTGAGACTGAGCTGTACTGCATCCGGGGCTATCGCCAGCGGATACATTGATTCA CGGTGGTGTATGGCTTGGTTCCGGCAAGCCCCTGGCAAGGAGCGCGAGGGCGTG GCGGCTATCTGGCCCGGCGGTGGACTGACCGTGTACGCTGACTCCGTCAAGGGC CGCTTTACTATCAGCCGCGACCACGCTAAGAACACGCTGTACCTCCAGATGAAC |

TABLE 1B-continued

| Name | SEQ ID NO: | Sequence |
|---|---|---|
| | | AATCTGAAGCCCGAGGACACCGCTATGTACTATTGCGCAGCTGGCTCACCTCGG ATGTGCCCTTCCCTTGAGTTTGGGTTCGATTACTGGGGCCAAGGCACCCAGGTG ACCGTTAGCAGT |
| hIL27 Ra_VH H20- DR591 | 1472 | CAGGTGCAGCTGCAAGAATCCGGCGGTGGCCTGGTGCAGCCAGGAGGCTCCCTG CGGCTGTCCTGTGCTGCGTCTGGCTTCACCCTTAGCTCTTATCCCATGTCTTGG GTGCGTCAGGCTCCGGGAAAGGGCTTGGAATGGGTGTCCACCATTTCTAGCGGA GGCGACACCACTCTCTACGCTGACTCCGTGAAAGGGCGCTTCACCTCCAGCAGA GACAACGCTAAGAACACCCTGTACTTGCAGCTTAATTCTCTGAAGACCGAGGAT ACAGCAATGTACTATTGCGCCAAGGGGATTGATTGCAACTCCGGCTATTGTTAC AAGAGGTCCTATTGGGGCCAGGGAACTCAGGTAACTGTTAGTTCAGGAGGCTCC GGTGGATCTGGCGGAAGCGGACAGGTGCAGCTTCAGGAATCTGGCGGTGGAAGC GTCCAGGCTGGAGGTTCCCAGAGGCTCAGCTGCACCGCCTCTGGTGCCATTGGG TCCGGGTACATTGATAGCCGCTGGTGCATGGCCTGGTTTAGACAAGCGCCAGGC AAGGAAAGAGAGGGTGTGGCAGCCATCTGGCCGGGCGGAGGTCTGACTGTGTAC GCCGACAGCGTGAAGGGCCGTTTCACTATCTCTCGCGACCACGCCAAGAACACT TTGTATCTTCAGATGAACAATCTGAAGCCCGAAGATACAGCCATGTATTACTGT GCAGCCGGTAGCCCTAGAATGTGCCCCAGTCTGGAGTTCGGCTTCGATTATTGG GGTCAGGGTACTCAGGTCACCGTCAGCTCT |
| hIL27 Ra_VH H20- DR592 | 1473 | CAGGTGCAGCTTCAAGAATCTGGAGGGGGCCTGGTTCAGCCAGGGGGTTCTCTG CGTCTGAGCTGTGCCGCGTCTGGATTCACATTCTCATCCTATCCAATGAGCTGG GTGCGTCAGGCTCCCGGTAAAGGGCTGGAATGGGTGTCTACTATCTCCAGCGGA GGCGACACTACCCAGTATGCGGACAGCGTCAAGGGACGCTTCACGTCCAGCAGA GACAACGCCAAAAATACCTTGTACTTGCAGCTGAACAGCCTGAAGACGGAGGAT ACAGCTATGTACTATTGCGCTAAAAGAATCGACTGCAACTCCGGCTACTGTTAC AAGAGAAGCTATTGGGGCCAGGGTACTCAGGTCACCGTGTCTAGCGGAGGTGGC TCCCAAGTGCAGTTGCAGGAGTCTGGGGCGGGGTTCCGTCCAGGCTGGGGCTCC TTGCGTCTTTCCTGTACTGCGCCGGGGTTTACCAGCAACTCATGCGGCATGGAT TGGTATCGTCAAGCGCCTGGTAAGGAGAGGGAATTTGTCTCATCCATCTCCACC GACGGCACGACCGGCTATGCTGACAGCGTAAAGGTCGTTTTACCATTTTCTAAG GATAAGGCCAAGGATACCGTCTACCTCCAGATGAACTCTCTGAAGCCTGAGGAT ACTGGCATGTACTCCTGCAAGACTAAGGATGGCACCATTGCCACGATGGAACTG TGTGATTTCGGGTACTGGGGTCAAGGCACCCAGGTTACCGTCTCCAGC |
| hIL27 Ra_VH H20- DR592 | 1474 | CAGGTCCAGCTTCAGGAAAGTGGCGGAGGCCTTGTCCAACCTGGGGGTTCACTC AGACTGTCTTGCGCTGCCAGTGGTTTCACCTTTTCTTCCTACCCCATGTCATGG GTGCGCCAGGCCCCAGGGAAGGGATTGGAATGGGTCTCCACAATCTCCTCTGGC GGTGATACCACACTGTACGCTGACTCTGTCAAGGGACGCTTCACCTCCAGCCGT GATAACGCCAAGAACACCCCGTACTTGCAACTGAACAGTTTGAAAACCGAGGAT ACCGCTATGTATTACTGGGCCAAGCGCATTGATTGCAACCCCGGCTATTGTTAC AAGCGCAGCTATTGGGGCCAGGGCACCCAGGTGACTGTCTCCTCTGGTGGCTCA GGCGGAAGCGGAGGCTCAGGGCAAGTACAGCTCCAGGAGTCAGGTGGCGGTTCC GTACAAGCCGGGGGCAGCCTGCGTCTTAGTTGCACCGCACCAGGGTTCACCTCT AACAGCTGCGGAATGGATTGGTACAGGCAAGCGCCCGGCAAGGAACGCGAGTTT GTAAGCTCCATCTCCACCGATGGCACAACCGGGTACGCAGACTCTGTGAAGGGG CGCTTCACGATCAGCAAGGACAAAGCGAAGGATACTGTGTACCTGCAAATGAAC TCCCTCAAGCCCGAAGACACCGGCATGTATTCCCGTAAGACCAAGGACGGCACC ATCGCCACTATGGAGCTGTGCGATTTTGGATACTGGGGACAGGGCACCCAGGTG ACTGTCTCCTCC |
| hIL27 Ra_VH H20- DR593 | 1475 | CAAGTACAGTTGCAGGAGAGCGGTGGCGGACTGGTACAGCCAGGCGGTTCCCTG CGCTTGAGCTGTGCTGCCTCCGGCTTCACCTTCCCCAGCTACCCTATGTCATGG GTGCGCCAGGCCCCTGGCAAAGGTCTGGAATGGGTCTCTACCATCTCATCTGGA GGGGACACAACCCTTTATGCAGACAGCGTCAAAGGACGTTTCACTTCTTCACGG GACAACGCGAAGAACACCCCGTACCTTCAGCTGAACTCCCTGAAGACTGAGGAT ACCGCAATGTACTATTGCGCCAAGCGGATTGATTGTAATTCCGGCTATTGTTAT AAGCGCTCCTATTGGGGGCAGGGGACCCAGGTAACTGTTTCCTCAGGAGGCGGT TCCCAGGTTCAGCTCCAGGAGTCTGGTGGAGGCTCCGTCCAAGCCGGGGGCTCA CTGCGCCTGTCATGCGCAGCCAGCGGTTACCCCTATAGCAACGGTTATATGGGT TGGTTCAGGCAGGCCCCCGGTAAAGAACGCGAGGCGCGTCGTACCATCTACACG GGCGACGGCAGGACTTATTACGCCGACTCTGTCAAGGGGCGTTTTACTATCTCA CGCGACAATGCCAAGAACACGGTGGACCTTCAAATGTCCAGTCTGAAGCCGGAA GACACTGCCATGTATTACTGCGCAGCGCGTGCGGCCCCTCTGTATTCCTCAGGC AGCCCTCTGACCCGCGCTCGCTACAACGTGTGGGGCCAAGGCACGCAAGTAACT GTGTCCTCT |
| hIL27 Ra_VH H20- DR593 | 1476 | CAGGTGCAGCCCCAGGAGTCTGGCGGTGGCCTGGTACAGCCGGGAGGCTCCCTG CGCCTGAGCTGTGCAGCTTCTGGCTTCACCTTCTCTTCCTACCCAATGTCCTGG GTGCGTCAGGCTCCCGGTAAGGGCCTTGAGTGGGTGTCTACCATTTCTTCCGGG GGTGATACCACGTTGTACGCAGACTCCGTGAAGGGCAGGCTCACCAGCTCTGGG GACAATGCCAAGAACACTCTGTACTTGCAGCTGAACTCTTTGAAGACCGAGGAT ACCGCAATGTACTATTGTGCAAAGAGGATCGACTGTAACTCTGGCTATTGTTAT AAGAGAAGCTACTGGGGGCAGGGTACTCAGGTGACCGTCTCAAGCGGCGGAAGC GGTGGGTCTGGAGGGAGTGGGCAGGTGCAGCTCCAGGAGTCTGGAGGGGGGGAGC GTGCAGGCAGGCGGTAGCCTCCGGCTGTCATGCGCCGCTTCCGGTTATCCCTAT AGCAACGGATACATGGGATGGTTCCGTCAGGCTCCCGGCAAGGAAAGGGAGGGT |

TABLE 1B-continued

| Name | SEQ ID NO: | Sequence |
|---|---|---|
| | | GTGGCCACGATCTACACAGGGGATGGAGAACTTATTACGCCGACTCCGTTAAG GGACGCTTCACTATCAGCCGCGACAACGCTAAAAACACTGTGGACCTTCAGATG TCCAGCTTGAAGCCTGAGGATACCGCCATGTATTACTGTGCAGCTCGCGCCGCT CCCCTGTACTCAAGCGGTTCACCCCTCACCCGCGCTCGCTACAACGTCTGGGGG CAGGGCACACAGGTGACTGTGTCCTCT |
| hIL27 Ra_VH H20- DR594 | 1477 | CAGGTGCAGTTGCAAGAGAGCGGGGGGGGCCTGGTCCAGCCTGGGGGCTCACTG CGTCTCTCCTGCGCCGCATCTGGATTTACCTTCTCCTCTTATCCTATGAGTTGG GTACGCCAGGCTCCTGGCAAGGGTTTGGAGTGGGTTTCCACAATCTCTAGCGGA GGTGACACTACACTTTACGCTGATAGCGTCAAGGGACGCTTTACCTCATCCAGG GACAACGCTAAGAACACCCTCCATCTCCAGCTGAACTCCCTCAAGACTGAGGAT ACAGCCATGTACTATTGCGCTAAACGCATCGACTGTAACAGCGGATACTGCTAC AAGCGTAGCTACTGGGGCCAGGGCACCCAGGTTACCGTCAGCTCTGGAGGTGGG TCCCAGGTCCAGTTGCAGGAAAGTGGCGGTGGCTCAGTGCAAGCTGGCGGATCT CTGCGCCTGTCCTGTGTGGCCAGCGCGTCTACCTACTGTACCTACGATATGCAC TGGTACAGACAAGCGCCTGGTAAAGGTAGGGAGTTTGTGAGCGCTATCGACTCC GATGGAACCACGAGGTATGCAGACTCCGTCAAGGGAAGGTTCACTATTTCCCAG GGCACAGCCAAAAACACCGTCTACTTGCAGATGAACAGCTTGCAGCCCGAGGAC ACCGCGATGTACTATTGCAAAACGGTGTGCGTAGTGGGGTCCCGCTGGAGCGAC TACTGGGGCCAGGGAACTCAGGTAACAGTCTCCTCC |
| hIL27 Ra_VH H20- DR594 | 1478 | CAGGTCCAGCTGCAAGAGTCTGGGGGGGGACTCGTTCAGCCTGGGGGCAGCCTG CGGCTCAGCTGTGCAGCCTCCGGCTTCACTTTTTCCAGCTACCCTATGTCCTGG GTGCGCCAGGCTCCCGGTAAGGGCCTGGAGTGGGTGTCCACGATTTCTAGTGGG GGTGATACGACCCTGTATGCCGACAGTGTAAAGGGTCGCTTCACAAGCAGTCGT GACAACGCTAAAAACACCCTGTACCTTCAGCTCAATTCCCTGAAAACAGAGGAC ACTGCTATGTATTACTGCGCGAAGCGTATCGACTGTAACAGCGGGTATTGCTAT AAGCGCAGTTATTGGGGCCAGGGCACGCAGGTCACCGTGAGTTCCGGGGGTTCT GGTGGCAGCGGCGGTTCTGGGCAGGTTCAGCTTCAGGAGAGTGGCGGGGGGTCC GTTCAGGCCGGGGGCTCTTTGCGGCTGTCATGCGTGGCGTCCGCTTCTACCTAC TGCACCTATGATATGCACTGGTATCGCCAAGCGCCCGGCAAGGGTCGCGAGTTT GTCAGCGCCATCGACTCCGACGGCACGACTCGGTACGCCGACTCTGTCAAGGGG CGGTTCACGATCTCCCAGGGCACCGCCAAGAACACAGTGTATCTTCAGATGAAC TCTCTGCAACCTGAAGATACTGCAATGTACTATTGTAAGACCGTGTGCGTGGTC GGCTCCAGATGGAGCGACTACTGGGGTCAGGGCACCCAGGTGACTGTGAGTAGT |
| hIL27 Ra_VH H20- DR595 | 1479 | CAGGTGCAACTGCAAGAGTCTGGAGGCGGTCTGGTGCAGCCAGGAGGTAGTCTT CGTCTGTCTTGCGCGGCCTCCGGCTTTACATTCTCCAGCTACCCAATGTCCTGG GTGCGTCAGGCCCCCGGCAAGGGCCTGGAGTGGGTTTCTACCATCTCTAGTGGC GGTGACACAACCCTGTACGCTGACTCTGTTAAAGGAAGATTTACCTCCAGTCGC GACAACGCCAAGAACACACTTTACTTGCAACTGAACTCTCTGAAAACCGAGGAC ACCGCCATGTATTACTGCGCTAAGCGTATTGACTGCAATTCAGGCTACTGTTAT AAGCGCTCTTACTGGGGCCAGGGCACTCAGGTCACCGTGTCTTCAGGCGGTGGC TCTCAGGTGCAGCTCCAGGAAAGCGGTGGGGGCTCCGTCCAAGCCGGTGGCAGC CTGACACTTTCCTGTGCTGCCTCCGAATACGCTTACTCAACCTGTAACATGGGC TGGTACAGACAGGCTCCTGGCAAGGAAAGAGAGTTGGTGTCCGCTTTCATCTCT GACGGCTCCACTTATTACGCCGACTCTGTAAAGGGCAGGTTCACGATCACCCGC GACAATGCCAAAAACACCGTCTACTTGCAGATGAACAGCCTGAAGCCGGAAGAC ACAGCAATCTACTATTGTAGCGCGAACTGCTATCGGCGTCTGCGCAACTATTGG GGCCAGGGCACCCAGGTCACCGTCTCCTCC |
| hIL27 Ra_VH H20- DR595 | 1480 | CAGGTGCAGCTCCAGGAATCTGGGGGGGGTCTGGTTCAGCCGGGGGGTAGTCTG CGGCTCTCCTGTGCCGCAAGCGGTTTTACTTTCTCTAGCTATCCCATGAGCTGG GTTCGGCAGGCCCCAGGTAAAGGGTTGGAGTGGGTATCTACCATCAGCTCTGGA GGTGACACTACCCTGTACGCCGACTCTGTGAAGGGCCGTTTCACCTCTTCACGC GACAACGCAAAAAATACGCTGTACCTCCAGCTCAATTCACTGAAAACTGAGGAC ACCGCTATGTATTACTGTGCGAAGCGCATTGATTGTAACAGCGGATATTGCTAC AAGCGCTCCTACTGGGGACAAGGTACGCAGGTGACTGTCTCCAGCGGCGGTAGC GGGGGTTCTGGAGGTTCCGGCCAGGTGCAACTGCAAGAGTCGGGGGGTGGCTCC GTGCAGGCCGGTGGGTCCCTGACTCTGTCCTGTGCTGCATCAGAATATGCGTAA TCCACTTGCAACATGGGTTGGTACAGGCAGGCTCCCGGAAAAGAGCGCGAGCTG GTCTCCGCCTTCATCAGTGACGGGTCTACCTATTACGCGGACAGTGTGAAGGGC CGCTTCACCATCACACGTGATAACGCCAAGAATACCGTGTATTTGCAAATGAAC TCTCTGAAACCCGAGGACACCGCAATCTATTACTGTAGCGCTAACTGCTACCGC CGTCTCAGGAACTATTGGGGACAGGGCACGCAGGTCACAGTTTCCTCC |
| hIL27 Ra_VH H20- DR596 | 1481 | CAGGTACAGCTTCAAGAGTCTGGGGGAGGTTTGGTGCAGCCTGGTGGGTCCTTG CGGCTGTCCTGTGCCGCGAGCGGGTTTACGTTCTCTTCCTATCCTATGTCCTGG GTGAGGCAAGCGCCGGGCAAGGGCCTTGAATGGGTGTCCACCATCTCTAGCGGA GGCGACACGACCCATTACGCTGACTCTGTGAAGGGACGCTTTACATCAAGTAGA GACAACGCCAAGAATTACACTGTATTTGCAGCTGAACCCCTGAAGACTGAGGAC ACTGCCATGTATTACTGCGCTAAGAGAATTGACTGCAACTCAGGCTACTGCTAC AAGCGCAGCTACTGGGGCCAGGGAACTCAGGTGACCGTTAGCTCCGGTGGCGGA TCTCAGGTACAGTTGCAAGAGTCAGGAGGTGGCCTGGTGCAGCCCGCGGGTAGC CTGCGTCTTAGCTGTACTGCCAGCGGCTTGACATTCGATGACTCCGTGATGGGT TGGTTTAGACAGGCCCCTGGCAAAGGACGGGAGGCTGTGAGCTGTATCAGCTCT TCAGGAGCTAATGCTTTCTACGCCGACTCCGTCAAGGGACGTTTTACAATCTCT |

TABLE 1B-continued

| Name | SEQ ID NO: | Sequence |
|---|---|---|
| | | CGTGATAACGCTAAGAATACTCTGTATTTGCAAATGAACTCTCTGAAGCCAGAG<br>GATACCGCTACCTATTACTGCAAGAGAGGCCACGCCTGCGGGGGCTATTACCCC<br>ATTCCCTACGACGATTACTGGGGTCAGGGTACACAGGTGACCGTCAGTTCT |
| hIL27 Ra_VH H20- DR596 | 1482 | CAGGTACAGTTGCAGGAGTCTGGAGGCGGACTGGTGCAACCCGGAGGCAGCCTG<br>AGGCTGAGCTGCGCAGCCAGCGGATTTACCTTCTCCTCTTATCCCATGAGCTGG<br>GTTCGCCAAGCGCCAGGTAAAGGTCTGGAATGGGTCAGCACAATCAGCTCAGGC<br>GGTGACACTACCCAGTACGCAGACTCTGTGAAAGGCCGGTTCACCTCTTCCAGG<br>GATAACGCCAAGAATACGCCCTACCTCCAGCTGAACTCCCTCAAGACTGAAGAC<br>ACCGCGATGTACTATTGCGCAAAGAGAATTGATTGTAACAGCGGTTATTGCTAC<br>AAACGTAGCTACTGGGGTCAGGGCACCCAGGTCACCGTGTCTTCCGGGGGAAGT<br>GGAGGTTCTGGTGGCTCTGGACAGGTACAGTTGCAGGAGAGCGGCGGTGGCCTG<br>GTGCAGCCTGGGGGAAGCCTGCGGCTGAGCTGCACTGCGAGCGGTTTGACTTTC<br>GATGACTCTGTTATGGGTTGGTTCCGTCAGGCCCCTGGTAAGGGCCGTGAGGCG<br>GTTTCCTGCATCTCTTCATCCGGTGCTAACGCTTTTTATGCAGACTCCGTGAAG<br>GGTCGCTTTACAATCAGCAGGGATAACGCGAAAAACACCCTCTACCTGCAAATG<br>AACTCCCTGAAACCCGAAGACACTGCTACCTATTACTGCAAGAGGGGGCACGCC<br>TGCGCCGGCTATTACCCTAACCCTTACGATGACTACTGGGGTCAGGGAACCCAG<br>GTCACCGTGTCCTCC |
| hIL27 Ra_VH H21- DR591 | 1483 | CAAGTGCAGTTGCAGGAAAGCGGAGGCGGACTTGTTCAGCCAGGGGGATCTTTG<br>CGCCTCAGCTGTGCCGCTTCAGGGTTTACATTCTCCCTGTCTAGCATGAGCTGG<br>GTCCGTCAGGCTCCTGGAAAGGGTCTGGAATGGGTTTCCGCCATTAGCTCCGGC<br>GGTGCCTCCACTTATTACACCGACAGTGTGAAAGGCCGCTTTACAATCAGCCGC<br>GACAACGCCAAGAACATGCCGTACTTGCAACTGAACAGCCTGAAAACCGAGGAC<br>ACCGCCATGTACTATTGTGCCAAGGGCGGGTCCGGCTACGGCGACGCGAGCCGG<br>ATGACCTCCCCAGGCTCCCAGGGCACCCAGGTCACCGTGAGCAGTGGCGGAGGC<br>TCCCAGGTTCAGTTGCAGGAGTCTGGAGGGGGCTCCGTGCAGGCTGGCGGAAGC<br>CTGCGCCTGAGCTGCACTGCCCCCGGCGCTATCGCTTCAGGATATATTGATTCC<br>CGTTGGTGTATGGCCTGGTTTAGGCAGGCTCCTGGAAAGGAGCGCGAAGGCGTG<br>GCAGCTATCTGGCCTGGCGGTGGCCTGACCGTATACGCAGATAGTGTCAAGGGC<br>CGCTTCACTATCTCCCGCGACCACGCAAAGAACACGCTGTACCTCCAGATGAAT<br>AACCTGAAGCCTGAGGACACCGCCATGTATTACTGTGCCGCTGGCTCACCTCGT<br>ATGTGCCCCTCCCTGGAGTTCGGCTTTGACTACTGGGGCCAGGGAACCCAGGTC<br>ACCGTCTCTTCT |
| hIL27 Ra_VH H21- DR591 | 1484 | CAGGTGCAGCCTCAGGAGAGCGGAGGTGGCCTGGTTCAGCCTGGTGGGTCACTC<br>CGCCTGAGTTGTGCGGCCTCAGGATTTACATTCTCCCTCTCCAGCATGTCTTGG<br>GTTAGACAAGCTCCTGGCAAAGGTCTGGAGTGGGTATCCGCCATTAGCTCCGGT<br>GGCGCTTCTACTTACTATACCGACAGCGTGAAGGGTCGCCTCACTATCTCCCGC<br>GACAATGCCAAGAACATGCTGTACCTTCAGCTCAATTCTCTGAAGACCGAGGAC<br>ACTGCGATGTACTATTGCGCCAAGGGAGGCTCTGGTTATGGCGACGCATCTCGC<br>ATGACCTCCCCCGGTTCCCAAGGCACCCAGGTCACGGTCTCCAGCGGAGGCAGT<br>GGCGGTTCAGGGGGGAGCGGACAGGTGCAGCTCCAGGAGTCCGGGGGGGGCTCT<br>GTGCAGGCTGGAGGCTCCCCTCGTCTGAGCTGCACTGCTTCCGGGGCAATCGCG<br>AGCGGCTACATTGATTCTCGTTGGTGTATGGCCTGGTTTCGTCAGGCACCCGGC<br>AAGGAGCGCGAAGGCGTTGCTGCAATTTGGCCGGGAGGGCGGTTGACGGTCTAT<br>GCGGACTCCGTGAAGGGCCGCTTCACTATCTCCCGCGACCATGCCAAGAACACA<br>CTGTATCTTCAGATGAATAACCTGAAGCCTGAGGACACTGCAATGTACTATTGT<br>GCCGCAGGCTCTCCCCGTATGTGCCCGTCACTGGAATTTGGGTTTGACTATTGG<br>GGCCAAGGCACACAAGTAACCGTGTCCAGC |
| hIL27 Ra_VH H21- DR592 | 1485 | CAGGTCCAGCTGCAAGAGTCTGGCGGTGGCCTCGTGCAGCCCGGAGGCAGCCTG<br>AGGCTCAGCTGTGCCGCAAGTGGATTTACCTTTTCACTCAGCTCTATGTCCTGG<br>GTGCGTCAGGCTCCAGGAAAGGGACTGGAGTGGGTGTCTGCTATCTCATCTGGA<br>GGGGCGTCTACATATTACACTGATAGTGTGAAGGGGCGGTTCACCATCAGTCGT<br>GATAACGCGAAAAACATGCTGTACCTGCAACTGAACAGTCTGAAGACTGAGGAC<br>ACCGCCATGTACTATTGTGCGAAGGCGGGAAGTGGCTACGGTGATGCGTCAAGA<br>ATGACCTCTCCCGGTAGTCAGGGAACTCAGGTCACTGTGTCCAGTGGCGGAGGC<br>AGCCAGGTGCAGCTCCAGGAAAGTGGAGGGGGTTCTGTCCAGGCAGGGGGCTCC<br>CTGCGCCTGAGCTGTACCGCCCCCGGCCTCACCTCCAACTCCTGTGGAATGGAT<br>TGGTACAGACAGGCTCCCGGCAAGGAGAGGGAGTTCGTTAGCTCCATCTCTACA<br>GACGGAACCACTGGGTACGCCGATAGCGTGAAGGGGCGTTTTACCATCTCCAAA<br>GATAAAGCCAAGGATACTGTGTATTTGCAGATGAACTCCCTCAAGCCCGAGGAT<br>ACCGGAATGTATAGCTGCAAAACCAAGGACGGTACTATCGCTACGATGGAGCTG<br>TGCGACTTTGGCTACTGGGGCCAAGGCACCCAGGTGACCGTTTCTAGC |
| hIL27 Ra_VH H21- DR592 | 1486 | CAGGTCCAGTTGCAGGAGTCCGGGGGGGGCCTGGTTCAGCCGGGTGGCTCTCTG<br>CGCCTGAGCTGCGCCGCTTCTGGCTTCACTTTCTCTCTCAGCTCTATGTCCTGG<br>GTCAGACAAGCGCCGGGCAAAGGTTTGGAGTGGGTGTCTGCTATTTCATCCGGT<br>GGCGCGAGTACCTACTATACCGATTCCGTGAAGGGCCGCTTCACTATTAGCCGG<br>GACAATGCTAAGAACATGCTGTACCTTCAGCTCAATTCTCTGAAAACCGAGGAC<br>ACTGCCATGTATTACTGCGCTAAGGGAGGTTCAGGATACGGCGATGCCTCCAGG<br>ATGACTAGCCCAGGCAGCCAAGGGACACAGGTCACCGTTTCCAGTGGGGGCTCC<br>GGCGGTTCTGGCGGTAGCGGCCAAGTGCAGCTGCAAGAGTCCGGGGGGGGCAGC<br>GTTCAAGCTGGGGGTAGCCTCAGGCTTTCCTGCACAGCTCCAGGTTTCACCAGC<br>AACAGTTGCGGAATGGACTGGTATCGCCAAGCGCCAGGTAAGGAGAGGGAGTTT |

TABLE 1B-continued

| Name | SEQ ID NO: | Sequence |
|---|---|---|
| | | GTTTCCAGCATCTCTACCGACGGCACCACGGGATATGCTGATTCTGTGAAGGGA<br>CGCTTTACCATCTCTAAGGATAAAGCGAAGGACACCGTGTACTTGCAGATGAAC<br>AGCCTGAAGCCCGAGGATACCGGCATGTATAGCTGCAAAACTAAGGACGGAACC<br>ATTGCGACAATGGAACTCTGCGATTTCGGATACTGGGGTCAGGGAACCCAGGTG<br>ACTGTGTCTAGC |
| hIL27 Ra_VH H21-DR593 | 1487 | CAGGTCCAGCTCCAGGAATCTGGCGGAGGGCTGGTGCAGCCGGGGGGTAGCCTC<br>CGGTTGTCCTGCGCTGCCAGCGGCTTTACCTTTTCCCTCAGCTCCATGTCTTGG<br>GTGCGCCAGGCACCCGGAAAAGGATTGGAGTGGGTGTCCGCTATCTCATCCGGG<br>GGAGCCAGCACGTATTACACTGATTCCGTGAAGGGCCGCTTCACCATTTCTCGC<br>GATAACGCTAAAAACATGCTGTATTTGCAGCTTAACTCCCTGAAAACAGAAGAT<br>ACCGCGATGTATTACTGTGCTAAGGCGGGGTCCGGCTACGGCGACGCATCTCGT<br>ATGACCAGCCCTGGCAGCCAGGGCACGCAGGTCACCGTGTCAAGCGGAGGCGGT<br>TCCCAGGTTCAGTTGCAGGAGAGCGGTGGGGGTAGCGTGCAGGCTGGGGGTTCC<br>CTTCGCCTCTCTTGCGCGGCTTCCGGTTATCCATACAGCAACGGCTATATGGGG<br>TGGTTCAGACAGGCACCCGGCAAGGAACGCGAAGGCGTGGCAACCATCTACACT<br>GGCGACGGACGCACGTACTATGCTGACAGCGTTAAAGGCCGTTTTACTATCAGC<br>CGCGACAATGCGAAGAACACCGTCGATTTGCAGATGTCAAGTCTGAAGCCAGAA<br>GACACAGCCATGTACTATTGCGCTGCGAGAGCCGCTCCCCTCTACTCTAGCGGC<br>AGCCCCCTGACCCGCGCACGTTACAATGTGTGGGGCCAGGGCACCCAGGTGACC<br>GTCTCCTCC |
| hIL27 Ra_VH H21-DR593 | 1488 | CAGGTGCAGCTTCAAGAATCTGGCGGCGGGCTTGGTGCAGCCCGGGGTAGCCTC<br>CGGTTGAGCTGCGCCGCTTCAGGGTTTACCTTCAGCTTGTCATCCATGTCATGG<br>GTGCGCCAGGCCCCCGGCAAGGGACTGGAGTGGGTCAGCGCCATCAGTAGCGGG<br>GGAGCGTCAACTTATTACACTGACTCCGTCAAGGGTCGCTTCACAATTAGCCGG<br>GACAACGCCAAGAACATGCTGTACCTCCAGTTGAACTCCCTGAAAACTGAGGAC<br>ACAGCCATGTACTATTGCGCCAAAGGGGGTAGCGGTTATGGCGACGCTTCCCGC<br>ATGACCTCTCCCGGCTCCCAAGGCACCCAGGTCACTGTAAGCTCAGGAGGGAGC<br>GGCGGTTCCGGTGGCAGCGGACAGGTCCAGCTCCAGGAGAGTGGAGGCGGATCA<br>GTGCAAGCCGGGGCTTCCCCCAGGCTCTCCCGCGCTGCGTCCGGCTACCCATAT<br>AGCAACGGCTACATGGGATGGTTCCGCCAGGCCCCAGGCAAAGAGGGGGAGGGC<br>GTTGCCACCATCTACACCGGGGATGGCCGTACCTATTACGCAGACTCCGTGAAG<br>GGGAGGTTTACCATCTCTCGGGACAATGCCAAAAACACGGTGGACCTCCAGATG<br>AGTTCCCTGAAGCCCGAAGACACCGCCATGTATTACTGCGCAGCCAGAGCCGCT<br>CCTTTGTACTCCTCAGGTAGCCCCCTCACCCGTGCTCGCTATAATGTATGGGGA<br>CAGGGCACTCAAGTGACCGTGTCCTCC |
| hIL27 Ra_VH H21-DR594 | 1489 | CAGGTTCAGCCTCAGGAGTCTGGTGGGGGCCTGGTGCAGCCAGGTGGCAGCTTG<br>CGCCTGTCCTGCGCGGCCAGCGGATTTACTTTCTCTCTCAGCTCCATGTCTTGG<br>GTGAGGCAGGCTCCAGGTAAGGGCCTGGAGTGGGTTTCTGCTATTAGCTCCGGG<br>GGAGCTTCCACATATTACACAGATTCTGTGAAAGGTCGTTTCACGATCTCTCGC<br>GACAACGCCAAAAACATGCTGTACCTTCAGCTGAACAGCCTGAAAACCGAAGAC<br>ACAGCTATGTACTATTGCGCCAAGGGAGGTAGCGGGTACGGCGACGCCTCCAGG<br>ATGACAAGTCCCGGTTCCCAGGGCACCCAGGTGACGGTCAGCTCCGGTGGAGGT<br>AGTCAAGTCCAACTTCAGGAGTCCGGCGGTGGCTCCGTTCAGGCTGGCGGTTCT<br>CTGCGTCTGTCTTGTGTGGCGTCCGCTTCCACCTACTGCACTTATGATATGCAC<br>TGGTACAGGCAAGCGCCCGGTAAGGGGCGCGAGTTTGTTTCCGCCATTGATTCC<br>GATGGGACCACTCGGTATGCGGACAGCGTCAAGGGCCGCTTCACTATCTCACAG<br>GGTACAGCCAAGAACACAGTGTACCTCCAGATGAACTCATTGCAACCCGAGGAC<br>ACGGCCATGTACTATTGTAAGACAGTCTGCGTGGTCGGTTCCAGATGGTCAGAC<br>TACTGGGGCCAAGGGACCCAAGTCACAGTCTCCTCA |
| hIL27 Ra_VH H21-DR594 | 1490 | CAGGTGCAACTCCAGGAAAGTGGGCGGGGCCTTGTTCAGCCTGGAGGCTCCCTG<br>CGGCTTAGCTGCGCTGCCTCCGGGTTTACTTTCTCACTGTCATCTATGAGCTGG<br>GTCCGGCAAGCTCCAGGGAAGGGCCTGGAATGGGTCAGCGCTATCTCTTCCGGC<br>GGAGCCTCAACTTACTATACTGACTCCGTGAAGGGCCGGTTTACCATCAGTCGC<br>GACAACGCTAAGAACATGCTGTACCTTCAGCTGAACAGCCTGAAGACTGAAGAT<br>ACTGCTATGTACTATTGCGCCAAAGGGGGTTCCGGGTACGGCGACGCCTCTCGG<br>ATGACCTCTCCGGGTTCCCAAGGCACCCAGGTTACCGTGTCCAGTGGGGGCTCC<br>GGGGGTAGCGGTGGCTCTGGCCAGGTGCAGCTCCAGGAATCCGGTGGGGGGTCC<br>GTGCAGGCTGGAGGGTCACTGCGCCTGTCCTGCGTGGCCAGCGCCTCTACCTAC<br>TGCACATACGACATGCACTGGTACAGGCAAGCTCCAGGTAAGGGTCGGGAGTTT<br>GTCAGCGCTATCGACAGCGACGGCACAACTCGCTATGCGGATAGCGTCAAGGGG<br>CGTTTTACCATCAGCCAAGGGACTGCCAAAAACACAGTGTATCTCCAGATGAAC<br>TCTCTCCAGCCAGAGGATACTGCCATGTATTACTGCAAGACCGTGTGCGTTGTG<br>GGTTCACGTTGGTCCGACTATTGGGGCCAAGGCACACAGGTGACCGTGTCCTCA |
| hIL27 Ra_VH H21-DR595 | 1491 | CAGGTGCAGCTCCAGGAATCTGGGCGGGGGTCTGGTGCAGCCCGGGGGTCTTTG<br>CGCCTCTCATGTGCAGCCTCTGGGTTTACCTTCTCTCTGCCCAGCATGTCTTGG<br>GTTAGGCAGGCCCCAGGTAAGGGGCTGGAGTGGGTTTCCGCCATCTCATCCGGC<br>GGTGCCAGCACATATTACACCGACTCCGTCAAGGGGAGATTCACCATCAGCCGG<br>GACAACGCCAAGAACATGCTGTATCTCCAGCTCAACCCCCTGAAAACCGAGGAC<br>ACCGCCATGTATTACTGCGCCAAGGGGGGTTCCGGCTATGGTGATGCTTCAAGG<br>ATGACTAGCCCCGGTTCCCAGGGCACCCAAGTCACTGTATCCAGCGGGGGAGGC<br>TCCCAGGTGCAGCTTCAGGAGTCTGGCGGTGGCAGCGTGCAGGCCGGGGGCTCC<br>CTGACACTGTCCTGTGCCGCTTCCGAGTACGCCTATTCCACGTGTAACATGGGA |

TABLE 1B-continued

| Name | SEQ ID NO: | Sequence |
|---|---|---|
| | | TGGTATCGCCAGGCTCCTGGCAAGGAGCGCGAGCTGGTCAGCGCCTTTATCTCC GACGGCAGCACTTATTACGCCGACTCCGTGAAGGGACGCTTCACAATCACTCGC GACAACGCCAAGAATACTGTGTACCTCCAGATGAACAGCCTCAAGCCTGAGGAT ACCGCCATCTATTACTGCTCTGCTAATTGCTATCGTCGGCTGCGCAACTACTGG GGACAAGGAACACAGGTGACCGTGTCATCT |
| hIL27 Ra_VH H21- DR595 | 1492 | CAGGTTCAACTCCAGGAAAGCGGAGGTGGACTTGTGCAGCCCGGCGGTTCCCTC CGGCTGTCCTGCGCTGCCTCTGGCTTCACTTTCTCACTCCCATCCATGAGCTGG GTCCGCCAGGCCCCCGGCAAAGGCCTGGAGTGGGTGAGTGCTATCTCCTCTGGC GGAGCTTCCACCTACTATACTGACTCTGTGAAGGGCCGCTTCACCATTAGTCGG GACAACGCCAAGAACATGCTGTACTTGCAGCTGAACTCACTGAAGACCGAGGAC ACTGCCATGTACTATTGCGCTAAGGGAGGCTCCGGGTACGGCGACGCCTCCAGA ATGACATCTCCCGGCTCTCAGGGGACCCAGGTCACGGTGTCCAGGGGGGGGTCC GGGGGCTCCGGCGGATCTGGTCAGGTACAACTTCAGGAGTCAGGCGGAGGCAGC GTTCAAGCCGGAGGCTCCTTGACACTGTCCTGCGCGGCCTCTGAGTACGCATAC AGTACCTGCAACATGGGCTGGTATCGGCAGGCCCCCGGAAAGGAGCGCGAATTG GTTTCTGCTTTCATCAGCGATGGATCTACTTATTACGCCGACTCTGTAAAAGGT AGATTCACTATTACTCGTGACAACGCTAAAAACACGGTGTATCTGCAAATGAAC AGCCTGAAGCCCGAGGACACTGCCATTTATTACTGTTCCGCTAATTGTTACCGT AGGCTGCGCAATTACTGGGGTCAGGGTACTCAGGTCACTGTATCCAGC |
| hIL27 Ra_VH H21- DR596 | 1493 | CAAGTCCAACTGCAAGAGTCTGGTGGAGGCTTGGTACAGCCCGGAGGGAGCCTG CGCCTCTCCTGCGCAGCCTCTGGCTTCACCTTCTCTCTCAGCTCAATGTCCTGG GTGAGGCAGGCCCCCGGAAAGGGCCTTGAGTGGGTGTCTGCTATCTCCTCTGGA GGGGCCAGCACCTACTATACAGACAGCGTCAAGGGCAGATTTACCATTAGTCGT GATAATGCTAAAAATATGCCTACTTGCAGCTTGAACTCCCTGAAAACAGAGGAC ACCGCCATGTACTATTGCGCCAAGGGGGGTTCAGGATATGGAGATGCCAGTCGC ATGACCAGCCCCGGTAGTCAGGGTACACAAGTGACCGTATCTAGCGGCGGAGGC TCTCAGGTGCAGCTCCAGGAGTCTGGAGGGGGCTTGGTGCAGCCGGGAGGCTCT CTCCGCCTTAGTTGTACTGCCTCTGGACTGACTTTCGATGACTCAGTGATGGGC TGGTTCCGCCAGGCCCCAGGCAAGGGCAGAGAGGCCGTGTCTTGTATCAGCAST AGCGGGGCCAACGCTTTCTATGCCGACTCTGTCAAGGGCCGTTTCACCATCTCT CGCGACAACGCTAAGAATACCCTGTACCTCCAAATGAACTCCCTGAAACCCGAG GACACAGCAACGTATTACTGTAAGAGAGGTCATGCTTGTGCGGGGTATTACCCA ATTCCCTATGACGATTACTGGGGCCAGGGGACCCAGGTAACAGTAAGCTCC |
| hIL27 Ra_VH H21- DR596 | 1494 | CAGGTGCAGTTGCAGGAGTCCGGGGGTGGGCTGGTCCAGCCTGGGGGCAGCCTG CGCCTTAGTTGCGCCGCTTCCGGCTTCACCTTTAGCCTTAGCAGTATGAGCTGG GTGAGACAGGCCCCAGGCAAGGGGCTGGAGTGGGTGTCCGCAATTTCTTCGGGG GGTGCGAGCACCTATTACACTGATAGCGTTAAGGGACGTTTCACCATTTCTCGC GACAACGCTAAGAACATGCTGTACCTCCAGCTCAACAGCCTGAAGACAGAAGAT ACTGCTATGTATTACTGTGCAAAGGGAGGCAGCGGCTACGGCGATGCGAGCCGG ATGACCAGTCCGGGGTCCCAGGGCACTCAGGTCACCGTTAGCTCCGGGGGGTCT GGCGGTTCCGGCGGTTCCGGTCAAGTTCAGCTGCAAGAGAGCGGTGGGGGACTG GTGCAGCCGGGAGGCTCCCTGCGCCTGAGTTGCACCGCTTCCGGTCTGACCTTT GACGATTCCGTTATGGGCTGGTTTCGCCAAGCCCCTGGCAAGGGGAGGGAAGCT GTGTCCTGCATTTCTAGCTCTGGCGCTAACGCCTTCTATGCCGATTCCGTGAAG GGCCGCTTCACGATCAGCCGCGACAACGCCAAGAACACCCTGTACCTGCAAATG AACTCATTGAAGCCCGAGGATACCGCCACCTATTACTGCAAACGCGGCCATGCC TGCGCGGGCTATTACCCGATTCCTTACGACGATTACTGGGGTCAAGGCACCCAG GTGACAGTCTCCTCC |
| hIL27 Ra_VH H22- DR591 | 1495 | CAGGTGCAGCTCCAGGAATCCGGCGGAGGCTCTGTGCAGGCTGGTGGCAGCCTG AGGCTGAGTTGCCGCGCTTCCGGCTCCACTTATAGCAACTACTGTCTGGGCTGG TTTCGCCAGACAACCGGAAAAGAAAGAGAAGGCGTGGCCGTGATTAACTGGGTC GGCGGGATGCTCTACTTTGCCGATAGTGTGAAAGGTCGTTTCACGGTCTCCCAG GACCAGGCCAAAAACACCGTCTACCTCCAGATGAACTCCCTCAAGCCTGAGGAT ACTGCGATGTATTACTGCGCCGCTGAGTCCGTCTCTTCCTTCTCCTGCGGGGGC TGGCTGACACGCCCCGACAGAGTCCCTTATTGGGGCCAAGGAACTCAGGTAACA GTGTCTTCCGGTGGCGGTTCCCAGGTACAGCTTCAGGAGTCTGGTGGCGGTTCT GTTCAGGCCGGGGGCTCCCTGCGCCTGTCCTGCACTGCTTCTGGCGCTATCGCA AGCGGATATATTGATAGTCGCTGGTGTATGGCATGGTTCAGACAAGCCCCTGGG AAGGAGCGCGAAGGCGTGGCGGCCATCTGGCCAGGGCGGGGGCTGACTGTCTAC GCTGACAGCGTTAAAGGTCGCTTCACCATCTCAAGAGATCATGCTAAGAACACT CTCTACCTCCAGATGAACAATCTGAAGCCTGAGGACACCGCCATGTATTACTGT GCTGCGGGAAGCCCCCGCATGTGTCCTAGCCTGGAGTTCGGGTTCGACTACTGG GGTCAGGGGACCCAGGTCACAGTGTCCAGC |
| hIL27 Ra_VH H22- DR591 | 1496 | CAAGTGCAACTCCAAGAATCTGGAGGTGGCTCTGTGCAGGGCGGGGGTTCCCTG AGACTGTCTTGCAGAGCAAGCGGCAGTACTTACTCTAACTACTGTTTGGGATGG TTCCGGCAGACAACCGGCAAAGAGAGGGAAGGCGTGGCCGTAATCAACTGGGTG GGTGGCATGTTGTACTTCGCGGATAGCGTTAAGGGCCGCTTCACAGTTTCCCAG GATCAGGCCAAGAACACCGTGTACTTGCAAATGAACTCTCAGAAGCCGGAGGAC ACCGCCATGTATTACTGCGCTGCCGAGTCAGTATCTTCATTTAGCTGTGGCGGA TGGTTGACTAGGCCGGACAGGGTCCCTTACTGGGGCCAGGGCACACAGGTGACT GTGTCCTCTGGCGGAAGCGGGGGTTCAGGAGGCCCTGGGCAGGTGCAGTTGCAG GAGAGCGGCGGGGGCTCTGTCCAGGCTGGAGGGAGCCTCAGGCTCTCATGCACA |

TABLE 1B-continued

| Name | SEQ ID NO: | Sequence |
|---|---|---|
| | | GCCTCTGGGGCTATCGCATCAGGATATATTGATTCTCGGTGGTGCATGGCTTGG TTCAGACAGGCACCGGGAAAGGAGCGCGAAGGTGTGGCGGCCATCTGGCCCGGC GGGGGCCTGACCGTGTATGCCGATTCCGTGAAGGGTCGTTTCACCATCTCCCGT GACCACGCGAAGAATACCCTGTATTTGCAGATGAATAACCTGAAGCCCGAAGAT ACCGCCATGTATTACTGCGCTGCCGGGAGCCCACGTATGTGCCCTTCATTGGAG TTCGGTTTCGATTACTGGGGTCAGGGGACCCAGGTGACCGTCTCCTCC |
| hIL27 Ra_VH H22- DR592 | 1497 | CAGGTGCAACTCCAGGAGAGCGGGGGGGGCAGTGTGCAGGCCGGAGGTTCCTTG CGCCTGTCTTGTCGTGCGTCAGGAAGCACATACAGCAACTACTGCCTCGGGTGG TTCAGGCAGACTACCGGCAAGGAACGTGAAGGTGTAGCCGTGATTAACTGGGTG GGCGGAATGCTGTACTTCGCGGACTCCGTGAAGGGCCGCTTCACCGTGTCTCAG GACCAGGCCAAGAACACCGTTTATCTCCAGATGAACTCCCTGAAGCCCGGAGGAC ACGGCCATGTATTACTGCGCTGCCGAGTCCGTGTCTTCATTCTCCTGCGGTGGC TGGTTGACTCGCCCTGATCGCGTGCCCTATTGGGGTCAGGGCACACAGGTGACA GTCAGCTCTGGTGGAGGTTCACAGGTCCAGCTCCAGGAGAGTGGGGGGGGTAGC GTTCAGGCCGGAGGCTCCCTGCGCCTGAGCTGTACCGCCCCAGGCTTTACCTCT AATAGCTGTGGAATGGACTGGTATCGTCAGGCTCCTGGTAAGGAACGCGAGTTC GTCTCTAGCATCTCAACCGACGGGACTACCGGCTATGCGGACTCTGTGAAGGGT CGTTTCACCATTAGCAAGGACAAGGCCAAGGACACAGTGTACCTTCAGATGAAC TCACTGAAGCCCGAGGACACTGGCATGTATAGCTGCAAAACTAAAGATGGAACC ATCGCCACTATGGAACTGTGCGATTTCGGCTACTGGGGCCAGGGCACGCAGGTG ACCGTGTCTTCC |
| hIL27 Ra_VH H22- DR592 | 1498 | CAGGTGCAGTTGCAGGAGAGTGGTGGAGGCAGTGTGCAGGCCGGTGGCTCTCTT AGACTGAGCTGCCGCGCCAGTGGCTCCACCTACTCCAACTATTGTCTGGGATGG TTTCGTCAGACCACTGGTAAAGAGCGGGAGGGGGTGGCCGTCATCAACTGGGTT GGGGGTATGCTGTACTTTGCTGACTCTGTCAAGGGGCGGTTCACAGTCTCACAG GACCAAGCCAAGAATACCGTGTACCTCCAGATGAACAGTCTGAAGCCGGAGGAT ACCGCTATGTATTACTGCGCAGCCGAATCCGTCAGCTCTTTCTCCCGCGGAGGC TGGCTCACGCGCCCTGACAGGGTTCCCTACTGGGGCCAAGGAACGCAGGTGACA GTTTCTAGTGGTGGGTCCGGGGGTAGCGGAGGCTCCGGCCAGGTGCAGCTCCAG GAATCCGGCGGAGGTTCCGTGCAGGCCGGAGGCTCCCTCCGCCTGAGCTGCACA GCCCCCGGTTTCACCTCCAATTCTTGCGGCATGGACTGGTATCGCCAGGCTCCG GGCAAGGAGCGTGAGTTCGTGTCCAGTATTTCTACGGACGGCACTACCGGGTAC GCTGACTCCGTTAAGGGCCGCTTTACCATTAGCAAAGACAAGGCGAAGGACACA GTCTATCTCCAGATGAATAGTCTGAAGCCGGAGGATACCGGCATGTACTCATGC AAAACAAAGGATGGCACGATTGCGACAATGGAGCTGTGCGACTTCGGGTATTGG GGCCAGGGCACGCAGGTGACGGTGTCCTCC |
| hIL27 Ra_VH H22- DR593 | 1499 | CAGGTACAGCTCCAGGAATCCGGTGGGGGTTCAGTTCAGGCCGGGGGTAGCCTT CGGCTGTCCTGCCGCGCGAGTGGCTCCACCTATAGCAACTACTGCCTGGGATGG TTCCGCCAGACCACAGGCAAGGAGCGTGAGGGCGTCGCTGTAATAAATTGGGTT GGGGGAATGTTGTACTTTGCGGACAGTGTGAAGGGACGTTTCACCGTCAGTCAG GACCAGGCCAAGAACACCGTTTACCTCCAGATGAACAGCCTCAAGCCCGAGGAT ACCGCCATGTATTACTGCGCGGCTGAGTCTGTTTCTTCCTTCTCTTGTGGGGGC TGGCTGACCAGGCCCGACAGAGTCCCATACTGGGGCCAGGGGACCCAGGTGACA GTTAGCTCCGGCGGTGGCTCACAGGTGCAGCTGCAAGAGAGCGGCGGTGGCTCC GTCCAAGGGGGGCGGGTCACTCAGACTGTCTTGCGCAGCTAGTGGTTACCCGTAT TCAAACGGTTACATGGGATGGTTTAGACAGGCACCAGGCAAAGAGCGCGAAGGC GTCGCTACCATCTACACAGGAGATGGCCGCACCTATTACGCCGACAGCGTGAAA GGCAGGTTTACAATTAGTCGCGACAACGCCAAGAACACTGTCGATCTTCAGATG TCTTCCTTGAAGCCAGAAGACACCGCCATGTATTACTGTGCAGCGCGGGCAGCC CCACTTTATTCCAGCGGCTCTCCCCTCACCCGCGCCCGGTATAACGTCTGGGGC CAAGGTACTCAGGTGACCGTGAGTTCT |
| hIL27 Ra_VH H22- DR593 | 1500 | CAGGTGCAGTTGCAGGAATCAGGTGGAGGCTCTGTGCAGGCCGGTGGATCTCTG CGGCTCAGCTGCCGGGCGTCCGGGAGCACTTACAGCAATTACTGTTTGGGGTGG TTTCGGCAGACCACTGGTAAGGAGAGAGAGGGAGTGGCCGTTATCAACTGGGTC GGAGGTATGCTCTACTTCGCTGACAGCGTCAAGGGACGCTTCACCGTGTCCCAG GACCAGGCTAAGAATACCGTTTATCTCCAGATGAATAGCCTGAAGCCTGAGGAC ACCGCTATGTATTACTGTGCGGCTGAGAGCGTCAGCTCTCTCTCCTGCGGTGGA TGGCTCACACGCCCCGACCGTGTCCCATATTGGGGACAAGGCACTCAGGTGACC GTCAGCTCAGGAGGCAGCGGGGGTAGCGGGGGTTCCGGCCAAGTGCAGCTCCAG GAGTCTGGGGGCGGAAGCGTGCAGGCCGGTGGGAGCTTGCGCCTGTCCTGTGCC GCGTCTGGCTACCCTTACAGTAACGGCTATATGGGCTGGTTCCGGCAGGCCCCC GGCAAGGAAAGGGAGGGTGTGGCCACTATCTACACTGGTGATGGTAGGACATAT TACGCCGATAGCGTGAAGGGCCGGTTCACGATCTCTCGTGATAACGCCAAAAAT ACCGTGGATCCTCAGATGTCATCCCTCAAGCCCGAGGATACCGCTATGTACTAT TGCGCAGCCCGCGCTGCCCCGCTCTACAGCAGTGGAAGCCCGTTGACCCGCGCC CGTTACAACGTGTGGGGTCAGGGCACACAAGTCACTGTCTCCTCA |
| hIL27 Ra_VH H22- DR594 | 1501 | CAAGTCCAACTTCAGGAGTCAGGGGGAGGTTCTGTTCAAGCCGGGGGTTCACTG AGGCTCTCTTGCCGCGCCTCCGGCTCAACATACTCCAACTATTGTCTGGGCTGG TTCAGGCAGACAACCGGGAAGGAGCGCGAGGGTGTGGCCGTCATCAACTGGGTC GGCGGGATGCTGTACTTTGCAGATTCCGTGAAGGGCCGGCTTACAGTGAGCCAG GACCAGGCTAAGAACACCGTGTACCTGCAAATGAACTCTCTGAAACCCGAGGAT ACAGCGATGTATTACTGCGCTGCGGAGTCCGTGTCTAGCTTCTCTTGCGGGGGC |

TABLE 1B-continued

| Name | SEQ ID NO: | Sequence |
|---|---|---|
| | | TGGCTGACCCGTCCTGATAGAGTCCCATACTGGGGACAGGGGACACAGGTGACC GTGAGCAGTGGGGGTGGCAGCCAGGTGCAGCTTCAGGAAAGCGGAGGTGGCTCA GTACAGGGGGGAGGCAGTCTGCGCCTGTCTTGCGTGGCCTCCGCATCCACCTAT TGCACCTACGACATGCACTGGTACAGGCAGGCACCTGGCAAGGGTCGCGAGTTT GTCAGTGCTATCGACTCCGACGGCACCACTCGGTACGCAGATTCCGTCAAGGGC CGGTTTACCATCTCCCAGGGCACAGCTAAAAACACTGTTTACCTCCAAATGAAC TCCCTCCAGCCTGAGGATACCGCTATGTATTACTGCAAGACAGTCTGTGTAGTG GGCTCCCGTTGGTCCGATTACTGGGGCCAGGGGACCCAAGTTACGGTTTCTAGC |
| hIL27 Ra_VH H22- DR594 | 1502 | CAAGTCCAACTCCAGGAAAGCGGGGGTGGCTCAGTCCAAGCAGGGGGCTCTCTC AGACTGAGTTGCAGGGCAAGCGGTTCCACCTACTCAAACTACTGCCTCGGTTGG TTTCGGCAGACTACCGGCAAGGAAAGGGAGGGCGTGGCGGTCATTAACTGGGTA GGGGGTATGCTCTACTTTGCAGACTCCGTGAAGGGCAGATTTACAGTATCCCAG GACCAGGCTAAGAACACGGTGTACCTGCAAATGAACTCTCTGAAGCCAGAGGAC ACCGCCATGTACTATTGCGCGGCAGAGTCAGTGAGCAGTTTTTCTTGTGGGGGC TGGCTCACCCGCCCGGACCGCGTGCCTTACTGGGGACAAGGAACGCAGGTTACA GTCTCTTCCGGCGGAAGCGGGGGCAGTGGTGGCAGCGGTCAGGTTCAGCTTCAG GAGAGTGGCGGAGGCAGCGTGCAGGCAGGGGGTTCCCTGAGGCTGTCCTGTGTG GCCTCTGCGAGTACGTATTGCACCTACGACATGCACTGGTATCGCCAGGCTCCT GGTAAGGGCCGTGAGTTCGTGTCCGCCATCGACAGCGACGGAACCACACGGTAC GCTGATTCCGTGAAAGGCAGGTTCACTATTTCCCAAGGAACTGCCAAAAACACT GTCTACCTCCAGATGAACAGCCTCCAGCCTGAGGATACAGCCATGTACTATTGC AAGACTGTGTGCGTGGTCGGCTCTCGTTGGTCCGACTACTGGGGCCAGGGCACC CAGGTCACCGTGTCCAGT |
| hIL27 Ra_VH H22- DR595 | 1503 | CAGGTGCAGCTCCAGGAGAGCGGTGGGGGGAGTGTTCAGGGGGGCGGTAGCCTG AGACTGTCATGCAGAGCATCTGGCTCTACGTACTCTAACTACTGTCTTGGCTGG TTCCGCCAGACGACCGGAAAGGAGCGTGAGGGCGTCGCTGTGATTAACTGGGTG GGCGGGATGTTGTACTTCGCCGATTCCGTGAAGGGCAGATTCACTGTGAGCCAG GATCAGGCTAAGAACACTGTGTACCTTCAGATGAACAGCCTGAAGCCCGAAGAC ACTGCCATGTACTATTGTGCAGCTGAATCTGTGAGCAGTTTCTCATGCGGTGGG TGGCTTACCAGACCGGATAGAGTGCCTTACTGGGGCCAGGGGACCCAGGTTACC GTGTCTAGCGGGGGTGGATCTCAGGTGCAGCTCCAGGAGTCCGGGGGGGGCTCC GTTCAGGCTGGGGGTAGTCTCACTCTGTCCTGTGCCGCTTCTGAGTACGCCTAC AGTACATGCAACATGGGCTGGTATCGCCAGGCTCCGGGGAAGGAACGCGAACTT GTGAGCGCCTTCATCTCCGATGGCTCTACCTATTACGCCGACTCCGTGAAGGGC AGGTTTACCATCACTCGCGACAACGCTAAGAACACTGTCTACTTGCAGATGAAC TCACTGAAACCCGAGGATACTGCCATCCATTACTGTTCCGCTAACTGCTATAGG CGGCTGAGAAACTATTGGGGACAGGGGACCCAGGTGACTGTCTCTAGC |
| hIL27 Ra_VH H22- DR595 | 1504 | CAAGTGCAACTCCAGGAAAGTGGAGGTGGCTCCGTGCAAGCCGGAGGCAGTCTC CGCCTGAGCTGTCGTGCGAGCGGTTCCACCTATAGCAACTACTGCCTGGGATGG TTTAGACAGACAACCGGGAAGGAGGGGGAGGGAGTCGCGGTGATAAATTGGGTG GGCGGTATGCTGTACTTCGCGGATTCTGTCAAGGGGAGATTCACCGTGAGCCAG GATCAGGCGAAGAACACTGTGTACCTTCAGATGAACTCTCTCAAGCCGGAGGAC ACAGCCATGTACTATTGTGCTGCCGAGCCTGTTTCATCCCTCTCCTGTGGCGGT TGGCTGACCCGCCCAGATCGCGTGCCTTACTGGGGCCAGGGTACTCAGGTCACC GTCTCTTCCGGGGGTTCAGGCGGTAGCGGTGGCTCCGGCCAGGTTCAACTCCAG GAAAGCGGAGGGGGTTCTGTGCAAGCCGGGGGCTCCCTGACCCTGTCCTGTGCT GCCAGCGAGTACGCCTATAGCACTTGTAACATGGGATGGTATCGCCAGGCCCCA GGAAAAGAACGCGAGCTTGTGAGTGCTTTTATCTCTGACGGGTCCACCTATTAC GCGGACTCTGTGAAAGGTCGCTTCACAATCACCCGCGATAACGCAAAGAACACT GTCTACCTTCAGATGAACTCCCTGAAGCCCGAGGACACTGCGATTTATTACTGT AGCGCCAACTGTTACCGCCGTCTCCGCAACTACTGGGGACAGGGGACCCAGGTG ACCGTCTCATCC |
| hIL27 Ra_VH H22- DR596 | 1505 | CAGGTCCAACTTCAGGAGTCTGGCGGAGGCAGCGTGCAAGGGGCGGGGAGCCTG CGCCTTTCCTGCCGCGCGTCTGGCAGCACCTACTCCAACTACTGCCTGGGATGG TTTCGCCAGACCACAGGTAAGGAGCGTGAAGGTGTGGCCGTCATCAACTGGGTC GGCGGTATGCTGTATTTCGCTGATTCCGTTAAGGGCAGATTTACTGTGAGTCAG GACCAGGCAAAGAACACAGTGTACCTTCAGATGAATAGCCTGAAGCCCGAAGAC ACTGCCATGTACTATTGCGCAGCCGAATCTGTGTCTAGCTTTTCCTGCGGTGGG TGGCTGACCCGCCCTGATCGCGTGCCATACTGGGGGCAGGGCACCCAGGTGACT GTATCTTCCGGGGGAGGCTCCCAGGTCCAGTTGCAGGAGTCCGGCGGAGGCCTG GTACAGCCTGGTGGATCTCTCCGCCTCTCTTGCACCGCGTCCGGGCTTACCTTC GATGACTCTGTCATGGGCTGGTTTCGGCAGGCTCCTGGTAAGGGCCGTGAAGCC GTGTCCTGCATCTCCTCTTCAGGAGCGAACGCTTTCTATGCTGATAGCGTTAAA GGCCGTTCACCATCTCCCGTGATAACGCTAAGAACACCCTTCTACCTTCAAATG AACTCCCTCAAGCCAGAGGACACCGCCACATATTACTGTAAACGCGGCCATGCT TGCGCGGGATATTACCCCATCCCTTATGACGATTACTGGGGTCAAGGGACACAG GTCACTGTCAGCTCC |
| hIL27 Ra_VH H22- DR596 | 1506 | CAGGTGCAACTTCAGGAGTCCGGTGGCGGTTCCGTGCAGGCTGGTGGCAGCCTG AGGCTGAGCTGTCGCGCCAGCGGGTCCACCTACTCTAACTATTGTCTGGGATGG TTCCGGCAGACCACAGGCAAGGAGCGCGAGGGAGTCGCTGTAATCAACTGGGTA GGTGGGATGCTGTACTTCGCCGATAGTGTAAAAGGCCGCTTCACCGTGTCACAG GACCAAGCCAAGAACACAGTCTACCTCCAGATGAACTCCCTGAAGCCAGAGGAC |

TABLE 1B-continued

| Name | SEQ ID NO: | Sequence |
|---|---|---|
| | | ACCGCCATGTATTACTGCGCCGCTGAATCCGTCAGCTCTTTCTCTTGCGGCGGT<br>TGGCTGACCCGCCCCGACCGTGTCCCCTACTGGGGCCAGGGCACTCAGGTGACT<br>GTGAGCAGTGGTGGCAGCGGGGGCTCCGGTGGAAGGGGCCAGGTTCAGCTCCAG<br>GAATCCGGGGGGGGACTCGTCCAGCCAGGGGGCAGCCTGCGGCTGTCCTGCACC<br>GCAAGCGGCCTGACCTTCGACGATAGCGTCATGGGATGGTTCCGTCAAGCCCCC<br>GGCAAGGGGAGGGAGGCCGTCAGCTGTATTAGCTCTAGCGGCGCTAACGCCTTC<br>TATGCCGATTCTGTTAAGGGTAGGTTCACAATCTCCCGCGACAACGCCAAAAAT<br>ACGCTGTATCTCCAGATGAACAGCCTGAAGCCCGAGGACACCGCAACCTATTAC<br>TGTAAGAGGGGACACGCATGTGCCGGTTATTACCCTATCCCCTACGATGACTAC<br>TGGGGGCAAGGTACTCAGGTCACCGTTTCCTCA |
| hIL27<br>Ra_VH<br>H23-<br>DR591 | 1507 | CAGGTGCAACTTCAGGAGAGTGGAGGCGGTAGCGTCCAAGCTGGGGGTTCCCTG<br>AGACTCTCATGTAGAGCTTCCCGTTCTCCTTACGGAAATTACTGTCTGGGCTGG<br>TTCCGCCAGTCCACTGGTAAGGAACGCGAGGGTGTGGCTGTGATAAATTGGCGG<br>GGTGGAATGCTGTACTTTGCCGACTCTGTTAAGGGTAGATTCACTGTGTCCCAA<br>GATCATGCCAAGAACACCGTCACCCTTCAGATGAACTCCCTGAAGCCGGAAGAC<br>ACCGCTATGTACTATTGTGCTGCCGAGTCCGTGTCCTCTTTCTCTTGCGGCGGT<br>TGGCTGACCAGACCGGACAGGGCTCCGTATTGGGGCCAAGGCACCCAGGTCACT<br>GTGAGTTCTGGAGGGGGTTCCCAGGTCCAACTCCAAGAAAGCGGAGGCGGCTCC<br>GTCCAGGCTGGCGGTTCTCTGCGCCTGAGCTGCACCGCCAGCGGGGCCATTGCG<br>TCTGGTTACATCGACAGTAGATGGTGTATGGCGTGGTTTCGGCAGGCTCCTGGA<br>AAGGAACGCGAGGGGGTTGCTGCCATCTGGCCAGGGGGTGGCCTGACAGTCTAT<br>GCGGACTCCGTGAAGGGGCGCTTCACCATTAGCAGAGACCACGCAAAAAACACT<br>CTGTATTTGCAGATGAATAACCTGAAGCCCGAAGACACTGCCATGTACTATTGC<br>GCTGCCGGTTCTCCGCGCATGTGCCCATCCCTGGAGTTCGGATTCGACTACTGG<br>GGACAGGGCACCCAGGTGACGGTGTCCAGT |
| hIL27<br>Ra_VH<br>H23-<br>DR591 | 1508 | CAGGTCCAGTTGCAGGAGTCAGGGGGGGGTAGCGTCCAGGCAGGGGGCAGCCTG<br>CGCCTGTCCTGCCGGGCCAGCAGAAGCCCCTACGGAAATTACTGTCTGGGCTGG<br>TTCCGGCAGAGCACTGGGAAGGAGCGCGAGGGCGTCGCCGTAATCAACTGGGTC<br>GGCGGGATGCTGTATTTCGCCGACAGTGTGAAGGGACGCTTTACTGTGAGTCAG<br>GACCACGCAAAGAATACAGTCACGTTGCAGATGAACTCCCTGAAGCCTGAGGAC<br>ACCGCTATGTACTATTGCGCGGCTGAGTCAGTGTCTAGCTTCAGCTGTGGTGGC<br>TGGCTCACTCGTCCTGATCGCGTACCATATTGGGGTCAGGGGACTCAGGTCACC<br>GTGAGTAGCGGCGGAAGTGGAGGCAGCGGTGGGAGCGGCCAAGTTCAGTTGCAG<br>GAGAGCGGCGGGGGCTCTGTGCAGGCTGGTGGCTCCCTGCGTCTGTCCTGCACC<br>GCGTCCGGGGCCATCGCCAGCGGATACATCGACAGTAGGTGGTGTATGGCATGG<br>TTCCGTCAGGCCCCTGGTAAGGAGCGCGAGGGCGTGGCCGCTATTTGGCCGGGT<br>GGGGGACTCACCGTGTATGCTGACTCCGTAAAGGGTCGCTTCACTATCTCTCGC<br>GATCACGCCAAGAACACCCTGTACTTGCAGATGAACAATCTGAAGCCCGAGGAC<br>ACCGCTATGTATTACTGGGCAGCTGGAAGCCCCAGGATGTGTCCGAGCCTGGAG<br>TTCGGCTTCGACTACTGGGGGCAGGGGACTCAGGTGACCGTGTCCTCT |
| hIL27<br>Ra_VH<br>H23-<br>DR592 | 1509 | CAAGTCCAGCTTCAGGAAAGCGGCGGTGGAAGCGTGCAGGCTGGAGGCAGCCTG<br>AGACTCAGCTGCCGCGCTTCAAGGTCCCCCTACGGTAACTACTGCCTGGGCTGG<br>TTTCGCCAGAGTACAGGCAAGGAAAGGGAAGGTGTGGCCGTTATCAACTGGGTG<br>GGCGGTATGCTGTACTTTGCCGACTCCGTCAAGGGCCGTTTTACAGTGTCCCAG<br>GACCACGCCAAGAACACGGTCACGCTTCAGATGAACAGCCTGAAGCCCGAGGAC<br>ACCGCTATGTATTACTGTGCTGCCGAGTCCGTTAGCAGTTTCTCCTGCGGCGGA<br>TGGCTGACCCGCCCTGACCGCGTTCCCTACTGGGGGCAGGGCACTCAGGTGACG<br>GTCAGCTCTGGGGGGGGGTCCCAGGTTCAGCTGCAAGAGAGTGGTGGAGGCTCC<br>GTACAGGCCGGGGGATCTCTTCGCCTGTCCTGTACTGCTCCGGGCTTCACGAGT<br>AACTCCTGTGGGATGGACTGGTATCGCCAAGCGCCCGGCAAGGAGCGCGAGTTC<br>GTAAGTAGCATCTCAACAGACGGCACGACCGGCTACGCCGATTCCGTGAAGGGC<br>CGCTTTACCATTAGCAAGGACAAGGCCAAGGACACTGTGTATCTGCAAATGAAC<br>TCCCTGAAACCCGAGGATACGGGCATGTACTCTTGCAAGACTAAGGATGGCACG<br>ATTGCCACAATGGAGCTGTGCGATTTCGGATATTGGGGCCAGGGCACCCAGGTG<br>ACTGTCTCCTCT |
| hIL27<br>Ra_VH<br>H23-<br>DR592 | 1510 | CAGGTGCAACTTCAGGAAAGTGGGGGGGGTTCCGTGCAGGCAGGGGGCTCTCTG<br>CGTCTGTCTTGCAGAGCCAGCAGGTCTCCTTATGGTAACTACTGCCTCGGGTGG<br>TTTCGTCAGTCTACCGGAAAGGAGCGCGAAGGAGTCGCAGTGATAAATTGGGTC<br>GGCGGTATGCTCTATTTCGCCGACAGCGTCAAGGGGCGTTTCACCGTCAGCCAA<br>GATCACGCTAAGAACACCGTAACACTGCAAATGAACTCCCTCAAACCTGAAGAC<br>ACGGCTATGTATTACTGCGCAGCGGAAAGTGTGAGCAGTTTCAGTTGTGGTGGA<br>TGGCTGACCCGCCCAGATCGCGTCCCTTACTGGGGGCAGGGCACCCAGGTGACT<br>GTCTCCAGTGGAGGGTCCGGTGGCAGCGGGGGAAGCGGCCAGGTGCAGTTGCAG<br>GAGTCTGGGGGCGGTTCTGTCCAGGCTGGAGGTAGCCTCCGCCTGTCTTGCACA<br>GCCCCCGGCTTTACGTCCAACTCTTGTGGCATGGACTGGTATCGGCAGGCTCCA<br>GGCAAAGAACGCGAGTTCGTCAGCTCTATCTCTACTGATGGAACTACAGGATAC<br>GCAGACAGCGTTAAGGGGCGTTTCACCATCTCCAAAGATAAAGCTAAGGACACC<br>GTTTACCTGCAAATGAACTCACTGAAGCCAGAGGATACAGGTATGTACTCTTGC<br>AAGACTAAGGATGGGACCATCGCCACTATGGAACTGTGTGATTTCGGCTACTGG<br>GGCCAGGGCACCCAGGTCACCGTGAGCAGC |
| hIL27<br>Ra_VH | 1511 | CAGGTGCAACTGCAAGAAAGTGGGGGTGGAAGCGTGCAGGCAGGTGGAAGCCTG<br>CGCCTCTCTTGTCGTGCTTCCAGAAGTCCGTATGGCAATTATTGTCTGGGCTGG |

TABLE 1B-continued

| Name | SEQ ID NO: | Sequence |
|---|---|---|
| H23-<br>DR593 | | TTTAGACAGTCCACTGGTAAGGAAAGGGAAGGAGTGGCTGTCATCAACTGGGTG<br>GGCGGTATGCTGTACTTCGCCGATTCCGTCAAGGGCCGTTTCACAGTCTCCCAA<br>GACCATGCAAAGAACACAGTGACACTCCAGATGAACTCCCTCAAGCCCGAGGAC<br>ACTGCTATGTATTACTGCGCCGCTGAGTCTGTCTCCAGCTTCTCTTGCGGCGGA<br>TGGCTGACTCGCCCGGATCGCGTTCCCTATTGGGGCCAGGGGACGCAGGTGACC<br>GTGTCCTCAGGCGGGGGCTCCCAGGTTCAGCTCCAGGAGTCTGGCGGGGGCTCA<br>GTACAGGCCGGTGGCTCCCTCCGCCTCTCATGCGCAGCCCCCGGCTACCCGTAT<br>AGCAACGGTTACATGGGCTGGTTCAGGCAGGCCCCTGGGAAGGAACGCGAGGGC<br>GTGGCGACTATCTACACTGGCGACGGTAGGACTTATTACGCTGATTCAGTGAAG<br>GGCAGGTTCACAATTTCTCGCGACAACGCTAAAAATACCGTGGATCTCCAGATG<br>TCCAGCCTGAAACCTGAGGATACTGCCATGTATTACTGTGCCGCTCGCGCAGCT<br>CCTCTGTATAGTAGCGGCAGCCCCTTGACCCGCGCTAGATACAATGTCTGGGGT<br>CAGGGCACCCAGGTAACCGTTAGTTCC |
| hIL27<br>Ra_VH<br>H23-<br>DR593 | 1512 | CAGGTACAACTTCAGGAAAGCGGAGGTGGGTCCGTGCAGGCCGGTGGCTCACTG<br>CGCTTGAGTTGTCGCGCCAGCCGCTCCCCTTATGGGAACTACTGCCTTGGGTGG<br>TTCCGCCAGAGCACTGGAAAGGAGCGCGAGGGCGTCGCAGTCATCAACTGGGTT<br>GGCGGGATGCTCTATTTCGCCGACAGCGTGAAAGGGCGGCTTACCGTTAGCCAA<br>GACCACGCCAAGAACACAGTGACCCTTCAAATGAACTCCCTGAAGCCCGAAGAC<br>ACCGCTATGTACTATTGCGCCGCAGAGTCAGTCTCCAGTTTTAGCTGCGGAGGC<br>TGGTTGACTCGCCCTGACCGCGTGCCTTATTGGGGCCAGGGCACCCAGGTGACA<br>GTAAGCAGTGGAGGCAGCGGCGGTTCCGGTGGAAGCGGCCAGGTGCAGCTTCAG<br>GAGAGCGGCGGTGGCAGTGTTCAGGCTGGGGGGTCCCTGAGGCTGTCCTGTGCA<br>GCCTCCGGCTACCCCTACTCCAACGGTTACATGGGTTGGTTCCGCCAAGCGCCA<br>GGAAAGGAACGCGAGGGTGTGGCTACCATCTACACCGGCGATGGTCGCACTTAT<br>TACGCTGACAGCGTGAAAGGCCGGTTCACAATCAGCCGGGACAACGCCAAGAAC<br>ACAGTGGACCTGCAAATGTCCAGTTTGAAGCCTGAAGACACAGCCATGTATTAC<br>TGTGCGGCTCGGGCCGCGCCCCTCTACAGCTCCGGCTCACCACTGACACGCGCG<br>AGATACAACGTGTGGGGACAGGGCACCCAGGTGACAGTTAGCAGC |
| hIL27<br>Ra_VH<br>H23-<br>DR594 | 1513 | CAGGTTCAGTTGCAGGAGTCTGGTGGCGGTTCCGTCCAGGCTGGCGGAAGTCTG<br>CGCCCCAGTTGTCGTGCCAGCCGCTCTCCTTACGGCAACTATTGCCTCGGCTGG<br>TTCCGGCAGTCCACTGGCAAGGAGAGGGAAGGAGTCGCCGTTATCAACTGGGTG<br>GGTGGAATGCTCTACTTTGCTGATAGCGTGAAGGGCCGCTTCACAGTTTCTCAG<br>GACCATGCGAAGAACACTGTTACTTTGCAGATGAACTCCCTGAAGCCAGAGGAT<br>ACGGCTATGTATTACTGTGCAGCCGAGTCCGTGAGTTCCTTTTCCTGGCGGGGT<br>TGGCTCACCCGTCCTGACCGTGTGCCTTATTGGGGCCAGGGTACGCAAGTCACC<br>GTAAGTAGCGGAGGGGGCAGCCAGGTCCAGTTGCAGGAGTCCGGCGGAGGCTCC<br>GTGCAGGCCGGGGGTTCTCTGCGTCTCTCATGTGTGGCATCTGCTTCTACTTAC<br>TGCACTTACGACATGCACTGGTATCGGCAGGCTCCTGGGAAAGGACGGGAGTTC<br>GTTAGTGCCATCGACAGCGACGGCACTACACGCTATGCTGATTCCGTTAAGGGC<br>CGCTTTACGATTTCACAGGGGACGGCCAAGAACACTGTGTACCTCCAGATGAAC<br>TCTTTGCAGCCTGAGGACACGGCTATGTATTACTGCAAAACCGTTTGTGTAGTG<br>GGCAGCCGCTGGTCAGACTATTGGGGCCAGGGCACACAGGTCACCGTGAGTTCT |
| hIL27<br>Ra_VH<br>H23-<br>DR594 | 1514 | CAGGTGCAACTGCAAGAGTCCGGCGGAGGCTCCGTGCAGGCTGGTGGCTCACTC<br>CGGCTCTCCTGTCGCGCCTCTCGCAGCCCTTATGGGAATTACTGCCTGGGTTGG<br>TTCCGTCAGAGTACCGGCAAGGAGCGTGAGGGAGTCGCAGTAATCAACTGGGTC<br>GGAGGTATGCTGTACTTCGCCGACTCCGTGAAGGGAAGGTTCACTGTGTCCCAG<br>GACCACGCCAAGAACACGGTAACGCTCCAGATGAACTCCCTGAAGCCCGAAGAC<br>ACCGCCATGTATTACTGTGCTGCCGAGCCCGTGTCCTCATTCTCCTGCGGCGGT<br>TGGCTGACACGCCCAGACCGCGTGCCCCATTGGGGACAGGGTACACAGGTTACC<br>GTCAGCTCTGGGGGGTCTGGTGGCAGTGGGGGCTCCGGTCAGGTGCAGTTGCAG<br>GAGTCCGGCGGAGGCTCTGTGCAGGCTGGTGGGAGTCTGCGCCTGTCTTGCGTC<br>GCCAGCGCCAGTACTTATTGTACTTACGACATGCACTGGTATAGACAGGCCCCC<br>GGTAAGGGAAGGGAGTTCGTGTCAGCTATCGACAGCGATGGGACCACTAGATAT<br>GCGGATAGCGTCAAGGGGCGCTTCACCATCACCCAGGGAACCGCAAAAAACACT<br>GTCTACCTTCAGATGAACAGCCTCCAGCCTGAGGACACGGCTATGTATTACTGC<br>AAGACCGTGTGTGTCGTTGGATCTCGCTGGTCTGACTATTGGGGGCAGGGCACC<br>CAGGTGACGGTGTCCAGC |
| hIL27<br>Ra_VH<br>H23-<br>DR595 | 1515 | CAGGTTCAGCTCCAGGAGTCTGGAGGGGGCAGCGTGCAGGCGGGAGGGTCTCTT<br>CGTCTTAGCTGCCGTGCCAGTCGCTCCCCCTACGGTAACTACTGCCTGGGGTGG<br>TTTCGCCAGAGTACCGGCAAGGAGCGCGAAGGTGTGGCTGTAATCAACTGGGTT<br>GGGGGTATGCTGTATTTCGCCGACTCCGTGAAAGGTAGGCTTACAGTGAGCCAG<br>GACCACGCTAAGAACACCGTCACCCTCCAGATGAACTCTCTCAAACCGGAGGAT<br>ACCGCTATGTATTACTGCGCTGCCGAGAGTGTGAGTAGCTTCTCTTGTGGCGGT<br>TGGCTGACCAGGCCTGACCGCGTACCCTACTGGGGCCAGGGCACCCAGGTCACA<br>GTCAGCTCTGGTGGAGGCTCACAGGTGCAGCTTCAGGAGTCCGGGGGGGGCAGC<br>GTGCAGGCCGGGGGCTCACTGACCCTGAGCTGTGCTGCCAGCGAATACGCATAC<br>TCTACCTGCAATATGGGCTGGTATCGGCAGGCCCCTGGGAAAGAAAGGGAACTG<br>GTTTCTGCCTTTATCAGCGATGGATCAACATATTACGCCGACTCCGTGAAAGGG<br>AGGTTCACGATCACCCGCGACAACGCCAAGAACACTGTGTACCTCCAAATGAAC<br>AGCCTGAAGCCTGAGGACACCGCGATCTATTACTGCTCTGCTAACTGCTACCGC<br>AGGCTGCGCAATTATTGGGGTCAAGGCACCCAGGTTACCGTGTCTTCC |

TABLE 1B-continued

| Name | SEQ ID NO: | Sequence |
|---|---|---|
| hIL27 Ra_VH H23-DR595 | 1516 | CAGGTCCAGCTCCAGGAGTGTGGCGGAGGCTCCGTGCAGGCTGGAGGCAGCCTC AGACTTTCTTGCAGAGCTTCCCGGTCTCCCTATGGAAACTACTGCTTGGGTTGG TTCCGCCAATCCACTGGCAAGGAGAGGGAGGGTGTTGCTGTCATCAACTGGGTG GGGGGGATGCTTTATTTCGCCGACAGTGTCAAGGGACGGTTCACCGTCTCTCAG GATCACGCCAAGAACACTGTGACCTTGCAGATGAACTCACTCAAACCCGAAGAT ACCGCTATGTACTATTGTGCCGCAGAAAGCGTGTCTAGCTTCAGCTGTGGTGGC TGGCTCACACGCCCTGACCGGGTGCCATACTGGGGCCAGGGCACGCAGGTGACC GTAAGCTCAGGGGGGAGTGGTGGCTCTGGAGGCTCTGGACAGGTGCAGCTCCAG GAGAGCGGGGGCGGGAGCGTGCAGGCTGGCGGTAGTCTGACCCTGTCATGCGCT GCAAGCGAATACGCCTACAGCACCTGCAATATGGGGTGGTATCGTCAGGCTCCT GGCAAGGAGCGTGAGCTGGTTTCCGCCTTCATCTCCGATGGCTCTACCTATTAC GCCGACTCAGTGAAGGGCCGCTTCACTATCACTAGGGACAATGCCAAGAACACA GTATACCTCCAGATGAACTCTCTGAAGCCAGAGGATACTGCCATCTATTACTGT AGCGCCAACTGTTATCGTCGCCCGCGCAACTATTGGGGTCAAGGCACACAGGTG ACAGTCTCTAGC |
| hIL27 Ra_VH H23-DR596 | 1517 | CAGGTGCAACTCCAGGAATCCGGGGGTGGATCAGTACAGGCAGGCGGAAGCCTG AGGCTGTCTTGTCGCGCTTCCCGTTCTCCCTACGGAAATTACTGTCTGGGCTGG TTCCGGCAGTCCACTGGAAAAGAGAGGGAGGGAGTGGCCGTTATCAACTGGGTA GGAGGTATGCTGTACTTTGCCGACAGCGTGAAAGGAAGGCTCACCGTGAGCCAG GACCACGCCAAGAATACCGTGACCTTGCAGATGAACAGCCTGAAGCCCGAAGAC ACTGCCATGTACTATTGTGCCGCTGAGAGTGTATCATCTTTCTCCTGCGGTGGC TGGTTGACTCGCCCAGACAGAGTGCCTTATTGGGGGCAGGGCACTCAGGTGACC GTGTCTTCCGGTGGAGGCTCCCAGGTTCAACTTCAGGAGTCCGGTGGAGGCCTG GTACAGCCTGGCGGATCTCTCAGGCTCAGCTGCACTGCCCCTGGACTGACCTTC GATGACTCTGTTATGGGCTGGTTTAGGCAGGCCCCTGGAAAAGGCCGGGAGGCG GTCAGCTGCATCAGCTCTAGCGGGGCCAATGCGTTTTACGCTGATTCCGTGAAG GGCCGCTTCACTATCTCTAGGGACAACGCGAAGAACACCCTCTACTTGCAGATG AACTCCCTCAAGCCCGAGGACACGGCGACTTATTACTGCAAAAGAGGACACGCC TGTGCCGGATATTACCCGATTCCCTATGATGACTATTGGGGCCAGGGCACCCAG GTGACAGTGAGCAGC |
| hIL27 Ra_VH H23-DR596 | 1518 | CAGGTGCAACTCCAGGAAAGCGGCGGTGGAAGCGTGCAGGCTGGAGGGTCCCTC AGACTGAGTTGCCGGGCCTCACGGTCCCCCTATGGGAACTATTGCCTGGGCTGG TTCCGTCAGTCCACTGGCAAGGAGCGCGAGGGCGTGGCCGTTATCAACTGGGTG GGAGGGATGCTGTACTTTGCAGACAGCGTTAAGGGTCGGTTTACCGTGAGCCAG GACCACGCCAAGAATACCGTGACCTTGCAGATGAACTCCCTGAAGCCTGAGGAC ACCGCCATGTATTACTGCGCTGCCGAATCCGTGTCTAGCTTTAGCTGTGGGGGC TGGCCCACCAGACCTGATCGCGTGCCGTACTGGGGCCAGGGCACTCAAGTGACG GTCAGCTCCGGTGGAAGCGGTGGCTCCGGGGGTTCCGGGCAGGTGCAGTTGCAG GAGTCAGGGGGAGGGTTGGTTCAGCCCGGTGGCTCCTTGCGTCTGTCCTGTACT GCAAGCGGGCTGACCTTCGACGATTCTGTGATGGGCTGGTTTCGTCAGGCTCCT GGCAAGGGCAGAGAGGCGGTGAGCTGTATCCCCAGCTCCGGCGCTAATGCCTTC TACGCAGACAGTGTTAAGGGTAGGTTTACTATCTCCAGGGACAATGCTAAAAAC ACTCTGTATCTTCAGATGAACAGCCTGAAGCCGGAGGATACTGCTACCTATTAC TGTAAGCGGGGCCATGCTTGCGCCGGGTACTATCCAATCCCCTACGATGACTAT TGGGGTCAAGGCACACAGGTGACAGTGTCCTCC |
| hIL27 Ra_VH H24-DR591 | 1519 | CAGGTCCAGTTGCAGGAGAGCGGTGGGGGCCTGGTGCAGCCTGGCGGTTCCCTG CGCCTGTCTTGTGCTGCGAGCGGGTTCACTTTCAGCCATTCTGGTATGAGTTGG GTACGCCAGGCTCCAGGCAAGGGCCTGGAATGGGTGAGCACCATCAACTCTGGA GGTGCCTCTACTTATTACACCGACAGTGTCAAGGGACGCTTTACAATCTCCAGA GACAACGCGAAGAATATGCTTTACTTGCAGCTCAACTCACTGAAGACCGAGGAT ACTGCCATGTATTACTGCGCTAAGGGAGGCTCAGGATATGGTGATGCCTCTCGC ATGACCTCTCCTGGCTCACAGGGAACCCAGGTGACCGTCAGTTCCGGTGGAGGT TCTCAGGTCCAGCTCCAGGAGTCCGGCGGTGGCAGCGTGCAGGCCGGAGGCAGC CTGCGCCTGTCATGCACAGCCTCTGGCGCTATCGCCAGTGGTTACATCGACAGC AGGTGGTGCATGGCCTGGTTCAGACAGGCCCCTGGTAAGGAACGCGAGGGAGTT GCTGCCATTTGGCCAGGCGGTGGCCTGACAGTGTACGCCGATAGCGTCAAGGGG CGCTTCACTATCTCACGGGATCACGCTAAAAACACTTTGTACCTCCAGATGAAT AACCTCAAACCAGAGGACACCGCGATGTATTACTGCGCTGGGGCTCTCCCCGC ATGTGTCCCTCTCTGGAGTTCGGGTTCGATTATTGGGGTCAGGGAACGCAGGTG ACTGTGTCCTCC |
| hIL27 Ra_VH H24-DR591 | 1520 | CAGGTGCAGCTTCAGGAGTCCGGGGGAGGCCTGGTTCAGCCCGGCGGTTCTCTC CGCCTCAGCTGTGCCGCTTCCGGGTTTACATTCAGCCACAGTGGAATGTCTTGG GTACGTCAAGCGCCAGGTAAGGGCCTGGAGTGGGTCTCTACAATCAACAGCGGT GGCGCAAGTACATACTATACCGACTCCGTGAAAGGGCGGTTTACCATCTCCCGT GACAACGCTAAGAATATGCTCTATCTTCAGCTGAACTCACTCAAGACTGAGGAT ACTGCTATGTATTACTGTGCGAAAGGGGGATCTGGGTACGGCGATGCGAGCCGC ATGACCTCCCCCGGCAGTCAGGGCACTCAAGTGACCGTATCATCCGGGGGTTCC GGTGGCTCAGGAGGTAGCGGCCAGGTTCAACTGCAAGAGAGTGGGGGGGGCTCC GTGCAGGGGGCGGGTTCCCTCAGGCTCTCTTGCACTGCAAGCGGCGCTATTGCG AGTGGGTACATCGACTCCAGATGGTGTATGGCCTGGTTCCGCCAGGCACCTGGC AAGGAGCGCGAAGGCGTGGCAGCCATCTGGCCTGGGGGGGTCTTACCGTCTAC GCTGACTCCGTGAAAGGCCGCTTCACTATTTCTCGCGACCATGCCAAGAACACC |

TABLE 1B-continued

| Name | SEQ ID NO: | Sequence |
|---|---|---|
| | | CTGTACTTGCAAATGAATAACCCGAAGCCTGAAGACACCGCGATGTATTACTGC<br>GCCGCTGGATCTCCCAGGATGTGCCCGAGCCTGGAGTTCGGTTTCGACTACTGG<br>GGCCAAGGCACACAGGTTACAGTCTCCTCC |
| hIL27<br>Ra_VH<br>H24-<br>DR592 | 1521 | CAAGTGCAGCTCCAGGAGAGCGGTGGCGGTCTCGTGCAACCAGGAGGTTCCTTG<br>CGGCTGAGCTGTGCCGCGTCAGGTTTTACATTTAGCCACAGTGGGATGTCTTGG<br>GTGAGACAGGCTCCGGGTAAGGGTCTCGAATGGGTCAGTACTATCAATTCCGGC<br>GGAGCAAGCACATACTATACCGACTCTGTCAAGGGGAGATTTACCATCTCCAGA<br>GACAATGCCAAAAACATGCTGTATTTGCAACTCAACAGTCTGAAGACCGAAGAC<br>ACCGCGATGTATTACTGCGCCAAGGGCGGTTCCGGGTACGGAGACGCGAGCCGC<br>ATGACTTCCCCTGGATCTCAGGGCACCCAGGTGACTGTCTCCAGCGGTGGCGGT<br>TCCCAAGTCCAACTCCAGGAAAGCGGAGGCGGTTCTGTGCAGGCAGGGGGGTCC<br>CTTCGGTTGAGCTGTACCGCACCCGGCCTTACCAGCAACCCTTGTGGTATGGAC<br>TGGTATCGGCAGGCTCCTGGCAAAGAGCGCGAGTTCGTGTCTTCCATTTCCACC<br>GACGGCACTACCGGGTACGCGGATTCCGTGAAGGGCAGGTTCACGATCAGCAAG<br>GATAAGGCAAAAGATACTGTTTATCTCCAGATGAACTCACTCAAGCCCGAAGAC<br>ACTGGCATGTACTCCTGCAAGACCAAAGACGGCACCATTGCCACTATGGAGCTG<br>TGCGATTTTGGCTACTGGGGTCAGGGCACCCAGGTCACCGTGTCATCC |
| hIL27<br>Ra_VH<br>H24-<br>DR592 | 1522 | CAGGTGCAGCTTCAGGAGAGTGGTGGGGGTCTGGTTCAGCCTGGGGGTAGCCTG<br>AGGCTGAGTTGTGCCGCGAGCGGATTTACTTTCTCTCATAGGGGCATGAGTTGG<br>GTGCGCCAGGCCCCTGGCAAGGGTCTGGAATGGGTGAGTACAATCAACTCTGGC<br>GGTGCCTCTACCTATTACACCGACAGCGTGAAGGGGAGATTCACTATTAGCCGC<br>GACAATGCTAAGAATATGCTCTATCTTCAGCTGAACTCCCTGAAAACCGAAGAC<br>ACCGCAATGTATTACTGTGCAAAGGGTGGAAGCGGCTACGGCGACGCCAGCCGC<br>ATGACTTCCCCCGGCTCTCAGGGAACTCAGGTTACCGTCTCTTCCGGCGGTAGC<br>GGGGGCTCTGGAGGCTCTGGCCAGGTTCAGTTGCAGGAAAGTGGAGGCGGTTCA<br>GTTCAGGCTGGAGGCAGCTTGCGCTTGTCCTGTACCGCGCCAGGCTTCACAAGT<br>AATAGCTGTGGCATGGATTGGTATCGTCAGGCACCGGGAAAGGAGCGCGAGTTT<br>GTGTCTAGCATCAGCACAGACGGGACAACCGGCTATGCGGATTCCGTAAAAGGA<br>CGGTTTACTATCTCCAAGGATAAGGCTAAGGACACAGTGTACCTGCAAATGAAC<br>AGCCTGAAGCCCGAAGATACTGGTATGTATAGCTGCAAGACCAAGGATGGCACA<br>ATCGCCACTATGGAGCTGTGTGACTTCGGCTATTGGGGTCAGGGCACCCAGGTG<br>ACAGTGTCTTCT |
| hIL27<br>Ra_VH<br>H24-<br>DR593 | 1523 | CAGGTGCAGCTCCAGGAAAGCGGAGGTGGCCTGGTACAGCCCGGCGGTAGTCTG<br>AGGCTGAGTTGTGCTGCCTCAGGTTTTACTTTCTCACACTCCGGGATGTCCTGG<br>GTGAGACAAGCGCCGGGCAAGGGCCTGGAGTGGGTATCAACTATTAACAGTGGC<br>GGGGCGTCTACCTATTACACTGACAGCGTGAAGGGCCGGTTCACTATCAGCAGA<br>GATAACGCTAAAAATATGTTGTATCTTCAGCTCAATTCCCTGAAAACCGAAGAT<br>ACCGCGATGTATTACTGTGCTAAAGGGGGGTTCTGGATACGGCGATGCGTCTCGC<br>ATGACCTCTCCTGGAAGCCAGGGCACCCAGGTCACCGTGTCTAGTGGCGGAGGT<br>AGTCAGGTTCAGCTCCAAGAGTCCGGCGGAGGTAGCGTCCAGGCCGGGGGCTCA<br>CTCCGCCTGTCCTGCGCAGCCAGCGGATACCCCTATTCAAACGGCTACATGGGC<br>TGGTTCCGCCAGGCCCCCGGAAAAGAGCGTGAAGGAGTGGCTACAATCTATACC<br>GGCGACGGGAGGACCTATTACGCAGATTCCGTGAAAGGCCGTTTCACCATCTCC<br>CGTGACAACGCCAAAAATACCGTGGACCTTCAGATGAGTTCTCTGAAGCCAGAG<br>GACACCGCTATGTACTATTGTGCTGCCAGAGCTGCACCACTGTATTCCTCTGGC<br>AGCCCCCTGACCAGAGCCCGCTACAACGTCTGGGGACAGGGCACCCAGGTCACA<br>GTCAGCTCT |
| hIL27<br>Ra_VH<br>H24-<br>DR593 | 1524 | CAGGTTCAGCTCCAGGAATCTGGCGGTGGCCTCGTTCAGCCGGGTGGCAGTCTT<br>CGTCTGAGCTGTGCAGCCTCTGGCTTCACCTTCTCTCACCCCGGCATGAGCTGG<br>GTCAGACAGGCCCCAGGCAAGGGTCTGGAGTGGGTGTCTACGATCAATAGCGGA<br>GGCGCTTCTACCTATTACACCGACAGCGTGAAGGGCAGATTTACCATTTCCCGT<br>GACAACGCCAAAAACATGCTGTATCTGCAACTGAACTCTCTGAAGACCGAGGAC<br>ACCGCCATGTACTATTGCGCTAAGGGGGGTAGCGGATATGGCGACGCGAGCAGA<br>ATGACTTCTCCGGGGAGCCAGGGTACACAGGTGACCGTGTCCAGCGGCGGTAGT<br>GGGGGCAGCGGTGGCAGCGGACAGGTCCAGTTGCAGGAATCCGGCGGAGGCAGC<br>GTGCAGGCTGGCGGTTCACTGAGACTCTCTGCGCGGCCAGCGGCTTATCCCTAT<br>TCTAACGGTTATATGGGCTGGTTTAGGCAGGCTCCCGGCAAGGAAAGGGAGGGC<br>GTGGCTACTATCTATACTGGCGATGGCCGCACTTACTATGCCGATAGTGTCAAG<br>GGCCGTTTCACTATCTCTCGCGACAACGCTAAGAACACAGTGGATCTTCAGATG<br>TCTTCCCTGAAGCCAGAGGATACCGCGATGTATTACTGTGCCGCGAGGGCTGCA<br>CCACTGTACTCTAGCGGATCTCCCCTGACCCGCGCCAGATACAACGTGTGGGGC<br>CAGGGGACGCAGGTTACCGTTTCTTCT |
| hIL27<br>Ra_VH<br>H24-<br>DR594 | 1525 | CAGGTGCAGTTGCAGGAGAGTGGAGGGGGACTGGTGCAGCCAGGAGGTTCACTG<br>CGTCTTTCTTGCGCAGCCAGCGGTTTTACATTCAGCCACTCTGGAATGTCTTGG<br>GTTCGCCAGGCACCGGGGAAGGGCCTGGAGTGGGTGTCCACAATCAACAGTGGG<br>GGTGCCTCTACTTACTATACAGACTCCGTGAAAGGCAGGTTTACCATCTCCAGG<br>GACAACGCCAAAAATATGCTTTATCTTCAGCTCAATTCTCTGAAGACCGAGGAT<br>ACTGCGATGTATTACTGTGCAAAAGGGGGCTCAGGATATGGCGATGCCTCCCGC<br>ATGACCAGCCCAGGGAGCCAGGGCACCCAGGTGACCGTCTCCAGTGGCGGAGGC<br>TCTCAGGTGCAGCTCCAGGAGTCAGGCGGTGGCCCCGTCCAGGCTGGGGGGAGC<br>TTGCGCTTGTCCTGTGTTGCCCCCGCTAGTACCTATTGCACCTATGATATGCAC<br>TGGTACAGACAGGCTCCGGGTAAGGGCCGTGAGTTCGTGTCCGCCATTGATAGC |

TABLE 1B-continued

| Name | SEQ ID NO: | Sequence |
|---|---|---|
| | | GACGGCACAACTCGCTACGCTGATTCCGTGAAAGGCCGCCTCACCATTAGCCAG |
| | | GGCACCGCTAAGAACACAGTGTACTTGCAGATGAACAGCTTGCAGCCAGAGGAT |
| | | ACCGCGATGTATTACTGCAAAACTGTGTGCGTAGTGGGCAGTAGATGGTCCGAC |
| | | TACTGGGGCCAGGGCACACAGGTCACCGTGAGCAGC |
| hIL27 | 1526 | CAGGTACAGCTCCAAGAGTCTGGCGGTGGCCTGGTGCAACCAGGGGGCTCATTG |
| Ra_VH | | AGATTGTCTTGCGCCGCTTCTGGATTCACATTCCCCCACTCAGGTATGAGTTGG |
| H24- | | GTGCGGCAAGCCCCAGGCAAGGGCCTGGAGTGGGTTTCTACCATCAACAGTGGG |
| DR594 | | GGAGCTAGTACCTACTATACAGACTCCGTGAAAGGCCGCCTCACCATTAGCCGC |
| | | GATAACGCTAAGAACATGCTGTACTTGCAGCTCAATTCCCTGAAGACCGAGGAC |
| | | ACAGCTATGTACTATTGCGCCAAGGGAGGCAGTGGTTACGGGGACGCCAGCCGG |
| | | ATGACCTCTCCCGGCTCTCAAGGGACGCAGGTTACCGTGTCAAGCGGGGGTTCC |
| | | GGTGGGTCCGGTGGCTCCGGTCAAGTGCAGCTCCAGGAGAGTGGGGGTGGCAGC |
| | | GTCCAGGCCGGAGGCTCCCTCAGGCTGTCCTGCGTGGCCTCTGCCAGCACATAT |
| | | TGCACATACGACATGCACTGGTATCGTCAGGCTCCTGGCAAAGGGCGCGAGTTC |
| | | GTGTCCGCTATTGATTCCGATGGTACAACCCGGTACGCTGACAGTGTGAAGGGC |
| | | CGTTTTCACAATAGCCAGGGCACCGCTAAAAACACCGTGTACCTCCAGATGAAC |
| | | TCCCTCCAACCTGAGGATACTGCCATGTATTACTGCAAAACGGTGTGCGTCGTG |
| | | GGCTCTCGCTGGTCCGATTACTGGGGGCAGGGCACTCAGGTGACCGTGTCCAGC |
| hIL27 | 1527 | CAGGTGCAGTTGCAGGAGAGCGGAGGGGGGCTGGTGCAGCCTGGAGGCTCTCTG |
| Ra_VH | | CGCCTGTCCTGCGCAGCCTCAGGATTTACATTCTCTCACAGTGGGATGTCTTGG |
| H24- | | GTGCGGCAGGCTCCGGGCAAAGGCCTGGAATGGGTGTCCACCATTAACTCTGGT |
| DR595 | | GGCGCGAGCACTTACTATACCGATAGTGTCAAAGGCCGCTTCACCATCAGCCGG |
| | | GACAACGCTAAGAACATGCTGTATCTCCAGCTGAACAGCCTGAAGACCGAAGAC |
| | | ACTGCTATGTATTACTGTGCCAAGGGGGGTTCAGGTTATGGGGACGCCTCTCGG |
| | | ATGACATCACCGGGCTCCCAAGGAACTCAGGTCACCGTCAGCAGTGGCGGTGGC |
| | | TCCCAGGTGCAACTTCAGGAGTCGGGGGGTGGAAGCGTGCAGGCTGGAGGCTCC |
| | | CTGACACTGTCTTGCGCTGCCAGCGAATACGCTTATTCCACCTGTAACATGGGG |
| | | TGGTATCGCCAAGCTCCTGGGAAGGAACGTGAACTGGTCAGTGCCTTCATCTCT |
| | | GATGGGTCCACGTATTACGCTGATTCAGTAAAGGGACGTTTCACAATCACCCGC |
| | | GACAACGCCAAAAACACTGTGTACTTGCAGATGAACAGCCTGAAGCCAGAGGAT |
| | | ACCGCTATCTACTATTGCAGCGCCAACTGTTACCGTCGGCTGCGCAACTACTGG |
| | | GGGCAGGGCACACAAGTCACAGTGTCCAGC |
| hIL27 | 1528 | CAGGTCCAGCTCCAGGAGTCAGGGGGTGGACTTGTTCAACCCGGTGGCTCCCTC |
| Ra_VH | | CGTCTCTCCTGTGCTGCGTCTGGTTTCACCTTCAGCCACTCTGGAATGAGCTGG |
| H24- | | GTTAGACAAGCACCTGGCAAAGGCCTCGAATGGGTCTCTACCATCAACAGCGGC |
| DR595 | | GGAGCCTCCACTTATTACACCGACTCCGTGAAGGGTCGCTTCACGATCAGCAGA |
| | | GACAACGCCAAGAACATGCTGTACCTCCAACTGAATAGCCTGAAAACCGAGGAT |
| | | ACTGCCATGTATTACTGTGCAAAGGGGGGAAGTGGTTACGGAGACGCCAGCAGG |
| | | ATGACATCTCCGGGTTCTCAAGGCACCCAGGTCACCGTGAGTAGCGGCGGATCT |
| | | GGGGGCAGCGGAGGCAGCGGCCAGGTGCAGCTTCAGGAAAGCGGAGGGGGTTCC |
| | | GTTCAGGCCGGGGGCTCACTGACACTGAGTTGCGCGGCCCCCGAATACGCCTAT |
| | | TCTACTTGTAACATGGGCTGGTACAGACAAGCTCCTGGGAAGGAGAGAGAACTG |
| | | GTGAGCGCTTTTATTTCTGACGGCTCAACCTATTACGCAGACTCCGTCAAGGGC |
| | | CGCTTCACCATTACCCGCGACAACGCTAAGAATACGGTGTACCTCCAGATGAAC |
| | | TCCCTGAAGCCCGAAGACACCGCAATTTACTATTGCAGCGCCAACTGCTACCGC |
| | | CGGTTGCGCAACTACTGGGGCCAGGGAACTCAGGTTACCGTATCCTCC |
| hIL27 | 1529 | CAGGTGCAACTCCAGGAGTCCGGGGGTGGACTGGTGCAGCCTGGCGGTAGCTTG |
| Ra_VH | | AGGCTGTCTTGCGCCGCATCCGGCTTCACATTCAGCCACTCTGGAATGTCATGG |
| H24- | | GTCAGACAGGCTCCGGGCAAGGGCCTGGAATGGGTCTCAACCATCAATAGTGGA |
| DR596 | | GGTGCCTCAACTTACTATACCGACTCCGTGAAAGGTCGTTTCACAATTTCACGC |
| | | GACAACGCTAAGAACATGCTGTACCTCCAGCTGAATAGTCTCAAAACTGAGGAC |
| | | ACCGCTATGTATTACTGTGCTAAGGGCGGTTCCGGGTATGGGGACGCCTCCAGG |
| | | ATGACTTCACCGGGTAGCCAGGGGACCCAGGTGACGGTTTCTAGCGGGGGGGGG |
| | | TCCCAGGTGCAGCTTCAGGAAAGCGGAGGGGGCCTGGTGCAGCCCGGGGGGTCC |
| | | CTGAGACTGAGCTGCACGGCAAGCGGCCTGACGTTTGATGACTCCGTGATGGGC |
| | | TGGTTCAGACAGGCCCCCGGCAAGGGGCGCGAAGCCGTCTCCTGTATTAGCTCC |
| | | AGCGGGGCCAACGCTTTCTACGCGGACAGCGTCAAAGGCCGCTTCACCATTAGC |
| | | AGAGACAACGCTAAGAACACTCCGTACCTCCAGATGAACAGCCTGAAACCAGAG |
| | | GATACCGCAACGTATTACTGCAAGCGCGGACATGCTTGCGCGGGCTATTACCCA |
| | | ATCCCTTATGACGATTACTGGGGCCAGGGCACTCAGGTGACGGTAAGCTCC |
| hIL27 | 1530 | CAGGTCCAACTCCAGGAGTCCGGCGGTGGCCTGGTTCAGCCAGGAGGTTCCCTG |
| Ra_VH | | CGCCTGTCCTGTGCCGCTTCCGGCTTTACCATCTCCCATTCCGGCATGAGCTGG |
| H24- | | GTGAGGCAGGCCCCTGGCAAAGGCCTGGAGTGGGTGTCTACCATTAACTCTGGC |
| DR596 | | GGAGCCAGCACATACTATACAGACTCAGTAAAGGGACGCTTCACCATCAGCAGG |
| | | GACAACGCCAAAAACATGCTGTATCTCCAGCTGAACTCTCTCAAGACCGAAGAC |
| | | ACCGCTATGTATTACTGTGCTAAGGGCGGTAGCGGCTATGGGGACGCATCTCGT |
| | | ATGACCTCTCCCGGCTCTCAAGGCACCCAGGTGACTGTGTCTAGTGGCGGGTCT |
| | | GGCGGGTCTGGCGGATCTGGTCAAGTCCAGTTGCAGGAGAGTGGAGGCGGTCTC |
| | | GTCCAGCCAGGCGGAAGCCTGCGCCTGTCTTGTACTGCCAGCGGTTTGACCTTT |
| | | GATGACTGTGTGATGGGCTGGTTTCGTCAGGCCCCCGGCAAGGGCCGTGAGGCC |
| | | GTGTCATGTATCTCATCTTCAGGAGCCAACGCCTTTTATGCCGATAGCGTGAAA |
| | | GGGAGATTCACCATCTCTCGTGATAACGCAAAGAACACCCTGTACCTTCAGATG |

TABLE 1B-continued

| Name | SEQ ID NO: | Sequence |
|---|---|---|
| | | AACTCTCTGAAGCCTGAGGACACTGCTACCTACTATTGTAAGCGTGGGCACGCC TGCGCTGGATATTACCCTATCCCTTACGATGACTATTGGGGGCAGGGCACTCAG GTGACCGTCAGCAGC |

In some embodiments, a bispecific $V_HH^2$ comprises:

an anti-gp130 $V_HH$ antibody comprising a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS:193-198; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS:199-204; and a CDR3 having at least 90% (e.g., 91%, 92%, 93%, 94%, 95%, 96%, 97%, 98%, 99%, or 100%) sequence identity, or having 0, 1, 2, or 3 amino acid changes optionally conservative amino acid changes relative, to the sequence of any one of SEQ ID NOS:205-210; and an anti-IL27Rα $V_HH$ antibody comprising a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS:211-217; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS:218-224; and a CDR3 having at least 90% (e.g., 91%, 92%, 93%, 94%, 95%, 96%, 97%, 98%, 99%, or 100%) sequence identity, or having 0, 1, 2, or 3 amino acid changes optionally conservative amino acid changes relative, to the sequence of any one of SEQ ID NOS:225-231.

In certain embodiments, a bispecific $V_HH^2$ described herein comprises an anti-gp130 $V_HH$ antibody comprising a CDR1, a CDR2, and a CDR3 and an anti-IL27Rα $V_HH$ antibody comprising a CDR1, a CDR2, and a CDR3 as described in each row of Table 1 below. In some embodiments, the CDR1, CDR2, and CDR3 in the anti-gp130 $V_HH$ antibody and CDR1, CDR2, and CDR-3 in the anti-IL27Rα $V_HH$ antibody can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in each row of Table 1.

In some embodiments, the bispecific $V_HH^2$ comprises an anti-gp130 $V_HH$ antibody at the N-terminus and an anti-IL27Rα. $V_HH$ antibody at the C-terminus. In some embodiments, the bispecific $V_HH^2$ comprises an anti-IL27Rα $V_HH$ antibody at the N-terminus and an anti-gp130 $V_HH$ antibody at the C-terminus.

TABLE 1

| Anti-gp130 $V_HH$ CDR1 | Anti-gp130 $V_HH$ CDR2 | Anti-gp130 $V_HH$ CDR3 | Anti-IL27Rα $V_HH$ CDR1 | Anti-IL27Rα $V_HH$ CDR2 | Anti-IL27Rα $V_HH$ CDR3 |
|---|---|---|---|---|---|
| ALASGYIDSR (SEQ ID NO: 193) | AIWPGGGLTVY ADSVKG (SEQ ID NO: 199) | GSPRMCPSLEFG FDY (SEQ ID NO: 205) | FTFSSYPMS (SEQ ID NO: 211) | TISAGGDTTLYA DSVKG (SEQ ID NO: 218) | GYCYRRNY (SEQ ID NO: 225) |
| ALASGYIDSR (SEQ ID NO: 193) | AIWPGGGLTVY ADSVKG (SEQ ID NO: 199) | GSPRMCPSLEFG FDY (SEQ ID NO: 205) | FTFSNYAMS (SEQ ID NO: 212) | GINVAYGITSYA DSVKG (SEQ ID NO: 219) | HSGTTIPRGFISY TK (SEQ ID NO: 226) |
| AIASGYIDSR (SEQ ID NO: 193) | AIWPGGGLTVY ADSVKG (SEQ ID NO: 199) | GSPRMCPSLEFG FDY (SEQ ID NO: 205) | FSFSSYAMK (SEQ ID NO: 213) | TISSGGSSTNYA DSVKG (SEQ ID NO: 220) | AIVPTGATME (SEQ ID NO: 227) |
| AIASGYIDSR (SEQ ID NO: 193) | AIWPGGGLTVY ADSVKG (SEQ ID NO: 199) | GSPRMCPSLEFG FDY (SEQ ID NO: 205) | FTYSTSNSWMA (SEQ ID NO: 214) | AIYTVGGSIFYA DSVRG (SEQ ID NO: 221) | ASGRLRGKWFW PYEYNY (SEQ ID NO: 228) |
| AIASGYIDSR (SEQ ID NO: 193) | AIWPGGGLTVY ADSVKG (SEQ ID NO: 199) | GSPRMCPSLEFG FDY (SEQ ID NO: 205) | YVSCDYFLPS (SEQ ID NO: 215) | IIDDGTGSTSYAA SVKG (SEQ ID NO: 222) | SCVRGRAISEY (SEQ ID NO: 229) |
| AIASGYIDSR (SEQ ID NO: 193) | AIWPGGGLTVY ADSVKG (SEQ ID NO: 199) | GSPRMCPSLEFG FDY (SEQ ID NO: 205) | STYSNYCLG (SEQ ID NO: 216) | VINWVGGMLYF ADSVKG (SEQ ID NO: 223) | ESVSSFSCGGWL TRPDRVPY (SEQ ID NO: 230) |
| AIASGYIDSR (SEQ ID NO: 193) | AIWPGGGLTVY ADSVKG (SEQ ID NO: 199) | GSPRMCPSLEFG FDY (SEQ ID NO: 205) | FTFSLSSMS (SEQ ID NO: 217) | AISSGGASTYYT DSVKG (SEQ ID NO: 224) | GGSGYGDASRM TSP (SEQ ID NO: 231) |
| FTSNSCGMD (SEQ ID NO: 194) | SISTDGTTGYAD SVKG (SEQ ID NO: 200) | KDGTIATMELC DFGY (SEQ ID NO: 206) | FTFSSYPMS (SEQ ID NO: 211) | TISAGGDTTLYA DSVKG (SEQ ID NO: 218) | GYCYRRNY (SEQ ID NO: 225) |
| FTSNSCGMD (SEQ ID NO: 194) | SISTDGTTGYAD SVKG (SEQ ID NO: 200) | KDGTIATMELC DFGY (SEQ ID NO: 206) | FTFSNYAMS (SEQ ID NO: 212) | GINVAYGITSYA DSVKG (SEQ ID NO: 219) | HSGTTIPRGFISY TK (SEQ ID NO: 226) |
| FTSNSCGMD (SEQ ID NO: 194) | SISTDGTTGYAD SVKG (SEQ ID NO: 200) | KDGTIATMELC DFGY (SEQ ID NO: 206) | FSFSSYAMK (SEQ ID NO: 213) | TISSGGSSTNYA DSVKG (SEQ ID NO: 220) | AIVPTGATME (SEQ ID NO: 227) |
| FTSNSCGMD (SEQ ID NO: 194) | SISTDGTTGYAD SVKG (SEQ ID NO: 200) | KDGTIATMELC DFGY (SEQ ID NO: 206) | FTYSTSNSWMA (SEQ ID NO: 214) | AIYTVGGSIFYA DSVRG (SEQ ID NO: 221) | ASGRLRGKWFW PYEYNY (SEQ ID NO: 228) |
| FTSNSCGMD (SEQ ID NO: 194) | SISTDGTTGYAD SVKG (SEQ ID NO: 200) | KDGTIATMELC DFGY (SEQ ID NO: 206) | YVSCDYFLPS (SEQ ID NO: 215) | IIDGTGSTSYAA SVKG (SEQ ID NO: 222) | SCVRGRAISEY (SEQ ID NO: 229) |

TABLE 1-continued

| Anti-gp130 $V_H$H CDR1 | Anti-gp130 $V_H$H CDR2 | Anti-gp130 $V_H$H CDR3 | Anti-IL27Rα $V_H$H CDR1 | Anti-IL27Rα $V_H$H CDR2 | Anti-IL27Rα $V_H$H CDR3 |
|---|---|---|---|---|---|
| FTSNSCGMD (SEQ ID NO: 194) | SISTDGTTGYAD SVKG (SEQ ID NO: 200) | KDGTIATMELC DFGY (SEQ ID NO: 206) | STYSNYCLG (SEQ ID NO: 216) | VINWVGGMLYF ADSVKG (SEQ ID NO: 223) | ESVSSFSCGGWL TRPDRVPY (SEQ ID NO: 230) |
| FTSNSCGMD (SEQ ID NO: 194) | SISTDGTTGYAD SVKG (SEQ ID NO: 200) | KDGTIATMELC DFGY (SEQ ID NO: 206) | FTFSLSSMS (SEQ ID NO: 217) | AISSGGASTYYT DSVKG (SEQ ID NO: 224) | GGSGYGDASRM TSP (SEQ ID NO: 231) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | FTFSSYPMS (SEQ ID NO: 211) | TISAGGDTTLYA DSVKG (SEQ ID NO: 218) | GYCYRRNY (SEQ ID NO: 225) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | FTFSNYAMS (SEQ ID NO: 212) | GINVAYGITSYA DSVKG (SEQ ID NO: 219) | HSGTTIPRGFISY TK (SEQ ID NO: 226) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | FSFSSYAMK (SEQ ID NO: 213) | TISSGGSSTNYA DSVKG (SEQ ID NO: 220) | AIVPTGATME (SEQ ID NO: 227) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | FTYSTSNSWMA (SEQ ID NO: 214) | AIYTVGGSIFYA DSVRG (SEQ ID NO: 221) | ASGRLRGKWFW PYEYNY (SEQ ID NO: 228) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | YVSCDYFLPS (SEQ ID NO: 215) | IIDGTGSTSYAA SVKG (SEQ ID NO: 222) | SCVRGRAISEY (SEQ ID NO: 229) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | STYSNYCLG (SEQ ID NO: 216) | VINWVGGMLYF ADSVKG (SEQ ID NO: 223) | ESVSSFSCGGWL TRPDRVPY (SEQ ID NO: 230) |
| YPYSNGYMG (SEQ ID NO: 195) | TIYTGDGRTYY ADSVKG (SEQ ID NO: 201) | RAAPLYSSGSPL TRARYNV (SEQ ID NO: 207) | FTFSLSSMS (SEQ ID NO: 217) | AISSGGASTYYT DSVKG (SEQ ID NO: 224) | GGSGYGDASRM TSP (SEQ ID NO: 231) |
| STYCTYDMH (SEQ ID NO: 196) | AIDSDGTTRYAD SVKG (SEQ ID NO: 202) | GSRWSDY (SEQ ID NO: 208) | FTFSSYPMS (SEQ ID NO: 211) | TISAGGDTTLYA DSVKG (SEQ ID NO: 218) | GYCYRRNY (SEQ ID NO: 225) |
| STYCTYDMH (SEQ ID NO: 196) | AIDSDGTTRYAD SVKG (SEQ ID NO: 202) | GSRWSDY (SEQ ID NO: 208) | FTFSNYAMS (SEQ ID NO: 212) | GINVAYGITSYA DSVKG (SEQ ID NO: 219) | HSGTTIPRGFISY TK (SEQ ID NO: 226) |
| STYCTYDMH (SEQ ID NO: 196) | AIDSDGTTRYAD SVKG (SEQ ID NO: 202) | GSRWSDY (SEQ ID NO: 208) | FSFSSYAMK (SEQ ID NO: 213) | TISSGGSSTNYA DSVKG (SEQ ID NO: 220) | AIVPTGATME (SEQ ID NO: 227) |

TABLE 1-continued

| Anti-gp130 $V_H$H CDR1 | Anti-gp130 $V_H$H CDR2 | Anti-gp130 $V_H$H CDR3 | Anti-IL27Rα $V_H$H CDR1 | Anti-IL27Rα $V_H$H CDR2 | Anti-IL27Rα $V_H$H CDR3 |
|---|---|---|---|---|---|
| STYCTYDMH (SEQ ID NO: 196) | AIDSDGTTRYAD SVKG (SEQ ID NO: 202) | GSRWSDY (SEQ ID NO: 208) | FTYSTSNSWMA (SEQ ID NO: 214) | AIYTVGGSIFYA DSVRG (SEQ ID NO: 221) | ASGRLRGKWFW PYEYNY (SEQ ID NO: 228) |
| STYCTYDMH (SEQ ID NO: 196) | AIDSDGTTRYAD SVKG (SEQ ID NO: 202) | GSRWSDY (SEQ ID NO: 208) | YVSCDYFLPS (SEQ ID NO: 215) | IIDGTGSTSYAA SVKG (SEQ ID NO: 222) | SCVRGRAISEY (SEQ ID NO: 229) |
| STYCTYDMH (SEQ ID NO: 196) | AIDSDGTTRYAD SVKG (SEQ ID NO: 202) | GSRWSDY (SEQ ID NO: 208) | STYSNYCLG (SEQ ID NO: 216) | VINWVGGMLYF ADSVKG (SEQ ID NO: 223) | ESVSSFSCGGWL TRPDRVPY (SEQ ID NO: 230) |
| STYCTYDMH (SEQ ID NO: 196) | AIDSDGTTRYAD SVKG (SEQ ID NO: 202) | GSRWSDY (SEQ ID NO: 208) | FTFSLSSMS (SEQ ID NO: 217) | AISSGGASTYYT DSVKG (SEQ ID NO: 224) | GGSGYGDASRM TSP (SEQ ID NO: 231) |
| YAYSTCNMG (SEQ ID NO: 197) | AFISDGSTYYAD SVKG (SEQ ID NO: 203) | NCYRRLRNY (SEQ ID NO: 209) | FTFSSYPMS (SEQ ID NO: 211) | TISAGGDTTLYA DSVKG (SEQ ID NO: 218) | GYCYRRNY (SEQ ID NO: 225) |
| YAYSTCNMG (SEQ ID NO: 197) | AFISDGSTYYAD SVKG (SEQ ID NO: 203) | NCYRRLRNY (SEQ ID NO: 209) | FTFSNYAMS (SEQ ID NO: 212) | GINVAYGITSYA DSVKG (SEQ ID NO: 219) | HSGTTIPRGFISY TK (SEQ ID NO: 226) |
| YAYSTCNMG (SEQ ID NO: 197) | AFISDGSTYYAD SVKG (SEQ ID NO: 203) | NCYRRLRNY (SEQ ID NO: 209) | FSFSSYAMK (SEQ ID NO: 213) | TISSGGSSTNYA DSVKG (SEQ ID NO: 220) | ATVPTGATME (SEQ ID NO: 227) |
| YAYSTCNMG (SEQ ID NO: 197) | AFISDGSTYYAD SVKG (SEQ ID NO: 203) | NCYRRLRNY (SEQ ID NO: 209) | FTYSTSNSWMA (SEQ ID NO: 214) | AIYTVGGSIFYA DSVRG (SEQ ID NO: 221) | ASGRLRGKWFW PYEYNY (SEQ ID NO: 228) |
| YAYSTCNMG (SEQ ID NO: 197) | AFISDGSTYYAD SVKG (SEQ ID NO: 203) | NCYRRLRNY (SEQ ID NO: 209) | YVSCDYELPS (SEQ ID NO: 215) | IIDGTGSTSYAA SVKG (SEQ ID NO: 222) | SCVRGRAISEY (SEQ ID NO: 229) |
| YAYSTCNMG (SEQ ID NO: 197) | AFISDGSTYYAD SVKG (SEQ ID NO: 203) | NCYRRLRNY (SEQ ID NO: 209) | STYSNYCLG (SEQ ID NO: 216) | VINWVGGMLYF ADSVKG (SEQ ID NO: 223) | ESVSSFSCGGWL TRPDRVPY (SEQ ID NO: 230) |
| YAYSTCNMG (SEQ ID NO: 197) | AFISDGSTYYAD SVKG (SEQ ID NO: 203) | NCYRRLRNY (SEQ ID NO: 209) | FTFSLSSMS (SEQ ID NO: 217) | AISSGGASTYYT DSVKG (SEQ ID NO: 224) | GGSGYGDASRM TSP (SEQ ID NO: 231) |
| LTFDDSVMG (SEQ ID NO: 198) | CISSSGANAFYA DSVKG (SEQ ID NO: 204) | GHACAGYYPIP YDDY (SEQ ID NO: 210) | FTFSSYPMS (SEQ ID NO: 211) | TISAGGDTTLYA DSVKG (SEQ ID NO: 218) | GYCYRRNY (SEQ ID NO: 225) |

TABLE 1-continued

| Anti-gp130 $V_HH$ CDR1 | Anti-gp130 $V_HH$ CDR2 | Anti-gp130 $V_HH$ CDR3 | Anti-IL27Rα $V_HH$ CDR1 | Anti-IL27Rα $V_HH$ CDR2 | Anti-IL27Rα $V_HH$ CDR3 |
|---|---|---|---|---|---|
| LIFDDSVMG (SEQ ID NO: 198) | CISSSGANAFYA DSVKG (SEQ ID NO: 204) | GHACAGYYPIP YDDY (SEQ ID NO: 210) | FTFSNYAMS (SEQ ID NO: 212) | GINVAYGITSYA DSVKG (SEQ ID NO: 219) | HSGTTIPRGFISY TK (SEQ ID NO: 226) |
| LIFDDSVMG (SEQ ID NO: 198) | CISSSGANAFYA DSVKG (SEQ ID NO: 204) | GHACAGYYPIP YDDY (SEQ ID NO: 210) | FSFSSYAMK (SEQ ID NO: 213) | TISSGGSSTNYA DSVKG (SEQ ID NO: 220) | ATVPTGATME (SEQ ID NO: 227) |
| LTFDDSVMG (SEQ ID NO: 198) | CISSSGANAFYA DSVKG (SEQ ID NO: 204) | GHACAGYYPIP YDDY (SEQ ID NO: 210) | FTYSTSNSWMA (SEQ ID NO: 214) | AIYTVGGSIFYA DSVRG (SEQ ID NO: 221) | ASGRLRGKWFW PYEYNY (SEQ ID NO: 228) |
| LTFDDSVMG (SEQ ID NO: 198) | CISSSGANAFYA DSVKG (SEQ ID NO: 204) | GHACAGYYPIP YDDY (SEQ ID NO: 210) | YVSCDYFLPS (SEQ ID NO: 215) | IIDGTGSTSYAA SVKG (SEQ ID NO: 222) | SCVRGRAISEY (SEQ ID NO: 229) |
| LTFDDSVMG (SEQ ID NO: 198) | CISSSGANAFYA DSVKG (SEQ ID NO: 204) | GHACAGYYPIP YDDY (SEQ ID NO: 210) | STYSNYCLG (SEQ ID NO: 216) | VINWVGGMLYF ADSVKG (SEQ ID NO: 223) | ESVSSFSCGGWL TRPDRVPY (SEQ ID NO: 230) |
| LTFDDSVMG (SEQ ID NO: 198) | CISSSGANAFYA DSVKG (SEQ ID NO: 204) | GHACAGYYPIP YDDY (SEQ ID NO: 210) | FTFSLSSMS (SEQ ID NO: 217) | AISSGGASTYYT DSVKG (SEQ ID NO: 224) | GGSGYGDASRM TSP (SEQ ID NO: 231) |

Anti-GP130-Linker-Anti-Il27Rα $V_HH$

A bispecific $V_HH^2$ can contain, from the N-terminus to the C-terminus, a first $V_HH$ binding to gp130 (an anti-gp130 $V_HH$ antibody), a linker, and a second $V_HH$ binding to IL27Rα (an anti-IL27Rα $V_HH$ antibody). In other words, the linker joins the C-terminus of the anti-gp130 $V_HH$ in the binding protein to the N-terminus of the anti-IL27Rα $V_HH$ in the binding protein. In some embodiments, a purification peptide, e.g., a six-histidine peptide ($(His)_6$ (SEQ ID NO: 1531) or His-tag) can be included, or not, in the bispecific $V_HH^2$.

In certain embodiments, a bispecific $V_HH^2$ described herein comprises an anti-gp130 $V_HH$ antibody comprising a sequence having at least 90% (e.g., 91%, 92%, 93%, 94%, 95%, 96%, 97%, 98%, 99%, or 100%) sequence identity to a sequence of any one of SEQ ID NOS:232-237; and an anti-IL27Rα $V_HH$ antibody comprising a sequence having at least 90% (e.g., 91%, 92%, 93%, 94%, 95%, 96%, 97%, 98%, 99%, or 100%) sequence identity to a sequence of any one of SEQ ID NOS:238-244.

In certain embodiments, a bispecific $V_HH^2$ described herein comprises an anti-gp130 $V_HH$ antibody and an anti-IL27Rα $V_HH$ antibody as described in each row of Table 2A below or Table 1A above. In some embodiments, in each row of Table 2A, the anti-gp130 $V_HH$ antibody and the anti-IL27Rα $V_HH$ antibody can each, independently, comprise at least 90% (e.g., 91%, 92%, 93%, 94%, 95%, 96%, 97%, 98%, 99%, or 100%) sequence identity to the sequence described in each row of Table 2A. In some embodiments, the bispecific $V_HH^2$ can comprise a linker (e.g., linkers described in Section IV) between the anti-gp130 $V_HH$ antibody and the anti-IL27Rα $V_HH$ antibody as described in each row of Table 2A below. In particular embodiments, the linker is GGGS (SEQ ID NO:108) or (GGGS)n (SEQ ID NO: 1532), (GGS)nG (SEQ ID NO: 1533), (GGGGS)n (SEQ ID NO: 1534) as described elwhere herein. The sequence of the anti-gp130 $V_HH$ is N-terminus to the linker and the sequence of the anti-IL27Rα $V_HH$ is C-terminus to the linker. Examples of linkers are further described in Section IV below. The CDR sequences in each $V_HH$ are underlined.

TABLE 2A

| N-terminal Anti-gp130 $V_HH$ | C-terminal Anti-IL27Rα $V_HH$ |
|---|---|
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVS (SEQ ID NO: 238) |
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVS (SEQ ID NO: 239) |
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVS (SEQ ID NO: 240) |
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVS (SEQ ID NO: 241) |
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVS (SEQ ID NO: 242) |
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVS (SEQ ID NO: 243) |
| QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS (SEQ ID NO: 232) | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVS (SEQ ID NO: 244) |
| QVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVSS (SEQ ID NO: 233) | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVS (SEQ ID NO: 238) |

TABLE 2A-continued

| N-terminal Anti-gp130 $V_HH$ | C-terminal Anti-IL27Rα $V_HH$ |
|---|---|
| QVQLQESGGGSVQAGGSLRLSCTAPGFTSNSC<br>GMDWYRQAPGKEREFVSSISTDGTTGYADSV<br>KGRFTISKDKAKDTVYLQMNSLKPEDIGMYS<br>CKTKDGTIATMELCDFGYWGQGTQVTVSS<br>(SEQ ID NO: 233) | QVQLQESGGGLVQPGESLRLSCTASGFTFSNY<br>AMSWVRQAPGKGLEWVSGINVAYGITSYADS<br>VKGRFTISRDNTKNTLYLQLNSLKTEDTAIYYC<br>VKHSGTTIPRGFISYTKRGQGTQVTVS (SEQ ID<br>NO: 239) |
| QVQLQESGGGSVQAGGSLRLSCTAPGFTSNSC<br>GMDWYRQAPGKEREFVSSISTDGTTGYADSV<br>KGRFTISKDKAKDTVYLQMNSLKPEDIGMYS<br>CKTKDGTIATMELCDFGYWGQGTQVTVSS<br>(SEQ ID NO: 233) | QVQLQESGGGLVQPGGSLRLSCAASGFSFSSY<br>AMKWVRQAPGKGLEWVSTISSGGSSTNYADS<br>VKGRFTISRDNAKNTLYLQLNSLKIEDTAMYY<br>CAKAIVPTGATMERGQGTQVTVS (SEQ ID<br>NO: 240) |
| QVQLQESGGGSVQAGGSLRLSCTAPGFTSNSC<br>GMDWYRQAPGKEREFVSSISTDGTTGYADSV<br>KGRFTISKDKAKDTVYLQMNSLKPEDIGMYS<br>CKTKDGTIATMELCDFGYWGQGTQVTVSS<br>(SEQ ID NO: 233) | QVQLQESGGGSVQSGGSLRLSCAASGFTYSTS<br>NSWMAWFRQAPGKEREGVAAIYTVGGSIFYA<br>DSVRGRFTISQDATKNMFYLQMNTLKPEDTA<br>MYYCAAASGRLRGKWFWPYEYNYWGQGTQ<br>VTVS (SEQ ID NO: 241) |
| QVQLQESGGGSVQAGGSLRLSCTAPGFTSNSC<br>GMDWYRQAPGKEREFVSSISTDGTTGYADSV<br>KGRFTISKDKAKDTVYLQMNSLKPEDIGMYS<br>CKTKDGTIATMELCDFGYWGQGTQVTVSS<br>(SEQ ID NO: 233) | QVQLQESGGGSVQAGGSLRLSCVASGYVSCD<br>YFLPSWYRQAPGKEREFVSIIDGTGSTSYAASV<br>KGRFTASQDKGKNIAYLQMNTLKPEDTAMYY<br>CKASCVRGRAISEYWGQGTQVTVS (SEQ ID<br>NO: 242) |
| QVQLQESGGGSVQAGGSLRLSCTAPGFTSNSC<br>GMDWYRQAPGKEREFVSSISTDGTTGYADSV<br>KGRFTISKDKAKDTVYLQMNSLKPEDIGMYS<br>CKTKDGTIATMELCDFGYWGQGTQVTVSS<br>(SEQ ID NO: 233) | QVQLQESGGGSVQAGGSLRLSCRASGSTYSNY<br>CLGWFRQITGKEREGVAVINWVGGMLYFADS<br>VKGRFTVSQDQAKNTVYLQMNSLKPEDTAMY<br>YCAAESVSSFSCGGWLTRPDRVPYWGQGTQV<br>TVS (SEQ ID NO: 243) |
| QVQLQESGGGSVQAGGSLRLSCTAPGFTSNSC<br>GMDWYRQAPGKEREFVSSISTDGTTGYADSV<br>KGRFTISKDKAKDTVYLQMNSLKPEDIGMYS<br>CKTKDGTIATMELCDFGYWGQGTQVTVSS<br>(SEQ ID NO: 233) | QVQLQESGGGLVQPGGSLRLSCAASGFTFSLSS<br>MSWVRQAPGKGLEWVSAISSGGASTYYTDSV<br>KGRFTISRDNAKNMLYLQLNSLKTEDTAMYY<br>CAKGGSGYGDASRMTSPGSQGTQVTVS (SEQ<br>ID NO: 244) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGLVQPGGSLRLSCAASGFTFSSY<br>PMSWVRQAPGKGLEWISTISAGGDTTLYADSV<br>KGRFTSSRDNAKNTLYLQLNSLKTEDAAIYYC<br>AKRIDCNSGYCYRRNYWGQGTQVTVS (SEQ<br>ID NO: 238) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGLVQPGESLRLSCTASGFTFSNY<br>AMSWVRQAPGKGLEWVSGINVAYGITSYADS<br>VKGRFTISRDNTKNTLYLQLNSLKTEDTAIYYC<br>VKHSGTTIPRGFISYTKRGQGTQVTVS (SEQ ID<br>NO: 239) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGLVQPGGSLRLSCAASGFSFSSY<br>AMKWVRQAPGKGLEWVSTISSGGSSTNYADS<br>VKGRFTISRDNAKNTLYLQLNSLKIEDTAMYY<br>CAKAIVPTGATMERGQGTQVTVS (SEQ ID<br>NO: 240) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGSVQSGGSLRLSCAASGFTYSTS<br>NSWMAWFRQAPGKEREGVAAIYTVGGSIFYA<br>DSVRGRFTISQDATKNMFYLQMNTLKPEDTA<br>MYYCAAASGRLRGKWFWPYEYNYWGQGTQ<br>VTVS (SEQ ID NO: 241) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGSVQAGGSLRLSCVASGYVSCD<br>YFLPSWYRQAPGKEREFVSIIDGTGSTSYAASV<br>KGRFTASQDKGKNIAYLQMNTLKPEDTAMYY<br>CKASCVRGRAISEYWGQGTQVTVS (SEQ ID<br>NO: 242) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGSVQAGGSLRLSCRASGSTYSNY<br>CLGWFRQITGKEREGVAVINWVGGMLYFADS<br>VKGRFTVSQDQAKNTVYLQMNSLKPEDTAMY<br>YCAAESVSSFSCGGWLTRPDRVPYWGQGTQV<br>TVS (SEQ ID NO: 243) |
| QVQLQESGGGSVQAGGSLRLSCAASGYPYSN<br>GYMGWFRQAPGKEREGVATIYTGDGRTYYAD<br>SVKGRFTISRDNAKNTVDLQMSSLKPEDTAMY<br>YCAARAAPLYSSGSPLTRARYNWWGQGTQVT<br>VSS (SEQ ID NO: 234) | QVQLQESGGGLVQPGGSLRLSCAASGFTFSLSS<br>MSWVRQAPGKGLEWVSAISSGGASTYYTDSV<br>KGRFTISRDNAKNMLYLQLNSLKTEDTAMYY<br>CAKGGSGYGDASRMTSPGSQGTQVTVS (SEQ<br>ID NO: 244) |

TABLE 2A-continued

| N-terminal Anti-gp130 $V_HH$ | C-terminal Anti-IL27Rα $V_HH$ |
|---|---|
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVS (SEQ ID NO: 238) |
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVS (SEQ ID NO: 239) |
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVS (SEQ ID NO: 240) |
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVS (SEQ ID NO: 241) |
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVS (SEQ ID NO: 242) |
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVS (SEQ ID NO: 243) |
| QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS (SEQ ID NO: 235) | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVS (SEQ ID NO: 244) |
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVS (SEQ ID NO: 238) |
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVS (SEQ ID NO: 239) |
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVS (SEQ ID NO: 240) |
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVS (SEQ ID NO: 241) |
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVS (SEQ ID NO: 242) |
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVS (SEQ ID NO: 243) |

TABLE 2A-continued

| N-terminal Anti-gp130 $V_HH$ | C-terminal Anti-IL27Rα $V_HH$ |
|---|---|
| QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVSS (SEQ ID NO: 236) | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVS (SEQ ID NO: 244) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVS (SEQ ID NO: 238) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVS (SEQ ID NO: 239) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVS (SEQ ID NO: 240) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVS (SEQ ID NO: 241) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVS (SEQ ID NO: 242) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVS (SEQ ID NO: 243) |
| QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS (SEQ ID NO: 237) | QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVS (SEQ ID NO: 244) |

In certain embodiments, the bispecific $V_HH^2$ comprises a sequence that is substantially identical to a sequence of any one of SEQ ID NOS:1-42. Such a bispecific $V_HH^2$ can have a sequence having at least 90% (e.g., 91%, 92%, 93%, 94%, 95%, 96%, 97%, 98%, 99%, or 100%) sequence identity to a sequence of any one of SEQ ID NOS:1-42, as shown in Table 2B below. In each of sequences of SEQ ID NOS:1-42, the linker GGGS (SEQ ID NO:108) is in bold. The sequence of the anti-gp130 $V_HH$ is N-terminus to the linker and the sequence of the anti-IL27Rα $V_HH$ is C-terminus to the linker. The CDR sequences in each $V_HH$ are underlined.

TABLE 2B

| SEQ ID NO | Sequence |
|---|---|
| 1 | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVSS**GGGS**QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS |

TABLE 2B-continued

| SEQ ID NO | Sequence |
|---|---|
| 2 | QVQLQESGGGSVQAGGSLRLSCTASGAIASGYIDSRWCMAWFRQAPGKEREGVAAIWPGG<br>GLTVYADSVKGRFTISRDHAKNTLYLQMNNLKPEDTAMYYCAAGSPRMCPSLEFGFDYW<br>GQGTQVTVSS**GGGS**QVQLQESGGGLVQPGESLRLSCTASGFTFSNYAMSWVRQAPGKGLE<br>WVSGINVAYGITSYADSVKGRFTISRDNIKNTLYLQLNSLKTEDTAIYYCVKHSGTTIPRGFI<br>SYTKRGQGTQVTVSS |
| 3 | QVQLQESGGGSVQAGGSLRLSCTASGAIASGYIDSRWCMAWFRQAPGKEREGVAAIWPGG<br>GLTVYADSVKGRFTISRDHAKNTLYLQMNNLKPEDTAMYYCAAGSPRMCPSLEFGFDYW<br>GQGTQVTVSS**GGGS**QVQLQESGGGLVQPGGSLRLSCAASGFSFSSYAMKWVRQAPGKGL<br>EWVSTISSGGSSTNYADSVKGRFTISRDNAKNTLYLQLNSLKIEDTAMYYCAKAIVPTGAT<br>MERGQGTQVTVSS |
| 4 | QVQLQESGGGSVQAGGSLRLSCTASGAIASGYIDSRWCMAWFRQAPGKEREGVAAIWPGG<br>GLTVYADSVKGRFTISRDHAKNTLYLQMNNLKPEDTAMYYCAAGSPRMCPSLEFGFDYW<br>GQGTQVTVSS**GGGS**QVQLQESGGGSVQSGGSLRLSCAASGFTYSTSNSWMAWFRQAPGK<br>EREGVAAIYTVGGSIFYADSVRGRFTISQDATKNMFYLQMNTLKPEDTAMYYCAAASGRL<br>RGKWFWPYEYNYWGQGTQVTVSS |
| 5 | QVQLQESGGGSVQAGGSLRLSCTASGAIASGYIDSRWCMAWFRQAPGKEREGVAAIWPGG<br>GLTVYADSVKGRFTISRDHAKNTLYLQMNNLKPEDTAMYYCAAGSPRMCPSLEFGFDYW<br>GQGTQVTVSS**GGGS**QVQLQESGGGSVQAGGSLRLSCVASGYVSCDYFLPSWYRQAPGKE<br>REFVSIIDGTGSTSYAASVKGRFTASQDKGKNIAYLQMNILKPEDTAMYYCKASCVRGRAI<br>SEYWGQGTQVTVSS |
| 6 | QVQLQESGGGSVQAGGSLRLSCTASGAIASGYIDSRWCMAWFRQAPGKEREGVAAIWPGG<br>GLTVYADSVKGRFTISRDHAKNTLYLQMNNLKPEDTAMYYCAAGSPRMCPSLEFGFDYW<br>GQGTQVTVSS**GGGS**QVQLQESGGGSVQAGGSLRLSCRASGSTYSNYCLGWFRQITGKERE<br>GVAVINWVGGMLYFADSVKGRFTVSQDQAKNTVYLQMNSLKPEDTAMYYCAAESVSSFS<br>CGGWLTRPDRVPYWGQGTQVTVSS |
| 7 | QVQLQESGGGSVQAGGSLRLSCTASGAIASGYIDSRWCMAWFRQAPGKEREGVAAIWPGG<br>GLTVYADSVKGRFTISRDHAKNTLYLQMNNLKPEDTAMYYCAAGSPRMCPSLEFGFDYW<br>GQGTQVTVSS**GGGS**QVQLQESGGGLVQPGGSLRLSCAASGFTFSLSSMSWVRQAPGKGLE<br>WVSAISSGGASTYYTDSVKGRFTISRDNAKNMLYLQLNSLKTEDTAMYYCAKGGSGYGDA<br>SRMTSPGSQGTQVTVSS |
| 8 | QVQLQESGGGSVQAGGSLRLSCTAPGFTSNSCGMDWYRQAPGKEREFVSSISTDGTTGYA<br>DSVKGRFTISKDKAKDIVYLQMNSLKPEDIGMYSCKTKDGTIATMELCDFGYWGQGTQV<br>TVSS**GGGS**QVQLQESGGGLVQPGGSLRLSCAASGFTFSSYPMSWVRQAPGKGLEWISTISA<br>GGDTILYADSVKGRFTSSRDNAKNTLYLQLNSLKTEDAAIYYCAKRIDCNSGYCYRRNYW<br>GQGTQVTVSS |
| 9 | QVQLQESGGGSVQAGGSLRLSCTAPGFTSNSCGMDWYRQAPGKEREFVSSISTDGTTGYA<br>DSVKGRFTISKDKAKDTVYLQMNSLKPEDIGMYSCKTKDGTIATMELCDFGYWGQGTQV<br>TVSS**GGGS**QVQLQESGGGLVQPGESLRLSCTASGFTFSNYAMSWVRQAPGKGLEWVSGIN<br>VAYGITSYADSVKGRFTISRDNTKNTLYLQLNSLKTEDTAIYYCVKHSGTTIPRGFISYTKRG<br>QGTQVTVSS |
| 10 | QVQLQESGGGSVQAGGSLRLSCTAPGFTSNSCGMDWYRQAPGKEREFVSSISTDGTTGYA<br>DSVKGRFTISKDKAKDTVYLQMNSLKPEDIGMYSCKTKDGTIATMELCDFGYWGQGTQV<br>TVSS**GGGS**QVQLQESGGGLVQPGGSLRLSCAASGFSFSSYAMKWVRQAPGKGLEWVSTIS<br>SGGSSTNYADSVKGRFTISRDNAKNTLYLQLNSLKIEDTAMYYCAKAIVPTGATMERGQGT<br>QVTVSS |
| 11 | QVQLQESGGGSVQAGGSLRLSCTAPGFTSNSCGMDWYRQAPGKEREFVSSISTDGTTGYA<br>DSVKGRFTISKDKAKDTVYLQMNSLKPEDIGMYSCKTKDGTIATMELCDFGYWGQGTQV<br>TVSS**GGGS**QVQLQESGGGSVQSGGSLRLSCAASGFTYSTSNSWMAWFRQAPGKEREGVA<br>AIYTVGGSIFYADSVRGRFTISQDATKNMFYLQMNTLKPEDTAMYYCAAASGRLRGKWFW<br>PYEYNYWGQGTQVTVSS |
| 12 | QVQLQESGGGSVQAGGSLRLSCTAPGFTSNSCGMDWYRQAPGKEREFVSSISIDGTTGYA<br>DSVKGRFTISKDKAKDTVYLQMNSLKPEDIGMYSCKTKDGTIATMELCDFGYWGQGTQV<br>TVSS**GGGS**QVQLQESGGGSVQAGGSLRLSCVASGYVSCDYELPSWYRQAPGKEREFVSIID<br>GTGSTSYAASVKGRFTASQDKGKNIAYLQMNTLKPEDTAMYYCKASCVRGRAISEYWGQ<br>GTQVTVSS |
| 13 | QVQLQESGGGSVQAGGSLRLSCTAPGFTSNSCGMDWYRQAPGKEREFVSSISTDGTTGYA<br>DSVKGRFTISKDKAKDTVYLQMNSLKPEDIGMYSCKTKDGTIATMELCDFGYWGQGTQV<br>TVSS**GGGS**QVQLQESGGGSVQAGGSLRLSCRASGSTYSNYCLGWFRQITGKEREGVAVIN<br>WVGGMLYFADSVKGRFTVSQDQAKNTVYLQMNSLKPEDTAMYYCAAESVSSFSCGGWL<br>TRPDRVPYWGQGTQVTVSS |
| 14 | QVQLQESGGGSVQAGGSLRLSCTAPGFTSNSCGMDWYRQAPGKEREFVSSISTDGTTGYA<br>DSVKGRFTISKDKAKDTVYLQMNSLKPEDIGMYSCKTKDGTIATMELCDFGYWGQGTQV<br>TVSS**GGGS**QVQLQESGGGLVQPGGSLRLSCAASGFTFSLSSMSWVRQAPGKGLEWVSAISS |

TABLE 2B-continued

| SEQ ID NO | Sequence |
|---|---|
| | GGASTYYTDSVKGRFTISRDNAKNMLYLQLNSLKTEDTAMYYCAKGGSGYGDASRMTSPGSQGTQVTVSS |
| 15 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGLVQPGGSLRLSCAASGFTFSSYPMSWVRQAPGKGLEWISTISAGGDITLYADSVKGRFTSSRDNAKNTLYLQLNSLKTEDAAIYYCAKRIDCNSGYCYRRNYWGQGTQVTVSS |
| 16 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGLVQPGESLRLSCTASGFTFSNYAMSWVRQAPGKGLEWVSGINVAYGITSYADSVKGRFTISRDNIKNTLYLQLNSLKTEDTAIYYCVKHSGTTIPRGFISYTKRGQGTQVTVSS |
| 17 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS |
| 18 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS |
| 19 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS |
| 20 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRYPYWGQGTQVTVSS |
| 21 | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVSS**GGGS**QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS |
| 22 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS**GGGS**QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS |
| 23 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS**GGG**SQVQLQESGGGLVQPGESLRLSCTASGFTFSNYAMSWVRQAPGKGLEWVSGINVAYGITSYADSVKGRFTISRDNIKNTLYLQLNSLKTEDTAIYYCVKHSGTTIPRGFISYTKRGQGTQVTVSS |
| 24 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS**GGGS**QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS |
| 25 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS**GGGS**QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS |
| 26 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS**GGGS**QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSS |

TABLE 2B-continued

| SEQ ID NO | Sequence |
|---|---|
| 27 | QVQLQESGGGSVQAGGSLRLSCVASASTYCTYDMHWYRQAPGKGREFVSAIDSDGITRYADSVKGRFTISQGTAKNTVYLQMNSLQPEDTAMYYCKTVCVVGSRWSDYWGQGTQVTVSS**GGGS**QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS |
| 28 | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVSS**GGGS**QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS |
| 29 | QVQLQESGGGSVQAGGSLTLSCAASEYAYSTQNMGWYRQAPGKERELVSAFISDGSTYYADSVKGRFTITRDNAKNTVYLQMNSLKPEDTAIYYCSANCYRRLRNYWGQGTQVTVSS**GGGS**QVQLQESGGGLVQPGGSLRLSCAASGFTFSSYPMSWVRQAPGKGLEWISTISAGGDITLYADSVKGRFTSSRDNAKNTLYLQLNSLKTEDAAIYYCAKRIDCNSGYCYRRNYWGQGTQVTVSS |
| 30 | QVQLQESGGGSVQAGGSLTLSCAASEYAYSTQNMGWYRQAPGKERELVSAFISDGSTYYADSVKGRFTITRDNAKNTVYLQMNSLKPEDTAIYYCSANCYRRLRNYWGQGTQVTVSS**GGGS**QVQLQESGGGLVQPGESLRLSCTASGFTFSNYAMSWVRQAPGKGLEWVSGINVAYGITSYADSVKGRFTISRDNIKNILYLQLNSLKTEDTAIYYCVKHSGTTIPRGFISYTKRGQGTQVTVSS |
| 31 | QVQLQESGGGSVQAGGSLTLSCAASEYAYSTQNMGWYRQAPGKERELVSAFISDGSTYYADSVKGRFTITRDNAKNTVYLQMNSLKPEDTAIYYCSANCYRRLRNYWGQGTQVTVSS**GGGS**QVQLQESGGGLVQPGGSLRLSCAASGFSFSSYAMKWVRQAPGKGLEWVSTISSGGSSINYADSVKGRFTISRDNAKNTLYLQLNSLKIEDTAMYYCAKAIVPTGATMERGQGTQVTVSS |
| 32 | QVQLQESGGGSVQAGGSLTLSCAASEYAYSTQNMGWYRQAPGKERELVSAFISDGSTYYADSVKGRFTITRDNAKNTVYLQMNSLKPEDTAIYCYRRLRNYWGQGTQVTVSS**GGGS**QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS |
| 33 | QVQLQESGGGSVQAGGSLILSCAASEYAYSTQNMGWYRQAPGKERELVSAFISDGSTYYADSVKGRFTITRDNAKNTVYLQMNSLKPEDTAIYYCSANCYRRLRNYWGQGTQVTVSS**GGGS**QVQLQESGGGSVQAGGSLRLSCVASGYVSCDYFLPSWYRQAPGKEREFVSIIDGTGSTSYAASVKGRFTASQDKGKNIAYLQMNILKPEDTAMYYCKASCVRGRAISEYWGQGTQVTVSS |
| 34 | QVQLQESGGGSVQAGGSLTLSCAASEYAYSTQNMGWYRQAPGKERELVSAFISDGSTYYADSVKGRFTITRDNAKNTVYLQMNSLKPEDTAIYYCSANCYRRLRNYWGQGTQVTVSS**GGGS**QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS |
| 35 | QVQLQESGGGSVQAGGSLTLSCAASEYAYSTQNMGWYRQAPGKERELVSAFISDGSTYYADSVKGRFTITRDNAKNTVYLQMNSLKPEDTAIYYCSANCYRRLRNYWGQGTQVTVSS**GGGS**QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS |
| 36 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS**GGGS**QVQLQESGGGLVQPGGSLRLSCAASGFTFSSYPMSWVRQAPGKGLEWISTISAGGDTILYADSVKGRFTSSRDNAKNTLYLQLNSLKTEDAAIYYCAKRIDCNSGYCYRRNYWGQGTQVTVSS |
| 37 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS**GGGS**QVQLQESGGGLVQPGESLRLSCTASGFTFSNYAMSWVRQAPGKGLEWVSGINVAYGITSYADSVKGRFTISRDNIKNILYLQLNSLKTEDTAIYYCVKHSGTTIPRGFISYTKRGQGTQVTVSS |
| 38 | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTVSS**GGGS**QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS |

TABLE 2B-continued

| SEQ ID NO | Sequence |
|---|---|
| 39 | QVQLQESGGGLVQPGGSLRLSCTASGLTFDDSVMGWFRQAPGKGREAVSCISSSGANAFY<br>ADSYKGRFTISRDNAKNTLYLQMNSLKPEDTATYYCKRGHACAGYYPIPYDDYWGQGTQ<br>VTVSS**GGGS**QVQLQESGGGSVQSGGSLRLSCAASGFTYSTSNSWMAWFRQAPGKEREGV<br>AAIYTVGGSIFYADSVRGRFTISQDATKNMFYLQMNTLKPEDTAMYYCAAASGRLRGKWF<br>WPYEYNYWGQGTQVTVSS |
| 40 | QVQLQESGGGLVQPGGSLRLSCTASGLTFDDSVMGWFRQAPGKGREAVSCISSSGANAFY<br>ADSVKGRFTISRDNAKNTLYLQMNSLKPEDTATYYCKRGHACAGYYPIPYDDYWGQGTQ<br>VTVSS**GGGS**QVQLQESGGGSVQAGGSLRLSCVASGYVSCDYFLPSWYRQAPGKEREFVSII<br>DGTGSTSYAASVKGRFTASQDKGKNIAYLQMNTLKPEDTAMYYCKASCVRGRAISEYWG<br>QGTQVTVSS |
| 41 | QVQLQESGGGLVQPGGSLRLSCTASGLTFDDSVMGWFRQAPGKGREAVSCISSSGANAFY<br>ADSVKGRFTISRDNAKNTLYLQMNSLKPEDTATYYCKRGHACAGYYPIPYDDYWGQGTQ<br>VTVSS**GGGS**QVQLQESGGGSVQAGGSLRLSCRASGSTYSNYCLGWFRQITGKEREGVAVI<br>NWVGGMLYFADSVKGRFTVSQDQAKNTVYLQMNSLKPEDTAMYYCAAESVSSFSCGGW<br>LTRPDRVPYWGQGTQVTVSS |
| 42 | QVQLQESGGGLVQPGGSLRLSCTASGLTFDDSVMGWFRQAPGKGREAVSCISSSGANAFY<br>ADSVKGRFTISRDNAKNTLYLQMNSLKPEDTATYYCKRGHACAGYYPIPYDDYWGQGTQ<br>VTVSS**GGGS**QVQLQESGGGLVQPGGSLRLSCAASGFTFSLSSMSWVRQAPGKGLEWVSAIS<br>SGGASTYYTDSVKGRFTISRDNAKNMLYLQLNSLKTEDTAMYYCAKGGSGYGDASRMTSP<br>GSQGTQVTVSS |

In some embodiments, an IL27R binding protein described herein (e.g., an IL27R binding protein comprising a sequence of any one of SEQ ID NOS: 1-42) is encoded by an isolated nucleic acid that is substantially identical to a sequence of any one of SEQ ID NOS: 109-150, as listed in Table 2C below. In some embodiments, an IL27R binding protein described herein (e.g., an IL27R binding protein comprising a sequence of any one of SEQ ID NOS: 1-42) is encoded by an isolated nucleic acid comprising a sequence having at least 90% (e.g., 91%, 92%, 93%, 94%, 95%, 96%, 97%, 98%, 99%, or 100%) sequence identity to a sequence of any one of SEQ ID NOS: 109-150, as listed in Table 2C below.

TABLE 2C

| SEQ ID NO | Sequence |
|---|---|
| 109 | CAGGTGCAGCTGCAGGAGAGCGGCGGQGGCAGCGTGCAGGCCGGCGGCAGCCTGAGG<br>CTGAGCTGCACCGCCAGCGGCGCCATCGCCAGCGGCTACATCGACAGCAGGTGGTGCA<br>TGGCCTGGTTCAGGCAGGCCCCCGGCAAGGAGAGGGAGGGCGTGGCCGCCATCTGGCC<br>CGGCGGCGGCCTGACCGTGTACGCCGACAGCGTGAAGGGCAGGTTCACCATCAGCAGG<br>GACCACGCCAAGAACACCCTGTACCTGCAGATGAACAACCTGAAGCCCGAGGACACCG<br>CCATGTACTACTGCGCCGCCGGCAGCCCCAGGATGTGCCCCAGCCTGGAGTTQGGCTTC<br>GACTACTGGGGCCAGGGCACCCAGGTGACCGTCTCGAGTGGCGGCGGATCCCAGGTGC<br>AGCTGCAGGAGAGCGGCGGCGGCCTGGTGCAGCCCGGCGGCAGCCTGAGGCTGAGCTG<br>CGCCGCCAGCGGCTTCACCTTCAGCAGCTACCCCATGAGCTGGGTGAGGCAGGCCCCC<br>GGCAAGGGCCTGGAGTGGATCAGCACCATCAGCGCCGGCGGCGACACCACCCTGTACG<br>CCGACAGCGTGAAGGGCAGGTTCACCAGCAGCAGGGACAACGCCAAGAACACCCTGTA<br>CCTGCAGCTGAACAGCCTGAAGACCGAGGACGQCGCCATCTACTACTGCGCCAAGAGG<br>ATCGACTGCAACAGCGGCTACTGCTACAGGAGGAACTACTGGGGCCAGGGCACCCAGG<br>TGACCGTGAGCGCTAGCCACCACCACCACCACCACCACCAC |
| 110 | CAGGTGCAGCTGCAGGAGAGCGGCGGCGGCAGCGTGCAGGCCGGCGGCAGCCTGAGG<br>CTGAGCTGCACCGCCAGCGGCGCCATCGCCAGCGGCTACATCGACAGCAGGTGGTGCA<br>TGGCCTGGTTCAGGCAGGCCCCCGGCAAGGAGAGGGAGGGCGTGGCCGCCATCTGGCC<br>CGGCGGCGGCCTGACCGTGTACGCCGACAGCGTGAAGGGCAGGTTCACCATCAGCAGG<br>GACCACGCCAAGAACACCCTGTACCTGCAGATGAACAACCTGAAGCCCGAGGACACCG<br>CCATGTACTACTGCGCCGCCGGCAGCCCCAGGATGTGCCCCAGCCTGGAGTTCGGCTTC<br>GACTACTGGGGCCAGGGCACCCAGGTGACCGTCTCGAGTGGCGGCGGATCCCAGGTGC<br>AGCTGCAGGAGAGCGGCGGCGGCCTGGTGCAGCCCGGCGAGAGCCTGAGGCTGAGCTG<br>CACCGCCAGCGGCTTCACCTTCAGCAACTACGCCATGAGCTGGGTGAGGCAGGCCCCC<br>GGCAAGGGCCTGGAGTGGGTGAGCGGCATCAACGTGGCCTACGGCATCACCAGCTACG<br>CCGACAGCGTGAAGGGCAGGTTCACCATCAGCAGGGACAACACCAAGAACACCCTGTA |

TABLE 2C-continued

| SEQ ID NO | Sequence |
|---|---|
| | CCTGCAGCTGAACAGCCTGAAGACCGAGGACACCGCCATCTACTACTGCGTGAAGCAC |
| | AGCGGCACCACCATCCCCAGGGGCTTCATCAGCTACACCAAGAGGGGCCAGGGCACCC |
| | AGGTGACCGTGAGCGCTAGCCACCACCACCACCACCACCACCAC |
| 111 | CAGGTGCAGCTGCAGGAGAGCGGGGCGGCAGCGTGCAGGCCGGCGGCAGCCTGAGG |
| | CTGAGCTGCACCGCCAGCGGCGCCATCGCCAGCGGCTACATCGACAGCAGGTGGTGCA |
| | TGGCCTGGTTCAGGCAGGCCCCCGGCAAGGAGAGGGAGGGCGTGGCCGCCATCTGGCC |
| | CGGCGGCGGCCTGACCGTGTACGCCGACAGCGTGAAGGGCAGGTTCACCATCAGCAGG |
| | GACCACGCCAAGAACACCCTGTACCTGCAGATGAACAACCTGAAGCCCGAGGACACCG |
| | CCATGTACTACTGCGCCGCCGGCAGCCCCAGGATGTGCCCCAGCCTGGAGTTCGGCTTC |
| | GACTACTGGGGCCAGGGCACCCAGGTGACCGTCTCGAGTGGCGGCGGATCCCAGGTGC |
| | AGCTGCAGGAGAGCGGCGGCGGCCTGGTGCAGCCCGGCGGCAGCCTGAGGCTGAGCTG |
| | CGCCGCCAGCGGCTTCAGCTTCAGCAGCTACGCCATGAAGTGGGTGAGGCAGGCCCCC |
| | GGCAAGGGCCTGGAGTGGGTGAGCACCATCAGCAGCGGCGGCAGCAGCACCAACTAC |
| | GCCGACAGCGTGAAGGGCAGGTTCACCATCAGCAGGGACAACGCCAAGAACACCCTGT |
| | ACCTGCAGCTGAACAGCCTGAAGATCGAGGACACCGCCATGTACTACTGCGCCAAGGC |
| | CATCGTGCCCACCGGCGCCACCATGGAGAGGGGCCAGGGCACCCAGGTGACCGTGAGC |
| | GCTAGCCACCACCACCACCACCACCACCAC |
| 112 | CAGGTGCAGCTGCAGGAGAGCGGCGGCGGCAGCGTGCAGGCCGGCGGCAGCCTGAGG |
| | CTGAGCTGCACCGCCAGCGGCGCCATCGCCAGCGGCTACATCGACAGCAGGTGGTGCA |
| | TGGCCTGGTTCAGGCAGGCCCCCGGCAAGGAGAGGGAGGGCGTGGCCGCCATCTGGCC |
| | CGGCGGCGGCCTGACCGTGTACGCCGACAGCGTGAAGGGCAGGTTCACCATCAGCAGG |
| | GACCACGCCAAGAACACCCTGTACCTGCAGATGAACAACCTGAAGCCCGAGGACACCG |
| | CCATGTACTACTGCGCCGCCGGCAGCCCCAGGATGTGCCCCAGCCTGGAGTTCGGCTTC |
| | GACTACTGGGGCCAGGGCACCCAGGTGACCGTCTCGAGTGGCGGCGGATCCCAGGTGC |
| | AGCTGCAGGAGAGCGGCGGCGGCAGCGTGCAGAGCGGCGGCAGCCTGAGGCTGAGCT |
| | GCGCCGCCAGCGGCTTCACCTACAGCACCAGCAACAGCTGGATGGCCTGGTTCAGGCA |
| | GGCCCCCGGCAAGGAGAGGGAGGGCGTGGCCGCCATCTACACCGTGGGCGGCAGCATC |
| | TTCTACGCCGACAGCGTGAGGGGCAGGTTCACCATCAGCCAGGACGCCACCAAGAACA |
| | TGTTCTACCTGCAGATGAACACCCTGAAGCCCGAGGACACCGCCATGTACTACTGCGCC |
| | GCCGCCAGCGGCAGGCTGAGGGGCAAGTGGTTCTGGCCCTACGAGTACAACTACTGGG |
| | GCCAGGGCACCCAGGTGACCGTGAGCGCTAGCCACCACCACCACCACCACCACCAC |
| 113 | CAGGTGCAGCTGCAGGAGAGCGGCGGCGGCAGCGTGCAGGCCGGCGGCAGCCTGAGG |
| | CTGAGCTGCACCGCCAGCGGCGCCATCGCCAGCGGCTACATCGACAGCAGGTGGTGCA |
| | TGGCCTGGTTCAGGCAGGCCCCCGGCAAGGAGAGGGAGGGCGTGGCCGCCATCTGGCC |
| | CGGCGGCGGCCTGACCGTGTACGCCGACAGCGTGAAGGGCAGGTTCACCATCAGCAGG |
| | GACCACGCCAAGAACACCCTGTACCTGCAGATGAACAACCTGAAGCCCGAGGACACCG |
| | CCATGTACTACTGCGCCGCCGGCAGCCCCAGGATGTGCCCCAGCCTGGAGTTCGGCTTC |
| | GACTACTGGGGCCAGGGCACCCAGGTGACCGTCTCGAGTGGCGGCGGATCCCAGGTGC |
| | AGCTGCAGGAGAGCGGCGGCGGCAGCGTGCAGGCCGGCGGCAGCCTGAGGCTGAGCT |
| | GCGTGGCCAGCGGCTACGTGAGCTGCGACTACTTCCTGCCCAGCTGGTACAGGCAGGC |
| | CCCCGGCAAGGAGAGGGAGTTCGTGAGCATCATCGACGGCACCGGCAGCACCAGCTAC |
| | GCCGCCAGCGTGAAGGGCAGGTTCACCGCCAGCCAGGACAAGGGCAAGAACATCGCCT |
| | ACCTGCAGATGAACACCCTGAAGCCCGAGGACACCGCCATGTACTACTGCAAGGCCAG |
| | CTGCGTGAGGGGCAGGGCCATCAGCGAGTACTGGGGCCAGGGCACCCAGGTGACCGTG |
| | AGCGCTAGCCACCACCACCACCACCACCACCAC |
| 114 | CAGGTGCAGCTGCAGGAGAGCGGCGGCGGCAGCGTGCAGGCCGGCGGCAGCCTGAGG |
| | CTGAGCTGCACCGCCAGCGGCGCCATCGCCAGCGGCTACATCGACAGCAGGTGGTGCA |
| | TGGCCTGGTTCAGGCAGGCCCCCGGCAAGGAGAGGGAGGGCGTGGCCGCCATCTGGCC |
| | CGGCGGCGGCCTGACCGTGTACGCCGACAGCGTGAAGGGCAGGTTCACCATCAGCAGG |
| | GACCACGCCAAGAACACCCTGTACCTGCAGATGAACAACCTGAAGCCCGAGGACACCG |
| | CCATGTACTACTGCGCCGCCGGCAGCCCCAGGATGTGCCCCAGCCTGGAGTTCGGCTTC |
| | GACTACTGGGGCCAGGGCACCCAGGTGACCGTCTCGAGTGGCGGCGGATCCCAGGTGC |
| | AGCTGCAGGAGAGCGGCGGCGGCAGCGTGCAGGCCGGCGGCAGCCTGAGGCTGAGCT |
| | GCAGGGCCAGCGGCAGCACCTACAGCAACTACTGCCTGGGCTGGTTCAGGCAGATCAC |
| | CGGCAAGGAGAGGGAGGGCGTGGCCGTGATCAACTGGGGGGCGGCATGCTGTACTTC |
| | GCCGACAGCGTGAAGGGCAGGTTCACCGTGAGCCAGGACCAGGCCAAGAACACCGTGT |
| | ACCTGCAGATGAACAGCCTGAAGCCCGAGGACACCGCCATGTACTACTGCGCCGCCGA |
| | GAGCGTGAGCAGCTTCAGCTGCGGCGGCTGGCTGACCAGGCCCGACAGGGTGCCCTAC |
| | TGGGGCCAGGGCACCCAGGTGACCGTGAGCGCTAGCCACCACCACCACCACCACCACC |
| | AC |
| 115 | CAGGTGCAGCTGCAGGAGAGCGGGGGGGGCAGCGTGCAGGCCGGCGGCAGCCTGAGG |
| | CTGAGCTGCACCGCCAGCGGCGCCATCGCCAGCGGCTACATCGACAGCAGGTGGTGCA |
| | TGGCCTGGTTCAGGCAGGCCCCCGGCAAGGAGAGGGAGGGCGTGGCCGCCATCTGGCC |
| | CGGCGGCGGCCTGACCGTGTACGCCGACAGCGTGAAGGGCAGGTTCACCATCAGCAGG |
| | GACCACGCCAAGAACACCCTGTACCTGCAGATGAACAACCTGAAGCCCGAGGACACCG |
| | CCATGTACTACTGCGCCGCCGGCAGCCCCAGGATGTGCCCCAGCCTGGAGTTCGGCTTC |
| | GACTACTGGGGCCAGGGCACCCAGGTGACCGTCTCGAGTGGCGGCGGATCCCAGGTGC |
| | AGCTGCAGGAGAGCGGGGGGGGCCTGGTGCAGCCCGGGGGCAGCCTGAGGCTGAGCTG |
| | CGCCGCCAGCGGCTTCACCTTCAGCCTGAGCAGCATGAGCTGGGTGAGGCAGGCCCCC |
| | GGCAAGGGCCTGGAGTGGGTGAGCGCCATCAGCAGCGGCGGCGCCAGCACCTACTACA |
| | CCGACAGCGTGAAGGGCAGGTTCACCATCAGCAGGGACAACGCCAAGAACATGCTGTA |

TABLE 2C-continued

| SEQ ID NO | Sequence |
|---|---|
| | CCTGCAGCTGAACAGCCTGAAGACCGAGGACACCGCCATGTACTACTGCGCCAAGGGC<br>GGCAGCGGCTACGGCGACGCCAGCAGGATGACCAGCCCCGGCAGCCAGGGCACCCAG<br>GTGACCGTGAGCGCTAGCCACCACCACCACCACCACCACCAC |
| 116 | CAGGTGCAGCTGCAGGAGAGCGGCGGCGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGCGGATCCCAGGTGCAGCTGCAGGAGAGCG<br>GCGGCGGCCTGGTGCAGCCCGGCGGCAGCCTGAGGCTGAGCTGCGCCGCCAGCGGCTT<br>CACCTTCAGCAGCTACCCCATGAGCTGGGTGAGGCAGGCCCCCGGCAAGGGCCTGGAG<br>TGGATCAGCACCATCAGCGCCGGCGGCGACACCACCCTGTACGCCGACAGCGTGAAGG<br>GCAGGTTCACCAGCAGCAGGGACAACGCCAAGAACACCCTGTACCTGCAGCTGAACAG<br>CCTGAAGACCGAGGACGCCGCCATCTACTACTGCGCCAAGAGGATCGACTGCAACAGC<br>GGCTACTGCTACAGGAGGAACTACTGGGGCCAGGGCACCCAGGTGACCGTGAGCGCTA<br>GCCACCACCACCACCACCACCACCAC |
| 117 | CAGGTGCAGCTGCAGGAGAGCGGCGGCGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGGGGATCCCAGGTGCAGCTGCAGGAGAGCG<br>GCGGCGGCCTGGTGCAGCCCGGCGAGAGCCTGAGGCTGAGCTGCACCGCCAGCGGCTT<br>CACCTTCAGCAACTACGCCATGAGCTGGGTGAGGCAGGCCCCCGGCAAGGGCCTGGAG<br>TGGGTGAGCGGCATCAACGTGGCCTACGGCATCACCAGCTACGCCGACAGCGTGAAGG<br>GCAGGTTCACCATCAGCAGGGACAACACCAAGAACACCCTGTACCTGCAGCTGAACAG<br>CCTGAAGACCGAGGACACCGCCATCTACTACTGCGTGAAGCACAGCGGCACCACCATC<br>CCCAGGGGCTTCATCAGCTACACCAAGAGGGGCCAGGGCACCCAGGTGACCGTGAGCG<br>CTAGCCACCACCACCACCACCACCACCAC |
| 118 | CAGGTGCAGCTGCAGGAGAGCGGCGGCGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGCGGATCCCAGGTGCAGCTGCAGGAGAGCG<br>GCGGCGGCCTGGTGCAGCCCGGCGGCAGCCTGAGGCTGAGCTGCGCCGCCAGCGGCTT<br>CAGCTTCAGCAGCTACGCCATGAAGTGGGTGAGGCAGGCCCCCGGCAAGGGCCTGGAG<br>TGGGTGAGCACCATCAGCAGCGGCGGCAGCAGCACCAACTACGCCGACAGCGTGAAGG<br>GCAGGTTCACCATCAGCAGGGACAACGCCAAGAACACCCTGTACCTGCAGCTGAACAG<br>CCTGAAGATCGAGGACACCGCCATGTACTACTGCGCCAAGGCCATCGTGCCCACCGGC<br>GCCACCATGGAGAGGGGCCAGGGCACCCAGGTGACCGTGAGCGCTAGCCACCACCACC<br>ACCACCACCACCAC |
| 119 | CAGGTGCAGCTGCAGGAGAGCGGCGGCGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGCGGATCCCAGGTGCAGCTGCAGGAGAGCG<br>GCGGCGGCAGCGTGCAGAGCGGCGGCAGCCTGAGGCTGAGCTGCGCCGCCAGCGGCTT<br>CACCTACAGCACCAGCAACAGCTGGATGGCCTGGTTCAGGCAGGCCCCCGGCAAGGAG<br>AGGGAGGGCGTGGCCGCCATCTACACCGTGGGCGGCAGCATCTTCTACGCCGACAGCG<br>TGAGGGGCAGGTTCACCATCAGCCAGGACGCCACCAAGAACATGTTCTACCTGCAGAT<br>GAACACCCTGAAGCCCGAGGACACCGCCATGTACTACTGCGCCGCCGCCAGCGGCAGG<br>CTGAGGGGCAAGTGGTTCTGGCCCTACGAGTACAACTACTGGGGCCAGGGCACCCAGG<br>TGACCGTGAGCGCTAGCCACCACCACCACCACCACCACCAC |
| 120 | CAGGTGCAGCTGCAGGAGAGCGGCGGCGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGAGGCTGAGCTGCGTGGCCAGCGGCTA<br>CGTGAGCTGCGACTACTTCCTGCCCAGCTGGTACAGGCAGGCCCCCGGCAAGGAGAGG<br>GAGTTCGTGAGCATCATCGACGGCACCGGCAGCACCAGCTACGCCGCCAGCGTGAAGG<br>GCAGGTTCACCGCCAGCCAGGACAAGGGCAAGAACATCGCCTACCTGCAGATGAACAC<br>CCTGAAGCCCGAGGACACCGCCATGTACTACTGCAAGGCCAGCTGCGTGAGGGGCAGG |

TABLE 2C-continued

| SEQ ID NO | Sequence |
|---|---|
| | GCCATCAGCGAGTACTGGGGCCAGGGCACCCAGGTGACCGTGAGCGCTAGCCACCACC<br>ACCACCACCACCACCAC |
| 121 | CAGGTGCAGCTGCAGGAGAGCGGGGGGGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGAGGCTGAGCTGCAGGGCCAGCGGCA<br>GCACCTACAGCAACTACTGCCTGGGCTGGTTCAGGCAGATCACCGGCAAGGAGAGGGA<br>GGGCGTGGCCGTGATCAACTGGGTGGGGGGCATGCTGTACTTCGCCGACAGCGTGAAG<br>GGCAGGTTCACCGTGAGCCAGGACCAGGCCAAGAACACCGTGTACCTGCAGATGAACA<br>GCCTGAAGCCCGAGGACACCGCCATGTACTACTGCGCCGCCGAGAGCGTGAGCAGCTT<br>CAGCTGCGGCGGCTGGCTGACCAGGCCCGACAGGGTGCCCTACTGGGGCCAGGGCACC<br>CAGGTGACCGTGAGCGCTAGCCACCACCACCACCACCACCACCAC |
| 122 | CAGGTGCAGCTGCAGGAGAGCGGCGGCGGCAGCGTGCAGGCCGGCGGCAGCCTGAGG<br>CTGAGCTGCACCGCCCCCGGCTTCACCAGCAACAGCTGCGGCATGGACTGGTACAGGC<br>AGGCCCCCGGCAAGGAGAGGGAGTTCGTGAGCAGCATCAGCACCGACGGCACCACCG<br>GCTACGCCGACAGCGTGAAGGGCAGGTTCACCATCAGCAAGGACAAGGCCAAGGACA<br>CCGTGTACCTGCAGATGAACAGCCTGAAGCCCGAGGACACCGGCATGTACAGCTGCAA<br>GACCAAGGACGGCACCATCGCCACCATGGAGCTGTGCGACTTCGGCTACTGGGGCCAG<br>GGCACCCAGGTGACCGTCTCGAGTGGCGGCGGATCCCAGGTGCAGCTGCAGGAGAGCG<br>GCGGCGGCCTGGTGCAGCCCGGCGGCAGCCTGAGGCTGAGCTGCGCCGCCAGCGGCTT<br>CACCTTCAGCCTGAGCAGCATGAGCTGGGTGAGGCAGGCCCCCGGCAAGGGCCTGGAG<br>TGGGTGAGCGCCATCAGCAGCGGCGGCGCCAGCACCTACTACACCGACAGCGTGAAGG<br>GCAGGTTCACCATCAGCAGGGACAACGCCAAGAACATGCTGTACCTGCAGCTGAACAG<br>CCTGAAGACCGAGGACACCGCCATGTACTACTGCGCCAAGGGCGGCAGCGGCTACGGC<br>GACGCCAGCAGGATGACCAGCCCCGGCAGCCAGGGCACCCAGGTGACCGTGAGCGCTA<br>GCCACCACCACCACCACCACCACCAC |
| 123 | CAGGTGCAGCTGCAGGAGAGCGGCGGCGGCAGCGTGCAGGCCGGCGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGGGGCGGATCCCAGGTGCA<br>GCTGCAGGAGAGCGGCGGCGGCCTGGTGCAGCCCGGCGGCAGCCTGAGGCTGAGCTGC<br>GCCGCCAGCGGCTTCACCTTCAGCAGCTACCCCATGAGCTGGGTGAGGCAGGCCCCCG<br>GCAAGGGCCTGGAGTGGATCAGCACCATCAGCGCCGGGGCGACACCACCCTGTACGC<br>CGACAGCGTGAAGGGCAGGTTCACCAGCAGCAGGGACAACGCCAAGAACACCCTGTAC<br>CTGCAGCTGAACAGCCTGAAGACCGAGGACGCCGCCATCTACTACTGCGCCAAGAGGA<br>TCGACTGCAACAGCGGCTACTGCTACAGGAGGAACTACTGGGGCCAGGGCACCCAGGT<br>GACCGTGAGCGCTAGCCACCACCACCACCACCACCACCAC |
| 124 | CAGGTGCAGCTGCAGGAGAGCGGGGGGGGCAGCGTGCAGGCCGGCGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGCGGCGGATCCCAGGTGCA<br>GCTGCAGGAGAGCGGCGGCGGCCTGGTGCAGCCCGGCGAGAGCCTGAGGCTGAGCTGC<br>ACCGCCAGCGGCTTCACCTTCAGCAACTACGCCATGAGCTGGGTGAGGCAGGCCCCCG<br>GCAAGGGCCTGGAGTGGGTGAGCGGCATCAACGTGGCCTACGGCATCACCAGCTACGC<br>CGACAGCGTGAAGGGCAGGTTCACCATCAGCAGGGACAACACCAAGAACACCCTGTAC<br>CTGCAGCTGAACAGCCTGAAGACCGAGGACACCGCCATCTACTACTGCGTGAAGCACA<br>GCGGCACCACCATCCCCAGGGGCTTCATCAGCTACACCAAGAGGGGCCAGGGCACCCA<br>GGTGACCGTGAGCGCTAGCCACCACCACCACCACCACCACCAC |
| 125 | CAGGTGCAGCTGCAGGAGAGCGGCGGCGGCAGCGTGCAGGCCGGCGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGCGGCGGATCCCAGGTGCA<br>GCTGCAGGAGAGCGGCGGCGGCCTGGTGCAGCCCGGCGGCAGCCTGAGGCTGAGCTGC<br>GCCGCCAGCGGCTTCAGCTTCAGCAGCTACGCCATGAAGTGGGTGAGGCAGGCCCCCG<br>GCAAGGGCCTGGAGTGGGTGAGCACCATCAGCAGCGGCGGCAGCAGCACCAACTACGC<br>CGACAGCGTGAAGGGCAGGTTCACCATCAGCAGGGACAACGCCAAGAACACCCTGTAC |

TABLE 2C-continued

| SEQ ID NO | Sequence |
|---|---|
| | CTGCAGCTGAACAGCCTGAAGATCGAGGACACCGCCATGTACTACTGCGCCAAGGCCA<br>TCGTGCCCACCGGCGCCACCATGGAGAGGGGCCAGGGCACCCAGGTGACCGTGAGCGC<br>TAGCCACCACCACCACCACCACCACCAC |
| 126 | CAGGTGCAGCTGCAGGAGAGCGGCGGCGGCAGCGTGCAGGCCGGGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGCGGCGGATCCCAGGTGCA<br>GCTGCAGGAGAGCGGCGGCGGCAGCGTGCAGAGCGGCGGCAGCCTGAGGCTGAGCTG<br>CGCCGCCAGCGGCTTCACCTACAGCACCAGCAACAGCTGGATGGCCTGGTTCAGGCAG<br>GCCCCCGGCAAGGAGAGGGAGGGCGTGGCCGCCATCTACACCGTGGGGGGCAGCATCT<br>TCTACGCCGACAGCGTGAGGGGCAGGTTCACCATCAGCCAGGACGCCACCAAGAACAT<br>GTTCTACCTGCAGATGAACACCCTGAAGCCCGAGGACACCGCCATGTACTACTGCGCCG<br>CCGCCAGCGGCAGGCTGAGGGGCAAGTGGTTCTGGCCCTACGAGTACAACTACTGGGG<br>CCAGGGCACCCAGGTGACCGTGAGCGCTAGCCACCACCACCACCACCACCACCAC |
| 127 | CAGGTGCAGCTGCAGGAGAGCGGCGGCGGCAGCGTGCAGGCCGGCGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGCGGCGGATCCCAGGTGCA<br>GCTGCAGGAGAGCGGCGGCGGCAGCGTGCAGGCCGGCGGCAGCCTGAGGCTGAGCTG<br>CGTGGCCAGCGGCTACGTGAGCTGCGACTACTTCCTGCCCAGCTGGTACAGGCAGGCCC<br>CCGGCAAGGAGAGGGAGTTCGTGAGCATCATCGACGGCACCGGCAGCACCAGCTACGC<br>CGCCAGCGTGAAGGGCAGGTTCACCGCCAGCCAGGACAAGGGCAAGAACATCGCCTAC<br>CTGCAGATGAACACCCTGAAGCCCGAGGACACCGCCATGTACTACTGCAAGGCCAGCT<br>GCGTGAGGGGCAGGGCCATCAGCGAGTACTGGGGCCAGGGCACCCAGGTGACCGTGA<br>GCGCTAGCCACCACCACCACCACCACCACCAC |
| 128 | CAGGTGCAGCTGCAGGAGAGCGGCGGCGGCAGCGTGCAGGCCGGCGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGCGGCGGATCCCAGGTGCA<br>GCTGCAGGAGAGCGGCGGCGGCAGCGTGCAGGCCGGCGGCAGCCTGAGGCTGAGCTG<br>CAGGGCCAGCGGCAGCACCTACAGCAACTACTGCCTGGGCTGGTTCAGGCAGATCACC<br>GGCAAGGAGAGGGAGGGCGTGGCCGTGATCAACTGGGTGGGCGGCATGCTGTACTTCG<br>CCGACAGCGTGAAGGGCAGGTTCACCGTGAGCCAGGACCAGGCCAAGAACACCGTGTA<br>CCTGCAGATGAACAGCCTGAAGCCCGAGGACACCGCCATGTACTACTGCGCCGCCGAG<br>AGCGTGAGCAGCTTCAGCTGCGGCGGCTGGCTGACCAGGCCCGACAGGGTGCCCTACT<br>GGGGCCAGGGCACCCAGGTGACCGTGAGCGCTAGCCACCACCACCACCACCACCACCA<br>C |
| 129 | CAGGTGCAGCTGCAGGAGAGCGGCGGCGGCAGCGTGCAGGCCGGCGGCAGCCTGAGG<br>CTGAGCTGCGCCGCCAGCGGCTACCCCTACAGCAACGGCTACATGGGCTGGTTCAGGC<br>AGGCCCCCGGCAAGGAGAGGGAGGGCGTGGCCACCATCTACACCGGCGACGGCAGGA<br>CCTACTACGCCGACAGCGTGAAGGGCAGGTTCACCATCAGCAGGGACAACGCCAAGAA<br>CACCGTGGACCTGCAGATGAGCAGCCTGAAGCCCGAGGACACCGCCATGTACTACTGC<br>GCCGCCAGGGCCGCCCCCCTGTACAGCAGCGGCAGCCCCCTGACCAGGGCCAGGTACA<br>ACGTGTGGGGCCAGGGCACCCAGGTGACCGTCTCGAGTGGCGGCGGATCCCAGGTGCA<br>GCTGCAGGAGAGCGGCGGCGGCCTGGTGCAGCCCGGCGGCAGCCTGAGGCTGAGCTGC<br>GCCGCCAGCGGCTTCACCTTCAGCCTGAGCAGCATGAGCTGGGTGAGGCAGGCCCCCG<br>GCAAGGGCCTGGAGTGGGTGAGCGCCATCAGCAGCGGCGGCGCCAGCACCTACTACAC<br>CGACAGCGTGAAGGGCAGGTTCACCATCAGCAGGGACAACGCCAAGAACATGCTGTAC<br>CTGCAGCTGAACAGCCTGAAGACCGAGGACACCGCCATGTACTACTGCGCCAAGGGCG<br>GCAGCGGCTACGGCGACGCCAGCAGGATGACCAGCCCCGGCAGCCAGGGCACCCAGGT<br>GACCGTGAGCGCTAGCCACCACCACCACCACCACCACCAC |
| 130 | CAGGTGCAGCTGCAGGAGAGCGGCGGCGGCAGCGTGCAGGCCGGCGGCAGCCTGAGG<br>CTGAGCTGCGTGGCCAGCGCCAGCACCTACTGCACCTACGACATGCACTGGTACAGGC<br>AGGCCCCCGGCAAGGGCAGGGAGTTCGTGAGCGCCATCGACAGCGACGGCACCACCAG<br>GTACGCCGACAGCGTGAAGGGCAGGTTCACCATCAGCCAGGGCACCGCCAAGAACACC<br>GTGTACCTGCAGATGAACAGCCTGCAGCCCGAGGACACCGCCATGTACTACTGCAAGA<br>CCGTGTGCGTGGTGGGCAGCAGGTGGAGCGACTACTGGGGCCAGGGCACCCAGGTGAC<br>CGTCTCGAGTGGCGGCGGATCCCAGGTGCAGCTGCAGGAGAGCGGCGGCGGCCTGGTG<br>CAGCCCGGCGGCAGCCTGAGGCTGAGCTGCGCCGCCAGCGGCTTCACCTTCAGCAGCT<br>ACCCCATGAGCTGGGTGAGGCAGGCCCCCGGCAAGGGCCTGGAGTGGATCAGCACCAT<br>CAGCGCCGGCGGCGACACCACCCTGTACGCCGACAGCGTGAAGGGCAGGTTCACCAGC<br>AGCAGGGACAACGCCAAGAACACCCTGTACCTGCAGCTGAACAGCCTGAAGACCGAGG |

TABLE 2C-continued

| SEQ ID NO | Sequence |
|---|---|
| | ACGCCGCCATCTACTACTGCGCCAAGAGGATCGACTGCAACAGCGGCTACTGCTACAG<br>GAGGAACTACTGGGGCCAGGGCACCCAGGTGACCGTGAGCGCTAGCCACCACCACCAC<br>CACCACCACCAC |
| 131 | CAGGTGCAGCTGCAGGAGAGCGGGGGGGGCAGCGTGCAGGCCGGCGGCAGCCTGAGG<br>CTGAGCTGCGTGGCCAGCGCCAGCACCTACTGCACCTACGACATGCACTGGTACAGGC<br>AGGCCCCCGGCAAGGGCAGGGAGTTCGTGAGCGCCATCGACAGCGACGGCACCACCAG<br>GTACGCCGACAGCGTGAAGGGCAGGTTCACCATCAGCCAGGGCACCGCCAAGAACACC<br>GTGTACCTGCAGATGAACAGCCTGCAGCCCGAGGACACCGCCATGTACTACTGCAAGA<br>CCGTGTGCGTGGTGGGCAGCAGGTGGAGCGACTACTGGGGCCAGGGCACCCAGGTGAC<br>CGTCTCGAGTGGCGGCGGATCCCAGGTGCAGCTGCAGGAGAGCGGCGGCGGCCTGGTG<br>CAGCCCGGCGAGAGCCTGAGGCTGAGCTGCACCGCCAGCGGCTTCACCTTCAGCAACT<br>ACGCCATGAGCTGGGTGAGGCAGGCCCCCGGCAAGGGCCTGGAGTGGGTGAGCGGCAT<br>CAACGTGGCCTACGGCATCACCAGCTACGCCGACAGCGTGAAGGGCAGGTTCACCATC<br>AGCAGGGACAACACCAAGAACACCCTGTACCTGCAGCTGAACAGCCTGAAGACCGAGG<br>ACACCGCCATCTACTACTGCGTGAAGCACAGCGGCACCACCATCCCCAGGGGCTTCATC<br>AGCTACACCAAGAGGGGCCAGGGCACCCAGGTGACCGTGAGCGCTAGCCACCACCACC<br>ACCACCACCACCAC |
| 132 | CAGGTGCAGCTGCAGGAGAGCGGCGGCGGCAGCGTGCAGGCCGGCGGCAGCCTGAGG<br>CTGAGCTGCGTGGCCAGCGCCAGCACCTACTGCACCTACGACATGCACTGGTACAGGC<br>AGGCCCCCGGCAAGGGCAGGGAGTTCGTGAGCGCCATCGACAGCGACGGCACCACCAG<br>GTACGCCGACAGCGTGAAGGGCAGGTTCACCATCAGCCAGGGCACCGCCAAGAACACC<br>GTGTACCTGCAGATGAACAGCCTGCAGCCCGAGGACACCGCCATGTACTACTGCAAGA<br>CCGTGTGCGTGGTGGGCAGCAGGTGGAGCGACTACTGGGGCCAGGGCACCCAGGTGAC<br>CGTCTCGAGTGGCGGCGGATCCCAGGTGCAGCTGCAGGAGAGCGGCGGCGGCCTGGTG<br>CAGCCCGGCGGCAGCCTGAGGCTGAGCTGCGCCGCCAGCGGCTTCAGCTTCAGCAGCT<br>ACGCCATGAAGTGGGTGAGGCAGGCCCCCGGCAAGGGCCTGGAGTGGGTGAGCACCAT<br>CAGCAGCGGCGGCAGCAGCACCAACTACGCCGACAGCGTGAAGGGCAGGTTCACCATC<br>AGCAGGGACAACGCCAAGAACACCCTGTACCTGCAGCTGAACAGCCTGAAGATCGAGG<br>ACACCGCCATGTACTACTGCGCCAAGGCCATCGTGCCCACCGGCGCCACCATGGAGAG<br>GGGCCAGGGCACCCAGGTGACCGTGAGCGCTAGCCACCACCACCACCACCACCACCAC |
| 133 | CAGGTGCAGCTGCAGGAGAGCGGCGGCGGCAGCGTGCAGGCCGGCGGCAGCCTGAGG<br>CTGAGCTGCGTGGCCAGCGCCAGCACCTACTGCACCTACGACATGCACTGGTACAGGC<br>AGGCCCCCGGCAAGGGCAGGGAGTTCGTGAGCGCCATCGACAGCGACGGCACCACCAG<br>GTACGCCGACAGCGTGAAGGGCAGGTTCACCATCAGCCAGGGCACCGCCAAGAACACC<br>GTGTACCTGCAGATGAACAGCCTGCAGCCCGAGGACACCGCCATGTACTACTGCAAGA<br>CCGTGTGCGTGGTGGGCAGCAGGTGGAGCGACTACTGGGGCCAGGGCACCCAGGTGAC<br>CGTCTCGAGTGGCGGCGGATCCCAGGTGCAGCTGCAGGAGAGCGGCGGCGGCAGCGTG<br>CAGAGCGGCGGCAGCCTGAGGCTGAGCTGCGCCGCCAGCGGCTTCACCTACAGCACCA<br>GCAACAGCTGGATGGCCTGGTTCAGGCAGGCCCCCGGCAAGGAGAGGGAGGGCGTGG<br>CCGCCATCTACACCGTGGGGGGCAGCATCTTCTACGCCGACAGCGTGAGGGGCAGGTT<br>CACCATCAGCCAGGACGCCACCAAGAACATGTTCTACCTGCAGATGAACACCCTGAAG<br>CCCGAGGACACCGCCATGTACTACTGCGCCGCCGCCAGCGGCAGGCTGAGGGGCAAGT<br>GGTTCTGGCCCTACGAGTACAACTACTGGGGCCAGGGCACCCAGGTGACCGTGAGCGC<br>TAGCCACCACCACCACCACCACCACCAC |
| 134 | CAGGTGCAGCTGCAGGAGAGCGGCGGCGGCAGCGTGCAGGCCGGCGGCAGCCTGAGG<br>CTGAGCTGCGTGGCCAGCGCCAGCACCTACTGCACCTACGACATGCACTGGTACAGGC<br>AGGCCCCCGGCAAGGGCAGGGAGTTCGTGAGCGCCATCGACAGCGACGGCACCACCAG<br>GTACGCCGACAGCGTGAAGGGCAGGTTTCACCATCAGCCAGGGCACCGCCAAGAACACC<br>GTGTACCTGCAGATGAACAGCCTGCAGCCCGAGGACACCGCCATGTACTACTGCAAGA<br>CCGTGTGCGTGGTGGGCAGCAGGTGGAGCGACTACTGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGAGGCTGAGCTGCGTGGCCAGCGGCTACGTGAGCTGCGACT<br>ACTTCCTGCCCAGCTGGTACAGGCAGGCCCCCGGCAAGGAGAGGGAGTTCGTGAGCAT<br>CATCGACGGCACCGGCAGCACCAGCTACGCCGCCAGCGTGAAGGGCAGGTTCACCGCC<br>AGCCAGGACAAGGGCAAGAACATCGCCTACCTGCAGATGAACACCCTGAAGCCCGAGG<br>ACACCGCCATGTACTACTGCAAGGCCAGCTGCGTGAGGGGCAGGGCCATCAGCGAGTA<br>CTGGGGCCAGGGCACCCAGGTGACCGTGAGCGCTAGCCACCACCACCACCACCACCAC<br>CAC |
| 135 | CAGGTGCAGCTGCAGGAGAGCGGCGGCGGCAGCGTGCAGGCCGGCGGCAGCCTGAGG<br>CTGAGCTGCGTGGCCAGCGCCAGCACCTACTGCACCTACGACATGCACTGGTACAGGC<br>AGGCCCCCGGCAAGGGCAGGGAGTTCGTGAGCGCCATCGACAGCGACGGCACCACCAG<br>GTACGCCGACAGCGTGAAGGGCAGGTTCACCATCAGCCAGGGCACCGCCAAGAACACC<br>GTGTACCTGCAGATGAACAGCCTGCAGCCCGAGGACACCGCCATGTACTACTGCAAGA<br>CCGTGTGCGTGGTGGGCAGCAGGTGGAGCGACTACTGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGAGGCTGAGCTGCAGGGCCAGCGGCAGCACCTACAGCAACT<br>ACTGCCTGGGCTGGTTCAGGCAGATCACCGGCAAGGAGAGGGAGGGCGTGGCCGTGAT<br>CAACTGGGTGGGCGGCATGCTGTACTTCGCCGACAGCGTGAAGGGCAGGTTCACCGTG<br>AGCCAGGACCAGGCCAAGAACACCGTGTACCTGCAGATGAACAGCCTGAAGCCCGAGG |

TABLE 2C-continued

| SEQ ID NO | Sequence |
|---|---|
| | ACACCGCCATGTACTACTGCGCCGCCGAGAGCGTGAGCAGCTTCAGCTGCGGCGGCTG GCTGACCAGGCCCGACAGGGTGCCCTACTGGGGCCAGGGCACCCAGGTGACCGTGAGC GCTAGCCACCACCACCACCACCACCACCAC |
| 136 | CAGGTGCAGCTGCAGGAGAGCGGCGGCGGCAGCGTGCAGGCCGGCGGCAGCCTGAGG CTGAGCTGCGTGGCCAGCGCCAGCACCTACTGCACCTACGACATGCACTGGTACAGGC AGGCCCCCGGCAAGGGCAGGGAGTTCGTGAGCGCCATCGACAGCGACGGCACCACCAG GTACGCCGACAGCGTGAAGGGCAGGTTCACCATCAGCCAGGGCACCGCCAAGAACACC GTGTACCTGCAGATGAACAGCCTGCAGCCCGAGGACACCGCCATGTACTACTGCAAGA CCGTGTGCGTGGTGGGCAGCAGGTGGAGCGACTACTGGGGCCAGGGCACCCAGGTGAC. CGTCTCGAGTGGCGGCGGATCCCAGGTGCAGCTGCAGGAGAGCGGCGGCGGCCTGGTG CAGCCCGGCGGCAGCCTGAGGCTGAGCTGCGCCGCCAGCGGCTTCACCTTCAGCCTGA GCAGCATGAGCTGGGTGAGGCAGGCCCCCGGCAAGGGCCTGGAGTGGGTGAGCGCCAT CAGCAGCGGCGGCGCCAGCACCTACTACACCGACAGCGTGAAGGGCAGGTTCACCATC AGCAGGGACAACGCCAAGAACATGCTGTACCTGCAGCTGAACAGCCTGAAGACCGAGG ACACCGCCATGTACTACTGCGCCAAGGGGGGCAGCGGCTACGGCGACGCCAGCAGGAT GACCAGCCCCGGCAGCCAGGGCACCCAGGTGACCGTGAGCGCTAGCCACCACCACCAC CACCACCACCAC |
| 137 | CAGGTGCAGCTGCAGGAGAGCGGCGGCGGCAGCGTGCAGGCCGGCGGCAGCCTGACC CTGAGCTGCGCCGCCAGCGAGTACGCCTACAGCACCTGCAACATGGGCTGGTACAGGC AGGCCCCCGGCAAGGAGAGGGAGCTGGTGAGCGCCTTCATCAGCGACGGCAGCACCTA CTACGCCGACAGCGTGAAGGGCAGGTTCACCATCACCAGGGACAACGCCAAGAACACC GTGTACCTGCAGATGAACAGCCTGAAGCCCGAGGACACCGCCATCTACTACTGCAGCG CCAACTGCTACAGGAGGCTGAGGAACTACTGGGGCCAGGGCACCCAGGTGACCGTCTC GAGTGGCGGCGGATCCCAGGTGCAGCTGCAGGAGAGCGGCGGCGGCCTGGTGCAGCCC GGCGGCAGCCTGAGGCTGAGCTGCGCCGCCAGCGGCTTCACCTTCAGCAGCTACCCCAT GAGCTGGGTGAGGCAGGCCCCCGGCAAGGGCCTGGAGTGGATCAGCACCATCAGCGCC GGCGGCGACACCACCCTGTACGCCGACAGCGTGAAGGGCAGGTTCACCAGCAGCAGGG ACAACGCCAAGAACACCCTGTACCTGCAGCTGAACAGCCTGAAGACCGAGGACGCCGC CATCTACTACTGCGCCAAGAGGATCGACTGCAACAGCGGCTACTGCTACAGGAGGAAC TACTGGGGCCAGGGCACCCAGGTGACCGTGAGCGCTAGCCACCACCACCACCACCACC ACCAC |
| 138 | CAGGTGCAGCTGCAGGAGAGCGGCGGCGGCAGCGTGCAGGCCGGCGGCAGCCTGACC CTGAGCTGCGCCGCCAGCGAGTACGCCTACAGCACCTGCAACATGGGCTGGTACAGGC AGGCCCCCGGCAAGGAGAGGGAGCTGGTGAGCGCCTTCATCAGCGACGGCAGCACCTA CTACGCCGACAGCGTGAAGGGCAGGTTCACCATCACCAGGGACAACGCCAAGAACACC GTGTACCTGCAGATGAACAGCCTGAAGCCCGAGGACACCGCCATCTACTACTGCAGCG CCAACTGCTACAGGAGGCTGAGGAACTACTGGGGCCAGGGCACCCAGGTGACCGTCTC GAGTGGCGGCGGATCCCAGGTGCAGCTGCAGGAGAGCGGCGGCGGCCTGGTGCAGCCC GGCGAGAGCCTGAGGCTGAGCTGCACCGCCAGCGGCTTCACCTTCAGCAACTACGCCA TGAGCTGGGTGAGGCAGGCCCCCGGCAAGGGCCTGGAGTGGGTGAGCGGCATCAACGT GGCCTACGGCATCACCAGCTACGCCGACAGCGTGAAGGGCAGGTTCACCATCAGCAGG GACAACACCAAGAACACCCTGTACCTGCAGCTGAACAGCCTGAAGACCGAGGACACCG CCATCTACTACTGCGTGAAGCACAGCGGCACCACCATCCCCAGGGGCTTCATCAGCTAC ACCAAGAGGGGCCAGGGCACCCAGGTGACCGTGAGCGCTAGCCACCACCACCACCACC ACCACCAC |
| 139 | CAGGTGCAGCTGCAGGAGAGCGGCGGCGGCAGCGTGCAGGCCGGCGGCAGCCTGACC CTGAGCTGCGCCGCCAGCGAGTACGCCTACAGCACCTGCAACATGGGCTGGTACAGGC AGGCCCCCGGCAAGGAGAGGGAGCTGGTGAGCGCCTTCATCAGCGACGGCAGCACCTA CTACGCCGACAGCGTGAAGGGCAGGTTCACCATCACCAGGGACAACGCCAAGAACACC GTGTACCTGCAGATGAACAGCCTGAAGCCCGAGGACACCGCCATCTACTACTGCAGCG CCAACTGCTACAGGAGGCTGAGGAACTACTGGGGCCAGGGCACCCAGGTGACCGTCTC GAGTGGCGGCGGATCCCAGGTGCAGCTGCAGGAGAGCGGCGGCGGCCTGGTGCAGCCC GGCGGCAGCCTGAGGCTGAGCTGCGCCGCCAGCGGCTTCAGCTTCAGCAGCTACGCCA TGAAGTGGGTGAGGCAGGCCCCCGGCAAGGGCCTGGAGTGGGTGAGCACCATCAGCAG CGGCGGCAGCAGCACCAACTACGCCGACAGCGTGAAGGGCAGGTTCACCATCAGCAGG GACAACGCCAAGAACACCCTGTACCTGCAGCTGAACAGCCTGAAGATCGAGGACACCG CCATGTACTACTGCGCCAAGGCCATCGTGCCCACCGGCGCCACCATGGAGAGGGGCCA GGGCACCCAGGTGACCGTGAGCGCTAGCCACCACCACCACCACCACCACCAC |
| 140 | CAGGTGCAGCTGCAGGAGAGCGGCGGCGGCAGCGTGCAGGCCGGCGGCAGCCTGACC CTGAGCTGCGCCGCCAGCGAGTACGCCTACAGCACCTGCAACATGGGCTGGTACAGGC AGGCCCCCGGCAAGGAGAGGGAGCTGGTGAGCGCCTTCATCAGCGACGGCAGCACCTA CTACGCCGACAGCGTGAAGGGCAGGTTCACCATCACCAGGGACAACGCCAAGAACACC GTGTACCTGCAGATGAACAGCCTGAAGCCCGAGGACACCGCCATCTACTACTGCAGCG CCAACTGCTACAGGAGGCTGAGGAACTACTGGGGCCAGGGCACCCAGGTGACCGTCTC GAGTGGCGGCGGATCCCAGGTGCAGCTGCAGGAGAGCGGGGGGCAGCGTGCAGAG CGGCGGCAGCCTGAGGCTGAGCTGCGCCGCCAGCGGCTTCACCTACAGCACCAGCAAC AGCTGGATGGCCTGGTTCAGGCAGGCCCCCGGCAAGGAGAGGGAGGGCGTGGCCGCCA TCTACACCGTGGGCGGCAGCATCTTCTACGCCGACAGCGTGAGGGGCAGGTTCACCATC AGCCAGGACGCCACCAAGAACATGTTCTACCTGCAGATGAACACCCTGAAGCCCGAGG |

TABLE 2C-continued

| SEQ ID NO | Sequence |
|---|---|
| | ACACCGCCATGTACTACTGCGCCGCCGCCAGCGGCAGGCTGAGGGGCAAGTGGTTCTG<br>GCCCTACGAGTACAACTACTGGGGCCAGGGCACCCAGGTGACCGTGAGCGCTAGCCAC<br>CACCACCACCACCACCACCAC |
| 141 | CAGGTGCAGCTGCAGGAGAGCGGCGGCGGCAGCGTGCAGGCCGGCGGCAGCCTGACC<br>CTGAGCTGCGCCGCCAGCGAGTACGCCTACAGCACCTGCAACATGGGCTGGTACAGGC<br>AGGCCCCCGGCAAGGAGAGGGAGCTGGTGAGCGCCTTCATCAGCGACGGCAGCACCTA<br>CTACGCCGACAGCGTGAAGGGCAGGTTCACCATCACCAGGGACAACGCCAAGAACACC<br>GTGTACCTGCAGATGAACAGCCTGAAGCCCGAGGACACCGCCATCTACTACTGCAGCG<br>CCAACTGCTACAGGAGGCTGAGGAACTACTGGGGCCAGGGCACCCAGGTGACCGTCTC<br>GAGTGGCGGCGGATCCCAGGTGCAGCTGCAGGAGAGCGGGGGGGGCAGCGTGCAGGC<br>CGGCGGCAGCCTGAGGCTGAGCTGCGTGGCCAGCGGCTACGTGAGCTGCGACTACTTC<br>CTGCCCAGCTGGTACAGGCAGGCCCCCGGCAAGGAGAGGGAGTTCGTGAGCATCATCG<br>ACGGCACCGGCAGCACCAGCTACGCCGCCAGCGTGAAGGGCAGGTTCACCGCCAGCCA<br>GGACAAGGGCAAGAACATCGCCTACCTGCAGATGAACACCCTGAAGCCCGAGGACACC<br>GCCATGTACTACTGCAAGGCCAGCTGCGTGAGGGGCAGGGCCATCAGCGAGTACTGGG<br>GCCAGGGCACCCAGGTGACCGTGAGCGCTAGCCACCACCACCACCACCACCACCAC |
| 142 | CAGGTGCAGCTGCAGGAGAGCGGCGGCGGCAGCGTGCAGGCCGGCGGCAGCCTGACC<br>CTGAGCTGCGCCGCCAGCGAGTACGCCTACAGCACCTGCAACATGGGCTGGTACAGGC<br>AGGCCCCCGGCAAGGAGAGGGAGCTGGTGAGCGCCTTCATCAGCGACGGCAGCACCTA<br>CTACGCCGACAGCGTGAAGGGCAGGTTCACCATCACCAGGGACAACGCCAAGAACACC<br>GTGTACCTGCAGATGAACAGCCTGAAGCCCGAGGACACCGCCATCTACTACTGCAGCG<br>CCAACTGCTACAGGAGGCTGAGGAACTACTGGGGCCAGGGCACCCAGGTGACCGTCTC<br>GAGTGGCGGCGGATCCCAGGTGCAGCTGCAGGAGAGCGGCGGCGGCAGCGTGCAGGC<br>CGGCGGCAGCCTGAGGCTGAGCTGCAGGGCCAGCGGCAGCACCTACAGCAACTACTGC<br>CTGGGCTGGTTCAGGCAGATCACCGGCAAGGAGAGGGAGGGCGTGGCCGTGATCAACT<br>GGGGGGCGGCATGCTGTACTTCGCCGACAGCGTGAAGGGCAGGTTCACCGTGAGCCA<br>GGACCAGGCCAAGAACACCGTGTACCTGCAGATGAACAGCCTGAAGCCCGAGGACACC<br>GCCATGTACTACTGCGCCGCCGAGAGCGTGAGCAGCTTCAGCTGCGGCGGCTGGCTGA<br>CCAGGCCCGACAGGGTGCCCTACTGGGGCCAGGGCACCCAGGTGACCGTGAGCGCTAG<br>CCACCACCACCACCACCACCACCAC |
| 143 | CAGGTGCAGCTGCAGGAGAGCGGGGGGGGCAGCGTGCAGGCCGGGGGCAGCCTGACC<br>CTGAGCTGCGCCGCCAGCGAGTACGCCTACAGCACCTGCAACATGGGCTGGTACAGGC<br>AGGCCCCCGGCAAGGAGAGGGAGCTGGTGAGCGCCTTCATCAGCGACGGCAGCACCTA<br>CTACGCCGACAGCGTGAAGGGCAGGTTCACCATCACCAGGGACAACGCCAAGAACACC<br>GTGTACCTGCAGATGAACAGCCTGAAGCCCGAGGACACCGCCATCTACTACTGCAGCG<br>CCAACTGCTACAGGAGGCTGAGGAACTACTGGGGCCAGGGCACCCAGGTGACCGTCTC<br>GAGTGGCGGCGGATCCCAGGTGCAGCTGCAGGAGAGCGGCGGCGGCCTGGTGCAGCCC<br>GGCGGCAGCCTGAGGCTGAGCTGCGCCGCCAGCGGCTTCACCTTCAGCCTGAGCAGCA<br>TGAGCTGGGTGAGGCAGGCCCCCGGCAAGGGCCTGGAGTGGGTGAGCGCCATCAGCAG<br>CGGCGGCGCCAGCACCTACTACACCGACAGCGTGAAGGGCAGGTTCACCATCAGCAGG<br>GACAACGCCAAGAACATGCTGTACCTGCAGCTGAACAGCCTGAAGACCGAGGACACCG<br>CCATGTACTACTGCGCCAAGGGCGGCAGCGGCTACGGCGACGCCAGCAGGATGACCAG<br>CCCCGGCAGCCAGGGCACCCAGGTGACCGTGAGCGCTAGCCACCACCACCACCACCAC<br>CACCAC |
| 144 | CAGGTGCAGCTGCAGGAGAGCGGGGGGGGCCTGGTGCAGCCCGGCGGCAGCCTGAGGC<br>TGAGCTGCACCGCCAGCGGCCTGACCTTCGACGACAGCGTGATGGGCTGGTTCAGGCA<br>GGCCCCCGGCAAGGGCAGGGAGGCCGTGAGCTGCATCAGCAGCAGCGGCGCCAACGC<br>CTTCTACGCCGACAGCGTGAAGGGCAGGTTCACCATCAGCAGGGACAACGCCAAGAAC<br>ACCCTGTACCTGCAGATGAACAGCCTGAAGCCCGAGGACACCGCCACCTACTACTGCA<br>AGAGGGGCCACGCCTGCGCCGGCTACTACCCCATCCCCTACGACGACTACTGGGGCCA<br>GGGCACCCAGGTGACCGTCTCGAGTGGCGGCGGATCCCAGGTGCAGCTGCAGGAGAGC<br>GGCGGCGGCCTGGTGCAGCCCGGCGGCAGCCTGAGGCTGAGCTGCGCCGCCAGCGGCT<br>TCACCTTCAGCAGCTACCCCATGAGCTGGGTGAGGCAGGCCCCCGGCAAGGGCCTGGA<br>GTGGATCAGCACCATCAGCGCCGGCGGCGACACCACCCTGTACGCCGACAGCGTGAAG<br>GGCAGGTTCACCAGCAGCAGGGACAACGCCAAGAACACCCTGTACCTGCAGCTGAACA<br>GCCTGAAGACCGAGGACGCCGCCATCTACTACTGCGCCAAGAGGATCGACTGCAACAG<br>CGGCTACTGCTACAGGAGGAACTACTGGGGCCAGGGCACCCAGGTGACCGTGAGCGCT<br>AGCCACCACCACCACCACCACCACCAC |
| 145 | CAGGTGCAGCTGCAGGAGAGCGGCGGCGGCCTGGTGCAGCCCGGCGGCAGCCTGAGGC<br>TGAGCTGCACCGCCAGCGGCCTGACCTTCGACGACAGCGTGATGGGCTGGTTCAGGCA<br>GGCCCCCGGCAAGGGCAGGGAGGCCGTGAGCTGCATCAGCAGCAGCGGCGCCAACGC<br>CTTCTACGCCGACAGCGTGAAGGGCAGGTTCACCATCAGCAGGGACAACGCCAAGAAC<br>ACCCTGTACCTGCAGATGAACAGCCTGAAGCCCGAGGACACCGCCACCTACTACTGCA<br>AGAGGGGCCACGCCTGCGCCGGCTACTACCCCATCCCCTACGACGACTACTGGGGCCA<br>GGGCACCCAGGTGACCGTCTCGAGTGGCGGCGGATCCCAGGTGCAGCTGCAGGAGAGC<br>GGCGGCGGCCTGGTGCAGCCCGGCGAGAGCCTGAGGCTGAGCTGCACCGCCAGCGGCT<br>TCACCTTCAGCAACTACGCCATGAGCTGGGTGAGGCAGGCCCCCGGCAAGGGCCTGGA<br>GTGGGTGAGCGGCATCAACGTGGCCTACGGCATCACCAGCTACGCCGACAGCGTGAAG<br>GGCAGGTTCACCATCAGCAGGGACAACACCAAGAACACCCTGTACCTGCAGCTGAACA |

TABLE 2C-continued

| SEQ ID NO | Sequence |
|---|---|
| | GCCTGAAGACCGAGGACACCGCCATCTACTACTGCGTGAAGCACAGCGGCACCACCAT CCCCAGGGGCTTCATCAGCTACACCAAGAGGGGCCAGGGCACCCAGGTGACCGTGAGC GCTAGCCACCACCACCACCACCACCACCACCAC |
| 146 | CAGGTGCAGCTGCAGGAGAGCGGCGGCGGCCTGGTGCAGCCCGGGGGCAGCCTGAGGC TGAGCTGCACCGCCAGCGGCCTGACCTTCGACGACAGCGTGATGGGCTGGTTCAGGCA GGCCCCCGGCAAGGGCAGGGAGGCCGTGAGCTGCATCAGCAGCAGCGGCGCCAACGC CTTCTACGCCGACAGCGTGAAGGGCAGGTTCACCATCAGCAGGGACAACGCCAAGAAC ACCCTGTACCTGCAGATGAACAGCCTGAAGCCCGAGGACACCGCCACCTACTACTGCA AGAGGGGCCACGCCTGCGCCGGCTACTACCCCATCCCCTACGACGACTACTGGGGCCA GGGCACCCAGGTGACCGTCTCGAGTGGGGCGGATCCCAGGTGCAGCTGCAGGAGAGC GGCGGCGGCCTGGTGCAGCCCGGCGGCAGCCTGAGGCTGAGCTGCGCCGCCAGCGGCT TCAGCTTCAGCAGCTACGCCATGAAGTGGGTGAGGCAGGCCCCCGGCAAGGGCCTGGA GTGGGTGAGCACCATCAGCAGCGGCGGCAGCAGCACCAACTACGCCGACAGCGTGAAG GGCAGGTTCACCATCAGCAGGGACAACGCCAAGAACACCCTGTACCTGCAGCTGAACA GCCTGAAGATCGAGGACACCGCCATGTACTACTGCGCCAAGGCCATCGTGCCCACCGG CGCCACCATGGAGAGGGGCCAGGGCACCCAGGTGACCGTGAGCGCTAGCCACCACCAC CACCACCACCACCAC |
| 147 | CAGGTGCAGCTGCAGGAGAGCGGCGGCGGCCTGGTGCAGCCCGGCGGCAGCCTGAGGC TGAGCTGCACCGCCAGCGGCCTGACCTTCGACGACAGCGTGATGGGCTGGTTCAGGCA GGCCCCCGGCAAGGGCAGGGAGGCCGTGAGCTGCATCAGCAGCAGCGGCGCCAACGC CTTCTACGCCGACAGCGTGAAGGGCAGGTTCACCATCAGCAGGGACAACGCCAAGAAC ACCCTGTACCTGCAGATGAACAGCCTGAAGCCCGAGGACACCGCCACCTACTACTGCA AGAGGGGCCACGCCTGCGCCGGCTACTACCCCATCCCCTACGACGACTACTGGGGCCA GGGCACCCAGGTGACCGTCTCGAGTGGCGGCGGATCCCAGGTGCAGCTGCAGGAGAGC GGCGGCGGCAGCGTGCAGAGCGGCGGCAGCCTGAGGCTGAGCTGCGCCGCCAGCGGCT TCACCTACAGCACCAGCAACAGCTGGATGGCCTGGTTCAGGCAGGCCCCCGGCAAGGA GAGGGAGGGCGTGGCCGCCATCTACACCGTGGGCGGCAGCATCTTCTACGCCGACAGC GTGAGGGGCAGGTTCACCATCAGCCAGGACGCCACCAAGAACATGTTTCTACCTGCAGA TGAACACCCTGAAGCCCGAGGACACCGCCATGTACTACTGCGCCGCCGCCAGCGGCAG GCTGAGGGGCAAGTGGTTCTGGCCCTACGAGTACAACTACTGGGGCCAGGGCACCCAG GTGACCGTGAGCGCTAGCCACCACCACCACCACCACCACCAC |
| 148 | CAGGTGCAGCTGCAGGAGAGCGGCGGCGGCCTGGTGCAGCCCGGGGGCAGCCTGAGGC TGAGCTGCACCGCCAGCGGCCTGACCTTCGACGACAGCGTGATGGGCTGGTTCAGGCA GGCCCCCGGCAAGGGCAGGGAGGCCGTGAGCTGCATCAGCAGCAGCGGCGCCAACGC CTTCTACGCCGACAGCGTGAAGGGCAGGTTCACCATCAGCAGGGACAACGCCAAGAAC ACCCTGTACCTGCAGATGAACAGCCTGAAGCCCGAGGACACCGCCACCTACTACTGCA AGAGGGGCCACGCCTGCGCCGGCTACTACCCCATCCCCTACGACGACTACTGGGGCCA GGGCACCCAGGTGACCGTCTCGAGTGGCGGCGGATCCCAGGTGCAGCTGCAGGAGAGC GGCGGCGGCAGCGTGCAGGCCGGCGGCAGCCTGAGGCTGAGCTGCGTGGCCAGCGGCT ACGTGAGCTGCGACTACTTCCTGCCCAGCTGGTACAGGCAGGCCCCCGGCAAGGAGAG GGAGTTCGTGAGCATCATCGACGGCACCGGCAGCACCAGCTACGCCGCCAGCGTGAAG GGCAGGTTCACCGCCAGCCAGGACAAGGGCAAGAACATCGCCTACCTGCAGATGAACA CCCTGAAGCCCGAGGACACCGCCATGTACTACTGCAAGGCCAGCTGCGTGAGGGGCAG GGCCATCAGCGAGTACTGGGGCCAGGGCACCCAGGTGACCGTGAGCGCTAGCCACCAC CACCACCACCACCACCAC |
| 149 | CAGGTGCAGCTGCAGGAGAGCGGCGGCGGCCTGGTGCAGCCCGGGGGCAGCCTGAGGC TGAGCTGCACCGCCAGCGGCCTGACCTTCGACGACAGCGTGATGGGCTGGTTCAGGCA GGCCCCCGGCAAGGGCAGGGAGGCCGTGAGCTGCATCAGCAGCAGCGGCGCCAACGC CTTCTACGCCGACAGCGTGAAGGGCAGGTTCACCATCAGCAGGGACAACGCCAAGAAC ACCCTGTACCTGCAGATGAACAGCCTGAAGCCCGAGGACACCGCCACCTACTACTGCA AGAGGGGCCACGCCTGCGCCGGCTACTACCCCATCCCCTACGACGACTACTGGGGCCA GGGCACCCAGGTGACCGTCTCGAGTGGCGGCGGATCCCAGGTGCAGCTGCAGGAGAGC GGCGGCGGCAGCGTGCAGGCCGGCGGCAGCCTGAGGCTGAGCTGCAGGGCCAGCGGC AGCACCTACAGCAACTACTGCCTGGGCTGGTTCAGGCAGATCACCGGCAAGGAGAGGG AGGGCGTGGCCGTGATCAACTGGGGGGCGGCATGCTGTACTTCGCCGACAGCGTGAA GGGCAGGTTCACCGTGAGCCAGGACCAGGCCAAGAACACCGTGTACCTGCAGATGAAC AGCCTGAAGCCCGAGGACACCGCCATGTACTACTGCGCCGCCGAGAGCGTGAGCAGCT TCAGCTGCGGCGGCTGGCTGACCAGGCCCGACAGGGTGCCCTACTGGGGCCAGGGCAC CCAGGTGACCGTGAGCGCTAGCCACCACCACCACCACCACCACCAC |
| 150 | CAGGTGCAGCTGCAGGAGAGCGGCGGCGGCCTGGTGCAGCCCGGGGGCAGCCTGAGGC TGAGCTGCACCGCCAGCGGCCTGACCTTCGACGACAGCGTGATGGGCTGGTTCAGGCA GGCCCCCGGCAAGGGCAGGGAGGCCGTGAGCTGCATCAGCAGCAGCGGCGCCAACGC CTTCTACGCCGACAGCGTGAAGGGCAGGTTCACCATCAGCAGGGACAACGCCAAGAAC ACCCTGTACCTGCAGATGAACAGCCTGAAGCCCGAGGACACCGCCACCTACTACTGCA AGAGGGGCCACGCCTGCGCCGGCTACTACCCCATCCCCTACGACGACTACTGGGGCCA GGGCACCCAGGTGACCGTCTCGAGTGGCGGCGGATCCCAGGTGCAGCTGCAGGAGAGC GGCGGCGGCCTGGTGCAGCCCGGCGGCAGCCTGAGGCTGAGCTGCGCCGCCAGCGGCT TCACCTTCAGCCTGAGCAGCATGAGCTGGGTGAGGCAGGCCCCCGGCAAGGGCCTGGA GTGGGTGAGCGCCATCAGCAGCGGCGGCGCCAGCACCTACTACACCGACAGCGTGAAG GGCAGGTTCACCATCAGCAGGGACAACGCCAAGAACATGCTGTACCTGCAGCTGAACA GCCTGAAGACCGAGGACACCGCCATGTACTACTGCGCCAAGGGGGGCAGCGGCTACGG |

TABLE 2C-continued

| SEQ ID NO | Sequence |
|---|---|
| | CGACGCCAGCAGGATGACCAGCCCCGGCAGCCAGGGCACCCAGGTGACCGTGAGCGCT AGCCACCACCACCACCACCACCACCAC |

Anti-IL27Rα $V_H$H-Linker-Anti-GP130 $V_H$H

A bispecific $V_HH^2$ can contain, from the N-terminus to the C-terminus, a first $V_H$H binding to IL27Rα (an anti-IL27Rα $V_H$H antibody), a linker, and a second $V_H$H binding to gp130 (an anti-gp130 $V_H$H antibody). In other words, the linker joins the C-terminus of the anti-IL27Rα $V_H$H in the binding protein to the N-terminus of the anti-gp130 $V_H$H in the binding protein. In some embodiments, a purification peptide, e.g., a six-histidine peptide ($(His)_6$ (SEQ ID NO: 1531) or His-tag) or an Fc tag can be included in the bispecific $V_HH^2$.

In certain embodiments, a bispecific $V_HH^2$ described herein comprises an anti-IL27Rα $V_H$H antibody comprising a sequence having at least 90% (e.g., 91%, 92%, 93%, 94%, 95%, 96%, 97%, 98%, 99%, or 100%) sequence identity to a sequence of any one of SEQ ID NOS:245-251; and an anti-gp130 $V_H$H antibody comprising a sequence having at least 90% (e.g., 91%, 92%, 93%, 94%, 95%, 96%, 97%, 98%, 99%, or 100%) sequence identity to a sequence of any one of SEQ ID NOS:252-257.

In certain embodiments, a bispecific $V_HH^2$ described herein comprises an anti-IL27Rα $V_H$H antibody and an anti-gp130 $V_H$H antibody as described in each row of Table 3A below or Table A above. In some embodiments, in each row of Table 3A, the anti-IL27Rα $V_H$H antibody and the anti-gp130 $V_H$H antibody can each, independently, comprise at least 90% (e.g., 91%, 92%, 93%, 94%, 95%, 96%, 97%, 98%, 99%, or 100%) sequence identity to the sequence described in each row of Table 3A. In some embodiments, the bispecific $V_HH^2$ can comprise a linker (e.g., linkers described in Section IV) between the anti-IL27Rα $V_H$H antibody and the anti-gp130 $V_H$H antibody as described in each row of Table 3A below. In particular embodiments, the linker is GGGS (SEQ ID NO:108). The sequence of the anti-IL27Rα $V_H$H is N-terminal to the linker and the sequence of the anti-gp130 $V_H$H is C-terminal to the linker. Examples of linkers are further described in Section IV below. The CDR sequences in each $V_H$H are underlined.

TABLE 3A

| N-terminal Anti-IL27Rα $V_H$H | C-terminal Anti-gp130 $V_H$H |
|---|---|
| QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS (SEQ ID NO: 245) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |
| QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS (SEQ ID NO: 245) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |
| QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS (SEQ ID NO: 245) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |
| QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS (SEQ ID NO: 245) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS (SEQ ID NO: 245) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS (SEQ ID NO: 245) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |
| QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS (SEQ ID NO: 246) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |

TABLE 3A-continued

| N-terminal Anti-IL27Rα $V_HH$ | C-terminal Anti-gp130 $V_HH$ |
|---|---|
| QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS (SEQ ID NO: 246) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |
| QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS (SEQ ID NO: 246) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |
| QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS (SEQ ID NO: 246) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS (SEQ ID NO: 246) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGLVQPGESLRLSCTASGFTFSNYAMSWVRQAPGKGLEWVSGINVAYGITSYADSVKGRFTISRDNTKNTLYLQLNSLKTEDTAIYYCVKHSGTTIPRGFISYTKRGQGTQVTVSS (SEQ ID NO: 246) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |
| QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS (SEQ ID NO: 247) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |
| QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS (SEQ ID NO: 247) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |
| QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS (SEQ ID NO: 247) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |
| QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS (SEQ ID NO: 247) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS (SEQ ID NO: 247) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS (SEQ ID NO: 247) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |
| QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS (SEQ ID NO: 248) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |
| QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS (SEQ ID NO: 248) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |

TABLE 3A-continued

| N-terminal Anti-IL27Rα $V_HH$ | C-terminal Anti-gp130 $V_HH$ |
|---|---|
| QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS (SEQ ID NO: 248) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |
| QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS (SEQ ID NO: 248) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS (SEQ ID NO: 248) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS (SEQ ID NO: 248) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |
| QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGOGTQVTVSS (SEQ ID NO: 249) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |
| QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGOGTQVTVSS (SEQ ID NO: 249) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |
| QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGOGTQVTVSS (SEQ ID NO: 249) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |
| QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGOGTQVTVSS (SEQ ID NO: 249) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGOGTQVTVSS (SEQ ID NO: 249) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGOGTQVTVSS (SEQ ID NO: 249) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |
| QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS (SEQ ID NO: 250) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |
| QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS (SEQ ID NO: 250) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |
| QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS (SEQ ID NO: 250) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |

TABLE 3A-continued

| N-terminal Anti-IL27Rα $V_HH$ | C-terminal Anti-gp130 $V_HH$ |
|---|---|
| QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS (SEQ ID NO: 250) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS (SEQ ID NO: 250) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGSVQAGGSLRLSCRASGSTYSNYCLGWFRQITGKEREGVAVINWVGGMLYFADSVKGRFTVSQDQAKNTVYLQMNSLKPEDTAMYYCAAESVSSFSCGGWLTRPDRVPYWGQGTQVTVSS (SEQ ID NO: 250) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |
| QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS (SEQ ID NO: 251) | QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS (SEQ ID NO: 252) |
| QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS (SEQ ID NO: 251) | QVQLQESGGGSVQAGGSLRLSCTAPGFTSNSCGMDWYRQAPGKEREFVSSISTDGTTGYADSVKGRFTISKDKAKDTVYLQMNSLKPEDTGMYSCKTKDGTIATMELCDFGYWGQGTQVTVS (SEQ ID NO: 253) |
| QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS (SEQ ID NO: 251) | QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS (SEQ ID NO: 254) |
| QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS (SEQ ID NO: 251) | QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS (SEQ ID NO: 255) |
| QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS (SEQ ID NO: 251) | QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS(SEQ ID NO: 256) |
| QVQLQESGGGLVQPGGSLRLSCAASGFTFSLSSMSWVRQAPGKGLEWVSAISSGGASTYYTDSVKGRFTISRDNAKNMLYLQLNSLKTEDTAMYYCAKGGSGYGDASRMTSPGSQGTQVTVSS (SEQ ID NO: 251) | QVQLQESGGGLVQPGGSLRLSCTASGLTFDDSVMGWFRQAPGKGREAVSCISSSGANAFYADSVKGRFTISRDNAKNTLYLQMNSLKPEDTATYYCKRGHACAGYYPIPYDDYWGQGTQVTYS (SEQ ID NO: 257) |

In certain embodiments, the bispecific $V_HH^2$ comprises a sequence that is substantially identical to a sequence of any one of SEQ ID NOS:43-84. Such a bispecific $V_HH^2$ can have a sequence having at least 90% (e.g., 91%, 92%, 93%, 94%, 95%, 96%, 97%, 98%, 99%, or 100%) sequence identity to the sequence of any one of SEQ ID NOS:43-84, as shown in Table 3B below. In each of sequences of SEQ ID NOS:43-84, the linker GGGS (SEQ ID NO: 108) is in bold. The sequence of the anti-IL27Rα $V_HH$ is N-terminus to the linker and the sequence of the anti-gp130 $V_HH$ is C-terminus to the linker. The CDR sequences in each $V_HH$ are underlined.

TABLE 3B

| SEQ ID NO | Sequence |
|---|---|
| 43 | QVQLQESGGGLVQPGGSLRLSCAASGFTFSSYPMSWVRQAPGKGLEWISTISAGGDTTLYADSVKGRFTSSRDNAKNTLYLQLNSLKTEDAAIYYCAKRIDCNSGYCYRRNYWGQGTQVTVSS**GGGS**QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS |

TABLE 3B-continued

| SEQ ID NO | Sequence |
|---|---|
| 44 | QVQLQESGGGLVQPGGSLRLSCAASGFTFSSYPMSWVRQAPGKGLEWISTISAGGDTTLYA DSVKGRFTSSRDNAKNTLYLQLNSLKTEDAAIYYCAKRIDCNSGYCYRRNYWGQGTQVTV SS**GGGS**QVQLQESGGGSVQAGGSLRLSCTAPGFTSNSCGMDWYRQAPGKEREFVSSISTDG TTGYADSVKGRFTISKDKAKDTVYLQMNSLKPEDTGMYSCKTKDGTIATMELCDFGYWG QGTQVTVS |
| 45 | QVQLQESGGGLVQPGGSLRLSCAASGFTFSSYPMSWVRQAPGKGLEWISTISAGGDTTLYA DSVKGRFTSSRDNAKNTLYLQLNSLKTEDAAIYYCAKRIDCNSGYCYRRNYWGQGTQVTV SS**GGGS**QVQLQESGGGSVQAGGSLRLSCAASGYPYSNGYMGWFRQAPGKEREGVATIYT GDGRTYYADSVKGRFTISRDNAKNTVDLQMSSLKPEDTAMYYCAARAAPLYSSGSPLTRA RYNVWGQGTQVTVS |
| 46 | QVQLQESGGGLVQPGGSLRLSCAASGFTFSSYPMSWVRQAPGKGLEWISTISAGGDTTLYA DSVKGRFTSSRDNAKNILYLQLNSLKTEDAAIYYCAKRIDCNSGYCYRRNYWGQGTQVTV SS**GGGS**QVQLQESGGGSVQAGGSLRLSCVASASTYCTYDMHWYRQAPGKGREFVSAIDSD GTTRYADSVKGRFTISQGTAKNTVYLQMNSLQPEDTAMYYCKTVCVVGSRWSDYWGQGT QVTVS |
| 47 | QVQLQESGGGLVQPGGSLRLSCAASGFTFSSYPMSWVRQAPGKGLEWISTISAGGDTTLYA DSVKGRFTSSRDNAKNTLYLQLNSLKTEDAAIYYCAKRIDCNSGYCYRRNYWGQGTQVTV SS**GGGS**QVQLQESGGGSVQAGGSLTLSCAASEYAYSTCNMGWYRQAPGKERELVSAFISD GSTYYADSVKGRFTITRDNAKNTVYLQMNSLKPEDTAIYYCSANCYRRLRNYWGQGTQVT VS |
| 48 | QVQLQESGGGLVQPGGSLRLSCAASGFTFSSYPMSWVRQAPGKGLEWISTISAGGDTTLYA DSVKGRFTSSRDNAKNTLYLQLNSLKTEDAAIYYCAKRIDCNSGYCYRRNYWGQGTQVTV SS**GGGS**QVQLQESGGGLVQPGGSLRLSCTASGLTFDDSVMGWFRQAPGKGREAVSCISSSG ANAFYADSVKGRFTISRDNAKNTLYLQMNSLKPEDTATYYCKRGHACAGYYPIPYDDYW GQGTQVTVS |
| 49 | QVQLQESGGGLVQPGESLRLSCTASGFTFSNYAMSWVRQAPGKGLEWVSGINVAYGITSY ADSVKGRFTISRDNTKNTLYLQLNSLKTEDTAIYYCVKHSGTTIPRGFISYTKRGQGTQVTV SS**GGGS**QVQLQESGGGSVQAGGSLRLSCTASGAIASGYIDSRWCMAWFRQAPGKEREGVA AIWPGGGLTVYADSVKGRFTISRDHAKNTLYLQMNNLKPEDTAMYYCAAGSPRMCPSLEF GFDYWGQGTQVTVS |
| 50 | QVQLQESGGGLVQPGESLRLSCTASGFTFSNYAMSWVRQAPGKGLEWVSGINVAYGITSY ADSVKGRFTISRDNTKNTLYLQLNSLKTEDTAIYYCVKHSGTTIPRGFISYTKRGQGTQVTV SS**GGGS**QVQLQESGGGSVQAGGSLRLSCTAPGFTSNSCGMDWYRQAPGKEREFVSSISTDG TTGYADSVKGRFTISKDKAKDTVYLQMNSLKPEDTGMYSCKTKDGTIATMELCDFGYWG QGTQVTVS |
| 51 | QVQLQESGGGLVQPGESLRLSCTASGFTFSNYAMSWVRQAPGKGLEWVSGINVAYGITSY ADSVKGRFTISRDNTKNTLYLQLNSLKTEDTAIYYCVKHSGTTIPRGFISYTKRGQGTQVTV SS**GGGS**QVQLQESGGGSVQAGGSLRLSCAASGYPYSNGYMGWFRQAPGKEREGVATIYT GDGRTYYADSVKGRFTISRDNAKNTVDLQMSSLKPEDTAMYYCAARAAPLYSSGSPLTRA RYNVWGQGTQVTVS |
| 52 | QVQLQESGGGLVQPGESLRLSCTASGFTFSNYAMSWVRQAPGKGLEWVSGINVAYGITSY ADSVKGRFTISRDNTKNTLYLQLNSLKTEDTAIYYCVKHSGTTIPRGFISYTKRGQGTQVTV SS**GGGS**QVQLQESGGGSVQAGGSLRLSCVASASTYCTYDMHWYRQAPGKGREFVSAIDSD GTTRYADSVKGRFTISQGTAKNTVYLQMNSLQPEDTAMYYCKTVCVVGSRWSDYWGQGT QVTVS |
| 53 | QVQLQESGGGLVQPGESLRLSCTASGFTFSNYAMSWVRQAPGKGLEWVSGINVAYGITSY ADSVKGRFTISRDNIKNILYLQLNSLKTEDTAIYYCVKHSGTTIPRGFISYTKRGQGTQVTV SS**GGGS**QVQLQESGGGSVQAGGSLTLSCAASEYAYSTCNMGWYRQAPGKERELVSAFISD GSTYYADSVKGRFTITRDNAKNTVYLQMNSLKPEDTAIYYCSANCYRRLRNYWGQGTQVT VS |
| 54 | QVQLQESGGGLVQPGESLRLSCTASGFTFSNYAMSWVRQAPGKGLEWVSGINVAYGITSY ADSVKGRFTISRDNTKNTLYLQLNSLKTEDTAIYYCVKHSGTTIPRGFISYTKRGQGTQVTV SS**GGGS**QVQLQESGGGLVQPGGSLRLSCTASGLTFDDSVMGWFRQAPGKGREAVSCISSSG ANAFYADSVKGRFTISRDNAKNTLYLQMNSLKPEDTATYYCKRGHACAGYYPIPYDDYW GQGTQVTVS |
| 55 | QVQLQESGGGLVQPGGSLRLSCAASGFSFSSYAMKWVRQAPGKGLEWVSTISSGGSSTNY ADSVKGRFTISRDNAKNTLYLQLNSLKIEDTAMYYCAKAIVPTGATMERGQGTQVTVSS**G GGS**QVQLQESGGGSVQAGGSLRLSCTASGAIASGYIDSRWCMAWFRQAPGKEREGVAAIW PGGGLTVYADSVKGRFTISRDHAKNTLYLQMNNLKPEDTAMYYCAAGSPRMCPSLEFGFD YWGQGTQVTVS |

TABLE 3B-continued

| SEQ ID NO | Sequence |
|---|---|
| 56 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS**GGGS**QVQLQESGGGSVQAGGSLRLSCTAPGFTSNSCGMDWYRQAPGKEREFVSSISIDGTTGYADSVKGRFTISKDKAKDTVYLQMNSLKPEDIGMYSCKTKDGTIATMELCDFGYWGQGTQVTVS |
| 57 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS**GGGS**QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS |
| 58 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS**GGGS**QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS |
| 59 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS**GGGS**QVQLQESGGGSVQAGGSLTLSCAASEYAYSTCNMGWYRQAPGKERELVSAFISDGSTYYADSVKGRFTITRDNAKNTVYLQMNSLKPEDTAIYYCSANCYRRLRNYWGQGTQVTVS |
| 60 | QVQLQESGGGLVQPGGSLRLSCAASGFSFSSYAMKWVRQAPGKGLEWVSTISSGGSSTNYADSVKGRFTISRDNAKNTLYLQLNSLKIEDTAMYYCAKAIVPTGATMERGQGTQVTVSS**GGGS**QVQLQESGGGLVQPGGSLRLSCTASGLTFDDSVMGWFRQAPGKGREAVSCISSSGANAFYADSYKGRFTISRDNAKNTLYLQMNSLKPEDTATYYCKRGHACAGYYPIPYDDYWGQGTQVTVS |
| 61 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS**GGGS**QVQLQESGGGSVQAGGSLRLSCTASGAIASGYIDSRWCMAWFRQAPGKEREGVAAIWPGGGLTVYADSVKGRFTISRDHAKNTLYLQMNNLKPEDTAMYYCAAGSPRMCPSLEFGFDYWGQGTQVTVS |
| 62 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS**GGGS**QVQLQESGGGSVQAGGSLRLSCTAPGFTSNSCGMDWYRQAPGKEREFVSSISTDGTTGYADSVKGRFTISKDKAKDTVYLQMNSLKPEDIGMYSCKTKDGTIATMELCDFGYWGQGTQVTVS |
| 63 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS**GGGS**QVQLQESGGGSVQAGGSLRLSCAASGYPYSNGYMGWFRQAPGKEREGVATIYTGDGRTYYADSVKGRFTISRDNAKNTVDLQMSSLKPEDTAMYYCAARAAPLYSSGSPLTRARYNVWGQGTQVTVS |
| 64 | QVQLQESGGGSVQSGGSLRLSCAASGFTYSTSSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS**GGGS**QVQLQESGGGSVQAGGSLRLSCVASASTYCTYDMHWYRQAPGKGREFVSAIDSDGTTRYADSVKGRFTISQGTAKNTVYLQMNSLQPEDTAMYYCKTVCVVGSRWSDYWGQGTQVTVS |
| 65 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSSG**GGS**QVQLQESGGGSVQAGGSLILSCAASEYAYSTCNMGWYRQAPGKERELVSAFISDGSTYYADSVKGRFTITRDNAKNTVYLQMNSLKPEDTAIYYCSANCYRRLRNYWGQGTQVTVS |
| 66 | QVQLQESGGGSVQSGGSLRLSCAASGFTYSTSNSWMAWFRQAPGKEREGVAAIYTVGGSIFYADSVRGRFTISQDATKNMFYLQMNTLKPEDTAMYYCAAASGRLRGKWFWPYEYNYWGQGTQVTVSS**GGGS**QVQLQESGGGLVQPGGSLRLSCTASGLTFDDSVMGWFRQAPGKGREAVSCISSSGANAFYADSVKGRFTISRDNAKNTLYLQMNSLKPEDIATYYCKRGHACAGYYPIPYDDYWGQGTQVTVS |
| 67 | QVQLQESGGGSVQAGGSLRLSCVASGYVSCDYFLPSWYRQAPGKEREFVSIIDGTGSTSYAASVKGRFTASQDKGKNIAYLQMNTLKPEDTAMYYCKASCVRGRAISEYWGQGTQVTVSSGGGSQVQLQES**GGGS**VQAGGSLRLSCTASGAIASGYIDSRWCMAWFRQAPGKEREGVAAIWPGGGLIVYADSVKGRFTISRDHAKNTLYLQMNNLKPEDTAMYYCAAGSPRMCPSLEFGFDYWGQGTQVTVS |

TABLE 3B-continued

| SEQ ID NO | Sequence |
|---|---|
| 68 | QYQLQESGGGSVQAGGSLRLSCVASGYVSCDYFLPSWYRQAPGKEREFVSIIDGIGSTSYA<br>ASVKGRFTASQDKGKNIAYLQMNTLKPEDTAMYYCKASCVRGRAISEYWGQGTQVTVSS<br>GGGSQVQLQES**GGGS**VQAGGSLRLSCTAPGFTSNSCGMDWYRQAPGKEREFVSSISTDGT<br>TGYADSVKGRFTISKDKAKDTVYLQMNSLKPEDIGMYSCKTKDGTIATMELCDFGYWGQ<br>GTQVTVS |
| 69 | QVQLQESGGGSVQAGGSLRLSCVASGYVSCDYFLPSWYRQAPGKEREFVSIIDGTGSTSYA<br>ASVKGRFTASQDKGKNIAYLQMNTLKPEDTAMYYCKASCVRGRAISEYWGQGTQVTVSS<br>GGGSQVQLQES**GGGS**VQAGGSLRLSCAASGYPYSNGYMGWFRQAPGKEREGVATIYTGD<br>GRTYYADSVKGRFTISRDNAKNTVDLQMSSLKPEDTAMYYCAARAAPLYSSGSPLTRARY<br>NVWGQGTQVTVS |
| 70 | QVQLQESGGGSVQAGGSLRLSCVASGYVSCDYFLPSWYRQAPGKEREFVSIIDGTGSTSYA<br>ASVKGRFTASQDKGKNIAYLQMNTLKPEDTAMYYCKASCVRGRAISEYWGQGTQVTVSS<br>GGGSQVQLQES**GGGS**VQAGGSLRLSCVASASTYCTYDMHWYRQAPGKGREFVSAIDSDG<br>TTRYADSVKGRFTISQGTAKNTVYLQMNSLQPEDTAMYYCKTVCVVGSRWSDYWGQGTQ<br>VTVS |
| 71 | QVQLQESGGGSVQAGGSLRLSCVASGYVSCDYFLPSWYRQAPGKEREFVSIIDGTGSTSYA<br>ASVKGRFTASQDKGKNIAYLQMNTLKPEDTAMYYCKASCVRGRAISEYWGQGTQVTVSS<br>GGGSQVQLQES**GGGS**VQAGGSLTLSCAASEYAYSTCNMGWYRQAPGKERELVSAFISDGS<br>TYYADSVKGRFTITRDNAKNTVYLQMNSLKPEDTAIYYCSANCYRRLRNYWGQGTQVTVS |
| 72 | QVQLQESGGGSVQAGGSLRLSCVASGYVSCDYFLPSWYRQAPGKEREFVSIIDGTGSTSYA<br>ASVKGRFTASQDKGKNIAYLQMNTLKPEDTAMYYCKASCVRGRAISEYWGQGTQVTVSS<br>**GGGS**QVQLQESGGGLVQPGGSLRLSCTASGLTFDDSVMGWFRQAPGKGREAVSCISSSGA<br>NAFYADSVKGRFTISRDNAKNTLYLQMNSLKPEDTATYYCKRGHACAGYYPIPYDDYWG<br>QGTQVTVS |
| 73 | QVQLQESGGGSVQAGGSLRLSCRASGSTYSNYCLGWFRQITGKEREGVAVINWVGGMLYF<br>ADSVKGRFTVSQDQAKNTVYLQMNSLKPEDTAMYYCAAESVSSFSCGGWLTRPDRVPYW<br>GQGTQVTVSS**GGGS**QVQLQESGGGSVQAGGSLRLSCTASGAIASGYIDSRWCMAWFRQAP<br>GKEREGVAAIWPGGGLTVYADSVKGRFTISRDHAKNTLYLQMNNLKPEDTAMYYCAAGS<br>PRMCPSLEFGFDYWGQGTQVTVS |
| 74 | QVQLQESGGGSVQAGGSLRLSCRASGSTYSNYCLGWFRQITGKEREGVAVINWVGGMLYF<br>ADSVKGRFTVSQDQAKNTVYLQMNSLKPEDTAMYYCAAESVSSFSCGGWLTRPDRVPYW<br>GQGTQVTVSS**GGGS**QVQLQESGGGSVQAGGSLRLSCTAPGFTSNSCGMDWYRQAPGKER<br>EFVSSISTDGTTGYADSVKGRFTISKDKAKDTVYLQMNSLKPEDIGMYSCKTKDGTIATME<br>LCDFGYWGQGTQVTVS |
| 75 | QVQLQESGGGSVQAGGSLRLSCRASGSTYSNYCLGWFRQITGKEREGVAVINWVGGMLYF<br>ADSVKGRFTVSQDQAKNTVYLQMNSLKPEDTAMYYCAAESVSSFSCGGWLTRPDRVPYW<br>GQGTQVTVSS**GGGS**QVQLQESGGGSVQAGGSLRLSCAASGYPYSNGYMGWFRQAPGKER<br>EGVATIYTGDGRTYYADSVKGRFTISRDNAKNTVDLQMSSLKPEDTAMYYCAARAAPLYS<br>SGSPLTRARYNVWGQGTQVTVS |
| 76 | QVQLQESGGGSVQAGGSLRLSCRASGSTYSNYCLGWFRQITGKEREGVAVINWVGGMLYF<br>ADSVKGRFTVSQDQAKNTVYLQMNSLKPEDTAMYYCAAESVSSFSCGGWLTRPDRVPYW<br>GQGTQVTVSS**GGGS**QVQLQESGGGSVQAGGSLRLSCVASASTYCTYDMHWYRQAPGKGR<br>EFVSAIDSDGTTRYADSVKGRFTISQGTAKNTVYLQMNSLQPEDTAMYYCKTVCVVGSRW<br>SDYWGQGTQVTVS |
| 77 | QVQLQESGGGSVQAGGSLRLSCRASGSTYSNYCLGWFRQITGKEREGVAVINWVGGMLYF<br>ADSVKGRFTVSQDQAKNTVYLQMNSLKPEDTAMYYCAAESVSSFSCGGWLTRPDRYPYW<br>GQGTQVTVSS**GGGS**QVQLQESGGGSVQAGGSLTLSCAASEYAYSTCNMGWYRQAPGKER<br>ELVSAFISDGSTYYADSVKGRFTITRDNAKNTVYLQMNSLKPEDTAIYYCSANCYRRLRNY<br>WGQGTQVTVS |
| 78 | QVQLQESGGGSVQAGGSLRLSCRASGSTYSNYCLGWFRQITGKEREGVAVINWVGGMLYF<br>ADSVKGRFTVSQDQAKNTVYLQMNSLKPEDTAMYYCAAESVSSFSCGGWLTRPDRVPYW<br>GQGTQVTVSS**GGGS**QVQLQESGGGLVQPGGSLRLSCTASGLTFDDSVMGWFRQAPGKGR<br>EAVSCISSSGANAFYADSYKGRFTISRDNAKNTLYLQMNSLKPEDTATYYCKRGHACAGY<br>YPIPYDDYWGQGTQVTVS |
| 79 | QVQLQESGGGLVQPGGSLRLSCAASGFTFSLSSMSWVRQAPGKGLEWVSAISSGGASTYYT<br>DSVKGRFTISRDNAKNMLYLQLNSLKTEDTAMYYCAKGGSGYGDASRMTSPGSQGTQVT<br>VSS**GGGS**QVQLQESGGGSVQAGGSLRLSCTASGAIASGYIDSRWCMAWFRQAPGKEREGV<br>AAIWPGGGLIVYADSVKGRFTISRDHAKNTLYLQMNNLKPEDTAMYYCAAGSPRMCPSLE<br>FGFDYWGQGTQVTVS |

TABLE 3B-continued

| SEQ ID NO | Sequence |
|---|---|
| 80 | QVQLQESGGGLVQPGGSLRLSCAASGFTFSLSSMSWVRQAPGKGLEWVSAISSGGASTYYT<br>DSVKGRFTISRDNAKNMLYLQLNSLKTEDTAMYYCAKGGSGYGDASRMTSPGSQGTQVT<br>VSS**GGGS**QVQLQESGGGSVQAGGSLRLSCTAPGFTSNSCGMDWYRQAPGKEREFVSSISTD<br>GTTGYADSVKGRFTISKDKAKDTVYLQMINSLKPEDIGMYSCKTKDGTIATMELCDFGYW<br>GQGTQVTVS |
| 81 | QVQLQESGGGLVQPGGSLRLSCAASGFTFSLSSMSWVRQAPGKGLEWVSAISSGGASTYYT<br>DSVKGRFTISRDNAKNMLYLQLNSLKTEDTAMYYCAKGGSGYGDASRMTSPGSQGTQVT<br>VSS**GGGS**QVQLQESGGGSVQAGGSLRLSCAASGYPYSNGYMGWFRQAPGKEREGVATIY<br>TGDGRTYYADSVKGRFTISRDNAKNTVDLQMSSLKPEDTAMYYCAARAAPLYSSGSPLTR<br>ARYNVWGQGTQVTVS |
| 82 | QVQLQESGGGLVQPGGSLRLSCAASGFTFSLSSMSWVRQAPGKGLEWVSAISSGGASTYYT<br>DSVKGRFTISRDNAKNMLYLQLNSLKTEDTAMYYCAKGGSGYGDASRMTSPGSQGTQVT<br>VSS**GGGS**QVQLQESGGGSVQAGGSLRLSCVASASTYCTYDMHWYRQAPGKGREFVSAIDS<br>DGTTRYADSVKGRFTISQGTAKNTVYLQMNSLQPEDTAMYYCKTVCVVGSRWSDYWGQ<br>GTQVTVS |
| 83 | QVQLQESGGGLVQPGGSLRLSCAASGFTFSLSSMSWVRQAPGKGLEWVSAISSGGASTYYT<br>DSVKGRFTISRDNAKNMLYLQLNSLKTEDTAMYYCAKGGSGYGDASRMTSPGSQGTQVT<br>VSS**GGGS**QVQLQESGGGSVQAGGSLTLSCAASEYAYSTCNMGWYRQAPGKERELVSAFIS<br>DGSTYYADSVKGRFTITRDNAKNTVYLQMNSLKPEDTAIYYCSANCYRRLRNYWGQGTQ<br>VTVS |
| 84 | QVQLQESGGGLVQPGGSLRLSCAASGFTFSLSSMSWVRQAPGKGLEWVSAISSGGASTYYT<br>DSVKGRFTISRDNAKNMLYLQLNSLKTEDTAMYYCAKGGSGYGDASRMTSPGSQGTQVT<br>VSS**GGGS**QVQLQESGGGLVQPGGSLRLSCTASGLTFDDSVMGWFRQAPGKGREAVSCISSS<br>GANAFYADSVKGRFTISRDNAKNTLYLQMNSLKPEDTATYYCKRGHACAGYYPIPYDDY<br>WGQGTQVTVS |

In some embodiments, an IL27R binding protein described herein (e.g., an IL27R binding protein comprising a sequence of any one of SEQ ID NOS:43-84) is encoded by an isolated nucleic acid that is substantially identical to a sequence of any one of SEQ ID NOS:151-192, as listed in Table 3C below. In some embodiments, an IL27R binding protein described herein (e.g., an IL27R binding protein comprising a sequence of any one of SEQ ID NOS:43-84) is encoded by an isolated nucleic acid comprising a sequence having at least 90% (e.g., 91%, 92%, 93%, 94%, 95%, 96%, 97%, 98%, 99%, or 100%) sequence identity to a sequence of any one of SEQ ID NOS: 151-192, as listed in Table 3C below.

TABLE 3C

| SEQ ID NO | Sequence |
|---|---|
| 151 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCAGCTACCCCATGAGCTGGGTGAGGCA<br>GGCCCCCGGCAAGGGCCTGGAGTGGATCAGCACCATCAGCGCCGGCGGCGACACCACC<br>CTGTACGCCGACAGCGTGAAGGGCAGGTTCACCAGCAGCAGGGACAACGCCAAGAAC<br>ACCCTGTACCTGCAGCTGAACAGCCTGAAGACCGAGGACGCCGCCATCTACTACTGCG<br>CCAAGAGGATCGACTGCAACAGCGGCTACTGCTACAGGAGGAACTACTGGGGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCACCGCCAGCGGCGCCA<br>TCGCCAGCGGCTACATCGACAGCAGGTGGTGCATGGCCTGGTTCAGGCAGGCCCCCGG<br>CAAGGAGAGGGAGGGCGTGGCCGCCATCTGGCCCGGCGGCGGCCTGACCGTGTACGCC<br>GACAGCGTGAAGGGCAGGTTCACCATCAGCAGGGACCACGCCAAGAACACCCTGTACC<br>TGCAGATGAACAACCTGAAGCCCGAGGACACCGCCATGTACTACTGCGCCGCCGGCAG<br>CCCCAGGATGTGCCCCAGCCTGGAGTTCGGCTTCGACTACTGGGGCCAGGGCACCCAG<br>GTGACCGTGAGCGCTAGCCACCACCACCACCACCACCACCAC |
| 152 | CAGGTGCAGCTGCAGGAGAGCGGCGGCGGCCTGGTGCAGCCCGGGGGCAGCCTGAGGC<br>TGAGCTGCGCCGCCAGCGGCTTCACCTTCAGCAGCTACCCCATGAGCTGGGTGAGGCA<br>GGCCCCCGGCAAGGGCCTGGAGTGGATCAGCACCATCAGCGCCGGCGGCGACACCACC<br>CTGTACGCCGACAGCGTGAAGGGCAGGTTCACCAGCAGCAGGGACAACGCCAAGAAC<br>ACCCTGTACCTGCAGCTGAACAGCCTGAAGACCGAGGACGCCGCCATCTACTACTGCG |

TABLE 3C-continued

| SEQ ID NO | Sequence |
|---|---|
| | CCAAGAGGATCGACTGCAACAGCGGCTACTGCTACAGGAGGAACTACTGGGGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCACCGCCCCCGGCTTCA<br>CCAGCAACAGCTGCGGCATGGACTGGTACAGGCAGGCCCCCGGCAAGGAGAGGGAGTT<br>CGTGAGCAGCATCAGCACCGACGGCACCACCGGCTACGCCGACAGCGTGAAGGGCAGG<br>TTCACCATCAGCAAGGACAAGGCCAAGGACACCGTGTACCTGCAGATGAACAGCCTGA<br>AGCCCGAGGACACCGGCATGTACAGCTGCAAGACCAAGGACGGCACCATCGCCACCAT<br>GGAGCTGTGCGACTTCGGCTACTGGGGCCAGGGCACCCAGGTGACCGTGAGCGCTAGC<br>CACCACCACCACCACCACCACCAC |
| 153 | CAGGTGCAGCTGCAGGAGAGCGGCGGCGGCCTGGTGCAGCCCGGGGGCAGCCTGAGGC<br>TGAGCTGCGCCGCCAGCGGCTTCACCTTCAGCAGCTACCCCATGAGCTGGGTGAGGCA<br>GGCCCCCGGCAAGGGCCTGGAGTGGATCAGCACCATCAGCGCCGGCGGCGACACCACC<br>CTGTACGCCGACAGCGTGAAGGGCAGGTTCACCAGCAGCAGGGACAACGCCAAGAAC<br>ACCCTGTACCTGCAGCTGAACAGCCTGAAGACCGAGGACGCCGCCATCTACTACTGCG<br>CCAAGAGGATCGACTGCAACAGCGGCTACTGCTACAGGAGGAACTACTGGGGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCGCCGCCAGCGGCTACC<br>CCTACAGCAACGGCTACATGGGCTGGTTCAGGCAGGCCCCCGGCAAGGAGAGGGAGGG<br>CGTGGCCACCATCTACACCGGCGACGGCAGGACCTACTACGCCGACAGCGTGAAGGGC<br>AGGTTCACCATCAGCAGGGACAACGCCAAGAACACCGTGGACCTGCAGATGAGCAGCC<br>TGAAGCCCGAGGACACCGCCATGTACTACTGCGCCGCCAGGGCCGCCCCCCTGTACAG<br>CAGCGGCAGCCCCCTGACCAGGGCCAGGTACAACGTGTGGGGCCAGGGCACCCAGGTG<br>ACCGTGAGCGCTAGCCACCACCACCACCACCACCACCAC |
| 154 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCAGCTACCCCATGAGCTGGGTGAGGCA<br>GGCCCCCGGCAAGGGCCTGGAGTGGATCAGCACCATCAGCGCCGGGGCGACACCACC<br>CTGTACGCCGACAGCGTGAAGGGCAGGTTCACCAGCAGCAGGGACAACGCCAAGAAC<br>ACCCTGTACCTGCAGCTGAACAGCCTGAAGACCGAGGACGCCGCCATCTACTACTGCG<br>CCAAGAGGATCGACTGCAACAGCGGCTACTGCTACAGGAGGAACTACTGGGGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCGTGGCCAGCGCCAGCA<br>CCTACTGCACCTACGACATGCACTGGTACAGGCAGGCCCCCGGCAAGGGCAGGGAGTT<br>CGTGAGCGCCATCGACAGCGACGGCACCACCAGGTACGCCGACAGCGTGAAGGGCAG<br>GTTCACCATCAGCCAGGGCACCGCCAAGAACACCGTGTACCTGCAGATGAACAGCCTG<br>CAGCCCGAGGACACCGCCATGTACTACTGCAAGACCGTGTGCGTGGTGGGCAGCAGGT<br>GGAGCGACTACTGGGGCCAGGGCACCCAGGTGACCGTGAGCGCTAGCCACCACCACCA<br>CCACCACCACCAC |
| 155 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCAGCTACCCCATGAGCTGGGTGAGGCA<br>GGCCCCCGGCAAGGGCCTGGAGTGGATCAGCACCATCAGCGCCGGCGGCGACACCACC<br>CTGTACGCCGACAGCGTGAAGGGCAGGTTCACCAGCAGCAGGGACAACGCCAAGAAC<br>ACCCTGTACCTGCAGCTGAACAGCCTGAAGACCGAGGACGCCGCCATCTACTACTGCG<br>CCAAGAGGATCGACTGCAACAGCGGCTACTGCTACAGGAGGAACTACTGGGGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGACCCTGAGCTGCGCCGCCAGCGAGTACG<br>CCTACAGCACCTGCAACATGGGCTGGTACAGGCAGGCCCCCGGCAAGGAGAGGGAGCT<br>GGTGAGCGCCTTCATCAGCGACGGCAGCACCTACTACGCCGACAGCGTGAAGGGCAGG<br>TTCACCATCACCAGGGACAACGCCAAGAACACCGTGTACCTGCAGATGAACAGCCTGA<br>AGCCCGAGGACACCGCCATCTACTACTGCAGCGCCAACTGCTACAGGAGGCTGAGGAA<br>CTACTGGGGCCAGGGCACCCAGGTGACCGTGAGCGCTAGCCACCACCACCACCACCAC<br>CACCAC |
| 156 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCAGCTACCCCATGAGCTGGGTGAGGCA<br>GGCCCCCGGCAAGGGCCTGGAGTGGATCAGCACCATCAGCGCCGGCGGCGACACCACC<br>CTGTACGCCGACAGCGTGAAGGGCAGGTTCACCAGCAGCAGGGACAACGCCAAGAAC<br>ACCCTGTACCTGCAGCTGAACAGCCTGAAGACCGAGGACGCCGCCATCTACTACTGCG<br>CCAAGAGGATCGACTGCAACAGCGGCTACTGCTACAGGAGGAACTACTGGGGCCAGGG<br>CACCCAGGTGACCGTCTCGAGTGGCGGCGGATCCCAGGTGCAGCTGCAGGAGAGCGGC<br>GGCGGCCTGGTGCAGCCCGGCGGCAGCCTGAGGCTGAGCTGCACCGCCAGCGGCCTGA<br>CCTTCGACGACAGCGTGATGGGCTGGTTCAGGCAGGCCCCCGGCAAGGGCAGGGAGGC<br>CGTGAGCTGCATCAGCAGCAGCGGCGCCAACGCCTTCTACGCCGACAGCGTGAAGGGC<br>AGGTTCACCATCAGCAGGGACAACGCCAAGAACACCCTGTACCTGCAGATGAACAGCC<br>TGAAGCCCGAGGACACCGCCACCTACTACTGCAAGAGGGGCCACGCCTGCGCCGGCTA<br>CTACCCCATCCCCTACGACGACTACTGGGGCCAGGGCACCCAGGTGACCGTGAGCGCT<br>AGCCACCACCACCACCACCACCACCAC |
| 157 | CAGGTGCAGCTGCAGGAGAGCGGCGGCGGCCTGGTGCAGCCCGGCGAGAGCCTGAGG<br>CTGAGCTGCACCGCCAGCGGCTTCACCTTCAGCAACTACGCCATGAGCTGGGTGAGGC<br>AGGCCCCCGGCAAGGGCCTGGAGTGGGTGAGCGGCATCAACGTGGCCTACGGCATCAC<br>CAGCTACGCCGACAGCGTGAAGGGCAGGTTCACCATCAGCAGGGACAACACCAAGAAC<br>ACCCTGTACCTGCAGCTGAACAGCCTGAAGACCGAGGACACCGCCATCTACTACTGCGT<br>GAAGCACAGCGGCACCACCATCCCCAGGGGCTTCATCAGCTACACCAAGAGGGGCCAG |

TABLE 3C-continued

| SEQ ID NO | Sequence |
|---|---|
| | GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGAGGCTGAGCTGCACCGCCAGCGGCGC<br>CATCGCCAGCGGCTACATCGACAGCAGGTGGTGCATGGCCTGGTTCAGGCAGGCCCCC<br>GGCAAGGAGAGGGAGGGCGTGGCCGCCATCTGGCCCGGCGGCGGCCTGACCGTGTACG<br>CCGACAGCGTGAAGGGCAGGTTCACCATCAGCAGGGACCACGCCAAGAACACCCTGTA<br>CCTGCAGATGAACAACCTGAAGCCCGAGGACACCGCCATGTACTACTGCGCCGCCGGC<br>AGCCCCAGGATGTGCCCCAGCCTGGAGTTCGGCTTCGACTACTGGGGCCAGGGCACCC<br>AGGTGACCGTGAGCGCTAGCCACCACCACCACCACCACCACCAC |
| 158 | CAGGTGCAGCTGCAGGAGAGCGGCGGCGGCCTGGTGCAGCCCGGCGAGAGCCTGAGG<br>CTGAGCTGCACCGCCAGCGGCTTCACCTTCAGCAACTACGCCATGAGCTGGGTGAGGC<br>AGGCCCCCGGCAAGGGCCTGGAGTGGGTGAGCGGCATCAACGTGGCCTACGGCATCAC<br>CAGCTACGCCGACAGCGTGAAGGGCAGGTTCACCATCAGCAGGGACAACACCAAGAAC<br>ACCCTGTACCTGCAGCTGAACAGCCTGAAGACCGAGGACACCGCCATCTACTACTGCGT<br>GAAGCACAGCGGCACCACCATCCCCAGGGGCTTCATCAGCTACACCAAGAGGGGCCAG<br>GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGAGGCTGAGCTGCACCGCCCCCGGCTT<br>CACCAGCAACAGCTGCGGCATGGACTGGTACAGGCAGGCCCCCGGCAAGGAGAGGGA<br>GTTCGTGAGCAGCATCAGCACCGACGGCACCACCGGCTACGCCGACAGCGTGAAGGGC<br>AGGTTCACCATCAGCAAGGACAAGGCCAAGGACACCGTGTACCTGCAGATGAACAGCC<br>TGAAGCCCGAGGACACCGGCATGTACAGCTGCAAGACCAAGGACGGCACCATCGCCAC<br>CATGGAGCTGTGCGACTTCGGCTACTGGGGCCAGGGCACCCAGGTGACCGTGAGCGCT<br>AGCCACCACCACCACCACCACCACCAC |
| 159 | CAGGTGCAGCTGCAGGAGAGCGGCGGCGGCCTGGTGCAGCCCGGCGAGAGCCTGAGG<br>CTGAGCTGCACCGCCAGCGGCTTCACCTTCAGCAACTACGCCATGAGCTGGGTGAGGC<br>AGGCCCCCGGCAAGGGCCTGGAGTGGGTGAGCGGCATCAACGTGGCCTACGGCATCAC<br>CAGCTACGCCGACAGCGTGAAGGGCAGGTTCACCATCAGCAGGGACAACACCAAGAAC<br>ACCCTGTACCTGCAGCTGAACAGCCTGAAGACCGAGGACACCGCCATCTACTACTGCGT<br>GAAGCACAGCGGCACCACCATCCCCAGGGGCTTCATCAGCTACACCAAGAGGGGCCAG<br>GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGAGGCTGAGCTGCGCCGCCAGCGGCTA<br>CCCCTACAGCAACGGCTACATGGGCTGGTTCAGGCAGGCCCCCGGCAAGGAGAGGGAG<br>GGCGTGGCCACCATCTACACCGGCGACGGCAGGACCTACTACGCCGACAGCGTGAAGG<br>GCAGGTTCACCATCAGCAGGGACAACGCCAAGAACACCGTGGACCTGCAGATGAGCAG<br>CCTGAAGCCCGAGGACACCGCCATGTACTACTGCGCCGCCAGGGCCGCCCCCCTGTAC<br>AGCAGCGGCAGCCCCCTGACCAGGGCCAGGTACAACGTGTGGGGCCAGGGCACCCAGG<br>TGACCGTGAGCGCTAGCCACCACCACCACCACCACCACCAC |
| 160 | CAGGTGCAGCTGCAGGAGAGCGGGGCGGCCTGGTGCAGCCCGGCGAGAGCCTGAGG<br>CTGAGCTGCACCGCCAGCGGCTTCACCTTCAGCAACTACGCCATGAGCTGGGTGAGGC<br>AGGCCCCCGGCAAGGGCCTGGAGTGGGTGAGCGGCATCAACGTGGCCTACGGCATCAC<br>CAGCTACGCCGACAGCGTGAAGGGCAGGTTCACCATCAGCAGGGACAACACCAAGAAC<br>ACCCTGTACCTGCAGCTGAACAGCCTGAAGACCGAGGACACCGCCATCTACTACTGCGT<br>GAAGCACAGCGGCACCACCATCCCCAGGGGCTTCATCAGCTACACCAAGAGGGGCCAG<br>GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGAGGCTGAGCTGCGTGGCCAGCGCCAG<br>CACCTACTGCACCTACGACATGCACTGGTACAGGCAGGCCCCCGGCAAGGGCAGGGAG<br>TTCGTGAGCGCCATCGACAGCGACGGCACCACCAGGTACGCCGACAGCGTGAAGGGCA<br>GGTTCACCATCAGCCAGGGCACCGCCAAGAACACCGTGTACCTGCAGATGAACAGCCT<br>GCAGCCCGAGGACACCGCCATGTACTACTGCAAGACCGTGTGCGTGGTGGGCAGCAGG<br>TGGAGCGACTACTGGGGCCAGGGCACCCAGGTGACCGTGAGCGCTAGCCACCACCACC<br>ACCACCACCACCAC |
| 161 | CAGGTGCAGCTGCAGGAGAGCGGCGGCGGCCTGGTGCAGCCCGGCGAGAGCCTGAGG<br>CTGAGCTGCACCGCCAGCGGCTTCACCTTCAGCAACTACGCCATGAGCTGGGTGAGGC<br>AGGCCCCCGGCAAGGGCCTGGAGTGGGTGAGCGGCATCAACGTGGCCTACGGCATCAC<br>CAGCTACGCCGACAGCGTGAAGGGCAGGTTCACCATCAGCAGGGACAACACCAAGAAC<br>ACCCTGTACCTGCAGCTGAACAGCCTGAAGACCGAGGACACCGCCATCTACTACTGCGT<br>GAAGCACAGCGGCACCACCATCCCCAGGGGCTTCATCAGCTACACCAAGAGGGGCCAG<br>GGCACCCAGGTGACCGTCTCGAGTGGCGGCGGATCCCAGGTGCAGCTGCAGGAGAGCG<br>GCGGCGGCAGCGTGCAGGCCGGCGGCAGCCTGACCCTGAGCTGCGCCGCCAGCGAGTA<br>CGCCTACAGCACCTGCAACATGGGCTGGTACAGGCAGGCCCCCGGCAAGGAGAGGGAG<br>CTGGTGAGCGCCTTCATCAGCGACGGCAGCACCTACTACGCCGACAGCGTGAAGGGCA<br>GGTTCACCATCACCAGGGACAACGCCAAGAACACCGTGTACCTGCAGATGAACAGCCT<br>GAAGCCCGAGGACACCGCCATCTACTACTGCAGCGCCAACTGCTACAGGAGGCTGAGG<br>AACTACTGGGGCCAGGGCACCCAGGTGACCGTGAGCGCTAGCCACCACCACCACCACC<br>ACCACCAC |
| 162 | CAGGTGCAGCTGCAGGAGAGCGGCGGCGGCCTGGTGCAGCCCGGCGAGAGCCTGAGG<br>CTGAGCTGCACCGCCAGCGGCTTCACCTTCAGCAACTACGCCATGAGCTGGGTGAGGC<br>AGGCCCCCGGCAAGGGCCTGGAGTGGGTGAGCGGCATCAACGTGGCCTACGGCATCAC<br>CAGCTACGCCGACAGCGTGAAGGGCAGGTTCACCATCAGCAGGGACAACACCAAGAAC<br>ACCCTGTACCTGCAGCTGAACAGCCTGAAGACCGAGGACACCGCCATCTACTACTGCGT<br>GAAGCACAGCGGCACCACCATCCCCAGGGGCTTCATCAGCTACACCAAGAGGGGCCAG<br>GGCACCCAGGTGACCGTCTCGAGTGGCGGCGGATCCCAGGTGCAGCTGCAGGAGAGCG |

TABLE 3C-continued

| SEQ ID NO | Sequence |
|---|---|
| | GCGGCGGCCTGGTGCAGCCCGGCGGCAGCCTGAGGCTGAGCTGCACCGCCAGCGGCCT<br>GACCTTCGACGACAGCGTGATGGGCTGGTTCAGGCAGGCCCCCGGCAAGGGCAGGGAG<br>GCCGTGAGCTGCATCAGCAGCAGCGGCGCCAACGCCTTCTACGCCGACAGCGTGAAGG<br>GCAGGTTCACCATCAGCAGGGACAACGCCAAGAACACCCTGTACCTGCAGATGAACAG<br>CCTGAAGCCCGAGGACACCGCCACCTACTACTGCAAGAGGGGCCACGCCTGCGCCGGC<br>TACTACCCCATCCCCTACGACGACTACTGGGGCCAGGGCACCCAGGTGACCGTGAGCG<br>CTAGCCACCACCACCACCACCACCACCAC |
| 163 | CAGGTGCAGCTGCAGGAGAGCGGCGGCGGCCTGGTGCAGCCCGGCGGCAGCCTGAGGC<br>TGAGCTGCGCCGCCAGCGGCTTCAGCTTCAGCAGCTACGCCATGAAGTGGGTGAGGCA<br>GGCCCCCGGCAAGGGCCTGGAGTGGGTGAGCACCATCAGCAGCGGCGGCAGCAGCACC<br>AACTACGCCGACAGCGTGAAGGGCAGGTTCACCATCAGCAGGGACAACGCCAAGAAC<br>ACCCTGTACCTGCAGCTGAACAGCCTGAAGATCGAGGACACCGCCATGTACTACTGCG<br>CCAAGGCCATCGTGCCCACCGGCGCCACCATGGAGAGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGAGGCTGAGCTGCACCGCCAGCGGCGCCATCGCCAGCGGCT<br>ACATCGACAGCAGGTGGTGCATGGCCTGGTTCAGGCAGGCCCCCGGCAAGGAGAGGGA<br>GGGCGTGGCCGCCATCTGGCCCGGGGGGGCCTGACCGTGTACGCCGACAGCGTGAAG<br>GGCAGGTTCACCATCAGCAGGGACCACGCCAAGAACACCCTGTACCTGCAGATGAACA<br>ACCTGAAGCCCGAGGACACCGCCATGTACTACTGCGCCGCCGGCAGCCCCAGGATGTG<br>CCCCAGCCTGGAGTTCGGCTTCGACTACTGGGGCCAGGGCACCCAGGTGACCGTGAGC<br>GCTAGCCACCACCACCACCACCACCACCAC |
| 164 | CAGGTGCAGCTGCAGGAGAGCGGCGGCGGCCTGGTGCAGCCCGGGGGCAGCCTGAGGC<br>TGAGCTGCGCCGCCAGCGGCTTCAGCTTCAGCAGCTACGCCATGAAGTGGGTGAGGCA<br>GGCCCCCGGCAAGGGCCTGGAGTGGGTGAGCACCATCAGCAGCGGCGGCAGCAGCACC<br>AACTACGCCGACAGCGTGAAGGGCAGGTTCACCATCAGCAGGGACAACGCCAAGAAC<br>ACCCTGTACCTGCAGCTGAACAGCCTGAAGATCGAGGACACCGCCATGTACTACTGCG<br>CCAAGGCCATCGTGCCCACCGGCGCCACCATGGAGAGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGAGGCTGAGCTGCACCGCCCCCGGCTTCACCAGCAACAGCT<br>GCGGCATGGACTGGTACAGGCAGGCCCCCGGCAAGGAGAGGGAGTTCGTGAGCAGCAT<br>CAGCACCGACGGCACCACCGGCTACGCCGACAGCGTGAAGGGCAGGTTCACCATCAGC<br>AAGGACAAGGCCAAGGACACCGTGTACCTGCAGATGAACAGCCTGAAGCCCGAGGAC<br>ACCGGCATGTACAGCTGCAAGACCAAGGACGGCACCATCGCCACCATGGAGCTGTGCG<br>ACTTCGGCTACTGGGGCCAGGGCACCCAGGTGACCGTGAGCGCTAGCCACCACCACCA<br>CCACCACCACCAC |
| 165 | CAGGTGCAGCTGCAGGAGAGCGGCGGCGGCCTGGTGCAGCCCGGCGGCAGCCTGAGGC<br>TGAGCTGCGCCGCCAGCGGCTTCAGCTTCAGCAGCTACGCCATGAAGTGGGTGAGGCA<br>GGCCCCCGGCAAGGGCCTGGAGTGGGTGAGCACCATCAGCAGCGGCGGCAGCAGCACC<br>AACTACGCCGACAGCGTGAAGGGCAGGTTCACCATCAGCAGGGACAACGCCAAGAAC<br>ACCCTGTACCTGCAGCTGAACAGCCTGAAGATCGAGGACACCGCCATGTACTACTGCG<br>CCAAGGCCATCGTGCCCACCGGCGCCACCATGGAGAGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGAGGCTGAGCTGCGCCGCCAGCGGCTACCCCTACAGCAACG<br>GCTACATGGGCTGGTTCAGGCAGGCCCCCGGCAAGGAGAGGGAGGGCGTGGCCACCAT<br>CTACACCGGCGACGGCAGGACCTACTACGCCGACAGCGTGAAGGGCAGGTTCACCATC<br>AGCAGGGACAACGCCAAGAACACCGTGGACCTGCAGATGAGCAGCCTGAAGCCCGAG<br>GACACCGCCATGTACTACTGCGCCGCCAGGGCCGCCCCCCTGTACAGCAGCGGCAGCC<br>CCCTGACCAGGGCCAGGTACAACGTGTGGGGCCAGGGCACCCAGGTGACCGTGAGCGC<br>TAGCCACCACCACCACCACCACCACCAC |
| 166 | CAGGTGCAGCTGCAGGAGAGCGGCGGCGGCCTGGTGCAGCCCGGGGGCAGCCTGAGGC<br>TGAGCTGCGCCGCCAGCGGCTTCAGCTTCAGCAGCTACGCCATGAAGTGGGTGAGGCA<br>GGCCCCCGGCAAGGGCCTGGAGTGGGTGAGCACCATCAGCAGCGGCGGCAGCAGCACC<br>AACTACGCCGACAGCGTGAAGGGCAGGTTCACCATCAGCAGGGACAACGCCAAGAAC<br>ACCCTGTACCTGCAGCTGAACAGCCTGAAGATCGAGGACACCGCCATGTACTACTGCG<br>CCAAGGCCATCGTGCCCACCGGCGCCACCATGGAGAGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGAGGCTGAGCTGCGTGGCCAGCGCCAGCACCTACTGCACCT<br>ACGACATGCACTGGTACAGGCAGGCCCCCGGCAAGGGCAGGGAGTTCGTGAGCGCCAT<br>CGACAGCGACGGCACCACCAGGTACGCCGACAGCGTGAAGGGCAGGTTCACCATCAGC<br>CAGGGCACCGCCAAGAACACCGTGTACCTGCAGATGAACAGCCTGCAGCCCGAGGACA<br>CCGCCATGTACTACTGCAAGACCGTGTGCGTGGTGGGCAGCAGGTGGAGCGACTACTG<br>GGGCCAGGGCACCCAGGTGACCGTGAGCGCTAGCCACCACCACCACCACCACCACCAC |
| 167 | CAGGTGCAGCTGCAGGAGAGCGGCGGCGGCCTGGTGCAGCCCGGCGGCAGCCTGAGGC<br>TGAGCTGCGCCGCCAGCGGCTTCAGCTTCAGCAGCTACGCCATGAAGTGGGTGAGGCA<br>GGCCCCCGGCAAGGGCCTGGAGTGGGTGAGCACCATCAGCAGCGGCGGCAGCAGCACC<br>AACTACGCCGACAGCGTGAAGGGCAGGTTCACCATCAGCAGGGACAACGCCAAGAAC<br>ACCCTGTACCTGCAGCTGAACAGCCTGAAGATCGAGGACACCGCCATGTACTACTGCG<br>CCAAGGCCATCGTGCCCACCGGCGCCACCATGGAGAGGGGCCAGGGCACCCAGGTGAC<br>CGTCTCGAGTGGCGGCGGATCCCAGGTGCAGCTGCAGGAGAGCGGCGGCGGCAGCGTG<br>CAGGCCGGCGGCAGCCTGACCCTGAGCTGCGCCGCCAGCGAGTACGCCTACAGCACCT<br>GCAACATGGGCTGGTACAGGCAGGCCCCCGGCAAGGAGAGGGAGCTGGTGAGCGCCTT |

TABLE 3C-continued

| SEQ ID NO | Sequence |
|---|---|
| | CATCAGCGACGGCAGCACCTACTACGCCGACAGCGTGAAGGGCAGGTTCACCATCACC AGGGACAACGCCAAGAACACCGTGTACCTGCAGATGAACAGCCTGAAGCCCGAGGAC ACCGCCATCTACTACTGCAGCGCCAACTGCTACAGGAGGCTGAGGAACTACTGGGGCC AGGGCACCCAGGTGACCGTGAGCGCTAGCCACCACCACCACCACCACCAC |
| 168 | CAGGTGCAGCTGCAGGAGAGCGGCGGCGGCCTGGTGCAGCCCGGCGGCAGCCTGAGGC TGAGCTGCGCCGCCAGCGGCTTCAGCTTCAGCAGCTACGCCATGAAGTGGGTGAGGCA GGCCCCCGGCAAGGGCCTGGAGTGGGTGAGCACCATCAGCAGCGGCGGCAGCAGCACC AACTACGCCGACAGCGTGAAGGGCAGGTTCACCATCAGCAGGGACAACGCCAAGAAC ACCCTGTACCTGCAGCTGAACAGCCTGAAGATCGAGGACACCGCCATGTACTACTGCG CCAAGGCCATCGTGCCCACCGGCGCCACCATGGAGAGGGGCCAGGGCACCCAGGTGAC CGTCTCGAGTGGCGGCGGATCCCAGGTGCAGCTGCAGGAGAGCGGCGGCGGCCTGGTG CAGCCCGGCGGCAGCCTGAGGCTGAGCTGCACCGCCAGCGGCCTGACCTTCGACGACA GCGTGATGGGCTGGTTCAGGCAGGCCCCCGGCAAGGGCAGGGAGGCCGTGAGCTGCAT CAGCAGCAGCGGCGCCAACGCCTTCTACGCCGACAGCGTGAAGGGCAGGTTCACCATC AGCAGGGACAACGCCAAGAACACCCTGTACCTGCAGATGAACAGCCTGAAGCCCGAGG ACACCGCCACCTACTACTGCAAGAGGGGCCACGCCTGCGCCGGCTACTACCCCATCCCC TACGACGACTACTGGGGCCAGGGCACCCAGGTGACCGTGAGCGCTAGCCACCACCACC ACCACCACCACCAC |
| 169 | CAGGTGCAGCTGCAGGAGAGCGGCGGCGGCAGCGTGCAGAGCGGCGGCAGCCTGAGG CTGAGCTGCGCCGCCAGCGGCTTCACCTACAGCACCAGCAACAGCTGGATGGCCTGGTT CAGGCAGGCCCCCGGCAAGGAGAGGGAGGGCGTGGCCGCCATCTACACCGTGGGCGG CAGCATCTTCTACGCCGACAGCGTGAGGGGCAGGTTCACCATCAGCCAGGACGCCACC AAGAACATGTTCTACCTGCAGATGAACACCCTGAAGCCCGAGGACACCGCCATGTACT ACTGCGCCGCCGCCAGCGGCAGGCTGAGGGGCAAGTGGTTCTGGCCCTACGAGTACAA CTACTGGGGCCAGGGCACCCAGGTGACCGTCTCGAGTGGCGGCGGATCCCAGGTGCAG CTGCAGGAGAGCGGCGGCGGCAGCGTGCAGGCCGGCGGCAGCCTGAGGCTGAGCTGC ACCGCCAGCGGCGCCATCGCCAGCGGCTACATCGACAGCAGGTGGTGCATGGCCTGGT TCAGGCAGGCCCCCGGCAAGGAGAGGGAGGGCGTGGCCGCCATCTGGCCCGGCGGCG GCCTGACCGTGTACGCCGACAGCGTGAAGGGCAGGTTCACCATCAGCAGGGACCACGC CAAGAACACCCTGTACCTGCAGATGAACAACCTGAAGCCCGAGGACACCGCCATGTAC TACTGCGCCGCCGGCAGCCCCAGGATGTGCCCCAGCCTGGAGTTCGGCTTCGACTACTG GGGCCAGGGCACCCAGGTGACCGTGAGCGCTAGCCACCACCACCACCACCACCACCAC |
| 170 | CAGGTGCAGCTGCAGGAGAGCGGCGGCGGCAGCGTGCAGAGCGGCGGCAGCCTGAGG CTGAGCTGCGCCGCCAGCGGCTTCACCTACAGCACCAGCAACAGCTGGATGGCCTGGTT CAGGCAGGCCCCCGGCAAGGAGAGGGAGGGCGTGGCCGCCATCTACACCGTGGGCGG CAGCATCTTCTACGCCGACAGCGTGAGGGGCAGGTTCACCATCAGCCAGGACGCCACC AAGAACATGTTCTACCTGCAGATGAACACCCTGAAGCCCGAGGACACCGCCATGTACT ACTGCGCCGCCGCCAGCGGCAGGCTGAGGGGCAAGTGGTTCTGGCCCTACGAGTACAA CTACTGGGGCCAGGGCACCCAGGTGACCGTCTCGAGTGGCGGCGGATCCCAGGTGCAG CTGCAGGAGAGCGGCGGCGGCAGCGTGCAGGCCGGCGGCAGCCTGAGGCTGAGCTGC ACCGCCCCCGGCTTCACCAGCAACAGCTGCGGCATGGACTGGTACAGGCAGGCCCCCG GCAAGGAGAGGGAGTTCGTGAGCAGCATCAGCACCGACGGCACCACCGGCTACGCCGA CAGCGTGAAGGGCAGGTTCACCATCAGCAAGGACAAGGCCAAGGACACCGTGTACCTG CAGATGAACAGCCTGAAGCCCGAGGACACCGGCATGTACAGCTGCAAGACCAAGGAC GGCACCATCGCCACCATGGAGCTGTGCGACTTCGGCTACTGGGGCCAGGGCACCCAGG TGACCGTGAGCGCTAGCCACCACCACCACCACCACCACCAC |
| 171 | CAGGTGCAGCTGCAGGAGAGCGGCGGCGGCAGCGTGCAGAGCGGCGGCAGCCTGAGG CTGAGCTGCGCCGCCAGCGGCTTCACCTACAGCACCAGCAACAGCTGGATGGCCTGGTT CAGGCAGGCCCCCGGCAAGGAGAGGGAGGGCGTGGCCGCCATCTACACCGTGGGCGG CAGCATCTTCTACGCCGACAGCGTGAGGGGCAGGTTCACCATCAGCCAGGACGCCACC AAGAACATGTTTCTACCTGCAGATGAACACCCTGAAGCCCGAGGACACCGCCATGTACT ACTGCGCCGCCGCCAGCGGCAGGCTGAGGGGCAAGTGGTTCTGGCCCTACGAGTACAA CTACTGGGGCCAGGGCACCCAGGTGACCGTCTCGAGTGGCGGCGGATCCCAGGTGCAG CTGCAGGAGAGCGGCGGCGGCAGCGTGCAGGCCGGCGGCAGCCTGAGGCTGAGCTGC GCCGCCAGCGGCTACCCCTACAGCAACGGCTACATGGGCTGGTTCAGGCAGGCCCCCG GCAAGGAGAGGGAGGGCGTGGCCACCATCTACACCGGCGACGGCAGGACCTACTACGC CGACAGCGTGAAGGGCAGGTTCACCATCAGCAGGGACAACGCCAAGAACACCGTGGA CCTGCAGATGAGCAGCCTGAAGCCCGAGGACACCGCCATGTACTACTGCGCCGCCAGG GCCGCCCCCCTGTACAGCAGCGGCAGCCCCCTGACCAGGGCCAGGTACAACGTGTGGG GCCAGGGCACCCAGGTGACCGTGAGCGCTAGCCACCACCACCACCACCACCACCAC |
| 172 | CAGGTGCAGCTGCAGGAGAGCGGCGGCGGCAGCGTGCAGAGCGGCGGCAGCCTGAGG CTGAGCTGCGCCGCCAGCGGCTTCACCTACAGCACCAGCAACAGCTGGATGGCCTGGTT CAGGCAGGCCCCCGGCAAGGAGAGGGAGGGCGTGGCCGCCATCTACACCGTGGGCGG CAGCATCTTCTACGCCGACAGCGTGAGGGGCAGGTTCACCATCAGCCAGGACGCCACC AAGAACATGTTCTACCTGCAGATGAACACCCTGAAGCCCGAGGACACCGCCATGTACT ACTGCGCCGCCGCCAGCGGCAGGCTGAGGGGCAAGTGGTTCTGGCCCTACGAGTACAA CTACTGGGGCCAGGGCACCCAGGTGACCGTCTCGAGTGGCGGCGGATCCCAGGTGCAG CTGCAGGAGAGCGGCGGCGGCAGCGTGCAGGCCGGCGGCAGCCTGAGGCTGAGCTGC GTGGCCAGCGCCAGCACCTACTGCACCTACGACATGCACTGGTACAGGCAGGCCCCCG GCAAGGGCAGGGAGTTCGTGAGCGCCATCGACAGCGACGGCACCACCAGGTACGCCGA CAGCGTGAAGGGCAGGTTCACCATCAGCCAGGGCACCGCCAAGAACACCGTGTACCTG |

TABLE 3C-continued

| SEQ ID NO | Sequence |
|---|---|
| | CAGATGAACAGCCTGCAGCCCGAGGACACCGCCATGTACTACTGCAAGACCGTGTGCG<br>TGGTGGGCAGCAGGTGGAGCGACTACTGGGGCCAGGGCACCCAGGTGACCGTGAGCGC<br>TAGCCACCACCACCACCACCACCACCAC |
| 173 | CAGGTGCAGCTGCAGGAGAGCGGCGGCGGCAGCGTGCAGAGCGGCGGCAGCCTGAGG<br>CTGAGCTGCGCCGCCAGCGGCTTCACCTACAGCACCAGCAACAGCTGGATGGCCTGGTT<br>CAGGCAGGCCCCCGGCAAGGAGAGGGAGGGCGTGGCCGCCATCTACACCGTGGGCGG<br>CAGCATCTTCTACGCCGACAGCGTGAGGGGCAGGTTCACCATCAGCCAGGACGCCACC<br>AAGAACATGTTCTACCTGCAGATGAACACCCTGAAGCCCGAGGACACCGCCATGTACT<br>ACTGCGCCGCCGCCAGCGGCAGGCTGAGGGGCAAGTGGTTCTGGCCCTACGAGTACAA<br>CTACTGGGGCCAGGGCACCCAGGTGACCGTCTCGAGTGGCGGCGGATCCCAGGTGCAG<br>CTGCAGGAGAGCGGCGGCGGCAGCGTGCAGGCCGGCGGCAGCCTGACCCTGAGCTGCG<br>CCGCCAGCGAGTACGCCTACAGCACCTGCAACATGGGCTGGTACAGGCAGGCCCCCGG<br>CAAGGAGAGGGAGCTGGTGAGCGCCTTCATCAGCGACGGCAGCACCTACTACGCCGAC<br>AGCGTGAAGGGCAGGTTCACCATCACCAGGGACAACGCCAAGAACACCGTGTACCTGC<br>AGATGAACAGCCTGAAGCCCGAGGACACCGCCATCTACTACTGCAGCGCCAACTGCTA<br>CAGGAGGCTGAGGAACTACTGGGGCCAGGGCACCCAGGTGACCGTGAGCGCTAGCCAC<br>CACCACCACCACCACCACCAC |
| 174 | CAGGTGCAGCTGCAGGAGAGCGGCGGCGGCAGCGTGCAGAGCGGCGGCAGCCTGAGG<br>CTGAGCTGCGCCGCCAGCGGCTTCACCTACAGCACCAGCAACAGCTGGATGGCCTGGTT<br>CAGGCAGGCCCCCGGCAAGGAGAGGGAGGGCGTGGCCGCCATCTACACCGTGGGGGG<br>CAGCATCTTCTACGCCGACAGCGTGAGGGGCAGGTTCACCATCAGCCAGGACGCCACC<br>AAGAACATGTTCTACCTGCAGATGAACACCCTGAAGCCCGAGGACACCGCCATGTACT<br>ACTGCGCCGCCGCCAGCGGCAGGCTGAGGGGCAAGTGGTTCTGGCCCTACGAGTACAA<br>CTACTGGGGCCAGGGCACCCAGGTGACCGTCTCGAGTGGCGGCGGATCCCAGGTGCAG<br>CTGCAGGAGAGCGGCGGCGGCCTGGTGCAGCCCGGCGGCAGCCTGAGGCTGAGCTGCA<br>CCGCCAGCGGCCTGACCTTCGACGACAGCGTGATGGGCTGGTTCAGGCAGGCCCCCGG<br>CAAGGGCAGGGAGGCCGTGAGCTGCATCAGCAGCAGCGGCGCCAACGCCTTCTACGCC<br>GACAGCGTGAAGGGCAGGTTCACCATCAGCAGGGACAACGCCAAGAACACCCTGTACC<br>TGCAGATGAACAGCCTGAAGCCCGAGGACACCGCCACCTACTACTGCAAGAGGGGCCA<br>CGCCTGCGCCGGCTACTACCCCATCCCCTACGACGACTACTGGGGCCAGGGCACCCAG<br>GTGACCGTGAGCGCTAGCCACCACCACCACCACCACCACCAC |
| 175 | CAGGTGCAGCTGCAGGAGAGCGGGGGGGGCAGCGTGCAGGCCGGCGGCAGCCTGAGG<br>CTGAGCTGCGTGGCCAGCGGCTACGTGAGCTGCGACTACTTCCTGCCCAGCTGGTACAG<br>GCAGGCCCCCGGCAAGGAGAGGGAGTTCGTGAGCATCATCGACGGCACCGGCAGCACC<br>AGCTACGCCGCCAGCGTGAAGGGCAGGTTCACCGCCAGCCAGGACAAGGGCAAGAAC<br>ATCGCCTACCTGCAGATGAACACCCTGAAGCCCGAGGACACCGCCATGTACTACTGCA<br>AGGCCAGCTGCGTGAGGGGCAGGGCCATCAGCGAGTACTGGGGCCAGGGCACCCAGGT<br>GACCGTCTCGAGTGGCGGCGGATCCCAGGTGCAGCTGCAGGAGAGCGGCGGCGGCAGC<br>GTGCAGGCCGGCGGCAGCCTGAGGCTGAGCTGCACCGCCAGCGGCGCCATCGCCAGCG<br>GCTACATCGACAGCAGGTGGTGCATGGCCTGGTTCAGGCAGGCCCCCGGCAAGGAGAG<br>GGAGGGCGTGGCCGCCATCTGGCCCGGCGGCGGCCTGACCGTGTACGCCGACAGCGTG<br>AAGGGCAGGTTCACCATCAGCAGGGACCACGCCAAGAACACCCTGTACCTGCAGATGA<br>ACAACCTGAAGCCCGAGGACACCGCCATGTACTACTGCGCCGCCGGCAGCCCCAGGAT<br>GTGCCCCAGCCTGGAGTTCGGCTTCGACTACTGGGGCCAGGGCACCCAGGTGACCGTG<br>AGCGCTAGCCACCACCACCACCACCACCACCAC |
| 176 | CAGGTGCAGCTGCAGGAGAGCGGCGGCGGCAGCGTGCAGGCCGGCGGCAGCCTGAGG<br>CTGAGCTGCGTGGCCAGCGGCTACGTGAGCTGCGACTACTTCCTGCCCAGCTGGTACAG<br>GCAGGCCCCCGGCAAGGAGAGGGAGTTCGTGAGCATCATCGACGGCACCGGCAGCACC<br>AGCTACGCCGCCAGCGTGAAGGGCAGGTTCACCGCCAGCCAGGACAAGGGCAAGAAC<br>ATCGCCTACCTGCAGATGAACACCCTGAAGCCCGAGGACACCGCCATGTACTACTGCA<br>AGGCCAGCTGCGTGAGGGGCAGGGCCATCAGCGAGTACTGGGGCCAGGGCACCCAGGT<br>GACCGTCTCGAGTGGCGGCGGATCCCAGGTGCAGCTGCAGGAGAGCGGCGGCGGCAGC<br>GTGCAGGCCGGCGGCAGCCTGAGGCTGAGCTGCACCGCCCCCGGCTTCACCAGCAACA<br>GCTGCGGCATGGACTGGTACAGGCAGGCCCCCGGCAAGGAGAGGGAGTTCGTGAGCAG<br>CATCAGCACCGACGGCACCACCGGCTACGCCGACAGCGTGAAGGGCAGGTTCACCATC<br>AGCAAGGACAAGGCCAAGGACACCGTGTACCTGCAGATGAACAGCCTGAAGCCCGAG<br>GACACCGGCATGTACAGCTGCAAGACCAAGGACGGCACCATCGCCACCATGGAGCTGT<br>GCGACTTCGGCTACTGGGGCCAGGGCACCCAGGTGACCGTGAGCGCTAGCCACCACCA<br>CCACCACCACCACCAC |
| 177 | CAGGTGCAGCTGCAGGAGAGCGGGGGGGGCAGCGTGCAGGCCGGCGGCAGCCTGAGG<br>CTGAGCTGCGTGGCCAGCGGCTACGTGAGCTGCGACTACTTCCTGCCCAGCTGGTACAG<br>GCAGGCCCCCGGCAAGGAGAGGGAGTTCGTGAGCATCATCGACGGCACCGGCAGCACC<br>AGCTACGCCGCCAGCGTGAAGGGCAGGTTCACCGCCAGCCAGGACAAGGGCAAGAAC<br>ATCGCCTACCTGCAGATGAACACCCTGAAGCCCGAGGACACCGCCATGTACTACTGCA<br>AGGCCAGCTGCGTGAGGGGCAGGGCCATCAGCGAGTACTGGGGCCAGGGCACCCAGGT<br>GACCGTCTCGAGTGGCGGCGGATCCCAGGTGCAGCTGCAGGAGAGCGGCGGCGGCAGC<br>GTGCAGGCCGGCGGCAGCCTGAGGCTGAGCTGCGCCGCCAGCGGCTACCCCTACAGCA<br>ACGGCTACATGGGCTGGTTCAGGCAGGCCCCCGGCAAGGAGAGGGAGGGCGTGGCCAC<br>CATCTACACCGGCGACGGCAGGACCTACTACGCCGACAGCGTGAAGGGCAGGTTCACC<br>ATCAGCAGGGACAACGCCAAGAACACCGTGGACCTGCAGATGAGCAGCCTGAAGCCCG<br>AGGACACCGCCATGTACTACTGCGCCGCCAGGGCCGCCCCCCTGTACAGCAGCGGCAG |

TABLE 3C-continued

| SEQ ID NO | Sequence |
|---|---|
| | CCCCCTGACCAGGGCCAGGTACAACGTGTGGGGCCAGGGCACCCAGGTGACCGTGAGC<br>GCTAGCCACCACCACCACCACCACCACCAC |
| 178 | CAGGTGCAGCTGCAGGAGAGCGGCGGCGGCAGCGTGCAGGCCGGCGGCAGCCTGAGG<br>CTGAGCTGCGTGGCCAGCGGCTACGTGAGCTGCGACTACTTCCTGCCCAGCTGGTACAG<br>GCAGGCCCCCGGCAAGGAGAGGGAGTTCGTGAGCATCATCGACGGCACCGGCAGCACC<br>AGCTACGCCGCCAGCGTGAAGGGCAGGTTCACCGCCAGCCAGGACAAGGGCAAGAAC<br>ATCGCCTACCTGCAGATGAACACCCTGAAGCCCGAGGACACCGCCATGTACTACTGCA<br>AGGCCAGCTGCGTGAGGGGCAGGGCCATCAGCGAGTACTGGGGCCAGGGCACCCAGGT<br>GACCGTCTCGAGTGGGGGGGGATCCCAGGTGCAGCTGCAGGAGAGCGGCGGCGGCAGC<br>GTGCAGGCCGGCGGCAGCCTGAGGCTGAGCTGCGTGGCCAGCGCCAGCACCTACTGCA<br>CCTACGACATGCACTGGTACAGGCAGGCCCCCGGCAAGGGCAGGGAGTTCGTGAGCGC<br>CATCGACAGCGACGGCACCACCAGGTACGCCGACAGCGTGAAGGGCAGGTTCACCATC<br>AGCCAGGGCACCGCCAAGAACACCGTGTACCTGCAGATGAACAGCCTGCAGCCCGAGG<br>ACACCGCCATGTACTACTGCAAGACCGTGTGCGTGGTGGGCAGCAGGTGGAGCGACTA<br>CTGGGGCCAGGGCACCCAGGTGACCGTGAGCGCTAGCCACCACCACCACCACCACCAC<br>CAC |
| 179 | CAGGTGCAGCTGCAGGAGAGCGGCGGCGGCAGCGTGCAGGCCGGCGGCAGCCTGAGG<br>CTGAGCTGCGTGGCCAGCGGCTACGTGAGCTGCGACTACTTCCTGCCCAGCTGGTACAG<br>GCAGGCCCCCGGCAAGGAGAGGGAGTTCGTGAGCATCATCGACGGCACCGGCAGCACC<br>AGCTACGCCGCCAGCGTGAAGGGCAGGTTCACCGCCAGCCAGGACAAGGGCAAGAAC<br>ATCGCCTACCTGCAGATGAACACCCTGAAGCCCGAGGACACCGCCATGTACTACTGCA<br>AGGCCAGCTGCGTGAGGGGCAGGGCCATCAGCGAGTACTGGGGCCAGGGCACCCAGGT<br>GACCGTCTCGAGTGGGGGGGGATCCCAGGTGCAGCTGCAGGAGAGCGGCGGCGGCAGC<br>GTGCAGGCCGGCGGCAGCCTGACCCTGAGCTGCGCCGCCAGCGAGTACGCCTACAGCA<br>CCTGCAACATGGGCTGGTACAGGCAGGCCCCCGGCAAGGAGAGGGAGCTGGTGAGCGC<br>CTTCATCAGCGACGGCAGCACCTACTACGCCGACAGCGTGAAGGGCAGGTTCACCATC<br>ACCAGGGACAACGCCAAGAACACCGTGTACCTGCAGATGAACAGCCTGAAGCCCGAGG<br>ACACCGCCATCTACTACTGCAGCGCCAACTGCTACAGGAGGCTGAGGAACTACTGGGG<br>CCAGGGCACCCAGGTGACCGTGAGCGCTAGCCACCACCACCACCACCACCAC |
| 180 | CAGGTGCAGCTGCAGGAGAGCGGCGGCGGCAGCGTGCAGGCCGGCGGCAGCCTGAGG<br>CTGAGCTGCGTGGCCAGCGGCTACGTGAGCTGCGACTACTTCCTGCCCAGCTGGTACAG<br>GCAGGCCCCCGGCAAGGAGAGGGAGTTCGTGAGCATCATCGACGGCACCGGCAGCACC<br>AGCTACGCCGCCAGCGTGAAGGGCAGGTTCACCGCCAGCCAGGACAAGGGCAAGAAC<br>ATCGCCTACCTGCAGATGAACACCCTGAAGCCCGAGGACACCGCCATGTACTACTGCA<br>AGGCCAGCTGCGTGAGGGGCAGGGCCATCAGCGAGTACTGGGGCCAGGGCACCCAGGT<br>GACCGTCTCGAGTGGCGGCGGATCCCAGGTGCAGCTGCAGGAGAGCGGCGGCGGCCTG<br>GTGCAGCCCGGCGGCAGCCTGAGGCTGAGCTGCACCGCCAGCGGCCTGACCTTCGACG<br>ACAGCGTGATGGGCTGGTTCAGGCAGGCCCCCGGCAAGGGCAGGGAGGCCGTGAGCTG<br>CATCAGCAGCAGCGGCGCCAACGCCTTCTACGCCGACAGCGTGAAGGGCAGGTTCACC<br>ATCAGCAGGGACAACGCCAAGAACACCCTGTACCTGCAGATGAACAGCCTGAAGCCCG<br>AGGACACCGCCACCTACTACTGCAAGAGGGGCCACGCCTGCGCCGGCTACTACCCCAT<br>CCCCTACGACGACTACTGGGGCCAGGGCACCCAGGTGACCGTGAGCGCTAGCCACCAC<br>CACCACCACCACCACCAC |
| 181 | CAGGTGCAGCTGCAGGAGAGCGGGGGGGGCAGCGTGCAGGCCGGCGGCAGCCTGAGG<br>CTGAGCTGCAGGGCCAGCGGCAGCACCTACAGCAACTACTGCCTGGGCTGGTTCAGGC<br>AGATCACCGGCAAGGAGAGGGAGGGCGTGGCCGTGATCAACTGGGGGGGGCATGCT<br>GTACTTCGCCGACAGCGTGAAGGGCAGGTTCACCGTGAGCCAGGACCAGGCCAAGAAC<br>ACCGTGTACCTGCAGATGAACAGCCTGAAGCCCGAGGACACCGCCATGTACTACTGCG<br>CCGCCGAGAGCGTGAGCAGCTTCAGCTGCGGCGGCTGGCTGACCAGGCCCGACAGGGT<br>GCCCTACTGGGGCCAGGGCACCCAGGTGACCGTCTCGAGTGGCGGCGGATCCCAGGTG<br>CAGCTGCAGGAGAGCGGGGGGGGCAGCGTGCAGGCCGGCGGCAGCCTGAGGCTGAGC<br>TGCACCGCCAGCGGCGCCATCGCCAGCGGCTACATCGACAGCAGGTGGTGCATGGCCT<br>GGTTCAGGCAGGCCCCCGGCAAGGAGAGGGAGGGCGTGGCCGCCATCTGGCCCGGCGG<br>CGGCCTGACCGTGTACGCCGACAGCGTGAAGGGCAGGTTCACCATCAGCAGGGACCAC<br>GCCAAGAACACCCTGTACCTGCAGATGAACAACCTGAAGCCCGAGGACACCGCCATGT<br>ACTACTGCGCCGCCGGCAGCCCCAGGATGTGCCCCAGCCTGGAGTTCGGCTTCGACTAC<br>TGGGGCCAGGGCACCCAGGTGACCGTGAGCGCTAGCCACCACCACCACCACCACCACC<br>AC |
| 182 | CAGGTGCAGCTGCAGGAGAGCGGCGGCGGCAGCGTGCAGGCCGGCGGCAGCCTGAGG<br>CTGAGCTGCAGGGCCAGCGGCAGCACCTACAGCAACTACTGCCTGGGCTGGTTCAGGC<br>AGATCACCGGCAAGGAGAGGGAGGGCGTGGCCGTGATCAACTGGGTGGGCGGCATGCT<br>GTACTTCGCCGACAGCGTGAAGGGCAGGTTCACCGTGAGCCAGGACCAGGCCAAGAAC<br>ACCGTGTACCTGCAGATGAACAGCCTGAAGCCCGAGGACACCGCCATGTACTACTGCG<br>CCGCCGAGAGCGTGAGCAGCTTCAGCTGCGGCGGCTGGCTGACCAGGCCCGACAGGGT<br>GCCCTACTGGGGCCAGGGCACCCAGGTGACCGTCTCGAGTGGCGGCGGATCCCAGGTG<br>CAGCTGCAGGAGAGCGGCGGCGGCAGCGTGCAGGCCGGCGGCAGCCTGAGGCTGAGC<br>TGCACCGCCCCCGGCTTCACCAGCAACAGCTGCGGCATGGACTGGTACAGGCAGGCCC<br>CCGGCAAGGAGAGGGAGTTCGTGAGCAGCATCAGCACCGACGGCACCACCGGCTACGC<br>CGACAGCGTGAAGGGCAGGTTCACCATCAGCAAGGACAAGGCCAAGGACACCGTGTAC |

TABLE 3C-continued

| SEQ ID NO | Sequence |
|---|---|
| | CTGCAGATGAACAGCCTGAAGCCCGAGGACACCGGCATGTACAGCTGCAAGACCAAGG<br>ACGGCACCATCGCCACCATGGAGCTGTGCGACTTCGGCTACTGGGGCCAGGGCACCCA<br>GGTGACCGTGAGCGCTAGCCACCACCACCACCACCACCAC |
| 183 | CAGGTGCAGCTGCAGGAGAGCGGCGGCGGCAGCGTGCAGGCCGGCGGCAGCCTGAGG<br>CTGAGCTGCAGGGCCAGCGGCAGCACCTACAGCAACTACTGCCTGGGCTGGTTCAGGC<br>AGATCACCGGCAAGGAGAGGGAGGGCGTGGCCGTGATCAACTGGGTGGGGGGCATGCT<br>GTACTTCGCCGACAGCGTGAAGGGCAGGTTCACCGTGAGCCAGGACCAGGCCAAGAAC<br>ACCGTGTACCTGCAGATGAACAGCCTGAAGCCCGAGGACACCGCCATGTACTACTGCG<br>CCGCCGAGAGCGTGAGCAGCTTCAGCTGCGGCGGCTGGCTGACCAGGCCCGACAGGGT<br>GCCCTACTGGGGCCAGGGCACCCAGGTGACCGTCTCGAGTGGCGGCGGATCCCAGGTG<br>CAGCTGCAGGAGAGCGGGGGGGGCAGCGTGCAGGCCGGCGGCAGCCTGAGGCTGAGC<br>TGCGCCGCCAGCGGCTACCCCTACAGCAACGGCTACATGGGCTGGTTCAGGCAGGCCC<br>CCGGCAAGGAGAGGGAGGGCGTGGCCACCATCTACACCGGCGACGGCAGGACCTACTA<br>CGCCGACAGCGTGAAGGGCAGGTTCACCATCAGCAGGGACAACGCCAAGAACACCGTG<br>GACCTGCAGATGAGCAGCCTGAAGCCCGAGGACACCGCCATGTACTACTGCGCCGCCA<br>GGGCCGCCCCCCTGTACAGCAGCGGCAGCCCCCTGACCAGGGCCAGGTACAACGTGTG<br>GGGCCAGGGCACCCAGGTGACCGTGAGCGCTAGCCACCACCACCACCACCACCACCAC |
| 184 | CAGGTGCAGCTGCAGGAGAGCGGCGGCGGCAGCGTGCAGGCCGGCGGCAGCCTGAGG<br>CTGAGCTGCAGGGCCAGCGGCAGCACCTACAGCAACTACTGCCTGGGCTGGTTCAGGC<br>AGATCACCGGCAAGGAGAGGGAGGGCGTGGCCGTGATCAACTGGGGGGGGCATGCT<br>GTACTTCGCCGACAGCGTGAAGGGCAGGTTCACCGTGAGCCAGGACCAGGCCAAGAAC<br>ACCGTGTACCTGCAGATGAACAGCCTGAAGCCCGAGGACACCGCCATGTACTACTGCG<br>CCGCCGAGAGCGTGAGCAGCTTCAGCTGCGGCGGCTGGCTGACCAGGCCCGACAGGGT<br>GCCCTACTGGGGCCAGGGCACCCAGGTGACCGTCTCGAGTGGCGGCGGATCCCAGGTG<br>CAGCTGCAGGAGAGCGGCGGCGGCAGCGTGCAGGCCGGCGGCAGCCTGAGGCTGAGC<br>TGCGTGGCCAGCGCCAGCACCTACTGCACCTACGACATGCACTGGTACAGGCAGGCCC<br>CCGGCAAGGGCAGGGAGTTCGTGAGCGCCATCGACAGCGACGGCACCACCAGGTACGC<br>CGACAGCGTGAAGGGCAGGTTCACCATCAGCCAGGGCACCGCCAAGAACACCGTGTAC<br>CTGCAGATGAACAGCCTGCAGCCCGAGGACACCGCCATGTACTACTGCAAGACCGTGT<br>GCGTGGTGGGCAGCAGGTGGAGCGACTACTGGGGCCAGGGCACCCAGGTGACCGTGAG<br>CGCTAGCCACCACCACCACCACCACCACCAC |
| 185 | CAGGTGCAGCTGCAGGAGAGCGGCGGCGGCAGCGTGCAGGCCGGCGGCAGCCTGAGG<br>CTGAGCTGCAGGGCCAGCGGCAGCACCTACAGCAACTACTGCCTGGGCTGGTTCAGGC<br>AGATCACCGGCAAGGAGAGGGAGGGCGTGGCCGTGATCAACTGGGTGGGGGGCATGCT<br>GTACTTCGCCGACAGCGTGAAGGGCAGGTTCACCGTGAGCCAGGACCAGGCCAAGAAC<br>ACCGTGTACCTGCAGATGAACAGCCTGAAGCCCGAGGACACCGCCATGTACTACTGCG<br>CCGCCGAGAGCGTGAGCAGCTTCAGCTGCGGCGGCTGGCTGACCAGGCCCGACAGGGT<br>GCCCTACTGGGGCCAGGGCACCCAGGTGACCGTCTCGAGTGGCGGCGGATCCCAGGTG<br>CAGCTGCAGGAGAGCGGCGGCGGCAGCGTGCAGGCCGGCGGCAGCCTGACCCTGAGCT<br>GCGCCGCCAGCGAGTACGCCTACAGCACCTGCAACATGGGCTGGTACAGGCAGGCCCC<br>CGGCAAGGAGAGGGAGCTGGTGAGCGCCTTCATCAGCGACGGCAGCACCTACTACGCC<br>GACAGCGTGAAGGGCAGGTTCACCATCACCAGGGACAACGCCAAGAACACCGTGTACC<br>TGCAGATGAACAGCCTGAAGCCCGAGGACACCGCCATCTACTACTGCAGCGCCAACTG<br>CTACAGGAGGCTGAGGAACTACTGGGGCCAGGGCACCCAGGTGACCGTGAGCGCTAGC<br>CACCACCACCACCACCACCACCAC |
| 186 | CAGGTGCAGCTGCAGGAGAGCGGCGGCGGCAGCGTGCAGGCCGGCGGCAGCCTGAGG<br>CTGAGCTGCAGGGCCAGCGGCAGCACCTACAGCAACTACTGCCTGGGCTGGTTCAGGC<br>AGATCACCGGCAAGGAGAGGGAGGGCGTGGCCGTGATCAACTGGGGGGCGGCATGCT<br>GTACTTCGCCGACAGCGTGAAGGGCAGGTTCACCGTGAGCCAGGACCAGGCCAAGAAC<br>ACCGTGTACCTGCAGATGAACAGCCTGAAGCCCGAGGACACCGCCATGTACTACTGCG<br>CCGCCGAGAGCGTGAGCAGCTTCAGCTGCGGGGCTGGCTGACCAGGCCCGACAGGGT<br>GCCCTACTGGGGCCAGGGCACCCAGGTGACCGTCTCGAGTGGCGGCGGATCCCAGGTG<br>CAGCTGCAGGAGAGCGGCGGCGGCCTGGTGCAGCCCGGCGGCAGCCTGAGGCTGAGCT<br>GCACCGCCAGCGGCCTGACCTTCGACGACAGCGTGATGGGCTGGTTCAGGCAGGCCCC<br>CGGCAAGGGCAGGGAGGCCGTGAGCTGCATCAGCAGCAGCGGCGCCAACGCCTTCTAC<br>GCCGACAGCGTGAAGGGCAGGTTCACCATCAGCAGGGACAACGCCAAGAACACCCTGT<br>ACCTGCAGATGAACAGCCTGAAGCCCGAGGACACCGCCACCTACTACTGCAAGAGGGG<br>CCACGCCTGCGCCGGCTACTACCCCATCCCCTACGACGACTACTGGGGCCAGGGCACCC<br>AGGTGACCGTGAGCGCTAGCCACCACCACCACCACCACCACCAC |
| 187 | CAGGTGCAGCTGCAGGAGAGCGGCGGCGGCCTGGTGCAGCCCGGGGGCAGCCTGAGGC<br>TGAGCTGCGCCGCCAGCGGCTTCACCTTCAGCCTGAGCAGCATGAGCTGGGTGAGGCA<br>GGCCCCCGGCAAGGGCCTGGAGTGGGTGAGCGCCATCAGCAGCGGCGGCGCCAGCACC<br>TACTACACCGACAGCGTGAAGGGCAGGTTCACCATCAGCAGGGACAACGCCAAGAACA<br>TGCTGTACCTGCAGCTGAACAGCCTGAAGACCGAGGACACCGCCATGTACTACTGCGC<br>CAAGGGCGGCAGCGGCTACGGCGACGCCAGCAGGATGACCAGCCCCGGCAGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCACCGCCAGCGGCGCCA<br>TCGCCAGCGGCTACATCGACAGCAGGTGGTGCATGGCCTGGTTCAGGCAGGCCCCCGG<br>CAAGGAGAGGGAGGGCGTGGCCGCCATCTGGCCCGGCGGCGGCCTGACCGTGTACGCC<br>GACAGCGTGAAGGGCAGGTTCACCATCAGCAGGGACCACGCCAAGAACACCCTGTACC<br>TGCAGATGAACAACCTGAAGCCCGAGGACACCGCCATGTACTACTGCGCCGCCGGCAG |

TABLE 3C-continued

| SEQ ID NO | Sequence |
|---|---|
| | CCCCAGGATGTGCCCCAGCCTGGAGTTCGGCTTCGACTACTGGGGCCAGGGCACCCAG<br>GTGACCGTGAGCGCTAGCCACCACCACCACCACCACCAC |
| 188 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCCTGAGCAGCATGAGCTGGGTGAGGCA<br>GGCCCCCGGCAAGGGCCTGGAGTGGGTGAGCGCCATCAGCAGCGGCGGCGCCAGCACC<br>TACTACACCGACAGCGTGAAGGGCAGGTTCACCATCAGCAGGGACAACGCCAAGAACA<br>TGCTGTACCTGCAGCTGAACAGCCTGAAGACCGAGGACACCGCCATGTACTACTGCGC<br>CAAGGGCGGCAGCGGCTACGGCGACGCCAGCAGGATGACCAGCCCCGGCAGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCACCGCCCCCGGCTTCA<br>CCAGCAACAGCTGCGGCATGGACTGGTACAGGCAGGCCCCCGGCAAGGAGAGGGAGTT<br>CGTGAGCAGCATCAGCACCGACGGCACCACCGGCTACGCCGACAGCGTGAAGGGCAGG<br>TTCACCATCAGCAAGGACAAGGCCAAGGACACCGTGTACCTGCAGATGAACAGCCTGA<br>AGCCCGAGGACACCGGCATGTACAGCTGCAAGACCAAGGACGGCACCATCGCCACCAT<br>GGAGCTGTGCGACTTCGGCTACTGGGGCCAGGGCACCCAGGTGACCGTGAGCGCTAGC<br>CACCACCACCACCACCACCACCAC |
| 189 | CAGGTGCAGCTGCAGGAGAGCGGCGGCGGCCTGGTGCAGCCCGGGGGCAGCCTGAGGC<br>TGAGCTGCGCCGCCAGCGGCTTCACCTTCAGCCTGAGCAGCATGAGCTGGGTGAGGCA<br>GGCCCCCGGCAAGGGCCTGGAGTGGGTGAGCGCCATCAGCAGCGGCGGCGCCAGCACC<br>TACTACACCGACAGCGTGAAGGGCAGGTTCACCATCAGCAGGGACAACGCCAAGAACA<br>TGCTGTACCTGCAGCTGAACAGCCTGAAGACCGAGGACACCGCCATGTACTACTGCGC<br>CAAGGGCGGCAGCGGCTACGGCGACGCCAGCAGGATGACCAGCCCCGGCAGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCGCCGCCAGCGGCTACC<br>CCTACAGCAACGGCTACATGGGCTGGTTCAGGCAGGCCCCCGGCAAGGAGAGGGAGGG<br>CGTGGCCACCATCTACACCGGCGACGGCAGGACCTACTACGCCGACAGCGTGAAGGGC<br>AGGTTCACCATCAGCAGGGACAACGCCAAGAACACCGTGGACCTGCAGATGAGCAGCC<br>TGAAGCCCGAGGACACCGCCATGTACTACTGCGCCGCCAGGGCCGCCCCCCTGTACAG<br>CAGCGGCAGCCCCCTGACCAGGGCCAGGTACAACGTGTGGGGCCAGGGCACCCAGGTG<br>ACCGTGAGCGCTAGCCACCACCACCACCACCACCACCAC |
| 190 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCCTGAGCAGCATGAGCTGGGTGAGGCA<br>GGCCCCCGGCAAGGGCCTGGAGTGGGTGAGCGCCATCAGCAGCGGCGGCGCCAGCACC<br>TACTACACCGACAGCGTGAAGGGCAGGTTCACCATCAGCAGGGACAACGCCAAGAACA<br>TGCTGTACCTGCAGCTGAACAGCCTGAAGACCGAGGACACCGCCATGTACTACTGCGC<br>CAAGGGGGCAGCGGCTACGGCGACGCCAGCAGGATGACCAGCCCCGGCAGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGAGGCTGAGCTGCGTGGCCAGCGCCAGCA<br>CCTACTGCACCTACGACATGCACTGGTACAGGCAGGCCCCCGGCAAGGGCAGGGAGTT<br>CGTGAGCGCCATCGACAGCGACGGCACCACCAGGTACGCCGACAGCGTGAAGGGCAG<br>GTTCACCATCAGCCAGGGCACCGCCAAGAACACCGTGTACCTGCAGATGAACAGCCTG<br>CAGCCCGAGGACACCGCCATGTACTACTGCAAGACCGTGTGCGTGGTGGGCAGCAGGT<br>GGAGCGACTACTGGGGCCAGGGCACCCAGGTGACCGTGAGCGCTAGCCACCACCACCA<br>CCACCACCACCAC |
| 191 | CAGGTGCAGCTGCAGGAGAGCGGCGGCGGCCTGGTGCAGCCCGGCGGCAGCCTGAGGC<br>TGAGCTGCGCCGCCAGCGGCTTCACCTTCAGCCTGAGCAGCATGAGCTGGGTGAGGCA<br>GGCCCCCGGCAAGGGCCTGGAGTGGGTGAGCGCCATCAGCAGCGGCGGCGCCAGCACC<br>TACTACACCGACAGCGTGAAGGGCAGGTTCACCATCAGCAGGGACAACGCCAAGAACA<br>TGCTGTACCTGCAGCTGAACAGCCTGAAGACCGAGGACACCGCCATGTACTACTGCGC<br>CAAGGGCGGCAGCGGCTACGGCGACGCCAGCAGGATGACCAGCCCCGGCAGCCAGGG<br>CACCCAGGTGACCGTCTCGAGTGGCGGCGGATCCCAGGTGCAGCTGCAGGAGAGCGGC<br>GGCGGCAGCGTGCAGGCCGGCGGCAGCCTGACCCTGAGCTGCGCCGCCAGCGAGTACG<br>CCTACAGCACCTGCAACATGGGCTGGTACAGGCAGGCCCCCGGCAAGGAGAGGGAGCT<br>GGTGAGCGCCTTCATCAGCGACGGCAGCACCTACTACGCCGACAGCGTGAAGGGCAGG<br>TTCACCATCACCAGGGACAACGCCAAGAACACCGTGTACCTGCAGATGAACAGCCTGA<br>AGCCCGAGGACACCGCCATCTACTACTGCAGCGCCAACTGCTACAGGAGGCTGAGGAA<br>CTACTGGGGCCAGGGCACCCAGGTGACCGTGAGCGCTAGCCACCACCACCACCACCAC<br>CACCAC |
| 192 | CAGGTGCAGCTGCAGGAGAGCGGGGCGGCCTGGTGCAGCCCGGGGGCAGCCTGAGGC<br>TGAGCTGCGCCGCCAGCGGCTTCACCTTCAGCCTGAGCAGCATGAGCTGGGTGAGGCA<br>GGCCCCCGGCAAGGGCCTGGAGTGGGTGAGCGCCATCAGCAGCGGCGGCGCCAGCACC<br>TACTACACCGACAGCGTGAAGGGCAGGTTCACCATCAGCAGGGACAACGCCAAGAACA<br>TGCTGTACCTGCAGCTGAACAGCCTGAAGACCGAGGACACCGCCATGTACTACTGCGC<br>CAAGGGCGGCAGCGGCTACGGCGACGCCAGCAGGATGACCAGCCCCGGCAGCCAGGG<br>CACCCAGGTGACCGTCTCGAGTGGCGGCGGATCCCAGGTGCAGCTGCAGGAGAGCGGC<br>GGCGGCCTGGTGCAGCCCGGCGGCAGCCTGAGGCTGAGCTGCACCGCCAGCGGCCTGA<br>CCTTCGACGACAGCGTGATGGGCTGGTTCAGGCAGGCCCCCGGCAAGGGCAGGGAGGC<br>CGTGAGCTGCATCAGCAGCAGCGGCGCCAACGCCTTCTACGCCGACAGCGTGAAGGGC<br>AGGTTCACCATCAGCAGGGACAACGCCAAGAACACCCTGTACCTGCAGATGAACAGCC |

TABLE 3C-continued

| SEQ ID NO | Sequence |
|---|---|
| | TGAAGCCCGAGGACACCGCCACCTACTACTGCAAGAGGGGCCACGCCTGCGCCGGCTA CTACCCCATCCCCTACGACGACTACTGGGGCCAGGGCACCCAGGTGACCGTGAGCGCT AGCCACCACCACCACCACCACCACCAC |

Additional IL27R Binding Proteins

Further, additional IL27R binding proteins can include three CDR sequences as underlined in an anti-IL27Rα $V_HH$ antibody listed in Table 4 below, and three CDR sequences as underlined in an anti-gp130 $V_HH$ antibody of anyone of SEQ ID NOS:232-237. Additional IL27R binding proteins can include an anti-IL27Rα $V_HH$ antibody (e.g., any one of the sequences listed in Table 4 below) and an anti-gp130 $V_HH$ antibody (e.g., any one of SEQ ID NOS:232-237. In some embodiments, the binding protein comprises the anti-IL27Rα $V_HH$ antibody at the N-terminus and the anti-gp130 $V_HH$ antibody at the C-terminus. In some embodiments, the binding protein comprise the anti-gp130 $V_HH$ antibody at the N-terminus and the anti-IL27Rα $V_HH$ antibody at the C-terminus. In some embodiments, the binding protein comprises a linker (e.g., any one of SEQ ID NOS:85-108 (e.g., SEQ ID NO: 108)) between the anti-IL27Rα $V_HH$ antibody and the anti-gp130 $V_HH$ antibody. In certain embodiments, the binding protein comprises a purification tag, such as as a six-histidine peptide $(His)_6$ (SEQ ID NO: 1531) (His-tag).

TABLE 4

| SEQ ID NO | Sequence |
|---|---|
| 258 | QVQLQESGGGSVQVGGSLRLSCAASGFTFSSYPMSWVRQAPGKGLEWISTISAGGDTTLYA DSVKGRFTSSRDNAKNTLYLLNSLKTEDTAIYYCAKRIDCNSGYCYRRNYWGQGTQVTV SS |
| 259 | QVQLQESGGGSVQAGGSLRLSCRASGSTYSNYCLGWFRQITGKEREGVAVINWVGGMLYF ADSVKGRFTVSQDQAKNTLYLMNSLKPEDTAMYYCAAESVSSFSCGGWLTRPDRVPYW GQGTQVTVSS |
| 260 | QVQLQESGGGSVQAGGSLRLSCVASGYVSCDYFLPSWYRQAPGKEREFVSIIDGTGSTSYA ASVKGRFTASQDKGKNIAYLQMNSLKPEDTAMYYCKASCVRGRGISEYWGQGTQVTVSS |
| 261 | QVQLQESGGGLVPGGSLRLSCAASGFTFSHSGMSWVRQAPGKGLEWVSTINSGGASTYY TDSVKGRFTISRDNAKNMLYLLNSLKTEDTAMYYCAKGGSGYGDASRMTSPGSQGTQV TVSS |
| 262 | QVQLQESGGGLVQPGGSLRLSCAASGFTFSLSGMSWVRQAPGKGLEWVSAISSGGASTYY TDSVKGRFTISRDNAKNILYLLNSLKTEDTAMYYCAKGGSGYGDASRMTSPGSQGTQVT VSS |
| 263 | QVQLQESGGGSVQAGGSLRLSCVASGYVSCDYFLPSWYRQAPGKEREFVSIIDGTGSTSYA ASVKGRFTASEDKGKNIAYLMNSLKPEDTAMYYCKASCVRGRAVSEYWGQGTQVTVSS |
| 264 | QVQLQESGGGSVQAGGSLRLSCTASGYVSCDYFLPSWYRQAPGKEREFVSVIDGTGSTSYA ASVKGRFTASQDKGKNIAYLQMNSLKPEDTAMYYCKASCVRGRAISEYWGQGTQVTVSS |
| 265 | QVQLQESGGGLVPGGSLRLSCAASGFTFSSYPMSWVRQAPGKGLEWISTISAGGDITLYA DSVKGRFTSSRDNAKNTLYLLNSLKTEDTAIYYCAKRIDCNSGYCYRRNYWGQGTQVTV SS |
| 266 | QVQLQESGGGSVQAGGSLRLSCRASGSTYSNYCLGWFRSTGKEREGVAVINWVGGMLY FADSVKGRFTVSQDHAKNTVTLQMNSLKPEDTAMYYCAAESVSSFSCGGWLTRPGRVPY WGQGTQVTVSS |
| 267 | QVQLQESGGGSVQAGESLRLSCRASGSTYSNYCLGWFRQITGKEREGVAVINWVGGMLYF ADSVKGRFTVSQDQAKNTVYLEMNSLKPEDTAMYYCATESVSSFSCGGWLTRPDRVPYW GQGTQVTVSS |
| 268 | QVQLQESGGGSVQAGGSLRLSCVASGYVSCDYFLPSWYRQAPGKEREFVSIIDGTGSTSYA ASVKGRFTASQDRGKNIAYLQMNSLKPEDTAMYYCKASCVRGRTISEYWGQGTQVTVSS |
| 269 | QVQLQESGGGSVQAGGSLRLSCVASGYVSCDYFLPSWYRQAPGKEREFVSIIDGTGSTSYA ASVKGRFTASQDKGKNIAYLQMNSLKPEDTAMYYCKASCVRGRAISEYWGQGTQVTVSS |
| 270 | QVQLQESGGGSVQAGGSLRLSCRASGSTYSNYCLGWFRITGKEREGVAVINWVGGMLYF ADSVKGRFTVSQDQAKNTVYLQMNSLKPEDTAMYYCAAESASSESCGGWLTRPDRVPYW GQGTQVTVSS |

TABLE 4-continued

| SEQ ID NO | Sequence |
|---|---|
| 271 | QVQLQESGGGLVPGGSLRLSCAASGFTFSLSGMSWVRAPGKGLEWVSAISSGGASTYYTDSVKGRFTISRDNAKNMLYLLNSLKTEDTAMYYCAKGGSGYGDASRMTSPGSQGTQVTVSS |
| 272 | QVQLQESGGGLVPGGSLRLSCAASGFTFSSYPMSWVRQAPGKGLEWVSTISSGGDTTLYADSVKGRFTSSRDNAKNTLYLLNSLKTEDTAMYYCAKRIDCNSGYCYKRSYWGQGTQVTVSS |
| 273 | QYQLQESGGGSVQAGGSLRLSCRASGSTYSNYCLGWFRQTTGKEREGVAVINWVGGMLYFADSVKGRFTVSQDQAKNIVYLQMNSLKPEDTAMYYCAAESVSSFSCGGWLTRPDRVPYWGQGTQVTVSS |
| 274 | QVQLQESGGGSVQAGGSLRLSCRASRSPYGNYCLGWFRSTGKEREGVAVINWVGGMLYFADSVKGRFTVSQDHAKNTVTLQMNSLKPEDTAMYYCAAESVSSFSCGGWLTRPDRVPYWGQGTQVTVSS |

An IL27R binding protein can comprise three CDR sequences as underlined in an anti-IL27Rα $V_H$H antibody and three CDR sequences as underlined in an anti-gp130 $V_H$H antibody as described in each row of Table 5 below. In some embodiments, an IL27R binding protein comprises an anti-IL27Rα $V_H$H antibody and an anti-gp130 $V_H$H antibody as described in each row of Table 5 below. In some embodiments, the binding protein comprises the anti-IL27Rα $V_H$H antibody at the N-terminus and the anti-gp130 $V_H$H antibody at the C-terminus. In some embodiments, the binding protein comprises the anti-gp130 $V_H$H antibody at the N-terminus and the anti-IL27Rα $V_H$H antibody at the C-terminus. In some embodiments, the binding protein comprises a linker (e.g., any one of SEQ ID NOS:85-108 (e.g., SEQ ID NO:108)) between the anti-IL27Rα $V_H$H antibody and the anti-gp130 $V_H$H antibody. In certain embodiments, the binding protein comprises a purification tag, such as as a six-histidine peptide $(His)_6$ (SEQ ID NO: 1531) (His-tag).

TABLE 5

| SEQ ID NO of Anti-IL27Rα $V_H$H antibody | SEQ ID NO of Anti-gp130 $V_H$H antibody |
|---|---|
| 258 | 232 |
| 259 | 232 |
| 260 | 232 |
| 261 | 232 |
| 262 | 232 |
| 263 | 232 |
| 264 | 232 |
| 265 | 232 |
| 266 | 232 |
| 267 | 232 |
| 268 | 232 |
| 269 | 232 |
| 270 | 232 |
| 271 | 232 |
| 272 | 232 |
| 273 | 232 |
| 274 | 232 |
| 258 | 233 |
| 259 | 233 |
| 260 | 233 |
| 261 | 233 |
| 262 | 233 |
| 263 | 233 |
| 264 | 233 |
| 265 | 233 |
| 266 | 233 |
| 267 | 233 |

TABLE 5-continued

| SEQ ID NO of Anti-IL27Rα $V_H$H antibody | SEQ ID NO of Anti-gp130 $V_H$H antibody |
|---|---|
| 268 | 233 |
| 269 | 233 |
| 270 | 233 |
| 271 | 233 |
| 272 | 233 |
| 273 | 233 |
| 274 | 233 |
| 258 | 234 |
| 259 | 234 |
| 260 | 234 |
| 261 | 234 |
| 262 | 234 |
| 263 | 234 |
| 264 | 234 |
| 265 | 234 |
| 266 | 234 |
| 267 | 234 |
| 268 | 234 |
| 269 | 234 |
| 270 | 234 |
| 271 | 234 |
| 272 | 234 |
| 273 | 234 |
| 274 | 234 |
| 258 | 235 |
| 259 | 235 |
| 260 | 235 |
| 261 | 235 |
| 262 | 235 |
| 263 | 235 |
| 264 | 235 |
| 265 | 235 |
| 266 | 235 |
| 267 | 235 |
| 268 | 235 |
| 269 | 235 |
| 270 | 235 |
| 271 | 235 |
| 272 | 235 |
| 273 | 235 |
| 274 | 235 |
| 258 | 236 |
| 259 | 236 |
| 260 | 236 |
| 261 | 236 |
| 262 | 236 |
| 263 | 236 |
| 264 | 236 |
| 265 | 236 |
| 266 | 236 |
| 267 | 236 |

TABLE 5-continued

| SEQ ID NO of Anti-IL27Rα $V_H$H antibody | SEQ ID NO of Anti-gp130 $V_H$H antibody |
|---|---|
| 268 | 236 |
| 269 | 236 |
| 270 | 236 |
| 271 | 236 |
| 272 | 236 |
| 273 | 236 |
| 274 | 236 |
| 258 | 237 |
| 259 | 237 |
| 260 | 237 |
| 261 | 237 |
| 262 | 237 |
| 263 | 237 |
| 264 | 237 |
| 265 | 237 |
| 266 | 237 |
| 267 | 237 |
| 268 | 237 |
| 269 | 237 |
| 270 | 237 |
| 271 | 237 |
| 272 | 237 |
| 273 | 237 |
| 274 | 237 |

Further, an IL27R binding protein can comprise a mouse Anti IL27Rα $V_H$H antibody and a mouse Anti gp130 $V_H$H antibody. In some instances, due to sequence or structural similarities between the extracellular domains of receptors from various mammalian species, immunization with an antigen derived from a IL27Rα or gp130 of a first mammalian species may provide antibodies which specifically bind to receptors of one or more additional mammalian species. Such antibodies are termed "cross reactive." For example, immunization of a camelid with a human derived antigen (e.g., the hIL27Rα-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL27Rα VHH" or "hIL27Rα VHH" merely denotes that the species of the IL27Rα antigen used for immunization of the camelid from which the VHH was derived was the human IL27Rα but should not be understood as limiting with respect to the specific binding affinity of the VHH for IL27Rα molecules of other mammalian species. Similarly, the use of the term "mouse IL27Rα VHH" or "mIL27Rα VHH" merely denotes that the species of the IL27Rα antigen used for immunization of the camelid from which the VHH was derived was the murine IL27Rα but should not be understood as limiting with respect to the specific binding affinity of the VHH for IL27Rα molecules of other mammalian species. In some embodiments, an IL27R binding protein can comprise three CDR sequences as underlined in a mouse anti-IL27Rα $V_H$H antibody sequence listed below and three CDR sequences as underlined in a mouse anti-gp130 $V_H$H antibody sequence listed below. In some embodiments, an IL27R binding protein comprises a mouse anti-IL27Rα $V_H$H antibody listed below and a mouse anti-gp130 $V_H$H antibody listed below. In some embodiments, the binding protein comprises the mouse anti-IL27Rα $V_H$H antibody at the N-terminus and the mouse anti-gp130 $V_H$H antibody at the C-terminus. In some embodiments, the binding protein comprises the mouse anti-gp130 $V_H$H antibody at the N-terminus and the mouse anti-IL27Rα $V_H$H antibody at the C-terminus. In some embodiments, the binding protein comprises a linker (e.g., any one of SEQ ID NOS:85-108 (e.g., SEQ ID NO:108)) between the mouse anti-IL27Rα $V_H$H antibody and the mouse anti-gp130 $V_H$H antibody. In certain embodiments, the binding protein comprises a purification tag, such as as a six-histidine peptide $(His)_6$ (SEQ ID NO: 1531)(His-tag).

Examples of mouse anti-IL27Rα $V_H$H antibody sequences:

>mouse anti-IL27Rα $V_H$H antibody_SEQ ID NO: 275
QVQLQESGGGSVQAGGSLRLSCAASKNSNFMGWFRQAPGKEREGVAAMMTKNNN
TYYADSVKGRFTISHDNAKNTVYLQMDSLKPEDTAVYYCAAVYRIRRLRVLEAAN
FDYWGQGTQVTVSS >mouse anti-IL27Rα $V_H$H antibody_SEQ ID NO: 276
QVQLQESGGGSVQAGGSLRLSCTASGYTSSRYCMGWFRQTPGKKREGVAAIYTGG
GTTFYHGSVKGRFTISQDNTTNTVYLQMHNLKPEDTAMYYCAAGPVTRACDEYNY
WGQGTQVTVSS >mouse anti-IL27Rα $V_H$H antibody_SEQ ID NO: 277
QVQLQESGGGSVQAGGSLRLSCAGSGYSLSNYCMGWFRQAPGQGREGVASLRFVS
GATFYADSVKGRFTIAQDNAKNTLYLQMNSLKPEDTAMYYCGIKSRGICGGRLVDV
DFGNWGQGTQVTVSS >mouse anti-IL27Rα $V_H$H antibody_SEQ ID NO: 278
QVQLQESGGGSVQAGGSLRLSCAASGYSINRMGWFRQAPGKEREGVAAISIGGGQT
YYADSVKGRFTISQDNAKNTVDLQMNSLKPEDTAMYYCAAGLVYGEAWLDSRHY
NKWGQGTQVTVSS >mouse anti-IL27Rα $V_H$H antibody_SEQ ID NO: 279
QVQLQESGGGSVQAGGSLRLSCAVSGDSTYSMGWFRQPPGKEREGVAAIAKDGITI
HADSVKGRFTISKDNAKNTLYLQMNSLKPEDTAMYYCAAHRPYGPPLNPRWYTYW
GQGTQVTVSS >mouse anti-IL27Rα $V_H$H antibody_SEQ ID NO: 280
QVQLQESGGGSVQAGGSLRLSCAASGYTYSSYCMAWFRQAPGKEREGVAAIDSDGS
TSYADSVKGRFTISKDNAKNTLYLQMNSLKPEDTAMYYCAAASGRCLGPGIRSLIW
GQGTQVTVSS -continued >mouse anti-IL27Rα $V_H$H antibody_SEQ ID NO: 281
QVQLQESGGGSVQAGGSLRLSCAVSGDSTYSMGWFRQPPGKEREGVAAITKDITIHA
DSVKGRFTISKDNAKNTLYLQMNSLKPEDTAMYYCAAHRPYGPPLNPRWYTYWGQ
GTQVTVSS >mouse anti-IL27Rα $V_H$H antibody_SEQ ID NO: 282
QVQLQESGGGSVQAGGSLRLSCAVSGDSTYSMGWFRQPPGKEREGVAAIPTDGITIH
ADSVKGRFTISKDNAKNTLYLQMNSLKPEDTAMYYCAAHRPYGPPLNPRWYTYWG
QGTQVTVSS >mouse anti-IL27Rα $V_H$H antibody_SEQ ID NO: 283
QVQLQESGGGSVQAGGSLRLSCAVSGDSTYSMGWFRQPPGKEREGVAAIAKDGITI
HADSVKGRFTISKDNAKNTLYLQMSSLKPEDTAMYYCAAHRPYGPPLNPRWYTYW
GQGTQVTVSS >mouse anti-IL27Rα $V_H$H antibody_SEQ ID NO: 284
QVQLQESGGGSVQAGGSLRLSCAVSGDSTYSMGWFRQPPGKEREGVAAIGKDGITI
HADSVKGRFTISKDNAKNTLYLQMNSLKPEDTAMYYCAAHRPYGPPLNPRWYTYW
GQGTQVTVSS >mouse anti-IL27Rα $V_H$H antibody_SEQ ID NO: 285
QVQLQESGGGSVQAGGSLRLSCAVSGDSTYSMGWFRQPPGKEREGVAAITKDITIHA
DSVKGRFTISKDNAKNILYLQMNSLRPEDTAMYYCAAHRPYGPPLNPRWYTYWGQ
GTQVTVSS >mouse anti-IL27Rα $V_H$H antibody_SEQ ID NO: 286
QVQLQESGGGSVQTGGSLRLSCAASGYSINRMAWFRQAPGKEREGVAAISIGGDRT
YYADSVKGRFTISQDNAKHTVDLQMNSLKPEDTAMYYCAAGLVYGEAWLDSRHY
NKWGQGTQVTVSS >mouse anti-IL27Rα $V_H$H antibody_SEQ ID NO: 287
QVQLQESGGGSVQAGGSLRLSCAASGYSINRMGWFRQAPGKEREGVAAISIGGGRT
YYADSVKGRFTISQDNAKNTVDLQMNSLKPEDTAMYYCAAGLVYGEAWLDSRHY
NKWGQGTQVTVSS >mouse anti-IL27Rα $V_H$H antibody_SEQ ID NO: 288
QVQLQESGGGSVQAGGSLRLSCAVSGDSTYSMGWFRQPPGKEREGVAAITKDGITIH
ADSVKGRFTISGDNAKNTLYLQMNNLKPEDTAMYYCAAHRPYGPPLNPRWYTYWG
QGTQVTVSS Examples of mouse anti-gp130 $V_H$H antibody sequences:
>mouse anti-gp130 $V_H$H antibody_SEQ ID NO: 289
QVQLQESGGGSVQAGGSLRLSCVISGFTYRQTFMGWFRQVLGKEREGVAAISTGGG
STVYADSVKGRFTISQDSSKNTVYLEMNGLKLEDTGMYYCAASTVITSVSINRGLYQ
YWGQGTQVTVSS >mouse anti-gp130 $V_H$H antibody_SEQ ID NO: 290
QVQLQESGGGSVQAGGSLRLSCAISGFTYRQTFMGWFRQVVGKEREGVAAISTGGG
STVYADSVKGRFTISQDSSKDTVYLEMNGLKLEDTGMYYCAASTVITSESINRNLYQ
YWGQGTQVTVSS >mouse anti-gp130 $V_H$H antibody_SEQ ID NO: 291
QVQLQESGGGLVQPGGSLRLSCAASGFTLSTYWIYWVRQAPGKGPEWVSTVSRSGG
TTYYADSVNGRFTISRDNAKNTVYLQMNNLKPEDAAVYYCLASVSNLGWPPVRAPS
PTGQGTQVTVSS >mouse anti-gp130 $V_H$H antibody_SEQ ID NO: 292
QVQLQESGGGLVQPGGSLRLSCAASGFTFSSYAMSWVRQAPGKGLEWVSAINSGGA
GTYYTDSVKGRFTISRDNAKNTLYLQLNSLKTEDTAMYYCAKHVTGDYDPSLRHGY
NVWSQGTQVTVSS >mouse anti-gp130 $V_H$H antibody_SEQ ID NO: 293
QVQLQESGGGSVQAGGSLRLSCVISGFTYRQTFMGWFRQVVGKEREGVAAISTGGG
STIYADSVKGRFTISQDSSKDTVYLEMNGLKLEDTGMYYCAASTVITSESINRNLYQY
WGQGTQVTVSS >mouse anti-gp130 $V_H$H antibody_SEQ ID NO: 294
QVQLQESGGGLVQPGGSLRLSCAASGFTLSTYWMYWVRQAPGKGPEWVSAVSRGG
FNTYYADSVKGRFTISRDNAKNTVYLQMNSLKPEDTAVYYCMSSVSFYGWPPDRVP
SPTGQGTQVTVSS >mouse anti-gp130 $V_H$H antibody_SEQ ID NO: 295
QVQLQESGGGLVQPGESLRLSCAASGFTFSSYAMSWVRQAPGKGLEWVSAINSGGA
GTYYTDSVKGRFTISRDNAKNTLYLQLNSLKTEDTAMYYCAKHVTGDYDPSLRYGY
NVWSQGTQVTVSS >mouse anti-gp130 $V_H$H antibody_SEQ ID NO: 296
QVQLQESGGGSVQAGGSLRLSCVISGFTYRPTFMGWFRQVLGKEREGVAAITTGGG
STVYADSVKGRFTISQDSSKNTVYLEMNGLKLEDTGMYYCAATTVITSVSINRNLYQ
YWGQGTQVTVSS -continued >mouse anti-gp130 $V_HH$ antibody_SEQ ID NO: 297
QVQLQESGGGSVQAGGSLRLSCGISGFTYRPTFMGWFRQVLGKEREGVAAISTGGGS
SVYADSVKGRFTVSQDSSKNTVYLEMNGLKLEDTGMYYCAASTVITSVSINRGLYQ
YWGQGTQVTVSS >mouse anti-gp130 $V_HH$ antibody_SEQ ID NO: 298
QVQLQESGGGLVQPGGSLRLSCTASGFTFRNYAMSWVRQAPGKGLEWVSAINSGG
GSTYYADSVKGRFTISRDNAKNILYLRLHSLKTEDTAMYYCAKHVTGDYDPSLRYE
YNYWSQGTQVTVSS >mouse anti-gp130 $V_HH$ antibody_SEQ ID NO: 299
QVQLQESGGGLVQPGGSLRLSCAASGFTFRNYAMSWVRQAPGKGLEWVSAINSGG
GSTYYADSVKGRFTISRDNAKNILYLQLNSLKTEDTAMYYCTKHVTGDYDPSLRYE
YNYWSQGTQVTVSS >mouse anti-gp 130 $V_HH$ antibody_SEQ ID NO: 300
QVQLQESGGGLVQPGGSLRLSCAASGFTFSSYAMSWVRQAPGKGLEWVSAINSGGG
STYYADSVKGRFTISRDNAKNTLYLQLNSLKTEDTAMYCCAKHVTGDYDPSLRYGY
NCWGPGTQVTVSS >mouse anti-gp130 $V_HH$ antibody_SEQ ID NO: 301
QVQLQESGGGSVQPGGSLRLSCAASGFTFSTYDMSWVRQAPGKGLEWVSTINYSGS
STYYVDSVLGRFTIARDNAKNTLYLQMNNLQTEDTAVYYCASVKERRSNGHPIVFG
DRGQGTQVTVSS >mouse anti-gp130 $V_HH$ antibody_SEQ ID NO: 302
QVQLQESGGGSVQAGGSLRLSCVISGFTYKQTFMGWFRQVPGKEREGVAAISTGGG
STVYADSVKGRFTISQDSSKNTVYLEMNGLKLEDTGMYYCAASTVITSVSINRGLYQ
YWGQGTQVTVSS >mouse anti-gp130 $V_HH$ antibody_SEQ ID NO: 303
QVQLQESGGGSVQAGGSLRLSCVISGFTYRQTFMGWFRQVVGKEREGVAAISTGGG
STVYADSVKGRFTISQDSSKDTVYLEMNGLKLEDTGMYYCAASTVITSESIYRNLYQ
YWGQGTQVTVSS >mouse anti-gp130 $V_HH$ antibody_SEQ ID NO: 304
QVQLQESGGGLVQPGGSLRLSCAASGFTFRNYAMSWVRQAPGKGLEWVSAINSGG
GSTYYADSVKGRFTISRDNAKNTLYLQMNSLKPEDTAMYYCAKHVTGDYDPSLRY
EYNYWSQGTQVTVSS >mouse anti-gp130 $V_HH$ antibody_SEQ ID NO: 305
QVQLQESGGGLVQPGGSLRLSCAASGFTFRNYAMSWVRQAPGKGLEWVSAINSGG
GSTYYADSVKGRFTISRDNAKNTLYLQLNSLKTEDTAMYYCAKHVTGDYDPSLRYE
YAYWSQGTQVTVSS >mouse anti-gp130 $V_HH$ antibody_SEQ ID NO: 306
QVQLQESGGGSVQAGGSLRLSCAASGFTFSSYAMSWVRQAPGKGLEWVSAINSGGG
STYYADSVKARFTISRDNAKNTLYLQLNSLKTEDTAMYYCAKHVTGDYDPSLRYDY
NYWGQGTQVTVSS >mouse anti-gp130 $V_HH$ antibody_SEQ ID NO: 307
QVQLQESGGGSVQAGGSLRLSCGISGFTYRPTFMGWFRQVLGKEREGVAAISTGGGS
SVYADSVKGRFTVSQDSSKNTVYLEMNGLKLEDTGMYYCAASTVITSVSINRALYQ
YWGQGTQVTVSS >mouse anti-gp130 $V_HH$ antibody_SEQ ID NO: 308
QVQLQESGGGLVQPGGSLRLSCAASGFTFSSYAVSWVRQAPGKGLEWVSTINSGGG
STYYADSVKGRFTISRDNAKNTLYLQLNSLKTEDTAMYYCTKHVTGDYDPSLRYEY
NVWSQGTQVTVSS >mouse anti-gp130 $V_HH$ antibody_SEQ ID NO: 309
QVQLQESGGGSVQAGGSLRVSCQISGFTYRQTFMGWFRQVPGKEREGVAAISTGGG
STVYADSVKGRFTISQDSSKNTVYLEMNGLKLEDTGMYYCAASTVITSPSINRNLYQ
YWGQGTQVTVSS >mouse anti-gp130 $V_HH$ antibody_SEQ ID NO: 310
QVQLQESGGGLVQPGGSLRLSCAVSGFTFSNYAMKWVRQAPGKGLEWVSSISGGG
GATYYADSVKGRFTISRDNTKNTLYLQMNSLKTEDTAVYYCAAQNLDYRGQGTQV
TVSS >mouse anti-gp130 $V_HH$ antibody_SEQ ID NO: 311
QVQLQESGGGLVQPGGSLRLSCTASGFTFNSAHMKWERQPPGKGLEWVSFITPGGA
STGYADSVKGRFTISRDNAKNTLYLQMNNLKTEDTAVYYCATGGLRGQGTQVTVSS >mouse anti-gp130 $V_HH$ antibody_SEQ ID NO: 312
QVQLQESGGGSVQAGGSLRLSCVISGFTYRPTFMGWFRQVLGKEREGVAAITTGGG
STLYADSVKGRFTISQDSSKNTVYLEMNGLKLEDTGMYYCAATTVITSVSINRNLYQ
YWGQGTQVTVSS -continued >mouse anti-gp130 $V_H$H antibody_SEQ ID NO: 313
QVQLQESGGGSVQAGGSLRLSCVISGFTYKQTFMGWFRQVPGKEREGVAAISTGGG
STVYADSVKGRFTISQDSSKNTVYLEMNGLKLEDTGMYYCAASTVITSVTINRGLYQ
YWGQGTQVTVSS >mouse anti-gp130 $V_H$H antibody_SEQ ID NO: 314
QVQLQESGGGSVQAGGSLRLSCVISGFVYKQTFMGWFRQVPGKEREGVAAISTGGG
STVYADSVKGRFTISQDSSKNTVYLEMNGLKLEDTGMYYCAASTVITSVSINRGLYQ
YWGQGTQVTVSS >mouse anti-gp130 $V_H$H antibody_SEQ ID NO: 315
QVQLQESGGGSVQAGGSLRVSCVISGFTYRQTFMGWFRQVPGKEREGVAAISTGGG
STVYADSVKGRFTISQDSSKNTVYLEMNGLKLEDTGMYYCAASTVITSVSINRGLYQ
YWGQGTQVTVSS >mouse anti-gp130 $V_H$H antibody_SEQ ID NO: 316
QVQLQESGGGLVQPGGSLRLSCAASGFTFSSYAMSWVRQAPGKGLEWVSAINSGGG
STYYADSVKGRFTISRDNAKSTLYLQLNSLKTEDTAMYYCTKHVTGDYDPSLRYEY
NYWSQGTQVTVSS >mouse anti-gp130 $V_H$H antibody_SEQ ID NO: 317
QVQLQESGGGLVQPGGSLRLSCAASGFTFSSYAMSWVRQAPGKGLEWVSAINSGGA
STYYADSVKGRFTISRDNAKNTLYLQLNSLKTEDTAMYCCAKHVTGDYDPSLRYEY
NCWGPGTQVTVSS >mouse anti-gp130 $V_H$H antibody_SEQ ID NO: 318
QVQLQESGGGLVQPGGSLRLSCAASGFTFSSYAMSWVRQAPGKGLEWVSAINSGGG
STYYADSVKGRFTISRDNAKNTLYLQLNSLKTEDTAMYYCAKHVTGDYDPSLRYEY
NYWSQGTQVTVSS >mouse anti-gp130 $V_H$H antibody_SEQ ID NO: 319
QVQLQESGGGSVQAGGSLRLSCVISGFTYRQTFMGWFRQVVGKEREGVAAISTGGG
STVYADSVKGRFTISQDSSKDTVYLEMNGLKLEDTGMYYCAASTVITSESINRNLYQ
YWGQGTQVTVSS >mouse anti-gp130 $V_H$H antibody_SEQ ID NO: 320
QVQLQESGGGSVQAGGSLRVSCVVSGFTYRQTFMGWFRQVPGKEREGVAAISTGG
GSTVYADSVKGRFTISQDSSKNTVYLEMNGLKLEDTGMYYCAASTVITSVSINRNLY
QYWGQGTQVTVSS >mouse anti-gp130 $V_H$H antibody_SEQ ID NO: 321
QVQLQESGGGLVQPGGSLRLSCAASGFTFSSYAMSWVRQAPGKGLEWVSAINSGGG
STYYADSVKGRFTISRDNAKNTMYLQLNSLKTEDTAMYYCAKHVAGDYDPSLRYE
WHVWGQGTQVTVSS >mouse anti-gp130 $V_H$H antibody_SEQ ID NO: 322
QVQLQESGGGLVQPGGSLRLSCAASGFTFRSYAMSWVRQAPGKGLEWVSAINSGGG
STYYADSVKARFTISRDNAKNTLYLQLNSLKTEDTAMYYCAKHVTGDYDPSLRYEY
NYWGQGTQVTVSS >mouse anti-gp130 $V_H$H antibody_SEQ ID NO: 323
QVQLQESGGGLVQPGGSLRLSCAASGFTFSSYAMSWVRQAPGKGLEWVSAINSGGG
STYYADSVKGRFTISRDNAKNTLYLQLNSLKTEDTAMYYCAKHITGDYDPSLRYEY
NYWGQGTQVTVSS >mouse anti-gp130 $V_H$H antibody_SEQ ID NO: 324
QVQLQESGGGSVQAGGSLRLSCVISGFTYRQTFMGWFRQVVGKEREGVAAISTGGG
SMVYADSVKGRFTISQDSSKDTVYLEMNGLKLEDTGMYYCAASTVITSESINRNLYQ
YWGQGTQVTVSS >mouse anti-gp130 $V_H$H antibody_SEQ ID NO: 325
QVQLQESGGGPVQAGGSLRLSCVISGFTYRQTFMGWFRQVPGKEREGVAAISTGGG
STVYADSVKGRFTISQDSSKNTVYLEMNGLKLEDTGMYYCAASTVITSESINRGLYQ
YWGQGTQVTVSS >mouse anti-gp130 $V_H$H antibody_SEQ ID NO: 326
QVQLQESGGGSVQAGGFLRLSCAFSGYTGCMGWFRQGPGQEREGVASINDGGSLTY
ADSVKGRFTISKDNAKKTLDLQMNTLKPEDTAMYYCAASLSYCLNPTLRVDGYNY
WGQGTQVTVSS >mouse anti-gp130 $V_H$H antibody_SEQ ID NO: 327
QVQLQESGGGSVQAGGSLRLSCVISGLTYKQTFMGWFRQVPGKEREGVAAISTGGG
STVYADSVKGRFTISQDNSKNTVYLEMNGLKLEDTGMYYCAASTVITSVSINRYLYQ
WWGQGTQVTVSS >mouse anti-gp130 $V_H$H antibody_SEQ ID NO: 328
QVQLQESGGGLVQPGGSLRLSCAASGFTFSNYAMSWVRQAPGKGVEWVSAINSGGS
VFYADSVKGRFTISRDNAKNTLYLQLSSLKTEDTAMYYCAKHVTGDYDPSLRYGYN
VWSQGTQVTVSS -continued

```
>mouse anti-gp130 VHH antibody_SEQ ID NO: 329
QVQLQESGGGSVQAGGSLRLSCGISGFTYRPTFMGWFRQVLGKEREGVAAISTGGGS
TVYADSVKGRFTISQDSSKDTVYLEMNGLKLEDTGMYYCAASTVITSESINRNLYQY
WGQGTQVTVSS

>mouse anti-gp130 VHH antibody_SEQ ID NO: 330
QVQLQESGGGLVQPGGSLRLSCAASGFTFSSYAMSWVRQAPGKGLEWVSAINSGGG
STYYADSVKGRFTISRDNAKNTLYLQLNSLKTEDTAMYYCAKHVTGDYDPSLRYGY
NVWSQGTQVTVSS

>mouse anti-gp130 VHH antibody_SEQ ID NO: 331
QVQLQESGGGLVQPGGSLRLSCAASGFTFSSYAMSWVRQAPGKGLEWVSAINLGGD
TTYYTDSVKGRFTISRDNAKNTLYLQLNSLKTEDTAMYYCAKHVTGDYDPSLRYEY
GYWSQGTQVTVSS

>mouse anti-gp130 VHH antibody_SEQ ID NO: 332
QVQLQESGGGLVQPGGSLRLSCTASGFTFNSAHLKWERQPPGKGLEWVSFITNGGAS
TGYADSVKGRFTISRDDAKNTLYLQMNNLKTEDTAVYYCATGGLRGQGTQVTVSS

>mouse anti-gp130 VHH antibody_SEQ ID NO: 333
QVQLQESGGGSVQAGGSLRVSCVISGFTYRQTFMGWFRQVPGKEREGVAAISTGGG
STIYANSVKGRFTISQDSSKNTVYLEMNGLKLEDTGMYYCAASTVITSVSINRGLYQ
YWGQGTQVTVSS

>mouse anti-gp130 VHH antibody_SEQ ID NO: 334
QVQLQESGGGLVQPGGSLRLSCAASGFTFSSYAMSWVRQAPGKGLEWVSAINSGGG
STYYADSVKGRFTISRDNAKNTLYLQLNSLKTEDTAMYCCAKHITGDYDPSLRYEY
NCWGQGTQVTVSS

>mouse anti-gp130 VHH antibody_SEQ ID NO: 335
QVQLQESGGGSVQAGGSLRLSCVISGFTYKQTFMGWFRQVPGKEREGVAAISTGGG
NTVYADSVKGRFTISQDSSKNTVYLEMNGLKLEDTGMYYCAASTVITSVTVNRGLY
QYWGQGTQVTVSS

>mouse anti-gp130 VHH antibody_SEQ ID NO: 336
QVQLQESGGALVQPGGSLRLSCAASGFTFSYYAMKWVRQAPGKGLEWVSSISGGG
GATYYADSVKGRFTISRDNINDTLYLQMNSLKTEDTAVYYCAAQNLDYRGQGTQV
TVSS

>mouse anti-gp130 VHH antibody_SEQ ID NO: 337
QVQLQESGGGSVQAGGSLRLSCVISGFTYKQTFMGWFRQVPGKEREGVAAISTGGG
STVYADSVKGRFTISQESSKNTVYLEMNGLKLEDTGMYYCAASTVITSVTINRGLYQ
YWGQGTQVTVSS
```

In some embodiments, a $V_H$H described herein can be humanized to contain human framework regions. Examples of human germlines that could be used to create humanized $V_H$Hs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

In some embodiments, the IL27R binding protein has a reduced $E_{max}$ compared to the $E_{max}$ caused by IL27. $E_{max}$ reflects the maximum response level in a cell type that can be obtained by a ligand (e.g., a binding protein described herein or the native cytokine (e.g., IL27)). In some embodiments, the IL27R binding protein described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IL27. In other embodiments, the $E_{max}$ of the IL27R binding protein described herein is greater (e.g., at least 1%, 5%, 10%, 15%, 20%, 25%, 30%, 35%, 40%, 45%, or 50% greater) than the $E_{max}$ of the natural ligand, IL27. In some embodiments, by varying the linker length of the IL27R binding protein, the $E_{max}$ of the IL27R binding protein can be changed. The IL27R binding protein can cause $E_{max}$ in the most desired cell types, and a reduced $E_{max}$ in other cell types.

IV. Linkers

As previously described, the binding domains of the binding proteins of the present disclosure may be joined contiguously (e.g., the C-terminal amino acid of the first $V_H$H in the binding protein to the N-terminal amino acid of the second $V_H$H in the binding protein) or the binding domains of the binding protein may optionally be joined via a linker. A linker is a linkage between two elements, e.g., protein domains. In a bispecific $V_HH^2$ binding protein described herein, a linker is a linkage between the two $V_H$Hs in the binding protein. A linker can be a covalent bond or a peptide linker. In some embodiments, the two $V_H$Hs in a binding protein are joined directly (i.e., via a covalent bond). The length of the linker between two $V_H$Hs in a binding protein can be used to modulate the proximity of the two $V_H$Hs of the binding protein. By varying the length of the linker, the overall size and length of the binding protein can be tailored to bind to specific cell receptors or domains or subunits thereof. For example, if the binding protein is designed to bind to two receptors or domains or subunits thereof that are located close to each other on the same cell, then a short linker can be used. In another example, if the binding protein is designed to bind to two receptors or domains or subunits there of that are located on two different cells, then a long linker can be used.

In some embodiments, the linker is a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids). A linker can also be a chemical linker, such as a synthetic polymer, e.g., a polyethylene glycol (PEG) polymer.

In some embodiments, a linker joins the C-terminus of the first $V_H$H in the binding protein to the N-terminus of the second $V_H$H in the binding protein. In other embodiments, a linker joins the C-terminus of the second $V_H$H in the binding protein to the N-terminus of the first $V_H$H in the binding protein.

Suitable peptide linkers are known in the art, and include, for example, peptide linkers containing flexible amino acid residues such as glycine and serine. In certain embodiments, a peptide linker can contain motifs, e.g., multiple or repeating motifs, of GS, GGS, GGGGS (SEQ ID NO:85), GGGGGS (SEQ ID NO:86), GGSG (SEQ ID NO:87), or SGGG (SEQ ID NO:88). In certain embodiments, a peptide linker can contain 2 to 12 amino acids including motifs of GS, e.g., GS, GSGS (SEQ ID NO:89), GSGSGS (SEQ ID NO:90), GSGSGSGS (SEQ ID NO:91), GSGSGSGSGS (SEQ ID NO:92), or GSGSGSGSGSGS (SEQ ID NO:93). In certain other embodiments, a peptide linker can contain 3 to 12 amino acids including motifs of GGS, e.g., GGS, GGSGGS (SEQ ID NO:94), GGSGGSGGS (SEQ ID NO:95), and GGSGGSGGSGGS (SEQ ID NO:96). In yet other embodiments, a peptide linker can contain 4 to 20 amino acids including motifs of GGSG (SEQ ID NO:87), e.g., GGSGGGSG (SEQ ID NO:97), GGSGGGSGGGSG (SEQ ID NO:98), GGSGGGSGGGSGGGSG (SEQ ID NO:99), or GGSGGGSGGGSGGGSGGGSG (SEQ ID NO:100). In other embodiments, a peptide linker can contain motifs of GGGGS (SEQ ID NO:85), e.g., GGGGSGGGGS (SEQ ID NO:101) or GGGGSGGGGSGGGGS (SEQ ID NO:102).

Examples of flexible linkers include glycine polymers (G)n, glycine-alanine polymers, alanine-serine polymers, glycine-serine polymers (for example, (GmSo)n (SEQ ID NO: 1535), (GSGGS)n (SEQ ID NO: 1536), (GmSoGm)n (SEQ ID NO: 1537), (GmSoGmSoGm)n (SEQ ID NO: 1538), (GSGGSm)n (SEQ ID NO: 1539), (GSGSmG)n (SEQ ID NO: 1540), (GGS)nG (SEQ ID NO: 1541) and (GGGSm)n (SEQ ID NO: 1542), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Glycine and glycine-serine polymers are relatively unstuctured, and therefore may serve as a neutral tether between components. Examples of flexible linkers include, but are not limited to GGSG (SEQ ID NO:87), GGSGG (SEQ ID NO:103), GSGSG (SEQ ID NO:104), GSGGG (SEQ ID NO:105), GGGSG (SEQ ID NO:106), and GSSSG (SEQ ID NO:107).

Additional examples of flexible linkers include glycine polymers (G)n or glycine-serine polymers (e.g., (GS)n (SEQ ID NO: 1543), (GSGGS)n (SEQ ID NO: 1544), (GGGS)n (SEQ ID NO: 1545) and (GGGGS)n (SEQ ID NO: 1546), where n=1 to 50, for example, 1, 2, 3, 4, 5, 6, 7, 8, 9, 10, 10-20, 20-30, 30-50). Exemplary flexible linkers include, but are not limited to GGGS (SEQ ID NO:108), GGGGS (SEQ ID NO:85), GGSG (SEQ ID NO:87), GGSGG (SEQ ID NO:103), GSGSG (SEQ ID NO:104), GSGGG (SEQ ID NO:105), GGGSG (SEQ ID NO:106), and GSSSG (SEQ ID NO:107).

V. Modifications to Extend Duration of Action In Vivo

The binding proteins described herein can be modified to provide for an extended lifetime in vivo and/or extended duration of action in a subject. In some embodiments, the binding protein can be conjugated to carrier molecules to provide desired pharmacological properties such as an extended half-life. In some embodiments, the binding protein can be covalently linked to the Fc domain of IgG, albumin, or other molecules to extend its half-life, e.g., by pegylation, glycosylation, and the like as known in the art.

In some embodiments, the binding protein is conjugated to a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The binding protein described herein can be conjugated to the entire Fc region, or a smaller portion that retains the ability to extend the circulating half-life of a chimeric polypeptide of which it is a part. In addition, full-length or fragmented Fc regions can be variants of the wild-type molecule. In a typical presentation, each monomer of the dimeric Fc can carry a heterologous polypeptide, the heterologous polypeptides being the same or different.

In some embodiments, when the binding protein described herein is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob"), and ii) in the CH3 domain of a second heavy chain, an amino acid residue is replaced with an amino acid residue having a smaller side chain (e.g., alanine or threonine), thereby generating a cavity ("hole") at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fc region (Carter, et al. (2001) Immunol Methods 248, 7-15). The knob-into-hole format is used to facilitate the expression of a first polypeptide on a first Fc monomer with a "knob" modification and a second polypeptide on the second Fc monomer possessing a "hole" modification to facilitate the expression of heterodimeric polypeptide conjugates.

In some embodiments, the binding protein can be conjugated to one or more water-soluble polymers. Examples of water soluble polymers useful in the practice of the present disclosure include polyethylene glycol (PEG), poly-propylene glycol (PPG), polysaccharides (polyvinylpyrrolidone, copolymers of ethylene glycol and propylene glycol, poly (oxyethylated polyol), polyolefinic alcohol), polysaccharides), poly-alpha-hydroxy acid), polyvinyl alcohol (PVA), polyphosphazene, polyoxazolines (POZ), poly(N-acryloylmorpholine), or a combination thereof.

In some embodiments, binding protein can be conjugated to one or more polyethylene glycol molecules or "PEGylated." Although the method or site of PEG attachment to the binding protein may vary, in certain embodiments the PEGylation does not alter, or only minimally alters, the activity of the binding protein.

In some instances, when employing the VHH sequences describe herein in the preparation of th IL27 binding molecules of the present disclosure, the VHH possesses an N-terminal glutamine ("IQ") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL27R binding molecules of the present disclosure, particularly when aldehyde chemistry is to be employed, the IL27Rα binding molecules possessing an amino acid at position 1 (e.g., 1Q) are substituted at position 1 with an alternative amino acid or are deleted at position 1 (e.g., des-1Q). In some embodiments, the IL27R binding molecules of the present disclosure comprise an amino acid substitution selected from the group Q1E and Q1D.

In some embodiments, selective PEGylation of the binding protein, for example, by the incorporation of non-natural amino acids having side chains to facilitate selective PEG conjugation, may be employed. Specific PEGylation sites can be chosen such that PEGylation of the binding protein does not affect its binding to the target receptors.

In certain embodiments, the increase in half-life is greater than any decrease in biological activity. PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the binding protein can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa, or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20.000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimdyl carbonate PEG (SC-PEG; see, e.g., Zalipsky, et al. (1992) *Biotelmol. Appl. Biochem* 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General PEGylation strategies known in the art can be applied herein.

The PEG can be bound to a binding protein of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the binding proteins is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin et al., PCT International Application No. PCT/US2018.045257 filed Aug. 3, 2018 and published Feb. 7, 2019 as International Publication Number WO 2019:028419A1.

The PEG conjugated to the polypeptide sequence can be linear or branched. Branched PEG derivatives. "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF), a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

In some embodiments, a linker can used to join the binding protein and the PEG molecule. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers are described in Section IV. Further, a multimer (e.g., 1, 2, 3, 4, 5, 6, 7, 8, 9, 10, 10-20, 20-30, or 30-50) of these linker sequences may be linked together to provide flexible linkers that may be used to conjugate two molecules. Alternative to a polypeptide linker, the linker can be a chemical linker, e.g., a PEG-aldehyde linker. In some embodiments, the binding protein is acetylated at the N-terminus by enzymatic reaction with N-terminal acetyltransferase and, for example, acetyl CoA. Alternatively, or in addition to N-terminal acetylation, the binding protein can be acetylated at one or more lysine residues, e.g., by enzymatic reaction with a lysine acetyltransferase. See, for example Choudhary et al. (2009) Science 325 (5942):834-840.

In other embodiments, the binding protein can be modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) *Science* 256:1014 and LeClair, et al. (1992) *PNAS-USA* 89:8145). In some embodiments, the binding protein further comprises a C-terminal c-myc epitope tag.

In some embodiments, the binding protein is expressed as a fusion protein with an albumin molecule (e.g., human serum albumin) which is known in the art to facilitate extended exposure in vivo.

In some embodiment, the binding proteins (including fusion proteins of the binding proteins) of the present disclosure are expressed as a fusion protein with one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present disclosure are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present disclosure are peptides comprising 3-6 contiguous histidine residues (SEQ ID NO: 1547) such as a six-histidine peptide $(His)_6$ (SEQ ID NO: 1531) and are frequently referred to in the art as "His-tags."

The foregoing fusion proteins may be readily produced by recombinant DNA methodology by techniques known in the art by constructing a recombinant vector comprising a nucleic acid sequence comprising a nucleic acid sequence encoding the binding protein in frame with a nucleic acid sequence encoding the fusion partner either at the N-terminus or C-terminus of the binding protein, the sequence optionally further comprising a nucleic acid sequence in frame encoding a linker or spacer polypeptide.

VI. Pharmaceutical Composition

The binding proteins of the present disclosure may be administered to a subject in a pharmaceutically acceptable dosage form. The preferred formulation depends on the intended mode of administration and therapeutic application. Pharmaceutical dosage forms of the binding proteins described herein comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The pharmaceutical compositions may also comprise pharmaceutically-acceptable, non-toxic carriers, excipients, stabilizers, or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present disclosure may readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, *Science* 249: 1527, 1990 and Hanes, *Advanced Drug Delivery Reviews* 28: 97-119, 1997). The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Administration of a binding protein described herein may be achieved through any of a variety of art recognized methods including but not limited to the topical, intravascular injection (including intravenous or intraarterial infusion), intadermal injection, subcutaneous injection, intramuscular injection, intraperitoneal injection, intracranial injection, intratumoral injection, intranodal injection, transdermal, transmucosal, iontophoretic delivery, intralymphatic injection (Senti and Kundig (2009) *Current Opinions in Allergy and Clinical Immunology* 9(6):537-543), intragastric infusion, intraprostatic injection, intravesical infusion (e.g., bladder), respiratory inhalers including nebulizers, intraocular injection, intraabdominal injection, intralesional injection, intraovarian injection, intracerebral infusion or injection, intracerebroventricular injection (ICVI), and the like. In some embodiments, administration includes the administration of the binding protein itself (e.g., parenteral), as well as the administration of a recombinant vector (e.g., viral or non-viral vector) to cause the in situ expression of the binding protein in the subject. Alternatively, a cell, such as a cell isolated from the subject, could also be recombinantly modified to express the binding protein of the present disclosure.

The dosage of the pharmaceutical compositions depends on factors including the route of administration, the disease to be treated, and physical characteristics, e.g., age, weight, general health, of the subject. Typically, the amount of a binding protein contained within a single dose may be an amount that effectively prevents, delays, or treats the disease without inducing significant toxicity. A pharmaceutical composition of the disclosure may include a dosage of a binding protein described herein ranging from 0.01 to 500 mg/kg (e.g., from 0.01 to 450 mg, from 0.01 to 400 mg, from 0.01 to 350 mg, from 0.01 to 300 mg, from 0.01 to 250 mg, from 0.01 to 200 mg, from 0.01 to 150 mg, from 0.01 to 100 mg, from 0.01 to 50 mg, from 0.01 to 10 mg, from 0.01 to 1 mg, from 0.1 to 500 mg/kg, from 1 to 500 mg/kg, from 5 to 500 mg/kg, from 10 to 500 mg/kg, from 50 to 500 mg/kg, from 100 to 500 mg/kg, from 150 to 500 mg/kg, from 200 to 500 mg/kg, from 250 to 500 mg/kg, from 300 to 500 mg/kg, from 350 to 500 mg/kg, from 400 to 500 mg/kg, or from 450 to 500 mg/kg) and, in a more specific embodiment, about 1 to about 100 mg/kg (e.g., about 1 to about 90 mg/kg, about 1 to about 80 mg/kg, about 1 to about 70 mg/kg, about 1 to about 60 mg/kg, about 1 to about 50 mg/g, about 1 to about 40 mg/kg, about 1 to about 30 mg/kg, about 1 to about 20 mg/kg, about 1 to about 10 mg/kg, about 10 to about 100 mg/kg, about 20 to about 100 mg/kg, about 30 to about 100 mg/kg, about 40 to about 100 mg/kg, about 50 to about 100 mg/kg, about 60 to about 100 mg/kg, about 70 to about 100 mg/kg, about 80 to about 100 mg/kg, or about 90 to about 100 mg/kg). In some embodiments, a pharmaceutical composition of the disclosure may include a dosage of a binding protein described herein ranging from 0.01 to 20 mg/kg (e.g., from 0.01 to 15 mg/kg, from 0.01 to 10 mg/kg, from 0.01 to 8 mg/kg, from 0.01 to 6 mg/kg, from 0.01 to 4 mg/kg, from 0.01 to 2 mg/kg, from 0.01 to 1 mg/kg, from 0.01 to 0.1 mg/kg, from 0.01 to 0.05 mg/kg, from 0.05 to 20 mg/kg, from 0.1 to 20 mg/kg, from 1 to 20 mg/kg, from 2 to 20 mg/kg, from 4 to 20 mg/kg, from 6 to 20 mg/kg, from 8 to 20 mg/kg, from 10 to 20 mg/kg, from 15 to 20 mg/kg). The dosage may be adapted by the physician in accordance with conventional factors such as the extent of the disease and different parameters of the subject.

A pharmaceutical composition containing a binding protein described herein can be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines. A course of therapy may be a single dose or in multiple doses over a period of time. In some embodiments, a single dose is used. In some embodiments, two or more split doses administered over a period of 1, 2, 3, 4, 5, 6, 7, 8, 9, 10, 11, 12, 13, 14, 21, 28, 30, 60, 90, 120 or 180 days are used. Each dose administered in such split dosing protocols may be the same in each administration or may be different. Multi-day dosing protocols over time periods may be provided by the skilled artisan (e.g., physician) monitoring the administration, taking into account the response of the subject to the treatment including adverse effects of the treatment and their modulation as discussed above.

VII. Indications

Immune Diseases

The present disclosure further provides methods of treating a subject suffering from a disease disorder or condition by the administration of a therapeutically effective amount of an IL27R binding protein (or nucleic acid encoding an IL27R binding protein including recombinant viruses encoding the IL27R binding protein) of the present disclosure. Disorders amenable to treatment with IL27R binding proteins (including pharmaceutically acceptable formulations comprising IL27R binding proteins and/or the nucleic acid molecules that encode them including recombinant viruses encoding such IL27R binding proteins) of the present disclosure include inflammatory or autoimmune diseases including but not limited to, viral infections (e.g., AIDS, influenza, chronic HCV, chronic viral hepatitis B, C or D), heliobacter pylori infection, HTLV, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome).

Other examples of proliferative and/or differentiative disorders amenable to treatment with IL27R binding proteins (including pharmaceutically acceptable formulations comprising IL27R binding proteins and/or the nucleic acid molecules that encode them including recombinant viruses encoding such IL27R binding proteins) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, *Pityriasis rubra* pilaris, *Pityriasis rosacea*, parapsoriasis, *Pityriasis* lichenoiders, *Lichen planus, Lichen nitidus*, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; *Lichen planus*; and keratitis. The skin disorder can be dermatitis, e.g., atopic dermatitis or allergic dermatitis, or psoriasis.

The compositions of the present disclosure (including pharmaceutically acceptable formulations comprising IL27R binding proteins and/or the nucleic acid molecules that encode them including recombinant viruses encoding such IL27R binding proteins) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Combination of IL27R Binding Proteins with Additional Therapeutic Agents for Autoimmune Disease:

The present disclosure provides for the use of the IL27R binding proteins of the present disclosure in combination with one or more additional active agents ("supplementary agents") in the treatment of autoimmune disease. As used herein, the term "supplementary agents" includes agents that can be administered or introduced separately, for example, formulated separately for separate administration (e.g., as may be provided in a kit) and/or therapies that can be administered or introduced in combination with the IL27R binding proteins.

As used herein, the term "in combination with" when used in reference to the administration of multiple agents to a subject refers to the administration of a first agent at least one additional (i.e., second, third, fourth, fifth, etc.) agent to a subject. For purposes of the present invention, one agent (e.g., IL27R binding protein) is considered to be administered in combination with a second agent (e.g. a therapeutic autoimmune antibody such as Humira®) if the biological effect resulting from the administration of the first agent persists in the subject at the time of administration of the second agent such that the therapeutic effects of the first agent and second agent overlap. For example, the therapeutic antibodies are sometimes administered by IV infusion every two weeks (e.g. adalimumab in the treatment of Crohn's disease) while the IL27R binding proteins of the present disclosure may be administered more frequently, e.g. daily, BID, or weekly. However, the administration of the first agent (e.g. entaercept) provides a therapeutic effect over an extended time and the administration of the second agent (e.g. an IL27R binding protein) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL27R binding protein and the supplementary agent(s) are administered or applied sequentially, e.g., where one agent is administered prior to one or more other agents. In other embodiments, the IL27R binding protein and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus). IMDH inhibitors (including but not limited to azathioprine, leflunomide and mycophenolate), biologics such as abatcept (Orencia®) or etanercept (Enbrel®), and therapeutic antibodies. Examples of therapeutic antibodies that may be administered as supplementary agents in combination with the IL27R binding proteins of the present disclosure in the treatment of autoimmune disease include but are not limited to anti-CD25 antibodies (e.g. daclizumiab and basiliximab), anti-VLA-4 antibodies (e.g. natalizumab), anti-CD52 antibodies (e.g. alemtuzunab), anti-CD20 antibodies (e.g. rituximab, ocrelizumab), anti-TNF antibodies (e.g. infliximab, and adalimumab), anti-IL6R antibodies (e.g. tocilizumab), anti-TNFα antibodies (e.g. adalimumab (Humira®), golimumab, and infliximab), anti-integrin-α4β7 antibodies (e.g. vedolizumab), anti-IL17a antibodies (e.g. brodalumab or secukinumab), anti-IL4Rα antibodies (e.g. dupilumab), anti-RANKL antibodies, IL6R antibodies, anti-IL1ß antibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IL27R binding proteins of the present disclosure (and optionally additional supplementary agents) for the treatment of the indicated autoimmune disease are provided in Table 4.

TABLE 4

| Name | Target | Indication |
|---|---|---|
| belimumab | BLyS | Systemic lupus erythematosus |
| efalizumab | CD11a | Psoriasis |
| ocrelizumab | CD20 | Multiple sclerosis |
| rituximab | CD20 | Multiple sclerosis |
| basiliximab | CD25 | Transplantation rejection |
| daclizumab | CD25 | Transplantation rejection |
| muromonab | CD3 | Transplantation rejection |
| alemtuzumab | CD52 | Multiple sclerosis |
| omalizumab | IgE | Asthma |
| ustekinumab | IL12/IL23 | Plaque psoriasis |
| brodalumab | IL17a | Psoriasis, psoriatic arthritis, ankylosing spondylitis |
| secukinumab | IL17a | Psoriasis, psoriatic arthritis, ankylosing spondylitis |
| ixekizumab | IL17a | Psoriasis, psoriatic arthritis, ankylosing spondylitis |
| canakinumab | ILIβ | Cryopyrin-associated periodic syndrome, tumor necrosis factor receptor associated periodic syndrome, hyperimmunoglobulin D syndrome, mevalonate kinase deficiency, familial Mediterranean fever, rheumatoid arthritis |
| dupilumab | IL4Rα | Asthma, dermatitis |
| mepolizumab | IL5 | Asthma |
| reslizumab | IL5 | Asthma |
| tocilizumab | IL6R | Rheumatoid arthritis |
| vedolizumab | Integrin-α4β7 | Ulcerative colitis, Crohn's disease |
| denosumab | RANKL | Osteoporosis |
| certolizumab | TNFα | Chron's disease, rheumatoid arthritis |
| golimumab | TNFα | Rheumatoid arthritis, psoriatic arthritis, ankylosing spondylitis |
| adalimumab | TNFα | Rheumatoid arthritis, juvenile idiopathic arthritis, psoriatic arthritis, ankylosing spondylitis, Crohn's disease, plaque psoriasis |
| infliximab | TNFα | Crohn's disease, ulcerative colitis, rheumatoid arthritis, ankylosing spondylitis, psoriatic arthritis, plaque psoriasis |
| ranibizumab | VEGF-A | Neovascular age-related macular degeneration, macular edema |
| natalizumab | VLA-4 | Multiple sclerosis, relapsing rultiple sclerosis, Crohn's disease |

Treatment of Neoplastic Disease

The present disclosure provides methods of use of IL-27R binding molecules in the treatment of subjects suffering from a neoplastic disease disorder or condition by the administration of a therapeutically effective amount of a IL-27R binding molecule (or nucleic acid encoding a IL-27R binding molecule including recombinant vectors encoding IL-27R binding molecules, and eucaryotic and procaryotic cells modified to express a IL-27R binding molecule) as described herein.

Neoplasms Amenable to Treatment:

The compositions and methods of the present disclosure are useful in the treatment of subject suffering from a neoplastic disease characterized by the presence neoplasms, including benign and malignant neoplasms, and neoplastic disease.

Examples of benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including but not limited to breast cancers; sarcomas (including but not limited to osteosarcomas and angiosarcomas and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas, astrocytomas, myelodysplastic disorders; cervical carcinoma-in-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis.

The term neoplastic disease includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic % neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML) and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease and Reed-Stemberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

Assessing Anti-Neoplastic Efficacy:

The determination of efficacy of the methods of the present disclosure in the treatment of cancer is generally associated with the achievement of one or more art recognized parameters such as reduction in lesions particularly reduction of metastatic lesion, reduction in metastasis, reduction in tumor volume, improvement in ECOG score, and the like. Determining response to treatment can be assessed through the measurement of biomarker that can provide reproducible information useful in any aspect of IL-27R binding molecule therapy, including the existence and extent of a subject's response to such therapy and the existence and extent of untoward effects caused by such therapy. By way of example, but not limitation, biomarkers include enhancement of IFNγ, and upregulation of granzyme A, granzyme B, and perforin; increase in CD8+ T-cell number and function; enhancement of IFNγ, an increase in ICOS expression on CD8+ T-cells, enhancement of IL-10 expressing $T_{Reg}$ cells. The response to treatment may be characterized by improvements in conventional measures of clinical efficacy may be employed such as Complete Response (CR), Partial Response (PR), Stable Disease (SD) and with respect to target lesions, Complete Response (CR)," Incomplete Response/Stable Disease (SD) as defined by RECIST as well as immune-related Complete Response (irCR), immune-related Partial Response (irPR), and immune-related Stable Disease (irSD) as defined Immune-Related Response Criteria (irRC) are considered by those of skill in the art as evidencing efficacy in the treatment of neoplastic disease in mammalian (e.g. human) subjects.

Maintenance of Serum Concentration:

In some embodiments of the invention the present disclosure provides methods and compositions for the treatment and/or prevention of neoplastic diseases, disorders or conditions by the administration of a therapeutically effective amount of an IL-27R binding molecules the serum concentration of the IL-27R binding molecule is maintained for a majority (i.e., greater than about 50% of the period of time, alternatively greater than about 60%, alternatively greater than about 70%, alternatively greater than about 80%, alternatively greater than about 90%) of a period of time (e.g. at least 24 hours, alternatively at least 48 hours, alternatively at least 72 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer) at a serum concentration at or above the therapeutically effective concentration with respect to such IL-27R binding molecule.

Combination of IL-27R Binding Molecules with Supplementary Therapeutic Agents:

The present disclosure provides for the use of the IL-27R binding molecules of the present disclosure in combination with one or more additional active agents ("supplementary agents"). Such further combinations are referred to interchangeably as "supplementary combinations" or "supplementary combination therapy" and those therapeutic agents that are used in combination with IL-27R binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IL-27R binding molecules.

Chemotherapeutic Agents:

In some embodiments, the supplementary agent is a chemotherapeutic agent. In some embodiments the supplementary agent is a "cocktail" of multiple chemotherapeutic agents. IN some embodiments the chemotherapeutic agent or cocktail is administered in combination with one or more physical methods (e.g. radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethyl olomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin $A_2$, cactinomycin, calicheamicin, carabicin, caminomycin, carzinophilin, chromomycins, dactinomycin, daunorubicin and derivatives such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; best rabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine, dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary agent is one or more chemical or biological agents identified in the art as useful in the treatment of neoplastic disease, including, but not limited to, a cytokines or cytokine antagonists such as IL-12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNT antagonists (e.g., Remicade® and Enbrel®), interferon-β1a (Avonex®), and interferon-β1b (Betaseron®) as well as combinations of one or more of the foregoing as practied in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the IL-27R binding molecule is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

Anti-Tumor Antigen Antibody Therapeutics as Supplementary Agents

In some embodiments, a "supplementary agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g. trastuzumab, pertuzumab, ado-trastuzumab emtansine), nectin-4 (e.g. enfortumab), CD79 (e.g. polatuzumab vedotin), CTLA4 (e.g. ipilumumab), CD22 (e.g. moxetumomab pasudotox), CCR4 (e.g. magamuizumab), IL23p19 (e.g. tildrakizumab), PDL1 (e.g. durvalumab, avelumab, atezolizumab), IL17a (e.g. ixekizumab), CD38 (e.g. daratumumab), SLAMF7 (e.g. elotuzumab), CD20 (e.g. rituximab, tositumomab, ibritumomab and ofatumumab), CD30 (e.g. brentuximab vedotin), CD33 (e.g. gemtuzumab ozogamicin), CD52 (e.g. alemtuzumab), EpCam, CEA, fpA33, TAG-72, CAIX, PSMA, PSA, folate binding protein, GD2 (e.g. dinuntuximab), GD3, IL6 (e.g. silutxumab) GM2, $Le^y$, VEGF (e.g. bevacizumab), VEGFR, VEGFR2 (e.g. ramucirumab), PDGFRα (e.g. olartumumab), EGFR (e.g. cetuximab, panitumumab and necitumumab), ERBB2 (e.g. trastuzumab), ERBB3, MET, IGF1R, EPHA3, TRAIL R1, TRAIL R2, RANKL RAP, tenascin, integrin αVβ3, and integrin α4β1.

Examples of antibody therapeutics which are FDA approved and may be used as supplementary agents for use in the treatment of neoplastic disease include those provided in the Table below.

TABLE

Approved Antineoplastic Disease Antibodies and Indications

| Name | Tradename(s) | Target; format | Indication |
|---|---|---|---|
| [fam]-trastuzumab deruxtecan | Enhertu ™ | HER2; Humanized IgG1 ADC | HER2+ breast cancer |
| Enfortumab vedotin | Padcev ™ | Nectin-4; Human IgG1 ADC | Urothelial cancer |
| Polatuzumab vedotin | Polivy ™ | CD79b; Humanized IgG1 ADC | Diffuse large B-cell lymphoma |
| Cemiplimab | Libtayo ™ | PD-1; Human mAb | Cutaneous squamous cell carcinoma |
| Moxetumomab pasudotox | Lumoxiti ™ | CD22; Murine IgG1 dsFv immunotoxin | Hairy cell leukemia |
| Mogamuizumab | Poteligeo ™ | CCR4; Humanized IgG1 | Cutaneous T cell lymphoma |
| Tildrakizumab | Ilumya ™ | IL23p19; Humanized IG1 | Plaque psoriasis |
| Ibalizumab | Trogarzo ™ | CD4; Humanized IgG4 | HIV infection |
| Durvalumab | IMFINZI ™ | PD-L1; Human IgG1 | Bladder cancer |
| Inotuzumab ozogamicin | BESPONSA ™ | CD22; Humanized IgG4, ADC | Hematological malignancy |
| Avelumab | Bavencio ™ | PD-L1; Human IgG1 | Merkel cell carcinoma |
| Atezolizumab | Tecentriq ™ | PD-L1; Humanized IgG1 | Bladder cancer |
| Olaratumab | Lartruvo ™ | PDGRFα; Human IgG1 | Soft tissue sarcoma |
| Ixekizumab | Taltz ™ | IL-17a; Humanized IgG4 | Psoriasis |
| Daratumumab | Darzalex ™ | CD38; Human IgG1 | Multiple myeloma |
| Elotuzumab | Empliciti ™ | SLAMF7; Humanized IgG1 | Multiple myeloma |
| Necitumumab | Portrazza ™ | EGFR; Human IgG1 | Non-small cell lung cancer |
| Dinutuximab | Unituxin ™ | GD2; Chimeric IgG1 | Neuroblastoma |
| Nivolumab | Opdivo ™ | PD1; Human IgG4 | Melanoma, non-small cell lung cancer |
| Blinatumomab | Blincyto ™ | CD19, CD3; Murine bispecific tandem scFv | Acute lymphoblastic leukemia |
| Pembrolizumab | Keytruda ™ | PD1; Humanized IgG4 | Melanoma |
| Ramucirumab | Cyramza ™ | VEGFR2; Human IgG1 | Gastric cancer |
| Siltuximab | Sylvant ™ | IL-6; Chimeric IgG1 | Castleman disease |
| Obinutuzumab | Gazyva ™ | CD20; Humanized IgG1; Glycoengineered | Chronic lymphocytic leukemia |
| Ado-trastuzumab emtansine | Kadcyla ™ | HER2; Humanized IgG1, ADC | Breast cancer |
| Pertuzumab | Perjeta ™ | HER2; Humanized IgG1 | Breast Cancer |
| Brentuximab vedotin | Adcetris ™ | CD30; Chimeric IgG1, ADC | Hodgkin lymphoma, systemic anaplastic large cell lymphoma |
| Ipilimumab | Yervoy ™ | CTLA-4; Human IgG1 | Metastatic melanoma |
| Ofatumumab | Arzerra ™ | CD20; Human IgG1 | Chronic lymphocytic leukemia |
| Certolizumab pegol | Cimzia ™ | TNF; Humanized Fab, pegylated | Crohn disease |
| Catumaxomab | Removab ™ | EPCAM/CD3; Rat/mouse bispecific mAb | Malignant ascites |
| Panitumumab | Vectibix ™ | EGFR; Human IgG2 | Colorectal cancer |
| Bevacizumab | Avastin ™ | VEGF; Humanized IgG1 | Colorectal cancer |
| Cetuximab | Erbitux ™ | EGFR; Chimeric IgG1 | Colorectal cancer |
| Tositumomab-I131 | Bexxar ™ | CD20; Murine IgG2a | Non-Hodgkin lymphoma |
| Ibrinunomab tiuxetan | Zevalin ™ | CD20; Murine IgG1 | Non-Hodgkin lymphoma |
| Gemtuzumab ozogamicin | Mylotarg ™ | CD33; Humanized IgG4, ADC | Acute myeloid leukemia |
| Trastuzumab | Herceptin ™ | HER2: Humanized IgG1 | Breast cancer |
| Infliximab | Remicade ™ | TNF: Chimeric IgG1 | Crohn disease |
| Rituximab | MabThera ™ Rituxan ™ | CD20; Chimeric IgG1 | Non-Hodgkin lymphoma |
| Edrecolomab | Panorex ™ | EpCAM; Murine IgG2a | Colorectal cancer |

Physical Methods

In some embodiments, a supplementary agent is one or more non-pharmacological modalities (e.g., localized radiation therapy or total body radiation therapy or surgery). By way of example, the present disclosure contemplates treatment regimens wherein a radiation phase is preceded or followed by treatment with a treatment regimen comprising a IL-27R binding molecule and one or more supplementary agents. In some embodiments, the present disclosure further contemplates the use of a IL-27R binding molecule in combination with surgery (e.g. tumor resection). In some embodiments, the present disclosure further contemplates the use of a IL-27R binding molecule in combination with bone marrow transplantation, peripheral blood stem cell transplantation or other types of transplantation therapy.

Combination with Immune Checkpoint Modulators:

In some embodiments, a "supplementary agent" is an immune checkpoint modulator for the treatment and/or prevention neoplastic disease in a subject as well as diseases, disorders or conditions associated with neoplastic disease. The term "immune checkpoint pathway" refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as "immune checkpoints." The biological responses modulated by such immune checkpoint pathways are mediated by intracellular signaling pathways that lead to downstream immune effector pathways, such as cell activation, cytokine production, cell migration, cytotoxic factor secretion, and antibody production. Immune checkpoint pathways are commonly triggered by the binding of a first cell surface expressed molecule to a second cell surface molecule associated with the immune checkpoint pathway (e.g. binding of PD1 to PDL1, CTLA4 to CD28, etc.). The activation of immune checkpoint pathways can lead to stimulation or inhibition of the immune response.

As used herein, the term "immune checkpoint pathway modulator" refers to a molecule that inhibits or stimulates the activity of an immune checkpoint pathway in a biological system including an immunocompetent mammal. An immune checkpoint pathway modulator may exert its effect by binding to an immune checkpoint protein (such as those immune checkpoint proteins expressed on the surface of an antigen presenting cell (APC) such as a cancer cell and/or immune T effector cell) or may exert its effect on upstream and/or downstream reactions in the immune checkpoint pathway. For example, an immune checkpoint pathway modulator may modulate the activity of SHP2, a tyrosine phosphatase that is involved in PD-1 and CTLA-4 signaling. The term "immune checkpoint pathway modulators" encompasses both immune checkpoint pathway modulator(s) capable of down-regulating at least partially the function of an inhibitory immune checkpoint (referred to herein as an "immune checkpoint pathway inhibitor" or "immune checkpoint pathway antagonist") and immune checkpoint pathway modulator(s) capable of up-regulating at least partially the function of a stimulatory immune checkpoint (referred to herein as an "immune checkpoint pathway effector" or "immune checkpoint pathway agonist.").

Immune checkpoint modulators include but are not limited to immune checkpoint antagonists (e.g. antagonist antibodies) that bind T-cell inhibitory receptors including but not limited to PD1 (also referred to as CD279), TIM3 (T-cell membrane protein 3; also known as HAVcr2), BTLA (B and T lymphocyte attenuator; also known as CD272), the VISTA (B7-H5) receptor, LAG3 (lymphocyte activation gene 3; also known as CD233) and CTLA4 (cytotoxic T-lymphocyte associated antigen 4; also known as CD152). In some embodiments, immune checkpoint modulators are agonists that trigger the checkpoint pathway resulting stimulation of the immune response. Examples of such agonist immune checkpoint modulators include, but is not limited to, agonist that modulate the binding of ICOSL to ICOS (CD278), B7-H6 to NKp30, CD155 to CD96, OX40L to OX40, CD70 to CD27, CD40 to CD40L, and GITRL to GITR. Examples of such positive immune checkpoint agonists include but are not limited to agonist antibodies that bind T-cell activating receptors such as ICOS (such as JTX-2011, Jounce Therapeutics). OX40 (such as MEDI6383, Medimmune), CD27 (such as varlilumab, Celldex Therapeutics), CD40 (such as dacetuzumab CP-870,893, Roche, Chi Lob 7/4), HVEM, CD28, CD137 4-1BB, CD226, and GITR (such as MEDI1873, Medimmune; INCAGN1876, Agenus).

Exemplary negative immune checkpoint pathway inhibitors include but are not limited to programmed death-1 (PD1) pathway inhibitors, programed death ligand-1 (PDL1) pathway inhibitors, TIM3 pathway inhibitors and anti-cytotoxic T-lymphocyte antigen 4 (CTLA4) pathway inhibitors.

In one embodiment, the immune checkpoint pathway modulator is an antagonist of a negative immune checkpoint pathway that inhibits the binding of PD1 to PDL1 and/or PDL2 ("PD1 pathway inhibitor). The term PD1 pathway inhibitors includes monoclonal antibodies that interfere with the binding of PD1 to PDL1 and/or PDL2. Examples of commercially available PD1 pathway inhibitors useful as supplementary agents in the treatment of neoplastic disease include antibodies that interfere with the binding of PD1 to PDL1 and/or PDL2 including but not limited to nivolumab (Opdivo®, BMS-936558, MDX1106, commercially available from BristolMyers Squibb, Princeton NJ), pembrolizumab (Keytruda® MK-3475, lambrolizumab, commercially available from Merck and Company, Kenilworth NJ), and atezolizumab (Tecentriq®, Genentech/Roche, South San Francisco CA). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105, BristolMyers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011. U.S. Pat. No. 7,943,743 (Medarex, Inc) issued May 17, 2011.

The term PD1 pathway inhibitors are not limited to antagonist antibodies. Non-antibody biologic PD1 pathway inhibitors are also under clinical development including AMP-224, a PD-L2 IgG2a fusion protein, and AMP-514, a PDL2 fusion protein, are under clinical development by Amplimmune and Glaxo SmithKline), aptamers (Wang, et al. (2018) 145:125-130), peptide PD1 pathway inhibitors (Sasikumar, et al., U.S. Pat. No. 9,422,339 issued Aug. 23, 2016, and Sasilkumar, et al., U.S. Pat. No. 8,907,053 issued Dec. 9, 2014), small molecules (CA-170, AUPM-170, Aurigene/Curis: Sasikumar, et al., 1,2,4-oxadiazole and thiadiazole compounds as immunomodulators (PCT/IB2016/051266 filed Mar. 7, 2016, published as WO2016142833A1 Sep. 15, 2016) and Sasikumar, et al PCT/IB2016/051343 filed Mar. 9, 2016 and published as WO2016142886A2), BMS-1166 and Chupak L S and Zheng X. (2015) WO 2015/034820 A1, EP3041822 B1 granted Aug. 9, 2017; WO2015034820 A1; and Chupak, et al. 2015) WO2015/160641 A2. WO2015/160641 A2, Chupak, et al. Sharpe, et al. WO 2011082400 A2 published Jul. 7, 2011; U.S. Pat. No. 7,488,802 issued Feb. 10, 2009:

In some embodiments, the IL-27R binding molecule is administered in combination with an antagonist of a negative immune checkpoint pathway that inhibits the binding of CTLA4 to CD28 ("CTLA4 pathway inhibitor"). Examples of CTLA4 pathway inhibitors are well known in the art (See, e.g., U.S. Pat. No. 6,682,736 (Abgenix) issued Jan. 27, 2004;

U.S. Pat. No. 6,984,720 (Medarex. Inc.) issued May 29, 2007; U.S. Pat. No. 7,605,238 (Medarex, Inc.) issued Oct. 20, 2009)

In some embodiments, the IL-27R binding molecule is administered in combination with an antagonist of a negative immune checkpoint pathway that inhibits the ability TIM3 to binding to TIM3-activating ligands ("TIM3 pathway inhibitor"). Examples of TIM3 pathway inhibitors are known in the art and with representative non-limiting examples described in PCT International Patent Publication No. WO 2016/144803 published Sep. 15, 2016; Lifke, et al. United States Patent Publication No. US 20160257749 A1 published Sep. 8, 2016 (F. Hoffman-LaRoche); Karunsky, U.S. Pat. No. 9,631,026 issued Apr. 27, 2017; Karunsky, Sabatos-Peyton, et al. U.S. Pat. No. 8,841,418 issued Sep. 23, 2014; U.S. Pat. No. 9,605,070; Takayanagi, et al., U.S. Pat. No. 8,552,156 issued Oct. 8, 2013.

In some embodiments, the IL-27R binding molecule is administered in combination with an inhibitor of both LAG3 and PD1 as the blockade of LAG3 and PD1 has been suggested to synergistically reverse anergy among tumor-specific CD8+ T-cells and virus-specific CD8+ T-cells in the setting of chronic infection. IMP321 (ImmuFact) is being evaluated in melanoma, breast cancer, and renal cell carcinoma. See generally Woo et al., (2012) Cancer Res 72:917-27; Goldberg et al., (2011) Cur. Top. Microbiol. Immunol. 344:269-78; Pardoll (2012) Nature Rev. Cancer 12:252-64; Grosso et al., (2007) J. Clin. Invest. 117:3383-392.

In some embodiments, the IL-27R binding molecule is administered in combination with an A2aR inhibitor. A2aR inhibits T-cell responses by stimulating CD4+ T-cells towards developing into $T_{Reg}$ cells. A2aR is particularly important in tumor immunity because the rate of cell death in tumors from cell turnover is high, and dying cells release adenosine, which is the ligand for A2aR. In addition, deletion of A2aR has been associated with enhanced and sometimes pathological inflammatory responses to infection. Inhibition of A2aR can be effected by the administration of molecules such as antibodies that block adenosine binding or by adenosine analogs. Such agents may be used in combination with the IL-27R binding molecules for use in the treatment disorders such as cancer and Parkinson's disease.

In some embodiments, the IL-27R binding molecule is administered in combination with an inhibitor of IDO (Indoleamine 2,3-dioxygenase). IDO down-regulates the immune response mediated through oxidation of thyptophan resulting in in inhibition of T-cell activation and induction of T-cell apoptosis, creating an environment in which tumor-specific cytotoxic T lymphocytes are rendered functionally inactive or are no longer able to attack a subject's cancer cells. Indoximod (NewLink Genetics) is an IDO inhibitor being evaluated in metastatic breast cancer.

As previously described, the present invention provides for a method of treatment of neoplastic disease (e.g. cancer) in a mammalian subject by the administration of a IL-27R binding molecule in combination with an agent(s) that modulate at least one immune checkpoint pathway including immune checkpoint pathway modulators that modulate two, three or more immune checkpoint pathways.

In some embodiments the IL-27R binding molecule is administered in combination with an immune checkpoint modulator that modulates multiple immune checkpoint pathways. Multiple immune checkpoint pathways may be modulated by the administration of multi-functional molecules which act as modulators of multiple immune checkpoint pathways. Examples of such multiple immune checkpoint pathway modulators include but are not limited to bi-specific or poly-specific antibodies. Examples of poly-specific antibodies capable of acting as modulators or multiple immune checkpoint pathways are known in the art. For example, United States Patent Publication No. 2013/0156774 describes bispecific and multispecific agents (e.g., antibodies), and methods of their use, for targeting cells that co-express PD1 and TIM3. Moreover, dual blockade of BTLA and PD1 has been shown to enhance antitumor immunity (Pardoll, (April 2012) Nature Rev. Cancer 12:252-64). The present disclosure contemplates the use of IL-27R binding molecules in combination with immune checkpoint pathway modulators that target multiple immune checkpoint pathways, including but limited to bi-specific antibodies which bind to both PD1 and LAG3. Thus, antitumor immunity can be enhanced at multiple levels, and combinatorial strategies can be generated in view of various mechanistic considerations.

In some embodiments, the IL-27R binding molecule may be administered in combination with two, three, four or more checkpoint pathway modulators. Such combinations may be advantageous in that immune checkpoint pathways may have distinct mechanisms of action, which provides the opportunity to attack the underlying disease, disorder or conditions from multiple distinct therapeutic angles.

It should be noted that therapeutic responses to immune checkpoint pathway inhibitors often manifest themselves much later than responses to traditional chemotherapies such as tyrosine kinase inhibitors. In some instance, it can take six months or more after treatment initiation with immune checkpoint pathway inhibitors before objective indicia of a therapeutic response are observed. Therefore, a determination as to whether treatment with an immune checkpoint pathway inhibitors(s) in combination with a IL-27R binding molecule of the present disclosure must be made over a time-to-progression that is frequently longer than with conventional chemotherapies. The desired response can be any result deemed favorable under the circumstances. In some embodiments, the desired response is prevention of the progression of the disease, disorder or condition, while in other embodiments the desired response is a regression or stabilization of one or more characteristics of the disease, disorder or conditions (e.g., reduction in tumor size). In still other embodiments, the desired response is reduction or elimination of one or more adverse effects associated with one or more agents of the combination.

Cell Therapy Agents and Methods as Supplementary Agents:

In some embodiments, the methods of the disclosure may include the combination of the administration of a IL-27R binding molecules with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more activated CAR-T cells, engineered TCR cells, tumor infiltrating lymphocytes (TILs), engineered Treg cells. As engineered T-cell products are commonly activated ex vivo prior to their administration to the subject and therefore provide upregulated levels of CD25, cell products comprising such activated engineered T cells types are amenable to further support via the administration of an CD25 biased IL-27R binding molecule as described herein.

In some embodiments of the methods of the present disclosure, the supplementary agent is a "chimeric antigen receptor T-cell" and "CAR-T cell" are used interchangeably to refer to a T-cell that has been recombinantly modified to express a chimeric antigen receptor. As used herein, the terms As used herein, the terms "chimeric antigen receptor" and "CAR" are used interchangeably to refer to a chimeric polypeptide comprising multiple functional domains arranged from amino to carboxy terminus in the sequence: (a) an antigen binding domain (ABD), (b) a transmembrane domain (TD); and (c) one or more cytoplasmic signaling domains (CSDs) wherein the foregoing domains may optionally be linked by one or more spacer domains. The CAR may also further comprise a signal peptide sequence which is conventionally removed during post-translational processing and presentation of the CAR on the cell surface of a cell transformed with an expression vector comprising a nucleic acid sequence encoding the CAR. CARs useful in the practice of the present invention are prepared in accordance with principles well known in the art. See e.g., Eshhaar et al. U.S. Pat. No. 7,741,465 B1 issued Jun. 22, 2010; Sadelain, et al (2013) Cancer Discovery 3(4):388-398; Jensen and Riddell (2015) Current Opinions in Immunology 33:9-15; Gross, et al. (1989) PNAS (USA) 86(24):10024-10028; Curran, et al. (2012) J Gene Med 14(6):405-15. Examples of commercially available CAR-T cell products that may be modified to incorporate an orthogonal receptor of the present invention include axicabtagene ciloleucel (marketed as Yescarta® commercially available from Gilead Pharmaceuticals) and tisagenlecleucel (marketed as Kymriah® commercially available from Novartis). In some embodiments, the CAR-T possesses a CAR specifically binds to a cell surface molecule associated with a tumor cell is selected from the group consisting of GD2, BCMA, CD19, CD33, CD38, CD70. GD2, IL3Rα2, CD19, mesothelin, Her2, EpCam, Muc1, ROR1, CD133, CEA, EGRFRVIII, PSCA, GPC3, Pan-ErbB and FAP Physical Methods:

In some embodiments, the supplementary agent is a anti-neoplastic physical methods including but not limited to radiotherapy, cryotherapy, hyperthermic therapy, surgery, laser ablation, and proton therapy.

Kits: The present disclosure also contemplates kits comprising pharmaceutical compositions IL-27R binding molecules and a pharmaceutical composition thereof. The kits are generally in the form of a physical structure housing various components, as described below, and can be utilized, for example, in practicing the methods described above. A kit may comprise a IL-27R binding molecule in the form of a pharmaceutical composition suitable for administration to a subject that is ready for use or in a form or requiring preparation for example, thawing, reconstitution or dilution prior to administration. When the IL-27R binding molecule is in a form that needs to be reconstituted by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL-27R binding molecule or kit comprising) in compliance with governmental regulations (e.g., HIPAA) are provided.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The foregoing antibodies useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

In some embodiments the supplementary agent is a vaccine. The IL27R binding proteins of the present invention may be administered to a subject in combination with vaccines as an adjuvant to enhance the immune response to the vaccine in accordance with the teaching of Doyle, et al U.S. Pat. No. 5,800,819 issued Sep. 1, 1998. Examples of vaccines that may be combined with the IL27R binding proteins of the present invention include are HSV vaccines, *Bordetella pertussis, Escherichia coli* vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, *Haemophilus influenzae* type B vaccines, human papilloma virus vaccines such as Garasil®, polio vaccines, Leptospirosis vaccines, combination respiratory vaccine, *Moraxella* vaccines, and attenuated live or killed virus vaccine products such as bovine respiratory disease vaccine (RSV), multivalent human influenza vaccines such as Fluzone® and Quadravlent Fluzone®), feline leukemia vaccine, transmissible gastroenteritis vaccine, COVID-19 vaccine, and rabies vaccine.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

EXAMPLES

Example 1

Camels were acclimated at research facility for at least 7 days before immunization. Antigen was diluted with 1×PBS (antigen total about 1 mg). The quality of the antigen was assessed by SDS-PAGE to ensure purity (e.g., >80%). For the first time, 10 mL CFA (then followed 6 times using IFA) was added into mortar, then 10 mL antigen in 1×PBS was slowly added into the mortar with the pestle grinding. The antigen and CFA/IFA were ground until the component showed milky white color and appeared hard to disperse. Camels were injected with antigen emulsified in CFA subcutaneously at at least six sites on the body, injecting about 2 mL at each site (total of 10 mL per camel). A stronger immune response was generated by injecting more sites and in larger volumes. The immunization was conducted every week (7 days), for 7 times. The needle was inserted into the subcutaneous space for 10 to 15 seconds after each injection to avoid leakage of the emulsion. Alternatively, a light pull on the syringe plunger also prevented leakage. The blood sample was collected three days later after $7^{th}$ immunization.

100 mL of blood was collected from the camel three days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with Psi I and Not I, subsequently, ligated to pMECS/Nb recombinant. After ligation, the products were transformed into *Escherichia coli* (*E. coli*) TG1 cells by electroporation. The transformants were enriched in growth medium, followed by transfer to 2YT+2% glucose agar plates.

Bio-panning of the phage library was conducted to identify VHHs that bind IL27Rα. A 96-well plate was coated with IL27Rα and the phage library was incubated in each well to allow phage-expressing IL27Rα reactive VHH to bind to the IL27Rα on the plate. Non-specifically bound phage were washed off and the specifically bound phage isolated. After the selection, the enriched phage library expressing IL27Rα reactive VHH were amplified in TG1 cells. The aforementioned bio-panning process was repeated for 2-3 rounds to enrich the library for VHH selective for IL27Rα. Once biopanning was complete, three 96-well plates of individual phage clones were isolated in order to perform periplasmic extract ELISA PE-ELISA) on antigen coated plates to identify positive VHH binders. Briefly, A 96-well plate was coated with antigen and PBS under the same conditions. Next, wells were blocked at 37° C. for 1 h. Then, 100 μl of extracted antibodies was added to each well and incubated for 1 h. Subsequently, 100 μl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader and antibodies with absorbance of the antigen-coated well at least threefold greater than PBS-coated control were specific binding molecules and subjected to sequence analysis.

Example 2—Recombinant Production and Purification

Codon optimized DNA inserts were cloned into modified pcDNA3.4 (Genewiz) for small scale expression in HEK293 cells in 24 well plates. The binding proteins were purified in substantial accordance with the following procedure. Using a Hamilton Star automated system, 96×4 mL of supernatants in 4×24-well blocks were re-arrayed into 4×96-well, 1 mL blocks. PhyNexus™ micropipette tips (Biotage, San Jose CA) holding 80 μL of Ni-Excel IMAC resin (Cytiva) are equilibrated wash buffer: PBS pH 7.4, 30 mM imidazole. PhyNexus™ tips were dipped and cycled through 14 cycles of 1 mL pipetting across all 4×96-well blocks. PhyNexus™ tips were washed in 2×1 mL blocks holding wash buffer. PhyNexus™ tips were eluted in 3×0.36 mL blocks holding elution buffer: PBS pH 7.4, 400 mM imidazole. PhyNexus™ tips were regenerated in 3×1 mL blocks of 0.5 M sodium hydroxide.

The purified protein eluates were quantified using a Biacore® T200 as in substantial accordance with the following procedure. 10 uL of the first 96×0.36 mL eluates were transferred to a Biacore® 96-well microplate and diluted to 60 uL in HBS-EP+ buffer (10 mM Hepes pH 7.4, 150 mM NaCl, 1 mM EDTA, 0.05% Tween™ 20). Each of the 96 samples was injected on a CM5 series S chip previously functionalized with anti-histidine capture antibody (Cytiva): injection is performed for 18 seconds at 5 μL/min. Capture levels were recorded 60 seconds after buffer wash. A standard curve of known $V_HH$ concentrations (270, 90, 30, 10, 3.3, 1.1 μg/mL) was acquired in each of the 4 Biacore® chip flow cells to eliminate cell-to-cell surface variability. The 96 captures were interpolated against the standard curve using a non-linear model including specific and unspecific, one-site binding. Concentrations in the first elution block varied from 12 to 452 μg/mL corresponding to a 4-149 μg, SDS-PAGE analysis of 5 randomly picked samples was performed to ensure molecular weight of eluates corresponded to expected values (~30 kDa).

The concentration of the proteins was normalized using the Hamilton Star automated system in substantial accordance with the following procedure. Concentration values are imported in an Excel spreadsheet where pipetting volumes were calculated to perform dilution to 50 μg/mL in 0.22 mL. The spreadsheet was imported in a Hamilton Star method dedicated to performing dilution pipetting using the first elution block and elution buffer as diluent. The final, normalized plate was sterile filtered using 0.22 μm filter plates (Corning).

Example 3

All experiments were conducted in 10 mM Hepes, 150 mM NaCl, 0.05% (v/v) Polysorbate 20 (PS20) and 3 mM EDTA (BBS-EP+ buffer) on a Biacore® T200 instrument equipped with a Protein A chip (Cytiva). Mono-Fc VIM ligands were flowed at 5 μl/min for variable time ranging from 18 to 300 seconds, reaching the capture loads listed in the tables below.

Following ligand capture, injections of a 2-fold dilution series of his-tagged cytokine receptors typically comprising at least five concentrations between 1 μM and 1 nM were performed in either high performance or single cycle kinetics mode. Surface regeneration was achieved by flowing 10 mM glycine-HCl, pH 1.5 (60 seconds, 50 μL/min). Buffer-subtracted sensograms were processed with Biacore® T200 Evaluation Software and globally fit with a 1:1 Langmuir binding model (bulk shift set to zero) to extract kinetics and affinity constants (ka, kd, KD). RMAX<100 RU indicates surface density compatible with kinetics analysis. Calculated Rmax were generated using the equation Rmax=Load (RU)×valency of ligand×(Molecular weight of analyte/Molecular weight of ligand. Surface activity was defined as the ratio experimental/calculated Rmax. See tables below for sample information and experimental results.

| Ligand | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|
| Anti-hGP130 Mono-Fc VHHs (ligand) binding to hGP130-his (Sino Biological, Catalog# 10974) | | | | | | | |
| 14-DR591 (SEQ ID NO. 232) | 5.9E+04 | 1.9E−03 | 33 | 52 | 84.6 | 252 | 21% |
| 15-DR592 (SEQ ID NO. 233) | 1.6E+05 | 5.9E−03 | 38 | 142.3 | 147 | 437 | 33% |
| 16-DR593 (SEQ ID NO. 234) | 2.5E+05 | 2.1E−02 | 82 | 64.2 | 110 | 326 | 20% |
| 17-DR594 (SEQ ID NO. 235) | 1.6E+05 | 9.5E−03 | 58 | 96.9 | 153 | 455 | 21% |
| 18-DR595 (SEQ ID NO. 236) | 1.8E+05 | 7.3E−03 | 41 | 127 | 128 | 379 | 33% |
| 19-DR596 (SEQ ID NO. 237) | 1.9E+05 | 8.2E−03 | 44 | 68.8 | 83.6 | 249 | 28% |

| Ligand | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|
| Anti-hIL27Ra Mono-Fc VHHs (ligand) binding to hIL27Ra-his (Origene, Catalog# TP307012) | | | | | | | |
| 20-DR597 (SEQ ID NO. 245) | 3.0E+04 | 5.7E−04 | 19.0 | 142* | 1319 | 3564 | 4% |
| 24-DR601 (SEQ ID NO. 249) | 9.1E+04 | 4.1E−04 | 4.5 | 102 | 305 | 824 | 12% |
| 23-DR600 (SEQ ID NO. 248) | 5.9E+04 | 1.0E−03 | 17 | 79 | 232 | 627 | 13% |
| 25-DR602 (SEQ ID NO. 250) | 1.5E+05 | 7.6E−04 | 5.2 | 115* | 210 | 568 | 20% |
| 26-DR603 (SEQ ID NO. 251) | 1.3E+05 | 7.7E−04 | 6.1 | 149* | 305 | 823 | 18% |

*Both association and dissociation kinetics constants might be suppressed at Rmax > 100.
If existing, this effect is likely cancelled in the kinetics ratio, i.e. affinity constant.

Example 4

Binding for all VHH was confirmed by ELISA. One representative VHH from each clonotype was selected for further analysis by surface plasmon resonance using Biacore® T200. See below.

| Dimer | hIL27 Ra arm | hgp130 arm | kON (1/Ms) hIL27Ra | kOFF (1/s) hIL27 Ra | Affinity (nM) hIL27Ra | kON (1/Ms) hgp130 | kOFF (1/s) hgp130 | Affinity (nM) hgp130 |
|---|---|---|---|---|---|---|---|---|
| hIL27Ra_VHH1-DR591 | VHH1 | DR591 | 3.00E+04 | 5.70E−04 | 19 | 5.90E+04 | 1.90E−03 | 33 |
| hIL27Ra_VHH4-DR591 | VHH4 | DR591 | — | — | — | 5.90E+04 | 1.90E−03 | 33 |
| hIL27Ra_VHH6-DR591 | VHH6 | DR591 | — | — | — | 5.90E+04 | 1.90E−03 | 33 |
| hIL27Ra_VHH9-DR591 | VHH9 | DR591 | 9.10E+04 | 4.10E−04 | 4.5 | 5.90E+04 | 1.90E−03 | 33 |
| hIL27Ra_VHH15-DR591 | VHH15 | DR591 | 5.90E+04 | 1.00E−03 | 17 | 5.90E+04 | 1.90E−03 | 33 |
| hIL27Ra_VHH19-DR591 | VHH19 | DR591 | 1.50E+05 | 7.60E−04 | 5.2 | 5.90E+04 | 1.90E−03 | 33 |
| hIL27Ra_VHH21-DR591 | VHA21 | DR591 | 1.30E+05 | 7.70E−04 | 6.1 | 5.90E+04 | 1.90E−03 | 33 |
| hIL27Ra_VHH1-DR592 | VHH1 | DR592 | 3.00E+04 | 5.70E−04 | 19 | 1.60E+05 | 5.90E−03 | 38 |
| hIL27Ra_VHH4-DR592 | VHH4 | DR592 | — | — | — | 1.60E+05 | 5.90E−03 | 38 |
| hIL27Ra_VHH6-DR592 | VHH6 | DR592 | — | — | — | 1.60E+05 | 5.90E−03 | 38 |

-continued

| Dimer | hIL27 Ra arm | hgp130 arm | kON (1/Ms) hIL27Ra | kOFF (1/s) hIL27 Ra | Affinity (nM) hIL27Ra | kON (1/Ms) hgp130 | kOFF (1/s) hgp130 | Affinity (nM) hgp130 |
|---|---|---|---|---|---|---|---|---|
| hIL27Ra_VHH9-DR592 | VHH9 | DR592 | 9.10E+04 | 4.10E−04 | 4.5 | 1.60E+05 | 5.90E−03 | 38 |
| hIL27Ra_VHH15-DR592 | VHH15 | DR592 | 5.90E+04 | 1.00E−03 | 17 | 1.60E+05 | 5.90E−03 | 38 |
| hIL27Ra_VHH19-DR592 | VHH19 | DR592 | 1.50E+05 | 7.60E−04 | 5.2 | 1.60E+05 | 5.90E−03 | 38 |
| hIL27Ra_VHH21-DR592 | VHH21 | DR592 | 1.30E+05 | 7.70E−04 | 6.1 | 1.60E+05 | 5.90E−03 | 38 |
| hIL27Ra_VHH1-DR593 | VHH1 | DR593 | 3.00E+04 | 5.70E−04 | 19 | 2.50E+05 | 2.10E−02 | 82 |
| hIL27Ra_VHH4-DR593 | VHH4 | DR593 | — | — | — | 2.50E+05 | 2.10E−02 | 82 |
| hIL27Ra_VHH6-DR593 | VHH6 | DR593 | — | — | — | 2.50E+05 | 2.10E−02 | 82 |
| hIL27Ra_VHH9-DR593 | VHH9 | DR593 | 9.10E+04 | 4.10E−04 | 4.5 | 2.50E+05 | 2.10E−02 | 82 |
| hIL27Ra_VHH15-DR593 | VHH15 | DR593 | 5.90E+04 | 1.00E−03 | 17 | 2.50E+0.5 | 2.10E−02 | 82 |
| hIL27Ra_VHH19-DR593 | VHH19 | DR593 | 1.50E+05 | 7.60E−04 | 5.2 | 2.50E+05 | 2.10E−02 | 82 |
| hIL27Ra_VHH21-DR593 | VHA21 | DR593 | 1.30E+05 | 7.70E−04 | 6.1 | 2.50E+05 | 2.10E−02 | 8.2 |
| hIL27Ra_VHH1-DR594 | VHH1 | DR594 | 3.00E+04 | 5.70E−04 | 19 | 1.60E+05 | 9.50E−03 | 58 |
| hIL27Ra_VHH4-DR594 | VHH4 | DR594 | — | — | — | 1.60E+05 | 9.50E−03 | 58 |
| hIL27Ra_VHH6-DR594 | VHH6 | DR594 | — | — | — | 1.60E+0.5 | 9.50E−03 | 58 |
| hIL27Ra_VHH9-DR594 | VHH9 | DR594 | 9.10E+04 | 4.10E−04 | 4.5 | 1.60E+05 | 9.50E−03 | 58 |
| hIL27Ra_VHH15-DR594 | VHH15 | DR594 | 5.90E+04 | 1.00E−03 | 17 | 1.60E+05 | 9.50E−03 | 58 |
| hIL27Ra_VHH19-DR594 | VHH19 | DR594 | 1.50E+05 | 7.60E−04 | 5.1 | 1.60E+05 | 9.50E−03 | 58 |
| hIL27Ra_VHH21-DR594 | VHH21 | DR594 | 1.30E+05 | 7.70E−04 | 6.1 | 1.60E+05 | 9.50E−03 | 58 |
| hIL27Ra_VHH1-DR595 | VHH1 | DR595 | 3.00E+04 | 5.70E−04 | 19 | 1.80E+05 | 7.30E−03 | 41 |
| hIL27Ra_VHH4-DR595 | VHH4 | DR595 | — | — | — | 1.80E+05 | 7.30E−03 | 41 |
| hIL27Ra_VHH6-DR595 | VHH6 | DR595 | — | — | — | 1.80E+05 | 7.30E−03 | 41 |
| hIL27Ra_VHH9-DR595 | VHA9 | DR595 | 9.10E+04 | 4.10E−04 | 4.5 | 1.80E+05 | 7.30E−03 | 41 |
| hIL27Ra_VHH15-DR595 | VHH15 | DR595 | 5.90E+04 | 1.00E−03 | 17 | 1.80E+05 | 7.30E−03 | 41 |
| hIL27Ra_VHH19-DR595 | VHH19 | DR595 | 1.50E+05 | 7.60E−04 | 5.2 | 1.80E+05 | 7.30E−03 | 41 |
| hIL27Ra_VHH21-DR595 | VHH21 | DR595 | 1.30E+05 | 7.70E−04 | 6.1 | 1.80E+05 | 7.30E−03 | 41 |
| hIL27Ra_VHH1-DR596 | VHH1 | DR596 | 3.00E+04 | 5.70E−04 | 19 | 1.90E+05 | 8.20E−03 | 44 |
| hIL27Ra_VHH4-DR596 | VHH4 | DR596 | — | — | — | 1.90E+05 | 8.20E−03 | 44 |
| hIL27Ra_VHH6-DR596 | VHH6 | DR596 | — | — | — | 1.90E+05 | 8.20E−03 | 44 |
| HIL27Ra_VHH9-DR596 | VHH9 | DR596 | 9.10E+04 | 4.10E−04 | 4.5 | 1.90E+05 | 8.20E−03 | 44 |
| hIL27Ra_VHH15-DR596 | VHH15 | DR596 | 5.90E+04 | 1.00E−03 | 17 | 1.90E+05 | 8.20E−03 | 44 |
| hIL27Ra_VHH19-DR596 | VHH19 | DR596 | 1.50E+05 | 7.60E−04 | 5.2 | 1.90E+05 | 8.20E−03 | 44 |
| hIL27Ra_VHH21-DR596 | VHR21 | DR596 | 1.30E+05 | 7.70E−04 | 6.1 | 1.90E+05 | 8.20E−03 | 44 |

SEQUENCE LISTING

The patent contains a lengthy sequence listing. A copy of the sequence listing is available in electronic form from the USPTO web site (https://seqdata.uspto.gov/?pageRequest=docDetail&DocID=US12209132B2). An electronic copy of the sequence listing will also be available from the USPTO upon request and payment of the fee set forth in 37 CFR 1.19(b)(3).

What is claimed is:

1. An isolated nucleic acid encoding an IL27 receptor (IL27R) binding protein that specifically binds to IL27Rα subunit (IL27Rα) and glycoprotein 130 subunit (gp130), wherein the binding protein comprises an anti-IL27Rα $V_H$H antibody and an anti-gp130 $V_H$H antibody, and wherein the anti-gp130 $V_H$H antibody comprises a set of a CDR1, a CDR2, and a CDR3, wherein the set is selected from the group consisting of:

SEQ ID NO: 193, SEQ ID NO: 199, SEQ ID NO: 205, respectively;

SEQ ID NO: 194, SEQ ID NO: 200, SEQ ID NO: 206, respectively;

SEQ ID NO: 195, SEQ ID NO: 201, SEQ ID NO: 207, respectively;

SEQ ID NO: 196, SEQ ID NO: 202, SEQ ID NO: 208, respectively;

SEQ ID NO: 197, SEQ ID NO: 203, SEQ ID NO: 209, respectively; and

SEQ ID NO: 198, SEQ ID NO: 204, SEQ ID NO: 210, respectively; and the anti-IL27Rα $V_H$H antibody comprises a set of a CDR1, a CDR2, and a CDR3, wherein the set is selected from the group consisting of SEQ ID NO: 211, SEQ ID NO: 218, SEQ ID NO: 225, respectively;

SEQ ID NO: 212, SEQ ID NO: 219, SEQ ID NO: 226, respectively;

SEQ ID NO: 213, SEQ ID NO: 220, SEQ ID NO: 227, respectively;

SEQ ID NO: 214, SEQ ID NO: 221, SEQ ID NO: 228, respectively;

SEQ ID NO: 215, SEQ ID NO: 222, SEQ ID NO: 229, respectively;

SEQ ID NO: 216, SEQ ID NO: 223, SEQ ID NO: 230, respectively; and

SEQ ID NO: 217, SEQ ID NO: 224, SEQ ID NO: 231, respectively.

2. An expression vector comprising the nucleic acid of claim 1.

3. An isolated cell comprising the vector of claim 2.

4. The isolated nucleic acid of claim 1, wherein the anti-gp130 $V_H$H antibody comprises the set of CDR1, CDR2, and CDR3 comprising amino acid sequences of SEQ ID NO: 196, SEQ ID NO: 202, and SEQ ID NO: 208, respectively.

5. The isolated nucleic acid of claim 4, wherein the anti-IL27Rα $V_H$H antibody CDR1 comprises the set of CDR1, CDR2, and CDR3 comprising amino acid sequences of SEQ ID NO: 214, SEQ ID NO: 221, SEQ ID NO: 228, respectively.

6. The isolated nucleic acid of claim 4, wherein the anti-IL27Rα $V_H$H antibody CDR1 comprises the set of CDR1, CDR2, and CDR3 comprising amino acid sequences of SEQ ID NO: 216, SEQ ID NO: 223 and SEQ ID NO: 230, respectively.

7. The isolated nucleic acid of claim 1, wherein the IL27 receptor (IL27R) binding protein comprises an amino acid sequence of SEQ ID NO: 64.

8. The isolated nucleic acid of claim 1, wherein the IL27 receptor (IL27R) binding protein comprises an amino acid sequence of SEQ ID NO: 76.

9. The expression vector of claim 2, wherein the anti-gp130 $V_H$H antibody comprises the set of CDR1, CDR2, and CDR3 comprising amino acid sequences of SEQ ID NO: 196, SEQ ID NO: 202, and SEQ ID NO: 208, respectively.

10. The expression vector of claim 9, wherein the anti-IL27Rα $V_H$H antibody CDR1 comprises the set of CDR1, CDR2, and CDR3 comprising amino acid sequences of SEQ ID NO: 214, SEQ ID NO: 221, SEQ ID NO: 228, respectively.

11. The expression vector of claim 9, wherein the anti-IL27Rα $V_H$H antibody CDR1 comprises the set of CDR1, CDR2, and CDR3 comprising amino acid sequences of SEQ ID NO: 216, SEQ ID NO: 223 and SEQ ID NO: 230, respectively.

12. The expression vector of claim 2, wherein the IL27 receptor (IL27R) binding protein comprises an amino acid sequence of SEQ ID NO: 64.

13. The expression vector of claim 2, wherein the IL27 receptor (IL27R) binding protein comprises an amino acid sequence of SEQ ID NO: 76.

14. The isolated cell of claim 3, wherein the anti-gp130 $V_H$H antibody comprises the set of CDR1, CDR2, and CDR3 comprising amino acid sequences of SEQ ID NO: 196, SEQ ID NO: 202, and SEQ ID NO: 208, respectively.

15. The isolated cell of claim 14, wherein the anti-IL27Rα $V_H$H antibody CDR1 comprises the set of CDR1, CDR2, and CDR3 comprising amino acid sequences of SEQ ID NO: 214, SEQ ID NO: 221, SEQ ID NO: 228, respectively.

16. The isolated cell of claim 3, wherein the anti-IL27Rα $V_H$H antibody CDR1 comprises the set of CDR1, CDR2, and CDR3 comprising amino acid sequences of SEQ ID NO: 216, SEQ ID NO: 223 and SEQ ID NO: 230, respectively.

17. The isolated cell of claim 3, wherein the IL27 receptor (IL27R) binding protein comprises an amino acid sequence of SEQ ID NO: 64.

18. The isolated cell of claim 3, wherein the IL27 receptor (IL27R) binding protein comprises an amino acid sequence of SEQ ID NO: 76.

19. A method of making the IL27 receptor (IL27R) binding protein that specifically binds to IL27Rα subunit (IL27Rα) and glycoprotein 130 subunit (gp130) from the cell of claim 3, the method comprising, culturing the cell to express the IL27 receptor (IL27R) binding protein.

* * * * *

UNITED STATES PATENT AND TRADEMARK OFFICE

CERTIFICATE OF CORRECTION

PATENT NO. : 12,209,132 B2
APPLICATION NO. : 18/464998
DATED : January 28, 2025
INVENTOR(S) : Kastelein et al.

It is certified that error appears in the above-identified patent and that said Letters Patent is hereby corrected as shown below:

In the Claims

Column 747, Line 62, In Claim 5, after "antibody", delete "CDR1"

Column 747, Line 67, In Claim 6, after "antibody", delete "CDR1"

Column 748, Line 31, In Claim 10, after "antibody", delete "CDR1"

Column 748, Line 37, In Claim 11, after "antibody", delete "CDR1"

Column 748, Line 53, In Claim 15, after "antibody", delete "CDR1"

Column 748, Line 56, In Claim 16, after "The isolated cell of claim", delete "3", and enter --14--

Column 748, Line 57, In Claim 16, after "antibody", delete "CDR1"

Signed and Sealed this
Third Day of February, 2026

John A. Squires
*Director of the United States Patent and Trademark Office*